(12) United States Patent
Babaoglu et al.

(10) Patent No.: US 8,987,250 B2
(45) Date of Patent: *Mar. 24, 2015

(54) THERAPEUTIC COMPOUNDS

(71) Applicant: Gilead Sciences, Inc., Foster City, CA (US)

(72) Inventors: Kerim Babaoglu, Lansdale, PA (US); Gediminas Brizgys, San Mateo, CA (US); Jake Cha, Burlingame, CA (US); Xiaowu Chen, Hillsborough, CA (US); Hongyan Guo, San Mateo, CA (US); Randall L. Halcomb, Foster City, CA (US); Xiaochun Han, San Mateo, CA (US); Richard Huang, San Mateo, CA (US); Hongtao Liu, Cupertino, CA (US); Ryan McFadden, Foster City, CA (US); Michael L. Mitchell, Hayward, CA (US); Yingmei Qi, Sunnyvale, CA (US); Paul A. Roethle, San Francisco, CA (US); Lianhong Xu, Palo Alto, CA (US); Hong Yang, Fremont, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/866,997

(22) Filed: Apr. 19, 2013

(65) Prior Publication Data
US 2013/0281433 A1 Oct. 24, 2013

Related U.S. Application Data

(60) Provisional application No. 61/636,602, filed on Apr. 20, 2012, provisional application No. 61/718,165, filed on Oct. 24, 2012.

(51) Int. Cl.
A01N 43/00 (2006.01)
A61K 31/00 (2006.01)
(Continued)

(52) U.S. Cl.
CPC ............ C07D 417/14 (2013.01); C07D 417/10 (2013.01); A61K 31/4439 (2013.01); A61K 31/444 (2013.01); A61K 31/506 (2013.01); A61K 31/496 (2013.01); A61K 31/428 (2013.01); C07D 471/04 (2013.01); A61K 31/437 (2013.01); A61K 31/513 (2013.01); A61K 31/497 (2013.01); A61K 31/5377 (2013.01); A61K 31/454 (2013.01);
(Continued)

(58) Field of Classification Search
USPC ......... 514/210.21, 211.05, 218, 230.5, 233.8, 514/249, 252.06, 252.11, 252.18, 253.1, 514/255.05, 256, 272, 274, 300, 303, 312, 514/313, 321, 333, 338, 367; 540/490, 575; 544/105, 122, 131, 238, 295, 318, 331, 544/333, 350, 357, 364, 405; 546/113, 119, 546/122, 157, 159, 198, 256, 270.1; 548/180
See application file for complete search history.

(56) References Cited

U.S. PATENT DOCUMENTS 3,895,028 A 7/1975 Wada et al.
3,900,486 A 8/1975 Suzuki et al.
(Continued)

FOREIGN PATENT DOCUMENTS

CA 1144556 A1 4/1983
CN 1123275 A 5/1996
(Continued)

OTHER PUBLICATIONS

Chen, S. et al. (2009). "Design, Synthesis and Biological Evaluation of Novel Quinolone Derivatives as HIV-1 Tat-TAR Interaction Inhibitors," *Bioorganic & Medicinal Chem.* 17:1948-1956.
Palella, F.J. et al. (Mar. 26, 1998). "Declining Morbidity and Mortality Among Patients with Advanced Human Immunodeficiency Virus Infection," *N. Engl. J. Med.* 338(13):853-860.
Pauwels, R. et al. (Jun. 1987). "Sensitive and Rapid Assay on MT-4 Cells for Detection of Antiviral Compounds Against the AIDS Virus," *J. Virol. Methods* 16(3):171-185.
Pendri, A. et al. (Aug. 2011, e-pub. May 20, 2011). "New First and Second Generation Inhibitors of Human Immunodeficiency Virus-1 Integrase," *Expert Opin. Ther. Pat.* 21(8):1173-1189.
Porto, S. et al. (2007). "Chiral Thiols: The Assignment of Their Absolute Configuration by H NMR," *Organic Letters* 9(24):5015-5018.
Richman, D.D. (2001). "HIV Chemotherapy," *Nature* 410:995-1001.
(Continued)

Primary Examiner — Wu-Cheng Winston Shen
Assistant Examiner — Jean Cornet
(74) Attorney, Agent, or Firm — Gilead Sciences, Inc.

(57) ABSTRACT

Compounds disclosed herein including compounds of formula I':

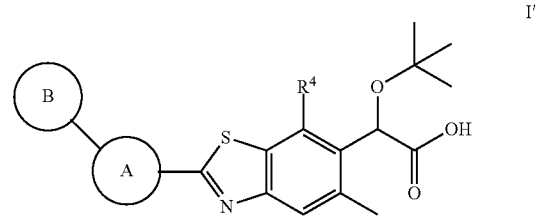

and salts thereof are provided. Pharmaceutical compositions comprising compounds disclosed herein, processes for preparing compounds disclosed herein, intermediates useful for preparing compounds disclosed herein and therapeutic methods for treating an HIV infection using compounds disclosed herein are also provided.

20 Claims, No Drawings

(51) Int. Cl.

| | | |
|---|---|---|
| *C07D 417/14* | (2006.01) | |
| *C07D 417/10* | (2006.01) | |
| *A61K 31/4439* | (2006.01) | |
| *A61K 31/444* | (2006.01) | |
| *A61K 31/506* | (2006.01) | |
| *A61K 31/496* | (2006.01) | |
| *A61K 31/428* | (2006.01) | |
| *C07D 471/04* | (2006.01) | |
| *A61K 31/437* | (2006.01) | |
| *A61K 31/513* | (2006.01) | |
| *A61K 31/497* | (2006.01) | |
| *A61K 31/5377* | (2006.01) | |
| *A61K 31/454* | (2006.01) | |
| *C07D 498/04* | (2006.01) | |
| *A61K 31/5383* | (2006.01) | |
| *A61K 31/4375* | (2006.01) | |
| *A61K 31/4709* | (2006.01) | |
| *A61K 31/501* | (2006.01) | |
| *C07D 487/04* | (2006.01) | |
| *A61K 31/4985* | (2006.01) | |
| *A61K 31/553* | (2006.01) | |
| *A61K 31/551* | (2006.01) | |
| *A61K 45/06* | (2006.01) | |
| *A61K 31/4741* | (2006.01) | |
| *C07D 277/82* | (2006.01) | |
| *C07D 491/06* | (2006.01) | |
| *C07D 417/04* | (2006.01) | |
| *C07D 277/66* | (2006.01) | |

(52) U.S. Cl.
CPC .......... *C07D498/04* (2013.01); *A61K 31/5383* (2013.01); *A61K 31/4375* (2013.01); *A61K 31/4709* (2013.01); *A61K 31/501* (2013.01); *C07D 487/04* (2013.01); *A61K 31/4985* (2013.01); *A61K 31/553* (2013.01); *A61K 31/551* (2013.01); *A61K 45/06* (2013.01); *A61K 31/4741* (2013.01); *C07D 277/82* (2013.01); *C07D 491/06* (2013.01); *C07D 417/04* (2013.01); *C07D 277/66* (2013.01)
USPC ............ 514/210.21; 514/211.05; 514/218.23; 514/230.5; 514/233.8; 514/249; 514/252.06; 514/252.11; 514/252.18; 514/253.1; 514/255.05; 514/256; 514/272; 514/274; 514/300; 514/303; 514/312; 514/313; 514/321; 514/333; 514/338; 514/367; 540/490; 540/575; 544/105; 544/122; 544/131; 544/238; 544/295; 544/318; 544/331; 544/333; 544/350; 544/357; 544/364; 544/405; 546/113; 546/119; 546/122; 546/158; 546/159; 546/198; 546/256; 546/270.1

(56) References Cited

U.S. PATENT DOCUMENTS

| | | | |
|---|---|---|---|
| 4,816,570 | A | 3/1989 | Farquhar |
| 4,968,788 | A | 11/1990 | Farquhar |
| 5,434,188 | A | 7/1995 | Boschelli et al. |
| 5,663,159 | A | 9/1997 | Starrett, Jr. et al. |
| 5,733,906 | A | 3/1998 | Jungheim et al. |
| 5,738,985 | A | 4/1998 | Miles et al. |
| 5,792,756 | A | 8/1998 | Starrett, Jr. et al. |
| 5,798,365 | A | 8/1998 | Kirsch et al. |
| 7,514,233 | B2 | 4/2009 | Debyser et al. |
| 8,008,470 | B2 | 8/2011 | Debyser et al. |
| 2005/0165052 | A1 | 7/2005 | Fakhfakh et al. |
| 2005/0239819 | A1 | 10/2005 | Satoh et al. |
| 2005/0261336 | A1 | 11/2005 | Mousnier et al. |
| 2006/0035926 | A1 | 2/2006 | Lee et al. |
| 2006/0094755 | A1 | 5/2006 | Rajagopalan et al. |
| 2006/0275748 | A1 | 12/2006 | Debyser et al. |
| 2009/0197862 | A1 | 8/2009 | Steinig et al. |
| 2009/0203742 | A1 | 8/2009 | Surleraux et al. |
| 2010/0311735 | A1 | 12/2010 | Tsantrizos et al. |
| 2011/0223131 | A1 | 9/2011 | Jin et al. |
| 2013/0203727 | A1 | 8/2013 | Babaoglu et al. |
| 2013/0210801 | A1 | 8/2013 | Babaoglu et al. |
| 2013/0231331 | A1 | 9/2013 | Pendri et al. |
| 2013/0281434 | A1 | 10/2013 | Babaoglu et al. |
| 2014/0045818 | A1 | 2/2014 | Mitchell et al. |

FOREIGN PATENT DOCUMENTS

| | | |
|---|---|---|
| CN | 1044117 C | 7/1999 |
| CN | 1466576 A | 1/2004 |
| CR | 20140213 A | 6/2014 |
| DE | 24 03 682 A1 | 7/1974 |
| EP | 0 017 543 A1 | 10/1980 |
| EP | 1 441 228 A1 | 7/2004 |
| EP | 1 541 558 A1 | 6/2005 |
| EP | 1 565 471 B1 | 10/2006 |
| EP | 1 873 238 A1 | 1/2008 |
| EP | 1 873 238 B1 | 1/2008 |
| GB | 2 154 583 A | 9/1985 |
| JP | 3-287558 A | 12/1991 |
| WO | WO-91/19721 A1 | 12/1991 |
| WO | WO-94/23041 A2 | 10/1994 |
| WO | WO-94/23041 A3 | 10/1994 |
| WO | WO-99/52850 A1 | 10/1999 |
| WO | WO-00/63152 A1 | 10/2000 |
| WO | WO-02/18341 A2 | 3/2002 |
| WO | WO-02/18341 A3 | 3/2002 |
| WO | WO-02/083657 A2 | 10/2002 |
| WO | WO-02/083657 A3 | 10/2002 |
| WO | WO-2004/014371 A1 | 2/2004 |
| WO | WO-2004/046115 A1 | 6/2004 |
| WO | WO-2004/087153 A2 | 10/2004 |
| WO | WO-2004/087153 A3 | 10/2004 |
| WO | WO-2005/120508 A1 | 12/2005 |
| WO | WO-2006/001958 A2 | 1/2006 |
| WO | WO-2006/001958 A3 | 1/2006 |
| WO | WO-2006/002185 A1 | 1/2006 |
| WO | WO-2006/045554 A1 | 5/2006 |
| WO | WO-2006/116412 A2 | 11/2006 |
| WO | WO-2006/116412 A3 | 11/2006 |
| WO | WO-2006/124780 A2 | 11/2006 |
| WO | WO-2006/124780 A3 | 11/2006 |
| WO | WO-2007/016392 A2 | 2/2007 |
| WO | WO-2007/016392 A3 | 2/2007 |
| WO | WO-2007/131350 A1 | 11/2007 |
| WO | WO-2007/138472 A2 | 12/2007 |
| WO | WO-2007/138472 A3 | 12/2007 |
| WO | WO-2007/147884 A1 | 12/2007 |
| WO | WO-2008/053478 A2 | 5/2008 |
| WO | WO-2008/071587 A2 | 6/2008 |
| WO | WO-2008/071587 A3 | 6/2008 |
| WO | WO-2009/062285 A1 | 5/2009 |
| WO | WO-2009/062288 A1 | 5/2009 |
| WO | WO-2009/062289 A1 | 5/2009 |
| WO | WO-2009/062308 A1 | 5/2009 |
| WO | WO-2009/095500 A1 | 8/2009 |
| WO | WO-2010/059658 A1 | 5/2010 |
| WO | WO-2010/130034 A1 | 11/2010 |
| WO | WO-2010/130842 A1 | 11/2010 |
| WO | WO-2011/002635 A1 | 1/2011 |
| WO | WO-2011/015641 A1 | 2/2011 |
| WO | WO-2011/047129 A1 | 4/2011 |
| WO | WO-2011/076765 A1 | 6/2011 |
| WO | WO-2011/106445 A1 | 9/2011 |
| WO | WO-2011/149950 A2 | 12/2011 |
| WO | WO-2011/149950 A3 | 12/2011 |
| WO | WO-2012/003497 A1 | 1/2012 |
| WO | WO-2012/003498 A1 | 1/2012 |
| WO | WO-2012/033735 A1 | 3/2012 |
| WO | WO-2012/065963 A2 | 5/2012 |
| WO | WO-2012/065963 A3 | 5/2012 |
| WO | WO-2012/066442 A1 | 5/2012 |
| WO | WO-2012/088365 A1 | 6/2012 |

(56) References Cited

FOREIGN PATENT DOCUMENTS

| WO | WO-2012/102985 A1 | 8/2012 |
|---|---|---|
| WO | WO-2012/137181 A1 | 10/2012 |
| WO | WO-2012/138669 A1 | 10/2012 |
| WO | WO-2012/138670 A1 | 10/2012 |
| WO | WO-2012/140243 A1 | 10/2012 |
| WO | WO-2012/145728 A1 | 10/2012 |
| WO | WO-2013/002357 A1 | 1/2013 |
| WO | WO-2013/025584 A1 | 2/2013 |
| WO | WO-2013/043553 A1 | 3/2013 |
| WO | WO-2013/058409 A1 | 4/2013 |
| WO | WO-2013/058448 A1 | 4/2013 |
| WO | WO-2013/062028 A1 | 5/2013 |
| WO | WO-2013/103724 A1 | 7/2013 |
| WO | WO-2013/103738 A1 | 7/2013 |
| WO | WO-2013/106643 A2 | 7/2013 |
| WO | WO-2013/106643 A3 | 7/2013 |
| WO | WO-2013/123148 A1 | 8/2013 |
| WO | WO-2013/134113 A1 | 9/2013 |
| WO | WO-2013/134142 A1 | 9/2013 |
| WO | WO-2013/157622 A1 | 10/2013 |
| WO | WO-2013/159064 A1 | 10/2013 |
| WO | WO-2014/009794 A1 | 1/2014 |
| WO | WO-2014/028384 A1 | 2/2014 |
| WO | WO-2014/055603 A1 | 4/2014 |
| WO | WO-2014/055618 A1 | 4/2014 |

OTHER PUBLICATIONS

Sagar, K.S. et al. (Aug. 1, 2004). "Preparation and Anti-HIV Activities of Retrojusticidin B Analogs and Azalignans," *Bioorg. Med. Chem.* 12(15):4045-4054.

Wang, C.Y. et al. (Dec. 2004). "Pharmacokinetic and Metabolic Studies of Retrojusticidin B, A Potential Anti-Viral Lignan, in Rats," *Planta Medica* 70(12):1161-1165.

Willgerodt, C. et al. (1900). "Regarding Quino-α:p-α-Phenyl and Quino-α:p-α Methyl Quinoline-γ-Hydroxy Acid," *Reports of the German Chemical Society* 33(3):2927-2935 (with full English Translation).

Zhan, P. et al. (2009). "Synthesis and Anti-HIV Activity Evaluation of 2-(4-(Naphthalen-2-yl)-1,2,3-thiadiazol-5-ylthio)-N-Acetamides as Novel Non-Nucleosides HIV-1 Reverse Transcriptase Inhibitors," *European Journal of Medicinal Chem.* 44:4648-4653.

Zouhiri, F. et al. (2001). "HIV-1 Replication Inhibitors of the Styrylquinoline Class: Incorporation of a Masked Diketo Acid Pharmacophore," *Tetrahedron Letters* 42:8189-8192.

International Search Report mailed on Feb. 21, 2013, for PCT Patent Application No. PCT/US2013/020172 filed on Jan. 3, 2013, four pages.

International Search Report mailed on Sep. 1, 2011, for PCT Patent Application No. PCT/US2011/042880 filed on Jul. 1, 2011, four pages.

International Search Report mailed on Sep. 14, 2011, for PCT Patent Application No. PCT/US2011/042881 filed on Jul. 1, 2011, seven pages.

International Search Report mailed on Mar. 26, 2013, for PCT Patent Application No. PCT/US2013/020151 filed on Jan. 3, 2013, five pages.

International Search Report mailed on Jul. 2, 2012, for PCT Patent Application No. PCT/US2012/034593 filed on Apr. 20, 2012, five pages.

International Search Report mailed on Aug. 5, 2013, for PCT Patent Application No. PCT/US2013/037483 filed on Apr. 19, 2013, three pages.

Written Opinion of the International Searching Authority mailed on Sep. 1, 2011, for PCT Patent Application No. PCT/US2011/042880 filed on Jul. 1, 2011, six pages.

Written Opinion of the International Searching Authority mailed on Sep. 14, 2011, for PCT Patent Application No. PCT/US2011/042881 filed on Jul. 1, 2011, 12 pages.

Written Opinion of the International Searching Authority mailed on Jul. 2, 2012, for PCT Patent Application No. PCT/US2012/034593 filed on Apr. 20, 2012, six pages.

International Preliminary Report on Patentability mailed on Jan. 17, 2013, for PCT Patent Application No. PCT/US2011/042880 filed on Jul. 1, 2011, 7 pages.

European Communication mailed on Oct. 15, 2013 for European Patent Application No. 11738878.5 filed on Jul. 1, 2011, four pages.

U.S. Appl. No. 14/112,473, filed Oct. 17, 2013, by Mitchell et al.

Benzaria, S. et al. (Dec. 6, 1996). "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," *J. Med. Chem.* 39(25):4958-4965.

De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," *J. Med. Chem.* 37(4):498-511.

Farquhar, D. et al. (Mar. 1983). "Biologically Reversible Phosphate-Protective Groups," *J. Pharm. Sci.* 72(3):324-325.

Khamnei, S. et al. (Sep. 27, 1996). "Neighboring Group Catalysis in the Design of Nucleotide Prodrugs," *J. Med. Chem.* 39(20):4109-4115.

Kocienski, P.J. (May 1994). "Protecting Groups: An Overview," Chapter 1 in *Protecting Groups*, Thieme Publishing Group: New York, NY, pp. 1-20.

Kocienski, P.J. (May 1994). "Hydroxyl Protecting Groups," Chapter 2 in *Protecting Groups*, Thieme Publishing Group: New York, NY, pp. 21-94.

Kocienski, P.J. (May 1994). "Diol Protecting Groups," Chapter 3 in *Protecting Groups*, Thieme Publishing Group: New York, NY, pp. 95-117.

Kocienski, P.J. (May 1994). "Carboxyl Protecting Groups," Chapter 4 in *Protecting Groups*, Thieme Publishing Group: New York, NY, pp. 118-154.

Kocienski, P.J. (May 1994). "Carbonyl Protecting Groups," Chapter 5 in *Protecting Groups*, Thieme Publishing Group: New York, NY, pp. 155-184.

Bundgaard, H. (1991). "Design and Application of Prodrugs," Chapter 5 in *A Textbook of Drug Design and Development*, Krogsgaard-Larsen, P. et al. eds., Harwood Academic Publishers, pp. 113-191.

McGinnity, D.F. et al. (Nov. 2004; e-pub. Jul. 30, 2004). "Evaluation of Fresh and Cryopreserved Hepatocytes as in Vitro Drug Metabolism Tools for the Prediction of Metabolic Clearance," *Drug Metab. Dispos.* 32(11):1247-1253.

Mitchell, A.G. et al. (1992). "Bioreversible Protection for the Phospho Group: Bioactivation of the Di (4-Acyloxybenzl) and Mono (4-Acyloxybenzl) Phosphoesters of Methylphosphonate and Phosphonoacetate," *J. Chem. Soc. Perkin Trans. II* 2345-2353.

Obach, R.S. et al. (Oct. 1997). "The Prediction of Human Pharmacokinetic Parameters from Preclinical and In Vitro Metabolism Data," *J. Pharmacol. Exp. Ther.* 283(1):46-58.

Puech, F. et al. (Oct. 1993). "Intracellular Delivery of Nucleoside Monophosphates Through a Reductase-Mediated Activation Process," *Antiviral Res.* 22(2-3):155-174.

Spivey, A.C. et al. (1999; e-pub. Dec. 4, 1999). "Configurationally Stable Biaryl Analogues of 4-(Dimethylamino) Pyridine: A Novel Class of Chiral Nucleophilic Catalysts," *J. Org. Chem.* 64(26):9430-9443.

Bolivian Opposition submitted to the Bolivian Patent Office for Bolivian Patent Application No. SP-0194-2011, filed on Jul. 1, 2011, two pages.

Bolivian Opposition submitted to the Bolivian Patent Office for Bolivian Patent Application No. SP-0195-2011, filed on Jul. 1, 2011, two pages.

Costa Rican Office Action mailed on Aug. 23, 2013 for Costa Rican Patent Application No. 20130045, filed on Jul. 1, 2011, three pages.

Costa Rican Opposition submitted to the Costa Rican Patent Office for Costa Rican Patent Application No. 20130043, filed on Jul. 1, 2011, three pages.

European Communication mailed on Feb. 8, 2013 for European Patent Application No. 11738878.5 filed on Jul. 1, 2011, two pages.

Pakistani Office Action mailed on Nov. 10, 2012 for Pakistani Patent Application No. 4932011, filed on Jul. 1, 2011, two pages.

Pakistani Office Action mailed on Nov. 10, 2012 for Pakistani Patent Application No. 4942011, filed on Jul. 1, 2011, two pages.

(56) References Cited

OTHER PUBLICATIONS

Taiwanese Office Action mailed on Nov. 5, 2013 for Taiwanese Patent Application No. 100123357, filed on Jul. 1, 2011, nine pages.
Al-Mawsawi, L.Q. et al. (Feb. 7, 2011; e-pub. Jan. 12, 2011). "Allosteric Inhibitor Development Targeting HIV-1 Integrase," *ChemMedChem.* 6(2):228-241.
Balakrishnan, M. et al. (Sep. 9, 2013). "Non-Catalytic Site HIV-1 Integrase Inhibitors Disrupt Core Maturation and Induce a Reverse Transcription Block in Target Cells," *PloS One* 8(9):e74163, 12 Total Pages.
Bartholomeeusen, K. et al. (Apr. 24, 2009; e-pub. Feb. 25, 2009). "Lens Epithelium-Derived Growth Factor/p75 Interacts with the Transposase-Derived DDE Domain of PogZ," *J. Biol. Chem.* 284(17):11467-11477.
Busschots, K. et al. (Feb. 2, 2007; e-pub. Nov. 3, 2006). "Identification of the LEDGF/p75 Binding Site in HIV-1 Integrase," *J. Mol. Biol.* 365(5):1480-1492.
Busschots, K. et al. (Jan. 2009; e-pub. Oct. 16, 2008). "In Search of Small Molecules Blocking Interactions Between HIV Proteins and Intracellular Cofactors," *Mol. Biosyst.* 5(1):21-31.
Chakraborty, A. et al. (Mar. 1, 2013; e-pub. Dec. 25, 2012). "Biochemical interactions between HIV-1 integrase and reverse transcriptase," *FEBS Letters* 587(5):425-429.
Cherepanov, P. et al. (Jun. 2005; e-pub. May 15, 2005). "Solution Structure of the HIV-1 Integrase-Binding Domain in LEDGF/p75," *Nat. Struct. Mol. Biol.* 12(6):526-532.
Cherepanov, P. et al. (Nov. 29, 2005; e-pub. Oct. 31, 2005). "Structural Basis for the Recognition Between HIV-1 Integrase and Transcriptional Coactivator p75," *PNAS* 102(48):17308-17313.
Christ, F. et al. (Aug. 2012; e-pub. Jun. 4, 2012). "Small-Molecule Inhibitors of the LEDGF/p75 Binding Site of Integrase Block HIV Replication and Modulate Integrase Multimerization," *Antimicrob. Agents Chemother.* 56(8):4365-4374.
Christ, F. et al. (Jun. 2010; e-pub. May 16, 2010). "Rational Design of Small-Molecule Inhibitors of the LEDGF/p75-Integrase Interaciton and HIV Replication," *Nat. Chem. Biol.*
De Luca, L. et al. (Feb. 2011; e-pub. Dec. 21, 2010). "HIV-1 integrase strand-transfer inhibitors: design, synthesis and molecular modeling investigation," *Eur. J. Med. Chem.* 46(2):756-764.
De Luca, L. et al. (Jul. 2011). "Inhibition of the Interaction Between HIV-1 Integrase and its Cofactor LEDGF/p75: A Promising Approach in Anti-Retroviral Therapy," *Mini Rev. Med. Chem.* 11(8):714-727.
Desimmie, B.A. et al. (May 30, 2013). "LEDGINs Inhibit Late Stage HIV-1 Replication by Modulating Integrase Multimerization in the Virions," *Retrovirology* 10:57, 16 Total Pages.
Engelman, A. et al. (Mar. 28, 2008). "The Lentiviral Integrase Binding Protein LEDGF/p75 and HIV-1 Replication," *PloS Pathog.* 4(3):e1000046, 9 Total Pages.
Graham, R.L.J. et al. (2011). "Proteomic Analysis of LEDGF/p75 Interactions with Nuclear Proteins," ASMS Poster, 1 page.
Hauser, F.M. et al. (1978). "Singlet Oxygen and Epoxidation from the Dehydration of Hydrogen Peroxide," *J. Org. Chem.* 43(1):180.
Hayouka, Z. et al. (2010). "Cyclic Peptide Inhibitors of HIV-1 Integrase Derived from the LEDGF/p75 Protein," *Bioorganic & Medicinal Chemistry* 18:8388-8395.
Hombrouck, A. et al. (Mar. 2007). "Virus Evolution Reveals an Exclusive Role for LEDGF/p75 in Chromosomal Tethering," *PloS* 3(3):e47, 13 Total Pages.
Huang, X. et al. (2007). "A Novel Multicomponent Reaction of Arynes, β-Keto Sulfones, and Michael-Type Acceptors: A Direct Synthesis of Polysubstituted Naphthols and Naphthalenes," *J. Org. Chem.* 72:3965-3968.
Johns, B.A. et al. (2013). "HIV Integrase Inhibitors," Chapter 6 in *Successful Strategies for the Discovery of Antiviral Drugs*, Desai, M.C. et al. eds., RSC Publishing, pp. 149-188.
Jurado, K.A. et al. (2013). "Allosteric Integrase Inhibitor Potency is Determined through the Inhibition of HIV-1 Particle Maturation," *PNAS* 110(21):8690-8695.
Kessl, J.J. et al. (2011). "FRET Analysis Reveals Distinct Conformations of IN Tetramers in the Presence of Viral DNA or LEDGF/p75," *Nuc. Acids Res.*, pp. 1-14.
Llano, M. et al. (Sep. 2004). "LEDGF/p75 Determines Cellular Trafficking of Diverse Lentiviral but Not Murine Oncoretroviral Integrase Proteins and is a Component of Functional Lentiviral Preintegration Complexes," *J. Virol.* 78(17):9524-9537.
Llano, M. et al. (Oct. 20, 2006; e-pub. Sep. 7, 2006). "An Essential Role for LEDGF/p75 in HIV Integration," *Science* 314(5798):461-464.
Mekouar, K. et al. (Jul. 16, 1998; e-pub. Jun. 25, 1998). "Styrylquinoline Derivatives: A New Class of Potent HIV-1 Integrase Inhibitors That Block HIV-1 Replication in CEM Cells," *J. Med. Chem.* 41(15):2846-2857.
Poeschla, E.M. et al. (2008). "Integrase, LEDGF/p75 and HIV Replication," *Cell. Mol. Life Sci.* 65:1403-1424.
Rain, J.C. et al. (2009). "Yeast-Two Hybrid Detection of Integrase-Host Factor Interactions," *Methods*, 7 Total Pages.
Rhodes, D.I. et al. (Oct. 17, 2011; e-pub. Aug. 17, 2011). "Crystal Structures of Novel Allosteric Peptide Inhibitors of HIV Integrase Identify New Interactions at the LEDGF Binding Site," *Chembiochem.* 12(15):2311-2315.
Shun, M.C. et al. (Jul. 15, 2007). "LEDGF/p75 Functions Downstream from Preintegration Complex Formation to Effect Gene-Specific HIV-1 Integration," *Genes Dev.* 21(14):1767-1778.
Suzuki, Y. et al. (Mar. 2007). "The Road to Chromatin—Nuclear Entry of Retroviruses," *Nat. Rev. Microbiol.* 5(3):187-196.
Tsiang, M. et al. (Jun. 15, 2012; e-pub. Apr. 25, 2012). "New Class of HIV-1 Integrase (IN) Inhibitors with a Dual Mode of Action," *J. Biol. Chem.* 287(25):21189-21203.
Vandekerckhove, L. et al. (Feb. 2006). "Transient and Stable Knockdown of the Integrase Cofactor LEDGF/p75 Reveals its Role in the Replication Cycle of Human Immunodeficiency Virus," *J. Virol.* 80(4):1886-1896.
Walker, M.A. (2009). "New Approaches for Inhibiting HIV Integrase: A Journey Beyond the Active Site," *Curr. Opin. Investig. Drugs* 10(2):129-136.
Wenhua, Z. et al. (2003). "Advances on Effects of Natural Products Against AIDS Virus," *Chinese Traditional Patent Medicine* 25(9):750-752 (with English Translation).
Restriction Requirement mailed on Apr. 24, 2014 for U.S. Appl. No. 14/112,473, filed Oct. 17, 2013, eight pages.
Notice of Allowance mailed on Aug. 15, 2014 for U.S. Appl. No. 14/112,473, filed Oct. 17, 2013, seven pages.
Australian Office Action mailed on Feb. 26, 2014, for Australian Patent Application No. 2011274323, filed on Jul. 1, 2011, three pages.
Australian Office Action mailed on Mar. 7, 2014, for Australian Patent Application No. 2011274322 filed on Jul. 1, 2011, three pages.
Chinese Office Action mailed on Mar. 3, 2014, for Chinese Patent Application No. 201180038442.X filed on Jul. 1, 2011, eight pages.
Chinese Office Action mailed on Mar. 25, 2014 for Chinese Patent Application No. 201180038443.4, filed on Jul. 1, 2011, eight pages.
Costa Rican Opposition filed Apr. 28, 2014 against Costa Rican Patent Application No. 201320102, filed Jul. 1, 2011, sixteen pages.
Columbian Office Action mailed on Feb. 20, 2014, for Columbian Patent Application No. 12236161 filed on Jul. 1, 2011, 10 pages.
Columbian Office Action mailed on Jun. 12, 2014 for Columbian Patent Application No. 12236158, filed on Jul. 1, 2011, twelve pages.
Eurasian Office Action mailed on Mar. 19, 2014, for Eurasian Patent Application No. 201291300 filed on Jul. 1, 2011, four pages.
Eurasian Office Action mailed in Apr. 9, 2014, for Eurasian Patent Application No. 201291301, filed on Jul. 1, 2011, three pages.
Israeli Office Action mailed on Mar. 3, 2014 for Israeli Patent Application No. 223558, filed on Jul. 1, 2011, two pages.
New Zealand Office Action mailed on Aug. 22, 2013 for New Zealand Patent Application No. 604598, filed on Jul. 1, 2011, two pages.
Ecuadoran Opposition filed Apr. 23, 2014 against Ecuadoran Patent Application No. SP1312418, filed Jul. 1, 2011, ten pages.
Ecuadoran Opposition from Jun. 2014, against Ecuadoran Patent Application No. SP1312417, filed Jul. 1, 2011, nine pages.

(56) References Cited

OTHER PUBLICATIONS

Philippine Office Action mailed on Aug. 1, 2014, for Philippine Patent Application No. 12013500011, filed on Jul. 1, 2011, two pages.
Written Opinion of the International Searching Authority mailed on Aug. 5, 2013, for PCT Patent Application No. PCT/US2013/037483 filed on Apr. 19, 2013, seven pages.
Written Opinion of the International Searching Authority mailed on Jul. 17, 2014, for PCT Patent Application No. PCT/US2013/020151 filed on Jan. 3, 2013, six pages.
Written Opinion of the International Searching Authority mailed on Jul. 17, 2014, for PCT Patent Application No. PCT/US2013/020172, filed on Jan. 3, 2013, seven pages.
European Communication mailed on Mar. 12, 2014 for European Patent Application No. 11738878.5 filed on Jul. 1, 2011, eight pages.
European Communication mailed on Feb. 15, 2013, for European Patent Application No. 11738339.8, filed on Jul. 1, 2011, two pages.
Philippines Office Action mailed on Mar. 14, 2014 for Philippine Patent Application No. 1/2013/500011, filed on Jul. 1, 2011, two pages.
Mexican Office Action mailed on Mar. 13, 2014 for Mexican Patent Application No. MX/a/2012/015293, filed on Jul. 1, 2011, seven pages.
Vietnamese Office Action mailed on Jul. 28, 2014, for Vietnamese Patent Application No. 1-201300326, filed on Jul. 1, 2011, two pages.
Non-Final Office Action mailed on Nov. 4, 2014, for U.S. Appl. No. 13/867,016, filed Apr. 19, 2013, seven pages.
European Office Action mailed on Oct. 20, 2014, for European Patent Application No. 13719355.3, filed on Apr. 19, 2013, four pages.
Costa Rican Opposition submitted by Asociacion De Genericos Farmaceuticos on Dec. 8, 2014, to the Costa Rican Patent Office against Costa Rican Patent Application No. 20140231, filed on Apr. 19, 2013, sixteen pages.

THERAPEUTIC COMPOUNDS

CROSS REFERENCE TO RELATED APPLICATIONS

This patent application claims the benefit of priority of U.S. Application Ser. No. 61/636,602, filed Apr. 20, 2012 and of U.S. application Ser. No. 61/718,165, filed Oct. 24, 2012. The content of each of these provisional applications is hereby incorporated herein in its entirety.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N Engl. J. Med.* (1998) 338:853-860; Richman, D. D. *Nature* (2001) 410:995-1001).

Accordingly, there is a need for new agents that inhibit the replication of HIV. There is also a need for agents that are directed against alternate sites in the viral life cycle including agents that target the integrase enzyme. There is also a need for new agents with appropriate levels of metabolic stability.

SUMMARY

Compounds and methods for the treatment of an HIV infection are disclosed. Accordingly, one embodiment provides a compound of formula I':

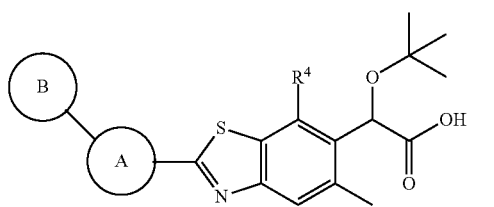

I' wherein:

$R^4$ is selected from aryl, heterocycle and heteroaryl, wherein any aryl, heterocycle and heteroaryl of $R^4$ is optionally substituted with one or more (e.g., 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, $-(C_1-C_6)$alkyl-$(C_3-C_7)$cycloalkyl, $-OH$, $-O(C_1-C_6)$alkyl, $-SH$, $-S(C_1-C_6)$alkyl, $NH_2$, $-NH(C_1-C_6)$alkyl and $-N((C_1-C_6)$alkyl$)_2$, wherein $(C_1-C_6)$alkyl is optionally substituted with hydroxy, $-O(C_1-C_6)$alkyl, cyano or oxo;

A is phenyl, monocyclic heteroaryl or monocyclic heterocycle, wherein any phenyl, monocyclic heteroaryl or monocyclic heterocycle of A is optionally substituted with one or more (e.g., 1, 2, 3, 4 or 5) $Z^{1a}$ groups, and B is aryl, heteroaryl or heterocycle, wherein any aryl, heteroaryl or heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle wherein bicyclic aryl, bicyclic heteroaryl or bicyclic heterocycle is optionally substituted with one or more (e.g., 1, 2, 3, 4 or 5) $Z^{1b}$ groups;

each $Z^{1a}$ is independently selected from halo, $(C_1-C_3)$alkyl, $(C_2-C_3)$alkenyl, $(C_2-C_3)$alkynyl, $(C_1-C_3)$haloalkyl, $(C_3-C_7)$carbocycle, heterocycle, $-O(C_1-C_3)$alkyl, $-O(C_2-C_3)$alkenyl, $-O(C_2-C_3)$alkynyl, $-NR_cR_d$, $-NR_aC(O)R_a$, $-C(O)OR_b$ and $-C(O)NR_cR_d$, wherein any $(C_3-C_7)$carbocycle and heterocycle of $Z^{1a}$ is optionally substituted with one or more (e.g., 1, 2, 3, 4 or 5) halogen or $(C_1-C_6)$alkyl;

each $Z^{1b}$ is independently selected from halo, CN, $(C_1-C_6)$alkyl, $(C_2-C_6)$alkenyl, $(C_2-C_6)$alkynyl, $(C_1-C_6)$haloalkyl, $(C_3-C_7)$carbocycle, heteroaryl, heterocycle, aryl$(C_1-C_6)$alkyl-, $-OH$, $-O(C_1-C_6)$alkyl, $-O(C_2-C_6)$alkenyl, $-O(C_2-C_6)$alkynyl, $-NR_cC(O)R_d$, $-NR_aC(O)R_a$, $-C(O)OR_b$ and $-C(O)NR_cR_d$, wherein any $(C_3-C_7)$carbocycle and heterocycle of $Z^{1b}$ is optionally substituted with one or more (e.g., 1, 2, 3, 4 or 5) halogen or $(C_1-C_6)$alkyl; and $R_a$, $R_b$, $R_c$ and $R_d$ are each independently H or $(C_1-C_6)$alkyl;

or a salt thereof.

One embodiment provides a pharmaceutical composition comprising a compound disclosed herein (e.g., a compound of formula I, I' etc.) or a pharmaceutically acceptable salt thereof, and a pharmaceutically acceptable carrier.

One embodiment provides methods for treating the proliferation of the HIV virus, treating AIDS or delaying the onset of AIDS or ARC symptoms in a mammal (e.g., a human), comprising administering a compound disclosed herein (e.g., a compound of formula I, I' etc.), or a pharmaceutically acceptable salt thereof, to the mammal.

One embodiment provides methods for treating an HIV infection in a mammal (e.g., a human) comprising administering a compound disclosed herein (e.g., a compound of formula I, I' etc.), or a pharmaceutically acceptable salt thereof, to the mammal.

One embodiment provides methods for treating an HIV infection in a mammal (e.g., a human) comprising administering to the mammal in need thereof a therapeutically effective amount of a compound disclosed herein (e.g., a compound of formula I, I' etc.), or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

One embodiment provides a compound disclosed herein (e.g., a compound of formula I, I' etc.), or a pharmaceutically acceptable salt thereof for use in medical therapy (e.g., for use in treating the proliferation of the HIV virus or AIDS or delaying the onset of AIDS or ARC symptoms in a mammal (e.g., a human)).

One embodiment provides a compound disclosed herein (e.g., a compound of formula I, I' etc.), or a pharmaceutically acceptable salt thereof for use in medical therapy (e.g., for use in treating an HIV infection in a mammal (e.g., a human)).

One embodiment provides a compound disclosed herein (e.g., a compound of formula I, I' etc.), or a pharmaceutically acceptable salt thereof for use in the manufacture of a medicament for treating the proliferation of the HIV virus or AIDS or delaying the onset of AIDS or ARC symptoms in a mammal (e.g., a human).

One embodiment provides a compound disclosed herein (e.g., a compound of formula I, I' etc.), or a pharmaceutically acceptable salt thereof, for use in the prophylactic or therapeutic treatment of the proliferation of the HIV virus or AIDS or for use in the therapeutic treatment of delaying the onset of AIDS or ARC symptoms.

One embodiment provides a compound disclosed herein (e.g., a compound of formula I, I' etc.), or a pharmaceutically acceptable salt thereof, for the manufacture of a medicament for treating an HIV infection in a mammal (e.g., a human).

One embodiment provides a compound disclosed herein (e.g., a compound of formula I, I' etc.) or a pharmaceutically acceptable salt thereof, for use in the prophylactic or therapeutic treatment of an HIV infection in a mammal (e.g., a human).

One embodiment provides processes and intermediates disclosed herein that are useful for preparing compounds disclosed herein or salts thereof.

DETAILED DESCRIPTION

Definitions

Unless stated otherwise, the following terms and phrases as used herein are intended to have the following meanings.

When trade names are used herein, applicants intend to independently include the tradename product and the active pharmaceutical ingredient(s) of the tradename product.

"Alkyl" is hydrocarbon containing normal, secondary or tertiary atoms. For example, an alkyl group can have 1 to 20 carbon atoms (i.e., ($C_1$-$C_{20}$)alkyl), 1 to 10 carbon atoms (i.e., ($C_1$-$C_{10}$)alkyl), 1 to 8 carbon atoms (i.e., ($C_1$-$C_8$)alkyl)or 1 to 6 carbon atoms (i.e., ($C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., ($C_1$-$C_{10}$)alkyl), or 1 to 6 carbon atoms (i.e., ($C_1$-$C_6$)alkyl) or 1-3 carbon atoms (i.e., ($C_1$-$C_3$)alkyl). Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g., an aryl fused to one or more aryl or carbocycle). Such bicyclic or multicyclic rings may be optionally substituted with one or more (e.g., 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Exemplary aryl groups include, but are not limited to, phenyl, indenyl, naphthyl, 1, 2, 3, 4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g., ring systems comprising 2 or 3 rings) wherein a heteroaryl group, as defined above, can be fused with one or more heteroaryls (e.g., naphthyridinyl), carbocycles (e.g., 5,6,7,8-tetrahydroquinolyl) or aryls (e.g., indazolyl) to form a multiple condensed ring. Such multiple condensed rings may be optionally substituted with one or more (e.g., 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl, benzofuranyl, benzimidazolyl, thianaphthenyl, pyrrolopyridinyl and pyrazolopyridinyl.

The term "N-heteroaryl" refers to a heteroaryl that contains at least one nitrogen atom within the ring system.

The term "heterocyclyl" or "heterocycle" as used herein refers to a single saturated or partially unsaturated ring or a multiple condensed ring. The term includes single saturated or partially unsaturated rings (e.g., 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g., 1, 2 or 3) oxo groups and the sulfur and nitrogen atoms may also be present in their oxidized forms. Such rings include but are not limited to azetidinyl, tetrahydrofuranyl or piperidinyl. The term also includes multiple condensed ring systems (e.g., ring systems comprising 2 or 3 rings) wherein a heterocycle group (as defined above) can be connected to two adjacent atoms (fused heterocycle) with one or more heterocycles (e.g., decahydronapthyridinyl), heteroaryls (e.g., 1,2,3,4-tetrahydronaphthyridinyl), carbocycles (e.g., decahydroquinolyl) or aryls. It is to be understood that the point of attachment of a heterocycle multiple condensed ring, as defined above, can be at any position of the ring including a heterocyle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, tetrahydropyrimidinyl-2-one, imidazolidinyl-2-one, pyrrolidinyl-2-one, 2,3-dihydropyrano[4,3,2-de]quinolonyl, 2,5-benzo[d][1,3]dioxolyl and chromanyl-4-one.

The term "bridged-heterocycle" as used herein refers to a 4, 5, 6, 7 or 8-membered heterocycle as defined herein connected at two non-adjacent atoms of the 4, 5, 6, 7 or 8-membered heterocycle with one or more (e.g., 1 or 2) 3, 4, 5 or 6-membered heterocycles or ($C_3$-$C_7$)carbocycles as defined herein. Such bridged-heterocycles include bicyclic and tricyclic ring systems (e.g., 2-azabicyclo[2.2.1]heptane and 4-azatricyclo[4.3.1.1$^{3,8}$]undecane).

The term "spiro-heterocycle" as used herein refers to a 3, 4, 5, 6, 7 or 8-membered heterocycle as defined herein connected to one or more (e.g., 1 or 2) single atoms of the 3, 4, 5, 6, 7 or 8-membered heterocycle with one or more (e.g., 1 or 2) 3, 4, 5, 6-membered heterocycles or a ($C_3$-$C_7$)carbocycles as defined herein. Such spiro-heterocycles include bicyclic and tricyclic ring systems (e.g., 1,4-dioxaspiro[4.5]dec-7-enyl).

The term "macroheterocycle" as used herein refers to a saturated or partially unsaturated 8, 9, 10, 11 or 12-membered ring comprising about 5 to 11 carbon atoms and about 1 to 3 heteroatoms selected from the group consisting of oxygen, nitrogen and sulfur in the ring which may be optionally fused at two adjacent atoms of the macroheterocycle to one or more (e.g., 1, 2 or 3) aryls, carbocycles, heteroaryls or heterocycles. The macroheterocycle may be substituted with one or more (e.g., 1, 2 or 3) oxo groups and the sulfur and nitrogen atoms may also be present in their oxidized forms.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e., heteroaryl ($C_1$-$C_6$)alkyl). Heteroarylalkyl groups include, but are not limited to heteroaryl-$CH_2$—, heteroaryl-CH($CH_3$)—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl($C_1$-$C_6$)alkyl). Typical heterocyclylalkyl groups include, but are not limited to heterocyclyl-$CH_2$—, heterocyclyl-CH($CH_3$)—, heterocyclyl-$CH_2CH_2$—, 2-(heterocyclyl) ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a saturated (i.e., cycloalkyl) or partially unsaturated (e.g., cycloalkenyl, cycloalkadienyl, etc.) ring having 3 to 7 carbon atoms as a monocycle or a mutlicyclic ring system. In one embodiment the carbocycle is a monocycle comprising 3-6 ring carbons (i.e. ($C_3$-$C_6$)carbocycle). Carbocycle includes multicyclic carbocyles having 7 to 12 carbon atoms as a bicycle, and up to about 20 carbon atoms as a polycycle provided that the largest single ring of a multicyclic carbocycle is 7 carbon atoms. The term "spiro-bicyclic carbocycle" refers to a carbocycle bicyclic ring system wherein the rings of the bicyclic ring system are connected to a single carbon atom (e.g., spiropentane, spiro[4,5]decane, spiro[4.5]decane, etc). The term "fused-bicyclic carbocycle" refers to a carbocycle bicyclic ring system wherein the rings of the bicyclic ring system are connected to two adjacent carbon atoms such as a bicyclo [4,5], [5,5], [5,6] or [6,6] system, or 9 or 10 ring atoms arranged as a bicyclo [5,6] or [6,6] system (e.g., decahydronaphthalene, norsabinane, norcarane). The term "bridged-bicyclic carbocycle" refers to a carbocycle bicyclic ring system wherein the rings of the bicyclic ring system are connected to two non-adjacent carbon (e.g., norbornane, bicyclo[2.2.2]octane, etc). The "carbocycle" or "carbocyclyl" may be optionally substituted with one or more (e.g., 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "halocarbocycle" as used herein refers to a carbocycle as defined herein, wherein one or more hydrogen atoms are each replaced by a halo substituent. For example, ($C_3$-$C_7$)halocarbocycle is a ($C_3$-$C_7$)carbocycle wherein one or more of the hydrogen atoms have been replaced by a halo substituent. Such a range includes one halo substituent on the carbocycle group to complete halogenation of the carbocycle group.

The term "macrocarbocycle" as used herein refers to a saturated or partially unsaturated 8, 9, 10, 11 or 12-membered ring comprising 8 to 12 carbon atoms which may be optionally fused at two adjacent atoms of the macrocarbocycle to one or more (e.g., 1, 2 or 3) aryls, carbocycles, heteroaryls or heterocycles. The macrocarbocycle may be substituted with one or more (e.g., 1, 2 or 3) oxo groups.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e.

carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl)ethan-1-yl, and the like, wherein the "carbocyclyl" portion includes any of the carbocyclyl groups described above.

It is to be understood that when a variable is substituted, for example, as described by the phrase "($C_1$-$C_6$)alkyl, either alone or as part of a group, is optionally substituted", the phrase means that the variable ($C_1$-$C_6$)alkyl can be substituted when it is alone and that it can also be substituted when the variable "($C_1$-$C_6$)alkyl" is part of a larger group such as for example an aryl($C_1$-$C_6$)alkyl or a —($C_1$-$C_6$)alkyl-$SO_2$—($C_1$-$C_6$)alkyl-($C_3$-$C_7$)carbocycle group. Similarly, when stated, other variables (e.g., ($C_1$-$C_6$)alkenyl, ($C_1$-$C_6$)alkynyl, aryl, heteroaryl, heterocycle, etc.) can also be substituted "either alone or as part of a group."

It is to be understood that certain variables of formula I, that connect two chemical groups may be oriented in either direction. Thus, for the X group of formula I (e.g., O, —C(O)—, —C(O)O—, —S—, —S(O)—, —$SO_2$—, —($C_1$-$C_6$)alkylO—, —($C_1$-$C_6$)alkylC(O)—, —($C_1$-$C_6$)alkylC(O)O—, —($C_1$-$C_6$)alkylS—, —($C_1$-$C_6$)alkylS(O)— and —($C_1$-$C_6$)alkyl$SO_2$—) certain values of X that are not symmetric can be oriented in either direction. For example, the —C(O)O—, can be oriented as either —C(O)O— or —OC(O)—, relative to the groups it connects.

It is to be understood that the nitrogen that is included in the core of the compound of formula I or formula I' can be present in an oxidized form. For example, the thiazole nitrogen of either $G^1$ or $G^2$ of formula I can be an N-oxide. Accordingly, the invention includes a compound of formula I or formula I' (as defined in the summary of the invention) or a salt or N-oxide thereof.

One skilled in the art will recognize that substituents and other moieties of the compounds disclosed herein should be selected in order to provide a compound which is sufficiently stable to provide a pharmaceutically useful compound which can be formulated into an acceptably stable pharmaceutical composition. Compounds disclosed herein which have such stability are contemplated as falling within the scope of the present invention.

The modifier "about" used in connection with a quantity is inclusive of the stated value and has the meaning dictated by the context (e.g., includes the degree of error associated with measurement of the particular quantity).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Certain compounds of the invention can exist as atropisomers. For example, it has been discovered that atropisomers exist for certain substituents at the $R^4$ position of compounds of the invention (e.g., compounds of formula I, I' and related formulas described herein) as marked by an asterisk in the formula below.

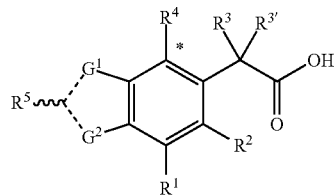

The chirality that results from the atropisomers at the asterisk position is a feature of certain compounds of the invention. Accordingly, the invention includes all atropisomers of compounds of the invention including mixtures of atropisomers and well as mixtures that are enriched in an atropisomer as well as single atropisomers, which mixtures or compounds possess the useful properties described herein.

In one embodiment, the compounds of the invention are greater than 50% a single atropisomer for the $R^4$ substituent at the asterisk position. In one embodiment, the compounds of the invention are at least 60% a single atropisomer for the $R^4$ substituent at the asterisk position. In another embodiment, the compounds of the invention are at least 70% a single atropisomer for the $R^4$ substituent at the asterisk position. In another embodiment, the compounds of the invention are at least 80% a single atropisomer for the $R^4$ substituent at the asterisk position. In another embodiment, the compounds of the invention are at least 90% a single atropisomer for the $R^4$ substituent at the asterisk position. In another embodiment, the compounds of the invention are at least 95% a single atropisomer for the $R^4$ substituent at the asterisk position. In one embodiment the stereochemistry for the $R^4$ substituent at the carbon marked with an asterisk as shown above for a compound of the invention (e.g., compounds of formula I or formula I') is the (R) stereochemistry. In another embodiment the stereochemistry for the $R^4$ substituent at the carbon marked with an asterisk as shown above for a compound of the invention (e.g., compounds of formula I or formula I') is the (S) stereochemistry.

For certain compounds of the invention the stereochemistry at the carbon bearing the $R^3$ substituent of compounds of the invention (e.g., compounds of formula I or formula I') as marked by an asterisk in the formula below is another aspect of the invention.

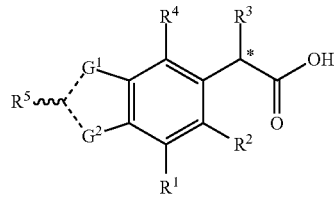

In one embodiment the stereochemistry at the carbon marked with an asterisk as shown in the formula above for a compound of the invention is the (S) stereochemistry. In another embodiment the stereochemistry at the carbon marked with an asterisk as shown in the formula above for a compound of the invention is the (R) stereochemistry.

In one embodiment, the compounds of the invention are greater than 50% a stereoisomer for the carbon at the asterisk position. In another embodiment, the compounds of the invention are at least 60% a single stereoisomer for the carbon at the asterisk position. In another embodiment, the compounds of the invention are at least 70% a single stereoisomer for the carbon at the asterisk position. In another embodiment, the compounds of the invention are at least 80% a single stereoisomer for the carbon at the asterisk position. In another embodiment, the compounds of the invention are at least 90% a single stereoisomer for the carbon at the asterisk position. In another embodiment, the compounds of the invention are at least 95% a single stereoisomer for the carbon at the asterisk position.

It is to be understood that for compounds disclosed herein when a bond is drawn in a non-stereochemical manner (e.g. flat) the atom to which the bond is attached includes all stereochemical possibilities. It is also to understood that when a bond is drawn in a stereochemical manner (e.g. bold, bold-wedge, dashed or dashed-wedge) the atom to which the stereochemical bond is attached has the stereochemistry as shown unless otherwise noted.

The term "treatment" or "treating," to the extent it relates to a disease or condition includes preventing the disease or condition from occurring, and/or inhibiting the disease or condition, and/or eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present disclosure, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. Protecting groups do not need to be, and generally are not, the same if the compound is substituted with multiple protecting groups. In general, protecting groups will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds described herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of pharmaceutically acceptable salts of the compounds described herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of disclosed herein. All salts, whether or not derived from a physiologically acceptable acid or base, are within the scope of the present invention.

Metal salts can be prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their un-ionized, as well as zwitterionic form, and combinations with water as in hydrates. In one embodiment the hydrates include a compound disclosed herein with stoichiometric amounts of water.

Certain embodiments provide salts of the compounds disclosed herein with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

Specific values listed below for radicals, substituents, and ranges in the embodiments of the invention are for illustration only; they do not exclude other defined values or other values within defined ranges for the radicals and substituents.

Compounds of Formula I.

A specific group of compounds of formula I are compounds of formula Ia:

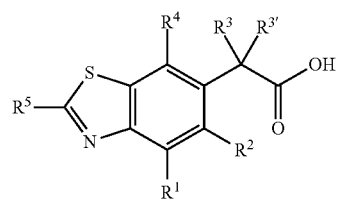

or a salt thereof.

Another specific group of compounds of formula I are compounds of formula Ib:

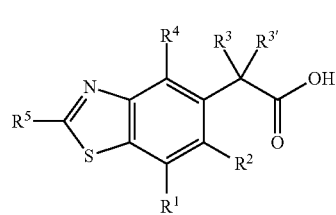

or a salt thereof.

Another specific group of compounds of formula I are compounds of formula Ic:

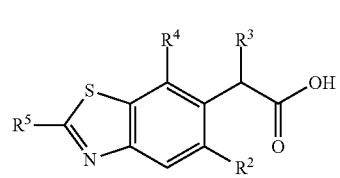

wherein $R^3$ is —$O(C_1$-$C_6)$alkyl or a salt thereof.

Another specific group of compounds of formula I are compounds of formula Ic':

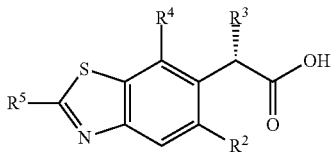

wherein R³ is —O(C₁-C₆)alkyl or a salt thereof

Another specific group of compounds of formula I are compounds of formula Id:

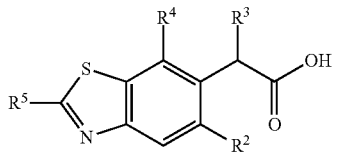

wherein R³ is —O(C₁-C₆)alkyl, or a salt thereof.

Another specific group of compounds of formula I are compounds of formula Id':

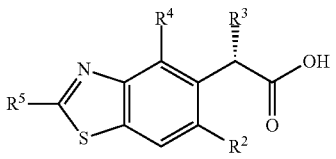

wherein R³ is —O(C₁-C₆)alkyl, or a salt thereof.

Another specific group of compounds of formula I are compounds of formula Ie:

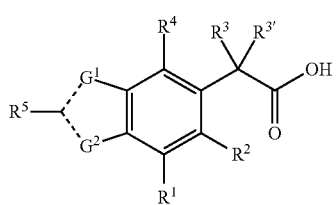

wherein:

G¹ is S; G² is N; the dashed bond connected to G¹ is a single bond and the dashed bond connected to G² is a double bond; or G¹ is N; G² is S; the dashed bond connected to G¹ is a double bond and the dashed bond connected to G² is a single bond;

or a salt thereof.

Another specific group of compounds of formula I are compounds of formula If:

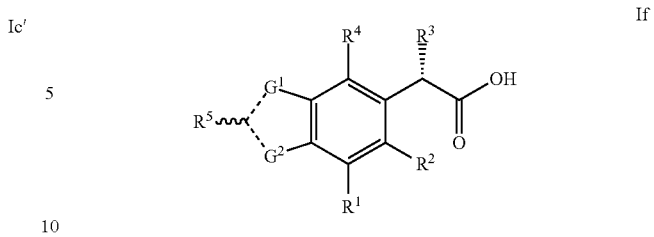

or a salt thereof.

Specific embodiments of the invention (e.g., embodiments) and specific values listed below are embodiments and values for compounds of formula I including all of the compounds of sub-formulas of formula I (e.g., the compounds of formulas Ia, Ib, Ic, Ic', Id, Id', Ie, If, Ia100-Ia145, etc.) and for compounds of formulas I' and subformulas or I' (e.g., formula Ia'). It is to be understood that two or more of the values listed herein below may be combined with one another.

A specific group of compounds of formula I are compounds wherein at least one of R¹, R², R³, R³' or R⁴ is selected from $R^{1b}$, $R^{2b}$, $R^{3b}$, $R_{3b'}$ or $R^{4b}$.

Another specific group of compounds of formula I are compounds wherein at least two of R¹, R², R³, R³' or R⁴ is selected from $R^{1b}$, $R^{2b}$, $R^{3b}$, $R^{3b'}$ or $R^{4b}$.

Another specific group of compounds of formula I are compounds wherein at least three of R¹, R², R³, R³' or R⁴ is selected from $R^{1b}$, $R^{2b}$, $R^{3b}$, $R^{3b'}$ or $R^{4b}$.

Another specific group of compounds of formula I are compounds wherein at least four of R¹, R², R³, R³' or R⁴ is selected from $R^{1b}$, $R^{2b}$, $R^{3b}$, $R^{3b'}$ or $R^{4b}$.

Another specific group of compounds of formula I are compounds wherein all five of R¹, R², R³, R³' or R⁴ is selected from $R^{1b}$, $R^{2b}$, $R^{3b}$, $R^{3b'}$ or $R^{4b}$.

Another specific group of compounds of formula I are compounds wherein R¹, R², R³, R³' and R⁴ are $R^{1b}$, $R^{2b}$, $R^{3b}$, $R^{3b'}$ or $R^{4b}$.

A specific value for R¹ is H.
Another specific value for R¹ is H or halo.
Another specific value for R¹ is H or F.
A specific value for R³' is H.
A specific value for R³ is $R^{3b}$.
A specific value for $R^{3b}$ is —OC(CH₃)₂CH₂OH, —OC(CH₃)₂CH₂OH, —O(C₁-C₆)alkyl-O—C(O)—NH₂, —O(C₁-C₆)alkyl-O—C(O)—N(CH₃)₂ or —O(C₁-C₆)alkyl-O—C(O)—NH(phenyl).
Another specific value for $R^{3b}$ is —(C₁-C₆)alkylOH or —O(C₁-C₆)alkyl-O—C(O)—NR_cR_d.
A specific value for R³ is $R^{3a}$.
A specific value for $R^{3a}$ is (C₁-C₆)alkyl, (C₂-C₆)alkenyl or —O(C₁-C₆)alkyl wherein any (C₁-C₆)alkyl or (C₂-C₆)alkenyl of $R^{3a}$ is optionally substituted with one or more groups selected from —O(C₁-C₆)alkyl, halo, oxo and —CN.
Another specific value for $R^{3a}$ is —OC(CH₃)₃.
A specific value for R³' is $R^{3b'}$.
A specific value for $R^{3b'}$ is (C₁-C₆)alkyl or —O(C₁-C₆)alkyl.
A specific value for R³' is $R^{3a'}$.
A specific value for $R^{3a'}$ is H.
A specific value for R³ is (C₁-C₆)alkyl, (C₂-C₆)alkenyl or —O(C₁-C₆)alkyl, wherein any (C₁-C₆)alkyl or (C₂-C₆)alkenyl of $R^{3a}$ is optionally substituted with one or more groups selected from —O(C₁-C₆)alkyl, halo, oxo and —CN.
Another specific value for R³ is (C₁-C₆)alkyl, (C₂-C₆)alkenyl or —O(C₁-C₆)alkyl, wherein the (C₁-C₆)alkyl, (C₂-C₆)alkenyl or —O(C₁-C₆)alkyl is branched.

A specific value for $R^3$ is —OC(CH$_3$)$_3$.

A specific group of compounds of formula I are compounds wherein $R^{3b}$ and $R^{3b'}$ together with the carbon to which they are attached form a (C$_3$-C$_7$)carbocycle or heterocycle; wherein the (C$_3$-C$_7$)carbocycle or heterocycle is optionally substituted with one or more $Z^1$ groups.

Another specific group of compounds of formula I are compounds wherein $R^{3b}$ and $R^{3b'}$ together with the carbon to which they are attached form a (C$_3$-C$_7$)carbocycle or a 4, 5 or 6-membered heterocycle; wherein the (C$_3$-C$_6$)carbocycle or the 4, 5 or 6-membered heterocycle is optionally substituted with one or more $Z^1$ groups.

Another specific group of compounds of formula I are compounds wherein $R^{3b}$ and $R^{3b'}$ together with the carbon to which they are attached form a (C$_4$-C$_6$)carbocycle or a 5 or 6-membered heterocycle; wherein the (C$_4$-C$_6$)carbocycle or the 5 or 6-membered heterocycle is optionally substituted with one or more $Z^1$ groups.

Another specific group of compounds of formula I are compounds wherein $R^{3b}$ and $R^{3b'}$ together with the carbon to which they are attached form a 5 or 6-membered heterocycle; wherein the 5 or 6-membered heterocycle is optionally substituted with one or more $Z^1$ group.

Another specific group of compounds of formula I are compounds wherein $R^{3b}$ and $R^{3b'}$ together with the carbon to which they are attached form a tetrahydropyran or tetrahydrofuran optionally substituted with one or more $Z^1$ groups.

Another specific group of compounds of formula I are compounds wherein $R^{3b}$ and $R^{3b'}$ together with the carbon to which they are attached form:

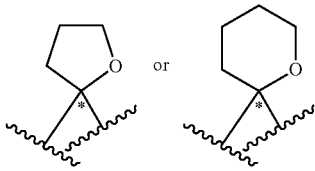 [SMILES: *C1(*)CCCO1 ; "or" ; *C1(*)CCCCO1]

each of which is optionally substituted with one or more $Z^1$ groups; and wherein "*" denotes the point of attachment to the carbon of the compound of formula I.

A specific value for $R^4$ is $R^{4b}$.

A specific value for $R^{4b}$ is (C$_1$-C$_6$)alkyl, (C$_2$-C$_6$)alkenyl or (C$_2$-C$_6$)alkynyl; wherein (C$_1$-C$_6$)alkyl, (C$_2$-C$_6$)alkenyl or (C$_2$-C$_6$)alkynyl are each optionally substituted with one or more $Z^1$ groups.

Another specific value for $R^{4b}$ is:

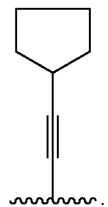

optionally substituted with one or more $Z^1$ groups.

Another specific value for $R^{4b}$ is (C$_3$-C$_7$)carbocycle; wherein (C$_3$-C$_7$)carbocycle is optionally substituted with one or more $Z^1$ groups; or wherein two $Z^1$ groups together with the atom or atoms to which they are attached optionally form a (C$_3$-C$_6$)carbocycle or 5-6-membered heterocycle.

Another specific value for $R^{4b}$ is:

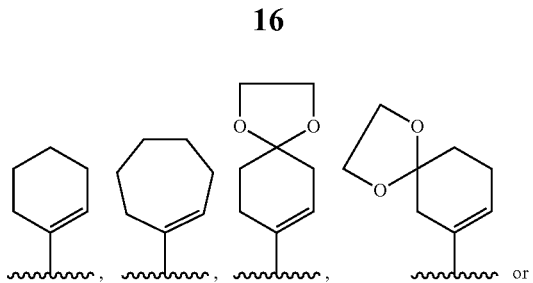

each of which is optionally substituted with one or more $Z^1$ groups.

Another specific value for $R^{4b}$ is aryl, heterocycle or heteroaryl; wherein aryl, heterocycle and heteroaryl are each independently substituted with one or more $Z^7$ groups and optionally substituted with one or more $Z^1$ groups.

Another specific value for $R^{4b}$ is:

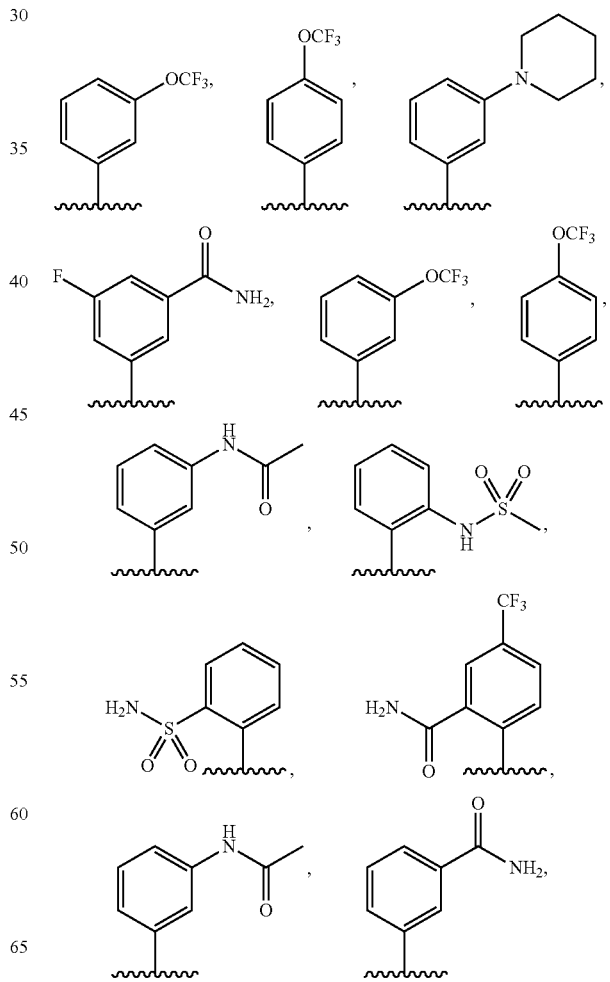

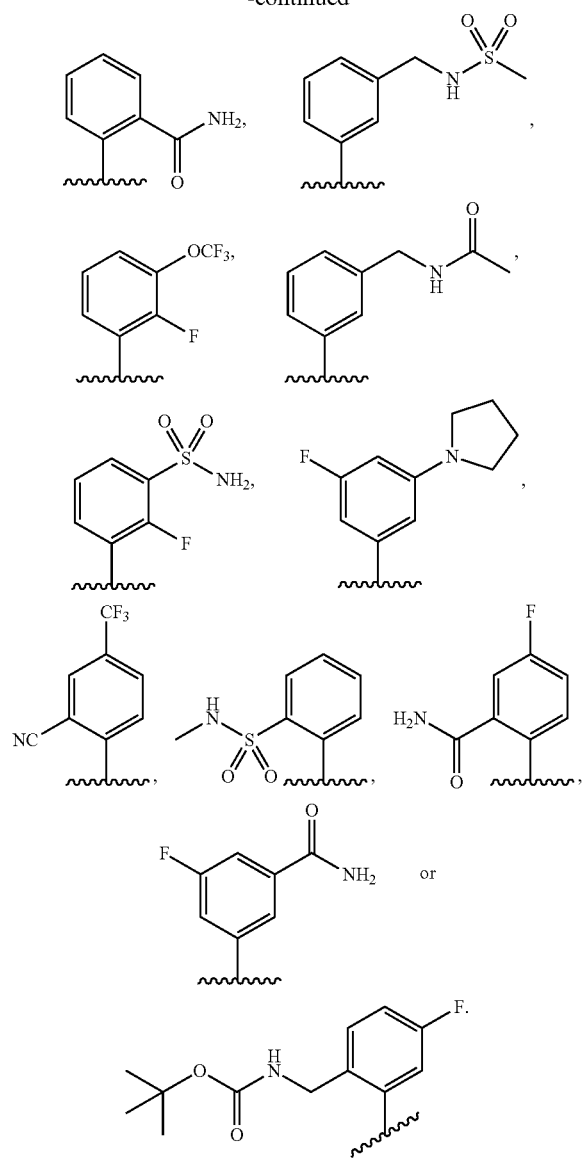
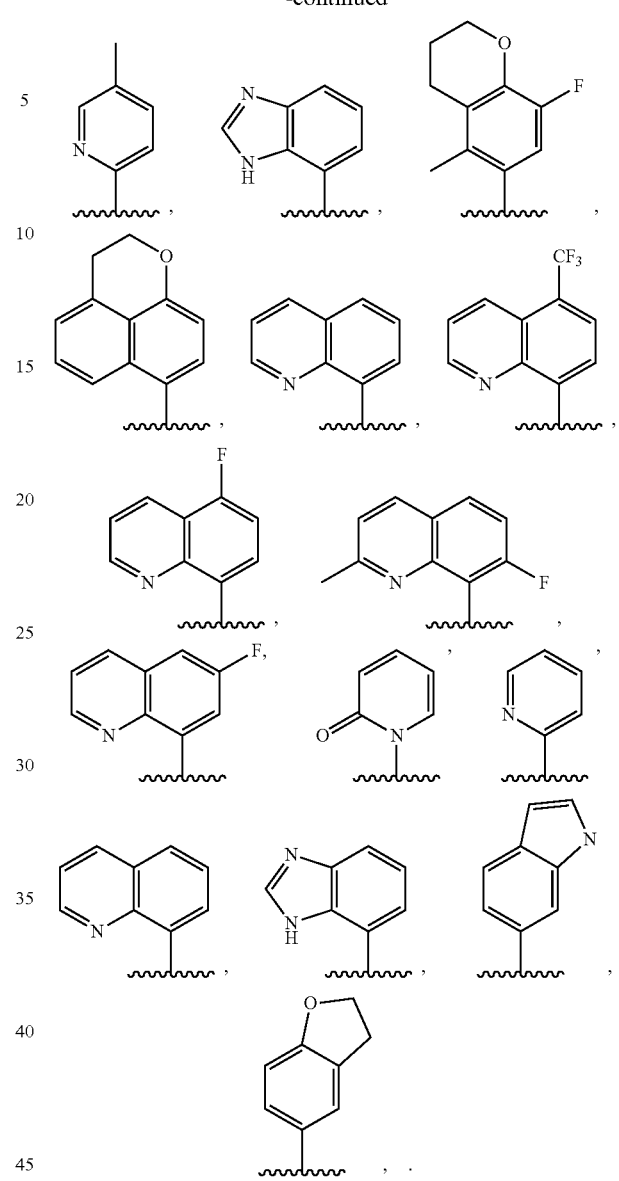
Another specific value for $R^4$ is $R^{4a}$.
A specific value for $R^{4a}$ is:
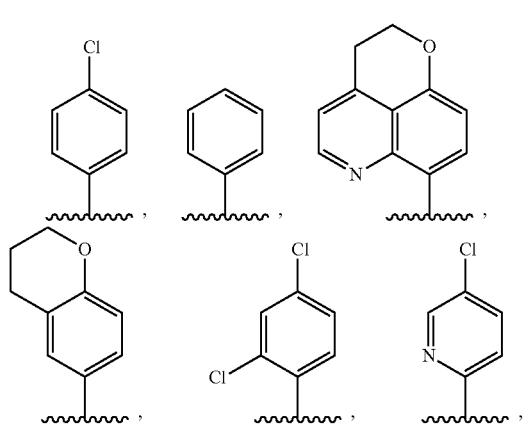
Another specific value for $R^{4a}$ is:

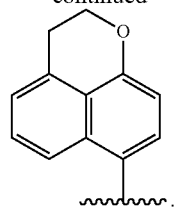

Another specific value for R⁴ᵃ is:

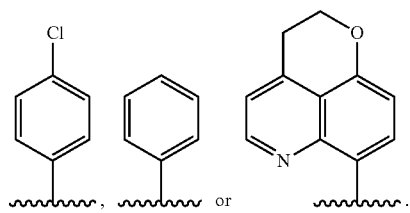

A specific value for R⁴ is selected from:

a) aryl, heterocycle and heteroaryl, wherein any aryl, heterocycle and heteroaryl of R⁴ is optionally substituted with one or more (e.g., 1, 2, 3, 4 or 5) groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, —NH₂, —NH($C_1$-$C_6$)alkyl and —N(($C_1$-$C_6$)alkyl)₂, wherein ($C_1$-$C_6$)alkyl is optionally substituted with hydroxy, —O($C_1$-$C_6$)alkyl, cyano or oxo; and b) aryl, heteroaryl, spiro-, fused-, or bridged-heterocycle; wherein aryl, heteroaryl, or spiro-, fused-, or bridged-heterocycle are each independently substituted with one or more $Z^7$ groups and optionally substituted with one or more (e.g., 1, 2, 3, 4 or 5) $Z^1$ groups.

Another specific value for R⁴ is selected from:

a) aryl, heterocycle and heteroaryl, wherein any aryl, heterocycle and heteroaryl of R⁴ is optionally substituted with one or more (e.g., 1, 2, 3, 4 or 5) groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, —NH($C_1$-$C_6$)alkyl and —N(($C_1$-$C_6$)alkyl)₂, wherein ($C_1$-$C_6$)alkyl is optionally substituted with hydroxy, —O($C_1$-$C_6$)alkyl, cyano or oxo; and b) aryl and heteroaryl, wherein aryl and heteroaryl are each independently substituted with one or more $Z^7$ groups and optionally substituted with one or more (e.g., 1, 2, 3, 4 or 5) $Z^1$ groups.

Another specific value for R⁴ is selected from aryl, heterocycle and heteroaryl, wherein any aryl, heterocycle and heteroaryl of R⁴ is optionally substituted with one or more (e.g., 1, 2, 3, 4 or 5) groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, —NH₂, —NH($C_1$-$C_6$)alkyl and —N(($C_1$-$C_6$)alkyl)₂, wherein ($C_1$-$C_6$)alkyl is optionally substituted with hydroxy, —O($C_1$-$C_6$)alkyl, cyano or oxo.

Another specific value for R⁴ is:

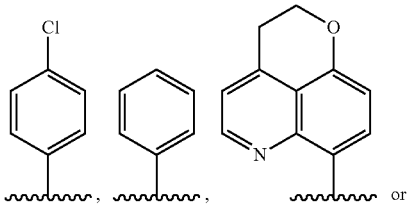

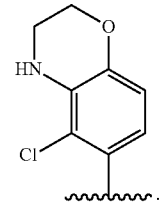

Another specific value for R⁴ is:

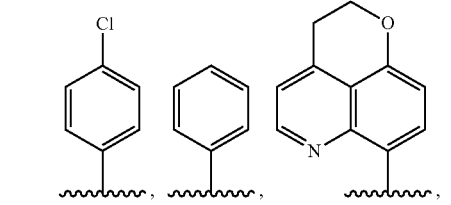

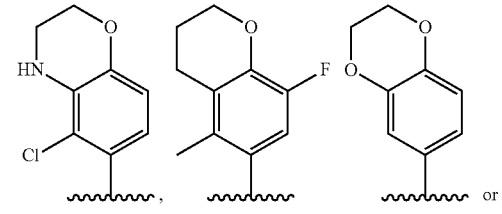

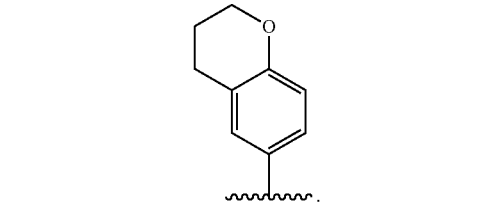

A specific group of compounds of formula I are compounds wherein R⁴ and R³ together with the atoms to which they are attached form a macroheterocycle or a macrocarbocycle wherein any macroheterocycle or macrocarbocycle of R⁴ and R³ together with the atoms to which they are attached may be optionally substituted with one or more $Z^1$ groups; and R³' is H, ($C_1$-$C_6$)alkyl or —O($C_1$-$C_6$)alkyl.

Another specific group of compounds of formula I are compounds wherein R⁴ and R³ together with the atoms to which they are attached form a macroheterocycle or a macrocarbocycle wherein any macroheterocycle or macrocarbocycle of R⁴ and R³ together with the atoms to which they are attached may be optionally substituted with one or more $Z^1$ groups; and R³' is H.

Another specific group of compounds of formula I are compounds wherein R⁴ and R³ together with the atoms to which they are attached form the macroheterocycle or a macrocarbocycle which is further fused to a Z group;

21 wherein:
Z is aryl, heteroaryl or $(C_3-C_6)$carbocycle;
n3 is 2, 3 or 4;
$W^1$ and $W^2$ are each independently O, NH or $CH_2$; and
wherein "*" denotes the $R^4$ point of attachment of the macroheterocycle or macrocarbocycle to the compound of formula I and "**" denotes the $R^3$ point of attachment of the macroheterocycle or macrocarbocycle to the compound of formula I; and wherein the macroheterocycle or a macrocarbocycle is optionally substituted with one or more $Z^1$ groups.

Another specific group of compounds of formula I are compounds wherein, $R^4$ and $R^3$ together with the atoms to which they are attached form the macroheterocycle:

wherein:
n1 is 3 or 4; n2 is 2, 3 or 4; n3 is 2, 3 or 4; W is O, NH or $N(C_1-C_4)$alkyl; and wherein "*" denotes the $R^4$ point of attachment of the macroheterocycle to the compound of formula I and "**" denotes the $R^3$ point of attachment of the macroheterocycle to the compound of formula I; and wherein the macroheterocycle or a macrocarbocycle is optionally substituted with one or more $Z^1$ groups.

A specific value for $R^2$ is $R^{2b}$.
Another specific value $R^2$ is $R^{2a}$.
A specific value for $R^{2a}$ is H, halo or $-CH_3$.
Another specific value for $R^{2a}$ is Cl.
A specific value for $R^2$ is halo, H or $(C_1-C_6)$alkyl.
Another specific value for $R^2$ is halo, H or $-CH_3$.
Another specific value for $R^2$ is H or $-CH_3$.
Another specific value for $R^2$ is H or $(C_1-C_6)$alkyl.
Another specific value for $R^2$ is $(C_1-C_6)$alkyl.
Another specific value for $R^2$ is $-CH_3$.
Another specific value for $R^5$ is $R^{5a}$.
A specific value for $R^{11}$ is aryl.
Another specific value for $R^{11}$ is carbocycle or aryl.
Another specific value for $R^{11}$ is carbocycle.
A specific value for $R^9$ is H or $(C_1-C_6)$alkyl.

22

A specific value for $R^{10}$ is H or $(C_1-C_6)$alkyl.
Another specific value for $R^9$ is H, $(C_1-C_6)$alkyl or $-C(=O)-R^{11}$.
Another specific value for $R^{10}$ is H, $(C_1-C_6)$alkyl or $-C(=O)-R^{11}$.
A value for $Z^9$ is "each $Z^9$ is independently selected from $-(C_1-C_6)$alkyl, $-O(C_1-C_6)$alkyl".
In one embodiment of $R^5$ does not include:

A specific value for $R^5$ is:

In one embodiment $R^5$ does not include:

In one embodiment the compounds of the invention do not include compounds 35, 36, 50, 51, 52, 53, 54, 55, 56, 57, 58, 76, and 89.
A specific group of compounds of formula I are compounds wherein $R^{4b}$ is selected from;
a) $(C_1-C_6)$alkyl, $(C_2-C_6)$alkenyl and $(C_2-C_6)$alkynyl, wherein any $(C_1-C_6)$alkyl, $(C_2-C_6)$alkenyl or $(C_2-C_6)$alkynyl is optionally substituted with one or more (e.g., 1, 2, 3, 4 or 5) $Z^1$ groups;
b) $(C_3-C_{14})$carbocycle, wherein $(C_3-C_{14})$carbocycle is optionally substituted with one or more (e.g., 1, 2, 3, 4 or 5) $Z^1$ groups;
c) Spiro-heterocycle or bridged-heterocycle, wherein Spiro-heterocycle or bridged-heterocycle is optionally substituted with one or more (e.g., 1, 2, 3, 4 or 5) $Z^1$ groups; and
d) aryl, heterocycle and heteroaryl, wherein aryl, heterocycle and heteroaryl are each independently substituted with one or more $Z^7$ groups and optionally substituted with one or more (e.g., 1, 2, 3, 4 or 5) $Z^1$ groups.

Another specific group of compounds of formula I are compounds wherein $R^{4b}$ is selected from:

a) $(C_1-C_6)$alkyl, $(C_2-C_6)$alkenyl and $(C_2-C_6)$alkynyl, wherein any $(C_1-C_6)$alkyl, $(C_2-C_6)$alkenyl or $(C_2-C_6)$alkynyl is optionally substituted with one or more (e.g., 1, 2, 3, 4 or 5) $Z^1$ groups;

b) $(C_3-C_{14})$carbocycle, wherein $(C_3-C_{14})$carbocycle is optionally substituted with one or more (e.g., 1, 2, 3, 4 or 5) $Z^1$ groups; wherein two $Z^1$ groups together with the atom or atoms to which they are attached optionally form a $(C_3-C_7)$ carbocycle or heterocycle; and c) aryl, heterocycle and heteroaryl, wherein aryl, heterocycle and heteroaryl are each independently substituted with one or more (e.g., 1, 2, 3, 4 or 5) $Z^7$ groups and optionally substituted with one or more (e.g., 1, 2, 3, 4 or 5) $Z^1$ groups.

Another specific group of compounds of formula I are compounds wherein $R^{4b}$ is selected from:

a) $(C_1-C_6)$alkyl, $(C_2-C_6)$alkenyl and $(C_2-C_6)$alkynyl, wherein any $(C_1-C_6)$alkyl, $(C_2-C_6)$alkenyl or $(C_2-C_6)$alkynyl is optionally substituted with one or more (e.g., 1, 2, 3, 4 or 5) $Z^1$ groups;

b) $(C_3-C_{14})$carbocycle, wherein $(C_3-C_{14})$carbocycle is optionally substituted with one or more (e.g., 1, 2, 3, 4 or 5) $Z^1$ groups; and c) aryl, heterocycle and heteroaryl, wherein aryl, heterocycle and heteroaryl are each independently substituted with one or more (e.g., 1, 2, 3, 4 or 5) $Z^7$ groups and optionally substituted with one or more (e.g., 1, 2, 3, 4 or 5) $Z^1$ groups.

In one embodiment, the compounds of the invention do not include the compounds selected from:

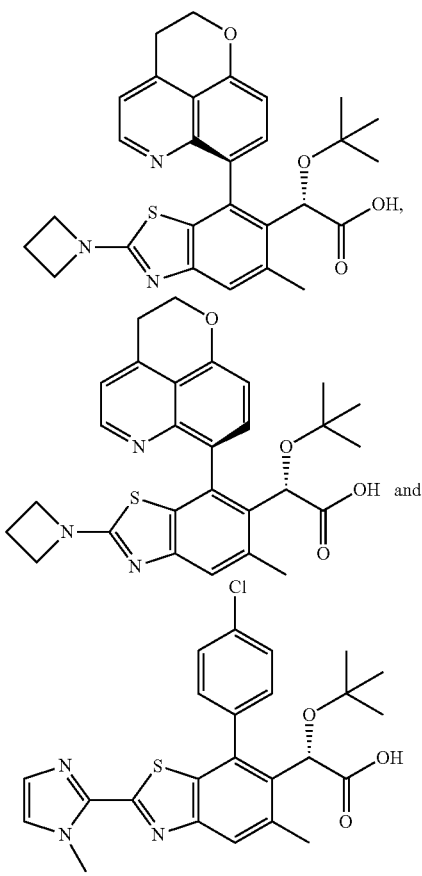

and salts thereof.

A specific value for $R^5$ is selected from:

a) aryl, heterocycle and heteroaryl, wherein aryl, heterocycle and heteroaryl are each optionally substituted with one or more (e.g., 1, 2 or 3) $Z^{11}$ groups;

b) aryl, heteroaryl and heterocycle, wherein aryl, heteroaryl and heterocycle are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle are each independently substituted with one or more (e.g., 1, 2, 3, 4 or 5) $Z^{15}$ groups and optionally substituted with one or more (e.g., 1, 2, 3, 4 or 5) $Z^1$ groups.

A specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups;

b) aryl, heteroaryl and heterocycle, wherein aryl, heteroaryl and heterocycle are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle are each independently substituted with one or more (e.g., 1, 2, 3, 4 or 5) $Z^{15}$ groups and optionally substituted with one or more (e.g., 1, 2, 3, 4 or 5) $Z^1$ groups; and $R^{3'}$ is H.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups;

b) aryl, heteroaryl and heterocycle, wherein aryl, heteroaryl and heterocycle are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups;

b) aryl, heteroaryl and heterocycle, wherein aryl, heteroaryl and heterocycle are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H;

$R^2$ is H or $(C_1-C_6)$alkyl; and
$R^3$ is —O$(C_1-C_6)$alkyl.

A specific value for $R^5$ is selected from:

a) aryl, heterocycle and heteroaryl, wherein aryl, heterocycle and heteroaryl are each optionally substituted with one or more (e.g., 1, 2 or 3) $Z^{11}$ groups; and b) aryl, heteroaryl and heterocycle, wherein aryl, heteroaryl and heterocycle are each independently substituted with one or more (e.g., 1, 2, 3, 4 or 5) $Z^{15}$ groups and optionally substituted with one or more (e.g., 1, 2, 3, 4 or 5) $Z^1$ groups.

A specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups; and b) aryl, heteroaryl and heterocycle, wherein aryl, heteroaryl and heterocycle are each independently substituted with one or more (e.g., 1, 2, 3, 4 or 5) $Z^{15}$ groups and optionally substituted with one or more (e.g., 1, 2, 3, 4 or 5) $Z^1$ groups; and $R^{3'}$ is H.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups; and b) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups; and b) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H;

$R^2$ is H or $(C_1-C_6)$alkyl; and $R^3$ is —O$(C_j-C_6)$alkyl.

Another specific value for $R^5$ is aryl, heteroaryl, heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

Another specific group of compounds of formula I are compounds wherein:

$R^5$ is selected from aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups; and $R^{3'}$ is H.

Another specific group of compounds of formula I are compounds wherein $R^5$ is selected from aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein $R^5$ is selected from aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H;

$R^2$ is H or $(C_1-C_6)$alkyl; and $R^3$ is —O$(C_1-C_6)$alkyl.

Another specific value for $R^5$ is selected from:

a) aryl, wherein aryl is optionally substituted with one or more (e.g., 1, 2 or 3) $Z^{11}$ groups;

b) aryl, heteroaryl and heterocycle, wherein aryl, heteroaryl are heterocycle, are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups.

Another specific group of compounds of formula I are compounds wherein:

$R^5$ is selected from:

a) aryl, wherein aryl is optionally substituted with one or more (e.g., 1, 2 or 3) $Z^{11}$ groups;

b) aryl, heteroaryl and heterocycle, wherein aryl, heteroaryl are heterocycle, are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups; and $R^{3'}$ is H.

Another specific group of compounds of formula I are compounds wherein:

$R^5$ is selected from:

a) aryl, wherein aryl is optionally substituted with one or more (e.g., 1, 2 or 3) $Z^{11}$ groups;

b) aryl, heteroaryl and heterocycle, wherein aryl, heteroaryl are heterocycle, are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, wherein aryl is optionally substituted with one or more (e.g., 1, 2 or 3) $Z^{11}$ groups;

b) aryl, heteroaryl and heterocycle, wherein aryl, heteroaryl are heterocycle, are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H;

$R^2$ is H or $(C_1-C_6)$alkyl; and $R^3$ is $-O(C_1-C_6)$alkyl.

Another specific value for $R^5$ is selected from:

a) aryl, heterocycle and heteroaryl, wherein aryl, heterocycle and heteroaryl are each optionally substituted with one or more (e.g., 1, 2 or 3) $Z^{11}$ groups;

b) aryl, heteroaryl and heterocycle, wherein aryl, heteroaryl and heterocycle are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

each $Z^{11}$ is independently selected from $Z^{10}$, $-C(=O)-NH_2$, $-C(=O)-NH(C_1-C_4)$alkyl, $-C(=O)-N((C_1-C_4)$alkyl$)_2$, $-C(=O)$-aryl, $-C(=O)$-heterocycle and $-C(=O)$-heteroaryl;

wherein each $Z^{10}$ is independently selected from:

i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, $-OH$, $-O(C_1-C_6)$alkyl, $-O(C_1-C_6)$haloalkyl, $-SH$, $-S(C_1-C_6)$alkyl, $-SO(C_1-C_6)$alkyl, $-SO_2(C_1-C_6)$alkyl, $-NH_2$, $-NH(C_1-C_6)$alkyl and $-N((C_1-C_6)$alkyl$)_2$;

ii) $(C_1-C_6)$alkyl substituted with $-OH$, $-O-(C_1-C_6)$haloalkyl, or $-O-(C_1-C_6)$alkyl; and iii) aryl, heterocycle and heteroaryl, which aryl, heterocycle and heteroaryl is optionally substituted with halo, $(C_1-C_6)$alkyl or COOH; and each $Z^{11}$ is independently selected from $Z^{10}$, $-C(=O)-NH_2$, $-C(=O)-NH(C_1-C_4)$alkyl, $-C(=O)-N((C_1-C_4)$alkyl$)_2$, $-C(=O)$-aryl, $-C(=O)$-heterocycle and $-C(=O)$-heteroaryl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups;

b) aryl, heteroaryl and heterocycle, wherein aryl, heteroaryl and heterocycle are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle, are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H;

each $Z^{10}$ is independently selected from:

i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, $-OH$, $-O(C_1-C_6)$alkyl, $-O(C_1-C_6)$haloalkyl, $-SH$, $-S(C_1-C_6)$alkyl, $-SO(C_1-C_6)$alkyl, $-SO_2(C_1-C_6)$alkyl, $-NH_2$, $-NH(C_1-C_6)$alkyl and $-N((C_1-C_6)$alkyl$)_2$;

ii) $(C_1-C_6)$alkyl substituted with $-OH$, $-O-(C_1-C_6)$haloalkyl, or $-O-(C_1-C_6)$alkyl; and iii) aryl, heterocycle and heteroaryl, which aryl, heterocycle and heteroaryl is optionally substituted with halo, $(C_1-C_6)$alkyl or COOH; and each $Z^{11}$ is independently selected from $Z^{10}$, $-C(=O)-NH_2$, $-C(=O)-NH(C_1-C_4)$alkyl, $-C(=O)-N((C_1-C_4)$alkyl$)_2$, $-C(=O)$-aryl, $-C(=O)$-heterocycle and $-C(=O)$-heteroaryl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g., 1, 2 or 3) $Z^{11}$ groups;

b) aryl, heteroaryl and heterocycle, wherein aryl, heteroaryl and heterocycle are each independently substituted with one or more (e.g., 1, 2, 3, 4 or 5) $Z^5$ groups and optionally substituted with one or more (e.g., 1, 2, 3, 4 or 5) $Z^1$ groups; and c) aryl, heteroaryl and heterocycle, wherein aryl, heteroaryl and heterocycle are each independently substituted with one or more (e.g., 1, 2, 3, 4 or 5) $Z^{15}$ groups and optionally substituted with one or more (e.g., 1, 2, 3, 4 or 5) $Z^1$ groups;

$R^{3'}$ is H; $R^1$ is H;

$R^2$ is H or $(C_1-C_6)$alkyl;

$R^3$ is $-O(C_1-C_6)$alkyl;

each $Z^{10}$ is independently selected from:

i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$)alkyl, —NH$_2$, —NH(C$_1$-C$_6$)alkyl and —N((C$_1$-C$_6$)alkyl)$_2$;

ii) (C$_1$-C$_6$)alkyl substituted with —OH, —O—(C$_1$-C$_6$)haloalkyl, or —O—(C$_1$-C$_6$)alkyl; and iii) aryl, heterocycle and heteroaryl, which aryl, heterocycle and heteroaryl is optionally substituted with halo, (C$_1$-C$_6$)alkyl or COOH; and each Z$^{11}$ is independently selected from Z$^{10}$, —C(=O)—NH$_2$, —C(=O)—NH(C$_1$-C$_4$)alkyl, —C(=O)—N((C$_1$-C$_4$)alkyl)$_2$, —C(=O)-aryl, —C(=O)-heterocycle and —C(=O)-heteroaryl.

Another specific value for R$^5$ is:

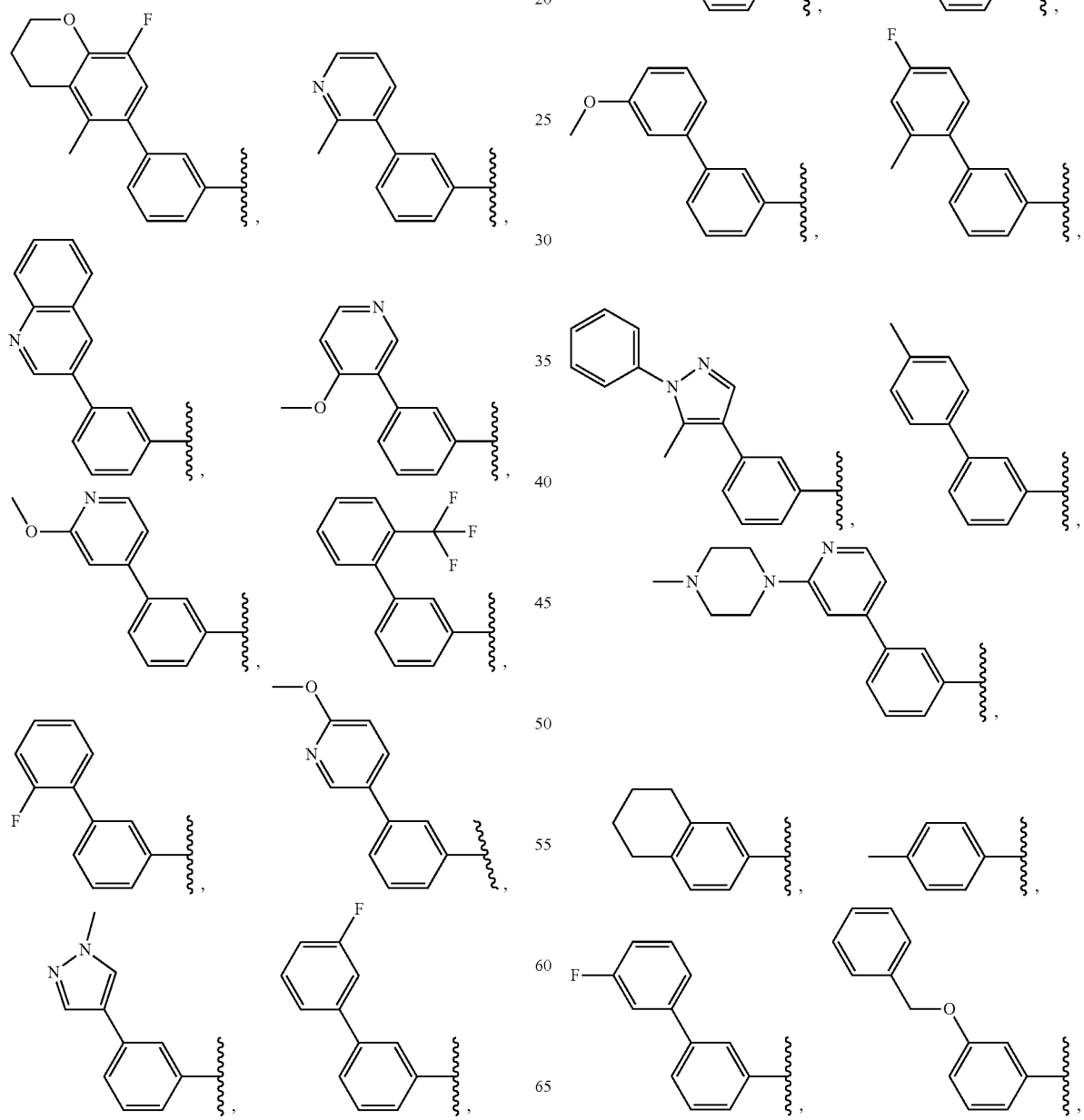

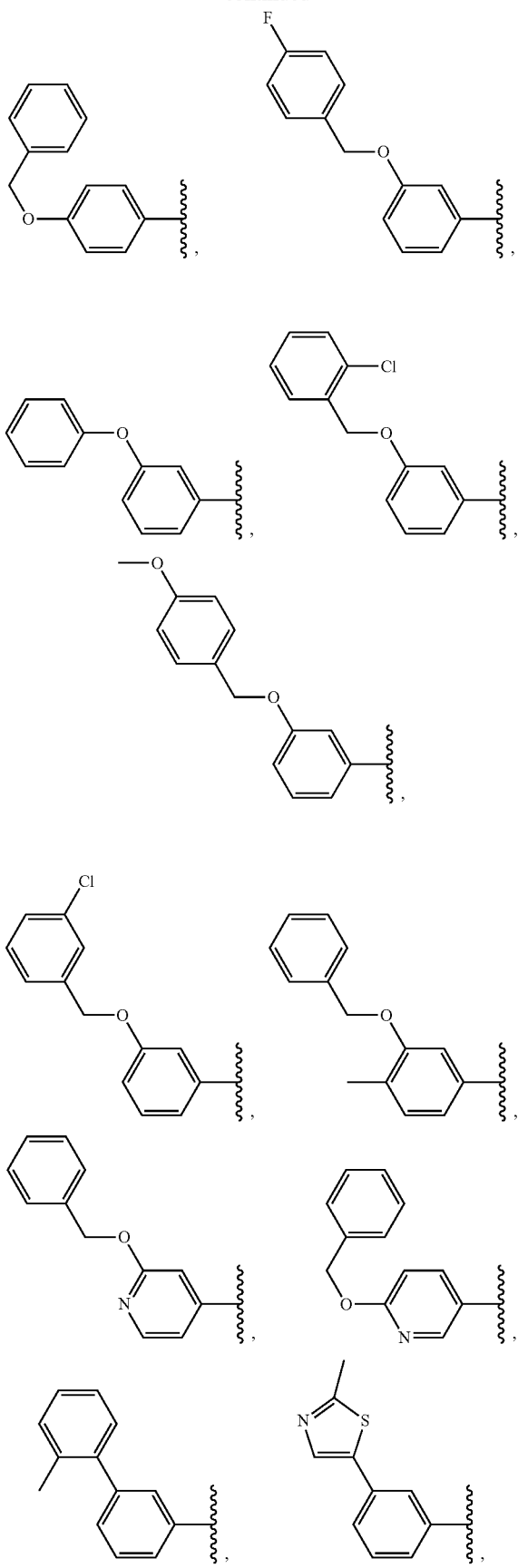
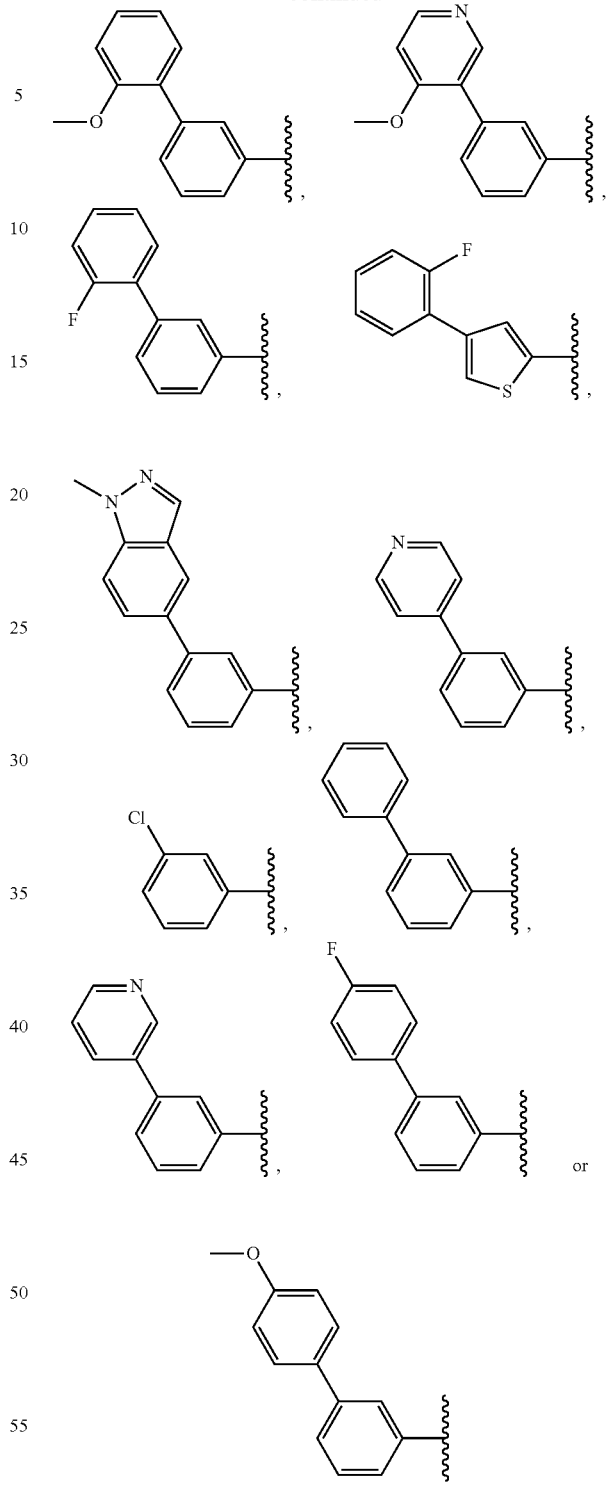
In one embodiment of the invention the compound of formula I is selected from a compound of formulas Ia100-Ia145 (e.g., compounds Ia100, Ia101, Ia102, Ia103, Ia104, Ia105, Ia106, Ia107, Ia108, Ia109, Ia110, Ia111, Ia112, Ia113, Ia114, Ia115, Ia116, Ia117, Ia118, Ia119, Ia120, Ia121, Ia122, Ia123, Ia124, Ia125, Ia126, Ia127, Ia128, Ia129, Ia130, Ia131, Ia132, Ia133, Ia134, Ia135, Ia136, Ia137, Ia138, Ia139, Ia140, Ia141, Ia142, Ia143, Ia144, Ia145):

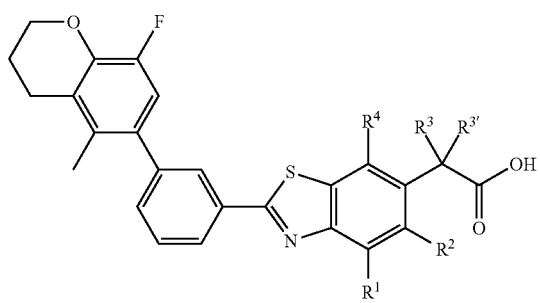
Ia100
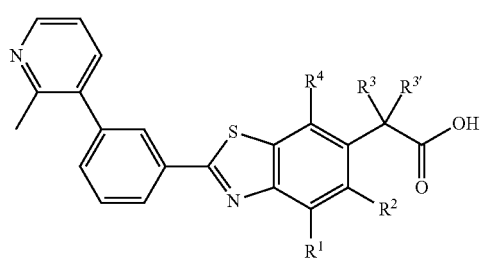
Ia101
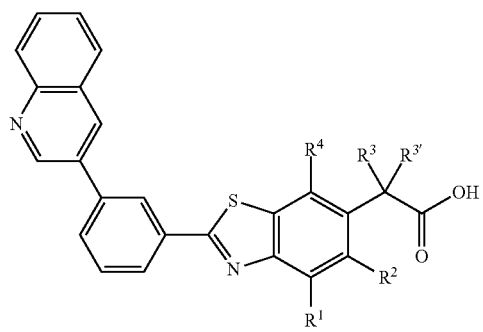
Ia102
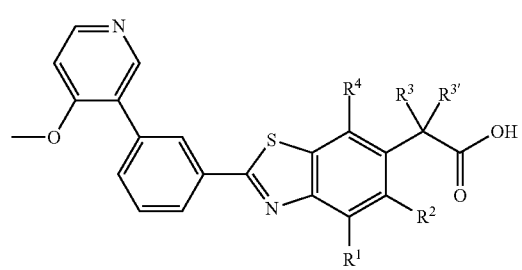
Ia103
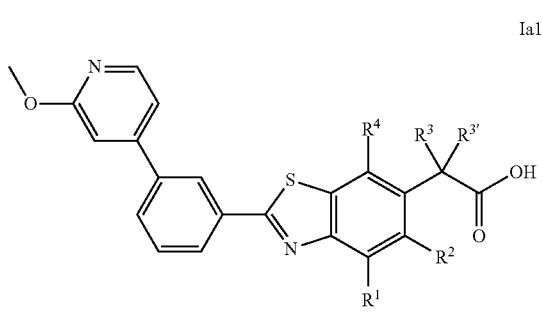
Ia104
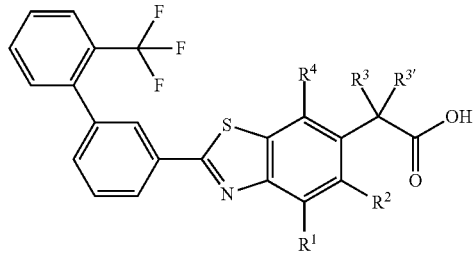
Ia105
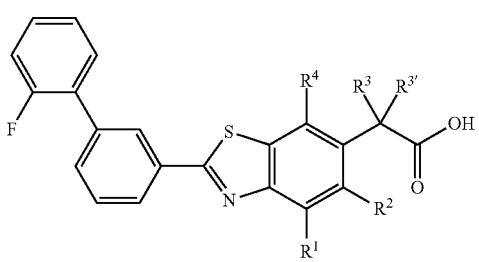
Ia106
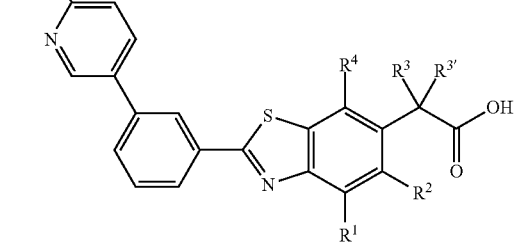
Ia107
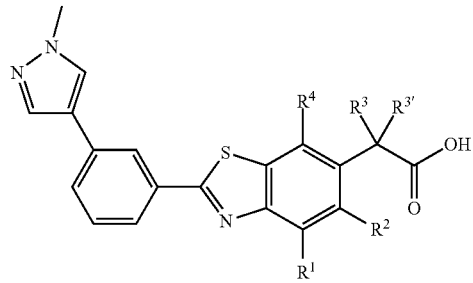
Ia108
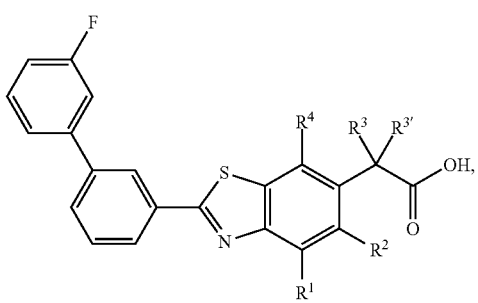
Ia109

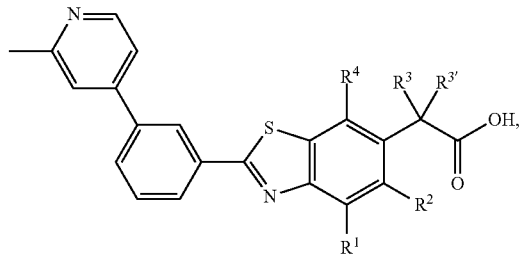
Ia110
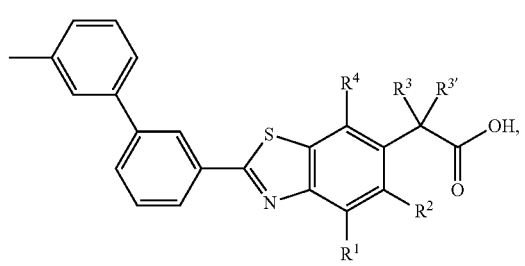
Ia111
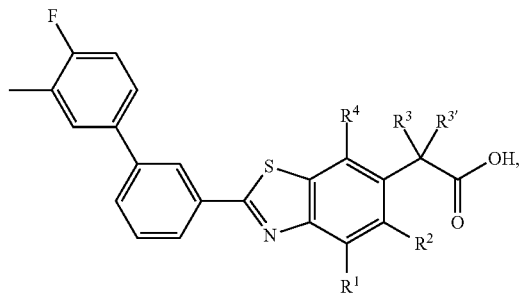
Ia112
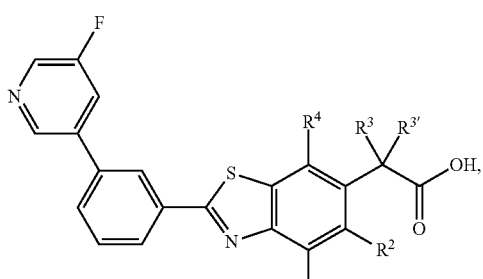
Ia113
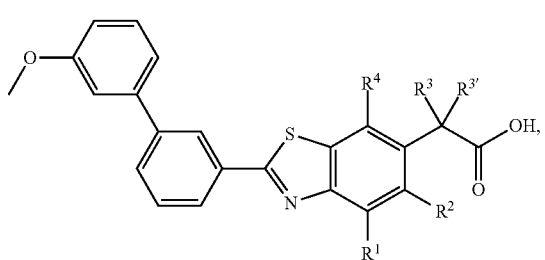
Ia114
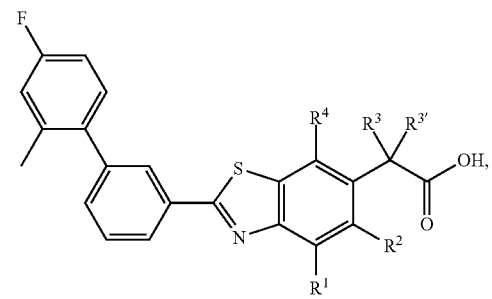
Ia115
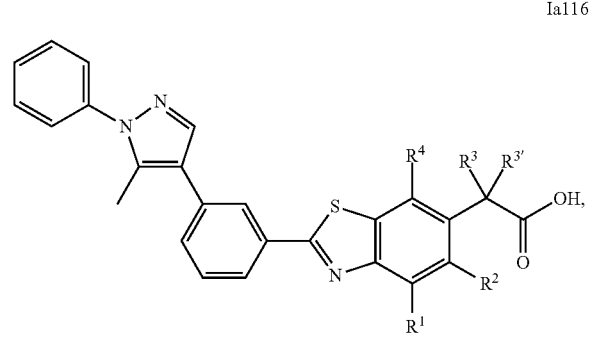
Ia116
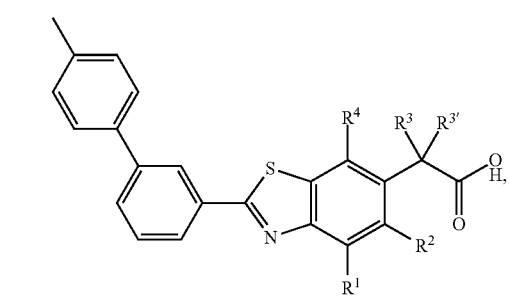
Ia117
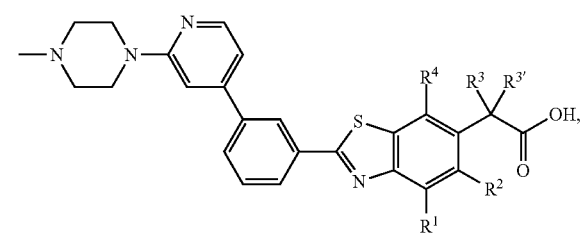
Ia118
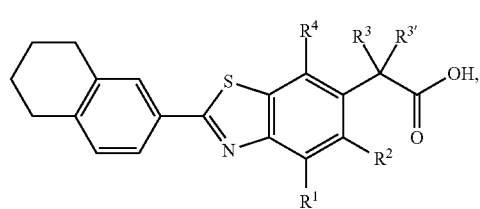
Ia119
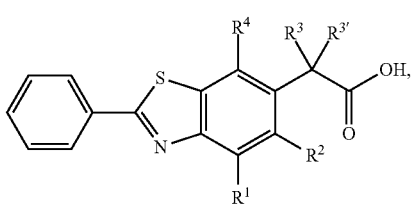
Ia120

Ia121
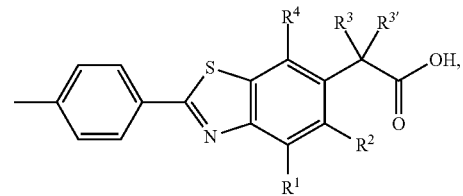
Ia122
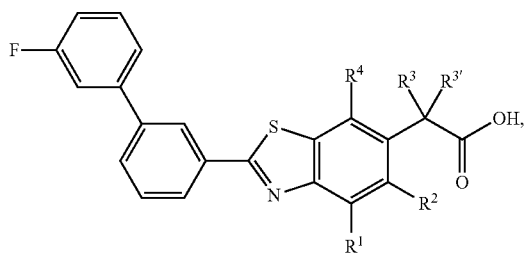
Ia123
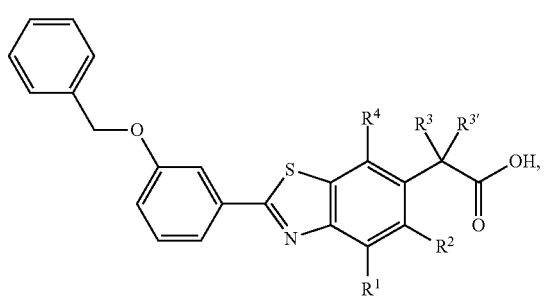
Ia124
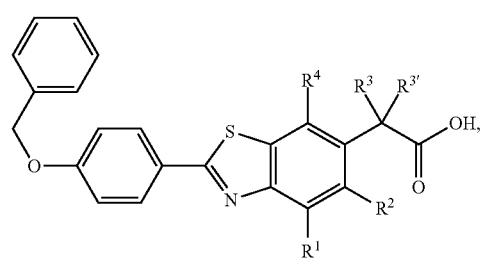
Ia125
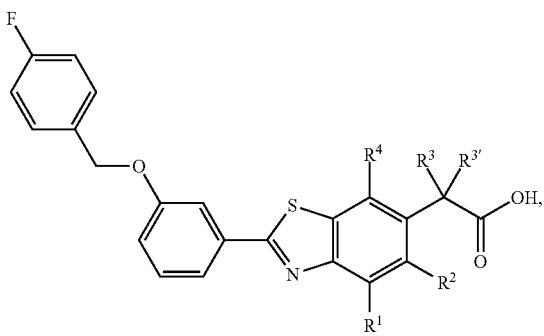
Ia126
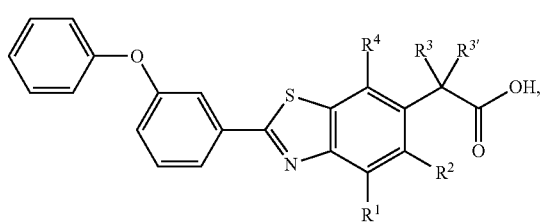
Ia127
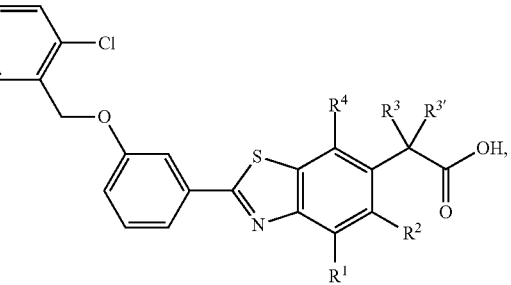
Ia128
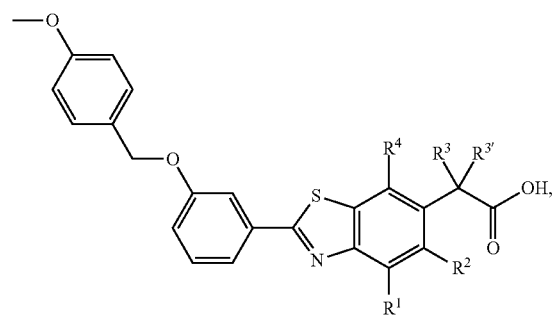
Ia129
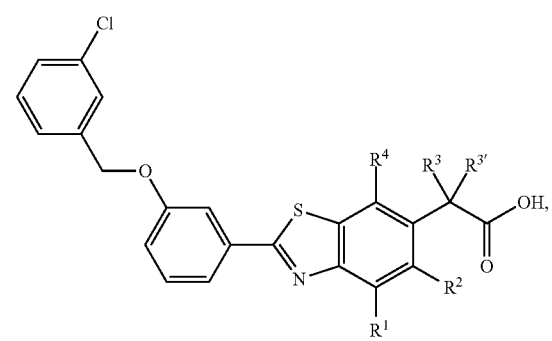
Ia130
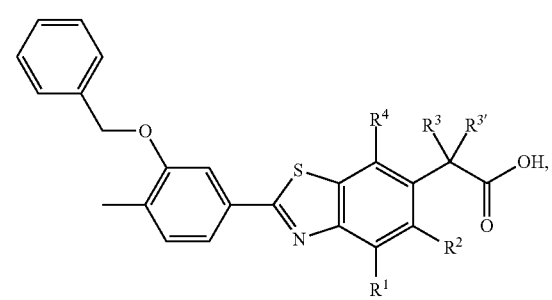
Ia131
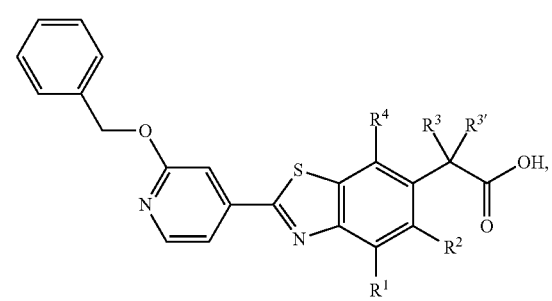

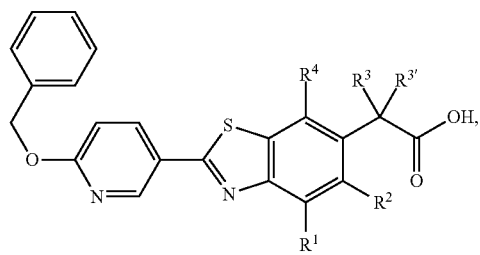
Ia132
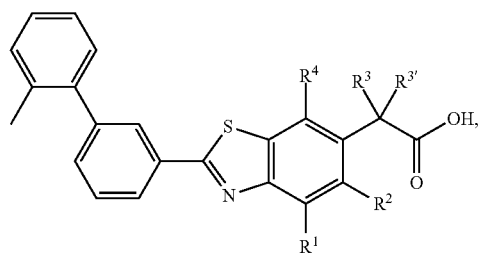
Ia133
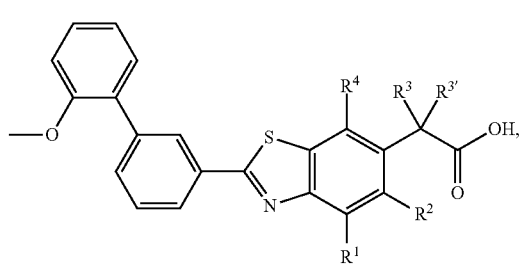
Ia134
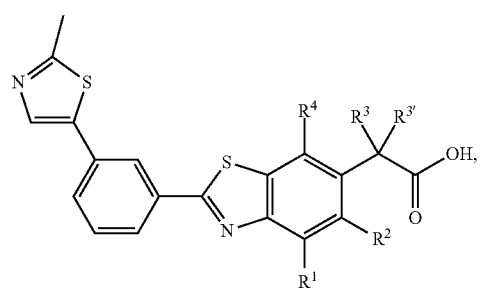
Ia135
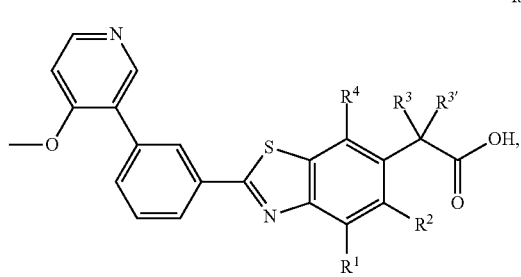
Ia136
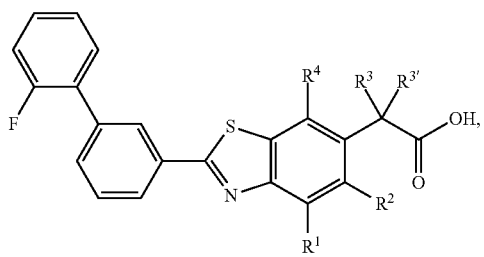
Ia137
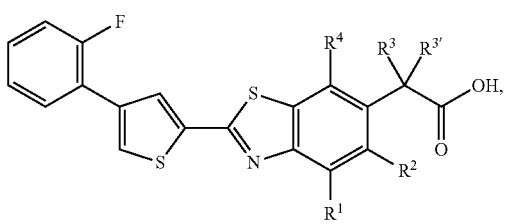
Ia138
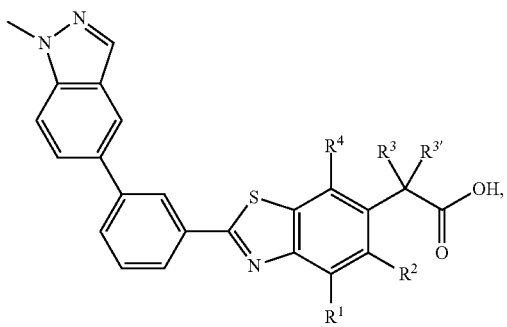
Ia139
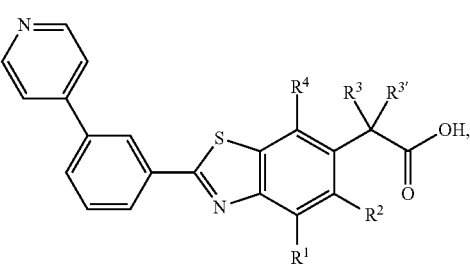
Ia140
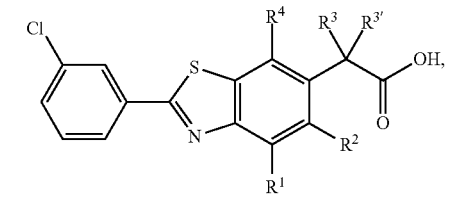
Ia141
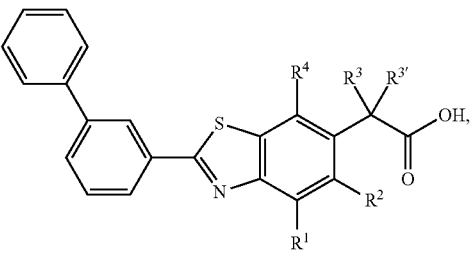
Ia142
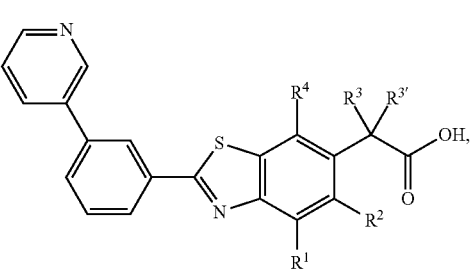
Ia143

-continued

Ia144

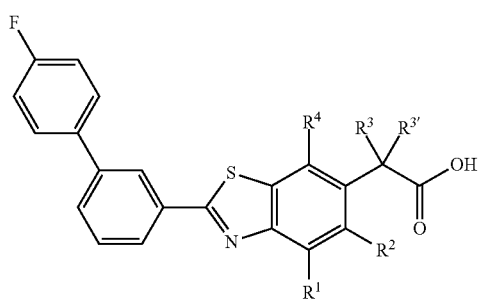

and

Ia145

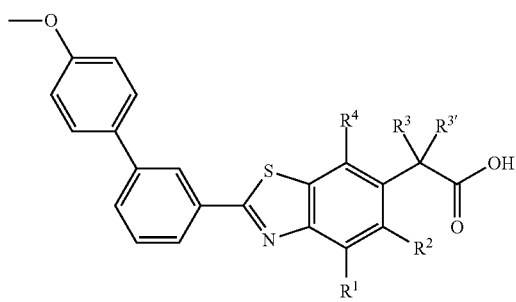

and salts thereof.

In one embodiment, the compounds of formula I are selected from the compounds of formulas Ia100-Ia145 wherein:
R$^1$ is H; R$^2$ is methyl, R$^{3'}$ is H; R$^3$ is —OtBu; and
R$^4$ is:

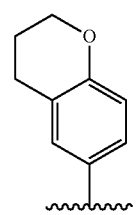

and salts thereof.

In another embodiment, the compounds of formula I are selected from the compounds of formulas Ia100-Ia145 wherein:
R$^1$ is H; R$^2$ is methyl, R$^{3'}$ is H; R$^3$ is —OtBu; and
R$^4$ is:

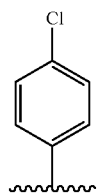

and salts thereof.

In another embodiment, the compounds of formula I are selected from the compounds of formulas Ia100-Ia145 wherein:
R$^1$ is H; R$^2$ is methyl, R$^{3'}$ is H; R$^3$ is —OtBu; and
R$^4$ is:

and salts thereof.

In another embodiment of the invention, the compounds of formula I are selected from the compounds of formulas Ia100-Ia145 wherein:
R$^1$ is H; R$^2$ is methyl, R$^{3'}$ is H; R$^3$ is —OtBu; and
R$^4$ is:

and salts thereof.

In one embodiment of the invention the compounds of formula I are selected from the compounds of formulas Ia100-Ia145 wherein R$^{3'}$ is H; R$^3$ is —O(C$_1$-C$_6$)alkyl and the stereochemistry of the carbon bearing the R$^3$ (—O(C$_1$-C$_6$)alkyl) group is (S).

In another embodiment of the invention the compounds of formula I are selected from the compounds of formulas Ia100-Ia145 wherein R$^{3'}$ is H; R$^3$ is —O(C$_1$-C$_6$)alkyl and the stereochemistry of the carbon bearing the R$^3$ (—O(C$_1$-C$_6$)alkyl) group is (R).

In one embodiment of the invention, the compounds of formula I are selected from:

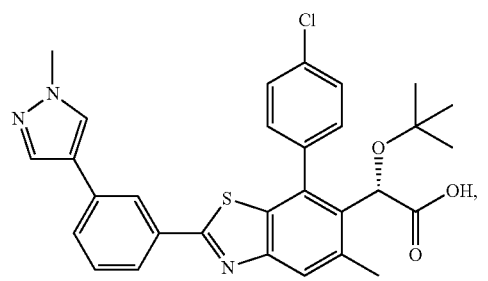

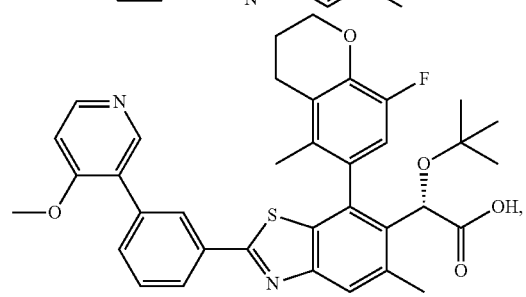

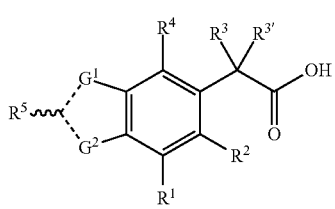

and salts thereof.

In one embodiment, the invention provides a compound of formula I:

I wherein:
$G^1$ is S, $G^2$ is N, the dashed bond connected to $G^1$ is a single bond, the dashed bond connected to $G^2$ is a double bond, and the wavy bond connected to $R^5$ is a single bond; or $G^1$ is N, $G^2$ is S, the dashed bond connected to $G^1$ is a double bond, the dashed bond connected to $G^2$ is a single bond, and the wavy bond connected to $R^5$ is a single bond;

$R^1$ is $R^{1a}$ or $R^{1b}$;
$R^2$ is $R^{2a}$ or $R^{2b}$;
$R^3$ is $R^{3a}$ or $R^{3b}$;
$R^{3'}$ is $R^{3a'}$ or $R^{3b'}$;
$R^4$ is $R^{4a}$ or $R^{4b}$;

$R^{1a}$ is selected from:
a) halo;
b) $R^{11}$, —C(=O)—$R^{11}$, —C(=O)—O—$R^{11}$, —O—$R^{11}$, —S—$R^{11}$, —S(O)—$R^{11}$, —SO$_2$—$R^{11}$, —(C$_1$-C$_6$)alkyl-$R^{11}$, —(C$_1$-C$_6$)alkyl-C(=O)—$R^{11}$, —(C$_1$-C$_6$)alkyl-C(=O)—O—$R^{11}$, —(C$_1$-C$_6$)alkyl-O—$R^{11}$, —(C$_1$-C$_6$)alkyl-S—$R^{11}$, —(C$_1$-C$_6$)alkyl-S(O)—$R^{11}$ and —(C$_1$-C$_6$)alkyl-SO$_2$—$R^{11}$, wherein each $R^{11}$ is independently selected from H, (C$_1$-C$_6$) alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle or heteroaryl are each optionally substituted with one or more (e.g. 1, 2 or 3) $Z^{11}$ groups; and
c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C (=O)—N(R$^9$)R$^{10}$ and —(C$_1$-C$_6$)alkyl-SO$_2$—N(R$^9$)R$^{10}$, wherein each $R^9$ is independently selected from H, (C$_1$-C$_6$) alkyl and (C$_3$-C$_7$)cycloalkyl, and each $R^{10}$ is independently selected from $R^{11}$, —(C$_1$-C$_6$)alkyl-$R^{11}$, —SO$_2$—$R^{11}$, —C(=O)—$R^{11}$, —C(=O)O$R^{11}$ and —C(=O)N(R$^9$)R$^{11}$, wherein each $R^{11}$ is independently selected from H, (C$_1$-C$_6$) alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

$R^{1b}$ is selected from:
a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_6$)carbocycle, —(C$_1$-C$_6$)alkyl-SO$_2$—(C$_1$-C$_6$)alkyl-(C$_3$-C$_7$)carbocycle, —(C$_1$-C$_6$) alkyl-SO$_2$—(C$_1$-C$_6$)alkyl-Z$^{13}$, —C(O)—(C$_1$-C$_6$)alkyl-Z$^{13}$, —O—(C$_1$-C$_6$)alkyl-Z$^{13}$, —S—(C$_1$-C$_6$)alkyl-Z$^{13}$, —S(O)—(C$_1$-C$_6$)alkyl-Z$^{13}$, —SO$_2$—(C$_1$-C$_6$)alkyl-Z$^{13}$, —(C$_1$-C$_6$) alkyl-Z$^{14}$, —(C$_1$-C$_6$)alkyl-C(O)—(C$_1$-C$_6$)alkyl-Z$^{13}$, —(C$_1$-C$_6$)alkyl-C(O)—O(C$_1$-C$_6$)alkyl-Z$^{13}$, —(C$_1$-C$_6$)alkyl-O—(C$_1$-C$_6$)alkyl-Z$^{13}$, —(C$_1$-C$_6$)alkyl-S—(C$_1$-C$_6$)alkyl-Z$^{13}$, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl —(C$_2$-C$_6$)alkynyl-heterocycle, —(C$_3$-C$_7$)carbocycle-Z$^1$ or —(C$_1$-C$_6$)haloalkyl-Z$^3$, wherein any (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl, either alone or as part of a group, is optionally substituted with one or more (e.g. 1, 2, 3, 4 or 5) $Z^1$ groups;
b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) $Z^1$ groups, or wherein two $Z^1$ groups together with the atom or atoms to which they are attached optionally form a carbocycle or heterocycle wherein the carbocycle or heterocycle is optionally substituted with one or more (e.g. 1, 2, 3, 4 or 5) $Z^1$ groups;
c) (C$_1$-C$_6$)alkyl, wherein (C$_1$-C$_6$)alkyl is substituted with one or more (e.g. 1, 2, 3, 4 or 5) $Z^2$ groups and optionally substituted with one or more (e.g. 1, 2, 3, 4 or 5) $Z^1$ groups;
d) —X(C$_1$-C$_6$)alkyl, —X(C$_1$-C$_6$)haloalkyl, —X(C$_2$-C$_6$) alkenyl, —X(C$_2$-C$_6$)alkynyl and —X(C$_3$-C$_7$)carbocycle, wherein —X(C$_1$-C$_6$)alkyl and —X(C$_1$-C$_6$)haloalkyl are each independently substituted with one or more $Z^3$ groups and optionally substituted with one or more $Z^1$ groups, and wherein —X(C$_2$-C$_6$)alkenyl, —X(C$_2$-C$_6$)alkynyl and —X(C$_3$-C$_7$)carbocycle, are each independently substituted with one or more (e.g. 1, 2, 3, 4 or 5) $Z^4$ groups and optionally substituted with one or more $Z^1$ groups;
e) aryl, heteroaryl, heterocycle, —Xaryl, —Xheteroaryl and —Xheterocycle; wherein aryl heteroaryl and heterocycle, either alone or as part of a group, are each independently substituted with one or more (e.g. 1, 2, 3, 4 or 5) $Z^5$ groups and optionally substituted with one or more $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more $Z^1$ groups;

g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—$C(O)$—$NR_eR_f$ and —$(C_1-C_6)$alkyl-$SO_2NR_eR_f$; wherein each $(C_1-C_6)$alkyl, as part of a group, is independently substituted with one or more (e.g. 1, 2, 3, 4 or 5) $Z^6$ groups and optionally substituted with one or more $Z^1$ groups; and h) nitro and cyano;

$R^{ea}$ is selected from:

a) halo;

b) $R^{11}$, $C(=O)$—$R^{11}$, —$C(=O)$—O—$R^{11}$, —O—$R^{11}$, —S—$R^{11}$, —$S(O)$—$R^{11}$, —$SO_2$—$R^{11}$, —$(C_1-C_6)$alkyl-$R^{11}$, —$(C_1-C_6)$alkyl-$C(=O)$—$R^{11}$, —$(C_1-C_6)$alkyl-$C(=O)$—O—$R^{11}$, —$(C_1-C_6)$alkyl-O—$R^{11}$, —$(C_1-C_6)$alkyl-S—$R^{11}$, —$(C_1-C_6)$alkyl-$S(O)$—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl and heterocycle and heteroaryl, wherein aryl, heterocycle or heteroaryl are each optionally substituted with one or more (e.g. 1, 2 or 3) $Z^{11}$ groups; and c) —$N(R^9)R^{10}$, —$C(=O)$—$N(R^9)R^{10}$, —O—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-$C(=O)$—$N(R^9)R^{10}$, —$(C_1-C_6)$alkyl-O—$C(=O)$—$N(R^9)R^{19}$, and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, wherein each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{2b}$ is selected from:

a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-$S(O)$—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_1-C_6)$alkyl-$SO_2$—$(C_1-C_6)$alkyl-$Z^{13}$, —$C(O)$—$(C_1-C_6)$alkyl-$Z^{13}$, —O—$(C_1-C_6)$alkyl-$Z^{13}$, —S—$(C_1-C_6)$alkyl-$Z^{13}$, —$S(O)$—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-$C(O)$—$(C_1-C_6)$alkyl-$Z^{13}$, —$(C_1-C_6)$alkyl-$C(O)$—$O(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_3-C_7)$halocarbocycle, —$NR_aSO_2NR_cR_d$, —$NR_aSO_2O(C_3-C_7)$carbocycle, —$NR_aSO_2O$aryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or —$(C_1-C_6)$haloalkyl-$Z^3$, wherein any $(C_1-C_6)$alkyl, —$(C_1-C_6)$haloalkyl, $(C_3-C_7)$carbocycle, $(C_2-C_6)$alkenyl, $(C_2-C_6)$alkynyl, aryl or heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$carbocycle or heterocycle wherein the $(C_3-C_6)$carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein —$X(C_1-C_6)$alkyl and $X(C_1-C_6)$haloalkyl are each independently substituted with one or more $Z^3$ groups and optionally substituted with one or more (e.g. 1, 2, 3, 4 or 5) $Z^1$ groups, and wherein —$X(C_2-C_6)$alkenyl, —$X(C_2-C_6)$alkynyl and —$X(C_3-C_7)$carbocycle are each independently substituted with one or more (e.g. 1, 2, 3, 4 or 5) $Z^4$ groups and optionally substituted with one or more $Z^1$ groups;

e) aryl, heteroaryl, heterocycle, —Xaryl, —Xheteroaryl and —Xheterocycle, wherein aryl heteroaryl and heterocycle, either alone or as part of a group, are each independently substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups;

g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—$C(O)$—$NR_eR_f$ and —$(C_1-C_6)$alkyl-$SO_2NR_eR_f$, wherein each $(C_1-C_6)$alkyl, as part of a group, is independently substituted with one or more (e.g. 1, 2, 3, 4 or 5) $Z^6$ groups and optionally substituted with one or more (e.g. 1, 2, 3, 4 or 5) $Z^1$ groups; and h) nitro and cyano;

or $R^1$ and $R^2$ together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are optionally substituted with one or more $Z^1$ groups;

or $R^1$ and $R^2$ together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are each independently substituted with one or more (e.g. 1, 2 or 3) $Z^7$ or $Z^8$ groups, or wherein when two $Z^7$ groups are on same atom the two $Z^7$ groups together with the atom to which they are attached optionally form a $(C_3-C_7)$carbocycle or 4, 5 or 6-membered heterocycle;

$R^{3a}$ is $(C_1-C_6)$alkyl, $(C_1-C_6)$haloalkyl, $(C_2-C_6)$alkenyl, $(C_2-C_6)$alkynyl, —$(C_1-C_6)$alkyl-$(C_3-C_7)$cycloalkyl, —$(C_1-C_6)$alkyl-aryl, —$(C_1-C_6)$alkyl-heterocycle, —$(C_1-C_6)$alkyl-heteroaryl, —$O(C_1-C_6)$alkyl, —$O(C_1-C_6)$haloalkyl, —$O(C_2-C_6)$alkenyl, —$O(C_2-C_6)$alkynyl, —$O(C_3-C_7)$cycloalkyl, —Oaryl, —$O(C_1-C_6)$alkyl-$(C_3-C_7)$cycloalkyl, —$O(C_1-C_6)$alkyl-aryl, —$O(C_1-C_6)$alkyl-heterocycle and —$O(C_1-C_6)$alkyl-heteroaryl, wherein any $(C_1-C_6)$alkyl, $(C_1-C_6)$haloalkyl, $(C_2-C_6)$alkenyl, $(C_2-C_6)$alkynyl, —$(C_1-C_6)$alkyl-$(C_3-C_7)$cycloalkyl, —$(C_1-C_6)$alkyl-aryl, —$(C_1-C_6)$alkyl-heterocycle, —$(C_1-C_6)$alkyl-heteroaryl, —$O(C_1-C_6)$alkyl, —$O(C_1-C_6)$haloalkyl, —$O(C_2-C_6)$alkenyl, —$O(C_2-C_6)$alkynyl, —$O(C_3-C_7)$cycloalkyl, —Oaryl, —$O(C_1-C_6)$alkyl-$(C_3-C_7)$cycloalkyl, —$O(C_1-C_6)$alkyl-aryl, —$O(C_1-C_6)$alkyl-heterocycle or —$O(C_1-C_6)$alkyl-heteroaryl of $R^{3a}$ is optionally substituted with one or more (e.g. 1, 2 or 3) groups selected from $(C_1-C_6)$alkyl, —$O(C_1-C_6)$alkyl, halo, oxo and —CN; and $R^{3a'}$ is H;

$R^{3b}$ is —($C_3$-$C_7$)carbocycle, aryl, heteroaryl, heterocycle, —($C_1$-$C_6$)alkylOH, —($C_1$-$C_6$)alkyl-O—($C_1$-$C_6$)alkyl-$Z^{12}$, —($C_1$-$C_6$)alkyl-O—($C_2$-$C_6$)alkenyl-$Z^{12}$, —($C_2$-$C_6$)alkyl-O—($C_2$-$C_6$)alkynyl-$Z^{12}$, —($C_1$-$C_6$)alkyl-S—($C_1$-$C_6$)alkyl-$Z^{12}$, —($C_1$-$C_6$)alkyl-S—($C_2$-$C_6$)alkenyl-$Z^{12}$, —($C_2$-$C_6$)alkyl-S—($C_2$-$C_6$)alkynyl-$Z^{12}$, —($C_1$-$C_6$)alkyl-S(O)—($C_1$-$C_6$)alkyl-$Z^{12}$, —($C_1$-$C_6$)alkyl-S(O)—($C_2$-$C_6$)alkenyl-$Z^{12}$, —($C_2$-$C_6$)alkyl-S(O)—($C_2$-$C_6$)alkynyl-$Z^{12}$, —($C_1$-$C_6$)alkyl-$SO_2$—($C_1$-$C_6$)alkyl-$Z^{12}$, —($C_1$-$C_6$)alkyl-$SO_2$—($C_2$-$C_6$)alkenyl-$Z^{12}$, —($C_2$-$C_6$)alkyl-$SO_2$—($C_2$-$C_6$)alkynyl-$Z^{12}$, —($C_2$-$C_6$)alkyl-$NR_aR_b$, —($C_2$-$C_6$)alkylOC(O)—$NR_cR_d$, —($C_2$-$C_6$)alkyl-$NR_a$—C(O)—$OR_b$, —($C_2$-$C_6$)alkyl-$NR_a$—C(O)—$NR_aR_b$, —($C_1$-$C_6$)alkyl-$SO_2$($C_1$-$C_6$)alkyl, —($C_1$-$C_6$)alkyl-$SO_2NR_cR_d$, —($C_1$-$C_6$)alkyl-$NR_aSO_2NR_cR_d$, —($C_1$-$C_6$)alkyl-$NR_aSO_2O$($C_3$-$C_7$)carbocycle, —($C_1$-$C_6$)alkyl-$NR_aSO_2$Oaryl, —($C_1$-$C_6$)alkyl-$NR_a$—$SO_2$—($C_1$-$C_6$)alkyl, —($C_1$-$C_6$)alkyl-$NR_a$—$SO_2$—($C_1$-$C_6$)haloalkyl, —($C_1$-$C_6$)alkyl-$NR_a$—$SO_2$—($C_2$-$C_6$)alkenyl, —($C_1$-$C_6$)alkyl-$NR_a$—$SO_2$—($C_2$-$C_6$)alkynyl, —($C_1$-$C_6$)alkyl-$NR_a$—$SO_2$—($C_3$-$C_7$)carbocycle, —($C_1$-$C_6$)alkyl-$NR_a$—$SO_2$—($C_3$-$C_7$)halocarbocycle, —($C_1$-$C_6$)alkyl-$NR_a$—$SO_2$-aryl, —($C_1$-$C_6$)alkyl-$NR_a$—$SO_2$-heteroaryl, —($C_1$-$C_6$)alkyl-$NR_a$—$SO_2$-heterocycle, —O($C_1$-$C_6$)alkyl-$NR_aR_b$, —O($C_1$-$C_6$)alkylOC(O)—$NR_cR_b$, —O($C_1$-$C_6$)alkyl-$NR_a$—C(O)—$OR_b$, —O($C_1$-$C_6$)alkyl-$NR_a$—C(O)—$NR_aR_b$, —O($C_1$-$C_6$)alkyl-$NR_a$—$SO_2$—($C_1$-$C_6$)alkyl, —O($C_1$-$C_6$)alkyl-$NR_a$—$SO_2$—($C_1$-$C_6$)haloalkyl, —O($C_1$-$C_6$)alkyl-$NR_a$—$SO_2$—($C_2$-$C_6$)alkenyl, —O($C_1$-$C_6$)alkyl-$NR_a$—$SO_2$—($C_2$-$C_6$)alkynyl, —O($C_1$-$C_6$)alkyl-$NR_a$—$SO_2$—($C_3$-$C_7$)carbocycle, —O($C_1$-$C_6$)alkyl-$NR_a$—$SO_2$—($C_3$-$C_7$)halocarbocycle, —O($C_1$-$C_6$)alkyl-$NR_a$—$SO_2$-aryl, —O($C_1$-$C_6$)alkyl-$NR_a$—$SO_2$-heteroaryl, —O($C_1$-$C_6$)alkyl-$NR_a$—$SO_2$-heterocycle, —O($C_1$-$C_6$)alkyl-$NR_a$—$SO_2$—$NR_aR_b$, —O($C_1$-$C_6$)alkyl-$NR_a$—$SO_2$—($C_3$-$C_7$)carbocycle, —O($C_1$-$C_6$)alkyl-$NR_a$—$SO_2$—($C_3$-$C_7$)halocarbocycle, —O($C_1$-$C_6$)alkyl-$NR_a$—$SO_2$-aryl, —O($C_1$-$C_6$)alkyl-$NR_aSO_2NR_cR_d$, —O($C_1$-$C_6$)alkyl-$NR_aSO_2O$($C_3$-$C_7$)carbocycle, —O($C_1$-$C_6$)alkyl-$NR_aSO_2$Oaryl, —Oheteroaryl, —Oheterocycle, —Sheteroaryl, —Sheterocycle, —S(O)heteroaryl, —S(O)heterocycle, —$SO_2$heteroaryl or —$SO_2$heterocycle, wherein any ($C_1$-$C_6$)alkyl, ($C_2$-$C_6$)alkenyl, ($C_2$-$C_6$)alkynyl, aryl, ($C_3$-$C_7$)carbocycle, heteroaryl or heterocycle of $R^{3b}$, either alone or as part of a group, is optionally substituted with one or more (e.g. 1, 2, 3, 4 or 5) $Z^1$ groups; and $R^{3b'}$ is H, ($C_1$-$C_6$)alkyl or —O($C_1$-$C_6$)alkyl; or $R^{3b}$ and $R^{3b'}$ together with the carbon to which they are attached form a heterocycle or ($C_3$-$C_7$)carbocycle, which heterocycle or ($C_3$-$C_7$)carbocycle of $R^{3b}$ and $R^{3b'}$ together with the carbon to which they are attached is optionally substituted with one or more (e.g. 1, 2, 3, 4 or 5) $Z^1$ groups;

$R^{4a}$ is selected from aryl, heterocycle and heteroaryl, wherein any aryl, heterocycle and heteroaryl of $R^{4a}$ is optionally substituted with one or more (e.g. 1, 2, 3, 4 or 5) groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, —$NH_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo;

$R^{4b}$ is selected from:

a) ($C_1$-$C_6$)alkyl, ($C_2$-$C_6$)alkenyl and ($C_2$-$C_6$)alkynyl, wherein ($C_1$-$C_6$)alkyl, ($C_2$-$C_6$)alkenyl or ($C_2$-$C_6$)alkynyl are each optionally substituted with one or more (e.g. 1, 2, 3, 4 or 5) $Z^1$ groups;

b) ($C_3$-$C_{14}$)carbocycle, wherein ($C_3$-$C_{14}$)carbocycle is optionally substituted with one or more (e.g. 1, 2, 3, 4 or 5) $Z^1$ groups, or wherein two $Z^1$ groups together with the atom or atoms to which they are attached optionally form a ($C_3$-$C_7$)carbocycle or heterocycle;

c) Spiro-heterocycle or bridged-heterocycle, wherein spiro-heterocycle or bridged-heterocycle is optionally substituted with one or more (e.g. 1, 2, 3, 4 or 5) $Z^1$ groups, or wherein two $Z^1$ groups together with the atom or atoms to which they are attached optionally form a ($C_3$-$C_7$)carbocycle or heterocycle; and d) aryl, heteroaryl, spiro-heterocycle, fused-heterocycle, or bridged-heterocycle, wherein aryl, heteroaryl, spiro-heterocycle, fused-heterocycle and bridged-heterocycle are each independently substituted with one or more $Z^7$ groups and optionally substituted with one or more (e.g. 1, 2, 3, 4 or 5) $Z^1$ groups; or $R^4$ and $R^3$ together with the atoms to which they are attached form a macroheterocycle or a macrocarbocycle, wherein any macroheterocycle or macrocarbocycle of $R^4$ and $R^3$ together with the atoms to which they are attached may be optionally substituted with one or more (e.g. 1, 2, 3, 4 or 5) $Z^1$ groups; and $R^{3b'}$ is H or ($C_1$-$C_6$)alkyl, —O($C_1$-$C_6$)alkyl;

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl and heterocycle are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl, heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

each X is independently selected from O, —C(O)—, —C(O)O—, —S—, —S(O)—, —$SO_2$—, —($C_1$-$C_6$)alkylO—, —($C_1$-$C_6$)alkylC(O)—, —($C_1$-$C_6$)alkylC(O)O—, —($C_1$-$C_6$)alkylS—, —($C_1$-$C_6$)alkylS(O)— and —($C_1$-$C_6$)alkyl$SO_2$—;

each $Z^1$ is independently selected from halo, —$NO_2$, —OH, =$NOR_a$, —SH, —CN, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2$($C_1$-$C_6$)alkyl, —S(O)aryl, —S(O)carbocycle, —S(O)heteroaryl, —S(O)heterocycle, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O$($C_3$-$C_7$)carbocycle, —$NR_aSO_2$Oaryl, —OS(O)$_2R_a$, —C(O)$R_a$, —C(O)$OR_b$, —C(O)$NR_cR_d$, and —OC(O)$NR_cR_d$, wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^1$, either alone or as part of a group, is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle or —S(O)$_2$NR$_c$R$_d$;

each $Z^2$ is independently selected from —NO$_2$, —CN, spiro-heterocycle, bridge-heterocycle, spiro-bicyclic carbocycle, bridged-bicyclic carbocycle, NR$_a$SO$_2$(C$_3$-C$_7$)carbocycle, —NR$_a$SO$_2$aryl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$Oaryl;

each $Z^3$ is independently selected from —NO$_2$, —CN, —OH, oxo, =NOR$_a$, thioxo, aryl, heterocycle, heteroaryl, (C$_3$-C$_7$)halocarbocycle, —O(C$_1$-C$_6$)alkyl, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each $Z^4$ is independently selected from halogen, —(C$_1$-C$_6$)alkyl, (C$_3$-C$_7$)carbocycle, —(C$_1$-C$_6$)haloalkyl, —NO$_2$, —CN, —OH, oxo, =NOR$_a$, thioxo, -aryl, -heterocycle, -heteroaryl, —(C$_3$-C$_7$)halocarbocycle, —O(C$_1$-C$_6$)alkyl, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_a$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each $Z^5$ is independently selected from —NO$_2$, —CN, —NR$_a$SO$_2$NR$_c$R$_d$, —NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$aryl, —NR$_a$SO$_2$heteraryl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each $Z^6$ is independently selected from —NO$_2$, —CN, —NR$_a$R$_a$, NR$_a$C(O)R$_b$, —C(O)NR$_c$R$_d$, (C$_3$-C$_7$)halocarbocycle, aryl, heteroaryl, heterocycle, —Oaryl, —Oheteroaryl, —Oheterocycle, —O(C$_3$-C$_7$)halocarbocycle, —O(C$_1$-C$_6$)alkyl, —O(C$_3$-C$_7$)carbocycle, —O(C$_1$-C$_6$)haloalkyl, —Saryl, —Sheteroaryl, —Sheterocycle, —S(C$_3$-C$_7$)halocarbocycle, —S(C$_1$-C$_6$)alkyl, —S(C$_3$-C$_7$)carbocycle, —S(C$_1$-C$_6$)haloalkyl, —S(O)aryl, —S(O)heteroaryl, —S(O)heterocycle, —S(O)(C$_3$-C$_7$)halocarbocycle, —S(O)(C$_1$-C$_6$)alkyl, —S(O)(C$_3$-C$_7$)carbocycle, —S(O)(C$_1$-C$_6$)haloalkyl, —SO$_2$aryl, —SO$_2$heteroaryl, —SO$_2$heterocycle, —SO$_2$(C$_1$-C$_6$)alkyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$NR$_c$R$_d$, —NR$_a$SO$_2$(C$_3$-C$_7$)halocarbocycle, —NR$_a$SO$_2$aryl, —NR$_a$SO$_2$heteraryl, —NR$_a$SO$_2$NR$_c$R$_d$, —NR$_a$SO$_2$O(C$_3$-C$_7$)carbocycle and —NR$_a$SO$_2$Oaryl, wherein any aryl, of $Z^6$, either alone or as part of a group, is optionally substituted with one or more (e.g. 1, 2, 3, 4 or 5) halogen, —OH, —O(C$_1$-C$_6$)alkyl, —CN or —(C$_1$-C$_6$)alkyl;

each $Z^7$ is independently selected from —NO$_2$, =NOR$_a$, —CN, —(C$_1$-C$_6$)alkyl-Z$^{12}$, —(C$_2$-C$_6$)alkenyl-Z$^{12}$, —(C$_2$-C$_6$)alkenylOH, —(C$_2$-C$_6$)alkynyl-Z$^{12}$, —(C$_2$-C$_6$)alkynylOH, —(C$_1$-C$_6$)haloalkyl-Z$^{12}$, —(C$_1$-C$_6$)haloalkylOH, —(C$_3$-C$_7$)carbocycle-Z$^{12}$, —(C$_3$-C$_7$)carbocycleOH, —(C$_3$-C$_7$)halocarbocycle, —(C$_1$-C$_6$)alkylNR$_c$R$_d$, —(C$_1$-C$_6$)alkylNR$_a$C(O)R$_a$, —(C$_1$-C$_6$)alkylNR$_a$SO$_2$R$_a$, aryl, heteroaryl, heterocycle, —O(C$_1$-C$_6$)alkyl-Z$^{12}$, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —O(C$_1$-C$_6$)alkylNR$_c$R$_d$, —O(C$_1$-C$_6$)alkylNR$_a$C(O)R$_a$, —O(C$_1$-C$_6$)alkylNR$_a$SO$_2$R$_a$, —Oheteroaryl, —Oheterocycle, —S(C$_1$-C$_6$)alkyl-Z$^{12}$, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —S(C$_1$-C$_6$)alkylNR$_c$R$_d$, —S(C$_1$-C$_6$)alkylNR$_a$C(O)R$_a$, —S(C$_1$-C$_6$)alkylNR$_a$SO$_2$R$_a$, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocyle, —S(O)(C$_3$-C$_7$)halocarbocycle, —SO$_2$(C$_1$-C$_6$)alkyl, —S(O)(C$_1$-C$_6$)alkylNR$_c$R$_d$, —S(O)(C$_1$-C$_6$)alkylNR$_a$C(O)R$_a$, —S(O)(C$_1$-C$_6$)alkylNR$_a$SO$_2$R$_a$, —S(O)aryl, —S(O)heteroaryl, —S(O)heterocycle, —SO$_2$(C$_1$-C$_6$)alkyl, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$(C$_1$-C$_6$)alkylNR$_c$R$_d$, —SO$_2$(C$_1$-C$_6$)alkylNR$_a$C(O)R$_a$, —SO$_2$(C$_1$-C$_6$)alkylNR$_a$SO$_2$R$_a$, —SO$_2$NR$_c$R$_d$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)NR$_c$R$_d$, and —OC(O)NR$_c$R$_d$, wherein any (C$_1$-C$_6$)alkyl, (C$_2$-C$_6$)alkenyl, (C$_2$-C$_6$)alkynyl, (C$_3$-C$_7$)carbocycle, (C$_3$-C$_7$)halocarbocycle, aryl, heteroaryl or heterocycle of $Z^7$, either alone or as part of a group, is optionally substituted with one or more (e.g. 1, 2, 3, 4 or 5) halogen, —OH, —OR$_b$, —CN, —NR$_a$C(O)$_2$R$_b$, heteroaryl, heterocycle, —Oheterocycle, —Oheterocycle, —NHheteroaryl, —NHheterocycle or —S(O)$_2$NR$_c$R$_d$;

each $Z^8$ is independently selected from —NO$_2$ or —CN;
each $Z^{10}$ is independently selected from
i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$)alkyl, —NH$_2$, —NH(C$_1$-C$_6$)alkyl and —N((C$_1$-C$_6$)alkyl)$_2$;
ii) (C$_1$-C$_6$)alkyl optionally substituted with —OH, —O—(C$_1$-C$_6$)haloalkyl, or —O—(C$_1$-C$_6$)alkyl; and
iii) aryl, heterocycle and heteroaryl, which aryl, heterocycle and heteroaryl is optionally substituted with halo, (C$_1$-C$_6$)alkyl or COOH;

each $Z^{11}$ is independently selected from $Z^{10}$, —C(=O)—NH$_2$, —C(=O)—NH(C$_1$-C$_4$)alkyl, —C(=O)—N((C$_1$-C$_4$)alkyl)$_2$, —C(=O)-aryl, —C(=O)-heterocycle and —C(=O)-heteroaryl;

each $Z^{12}$ is independently selected from —NO$_2$, =NOR$_a$, thioxo, aryl, heterocycle, heteroaryl, (C$_3$-C$_7$)halocarbocycle, (C$_3$-C$_7$)carbocycle, —O(C$_3$-C$_7$)carbocycle, —O(C$_3$-C$_7$)halocarbocyle, —Oaryl, —Oheterocycle, —Oheteroaryl, —S(C$_1$-C$_6$)alkyl, —S(C$_3$-C$_7$)carbocyle, —S(C$_3$-C$_7$)halocarbocyle, —Saryl, —Sheterocycle, —Sheteroaryl, —S(O)(C$_1$-C$_6$)alkyl, —S(O)(C$_3$-C$_7$)carbocyle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-

$C_7$)halocarbocycle, —$SO_2$aryl, —$SO_2$heterocycle, —$SO_2$heteroaryl, —$NR_aR_a$, —$NR_aC(O)R_b$, —$C(O)NR_cR_d$, —$SO_2NR_cR_d$, —$NR_aSO_2NR_cR_d$, —$NR_aSO_2O(C_3-C_7)$carbocyle and —$NR_aSO_2O$aryl;

each $Z^{13}$ is independently selected from —$NO_2$, —OH, =$NOR_a$, —SH, —CN, $(C_3-C_7)$halocarbocycle, —$O(C_1-C_6)$alkyl, —$O(C_2-C_6)$alkenyl, —$O(C_2-C_6)$alkynyl, —$O(C_1-C_6)$haloalkyl, —$O(C_3-C_7)$carbocycle, —$O(C_3-C_7)$halocarbocycle, —Oaryl, —Oheteroaryl, —Oheterocycle, —$S(C_1-C_6)$alkyl, —$S(C_2-C_6)$alkenyl, —$S(C_2-C_6)$alkynyl, —$S(C_1-C_6)$haloalkyl, —$S(C_3-C_7)$carbocycle, —$S(C_3-C_7)$halocarbocycle, —Saryl, —Sheteroaryl, —Sheterocycle, —$S(O)(C_1-C_6)$alkyl, —$S(O)(C_2-C_6)$alkenyl, —$S(O)(C_2-C_6)$alkynyl, —$S(O)(C_1-C_6)$haloalkyl, —$S(O)(C_3-C_7)$carbocycle, —$S(O)(C_3-C_7)$halocarbocycle, —$S(O)$aryl, —$S(O)$heteroaryl, —$S(O)$heterocycle, —$SO_2(C_1-C_6)$alkyl, —$SO_2(C_2-C_6)$alkenyl, —$SO_2(C_2-C_6)$alkynyl, —$SO_2(C_1-C_6)$haloalkyl, —$SO_2(C_3-C_7)$carbocycle, —$SO_2(C_3-C_7)$halocarbocycle, —$SO_2$aryl, —$SO_2$heteroaryl, —$SO_2$heterocycle, —$SO_2NR_cR_d$, —$NR_aR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O(C_3-C_7)$carbocycle, —$NR_aSO_2O$aryl, —$OS(O)_2R_a$, —$C(O)R_a$, —$C(O)OR_b$, —$C(O)NR_cR_d$, and —$OC(O)NR_cR_d$, wherein any $(C_1-C_6)$alkyl, $(C_2-C_6)$alkenyl, $(C_2-C_6)$alkynyl, $(C_3-C_7)$halocarbocycle, $(C_3-C_7)$carbocycle, $(C_3-C_7)$halocarbocycle, aryl, heteroaryl or heterocycle of $Z^{13}$, either alone or as part of a group, is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $Z^{14}$ is independently selected from —$NO_2$, =$NOR_a$, —CN, —$(C_3-C_7)$halocarbocycle, —$O(C_3-C_7)$halocarbocycle, —$S(C_3-C_7)$halocarbocycle, —$S(O)(C_3-C_7)$halocarbocycle, —$SO_2(C_3-C_7)$halocarbocycle, —$NR_aSO_2NR_cR_d$, —$NR_aSO_2O(C_3-C_7)$carbocycle, —$NR_aSO_2O$aryl, —$OS(O)_2R_a$, wherein any —$(C_3-C_7)$halocarbocycle of $Z^{14}$, either alone or as part of a group, is optionally substituted with one or more (e.g. 1, 2, 3, 4 or 5) halogen, —OH, —$OR_b$, —CN, —$NR_aC(O)_2R_b$, heteroaryl, -heterocycle, —Oheteroaryl, —Oheterocycle, —NHheteroaryl, —NHheterocycle, or —$S(O)_2NR_cR_d$;

each $Z^{15}$ is independently selected from aryl, heteroaryl, heterocycle, —Oaryl, —Oheteroaryl, —Oheterocycle, —$O(C_1-C_6)$alkyl-aryl, —$O(C_1-C_6)$alkyl-heteroaryl, —$O(C_1-C_6)$alkyl-heterocycle, wherein aryl, heteroaryl and heterocycle are each independently substituted with one or more (e.g. 1, 2, 3, 4 or 5) $Z^{16}$ groups and optionally substituted with one or more (e.g. 1, 2, 3, 4 or 5) $Z^1$ groups, and wherein any —Oaryl, —Oheteroaryl, —Oheterocycle, —$O(C_1-C_6)$alkyl-aryl, —$O(C_1-C_6)$alkyl-heteroaryl or —$O(C_1-C_6)$alkyl-heterocycle is optionally substituted with one or more (e.g. 1, 2, 3, 4 or 5) $Z^1$ groups;

each $Z^{16}$ is independently selected from —$NO_2$, —OH, =$NOR_a$, —SH, —CN, $(C_2-C_6)$alkenyl, $(C_2-C_6)$alkynyl, $(C_1-C_6)$haloalkyl, $(C_3-C_7)$carbocycle, $(C_3-C_7)$halocarbocycle, aryl, heteroaryl, heterocycle, —$O(C_1-C_6)$alkyl, —$O(C_2-C_6)$alkenyl, —$O(C_2-C_6)$alkynyl, —$O(C_1-C_6)$haloalkyl, —$O(C_3-C_7)$carbocycle, —$O(C_3-C_7)$halocarbocycle, —Oaryl, —Oheteroaryl, —Oheterocycle, —$S(C_1-C_6)$alkyl, —$S(C_2-C_6)$alkenyl, —$S(C_2-C_6)$alkynyl, —$S(C_1-C_6)$haloalkyl, —$S(C_3-C_7)$carbocycle, —$S(C_3-C_7)$halocarbocycle, —Saryl, —Sheteroaryl, —Sheterocycle, —$S(O)(C_1-C_6)$alkyl, —$S(O)(C_2-C_6)$alkenyl, —$S(O)(C_2-C_6)$alkynyl, —$S(O)(C_1-C_6)$haloalkyl, —$S(O)(C_3-C_7)$carbocycle, —$S(O)(C_3-C_7)$halocarbocycle, —$SO_2(C_1-C_6)$alkyl, —$S(O)$aryl, —$S(O)$carbocycle, —$S(O)$heterocycle, —$S(O)$heterocycle, —$SO_2(C_2-C_6)$alkenyl, —$SO_2(C_2-C_6)$alkynyl, —$SO_2(C_1-C_6)$haloalkyl, —$SO_2(C_3-C_7)$carbocycle, —$SO_2(C_3-C_7)$halocarbocycle, —$SO_2$aryl, —$SO_2$heterocycle, —$SO_2$heterocycle, —$SO_2NR_cR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O(C_3-C_7)$carbocycle, —$NR_aSO_2O$aryl, —$OS(O)_2R_a$, —$C(O)R_a$, —$C(O)OR_b$, —$C(O)NR_cR_d$, and —$OC(O)NR_cR_d$, wherein any $(C_1-C_6)$alkyl, $(C_2-C_6)$alkenyl, $(C_2-C_6)$alkynyl, —$(C_3-C_7)$halocarbocycle, $(C_3-C_7)$carbocycle, $(C_3-C_7)$halocarbocycle, aryl, heteroaryl or heterocycle of $Z^{16}$, either alone or as part of a group, is optionally substituted with one or more (e.g. 1, 2, 3, 4 or 5) halogen, $(C_1-C_6)$alkyl, —OH, —$OR_b$, —CN, —$NR_aC(O)_2R_b$, heteroaryl, heterocycle, —Oheteroaryl, —Oheterocycle, —NHheteroaryl, —NHheterocycle or —$S(O)_2NR_cR_d$;

each $R_a$ is independently H, $(C_1-C_6)$alkyl, $(C_2-C_6)$alkenyl, $(C_2-C_6)$alkynyl, $(C_3-C_7)$carbocycle, heterocycle, aryl, aryl$(C_1-C_6)$alkyl-, heteroaryl or heteroaryl$(C_1-C_6)$alkyl-, wherein any $(C_1-C_6)$alkyl, $(C_2-C_6)$alkenyl, $(C_2-C_6)$alkynyl, $(C_3-C_7)$carbocycle, heterocycle, aryl, or heteroaryl of $R_a$, either alone or as part of a group, is optionally substituted with one or more (e.g. 1, 2, 3, 4 or 5) halogen, OH or cyano;

each $R_b$ is independently $(C_1-C_6)$alkyl, $(C_2-C_6)$alkenyl, $(C_2-C_6)$alkynyl, $(C_3-C_7)$carbocycle, heterocycle, aryl, aryl$(C_1-C_6)$alkyl-, heteroaryl or heteroaryl$(C_1-C_6)$alkyl-, wherein any $(C_1-C_6)$alkyl, $(C_2-C_6)$alkenyl, $(C_2-C_6)$alkynyl, $(C_3-C_7)$carbocycle, heterocycle, aryl, or heteroaryl of $R_b$, either alone or as part of a group, is optionally substituted with one or more (e.g. 1, 2, 3, 4 or 5) halogen, OH and cyano;

$R_c$ and $R_d$ are each independently selected from H, $(C_1-C_6)$alkyl, $(C_2-C_6)$alkenyl, $(C_2-C_6)$alkynyl, $(C_3-C_7)$carbocycle, aryl, aryl$(C_1-C_6)$alkyl-, heterocycle, heteroaryl or heteroaryl$(C_1-C_6)$alkyl-, wherein any $(C_1-C_6)$alkyl, $(C_2-C_6)$alkenyl, $(C_2-C_6)$alkynyl, $(C_3-C_7)$carbocycle, heterocycle, aryl, or heteroaryl of $R_c$ or $R_d$, either alone or as part of a group, is optionally substituted with one or more (e.g. 1, 2, 3, 4 or 5) halogen, OH or cyano; or $R_c$ and $R_d$ together with the nitrogen to which they are attached form a heterocycle, wherein any heterocycle of $R_c$ and $R_d$ together with the nitrogen to which they are attached is optionally substituted with one or more (e.g. 1, 2, 3, 4 or 5) halogen, OH or cyano;

each $R_e$ is independently selected from –$OR_a$, $(C_1-C_6)$alkyl or $(C_3-C_7)$carbocycle, wherein $(C_1-C_6)$alkyl and $(C_3-C_7)$carbocycle are each independently substituted with one or more (e.g. 1, 2, 3, 4 or 5) $Z^6$ groups and optionally substituted with one or more (e.g. 1, 2, 3, 4 or 5) $Z^1$ groups; $(C_2-C_6)$haloalkyl, $(C_2-C_6)$alkenyl and $(C_2-C_6)$alkynyl, wherein any $(C_2-C_6)$haloalkyl, $(C_2-C_6)$alkenyl or $(C_2-C_6)$alkynyl is optionally substituted with one or more (e.g. 1, 2, 3, 4 or 5) $Z_1$ groups; and aryl, heterocycle and heteroaryl wherein aryl, heterocycle and heteroaryl are each independently substituted with one or more (e.g. 1, 2, 3, 4 or 5) $Z_5$ groups;

each $R_f$ is independently selected from —$R_g$, —$OR_a$, —$(C_1-C_6)$alkyl-$Z^6$, —$SO_2R_g$, —$C(O)R_g$, $C(O)OR_g$ and —$C(O)NR_cR_g$; and each $R_g$ is independently selected from $(C_1-C_6)$alkyl, $(C_3-C_7)$carbocycle $(C_1-C_6)$haloalkyl, $(C_2-C_6)$alkenyl, $(C_2-C_6)$alkynyl, aryl, heterocycle and heteroaryl, wherein any $(C_1-C_6)$alkyl, $(C_3-C_7)$carbocycle —$(C_1-C_6)$haloalkyl, $(C_2-C_6)$alkenyl, $(C_2-C_6)$alkynyl, aryl, heterocycle or heteroaryl of $R_g$ is optionally substituted with one or more (e.g. 1, 2, 3, 4 or 5) $Z_1$ groups;

or a salt thereof.

In one embodiment, the invention provides a compound of formula Ia:

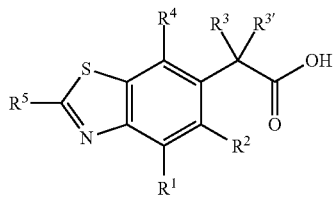

Ia wherein:
$R^1$ is H;
$R^2$ is $(C_1\text{-}C_6)$alkyl;
$R^3$ is —O$(C_1\text{-}C_6)$alkyl;
$R^{3'}$ is H;
$R^4$ is selected from aryl, heterocycle and heteroaryl, wherein any aryl, heterocycle and heteroaryl of $R^4$ is optionally substituted with one or more groups each independently selected from halo, $(C_1\text{-}C_6)$alkyl, $(C_2\text{-}C_6)$alkenyl, $(C_1\text{-}C_6)$haloalkyl, $(C_3\text{-}C_7)$cycloalkyl, —$(C_1\text{-}C_6)$alkyl-$(C_3\text{-}C_7)$cycloalkyl, —OH, —O$(C_1\text{-}C_6)$alkyl, —SH, —S$(C_1\text{-}C_6)$alkyl, NH$_2$, —NH$(C_1\text{-}C_6)$alkyl and —N($(C_1\text{-}C_6)$alkyl)$_2$, wherein $(C_1\text{-}C_6)$alkyl is optionally substituted with hydroxy, —O$(C_1\text{-}C_6)$alkyl, cyano or oxo;
$R^5$ is selected from:
a) aryl, heterocycle and heteroaryl, wherein aryl, heterocycle and heteroaryl are each optionally substituted with one or more (e.g. 1, 2, 3, 4 or 5) $Z^{11}$ groups;
b) aryl, heteroaryl and heterocycle, wherein aryl, heteroaryl and heterocycle are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl, and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
each $Z^1$ is independently selected from halo, —NO$_2$, —OH, =NOR$_a$, —SH, —CN, $(C_1\text{-}C_6)$alkyl, $(C_2\text{-}C_6)$alkenyl, $(C_2\text{-}C_6)$alkynyl, $(C_1\text{-}C_6)$haloalkyl, $(C_3\text{-}C_7)$carbocycle, $(C_3\text{-}C_7)$halocarbocycle, aryl, heteroaryl, heterocycle, —O$(C_1\text{-}C_6)$alkyl, —O$(C_2\text{-}C_6)$alkenyl, —O$(C_2\text{-}C_6)$alkynyl, —O$(C_1\text{-}C_6)$haloalkyl, —O$(C_3\text{-}C_7)$carbocycle, —O$(C_3\text{-}C_7)$halocarbocycle, —Oaryl, —Oheteroaryl, —Oheterocycle, —S$(C_1\text{-}C_6)$alkyl, —S$(C_2\text{-}C_6)$alkenyl, —S$(C_2\text{-}C_6)$alkynyl, —S$(C_1\text{-}C_6)$haloalkyl, —S$(C_3\text{-}C_7)$carbocycle, —S$(C_3\text{-}C_7)$halocarbocycle, —Saryl, —Sheteroaryl, —Sheterocycle, —S(O)$(C_1\text{-}C_6)$alkyl, —S(O)$(C_2\text{-}C_6)$alkenyl, —S(O)$(C_2\text{-}C_6)$alkynyl, —S(O)$(C_1\text{-}C_6)$haloalkyl, —S(O)$(C_3\text{-}C_7)$carbocycle, —S(O)$(C_3\text{-}C_7)$halocarbocycle, —SO$_2$$(C_1\text{-}C_6)$alkyl, —S(O)aryl, —S(O)carbocycle, —S(O)heterocycle, —S(O)heterocycle, —SO$_2$$(C_2\text{-}C_6)$alkenyl, —SO$_2$$(C_2\text{-}C_6)$alkynyl, —SO$_2$$(C_1\text{-}C_6)$haloalkyl, —SO$_2$$(C_3\text{-}C_7)$carbocycle, —SO$_2$$(C_3\text{-}C_7)$halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O$(C_3\text{-}C_7)$carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any $(C_1\text{-}C_6)$alkyl, $(C_2\text{-}C_6)$alkenyl, $(C_2\text{-}C_6)$alkynyl, —$(C_3\text{-}C_7)$halocarbocycle, $(C_3\text{-}C_7)$carbocycle, $(C_3\text{-}C_7)$halocarbocycle, aryl, heteroaryl or heterocycle of $Z^1$, either alone or as part of a group, is optionally substituted with one or more halogen, —OH, —OR$_b$, —CN, —NR$_a$C(O)$_2$R$_b$, heteroaryl, heterocycle, —Oheteroaryl, —Oheterocycle, —NHheteroaryl, —NHheterocycle or —S(O)$_2$NR$_c$R$_d$;

each $Z^5$ is independently selected from —NO$_2$, —CN, —NR$_a$SO$_2$NR$_c$R$_d$, —NR$_a$SO$_2$O$(C_3\text{-}C_7)$carbocycle, —NR$_a$SO$_2$Oaryl, —NR$_a$SO$_2$$(C_1\text{-}C_6)$alkyl, —NR$_a$SO$_2$$(C_2\text{-}C_6)$alkenyl, —NR$_a$SO$_2$$(C_2\text{-}C_6)$alkynyl, —NR$_a$SO$_2$$(C_3\text{-}C_7)$carbocycle, —NR$_a$SO$_2$$(C_3\text{-}C_7)$halocarbocycle, —NR$_a$SO$_2$aryl, —NR$_a$SO$_2$heteraryl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)$(C_3\text{-}C_7)$carbocycle, —NR$_a$C(O)$(C_3\text{-}C_7)$halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each $Z^{10}$ is independently selected from
i) halo, oxo, thioxo, $(C_2\text{-}C_6)$alkenyl, $(C_1\text{-}C_6)$haloalkyl, $(C_3\text{-}C_7)$cycloalkyl, $(C_3\text{-}C_7)$cycloalkyl-$(C_1\text{-}C_6)$alkyl-, —OH, —O$(C_1\text{-}C_6)$alkyl, —O$(C_1\text{-}C_6)$haloalkyl, —SH, —S$(C_1\text{-}C_6)$alkyl, —SO$(C_1\text{-}C_6)$alkyl, —SO$_2$$(C_1\text{-}C_6)$alkyl, —NH$_2$, —NH$(C_1\text{-}C_6)$alkyl and —N($(C_1\text{-}C_6)$alkyl)$_2$;
ii) $(C_1\text{-}C_6)$alkyl optionally substituted with one or more —OH, —O—$(C_1\text{-}C_6)$haloalkyl, or —O—$(C_1\text{-}C_6)$alkyl; and
iii) aryl, heterocycle and heteroaryl, which aryl, heterocycle and heteroaryl is optionally substituted with one or more halo, $(C_1\text{-}C_6)$alkyl or COOH;

each $Z^{11}$ is independently selected from $Z^{10}$, —C(=O)—NH$_2$, —C(=O)—NH$(C_1\text{-}C_4)$alkyl, —C(=O)—N($(C_1\text{-}C_4)$alkyl)$_2$, —C(=O)-aryl, —C(=O)-heterocycle and —C(=O)-heteroaryl;

each $Z^{15}$ is independently selected from aryl, heteroaryl, heterocycle, —Oaryl, —Oheteroaryl, —Oheterocycle, —O$(C_1\text{-}C_6)$alkyl-aryl, —O$(C_1\text{-}C_6)$alkyl-heteroaryl, —O$(C_1\text{-}C_6)$alkyl-heterocycle, wherein aryl, heteroaryl and heterocycle are each independently substituted with one or more $Z^{16}$ groups and optionally substituted with one or more $Z^1$ groups, and wherein any —Oaryl, —Oheteroaryl, —Oheterocycle, —O$(C_1\text{-}C_6)$alkyl-aryl, —O$(C_{1\text{-}r}$ $C_6)$alkyl-heteroaryl or —O$(C_1\text{-}C_6)$alkyl-heterocycle is optionally substituted with one or more $Z^1$ groups;

each $Z^{16}$ is independently selected from —NO$_2$, —OH, =NOR$_a$, —SH, —CN, $(C_2\text{-}C_6)$alkenyl, $(C_2\text{-}C_6)$alkynyl, $(C_1\text{-}C_6)$haloalkyl, $(C_3\text{-}C_7)$carbocycle, $(C_3\text{-}C_7)$halocarbocycle, aryl, heteroaryl, heterocycle, aryl$(C_1\text{-}C_6)$alkyl-, —O$(C_1\text{-}C_6)$alkyl, —O$(C_2\text{-}C_6)$alkenyl, —O$(C_2\text{-}C_6)$alkynyl, —O$(C_1\text{-}C_6)$haloalkyl, —O$(C_3\text{-}C_7)$carbocycle, —O$(C_3\text{-}C_7)$halocarbocycle, —Oaryl, —Oheteroaryl, —Oheterocycle, —S$(C_1\text{-}C_6)$alkyl, —S$(C_2\text{-}C_6)$alkenyl, —S$(C_2\text{-}C_6)$alkynyl, —S$(C_1\text{-}C_6)$haloalkyl, —S$(C_3\text{-}C_7)$carbocycle, —S$(C_3\text{-}C_7)$halocarbocycle, —Saryl, —Sheteroaryl, —Sheterocycle, —S(O)$(C_1\text{-}C_6)$alkyl, —S(O)$(C_2\text{-}C_6)$alkenyl, —S(O)$(C_2\text{-}C_6)$alkynyl, —S(O)$(C_1\text{-}C_6)$haloalkyl, —S(O)$(C_3\text{-}C_7)$carbocycle, —S(O)$(C_3\text{-}C_7)$halocarbocycle, —SO$_2$$(C_1\text{-}C_6)$alkyl, —S(O)aryl, —S(O)carbocycle, —S(O)heterocycle, —S(O)heterocycle, —SO$_2$$(C_2\text{-}C_6)$alkenyl, —SO$_2$$(C_2\text{-}C_6)$alkynyl, —SO$_2$$(C_1\text{-}C_6)$haloalkyl, —SO$_2$$(C_3\text{-}C_7)$carbocycle, —SO$_2$$(C_3\text{-}C_7)$halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O$(C_3\text{-}C_7)$carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any $(C_1\text{-}C_6)$alkyl, $(C_2\text{-}C_6)$alkenyl, $(C_2\text{-}C_6)$alkynyl, $(C_3\text{-}C_7)$carbocycle, $(C_3\text{-}C_7)$halocarbocycle, aryl, heteroaryl or heterocycle of $Z^{16}$, either alone or as part of a group, is optionally substituted with one or more halogen, $(C_1\text{-}C_6)$alkyl, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each $R_a$ is independently H, $(C_1-C_6)$alkyl, $(C_2-C_6)$alkenyl, $(C_2-C_6)$alkynyl, $(C_3-C_7)$carbocycle, heterocycle, aryl, aryl$(C_1-C_6)$alkyl-, heteroaryl or heteroaryl$(C_1-C_6)$alkyl-, wherein any $(C_1-C_6)$alkyl, $(C_2-C_6)$alkenyl, $(C_2-C_6)$alkynyl, $(C_3-C_7)$carbocycle, heterocycle, aryl, or heteroaryl of $R_a$, either alone or as part of a group, is optionally substituted with one or more halogen, OH or cyano;

each $R_b$ is independently $(C_1-C_6)$alkyl, $(C_2-C_6)$alkenyl, $(C_2-C_6)$alkynyl, $(C_3-C_7)$carbocycle, heterocycle, aryl, aryl$(C_1-C_6)$alkyl-, heteroaryl or heteroaryl$(C_1-C_6)$alkyl-, wherein any $(C_1-C_6)$alkyl, $(C_2-C_6)$alkenyl, $(C_2-C_6)$alkynyl, $(C_3-C_7)$carbocycle, heterocycle, aryl, or heteroaryl of $R_b$, either alone or as part of a group, is optionally substituted with one or more halogen, OH and cyano; and $R_c$ and $R_d$ are each independently selected from H, $(C_1-C_6)$ alkyl, $(C_2-C_6)$alkenyl, $(C_2-C_6)$alkynyl, $(C_3-C_7)$carbocycle, aryl, aryl$(C_1-C_6)$alkyl-, heterocycle, heteroaryl or heteroaryl $(C_1-C_6)$alkyl-, wherein any $(C_1-C_6)$alkyl, $(C_2-C_6)$alkenyl, $(C_2-C_6)$alkynyl, $(C_3-C_7)$carbocycle, heterocycle, aryl, or heteroaryl of $R_c$ or $R_d$, either alone or as part of a group, is optionally substituted with one or more halogen, OH or cyano; or $R_c$ and $R_d$ together with the nitrogen to which they are attached form a heterocycle, wherein any such heterocycle is optionally substituted with one or more halogen, OH or cyano;

or a salt thereof;

provided $R^5$ is not azetidinyl or 1-methyl-imidazo-2-yl.

In one embodiment, the invention provides a compound of formula Ia:

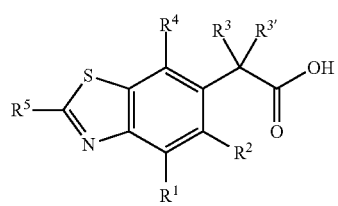

Ia wherein:
$R^1$ is H;
$R^2$ is $(C_1-C_6)$alkyl;
$R^3$ is —O$(C_1-C_6)$alkyl;
$R^{3'}$ is H;
$R^4$ is selected from aryl, heterocycle and heteroaryl, wherein any aryl, heterocycle and heteroaryl of $R^4$ is optionally substituted with one or more groups each independently selected from halo, $(C_1-C_6)$alkyl, $(C_2-C_6)$alkenyl, $(C_1-C_6)$ haloalkyl, $(C_3-C_7)$cycloalkyl, —$(C_1-C_6)$alkyl-$(C_3-C_7)$cycloalkyl, —OH, —O$(C_1-C_6)$alkyl, —SH, —S$(C_1-C_6)$alkyl, NH$_2$, —NH$(C_1-C_6)$alkyl and —N$((C_1-C_6)$alkyl$)_2$, wherein $(C_1-C_6)$alkyl is optionally substituted with hydroxy, —O$(C_1-C_6)$alkyl, cyano or oxo;

$R^5$ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl and heterocycle are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl, heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

each $Z^1$ is independently selected from halo, —NO$_2$, —OH, =NOR$_a$, —SH, —CN, $(C_1-C_6)$alkyl, $(C_2-C_6)$alkenyl, $(C_2-C_6)$alkynyl, $(C_1-C_6)$haloalkyl, $(C_3-C_7)$carbocycle, $(C_3-C_7)$halocarbocycle, aryl, heteroaryl, heterocycle, —O$(C_1-C_6)$alkyl, —O$(C_2-C_6)$alkenyl, —O$(C_2-C_6)$alkynyl, —O$(C_1-C_6)$haloalkyl, —O$(C_3-C_7)$carbocycle, —O$(C_3-C_7)$halocarbocycle, —Oaryl, —Oheteroaryl, —Oheterocycle, —S$(C_1-C_6)$alkyl, —S$(C_2-C_6)$alkenyl, —S$(C_2-C_6)$alkynyl, —S$(C_1-C_6)$haloalkyl, —S$(C_3-C_7)$carbocycle, —S$(C_3-C_7)$halocarbocycle, —Saryl, —Sheteroaryl, —Sheterocycle, —S(O)$(C_1-C_6)$alkyl, —S(O)$(C_2-C_6)$alkenyl, —S(O)$(C_2-C_6)$alkynyl, —S(O)$(C_1-C_6)$haloalkyl, —S(O)$(C_3-C_7)$carbocycle, —S(O)$(C_3-C_7)$halocarbocycle, —SO$_2(C_1-C_6)$alkyl, —S(O)aryl, —S(O)carbocycle, —S(O)heteroaryl, —S(O) heterocycle, —SO$_2(C_2-C_6)$alkenyl, —SO$_2(C_2-C_6)$alkynyl, —SO$_2(C_1-C_6)$haloalkyl, —SO$_2(C_3-C_7)$carbocycle, —SO$_2$ $(C_3-C_7)$halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O$(C_3-C_7)$carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any $(C_1-C_6)$ alkyl, $(C_2-C_6)$alkenyl, $(C_2-C_6)$alkynyl, —$(C_3-C_7)$halocarbocycle, $(C_3-C_7)$carbocycle, $(C_3-C_7)$halocarbocycle, aryl, heteroaryl or heterocycle of $Z^1$, either alone or as part of a group, is optionally substituted with one or more halogen, —OH, —OR$_b$, —CN, —NR$_a$C(O)$_2$R$_b$, heteroaryl, heterocycle, —Oheteroaryl, —Oheterocycle, —NHheteroaryl, —NHheterocycle or —S(O)$_2$NR$_c$R$_d$;

each $Z^5$ is independently selected from —NO$_2$, —CN, —NR$_a$SO$_2$NR$_c$R$_d$, —NR$_a$SO$_2$O$(C_3-C_7)$carbocycle, —NR$_a$SO$_2$Oaryl, —NR$_a$SO$_2(C_1-C_6)$alkyl, —NR$_a$SO$_2(C_2-C_6)$alkenyl, —NR$_a$SO$_2(C_2-C_6)$alkynyl, —NR$_a$SO$_2(C_3-C_7)$ carbocycle, —NR$_a$SO$_2(C_3-C_7)$halocarbocycle, —NR$_a$SO$_2$aryl, —NR$_a$SO$_2$hetaryl, —NR$_a$SO$_2$heterocycle, —NR$_a$SO$_2$heterocycle, —NR$_a$C(O)alkyl, —NR$_a$C(O)alkenyl, —NR$_a$C(O)alkynyl, —NR$_a$C(O)$(C_3-C_7)$carbocycle, —NR$_a$C(O)$(C_3-C_7)$halocarbocycle, —NR$_a$C(O)aryl, —NR$_a$C(O)heteroaryl, —NR$_a$C(O)heterocycle, —NR$_a$C(O) NR$_c$R$_d$ and —NR$_a$C(O)OR$_b$;

each $Z^{10}$ is independently selected from
i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, —OH, —O$(C_1-C_6)$alkyl, —O$(C_1-C_6)$haloalkyl, —SH, —S$(C_1-C_6)$alkyl, —SO$(C_1-C_6)$alkyl, —SO$_2(C_1-C_6)$ alkyl, —NH$_2$, —NH$(C_1-C_6)$alkyl and —N$((C_1-C_6)$ alkyl$)_2$;
ii) $(C_1-C_6)$alkyl optionally substituted with one or more —OH, —O—$(C_1-C_6)$haloalkyl, or —O—$(C_1-C_6)$alkyl; and
iii) aryl, heterocycle and heteroaryl, which aryl, heterocycle and heteroaryl is optionally substituted with one or more halo, $(C_1-C_6)$alkyl or COOH;

each $Z^{11}$ is independently selected from $Z^{10}$, —C(=O)—NH$_2$, —C(=O)—NH$(C_1-C_4)$alkyl, —C(=O)—N$((C_1-C_4)$ alkyl$)_2$, —C(=O)-aryl, —C(=O)-heterocycle and —C(=O)-heteroaryl;

each $Z^{15}$ is independently selected from aryl, heteroaryl, heterocycle, —Oaryl, —Oheteroaryl, —Oheterocycle, —O$(C_1-C_6)$alkyl-aryl, —O$(C_1-C_6)$alkyl-heteroaryl, —O$(C_1-C_6)$alkyl-heterocycle, wherein aryl, heteroaryl and heterocycle are each independently substituted with one or more $Z^{16}$ groups and optionally substituted with one or more $Z^1$ groups, and wherein any —Oaryl, —Oheteroaryl, —Oheterocycle, —O$(C_1-C_6)$alkyl-aryl, —O$(C_1-C_6)$alkyl-heteroaryl or —O(C$_1$-C$_6$)alkyl-heterocycle is optionally substituted with one or more Z$^1$ groups;

each Z$^{16}$ is independently selected from —NO$_2$, —OH, =NOR$_a$, —SH, —CN, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, aryl(C$_1$-C$_6$)alkyl-, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)aryl, —S(O)carbocycle, —S(O)heteroaryl, —S(O)heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^{16}$, either alone or as part of a group, is optionally substituted with one or more halogen, (C$_1$-C$_6$)alkyl, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each R$_a$ is independently H, (C$_1$-C$_6$)alkyl, (C$_2$-C$_6$)alkenyl, (C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_a$, either alone or as part of a group, is optionally substituted with one or more halogen, OH or cyano;

each R$_b$ is independently (C$_1$-C$_6$)alkyl, (C$_2$-C$_6$)alkenyl, (C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_b$, either alone or as part of a group, is optionally substituted with one or more halogen, OH and cyano; and R$_c$ and R$_d$ are each independently selected from H, (C$_1$-C$_6$)alkyl, (C$_2$-C$_6$)alkenyl, (C$_2$-C$_6$)alkynyl, (C$_3$-C$_7$)carbocycle, aryl, aryl(C$_1$-C$_6$)alkyl-, heterocycle, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_c$ or R$_d$, either alone or as part of a group, is optionally substituted with one or more halogen, OH or cyano; or R$_c$ and R$_d$ together with the nitrogen to which they are attached form a heterocycle, wherein any heterocycle of R$_c$ and R$_d$ together with the nitrogen to which they are attached is optionally substituted with one or more halogen, OH or cyano;

or a salt thereof;

provided R$^5$ is not azetidinyl or 1-methyl-imidazo-2-yl.

In one embodiment, the invention provides a compound of formula Ia:

wherein:
R$^1$ is H;
R$^2$ is (C$_1$-C$_6$)alkyl;
R$^3$ is —O(C$_1$-C$_6$)alkyl;
R$^{3'}$ is H;

R$^4$ is selected from aryl, heterocycle and heteroaryl, wherein any aryl, heterocycle and heteroaryl of R$^4$ is optionally substituted with one or more groups each independently selected from halo, (C$_1$-C$_6$)alkyl, (C$_2$-C$_6$)alkenyl, (C$_1$-C$_6$)haloalkyl, (C$_3$-C$_7$)cycloalkyl, —(C$_1$-C$_6$)alkyl-(C$_3$-C$_7$)cycloalkyl, —OH, —O(C$_1$-C$_6$)alkyl, —SH, —S(C$_1$-C$_6$)alkyl, NH$_2$, —NH(C$_1$-C$_6$)alkyl and —N((C$_1$-C$_6$)alkyl)$_2$, wherein (C$_1$-C$_6$)alkyl is optionally substituted with hydroxy, —O(C$_1$-C$_6$)alkyl, cyano or oxo;

R$^5$ is selected from:

a) aryl, heterocycle and heteroaryl, wherein aryl, heterocycle and heteroaryl are each optionally substituted with one or more (e.g. 1, 2 or 3) Z$^{11}$ groups;

b) aryl, heteroaryl and heterocycle, wherein aryl, heteroaryl and heterocycle are each independently substituted with one or more (e.g. 1, 2, 3, 4 or 5) Z$^5$ groups and optionally substituted with one or more (e.g. 1, 2, 3, 4 or 5) Z$^1$ groups; and c) aryl, heteroaryl, heterocycle, wherein aryl, heteroaryl and heterocycle, are each independently substituted with one or more (e.g. 1, 2, 3, 4 or 5) Z$^{15}$ groups and optionally substituted with one or more (e.g. 1, 2, 3, 4 or 5) Z$^1$ groups;

each Z$^1$ is independently selected from halo, —NO$_2$, —OH, =NOR$_a$, —SH, —CN, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)aryl, —S(O)carbocycle, —S(O)heteroaryl, —S(O)heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^1$, either alone or as part of a group, is optionally substituted with one or more halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each Z$^5$ is independently selected from —NO$_2$, —CN, —NR$_a$SO$_2$NR$_c$R$_d$, —NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$aryl, —NR$_a$SO$_2$hetearyl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each Z$^{10}$ is independently selected from i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S($C_1$-$C_6$)alkyl, —SO($C_1$-$C_6$)alkyl, —$SO_2$($C_1$-$C_6$)alkyl, —$NH_2$, —NH($C_1$-$C_6$)alkyl and —N(($C_1$-$C_6$)alkyl)$_2$;

ii) ($C_1$-$C_6$)alkyl optionally substituted with one or more —OH, —O—($C_1$-$C_6$)haloalkyl, or —O—($C_1$-$C_6$)alkyl; and iii) aryl, heterocycle and heteroaryl, which aryl, heterocycle and heteroaryl is optionally substituted with halo, ($C_1$-$C_6$)alkyl or COOH;

each $Z^{11}$ is independently selected from $Z^{10}$, —C(=O)—$NH_2$, —C(=O)—NH($C_1$-$C_4$)alkyl, —C(=O)—N(($C_1$-$C_4$)alkyl)$_2$, —C(=O)-aryl, —C(=O)-heterocycle and —C(=O)-heteroaryl;

each $Z^{15}$ is independently selected from aryl, heteroaryl, heterocycle, —Oaryl, —Oheteroaryl, —Oheterocycle, —O($C_1$-$C_6$)alkyl-aryl, —O($C_1$-$C_6$)alkyl-heteroaryl, —O($C_1$-$C_6$)alkyl-heterocycle, wherein aryl, heteroaryl and heterocycle are each independently substituted with one or more $Z^{16}$ groups and optionally substituted with one or more $Z^1$ groups, and wherein any —Oaryl, —Oheteroaryl, —Oheterocycle, —O($C_1$-$C_6$)alkyl-aryl, —O($C_1$-$C_6$)alkyl-heteroaryl or —O($C_1$-$C_6$)alkyl-heterocycle is optionally substituted with one or more $Z^1$ groups;

each $Z^{16}$ is independently selected from —$NO_2$, —OH, =$NOR_a$, —SH, —CN, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2$($C_1$-$C_6$)alkyl, —S(O)aryl, —S(O)carbocycle, —S(O)heteroaryl, —S(O)heterocycle, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O(C_3$-$C_7)$carbocycle, —$NR_aSO_2$Oaryl, —OS(O)$_2R_a$, —C(O)$R_a$, —C(O)$OR_b$, —C(O)$NR_cR_d$, and —OC(O)$NR_cR_d$, wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^{16}$, either alone or as part of a group, is optionally substituted with one or more halogen, ($C_1$-$C_6$)alkyl, —OH, —$OR_b$, —CN, —$NR_aC(O)_2R_b$, -heteroaryl, -heterocycle, —Oheteroaryl, —Oheterocycle, —NHheteroaryl, —NHheterocycle or —S(O)$_2NR_cR_d$;

each $R_a$ is independently H, ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_a$, either alone or as part of a group, is optionally substituted with one or more halogen, OH or cyano;

each $R_b$ is independently ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_b$, either alone or as part of a group, is optionally substituted with one or more halogen, OH and cyano; and $R_c$ and $R_d$ are each independently selected from H, ($C_1$-$C_6$)alkyl, ($C_2$-$C_6$)alkenyl, ($C_2$-$C_6$)alkynyl, ($C_3$-$C_7$)carbocycle, aryl, aryl($C_1$-$C_6$)alkyl-, heterocycle, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_c$ or $R_d$, either alone or as part of a group, is optionally substituted with one or more halogen, OH or cyano; or $R_c$ and $R_d$ together with the nitrogen to which they are attached form a heterocycle, wherein any heterocycle of $R_c$ and $R_d$ together with the nitrogen to which they are attached is optionally substituted with one or more halogen, OH or cyano;

or a salt thereof.

In one embodiment, the invention provides a compound of formula I':

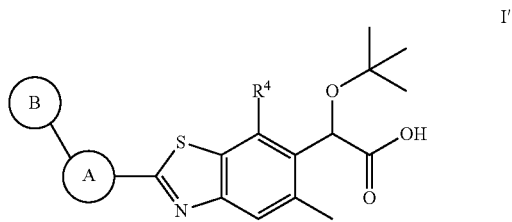

wherein:

$R^4$ is selected from aryl, heterocycle and heteroaryl, wherein any aryl, heterocycle and heteroaryl of $R^4$ is optionally substituted with one or more groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —($C_1$-$C_6$)alkyl-($C_3$-$C_7$)cycloalkyl, —OH, —O($C_1$-$C_6$)alkyl, —SH, —S($C_1$-$C_6$)alkyl, $NH_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo;

A is phenyl, monocyclic heteroaryl or monocyclic heterocycle, wherein any phenyl, monocyclic heteroaryl or monocyclic heterocycle of A is optionally substituted with one or more $Z^{1a}$ groups, and B is aryl, heteroaryl or heterocycle wherein any aryl, heteroaryl or heterocycle of B is optionally substituted with one or more $Z^{1b}$ groups; or A and B together form a bicyclic aryl, bicyclic heteroaryl or bicyclic heterocycle wherein bicyclic aryl, bicyclic heteroaryl or bicyclic heterocycle is optionally substituted with one or more $Z^{1b}$ groups;

each $Z^{1a}$ is independently selected from halo, ($C_1$-$C_3$)alkyl, ($C_2$-$C_3$)alkenyl, ($C_2$-$C_3$)alkynyl, ($C_1$-$C_3$)haloalkyl, ($C_3$-$C_7$)carbocycle, heterocycle, —O($C_1$-$C_3$)alkyl, —O($C_2$-$C_3$)alkenyl, —O($C_2$-$C_3$)alkynyl, —$NR_cR_d$, —$NR_aC(O)R_a$, —C(O)$OR_b$, and —C(O)$NR_cR_d$, wherein any ($C_3$-$C_7$)carbocycle or heterocycle of $Z^{1a}$, either alone or as part of a group, is optionally substituted with one or more halogen or ($C_1$-$C_6$)alkyl;

each $Z^{1b}$ is independently selected from halo, CN, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)carbocycle, heteroaryl, heterocycle, aryl($C_1$-$C_6$)alkyl-, —OH, —O($C_1$-$C_6$)alkyl, —O($C_2$-$C_6$)alkenyl, —O($C_2$-$C_6$)alkynyl, —$NR_cR_d$, —$NR_aC(O)R_a$, —C(O)$OR_b$, and —C(O)$NR_cR_d$, wherein any ($C_3$-$C_7$)carbocycle or heterocycle of $Z^{1b}$, either alone or as part of a group, is optionally substituted with one or more halogen or ($C_1$-$C_6$)alkyl; and $R_a$, $R_b$, $R_c$ and $R_d$ are each independently H or ($C_1$-$C_6$)alkyl;

or a salt thereof

A specific group of compounds of formula I' are compounds of formula Ia':

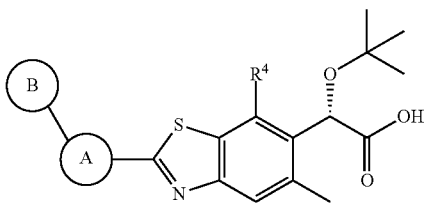

or a pharmaceutically acceptable salt thereof.

In one embodiment, the invention provides a compound of formula I':
wherein:
$R^4$ is selected from aryl, heterocycle and heteroaryl, wherein any aryl, heterocycle and heteroaryl of $R^4$ is optionally substituted with one or more (e.g., 1, 2, 3, 4 or 5) groups each independently selected from halo, $(C_1-C_6)$alkyl, $(C_1-C_6)$haloalkyl, $(C_3-C_7)$cycloalkyl, —$(C_1-C_6)$alkyl-$(C_3-C_7)$cycloalkyl, —OH, —O$(C_1-C_6)$alkyl, —SH, —S$(C_1-C_6)$alkyl, $NH_2$, —NH$(C_1-C_6)$alkyl and —N$((C_1-C_6)$alkyl$)_2$, wherein $(C_1-C_6)$alkyl is optionally substituted with hydroxy, —O$(C_1-C_6)$alkyl, cyano or oxo;

A is phenyl, monocyclic heteroaryl or monocyclic heterocycle, wherein any phenyl, monocyclic heteroaryl or monocyclic heterocycle of A is optionally substituted with one or more (e.g., 1, 2, 3, 4 or 5) $Z^{1a}$ groups, and B is aryl, heteroaryl or heterocycle, wherein any aryl, heteroaryl or heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle, wherein bicyclic aryl, bicyclic heteroaryl or bicyclic heterocycle is optionally substituted with one or more (e.g., 1, 2, 3, 4 or 5) $Z^{1b}$ groups;

each $Z^{1a}$ is independently selected from halo, $(C_1-C_3)$alkyl, $(C_1-C_3)$haloalkyl, $(C_3-C_7)$carbocycle, heterocycle, —O$(C_1-C_3)$alkyl, —$NR_cR_d$, —$NR_aC(O)R_a$, —$C(O)OR_b$ and —$C(O)NR_cR_d$, wherein any $(C_3-C_7)$carbocycle and heterocycle of $Z^{1a}$ is optionally substituted with one or more (e.g., 1, 2, 3, 4 or 5) halogen or $(C_1-C_6)$alkyl;

each $Z^{1b}$ is independently selected from halo, CN, $(C_1-C_6)$alkyl, $(C_1-C_6)$haloalkyl, $(C_3-C_7)$carbocycle, heterocycle, aryl, aryl$(C_1-C_6)$alkyl-, —OH, —O$(C_1-C_6)$alkyl, —$NR_cR_d$, —$NR_aC(O)R_a$, —$C(O)OR_b$ and —$C(O)NR_cR_d$, wherein any $(C_3-C_7)$carbocycle and heterocycle of $Z^{1b}$ is optionally substituted with one or more (e.g., 1, 2, 3, 4 or 5) halogen or $(C_1-C_6)$alkyl; and $R_a$, $R_b$, $R_c$ and $R_d$ are each independently H or $(C_1-C_6)$alkyl;

or a salt thereof.

Specific embodiments of the invention (e.g., embodiments) and specific values listed below are embodiments and values for compounds of formula I' and subformulas of formula I' I' (e.g., formula Ia'). It is to be understood that two or more of the values listed herein below may be combined with one another.

A specific value for A is phenyl, monocyclic heteroaryl or monocyclic heterocycle wherein any phenyl, monocyclic heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is phenyl, monocyclic N-heteroaryl or monocyclic heterocycle wherein any phenyl, monocyclic N-heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic heteroaryl or monocyclic heterocycle, wherein any monocyclic heteroaryl or monocyclic heterocycle of A is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic N-heteroaryl or monocyclic heterocycle, wherein any monocyclic N-heteroaryl or monocyclic heterocycle of A is optionally substituted with one or more $Z^{1a}$ groups, and B is aryl, heteroaryl or heterocycle wherein any aryl, heteroaryl or heterocycle of B is optionally substituted with one or more $Z^{1b}$ groups.

Another specific value for A is monocyclic heteroaryl, wherein monocyclic heteroaryl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic N-heteroaryl, wherein monocyclic N-heteroaryl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is monocyclic heterocycle, wherein monocyclic heterocycle is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridinyl, pyrimidinyl, pyrazinyl, pyridinyl-2-one, tetrahydropyrimidinyl-2-one, imidazolidinyl-2-one, pyrrolidinyl-2-one or pyrrolidinyl, wherein pyridinyl, pyrimidinyl, pyrazinyl, pyridinyl-2-one, tetrahydropyrimidinyl-2-one, imidazolidinyl-2-one, pyrrolidinyl-2-one or pyrrolidinyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridinyl, pyrimidinyl or pyrazinyl wherein pyridinyl, pyrimidinyl or pyrazinyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridinyl, wherein pyridinyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridin-4-yl, wherein pyridin-4-yl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

Another specific value for A is pyridinyl-2-one, tetrahydropyrimidinyl-2-one, imidazolidinyl-2-one, pyrrolidinyl-2-one or pyrrolidinyl, wherein pyridinyl-2-one, tetrahydropyrimidinyl-2-one, imidazolidinyl-2-one, pyrrolidinyl-2-one or pyrrolidinyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

A specific group of compounds of formula I' are compounds wherein A is not substituted with $Z^{1a}$.

A specific value for B is phenyl, pyridinyl, pyrazolyl, pyrimidinyl, indazolyl, pyrazolopyridine or benzimidazolyl, wherein any phenyl, pyridinyl, pyrazolyl, pyrimidinyl, indazolyl, pyrazolopyridine or benzimidazolyl of B is optionally substituted with one or more $Z^{1b}$ groups.

Another specific value for B is phenyl or indazolyl, wherein any phenyl or indazolyl of B is optionally substituted with one or more $Z^{1b}$ groups.

A specific group of compounds of formula I' are compounds wherein A and B together form a bicyclic aryl, bicyclic heteroaryl or bicyclic heterocycle, wherein bicyclic aryl, bicyclic heteroaryl or bicyclic heterocycle is optionally substituted with one or more $Z^{1b}$ groups.

Another specific group of compounds of formula I' are compounds wherein A and B together form a bicyclic heteroaryl, wherein bicyclic heteroaryl is optionally substituted with one or more $Z^{1b}$ groups.

Another specific group of compounds of formula I' are compounds wherein A and B together form a pyrrolopyridinyl, pyrazolopyridine or indazolyl, wherein pyrrolopyridinyl or indazolyl is optionally substituted with one or more $Z^{1b}$ groups.

Another specific value for A is phenyl, wherein phenyl is optionally substituted with one or more $Z^{1a}$ groups, and B is aryl, heteroaryl or heterocycle, wherein any aryl, heteroaryl or heterocycle of B is optionally substituted with one or more $Z^{1b}$ groups.

A specific value for $Z^{1a}$ is halo.

Another specific value for $Z^{1a}$ is fluoro or chloro.

Another specific value for B is phenyl, pyridinyl, pyrazolyl, pyrimidinyl, indazolyl or pyrazolopyridine, wherein any phenyl, pyridinyl, pyrazolyl, pyrimidinyl, indazolyl or pyrazolopyridine of B is optionally substituted with one or more $Z^{1b}$ groups.

A specific group of compounds of formula I' are compounds wherein each $Z^{1b}$ is independently selected from methyl, isobutyl, isopropyl, cyclopropyl, cyclobutyl, cyclopentyl, N-methylpiperazinyl, morpholinyl, tetrazolyl, —OCH$_3$, t-butyl, —C(O)OH, —NH$_2$, —N(CH$_3$)$_2$, —OH, —C(O)NH$_2$, benzyl and CN.

Another specific group of compounds of formula I' are compounds wherein each $Z^{1b}$ is independently selected from methyl, cyclopropyl, cyclobutyl, N-methylpiperazinyl, morpholinyl, tetrazolyl, —OCH$_3$, —C(O)OH, —OH, —C(O)NH$_2$, NH$_2$ and CN.

Another specific group of compounds of formula I' are compounds wherein each $Z^{1b}$ is independently selected from methyl, cyclopropyl, cyclobutyl, N-methylpiperazinyl, morpholinyl, tetrazolyl, —OCH$_3$, —C(O)OH, —OH, —C(O)NH$_2$ and CN.

Another specific group of compounds of formula I' are compounds wherein each $Z^{1'''}$ is independently selected from methyl and NH$_2$.

Another specific group of compounds of formula I' are compounds wherein each $Z^{1b}$ is independently selected from methyl, isobutyl, isopropyl, cyclopentyl, N-methylpiperazinyl, —OCH$_3$, t-butyl, —N(CH$_3$)$_2$, —OH and benzyl.

A specific group of compounds of formula I' are compounds wherein A-B is selected from:

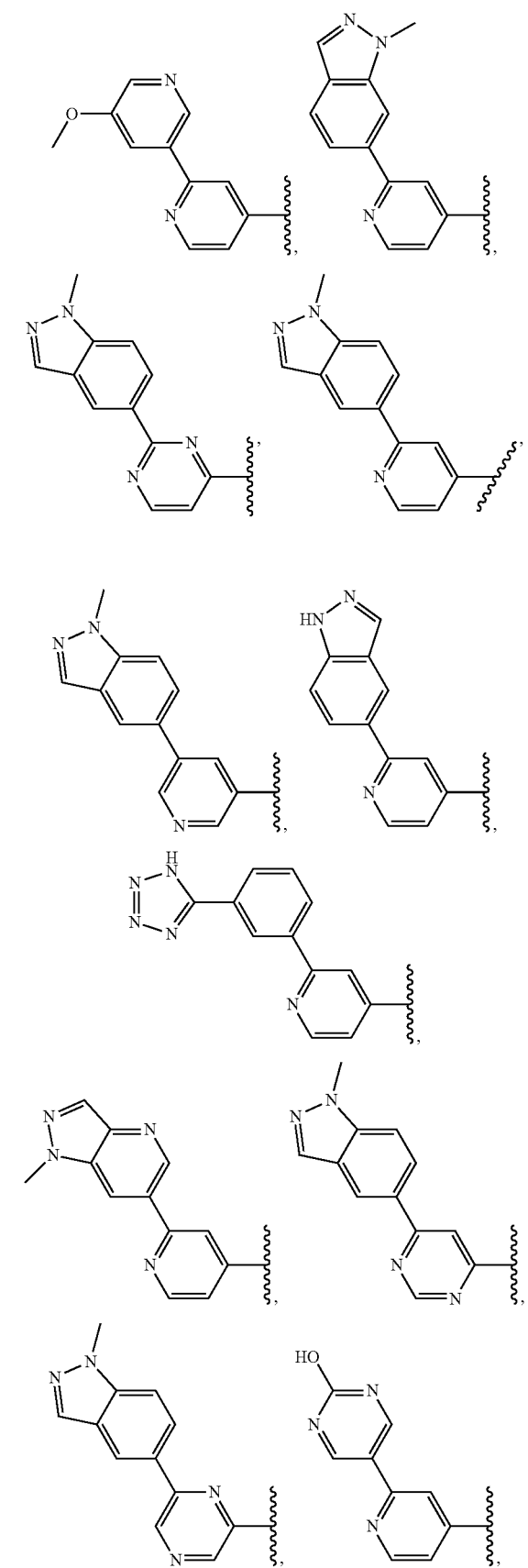

65
-continued
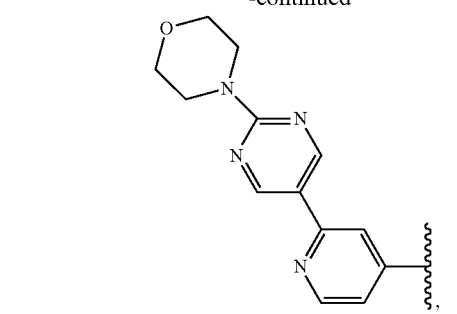
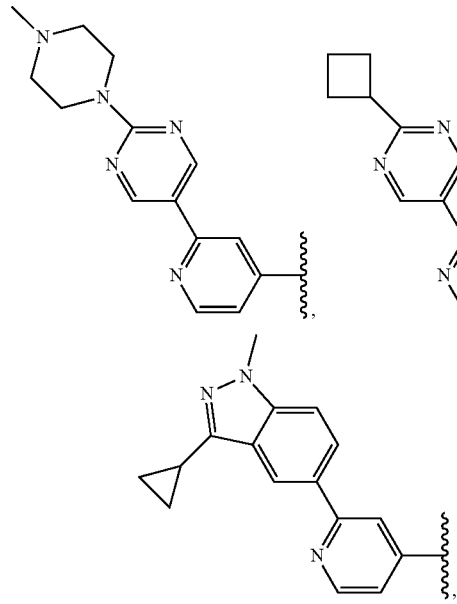
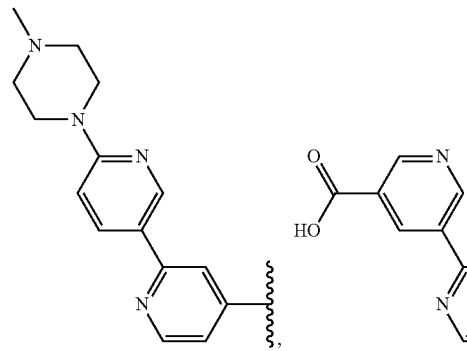
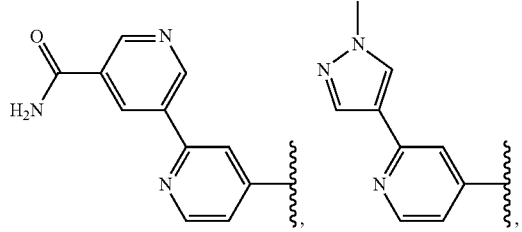
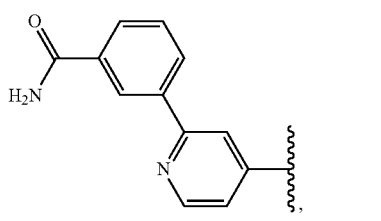
66
-continued
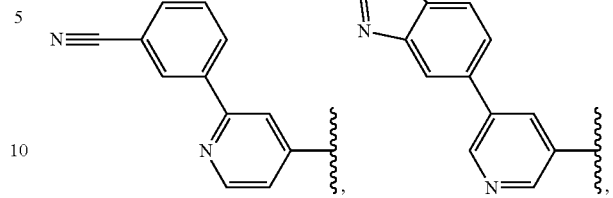
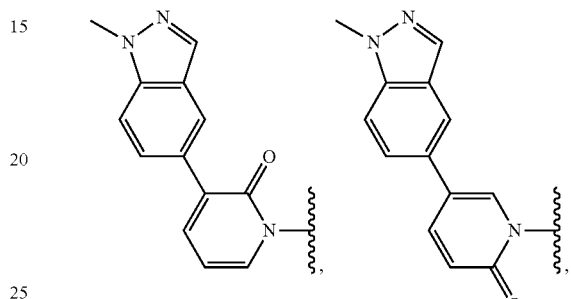
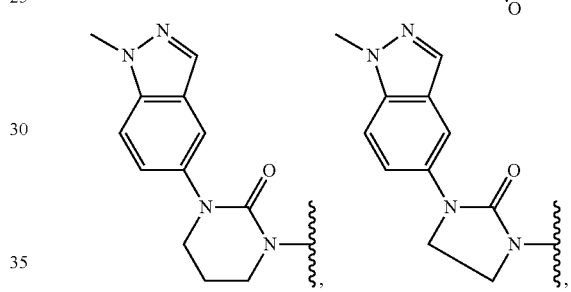
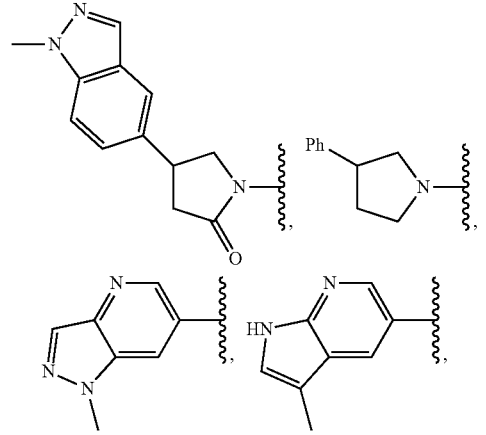
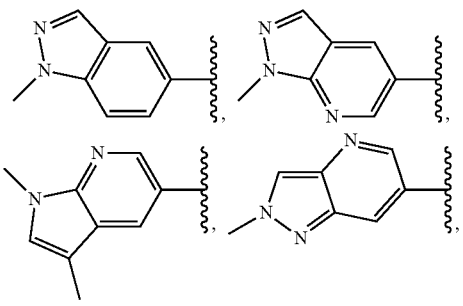

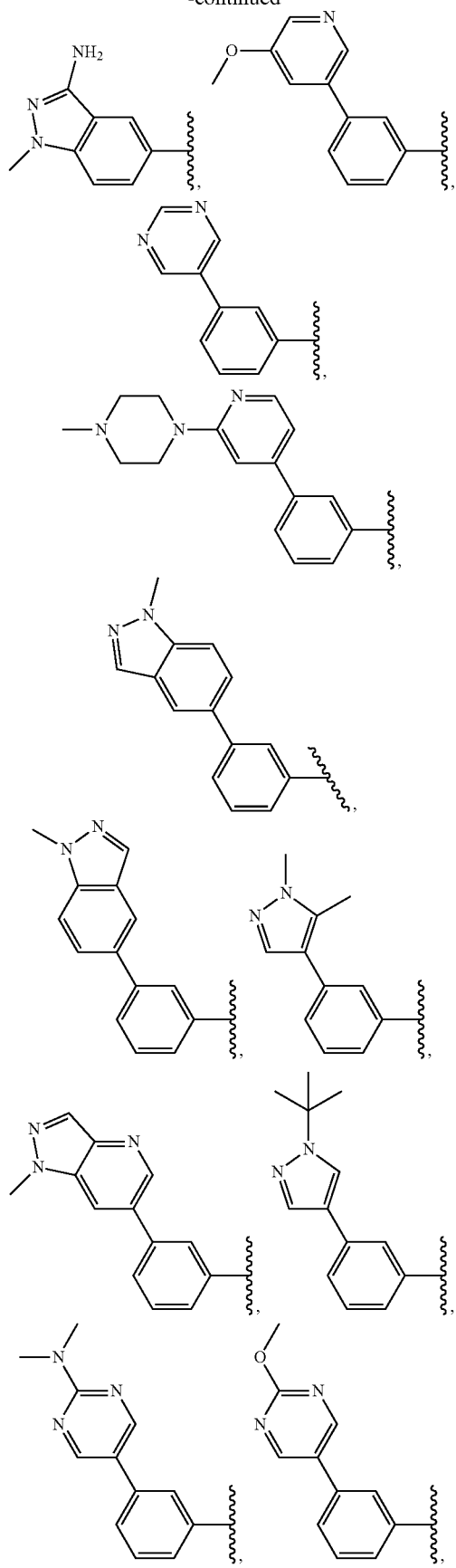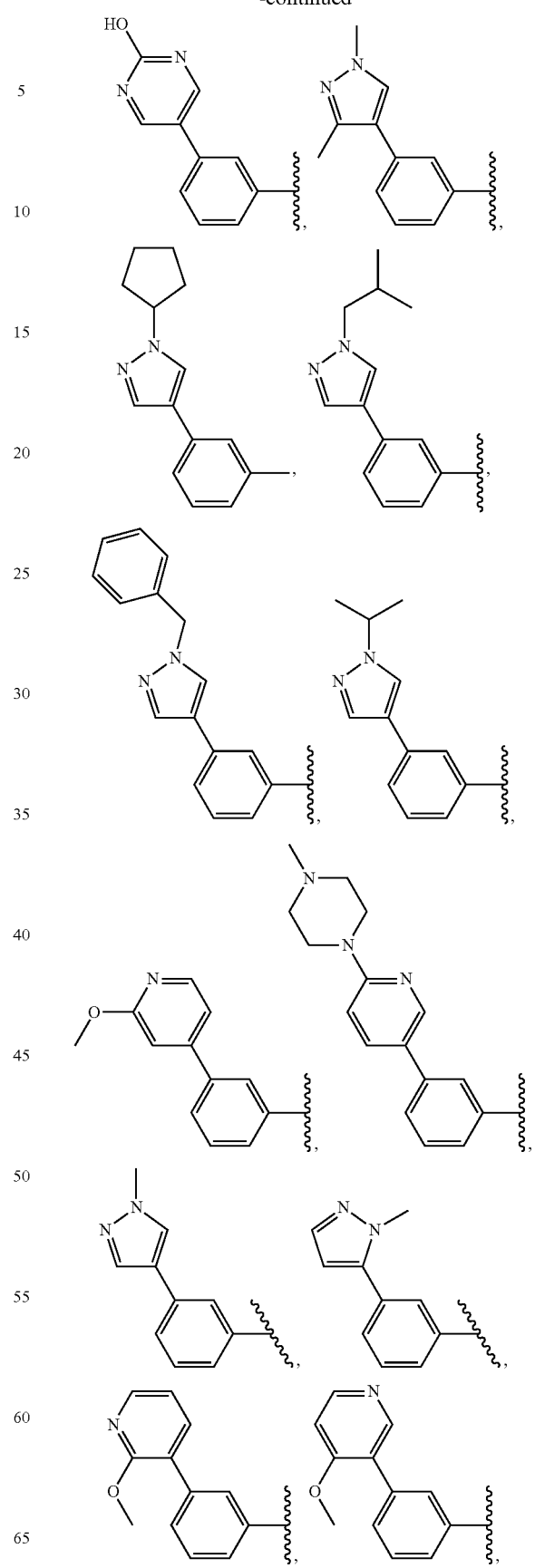

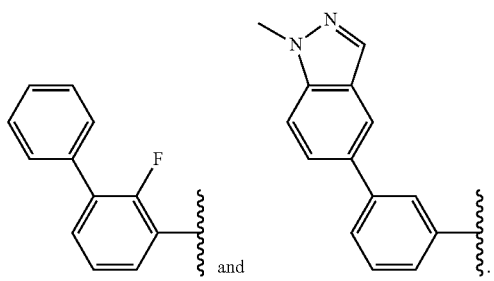
and
A specific group of compounds of formula I' are compounds wherein A-B is selected from:
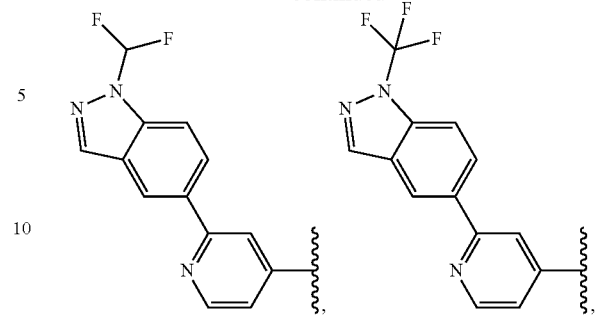
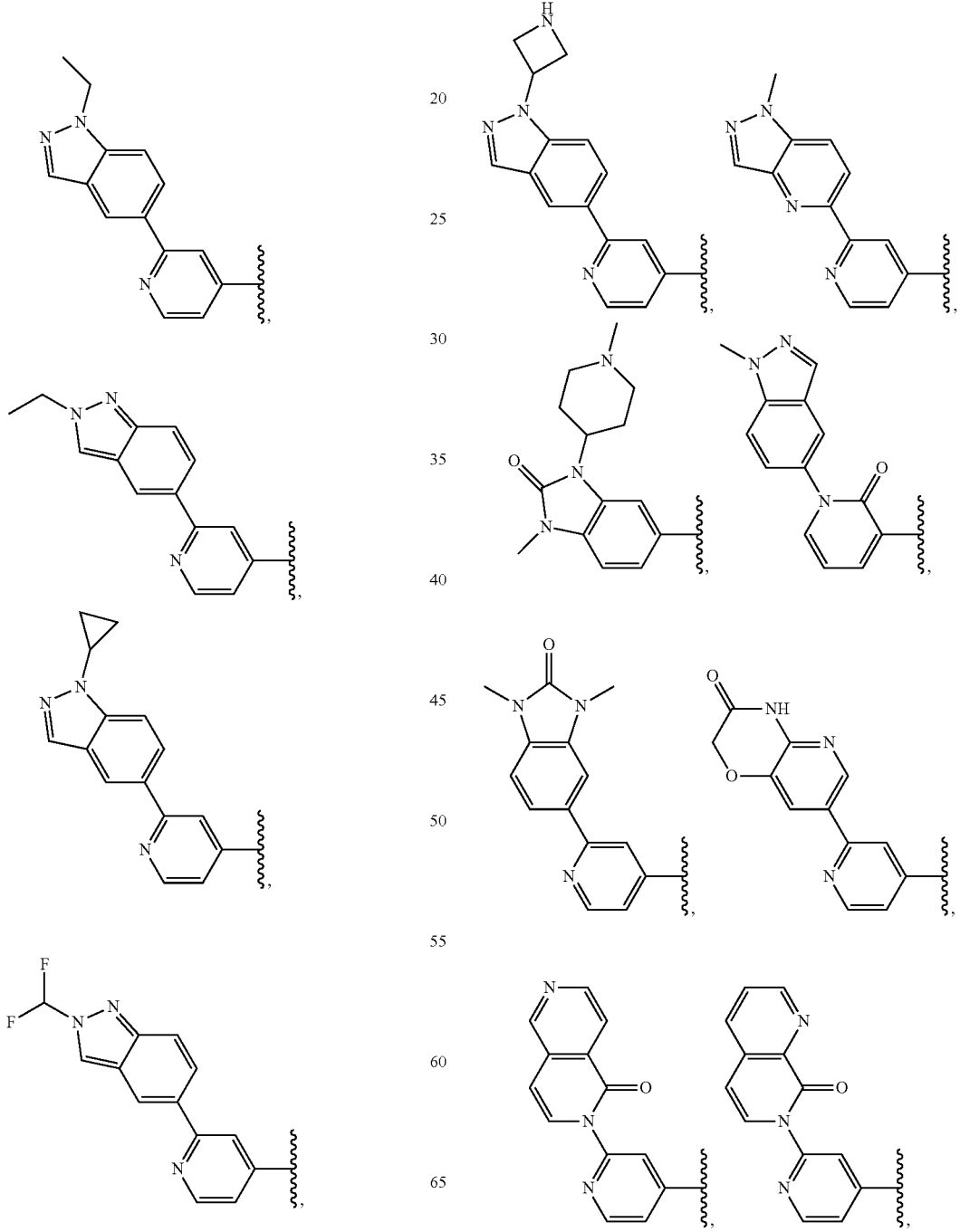

71
-continued
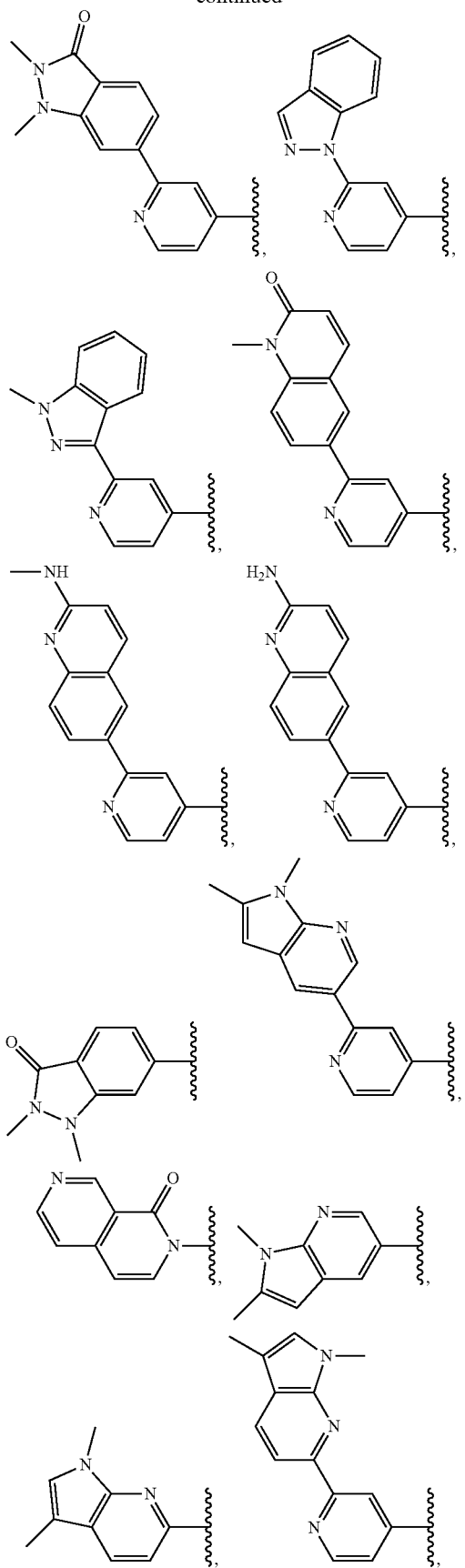
72
-continued
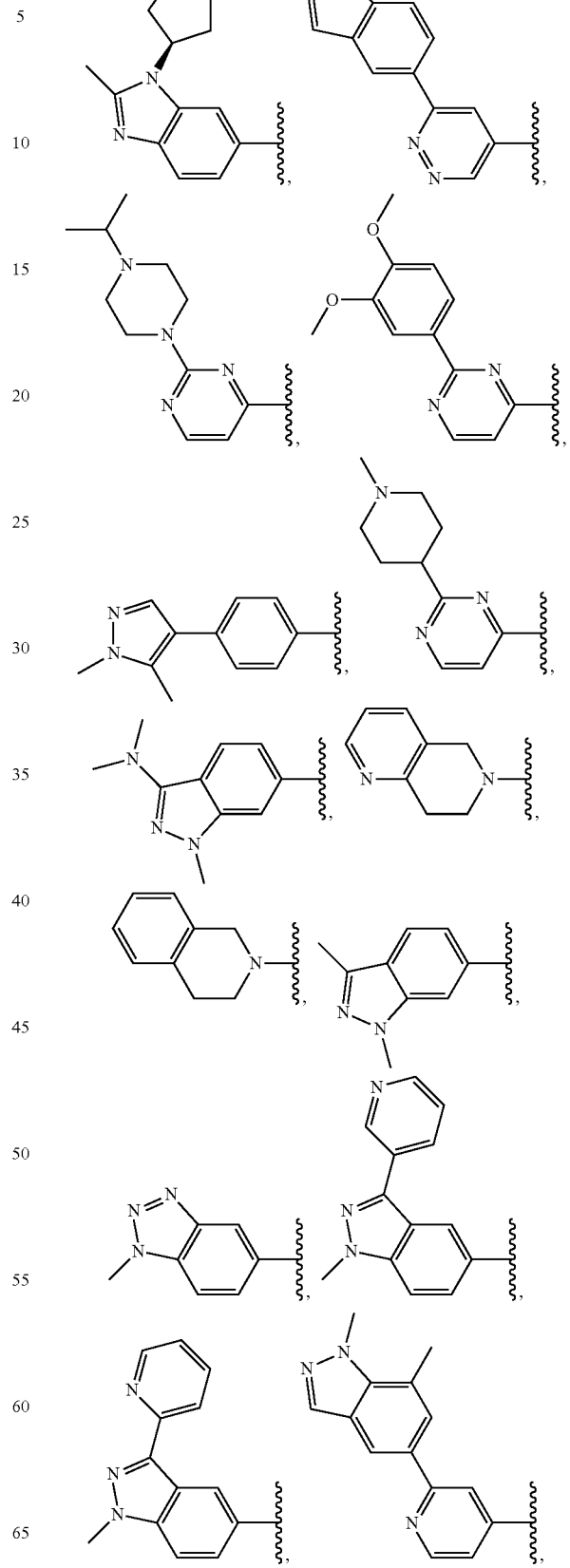

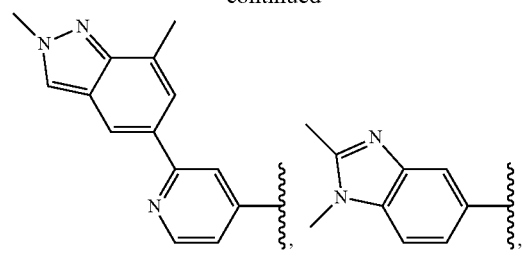
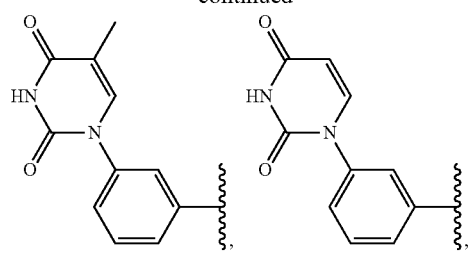
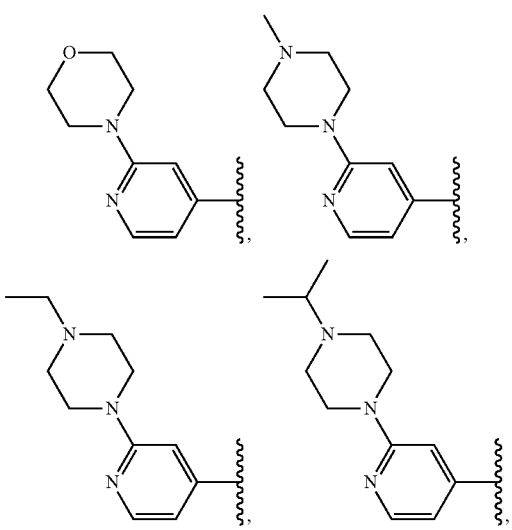
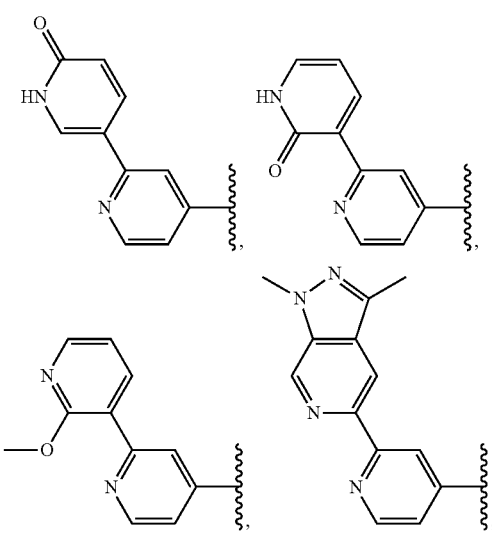
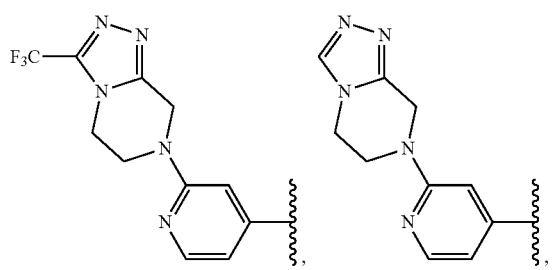
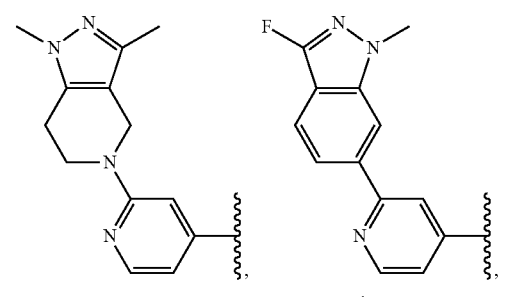
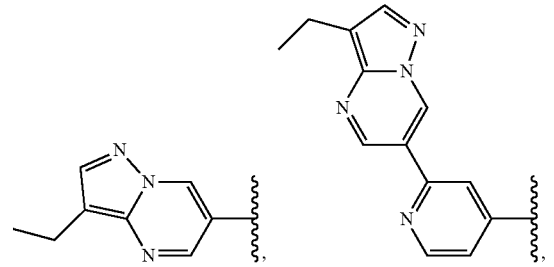
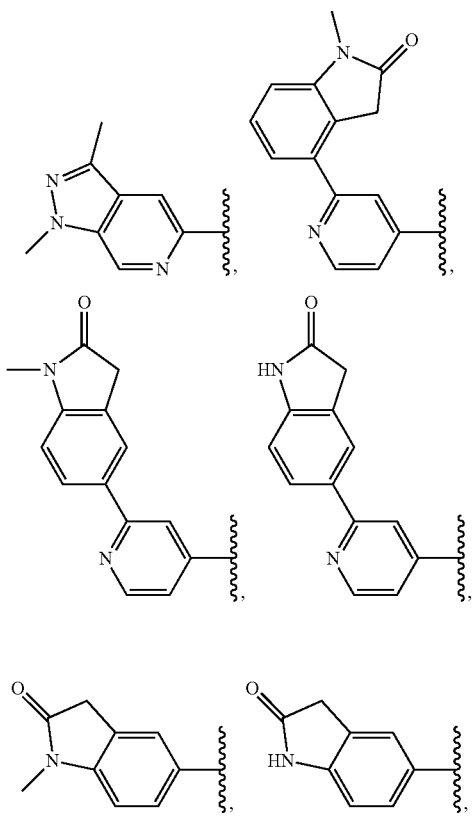

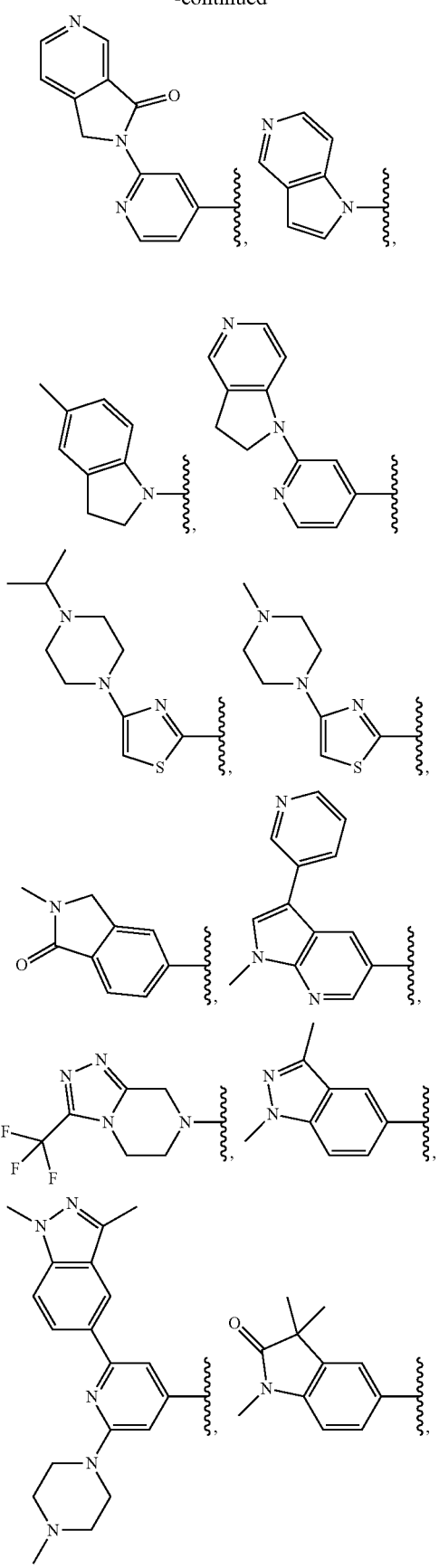
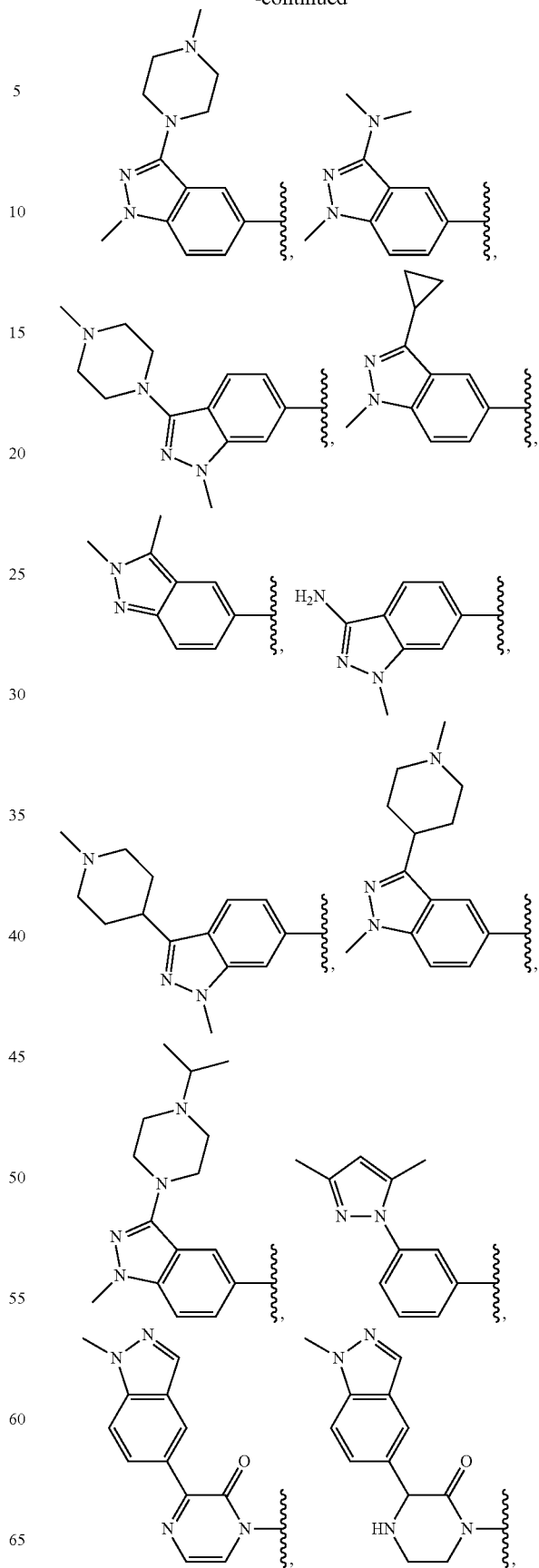

-continued
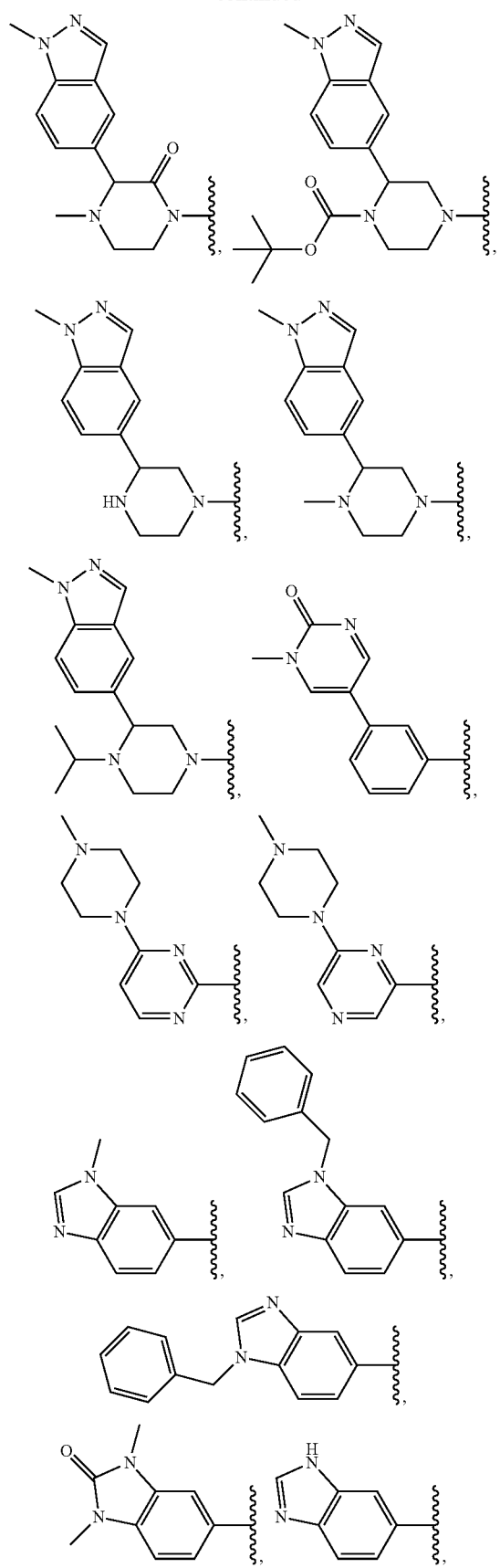
-continued
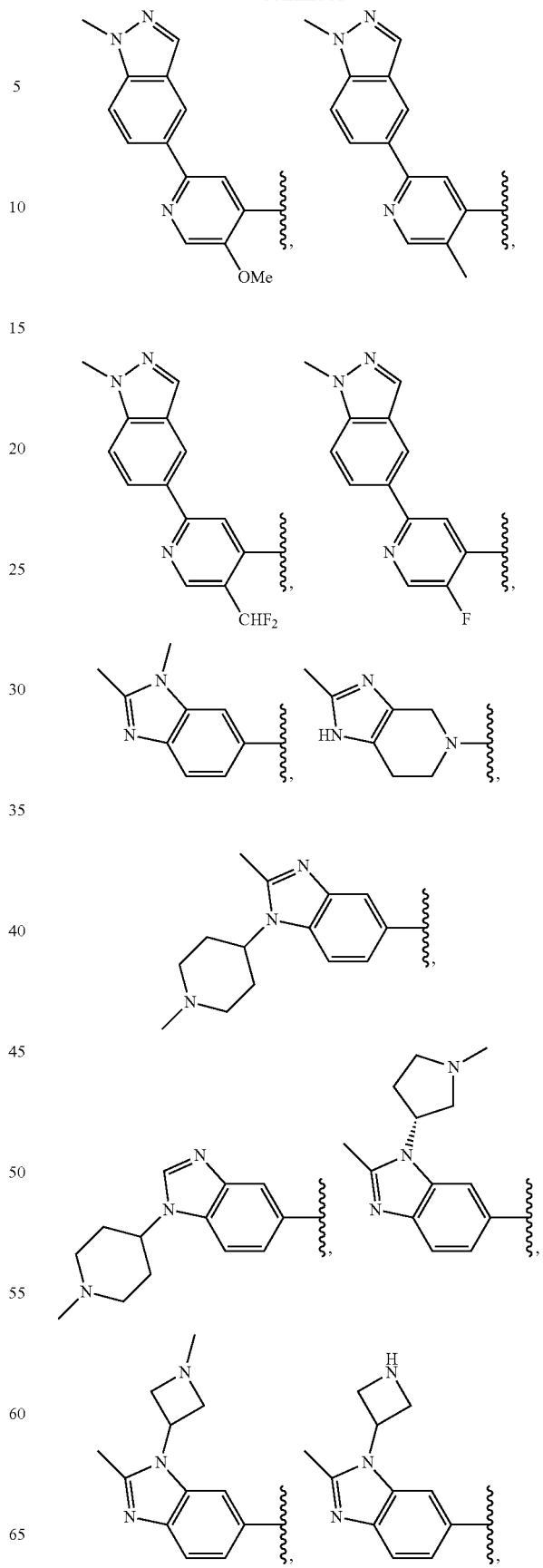

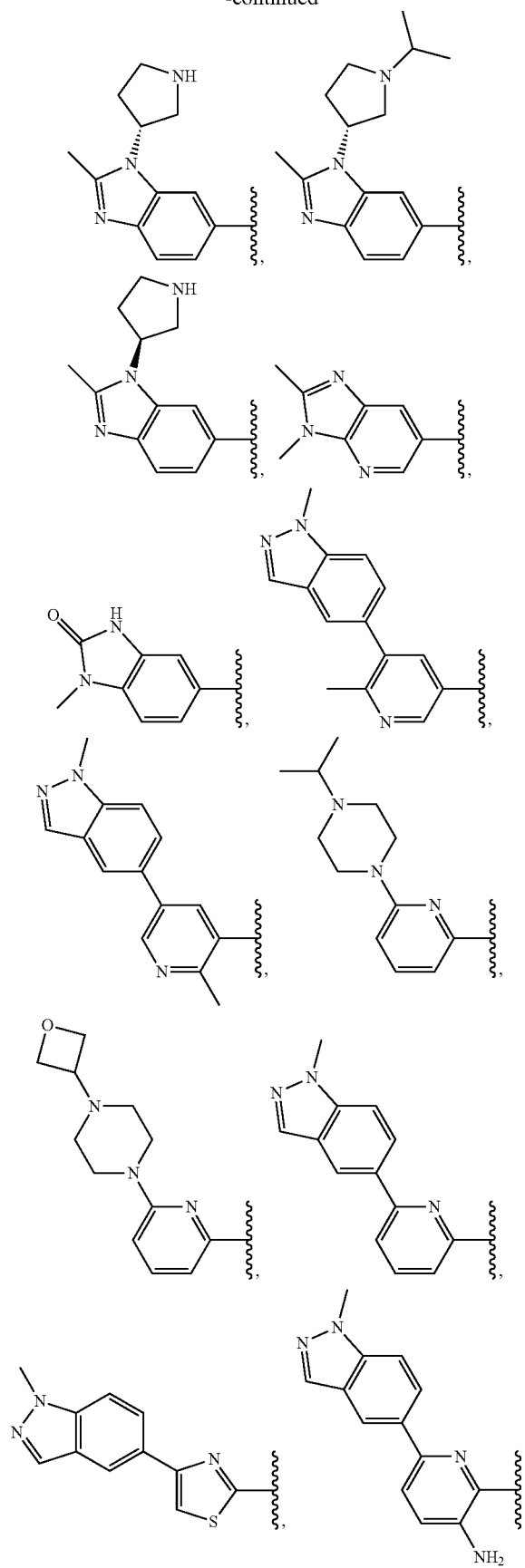
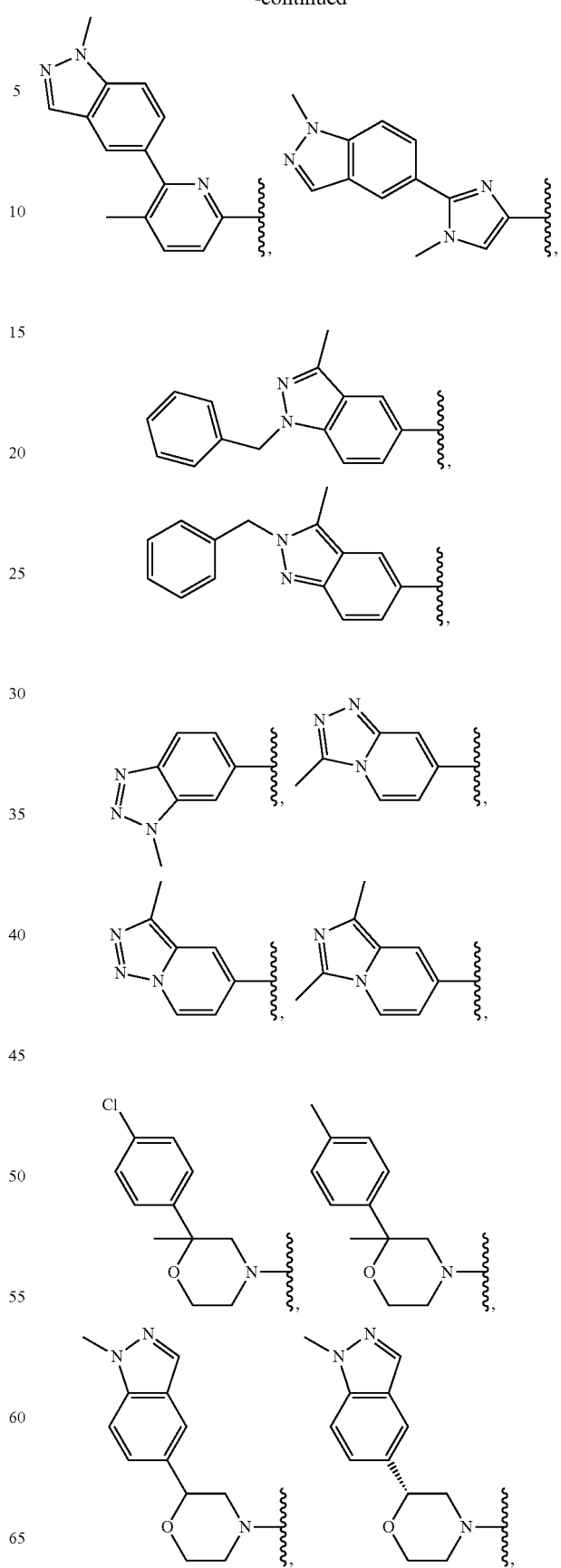

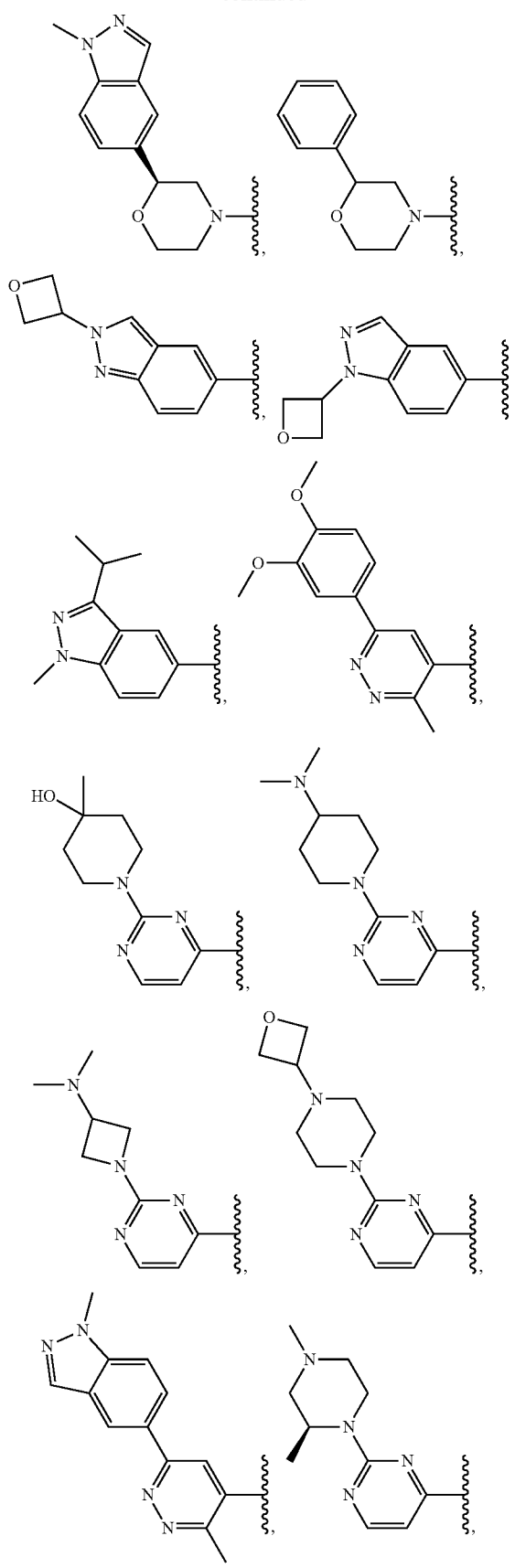
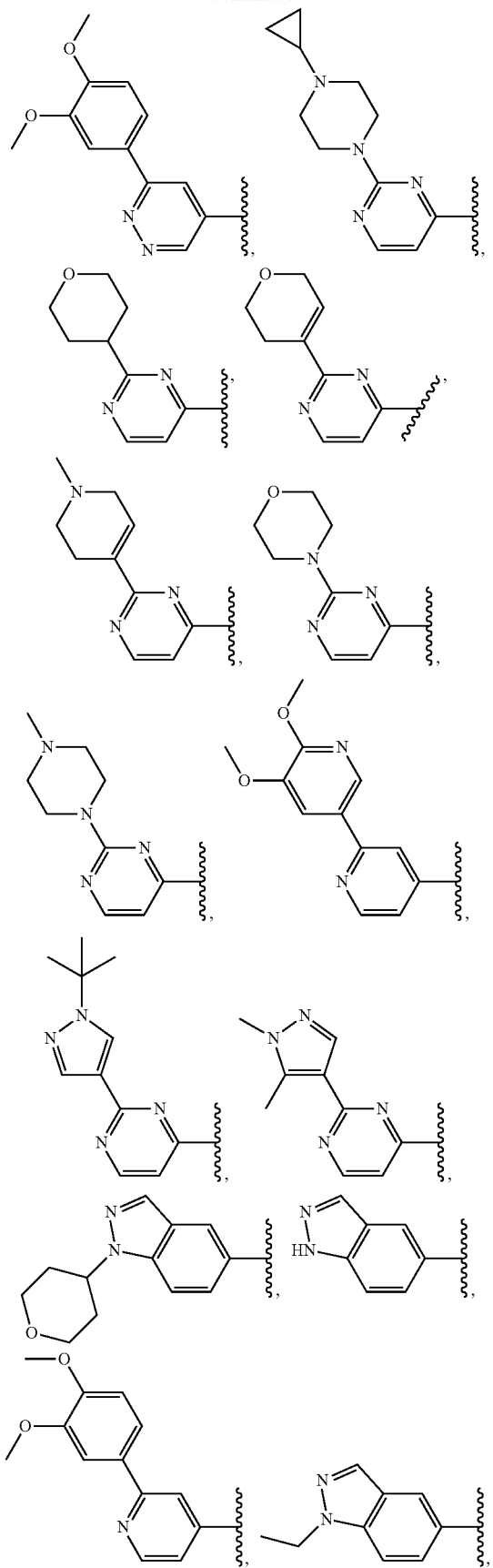

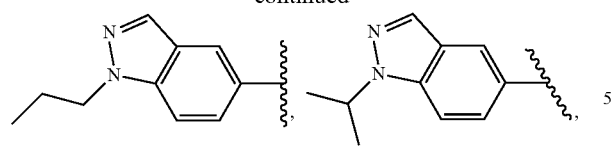
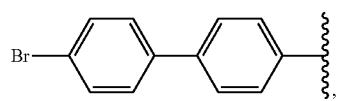
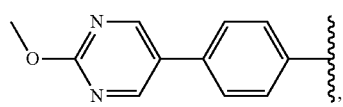
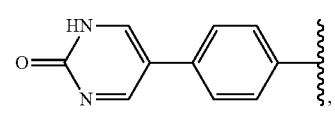
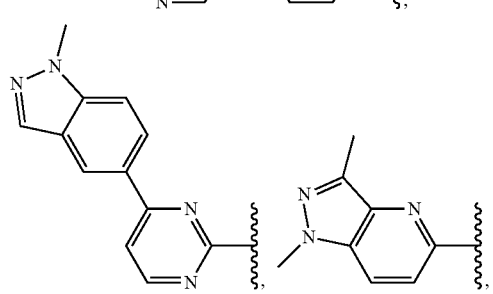
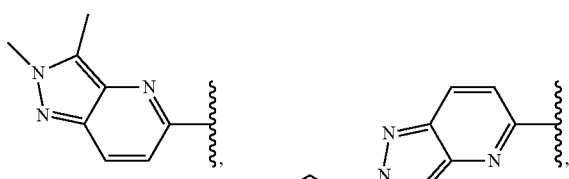
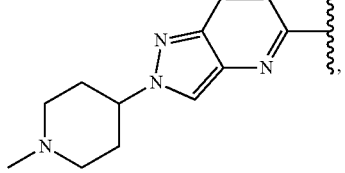
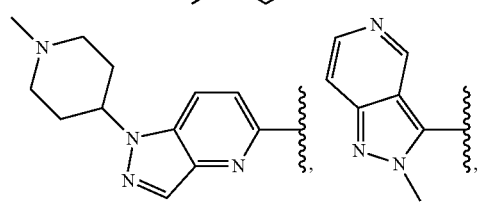
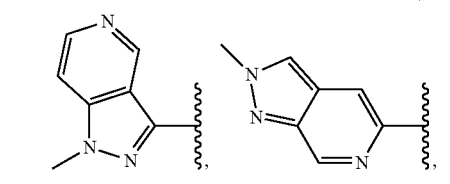
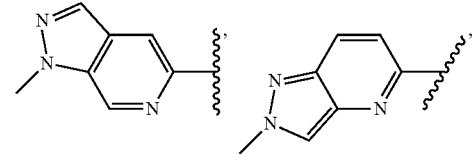
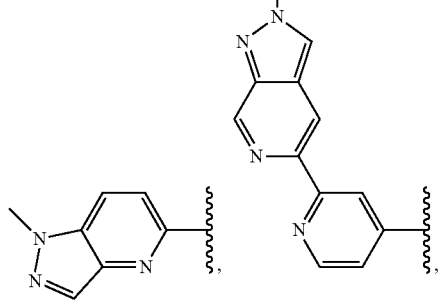
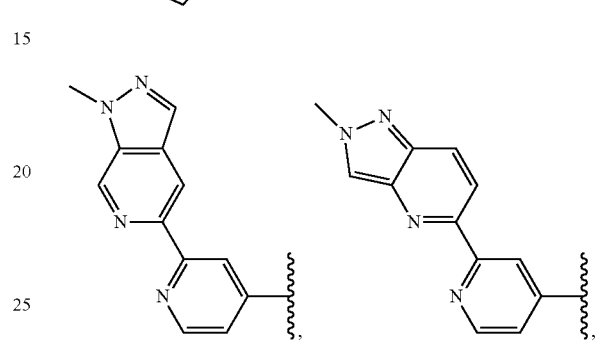
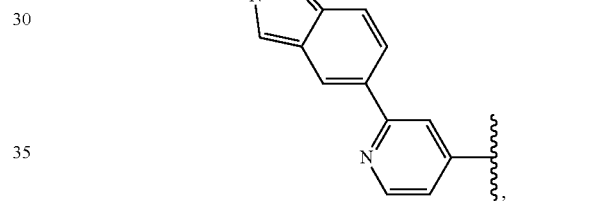
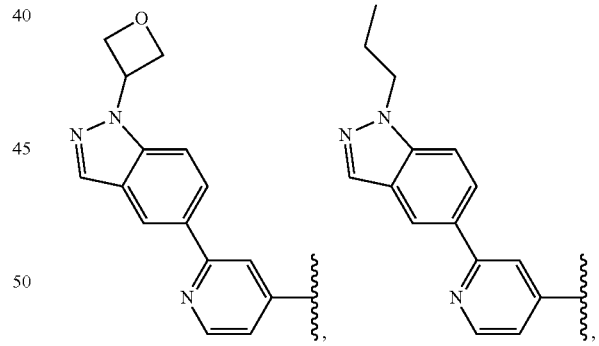
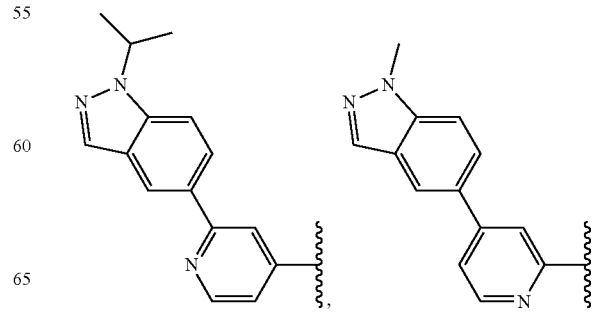

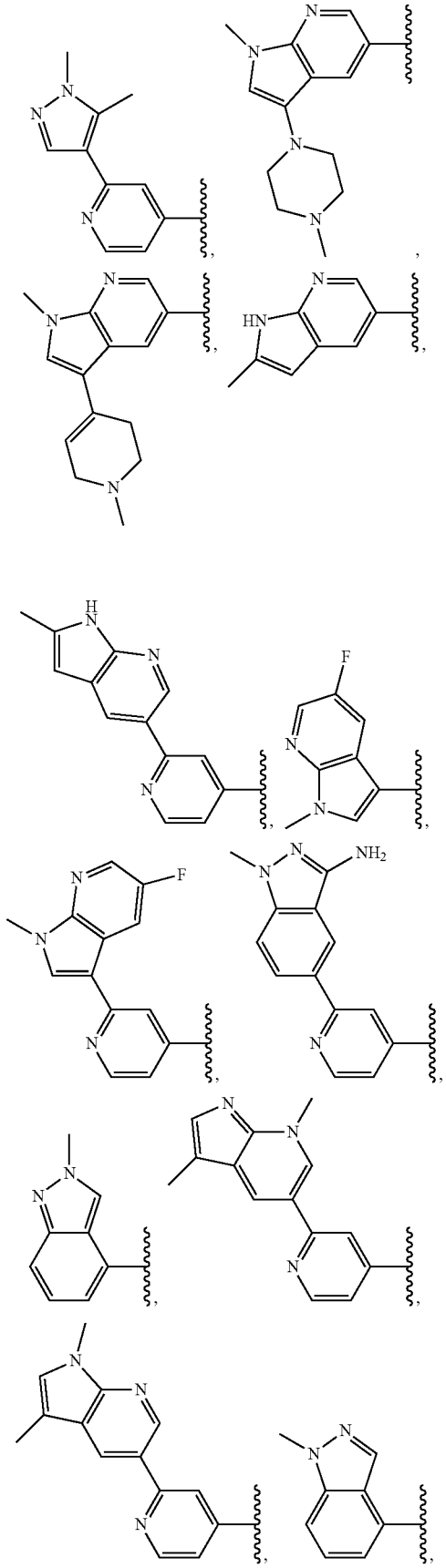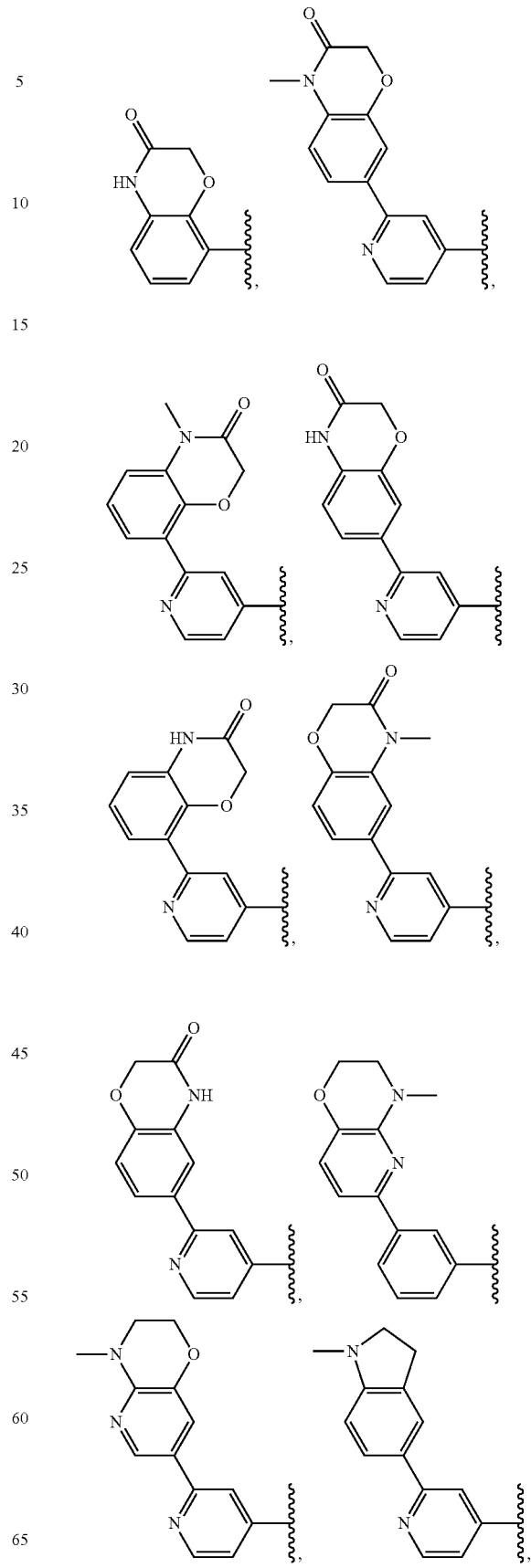

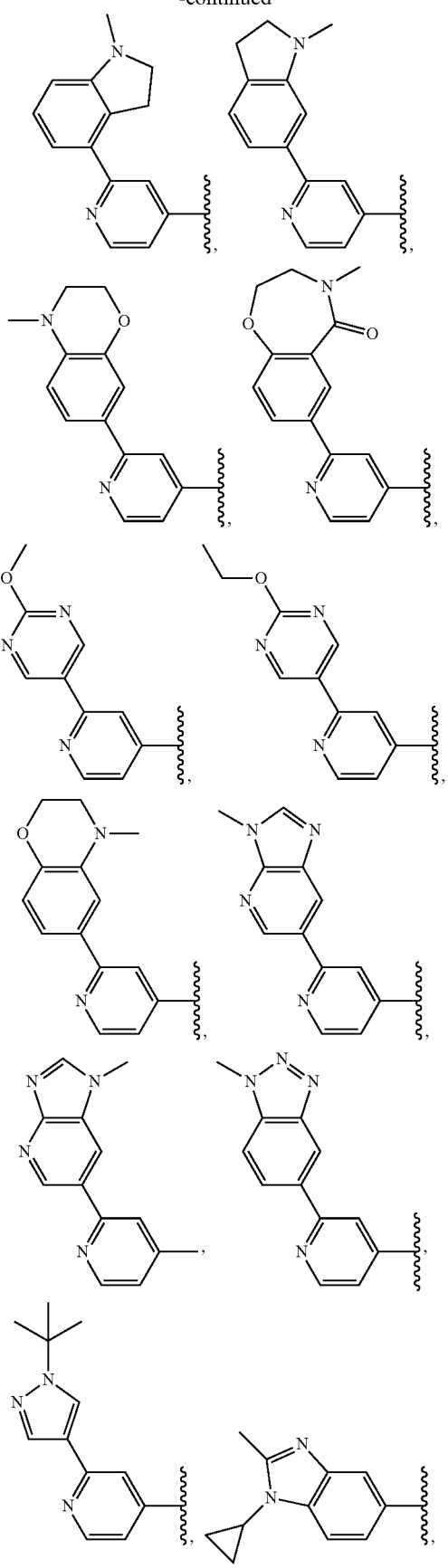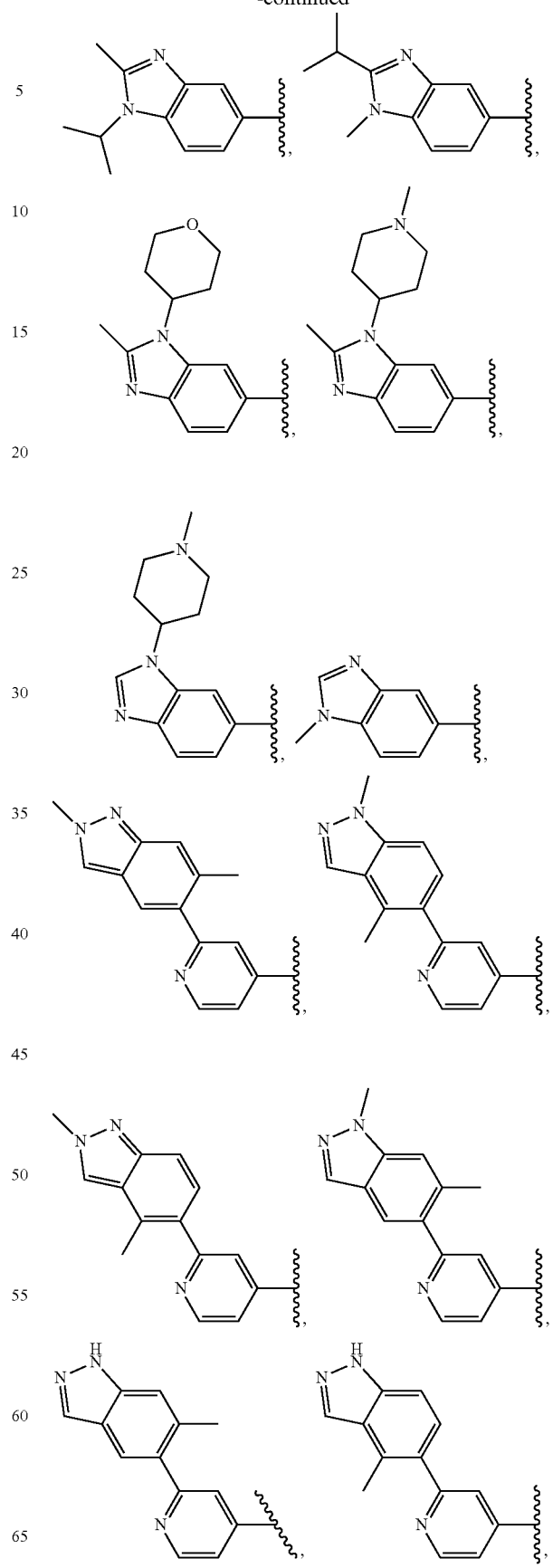

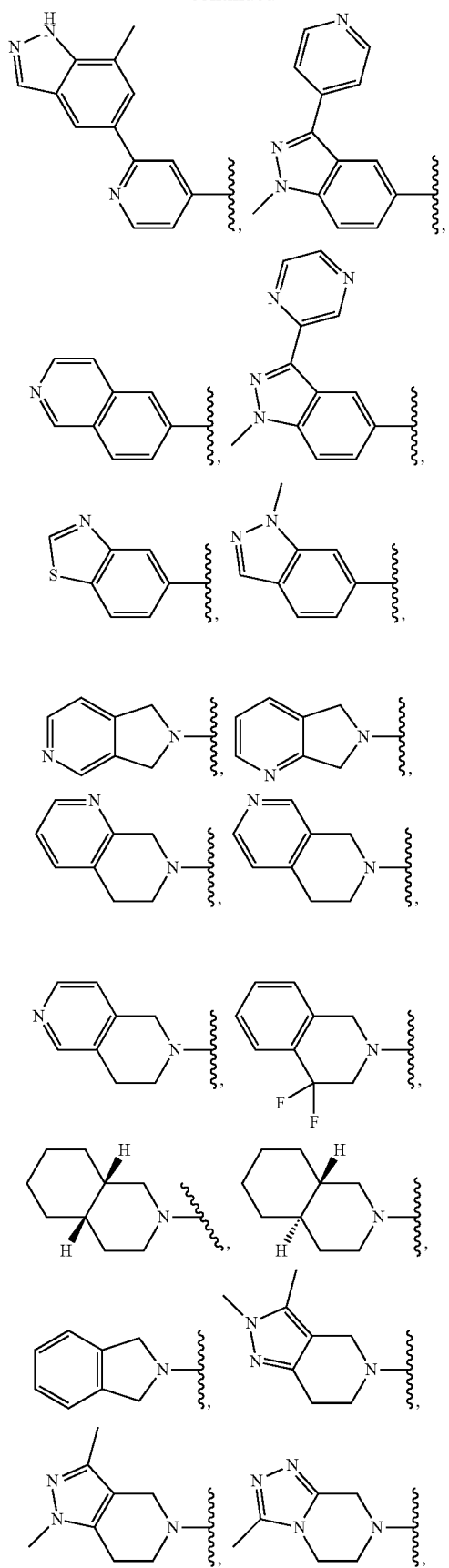
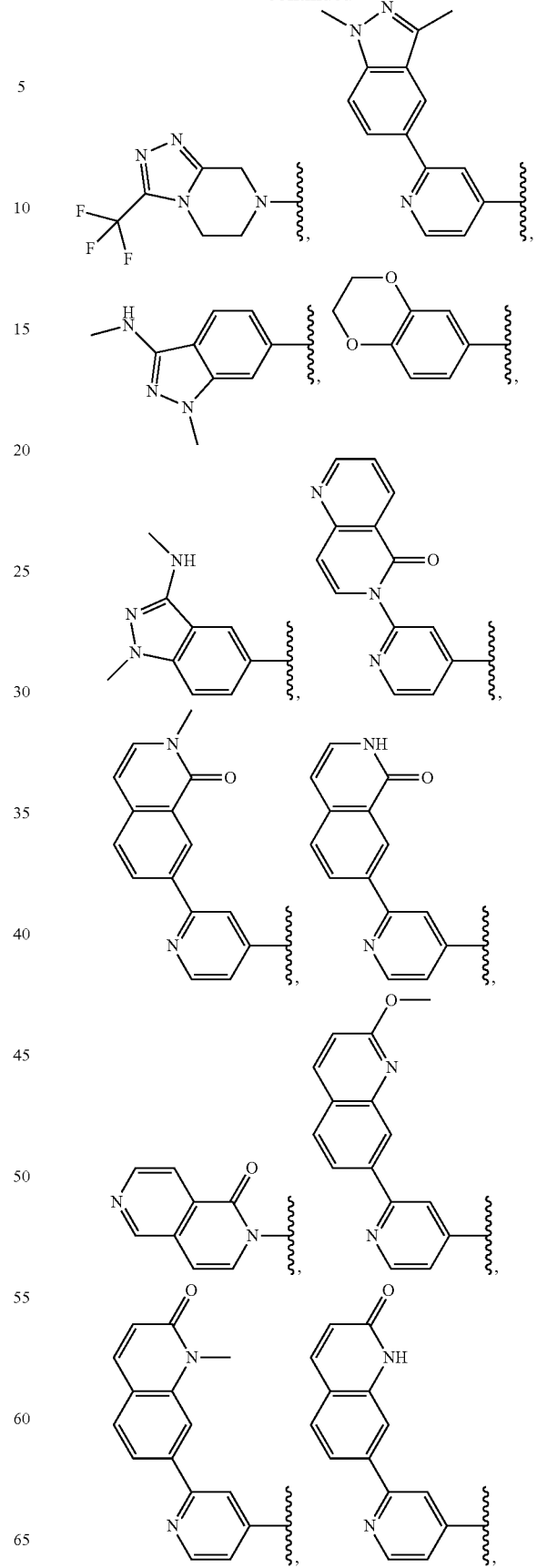

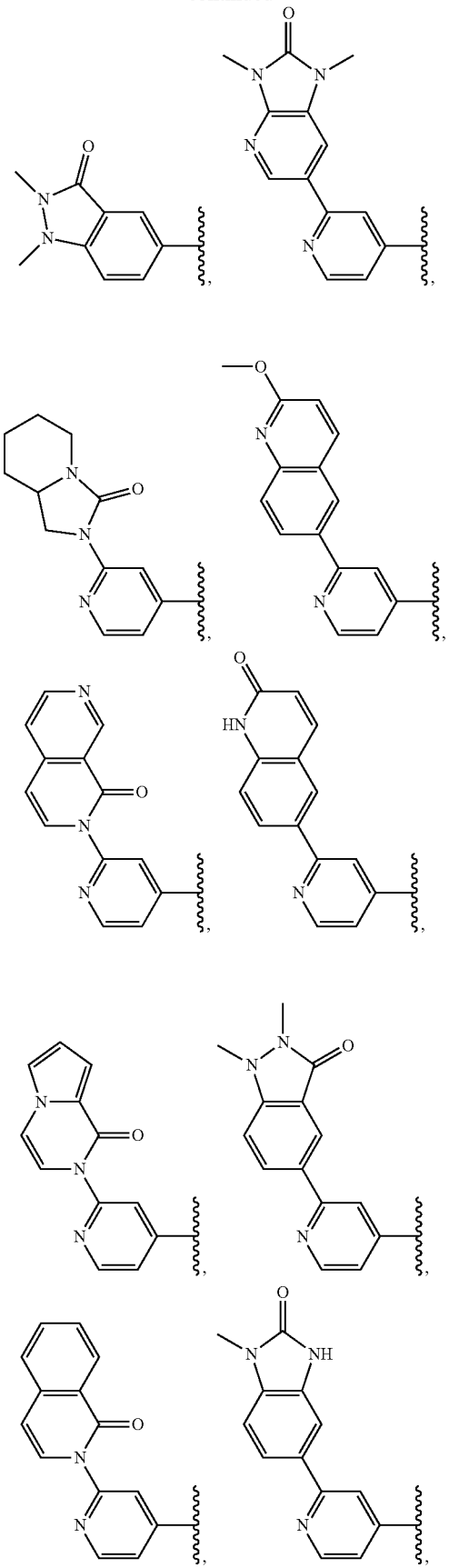
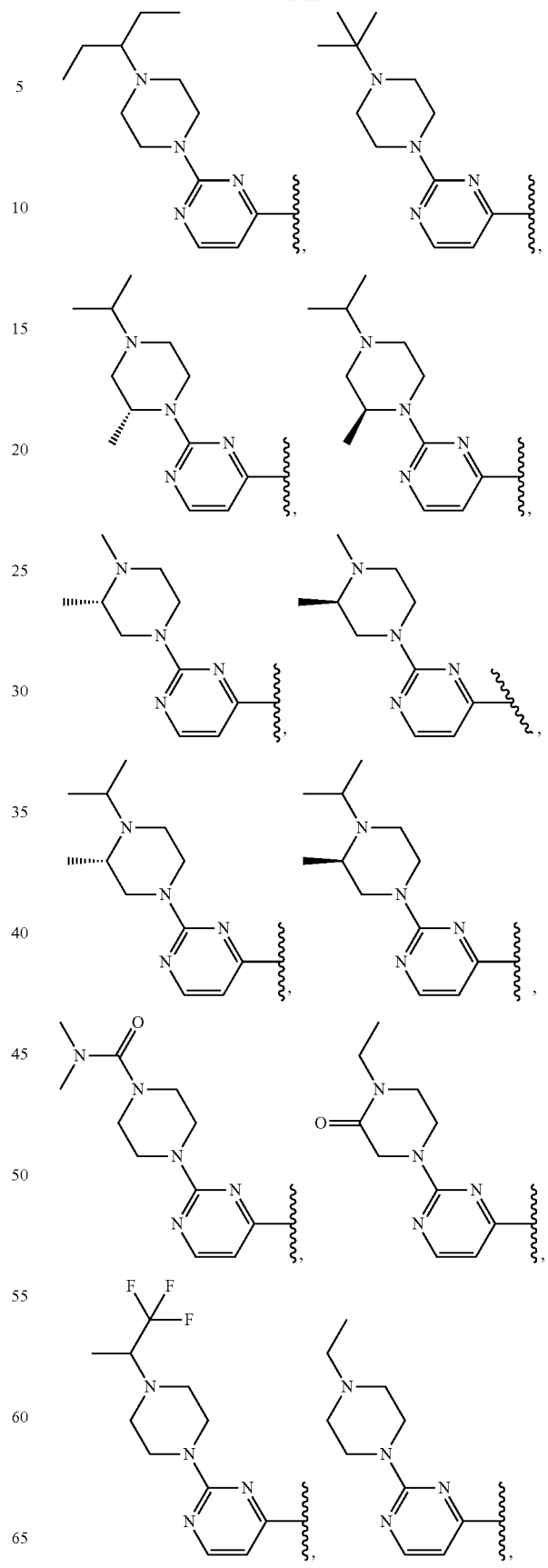

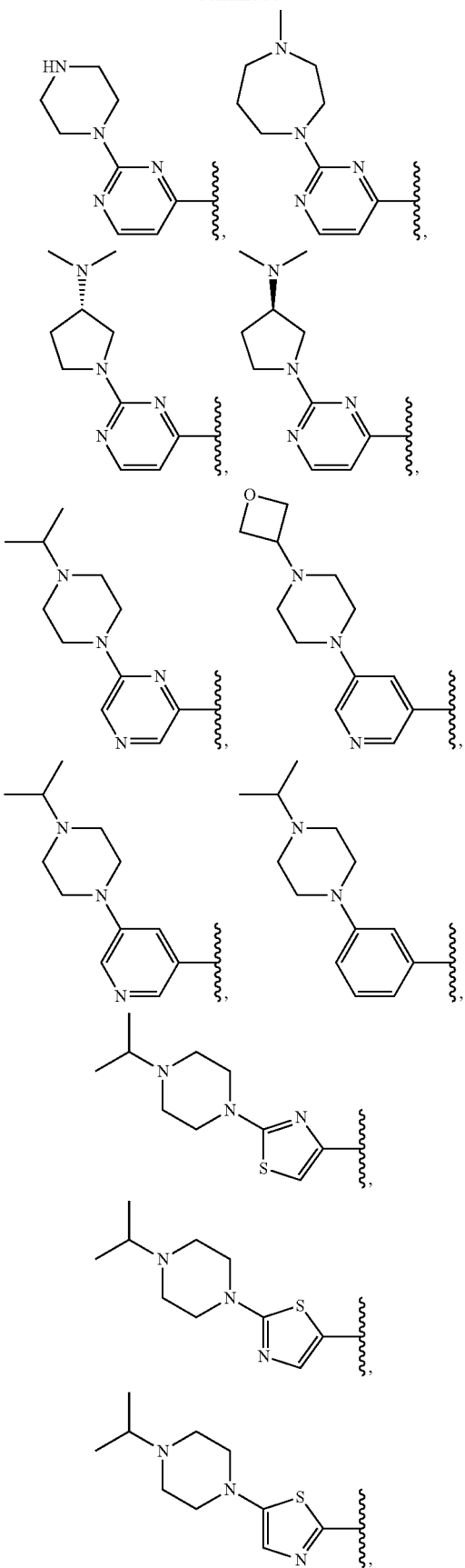
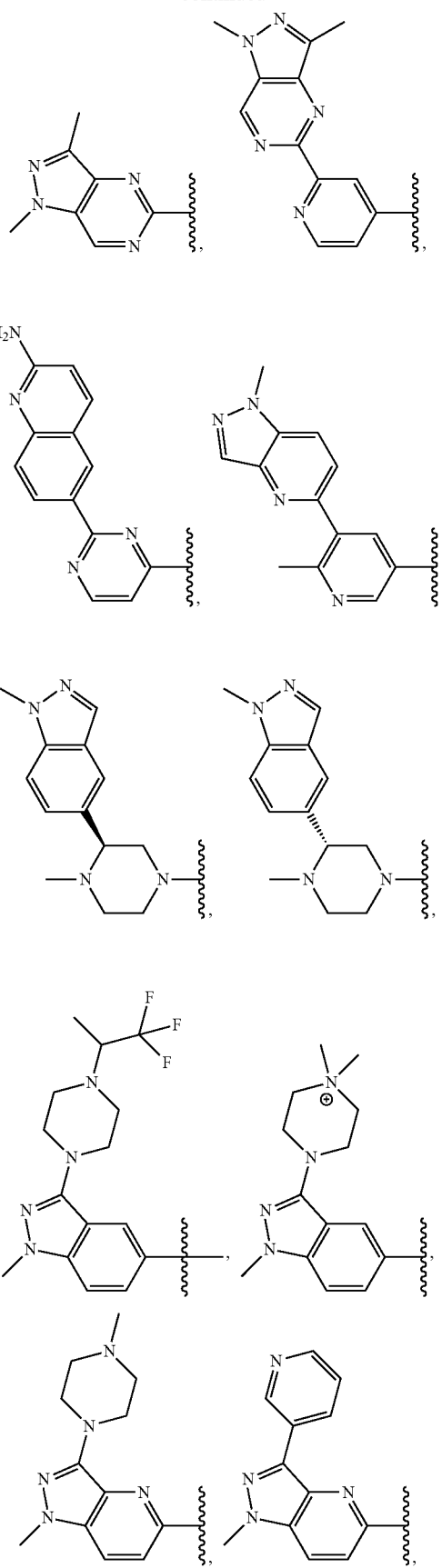

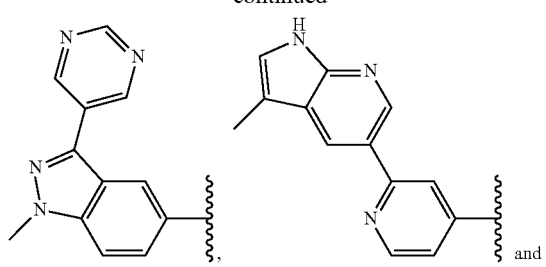
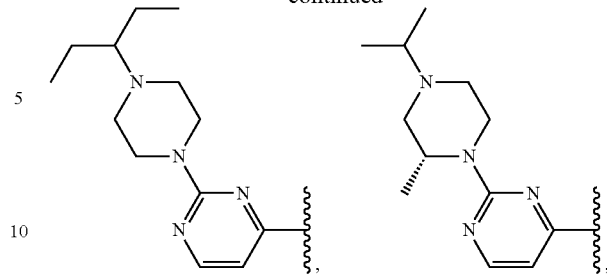 and
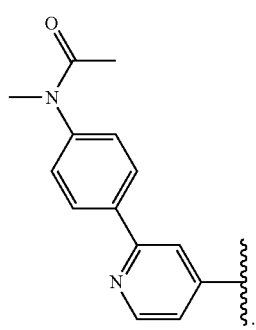
A specific group of compounds of formula I' are compounds wherein A-B is selected from:
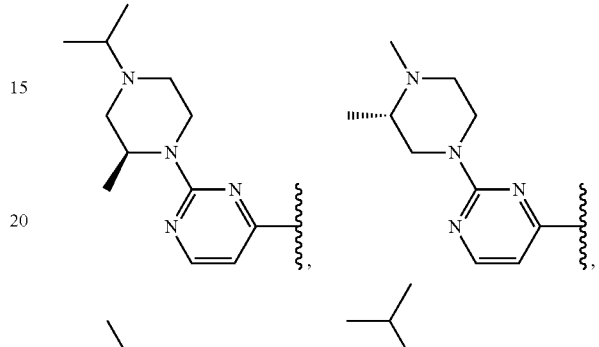
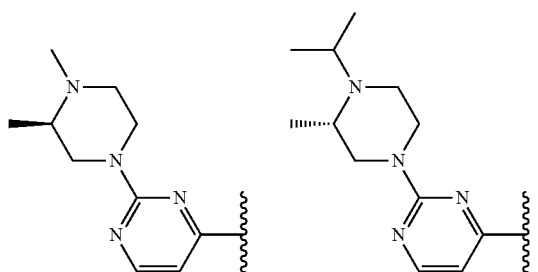
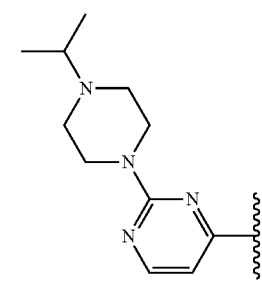, 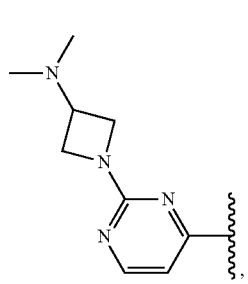,
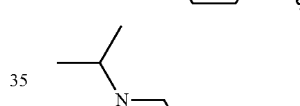
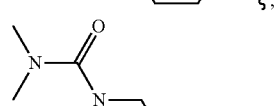
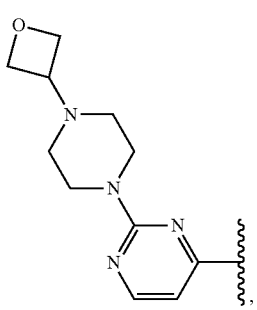, 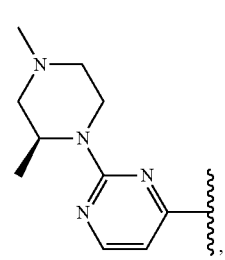, 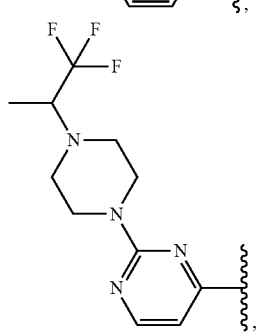, 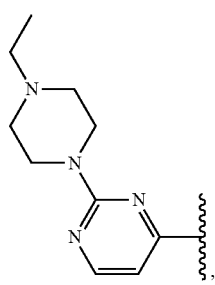,
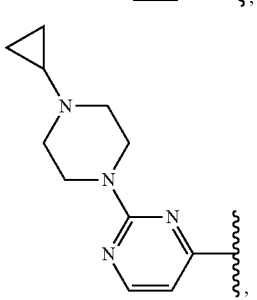, 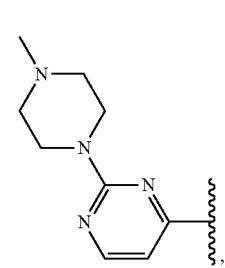, 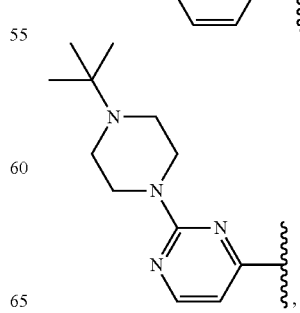 and 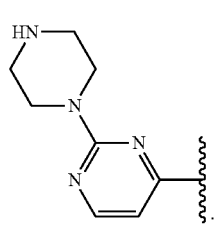.

A specific group of compounds of formula I' are compounds wherein A-B is selected from:

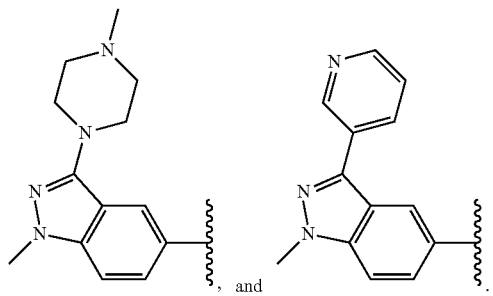 [SMILES: *c1ccc2c(c1)c(N1CCN(C)CC1)nn2C ; *c1ccc2c(c1)c(-c1cccnc1)nn2C], and

A specific value for $R^4$ is selected from aryl, heterocycle and heteroaryl, wherein any aryl, heterocycle and heteroaryl of $R^4$ is optionally substituted with one or more halo or $(C_1-C_6)$alkyl.

Another specific value for $R^4$ is selected from aryl and heterocycle, wherein any aryl and heterocycle of $R^4$ is optionally substituted with one or more chloro, fluoro or methyl.

Another specific value for $R^4$ is phenyl, wherein phenyl is optionally substituted with one or more halo or $(C_1-C_6)$alkyl.

Another specific value for $R^4$ is phenyl wherein phenyl is optionally substituted with one or more chloro, fluoro or methyl.

A specific value for $R^4$ is:

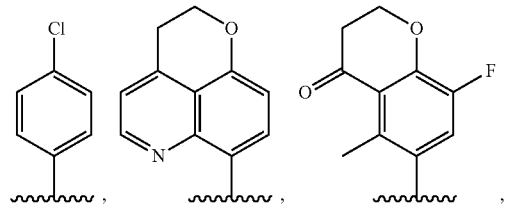

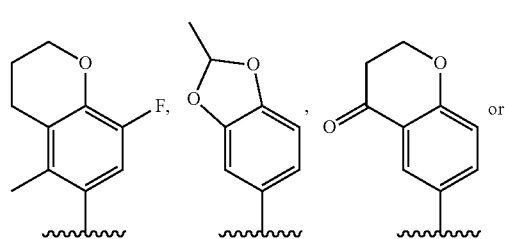

Another specific value for $R^4$ is:

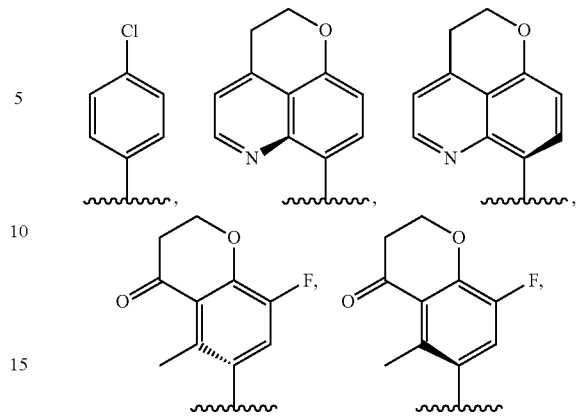

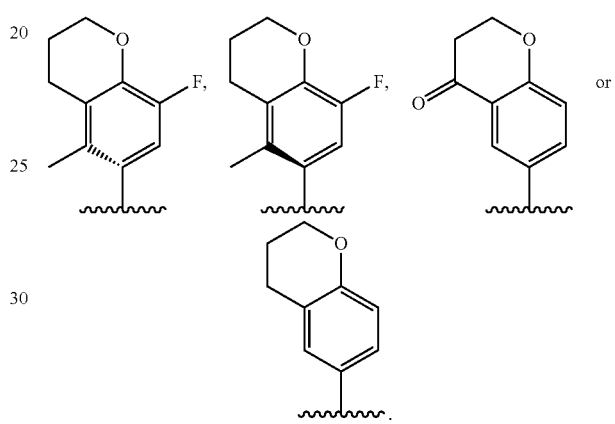

Another specific value for $R^4$ is:

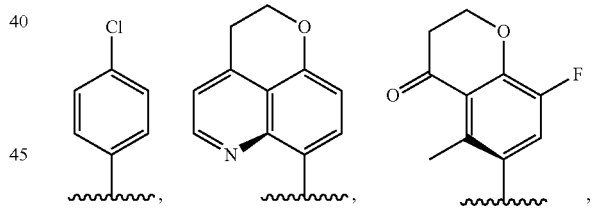

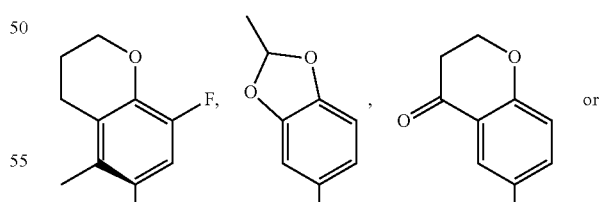

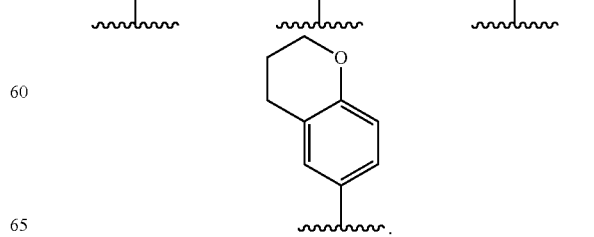

A specific value for R$^4$ is:

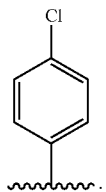

One embodiment provides a specific group of compounds of formula I' wherein the configuration of the R$^3$ group of formula I' is the (S) stereochemistry.

One embodiment provides a specific group of compounds of formula I' wherein the configuration of the —OC(CH$_3$)$_3$ group as shown in formula I' is the (S) stereochemistry.

A specific group or compounds of formula I' are compounds wherein:

R$^4$ is selected from phenyl, 9-10 membered bicyclic heterocycle and 12-13 membered tricyclic heterocycle, wherein any phenyl, 9-10 membered bicyclic heterocycle and 12-13 membered tricyclic heterocycle of R$^4$ is optionally substituted with one or more (e.g., 1, 2, 3, 4 or 5) groups independently selected from selected from halo and (C$_1$-C$_6$)alkyl;

A is phenyl, 5-6 membered monocyclic heteroaryl or 3-7 membered monocyclic heterocycle, wherein any phenyl, 5-6 membered monocyclic heteroaryl or 3-7 membered monocyclic heterocycle of A is optionally substituted with one or more (e.g., 1, 2, 3, 4 or 5) Z$^{1a}$ groups, and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) Z$^{1b}$ groups; or A and B together form a 8-11 membered bicyclic aryl, 7-11 membered bicyclic heteroaryl or 6-11 membered bicyclic heterocycle, wherein any 8-11 membered bicyclic aryl, 7-11 membered bicyclic heteroaryl or 6-11 membered bicyclic heterocycle is optionally substituted with one or more (e.g., 1, 2, 3, 4 or 5) Z$^{1b}$ groups;

each Z$^{1a}$ is independently selected from halo, (C$_1$-C$_3$)alkyl, (C$_2$-C$_3$)alkenyl, (C$_2$-C$_3$)alkynyl, (C$_1$-C$_3$)haloalkyl, (C$_3$-C$_7$)carbocycle, 3-7 membered monocyclic heterocycle, —O(C$_1$-C$_3$)alkyl, —O(C$_2$-C$_3$)alkenyl, —O(C$_2$-C$_3$)alkynyl, —NR$_c$R$_d$, —NR$_a$C(O)R$_a$, —C(O)OR$_b$ and —C(O)NR$_c$R$_d$, wherein any (C$_3$-C$_7$)carbocycle or 3-7 membered monocyclic heterocycle of Z$^{1a}$ is optionally substituted with one or more (e.g., 1, 2, 3, 4 or 5) halogen or (C$_1$-C$_6$)alkyl;

each Z$^{1b}$ is independently selected from halo, CN, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, 5-6 membered monocyclic heteroaryl, 7-12 membered bicyclic heteroaryl, 3-7 membered monocyclic heterocycle, 6-11 membered bicyclic heterocycle, phenyl (C$_1$-C$_6$)alkyl-, —OH, —O(C$_1$-C$_6$)alkyl, —O(C$_2$-C$_6$)alkenyl, —O(C$_2$-C$_6$)alkynyl, —NR$_c$R$_d$, —NR$_a$C(O)R$_a$, —C(O)OR$_b$ and —C(O)NR$_c$R$_d$, wherein any (C$_3$-C$_7$)carbocycle, 3-7 membered monocyclic heterocycle or 6-11 membered bicyclic heterocycle of Z$^{1b}$ is optionally substituted with one or more (e.g., 1, 2, 3, 4 or 5) halogen or (C$_1$-C$_6$)alkyl; and R$_a$, R$_b$, R$_c$ and R$_d$ are each independently H or (C$_1$-C$_6$)alkyl;

or a salt thereof.

A specific value for R$^4$ is selected from phenyl, bicyclic aryl, monocyclic heterocycle, bicyclic heterocycle, tricyclic heterocycle, monocyclic heteroaryl, bicyclic heteroaryl and tricyclic heteroaryl, wherein any phenyl, bicyclic aryl, monocyclic heterocycle, bicyclic heterocycle, tricyclic heterocycle, monocyclic heteroaryl, bicyclic heteroaryl and tricyclic heteroaryl of R$^4$ is optionally substituted with one or more (e.g., 1, 2, 3, 4 or 5) groups independently selected from halo and (C$_1$-C$_6$)alkyl.

A specific value for R$^4$ is selected from phenyl, bicyclic aryl, monocyclic heterocycle, bicyclic heterocycle, tricyclic heterocycle, monocyclic heteroaryl, bicyclic heteroaryl and tricyclic heteroaryl, wherein any phenyl, bicyclic aryl, monocyclic heterocycle, bicyclic heterocycle, tricyclic heterocycle, monocyclic heteroaryl, bicyclic heteroaryl and tricyclic heteroaryl of R$^4$ is optionally substituted with one or more (e.g., 1, 2, 3, 4 or 5) groups independently selected from halo and methyl.

A specific value for R$^4$ is selected from phenyl, bicyclic heterocycle and tricyclic heterocycle, wherein any phenyl, bicyclic heterocycle and tricyclic heterocycle of R$^4$ is optionally substituted with one or more (e.g., 1, 2, 3, 4 or 5) groups independently selected from halo, (C$_1$-C$_6$)alkyl, (C$_2$-C$_6$)alkenyl, (C$_1$-C$_6$)haloalkyl, (C$_3$-C$_7$)cycloalkyl, —(C$_1$-C$_6$)alkyl-(C$_3$-C$_7$)cycloalkyl, —OH, —O(C$_1$-C$_6$)alkyl, —SH, —S(C$_1$-C$_6$)alkyl, NH$_2$, —NH(C$_1$-C$_6$)alkyl and —N((C$_1$-C$_6$)alkyl)$_2$, wherein (C$_1$-C$_6$)alkyl is optionally substituted with hydroxy, —O(C$_1$-C$_6$)alkyl, cyano or oxo.

A specific value for R$^4$ is selected from phenyl, bicyclic heterocycle and tricyclic heterocycle, wherein any phenyl, bicyclic heterocycle and tricyclic heterocycle of R$^4$ is optionally substituted with one or more (e.g., 1, 2, 3, 4 or 5) groups independently selected from halo and (C$_1$-C$_6$)alkyl.

A specific value for R$^4$ is selected from phenyl, bicyclic heterocycle and tricyclic heterocycle, wherein any phenyl, bicyclic heterocycle and tricyclic heterocycle of R$^4$ is optionally substituted with one or more (e.g., 1, 2, 3, 4 or 5) groups independently selected from halo and methyl.

A specific value for R$^4$ is selected from phenyl, bicyclic heterocycle and tricyclic heterocycle, wherein any phenyl, bicyclic heterocycle and tricyclic heterocycle of R$^4$ is optionally substituted with one or more (e.g., 1, 2, 3, 4 or 5) groups independently selected from fluoro, chloro or methyl.

A specific value for R$^4$ is selected from phenyl, 9-10 membered bicyclic heterocycle and 12-13 membered tricyclic heterocycle, wherein any phenyl, 9-10 membered bicyclic heterocycle and 12-13 membered tricyclic heterocycle of R$^4$ is optionally substituted with one or more (e.g., 1, 2, 3, 4 or 5) groups independently selected from halo, (C$_1$-C$_6$)alkyl, (C$_2$-C$_6$)alkenyl, (C$_1$-C$_6$)haloalkyl, (C$_3$-C$_7$)cycloalkyl, —(C$_1$-C$_6$)alkyl-(C$_3$-C$_7$)cycloalkyl, —OH, —O(C$_1$-C$_6$)alkyl, —SH, —S(C$_1$-C$_6$)alkyl, NH$_2$, —NH(C$_1$-C$_6$)alkyl and —N((C$_1$-C$_6$)alkyl)$_2$, wherein (C$_1$-C$_6$)alkyl is optionally substituted with hydroxy, —O(C$_1$-C$_6$)alkyl, cyano or oxo.

A specific value for R$^4$ is selected from phenyl, 9-10 membered bicyclic heterocycle and 12-13 membered tricyclic heterocycle, wherein any phenyl, 9-10 membered bicyclic heterocycle and 12-13 membered tricyclic heterocycle of R$^4$ is optionally substituted with one or more (e.g., 1, 2, 3, 4 or 5) groups independently selected from selected from halo and (C$_1$-C$_6$)alkyl.

A specific value for R$^4$ is selected from phenyl, 9-10 membered bicyclic heterocycle and 12-13 membered tricyclic heterocycle, wherein any phenyl, 9-10 membered bicyclic heterocycle and 12-13 membered tricyclic heterocycle of R$^4$ is optionally substituted with one or more (e.g., 1, 2, 3, 4 or 5) groups independently selected from halo and methyl.

A specific value for $R^4$ is selected from phenyl, 9-10 membered bicyclic heterocycle and 12-13 membered tricyclic heterocycle, wherein any phenyl, 9-10 membered bicyclic heterocycle and 12-13 membered tricyclic heterocycle of $R^4$ is optionally substituted with one or more (e.g., 1, 2, 3, 4 or 5) groups independently selected from fluoro, chloro or methyl.

A specific value for $R^4$ is selected from phenyl, 9-10 membered bicyclic heterocycle and 13 membered tricyclic heterocycle, wherein any phenyl, 9-10 membered bicyclic heterocycle and 13 membered tricyclic heterocycle of $R^4$ is optionally substituted with one or more (e.g., 1, 2, 3, 4 or 5) groups independently selected from selected from halo and $(C_1-C_6)$alkyl.

A specific value for $R^4$ is selected from phenyl, 9-10 membered bicyclic heterocycle and 13 membered tricyclic heterocycle, wherein any phenyl, 9-10 membered bicyclic heterocycle and 13 membered tricyclic heterocycle of $R^4$ is optionally substituted with one or more (e.g., 1, 2, 3, 4 or 5) groups independently selected from halo and methyl.

A specific value for $R^4$ is selected from phenyl, 9-10 membered bicyclic heterocycle and 13 membered tricyclic heterocycle, wherein any phenyl, 9-10 membered bicyclic heterocycle and 13 membered tricyclic heterocycle of $R^4$ is optionally substituted with one or more (e.g., 1, 2, 3, 4 or 5) groups independently selected from fluoro, chloro or methyl.

A specific value for $R^4$ is selected from phenyl, 2,3-dihydropyrano[4,3,2-de]quinolinyl, chromanyl-4-one, chromanyl and 2-methylbenzo[d][1,3]dioxolyl wherein any phenyl, 2,3-dihydropyrano[4,3,2-de]quinolinyl, chromanyl-4-one, chromanyl and 2-methylbenzo[d][1,3]dioxolyl of $R^4$ is optionally substituted with one or more (e.g., 1, 2, 3, 4 or 5) groups independently selected from halo and $(C_1-C_6)$alkyl.

A specific value for $R^4$ is selected from phenyl, 2,3-dihydropyrano[4,3,2-de]quinolinyl, chromanyl-4-one, chromanyl and 2-methylbenzo[d][1,3]dioxolyl wherein any phenyl, 2,3-dihydropyrano[4,3,2-de]quinolinyl, chromanyl-4-one, chromanyl and 2-methylbenzo[d][1,3]dioxolyl of $R^4$ is optionally substituted with one or more (e.g., 1, 2, 3, 4 or 5) groups independently selected from halo and methyl.

A specific value for $R^4$ is selected from phenyl, 2,3-dihydropyrano[4,3,2-de]quinolinyl, chromanyl-4-one, chromanyl and 2-methylbenzo[d][1,3]dioxolyl wherein any phenyl, 2,3-dihydropyrano[4,3,2-de]quinolinyl, chromanyl-4-one, chromanyl and 2-methylbenzo[d][1,3]dioxolyl of $R^4$ is optionally substituted with one or more (e.g., 1, 2, 3, 4 or 5) groups independently selected from fluoro, chloro and methyl.

A specific value for $R^4$ is phenyl, wherein phenyl is optionally substituted with one or more (e.g., 1, 2, 3, 4 or 5) groups independently selected from halo and $(C_1-C_6)$alkyl.

A specific value for $R^4$ is phenyl, wherein phenyl is optionally substituted with one or more (e.g., 1, 2, 3, 4 or 5) groups independently selected from halo and methyl.

A specific value for $R^4$ is phenyl, wherein phenyl is optionally substituted with one or more (e.g., 1, 2, 3, 4 or 5) groups independently selected from fluoro and chloro.

A specific value for $R^4$ is phenyl, wherein phenyl is optionally substituted with one or more (e.g., 1, 2, 3, 4 or 5) chloro.

A specific group of compounds of formula I' include compounds wherein A is phenyl, monocyclic heteroaryl or monocyclic heterocycle, wherein any phenyl, monocyclic heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, tricyclic heteroaryl, monocyclic heterocycle, bicyclic heterocycle or tricyclic heterocycle, wherein any phenyl, bicyclic aryl, monocyclic heteroaryl, bicyclic heteroaryl, tricyclic heteroaryl, monocyclic heterocycle, bicyclic heterocycle or tricyclic heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle, wherein any bicyclic aryl, bicyclic heteroaryl or bicyclic heterocycle is optionally substituted with one or more (e.g., 1, 2, 3, 4 or 5) $Z^{1b}$ groups.

A specific group of compounds of formula I' include compounds wherein A is phenyl, monocyclic heteroaryl or monocyclic heterocycle, wherein any phenyl, monocyclic heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, monocyclic heterocycle, or bicyclic heterocycle, wherein any phenyl, bicyclic aryl, monocyclic heteroaryl, bicyclic heteroaryl, monocyclic heterocycle or bicyclic heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle, wherein any bicyclic aryl, bicyclic heteroaryl or bicyclic heterocycle is optionally substituted with one or more (e.g., 1, 2, 3, 4 or 5) $Z^{1b}$ groups.

A specific group of compounds of formula I' include compounds wherein A is phenyl, 5-6 membered monocyclic heteroaryl or 3-7 membered monocyclic heterocycle, wherein any phenyl, 5-6 membered monocyclic heteroaryl or 3-7 membered monocyclic heterocycle of A is optionally substituted with one or more (e.g., 1, 2, 3, 4 or 5) $Z^{1a}$ groups, and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) $Z^{1b}$ groups; or A and B together form a 8-11 membered bicyclic aryl, 7-11 membered bicyclic heteroaryl or 6-11 membered bicyclic heterocycle, wherein any 8-11 membered bicyclic aryl, 7-11 membered bicyclic heteroaryl or 6-11 membered bicyclic heterocycle is optionally substituted with one or more (e.g., 1, 2, 3, 4 or 5) $Z^{1b}$ groups.

A specific group of compounds of formula I' include compounds wherein A is phenyl, monocyclic heteroaryl or monocyclic heterocycle, wherein any phenyl, monocyclic heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, tricyclic heteroaryl, monocyclic heterocycle, bicyclic heterocycle or tricyclic heterocycle, wherein any phenyl, bicyclic aryl, monocyclic heteroaryl, bicyclic heteroaryl, tricyclic heteroaryl, monocyclic heterocycle, bicyclic heterocycle or tricyclic heterocycle of B is optionally substituted with one or more (e.g., 1, 2, 3, 4 or 5) $Z^{1b}$ groups.

A specific group of compounds of formula I' include compounds wherein A is phenyl, monocyclic heteroaryl or monocyclic heterocycle, wherein any phenyl, monocyclic heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, monocyclic heterocycle, or bicyclic heterocycle, wherein any phenyl, bicyclic aryl, monocyclic heteroaryl, bicyclic heteroaryl, monocyclic heterocycle or bicyclic heterocycle of B is optionally substituted with one or more (e.g., 1, 2, 3, 4 or 5) $Z^{1b}$ groups.

A specific group of compounds of formula I' include compounds wherein A is phenyl, 5-6 membered monocyclic heteroaryl or 3-7 membered monocyclic heterocycle, wherein any phenyl, 5-6 membered monocyclic heteroaryl or 3-7 membered monocyclic heterocycle of A is optionally substituted with one or more (e.g., 1, 2, 3, 4 or 5) $Z^{1a}$ groups, and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) $Z^{1b}$ groups.

A specific group of compounds of formula I' include compounds wherein A is monocyclic N-heteroaryl or monocyclic heterocycle, wherein any monocyclic N-heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, tricyclic heteroaryl, monocyclic heterocycle, bicyclic heterocycle or tricyclic heterocycle, wherein any phenyl, bicyclic aryl, monocyclic heteroaryl, bicyclic heteroaryl, tricyclic heteroaryl, monocyclic heterocycle, bicyclic heterocycle or tricyclic heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle, wherein any bicyclic aryl, bicyclic heteroaryl or bicyclic heterocycle is optionally substituted with one or more (e.g., 1, 2, 3, 4 or 5) $Z^{1b}$ groups.

A specific group of compounds of formula I' include compounds wherein A is monocyclic N-heteroaryl or monocyclic heterocycle, wherein any monocyclic N-heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, monocyclic heterocycle, or bicyclic heterocycle, wherein any phenyl, bicyclic aryl, monocyclic heteroaryl, bicyclic heteroaryl, monocyclic heterocycle or bicyclic heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle, wherein any bicyclic aryl, bicyclic heteroaryl or bicyclic heterocycle is optionally substituted with one or more (e.g., 1, 2, 3, 4 or 5) $Z^{1b}$ groups.

A specific group of compounds of formula I' include compounds wherein A is 5-6 membered monocyclic N-heteroaryl or 3-7 membered monocyclic heterocycle, wherein any 5-6 membered monocyclic N-heteroaryl or 3-7 membered monocyclic heterocycle of A is optionally substituted with one or more (e.g., 1, 2, 3, 4 or 5) $Z^{1a}$ groups, and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) $Z^{1b}$ groups; or A and B together form a 8-11 membered bicyclic aryl, 7-11 membered bicyclic heteroaryl or 6-11 membered bicyclic heterocycle, wherein any 8-11 membered bicyclic aryl, 7-11 membered bicyclic heteroaryl or 6-11 membered bicyclic heterocycle is optionally substituted with one or more (e.g., 1, 2, 3, 4 or 5) $Z^{1b}$ groups.

A specific group of compounds of formula I' include compounds wherein A is monocyclic N-heteroaryl or monocyclic heterocycle, wherein any monocyclic N-heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, tricyclic heteroaryl, monocyclic heterocycle, bicyclic heterocycle or tricyclic heterocycle, wherein any phenyl, bicyclic aryl, monocyclic heteroaryl, bicyclic heteroaryl, tricyclic heteroaryl, monocyclic heterocycle, bicyclic heterocycle or tricyclic heterocycle of B is optionally substituted with one or more (e.g., 1, 2, 3, 4 or 5) $Z^{1b}$ groups.

A specific group of compounds of formula I' include compounds wherein A is monocyclic N-heteroaryl or monocyclic heterocycle, wherein any monocyclic N-heteroaryl or monocyclic heterocycle of A is optionally substituted with one or more (e.g., 1, 2, 3, 4 or 5) $Z^{1a}$ groups, and B is phenyl, bicyclic aryl, monocyclic heteroaryl, bicyclic heteroaryl, monocyclic heterocycle, or bicyclic heterocycle, wherein any phenyl, bicyclic aryl, monocyclic heteroaryl, bicyclic heteroaryl, monocyclic heterocycle or bicyclic heterocycle of B is optionally substituted with one or more (e.g., 1, 2, 3, 4 or 5) $Z^{1b}$ groups.

A specific group of compounds of formula I' include compounds wherein A is 5-6 membered monocyclic N-heteroaryl or 3-7 membered monocyclic heterocycle, wherein any 5-6 membered monocyclic N-heteroaryl or 3-7 membered monocyclic heterocycle of A is optionally substituted with one or more (e.g., 1, 2, 3, 4 or 5) $Z^{1a}$ groups, and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) $Z^{1b}$ groups.

A specific group of compounds of formula I' include compounds wherein A is monocyclic N-heteroaryl, wherein any monocyclic N-heteroaryl of A is optionally substituted with one or more (e.g., 1, 2, 3, 4 or 5) $Z^{1a}$ groups, and B is phenyl, bicyclic aryl, monocyclic heteroaryl, bicyclic heteroaryl, tricyclic heteroaryl, monocyclic heterocycle, bicyclic heterocycle or tricyclic heterocycle, wherein any phenyl, bicyclic aryl, monocyclic heteroaryl, bicyclic heteroaryl, tricyclic heteroaryl, monocyclic heterocycle, bicyclic heterocycle or tricyclic heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle, wherein any bicyclic aryl, bicyclic heteroaryl or bicyclic heterocycle is optionally substituted with one or more (e.g., 1, 2, 3, 4 or 5) $Z^{1b}$ groups.

A specific group of compounds of formula I' include compounds wherein A is monocyclic N-heteroaryl, wherein any monocyclic N-heteroaryl of A is optionally substituted with one or more (e.g., 1, 2, 3, 4 or 5) $Z^{1a}$ groups, and B is phenyl, bicyclic aryl, monocyclic heteroaryl, bicyclic heteroaryl, monocyclic heterocycle or bicyclic heterocycle, wherein any phenyl, bicyclic aryl, monocyclic heteroaryl, bicyclic heteroaryl, monocyclic heterocycle or bicyclic heterocycle of B is optionally substituted with one or more (e.g., 1, 2, 3, 4 or 5) $Z^{1b}$ groups; or A and B together form a bicyclic aryl, bicyclic heteroaryl or bicyclic heterocycle, wherein any bicyclic aryl, bicyclic heteroaryl or bicyclic heterocycle is optionally substituted with one or more (e.g., 1, 2, 3, 4 or 5) $Z^{1b}$ groups.

A specific group of compounds of formula I' include compounds wherein A is 5-6 membered monocyclic N-heteroaryl, wherein any 5-6 membered monocyclic N-heteroaryl of A is optionally substituted with one or more (e.g., 1, 2, 3, 4 or 5) $Z^{1a}$ groups, and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) $Z^{1b}$ groups; or A and B together form a 8-11 membered bicyclic aryl, 7-11 membered bicyclic heteroaryl or 6-11 membered bicyclic heterocycle, wherein any 8-11 membered bicyclic aryl, 7-11 membered bicyclic heteroaryl or 6-11 membered bicyclic heterocycle is optionally substituted with one or more (e.g., 1, 2, 3, 4 or 5) $Z^{1b}$ groups.

A specific group of compounds of formula I' include compounds wherein A is monocyclic N-heteroaryl, wherein any monocyclic N-heteroaryl of A is optionally substituted with one or more (e.g., 1, 2, 3, 4 or 5) $Z^{1a}$ groups, and B is phenyl, bicyclic aryl, monocyclic heteroaryl, bicyclic heteroaryl, tricyclic heteroaryl, monocyclic heterocycle, bicyclic heterocycle or tricyclic heterocycle, wherein any phenyl, bicyclic aryl, monocyclic heteroaryl, bicyclic heteroaryl, tricyclic heteroaryl, monocyclic heterocycle, bicyclic heterocycle or tricyclic heterocycle of B is optionally substituted with one or more (e.g., 1, 2, 3, 4 or 5) $Z^{1b}$ groups.

A specific group of compounds of formula I' include compounds wherein A is monocyclic N-heteroaryl, wherein any monocyclic N-heteroaryl of A is optionally substituted with one or more (e.g., 1, 2, 3, 4 or 5) $Z^{1a}$ groups, and B is phenyl, bicyclic aryl, monocyclic heteroaryl, bicyclic heteroaryl, monocyclic heterocycle, or bicyclic heterocycle, wherein any phenyl, bicyclic aryl, monocyclic heteroaryl, bicyclic heteroaryl, monocyclic heterocycle or bicyclic heterocycle of B is optionally substituted with one or more (e.g., 1, 2, 3, 4 or 5) $Z^{1b}$ groups.

A specific group of compounds of formula I' include compounds wherein A is 5-6 membered monocyclic N-heteroaryl, wherein any 5-6 membered monocyclic N-heteroaryl of A is optionally substituted with one or more (e.g., 1, 2, 3, 4 or 5) $Z^{1a}$ groups, and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) $Z^{1b}$ groups.

A specific group of compounds of formula I' include compounds wherein A is 5-6 membered monocyclic N-heteroaryl, wherein any 5-6 membered monocyclic N-heteroaryl of A is optionally substituted with one or more (e.g., 1, 2, 3, 4 or 5) $Z^{1a}$ groups, and B is 3-7 membered monocyclic heterocycle, wherein any 3-7 membered monocyclic heterocycle of B is optionally substituted with one or more (e.g., 1, 2, 3, 4 or 5) $Z^{1b}$ groups; or A and B together form a 8-11 membered bicyclic aryl, 7-11 membered bicyclic heteroaryl or 6-11 membered bicyclic heterocycle, wherein any 8-11 membered bicyclic aryl, 7-11 membered bicyclic heteroaryl or 6-11 membered bicyclic heterocycle is optionally substituted with one or more (e.g., 1, 2, 3, 4 or 5) $Z^{1b}$ groups.

A specific group of compounds of formula I' include compounds wherein A is 5-6 membered monocyclic N-heteroaryl, wherein any 5-6 membered monocyclic N-heteroaryl of A is optionally substituted with one or more (e.g., 1, 2, 3, 4 or 5) $Z^{1a}$ groups, and B is 3-7 membered monocyclic heterocycle, wherein any 3-7 membered monocyclic heterocycle of B is optionally substituted with one or more (e.g., 1, 2, 3, 4 or 5) $Z^{1b}$ groups.

In one embodiment a monocyclic N-heteroaryl includes monocyclic heteroaryls which include one or two nitrogens in the monocyclic ring and which may optionally include one oxygen or one sulfur in the monocyclic ring.

In one embodiment a monocyclic N-heteroaryl includes monocyclic heteroaryls which include one or two nitrogens in the monocyclic ring.

In one embodiment a N-heteroaryl includes heteroaryls which include one or two nitrogens in the heteroary ring and which may optionally include one oxygen or one sulfur in the heteroaryl ring.

A specific value for A is phenyl, pyridinyl, pyrimidinyl, pyrazinyl, pyridinyl-2(1H)-one, tetrahydropyrimidin-2(1H)-one, imidazolidinyl-2-one, pyrrolidinyl-2-one , pyrrolidinyl, pyridazinyl, thiazolyl, pyrazin-2(1H)-one, piperazinyl-2-one, piperazinyl, imidazolyl, morpholinyl, 1,2,3,6-tetrahydropyridinyl or piperidinyl, wherein any phenyl, pyridinyl, pyrimidinyl, pyrazinyl, pyridinyl-2(1H)-one, tetrahydropyrimidin-2(1H)-one, imidazolidinyl-2-one, pyrrolidinyl-2-one , pyrrolidinyl, pyridazinyl, thiazolyl, pyrazin-2(1H)-one, piperazinyl-2-one, piperazinyl, imidazolyl, morpholinyl, 1,2,3,6-tetrahydropyridinyl or piperidinyl of A is optionally substituted with one or more (e.g., 1, 2, 3, 4 or 5) $Z^{1a}$ groups.

A specific value for A is 5-6 membered monocyclic N-heteroaryl, wherein any 5-6 membered monocyclic N-heteroaryl of A is optionally substituted with one or more (e.g., 1, 2, 3, 4 or 5) $Z^{1a}$ groups.

A specific value for A is 6 membered monocyclic N-heteroaryl, wherein any 6 membered monocyclic N-heteroaryl of A is optionally substituted with one or more (e.g., 1, 2, 3, 4 or 5) $Z^{1a}$ groups.

A specific value for A is pyridinyl or pyrimidinyl, wherein pyridinyl, or pyrimidinyl is optionally substituted with one or more (e.g., 1, 2, 3, 4 or 5) $Z^{1a}$ groups.

A specific value for A is pyridinyl, pyrimidinyl, pyrazinyl or pyridizinyl wherein the pyridinyl, pyrimidinyl, pyrazinyl or pyradizinyl is optionally substituted with one or more (e.g., 1, 2, 3, 4 or 5) $Z^{1a}$ groups.

A specific value for A is pyrimidinyl wherein the pyrimidinyl is optionally substituted with one or more (e.g., 1, 2, 3, 4 or 5) $Z^{1a}$ groups.

A specific value for B is selected from phenyl, pyridinyl, indazolyl, pyrazolo[4,3-b]pyridinyl, pyrimidinyl, pyrazolyl, benzo[d]imidazolyl, indazolyl, 1H-benzo[d]imidazolyl-2 (3H)-one, 2H-pyrido[3,2-b][1,4]oxazinyl-3(4H)-one, 2,6-naphthyridin-1(2H)-one, 1,7-naphthyridinyl-8(7H)-one, 1H-indazolyl-3 (2H)-one, quinolinyl-2(1H)-one, quinolinyl, pyrrolo[2,3-b]pyridinyl, pyrrolidinyl, piperazinyl, phenyl, imidazolyl, piperidinyl, morpholinyl, 5,6,7,8-tetrahydro-[1,2,4]triazolo[4,3-a]pyrazinyl, 4,5,6,7-tetrahydro-pyrazolo[4,3-c]pyridinyl, pyrazolo[1,5a]pyrimidinyl, pyrimidinyl-2,4(1H,3H)-dionyl, pyridinyl-2(1H)-one, 1H-pyrazolo[3,4-c]pyridinyl, indolinyl-2-one, 1H-pyrrolo[3,4-c]pyridinyl-3(2H)-one, 2,3-dihydro-1H-pyrrolo[3,2-c]pyridinyl, pyrazolyl, pyrimidinyl-2(1H)-one, azetidinyl, tetrahydro-2H-pyranyl, 3,6-dihydro-2,1-pyranyl, 1,2,3,6-tetrahydropyridine, 1H-pyrazolo[3,4-b]pyridinyl, 2H-benzo[b][1,4]oxaziyl-3(4H)-one, 3,4-dihydro-2H-pyrido[3,2-b][1,4]oxazinyl, indolinyl, 3,4-dihydrobenzo[f][1,4]oxazepin-5(2H)-one, 3H-imidazo[4,5-b]pyridinyl and 1H-benzo[d][1,2,3]triazolyl, wherein any phenyl, pyridinyl, indazolyl, pyrazolo[4,3-b]pyridinyl, pyrimidinyl, pyrazolyl, benzo[d]imidazolyl, indazolyl, 1H-benzo[d]imidazolyl-2(3H)-one, 2H-pyrido[3,2-b][1,4]oxazinyl-3(4H)-one, 2,6-naphthyridin-1(2H)-one, 1,7-naphthyridinyl-8(7H)-one, 1H-indazolyl-3(2H)-one, quinolinyl-2(1H)-one, quinolinyl, pyrrolo[2,3-b]pyridinyl, pyrrolidinyl, piperazinyl, phenyl, imidazolyl, piperidinyl, morpholinyl, 5,6,7,8-tetrahydro-[1,2,4]triazolo[4,3-a]pyrazinyl, 4,5,6,7-tetrahydro-pyrazolo[4,3-c]pyridinyl, pyrazolo[1,5-a]pyrimidinyl, pyrimidinyl-2,4 (1H,3H)-dionyl, pyridinyl-2(1H)-one, 1H-pyrazolo[3,4-c]pyridinyl, indolinyl-2-one, 1H-pyrrolo[3,4-c]pyridinyl-3 (2H)-one, 2,3-dihydro-1H-pyrrolo[3,2-c]pyridinyl, pyrazolyl, pyrimidinyl-2(1H)-one, azetidinyl, tetrahydro-2H-pyranyl, 3,6-dihydro-2H-pyranyl, 1,2,3,6-tetrahydropyridine, 1H-pyrazolo[3,4-b]pyridinyl, 2H-benzo[b][1,4]oxaziyl-3(4H)-one, 3,4-dihydro-2H-pyrido[3,2-b][1,4]oxazinyl, indolinyl, 3,4-dihydrobenzo[f][1,4]oxazepin-5(2H)-one, 3H-imidazo[4,5-b]pyridinyl, and 1H-benzo[d][1,2,3]triazolyl of B is optionally substituted with one or more (e.g., 1, 2, 3, 4 or 5) $Z^{1b}$ groups.

A specific value for B is 3-7 membered monocyclic heterocycle, wherein any 3-7 membered monocyclic heterocycle of B is optionally substituted with one or more (e.g., 1, 2, 3, 4 or 5) $Z^{1b}$ groups.

A specific value for B is 4-7 membered monocyclic heterocycle, wherein any 4-7 membered monocyclic heterocycle of B is optionally substituted with one or more (e.g., 1, 2, 3, 4 or 5) $Z^{1b}$ groups.

A specific value for B is 4-6 membered monocyclic heterocycle, wherein any 4-6 membered monocyclic heterocycle of B is optionally substituted with one or more (e.g., 1, 2, 3, 4 or 5) $Z^{1b}$ groups.

A specific value for B is piperazinyl or azetidinyl, wherein any piperazinyl or azetidinyl of B is optionally substituted with one or more (e.g., 1, 2, 3, 4 or 5) $Z^{1b}$ groups.

A specific group or compounds of formula I' include compounds wherein A-B is:

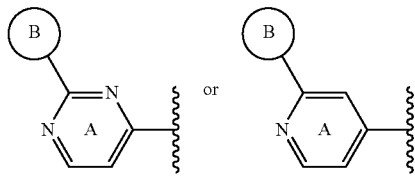

wherein A is optionally substituted with one or more (e.g., 1, 2, 3, 4 or 5) $Z^{1a}$ groups and B is phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle, wherein any phenyl, 8-11 membered bicyclic aryl, 5-6 membered monocyclic heteroaryl, 7-11 membered bicyclic heteroaryl, 3-7 membered monocyclic heterocycle or 6-11 membered bicyclic heterocycle of B is optionally substituted with one or more (e.g., 1, 2, 3, 4 or 5) $Z^{1b}$ groups.

A specific group of compounds of formula I' include compounds wherein A-B is:

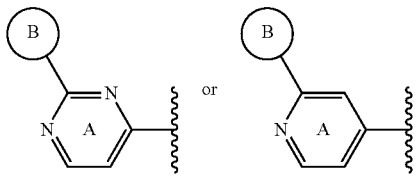

wherein A is optionally substituted with one or more (e.g., 1, 2, 3, 4 or 5) $Z^{1a}$ groups and B is 3-7 membered monocyclic heterocycle wherein any 3-7 membered monocyclic heterocycle of B is optionally substituted with one or more (e.g., 1, 2, 3, 4 or 5) $Z^{1b}$ groups.

A specific group of compounds of formula I' include compounds wherein A-B is:

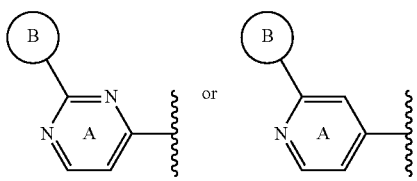

wherein B is azetidinyl or piperazinyl, wherein any azetidinyl or piperazinyl of B is optionally substituted with one or more (e.g., 1, 2, 3, 4 or 5) $Z^{1b}$ groups.

A specific group of compounds of formula I' are compounds wherein A and B together form a pyrrolopyridinyl, pyrazolopyridine or indazolyl, wherein the pyrrolopyridinyl, pyrazolopyridine or indazolyl is optionally substituted with one or more $Z^{1b}$ groups.

A specific group of compounds of formula I' include compounds wherein A and B together form a bicyclic aryl, bicyclic heteroaryl or bicyclic heterocycle, wherein the bicyclic aryl, bicyclic heteroaryl or bicyclic heterocycle is optionally substituted with one or more (e.g., 1, 2, 3, 4 or 5) $Z^{1b}$ groups.

A specific group of compounds of formula I' include compounds wherein A and B together form a 8-11 membered bicyclic aryl, 7-11 membered bicyclic heteroaryl or 6-11 membered bicyclic heterocycle, wherein the 8-11 membered bicyclic aryl, 7-11 membered bicyclic heteroaryl or 6-11 membered bicyclic heterocycle is optionally substituted with one or more (e.g., 1, 2, 3, 4 or 5) $Z^{1b}$ groups.

A specific group of compounds of formula I' include compounds wherein A and B together form a 7-11 membered bicyclic heteroaryl or 6-11 membered bicyclic heterocycle, wherein the 7-11 membered bicyclic heteroaryl or 6-11 membered bicyclic heterocycle is optionally substituted with one or more (e.g., 1, 2, 3, 4 or 5) $Z^{1b}$ groups.

A specific group of compounds of formula I' include compounds wherein A and B together form a 7-11 membered bicyclic heteroaryl, wherein the 7-11 membered bicyclic heteroaryl is optionally substituted with one or more (e.g., 1, 2, 3, 4 or 5) $Z^{1b}$ groups.

A specific group of compounds of formula I' include compounds wherein A and B together form a 9-10 membered bicyclic heteroaryl or 9-11 membered bicyclic heterocycle, wherein the 9-10 membered bicyclic heteroaryl or 9-11 membered bicyclic heterocycle is optionally substituted with one or more (e.g., 1, 2, 3, 4 or 5) $Z^{1b}$ groups.

A specific group of compounds of formula I' include compounds wherein A and B together form a 9-10 membered bicyclic heteroaryl, wherein the 9-10 membered bicyclic heteroaryl is optionally substituted with one or more (e.g., 1, 2, 3, 4 or 5) $Z^{1b}$ groups.

A specific group of compounds of formula I' include compounds wherein A and B together form a 9-10 membered bicyclic heteroaryl, wherein the 9-10 membered bicyclic heteroaryl includes 1-4 nitrogen atoms, and wherein the 9-10 membered bicyclic heteroaryl is optionally substituted with one or more (e.g., 1, 2, 3, 4 or 5) $Z^{1b}$ groups.

A specific group of compounds of formula I' include compounds wherein A and B together form a 9-10 membered bicyclic heteroaryl, wherein the 9-10 membered bicyclic heteroaryl includes 2 or 3 nitrogen atoms, and wherein the 9-10 membered bicyclic heteroaryl is optionally substituted with one or more (e.g., 1, 2, 3, 4 or 5) $Z^{1b}$ groups.

A specific group of compounds of formula I' include compounds wherein A and B together form an indazolyl, wherein the indazolyl is optionally substituted with one or more (e.g., 1, 2, 3, 4 or 5) $Z^{1b}$ groups.

A specific group of compounds of formula I' are compounds wherein A and B together form a pyrazolo[4,3-b]pyridinyl, pyrrolo[2,3-b]pyridinyl, indazolyl, pyrazolo[3,4-b]pyridinyl, 2,7-naphthyridinyl-1(2H)-one, benzoimidazolyl, benzo[1,2,3]triazolyl, pyrazolo[3,4-c]pyridinyl, pyrrolo[3,2-c]pyridinyl, [1,2,4]triazolo[4,3-a]pyridinyl, [1,2,3]triazolo[1,5-a]pyridinyl, imidazo[1,5-a]pyridinyl, pyrazolo[4,3-c]pyridinyl, isoquinolinyl, benzothiazolyl, 1H-pyrazolo[4,3-d]pyrimidinyl or 2,6-naphthyridin-1(2H)-one, wherein the pyrazolo[4,3-b]pyridinyl, pyrrolo[2,3-b]pyridinyl, indazolyl, pyrazolo[3,4-b]pyridinyl, 2,7-naphthyridinyl-1(2H)-one, benzoimidazolyl, benzo[1,2,3]triazolyl, pyrazolo[3,4-c]pyridinyl, pyrrolo[3,2-c]pyridinyl, [1,2,4]triazolo[4,3-a]pyridinyl, [1,2,3]triazolo[1,5-a]pyridinyl, imidazo[1,5-a]pyridinyl, pyrazolo[4,3-c]pyridinyl, isoquinolinyl, benzothiazolyl, 1H-pyrazolo[4,3-d]pyrimidinyl or 2,6-naphthyridin-1(2H)-one is optionally substituted with one or more (e.g., 1, 2, 3, 4 or 5) $Z^{1b}$ groups.

A specific group of compounds of formula I' are compounds wherein A and B together form a 1H-benzo[d]imidazolyl-2(3H)-one, 1H-indazolyl-3(2H)-one, 5,6,7,8-tetrahydro-1,6-naphthyridinyl, 1,2,3,4-tetrahydroisoquinolinyl, indolinyl-2-one, isoindolinyl-1-one, indolinyl, 4,5,6,7-tetrahydro-1H-imidazo[4,5-c]pyridinyl, 5,6,7,8-tetrahydro-[1,2,4]triazolo[4,3-a]pyrazinyl, 2H-benzo[b][1,4]oxazinyl-3(4H)-one, 5,6,7,8-tetrahydro-1,7-naphthyridinyl, 2,3-dihydro-1H-pyrrolo[3,4-c]pyridinyl, 1,2,3,4-tetrahydro-2,7-naphthyridinyl, 6,7-dihydro-5H-pyrrolo[3,4-b]pyridinyl, 1,2,3,4-tetrahydro-2,6-naphthyridinyl, decahydroisoquinolinyl, 4,5,6,7-tetrahydro-1H-pyrazolo[4,3-c]pyridinyl, isoindolinyl or 2,3-dihydrobenzo[b][1,4]dioxinyl, wherein the 1H-benzo[d]imidazolyl-2(3H)-one, 1H-indazolyl-3(2H)-one, 5,6,7,8-tetrahydro-1,6-naphthyridinyl, 1,2,3,4-tetrahydroisoquinolinyl, indolinyl-2-one, isoindolinyl-1-one, indolinyl, 4,5,6,7-tetrahydro-1H-imidazo[4,5-c]pyridinyl, 5,6,7,8-tetrahydro-[1,2,4]triazolo[4,3-a]pyrazinyl, 2H-benzo[b][1,4]oxazinyl-3(4H)-one, 5,6,7,8-tetrahydro-1,7-naphthyridinyl, 2,3-dihydro-1H-pyrrolo[3,4-c]pyridinyl, 1,2,3,4-tetrahydro-2,7-naphthyridinyl, 6,7-dihydro-5H-pyrrolo[3,4-b]pyridinyl, 1,2,3,4-tetrahydro-2,6-naphthyridinyl, decahydroisoquinolinyl, 4,5,6,7-tetrahydro-1H-pyrazolo[4,3-c]pyridinyl, isoindolinyl or 2,3-dihydrobenzo[b][1,4]dioxinyl, is optionally substituted with one or more (e.g., 1, 2, 3, 4 or 5) $Z^{1b}$ groups.

A specific group of compounds of formula I' are compounds wherein A and B together form a pyrazolo[4,3-b]pyridinyl, pyrrolo[2,3-b]pyridinyl, indazolyl, pyrazolo[3,4-b]pyridinyl, 2,7-naphthyridinyl-1(2H)-one, benzoimidazolyl, benzo[1,2,3]triazolyl, pyrazolo[3,4-c]pyridinyl, pyrrolo[3,2-c]pyridinyl, [1,2,4]triazolo[4,3-a]pyridinyl, [1,2,3]triazolo[1,5-a]pyridinyl, imidazo[1,5-a]pyridinyl, pyrazolo[4,3-c]pyridinyl, isoquinolinyl, benzothiazolyl, 1H-pyrazolo[4,3-d]pyrimidinyl, 2,6-naphthyridin-1 (2H)-one, 1H-benzo[d]imidazolyl-2(3H)-one, 1H-indazolyl-3(2H)-one, 5,6,7,8-tetrahydro-1,6-naphthyridinyl, 1,2,3,4-tetrahydroisoquinolinyl, indolinyl-2-one, isoindolinyl-1-one, indolinyl, 4,5,6,7-tetrahydro-1H-imidazo[4,5-c]pyridinyl, 5,6,7,8-tetrahydro-[1,2,4]triazolo[4,3-a]pyrazinyl, 2H-benzo[b][1,4]oxazinyl-3(4H)-one, 5,6,7,8-tetrahydro-1,7-naphthyridinyl, 2,3-dihydro-1H-pyrrolo[3,4-c]pyridinyl, 1,2,3,4-tetrahydro-2,7-naphthyridinyl, 6,7-dihydro-5H-pyrrolo[3,4-b]pyridinyl, 1,2,3,4-tetrahydro-2,6-naphthyridinyl, decahydroisoquinolinyl, 4,5,6,7-tetrahydro-1H-pyrazolo[4,3-c]pyridinyl, isoindolinyl or 2,3-dihydrobenzo[b][1,4]dioxinyl, wherein the pyrazolo[4,3-b]pyridinyl, pyrrolo[2,3-b]pyridinyl, indazolyl, pyrazolo[3,4-b]pyridinyl, 2,7-naphthyridinyl-1(2H)-one, benzoimidazolyl, benzo[1,2,3]triazolyl, pyrazolo[3,4-c]pyridinyl, pyrrolo[3,2-c]pyridinyl, [1,2,4]triazolo[4,3-a]pyridinyl, [1,2,3]triazolo[1,5-a]pyridinyl, imidazo[1,5-a]pyridinyl, pyrazolo[4,3-c]pyridinyl, isoquinolinyl, benzothiazolyl, 1H-pyrazolo[4,3-d]pyrimidinyl, 2,6-naphthyridin-1 (2H)-one, 1H-benzo[d]imidazolyl-2(3H)-one, 1H-indazolyl-3(2H)-one, 5,6,7,8-tetrahydro-1,6-naphthyridinyl, 1,2,3,4-tetrahydroisoquinolinyl, indolinyl-2-one, isoindolinyl-1-one, indolinyl, 4,5,6,7-tetrahydro-1H-imidazo[4,5-c]pyridinyl, 5,6,7,8-tetrahydro-[1,2,4]triazolo[4,3-a]pyrazinyl, 2H-benzo[b][1,4]oxazinyl-3 (4H)-one, 5,6,7,8-tetrahydro-1,7-naphthyridinyl, 2,3-dihydro-1H-pyrrolo[3,4-c]pyridinyl, 1,2,3,4-tetrahydro-2,7-naphthyridinyl, 6,7-dihydro-5H-pyrrolo[3,4-b]pyridinyl, 1,2,3,4-tetrahydro-2,6-naphthyridinyl, decahydroisoquinolinyl, 4,5,6,7-tetrahydro-1H-pyrazolo[4,3-c]pyridinyl, isoindolinyl or 2,3-dihydrobenzo[b][1,4]dioxinyl is optionally substituted with one or more (e.g., 1, 2, 3, 4 or 5) $Z^{1b}$ groups.

A specific group of compounds of formula I' include compounds wherein A-B is:

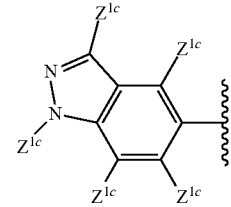

wherein each $Z^{1c}$ is H or $Z^{1b}$.

A specific group of compounds of formula I' include compounds wherein A-B is:

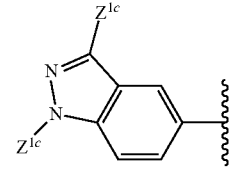

wherein each $Z^{1c}$ is H or $Z^{1b}$.

A specific value for each $Z^{1a}$ is halo, $(C_1-C_3)$alkyl, $(C_1-C_3)$haloalkyl, $(C_3-C_7)$carbocycle, 3-7 membered monocyclic heterocycle, —O$(C_1-C_3)$alkyl, —O$(C_2-C_3)$alkenyl, —O$(C_2-C_3)$alkynyl, —NR$_c$R$_d$, —NR$_d$C(O)R$_a$, —C(O)OR$_b$, and —C(O)NR$_c$R$_d$, wherein any $(C_3-C_7)$carbocycle or 3-7 membered monocyclic heterocycle of $Z^{1a}$ is optionally substituted with one or more (e.g., 1, 2, 3, 4 or 5) halogen or $(C_1-C_6)$alkyl.

A specific value for $Z^{1a}$ is halo, $(C_1-C_3)$alkyl, $(C_1-C_3)$haloalkyl, —O$(C_1-C_3)$alkyl or —C(O)OR$_b$.

A specific value for each $Z^{1b}$ is independently selected from halo, CN, $(C_1-C_6)$alkyl, $(C_1-C_6)$haloalkyl, $(C_3-C_7)$carbocycle, heteroaryl, heterocycle, aryl$(C_1-C_6)$alkyl-, —OH, —O$(C_1-C_6)$alkyl, —NR$_c$R$_d$, —C(O)OR$_b$, and —C(O)NR$_c$R$_d$, wherein any $(C_3-C_7)$carbocycle or heterocycle of $Z^{1b}$ is optionally substituted with one or more (e.g., 1, 2, 3, 4 or 5) halogen or $(C_1-C_6)$alkyl.

A specific value for $Z^{1b}$ is halo, CN, $(C_1-C_6)$alkyl, $(C_1-C_6)$haloalkyl, $(C_3-C_7)$carbocycle, monocyclic heteroaryl, monocyclic heterocycle, phenyl$(C_1-C_6)$alkyl-, —OH, —O$(C_1-C_6)$alkyl, —NR$_c$R$_d$, —C(O)OR$_b$ and —C(O)NR$_c$R$_d$, wherein any $(C_3-C_7)$carbocycle or monocyclic heterocycle of $Z^{1b}$ is optionally substituted with one or more (e.g., 1, 2, 3, 4 or 5) halogen or $(C_1-C_6)$alkyl.

A specific value for $Z^{1b}$ is halo, CN, $(C_1-C_6)$alkyl, $(C_1-C_6)$haloalkyl, $(C_3-C_7)$carbocycle, 5-6 membered monocyclic heteroaryl, 3-7 membered monocyclic heterocycle, aryl$(C_1-C_6)$alkyl-, —OH, —O$(C_1-C_6)$alkyl, —C(O)OR$_b$ or —C(O)NR$_c$R$_d$, wherein any $(C_3-C_7)$carbocycle or 5-6 membered monocyclic heterocycle of $Z^{1b}$ is optionally substituted with one or more (e.g., 1, 2, 3, 4 or 5) halogen or $(C_1-C_6)$alkyl.

A specific value for each $Z^{1b}$ is $(C_1-C_6)$alkyl, heteroaryl, heterocycle or —NR$_c$R$_d$, wherein any heterocycle of $Z^{1b}$ is optionally substituted with one or more (e.g., 1, 2, 3, 4 or 5) halogen or $(C_1-C_6)$alkyl.

A specific value for $Z^{1b}$ is $(C_1-C_6)$alkyl, monocyclic heteroaryl, monocyclic heterocycle or —NR$_c$R$_d$, wherein any monocyclic heterocycle of $Z^{1b}$ is optionally substituted with one or more (e.g., 1, 2, 3, 4 or 5) halogen or $(C_1-C_6)$alkyl.

A specific value for $Z^{1b}$ is $(C_1-C_6)$alkyl, 5-6 membered monocyclic heteroaryl, 3-7 membered monocyclic heterocycle or —NR$_c$R$_d$, wherein any 5-6 membered monocyclic heterocycle of $Z^{1b}$ is optionally substituted with one or more (e.g., 1, 2, 3, 4 or 5) halogen or $(C_1-C_6)$alkyl.

A specific value for $Z^{1b}$ is methyl, isopropyl, —N(CH$_3$)$_2$, oxetanyl, pyridinyl, N-methylpiperazinyl.

A specific value for $Z^{1b}$ is methyl, pyridinyl or N-methylpiperazinyl.

A specific value for $Z^{1b}$ isopropyl, —N(CH$_3$)$_2$ or oxetanyl.

In one embodiment a compound is selected from:

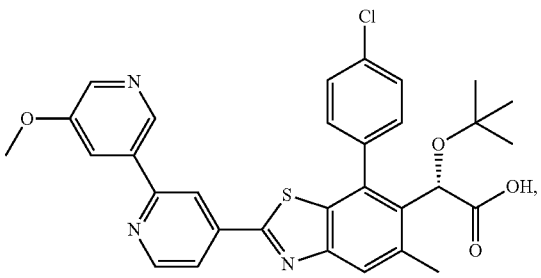

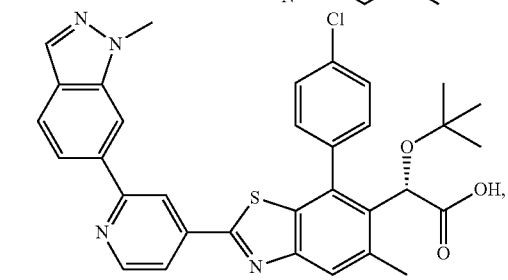

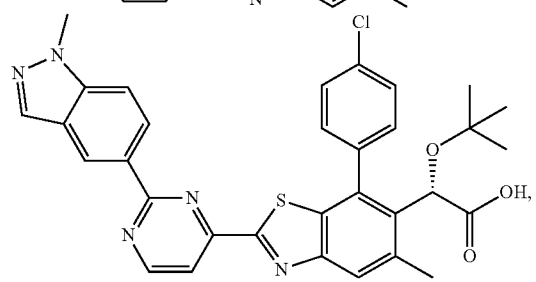

-continued

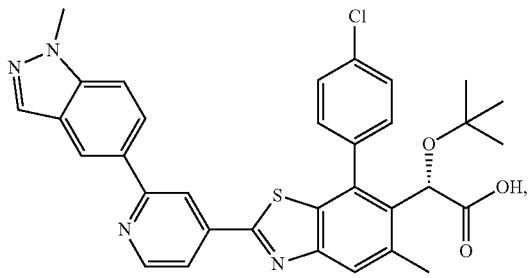

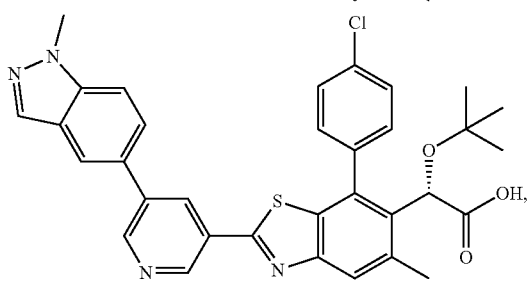

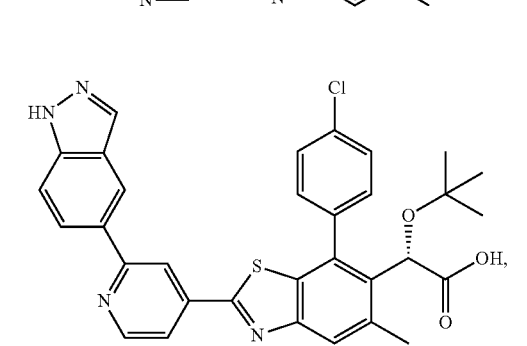

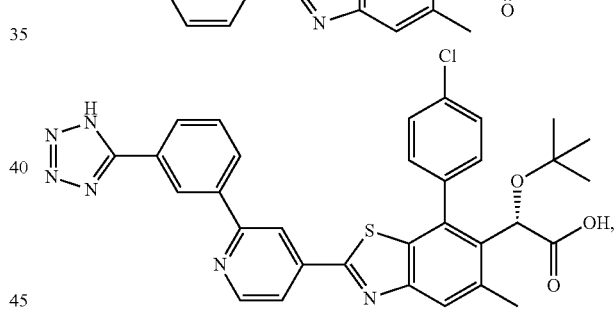

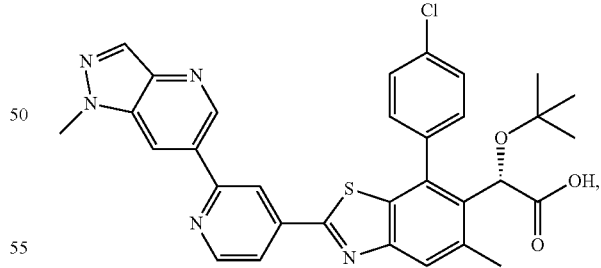

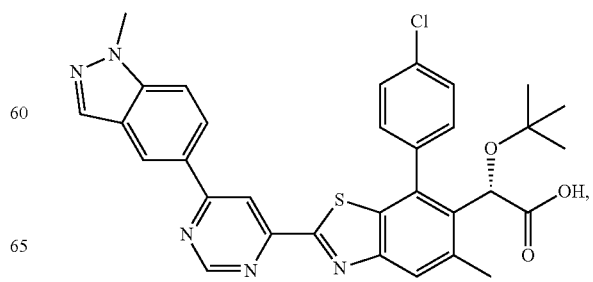

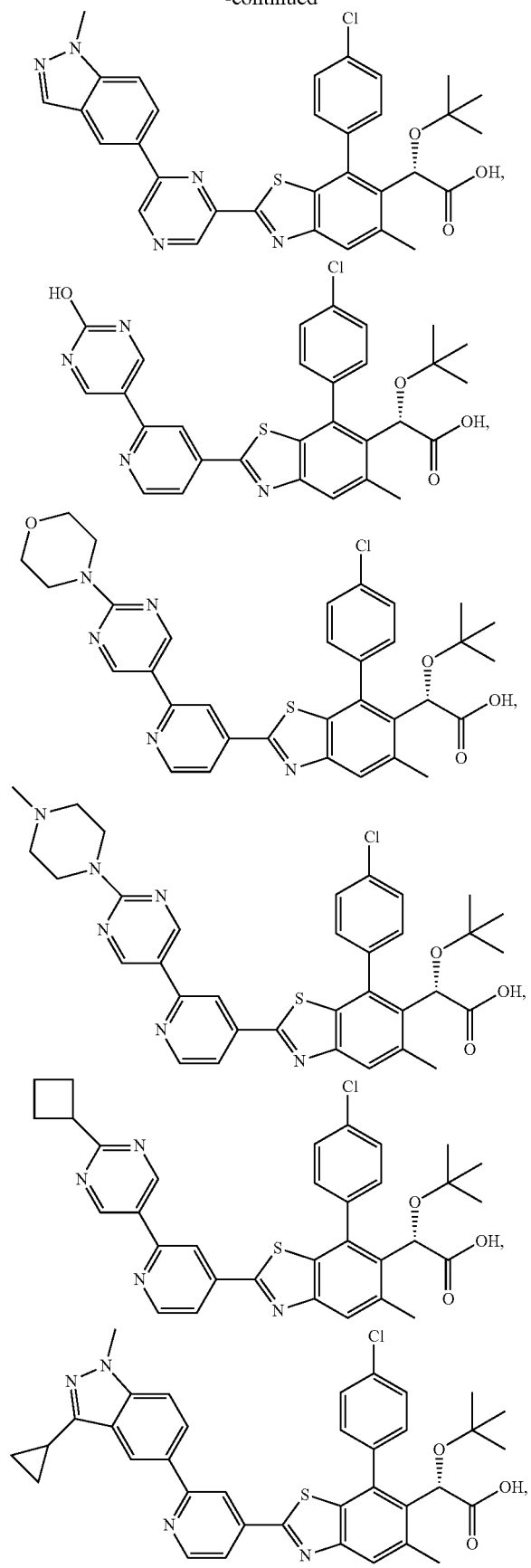
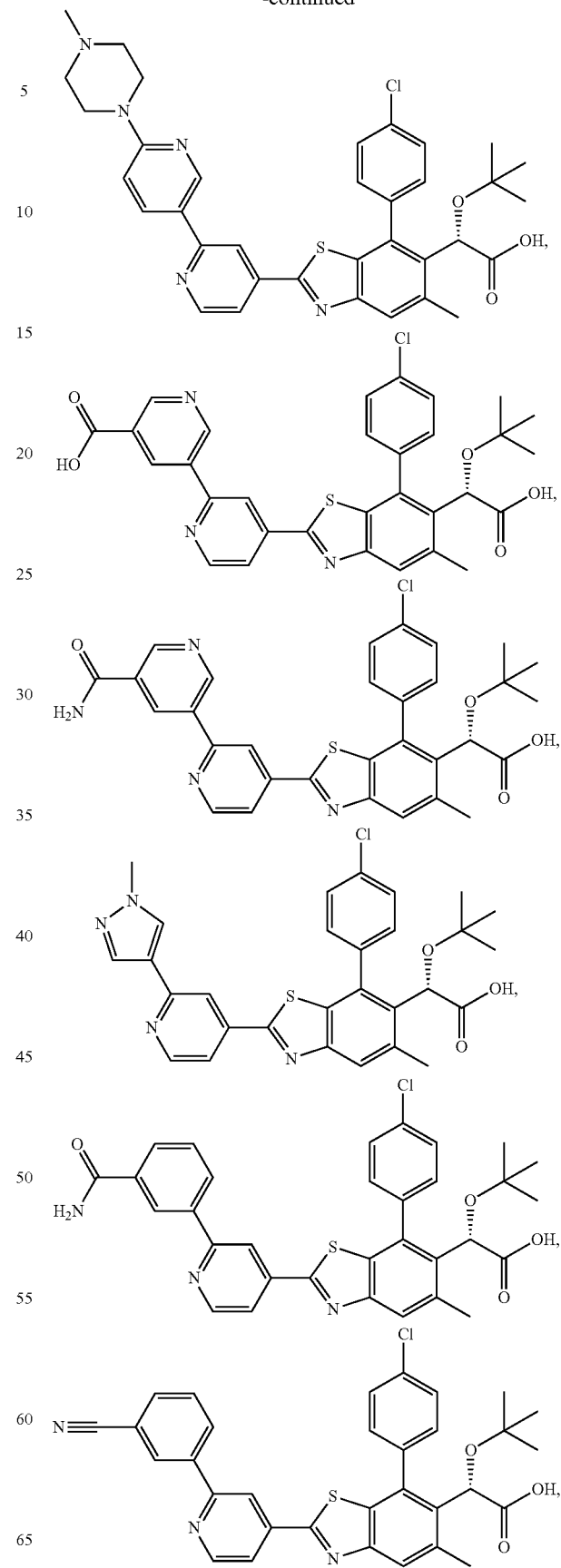

115
-continued
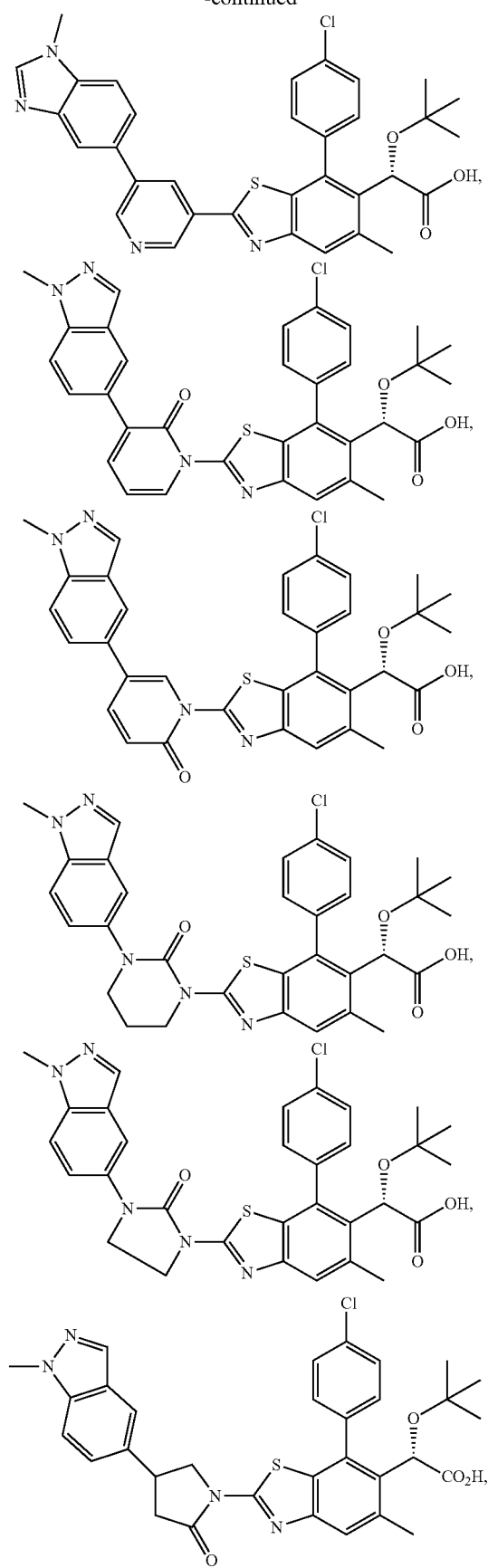
116
-continued
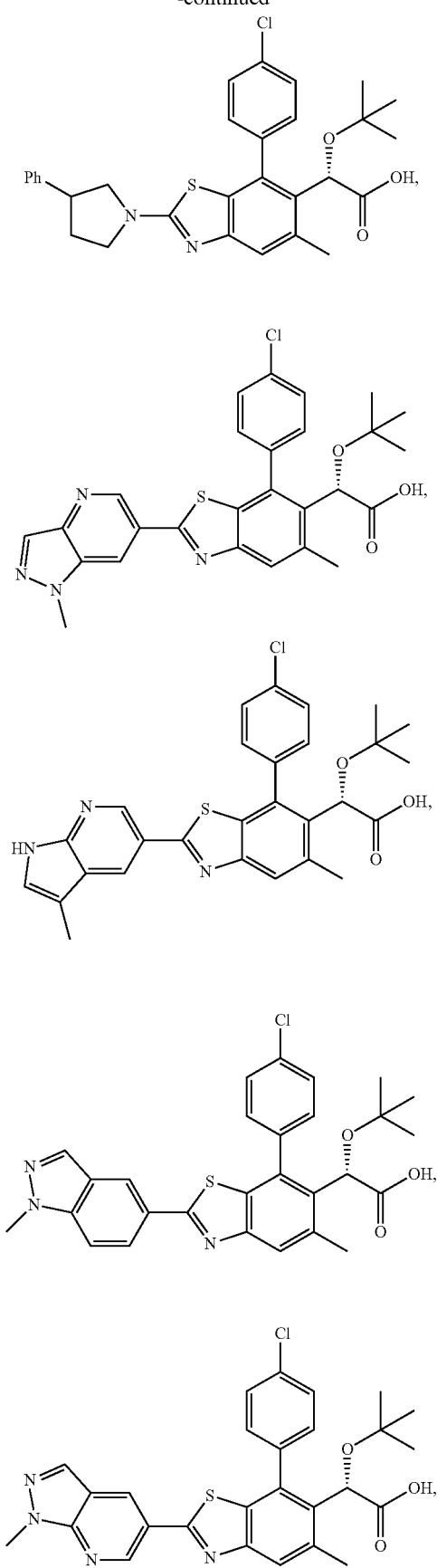

117
-continued
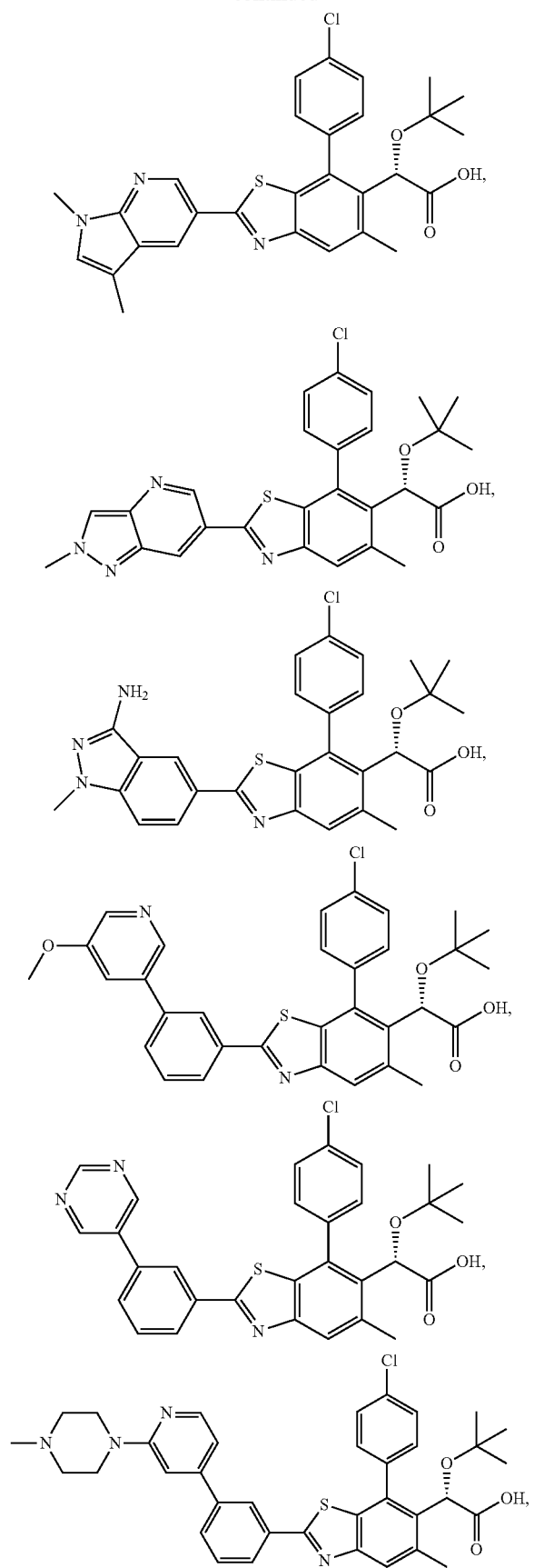
118
-continued
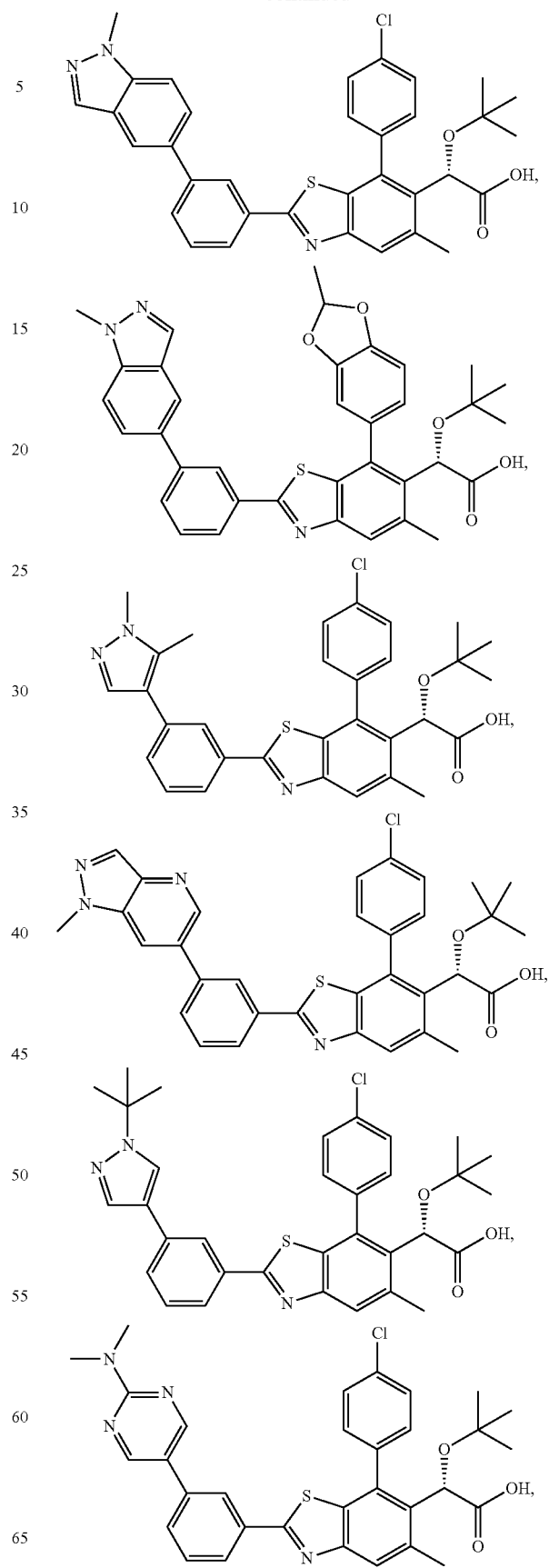

119
-continued
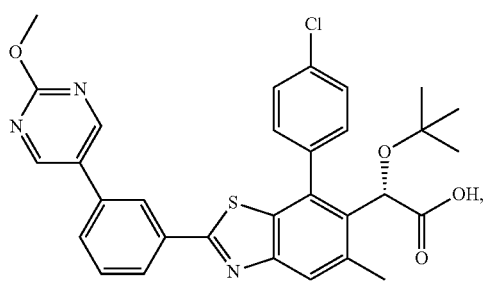
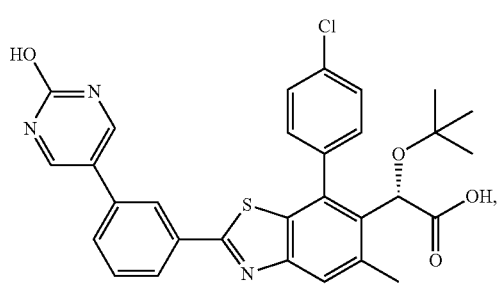
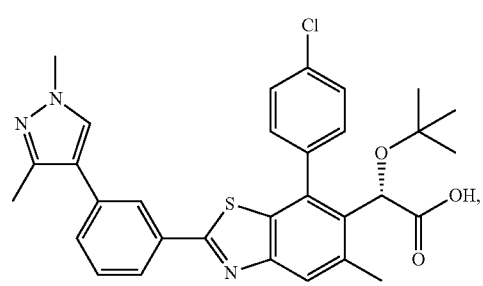
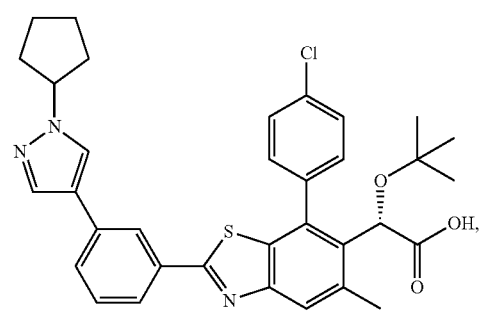
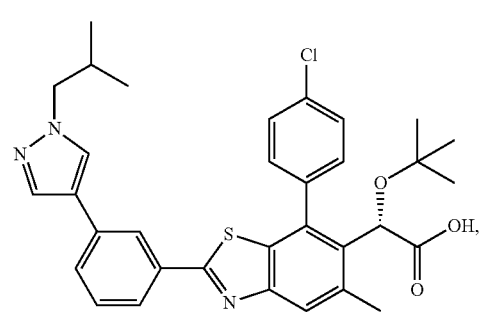
120
-continued
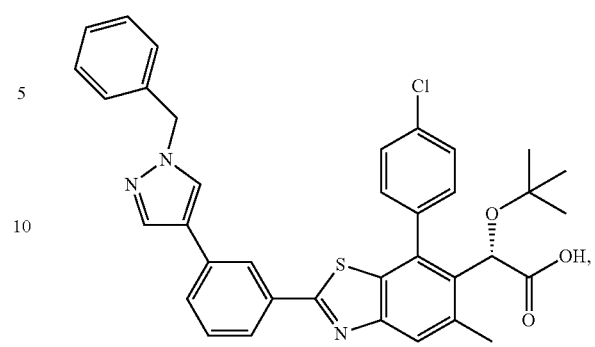
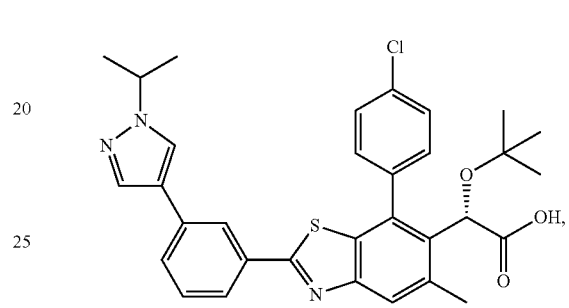
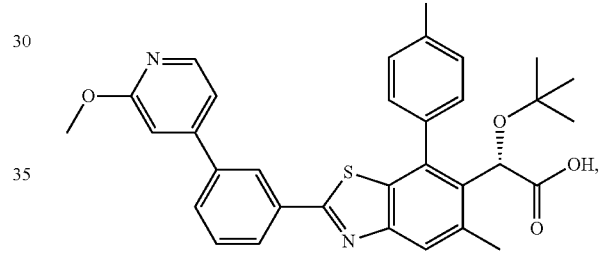
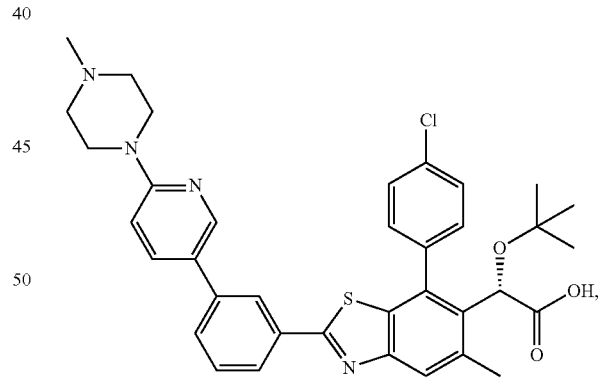
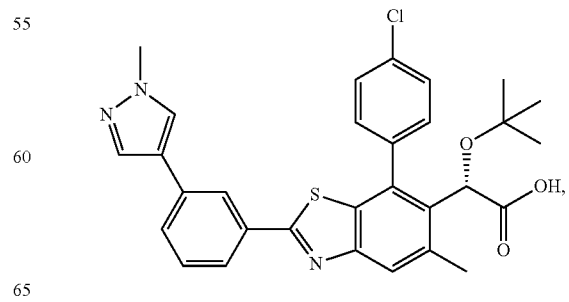

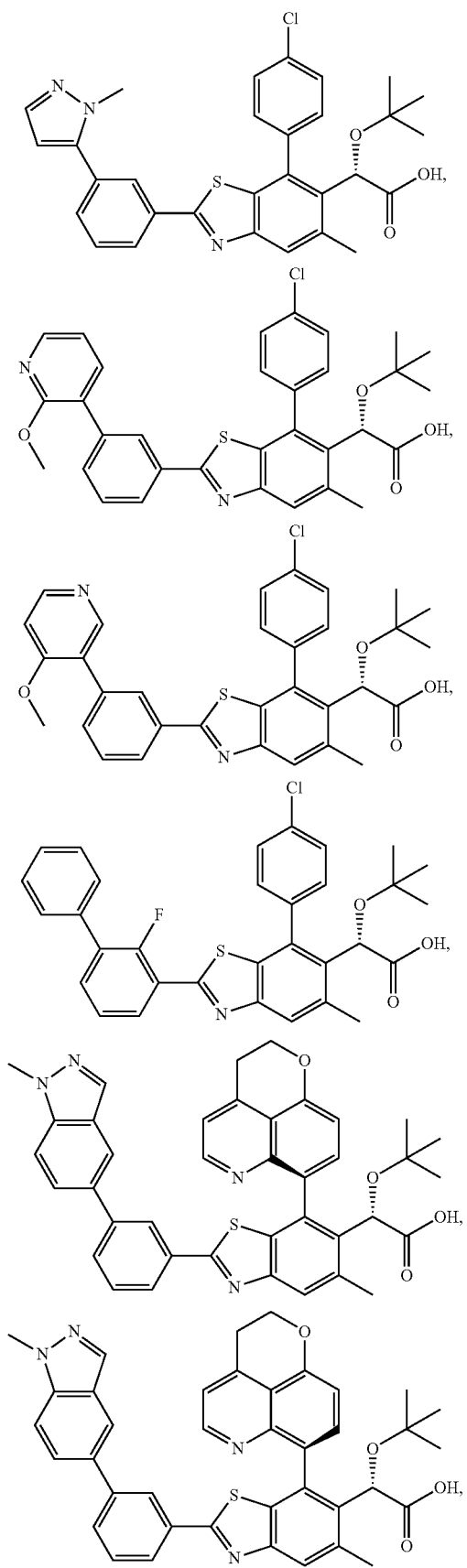
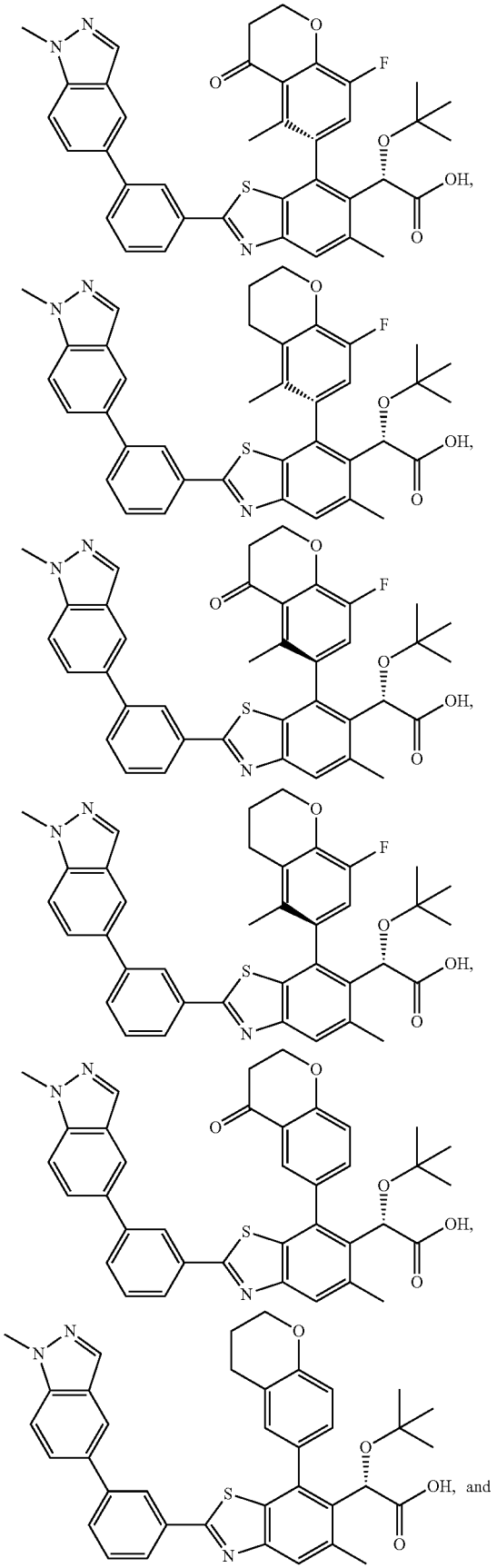

123
-continued
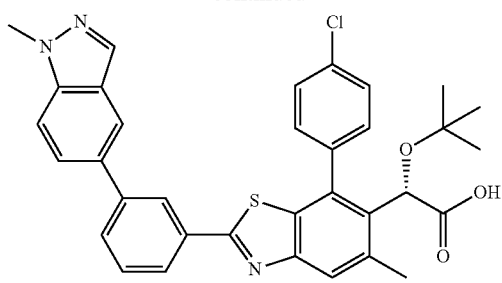
and salts thereof.
In one embodiment a compound is selected from:
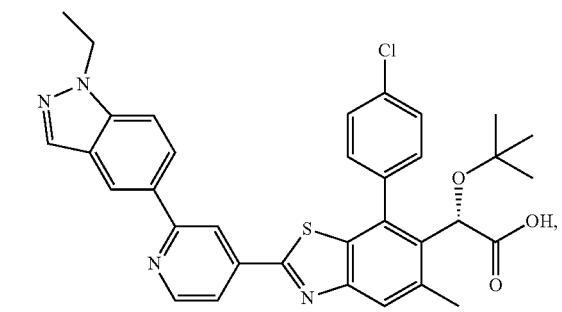
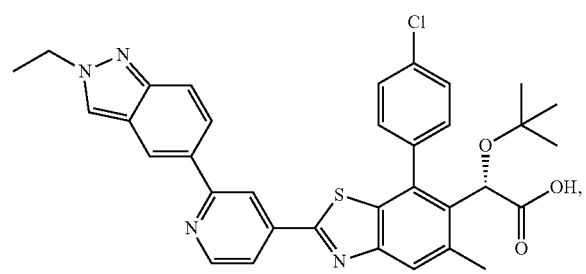
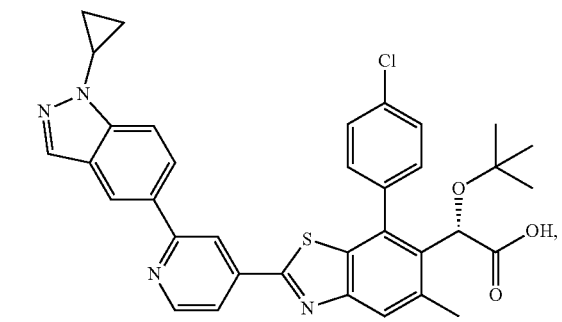
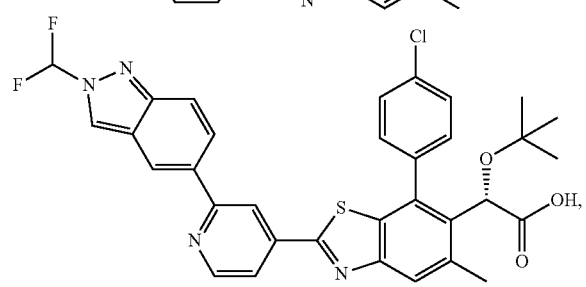
124
-continued
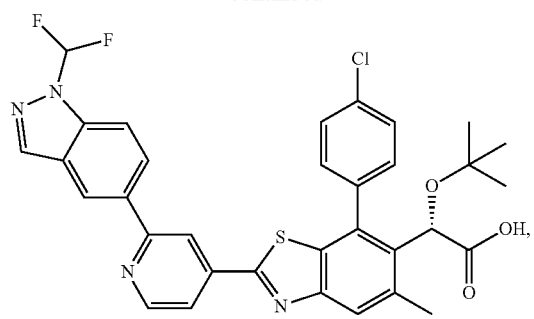
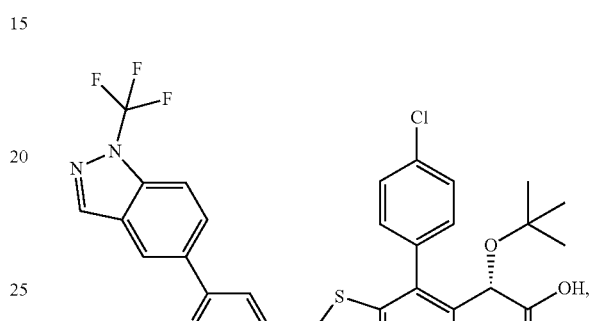
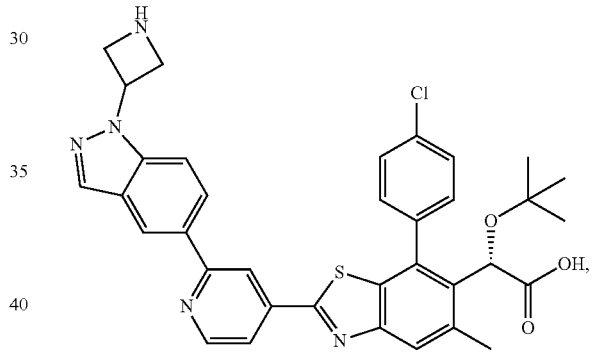
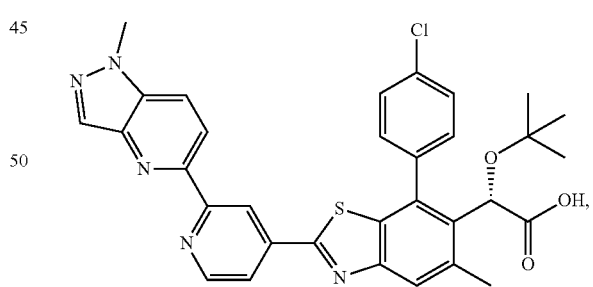
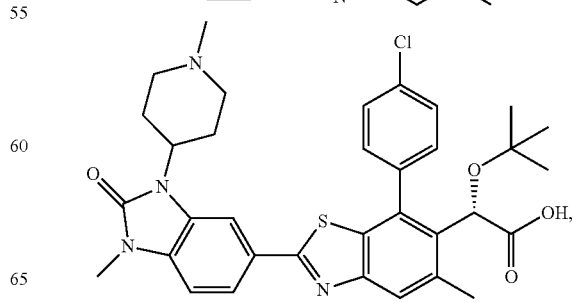

125
-continued
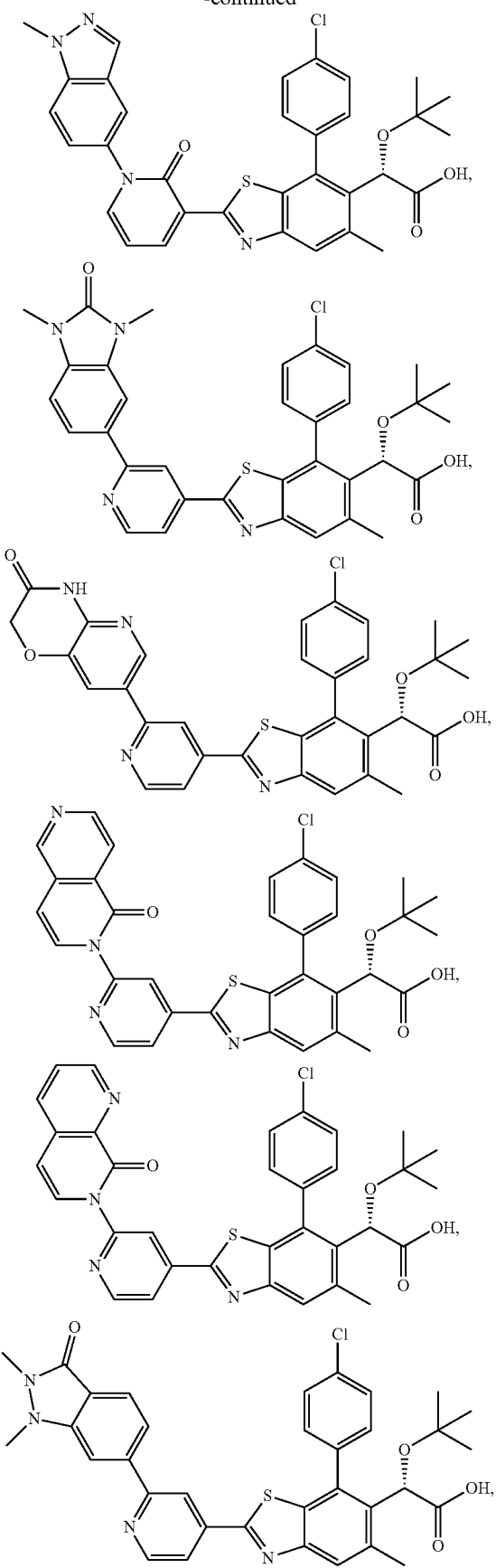
126
-continued
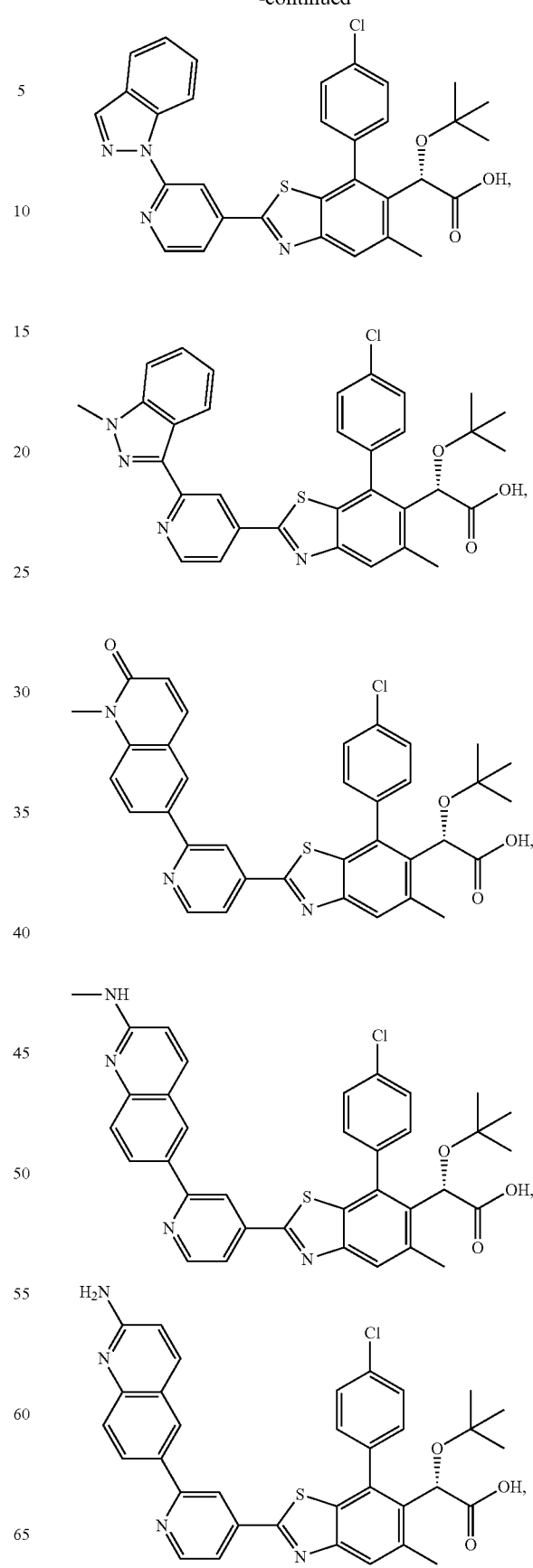

127
-continued
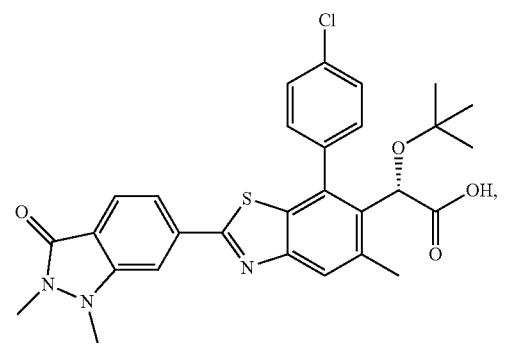
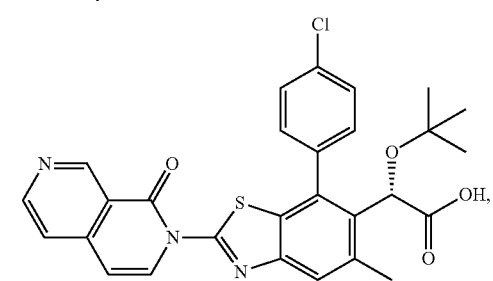
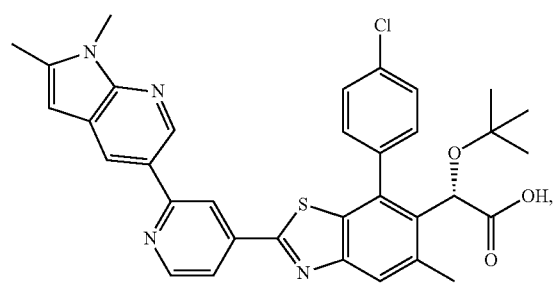
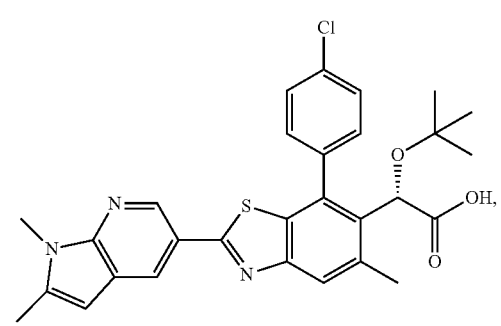
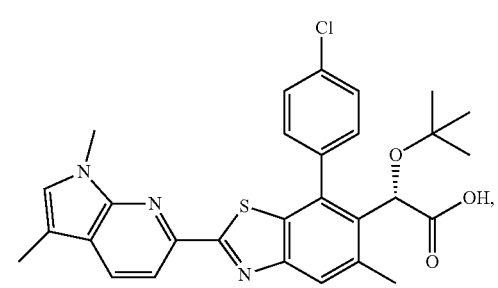
128
-continued
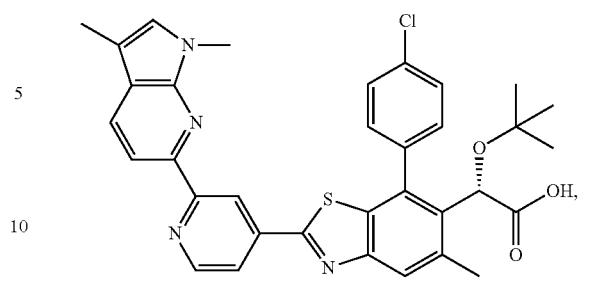
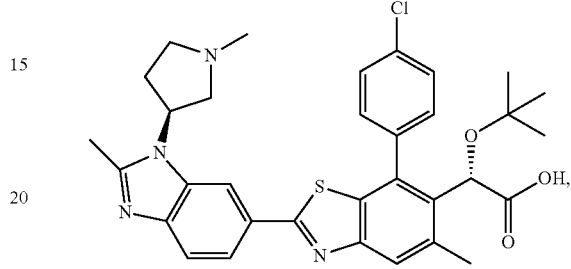
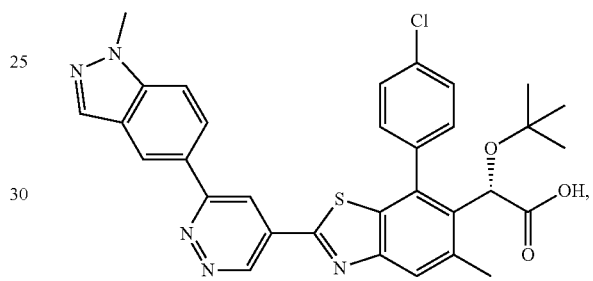
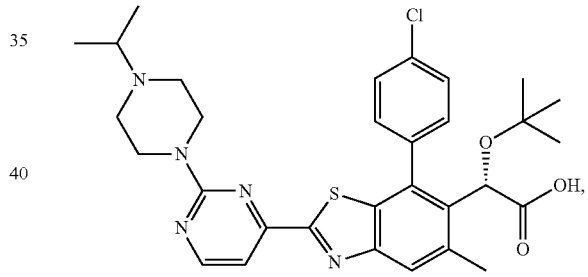
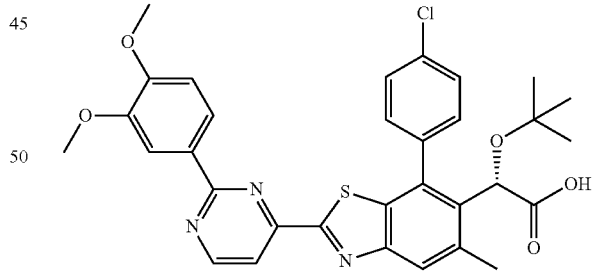
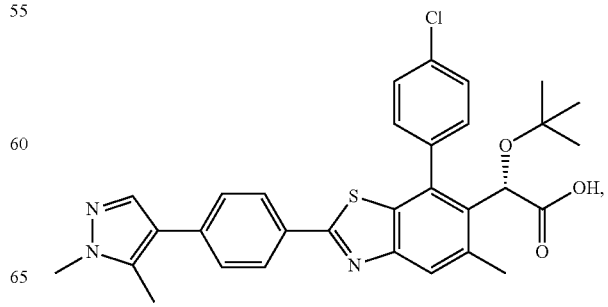

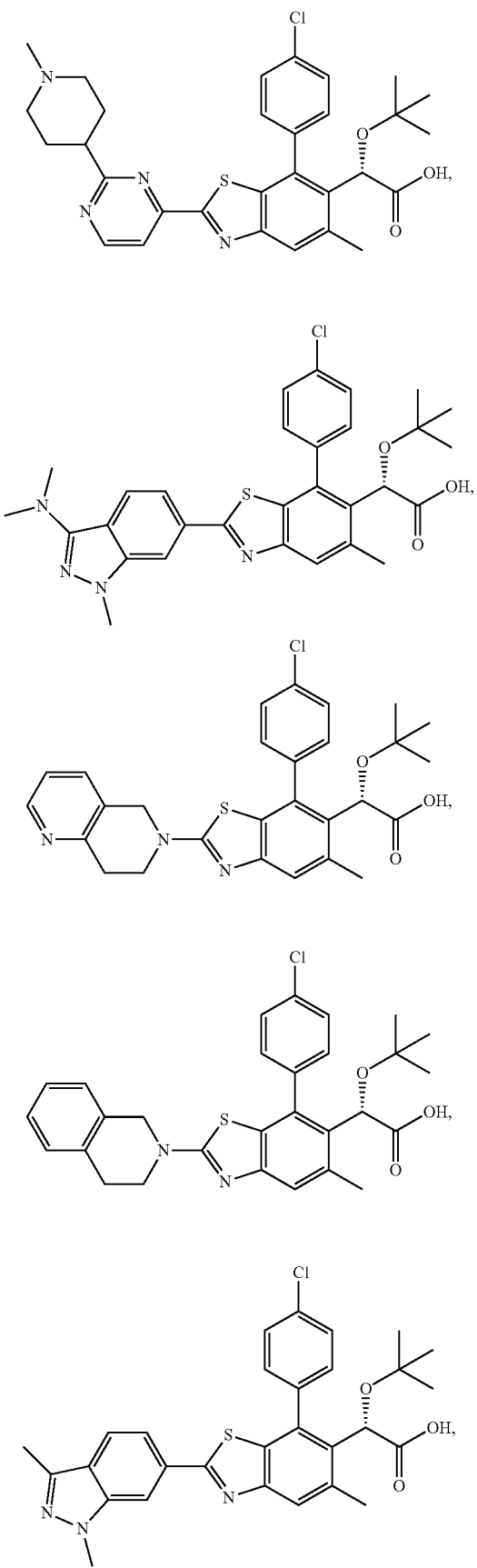
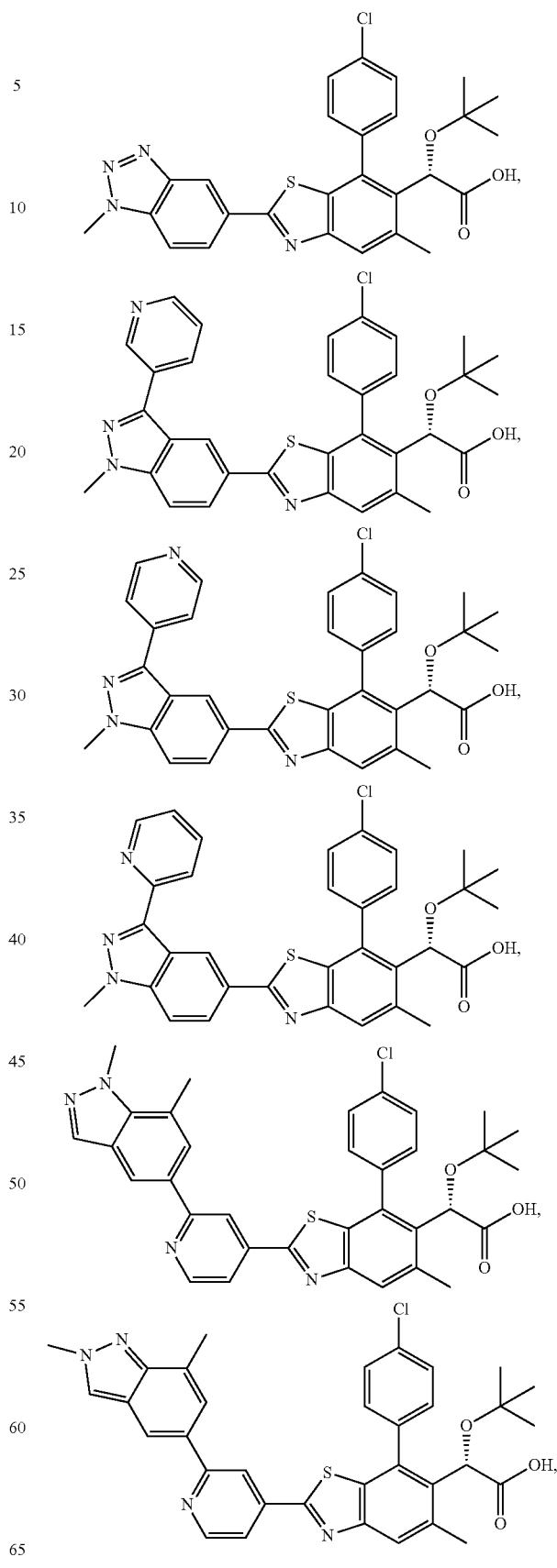

131
-continued
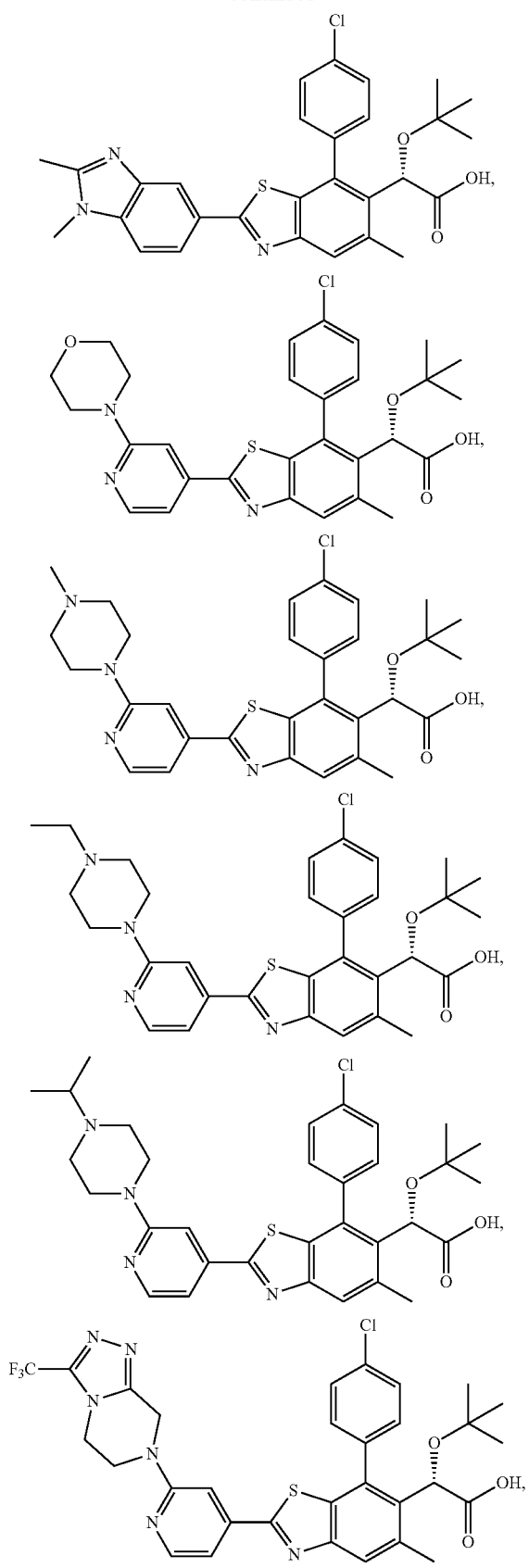
132
-continued
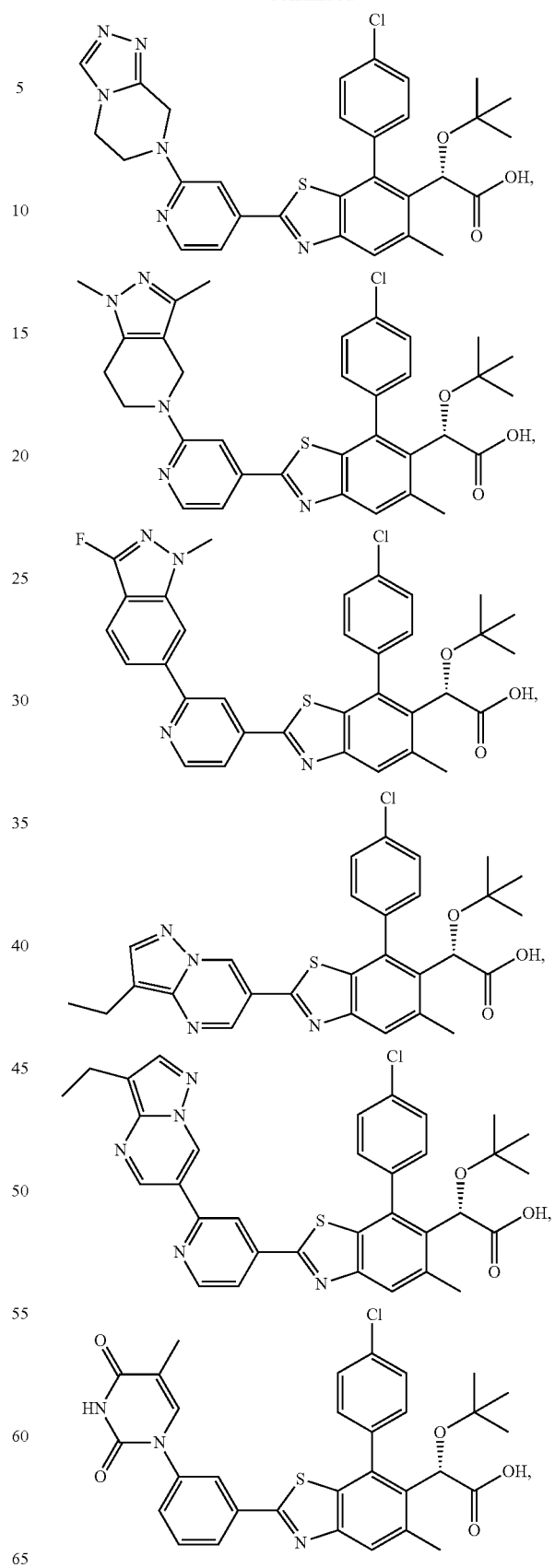

133
-continued
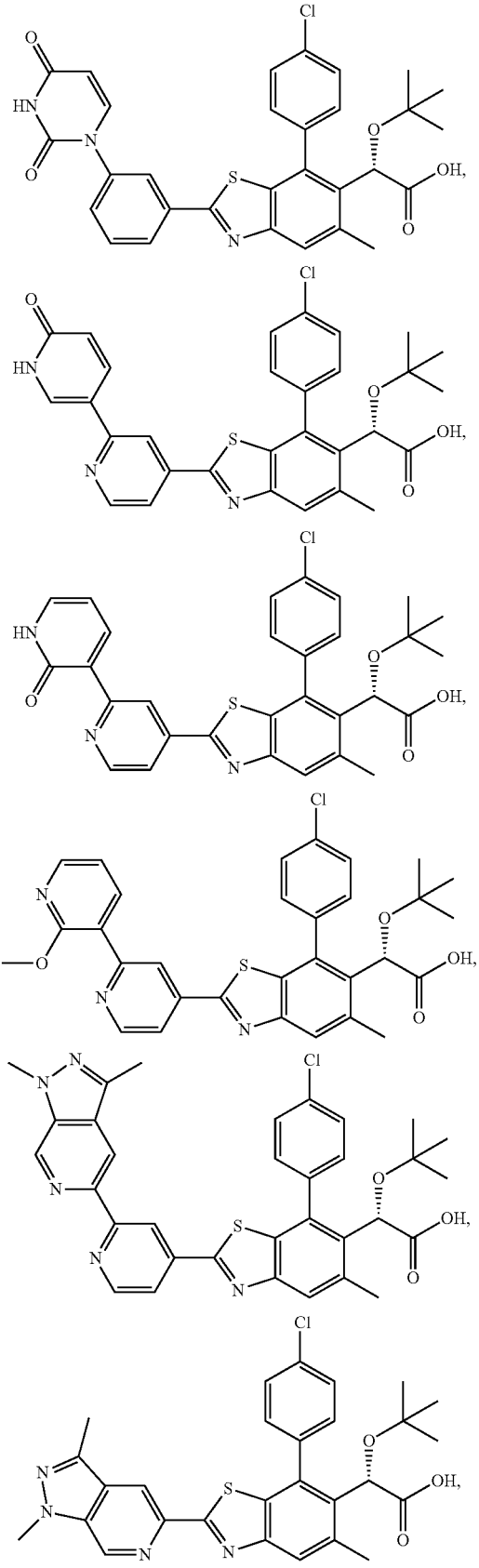
134
-continued
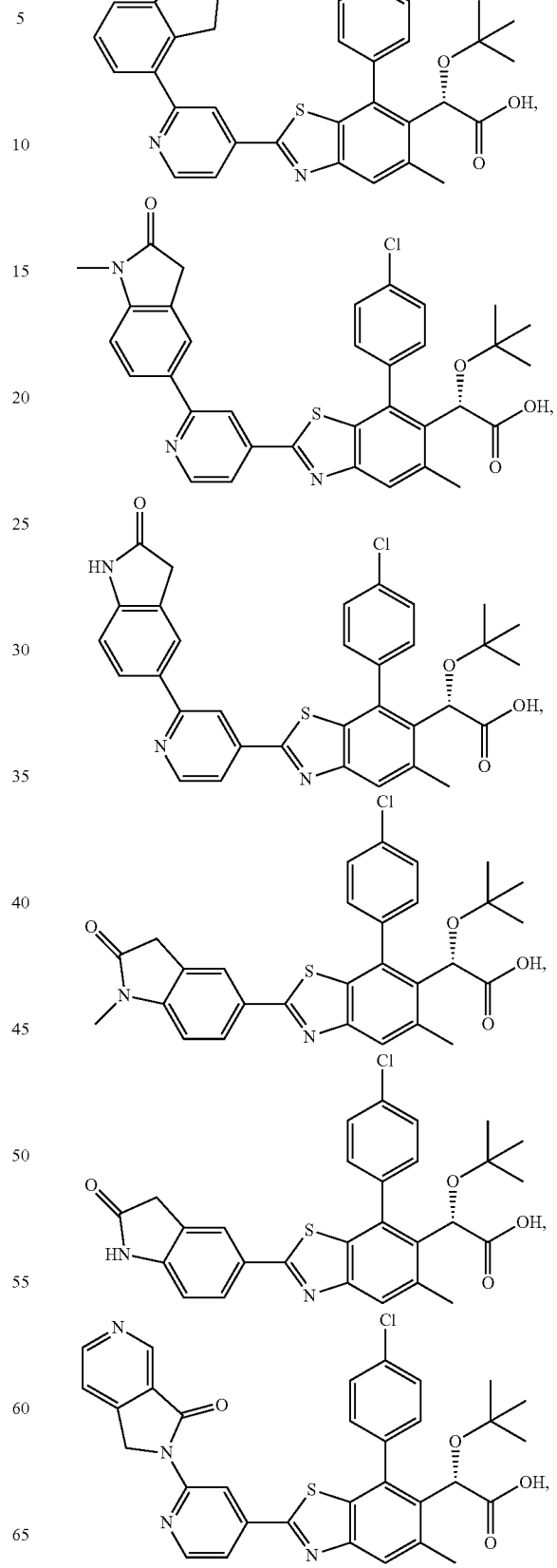

135
-continued
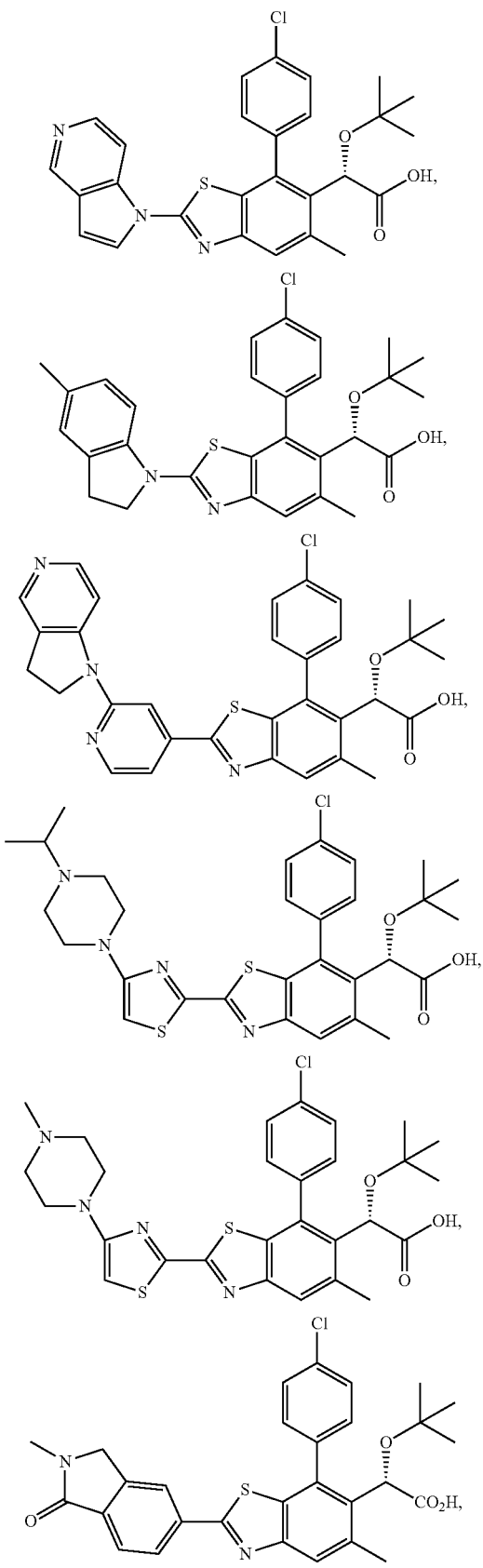
136
-continued
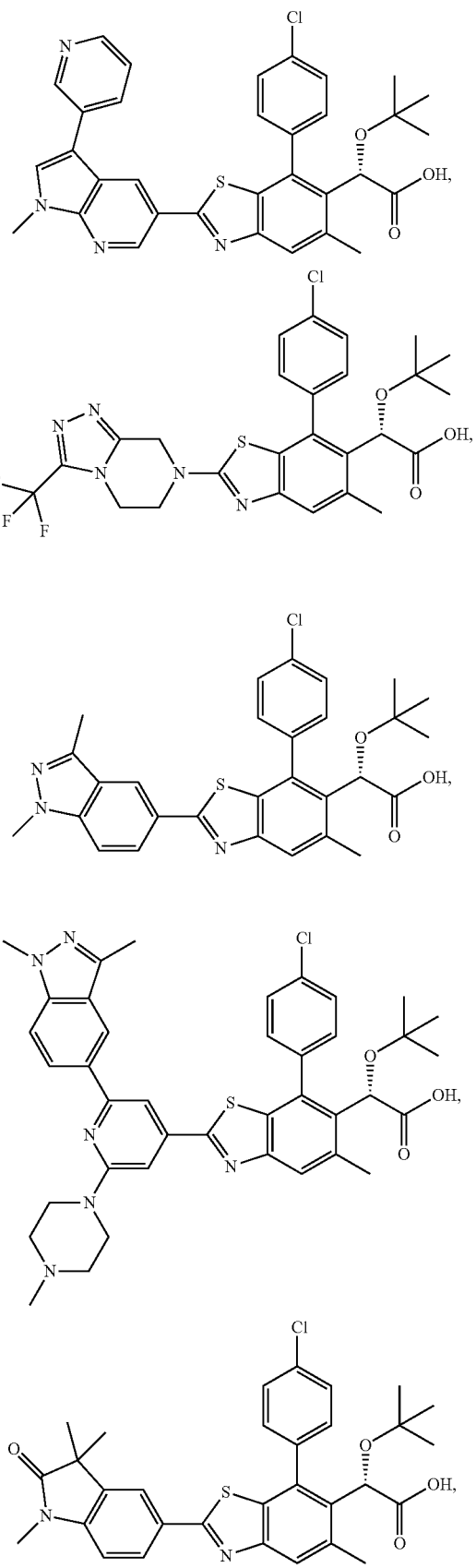

137
-continued
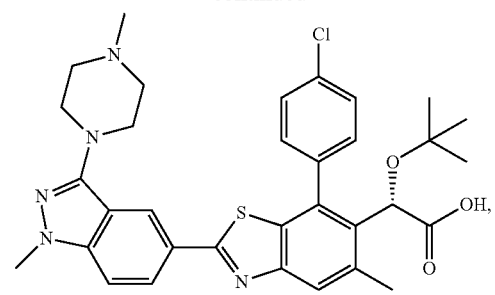
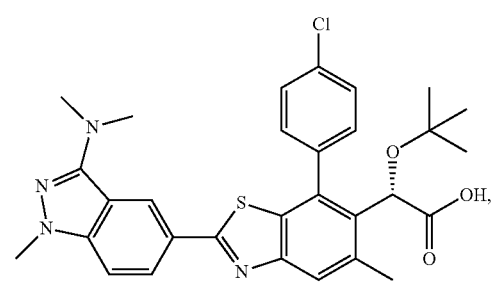
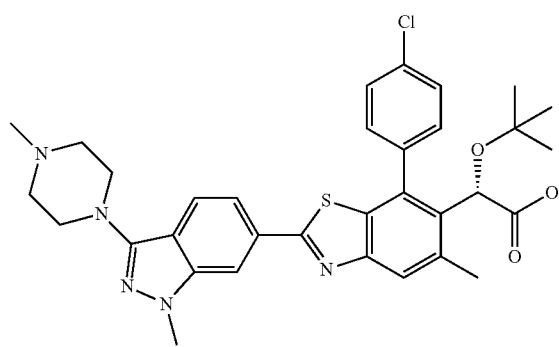
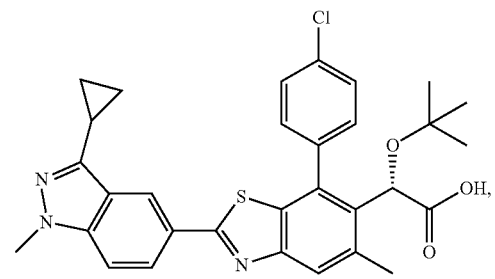
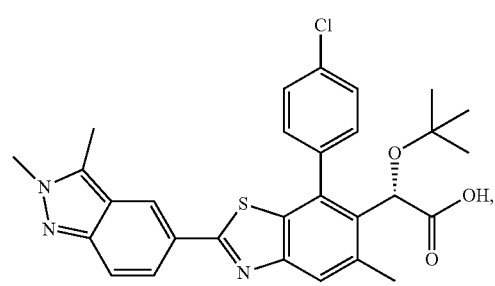
138
-continued
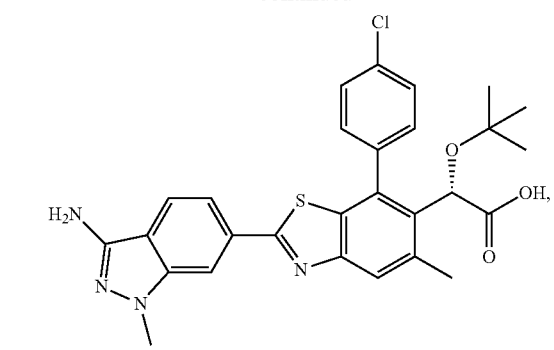
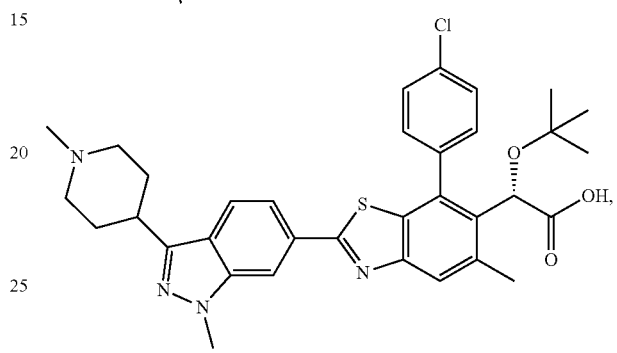
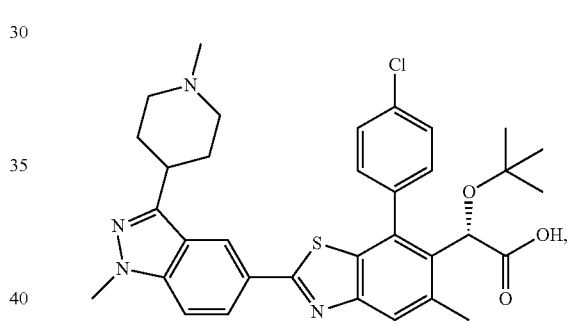
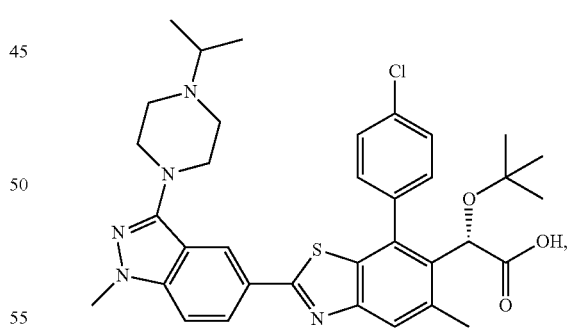
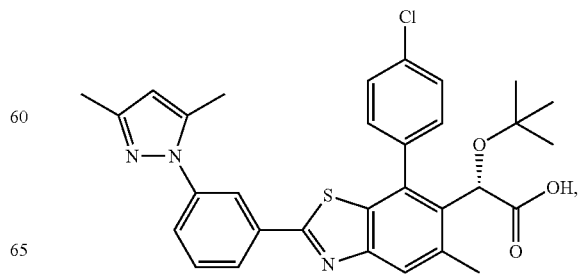

139
-continued
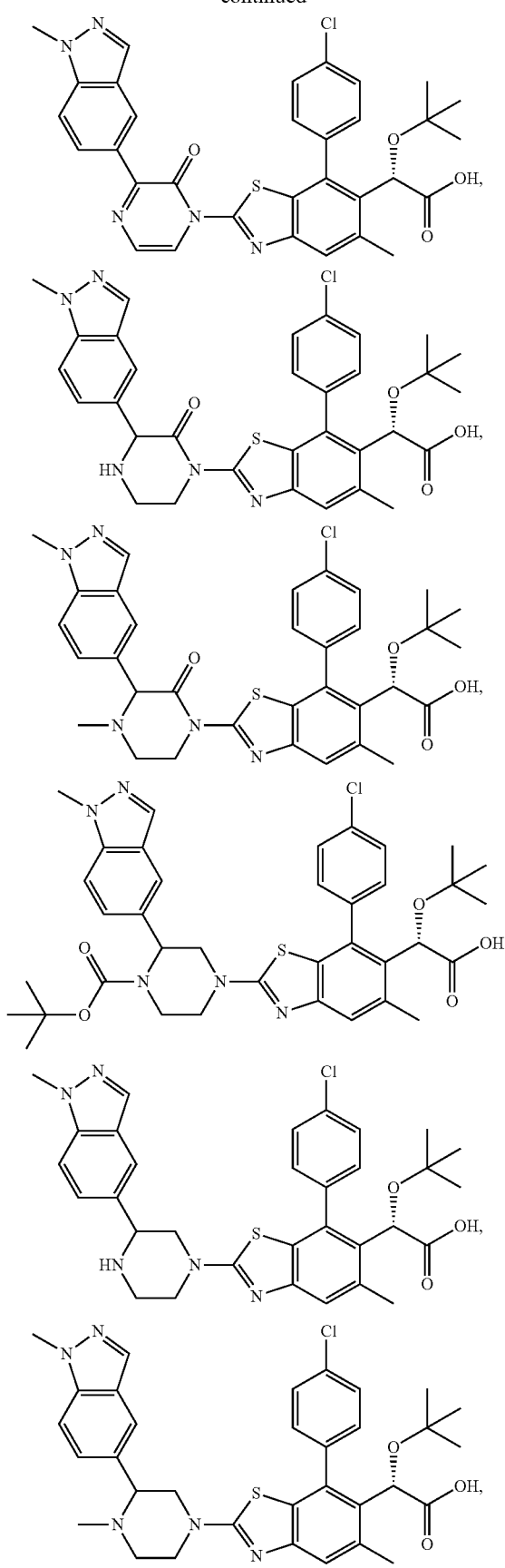
140
-continued
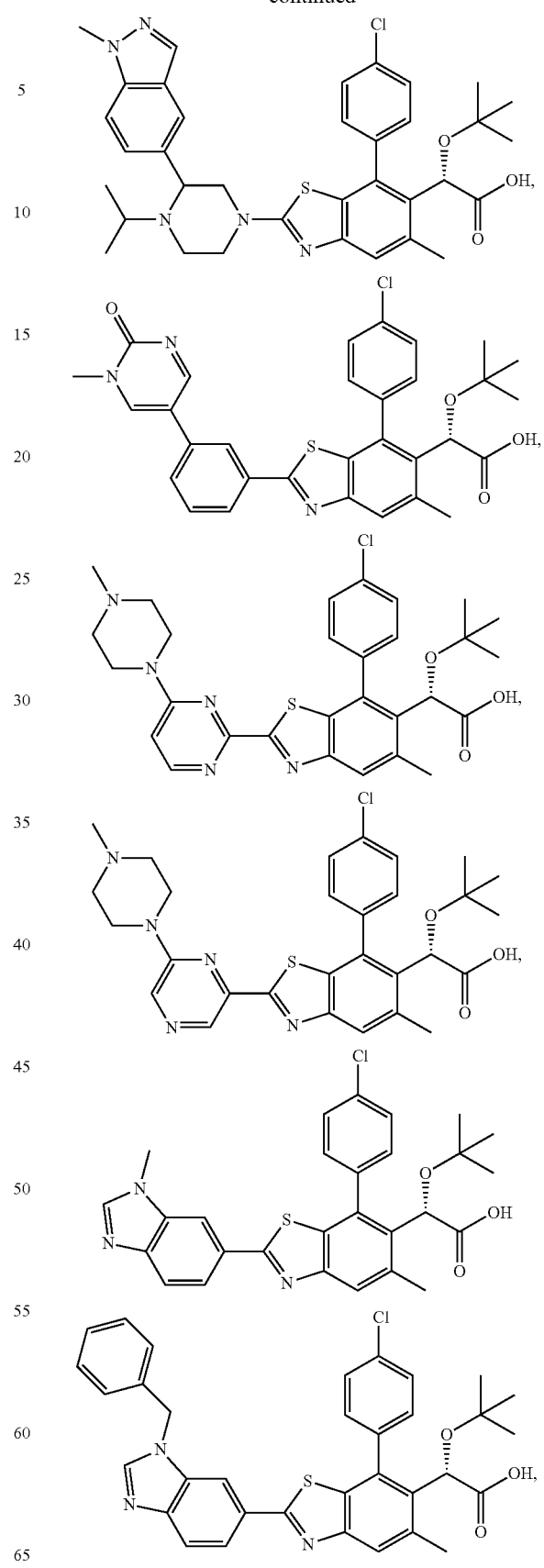

141
-continued
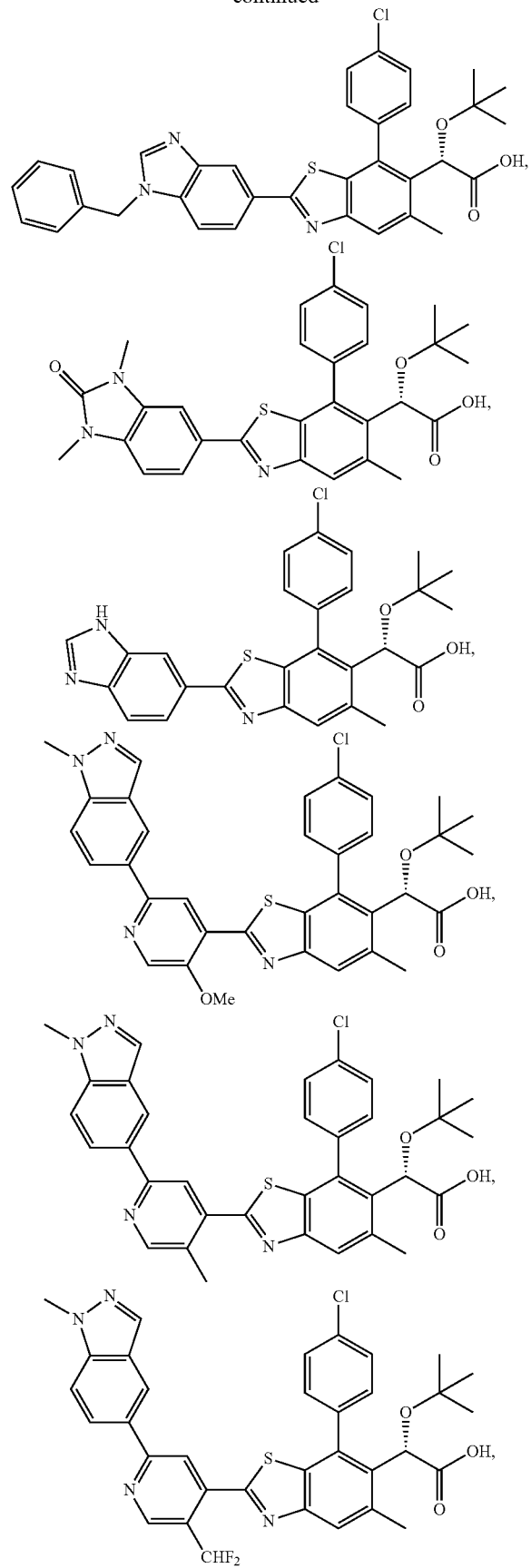
142
-continued
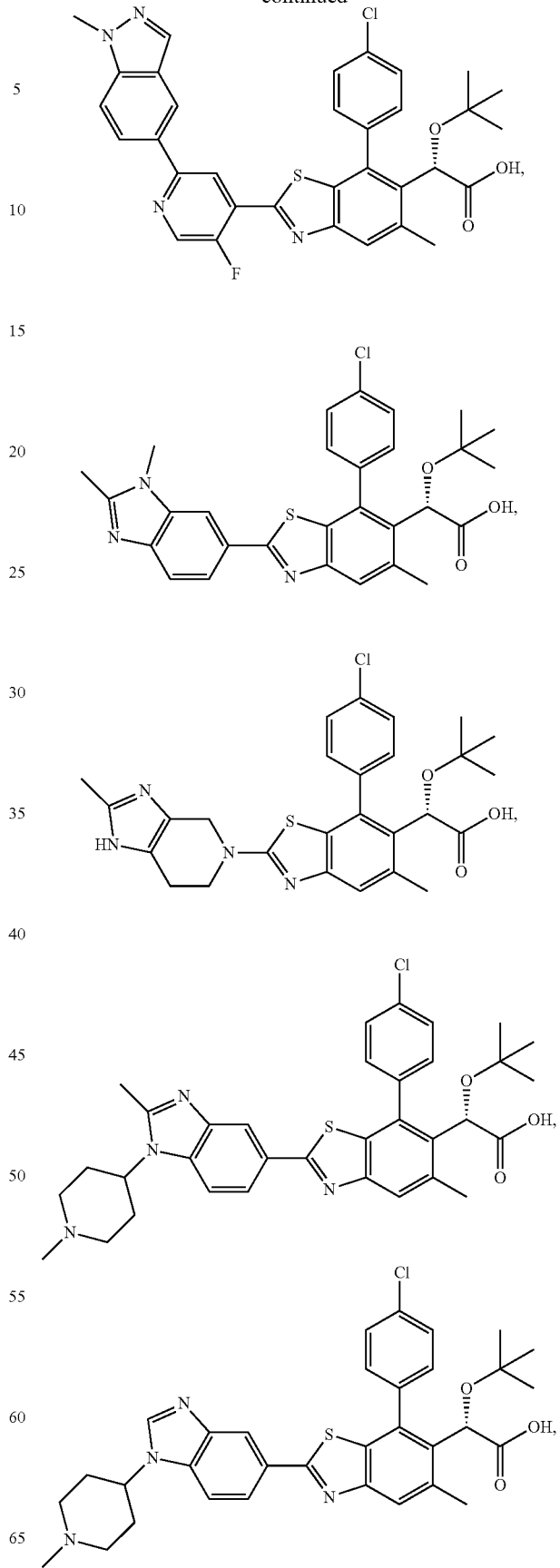

143
-continued
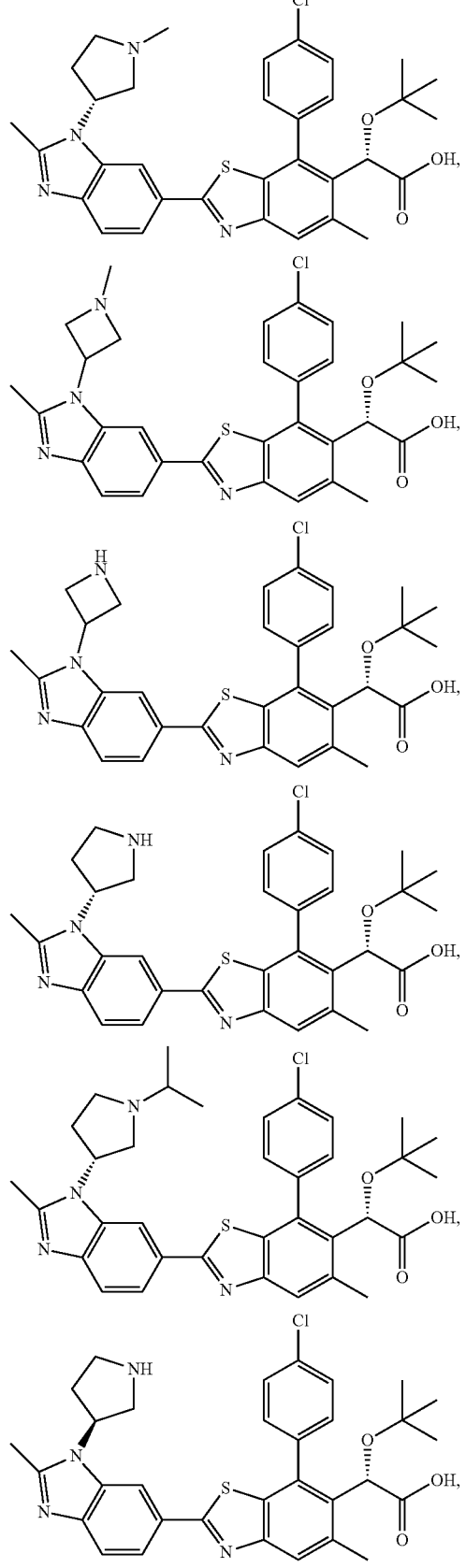
144
-continued
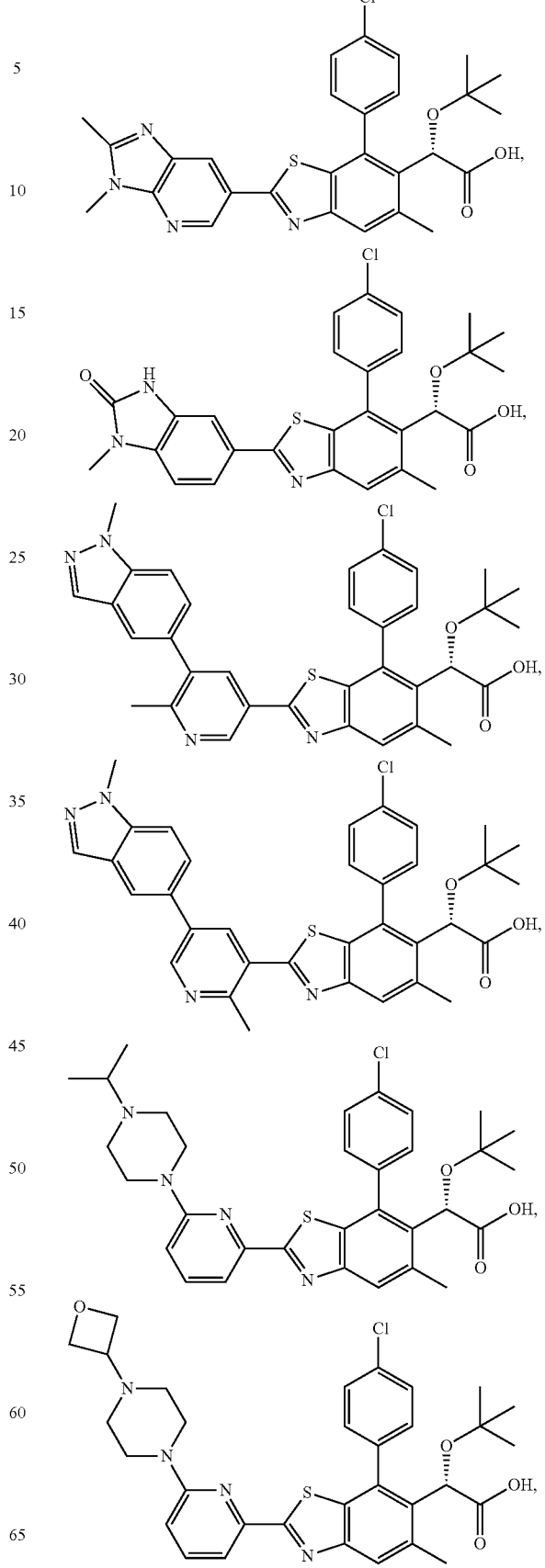

145
-continued
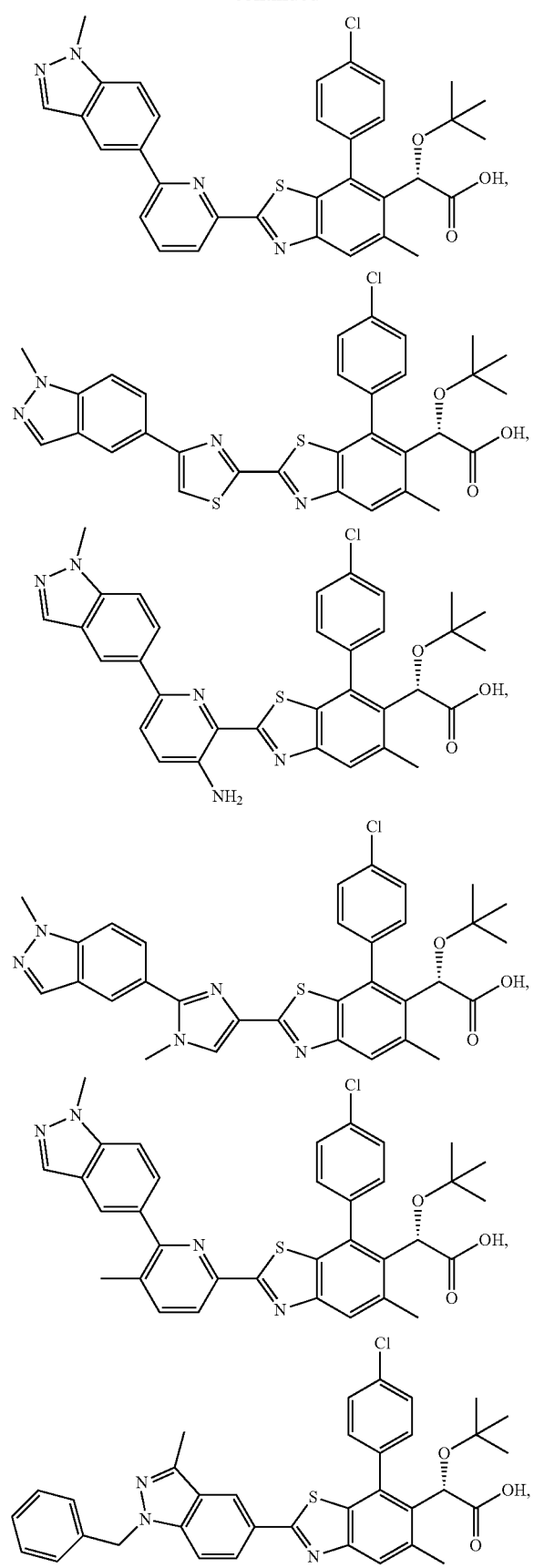
146
-continued
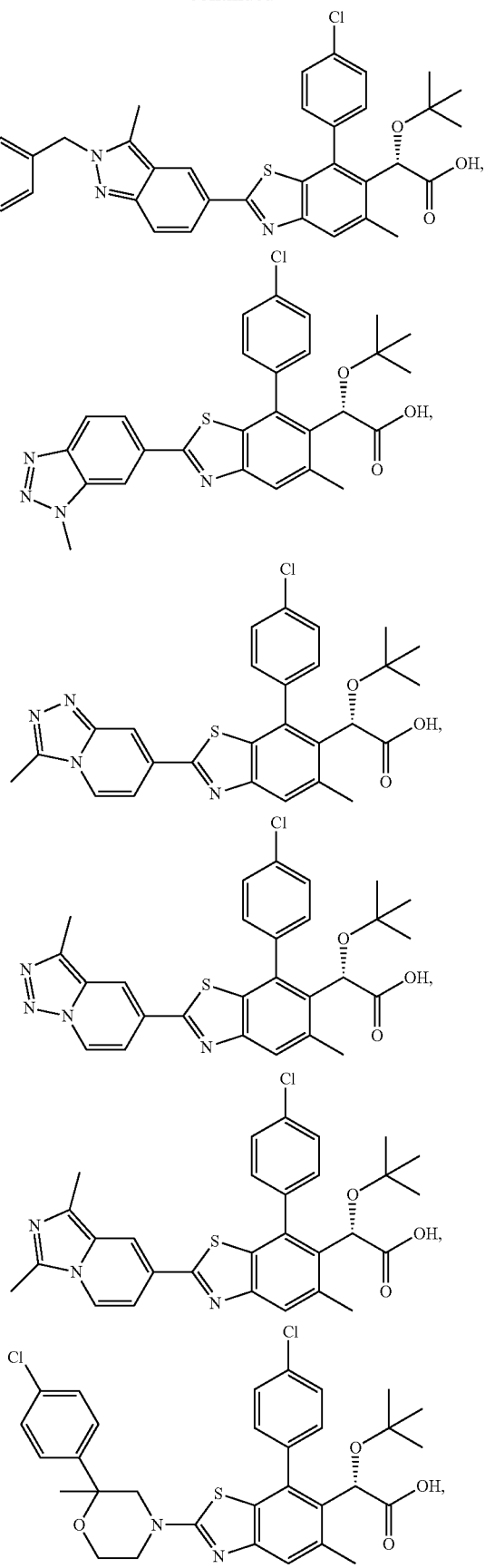

147
-continued
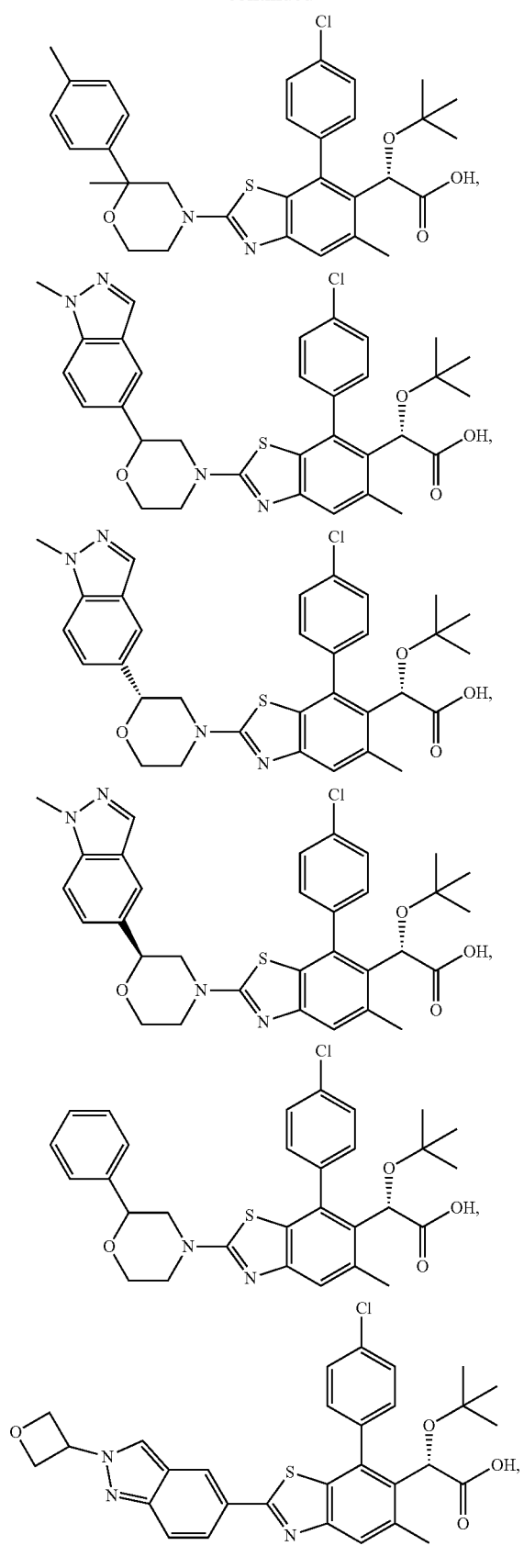
148
-continued
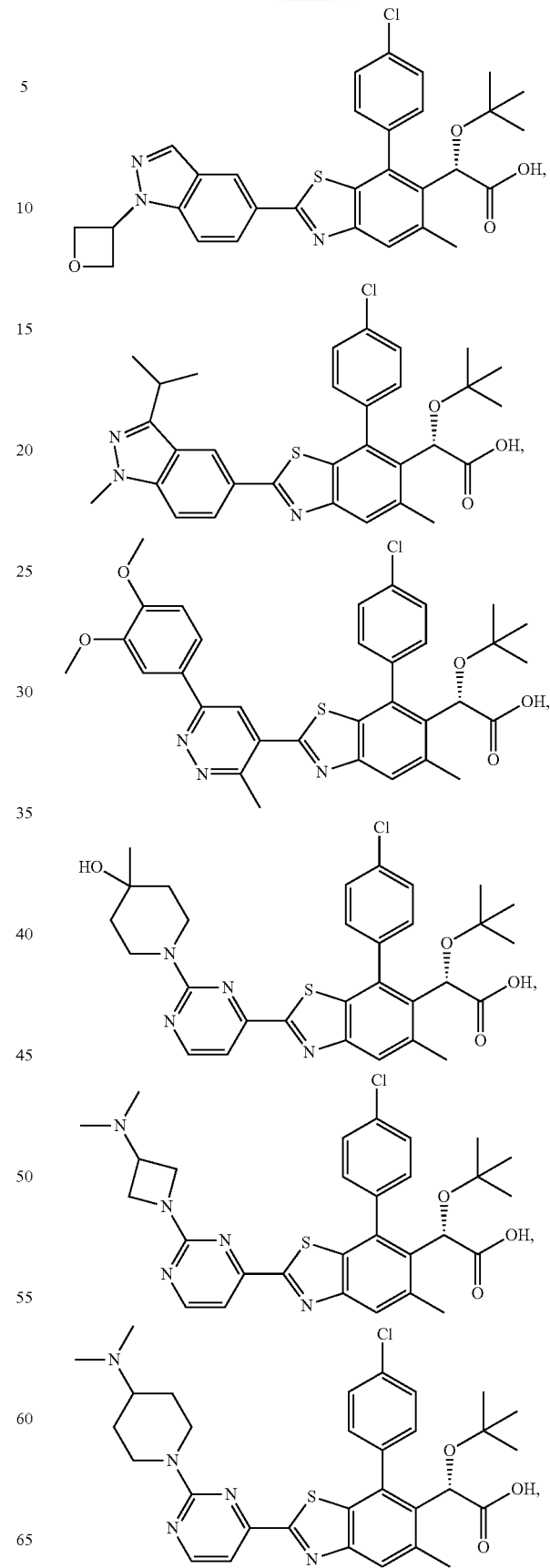

149
-continued
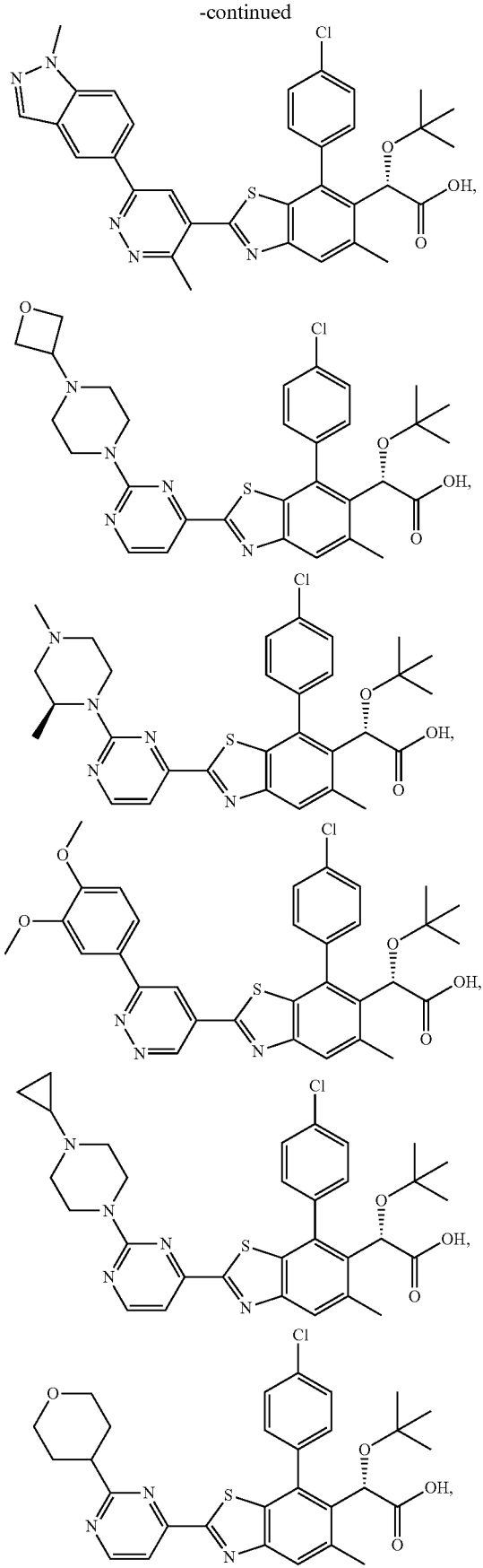
150
-continued
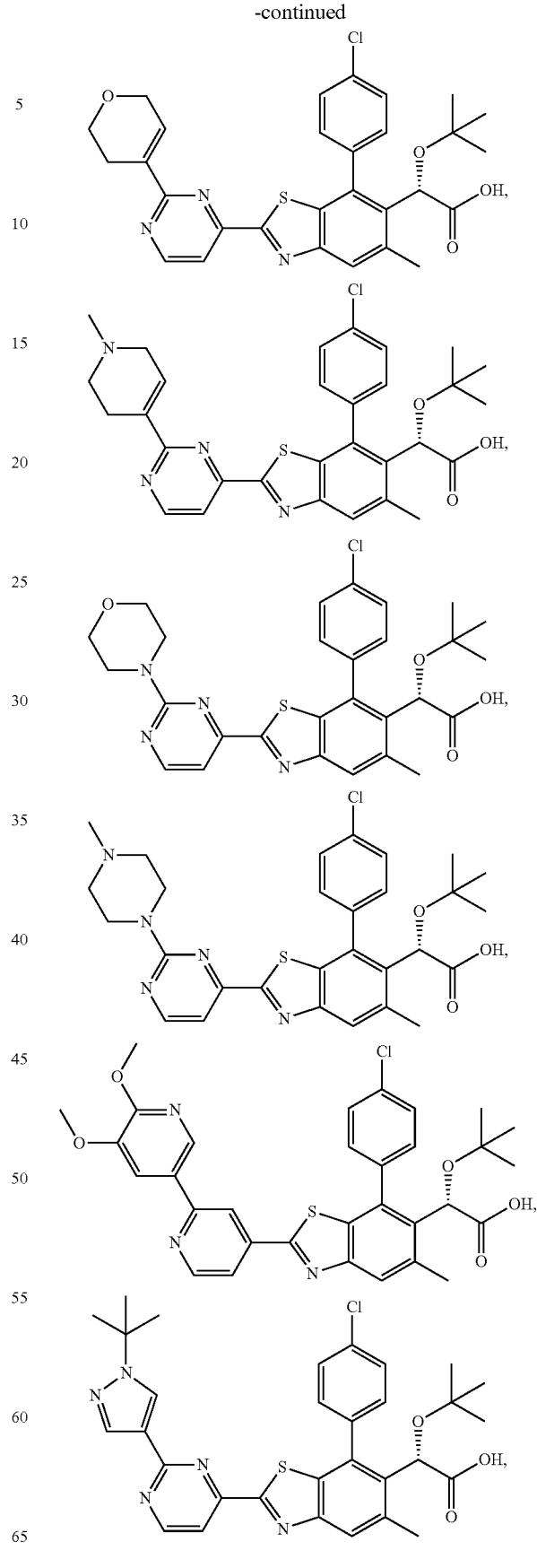

151
-continued
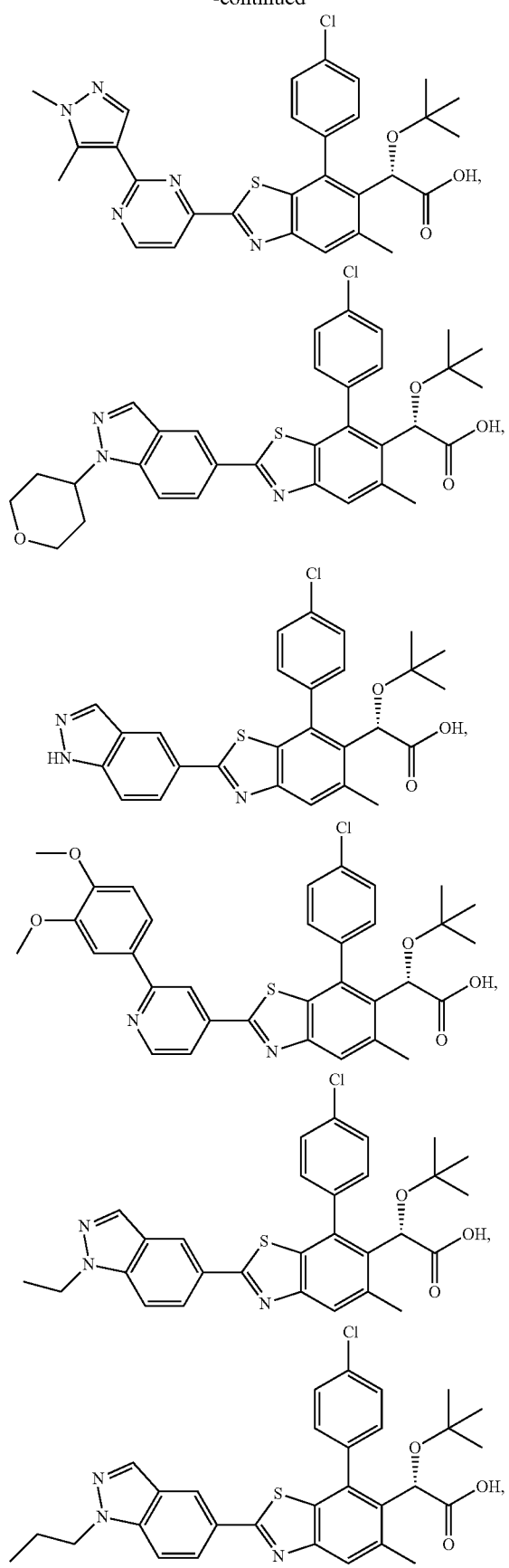
152
-continued
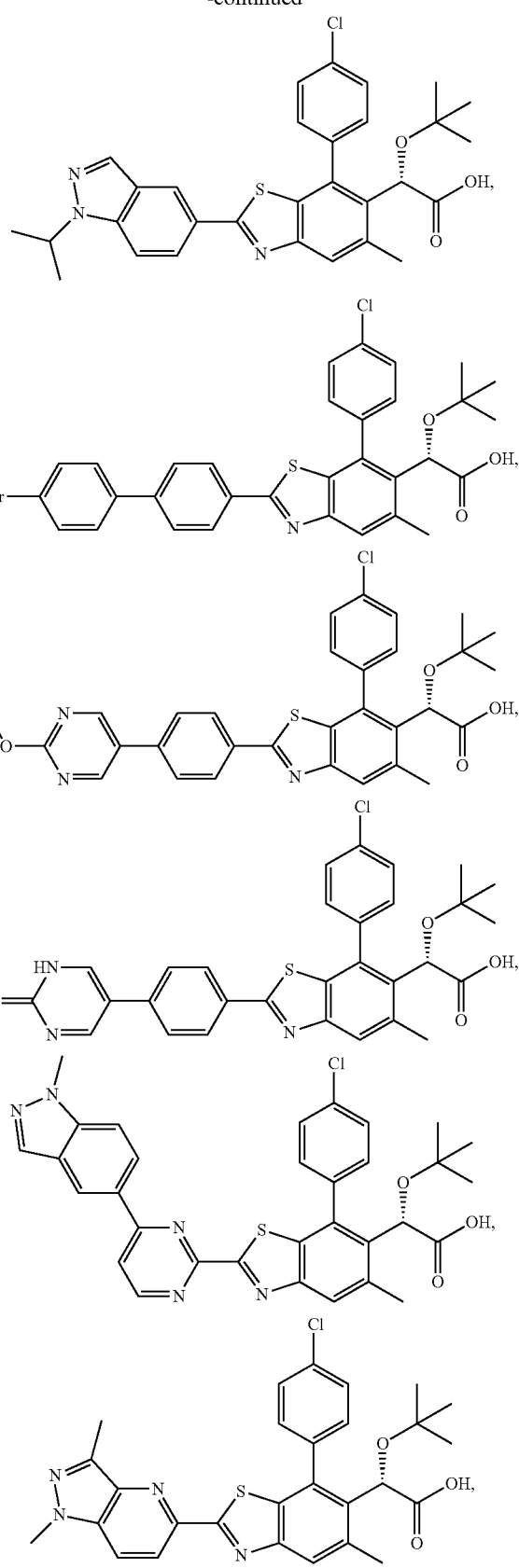

153
-continued
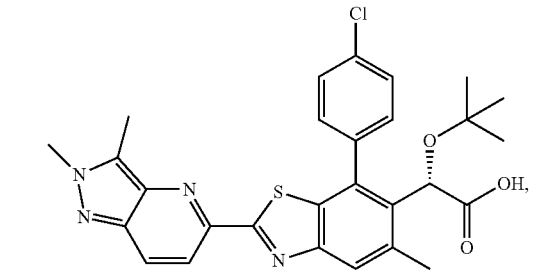
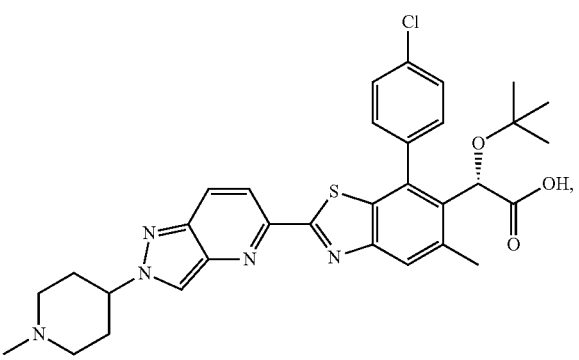
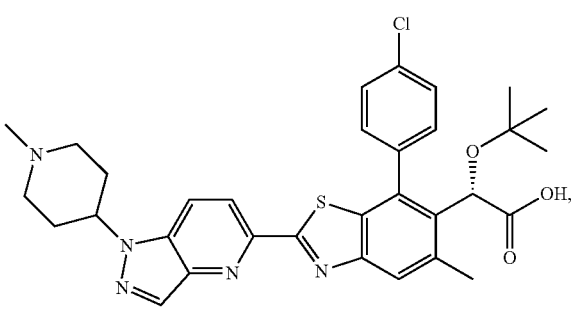
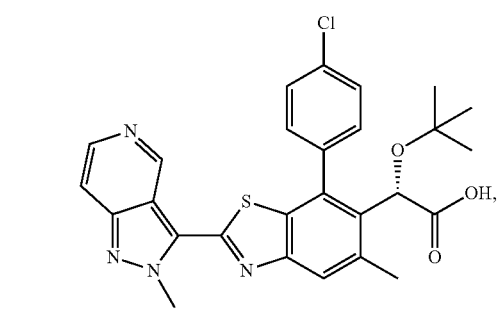
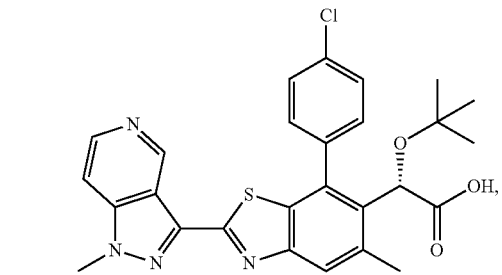
154
-continued
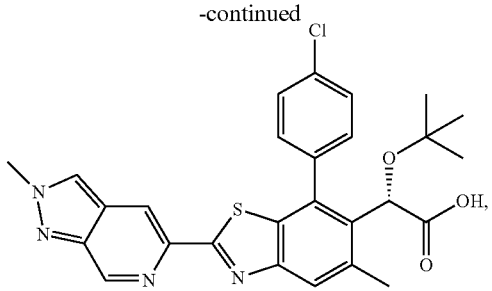
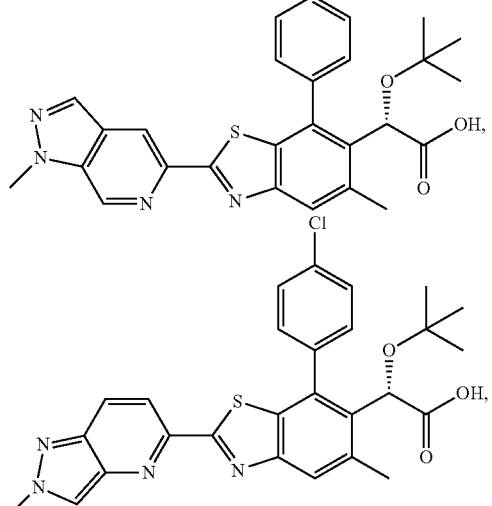
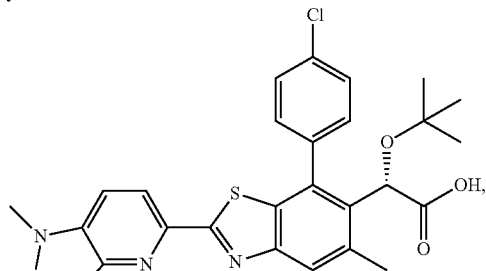

155
-continued
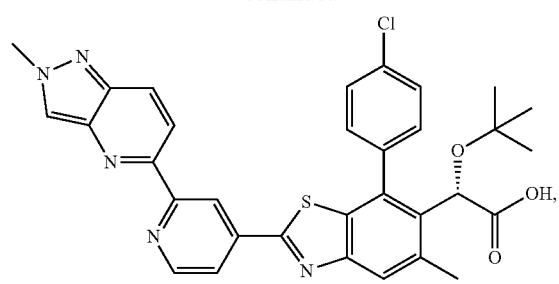
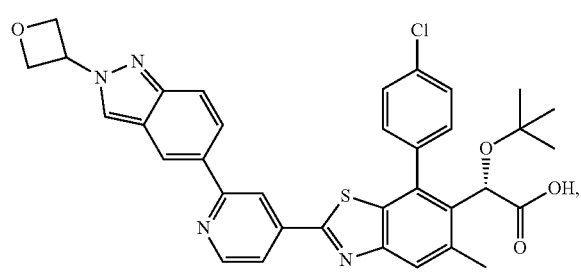
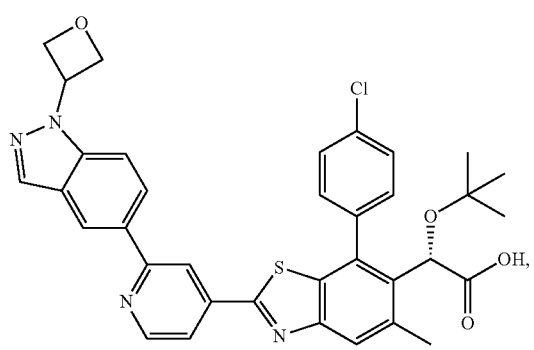
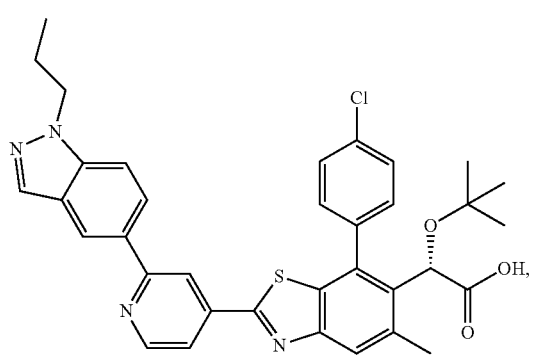
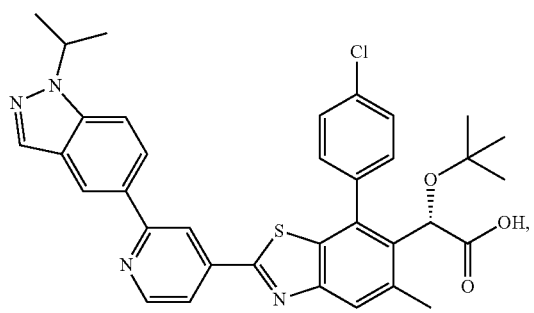
156
-continued
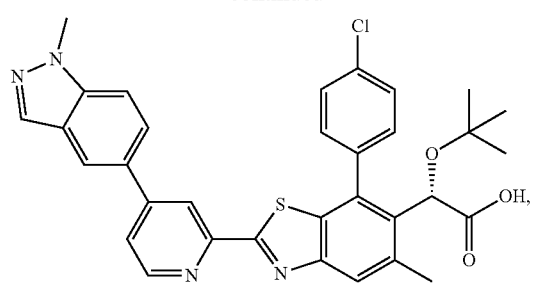
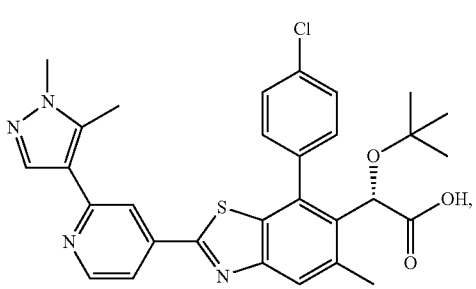
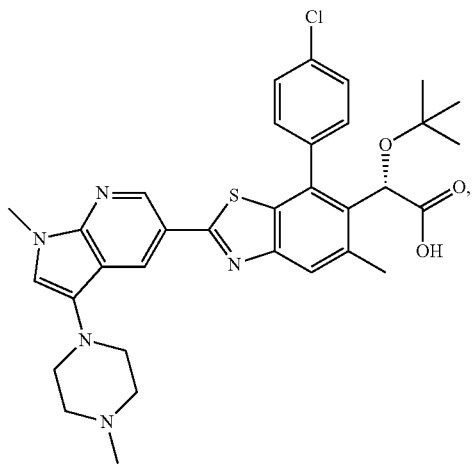
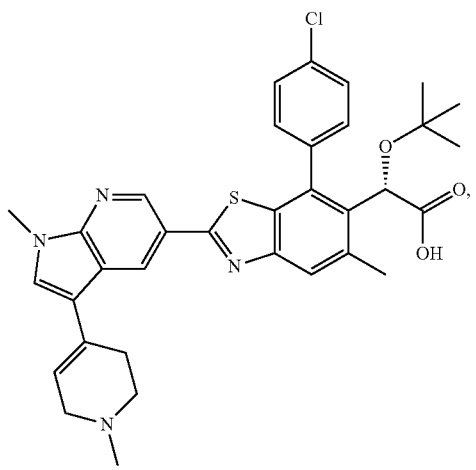

157
-continued
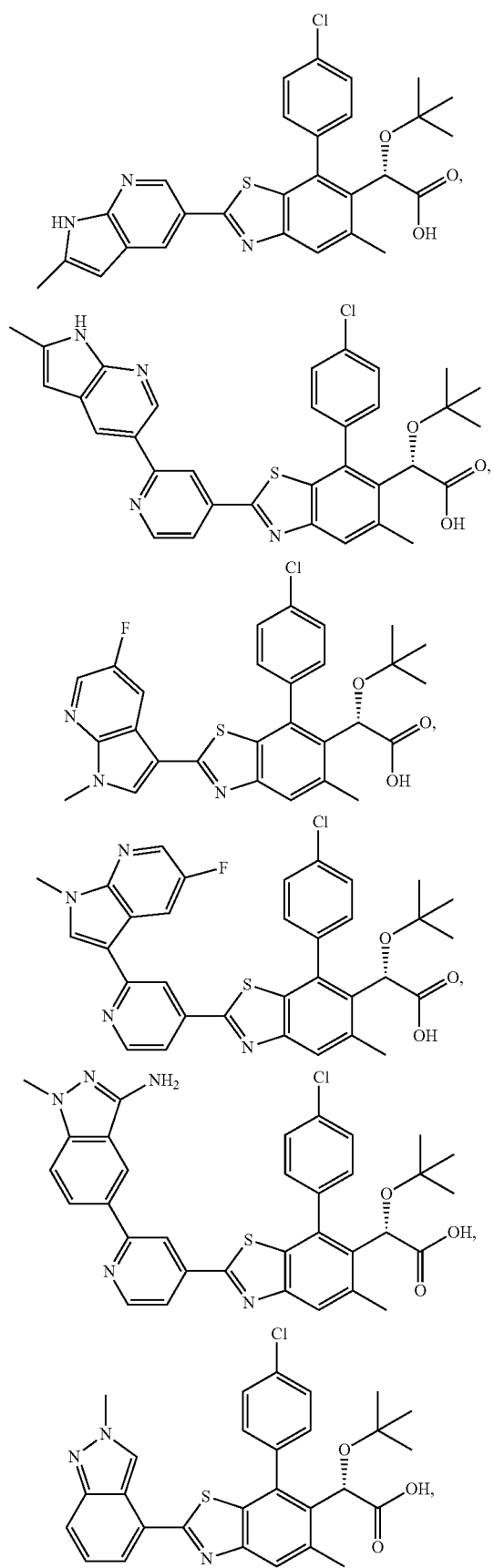
158
-continued
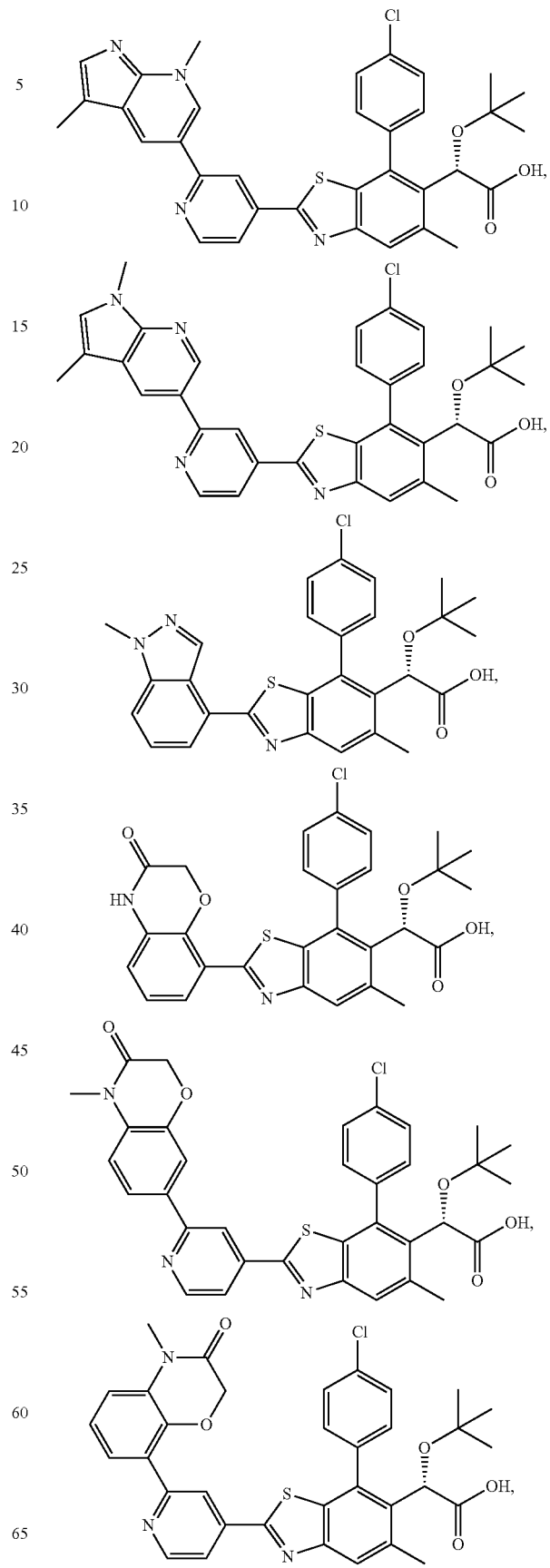

159
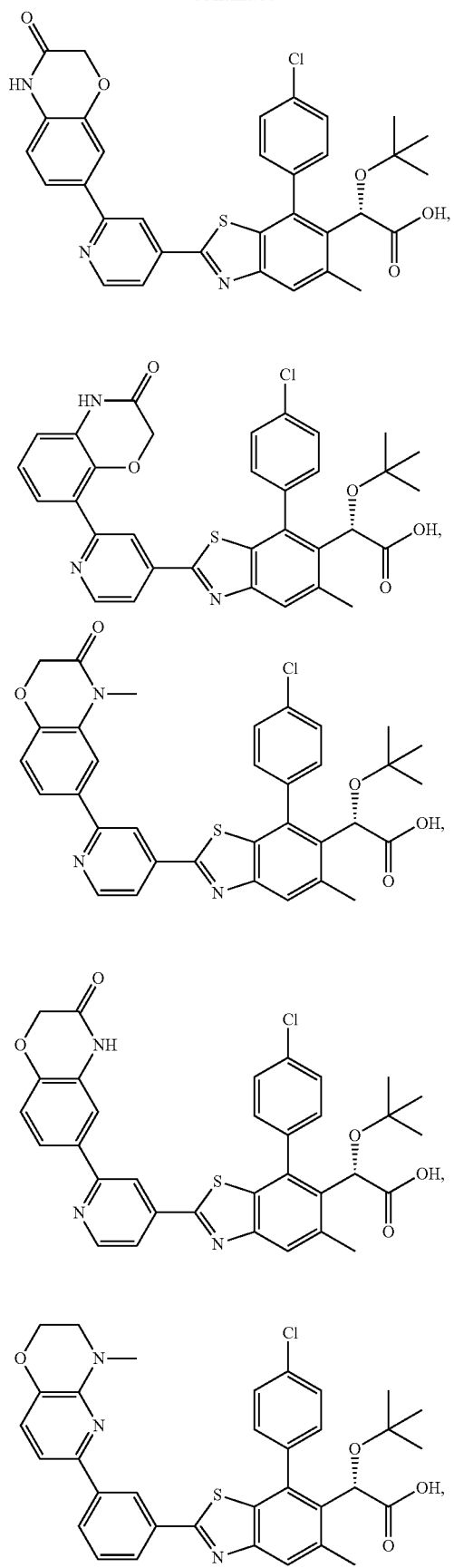
160
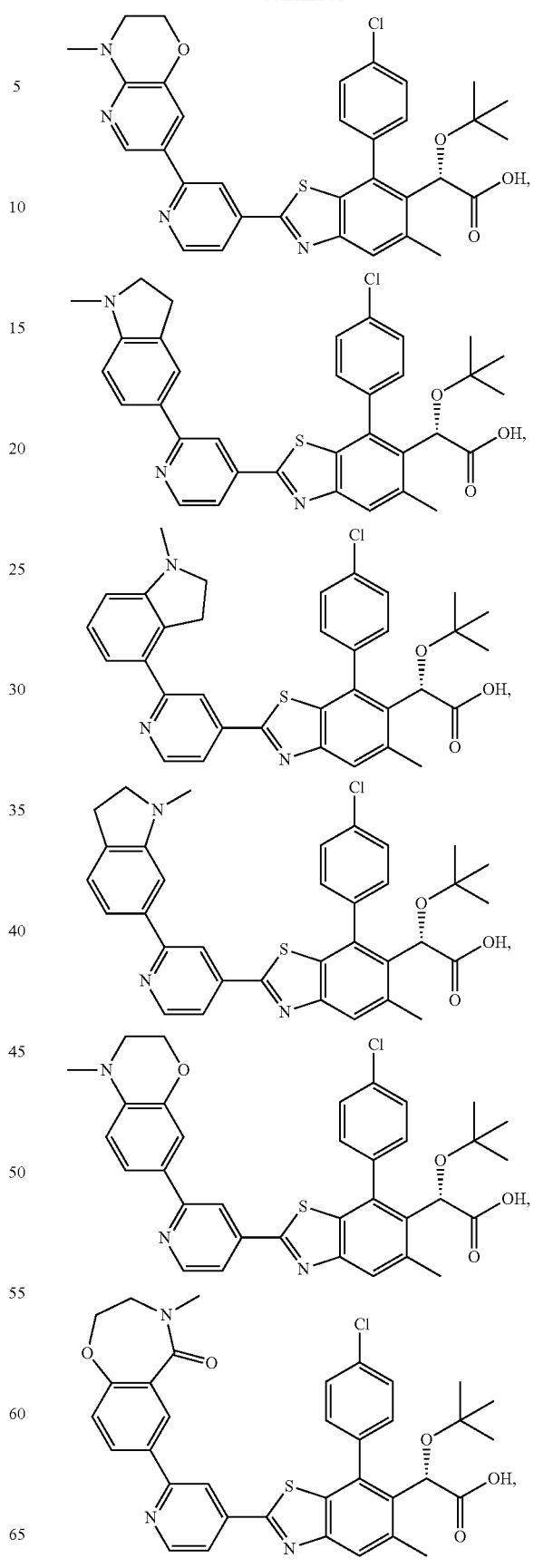

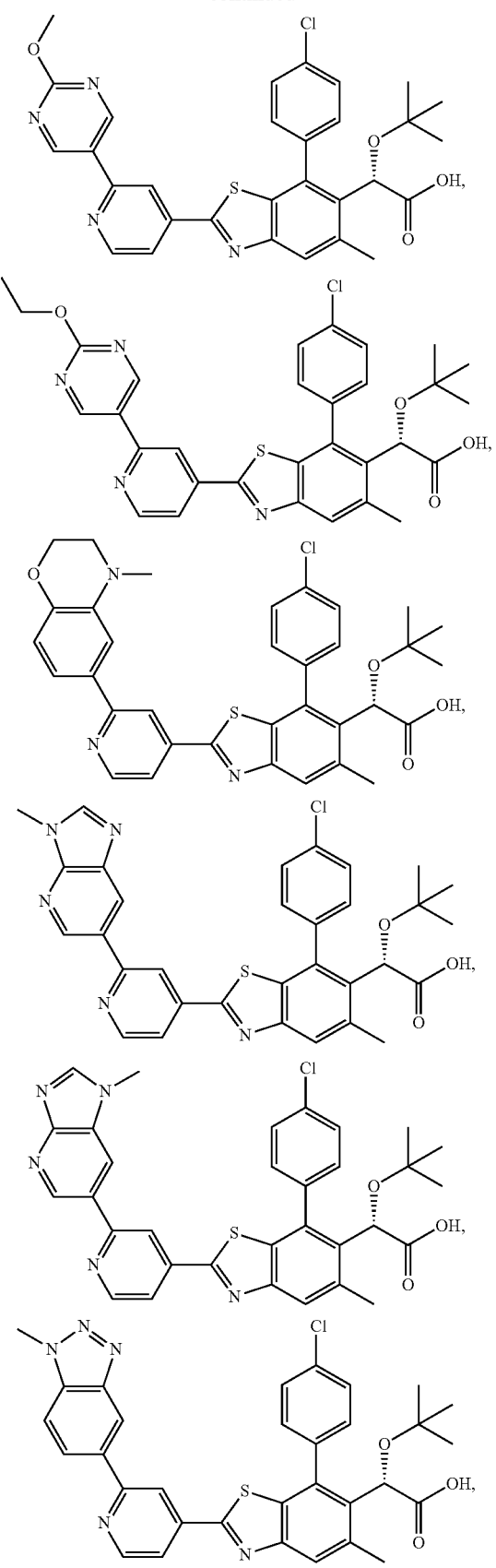
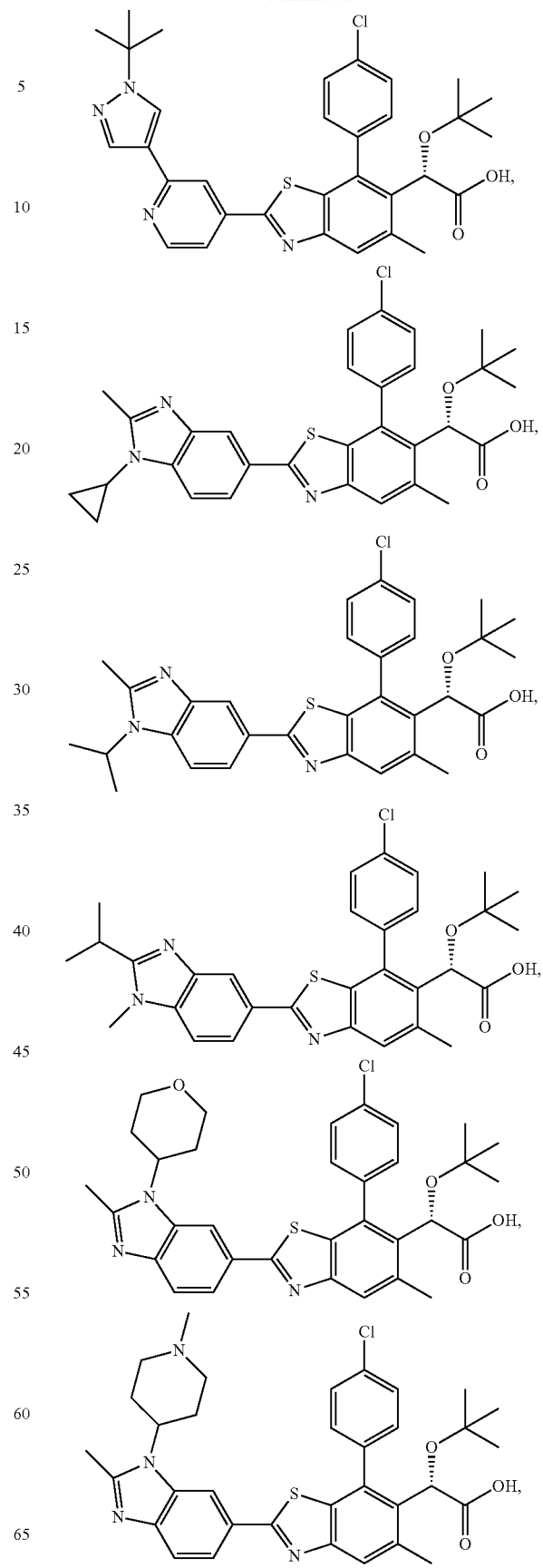

163
-continued
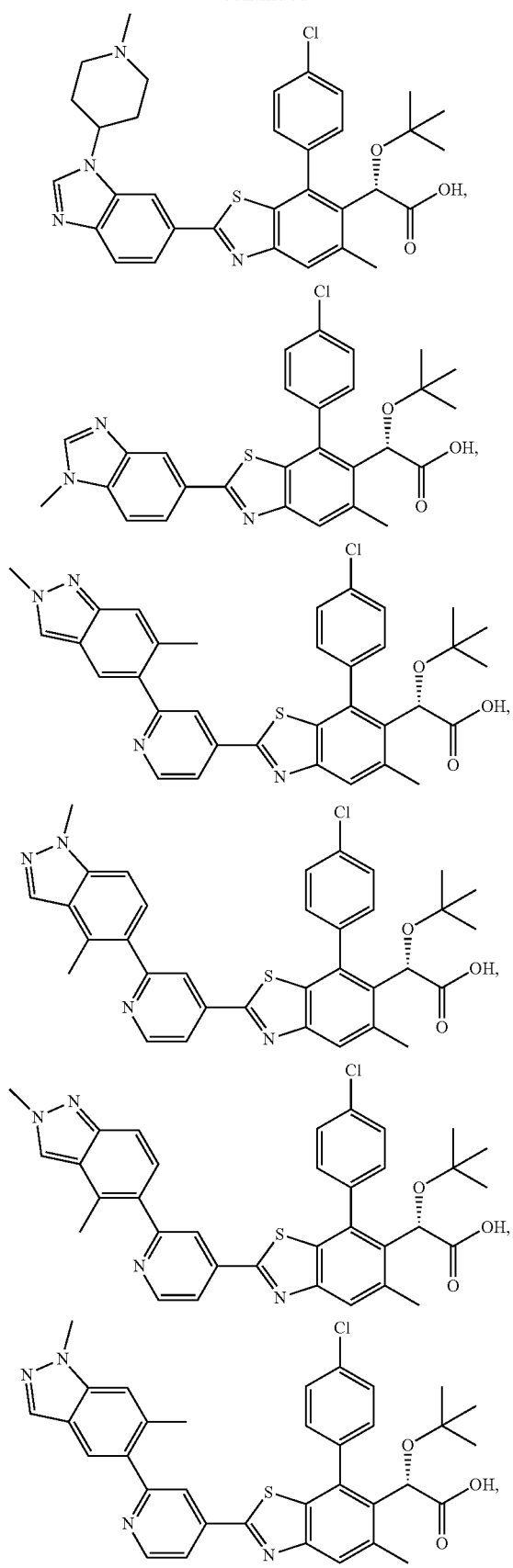
164
-continued
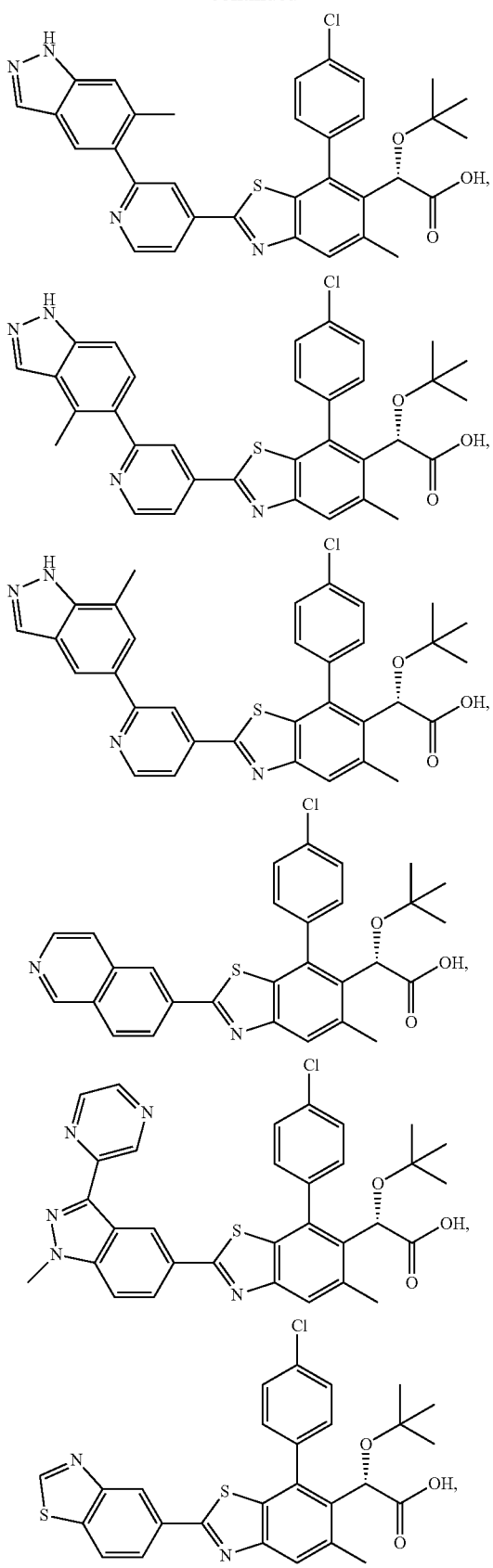

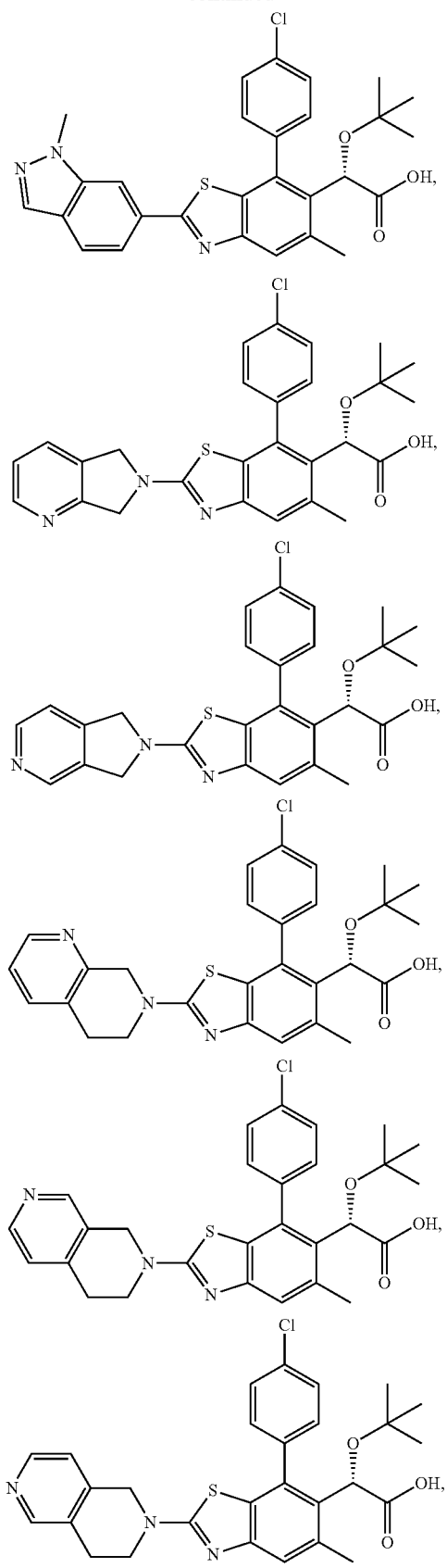
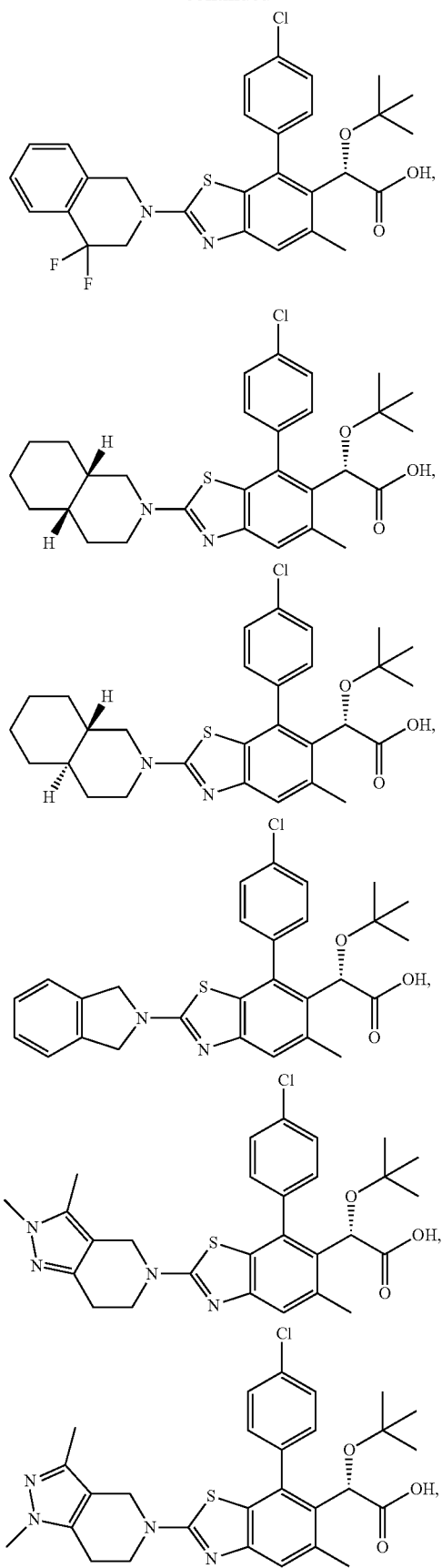

167
-continued
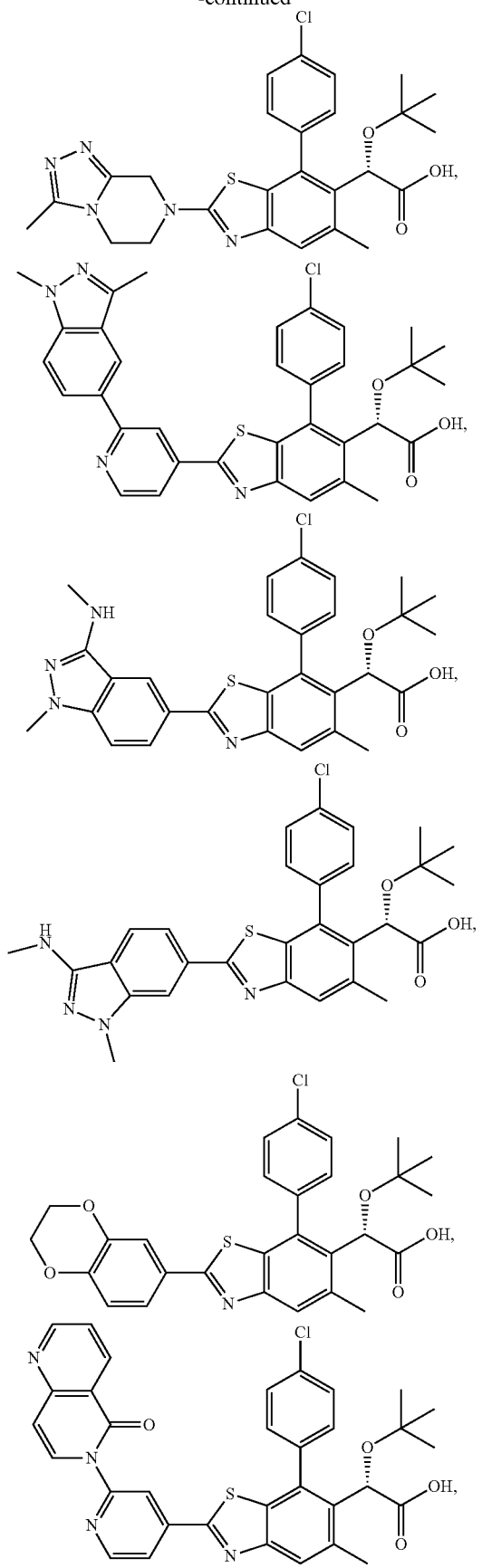
168
-continued
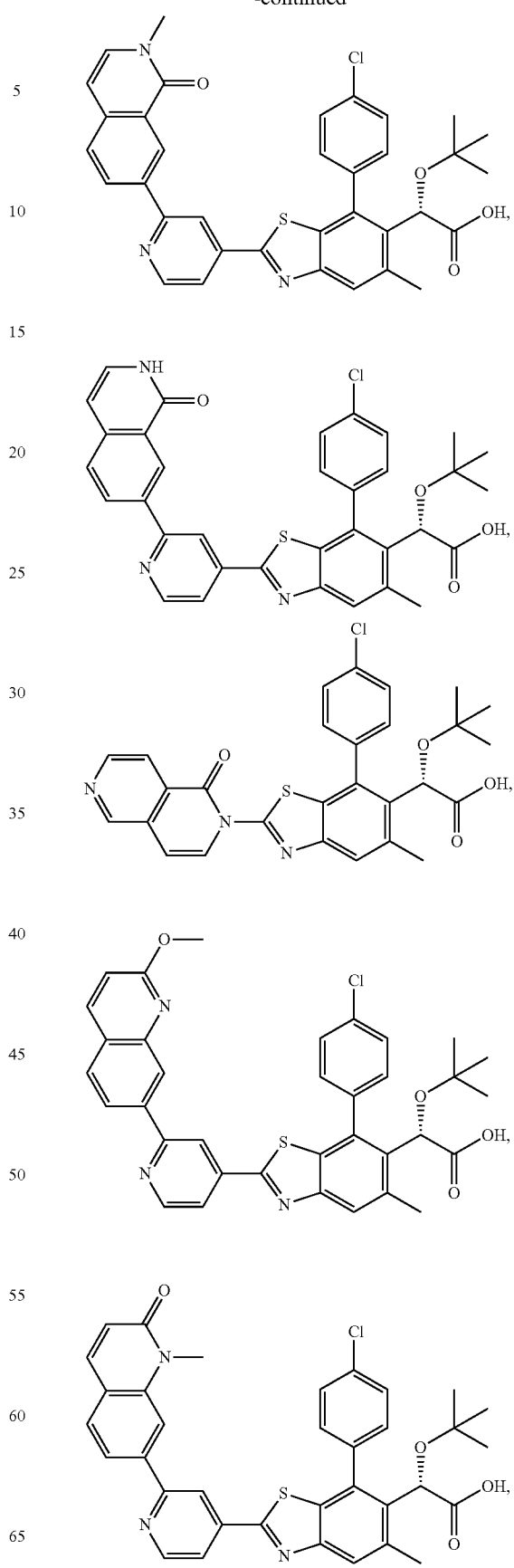

169
-continued
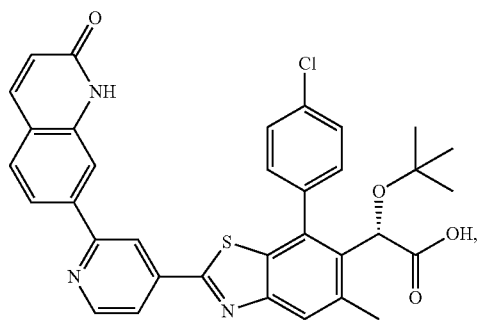
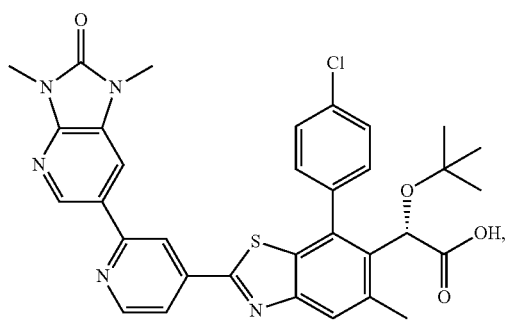
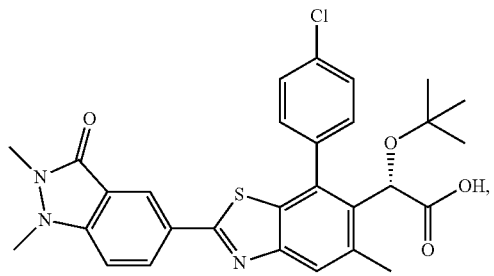
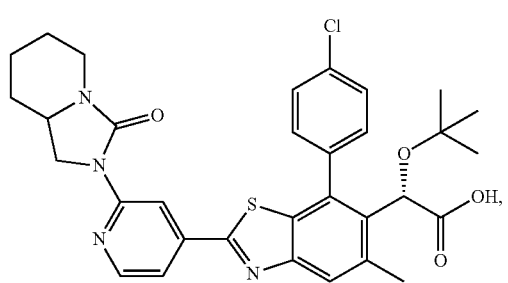
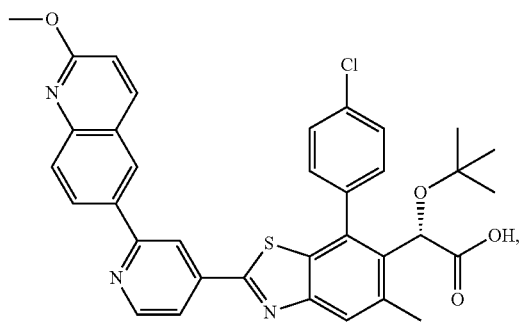
170
-continued
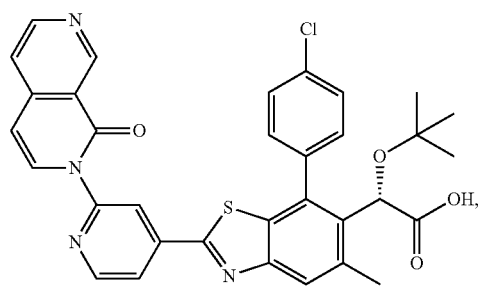
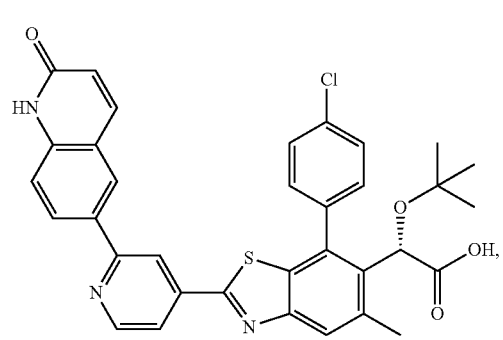
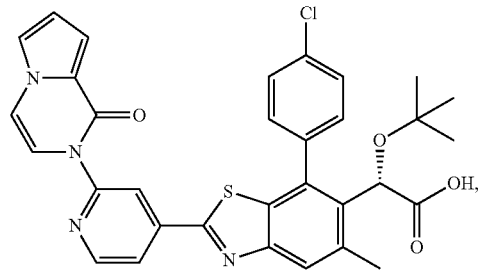
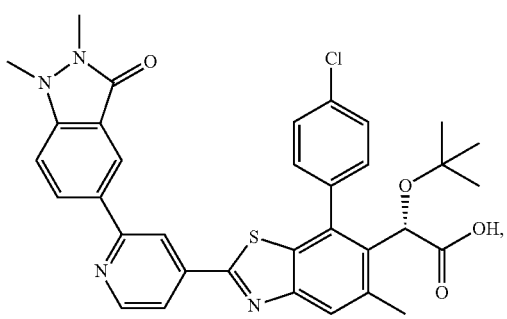
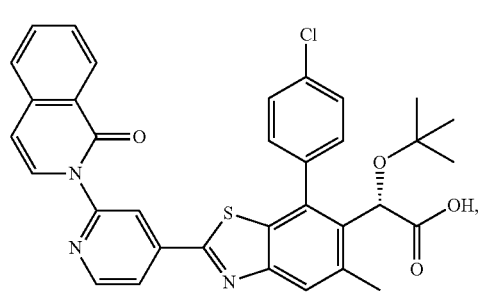

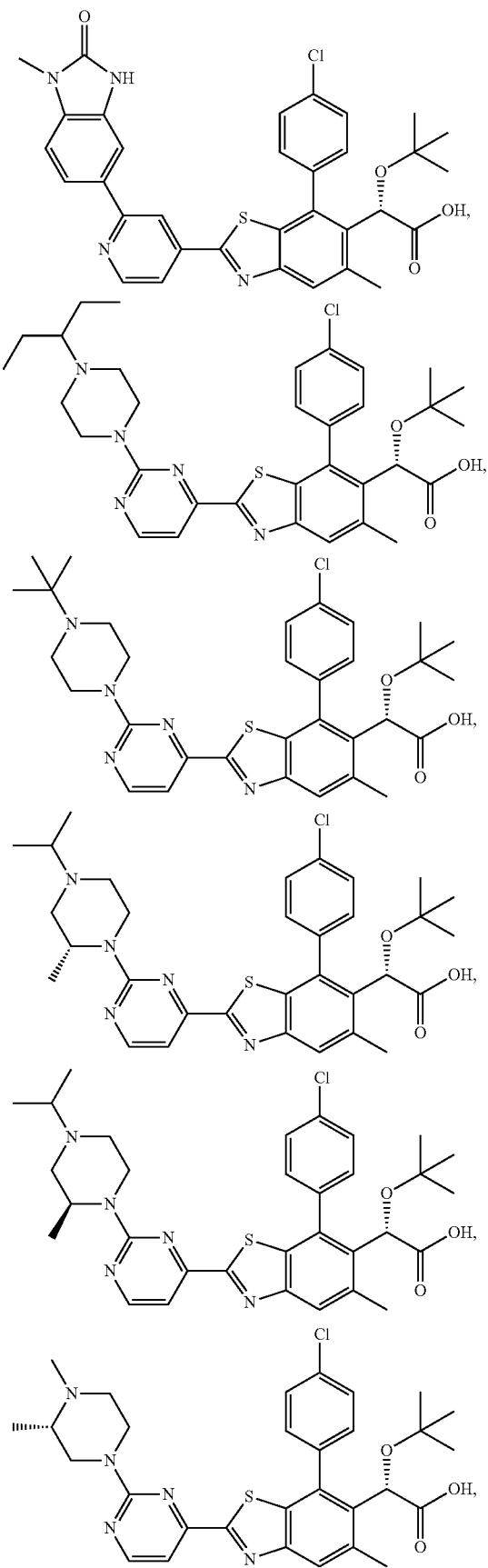
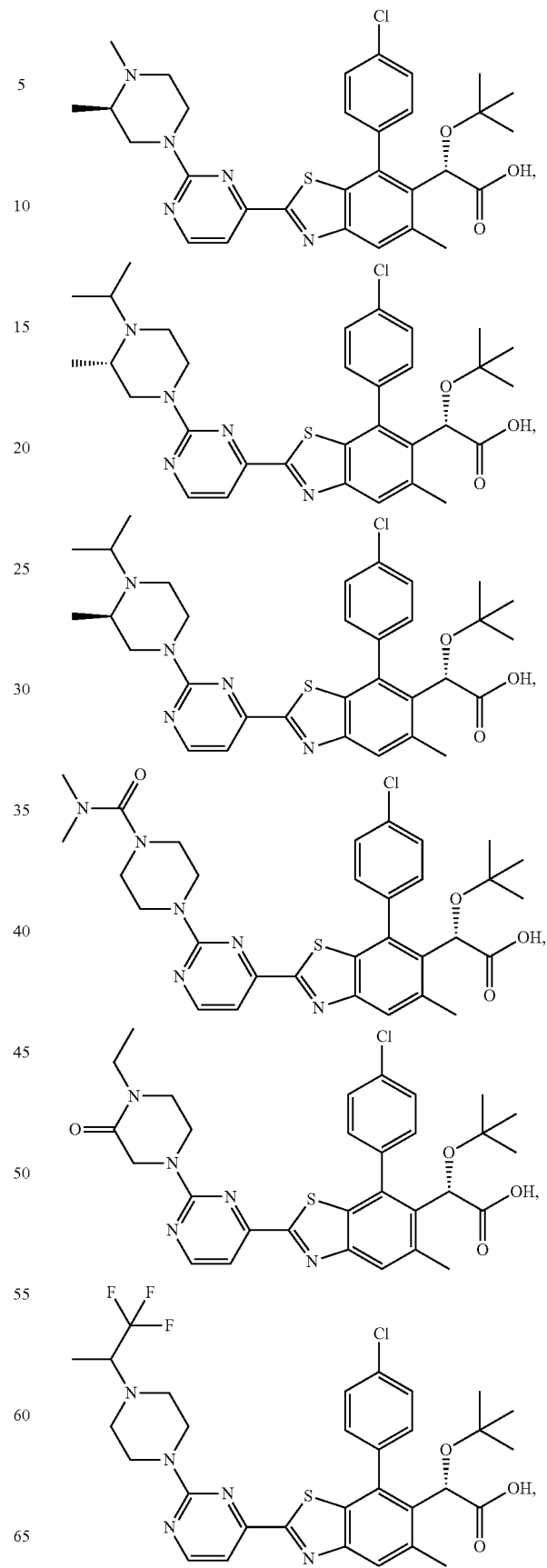

173
-continued
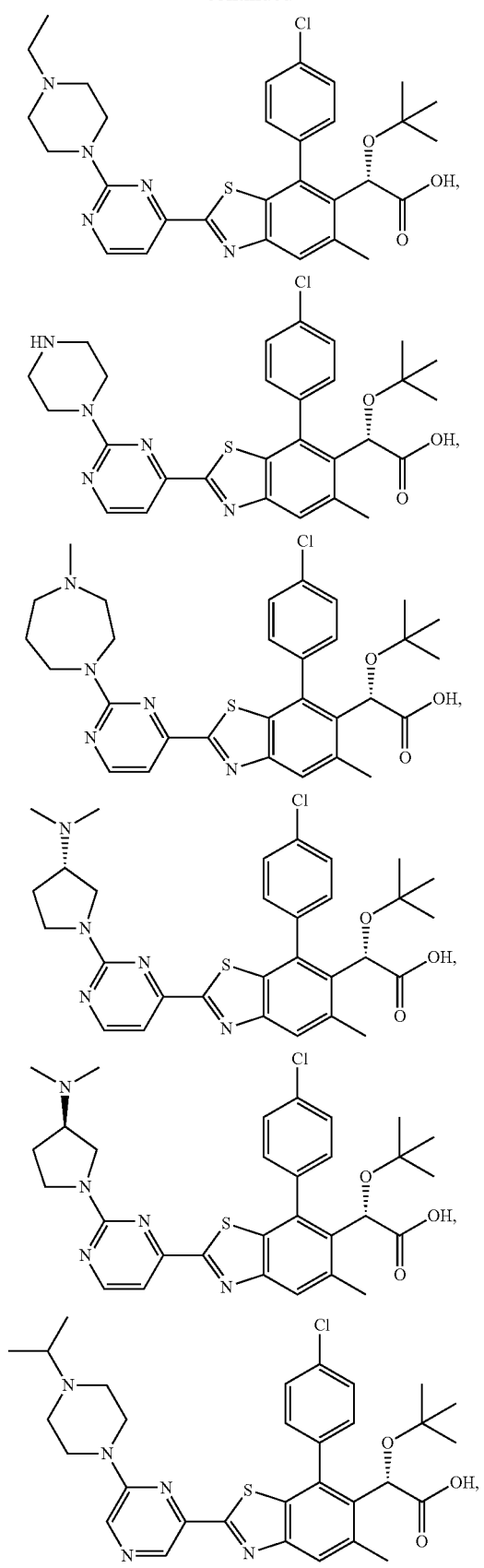
174
-continued
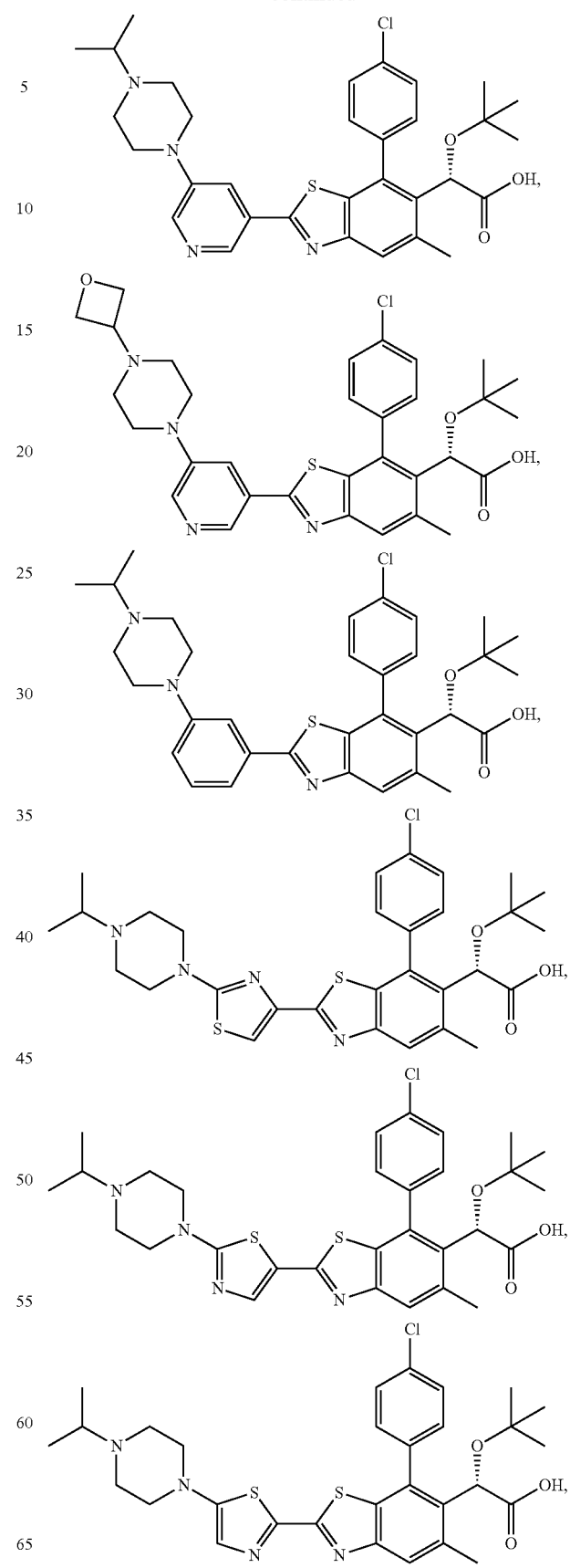

175
-continued
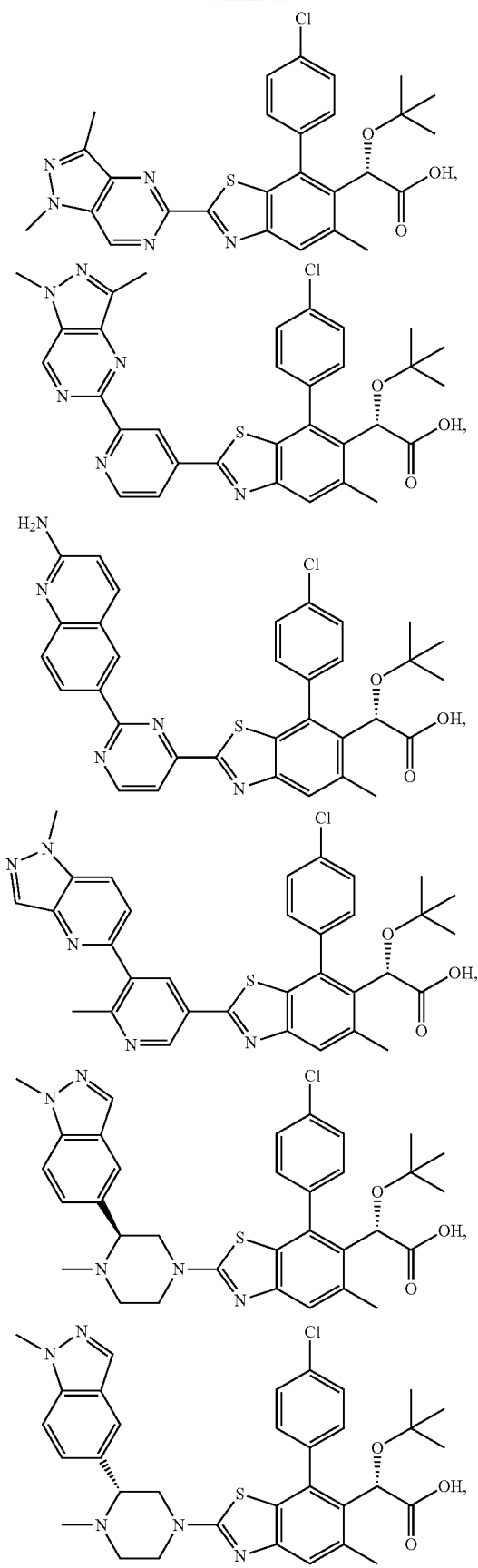
176
-continued
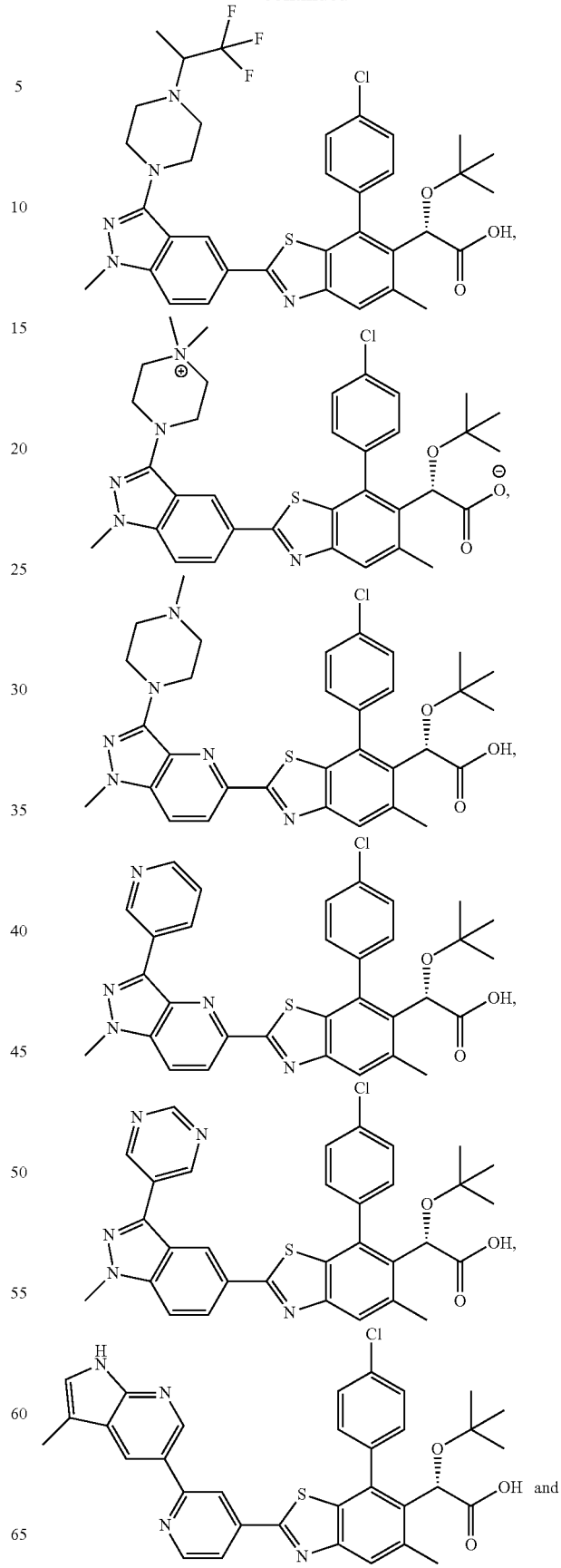

177
-continued
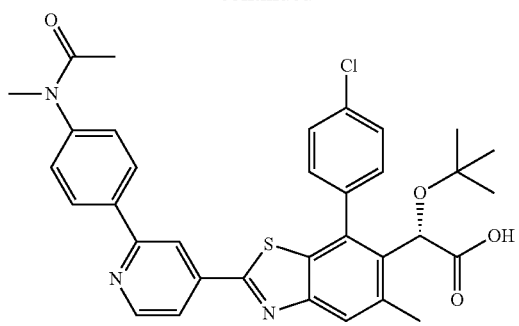
and pharmaceutically acceptable salts thereof.
In one embodiment a compound is selected from:
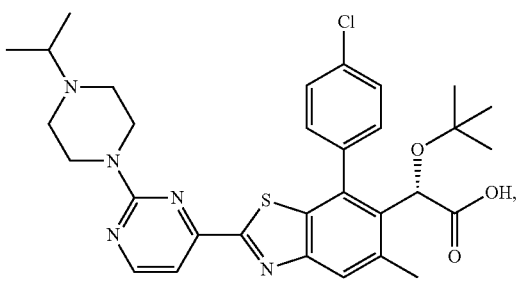
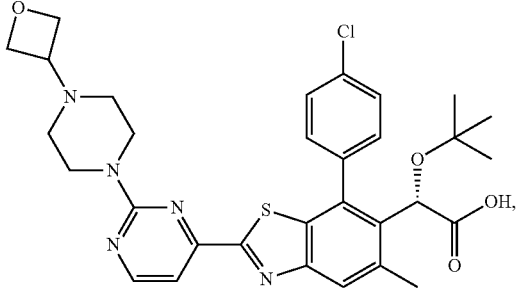
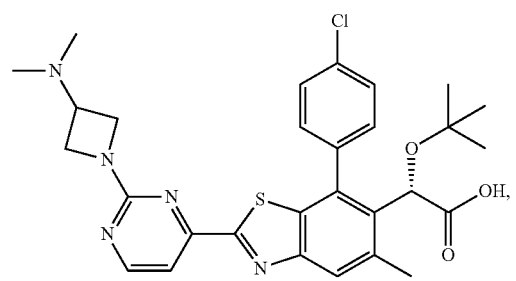
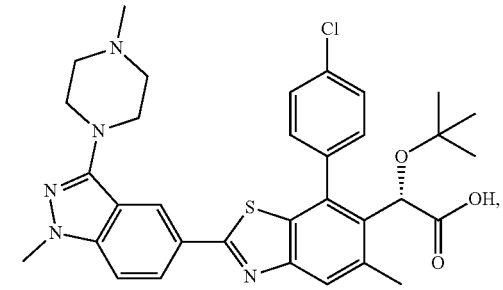
178
-continued
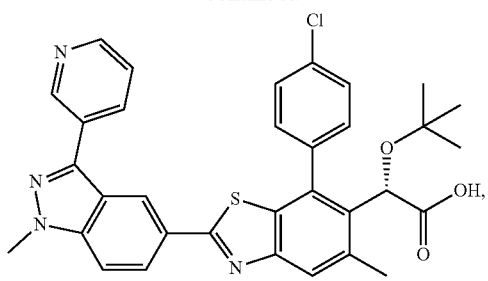
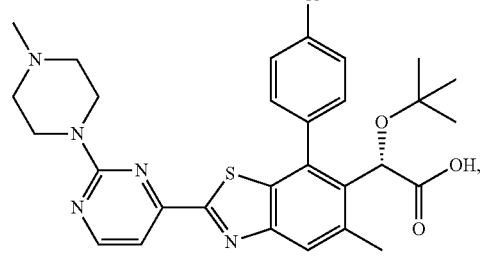
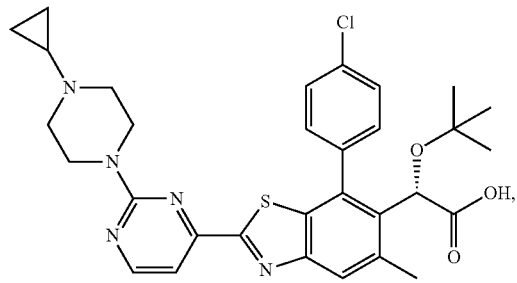
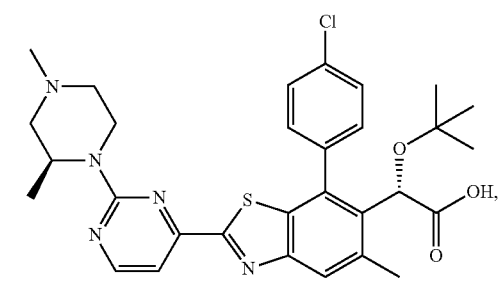
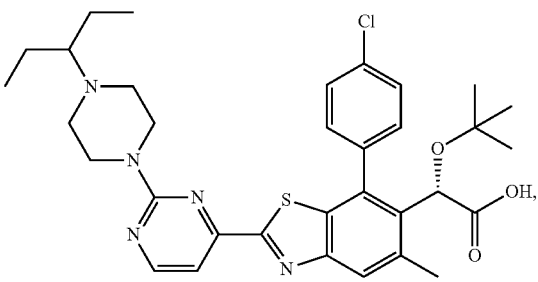
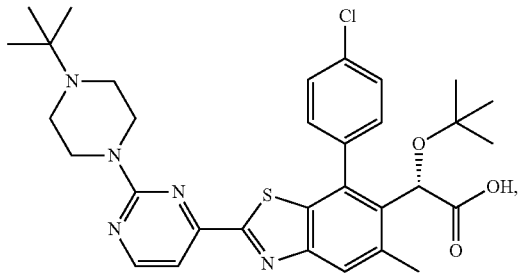

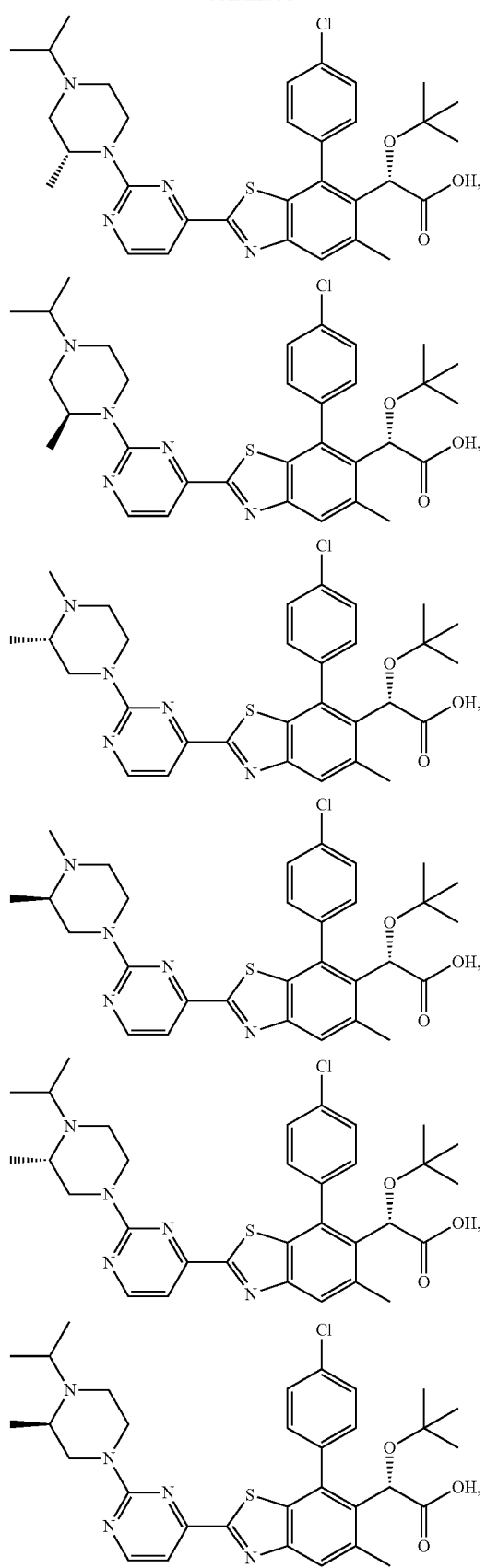
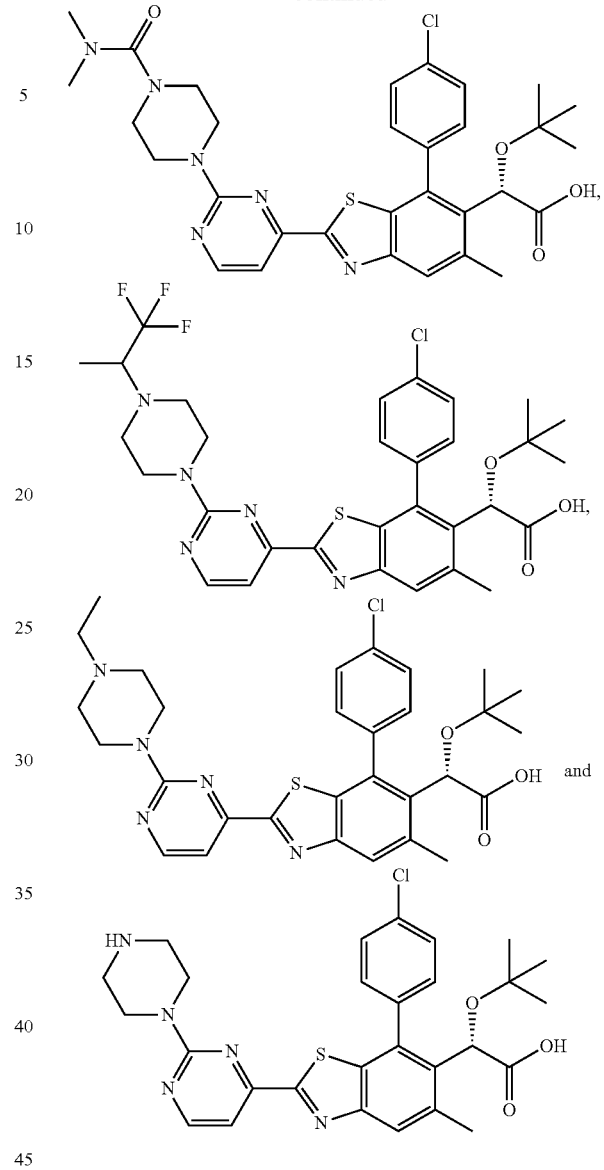

and pharmaceutically acceptable salts thereof.

In one embodiment the compounds of the invention do not include compounds wherein A is thiophene.

In another embodiment the compounds of the invention do not include compounds wherein A is thiophenyl and B is phenyl, wherein phenyl is optionally substituted with one or $Z^{1b}$ groups.

In another embodiment the compounds of the invention do not include compounds wherein A-B is:

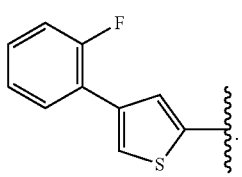 [SMILES: *c1cc(-c2ccccc2F)cs1]

In another embodiment the compounds of the invention do not include the compounds of the following formula:

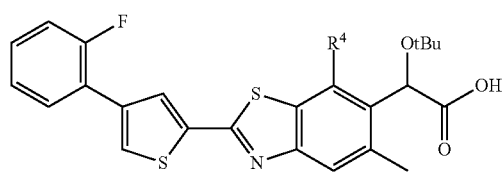
wherein R⁴ is:
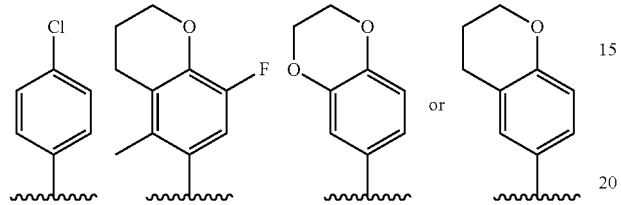
or salts thereof.
General Synthetic Procedures
Schemes 1-17 are provided as further embodiments of the invention and illustrate general methods which were used to prepare compounds of the invention and which can be used to prepare additional compounds of the invention.
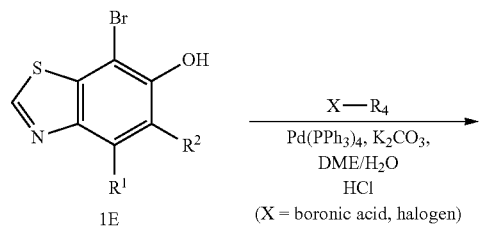
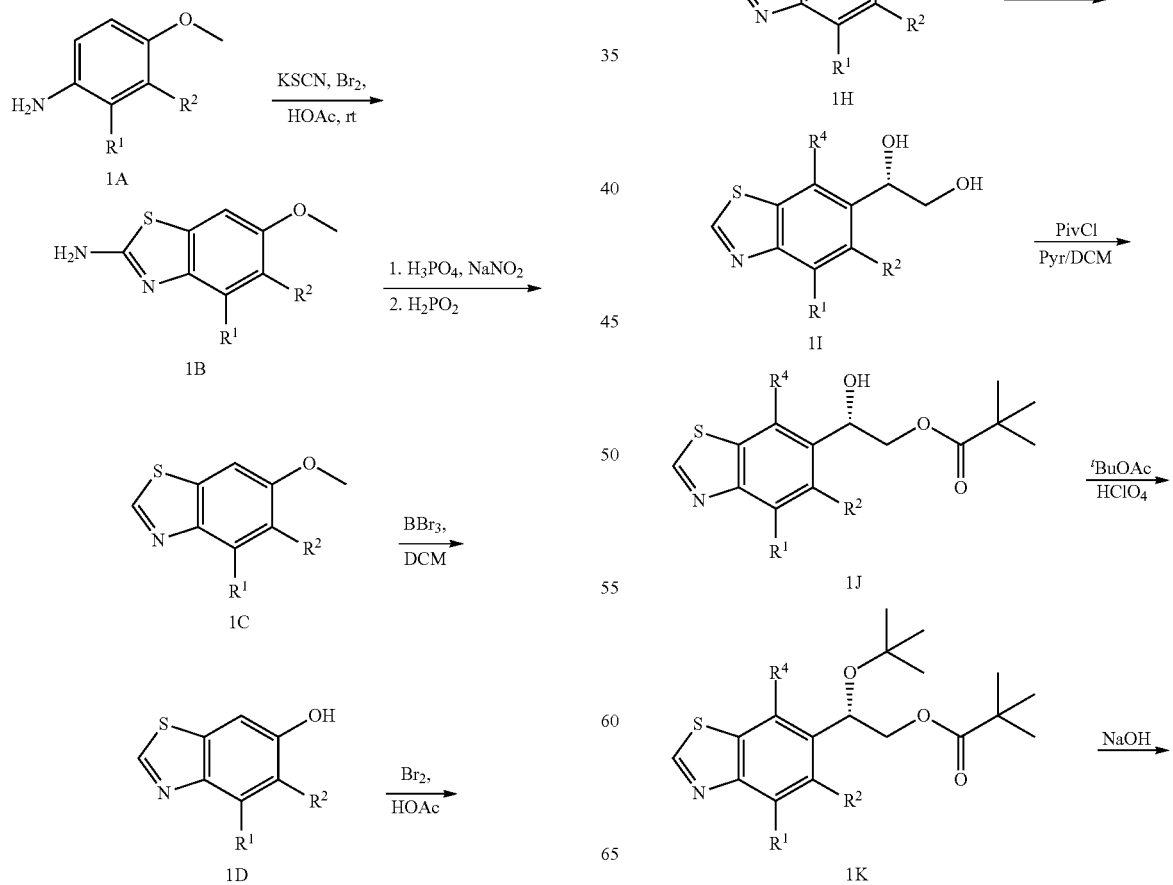

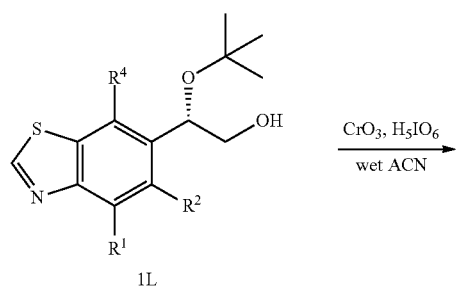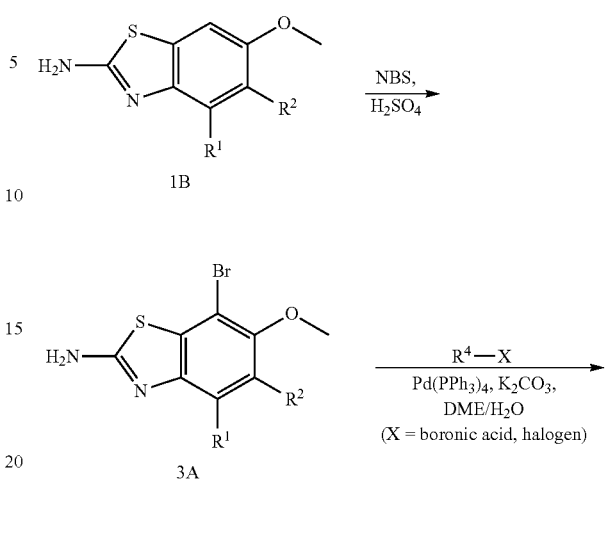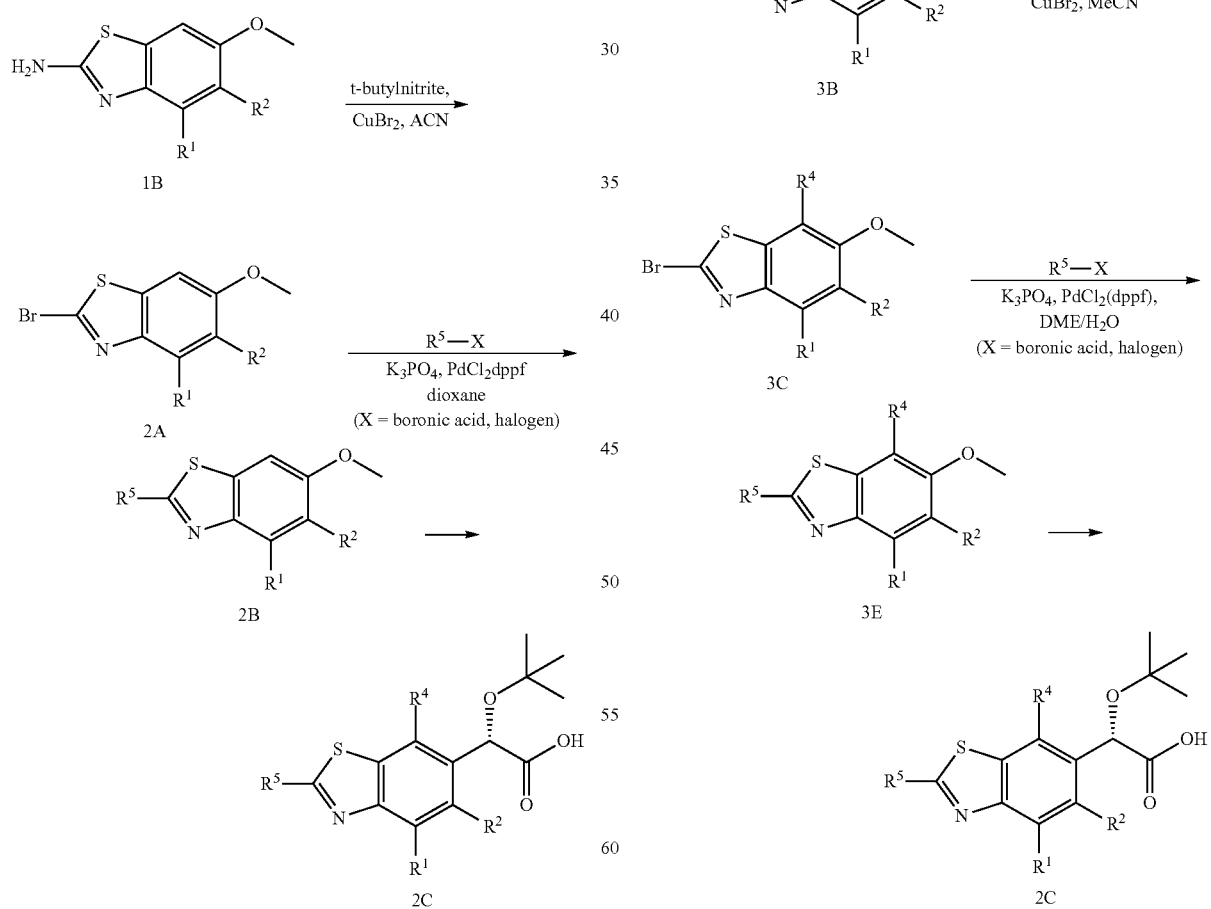
In certain embodiments, the benzothiazole intermediate 2B is converted to the final compound 2C by the methods used to convert 1C to 1M as outlined in Scheme 1.
In certain embodiments, the benzothiazole intermediate 3E is converted to the final compound 2C by the methods used to convert 1C to 1D and 1F to 1M as outlined in Scheme 1.

Scheme 4

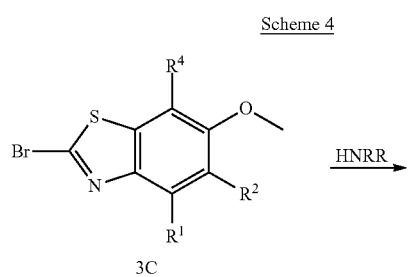

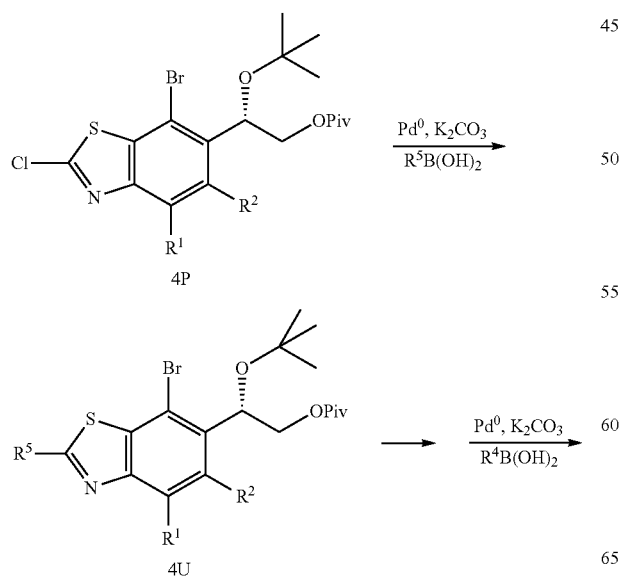

In certain embodiments the benzothiazole intermediate 4A is converted to the final compound 4B by the methods used to convert 1C to 1D and 1F to 1M as outlined in Scheme 1 wherein HNRR a heterocycle (i.e., when R and R taken together with the nitrogen to which they are attached form a ring).

Scheme 5

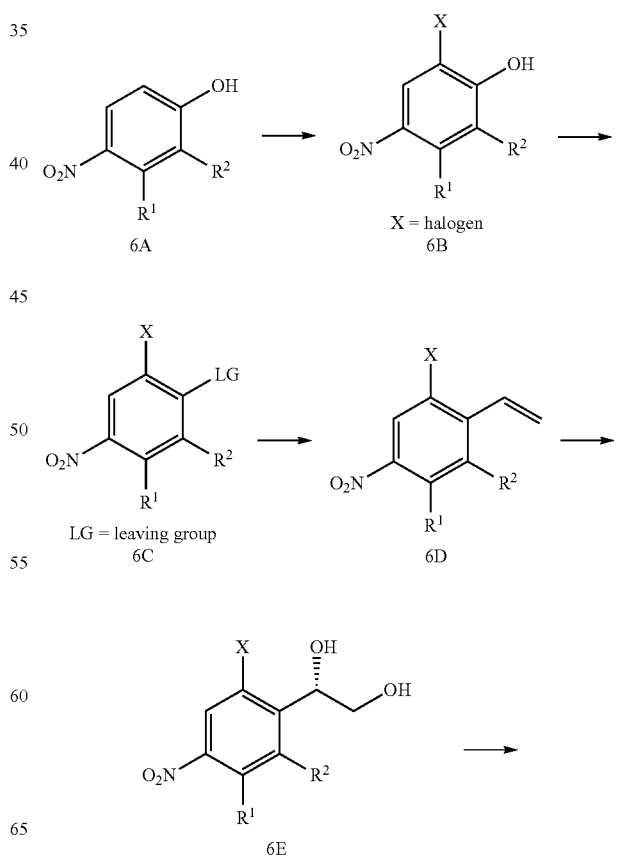

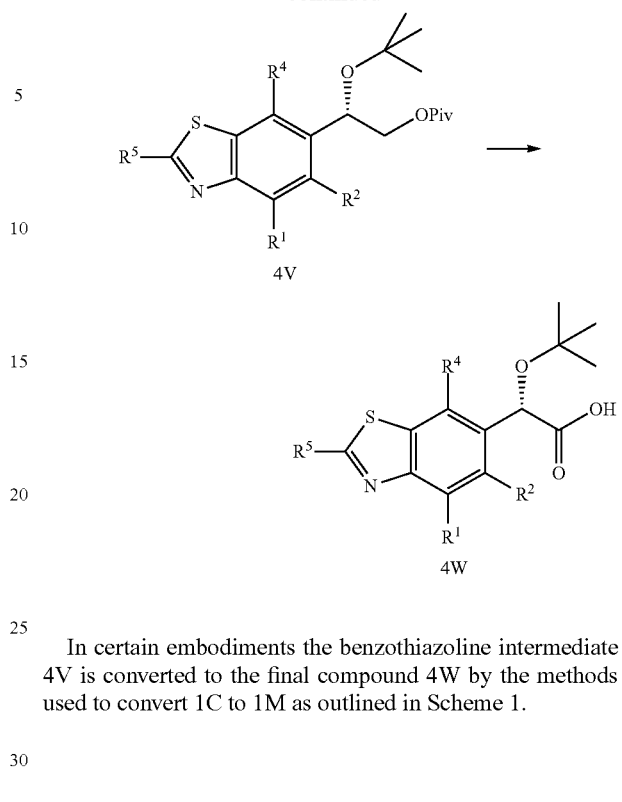

In certain embodiments the benzothiazoline intermediate 4V is converted to the final compound 4W by the methods used to convert 1C to 1M as outlined in Scheme 1.

Scheme 6

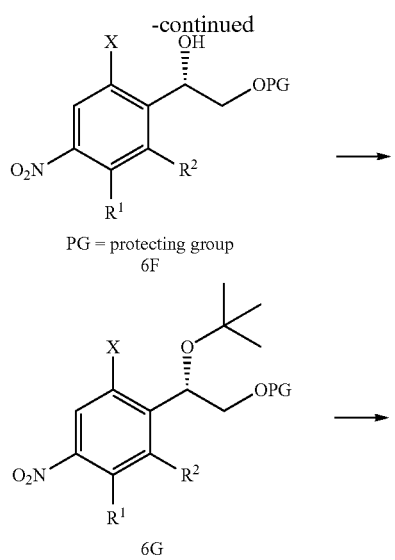

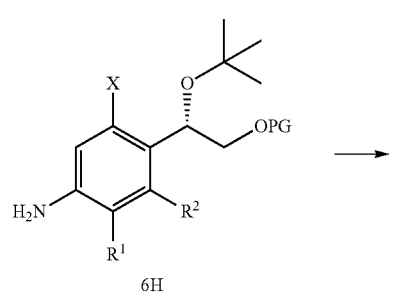

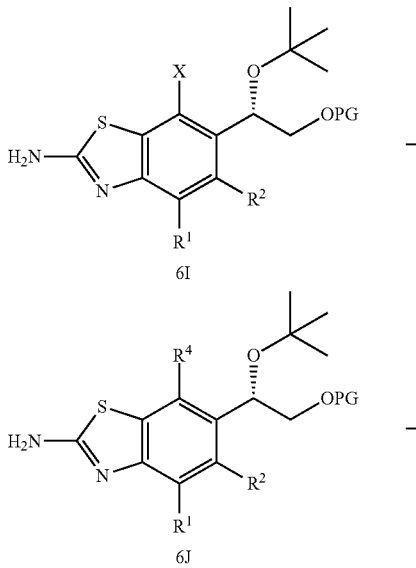

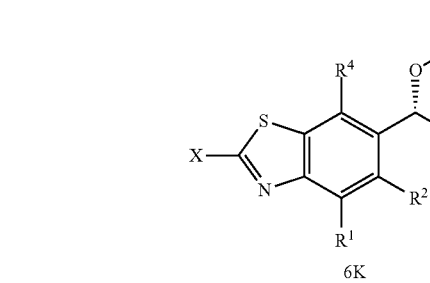

In certain embodiments, an appropriately substituted phenol 6A is halogenated by the treatment of dihalide, for example bromine, in a suitable solvent such as, for example acetic acid. The phenol 6B is converted to a leaving group (e.g., triflate) known to undergo cross-coupling reactions. The corresponding activated phenol 6C undergoes a selective cross-coupling reaction such as, for example Stille cross-coupling using a tin reagent such as tributyl(vinyl)tin and a palladium catalyst such as bis(triphenylphosphine) palladium(II) dichloride to give the corresponding cross-coupled naphthalene such as styrene 6D. The styrene is dihydroxylated to provide 6E by methods known to those skilled in the art such as, Sharpless asymmetric dihydroxylation using, for example, commercially available AD mix-α. The resulting diol 6E is protected at the primary hydroxyl by suitable protecting groups such as pivalate ester using pivaloyl chloride and pyridine to provide 6F. The secondary hydroxyl is converted to the corresponding ether such as tert-butyl ether using methods known to those skilled in the art such as, tert-butyl acetate and perchloric acid to provide 6G.

The nitro group of 6G is reduced to the corresponding aniline 6H by catalytic hydrogenation using platinum on carbon, for example, under a hydrogen atmosphere. Benzothiazole 6I is formed by methods known to those skilled in the art such as potassium thiocyanate and pyridinium perbromide, for example. The resulting benzothiazole undergoes cross-coupling reaction such as Suzuki cross-coupling using a boronic acid or ester and a palladium catalyst such as tetrakis(triphenylphosphine)palladium(0) to give the corresponding cross-coupled benzothiazole 6J. The corresponding halobenzothiazole 6K is formed by methods known to those skilled in the art such as tert-butyl nitrite and a copper(II) halide such as copper(II) bromide, for example.

Scheme 7

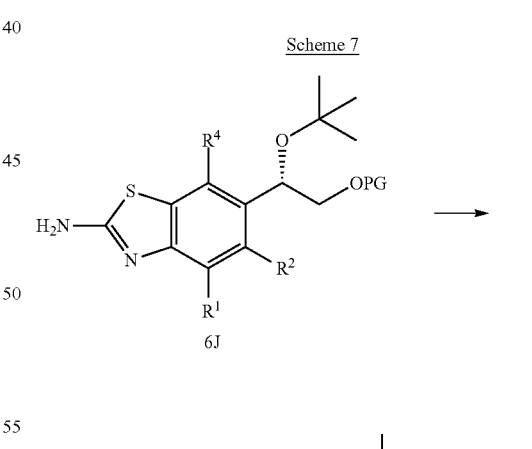

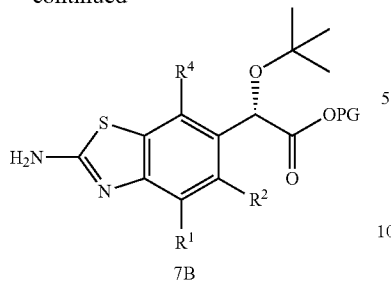

7B

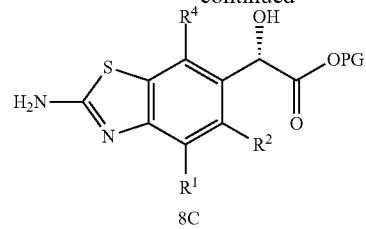

8C

In certain embodiments the protected primary hydroxyl 6J is deprotected by methods known to those skilled in the art such as the deprotection of a pivalate protecting group under basic conditions for example, using sodium hydroxide, to give the corresponding primary hydroxyl compound 7A. The primary hydroxyl is oxidized to the corresponding carboxylic acid 7B by methods known to those skilled in the art such as, for example, periodic acid and chromium trioxide. The resulting carboxylic acid is protected by formation of corresponding carboxylic ester 7B with treatment of, for example, trimethylsilyldiazomethane, to form the corresponding methyl ester.

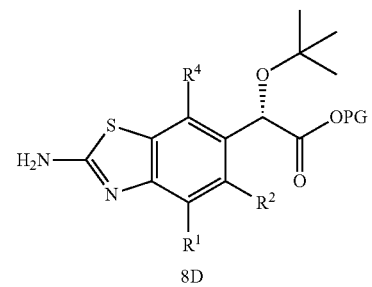

8D

Scheme 8

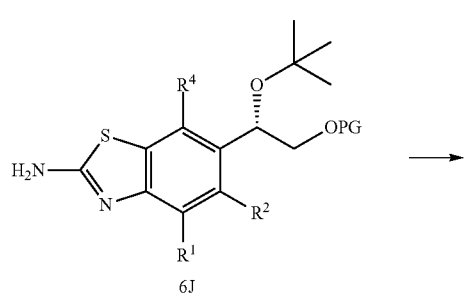

6J

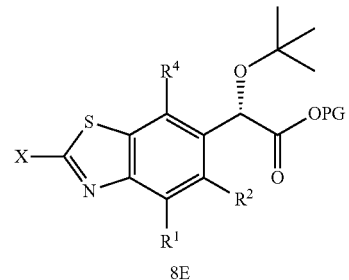

8E

In certain embodiments the protected primary hydroxyl 6J is deprotected by methods known to those skilled in the art such as the deprotection of a pivalate protecting group under basic conditions for example, using sodium hydroxide, to give the corresponding primary hydroxyl compound 8A. The primary hydroxyl is oxidized to the corresponding carboxylic acid 8B by periodic acid and chromium trioxide, for example. The carboxylic acid is protected as, for example, a methyl ester by treatment with sulfuric acid in methanol. The tert-butyl ether is re-installed by treating 8C with tert-butyl acetate and perchloric acid, for example, to provide 8D. The corresponding halobenzothiazole 8E is formed by methods known to those skilled in the art such as tert-butyl nitrite and a copper(II)halide such as copper(II)bromide, for example.

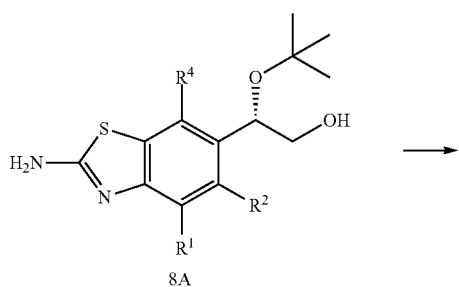

8A

Scheme 9

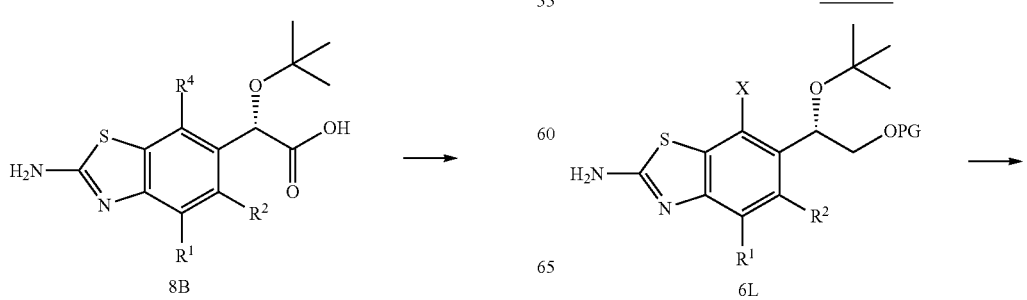

8B        6L

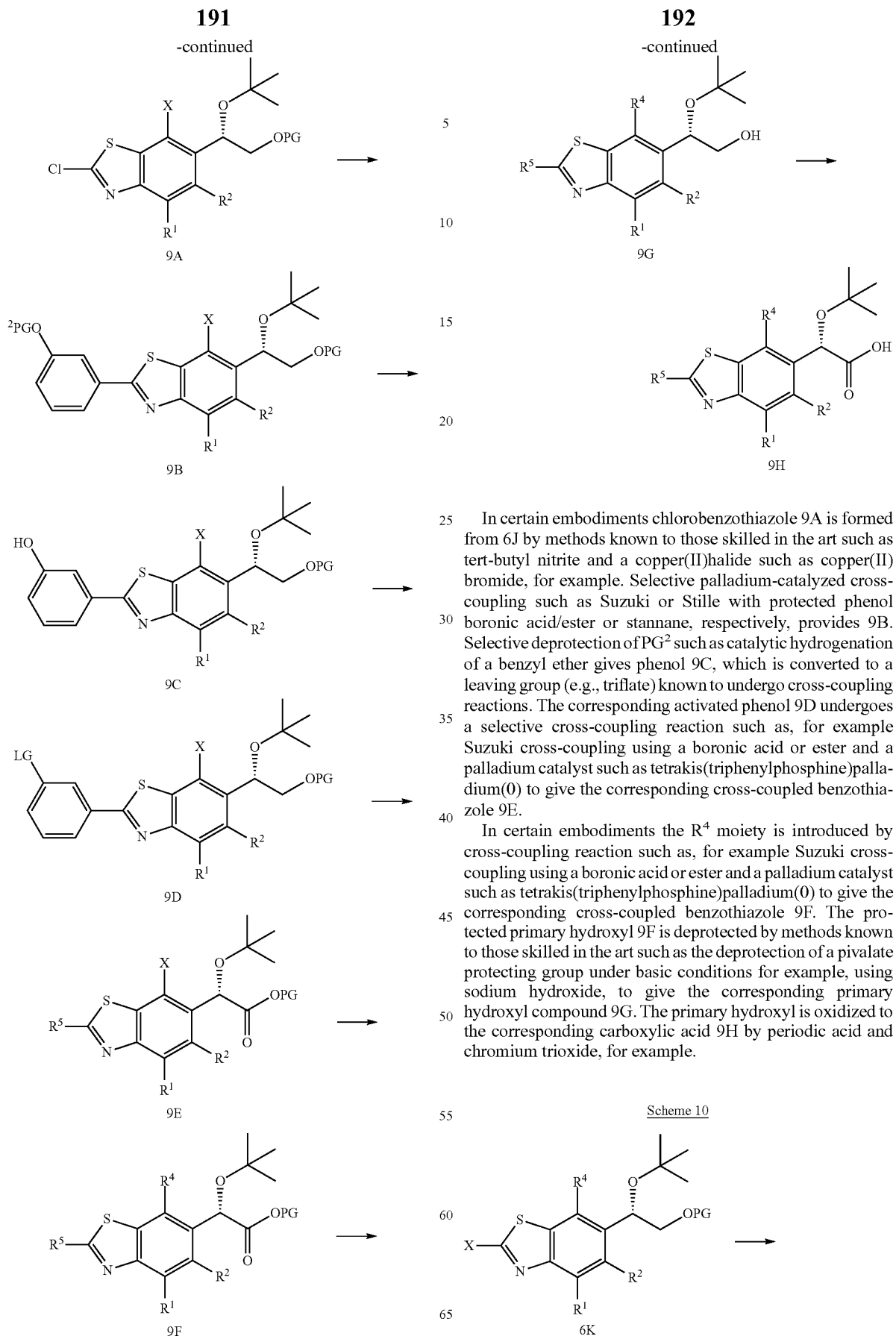

In certain embodiments chlorobenzothiazole 9A is formed from 6J by methods known to those skilled in the art such as tert-butyl nitrite and a copper(II)halide such as copper(II) bromide, for example. Selective palladium-catalyzed cross-coupling such as Suzuki or Stille with protected phenol boronic acid/ester or stannane, respectively, provides 9B. Selective deprotection of $PG^2$ such as catalytic hydrogenation of a benzyl ether gives phenol 9C, which is converted to a leaving group (e.g., triflate) known to undergo cross-coupling reactions. The corresponding activated phenol 9D undergoes a selective cross-coupling reaction such as, for example Suzuki cross-coupling using a boronic acid or ester and a palladium catalyst such as tetrakis(triphenylphosphine)palladium(0) to give the corresponding cross-coupled benzothiazole 9E.

In certain embodiments the $R^4$ moiety is introduced by cross-coupling reaction such as, for example Suzuki cross-coupling using a boronic acid or ester and a palladium catalyst such as tetrakis(triphenylphosphine)palladium(0) to give the corresponding cross-coupled benzothiazole 9F. The protected primary hydroxyl 9F is deprotected by methods known to those skilled in the art such as the deprotection of a pivalate protecting group under basic conditions for example, using sodium hydroxide, to give the corresponding primary hydroxyl compound 9G. The primary hydroxyl is oxidized to the corresponding carboxylic acid 9H by periodic acid and chromium trioxide, for example.

Scheme 10

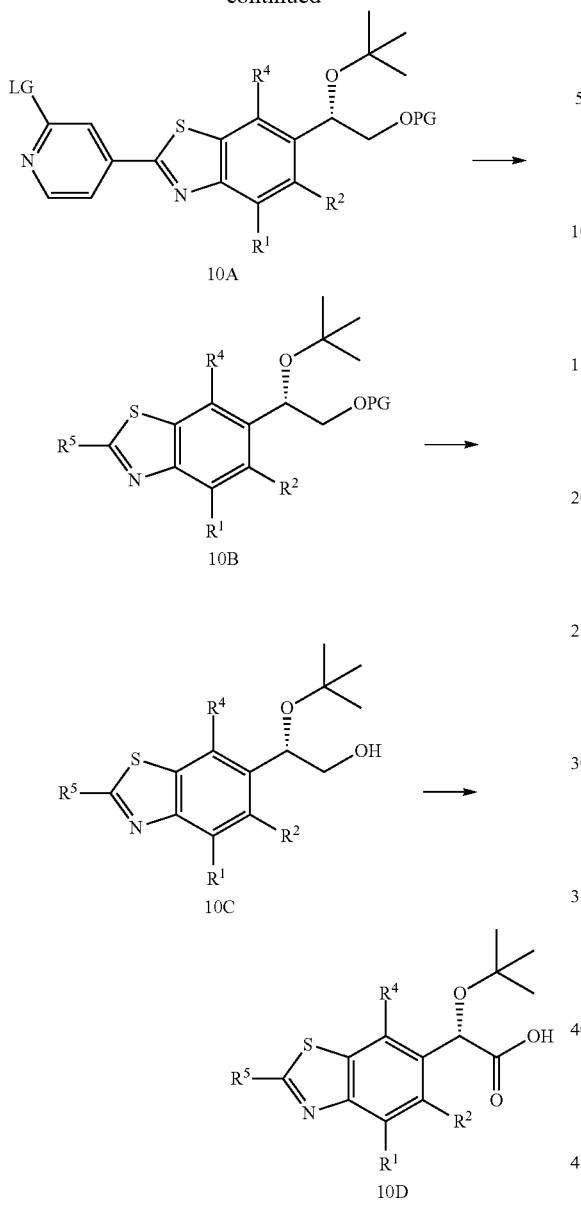

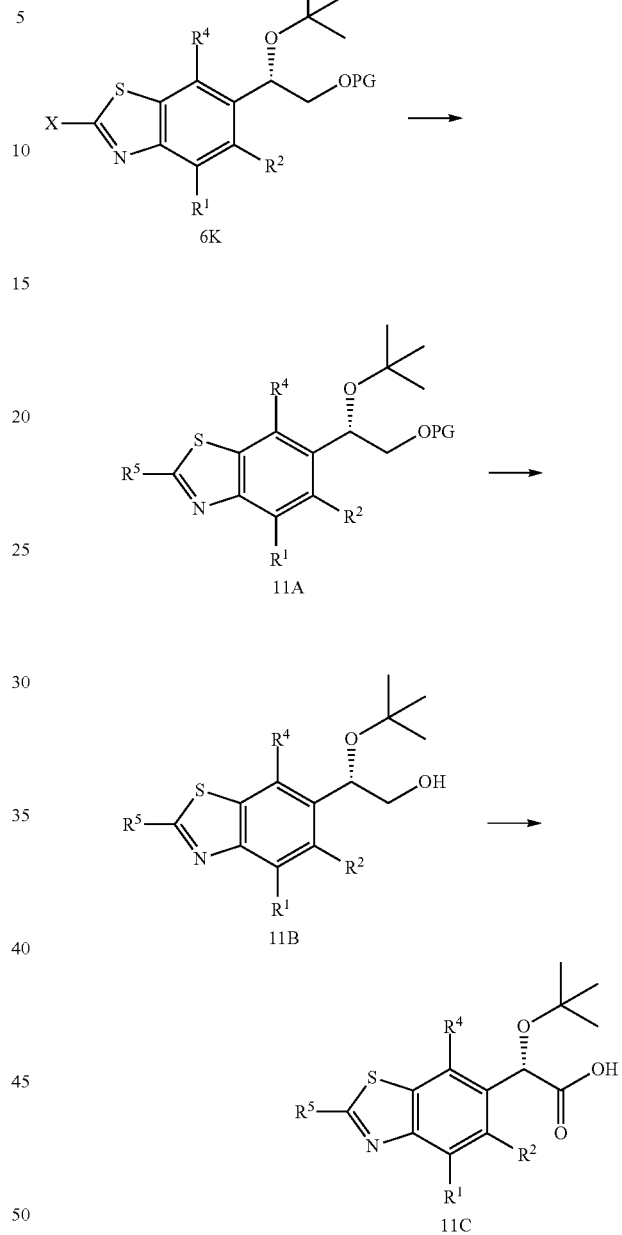

Scheme 11

In certain embodiments halobenzothiazole 6K undergoes selective palladium-catalyzed cross-coupling such as Suzuki or Stille with a boronic acid/ester or stannane that also contains a leaving group such as for example, a chloropyridylboronic acid, known to undergo cross-coupling reactions to give 10A. The activated moiety 10A undergoes a cross-coupling reaction such as, for example Suzuki or Stille cross-coupling using a boronic acid/ester or stannane, respectively and a palladium catalyst such as tetrakis(triphenylphosphine)palladium(0) to give the corresponding cross-coupled benzothiazole 10B. The protected primary hydroxyl 10B is deprotected by methods known to those skilled in the art such as the deprotection of a pivalate protecting group under basic conditions for example, using sodium hydroxide, to give the corresponding primary hydroxyl compound 10C. The primary hydroxyl is oxidized to the corresponding carboxylic acid 10D by periodic acid and chromium trioxide, for example.

In certain embodiments halobenzothiazole 6K undergoes palladium-catalyzed cross-coupling such as Suzuki with a boronic acid or ester; Stille with a stannane; palladium-catalyzed carbonylation using carbon monoxide, for example in the presence of an amine; copper(I)halide catalyzed or Buchwald-Hartwig amination; palladium-catalyzed amidation; $S_NAr$ with an amine; to introduce the $R^5$ moiety in 11A. The protected primary hydroxyl of 11A is deprotected by methods known to those skilled in the art such as the deprotection of a pivalate protecting group under basic conditions for example, using sodium hydroxide, to give the corresponding primary hydroxyl compound 11B. The primary hydroxyl is oxidized to the corresponding carboxylic acid 11C by periodic acid and chromium trioxide, for example.

Scheme 12

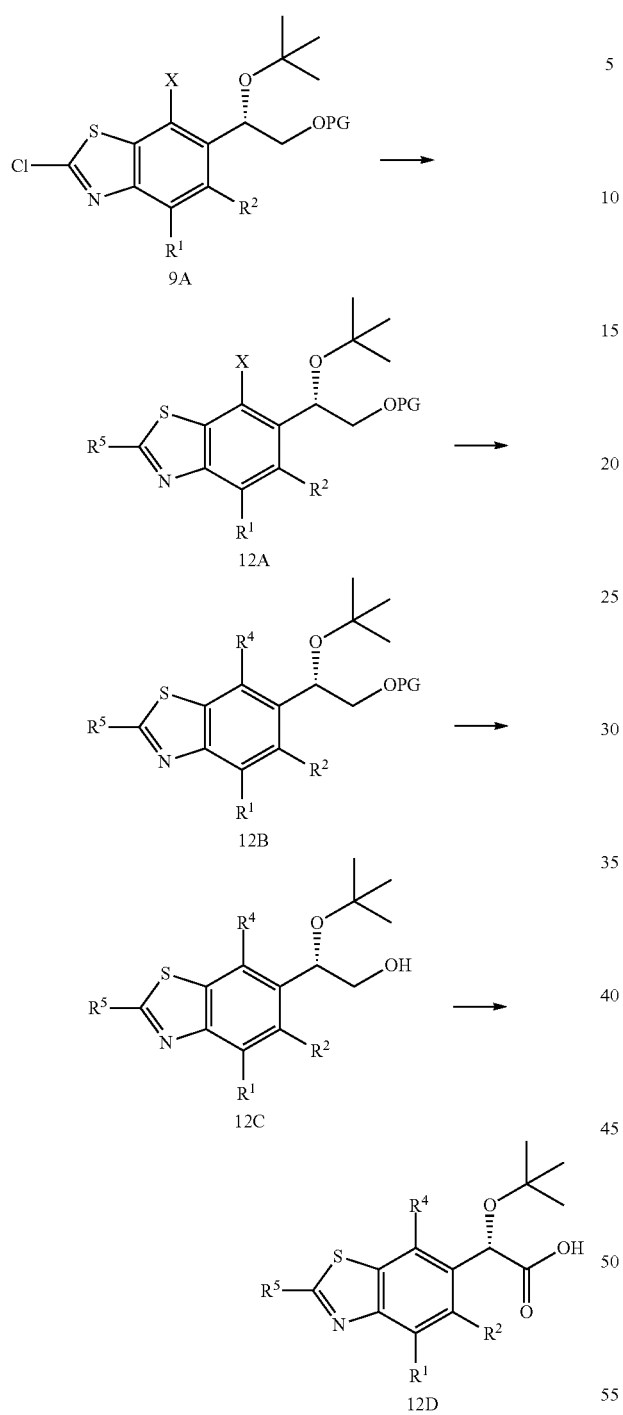

deprotection of a pivalate protecting group under basic conditions for example, using sodium hydroxide, to give the corresponding primary hydroxyl compound 12C. The primary hydroxyl is oxidized to the corresponding carboxylic acid 12D by periodic acid and chromium trioxide, for example.

Scheme 13

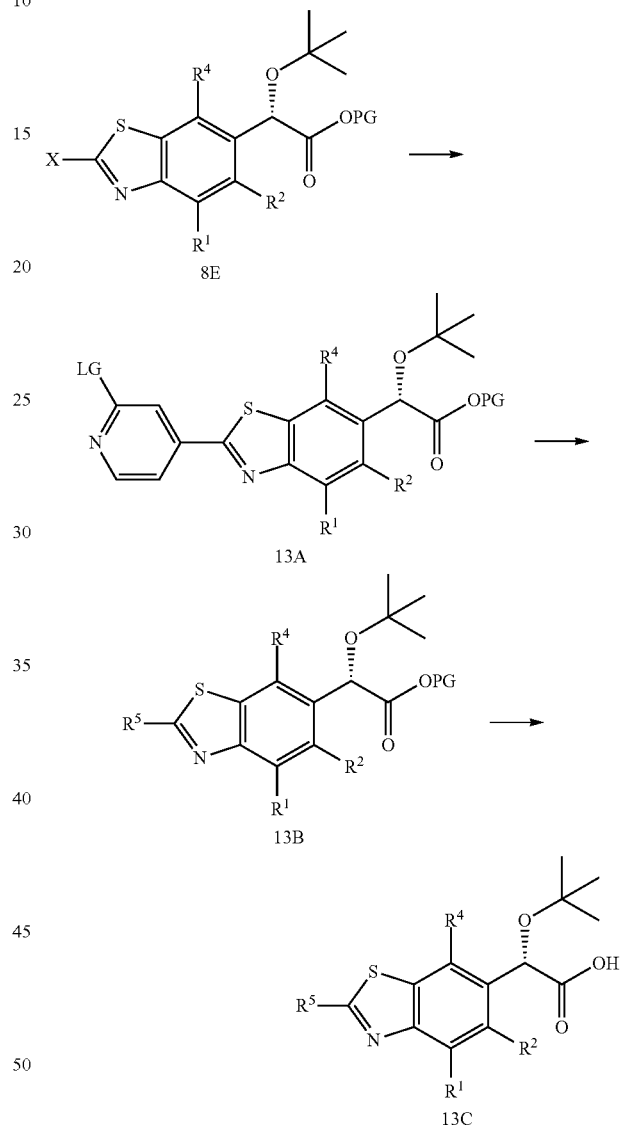

In certain embodiments chlorobenzothiazole 9A undergoes selective palladium-catalyzed cross-coupling such as Suzuki or Stille with protected phenol boronic acid/ester or stannane, respectively, to provide 12A. The $R^4$ moiety is introduced by cross-coupling reaction such as, for example Suzuki cross-coupling using a boronic acid or ester and a palladium catalyst such as tetrakis(triphenylphosphine)palladium(0) to give the corresponding cross-coupled benzothiazole 12B. The protected primary hydroxyl in 12B is deprotected by methods known to those skilled in the art such as the In certain embodiments halobenzothiazole 8E undergoes selective palladium-catalyzed cross-coupling such as Suzuki or Stille with a boronic acid/ester or stannane that also contains a leaving group such as for example, a chloropyridylboronic acid, known to undergo cross-coupling reactions to give 13A. The activated moiety 13A undergoes an $S_NAr$ reaction with for example a secondary amine, or a cross-coupling reaction such as, for example Suzuki or Stille cross-coupling using a boronic acid/ester or stannane, respectively, and a palladium catalyst such as tetrakis(triphenylphosphine) palladium(0) to give the corresponding cross-coupled benzothiazole 13B. The protected carboxylic acid 13B is deprotected by methods known to those skilled in the art such as the deprotection of a carboxylic ester under basic conditions for example, using sodium hydroxide, or treatment with lithium iodide in pyridine, to give the corresponding carboxylic acid 13C.

Scheme 14

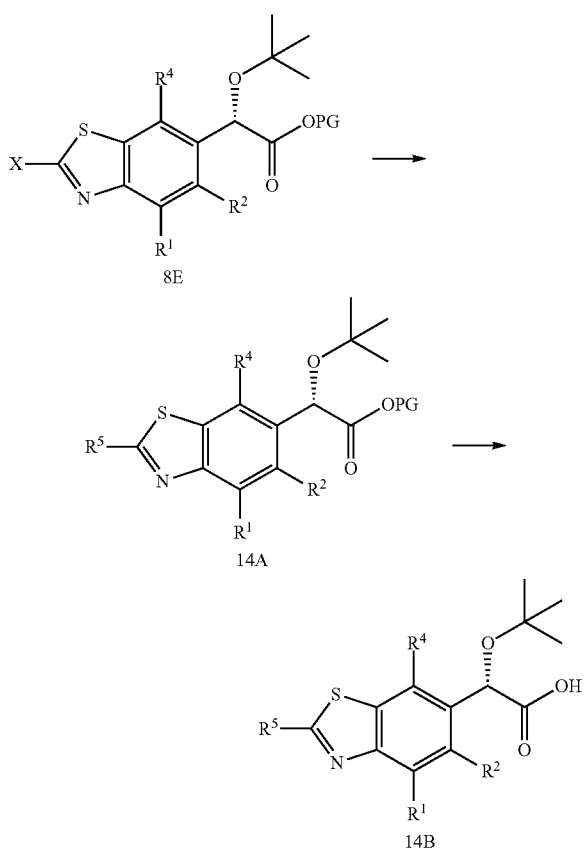

In certain embodiments halobenzothiazole 8E undergoes palladium-catalyzed cross-coupling such as Suzuki with a boronic acid or ester; Stille with a stannane; palladium-catalyzed carbonylation using carbon monoxide, for example in the presence of an amine; copper(I)halide catalyzed or Buchwald-Hartwig amination; palladium-catalyzed amidation; $S_NAr$ with an amine or alcohol; to introduce the $R^5$ moiety in 14A. The protected carboxylic acid 14A is deprotected by methods known to those skilled in the art such as the deprotection of a carboxylic ester under basic conditions for example, using sodium hydroxide, or treatment with lithium iodide in pyridine to give the corresponding carboxylic acid 14B.

Scheme 15

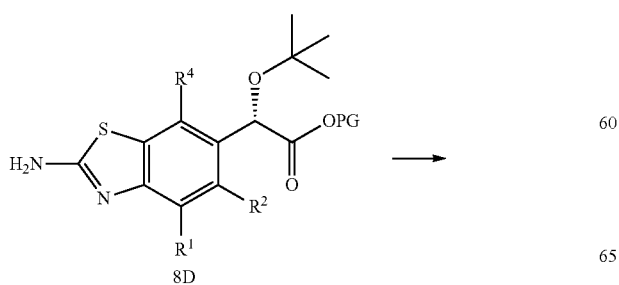

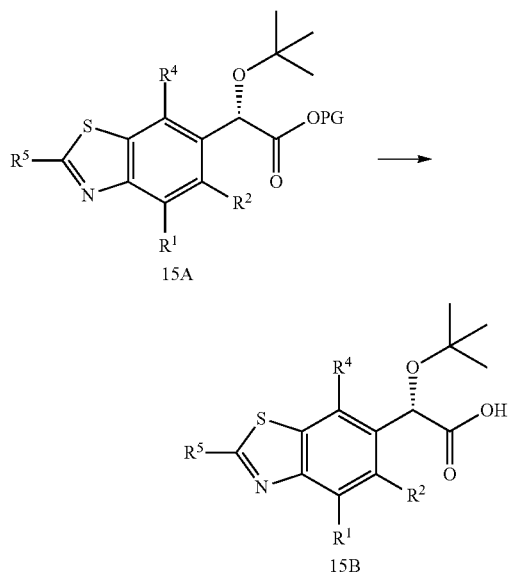

In certain embodiments aminobenzothiazole 8D undergoes reactions known to those skilled in the art such as amide formation using carboxylic acid EDCI, for example; sulfonamide formation using a sulfonyl chloride; urea formation using CDI in the presence of an amine; to introduce the $R^5$ moiety in 15A. The protected carboxylic acid 15A is deprotected by methods known to those skilled in the art such as the deprotection of a carboxylic ester under basic conditions for example, using sodium hydroxide, to give the corresponding carboxylic acid 15B.

Scheme 16

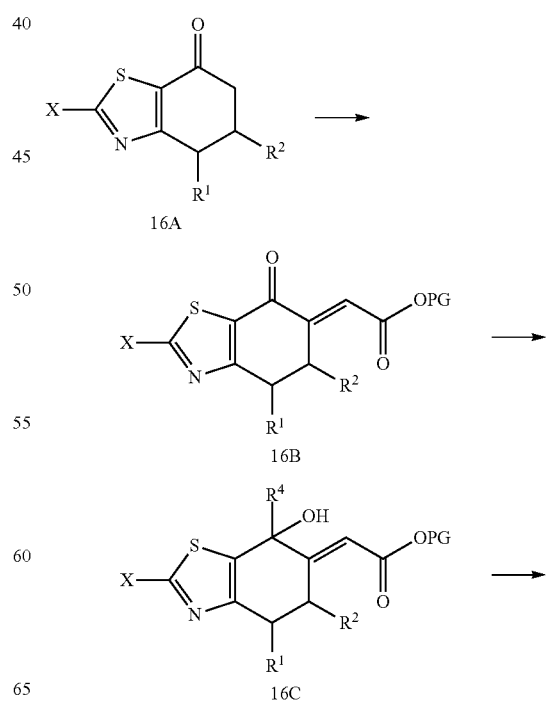

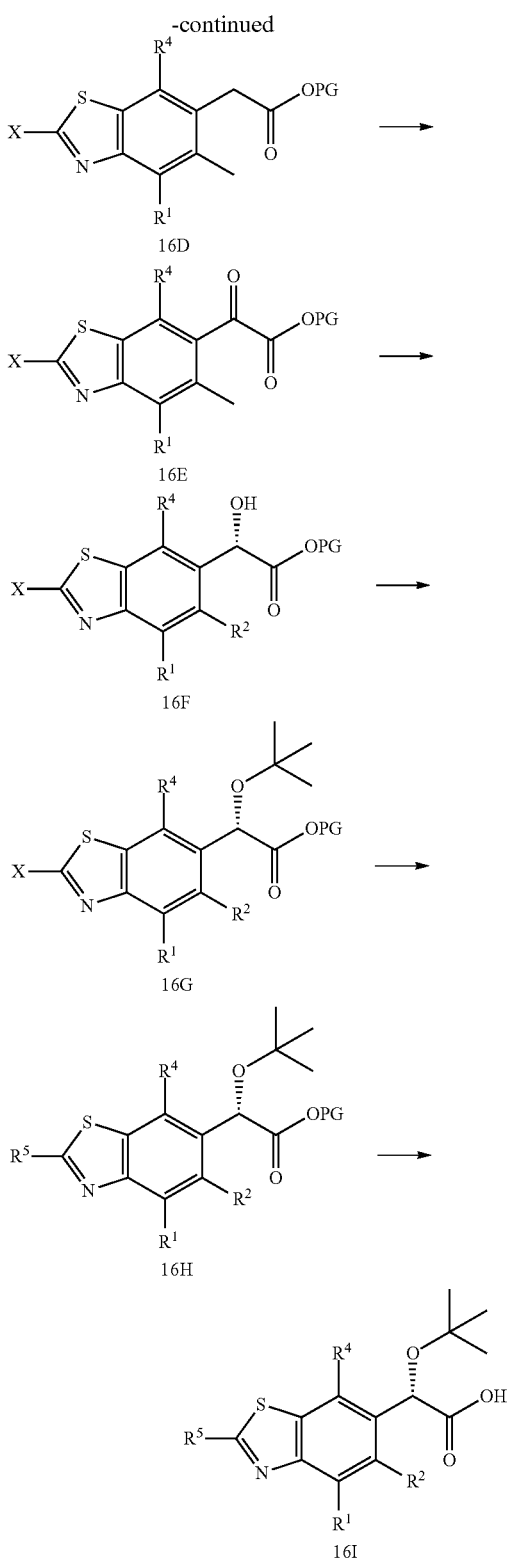

presence of oxaziridine such as Davis reagent, followed oxidation with an oxidant such as Dess-Martin periodinane can give ketoester 16E. Chiral reductions of 16E such as CBS or Noyori can give chiral alcohol 16F. The secondary hydroxyl is converted to the corresponding ether such as tert-butyl ether using methods known to those skilled in the art such as, tert-butyl acetate and perchloric acid to provide 16G. The activated benzthiazole 16G undergoes a cross-coupling reaction such as, for example Buchwald, Heck, Negishi, Suzuki or Stille cross-coupling using a palladium catalyst such as tetrakis(triphenylphosphine)palladium(0); $S_NAr$ reactions with for example, a secondary amine; to give the corresponding benzothiazole 16H. The protected carboxylic acid 16H is deprotected by methods known to those skilled in the art such as the deprotection of a carboxylic ester under basic conditions for example, using sodium hydroxide, or treatment with lithium iodide in pyridine to give the corresponding carboxylic acid 16I.

Scheme 17

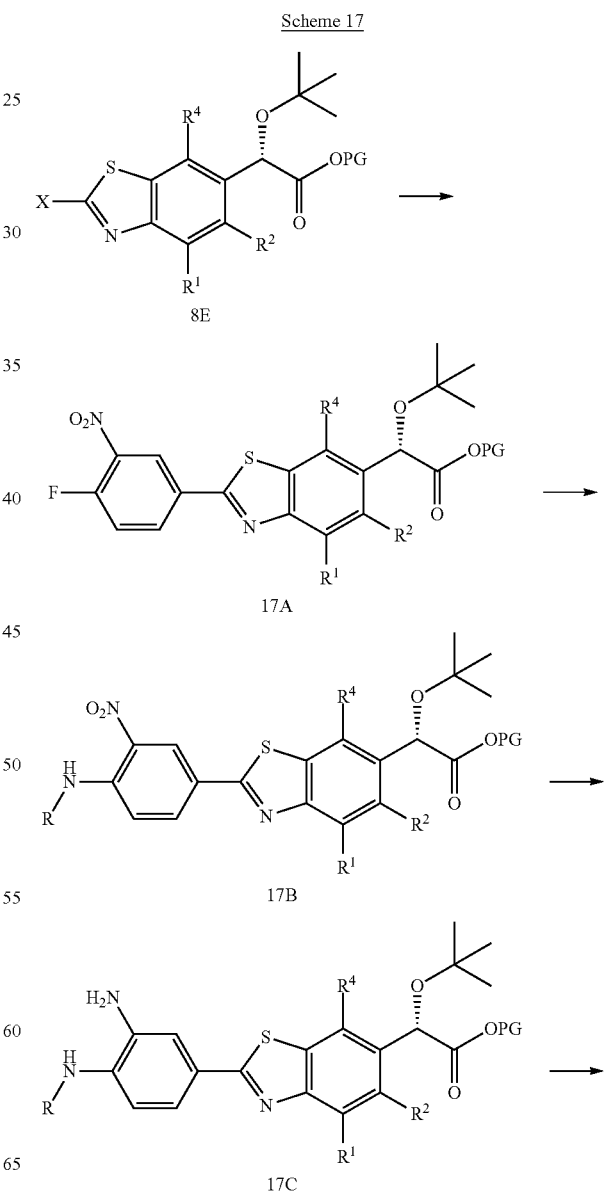

In certain embodiments, ketone 16A undergoes reactions known to those skilled in the art such as aldol condensation to give enone 16B. Enone 16B can undergo 1,2 organometallic additions such as Grignard additions to give tertiary alcohol 16C. Under the action of an acid such as polyphosphoric acid, 16C is converted to benzthiazole 16D. Reaction of 16D under basic conditions such as lithium hexamethyldisilazane in the

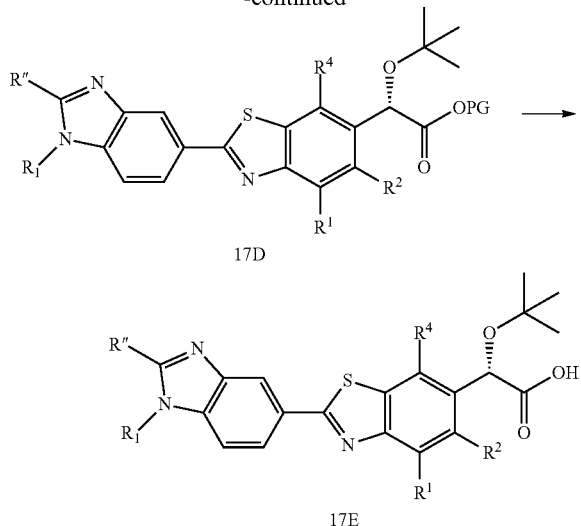

17D

17E

In certain embodiments, halobenzthiazole 8E undergoes palladium-catalyzed cross-coupling such as Suzuki with a boronic acid or ester, for Example 2-(4-fluoro-3-nitrophenyl)-4,4,5,5-tetramethyl-1,3,2-dioxaborolane to give 17A, known to those skilled in the art to undergo SnAr reaction with nucleophiles, such as, for example methylamine, to give 17B. Hydrogenation under platinum on carbon, for example provides the bis-aniline 17C. Cyclization with an orthoformate, such as triethylorthoformate in acetic acid, for example gives benzimidazole 17D. The protected carboxylic acid 17D is deprotected by methods known to those skilled in the art such as the deprotection of a carboxylic ester under basic conditions for example, using sodium hydroxide, or treatment with lithium iodide in pyridine to give the corresponding carboxylic acid 17E.

Prodrugs

In one embodiment, a prodrug of a compound described herein is provided. The term "prodrug" as used herein refers to any compound that when administered to a biological system generates a compound of the invention that inhibits the replication of HIV ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2C(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 24; also U.S. Pat. Nos. 4,816,570, 4,968,788, 5663159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Combination Therapy

In one embodiment, a method for treating an HIV infection is provided, comprising administering to a patient in need thereof a therapeutically effective amount of a compound disclosed herein, or a pharmaceutically acceptable salt, thereof, in combination with a therapeutically effective amount of one or more additional therapeutic agents which are suitable for treating an HIV infection.

In one embodiment, pharmaceutical compositions comprising a compound disclosed herein, or a pharmaceutically acceptable salt thereof, in combination with at least one additional therapeutic agent, and a pharmaceutically acceptable carrier are provided. For example, the therapeutic agent used in combination with the compound disclosed herein can be any anti-HIV agent.

One embodiment provides pharmaceutical compositions comprising a compound disclosed herein, or a pharmaceutically acceptable salt thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof, and a pharmaceutically acceptable carrier.

One embodiment provides pharmaceutical compositions comprising a compound disclosed herein, or a pharmaceutically acceptable salt thereof, in combination with at least one additional therapeutic agent selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, RDEA806, KM023 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), adefovir, adefovir dipivoxil, CMX-001 (Chimerix) or CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, GS-5696, elvitegravir and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5 mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

Another embodiment provides pharmaceutical compositions comprising a compound disclosed herein, or a pharmaceutically acceptable salt thereof, in combination with at least one additional therapeutic agent selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5 mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In another embodiment, the invention provides pharmaceutical compositions comprising a compound disclosed herein, or a pharmaceutically acceptable salt thereof, in combination with two, three, four or more additional therapeutic agents. For example, a compound disclosed herein, or a pharmaceutically acceptable salt, thereof, is combined with two, three, four or more additional therapeutic agents selected from the classes of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drugs for treating HIV. The two, three four or more additional therapeutic agents can be different therapeutic agents selected from the same class of therapeutic agents, or they can be selected from different classes of therapeutic agents.

One embodiment provides for a combination pharmaceutical agent comprising:

a) a compound disclosed herein, or a pharmaceutically acceptable salt, thereof; and b) at least one additional active agent which is suitable for treating an HIV infection.

Another embodiment provides a combination pharmaceutical agent comprising:

a) a compound disclosed herein, or a pharmaceutically acceptable salt thereof; and b) at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drugs for treating HIV.

It is also possible to combine any compound disclosed herein with one or more other active therapeutic agents in a unitary dosage form for simultaneous or sequential administration to a patient. The combination therapy may be administered as a simultaneous or sequential regimen. When administered sequentially, the combination may be administered in two or more administrations.

It is also possible to co-administer a compound disclosed herein with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of the compound disclosed herein and one or more other active therapeutic agents are both present in the body of the patient.

Co-administration includes administration of unit dosages of the compounds disclosed herein before or after administration of unit dosages of one or more other active therapeutic agents, for example, administration of the compound disclosed herein within seconds, minutes, or hours of the administration of one or more other active therapeutic agents. For example, a unit dose of a compound disclosed herein can be administered first, followed within seconds or minutes by administration of a unit dose of one or more other active therapeutic agents. Alternatively, a unit dose of one or more other active therapeutic agents can be administered first, followed by administration of a unit dose of a compound disclosed herein within seconds or minutes. In some cases, it may be desirable to administer a unit dose of a compound disclosed herein first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound disclosed herein.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Another embodiment provides a method for treating an HIV infection comprising administering to a patient in need thereof a therapeutically effective amount of a compound disclosed herein, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV.

Another embodiment provides a method for treating an HIV infection comprising administering to a patient in need thereof a therapeutically effective amount of a compound disclosed herein, or a pharmaceutically acceptable salt, thereof, in combination with a therapeutically effective amount of one or more additional therapeutic agents selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, RDEA806, KM023 and MK-1439;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), adefovir, adefovir dipivoxil, CMX-001 (Chimerix) or CMX-157 (Chimerix);

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, GS-9696, elvitegravir and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5 mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221

HIV, DEBIO-025, BAY 50-4798, MDX010 (ipilimumab), PBS 119, ALG 889, and PA-1050040 (PA-040).

Another embodiment provides a method for treating an HIV infection comprising administering to a patient in need thereof a therapeutically effective amount of a compound disclosed herein, or a pharmaceutically acceptable salt, thereof, in combination with a therapeutically effective amount of one or more additional therapeutic agents selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003),;

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5 mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

Pharmaceutical Formulations

The compounds disclosed herein are formulated with conventional carriers (e.g., inactive ingredient or excipient material), which will be selected in accord with ordinary practice. Tablets will contain excipients, including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations described herein that are suitable for oral administration may be presented as discrete units including but not limited to capsules, cachets or tablets each containing a predetermined amount of the active ingredient.

Pharmaceutical formulations disclosed herein comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate amount of carrier material (e.g., inactive ingredient or excipient material). In certain embodiments, the carrier material varies from about 5 to about 95% of the total composition (weight:weight).

It should be understood that in addition to the ingredients particularly mentioned above the formulations of this invention may include other agents conventional in the art having regard to the type of formulation in question, for example those suitable for oral administration may include flavoring agents.

Certain embodiments provide veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound of the invention may be determined using Test A described below.

Test A: Antiviral Assay in MT4 Cells

For the antiviral assay utilizing MT-4 cells, 0.4 µL of 189× test concentration of 3-fold serially diluted compound in DMSO was added to 40 µL of cell growth medium (RPMI 1640, 10% FBS, 1% penicilline/Streptomycine, 1% L-Glutamine, 1% HEPES) in each well of 384-well assay plates (10 concentrations) in quadruplicate.

One mL aliquots of 2×10e6 MT-4 cells were pre-infected for 1 and 3 hours respectively, @ 37° C. with 25 uL (MT4) or of either cell growth medium (mock-infected) or a fresh 1:250 dilution of an HIV-IIIb concentrated ABI stock (0.004m.o.i. for MT4 cells). Infected and uninfected cells were diluted in cell growth medium and 35 uL of 2000 (for MT4) cells was added to each well of the assay plates.

Assay plates were then incubated in a 37° C. incubator. After 5 days of incubation, 25 µA of 2× concentrated CellTiter-Glo™ Reagent (catalog #G7573, Promega Biosciences, Inc., Madison, Wis.) was added to each well of the assay plate. Cell lysis was carried out by incubating at room temperature for 2-3 min and then chemiluminescence was read using the Envision reader (PerkinElmer).

Compounds disclosed herein demonstrate antiviral activity in this assay (Test A) as depicted in Table 1 and Table 2 below.

Accordingly, the compounds may be useful for treating an HIV infection, the proliferation of the HIV virus, treating AIDS or delaying the onset of AIDS or ARC symptoms.

TABLE 1

| Compound Number | EC50 (nM) |
| --- | --- |
| 50 | 52.8 |
| 51 | 5250 |
| 52 | 53.4 |
| 53 | 37500 |
| 54 | 274 |
| 55 | 53000 |
| 56 | 62.4 |
| 57 | 147 |
| 58 | 3520 |
| 76 | 26 |
| 78 | 726 |
| 89 | 36.6 |
| 104 | 42 |
| 105 | 16 |
| 106 | 103 |
| 107 | 46 |
| 108 | 33 |
| 109 | 82 |
| 110 | 14 |
| 111 | 8 |
| 112 | 28 |
| 113a | 16 |
| 113b | 18 |
| 114 | 13 |
| 115 | 13 |
| 116 | 19 |
| 117 | 14 |
| 118 | 101 |
| 119 | 237 |
| 120 | 23 |
| 121 | 27 |
| 122 | 5518 |
| 123 | 18 |
| 124 | 21 |
| 125 | 205 |
| 126 | 722 |
| 129 | 48 |
| 130 | 100 |
| 131 | 8 |
| 132 | 12 |
| 133 | 18 |
| 134 | 3226 |
| 135 | 17 |
| 136 | 12 |
| 137 | 21 |
| 138 | 65 |
| 139 | 61 |
| 140 | 5 |
| 141 | 77 |
| 142 | 48 |
| 143 | 24 |
| 144 | 2608 |
| 145 | 34 |
| 146 | 92 |
| 147 | 59 |
| 148 | 2698 |
| 149 | 153 |
| 150 | 91 |
| 151 | 32 |
| 152 | 46 |
| 153 | 15 |
| 154 | 16 |
| 155 | 66 |
| 156 | 26 |
| 157 | 29 |
| 158 | 17 |
| 159 | 46 |
| 160 | 136 |
| 161 | 116 |
| 162 | 350 |
| 163 | 18 |
| 164 | 483 |
| 167 | 39 |

TABLE 1-continued

| Compound Number | EC50 (nM) |
|---|---|
| 168 | 42 |
| 169 | 33 |
| 170 | 35 |

TABLE 2

| Compound Number | EC50 (nM) |
|---|---|
| 173 | 11 |
| 174 | 26 |
| 175 | 33 |
| 176 | 18 |
| 177 | 39 |
| 178 | 89 |
| 179 | 73 |
| 180 | 5 |
| 181 | 27 |
| 182 | 80 |
| 183 | 18 |
| 184 | 19 |
| 186 | 4 |
| 187 | 25 |
| 188 | 12 |
| 189 | 249 |
| 190 | 112 |
| 191 | 10 |
| 192 | 12 |
| 193 | 9 |
| 194 | 21 |
| 195 | 11 |
| 196 | 33 |
| 197 | 12 |
| 198 | 39 |
| 199 | 95 |
| 200 | 14 |
| 201 | 7 |
| 202 | 2 |
| 203 | 12 |
| 204 | 155 |
| 205 | 18 |
| 206 | 24 |
| 207 | 19 |
| 208 | 62 |
| 209 | 16 |
| 210 | 6 |
| 212 | 6 |
| 213 | 4 |
| 214 | 17 |
| 215 | 27 |
| 216 | 15 |
| 217 | 7 |
| 218 | 116 |
| 219 | 39 |
| 220 | 43 |
| 221 | 24 |
| 222 | 49 |
| 223 | 312 |
| 224 | 12 |
| 225 | 96 |
| 226 | 36 |
| 227 | 85 |
| 228 | 910 |
| 229 | 1737 |
| 230 | 131 |
| 232 | 86 |
| 233 | 33 |
| 234 | 13 |
| 235 | 14 |
| 236 | 31 |
| 237 | 10 |
| 238 | 25 |
| 239 | 26 |
| 240 | 76 |
| 241 | 3 |
| 242 | 494 |

TABLE 2-continued

| Compound Number | EC50 (nM) |
|---|---|
| 243 | 424 |
| 245 | 9 |
| 246 | 9 |
| 247 | 10 |
| 248 | 13 |
| 249 | 7 |
| 250 | 235 |
| 254 | 8 |
| 255 | 12 |
| 256 | 9 |
| 257 | 5 |
| 258 | 13 |
| 259 | 12 |
| 264 | 17 |
| 265 | 15 |
| 266 | 10 |
| 267 | 11 |
| 268 | 12 |
| 269 | 12 |
| 272 | 78 |
| 273 | 53 |
| 274 | 31 |
| 275 | 21 |
| 276 | 37 |
| 277 | 26 |
| 278 | 4 |
| 279 | 16 |
| 280 | 248 |
| 281 | 31 |
| 282 | 3 |
| 283 | 51 |
| 284/285 | 23 |
| 286 | 10 |
| 287 | 113 |
| 288 | 65 |
| 289 | 25 |
| 290 | 87 |
| 291 | 76 |
| 292 | 23 |
| 293 | 215 |
| 294 | 36 |
| 295 | 34 |
| 296 | 13 |
| 297 | 17 |
| 298 | 181 |
| 299 | 130 |
| 300 | 12 |
| 301 | 109 |
| 302 | 8 |
| 303 | 19 |
| 305 | 10 |
| 306 | 14 |
| 307 | 4 |
| 308 | 6 |
| 309 | 37 |
| 310 | 26 |
| 311 | 45 |
| 312 | 37 |
| 313 | 14 |
| 314 | 42 |
| 315 | 34 |
| 316 | 18 |
| 317 | 13 |
| 318 | 10 |
| 319 | 5 |
| 322 | 640 |
| 323 | 384 |
| 324 | 13 |
| 325 | 10 |
| 326 | 66 |
| 327 | 162 |
| 328 | 44 |
| 329 | 14 |
| 330 | 19 |
| 331 | 44 |
| 332 | 5 |
| 333 | 3 |
| 334 | 5 |

TABLE 2-continued

| Compound Number | EC50 (nM) |
|---|---|
| 335 | 14 |
| 336 | 2 |
| 337 | 4 |
| 338 | 11 |
| 339 | 11 |
| 340 | 9 |
| 341 | 14 |
| 342 | 5 |
| 343 | 26 |
| 344 | 6 |
| 345 | 28 |
| 346 | 11 |
| 347 | 42 |
| 348 | 30 |
| 349 | 42 |
| 350 | 14 |
| 351 | 21 |
| 352 | 29 |
| 353 | 31 |
| 354 | 1372 |
| 355 | 182 |
| 356 | 3332 |
| 357 | 12 |
| 358 | 241 |
| 359 | 21 |
| 360 | 13 |
| 361 | 20 |
| 362 | 21 |
| 363 | 15 |
| 364 | 9 |
| 365 | 29 |
| 366 | 6 |
| 367 | 6 |
| 368 | 5 |
| 369 | 8 |
| 370 | 4 |
| 371 | 7 |
| 372 | 7 |
| 373 | 37 |
| 374 | 45 |
| 375 | 228 |
| 376 | 19 |
| 377 | 32 |
| 378 | 51 |
| 379 | 15 |
| 380 | 25 |
| 381 | 47 |
| 382 | 91 |
| 383 | 18 |
| 384 | 332 |
| 385 | 143 |
| 386 | 56 |
| 387 | 530 |
| 388 | 28 |
| 389 | 7 |
| 390 | 9 |
| 391 | 11 |
| 392 | 27 |
| 393 | 33 |
| 394 | 25 |
| 395 | 61 |
| 396 | 10 |
| 397 | 32 |
| 398 | 36 |
| 399 | 43 |
| 400 | 16 |
| 401 | 23 |
| 402 | 35 |
| 403 | 42 |
| 404 | 41 |
| 405 | 37 |
| 406 | 149 |
| 407 | 14 |
| 408 | 27 |
| 409 | 10 |
| 410 | 9 |
| 411 | 8 |
| 412 | 16 |
| 413 | 33 |
| 414 | 32 |
| 415 | 10 |
| 416 | 25 |
| 417 | 18 |
| 418 | 11 |
| 419 | 13 |
| 420 | 14 |
| 421 | 20 |
| 422 | 32 |
| 427 | 14 |
| 428 | 7 |
| 429 | 43 |
| 430 | 29 |
| 431 | 18 |
| 432 | 18 |
| 433 | 38 |
| 434 | 42 |
| 435 | 39 |
| 436 | 67 |
| 437 | 309 |
| 438 | 258 |
| 439 | 20 |
| 440 | 11 |
| 441 | 4 |
| 442 | 1159 |
| 443 | 24 |
| 444 | 10 |
| 445 | 5 |
| 446 | 173 |
| 447 | 5 |
| 448 | 9 |
| 449 | 30 |
| 450 | 25 |
| 451 | 86 |
| 452 | 16 |
| 453 | 36 |
| 454 | 18 |
| 455 | 17 |
| 456 | 20 |
| 457 | 96 |
| 458 | 5 |
| 459 | 28 |
| 460 | 31 |
| 461 | 14 |
| 462 | 42 |
| 463 | 52 |
| 464 | 12 |
| 465 | 2 |
| 466 | 5 |
| 467 | 5 |
| 468 | 8 |
| 469 | 8 |
| 470 | 3 |
| 471 | 3 |
| 472 | 4 |
| 473 | 8 |
| 474 | 40 |
| 475 | 6 |
| 476 | 128 |
| 477 | 14 |
| 478 | 4 |
| 479 | 4 |
| 480 | 2 |
| 481 | 17 |
| 482 | 14 |
| 483 | 37 |
| 484 | 9 |
| 485 | 15 |
| 486 | 31 |
| 487 | 12 |
| 488 | 11 |
| 489 | 20 |
| 490 | 3 |
| 491 | 51 |
| 492 | 3 |
| 493 | 51 |
| 494 | 2878 |

TABLE 2-continued

| Compound Number | EC50 (nM) |
|---|---|
| 495 | 4 |
| 496 | 5 |
| 497 | 4 |
| 498 | 34 |
| 499 | 12 |

In certain embodiments, the compounds demonstrate an EC50 of <50 µM. In certain embodiments, the compounds demonstrate an EC50 of <30 µM. In certain embodiments, the compounds demonstrate an EC50 of <10 µM. In certain embodiments, the compounds demonstrate an EC50 of <1 µM. In certain embodiments, the compounds demonstrate an EC50 of <0.5 µM. In certain embodiments, the compounds demonstrate an EC50 of <0.1 µM. In certain embodiments, the compounds demonstrate an EC50 of <0.05 µM. In certain embodiments, the compounds demonstrate an EC50 of <0.01 µM. It is to be understood that the compounds disclosed herein can be grouped according to their % inhibition as described above.

Test B: Metabolic Stability Assay with Human Liver Microsomes

Effective viral suppression in the HIV infected patient requires that the antiviral drug persists in the patient's body at concentrations exceeding the minimum concentration required to inhibit viral proliferation. One of the factors controlling the drug levels after dosing is metabolic conversion. The liver is one site of drug metabolism. Approximately 60% of marketed drugs are cleared by hepatic metabolism (McGinnity D F et al. (2004) Drug Metab Dispos 32; 1247-1253). Liver microsomes are subcellular fractions which contain membrane bound drug metabolising enzymes. Human liver microsomes provide a convenient and concentrated source of the key liver metabolic enzymes (e.g., cytochromes P450, UDP-glucuronosyltransferases, and many others) and can be used to predict the metabolic stability of drug candidates (e.g., agents).

Cluster tubes containing 500 uL of 1 uM compound with 1 mg/mL human liver microsomal proteins (BD Biosciences, BD452117)/50 mM K-phosphate buffer pH7.4/NADPH regenerating system/and UDP-glucuronosyltransferase cofactors, were incubated on the Precision-2000 workstation at 37° C. for 0, 10, 25, 60 minutes. The reactions were quenched with 100 uL of 0.2% formic acid in 90% ACN; containing 50 nM of an internal standard. The samples were analyzed on LC/MS/MS instrument (Q-Trap). Metabolic stabilities in microsomal fractions and hepatocytes were determined by measuring the rate of disappearance of the compound. Data (% of parent remaining) were plotted on a semi logarithmic scale and fitted using an exponential fit. The predicted hepatic half-life was calculated from these data (Obach R S, Baxter J G, Liston T E, Silber B M, Jones B C, MacIntyre F, et al. J Pharmacol Exp Ther 1997; 283 (1):46-58). These results are shown in Table 3. Human microsomal stability equal to A refers to a compound having a human microsomal stability half-life of greater than or equal to 300 minutes. Humun microsomal stability equal to B refers to a compound having a human microsomal stability half-life of less than 300 minutes but greater than or equal to 150 minutes. Humun microsomal stability equal to C refers to a compound having a human microsomal stability half-life of less than 150 minutes.

TABLE 3

| Compound Number | Human Microsomal stability |
|---|---|
| 104 | C |
| 107 | C |
| 109 | B |
| 141 | B |
| 152 | C |
| 158 | C |
| 163 | C |
| 186 | C |
| 202 | A |
| 206 | C |
| 212 | A |
| 257 | A |
| 278 | B |
| 285 | A |
| 333 | A |
| 336 | A |
| 113a | A |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

The invention will now be illustrated by the following non-limiting examples of compounds (including compounds of the invention) and intermediates useful for preparing compounds of the invention.

Example 1

Preparation of Intermediates 24-32

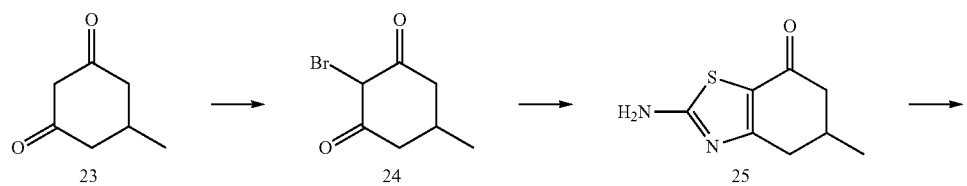

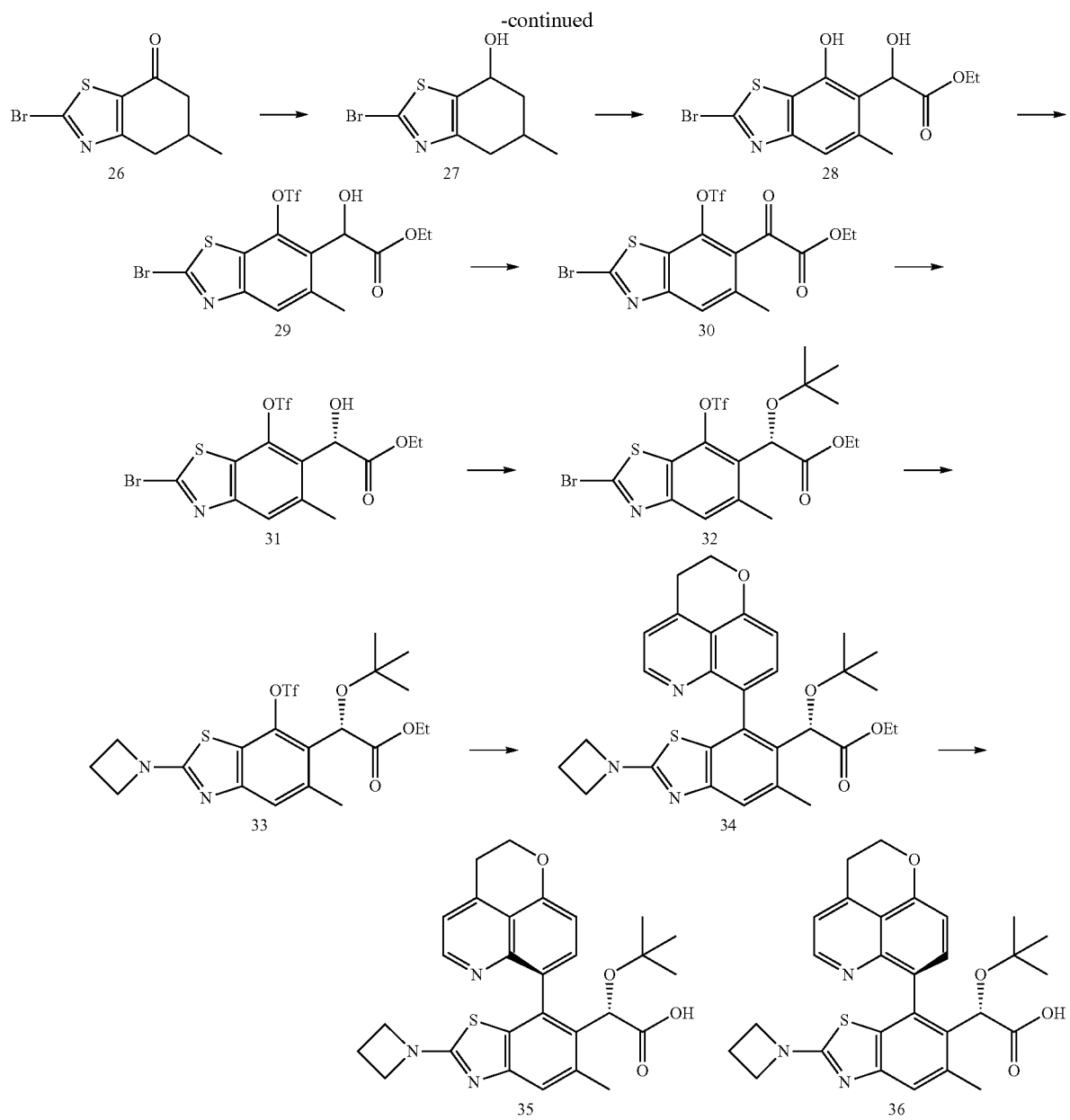

To a solution of 34 (23 mg, 0.043 mmol) in THF (1 mL) and MeOH (1 mL) was added a solution of NaOH (2 M, ~400 μL). The reaction mixture was heated at 70° C. for 4 h. The reaction was brought to ~pH 5 with TFA and was then purified by reverse phase HPLC (ACN/H$_2$O containing 0.1% TFA) to give 6 mg of compound 35 and 10 mg of compound 36.

Compound 35: $^1$H-NMR: 400 MHz, (CD$_3$OD) δ: 8.75 (d, J=2.6 Hz, 1H), 7.80 (d, J=4.0 Hz, 1H), 7.72 (d, J=2.6 Hz, 1H), 7.47 (s, 1H), 7.34 (d, J=4.0 Hz, 1H), 5.13 (s, 1H), 4.67-4.65 (m, 2H), 4.17 (t, J=7.6 Hz, 4H), 3.59-3.58 (m, 2H), 2.66 (s, 3H), 2.52-2.50 (m, 2H), 0.88 (s, 9H). LCMS-ESI$^+$: calc'd for C$_{28}$H$_{29}$N$_3$O$_4$S: 504.2 (M+H$^+$); Found: 504.0 (M+H$^+$).

Compound 36: $^1$H-NMR: 400 MHz, (CD$_3$OD) δ: 8.67 (d, J=2.2 Hz, 1H), 8.01 (d, J=4.0 Hz, 1H), 7.49 (d, J=2.6 Hz, 1H), 7.40 (s, 1H), 7.27 (d, J=4.2 Hz, 1H), 5.18 (s, 1H), 4.60-4.57 (m, 2H), 4.27 (t, J=7.8 Hz, 4H), 3.48-3.45 (m, 2H), 2.61 (s, 3H), 2.58-2.54 (m, 2H), 0.80 (s, 9H). LCMS-ESI$^+$: calc'd for C$_{28}$H$_{29}$N$_3$O$_4$S: 504.2 (M+H$^+$); Found: 504.1 (M+H$^+$).

Preparation of (2S)-ethyl 2-(2-(azetidin-1-yl)-7-(2,3-dihydropyrano[4,3,2-de]quinolin-7-yl)-5-methyl-benzo[d]thiazol-6-yl)-2-tert-butoxyacetate (34)

Step 1.

Preparation of 2-bromo-5-methylcyclohexane-1,3-dione (24). To a solution of 5-methyl-1,3-cyclohexanedione (23) (45.4 g, 360 mmol) in acetic acid (540 mL) was added bromine (19.4 mL, 378 mmol) over 5 min. After 30 min of stirring (with mechanical stirrer), the reaction mixture was filtered. The solid was left under high vacuum overnight and used in the subsequent step without further purification.

Step 2.

Preparation of 2-amino-5-methyl-5,6-dihydrobenzo[d]thiazol-7(4H)-one (25). To a solution of 24 in acetic acid (540 mL) was added sodium acetate (44.3 g, 540 mmol) and thiourea (28.8 g, 378 mmol). The reaction mixture was stirred with a mechanical stirrer at 100° C. for 3 h. The reaction mixture was partially concentrated in vacuo. EtOAc was added (500 mL). The mixture was made basic with 1 M NaOH, and the layers were separated. The aqueous layer was extracted with EtOAc (2×300 mL). The combined organic layers were dried, filtered, and concentrated in vacuo to give 49.3 g of 25, which was taken on without further purification. LCMS-ESI$^+$: calc'd for $C_8H_{11}N_2OS$: 183.1 (M+H$^+$); Found: 183.1 (M+H$^+$).

Step 3.

Preparation of 2-bromo-5-methyl-5,6-dihydrobenzo[d]thiazol-7(4H)-one (26). To a solution of 25 (53.9 g, 296 mmol) in ACN (600 mL) at 0° C., while mechanically stirred), was added copper (II) bromide (79.2 g, 355 mmol) then t-butyl nitrite (46.8 mL, 355 mmol). The reaction mixture was stirred from 0° C. to room temperature over 2 h and was then partially concentrated. EtOAc (400 mL) and a 0.5 M HCl solution were added. The layers were separated, and the organic layer was washed with a brine solution. The combined organic layers were dried, filtered, and concentrated in vacuo. The crude product was adsorbed on ~150 g of silica then run through a plug of silica with 40% EtOAc/hexanes to give 58.3 g of 26. $^1$H-NMR: 400 MHz, (CDCl$_3$) δ: 3.16 (dd, 1H. J=18, 4 Hz), 2.66 (m, 2H), 2.47 (m, 1H), 2.34 (dd, 1H, J=16, 12 Hz), 1.19 (d, 3H, J=7 Hz). LCMS-ESI$^+$: calc'd for $C_8H_9BrNOS$: 245.9 (M+H$^+$); Found: 246.1 (M+H$^+$).

Step 4.

Preparation of 2-bromo-5-methylbenzo[d]thiazol-7-ol (27). To a solution of 26 (7.38 g, 30.0 mmol) in CCl$_4$ (90 mL) was added NBS (5.61 g, 31.5 mmol) and dibenzoyl peroxide (727 mg, 3.0 mmol). The reaction was heated at 90° C. in a sealed reaction vessel for about 4 h. Then DBU (6.73 mL, 45.0 mmol) in $CH_2Cl_2$ (15 mL) was added. The mixture was heated a reflux for 30 min, then a 1 M HCl solution was added. The layers were separated, and the aqueous layer was extracted with $CH_2Cl_2$. The combined organic layers were washed with a brine solution. The organic layer was then dried, filtered, and concentrated in vacuo. The crude product was adsorbed on ~30 g of silica then run through a plug of silica with 40% EtOAc/hexanes to give 5.2 g of 27. $^1$H-NMR: 400 MHz, (CD$_3$OH) δ: 7.25 (s, 1H), 6.69 (s, 1H), 2.40 (s, 3H). LCMS-ESI$^+$: calc'd for $C_8H_7BrNOS$: 243.9 (M+H$^+$); Found: 244.1 (M+H$^+$).

Step 5.

Preparation of ethyl 2-(2-bromo-7-hydroxy-5-methylbenzo[d]thiazol-6-yl)-2-hydroxyacetate (28). To a solution of 27 (3.90 g, 16.0 mmol) in $CH_2Cl_2$ (80 mL) at 0° C. was added triethylamine (2.45 mL, 16.8 mmol) then a solution of titanium tetrachloride in $CH_2Cl_2$ (1.0 M, 16.8 mL, 16.8 mmol). After 15 min, ethyl glyoxalate (50% in toluene, 3.49 mL, 17.6 mmol) was added. The reaction mixture was stirred for 2 h while warming to room temperature. Water (50 mL) and a saturated solution of potassium sodium tartrate (50 mL) were added. The mixture was stirred vigorously for 2 h. The layers were separated, and the aqueous layer was extracted with $CH_2Cl_2$. The combined organic layers were dried, filtered, and concentrated in vacuo. The crude material was purified by column chromatography to give 2.48 g of 28 and recovered ~500 mg of 27. $^1$H-NMR: 400 MHz, (CD$_3$OH) δ: 7.33 (s, 1H), 5.69 (s, 1H), 4.17 (m, 2H), 2.50 (s, 3H), 1.18 (t, 3H, J=7 Hz). LCMS-ESI$^+$: calc'd for $C_{12}H_{13}BrNO_4S$: 346.0 (M+H$^+$); Found: 346.1 (M+H$^+$).

Step 6.

Preparation of ethyl 2-(2-bromo-5-methyl-7-(trifluoromethylsulfonyloxy)benzo[d]thiazol-6-yl)-2-hydroxyacetate (29). To a solution of 28 (2.42 g, 7.00 mmol) in $CH_2Cl_2$ (30 mL) at −78° C. was added triethylamine (1.02 mL, 7.70 mmol) followed by trifluoromethanesulfonic anhydride (1.24 mL, 7.35 mmol). After 15 min, saturated NH$_4$Cl was added. The layers were separated. The organic layer was dried, filtered, and concentrated in vacuo. The crude material was purified by column chromatography to give 2.17 g of 29. $^1$H-NMR: 400 MHz, (CDCl$_3$) δ: 7.84 (s, 1H), 5.67 (s, 1H), 4.27 (m, 2H), 2.50 (s, 3H), 1.23 (t, 3H, J=7 Hz). LCMS-ESI$^+$: calc'd for $C_{13}H_{12}BrF_3NO_6S_2$: 477.9 (M+H$^+$); Found: 478.2 (M+H$^+$).

Step 7.

Preparation of ethyl 2-(2-bromo-5-methyl-7-(trifluoromethylsulfonyloxy)benzo[d]thiazol-6-yl)-2-oxoacetate (30). To a solution of 29 (9.85 g, 20.6 mmol) in $CH_2Cl_2$ (100 mL) was added Dess-Martin periodinane (9.61 g, 22.6 mmol). After 30 min, water (75 mL) and saturated $Na_2S_2O_4$ solution (75 mL) was added. The mixture was stirred vigorously for 30 min. The layers were separated, and the aqueous layer was extracted with $CH_2Cl_2$. The combined organic layers were dried, filtered, and concentrated in vacuo. The crude material was purified by column chromatography to give 8.32 g of 30. $^1$H-NMR: 400 MHz, (CDCl$_3$) δ: 7.91 (s, 1H), 4.40 (q, 2H, J=7 Hz), 2.49 (s, 3H), 1.39 (t, 3H, J=7 Hz).

LCMS-ESI$^+$: calc'd for $C_{13}H_{10}BrF_3NO_6S_2$: 475.9 (M+H$^+$); Found: 476.1 (M+H$^+$).

Step 8.

Preparation of (S)-ethyl 2-(2-bromo-5-methyl-7-(trifluoromethylsulfonyloxy)benzo[d]thiazol-6-yl)-2-hydroxyacetate (31). To a solution of 30 (8.30 g, 17.4 mmol) in toluene (70 mL) was added ((R)-2-methyl-CBS-oxazaborolidine (725 mg, 2.61 mmol). The reaction mixture was then cooled to −35° C. and a solution of catecholborane (freshly distilled) (1 M in toluene, 20.9 mL, 20.9 mmol) was added via addition funnel over 30 min. The reaction was stirred for 20 min while warming to −20° C. A 2 M solution of Na$_2$CO$_3$ was added (50 mL). The layers were separated, and the organic layer was washed with additional Na$_2$CO$_3$ solution (3×25 mL). The organic layer was dried, filtered, and concentrated in vacuo to give 31, which had analytical data to match 29. The compound was taken on to the next step without further purification.

Step 9.

Preparation of (S)-ethyl 2-(2-bromo-5-methyl-7-(trifluoromethylsulfonyloxy)benzo[d]thiazol-6-yl)-2-tert-butoxyacetate (32).

To a solution of 31 (~17 mmol) in t-butylacetate (70 mL) was added perchloric acid (1.23 mL, 20.4 mmol). After 3 h, water was added (50 mL). The layers were separated. The organic layer was washed with a saturated solution of NaHCO$_3$. The organic layer was dried, filtered, and concentrated in vacuo. The crude material was purified by column chromatography (EtOAc/hexanes) to give 7.22 g of 32 and 1.58 g of 31. $^1$H-NMR: 400 MHz, (CD$_3$OH) δ: 7.82 (s, 1H), 5.59 (s, 1H), 4.08-4.25 (m, 2H), 2.55 (s, 3H), 1.20 (s, 9H), 1.16 (t, 3H, J=7 Hz).

LCMS-ESI$^+$: calc'd for $C_{17}H_{20}BrF_3NO_6S_2$: 534.0 (M+H$^+$); Found: 534.1 (M+H$^+$).

Step 10.

Preparation of (S)-ethyl 2-(2-(azetidin-1-yl)-5-methyl-7-(trifluoromethylsulfonyloxy)benzo[d]thiazol-6-yl)-2-tert-butoxyacetate (33). To a solution of 32 (50 mg, 0.094 mmol) in THF (1 mL) was added azetidine (20 µL). The reaction mixture was heated at 70° C. for 30 min. A saturated solution of NH$_4$Cl (3 mL) was added, and the layers were separated. The aqueous layer was extracted with EtOAc. The combined organic layer were dried, filtered, and concentrated in vacuo.

The crude material was purified by column chromatography (EtOAc/hexanes) to give 38 mg of 33. LCMS-ESI+: calc'd for $C_{20}H_{25}F_3N_2O_6S_2$: 511.1 (M+H+); Found: 511.0 (M+H+).

Step 11.

Preparation of (2S)-ethyl 2-(2-(azetidin-1-yl)-7-(2,3-dihydropyrano[4,3,2-de]quinolin-7-yl)-5-methylbenzo[d]thiazol-6-yl)-2-tert-butoxyacetate (34). To a solution of 33 (38 mg, 0.075 mmol) in freshly distilled DME (1 mL) was added 2,3-dihydropyrano[4,3,2-de]quinolin-7-ylboronic acid hydrochloride (24 mg, 0.097 mmol), chloro(2-dicyclohexylphosphino-2',6'-dimethoxy-1,1'-biphenyl)[2-(2-aminoethylphenyl)]palladium(II) methyl-t-butylether adduct, [SPhos Palladacycle] (5 mg, 0.0075 mmol), and cesium fluoride (46 mg, 0.3 mmol). The reaction mixture was heated in the microwave at 110° C. for 45 min. A saturated solution of NaHCO₃ (3 mL) was added, and the layers were separated. The aqueous layer was extracted with EtOAc. The combined organic layer were dried, filtered, and concentrated in vacuo. The crude material was purified by column chromatography (EtOAc/hexanes) to give 21 mg of 34. LCMS-ESI+: calc'd for $C_{30}H_{33}N_3O_4S$: 532.2 (M+H+); Found: 532.0 (M+H+).

Example 2

Preparation of (S)-2-tert-butoxy-2-((S)-7-(2,3-dihydropyrano[4,3,2-de]quinolin-7-yl)-5-methyl-2-(pyrrolidin-1-yl)benzo[d]thiazol-6-yl)acetic acid (50) and (S)-2-tert-butoxy-2-((R)-7-(2,3-dihydropyrano [4,3,2-de]quinolin-7-yl)-5-methyl-2-(pyrrolidin-1-yl)benzo[d]thiazol-6-yl)acetic acid (51)

Compounds 50 and 51 were prepared from compound 32 according to the procedure used to prepare compound 35 (except that pyrrolidine was used instead of azetidine) in Example 1.

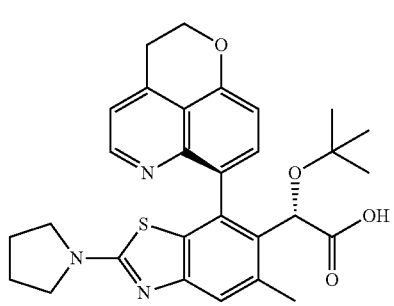

Compound 50: ¹H-NMR: 400 MHz, (CD₃OD) δ 8.76 (d, J=5.3 Hz, 1H), 7.80 (d, J=8.1 Hz, 1H), 7.69 (d, J=5.1 Hz, 1H), 7.50 (s, 1H), 7.33 (d, J=8.0 Hz, 1H), 5.15 (s, 1H), 9.03-0.64 (m, 79H), 4.70-4.60 (m, 2H), 3.56 (dd, J=13.8, 7.7 Hz, 6H), 2.68 (s, 3H), 2.10 (t, J=6.7 Hz, 4H), 0.89 (s, 10H). LCMS-ESI+ (m/z): [M+H]+ calcd for $C_{29}H_{32}N_3O_4S$: 518.21 (M+H+); Found: 517.99, 518.97 (M+H+).

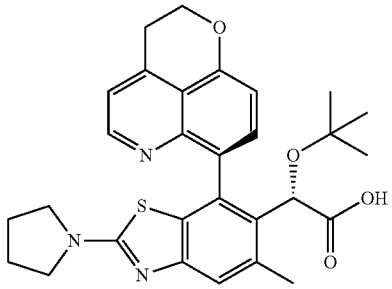

Compound 51: ¹H-NMR: 400 MHz, (CD₃OD) δ 8.67 (d, J=4.7 Hz, 1H), 8.01 (d, J=8.1 Hz, 1H), 7.46 (d, J=4.8 Hz, 1H), 7.44 (s, 1H), 7.27 (d, J=8.1 Hz, 1H), 5.20 (s, 1H), 4.68-4.50 (m, 2H), 3.57 (s, 3H), 3.45 (t, J=5.8 Hz, 2H), 2.63 (s, 4H), 2.14 (t, J=6.3 Hz, 4H), 0.79 (s, 9H). LCMS-ESI+ (m/z): [M+H]+ calcd for $C_{29}H_{32}N_3O_4S$: 518.21 (M+H+); Found: 518.07, 519.07 (M+H+).

Example 3

Preparation of (S)-2-tert-butoxy-2-((S)-2-(3,3-difluoroazetidin-1-yl)-7-(2,3-dihydropyrano[4,3,2-de] quinolin-7-yl)-5-methylbenzo[d]thiazol-6-yl)acetic acid (52) and (S)-2-tert-butoxy-2-((R)-2-(3,3-difluoroazetidin-1-yl)-7-(2,3-dihydropyrano[4,3,2-de] quinolin-7-yl)-5-methylbenzo[d]thiazol-6-yl)acetic acid (53)

Compounds 52 and 53 were prepared from compound 32 according to the procedure used to prepare compound 35 (except that 2,2-difluoroazetidine was used instead of azetidine) in Example 1.

Compound 52: ¹H-NMR: 400 MHz, (CD₃OD) δ 8.80 (d, J=5.6 Hz, 1H), 7.87 (d, J=8.2 Hz, 1H), 7.83 (d, J=5.6 Hz, 1H), 7.61 (s, 1H), 7.41 (d, J=8.2 Hz, 1H), 5.17 (s, 1H), 4.76-4.64 (m, 2H), 4.56-4.43 (m, 4H), 3.65 (t, J=5.9 Hz, 2H), 2.69 (s, 3H), 0.91 (s, 9H). ¹⁹F NMR (377 MHz, CD₃OD) δ-77.88 (s). LCMS-ESI+ (m/z): [M+H]+ calcd for $C_{28}H_{28}F_2N_3O_4S$: 540.18 (M+H+); Found: 539.96, 540.96 (M+H+)

53

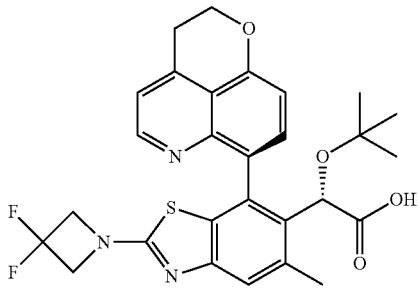

Compound 53: ¹H-NMR: 400 MHz, (CD₃OD) δ 8.71 (d, J=5.4 Hz, 1H), 8.14 (d, J=8.2 Hz, 1H), 7.69 (d, J=5.4 Hz, 1H), 7.57 (s, 1H), 7.40 (d, J=8.2 Hz, 1H), 5.21 (s, 1H), 4.72-4.60 (m, 2H), 4.56-4.42 (m, 4H), 3.58 (t, J=6.0 Hz, 2H), 2.65 (s, 3H), 0.91 (s, 9H). LCMS-ESI⁺ (m/z): [M+H]⁺ calcd for $C_{28}H_{28}F_2N_3O_4S$: 540.18 (M+H⁺); Found: 539.98, 541.02 (M+H⁺).

Example 4

Preparation of (S)-2-tert-butoxy-2-((S)-7-(2,3-dihydropyrano[4,3,2-de]quinolin-7-yl)-2-(3-methoxyazetidin-1-yl)-5-methylbenzo[d]thiazol-6-yl)acetic acid (54) and (S)-2-tert-butoxy-2-((R)-7-(2,3-dihydropyrano[4,3,2-de]quinolin-7-yl)-2-(3-methoxyazetidin-1-yl)-5-methylbenzo[d]thiazol-6-yl)acetic acid (55)

Compounds 54 and 55 were prepared from compound 32 according to the procedure used to prepare compound 35 (except that 2-methoxyazetidine was used instead of azetidine) in Example 1.

54

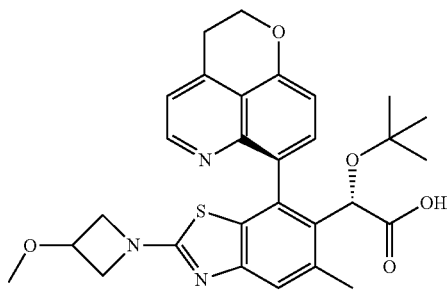

Compound 54: ¹H-NMR: 400 MHz, (CD₃OD) δ: 8.78 (d, J=5.5 Hz, 1H), 7.84 (d, J=8.5 Hz, 1H), 7.77 (d, J=6.1 Hz, 1H), 7.52 (s, 1H), 7.37 (d, J=7.8 Hz, 1H), 5.16 (s, 1H), 4.73-4.64 (m, 2H), 4.41 (ddd, J=9.9, 6.2, 3.4 Hz, 1H), 4.31 (td, J=7.7, 1.0 Hz, 2H), 4.02-3.90 (m, 2H), 3.62 (t, J=5.7 Hz, 2H), 2.68 (s, 4H), 0.91 (s, 11H). LCMS-ESI⁺ (m/z): [M+H]⁺ calcd for $C_{29}H_{32}N_3O_5S$: 534.21 (M+H⁺); Found: 533.95, 534.97 (M+H⁺).

55

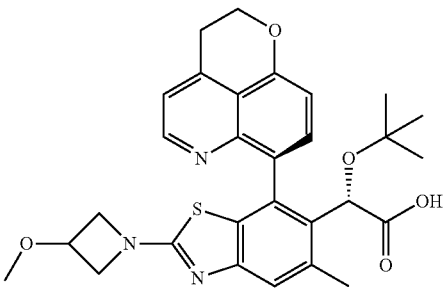

Compound 55: ¹H-NMR: 400 MHz, (CD₃OD) δ 8.67 (d, J=5.1 Hz, 1H), 8.04 (d, J=8.2 Hz, 1H), 7.52 (d, J=4.7 Hz, 1H), 7.43 (s, 1H), 7.30 (d, J=8.1 Hz, 1H), 5.19 (s, 1H), 4.66-4.56 (m, 2H), 4.42 (m, 1H), 4.38-4.32 (m, 2H), 4.08-4.01 (m, 2H), 3.49 (t, J=6.0 Hz, 3H), 2.61 (s, 3H), 0.82 (s, 10H). LCMS-ESI⁺ (m/z): [M+H]⁺ calcd for $C_{29}H_{32}N_3O_5S$: 534.21 (M+H⁺). Found: 534.03, 535.08 (M+H⁺).

Example 5

Preparation of (S)-2-tert-butoxy-2-((S)-7-(2,3-dihydropyrano[4,3,2-de]quinolin-7-yl)-2-(3-fluoroazetidin-1-yl)-5-methylbenzo[d]thiazol-6-yl)acetic acid (56)

Compound 56 was prepared from compound 32 according to the procedure used to prepare compound 35 (except that 2-fluoroazetidine was used instead of azetidine) in Example 1.

56

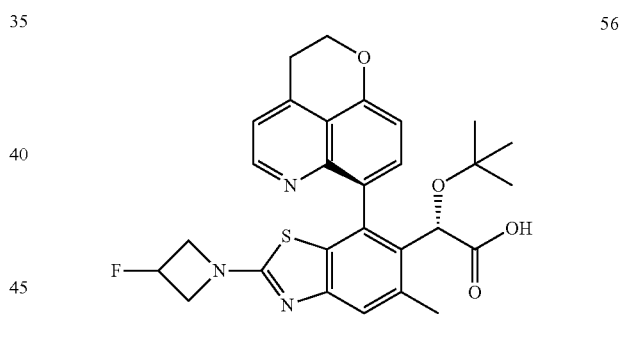

Compound 56: ¹H-NMR: 400 MHz, (CD₃OD) δ 8.79 (d, J=5.5 Hz, 1H), 7.85 (d, J=8.1 Hz, 1H), 7.79 (d, J=5.1 Hz, 1H), 7.55 (s, 1H), 7.39 (d, J=7.9 Hz, 1H), 5.58-5.38 (m, 1H), 5.16 (s, 1H), 4.70 (td, J=5.9, 3.1 Hz, 2H), 4.49-4.35 (m, 2H), 4.28-4.12 (m, 2H), 3.63 (t, J=6.0 Hz, 2H), 2.68 (s, 3H), 0.91 (s, 9H).
LCMS-ESI⁺ (m/z): [M+H]⁺ calcd for $C_{28}H_{29}FN_3O_4S$: 522.19 (M+H⁺); Found: 521.97, 523.02 (M+H⁺).

Example 6

Preparation of (S)-2-tert-butoxy-2-((S)-7-(2,3-dihydropyrano[4,3,2-de]quinolin-7-yl)-5-methyl-2-(3-methylazetidin-1-yl)benzo[d]thiazol-6-yl)acetic acid (57)

Compound 57 was prepared from compound 32 according to the procedure used to prepare compound 35 (except that 2-methylazetidine was used instead of azetidine) in Example 1.

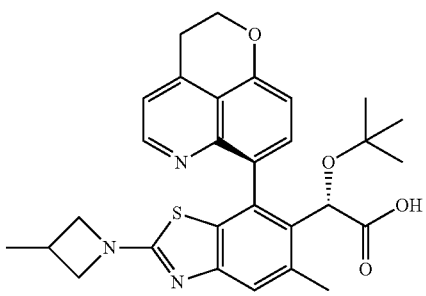

57

Compound 57: ¹H-NMR: 400 MHz, (CD₃OD) δ 8.92 (s, 1H), 7.90 (d, J=7.6 Hz, 2H), 7.56 (s, 1H), 7.44 (d, J=7.3 Hz, 1H), 5.18 (s, 1H), 4.73 (s, 2H), 4.48 (s, 2H), 3.99 (s, 2H), 3.68 (s, 2H), 3.12 (m, 1H), 2.73 (s, 3H), 1.35 (d, J=5.6 Hz, 3H), 0.91 (s, 9H). LCMS-ESI⁺ (m/z): [M+H]⁺ calcd for $C_{29}H_{32}N_3O_4S$: 518.21 (M+H⁺); Found: 518.09, 519.12 (M+H⁺).

Example 7

Preparation of (S)-2-tert-butoxy-2-((S)-7-(2,3-dihydropyrano[4,3,2-de]quinolin-7-yl)-5-methyl-2-(3-(methylsulfonyl)azetidin-1-yl)benzo[d]thiazol-6-yl)acetic acid (58)

Compound 58 was prepared from compound 32 according to the procedure used to prepare compound 35 (except that 2-methylsulfonylazetidine was used instead of azetidine) in Example 1.

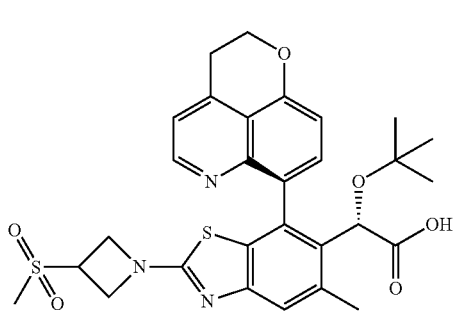

58

Compound 58: ¹H-NMR: 400 MHz, (CD₃OD) δ: ¹H NMR (400 MHz, CD₃OD) δ 8.85 (d, J=5.3 Hz, 1H), 7.89 (t, J=6.7 Hz, 2H), 7.61 (s, 1H), 7.44 (d, J=8.1 Hz, 1H), 5.18 (s, 1H), 4.72 (dd, J=9.0, 6.2 Hz, 2H), 4.59-4.35 (m, 5H), 3.01 (s, 3H), 2.72 (s, 3H), 0.92 (s, 9H). LCMS-ESI⁺ (m/z): [M+H]⁺ calcd for $C_{29}H_{32}N_3O_6S$: 582.17 (M+H⁺); Found: 581.95, 583.02 (M+H⁺).

Example 8

Preparation of (S)-2-((S)-2-(azetidin-1-yl)-7-(2,3-dihydropyrano[4,3,2-de]quinolin-7-yl)-4-fluoro-5-methylbenzo[d]thiazol-6-yl)-2-tert-butoxyacetic acid (76)

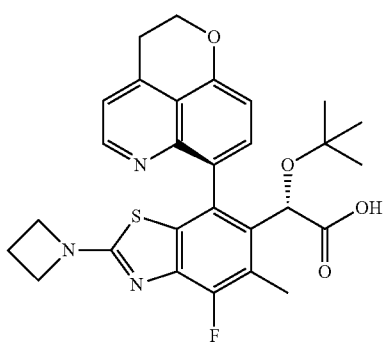

76

Compound 76: ¹H-NMR: 400 MHz, (CD₃OD) δ: 8.65 (d, J=4.4 Hz, 1H); 7.70 (d, J=7.6 Hz, 1H); 7.39 (d, J=4.4 Hz, 1H); 7.16 (d, J=7.6 Hz, 1H); 5.04 (s, 1H); 4.57 (t, J=6.0 Hz, 2H); 4.15-4.10 (m, 4H); 3.41 (t, J=6.0 Hz, 2H); 2.50-2.46 (m, 6H); 0.90 (s, 9H). LCMS-ESI⁺ (m/z): [M+H]⁺ calcd for $C_{28}H_{29}FN_3O_4S$: 522.19 (M+H⁺); Found: 521.99, 523.00 (M+H⁺).

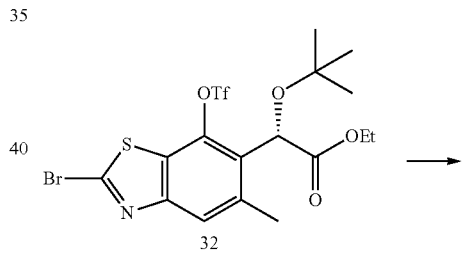

32

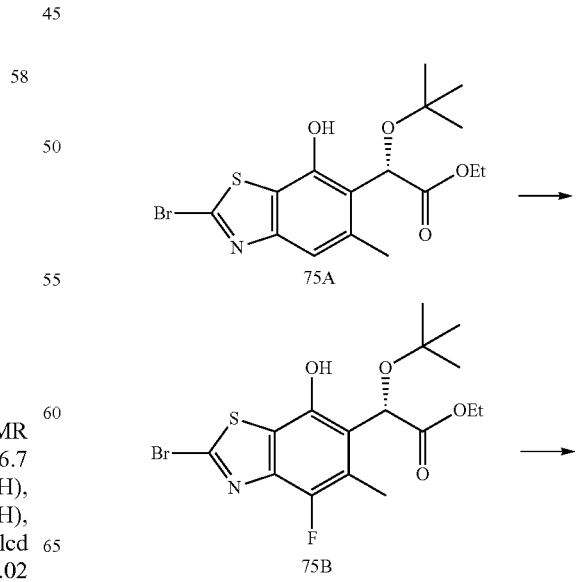

75A

75B

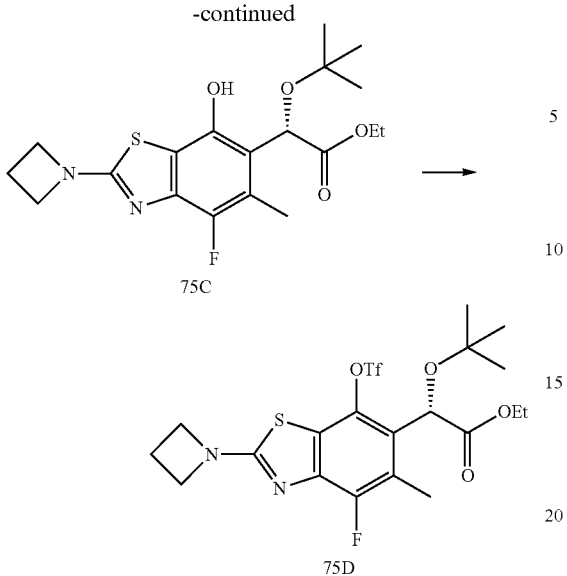

Step 1.

Preparation of (S)-ethyl 2-(2-bromo-7-hydroxy-5-methyl-benzo[d]thiazol-6-yl)-2-tert-butoxyacetate (75A): To a solution of (S)-ethyl 2-(2-bromo-5-methyl-7-(trifluoromethylsulfonyloxy)benzo[d]thiazol-6-yl)-2-tert-butoxyacetate (32): (500 mg, 0.938 mmol) in THF (5 mL) was added TBAF (1.0 M in THF, 4 mL) slowly. The reaction mixture was stirred at room temperature for 1 h. The reaction mixture was washed by a mixture of $H_2O$ (20 mL) and HOAc (200 ul), extracted by EtOAc, the organic phase was washed by sat. $NaHCO_3$, dried over $MgSO_4$, filtered, concentrated down and purified by silica gel column, eluting by 0-40% EtOAc in hexanes to give 75A (380 mg). LCMS-ESI$^+$: calc'd for $C_{16}H_{20}BrNO_4S$: 402.0 (M+H$^+$); Found: 401.9 (M+H$^+$).

Step 2.

Preparation of (S)-ethyl 2-(2-bromo-4-fluoro-7-hydroxy-5-methylbenzo[d]thiazol-6-yl)-2-tert-butoxyacetate (75B): The reaction mixture of (S)-ethyl 2-(2-bromo-7-hydroxy-5-methylbenzo[d]thiazol-6-yl)-2-tert-butoxyacetate (75A) (380 mg, 0.948 mmol), Selectfluor (1.9 g, 4.74 mmol) in acetonitrile (7 mL) was reacted at 0° C. for 5 days. The reaction mixture was washed by 1.5 M $KH_2PO_4$, extracted by EtOAc, the organic phase was dried over $MgSO_4$, filtered, concentrated down and purified by silica gel column, eluting by 0-40% EtOAc in hexanes to give 75B (137 mg, 35%). LCMS-ESI$^+$: calc'd for $C_{16}H_{19}FNO_4S$: 420.0 (M+H$^+$). Found: 420.1 (M+H$^+$).

Step 3.

Preparation of (S)-ethyl 2-(2-(azetidin-1-yl)-4-fluoro-7-hydroxy-5-methylbenzo[d]thiazol-6-yl)-2-tert-butoxyacetate (75C): Prepared by the similar method to make (S)-ethyl 2-(2-(azetidin-1-yl)-5-methyl-7-(trifluoromethylsulfonyloxy)benzo[d]thiazol-6-yl)-2-tert-butoxyacetate (33) in Example 10. LCMS-ESI$^+$: calc'd for $C_{19}H_{25}FN_2O_4S$: 397.2 (M+H$^+$); Found: 397.0 (M+H$^+$).

Step 4.

Preparation of (S)-ethyl 2-(2-(azetidin-1-yl)-4-fluoro-5-methyl-7-(trifluoromethylsulfonyloxy)benzo[d]thiazol-6-yl)-2-tert-butoxyacetate (75D): The reaction mixture of S)-ethyl 2-(2-(azetidin-1-yl)-4-fluoro-7-hydroxy-5-methylbenzo[d]thiazol-6-yl)-2-tert-butoxyacetate (75C) (50 mg, 0.126 mmol), N-phenyl triflate (90 mg, 0.252 mmol), $Cs_2CO_3$ (82 mg, 0.126 mmol) in THF (2 mL) was stirred at rt. After the reaction finished, the reaction was washed by sat $NaHCO_3$, extracted by EtOAc, the organic phase was dried over $MgSO_4$, filtered, concentrated down and purified by silica gel column, eluting by 0-40% EtOAc in hexanes to give 75D (50 mg, 75%). LCMS-ESI$^+$: calc'd for $C_{20}H_{24}F_4N_2O_6S_2$: 529.1 (M+H$^+$); Found: 529.0 (M+H$^+$).

The remainder of the synthesis of compound 76 is analogous to the preparation of compound 35 from compound 33 in example 1.

Example 9

Preparation of (S)-2-((S)-2-(azetidin-1-yl)-7-(2,3-dihydropyrano[4,3,2-de]quinolin-7-yl)-5-methyl-benzo[d]thiazol-6-yl)-2-(tert-pentyloxy)acetic acid (89)

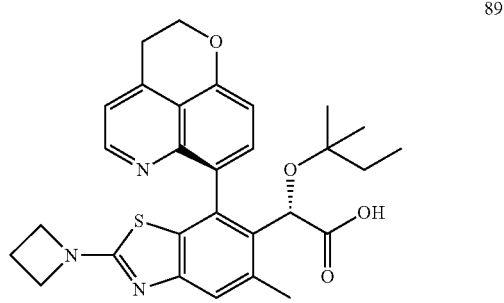

Compound 89: $^1$H NMR (400 MHz, CD$_3$OD) δ 8.75 (d, J=5.1 Hz, 1H), 7.82 (d, J=8.3 Hz, 1H), 7.71 (d, J=5.6 Hz, 1H), 7.47 (s, 1H), 7.35 (d, J=8.1 Hz, 1H), 5.09 (d, J=0.6 Hz, 1H), 4.69-4.62 (m, 2H), 4.17 (t, J=7.7 Hz, 4H), 3.61-3.55 (m, 2H), 2.66 (s, 3H), 2.58-2.42 (m, 2H), 0.87 (d, J=2.9 Hz, 6H), 0.59 (t, J=7.0 Hz, 3H). $^{19}$F NMR (377 MHz, CD$_3$OD) 6-77.77. LCMS: calc'd=518.64, observed: 518.08

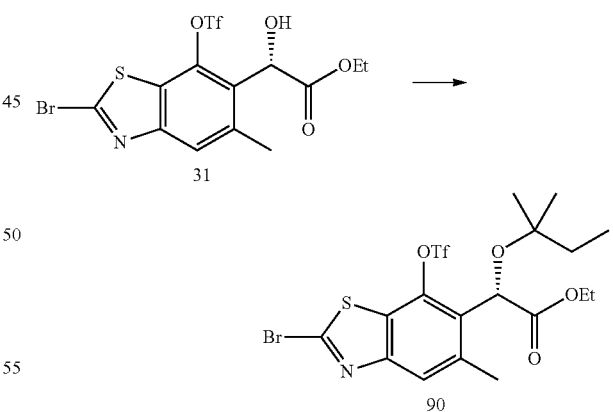

Preparation of 90: A slurry of 31 (740 mg, 1.55 mmol) in tert-amyl acetate (7.0 mL) was treated with 70% aq. $HClO_4$ (5 µL) was added at 23° C. Reaction became cloudy, but LCMS analysis indicated minimal conversion. More 70% aq. $HClO_4$ (50 µL) was introduced. After 2 h, the reaction was added dropwise over 5 min to sat. aq. $NaHCO_3$ (20 mL). $H_2O$ (10 mL) was added, and the system was extracted with DCM (3×20 mL). Combined organic layers were dried ($Na_2SO_4$), filtered, concentrated, and treated with hexane (10 mL). The system was concentrated again to remove some residual t-amyl alcohol. The residue was treated with Benzene and loaded onto a 12 gram "gold" ISCO silica gel column. Chromatography (eluent: Hexanes/Ethyl Acetate) gave 90 (134 mg, 16% yield) along with some recovered 31. $^1$H-NMR: 400 MHz, (CDCl$_3$) δ: 7.80 (s, 1H), 5.49 (s, 1H), 4.24-4.06 (m, 2H), 2.57 (s, 3H), 1.60-1.40 (m, 2H), 1.17 (s, 3H), 1.16 (t, J=7.0 Hz, 3H), 1.05 (s, 3H), 0.80 (t, J=7.0 Hz, 3H). $^{19}$F-NMR: 376 MHz, (CDCl$_3$) δ: −73.8

The remainder of the synthesis of 89 follows the same route as Example 10 from compound 32.

Example 10

Preparation of (S)-2-(2-amino-7-bromo-5-methyl-benzo[d]thiazol-6-yl)-2-tert-butoxyethyl pivalate (100)

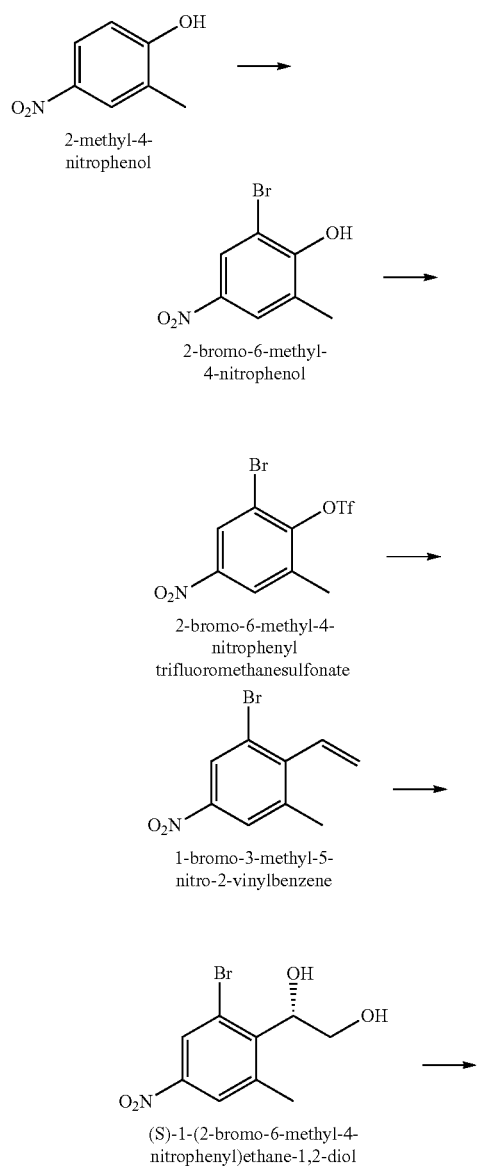

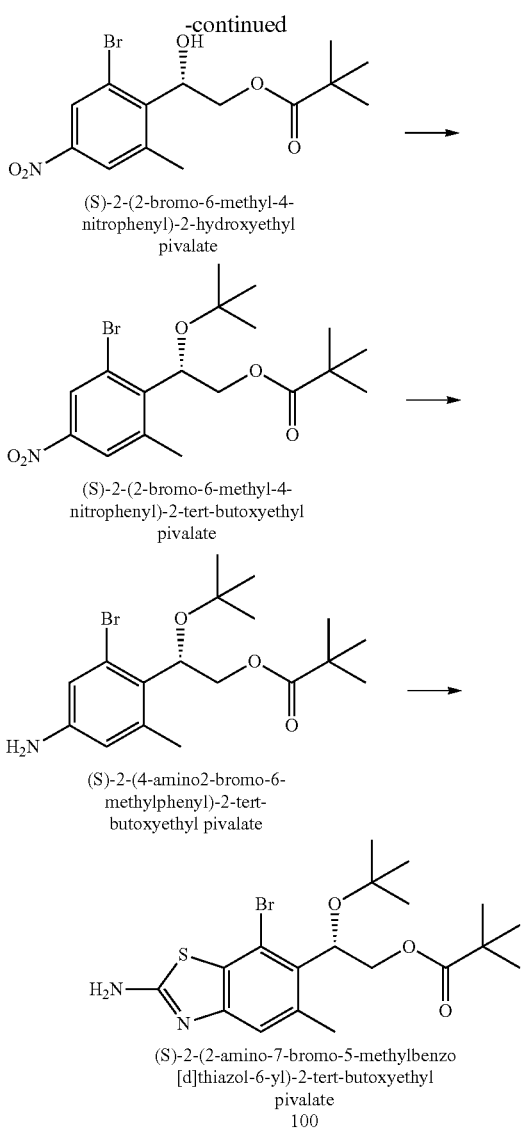

Preparation of 2-bromo-6-methyl-4-nitrophenol: Br$_2$ (122.2 g, 0.765 mol) was added into a solution of 2-methyl-4-nitrophenol (90.0 g, 0.588 mol) in HOAc (1.17 L) at room temperature. The resulting solution was stirred at room temperature for 4 h. TLC showed the reaction was complete. The solution was added into ice-water (3 L) slowly and filtered. The filter cake was dissolved into EA (2.5 L) and washed with saturated NaHSO$_3$ (3×500 mL). The EtOAc layer was dried over anhydrous Na$_2$SO$_4$, filtered and concentrated in vacuo to afford 2-bromo-6-methyl-4-nitrophenol (110 g, 80%) as yellow solid. $^1$H-NMR: 400 MHz, (CDCl$_3$) δ: 8.30 (d, J=2.0 Hz, 1H), 8.05 (s, 1H), 6.22 (s, broad, 1H), 2.41 (s, 3H).

Preparation of 2-Bromo-6-methyl-4-nitrophenyl trifluoromethanesulfonate: To a solution of 2-bromo-6-methyl-4-nitrophenol (110.0 g, 0.474 mol) in DCM (950 mL) at −70° C. was added Et$_3$N (62.3 g, 0.616 mol) and Tf$_2$O (147.1 g, 0.521 mol). The resulting solution was stirred at −70° C. for 20 min. TLC showed the reaction was complete. Aqueous HCl (0.5 M, 1 L) was added to quench the reaction. The DCM layers were separated, dried over anhydrous Na$_2$SO$_4$, filtered, concentrated in vacuo and purified by silica gel column (Petroleum Ether→Petroleum Ether:EtOAc (20:1)) to afford desired 2-Bromo-6-methyl-4-nitrophenyl trifluoromethanesulfonate (146.7 g, 85%) as yellow solid. $^1$H-NMR: 400 MHz, (CDCl$_3$) δ: 8.41 (d, J=2.0 Hz, 1H), 8.16 (d, J=2.8 Hz, 1H), 2.59 (s, 3H).

Preparation of 1-Bromo-3-methyl-5-nitro-2-vinylbenzene: The reaction mixture of 2-Bromo-6-methyl-4-nitrophenyl trifluoromethanesulfonate (10.0 g, 27.5 mmol), vinyl-tri-n-butyltin (8.7 g, 27.5 mmol), LiCl (1.4 g, 33.0 mmol), Pd(dppf)Cl$_2$ (673 mg, 0.92 mmol) and DMF (50 mL) was stirred at 70° C. for 3 h under N$_2$. Then 2 N aq. NaOH (30 mL) was added and stirred at 70° C. for 10 min. The reaction mixture was cooled down, washed with saturated aqueous NaHCO$_3$ (100 mL), and extracted with EtOAc (3×50 mL). The combined organic layer was dried over anhydrous Na$_2$SO$_4$, filtered, concentrated in vacuo, and purified by silica gel column (Petroleum Ether→Petroleum Ether:EtOAc (50:1)) to afford 1-Bromo-3-methyl-5-nitro-2-vinylbenzene (2.01 g, 30%) as yellow oil. $^1$H-NMR: 400 MHz, (CDCl$_3$) δ: 8.29 (d, J=2.0 Hz, 1H), 8.02 (s, 1H), 6.67 (dd, J=17.6, 11.6 Hz, 1H), δ 5.75 (d, J=11.6 Hz, 1H), δ 5.49 (d, J=18.0 Hz, 1H), δ 2.48 (s, 3H).

Preparation of (S)-1-(2-Bromo-6-methyl-4-nitrophenyl)ethane-1,2-diol: The reaction mixture of 1-Bromo-3-methyl-5-nitro-2-vinylbenzene (30.0 g, 0.124 mol), AD-mix α (173.5 g: 0.104 g of K$_2$OsO$_4$.2H$_2$O; 1.389 g of (DHQ)$_2$PHAL; 51.038 g of K$_2$CO$_3$ and 120.99 g of K$_4$Fe(CN)$_6$), MeSO$_2$NH$_2$ (11.8 g, 0.124 mol) in t-BuOH (250 mL) and H$_2$O (250 mL) was stirred at 0° C. for 3 days. Na$_2$SO$_3$ (15 g) was added and stirred at room temperature for 40 min to quench the reaction. The reaction mixture was treated with water (1 L) and the resulting mixture was extracted with EtOAc (3×200 mL). The combined organic layers were dried over anhydrous Na$_2$SO$_4$, filtered, concentrated in vacuo, and purified by silica gel column (Petroleum Ether:EtOAc (2:1), isocratic) to afford (S)-1-(2-Bromo-6-methyl-4-nitrophenyl)ethane-1,2-diol (17 g, 50%) as yellow solid. $^1$H-NMR: 400 MHz, (CDCl$_3$) δ: 8.26 (s, 1H), 7.99 (s, 1H), 5.56-5.54 (m, 1H), 3.94-3.92 (m, 1H), 3.81-3.78 (m, 1H), 2.82 (d, broad, 1H), 2.67 (s, 3H), 2.18-2.15 (m, 1H).

Preparation of (S)-2-(2-Bromo-6-methyl-4-nitrophenyl)-2-hydroxyethyl pivalate: To a suspension of (S)-1-(2-Bromo-6-methyl-4-nitrophenyl)ethane-1,2-diol (17.0 g, 61.6 mmol) in DCM (435 mL) at 0° C. was added pyridine (18.6 g, 235.4 mmol) and PivCl (13.4 g, 110.8 mmol) slowly. After stirring at 0° C. for 5 min, the system was raised to room temperature and stirred at this temperature for 5 h. TLC showed the reaction was complete. The reaction mixture was treated with saturated aqueous NaHCO$_3$ (500 mL), and the resulting system was extracted with DCM (2×200 mL). The combined organic layer was dried over anhydrous Na$_2$SO$_4$, filtered, concentrated in vacuum, and purified by silica gel column (Petroleum Ether:EtOAc (30:1)) to afford (S)-2-(2-Bromo-6-methyl-4-nitrophenyl)-2-hydroxyethyl pivalate (17 g, 77%) as yellow solid. $^1$H-NMR: 400 MHz, (CDCl$_3$) δ: 8.28 (s, 1H), 8.00 (d, J=2.0 Hz, 1H), 5.70-5.66 (m, 1H), 4.58-4.53 (m, 1H), 4.31-4.26 (m, 1H), 2.84 (d, J=5.6 Hz, 2H), 2.68 (s, 3H), 1.22 (s, 9H).

Preparation of (S)-2-(2-Bromo-6-methyl-4-nitrophenyl)-2-tert-butoxyethyl pivalate: To a solution of (S)-2-(2-Bromo-6-methyl-4-nitrophenyl)-2-hydroxyethyl pivalate (13 g, 0.036 mol) in t-BuOAc (300 mL) at 0° C. was added HClO$_4$ (20.7 g, 0.144 mol) slowly. The solution was stirred at 0° C. for 5 min, then warmed to room temperature and stirred at this temperature for 1.5 h. The solution was alkalized by saturated aqueous NaHCO$_3$ until the pH of solution >8. The mixture was extracted with EtOAc (3×1 L). The combined organic layers were dried over anhydrous Na$_2$SO$_4$, filtered, concentrated in vacuo, and purified by silica gel column (Petroleum Ether:EtOAc (50:1)) to afford (S)-2-(2-Bromo-6-methyl-4-nitrophenyl)-2-tert-butoxyethyl pivalate (9.3 g, 62%) as yellow solid. $^1$H-NMR: 400 MHz, (CDCl$_3$) δ: 8.26 (s, 1H), 7.98 (s, 1H), 5.60-5.57 (m, 1H), 4.32-4.27 (m, 1H), 4.18-4.14 (m, 1H), 2.73 (s, 3H), 1.17 (s, 9H), 1.14 (s, 9H).

Preparation of (S)-2-(4-amino-2-bromo-6-methylphenyl)-2-tert-butoxyethyl pivalate: To a solution of (S)-2-(2-Bromo-6-methyl-4-nitrophenyl)-2-tert-butoxyethyl pivalate (9 g, 0.022 mol) in EtOH (50 mL) and EtOAc (50 mL) was added Pt/C (1.4 g), and the reaction was fitted with a balloon of H$_2$. The reaction mixture was stirred at room temperature for 3 h. TLC showed the reaction was complete. The reaction mixture was filtered over Celite. The filtrate was concentrated in vacuo to give (S)-2-(4-amino-2-bromo-6-methylphenyl)-2-tert-butoxyethyl pivalate (7 g, 82%) as brown oil, which was immediately used for next step without further purification. $^1$H-NMR: 400 MHz, (CDCl$_3$) δ: 6.70 (s, 1H), 6.40 (s, 1H), 5.38 (app. s, broad, 1H), 4.22 (app. s, broad, 1H), 4.05 (app. s, broad, 1H), 3.60 (app. s, broad, 2H), 2.47 (s, 3H), 1.17 (s, 9H), 1.13 (s, 9H).

Preparation of (S)-2-(2-amino-7-bromo-5-methylbenzo[d]thiazol-6-yl)-2-tert-butoxyethyl pivalate: To a solution of freshly prepared (S)-2-(4-amino-2-bromo-6-methylphenyl)-2-tert-butoxyethyl pivalate (7 g, 18.1 mmol) in HOAc (90 mL) was added KSCN (1.76 g, 18.1 mmol) at r.t. The reaction mixture was stirred at r.t. for 0.5 h. Pyridinium perbromide (5.79 g, 18.1 mmol) was added slowly over a period of 10 min, and stirred at r.t for 2 h. The mixture was alkalized to pH=8 using saturated aqueous NaHCO$_3$ solution, then extracted with EtOAc (3×600 mL). The combined organic layers were dried over anhydrous Na$_2$SO$_4$, filtered, concentrated in vacuo, and purified by silica gel column (Petroleum Ether:EtOAc (10:1→5:1)) to afford (S)-2-(2-amino-7-bromo-5-methylbenzo[d]thiazol-6-yl)-2-tert-butoxyethyl pivalate (2.74 g, 34.3%) as yellow solid. LCMS-ESI$^+$: calc'd for C$_{19}$H$_{27}$BrN$_2$O$_3$S: 443.1 and 445.1 (M+H$^+$); found: 443.1 and 445.1 (M+H$^+$). $^1$H-NMR: 400 MHz, (CD$_3$OD) δ: 7.15 (s, 1H), 5.53-5.49 (m, 1H), 4.31-4.26 (m, 1H), 4.17-4.13 (m, 1H), 2.64 (s, 3H), 1.15 (s, 9H), 1.11 (s, 9H).

Example 11

Preparation of (S)-2-(2-bromo-7-(4-chlorophenyl)-5-methylbenzo[d]thiazol-6-yl)-2-tert-butoxyethyl pivalate (101)

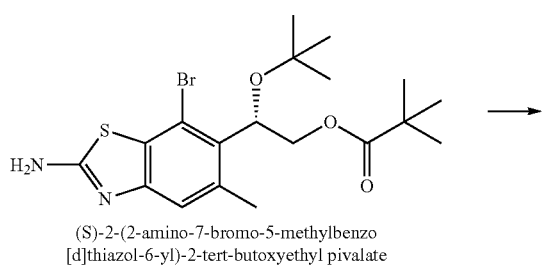

(S)-2-(2-amino-7-bromo-5-methylbenzo[d]thiazol-6-yl)-2-tert-butoxyethyl pivalate

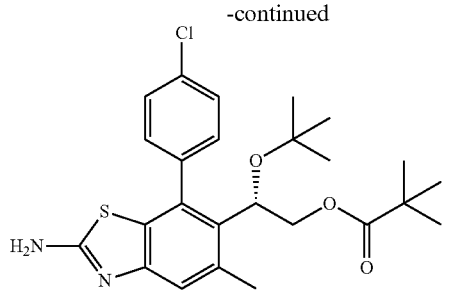

(S)-2-(2-amino-7-(4-chlorophenyl)-5-methylbenzo[d]thiazol-6-yl)-2-tert-butoxyethyl pivalate

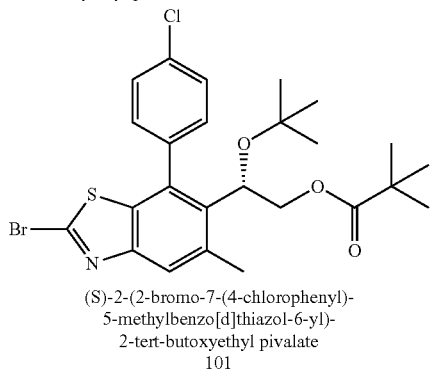

(S)-2-(2-bromo-7-(4-chlorophenyl)-5-methylbenzo[d]thiazol-6-yl)-2-tert-butoxyethyl pivalate
101

Preparation of (S)-2-(2-Amino-7-(4-chlorophenyl)-5-methylbenzo[d]thiazol-6-yl)-2-tert-butoxyethyl pivalate: 2 separate microwave tubes were each charged with (S)-2-(2-Amino-7-bromo-5-methylbenzo[d]thiazol-6-yl)-2-tert-butoxyethyl pivalate (768 mg, 1.74 mmol), $K_2CO_3$ (960 mg, 6.96 mmol), 4-chlorophenylboronic acid (325 mg, 2.09 mmol), Pd(PPh$_3$)$_4$ (200 mg, 0.174 mmol), dioxane (8.0 mL), and $H_2O$ (2.0 mL). The two sealed vessels were separately heated at 110° C. for 3 h. The reactions were cooled to 23° C. and combined. $H_2O$ (50 mL) was added, and the system was extracted with EtOAc (3×50 mL). The combined extracts were dried (Na$_2$SO$_4$), filtered, and concentrated. The residue was treated with benzene and purified via chromatography on silica gel (80 g "gold" ISCO column; Hex/EtOAc) giving (S)-2-(2-Amino-7-(4-chlorophenyl)-5-methylbenzo[d]thiazol-6-yl)-2-tert-butoxyethyl pivalate (1.55 g, 90% yield). LCMS-ESI$^+$: calc'd for $C_{25}H_{31}ClN_2O_3S$: 475.2 and 477.2 (M+H$^+$); found: 475.3 and 477.3 (M+H$^+$). $^1$H-NMR: 400 MHz, (CDCl$_3$) δ: 7.49-7.41 (m, 2H), 7.36-7.32 (m, 2H), 7.22 (d, J=7.3 Hz, 1H), 5.19 (s, broad, 2H), 4.67 (dd, J=9.0, 2.7 Hz, 1H), 4.36 (dd, J=11.7, 9.0 Hz, 1H), 4.23 (dd, J=11.7, 2.7 Hz, 1H), 2.68 (s, 3H), 1.14 (s, 9H), 0.94 (s, 9H).

Preparation of (S)-2-(2-bromo-7-(4-chlorophenyl)-5-methylbenzo[d]thiazol-6-yl)-2-tert-butoxyethyl pivalate: At 23° C., in a water bath, a solution of (S)-2-(2-amino-7-(4-chlorophenyl)-5-methylbenzo[d]thiazol-6-yl)-2-tert-butoxyethyl pivalate (1.13 g, 2.37 mmol) in CH$_3$CN (22 mL) was treated with solid anhydrous CuBr$_2$ (635 mg, 2.84 mmol). Reaction was fitted with a mineral oil bubbler. A freshly prepared solution of t-butyl nitrite (269 mg, 2.61 mmol) in CH$_3$CN (2.0 mL) was added dropwise over a 5 min period. The water bath was removed. Gas evolution was monitored using the bubbler. At 1 h, gas evolution ceased. The reaction was poured into EtOAc (50 mL) and treated with H$_2$O (50 mL). A brown solid precipitated. The suspension was filtered over Celite, which was thoroughly washed with EtOAc. The filtrate was transferred to a separatory funnel. The organic phase was collected. The aq. phase was extracted with EtOAc. The total organic layers were combined, dried (Na$_2$SO$_4$), filtered, and concentrated. The residue was treated with benzene and purified via chromatography on silica gel (80 g "gold" ISCO column; Hex/EtOAc) giving (S)-2-(2-bromo-7-(4-chlorophenyl)-5-methylbenzo[d]thiazol-6-yl)-2-tert-butoxyethyl pivalate (675 mg, 53% yield). LCMS-ESI$^+$: calc'd for $C_{25}H_{29}BrClNO_3S$: 538.1, 540.1, and 542.1.1 (M+H$^+$); found: 538.2, 540.2, and 542.2 (M+H$^+$). $^1$H-NMR: 400 MHz, (CDCl$_3$) δ: 7.76 (s, 1H), 7.51 (d, J=8.2 Hz, 1H), 7.47 (d, J=7.8 Hz, 1H), 7.34 (d, J=8.2 Hz, 1H), 7.24 (d, J=7.8 Hz, 1H), 4.76 (dd, J=9.0, 3.5 Hz, 1H), 4.39 (dd, J=11.7, 9.0 Hz, 1H), 4.25 (dd, J=11.7, 3.5 Hz, 1H), 2.76 (s, 3H), 1.14 (s, 9H), 0.94 (s, 9H).

Example 12

Preparation of (S)-methyl 2-(2-amino-7-(4-chlorophenyl)-5-methylbenzo[d]thiazol-6-yl)-2-tert-butoxyacetate (102)

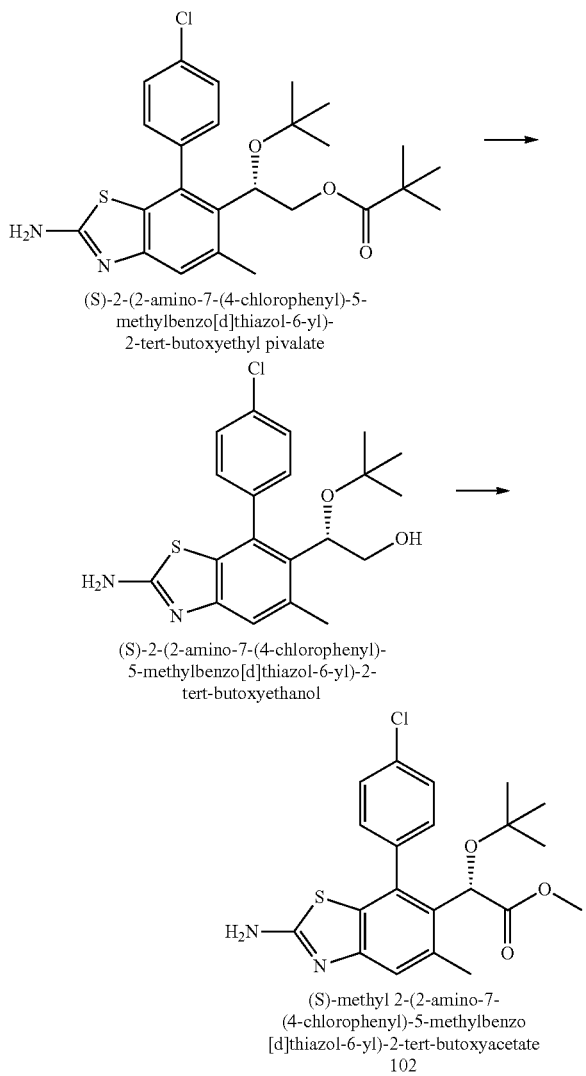

(S)-2-(2-amino-7-(4-chlorophenyl)-5-methylbenzo[d]thiazol-6-yl)-2-tert-butoxyethyl pivalate (S)-2-(2-amino-7-(4-chlorophenyl)-5-methylbenzo[d]thiazol-6-yl)-2-tert-butoxyethanol (S)-methyl 2-(2-amino-7-(4-chlorophenyl)-5-methylbenzo[d]thiazol-6-yl)-2-tert-butoxyacetate
102

Preparation of (S)-2-(2-amino-7-(4-chlorophenyl)-5-methylbenzo[d]thiazol-6-yl)-2-tert-butoxyethanol: A flask was charged with (S)-2-(2-Amino-7-(4-chlorophenyl)-5-methylbenzo[d]thiazol-6-yl)-2-tert-butoxyethyl pivalate (2.15 g, 4.52 mmol), LiOH monohydrate (2.00 g, 47.4 mmol), H$_2$O (4 mL), EtOH (absolute, 4.0 mL), and THF (8.0 mL). The reaction was placed under N$_2$ and heated to 100° C. After 2 h, the reaction was cooled to 23° C., diluted with H$_2$O, and extracted with EtOAc several times. The combined organic phases were dried (Na$_2$SO$_4$), filtered, and concentrated. The residue was treated with benzene and purified via chromatography on silica gel (80 g "gold" ISCO column; Hex/EtOAc) giving (S)-2-(2-amino-7-(4-chlorophenyl)-5-methylbenzo[d]thiazol-6-yl)-2-tert-butoxyethanol (1.10 g, 62% yield). LCMS-ESI$^+$: calc'd for C$_{20}$H$_{23}$ClN$_2$O$_2$S: 391.1 and 393.1 (M+H$^+$); found: 391.2 and 393.2 (M+H$^+$). $^1$H-NMR: 400 MHz, (CDCl$_3$) δ: 7.49-7.41 (m, 2H), 7.36-7.32 (m, 2H), 7.20 (d, J=7.3 Hz, 1H), 5.39 (s, broad, 2H), 4.52-4.50 (m, 1H), 3.85-3.70 (m, 2H), 2.63 (s, 3H), 0.99 (s, 9H).

Preparation of (S)-methyl 2-(2-amino-7-(4-chlorophenyl)-5-methylbenzo[d]thiazol-6-yl)-2-tert-butoxyacetate: A solution of (S)-2-(2-amino-7-(4-chlorophenyl)-5-methylbenzo[d]thiazol-6-yl)-2-tert-butoxyethanol (1.10 g, 2.81 mmol) in CH$_3$CN (40 mL) and H$_2$O (10 mL) was treated with H$_5$IO$_6$ (2.00 g, 8.77 mmol) at 0° C. Then solid CrO$_3$ (500 mg, 5.00 mmol) was added in one portion. All solids dissolved initially, then precipitate developed. Reaction was warmed to 23° C. After 1.5 h, the reaction was treated with 1.0 M aq. Na$_2$HPO$_4$ until the pH was ~8. Then 1.0 M aq. NaH$_2$PO$_4$ was added to pH=5. The resulting system was extracted with DCM (50 mL). The organic phase was dried (Na$_2$SO$_4$), filtered, and treated with MeOH (20 mL). Trimethylsilyldiazomethane (2.0 M in hexane, 3.0 mL) was added slowly. The reaction was then stirred for 5 min. Glacial AcOH (300 μL) was added carefully. Saturated aq. Na$_2$HPO$_4$ (50 mL) was added. The organic phase was collected, and the aq. layer was extracted with DCM. Combined organic layers were dried (Na$_2$SO$_4$), filtered, and concentrated. The residue was purified via chromatography on silica gel (80 g "gold" ISCO column; Hex/EtOAc) giving (S)-methyl 2-(2-amino-7-(4-chlorophenyl)-5-methylbenzo[d]thiazol-6-yl)-2-tert-butoxyacetate (206 mg, 19% yield). LCMS-ESI$^+$: calc'd for C$_{21}$H$_{23}$ClN$_2$O$_3$S: 419.1 and 421.1 (M+H$^+$); found: 419.2 and 421.2 (M+H$^+$). $^1$H-NMR: 400 MHz, (CDCl$_3$) δ: 7.50-7.31 (m, 5H), 5.17 (s, broad, 2H), 5.10 (s, 1H), 3.72 (s, 3H), 2.49 (s, 3H), 0.95 (s, 9H).

Example 13

Preparation of (S)-methyl 2-(2-bromo-7-(4-chlorophenyl)-5-methylbenzo[d]thiazol-6-yl)-2-tert-butoxyacetate (103)

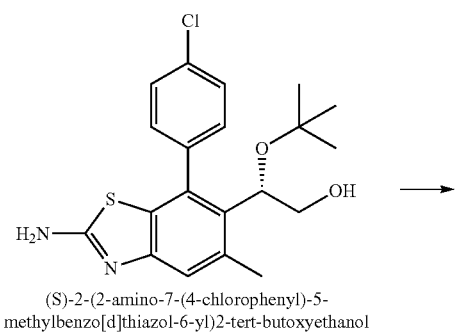

(S)-2-(2-amino-7-(4-chlorophenyl)-5-methylbenzo[d]thiazol-6-yl)2-tert-butoxyethanol

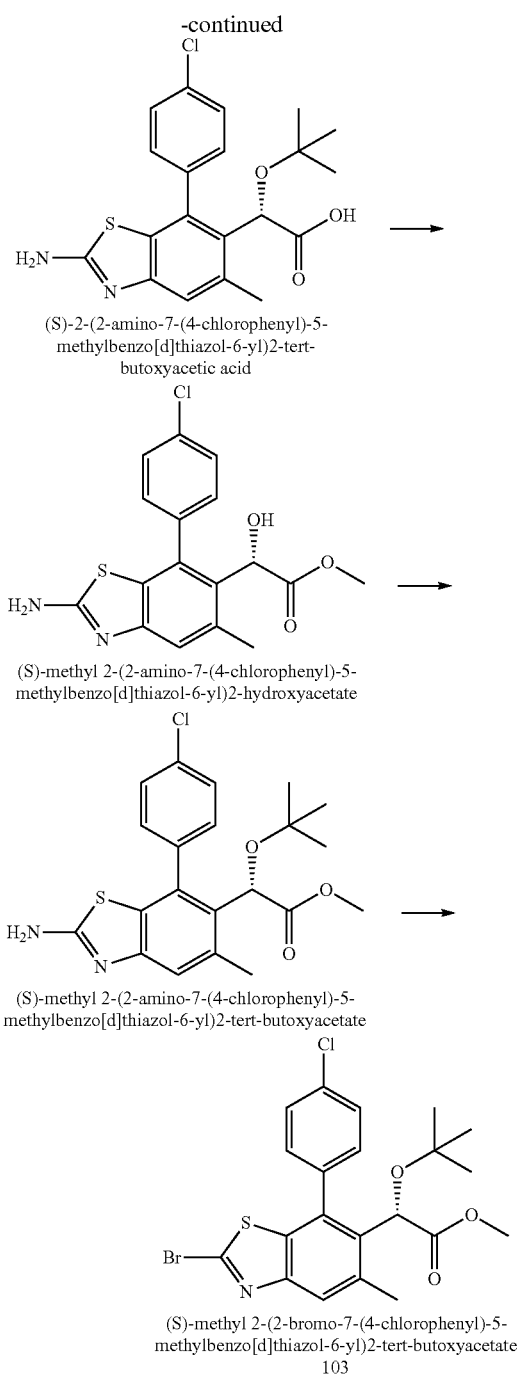

(S)-2-(2-amino-7-(4-chlorophenyl)-5-methylbenzo[d]thiazol-6-yl)2-tert-butoxyacetic acid (S)-methyl 2-(2-amino-7-(4-chlorophenyl)-5-methylbenzo[d]thiazol-6-yl)2-hydroxyacetate (S)-methyl 2-(2-amino-7-(4-chlorophenyl)-5-methylbenzo[d]thiazol-6-yl)2-tert-butoxyacetate (S)-methyl 2-(2-bromo-7-(4-chlorophenyl)-5-methylbenzo[d]thiazol-6-yl)2-tert-butoxyacetate
103

Preparation of (S)-2-(2-amino-7-(4-chlorophenyl)-5-methylbenzo[d]thiazol-6-yl)-2-tert-butoxyacetic acid. To a solution of (S)-2-(2-amino-7-(4-chlorophenyl)-5-methylbenzo[d]thiazol-6-yl)-2-tert-butoxyethanol (1.95 g, 5.00 mmol) in acetonitrile (25 mL) and water (1 mL) was added H$_5$IO$_6$ (1.37 g, 6.00 mmol) and CrO$_3$ (1.00 g, 10.0 mmol). The mixture was stirred at room temperature for 1 h and was diluted with EtOAc (50 mL) and a saturated solution of Na$_2$SO$_3$ (50 mL). The layers were separated, and the aqueous layer was extracted with EtOAc. The crude material was taken on without further purification. $^1$H-NMR: 400 MHz, (CDCl$_3$) δ: 7.42-7.61 (m, 4H), 7.20 (s, 1H), 5.11 (s, 1H), 2.47 (s, 3H), 0.93 (s, 9H).

Preparation of (S)-methyl 2-(2-amino-7-(4-chlorophenyl)-5-methylbenzo[d]thiazol-6-yl)-2-tert-butoxyacetate. To a solution of Preparation of (S)-2-(2-amino-7-(4-chlorophenyl)-5-methylbenzo[d]thiazol-6-yl)-2-tert-butoxyacetic acid from above in MeOH (25 mL) was added H$_2$SO$_4$ (200 μL). The reaction mixture was stirred at overnight. EtOAc (20 mL) and saturated NaHCO$_3$ solution (50 mL) were added. The layers were separated, dried, filtered, and concentrated in vacuo. The crude mixture was a mixture of the desired (S)-methyl 2-(2-amino-7-(4-chlorophenyl)-5-methylbenzo[d]thiazol-6-yl)-2-tert-butoxyacetate and (S)-methyl 2-(2-amino-7-(4-chlorophenyl)-5-methylbenzo[d]thiazol-6-yl)-2-hydroxyacetate. t-Butyl acetate was added (20 mL) and perchloric acid (500 μL). The mixture was stirred at rt for 3 hr, where all (S)-methyl 2-(2-amino-7-(4-chlorophenyl)-5-methylbenzo[d]thiazol-6-yl)-2-hydroxyacetate was converted to (S)-methyl 2-(2-amino-7-(4-chlorophenyl)-5-methylbenzo[d]thiazol-6-yl)-2-tert-butoxyacetate. EtOAc (10 mL) and saturated NaHCO$_3$ solution (50 mL) were added. The layers were separated, dried, filtered, and concentrated in vacuo. LCMS-ESI$^+$: calc'd for C$_{21}$H$_{23}$ClN$_2$O$_3$S: 419.1 and 421.1 (M+H$^+$); found: 419.2 and 421.2 (M+H$^+$).

Preparation of (S)-methyl 2-(2-bromo-7-(4-chlorophenyl)-5-methylbenzo[d]thiazol-6-yl)-2-tert-butoxyacetate. To a solution of (S)-methyl 2-(2-amino-7-(4-chlorophenyl)-5-methylbenzo[d]thiazol-6-yl)-2-tert-butoxyacetate from above in acetonitrile (25 mL) was added CuBr$_2$ (1.1 g, 5.0 mmol) and t-butyl nitrite (600 μL, 5.0 mmol). The reaction was stirred at room temperature for 30 min, and then a saturated solution of Na$_2$SO$_3$ (25 mL) was added. The layers were separated, dried, filtered, and concentrated in vacuo. The crude material was purified by column chromatography (EtOAc/hexanes) to give 642 mg of (S)-methyl 2-(2-bromo-7-(4-chlorophenyl)-5-methylbenzo[d]thiazol-6-yl)-2-tert-butoxyacetate. LCMS-ESI$^+$: calc'd for C$_{21}$H$_{21}$BrClNO$_3$S: 482.0 and 484.0 (M+H$^+$); found: 482.1 and 484.1 (M+H$^+$). $^1$H-NMR: 400 MHz, (CDCl$_3$) δ: 7.70 (s, 1H), 7.41 (br s, 3H), 7.19 (s, 1H), 5.09 (s, 1H), 3.67 (s, 3H), 2.49 (s, 3H), 0.88 (s, 9H).

Example 14

Method B: Preparation of (S)-2-tert-butoxy-2-(7-(4-chlorophenyl)-2-(3-(5-methoxypyridin-3-yl)phenyl)-5-methylbenzo[d]thiazol-6-yl)acetic acid (104)

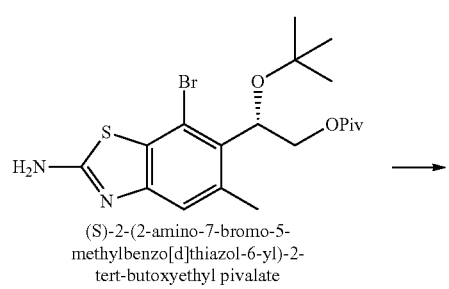

(S)-2-(2-amino-7-bromo-5-methylbenzo[d]thiazol-6-yl)-2-tert-butoxyethyl pivalate -continued

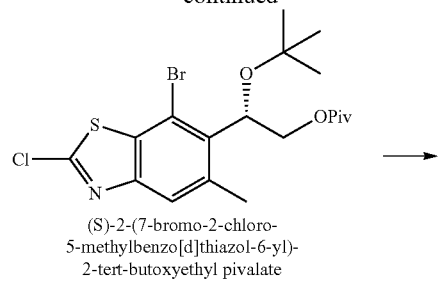

(S)-2-(7-bromo-2-chloro-5-methylbenzo[d]thiazol-6-yl)-2-tert-butoxyethyl pivalate

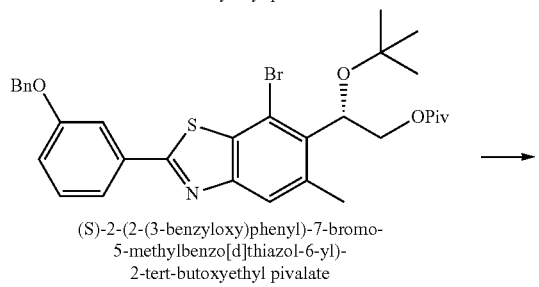

(S)-2-(2-(3-benzyloxy)phenyl)-7-bromo-5-methylbenzo[d]thiazol-6-yl)-2-tert-butoxyethyl pivalate

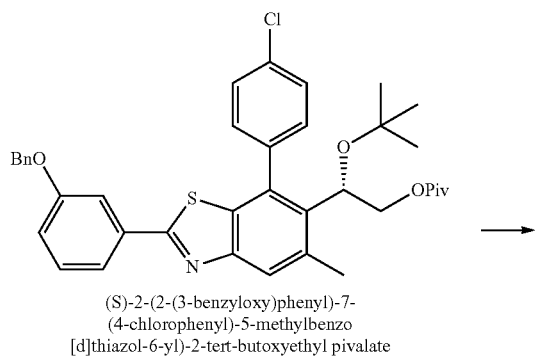

(S)-2-(2-(3-benzyloxy)phenyl)-7-(4-chlorophenyl)-5-methylbenzo[d]thiazol-6-yl)-2-tert-butoxyethyl pivalate

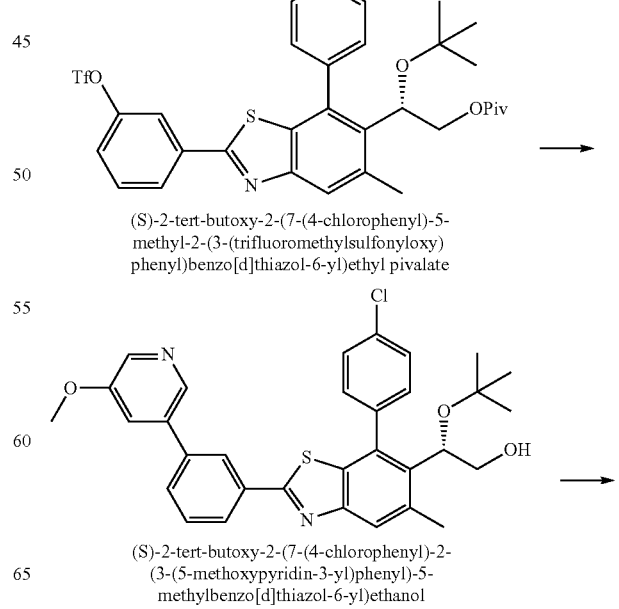

(S)-2-tert-butoxy-2-(7-(4-chlorophenyl)-5-methyl-2-(3-(trifluoromethylsulfonyloxy)phenyl)benzo[d]thiazol-6-yl)ethyl pivalate (S)-2-tert-butoxy-2-(7-(4-chlorophenyl)-2-(3-(5-methoxypyridin-3-yl)phenyl)-5-methylbenzo[d]thiazol-6-yl)ethanol -continued

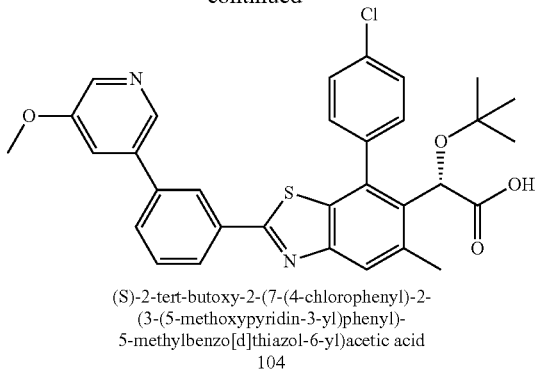

(S)-2-tert-butoxy-2-(7-(4-chlorophenyl)-2-
(3-(5-methoxypyridin-3-yl)phenyl)-
5-methylbenzo[d]thiazol-6-yl)acetic acid
104

Preparation of (S)-2-(7-bromo-2-chloro-5-methylbenzo[d]thiazol-6-yl)-2-tert-butoxyethyl pivalate: To a solution of (S)-2-(2-amino-7-bromo-5-methylbenzo[d]thiazol-6-yl)-2-tert-butoxyethyl pivalate (1 g, 2.26 mmol) in acetonitrile (15 mL) was added t-butyl nitrite (350 µL, 2.94 mmol) and CuCl$_2$ (364 mg, 2.7 mmol). The reaction mixture was stirred at room temperature for 5 hours. After the reaction finished, the reaction mixture was diluted by EtOAc, washed by water, extracted by EtOAc. The organic phase was dried over MgSO$_4$, filtered, concentrated down and purified by silica gel column, eluting be 0-50% EtOAc in hexanes to give the product (850 mg, 81%). LCMS-ESI$^+$: calc'd for $C_{19}H_{25}BrClNO_3S$: 462.0 (M+H$^+$); Found: 462.14 (M+H$^+$).

Preparation of (S)-2-(2-(3-(benzyloxy)phenyl)-7-bromo-5-methylbenzo[d]thiazol-6-yl)-2-tert-butoxyethyl pivalate: To a solution of (S)-2-(7-bromo-2-chloro-5-methylbenzo[d]thiazol-6-yl)-2-tert-butoxyethyl pivalate (130 mg, 0.282 mmol) in dioxane, was added 3-benzyloxyphenylboronic acid pinacol ester (105 mg, 0.338 mmol), Pd(PPh$_3$)$_4$ (16 mg, 0.014 mmol), 2N K$_2$CO$_3$ (700 µL). The reaction mixture in sealed tube was heated at 95° C. for 1.5hs. Then the reaction was cooled down. The reaction mixture was washed by sat. NaHCO$_3$, and extracted by EtOAc. The organic phase was filtered, concentrated down, purified by silica gel column, eluting by 0-50% EtOAc in hexanes to give the product (100 mg, 58%). LCMS-ESI$^+$: calc'd for $C_{32}H_{36}BrNO_4S$: 610.2 (M+H$^+$); Found: 610.2 (M+H$^+$).

Preparation of (S)-2-(2-(3-(benzyloxy)phenyl)-7-(4-chlorophenyl)-5-methylbenzo[d]thiazol-6-yl)-2-tert-butoxyethyl pivalate: The mixture of (S)-2-(2-(3-(benzyloxy)phenyl)-7-bromo-5-methylbenzo[d]thiazol-6-yl)-2-tert-butoxyethyl pivalate (100 mg, 0.164 mmol), 4-cholorophenylboronic acid (38 mg, 0.246 mmol), 2N K$_2$CO$_3$ (400 µL), Pd(PPh$_3$)$_4$ (18 mg, 0.016 mmol) in dioxane in sealed tube was heated at 120° C. After the reaction is finished, the reaction mixture was washed by sat. NaHCO$_3$, extracted by EtOAc, the organic phase was dried over MgSO$_4$, filtered, concentrated down and purified by silica gel column by (0-50% EtOAc in Hexanes) to give the product (103 mg, 97%). LCMS-ESI$^+$: calc'd for $C_{38}H_{40}ClNO_4S$: 642.2 (M+H$^+$); Found: 642.3 (M+H$^+$).

Preparation of (S)-2-tert-butoxy-2-(7-(4-chlorophenyl)-5-methyl-2-(3-(trifluoromethylsulfonyloxy)phenyl)benzo[d]thiazol-6-yl)ethyl pivalate: To a solution of (S)-2-(2-(3-(benzyloxy)phenyl)-7-(4-chlorophenyl)-5-methylbenzo[d]thiazol-6-yl)-2-tert-butoxyethyl pivalate (410 mg, 0.638 mmol) in EtOH/EtOAc (1:1, 4 mL) was added Pd/C (10%, 600 mg). Then hydrogen balloon was attached to the flask, and the reaction was reacted at room temperature for 1 h. After the reaction was finished, the catalyst was removed over Celite pad and the solution was concentrated down to dryness. The residue was dissolved in DCM (5 mL), to the solution was added pyridine (2 mL), Tf$_2$O (210 µL, 1.25 mmol) at 0° C. and the reaction was stirred at 0° C. for 1 h. Then the reaction was quenched by sat. NaHCO$_3$, extracted by DCM, dried over MgSO$_4$, filtered, concentrated down and purified by silica gel column (0-40% EtOAc in hexanes) to give the product (360 mg, 82%). LCMS-ESI$^+$: calc'd for $C_{32}H_{33}ClF_3NO_6S_2$: 684.1 (M+H$^+$); Found: 684.1 (M+H$^+$).

Preparation of (S)-2-tert-butoxy-2-(7-(4-chlorophenyl)-2-(3-(5-methoxypyridin-3-yl)phenyl)-5-methylbenzo[d]thiazol-6-yl)ethanol: The reaction mixture of (S)-2-tert-butoxy-2-(7-(4-chlorophenyl)-5-methyl-2-(3-(trifluoromethylsulfonyloxy)phenyl)benzo[d]thiazol-6-yl)ethyl pivalate (20 mg, 0.029 mmol), 3-methoxypyridine-5-boronic acid pinacol ester (10 mg, 0.043 mmol), 2N K$_2$CO$_3$ (70 µL), Pd(PPh$_3$)$_4$ (3.3 mg, 0.0029 mmol) in dioxane (1 mL) was heated at 120° C. in sealed tube for 2 hours. After the reaction finished, the reaction was cooled down, to the reaction mixture was added MeOH (1 mL), 2N NaOH (500 µL) and heated at 45° C. for 3 hours. Then reaction mixture was washed by sat. NaHCO$_3$, extracted by EtOAc, the organic phase was dried over MgSO$_4$, filtered, concentrated down and purified by silica gel column, eluting by 0-100% EtOAc in hexanes to give the product (10 mg, 62%). LCMS-ESI$^+$: calc'd for $C_{32}H_{31}ClN_2O_3S$: 559.2 (M+H$^+$); Found: 559.2 (M+H$^+$).

Preparation of (S)-2-tert-butoxy-2-(7-(4-chlorophenyl)-2-(3-(5-methoxypyridin-3-yl)phenyl)-5-methylbenzo[d]thiazol-6-yl)acetic acid: To a solution of (S)-2-tert-butoxy-2-(7-(4-chlorophenyl)-2-(3-(5-methoxypyridin-3-yl)phenyl)-5-methylbenzo[d]thiazol-6-yl)ethanol (10 mg, 0.0179 mmol) in wet acetonitrile (0.75 w % H$_2$O, 1 mL), was added stock solution of H$_5$IO$_6$/CrO$_3$ (0.439 M in 0.75% H$_2$O in acetonitrile, 400 µL) at 0° C. for ½ hour. The reaction mixture was filtered and purified by reverse phase HPLC, eluting by 0-100% acetonitrile in H$_2$O with 0.1% TFA give the product (5 mg, 40%). LCMS-ESI$^+$: calc'd for $C_{32}H_{29}ClN_2O_4S$: 573.2 (M+H$^+$); Found: 573.2 (M+H$^+$). $^1$H NMR (400 MHz, CD$_3$OD): δ 8.59 (s, 1H), 8.40-8.38 (m, 2H), 8.09 (d, J=4.2 Hz, 1H), 7.97 (s, 1H), 7.89-7.88 (m, 2H), 7.70-7.60 (m, 5H), 5.26 (s, 1H), 4.03 (s, 3H), 2.62 (s, 3H), 0.97 (s, 9H).

Example 15

Method C: Preparation of (S)-2-tert-butoxy-2-(7-(4-chlorophenyl)-2-(5'-methoxy-2,3'-bipyridin-4-yl)-5-methylbenzo[d]thiazol-6-yl)acetic acid (105)

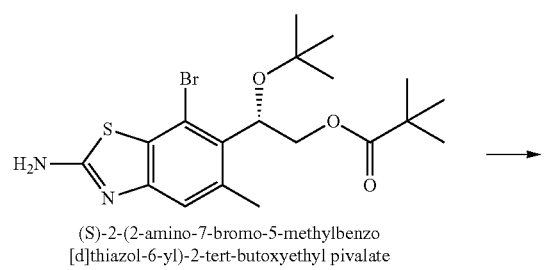

(S)-2-(2-amino-7-bromo-5-methylbenzo
[d]thiazol-6-yl)-2-tert-butoxyethyl pivalate -continued

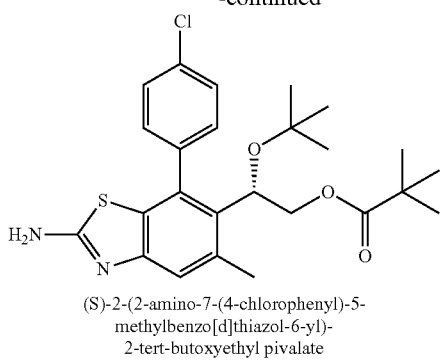

(S)-2-(2-amino-7-(4-chlorophenyl)-5-methylbenzo[d]thiazol-6-yl)-2-tert-butoxyethyl pivalate

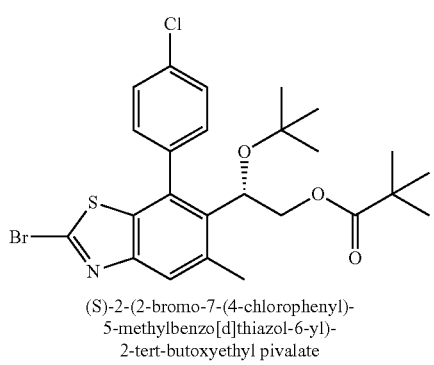

(S)-2-(2-bromo-7-(4-chlorophenyl)-5-methylbenzo[d]thiazol-6-yl)-2-tert-butoxyethyl pivalate

+

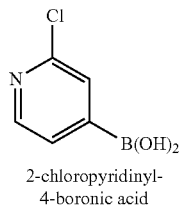

2-chloropyridinyl-4-boronic acid

→

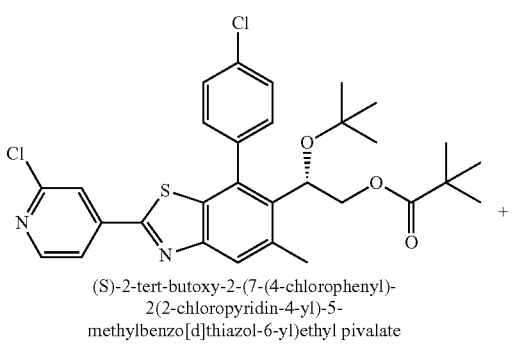

(S)-2-tert-butoxy-2-(7-(4-chlorophenyl)-2(2-chloropyridin-4-yl)-5-methylbenzo[d]thiazol-6-yl)ethyl pivalate

+

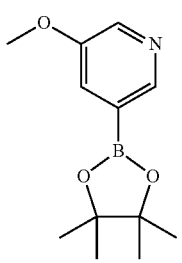

5-methoxy-3-pyridineboronic acid pinacol ester

→

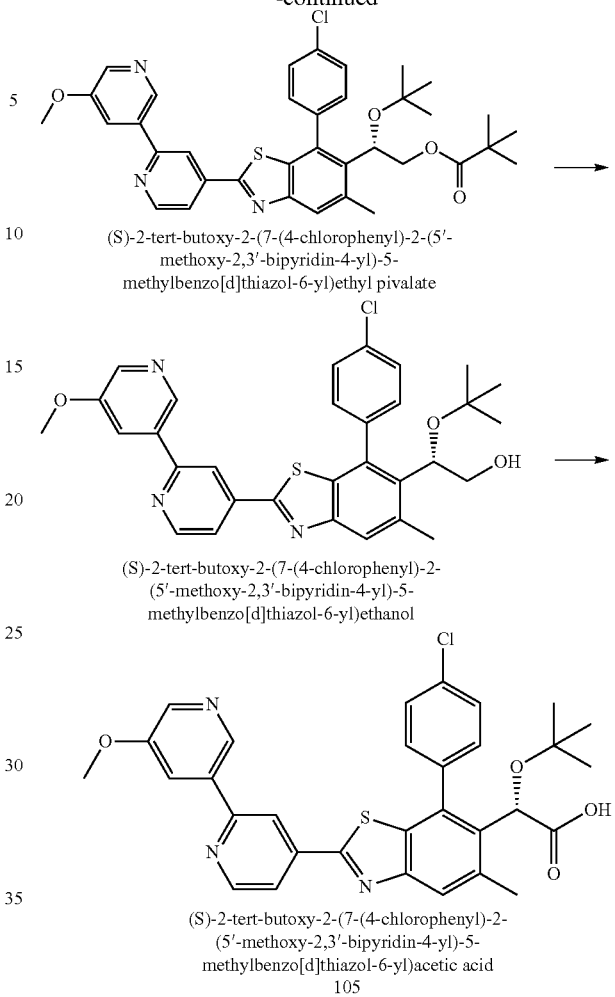

Preparation of (S)-2-(2-Amino-7-(4-chlorophenyl)-5-methylbenzo[d]thiazol-6-yl)-2-tert-butoxyethyl pivalate: 2 separate microwave tubes were each charged with (S)-2-(2-Amino-7-bromo-5-methylbenzo[d]thiazol-6-yl)-2-tert-butoxyethyl pivalate (768 mg, 1.74 mmol), $K_2CO_3$ (960 mg, 6.96 mmol), 4-chlorophenylboronic acid (325 mg, 2.09 mmol), $Pd(PPh_3)_4$ (200 mg, 0.174 mmol), dioxane (8.0 mL), and $H_2O$ (2.0 mL). The two sealed vessels were separately heated at 110° C. for 3 h. The reactions were cooled to 23° C. and combined. $H_2O$ (50 mL) was added, and the system was extracted with EtOAc (3×50 mL). The combined extracts were dried ($Na_2SO_4$), filtered, and concentrated. The residue was treated with benzene and purified via chromatography on silica gel (80 g "gold" ISCO column; Hex/EtOAc) giving (S)-2-(2-Amino-7-(4-chlorophenyl)-5-methylbenzo[d]thiazol-6-yl)-2-tert-butoxyethyl pivalate (1.55 g, 90% yield). LCMS-ESI$^+$: calc'd for $C_{25}H_{31}ClN_2O_3S$: 475.2 and 477.2 (M+H$^+$); found: 475.3 and 477.3 (M+H$^+$). $^1$H-NMR: 400 MHz, (CDCl$_3$) δ: 7.49-7.41 (m, 2H), 7.36-7.32 (m, 2H), 7.22 (d, J=7.3 Hz, 1H), 5.19 (s, broad, 2H), 4.67 (dd, J=9.0, 2.7 Hz, 1H), 4.36 (dd, J=11.7, 9.0 Hz, 1H), 4.23 (dd, J=11.7, 2.7 Hz, 1H), 2.68 (s, 3H), 1.14 (s, 9H), 0.94 (s, 9H).

Preparation of (S)-2-(2-bromo-7-(4-chlorophenyl)-5-methylbenzo[d]thiazol-6-yl)-2-tert-butoxyethyl pivalate: At 23° C., in a water bath, a solution of (S)-2-(2-amino-7-(4-chlorophenyl)-5-methylbenzo[d]thiazol-6-yl)-2-tert-butoxyethyl pivalate (1.13 g, 2.37 mmol) in CH$_3$CN (22 mL) was treated with solid anhydrous CuBr$_2$ (635 mg, 2.84 mmol). Reaction was fitted with a mineral oil bubbler. A freshly prepared solution of t-butyl nitrite (269 mg, 2.61 mmol) in CH$_3$CN (2.0 mL) was added dropwise over a 5 min period. The water bath was removed. Gas evolution was monitored using the bubbler. At 1 h, gas evolution ceased. The reaction was poured into EtOAc (50 mL) and treated with H$_2$O (50 mL). A brown solid precipitated. The suspension was filtered over Celite, which was thoroughly washed with EtOAc. The filtrate was transferred to a separatory funnel. The organic phase was collected. The aq. phase was extracted with EtOAc. The total organic layers were combined, dried (Na$_2$SO$_4$), filtered, and concentrated. The residue was treated with benzene and purified via chromatography on silica gel (80 g "gold" ISCO column; Hex/EtOAc) giving (S)-2-(2-bromo-7-(4-chlorophenyl)-5-methylbenzo[d]thiazol-6-yl)-2-tert-butoxyethyl pivalate. LCMS-ESI$^+$: calc'd for C$_{25}$H$_{29}$BrClNO$_3$S: 538.1, 540.1, and 542.1.1 (M+H$^+$); found: 538.2, 540.2, and 542.2 (M+H$^+$). $^1$H-NMR: 400 MHz, (CDCl$_3$) S: 7.76 (s, 1H), 7.51 (d, J=8.2 Hz, 1H), 7.47 (d, J=7.8 Hz, 1H), 7.34 (d, J=8.2 Hz, 1H), 7.24 (d, J=7.8 Hz, 1H), 4.76 (dd, J=9.0, 3.5 Hz, 1H), 4.39 (dd, J=11.7, 9.0 Hz, 1H), 4.25 (dd, J=11.7, 3.5 Hz, 1H), 2.76 (s, 3H), 1.14 (s, 9H), 0.94 (s, 9H).

Preparation of (S)-2-tert-butoxy-2-(7-(4-chlorophenyl)-2-(2-chloropyridin-4-yl)-5-methylbenzo[d]thiazol-6-yl)ethyl pivalate: (S)-2-(2-bromo-7-(4-chlorophenyl)-5-methylbenzo[d]thiazol-6-yl)-2-tert-butoxyethyl pivalate (400.0 mg, 0.742 mmol), 2-chloro-4-pyridinylboronic acid (140.2 mg, 0.891 mmol), potassium carbonate (307.7 mg, 2.227 mmol), and Pd(PPh$_3$)$_4$ (128.7 mg, 0.111 mmol) were placed in a microwave vial and the vial was vacuum pumped and flushed with argon three times. To this mixture was added degassed 1,4-dioxane (3.5 mL) and water (0.7 mL). The reaction mixture was heated at 90° C. for 4.5 h then cooled to rt. The aqueous layer was separated and extracted three times with ethyl acetate. All organic layers were combined, dried over Na$_2$SO$_4$, and concentrated. Purification by flash column chromatography on silica gel (hexanes/ethyl acetate eluent) provided the final compound. LCMS-ESI$^+$: calc'd for C$_{30}$H$_{33}$Cl$_2$N$_2$O$_3$S: 571.2 (M+H$^+$); Found: 571.1 (M+H$^+$); $^1$H NMR (400 MHz, CDCl$_3$) δ 8.49 (d, J=4.9 Hz, 1H), 7.93 (s, 2H), 7.77 (d, J=5.0 Hz, 1H), 7.55 (d, J=9.2 Hz, 1H), 7.50 (d, J=7.4 Hz, 1H), 7.40 (d, J=7.4 Hz, 1H), 7.29 (d, J=8.9 Hz, 1H), 4.82 (dd, J=8.9, 2.7 Hz, 1H), 4.42 (dd, J=11.2, 9.3 Hz, 1H), 4.29 (dd, J=11.5, 3.2 Hz, 1H), 2.80 (s, 3H), 1.14 (s, 9H), 0.97 (s, 9H).

Preparation of (S)-2-tert-butoxy-2-(7-(4-chlorophenyl)-2-(5'-methoxy-2,3'-bipyridin-4-yl)-5-methylbenzo -yl)ethyl pivalate: (S)-2-tert-butoxy-2-(7-(4-chlorophenyl)-2-(2-chloropyridin-4-yl)-5-methylbenzo[d]thiazol-6-yl)ethyl pivalate (40.0 mg, 0.070 mmol), 5-methoxy-3-pyridineboronic acid pinacol ester (19.7 mg, 0.084 mmol), potassium carbonate (29.0 mg, 0.210 mmol), and Pd(PPh$_3$)$_4$ (12.1 mg, 0.010 mmol) were placed in a microwave vial and the vial was vacuum pumped and flushed with argon three times. To this mixture was added degassed 1,4-dioxane (0.8 mL) and water (0.2 mL). The reaction mixture was heated at 110° C. for 1 h then cooled to rt. The aqueous layer was separated and extracted three times with ethyl acetate. All organic layers were combined, dried over Na$_2$SO$_4$, and concentrated. Purification by flash column chromatography on silica gel (hexanes/ethyl acetate eluent) provided the product. LCMS-ESI$^+$: calc'd for C$_{36}$H$_{39}$ClN$_3$O$_4$S: 644.2 (M+H$^+$); Found: 644.1 (M+H$^+$); $^1$H NMR (400 MHz, CDCl$_3$) δ 8.89 (s, 1H), 8.81 (d, J=4.9 Hz, 1H), 8.40 (d, J=2.7 Hz, 1H), 8.35 (s, 1H), 8.02 (s, 1H), 7.95 (s, 1H), 7.83 (d, J=5.2 Hz, 1H), 7.57 (d, J=8.4 Hz, 1H), 7.51 (d, J=8.5 Hz, 1H), 7.43 (d, J=8.4 Hz, 1H), 7.31 (d, J=8.7 Hz, 1H), 4.83 (dd, J=9.4, 2.7 Hz, 1H), 4.43 (dd, J=11.2, 9.5 Hz, 1H), 4.30 (dd, J=12.1, 2.9 Hz, 1H), 3.99 (s, 3H), 2.81 (s, 3H), 1.15 (s, 9H), 0.97 (s, 9H).

Preparation of (S)-2-tert-butoxy-2-(7-(4-chlorophenyl)-2-(5'-methoxy-2,3'-bipyridin-4-yl)-5-methylbenzo[d]thiazol-6-yl)ethanol: To a solution of (S)-2-tert-butoxy-2-(7-(4-chlorophenyl)-2-(5'-methoxy-2,3'-bipyridin-4-yl)-5-methylbenzo[d]thiazol-6-yl)ethyl pivalate (40.5 mg, 0.063 mmol) in THF (0.5 mL) and methanol (0.5 mL) was added NaOH (0.5 mL, 2N solution). The reaction mixture was heated at 40° C. for 4 h, cooled, diluted with satd. aqueous NH$_4$Cl, and extracted with ethyl acetate. The organic layer was dried over Na$_2$SO$_4$, filtered and concentrated to give the crude product which was used without further purification. LCMS-ESI$^+$: calc'd for C$_{31}$H$_{31}$ClN$_3$O$_3$S: 560.2 (M+H$^+$); Found: 560.0 (M+H$^+$).

Preparation of (S)-2-tert-butoxy-2-(7-(4-chlorophenyl)-2-(5'-methoxy-2,3'-bipyridin-4-yl)-5-methylbenzo[d]thiazol-6-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. To a solution of crude (S)-2-tert-butoxy-2-(7-(4-chlorophenyl)-2-(5'-methoxy-2,3'-bipyridin-4-yl)-5-methylbenzo[d]thiazol-6-yl)ethanol from the previous reaction (assume 0.063 mmol) in 25% water/acetonitrile (1.6 mL) was added sequentially, a stock solution of CrO$_3$/H$_5$IO$_6$ (0.72 mL, 0.439 M solution) and CrO$_3$ (9.4 mg, 0.094 mmol) at room temperature. The reaction was stirred for 1 h and quenched with aqueous Na$_2$SO$_3$ (10% w/v). When the reaction mixture turned green, it was extracted 3 times with ethyl acetate. The combined organic layers were dried over Na$_2$SO$_4$, concentrated, taken up in THF (0.3 mL), methanol (0.3 mL), and water (0.15 mL), filtered, and purified by reverse phase HPLC. Fractions containing the product were pooled and lyophilized to provide the TFA salt of the product. $^1$H NMR (400 MHz, CD$_3$OD) δ 9.03 (s, 1H), 8.84 (d, J=5.1 Hz, 1H), 8.61 (s, 1H), 8.50 (s, 2H), 8.02 (d, J=5.2 Hz, 1H), 7.94 (s, 1H), 7.70 (d, J=9.6 Hz, 1H), 7.64-7.56 (m, 3H), 5.28 (s, 1H), 4.08 (s, 3H), 2.64 (s, 3H), 0.98 (s, 9H). LCMS-ESI$^+$: calc'd for C$_{31}$H$_{29}$ClN$_3$O$_4$S: 574.1 (M+H$^+$); Found: 574.0 (M+H$^+$).

Example 16

Method D: Preparation of (S)-2-tert-butoxy-2-(7-(4-chlorophenyl)-5-methyl-2-(3-(pyrimidin-5-yl)phenyl)benzo[d]thiazol-6-yl)acetic acid (106)

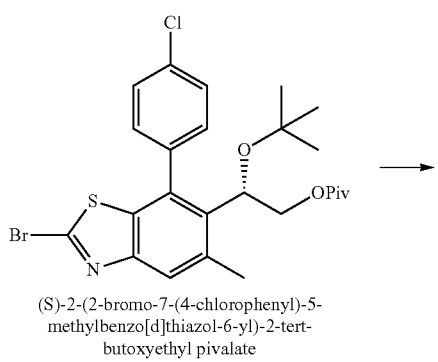

(S)-2-(2-bromo-7-(4-chlorophenyl)-5-methylbenzo[d]thiazol-6-yl)-2-tert-butoxyethyl pivalate -continued

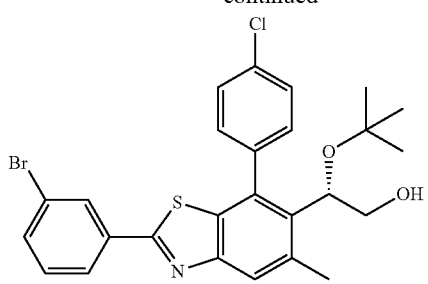

(S)-2-(2-(3-bromophenyl)-7-
(4-chlorophenyl)-5-methylbenzo
[d]thiazol-6-yl)-2-tert-butoxyethanol


(S)-2-(2-(3-bromophenyl)-7-
(4-chlorophenyl)-5-methylbenzo
[d]thiazol-6-yl)-2-tert-butoxyacetic acid

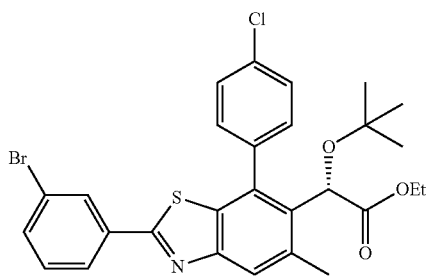

(S)-ethyl 2-(2-(3-bromophenyl)-7-
(4-chlorophenyl)-5-methylbenzo
[d]thiazol-6-yl)-2-tert-butoxyacetate

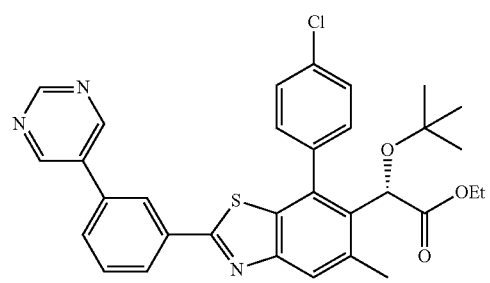

(S)-ethyl 2-tert-butoxy-2-(7-(4-chlorophenyl)-
5-methyl-2-(3-(pyrimidin-5-yl)phenyl)
benzo[d]thiazol-6-yl)acetate -continued

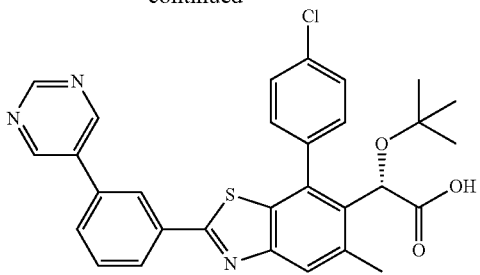

(S)-2-tert-butoxy-2-(7-(4-chlorophenyl)-
5-methyl-2-(3-(pyrimidin-5-yl)phenyl)
benzo[d]thiazol-6-yl)acetic acid
106

Preparation of (S)-2-(2-(3-bromophenyl)-7-(4-chlorophenyl)-5-methylbenzo[d]thiazol-6-yl)-2-tert-butoxyethanol: To a solution of (S)-2-(2-bromo-7-(4-chlorophenyl)-5-methylbenzo[d]thiazol-6-yl)-2-tert-butoxyethyl pivalate (310 mg, 0.577 mmol) in dioxane (5 mL), was added 3-bromophenylboronic acid (173 mg, 0.865 mmol), Ph(PPh$_3$)$_4$ (33 mg, 0.029 mmol) 2N K$_2$CO$_3$ (850 µL) in sealed tube. The reaction mixture was heated at 90° C. for 3hs. Then the reaction was cooled down and to the mixture was added MeOH (5 mL), 2N NaOH (1.5 mL) and heated at 45° C. After the reaction was finished, the reaction was washed by water, extracted by EtOAc. The organic phase was dried over MgSO$_4$, filtered, concentrated down and purified by silica gel column, eluting by 0-50% EtOAc in hexanes to give the product (110 mg, 36%). LCMS-ESI$^+$: calc'd for C$_{26}$H$_{25}$BrClNO$_2$S: 530.0 (M+H$^+$); Found: 530.2 (M+H$^+$).

Preparation of (S)-2-(2-(3-bromophenyl)-7-(4-chlorophenyl)-5-methylbenzo[d]thiazol-6-yl)-2-tert-butoxyacetic acid: To a solution of (S)-2-(2-(3-bromophenyl)-7-(4-chlorophenyl)-5-methylbenzo[d]thiazol-6-yl)-2-tert-butoxyethanol (110 mg, 0.208 mmol) in wet acetonitrile (0.75% H$_2$O, 2.5 mL), was added H$_5$IO$_6$/CrO$_3$ stock solution (0.439 M in wet acetonitrile, 2.4 mL) at 0° C. The reaction was stirred at 0° C. for ½ h. The reaction mixture was washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{26}$H$_{23}$BrClNO$_3$S: 544.0 (M+H$^+$); Found: 544.1 (M+H$^+$).

Preparation of (S)-ethyl 2-(2-(3-bromophenyl)-7-(4-chlorophenyl)-5-methylbenzo[d]thiazol-6-yl)-2-tert-butoxyacetate: To a solution of (S)-2-(2-(3-bromophenyl)-7-(4-chlorophenyl)-5-methylbenzo[d]thiazol-6-yl)-2-tert-butoxyacetic acid (104 mg, 0.191 mmol) in DMF, was added Cs$_2$CO$_3$ (152 mg, 0.467 mmol), ethyl iodide (30 µL, 0.343 mmol). The reaction was stirred at room temperature for 2hs. The reaction mixture was washed by sat. NaHCO$_3$, extracted by EtOAc, dry over MgSO$_4$, filtered, purified by silica gel column, eluting by 0-50% EtOAc in hexanes to give the product. LCMS-ESI$^+$: calc'd for C$_{28}$H$_{27}$BrClNO$_3$S: 572.1 (M+H$^+$); Found: 572.2 (M+H$^+$).

Preparation of (S)-ethyl 2-tert-butoxy-2-(7-(4-chlorophenyl)-5-methyl-2-(3-(pyrimidin-5-yl)phenyl)benzo[d]thiazol-6-yl)acetate: The reaction mixture of (S)-ethyl 2-(2-(3-bromophenyl)-7-(4-chlorophenyl)-5-methylbenzo[d]thiazol-6-yl)-2-tert-butoxyacetate (12 mg, 0.025 mmol), 5-pyrimidineboronic acid (5 mg, 0.0375 mmol), 2N K$_2$CO$_3$ (60 µL), Pd(PPh$_3$)$_4$ (3 mg, 0.0025 mmol) in dioxane (1 mL) was heated at 120° C. in sealed tube. After the reaction was finished, the reaction was washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{32}$H$_{30}$ClN$_3$O$_3$S: 572.2 (M+H$^+$); Found: 572.2 (M+H$^+$).

Preparation of (S)-2-tert-butoxy-2-(7-(4-chlorophenyl)-5-methyl-2-(3-(pyrimidin-5-yl)phenyl)benzo[d]thiazol-6-yl)acetic acid: The reaction mixture of (S)-ethyl 2-tert-butoxy-2-(7-(4-chlorophenyl)-5-methyl-2-(3-(pyrimidin-5-yl)phenyl)benzo[d]thiazol-6-yl)acetate (9 mg, 0.0157 mmol), excess NaOH, in MeOH/THF (1:1, 2 mL) was heated at 45° C. overnight. After reaction finished, the solvent was removed and the residue was dissolved in MeOH and purified by reverse phase HPLC, eluting by 0-100% acetonitrile in H$_2$O with 0.1% TFA to give the product. LCMS-ESI$^+$: calc'd for C$_{30}$H$_{26}$ClN$_3$O$_3$S: 544.1 (M+H$^+$); Found: 544.2 (M+H$^+$). $^1$H NMR (400 MHz, CD$_3$OD): δ 9.18 (s, 1H), 9.16 (s, 2H), 8.40 (s, 1H), 8.12 (d, J=4 Hz, 1H), 7.91-7.88 (m, 2H), 7.71-7.67 (m, 2H), 7.60-7.58 (m, 3H), 5.26 (s, 1H), 2.62 (s, 3H), 0.97 (s, 9H).

Example 17

Method E: Preparation of (S)-2-tert-butoxy-2-(7-(4-chlorophenyl)-2-(3-(2-chloropyridin-4-yl)phenyl)-5-methylbenzo[d]thiazol-6-yl)acetic acid (107)

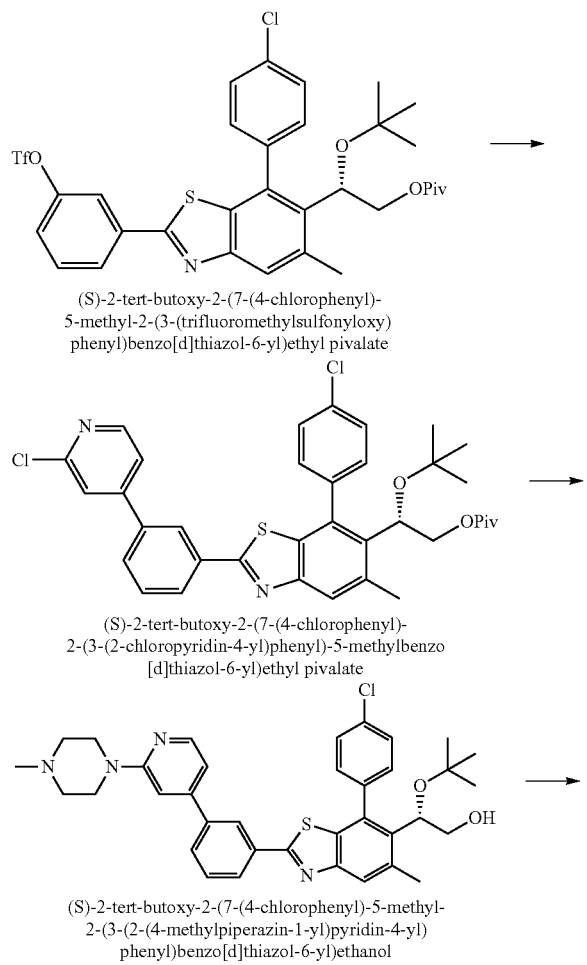

(S)-2-tert-butoxy-2-(7-(4-chlorophenyl)-5-methyl-2-(3-(trifluoromethylsulfonyloxy)phenyl)benzo[d]thiazol-6-yl)ethyl pivalate (S)-2-tert-butoxy-2-(7-(4-chlorophenyl)-2-(3-(2-chloropyridin-4-yl)phenyl)-5-methylbenzo[d]thiazol-6-yl)ethyl pivalate (S)-2-tert-butoxy-2-(7-(4-chlorophenyl)-5-methyl-2-(3-(2-(4-methylpiperazin-1-yl)pyridin-4-yl)phenyl)benzo[d]thiazol-6-yl)ethanol

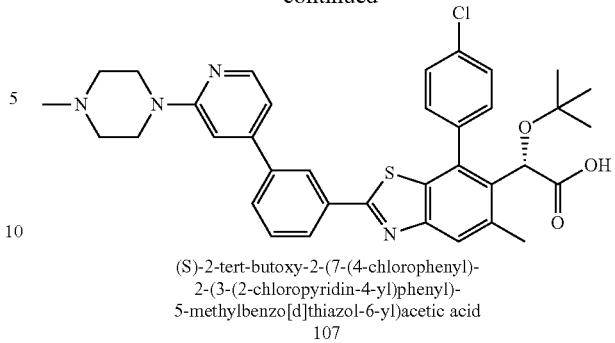

(S)-2-tert-butoxy-2-(7-(4-chlorophenyl)-2-(3-(2-chloropyridin-4-yl)phenyl)-5-methylbenzo[d]thiazol-6-yl)acetic acid 107

Preparation of (S)-2-tert-butoxy-2-(7-(4-chlorophenyl)-2-(3-(2-chloropyridin-4-yl)phenyl)-5-methylbenzo[d]thiazol-6-yl)ethyl pivalate: The reaction mixture of (S)-2-tert-butoxy-2-(7-(4-chlorophenyl)-5-methyl-2-(3-(trifluoromethylsulfonyloxy)phenyl)benzo[d]thiazol-6-yl)ethyl pivalate (30 mg, 0.0438 mmol), 2-chloropyridine-4-boronic acid (10 mg, 0.0657 mmol), 2N K$_2$CO$_3$ (100 μL), Pd(PPh$_3$)$_4$ (5.0 mg, 0.0044 mmol) in dioxane (2 mL) was heated at 120° C. in sealed tube for 2hs. The reaction was washed by sat. NaHCO$_3$, extracted by EtOAc, dried by MgSO$_4$, filtered, concentrated down and purified by silica gel column, eluting by 0-100% EtOAc in hexanes to give the product. LCMS-ESI$^+$: calc'd for C$_{36}$H$_{36}$Cl$_2$N$_2$O$_3$S: 647.2 (M+H$^+$); Found: 647.3 (M+H$^+$).

Preparation of (S)-2-tert-butoxy-2-(7-(4-chlorophenyl)-5-methyl-2-(3-(2-(4-methylpiperazin-1-yl)pyridin-4-yl)phenyl)benzo[d]thiazol-6-yl)ethanol: The reaction mixture of (S)-2-tert-butoxy-2-(7-(4-chlorophenyl)-2-(3-(2-chloropyridin-4-yl)phenyl)-5-methylbenzo[d]thiazol-6-yl)ethyl pivalate (16 mg, 0.025 mmol), 1-methylpiperazine (1 mL) was heated at 120° C. overnight. Then the reaction mixture was washed by sat. NaHCO$_3$, extracted by EtOAc, the organic phase was dried over MgSO$_4$, filtered, concentrated. To the residue was added THF, MeOH, 2N NaOH, the mixture was heated at 45° C. After the reaction finished, the reaction was washed by sat NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{36}$H$_{39}$ClN$_4$O$_2$S: 627.2 (M+H$^+$); Found: 627.3 (M+H$^+$).

Preparation of (S)-2-tert-butoxy-2-(7-(4-chlorophenyl)-2-(3-(2-chloropyridin-4-yl)phenyl)-5-methylbenzo[d]thiazol-6-yl)acetic acid: To a solution of (S)-2-tert-butoxy-2-(7-(4-chlorophenyl)-5-methyl-2-(3-(2-(4-methylpiperazin-1-yl)pyridin-4-yl)phenyl)benzo[d]thiazol-6-yl)ethanol in DCM (1 mL) was added Dess-Martin periodinane (8.8 mg, 0.020 mmol). After 1 h, more Dess-Martin periodinane was added (10 mg) and the reaction mixture was reacted at room temperature overnight. The mixture was washed by sat. NaHCO$_3$, 1M Na$_2$S$_2$O$_3$, extracted by DCM, dried over MgSO$_4$, filtered, concentrated down. To the residue was added t-BuOH (600 μL), 1M NaH$_2$PO4 (300 μL), 2-methylbut-2-ene (500 μL) and NaClO$_2$ (14 mg). The reaction mixture was reacted at room temperature. After the reaction finished, the mixture was treated with MeOH, filtered, purified by reverse phase HPLC to give the product. LCMS-ESI$^+$: calc'd for C$_{36}$H$_{37}$ClN$_4$O$_3$S: 641.2 (M+H$^+$); Found: 641.2 (M+H$^+$).

Example 18

Method F: Preparation of (S)-2-tert-butoxy-2-(7-(4-chlorophenyl)-5-methyl-2-(2-(1-methyl-1H-indazol-6-yl)pyridin-4-yl)benzo[d]thiazol-6-yl)acetic acid (108)

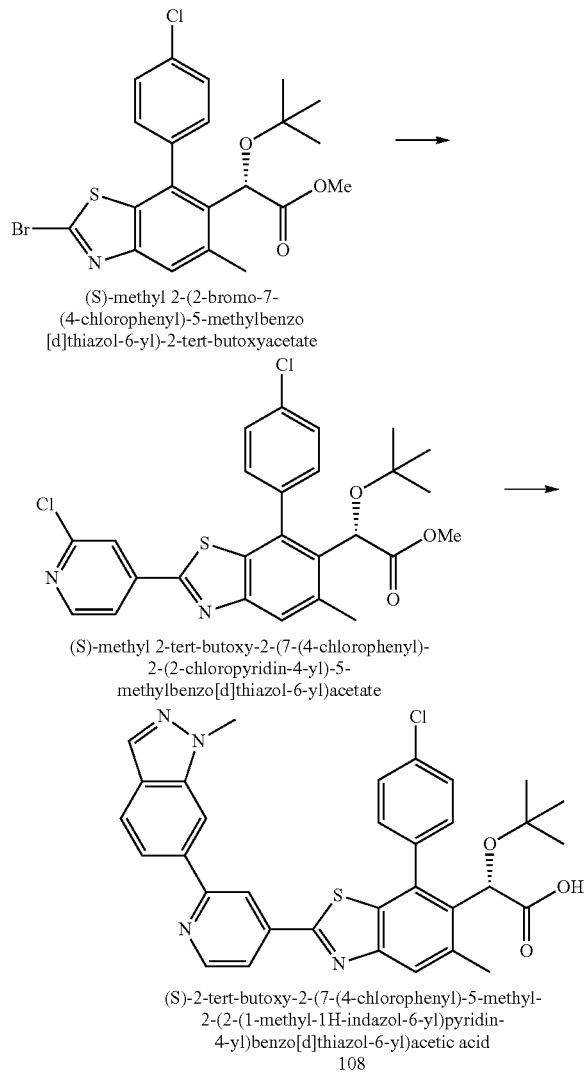

(S)-methyl 2-(2-bromo-7-(4-chlorophenyl)-5-methylbenzo[d]thiazol-6-yl)-2-tert-butoxyacetate (S)-methyl 2-tert-butoxy-2-(7-(4-chlorophenyl)-2-(2-chloropyridin-4-yl)-5-methylbenzo[d]thiazol-6-yl)acetate (S)-2-tert-butoxy-2-(7-(4-chlorophenyl)-5-methyl-2-(2-(1-methyl-1H-indazol-6-yl)pyridin-4-yl)benzo[d]thiazol-6-yl)acetic acid 108

Preparation of (S)-methyl 2-tert-butoxy-2-(7-(4-chlorophenyl)-2-(2-chloropyridin-4-yl)-5-methylbenzo[d]thiazol-6-yl)acetate: The reaction mixture of (S)-methyl 2-(2-bromo-7-(4-chlorophenyl)-5-methylbenzo[d]thiazol-6-yl)-2-tert-butoxyacetate (370 mg, 0.769 mol), 2-chloropyridine-4-boronic acid (157 mg, 0.99 mmol), 2N $K_2CO_3$ (1.9 mL), Pd(PPh$_3$)$_4$ (80 mg, 0.077 mmol) in dioxane (10 mL) was heated at 95° C. for 2 h. The reaction mixture was diluted by EtOAc, washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for $C_{26}H_{24}Cl_2N_2O_3S$: 515.1 (M+H$^+$). Found: 515.1 (M+H$^+$).

Preparation of (S)-2-tert-butoxy-2-(7-(4-chlorophenyl)-5-methyl-2-(2-(1-methyl-1H-indazol-6-yl)pyridin-4-yl)benzo[d]thiazol-6-yl)acetic acid: The reaction mixture of (S)-methyl 2-tert-butoxy-2-(7-(4-chlorophenyl)-2-(2-chloropyridin-4-yl)-5-methylbenzo[d]thiazol-6-yl)acetate (20 mg, 0.039 mmol), 1-methyl-1H-indazole-6-boronic acid (10.3 mg, 0.058 mmol), 2N $K_2CO_3$ (100 µL, 0.19 mmol), Pd(PPh$_3$)$_4$ (4.3 mg, 0.004 mmol) in dioxane (1.5 mL) in sealed tube was heated at 110° C. for 2 h. After the starting material consumed, the reaction was cooled down, to the mixture was added MeOH, excess NaOH, the reaction mixture was heated at 45° C. overnight. Then the reaction mixture was neutralized by acetic acid, concentrated down, then treated by MeOH, and purified by reverse phase HPLC, eluting by 0-100% acetonitrile in H$_2$O with 0.1% TFA to give the product. LCMS-ESI$^+$: calc'd for $C_{33}H_{29}ClN_4O_3S$: 597.2 (M+H$^+$). Found: 597.2 (M+H$^+$). $^1$H NMR (400 MHz, CD$_3$OD): δ 8.78 (d, J=2.6 Hz, 1H), 8.60 (s, 1H), 8.26 (s, 1H), 8.06 (s, 1H), 8.03-7.82 (m, 4H), 7.71-7.69 (m, 1H), 7.61-7.60 (m, 3H), 5.28 (s, 1H), 4.16 (s, 3H), 2.64 (s, 3H), 0.98 (s, 9H).

Example 19

Method G: Preparation of (S)-2-tert-butoxy-2-(7-(4-chlorophenyl)-5-methyl-2-(3-(1-methyl-1H-indazol-5-yl)phenyl)benzo[d]thiazol-6-yl)acetic acid (109)

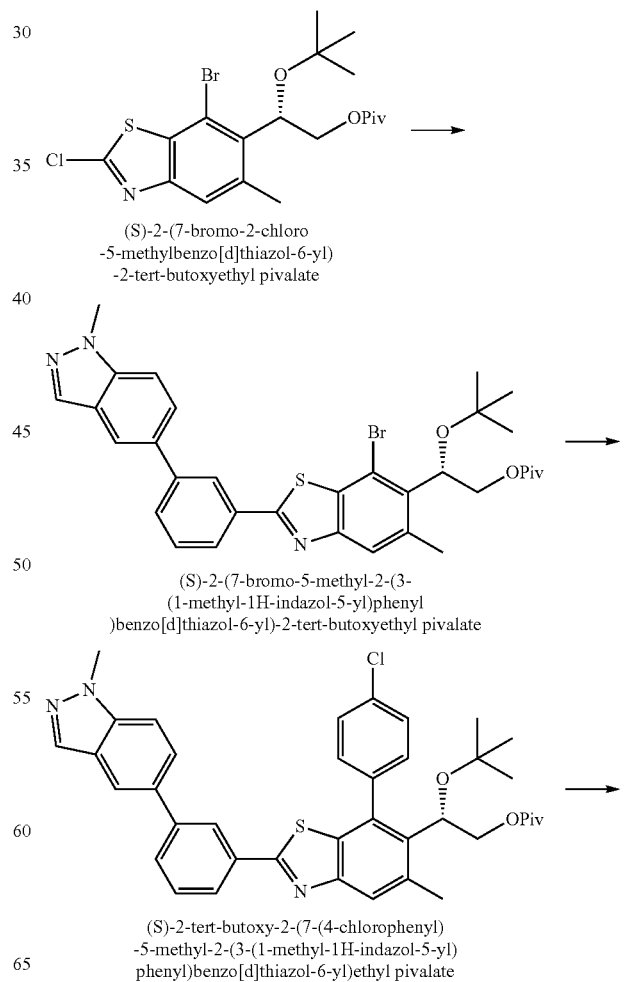

(S)-2-(7-bromo-2-chloro-5-methylbenzo[d]thiazol-6-yl)-2-tert-butoxyethyl pivalate (S)-2-(7-bromo-5-methyl-2-(3-(1-methyl-1H-indazol-5-yl)phenyl)benzo[d]thiazol-6-yl)-2-tert-butoxyethyl pivalate (S)-2-tert-butoxy-2-(7-(4-chlorophenyl)-5-methyl-2-(3-(1-methyl-1H-indazol-5-yl)phenyl)benzo[d]thiazol-6-yl)ethyl pivalate -continued

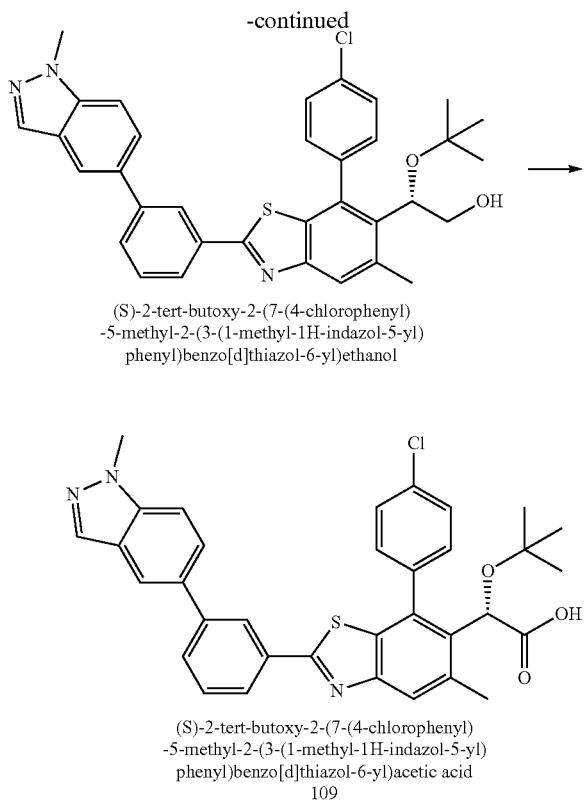

(S)-2-tert-butoxy-2-(7-(4-chlorophenyl)
-5-methyl-2-(3-(1-methyl-1H-indazol-5-yl)
phenyl)benzo[d]thiazol-6-yl)ethanol (S)-2-tert-butoxy-2-(7-(4-chlorophenyl)
-5-methyl-2-(3-(1-methyl-1H-indazol-5-yl)
phenyl)benzo[d]thiazol-6-yl)acetic acid
109

Preparation of (S)-2-(7-bromo-5-methyl-2-(3-(1-methyl-1H-indazol-5-yl)phenyl)benzo[d]thiazol-6-yl)-2-tert-butoxyethyl pivalate: The reaction mixture of (S)-2-(7-bromo-2-chloro-5-methylbenzo[d]thiazol-6-yl)-2-tert-butoxyethyl pivalate (300 mg, 0.65 mmol), 1-methyl-5-(3-(4,4,5,5-tetramethyl-1,3,2-dioxaborolan-2-yl)phenyl)-1H-indazole (260 mg, 0.78 mmol), Pd(PPh$_3$)$_4$ (75 mg, 0.065 mmol), 2N K$_2$CO$_3$ (1.6 mL) in dioxane (5 mL) was heated at 95° C. for 40 hours. After the reaction finished, the reaction mixture was diluted by EtOAc, washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{33}$H$_{36}$BrN$_3$O$_3$S: 634.2 (M+H$^+$); Found: 634.1 (M+H$^+$).

Preparation of (S)-2-tert-butoxy-2-(7-(4-chlorophenyl)-5-methyl-2-(3-(1-methyl-1H-indazol-5-yl)phenyl)benzo[d]thiazol-6-yl)ethyl pivalate: The mixture of (S)-2-(7-bromo-5-methyl-2-(3-(1-methyl-1H-indazol-5-yl)phenyl)benzo[d]thiazol-6-yl)-2-tert-butoxyethyl pivalate (24 mg, 0.0379 mmol), 4-chlorophenylboronic acid (9 mg, 0.0568 mmol), 2N NaHCO$_3$ (100 μL), Pd(PPh$_3$)$_4$ (4 mg, 0.0038 mmol) in dioxane (2 mL) was heated at 120° C. for 3 h. The reaction mixture was diluted by EtOAc, washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{39}$H$_{40}$ClN$_3$O$_3$S: 666.2 (M+H$^+$); Found: 666.1 (M+H$^+$).

Preparation of (S)-2-tert-butoxy-2-(7-(4-chlorophenyl)-5-methyl-2-(3-(1-methyl-1H-indazol-5-yl)phenyl)benzo[d]thiazol-6-yl)ethanol: The reaction mixture of (S)-2-tert-butoxy-2-(7-(4-chlorophenyl)-5-methyl-2-(3-(1-methyl-1H-indazol-5-yl)phenyl)benzo[d]thiazol-6-yl)ethyl pivalate (10 mg, 0.015 mmol), 2N NaOH (150 μL) in THF/MeOH (1:1, 1 mL) was heated at 40° C. After reaction finished, the reaction mixture was diluted by EtOAc, washed by sat. NaHCO$_3$, extracted by EtOAc, the organic phase was dried over MgSO$_4$, filtered, concentrated down and purified by silica gel column, eluting by 0-100% EtOAc in hexanes to give the product. LCMS-ESI$^+$: calc'd for C$_{34}$H$_{32}$ClN$_3$O$_2$S: 582.2 (M+H$^+$); Found: 582.2 (M+H$^+$).

Preparation of (S)-2-tert-butoxy-2-(7-(4-chlorophenyl)-5-methyl-2-(3-(1-methyl-1H-indazol-5-yl)phenyl)benzo[d]thiazol-6-yl)acetic acid: To the solution of (S)-2-tert-butoxy-2-(7-(4-chlorophenyl)-5-methyl-2-(3-(1-methyl-1H-indazol-5-yl)phenyl)benzo[d]thiazol-6-yl)ethanol (6 mg, 0.010 mmol) in wet acetonitrile (0.75 w % H$_2$O, 1 mL), was added stock solution of H$_5$IO$_6$/CrO$_3$ (0.439 M in wet acetonitrile, 150 μL) at 0° C. for ½ hour. The reaction mixture was filtered and purified by reverse phase HPLC, eluting by 0-100% acetonitrile in H$_2$O with 0.1% TFA give the product. LCMS-ESI$^+$: calc'd for C$_{34}$H$_{30}$ClN$_3$O$_3$S: 596.2 (M+H$^+$); Found: 596.2 (M+H$^+$). $^1$H NMR (300 MHz, CD$_3$OD): δ 8.24 (s, 1H), 7.95-7.98 (m, 2H), 7.88-7.50 (m, 10H), 5.17 (s, 1H), 4.01 (s, 3H), 2.52 (s, 3H), 0.88 (s, 9H).

Example 20

Method H: Preparation of (S)-2-tert-butoxy-2-(7-(4-chlorophenyl)-5-methyl-2-(2-(1-methyl-1H-indazol-5-yl)pyrimidin-4-yl)benzo[d]thiazol-6-yl)acetic acid (110)

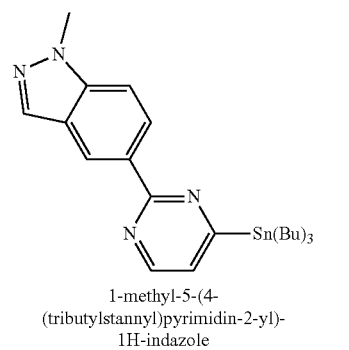

1-methyl-5-(4-(tributylstannyl)pyrimidin-2-yl)-1H-indazole

+

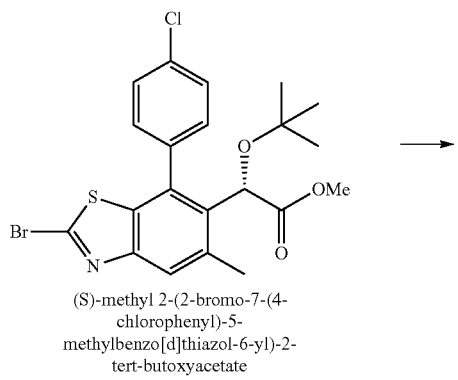

(S)-methyl 2-(2-bromo-7-(4-chlorophenyl)-5-methylbenzo[d]thiazol-6-yl)-2-tert-butoxyacetate

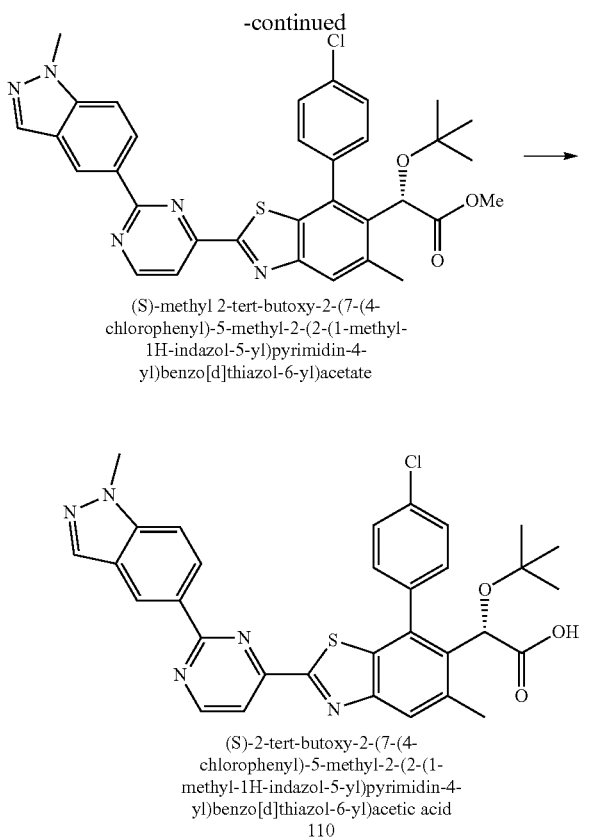

(S)-methyl 2-tert-butoxy-2-(7-(4-chlorophenyl)-5-methyl-2-(2-(1-methyl-1H-indazol-5-yl)pyrimidin-4-yl)benzo[d]thiazol-6-yl)acetate (S)-2-tert-butoxy-2-(7-(4-chlorophenyl)-5-methyl-2-(2-(1-methyl-1H-indazol-5-yl)pyrimidin-4-yl)benzo[d]thiazol-6-yl)acetic acid
110

Preparation of (S)-methyl 2-tert-butoxy-2-(7-(4-chlorophenyl)-5-methyl-2-(2-(1-methyl-1H-indazol-5-yl)pyrimidin-4-yl)benzo[d]thiazol-6-yl)acetate: (S)-methyl 2-(2-bromo-7-(4-chlorophenyl)-5-methylbenzo[d]thiazol-6-yl)-2-tert-butoxyacetate (17.4 mg, 0.036 mmol), Pd(PPh$_3$)$_4$ (2.1 mg, 0.002 mmol), lithium chloride (2.3 mg, 0.054 mmol), and copper(I) iodide (1.0 mg, 0.005 mmol) were taken in a microwave vial and the vial was vacuum pumped and flushed with argon three times. To this mixture was added 1-methyl-5-(4-(tributylstannyl)pyrimidin-2-yl)-1H-indazole (9.0 mg, 0.018 mmol) in degassed 1,4-dioxane (0.5 mL). The reaction mixture was heated at 100° C. for 5 h, cooled, filtered through celite (ethyl acetate eluent), and concentrated. Purification by flash column chromatography on silica gel (hexanes/ethyl acetate eluent) provided the product. LCMS-ESI$^+$: calc'd for C$_{33}$H$_{31}$ClN$_5$O$_3$S: 612.2 (M+H$^+$); Found: 611.9 (M+H$^+$).

Preparation of (S)-2-tert-butoxy-2-(7-(4-chlorophenyl)-5-methyl-2-(2-(1-methyl-1H-indazol-5-yl)pyrimidin-4-yl)benzo[d]thiazol-6-yl)acetic acid: To a solution of (S)-methyl 2-tert-butoxy-2-(7-(4-chlorophenyl)-5-methyl-2-(2-(1-methyl-1H-indazol-5-yl)pyrimidin-4-yl)benzo[d]thiazol-6-yl)acetate (4.8 mg, 0.008 mmol) in THF (0.3 mL) and methanol (0.3 mL) was added NaOH (0.3 mL of a 2N solution). The reaction mixture was heated at 45° C. for 6 h, cooled, filtered, and purified by reverse phase HPLC. Fractions containing the product were pooled and lyophilized to provide the TFA salt of the product. $^1$H NMR (400 MHz, CD$_3$OD) δ 8.94 (d, J=5.1 Hz, 1H), 8.83 (s, 1H), 8.49 (dd, J=9.0, 1.4 Hz, 1H), 8.12 (s, 1H), 8.05 (d, J=5.1 Hz, 1H), 7.87 (s, 1H), 7.76-7.71 (m, 1H), 7.68-7.59 (m, 3H), 7.57 (d, J=8.9 Hz, 1H), 5.29 (s, 1H), 4.07 (s, 3H), 2.63 (s, 3H), 0.99 (s, 9H). LCMS-ESI$^+$: calc'd for C$_{32}$H$_{29}$ClN$_5$O$_3$S: 598.2 (M+H$^+$); Found: 598.3 (M+H$^+$).

Example 21

Method I: Preparation of (S)-2-tert-butoxy-2-(7-(4-chlorophenyl)-5-methyl-2-(1-methyl-1H-pyrazolo[4,3-b]pyridin-6-yl)benzo[d]thiazol-6-yl)acetic acid (111)

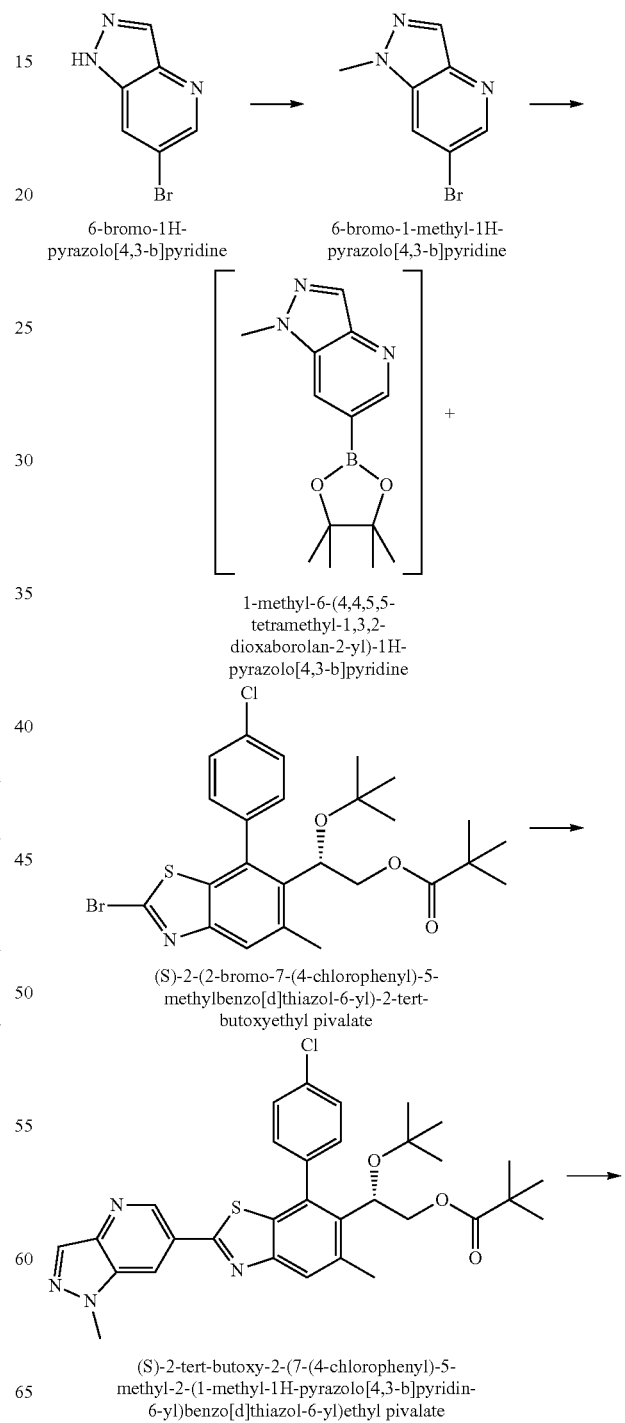

6-bromo-1H-pyrazolo[4,3-b]pyridine 6-bromo-1-methyl-1H-pyrazolo[4,3-b]pyridine 1-methyl-6-(4,4,5,5-tetramethyl-1,3,2-dioxaborolan-2-yl)-1H-pyrazolo[4,3-b]pyridine (S)-2-(2-bromo-7-(4-chlorophenyl)-5-methylbenzo[d]thiazol-6-yl)-2-tert-butoxyethyl pivalate (S)-2-tert-butoxy-2-(7-(4-chlorophenyl)-5-methyl-2-(1-methyl-1H-pyrazolo[4,3-b]pyridin-6-yl)benzo[d]thiazol-6-yl)ethyl pivalate

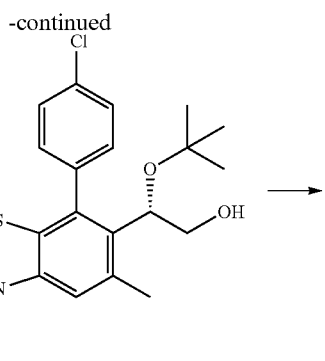

(S)-2-tert-butoxy-2-(7-(4-chlorophenyl)-5-methyl-
2-(1-methyl-1H-pyrazolo[4,3-b]pyridin-6-
yl)benzo[d]thiazol-6-yl)ethanol

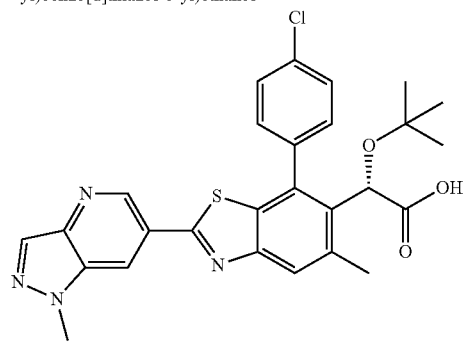

(S)-2-tert-butoxy-2-(7-(4-chlorophenyl)-5-
methyl-2-(1-methyl-1H-pyrazolo[4,3-b]pyridin-
6-yl)benzo[d]thiazol-6-yl)acetic acid
111

Preparation of 6-bromo-1-methyl-1H-pyrazolo[4,3-b]pyridine: To a solution of 6-bromo-1H-pyrazolo[4,3-b]pyridine (200 mg, 1.01 mmol) in DMF (5 mL) was added cesium carbonate (494 mg, 1.515 mmol). The reaction solution was stirred at room temperature for 5 minutes, iodomethane (215 mg, 1.515 mmol) was added. The reaction solution was stirred for 2 h and quenched with water. Volatiles were removed and the residue partitioned between ethyl acetate and water. The organic phase was washed with brine, dried (MgSO$_4$), filtered and concentrated to give crude product which was purified by chromatographic column to afford the desired product 6-bromo-1-methyl-1H-pyrazolo[4,3-b]pyridine. LCMS-ESI$^+$: calc'd for C$_7$H$_6$BrN$_3$: 211.98 (M+H$^+$); Found: 212.1 (M+H$^+$).

Preparation of (S)-2-tert-butoxy-2-(7-(4-chlorophenyl)-5-methyl-2-(1-methyl-1H-pyrazolo[4,3-b]pyridine-6-yl)benzo[d]thiazol-6-yl)ethyl pivalate: To a solution of 6-bromo-1-methyl-1H-pyrazolo[4,3-b]pyridine (20 mg, 0.094 mmol) in dioxane (2 mL) was added bis(pinacolato)diboron (29 mg, 0.113 mmol), [1,1'-Bis(diphenylphosphino)ferrocene]dichloropalladium(II) complex with dichloromethane (8 mg, 0.0094 mmol), potassium acetate (19 mg, 0.189 mmol). The mixture was degassed and heated at 100° C. for 2 h. The mixture was cooled, and then added (S)-2-(2-bromo-7-(4-chlorophenyl)-5-methylbenzo[d]thiazol-6-yl)-2-tert-butoxyethyl pivalate (25 mg, 0.046 mmol), tetrakis(triphenylphosphine)palladium(0) (6 mg, 0.005 mmol), K$_2$CO$_3$ (33 mg, 0.23 mmol) and water (0.3 mL, degassed). The reaction mixture was heated at 90° C. for 1 h, cooled and partitioned between ethyl acetate and brine. The organic layer was separated, dried over Na$_2$SO$_4$, filtered and concentrated to give crude product which was purified by chromatographic column to afford the desired product. LCMS-ESI$^+$: calc'd for C$_{32}$H$_{35}$ClN$_4$O$_3$S: 591.22 (M+H$^+$); Found: 591.2 (M+H$^+$).

Preparation of (S)-2-tert-butoxy-2-(7-(4-chlorophenyl)-5-methyl-2-(1-methyl-1H-pyrazolo[4,3-b]pyridin-6-yl)benzo[d]thiazol-6-yl)ethanol: To a solution of (S)-2-tert-butoxy-2-(7-(4-chlorophenyl)-5-methyl-2-(1-methyl-1H-pyrazolo[4,3-b]pyridine-6-yl)benzo[d]thiazol-6-yl)ethyl pivalate: (68 mg, 0.115 mmol) in THF/CH$_3$OH (1.5 mL/1.5 mL) was added 2N NaOH (0.57 mL, 1.15 mmol). The reaction mixture was heated at 45° C. for 2 h and cooled to rt. The reaction solution is quenched with saturated ammonium chloride solution and extracted with ethyl acetate. The organic solution is washed with water, brine, dried and concentrated to give crude product which was carried to next reaction without further purification. LCMS-ESI$^+$: calc'd for C$_{27}$H$_{27}$ClN$_4$O$_2$S: 507.16 (M+H$^+$); Found: 507.2 (M+H$^+$).

Preparation of (S)-2-tert-butoxy-2-(7-(4-chlorophenyl)-5-methyl-2-(1-methyl-1H-pyrazolo[4,3-b]pyridin-6-yl)benzo[d]thiazol-6-yl)acetic acid: To a solution of (S)-2-tert-butoxy-2-(7-(4-chlorophenyl)-5-methyl-2-(1-methyl-1H-pyrazolo[4,3-b]pyridin-6-yl)benzo[d]thiazol-6-yl)ethanol (50 mg, 0.099 mmol) in acetonitrile/water (2 mL/0.5 mL) was added CrO$_3$/H$_5$IO$_6$ (0.439M, 1.1 mL, 0.483 mmol) and CrO$_3$ (20 mg, 0.198 mmol). The reaction solution was stirred at room temperature for 1 h and quenched with 5% Na$_2$S$_2$O$_3$ solution. The mixture was extracted with ethyl acetate, washed with water and brine. The organic solution was dried and concentrated to give crude which was purified by reverse phase HPLC, eluting by 5-100% acetonitrile in H$_2$O with 0.1% TFA to give the desired product. LCMS-ESI$^+$: calc'd for C$_{27}$H$_{25}$ClN$_4$O$_3$S: 521.14 (M+H$^+$); Found: 521.2 (M+H$^+$), $^1$H NMR (400 MHz, CD$_3$OD) δ 9.20 (d, J=8 Hz, 1H), 8.67 (s, 1H), 8.24 (s, 1H), 7.88 (s, 1H), 7.71-7.59 (m, 4H), 5.27 (s, 1H), 4.16 (s, 3H), 2.62 (s, 3H), 0.98 (s, 9H).

Example 22

Method J: Preparation of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetic acid (112)

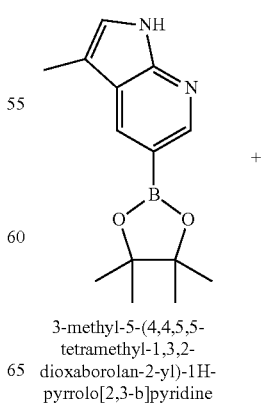

3-methyl-5-(4,4,5,5-
tetramethyl-1,3,2-
dioxaborolan-2-yl)-1H-
pyrrolo[2,3-b]pyridine

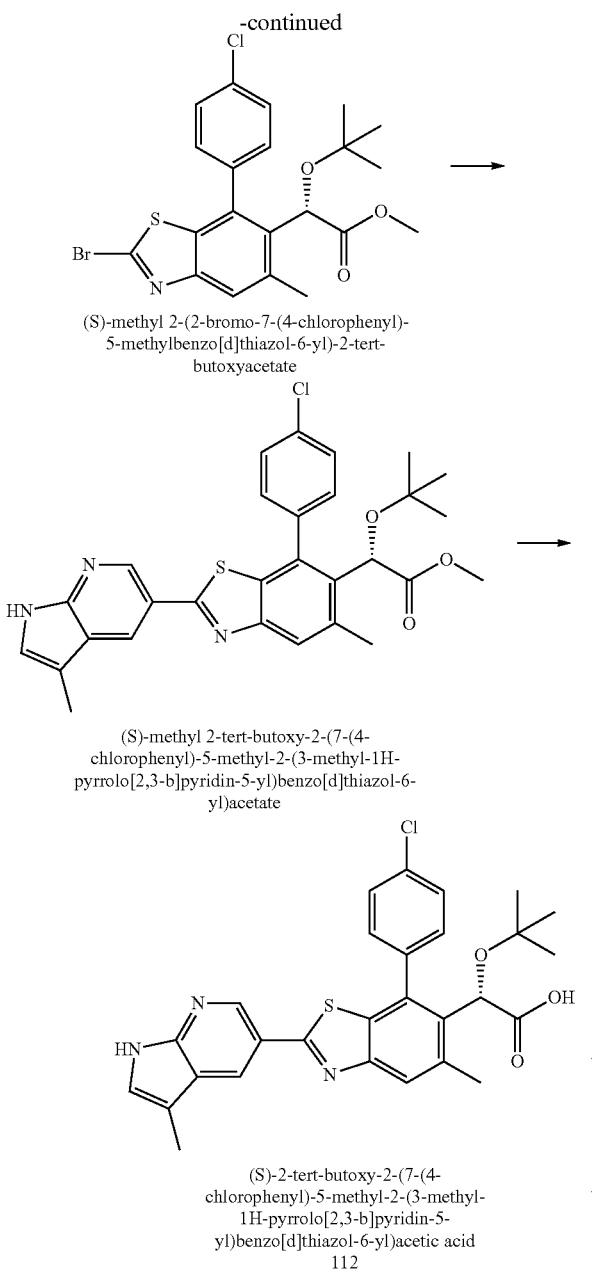

(S)-methyl 2-(2-bromo-7-(4-chlorophenyl)-
5-methylbenzo[d]thiazol-6-yl)-2-tert-
butoxyacetate (S)-methyl 2-tert-butoxy-2-(7-(4-
chlorophenyl)-5-methyl-2-(3-methyl-1H-
pyrrolo[2,3-b]pyridin-5-yl)benzo[d]thiazol-6-
yl)acetate (S)-2-tert-butoxy-2-(7-(4-
chlorophenyl)-5-methyl-2-(3-methyl-
1H-pyrrolo[2,3-b]pyridin-5-
yl)benzo[d]thiazol-6-yl)acetic acid
112

Preparation of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate: To a solution of (S)-methyl-5-(4,4,5,5-tetramethyl-1,3,2-dioxaborolan-2-yl)-1H-pyrrolo[2,3-b]pyridine (22 mg, 0.085 mmol) and (S)-methyl 2-(2-bromo-7-(4-chlorophenyl)-5-methylbenzo[d]thiazol-6-yl)-2-tert-butoxyacetate (20 mg, 0.041 mmol) in dioxane (1.2 mL, degassed) was added tetrakis(triphenylphosphine)palladium(0) (2.4 mg, 0.00207 mmol), K$_2$CO$_3$ (29 mg, 0.207 mmol) and water (0.4 mL, degassed). The reaction mixture was heated at 90° C. for 1 h, cooled and partitioned between ethyl acetate and brine. The organic layer was separated, dried over Na$_2$SO$_4$, filtered and concentrated to give crude which was purified by chromatographic column to afford the desired product. LCMS-ESI$^+$: calc'd for C$_{29}$H$_{28}$ClN$_3$O$_3$S: 534.16 (M+H$^+$); Found: 534.4 (M+H$^+$).

Preparation of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetic acid: To a solution of (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate: (8 mg, 0.015 mmol) in THF/CH$_3$OH (0.5 mL/0.5 mL) was added 2N NaOH (75 μL, 0.15 mmol). The reaction mixture was heated at 50° C. for 2 h and the crude was purified by reverse phase HPLC, eluting by 0-100% acetonitrile in H2O with 0.1% TFA to give the product. LCMS-ESI$^+$: calc'd for C$_{28}$H$_{26}$ClN$_3$O$_3$S: 520.14 (M+H$^+$); Found: 520.2 (M+H$^+$). $^1$H NMR (400 MHz, CD$_3$OD): δ 8.86 (d, J=1 Hz, 1H), 8.57 (d, J=1 Hz, 1H), 7.84 (s, 1H), 7.71-7.26 (m, 5H), 5.26 (s, 1H), 2.62 (s, 3H), 2.36 (s, 3H), 0.94 (s, 9H).

Example 23

Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)acetic acid (113a) and (S)-2-tert-butoxy-2-(7-(4-chlorophenyl)-5-methyl-2-(1-methyl-1H-indazol-5-yl)benzo[d]thiazol-6-yl) acetic acid (113b)

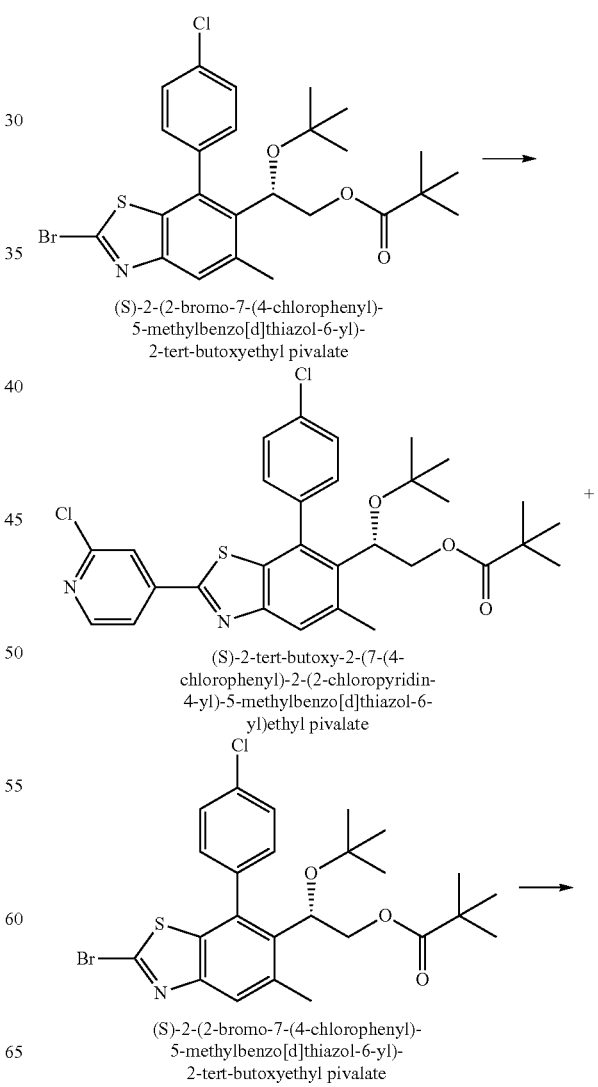

(S)-2-(2-bromo-7-(4-chlorophenyl)-
5-methylbenzo[d]thiazol-6-yl)-
2-tert-butoxyethyl pivalate (S)-2-tert-butoxy-2-(7-(4-
chlorophenyl)-2-(2-chloropyridin-
4-yl)-5-methylbenzo[d]thiazol-6-
yl)ethyl pivalate (S)-2-(2-bromo-7-(4-chlorophenyl)-
5-methylbenzo[d]thiazol-6-yl)-
2-tert-butoxyethyl pivalate

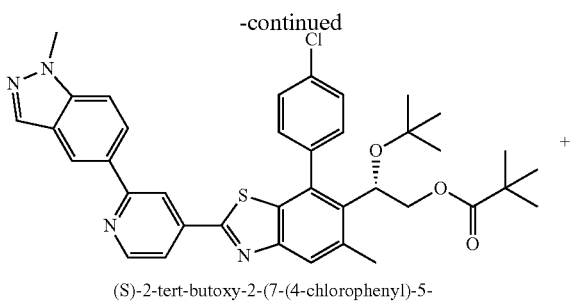

(S)-2-tert-butoxy-2-(7-(4-chlorophenyl)-5-methyl-2-(2-(1-methyl-1H-indazol-5-yl)pyridin-4-yl)benzo[d]thiazol-6-yl)ethyl pivalate

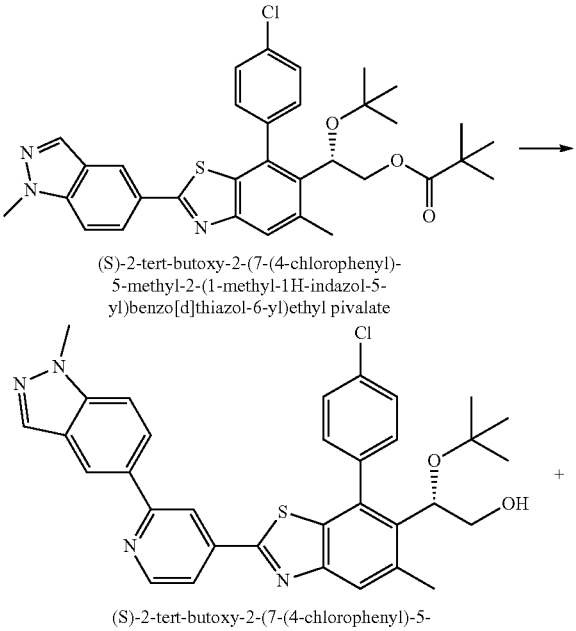

(S)-2-tert-butoxy-2-(7-(4-chlorophenyl)-5-methyl-2-(1-methyl-1H-indazol-5-yl)benzo[d]thiazol-6-yl)ethyl pivalate (S)-2-tert-butoxy-2-(7-(4-chlorophenyl)-5-methyl-2-(2-(1-methyl-1H-indazol-5-yl)pyridin-4-yl)benzo[d]thiazol-6-yl)ethanol

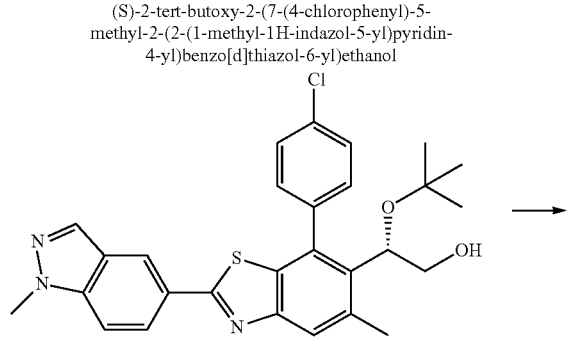

(S)-2-tert-butoxy-2-(7-(4-chlorophenyl)-5-methyl-2-(1-methyl-1H-indazol-5-yl)benzo[d]thiazol-6-yl)ethanol

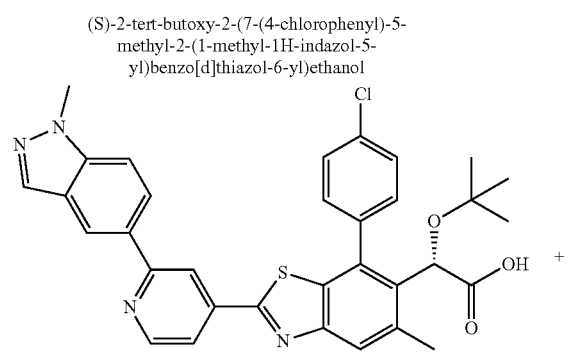

(S)-2-tert-butoxy-2-(7-(4-chlorophenyl)-5-methyl-2-(2-(1-methyl-1H-indazol-5-yl)pyridin-4-yl)benzo[d]thiazol-6-yl)acetic acid
113a

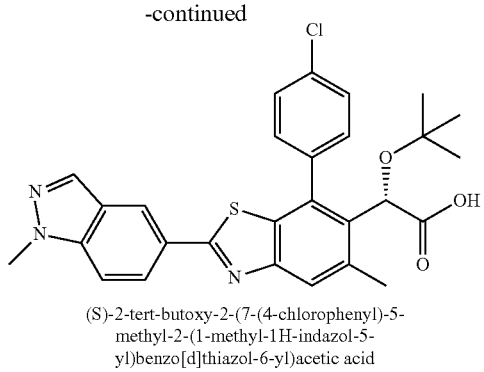

(S)-2-tert-butoxy-2-(7-(4-chlorophenyl)-5-methyl-2-(1-methyl-1H-indazol-5-yl)benzo[d]thiazol-6-yl)acetic acid
113b Preparation of (S)-2-tert-butoxy-2-(7-(4-chlorophenyl)-5-methyl-2-(2-(1-methyl-1H-indazol-6-yl)pyridin-4-yl)benzo[d]thiazol-6-yl)ethanol: A mixture of (S)-2-(2-bromo-7-(4-chlorophenyl)-5-methylbenzo[d]thiazol-6-yl)-2-tert-butoxyethyl pivalate (0.190 g, 0.35 mmol), 2-chloropyridin-4-ylboronic acid (0.66 g, 0.42 mmol), Pd(PPh$_3$)$_4$ (0.020 g, 0.0175, aq. 2M potassium carbonate solution (0.7 mL, 1.4 mmol) in degassed dioxane (2.0 mL) was heated at 90° C. for 3 hr. LC/MS indicated a 1.5:1 ratio of (S)-2-tert-butoxy-2-(7-(4-chlorophenyl)-2-(2-chloropyridin-4-yl)-5-methylbenzo[d]thiazol-6-yl)ethyl pivalate to (S)-2-(2-bromo-7-(4-chlorophenyl)-5-methylbenzo[d]thiazol-6-yl)-2-tert-butoxyethyl pivalate. Reaction mixture was used in next step without further purification.

(S)-2-tert-butoxy-2-(7-(4-chlorophenyl)-2-(2-chloropyridin-4-yl)-5-methylbenzo[d]thiazol-6-yl)ethyl pivalate: LCMS-ESI$^+$: calc'd for C$_{30}$H$_{33}$Cl$_2$N$_2$O$_3$S: 571.2 (M+H$^+$); found: 571.2 (M+H$^+$).

(S)-2-(2-bromo-7-(4-chlorophenyl)-5-methylbenzo[d]thiazol-6-yl)-2-tert-butoxyethyl pivalate: LCMS-ESI$^+$: calc'd for C$_{25}$H$_{29}$BrClNO$_3$S: 538.1, 540.1, and 542.1.1 (M+H$^+$); found: 538.2, 540.2, and 542.2 (M+H$^+$).

Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)ethyl pivalate and (S)-2-tert-butoxy-2-(7-(4-chlorophenyl)-5-methyl-2-(1-methyl-1H-indazol-5-yl)benzo[d]thiazol-6-yl)ethyl pivalate: One-half of above reaction mixture containing S)-2-tert-butoxy-2-(7-(4-chlorophenyl)-2-(2-chloropyridin-4-yl)-5-methylbenzo[d]thiazol-6-yl)ethyl pivalate to (S)-2-(2-bromo-7-(4-chlorophenyl)-5-methylbenzo[d]thiazol-6-yl)-2-tert-butoxyethyl pivalate (1.5:1 ratio) was telescoped into the subsequent reaction. 1-Methyl-1H-indazol-5-ylboronic acid was added to the previous reaction mixture and reaction continued was heated at 120° C. for 30 minutes to give (S)-2-tert-butoxy-2-(7-(4-chlorophenyl)-5-methyl-2-(2-(1-methyl-1H-indazol-5-yl)pyridin-4-yl)benzo[d]thiazol-6-yl)ethyl pivalate and (S)-2-tert-butoxy-2-(7-(4-chlorophenyl)-5-methyl-2-(1-methyl-1H-indazol-5-yl)benzo[d]thiazol-6-yl)ethyl pivalate.

(S)-2-tert-butoxy-2-(7-(4-chlorophenyl)-5-methyl-2-(2-(1-methyl-1H-indazol-5-yl)pyridin-4-yl)benzo[d]thiazol-6-yl)ethyl pivalate: LCMS-ESI$^+$: calc'd for C$_{38}$H$_{40}$ClN$_4$O$_3$S: 667.2 (M+H$^+$); found: 667.4 (M+H$^+$).

(S)-2-tert-butoxy-2-(7-(4-chlorophenyl)-5-methyl-2-(1-methyl-1H-indazol-5-yl)benzo[d]thiazol-6-yl)ethyl pivalate: LCMS-ESI$^+$: calc'd for C$_{33}$H$_{36}$ClN$_3$O$_3$S: 590.2 (M+H$^+$); found: 590.2 (M+H$^+$).

Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)ethanol and (S)-2-tert-butoxy-2-(7-(4-chlorophenyl)-5-methyl-2-(1-methyl-1H-indazol-5-yl)benzo[d]thiazol-6-yl)ethanol: (S)-2-tert-butoxy-2-(7-(4- chlorophenyl)-5-methyl-2-(2-(1-methyl-1H-indazol-6-yl) pyridin-4-yl)benzo[d]thiazol-6-yl)ethyl pivalate and (S)-2-tert-butoxy-2-(7-(4-chlorophenyl)-5-methyl-2-(1-methyl-1H-indazol-5-yl)benzo[d]thiazol-6-yl)ethyl pivalate was telescoped into the subsequent reaction. To the previous reaction mixture, methanol and 2M NaOH were added and reaction mixture was heated at 55° C. overnight. Reaction mixture was cooled to rt, diluted with ethyl acetate and washed with brine. The organic layer was dried (MgSO₄), filtered, concentrated and purified by CombiFlash (Hex/EtOAc) to give (S)-2-tert-butoxy-2-(7-(4-chlorophenyl)-5-methyl-2-(2-(1-methyl-1H-indazol-5-yl)pyridin-4-yl)benzo[d]thiazol-6-yl) ethanol.

LCMS-ESI⁺: calc'd for $C_{33}H_{32}ClN_4O_2S$: 583.2 (M+H⁺); found: 583.2 (M+H⁺).

(S)-2-tert-butoxy-2-(7-(4-chlorophenyl)-5-methyl-2-(1-methyl-1H-indazol-5-yl)benzo[d]thiazol-6-yl)ethanol was also isolated.

LCMS-ESI⁺: calc'd for $C_{28}H_{29}ClN_3O_2S$: 506.2 (M+H⁺); found: 506.2 (M+H⁺).

Preparation of (S)-2-tert-butoxy-2-(7-(4-chlorophenyl)-5-methyl-2-(2-(1-methyl-1H-indazol-5-yl)pyridin-4-yl)benzo[d]thiazol-6-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H₂O) to a volume of 114 mL. This stock solution (0.6 mL) was added to a solution of (S)-2-tert-butoxy-2-(7-(4-chlorophenyl)-5-methyl-2-(2-(1-methyl-1H-indazol-6-yl)pyridin-4-yl)benzo[d]thiazol-6-yl)ethanol (25 mg, 0.049 mmol) in ACN (3 mL) at room temperature and stirred for one hour. The reaction mixture was quenched with saturated Na₂SO₃ solution and extracted with EtOAc. The organic layer was dried (MgSO₄), filtered, concentrated and purified by reverse phase HPLC (H₂O/ACN+0.1% TFA) to give the desired product after lyophilization. LCMS-ESI⁺: calc'd for $C_{33}H_{30}ClN_4O_3S$: 597.2 (M+H⁺); found: 597.2, 599.2. ¹H NMR (400 MHz, CD₃OD) δ 8.72 (d, J=5.3 Hz, 1H), 8.46 (s, 1H), 8.43 (s, 1H), 8.14-8.08 (m, 2H), 7.94-7.87 (m, 2H), 7.73-7.63 (m, 2H), 7.61-7.54 (m, 3H), 5.26 (s, 1H), 4.10 (s, 3H), 2.63 (s, 3H), 0.97 (s, 9H).

The preparation of (S)-2-tert-butoxy-2-(7-(4-chlorophenyl)-5-methyl-2-(1-methyl-1H-indazol-5-yl)benzo[d]thiazol-6-yl)acetic acid (114b) followed the procedure described above for (S)-2-tert-butoxy-2-(7-(4-chlorophenyl)-5-methyl-2-(2-(1-methyl-1H-indazol-5-yl)pyridin-4-yl)benzo[d]thiazol-6-yl)acetic acid. LCMS-ESI⁺: calc'd for $C_{33}H_{30}ClN_4O_3S$: 520.05 (M+H⁺). Found: 520.2, 522.1. ¹H NMR (400 MHz, CD₃OD) δ 8.38 (s, 1H), 8.09 (d, J=11.2 Hz, 2H), 7.78 (s, 1H), 7.68 (d, J=8.7 Hz, 1H), 7.63 (d, J=8.9 Hz, 1H), 7.60-7.53 (m, 3H), 5.24 (s, 1H), 4.08 (s, 3H), 2.59 (s, 3H), 0.97 (s, 9H).

Example 24
Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)acetic acid (114)

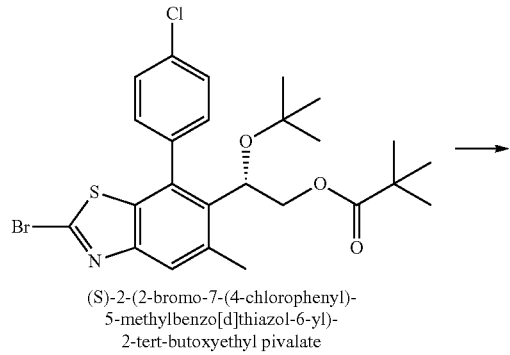

(S)-2-(2-bromo-7-(4-chlorophenyl)-5-methylbenzo[d]thiazol-6-yl)-2-tert-butoxyethyl pivalate (S)-2-(2-(5-bromopyridin-3-yl)-7-(4-chlorophenyl)-5-methylbenzo[d]thiazol-6-yl)-2-tert-butoxyethyl pivalate (S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate (S)-2-tert-butoxy-2-(7-(4-chlorophenyl)-5-methyl-2-(5-(1-methyl-1H-indazol-5-yl)pyridin-3-yl)benzo[d]thiazol-6-yl)ethanol (S)-2-tert-butoxy-2-(7-(4-chlorophenyl)-5-methyl-2-(5-(1-methyl-1H-indazol-5-yl)pyridin-3-yl)benzo[d]thiazol-6-yl) acetic acid
114

Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate: (S)-2-(2-(5-bromopyridin-3-yl)-7-(4-chlorophenyl)-5-methylbenzo[d]thiazol-6-yl)-2-tert-butoxyethyl pivalate was telescoped into the subsequent reaction. 1-Methyl-1H-indazol-5-ylboronic acid (0.024 g, 0.14 mmol) was added to the one-half of the previous reaction mixture and reaction heated in microwave at 115° C. for 30 minutes. Reaction mixture was portioned between ethyl acetate and H$_2$O, the organic layer removed and concentrated to give (S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate. LCMS-ESI$^+$: calc'd for C$_{38}$H$_{40}$ClN$_4$O$_3$S: 667.2 (M+H$^+$); found: 667.3 (M+H$^+$).

Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)ethanol: To a solution of (S)-2-tert-butoxy-2-(7-(4-chlorophenyl)-5-methyl-2-(5-(1-methyl-1H-indazol-5-yl)pyridin-3-yl)benzo[d]thiazol-6-yl)ethyl pivalate from above reaction was added THF:MeOH (1:1, 2 mL) and 2M NaOH (0.5 mL) were added and reaction mixture was heated at 55° C. for 3 h. Reaction mixture was cooled to rt, diluted with ethyl acetate and washed with saturated ammonium chloride solution. The organic layer was dried (MgSO$_4$), filtered, concentrated and purified by CombiFlash (EtOAC/Hex) to give (S)-2-tert-butoxy-2-(7-(4-chlorophenyl)-5-methyl-2-(5-(1-methyl-1H-indazol-5-yl)pyridin-3-yl)benzo[d]thiazol-6-yl)ethanol (15 mg). LCMS-ESI$^+$: calc'd for C$_{33}$H$_{32}$ClN$_4$O$_2$S: 583.2 (M+H$^+$); found: 583.3 (M+H$^+$).

Preparation of (S)-2-tert-butoxy-2-(7-(4-chlorophenyl)-5-methyl-2-(5-(1-methyl-1H-indazol-5-yl)pyridin-3-yl)benzo[d]thiazol-6-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (0.3 mL) was added to a solution of (S)-2-tert-butoxy-2-(7-(4-chlorophenyl)-5-methyl-2-(2-(1-methyl-1H-indazol-6-yl)pyridin-5-yl)benzo[d]thiazol-6-yl)ethanol (15 mg, 0.027 mmol) in 0.75% H$_2$O in ACN (3 mL). The reaction mixture was stirred at room temperature for 45 minutes, quenched with saturated Na$_2$SO$_3$ solution and extracted with EtOAc. The organic layer was dried (MgSO$_4$), filtered, concentrated and purified by reverse phase HPLC (H$_2$O/ACN+0.1% TFA) to give the desired product after lyophilization. LCMS-ESI$^+$: calc'd for C$_{33}$H$_{30}$ClN$_4$O$_3$S: 597.2 (M+H$^+$); found: 597.2, 599.2. $^1$H NMR (400 MHz, CD$_3$OD) δ 9.13 (s, 1H), 8.98 (s, 1H), 8.67 (s, 1H), 8.16 (s, 1H), 8.12 (s, 1H), 7.92 (s, 1H), 7.83 (dd, J=8.8, 1.6 Hz, 1H), 7.73 (dd, J=13.4, 5.2 Hz, 2H), 7.60 (d, J=8.0 Hz, 3H), 5.27 (s, 1H), 4.11 (s, 3H), 2.63 (s, 3H), 0.98 (s, 9H) (115).

Example 25

Preparation of (S)-2-(2-(2-(1H-indazol-5-yl)pyridin-4-yl)-7-(4-chlorophenyl)-5-methylbenzo[d]thiazol-6-yl)-2-tert-butoxyacetic acid (115)

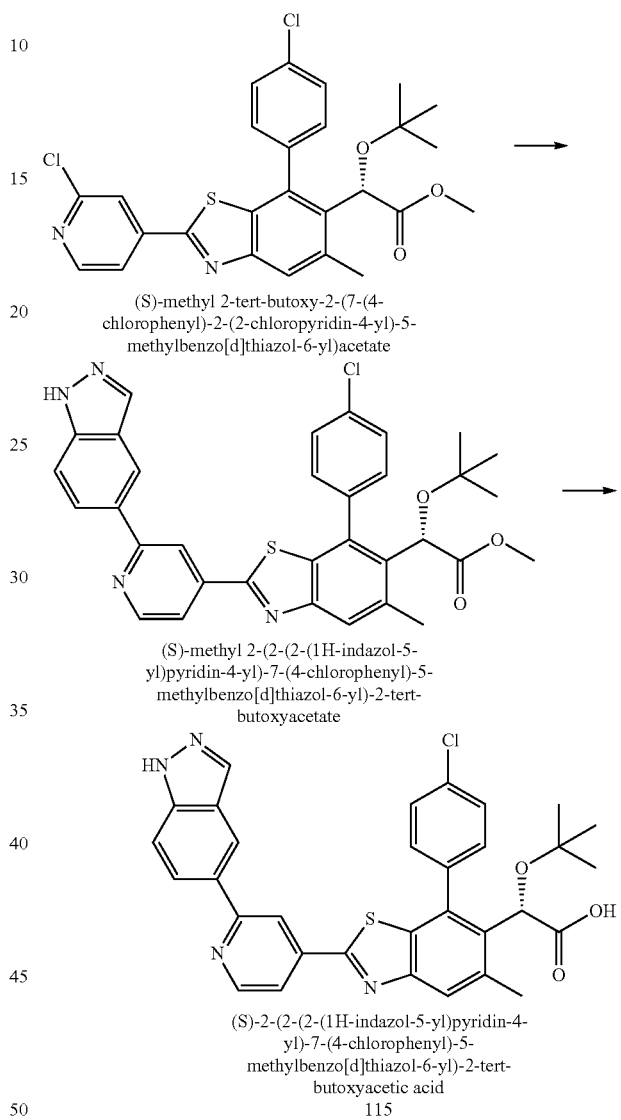

(S)-methyl 2-tert-butoxy-2-(7-(4-chlorophenyl)-2-(2-chloropyridin-4-yl)-5-methylbenzo[d]thiazol-6-yl)acetate (S)-methyl 2-(2-(2-(1H-indazol-5-yl)pyridin-4-yl)-7-(4-chlorophenyl)-5-methylbenzo[d]thiazol-6-yl)-2-tert-butoxyacetate (S)-2-(2-(2-(1H-indazol-5-yl)pyridin-4-yl)-7-(4-chlorophenyl)-5-methylbenzo[d]thiazol-6-yl)-2-tert-butoxyacetic acid
115

Preparation of (S)-methyl 2-(2-(2-(1H-indazol-5-yl)pyridin-4-yl)-7-(4-chlorophenyl)-5-methylbenzo[d]thiazol-6-yl)-2-tert-butoxyacetate: A microwave tube was charged with (S)-methyl 2-tert-butoxy-2-(7-(4-chlorophenyl)-2-(2-chloropyridin-4-yl)-5-methylbenzo[d]thiazol-6-yl)acetate (25.0 mg, 48.5 μmol), 5-(4',4',5',5'-tetramethyl-1',3',2'-dioxaborolan-2'-yl)-1H-indazole (14.2 mg, 58.2 μmol), Pd(PPh$_3$)$_4$ (5.6 mg, 4.86 μmol), K$_2$CO$_3$ (27 mg, 0.19 mmol), H$_2$O (400 μL), and dioxane (1.6 mL). The reaction was sealed and heated to 110° C. The reaction failed to reach completion during the next 2 h (boronate ester was fully consumed (LCMS analysis), yet (S)-methyl 2-tert-butoxy-2-(7-(4-chlorophenyl)-2-(2-chloropyridin-4-yl)-5-methylbenzo[d]thiazol-6-yl)acetate remained.). The reaction was cooled to 23° C. and charged with more 5-(4',4',5',5'-tetramethyl-1',3',2'-dioxaborolan-2'-yl)-1H-indazole (10 mg, 41 μmol). Heating to 110° C. was continued. Reaction progressed further, but was still incomplete after 1 h. Again, the reaction was cooled to 23° C. and this time charged with 1H-indazole-5-boronic acid (20 mg, 120 μmol) and K$_2$CO$_3$ (15 mg, 0.11 mmol); heating to 110° C. was resumed. Reaction reached completion in 1 h. The crude product (S)-methyl 2-(2-(2-(1H-indazol-5-yl)pyridin-4-yl)-7-(4-chlorophenyl)-5-methylbenzo[d]thiazol-6-yl)-2-tert-butoxyacetate was detected in solution. The solution was used crude in the next reaction. LCMS-ESI$^+$: calc'd for C$_{33}$H$_{29}$ClN$_4$O$_3$S: 597.2 and 599.2 (M+H$^+$); found: 597.3 and 599.3 (M+H$^+$).

Preparation of (S)-2-(2-(2-(1H-indazol-5-yl)pyridin-4-yl)-7-(4-chlorophenyl)-5-methylbenzo[d]thiazol-6-yl)-2-tert-butoxyacetic acid: The solution of crude (S)-methyl 2-(2-(2-(1H-indazol-5-yl)pyridin-4-yl)-7-(4-chlorophenyl)-5-methylbenzo[d]thiazol-6-yl)-2-tert-butoxyacetate from the previous reaction was treated directly with LiOH monohydrate (60 mg, 1.42 mmol), H$_2$O (500 μL), and MeOH (500 μL). The reaction was heated to 50° C. for 15 h. The reaction failed to reach completion (LCMS analysis). The reaction was then heated to 100° C. for 30 min and reached completion. The system was cooled to 23° C. and filtered (0.45 micron Teflon® filter). The filtrate was purified directly on a C-18 Gemini column using a Gilson liquid handler (Eluent H$_2$O/CH$_3$CN gradient with both mobile phase components spiked 0.1% v/v with TFA). The title compound was obtained as a mono-trifluoroacetic acid salt. LCMS-ESI$^+$: calc'd for C$_{32}$H$_{27}$ClN$_4$O$_3$S: 583.2 and 585.2 (M+H$^+$); Found: 583.3 and 585.3 (M+H$^+$). $^1$H NMR (400 MHz, CD$_3$OD) δ: 8.78 (d, J=5.5 Hz, 1H), 8.58 (s, 1H), 8.51 (s, 1H), 8.22 (s, 1H), 8.11 (dd, J=8.6, 1.2 Hz, 1H), 8.04 (dd, J=5.4, 1.2 Hz, 1H), 7.99 (s, 1H), 7.74-7.70 (m, 2H), 7.65-7.60 (m, 3H), 5.23 (s, 1H), 2.65 (s, 3H), 0.99 (s, 9H).

Example 26

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)acetic acid (116)

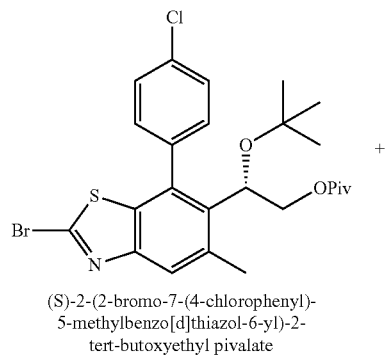

(S)-2-(2-bromo-7-(4-chlorophenyl)-5-methylbenzo[d]thiazol-6-yl)-2-tert-butoxyethyl pivalate

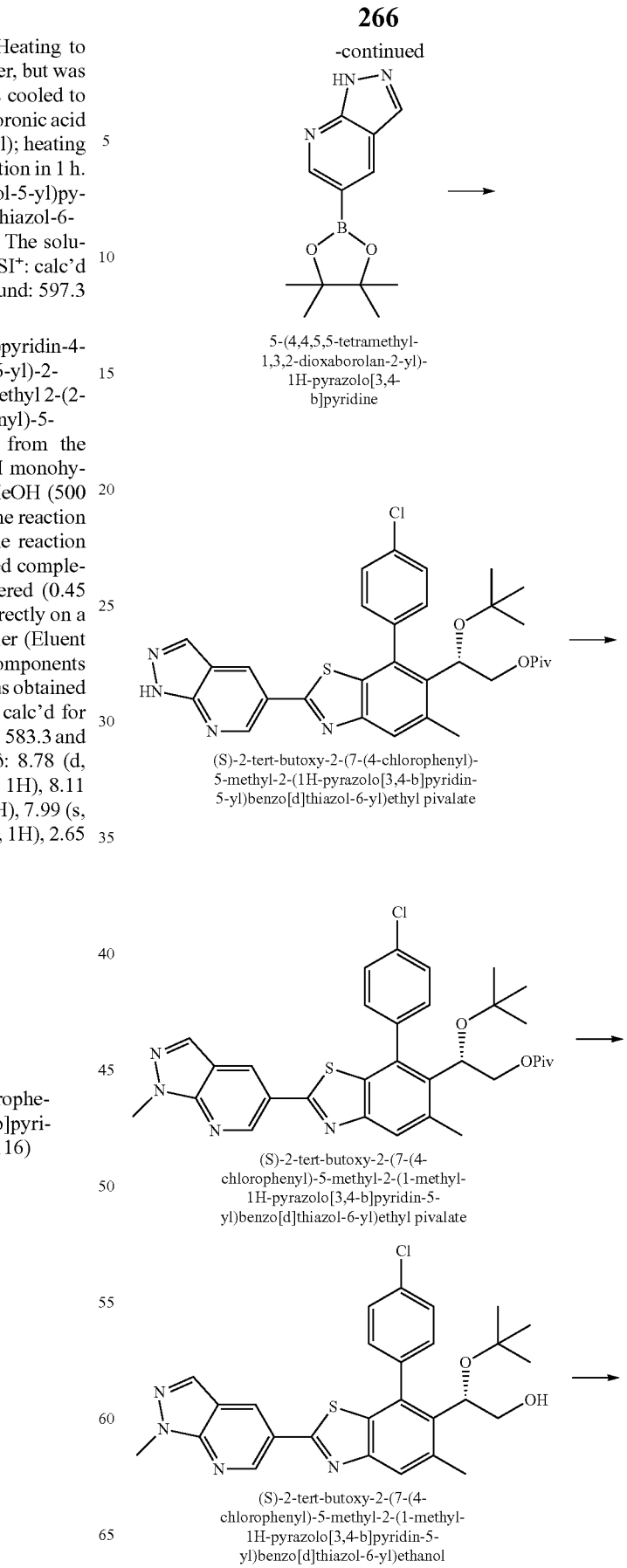

5-(4,4,5,5-tetramethyl-1,3,2-dioxaborolan-2-yl)-1H-pyrazolo[3,4-b]pyridine (S)-2-tert-butoxy-2-(7-(4-chlorophenyl)-5-methyl-2-(1H-pyrazolo[3,4-b]pyridin-5-yl)benzo[d]thiazol-6-yl)ethyl pivalate (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethyl pivalate (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethanol

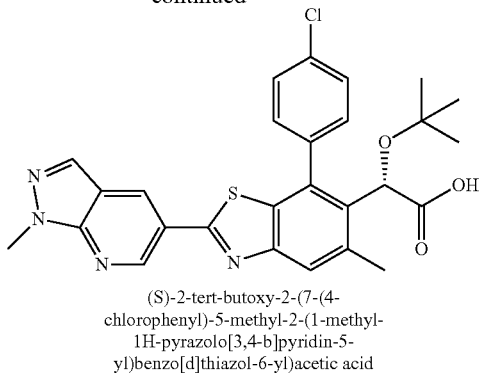

(S)-2-tert-butoxy-2-(7-(4-
chlorophenyl)-5-methyl-2-(1-methyl-
1H-pyrazolo[3,4-b]pyridin-5-
yl)benzo[d]thiazol-6-yl)acetic acid
116

Preparation of (S)-2-tert-butoxy-2-(7-(4-chlorophenyl)-5-methyl-2-(1H-pyrazolo[3,4-b]pyridin-5-yl)benzo[d]thiazol-6-yl)ethyl pivalate: To a solution of (S)-2-(2-bromo-7-(4-chlorophenyl)-5-methylbenzo[d]thiazol-6-yl)-2-tert-butoxyethyl pivalate (51 mg, 0.095 mmol) and 5-(4,4,5,5-tetramethyl-1,3,2-dioxaborolan-2-yl)-1H-pyrazolo[3,4-b]pyridine (28 mg, 0.123 mmol) in degassed 1,4-dioxane (250 µL) and water (25 µL) was added aqueous $K_2CO_3$ (95 µL of a 2.0 M solution) and tetrakis(triphenylphosphine)palladium (0) (6 mg, 0.005 mmol). The reaction mixture was heated at 100° C. for 6 h, cooled and partitioned between ethyl acetate and brine. The organic layer was separated, dried over $Na_2SO_4$ and concentrated. The crude material was used without any further purification. LCMS-ESI$^+$: calc'd for $C_{31}H_{34}ClN_4O_3S$: 577.2 (M+H$^+$); Found: 577.3 (M+H$^+$).

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethyl pivalate: To a solution of the crude material from the previous reaction (assume 0.095 mmol) in dry DMF (1.0 mL) was added $Cs_2CO_3$ (60 mg, 0.185 mmol) at room temperature. After 15 min, neat methyl iodide (12 µL, 0.19 mmol) was added and the reaction was allowed to stir for 6 h. The reaction was then partitioned between ethyl acetate and water and extracted. The organic layer was washed sequentially with aqueous 5% LiCl, brine, dried over $Na_2SO_4$ and concentrated to give the desired product. Purification by flash column chromatography on silica gel using 30% ethyl acetate in hexanes provided a pale foam (14 mg, 25% for two steps). LCMS-ESI$^+$: calc'd for $C_{32}H_{36}ClN_4O_3S$: 591.2 (M+H$^+$); Found: 591.3 (M+H$^+$).

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethanol: To a solution of compound (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethyl pivalate (14 mg, 0.024 mmol) in THF (0.50 mL) and MeOH (0.50 mL) was added aqueous NaOH (0.10 mL of a 2 N solution). The reaction mixture was heated at 50° C. for 17 h, cooled, diluted with satd. aqueous $NH_4Cl$ and extracted with ethyl acetate. The organic layer was dried and concentrated to give the desired product which was used without any further purification. LCMS-ESI$^+$: calc'd for $C_{27}H_{28}ClN_4O_2S$: 507.2 (M+H$^+$); 507.2 (M+H$^+$).

Preparation of (S)-2-tert-butoxy-2-(7-(4-chlorophenyl)-5-methyl-2-(1-methyl-1H-pyrazolo[3,4-b]pyridin-5-yl)benzo[d]thiazol-6-yl)acetic acid: To a solution of (S)-2-tert-butoxy-2-(7-(4-chlorophenyl)-5-methyl-2-(1-methyl-1H-pyrazolo[3,4-b]pyridin-5-yl)benzo[d]thiazol-6-yl)ethanol from previous reaction (assume 0.024 mmol) in 25% water/acetonitrile (0.70 mL) was added sequentially, a stock solution of $CrO_3/H_5IO_6$ (296 µL, 0.439 M solution) and $CrO_3$ (3 mg, 0.030 mmol) at room temperature. The reaction was stirred for 1 h, diluted with acetonitrile, filtered and purified by reverse phase HPLC. Fractions containing product were pooled and evaporated to the desired product. LCMS-ESI$^+$: calc'd for $C_{27}H_{26}ClN_4O_3S$: 521.1 (M+H$^+$); 521.2 (M+H$^+$); $^1$H NMR (400 MHz, CD$_3$OD): δ 9.26 (d, J=1.9 Hz, 1H), 8.79 (d, J=1.9 Hz, 1H), 8.20 (s, 1H), 7.87 (s, 1H), 7.69 (d, J=9.4 Hz, 1H), 7.61-7.59 (m, 3H), 5.26 (s, 1H), 4.15 (s, 3H), 2.61 (s, 3H), 0.97 (s, 9H).

Example 27

Preparation of (S)-2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetic acid (117)

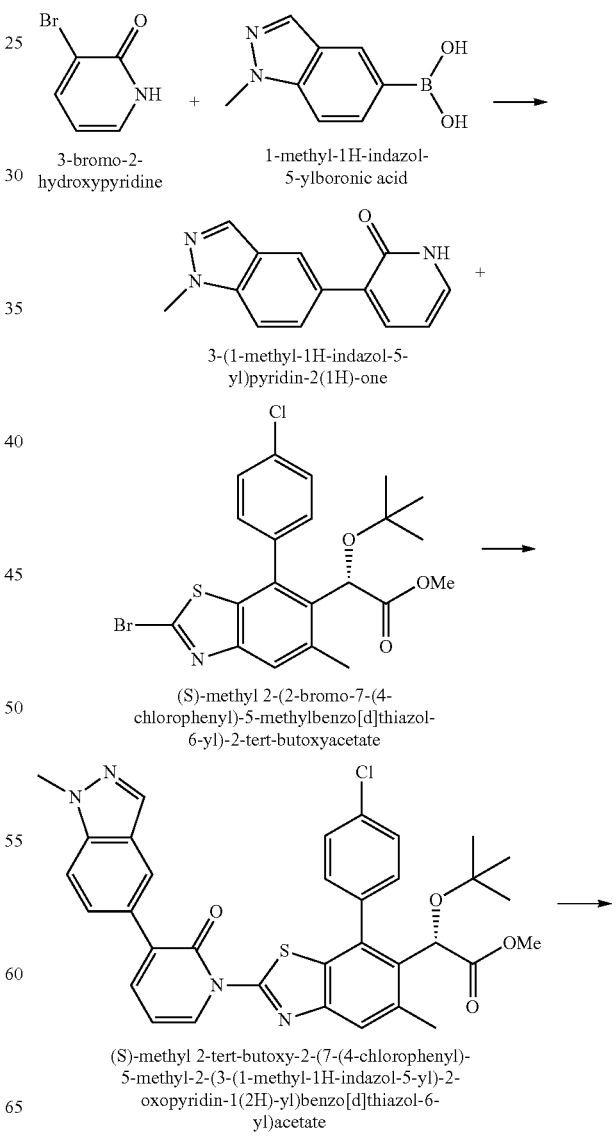

-continued

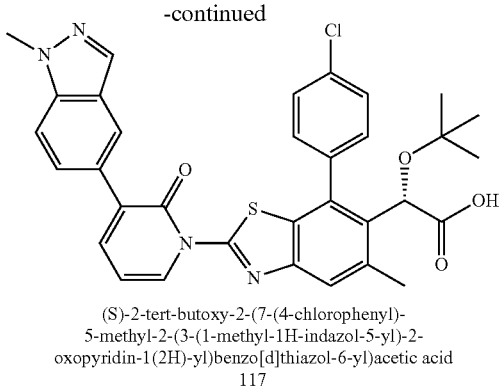

(S)-2-tert-butoxy-2-(7-(4-chlorophenyl)-
5-methyl-2-(3-(1-methyl-1H-indazol-5-yl)-2-
oxopyridin-1(2H)-yl)benzo[d]thiazol-6-yl)acetic acid
117

Preparation of 3-(1-methyl-1H-indazol-5-yl)pyridin-2(1H)-one: The suspension of 3-bromo-2-hydroxypyridine (80 mg, 0.46 mmol), 1-methyl-1H-indazol-5-ylboronic acid (121 mg, 0.69 mmol) and sodium carbonate (146 mg, 1.38 mmol) in DMF (2.0 mL) and H$_2$O (0.4 mL) was degassed with N$_2$ for 5 minutes. To the mixture was added bis(triphenylphosphine)palladium (II) dichloride (67 mg, 0.09 mmol), and the resulting mixture was heated at 90° C. for 2 h. The reaction mixture was filtered and purified by reverse phase HPLC (Gemini, 5 to 100% ACN/H$_2$O+0.1% TFA) to give the product. LCMS-ESI$^+$ (m/z): [M+H]$^+$ calcd for C$_{13}$H$_{12}$N$_3$O: 226.25; Found: 226.2.

Preparation of (S)-methyl 2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetate: To a solution of 3-(1-methyl-1H-indazol-5-yl)pyridin-2(1H)-one (13.0 mg, 0.055 mmol), (S)-methyl 2-(2-bromo-7-(4-chlorophenyl)-5-methylbenzo[d]thiazol-6-yl)-2-tert-butoxyacetate (22 mg, 0.046 mmol), trans-N1,N2-dimethylcyclohexane-1,2-diamine (9 μL, 0.055 mmol) and potassium carbonate (13 mg, 0.091 mmol) in DMF (0.5 mL) was added copper(I) iodide (5.0 mg, 0.026 mmol). The mixture was degassed with N$_2$ for 5 minutes and then heated at 110° C. for 3 h. The mixture was then diluted with EtOAc, extracted with H$_2$O, brine, dried over Na$_2$SO$_4$, filtered and concentrated and purified by flash column chromatography (silica gel, 0 to 100% ethyl acetate/hexanes) to give the product. LCMS-ESI$^+$ (m/z): [M+H]$^+$ calcd for C$_{34}$H$_{32}$ClN$_4$O$_4$S: 627.18; Found: 627.2.

Preparation of (S)-2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetic acid: To a stirred solution of (S)-methyl 2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl)acetate (12.6 mg, 0.020 mmol) in THF (1.2 mL) and methanol (0.5 mL) was added 1 M NaOH solution (0.3 mL, excess). The reaction mixture was stirred at 37° C. for 6 h. The reaction mixture was purified by reverse phase HPLC (Gemini, 5 to 100% ACN/H$_2$O+0.1% TFA) to give the product. LCMS-ESI$^+$ (m/z): [M+H]$^+$ calcd for C$_{33}$H$_{30}$ClN$_4$O$_4$S: 613.17; Found: 613.2; $^1$H-NMR: 400 MHz, (CD$_3$OD) δ 8.89 (dd, J=7.6, 2 Hz, 1H), 8.02 (s, 2H), 7.75 (s, 1H), 7.70-7.63 (m, 3H), 7.53-7.49 (m, 4H), 6.61 (t, J=7.2 Hz, 1H), 5.27 (s, 1H), 4.06 (s, 3H), 2.60 (s, 3H), 0.95 (s, 9H).

Example 28

Preparation of (S)-2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetic acid (118)

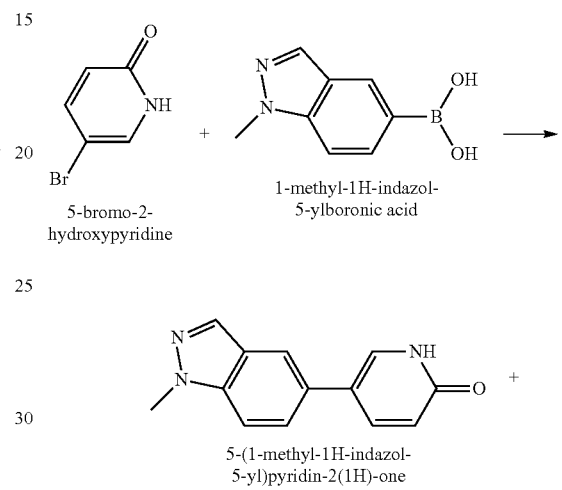

5-bromo-2-hydroxypyridine    1-methyl-1H-indazol-5-ylboronic acid 5-(1-methyl-1H-indazol-5-yl)pyridin-2(1H)-one

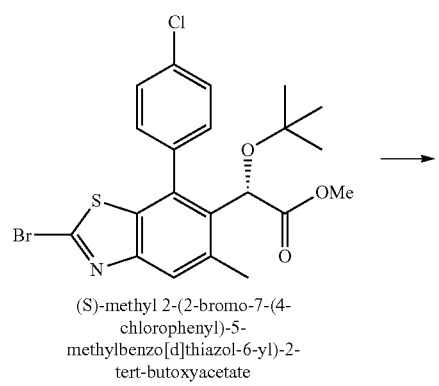

(S)-methyl 2-(2-bromo-7-(4-chlorophenyl)-5-methylbenzo[d]thiazol-6-yl)-2-tert-butoxyacetate

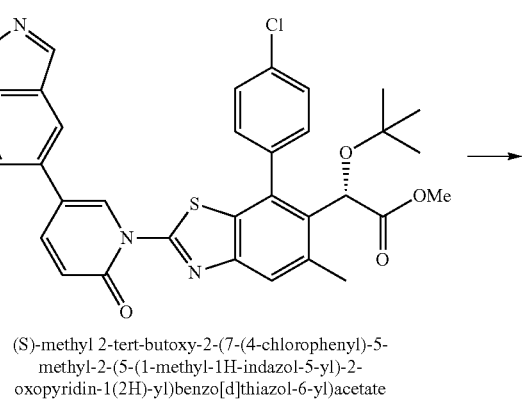

(S)-methyl 2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetate

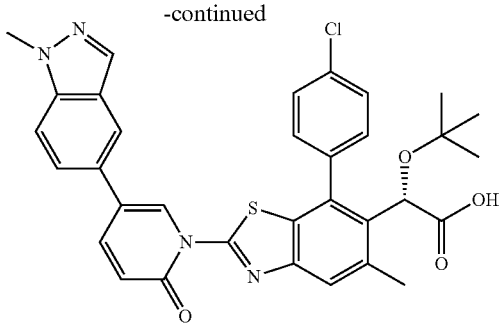

(S)-2-tert-butoxy-2-(7-(4-chlorophenyl)-5-
methyl-2-(5-(1-methyl-1H-indazol-5-yl)-2-
oxopyridin-1(2H)-yl)benzo[d]thiazol-6-yl)acetic acid
118

Preparation of 5-(1-methyl-1H-indazol-5-yl)pyridin-2 (1H)-one: The suspension of 5-bromo-2-hydroxypyridine (80 mg, 0.46 mmol), 1-methyl-1H-indazol-5-ylboronic acid (121 mg, 0.69 mmol) and 2N sodium carbonate solution (1.0 mL, 2 mmol) in DMF (2.1 mL) was degassed with $N_2$ for 5 minutes. To the mixture was added tetrakis(triphenylphosphine)palladium(0) (53 mg, 0.04 mmol), and the resulting mixture was heated at 80° C. overnight. The mixture was then diluted with $CH_2Cl_2$, extracted with $H_2O$, brine, dried over $Na_2SO_4$, filtered and concentrated and purified by reverse phase HPLC (Gemini, 5 to 100% ACN/$H_2O$+0.1% TFA) to give the product. LCMS-ESI$^+$ (m/z): [M+H]$^+$ calcd for $C_{13}H_{12}N_3O$: 226.25; Found: 226.3.

Preparation of (S)-methyl 2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetate:

Compound (S)-methyl 2-tert-butoxy-2-(7-(4-chlorophenyl)-5-methyl-2-(5-(1-methyl-1H-indazol-5-yl)-2-oxopyridin-1(2H)-yl)benzo[d]thiazol-6-yl)acetate was prepared following the procedure used to prepare (S)-methyl 2-tert-butoxy-2-(7-(4-chlorophenyl)-5-methyl-2-(3-(1-methyl-1H-indazol-5-yl)-2-oxopyridin-1(2H)-yl)benzo[d]thiazol-6-yl) acetate of Example 27, except that 5-(1-methyl-1H-indazol-5-yl)pyridin-2(1H)-one was used instead of 3-(1-methyl-1H-indazol-5-yl)pyridin-2(1H)-one. LCMS-ESI$^+$ (m/z): [M+H]$^+$ calcd for $C_{34}H_{32}ClN_4O_4S$: 627.18; Found: 627.2.

Preparation of (S)-2-tert-butoxy-2-(7-(4-chlorophenyl)-5-methyl-2-(5-(1-methyl-1H-indazol-5-yl)-2-oxopyridin-1 (2H)-yl)benzo[d]thiazol-6-yl)acetic acid: Compound (S)-2-tert-butoxy-2-(7-(4-chlorophenyl)-5-methyl-2-(5-(1-methyl-1H-indazol-5-yl)-2-oxopyridin-1(2H)-yl)benzo[d] thiazol-6-yl)acetic acid was prepared following the procedure used to (S)-2-tert-butoxy-2-(7-(4-chlorophenyl)-5-methyl-2-(3-(1-methyl-1H-indazol-5-yl)-2-oxopyridin-1 (2H)-yl)benzo[d]thiazol-6-yl)acetic acid of Example 27, except that (S)-methyl 2-tert-butoxy-2-(7-(4-chlorophenyl)-5-methyl-2-(5-(1-methyl-1H-indazol-5-yl)-2-oxopyridin-1 (2H)-yl)benzo[d]thiazol-6-yl)acetate was used instead of (S)-methyl 2-tert-butoxy-2-(7-(4-chlorophenyl)-5-methyl-2-(3-(1-methyl-1H-indazol-5-yl)-2-oxopyridin-1(2H)-yl) benzo[d]thiazol-6-yl)acetate. $^1$H-NMR: 400 MHz, (CD$_3$OD) δ 9.07 (d, J=2.8 Hz, 1H), 8.04 (s, 1H), 7.97 (s, 1H), 7.93 (dd, J=9.2, 2.4 Hz, 1H), 7.69-7.62 (m, 4H), 7.55-7.51 (m, 3H), 6.72 (d, J=9.6 Hz, 1H), 5.25 (s, 1H), 4.09 (s, 3H), 2.56 (s, 3H), 0.96 (s, 9H); LCMS-ESI$^+$(m/z): [M+H]$^+$ calcd for $C_{33}H_{30}ClN_4O_4S$: 613.17; Found: 613.2.

Example 29

Preparation of (2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)acetic acid (119)

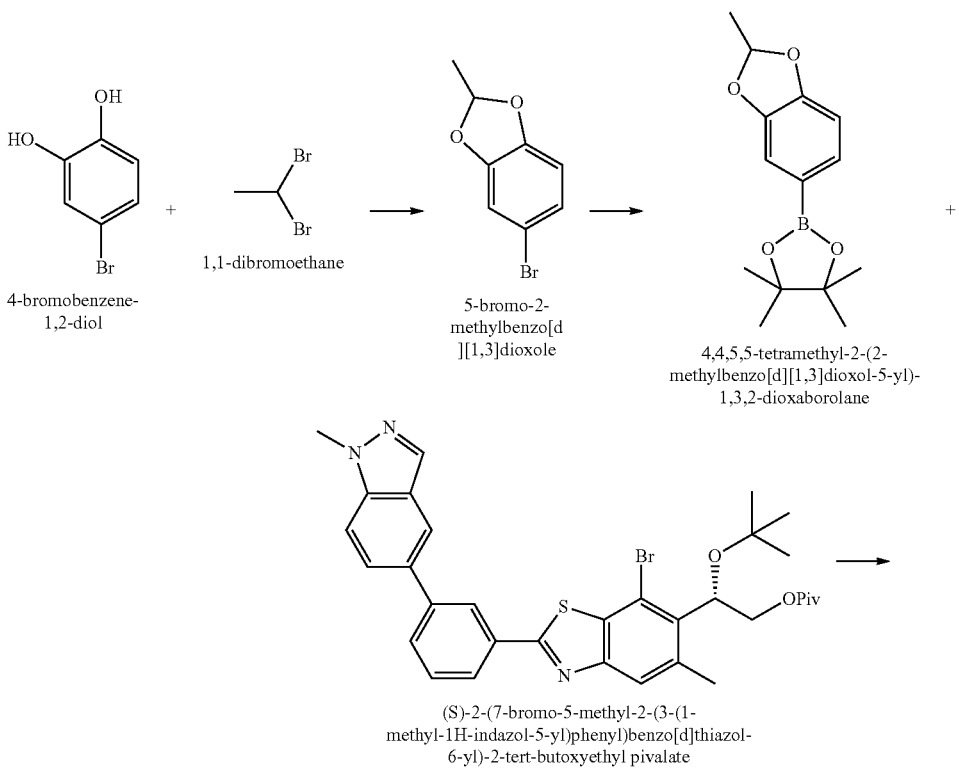

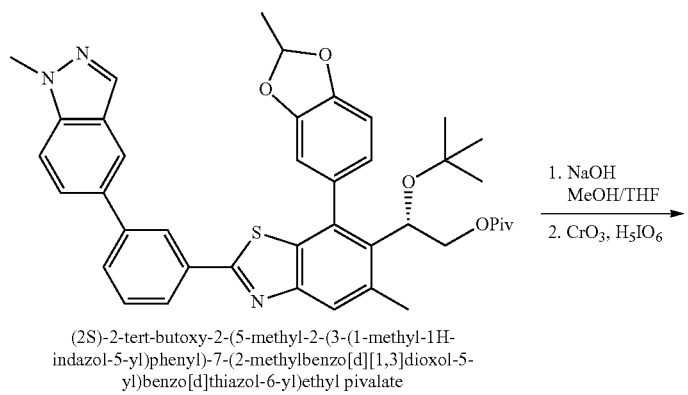

(2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)ethyl pivalate 1. NaOH MeOH/THF
2. CrO₃, H₅IO₆

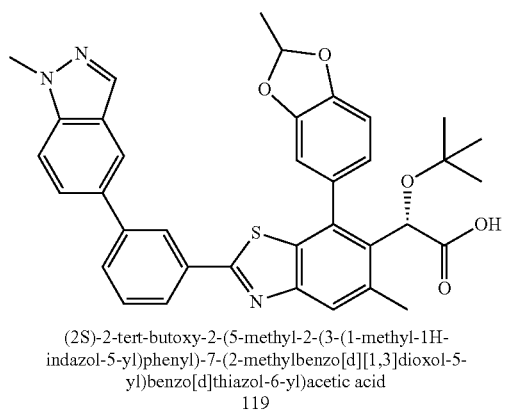

(2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)acetic acid
119

Preparation of 5-bromo-2-methylbenzo[d][1,3]dioxole: To a solution of 4-bromobenzene-1,2-diol (500 mg, 2.65 mmol) in acetone (4 mL) was added cesium carbonate (1.90 g, 5.82 mmol) and 1,1-dibromoethane (1.09 g, 5.82 mmol). The mixture was microwaved to 120° C. for 3 h. After cooling, the reaction mixture was diluted with EtOAc, extracted with H₂O, brine, dried over Na₂SO₄, filtered and concentrated and purified by flash column chromatography (silica gel, 0 to 10% ethyl acetate/hexanes) to give the product. ¹H-NMR: 400 MHz, (CDCl₃) δ 6.93-6.89 (m, 2H), 6.63 (d, J=8 Hz, 1H), 6.27 (q, J=9.6 Hz, 1H), 1.67 (d, J=4.4 Hz, 3H).

Preparation of 4,4,5,5-tetramethyl-2-(2-methylbenzo[d][1,3]dioxol-5-yl)-1,3,2-dioxaborolane: The suspension of 5-bromo-2-methylbenzo[d][1,3]dioxole (36 mg, 0.17 mmol), bis(pinacolato)diboron (56 mg, 0.22 mmol) and potassium carbonate (50 mg, 0.51 mmol) in DME (0.4 mL) was degassed with N₂ for 5 minutes. To the mixture was added [1,1'-bis(diphenylphosphino)ferrocene]dichloropalladium (II) (12 mg, 0.02 mmol), and the resulting mixture was heated at 90° C. for 2 h. Concentrated in vacuo and then purified by flash column chromatography (silica gel, 0 to 50% ethyl acetate/hexanes) to give the product. ¹H-NMR: 400 MHz, (CDCl₃) δ 7.34-7.32 (m, 1H), 7.19 (d, J=0.8 Hz, 1H), 6.78-6.75 (m, 1H), 6.29-6.23 (m, 1H), 1.68-1.64 (m, 3H), 1.32 (s, 12H).

Preparation of (2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)ethyl pivalate: To a solution of (S)-2-(7-bromo-5-methyl-2-(3-(1-methyl-1H-indazol-5-yl)phenyl)benzo[d]thiazol-6-yl)-2-tert-butoxyethyl pivalate (16 mg, 0.025 mmol) and 4,4,5,5-tetramethyl-2-(2-methylbenzo[d][1,3]dioxol-5-yl)-1,3,2-dioxaborolane (13 mg, 0.050 mmol) in 1,4-dioxane was added Pd(PPh₃)₄ (4 mg, 3.1×10⁻³ mmol) and 2M K₂CO₃ (66 μL, 0.133 mmol). The reaction was degassed for 5 minutes with N₂ and then heated to 110° C. for 1 h. After cooling, the reaction mixture was diluted with EtOAc, extracted with saturated NaHCO₃, brine, dried over Na₂SO₄, filtered and concentrated and purified by flash column chromatography (silica gel, 0 to 10% ethyl acetate/hexanes) to give the product. LCMS-ESI+ (m/z): [M+H]+ calcd for C₄₁H₄₄N₃O₅S: 690.30; found: 690.4.

Preparation of (2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)acetic acid: prepared in a similar manner as (S)-2-tert-butoxy-2-(7-(4-chlorophenyl)-5-methyl-2-(3-(1-methyl-1H-indazol-5-yl)phenyl)benzo[d]thiazol-6-yl)acetic acid in Method G, except using (2S)-2-tert-butoxy-2-(5-methyl-2-(3-(1-methyl-1H-indazol-5-yl)phenyl)-7-(2-methylbenzo[d][1,3]dioxol-5-yl)benzo[d]thiazol-6-yl)ethyl pivalate instead of (S)-2-tert-butoxy-2-(7-(4-chlorophenyl)-5-methyl-2-(3-(1-methyl-1H-indazol-5-yl)phenyl)benzo[d]thiazol-6-yl)ethyl pivalate. LCMS-ESI⁺ (m/z): [M+H]⁺ calcd for C₃₆H₃₄N₃O₅S: 620.2; Found: 620.3; ¹H-NMR: 400 MHz, (CD₃OD) δ 8.34-8.32 (m, 1H), 8.08 (s, 2H), 8.00-7.94 (m, 1H), 7.85-7.84 (m, 3H), 7.66 (d, J=8.8 Hz, 1H), 7.59 (t, J=7.2 Hz, 1H), 7.17-7.11 (m, 1H), 7.06-7.00 (m, 1H), 6.97-6.94 (m, 1H), 6.43-6.37 (m, 1H), 5.46-5.36 (m, 1H), 4.10 (s, 3H), 2.60 (s, 3H), 1.74-1.68 (m, 3H), 0.99 (s, 9H).

Example 30

Preparation of (S)-2-tert-butoxy-2-(7-(4-chlorophenyl)-2-(3-(1,5-dimethyl-1H-pyrazol-4-yl)phenyl)-5-methylbenzo[d]thiazol-6-yl)acetic acid (120)

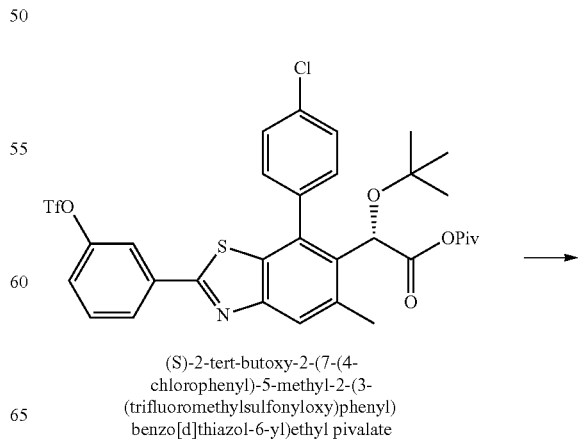

(S)-2-tert-butoxy-2-(7-(4-chlorophenyl)-5-methyl-2-(3-(trifluoromethylsulfonyloxy)phenyl)benzo[d]thiazol-6-yl)ethyl pivalate

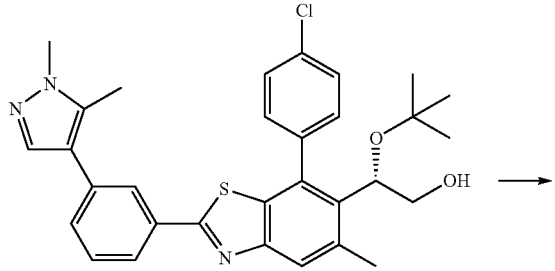

(S)-2-tert-butoxy-2-(7-(4-chlorophenyl)-2-(3-(1,5-dimethyl-1H-pyrazol-4-yl)phenyl)-5-methyl benzo[d]thiazol-6-yl)ethanol

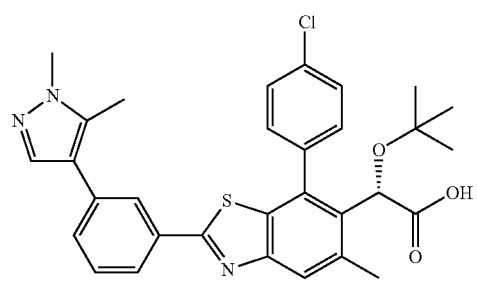

(S)-2-tert-butoxy-2-(7-(4-chlorophenyl)-2-(3-(1,5-dimethyl-1H-pyrazol-4-yl)phenyl)-5-methylbenzo[d]thiazol-6-yl)acetic acid
120

Preparation of (S)-2-tert-butoxy-2-(7-(4-chlorophenyl)-5-methyl-2-(3-(trifluoromethylsulfonyloxy)phenyl)benzo[d]thiazol-6-yl)ethyl pivalate: The reaction mixture of (S)-2-tert-butoxy-2-(7-(4-chlorophenyl)-5-methyl-2-(3-(trifluoromethylsulfonyloxy)phenyl)benzo[d]thiazol-6-yl) ethyl pivalate (20 mg, 0.029 mmol), 1,5-dimethyl-1H-pyrazole-5-boronic acid pinnacle ester (13 mg, 0.058 mmol), 2N $K_2CO_3$ (80 μL), Pd(PPh$_3$)$_4$ (3.3 mg, 0.0029 mmol) in dioxane (1 mL) was heated at 120° C. in sealed tube for 2 hours. After the reaction finished, the reaction was cooled down, to the reaction mixture was added MeOH (1 mL), 2N NaOH (500 μL) and heated at 45° C. overnight. Then reaction mixture was washed by sat. NaHCO$_3$, extracted by EtOAc, the organic phase was dried over MgSO$_4$, filtered, concentrated down and purified by silica gel column, eluting by 0-100% EtOAc in hexanes to give the desired product. LCMS-ESI$^+$: calc'd for $C_{31}H_{32}ClN_3O_2S$: 546.2 (M+H$^+$);. Found: 546.3 (M+H$^+$).

Preparation of (S)-2-tert-butoxy-2-(7-(4-chlorophenyl)-2-(3-(1,5-dimethyl-1H-pyrazol-4-yl)phenyl)-5-methylbenzo[d]thiazol-6-yl)acetic acid: To a solution of (S)-2-tert-butoxy-2-(7-(4-chlorophenyl)-2-(3-(1,5-dimethyl-1H-pyrazol-4-yl)phenyl)-5-methylbenzo[d]thiazol-6-yl)ethanol (11 mg, 0.020 mmol) in wet acetonitrile (0.75 w % H$_2$O, 1 mL), was added stock solution of $H_5IO_6$/CrO$_3$ (0.439 M in wet acetonitrile, 400 μL) at 0° C. for ½ hour. The reaction mixture was filtered and purified by reverse phase HPLC, eluting by 0-100% acetonitrile in H$_2$O with 0.1% TFA give the product. LCMS-ESI$^+$: calc'd for $C_{31}H_{30}ClN_3O_3S$: 560.2 (M+H$^+$). Found: 560.2 (M+H$^+$). $^1$H NMR (400 MHz, CD$_3$OD): δ 8.05 (s, 1H), 7.88 (d, J=3.4 Hz, 1H), 7.84 (s, 1H), 7.69-7.66 (m, 2H), 7.59-7.51 (m, 5H), 5.25 (s, 1H), 3.86 (s, 3H), 2.61 (s, 3H), 2.45 (s, 3H), 0.97 (S, 9H).

Example 31

Preparation of (S)-2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetic acid (121)

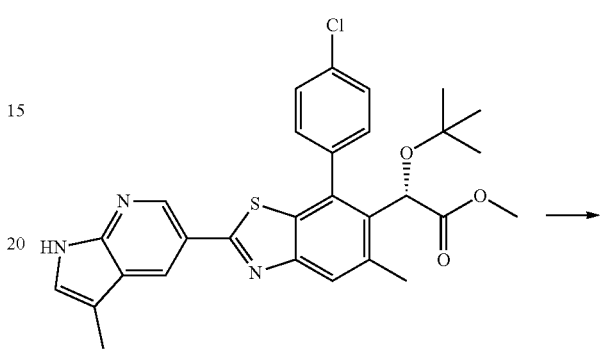

(S)-methyl 2-tert-butoxy-2-(7-(4-chlorophenyl)-5-methyl-2-(3-methyl-1H-pyrrolo[2, 3-b]pyridin-5-yl)benzo[d]thiazol-6-yl)acetate

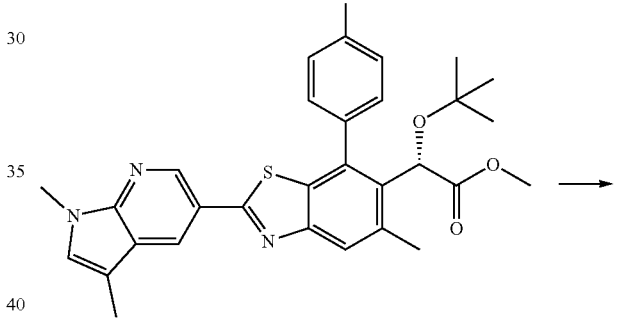

(S)-methyl 2-tert-butoxy-2-(7-(4-chlorophenyl)-2-(1, 3-dimethyl-1H-pyrrolo[2, 3-b]pyridin-5-yl)-5-methylbenzo[d]thiazol-6-yl)acetate

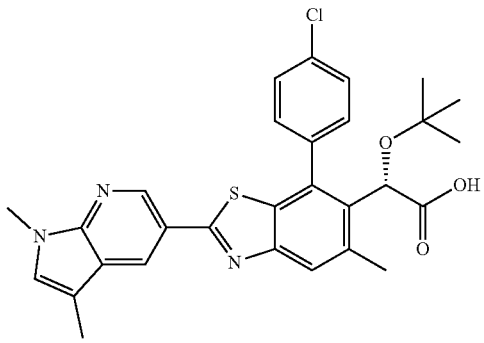

(S)-2-tert-butoxy-2-(7-(4-chlorophenyl)-2-(1, 3-dimethyl-1H-pyrrolo[2, 3-b]pyridin-5-yl)-5-methylbenzo[d]thiazol-6-yl)acetic acid
121

Preparation (S)-methyl 2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetate: To a solution of (S)-methyl 2-tert-butoxy-2-(7-(4-chlorophenyl)-5-methyl-2-(3-methyl- 1H-pyrrolo[2,3-b]pyridin-5-yl)benzo[d]thiazol-6-yl)acetate (12 mg, 0.022 mmol) in DMF (5 mL) was added cesium carbonate (11 mg, 0.033 mmol). The reaction solution was stirred at room temperature for 5 minutes, iodomethane (4.7 mg, 0.033 mmol) was added. The reaction solution was stirred for 30 minutes and quenched with water. Volatiles were removed and the residue partitioned between ethyl acetate and water. The organic phase was washed with brine, dried (MgSO$_4$), filtered and concentrated to give crude product which was purified by chromatographic column to afford the desired product. LCMS-ESI$^+$: calc'd for C$_{30}$H$_{30}$ClN$_3$O$_3$S: 548.17 (M+H$^+$); Found: 548.4 (M+H$^+$).

Preparation (S)-2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetic acid: To a solution of (S)-methyl 2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetate: (4 mg, 0.0073 mmol) in THF/CH$_3$OH (0.5 mL/0.5 mL) was added 2N NaOH (37 uL, 0.073 mmol). The reaction mixture was heated at 50° C. for 2 h and the crude was purified by reverse phase HPLC, eluting with 5-100% acetonitrile in H$_2$O with 0.1% TFA to give desired product. LCMS-ESI$^+$: calc'd for C$_{29}$H$_{28}$ClN$_3$O$_3$S: 534.16 (M+H$^+$). Found: 534.2 (M+H$^+$). $^1$H NMR (400 MHz, CD$_3$OD): δ 8.88 (d, J=1 Hz, 1H), 8.51 (d, J=1 Hz, 1H), 7.82 (s, 1H), 7.71-7.58 (m, 4H), 7.21 (s, 1H), 5.26 (s, 1H), 3.83 (s, 3H), 2.61 (s, 3H), 2.34 (s, 3H), 0.97 (s, 9H).

Example 32

Preparation of (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyacetic acid (122)

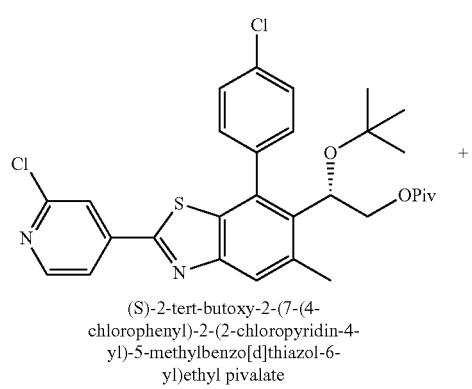

(S)-2-tert-butoxy-2-(7-(4-chlorophenyl)-2-(2-chloropyridin-4-yl)-5-methylbenzo[d]thiazol-6-yl)ethyl pivalate

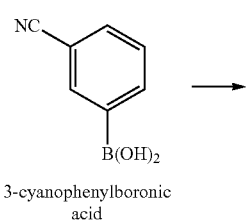

3-cyanophenylboronic acid

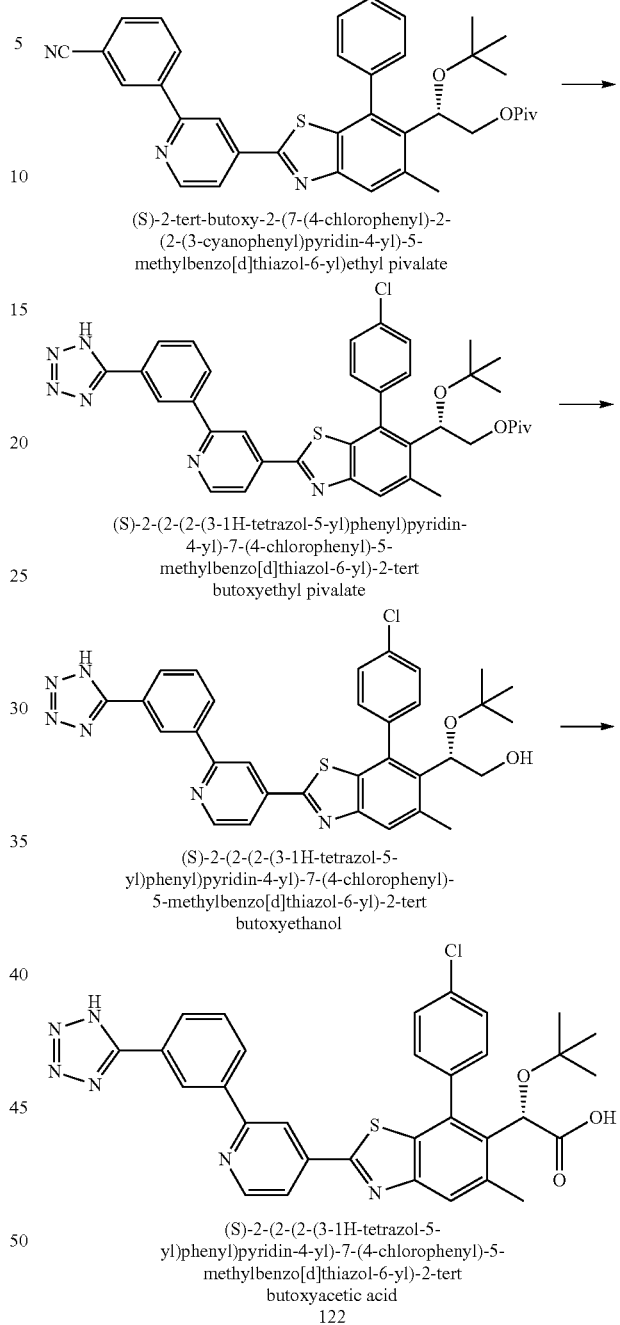

Preparation of (S)-2-tert-butoxy-2-(7-(4-chlorophenyl)-2-(2-(3-cyanophenyl)pyridin-4-yl)-5-methylbenzo[d]thiazol-6-yl)ethyl pivalate: (S)-2-tert-butoxy-2-(7-(4-chlorophenyl)-2-(2-chloropyridin-4-yl)-5-methylbenzo[d]thiazol-6-yl) ethyl pivalate (19.7 mg, 0.034 mmol), 3-cyanophenylboronic acid (6.1 mg, 0.041 mmol), Pd(PPh$_3$)$_4$, and K$_2$CO$_3$ (14.3 mg, 0.103 mmol) were placed in a microwave vial and the vial was vacuum pumped and flushed with argon three times. To this mixture was added degassed 1,4-dioxane (0.4 mL) and degassed water (0.1 mL). The reaction mixture was heated at 110° C. for 1.5 h, cooled, diluted with ethyl acetate, filtered through Celite (ethyl acetate eluent), and concentrated. Purification by flash column chromatography on silica gel (hexanes/ethyl acetate eluent) provided the product. LCMS-ESI⁺: calc'd for $C_{37}H_{37}ClN_3O_3S$: 638.2 (M+H⁺); Found: 637.9 (M+H⁺).

Preparation of (S)-2-(2-(2-(3-(1H-tetrazol-5-yl)phenyl) pyridin-4-yl)-7-(4-chlorophenyl)-5-methylbenzo[d]thiazol-6-yl)-2-tert-butoxyethyl pivalate: To a solution of (S)-2-tert-butoxy-2-(7-(4-chlorophenyl)-2-(2-(3-cyanophenyl)pyridin-4-yl)-5-methylbenzo[d]thiazol-6-yl)ethyl pivalate (17.2 mg, 0.027 mmol) in DMF (0.5 mL) was added ammonium chloride (7.2 mg, 0.135 mmol) and sodium azide (9.4 mg, 0.144 mmol). The reaction mixture was heated at 120° C. for 6 h then cooled. The crude reaction mixture was passed through a silica gel plug (hexanes/ethyl acetate eluent) to remove the DMF and salts, concentrated, and used without further purification. LCMS-ESI⁺: calc'd for $C_{37}H_{38}ClN_6O_3S$: 681.2 (M+H⁺); Found: 680.9 (M+H⁺).

Preparation of (S)-2-(2-(2-(3-(1H-tetrazol-5-yl)phenyl) pyridin-4-yl)-7-(4-chlorophenyl)-5-methylbenzo[d]thiazol-6-yl)-2-tert-butoxyethanol: To a solution of crude (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyethyl pivalate from the previous reaction (assume 0.027 mmol) in THF (0.4 mL) and methanol (0.4 mL) was added NaOH (0.4 mL of a 2N solution). The reaction mixture was heated at 40° C. for 2 h, cooled, quenched with NH₄Cl (sat. aq.), and extracted with ethyl acetate. The combined organic layers were dried over Na₂SO₄ and concentrated to give the crude product which was used without further purification. LCMS-ESI⁺: calc'd for $C_{32}H_{30}ClN_6O_2S$: 597.2 (M+H⁺); Found: 597.0 (M+H⁺).

Preparation of (S)-2-(2-(2-(3-(1H-tetrazol-5-yl)phenyl) pyridin-4-yl)-7-(4-chlorophenyl)-5-methylbenzo[d]thiazol-6-yl)-2-tert-butoxyacetic acid: To a solution of crude (S)-2-(2-(2-(3-(1H-tetrazol-5-yl)phenyl)pyridin-4-yl)-7-(4-chlorophenyl)-5-methylbenzo[d]thiazol-6-yl)-2-tert-butoxyethanol from the previous reaction (assume 0.023 mmol) in 25% water/acetonitrile (0.75 mL) was added sequentially, a stock solution of $CrO_3/H_5IO_6$ (0.27 mL, 0.439 M solution) and $CrO_3$ (3.5 mg, 0.035 mmol) at room temperature. The reaction was stirred for 2 h, filtered, and purified by reverse phase HPLC. Fractions containing the product were pooled and lyophilized to provide the TFA salt of the product. ¹H NMR (400 MHz, CD₃OD) δ 8.84 (dd, J=5.2, 0.6 Hz, 1H), 8.80-8.77 (m, 1H), 8.58 (s, 1H), 8.37-8.31 (m, 1H), 8.19-8.14 (m, 1H), 8.01 (dd, J=5.2, 1.6 Hz, 1H), 7.98 (s, 1H), 7.77 (t, J=7.9 Hz, 1H), 7.73-7.68 (m, 1H), 7.65-7.59 (m, 3H), 5.29 (s, 1H), 2.65 (s, 3H), 0.99 (s, 9H). LCMS-ESI⁺: calc'd for $C_{32}H_{28}ClN_6O_3S$: 611.2 (M+H⁺); Found: 610.9 (M+H⁺).

Example 33

Preparation of (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid (123)

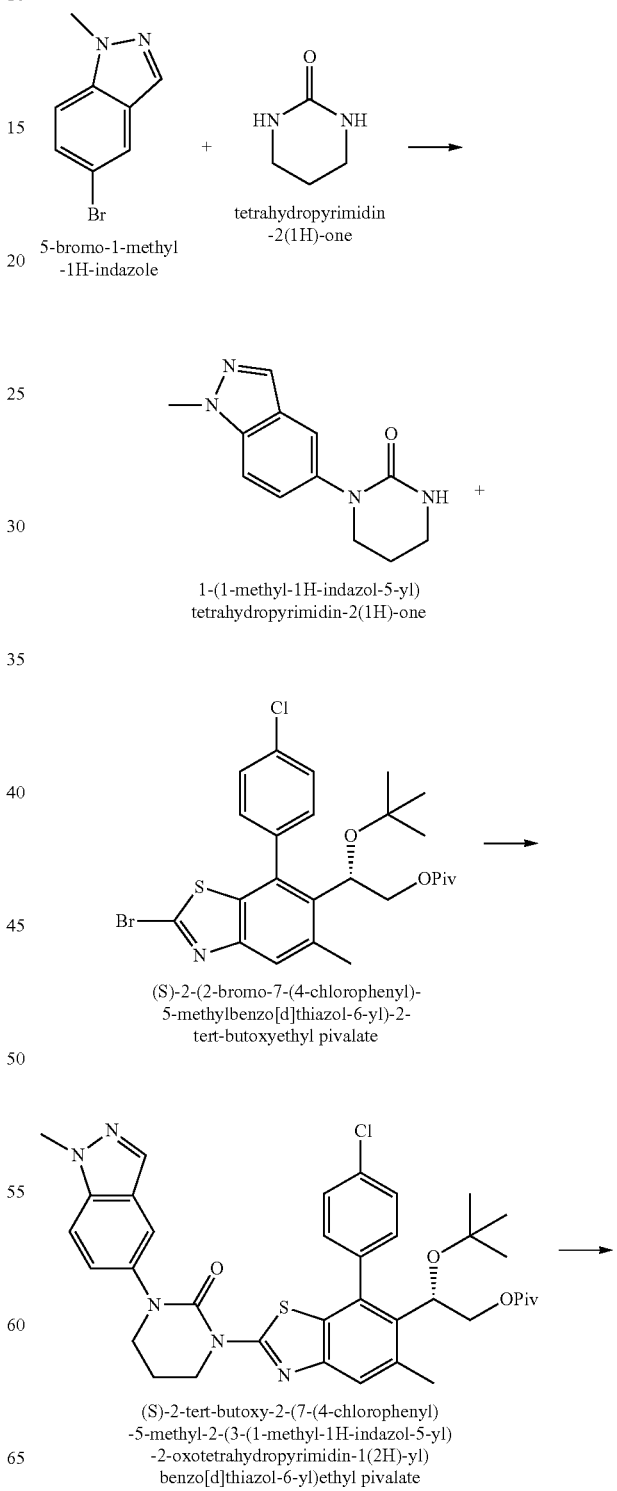

-continued

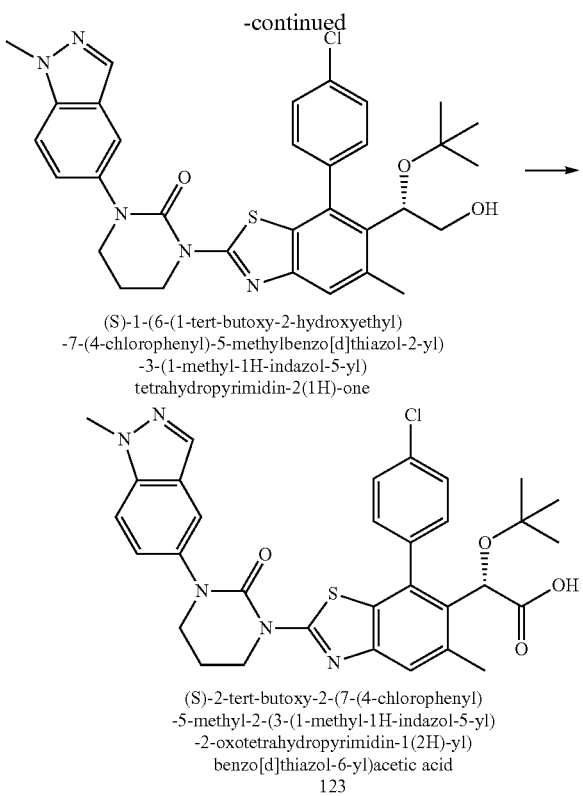

(S)-1-(6-(1-tert-butoxy-2-hydroxyethyl)
-7-(4-chlorophenyl)-5-methylbenzo[d]thiazol-2-yl)
-3-(1-methyl-1H-indazol-5-yl)
tetrahydropyrimidin-2(1H)-one (S)-2-tert-butoxy-2-(7-(4-chlorophenyl)
-5-methyl-2-(3-(1-methyl-1H-indazol-5-yl)
-2-oxotetrahydropyrimidin-1(2H)-yl)
benzo[d]thiazol-6-yl)acetic acid
123

Preparation of 1-(1-methyl-1H-indazol-5-yl)tetrahydropyrimidin-2(1H)-one: To a solution of 5-bromo-1-methyl-1H-indazole (76 mg, 0.36 mmol) in 1,4-dioxane (5 mL) was added tetrahydropyrimidin-2(1H)-one (Aldrich, 216 mg, 2.16 mmol), followed by Pd$_2$(dba)$_3$ (16 mg, 0.02 mmol), 4,5-bis(diphenylphosphino)-9,9-dimethylxanthene (31 mg, 0.06 mmol) and cesium carbonate (176 mg, 0.54 mmol). The reaction mixture was degassed with nitrogen and heated at 100° C. for 16 hours. The mixture was diluted with ethyl acetate, washed with water and brine, and dried over Na$_2$SO$_4$ and filtered. Concentration and purification by flash column chromatography (hexanes/EtOAc) yielded 1-(1-methyl-1H-indazol-5-yl)tetrahydropyrimidin-2(1H)-one. LCMS-ESI$^+$: calc'd for C$_{12}$H$_{14}$N$_4$O: 231.2 (M+H$^+$); Found: 231.2 (M+H$^+$).

Preparation of ((S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)ethyl pivalate: To a solution of (S)-2-(2-bromo-7-(4-chlorophenyl)-5-methylbenzo[d]thiazol-6-yl)-2-tert-butoxyethyl pivalate (27 mg, 0.05 mmol) in 1,4-dioxane (1.5 mL) was added 1-(1-methyl-1H-indazol-5-yl)tetrahydropyrimidin-2(1H)-one (23 mg, 0.1 mmol), followed by Pd$_2$(dba)$_3$ (5 mg, 0.006 mmol), 4,5-bis(diphenylphosphino)-9,9-dimethylxanthene (10 mg, 0.02 mmol) and cesium carbonate (60 mg, 0.18 mmol). The reaction mixture was degassed with nitrogen and heated at 100° C. for 16 hours. The mixture was diluted with ethyl acetate, washed with water and brine, and dried over Na$_2$SO$_4$ and filtered. Concentration and purification by flash column chromatography (hexanes/EtOAc) yielded ((S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)ethyl pivalate. LCMS-ESI$^+$: calc'd for C$_{37}$H$_{42}$ClN$_5$O$_4$S: 688.3 (M+H$^+$); Found: 688.4 (M+H$^+$).

Preparation of (S)-1-(6-(1-tert-butoxy-2-hydroxyethyl)-7-(4-chlorophenyl)-5-methylbenzo[d]thiazol-2-yl)-3-(1-methyl-1H-indazol-5-yl)tetrahydropyrimidin-2(1H)-one: To the solution of ((S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)ethyl pivalate (20 mg) in THF/MeOH (1 mL/1 mL) was added sodium hydroxide solution (1 mL, 1 N, 1 mmol). The mixture was heated at 50° C. for 12 hours. The mixture was diluted with water, and extracted with ethyl acetate. The organic phase was washed with water and brine, dried over sodium sulfate and filtered. Concentration gave (S)-1-(6-(1-tert-butoxy-2-hydroxyethyl)-7-(4-chlorophenyl)-5-methylbenzo[d]thiazol-2-yl)-3-(1-methyl-1H-indazol-5-yl)tetrahydropyrimidin-2(1H)-one. LCMS-ESI$^+$: calc'd for C$_{32}$H$_{34}$ClN$_5$O$_3$S: 604.2 (M+H$^+$); Found: 604.3 (M+H$^+$).

Preparation of (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid:. A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O, 114 mL). To a solution of (S)-1-(6-(1-tert-butoxy-2-hydroxyethyl)-7-(4-chlorophenyl)-5-methylbenzo[d]thiazol-2-yl)-3-(1-methyl-1H-indazol-5-yl)tetrahydropyrimidin-2(1H)-one (16 mg) in wet acetonitrile (1.0 mL, 0.75% H$_2$O) at 0° C. was added the above stock solution (0.6 mL) at 0° C. Filtration and purification by reverse phase HPLC gave (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid. LCMS-ESI$^+$: calc'd for C$_{32}$H$_{32}$ClN$_5$O$_4$S: 618.2 (M+H$^+$); Found: 618.3 (M+H$^+$), 615.8 (M+H$^+$); $^1$H-NMR 400 MHz, (CD$_3$OD) δ 7.99 (s, 1H), 7.70 (s, 1H), 7.62-7.50 (m, 3H), 7.50-7.47 (m, 3H), 7.37 (m, 1H), 5.20 (s, 1H), 4.40 (m, 2H), 4.07 (s, 3H), 3.85 (m, 2H), 2.55 (s, 3H), 2.34 (m, 2H), 0.94 (s, 9H).

Example 34

Preparation of (S)-2-tert-butoxy-2-(7-(4-chlorophenyl)-5-methyl-2-(3-(1-methyl-1H-indazol-5-yl)-2-oxoimidazolidin-1-yl)benzo[d]thiazol-6-yl)acetic acid (124)

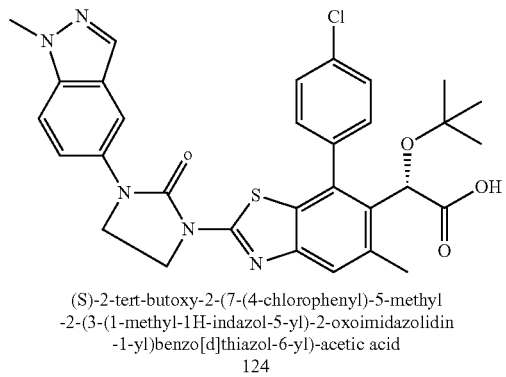

(S)-2-tert-butoxy-2-(7-(4-chlorophenyl)-5-methyl
-2-(3-(1-methyl-1H-indazol-5-yl)-2-oxoimidazolidin
-1-yl)benzo[d]thiazol-6-yl)-acetic acid
124

Preparation of (S)-2-tert-butoxy-2-(7-(4-chlorophenyl)-5-methyl-2-(3-(1-methyl-1H-indazol-5-yl)-2-oxoimidazolidin-1-yl)benzo[d]thiazol-6-yl)acetic acid: (S)-2-tert-butoxy-2-(7-(4-chlorophenyl)-5-methyl-2-(3-(1-methyl-1H- indazol-5-yl)-2-oxoimidazolidin-1-yl)benzo[d]thiazol-6-yl) acetic acid (1.3 mg) was prepared in a similar manner as compound (S)-2-tert-butoxy-2-(7-(4-chlorophenyl)-5-methyl-2-(3-(1-methyl-1H-indazol-5-yl)-2-oxotetrahydropyrimidin-1(2H)-yl)benzo[d]thiazol-6-yl)acetic acid except using imidazolidin-2-one instead of tetrahydropyrimidin-2 (1H)-one. LCMS-ESI+: calc'd for $C_{31}H_{30}ClN_5O_4S$: 604.2 (M+H+); Found: 604.2 (M+H+); $^1$H-NMR 400 MHz, (CD$_3$OD) δ 7.99 (s, 1H), 7.82 (m, 1H), 7.66 (m, 1H), 7.60-7.48 (m, 5H), 7.42 (m, 1H), 5.21 (s, 1H), 4.33 (m, 1H), 4.22 (m, 2H), 4.06 (s, 3H), 3.64 (m, 1H), 2.55 (s, 3H), 0.96 (s, 9H).

Example 35

Preparation of (2S)-2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetic acid (125)

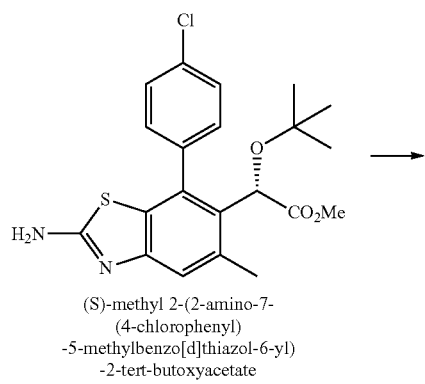

(S)-methyl 2-(2-amino-7-(4-chlorophenyl)-5-methylbenzo[d]thiazol-6-yl)-2-tert-butoxyacetate

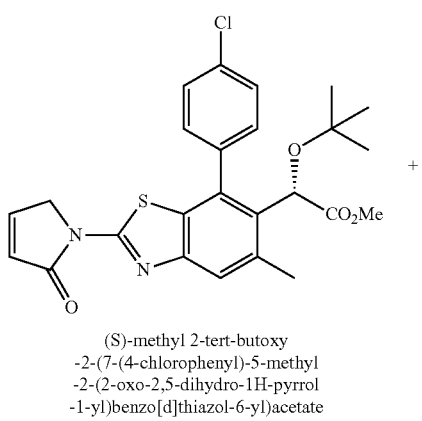

(S)-methyl 2-tert-butoxy-2-(7-(4-chlorophenyl)-5-methyl-2-(2-oxo-2,5-dihydro-1H-pyrrol-1-yl)benzo[d]thiazol-6-yl)acetate

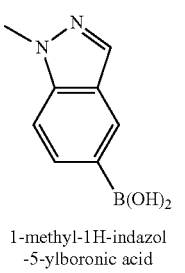

1-methyl-1H-indazol-5-ylboronic acid

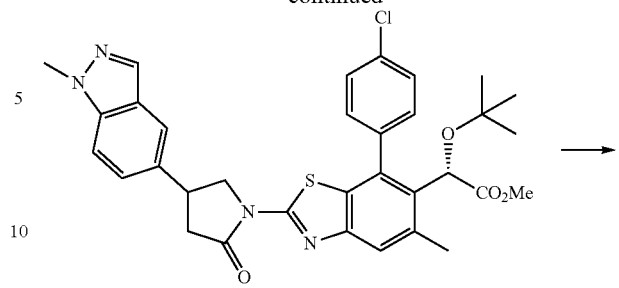

(2S)-methyl 2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetate

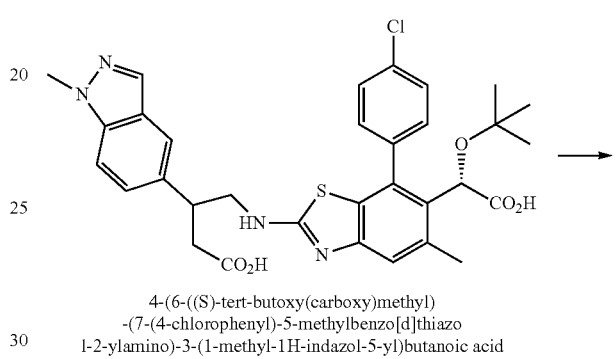

4-(6-((S)-tert-butoxy(carboxy)methyl)-(7-(4-chlorophenyl)-5-methylbenzo[d]thiazol-2-ylamino)-3-(1-methyl-1H-indazol-5-yl)butanoic acid

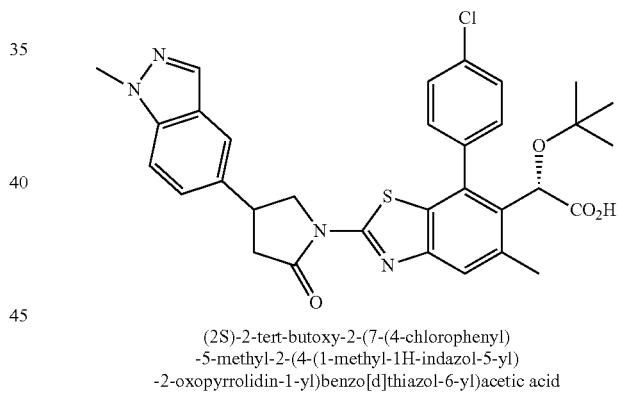

(2S)-2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetic acid
125

Preparation of (S)-methyl 2-tert-butoxy-2-(7-(4-chlorophenyl)-5-methyl-2-(2-oxo-2,5-dihydro-1H-pyrrol-1-yl)benzo[d]thiazol-6-yl)acetate: To a solution of (S)-methyl 2-(2-amino-7-(4-chlorophenyl)-5-methylbenzo[d]thiazol-6-yl)-2-tert-butoxyacetate (40 mg, 0.1 mmol) in acetonitrile (1 mL) was added 2,5-dimethoxy-2,5-dihydrofuran (26 μL, 0.2 mmol), followed by hydrochloric acid (0.2 N, 0.8 mL, 0.16 mmol). The mixture was stirred for 24 hours, and was diluted with EtOAc and quenched with saturated sodium bicarbonate solution. The organic layer was separated, and was washed with water and brine, dried with sodium sulfate and filtered. Concentration and purification by flash column chromatography (hexanes/EtOAc) gave (S)-methyl 2-tert-butoxy-2-(7-(4-chlorophenyl)-5-methyl-2-(2-oxo-2,5-dihydro-1H-pyrrol-1-yl)benzo[d]thiazol-6-yl)acetate. LCMS-ESI+: calc'd for $C_{25}H_{25}ClN_2O_4S$: 485.1 (M+H+); Found: 485.2 (M+H+).

Preparation of (2S)-methyl 2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetate: To a solution of (S)-methyl 2-tert-butoxy-2-(7-(4-chlorophenyl)-5-methyl-2-(2-oxo-2,5-dihydro-1H-pyrrol-1-yl)benzo[d]thiazol-6-yl)acetate (12 mg, 0.025 mmol) in 1,4-dioxane/water (0.5 mL/50 μL) was added 1-methyl-1H-indazol-5-ylboronic acid (8 mg, 0.050 mmol), followed by chloro(1,5-cyclooctadiene) rhodium (I) dimer (1 mg), BINAP (5 mg), and potassium carbonate solution (2 N, 6 μL). The mixture was purged with nitrogen and heated at 80° C. for 24 hours. The mixture was diluted with EtOAc, and was washed with water and brine, dried with sodium sulfate and filtered. Concentration and purification by flash column chromatography (hexanes/EtOAc) gave (2S)-methyl 2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetate. LCMS-ESI+: calc'd for $C_{33}H_{33}ClN_4O_4S$: 617.2 (M+H+); Found: 617.2 (M+H+).

Preparation of 4-(6-((S)-tert-butoxy(carboxy)methyl)-7-(4-chlorophenyl)-5-methylbenzo[d]thiazol-2-ylamino)-3-(1-methyl-1H-indazol-5-yl)butanoic acid: To a solution of (2S)-methyl 2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetate (5 mg) in THF/MeOH (0.5 mL/0.5 mL) was added sodium hydroxide solution (1.0 N, 0.5 mL). The mixture was stirred at 25° C. for 2 hours and heated at 50° C. for 16 hours. The mixture was cooled and neutralized with 0.1 N hydrochloric acid until pH=5. The reaction mixture was freeze-dried and used for next step without further purification. LCMS-ESI+: calc'd for $C_{32}H_{33}ClN_4O_5S$: 621.2 (M+H+); Found: 621.2 (M+H+).

Preparation of (2S)-2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetic acid: To a solution of 4-(6-((S)-tert-butoxy(carboxy)methyl)-7-(4-chlorophenyl)-5-methylbenzo[d]thiazol-2-ylamino)-3-(1-methyl-1H-indazol-5-yl)butanoic acid in DMF (1 mL) was added di-isopropylethylamine (86 μL), followed by N-(3-dimethylaminopropyl)-N-ethylcarbodiimide hydrochloride (19 mg). The mixture was stirred for 2 hours and purified with reverse phase HPLC to give an intermediate (6 mg). The intermediate was dissolved in pyridine (1 mL), water (1 mL) and 1-hydroxybenzotriazole hydrate (1 mg) were added. The mixture was heated at 100° C. for 48 hours. Concentration and purification by reverse phase HPLC gave (2S)-2-tert-butoxy-2-(7-(4-chlorophenyl)-5-methyl-2-(4-(1-methyl-1H-indazol-5-yl)-2-oxopyrrolidin-1-yl)benzo[d]thiazol-6-yl)acetic acid. LCMS-ESI+: calc'd for $C_{32}H_{31}ClN_4O_4S$: 603.2 (M+H+); Found: 603.4 (M+H+); 1H-NMR 400 MHz, (CD3OD) δ 7.97 (m, 1H), 7.74 (m, 1H), 7.60-7.47 (m, 7H), 5.22 (s, 1H), 4.68 (m, 1H), 4.19 (m, 1H), 4.06 (m, 3H), 4.0 (m, 1H), 3.10 (m, 1H), 2.95 (m, 1H), 2.55 (s, 3H), 0.95 (s, 9H).

Example 36

Preparation of (2S)-2-tert-butoxy-2-(7-(4-chlorophenyl)-5-methyl-2-(3-phenoxypyrrolidin-1-yl)benzo[d]thiazol-6-yl)acetic acid (126)

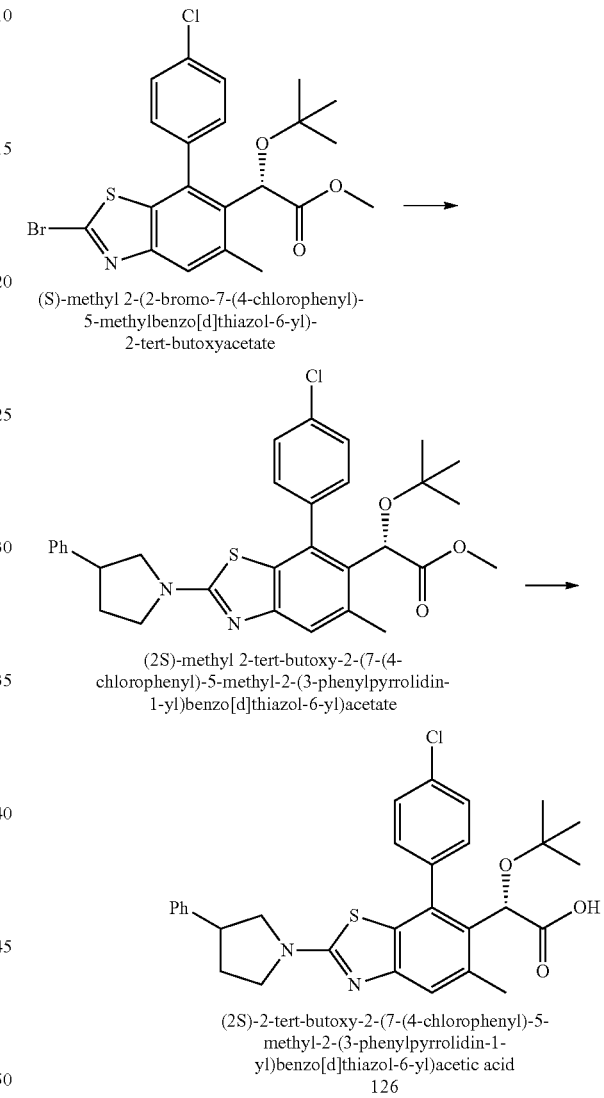

(S)-methyl 2-(2-bromo-7-(4-chlorophenyl)-5-methylbenzo[d]thiazol-6-yl)-2-tert-butoxyacetate (2S)-methyl 2-tert-butoxy-2-(7-(4-chlorophenyl)-5-methyl-2-(3-phenylpyrrolidin-1-yl)benzo[d]thiazol-6-yl)acetate (2S)-2-tert-butoxy-2-(7-(4-chlorophenyl)-5-methyl-2-(3-phenylpyrrolidin-1-yl)benzo[d]thiazol-6-yl)acetic acid
126

Preparation of (2S)-methyl 2-tert-butoxy-2-(7-(4-chlorophenyl)-5-methyl-2-(3-phenylpyrrolidin-1-yl)benzo[d]thiazol-6-yl)acetate: To a solution of (9-methyl 2-(2-bromo-7-(4-chlorophenyl)-5-methylbenzo[d]thiazol-6-yl)-2-tert-butoxyacetate (46.1 mg, 0.095 mmol) in THF (2 mL) was added 3-phenylpyrrolidine (16.9 mg, 0.115 mmol) and diethylpropylamine (24.8 μL, 0.143 mmol). The resulting reaction mixture was heated at 50° C. for 16 hr then evaporated to dryness. The residue was purified via chromatography on silica gel (4 g "gold" ISCO column; 0-60% EtOAc/Hex) to give (2S)-methyl 2-tert-butoxy-2-(7-(4-chlorophenyl)-5-methyl-2-(3-phenylpyrrolidin-1-yl)benzo[d]thiazol-6-yl)acetate. LCMS-ESI+: calc'd for $C_{31}H_{34}ClN_2O_3S$: 548.2 550.2 (M+H+); found: 549.3, 551.3 (M+H+).

Preparation of (2S)-2-tert-butoxy-2-(7-(4-chlorophenyl)-5-methyl-2-(3-phenoxypyrrolidin-1-yl)benzo[d]thiazol-6-yl)acetic acid: To a solution of (2S)-methyl 2-tert-butoxy-2-(7-(4-chlorophenyl)-5-methyl-2-(3-phenylpyrrolidin-1-yl)benzo[d]thiazol-6-yl)acetate (29.3 mg, 0.653 mmol) in $CH_3OH$ (1 mL) was added NaOH (1N, 1 mL, 1 mmol), the resulting mixture was heated at 50 C for 10 hr. The mixture was acidified to pH 3 and evaporated to a small volume, and the residue was partitioned between $CH_2Cl_2$ and brine. The organic layer was separated, dried, filtered and evaporated to dryness. The residue was purified on TLC (50% EtOAc/Hex) to give (2S)-2-tert-butoxy-2-(7-(4-chlorophenyl)-5-methyl-2-(3-phenoxypyrrolidin-1-yl)benzo[d]thiazol-6-yl)acetic acid. LCMS-ESI$^+$: calc'd for $C_{30}H_{32}ClN_2O_3S$: 534.2, 536.2 (M+H$^+$); found: 535.2, 537.2 (M+H$^+$). $^1$H-NMR: 400 MHz, (CD$_3$OD) δ: 7.63 (dd, J=2.0, 7.2 Hz, 1H), 7.49-7.52 (m, 3H), 7.30-7.34 (m, 5H), 7.24 (m, 1H), 5.13 (s, 1H), 3.94 (m, 1H), 3.70 (m, 1H), 3.52-3.63 (m, 4H), 2.48 (s, 3H), 2.46 (m, 1H), 2.20 (m, 1H), 0.94 (s, 9H).

Example 37

Preparation of 6-(3-bromophenyl)-1-methyl-1H-pyrazolo[4,3-b]pyridine: To a solution of 6-bromo-1-methyl-1H-pyrazolo[4,3-b]pyridine (127)

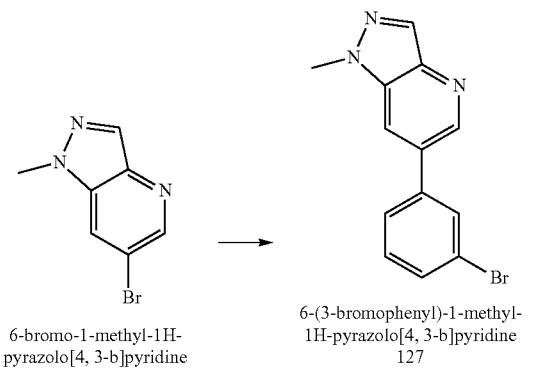 [SMILES: Cn1ncc2ncc(Br)cc21 ; Cn1ncc2ncc(-c3cccc(Br)c3)cc21]

6-bromo-1-methyl-1H-pyrazolo[4, 3-b]pyridine 6-(3-bromophenyl)-1-methyl-1H-pyrazolo[4, 3-b]pyridine
127

Preparation of 6-(3-bromophenyl)-1-methyl-1H-pyrazolo[4,3-b]pyridine: To a solution of 6-bromo-1-methyl-1H-pyrazolo[4,3-b]pyridine (120 mg, 0.566 mmol) and 3-bromophenylboronic acid (136 mg, 0.679 mmol) in degassed 1,4-dioxane (6 mL) and water (2 mL) was added $K_2CO_3$ (391 mg, 2.83 mmol) and tetrakis(triphenylphosphine)palladium(0) (32 mg, 0.028 mmol). The reaction mixture was heated at 90° C. for 1 h, cooled and partitioned between ethyl acetate and brine. The organic layer was separated, dried over $Na_2SO_4$ and concentrated to give crude which was purified by chromatographic column to afford the desired product. LCMS-ESI$^+$: calc'd for $C_{13}H_{10}BrN_3$: 288.01 (M+H$^+$); Found: 288.2 (M+H$^+$).

Example 38

Representative procedure for the synthesis of stannane intermediates used in Method H. Preparation of 1-methyl-5-(4-(tributylstannyl)pyrimidin-2-yl)-1H-indazole (128).

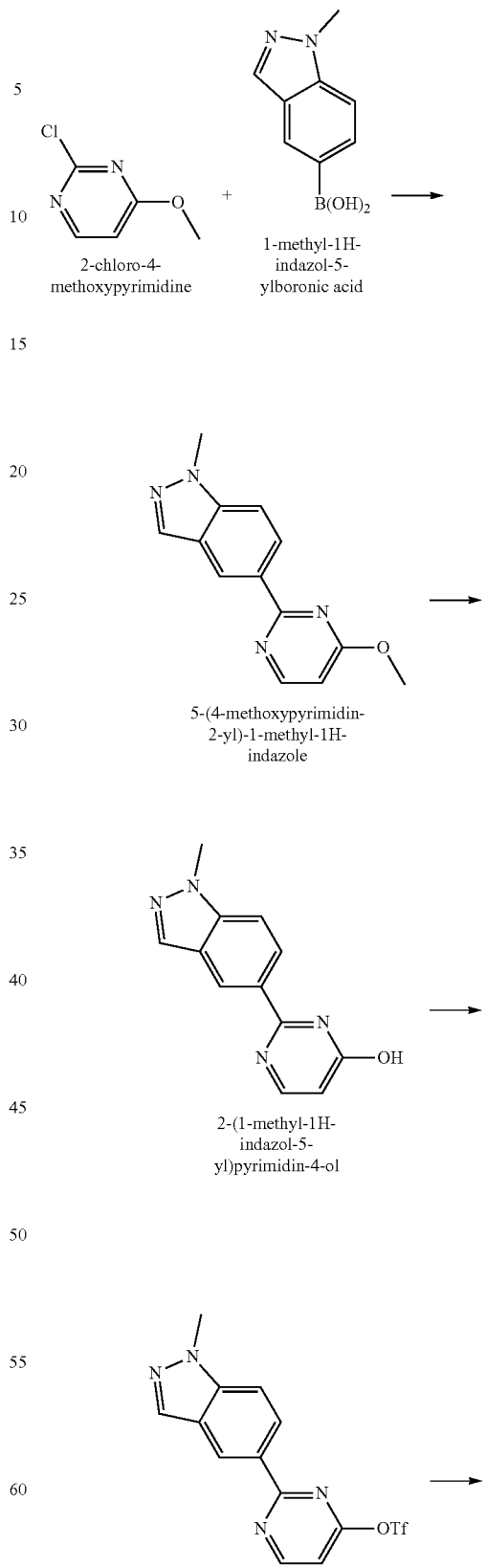

2-chloro-4-methoxypyrimidine 1-methyl-1H-indazol-5-ylboronic acid 5-(4-methoxypyrimidin-2-yl)-1-methyl-1H-indazole 2-(1-methyl-1H-indazol-5-yl)pyrimidin-4-ol 2-(1-methyl-1H-indazol-5-yl)pyrimidin-4-yl trifluoromethanesulfonate

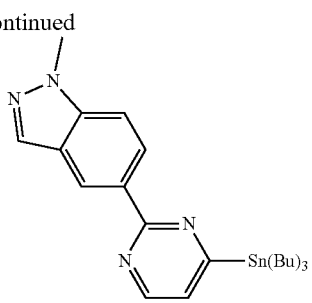

1-methyl-5-(4-
(tributylstannyl)pyrimidin-2-
yl)-1H-indazole
128

Preparation of 5-(4-methoxypyrimidin-2-yl)-1-methyl-1H-indazole: 2-chloro-4-methoxypyrimidine (100.0 mg, 0.69 mmol), 1-methyl-1H-indazol-5-ylboronic acid (133.9 mg, 0.76 mmol), Pd(PPh$_3$)$_4$ (79.9 mg, 0.069 mmol), and K$_2$CO$_3$ (286.8 mg, 2.075 mmol) were taken in a microwave vial and the vial was vacuum pumped and flushed with argon three times. To this mixture was added degassed toluene (2.5 mL) and DMF (0.28 mL). The reaction mixture was heated in a microwave at 185° C. for 30 min, diluted with ethyl acetate, filtered through Celite (ethyl acetate eluent), and concentrated. Purification by flash column chromatography on silica gel (hexanes/ethyl acetate eluent) provided the product. $^1$H NMR (400 MHz, CDCl$_3$) δ 8.92 (s, 1H), 8.56 (dd, J=8.9, 1.3 Hz, 1H), 8.52 (d, J=5.8 Hz, 1H), 8.10 (s, 1H), 7.47 (d, J=8.9 Hz, 1H), 6.64 (d, J=5.8 Hz, 1H), 4.14 (s, 3H), 4.12 (s, 3H). LCMS-ESI$^+$: calc'd for C$_{13}$H$_{13}$N$_4$O: 241.1 (M+H$^+$); Found: 241.2 (M+H$^+$).

Preparation of 2-(1-methyl-1H-indazol-5-yl)pyrimidin-4-ol: 5-(4-methoxypyrimidin-2-yl)-1-methyl-1H-indazole (30.2 mg, 0.126 mmol) was suspended in hydrochloric acid (1.25 mL of a 2N solution) and heated at 85° C. for 14 h, cooled, and neutralized by dropwise addition of NaOH (2N solution). The mixture was extracted six times with 1:1 chloroform/isopropanol and the combined organic layers were dried over Na$_2$SO$_4$ and concentrated to provide the crude product which was used without further purification. LCMS-ESI$^+$: calc'd for C$_{12}$H$_{11}$N$_4$O: 227.1 (M+H$^+$); Found: 227.2 (M+H$^+$).

Preparation of 2-(1-methyl-1H-indazol-5-yl)pyrimidin-4-yl trifluoromethanesulfonate: To a solution of crude 2-(1-methyl-1H-indazol-5-yl)pyrimidin-4-ol (41.5 mg, 0.183 mmol) in DCM (2.0 mL) was added triethylamine (0.15 mL, 1.101 mmol) followed by trifluoromethanesulfonic anhydride (91.3 μL, 0.550 mmol) at −78° C. The reaction mixture was stirred for 16 h and allowed to slowly warm to room temperature during this time then concentrated. Purification by flash column chromatography on silica gel (hexanes/ethyl acetate eluent) provided the product. $^1$H NMR (400 MHz, CDCl$_3$) δ 8.92 (d, J=5.4 Hz, 1H), 8.90 (s, 1H), 8.49 (dd, J=8.9, 1.5 Hz, 1H), 8.13 (s, 1H), 7.49 (d, J=8.9 Hz, 1H), 7.00 (d, J=5.4 Hz, 1H), 4.13 (s, 3H). LCMS-ESI$^+$: calc'd for C$_{13}$H$_{10}$F$_3$N$_4$O$_3$S: 359.0 (M+H$^+$); Found: 359.1 (M+H$^+$).

Preparation of 1-methyl-5-(4-(tributylstannyl)pyrimidin-2-yl)-1H-indazole: 2-(1-methyl-1H-indazol-5-yl)pyrimidin-4-yl trifluoromethanesulfonate (43.4 mg, 0.121 mmol), Pd(PPh$_3$)$_4$ (7.0 mg, 0.006 mmol), and lithium chloride (25.6 mg, 0.604 mmol) were taken in a microwave vial and the vial was vacuum pumped and flushed with argon three times. To this mixture was added degassed toluene (2.0 mL) and bis(tributyltin) (61 μL, 0.121 mmol). The reaction mixture was heated at 110° C. for 16 h, cooled, quenched with water, and diluted with ethyl acetate. The aqueous layer was removed and twice extracted with ethyl acetate. The combined organic layers were dried over Na$_2$SO$_4$ and concentrated. Purification by flash column chromatography on silica gel (hexanes/ethyl acetate eluent) provided the product. LCMS-ESI$^+$: calc'd for C$_{24}$H$_{37}$N$_4$Sn: 501.2 (M+H$^+$); Found: 501.3 (M+H$^+$).

Example 39

The compounds in the table below were prepared by the general method noted (Method B (example 14), Method C (example 15), Method D (example 16), Method E (example 17), Method F (example 18), Method G (example 19), Method H (example 20), Method I (example 21) and Method J (example 22)).

| Compound Number | Structure | Method | Parent MW | LCMS-ESI+ | 1H NMR |
|---|---|---|---|---|---|
| 129 | 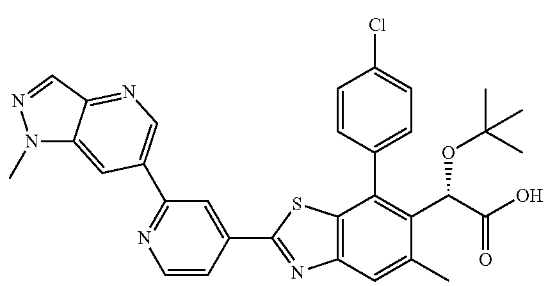 [SMILES: Cc1cc2nc(-c3ccnc(-c4cnc5cnn(C)c5c4)c3)sc2c(-c2ccc(Cl)cc2)c1[C@H](OC(C)(C)C)C(=O)O] | C | 598.1 | 598.2 | $^1$H NMR (400 MHz, CD$_3$OD): δ 9.31 (s, 1H), 8.85-8.84 (m, 2H), 8.64 (s, 1H), 8.25 (s, 1H), 8.01-7.954 (m, 2H), 7.71-7.60 (m, 4H), 5.28 (s, 1H), 4.22 (d, J = 1 Hz, 3H), 2.64 s, 3H), 0.97 (s, 9H) |

-continued

| Compound Number | Structure | Method | Parent MW | LCMS-ESI+ | 1H NMR |
|---|---|---|---|---|---|
| 130 | 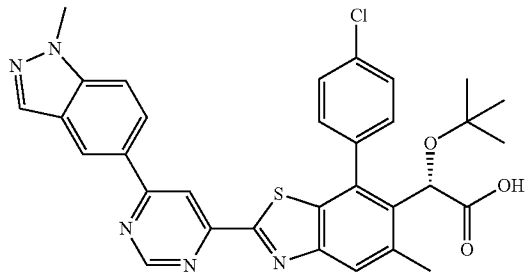 | H | 598.1 | 597.9 | $^1$H NMR (400 MHz, CD$_3$OD) δ 9.19 (d, J = 0.9 Hz, 1H), 8.84 (d, J = 1.0 Hz, 1H), 8.78 (s, 1H), 8.38 (dd, J = 8.9, 1.6 Hz, 1H), 8.21 (s, 1H), 7.98 (s, 1H), 7.75 (d, J = 9.2 Hz, 1H), 7.72-7.69 (m, 1H), 7.65-7.59 (m, 3H), 5.30 (s, 1H), 4.14 (s, 3H), 2.65 (s, 3H), 0.98 (s, 9H). |
| 131 | 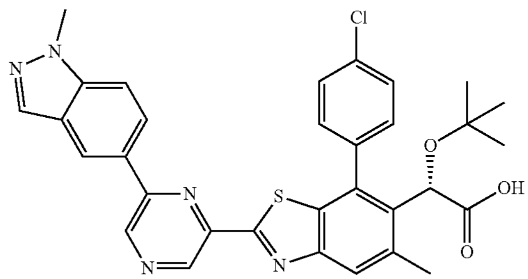 | H | 598.1 | 598 | $^1$H NMR (400 MHz, CD$_3$OD) δ 9.37 (s, 1H), 9.29 (s, 1H), 8.62 (s, 1H), 8.28 (dd, J = 8.9, 1.6 Hz, 1H), 8.16 (s, 1H), 7.94 (s, 1H), 7.73-7.72 (m, 1H), 7.17-7.69 (m, 1H), 7.67-7.60 (m, 3H), 5.29 (s, 1H), 4.11 (s, 3H), 2.64 (s, 3H), 0.99 (s, 9H). |
| 132 | 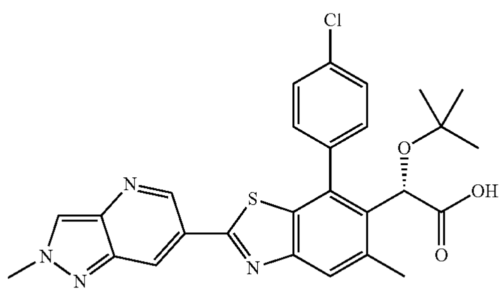 [SMILES: Cc1cc2nc(-c3cnc4cn(C)nc4c3)sc2c(-c2ccc(Cl)cc2)c1[C@H](OC(C)(C)C)C(=O)O] | I | 521 | 521.3 | $^1$H NMR (400 MHz, CD$_3$OD) δ 9.23 (d, J = 1 Hz, 1H), 8.65 (s, 1H), 8.54 (s, 1H), 7.90 (s, 1H), 7.71-7.59 (m, 4H), 5.27 (s, 1H), 4.31 (s, 3H), 2.62 (s, 3H), 0.97 (s, 9H). |
| 133 | 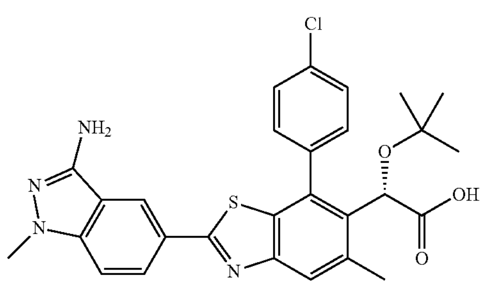 [SMILES: Cc1cc2nc(-c3ccc4c(c3)c(N)nn4C)sc2c(-c2ccc(Cl)cc2)c1[C@H](OC(C)(C)C)C(=O)O] | J | 535.1 | 535.3 | $^1$H NMR (400 MHz, CD$_3$OD): δ 8.40 (s, 1H), 8.09-8.07 (m, 1H), 7.79 (s, 1H), 7.69 (d, J = 4.2 Hz, 1H), 7.60-7.41 (m, 4H), 5.25 (s, 1H), 3.83 (s, 3H), 2.60 (s, 3H), 0.97 (s, 9H). |
| 134 | 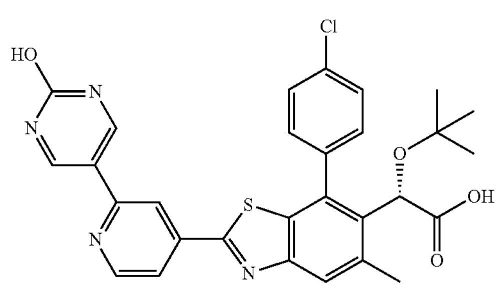 [SMILES: Cc1cc2nc(-c3ccnc(-c4cnc(O)nc4)c3)sc2c(-c2ccc(Cl)cc2)c1[C@H](OC(C)(C)C)C(=O)O] | F | 561.13 | 561.1 | $^1$H NMR (400 MHz, CD$_3$OD): δ 9.13 (bs, 2H), 8.72 (bs, 1H), 8.36 (bs, 1H), 7.92-7.90 (m, 2H), 7.69-7.56 (m, 4H), 5.27 (s, 1H), 2.62 (s, 3H), 0.97 (s, 9H). |

| Compound Number | Structure | Method | Parent MW | LCMS-ESI+ | 1H NMR |
|---|---|---|---|---|---|
| 135 | 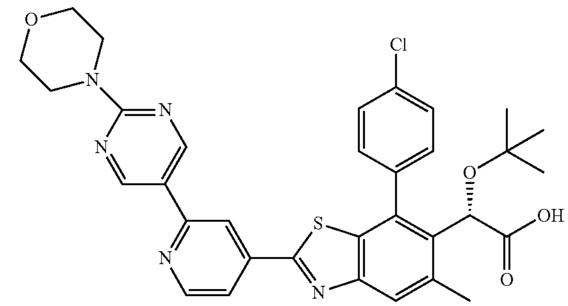 [SMILES: Cc1cc2nc(-c3ccnc(-c4cnc(N5CCOCC5)nc4)c3)sc2c(-c2ccc(Cl)cc2)c1[C@H](OC(C)(C)C)C(=O)O] | F | 630.29 | 630.2 | ¹H NMR (400 MHz, CD₃OD): δ 9.03 (s, 2H), 8.71 (d, J = 2.4 Hz, 1H), 8.43 (s, 1H), 7.95-7.93 (m, 2H), 7.70-7.68 (m, 1H), 7.60 (s, 3H), 5.27 (s, 1H), 3.92-3.89 (m, 4H), 3.78-3.75 (m, 4H), 2.63 (s, 3H), 0.97 (s, 9H). |
| 136 | 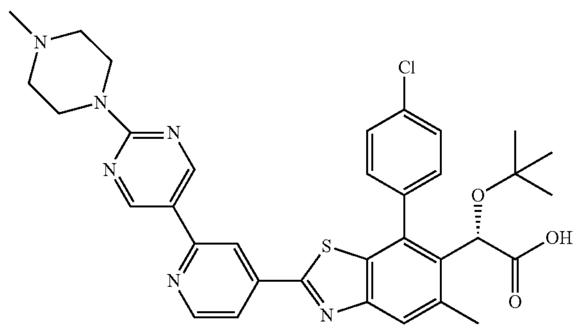 [SMILES: Cc1cc2nc(-c3ccnc(-c4cnc(N5CCN(C)CC5)nc4)c3)sc2c(-c2ccc(Cl)cc2)c1[C@H](OC(C)(C)C)C(=O)O] | F | 643.22 | 643.2 | ¹H NMR (400 MHz, CD₃OD): δ 9.10 (s, 2H), 8.72 (d, J = 2.6 Hz, 1H), 8.38 (s, 1H), 7.92 (s, 1H), 7.87-7.7.86 (m, 1H), 7.70-7.68 (m, 1H), 7.62-7.58 (m, 3H), 5.27 (s, 1H), 5.10-5.04 (m, 2H), 3.61-3.34 (m, 4H), 3.29-3.18 (m, 2H), 2.97 (s, 3H), 2.62 (s, 3H), 0.97 (s, 9H). |
| 137 | 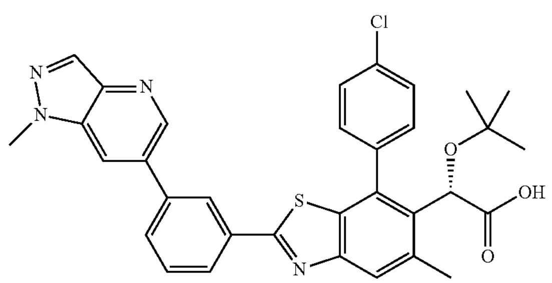 [SMILES: Cc1cc2nc(-c3cccc(-c4cnc5cnn(C)c5c4)c3)sc2c(-c2ccc(Cl)cc2)c1[C@H](OC(C)(C)C)C(=O)O] | I | 597.1 | 597.2 | ¹H NMR (400 MHz, CD₃OD) δ 8.92 (s, 1H), 8.51-8.45 (m, 2H), 8.25 (s, 1H), 8.10-7.94 (m, 2H), 7.87-7.58 (m, 6H), 5.26 (s, 1H), 4.20 (s, 3H), 2.62 (s, 3H), 0.98 (s, 9H). |
| 138 | 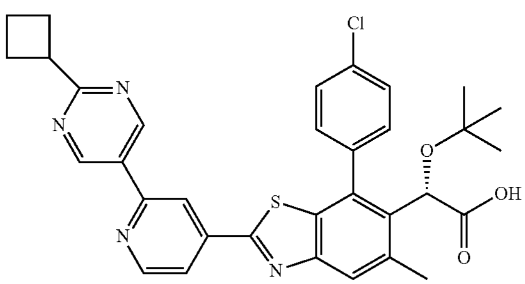 [SMILES: Cc1cc2nc(-c3ccnc(-c4cnc(C5CCC5)nc4)c3)sc2c(-c2ccc(Cl)cc2)c1[C@H](OC(C)(C)C)C(=O)O] | F | 599.15 | 599.1 | ¹H NMR (400 MHz, CD₃OD): δ 9.43 (s, 2H), 8.83 (d, J = 2.4 Hz, 1H), 8.57 (s, 1H), 8.02-8.8.00 (m, 1H), 7.95 (s, 1H), 7.70-7.68 (m, 1H), 7.60-7.59 (m, 3H), 5.27 (s, 1H), 3.92-3.31 (m, 1H), 2.63 (s, 3H), 2.59-2.42 (m, 4H), 2.20-2.2.12 (m, 2H), 2.03-1.97 (m, 2H), 0.97 (s, 9H). |
| 139 | 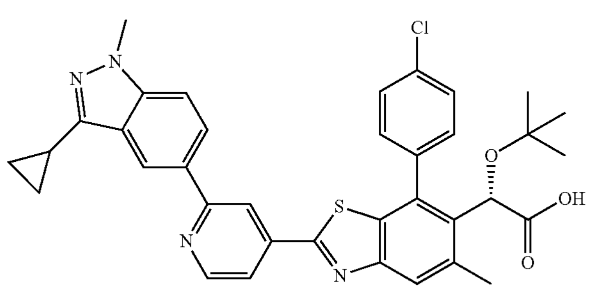 [SMILES: Cc1cc2nc(-c3ccnc(-c4ccc5c(c4)c(C4CC4)nn5C)c3)sc2c(-c2ccc(Cl)cc2)c1[C@H](OC(C)(C)C)C(=O)O] | F | 637.2 | 637.2 | ¹H NMR (400 MHz, CD₃OD): δ 8.60 (d, J = 2.6 Hz, 1H), 8.40 (s, 1H), 8.34 (s, 1H), 7.93-7.91 (m, 1H), 7.86-7.83 (m, 2H), 7.61-7.59 (m, 1H), 7.50-7.45 (m, 4H), 5.28 (s, 1H), 3.86 (s, 3H), 2.53 (s, 3H), 2.24-2.21 (m, 1H), 0.99-0.97 (m, 4H), 0.88 (s, 9H). |

| Compound Number | Structure | Method | Parent MW | LCMS-ESI+ | 1H NMR |
|---|---|---|---|---|---|
| 140 | 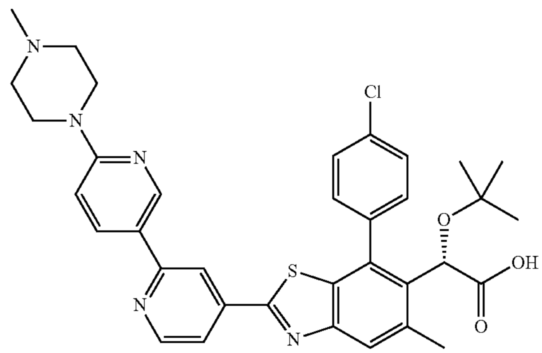 [SMILES: Cc1cc2nc(-c3ccnc(-c4ccc(N5CCN(C)CC5)nc4)c3)sc2c(-c2ccc(Cl)cc2)c1[C@H](OC(C)(C)C)C(=O)O] | F | 642.22 | 642.2 | $^1$H NMR (400 MHz, CD$_3$OD): δ 8.79 (d, J = 1.2 Hz, 1H), 8.61 (d, J = 2.8 Hz, 1H), 8.29 (s, 1H), 8.23-8.21 (m, 1H), 7.83 (s, 1H), 7.77-7.76 (m, 1H), 7.61-7.58 (m, 1H), 7.52-7.48 (m, 3H), 6.98 (d, J = 4.4 Hz, 1H), 5.18 (s, 1H), 4.55-4.52 (m, 2H), 3.39-3.21 (m, 6H), 2.88 (s, 3H), 2.53 (s, 3H), 0.87 (s, 9H). |
| 141 | 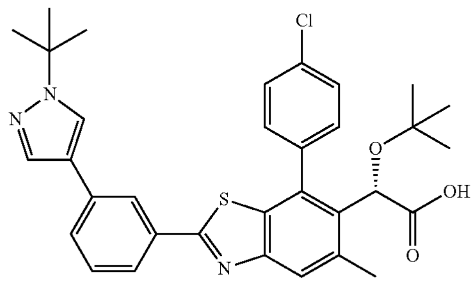 [SMILES: Cc1cc2nc(-c3cccc(-c4cnn(C(C)(C)C)c4)c3)sc2c(-c2ccc(Cl)cc2)c1[C@H](OC(C)(C)C)C(=O)O] | B | 588.17 | 588.3 | $^1$H NMR (400 MHz, CD$_3$OD): δ (8.23-8.22 (m, 2H), 7.93 (s, 1H), 7.83-7.80 (m, 2H), 7.74-7.67 (m, 2H), 7.58 (m, 3H), 7.48-7.45 (m, 1H), 5.25 (s, 1H), 2.61 (s, 3H), 1.64 (s, 9H), 0.97 (s, 9H). |
| 142 | 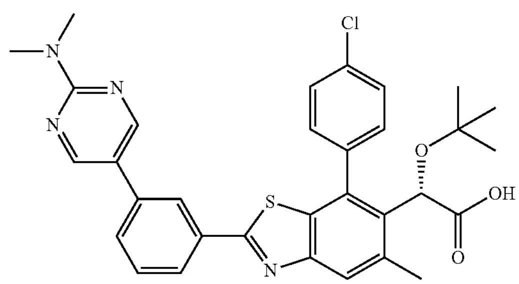 [SMILES: Cc1cc2nc(-c3cccc(-c4cnc(N(C)C)nc4)c3)sc2c(-c2ccc(Cl)cc2)c1[C@H](OC(C)(C)C)C(=O)O] | D | 587.14 | 587.2 | $^1$H NMR (400 MHz, CD$_3$OD): δ 8.57 (s, 2H), 8.10 (s, 1H), 7.81 (d, J = 4 Hz, 1H), 7.72 (s, 1H), 7.58 (d, J = 4 Hz, 1H), 7.47-7.42 (m, 4H), 5.16 (s, 1H), 3.14 (s, 6H), 2.61 (s, 3H), 0.97 (s, 9H). |
| 143 | 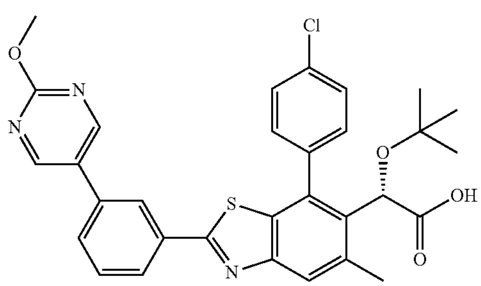 [SMILES: COc1ncc(-c2cccc(-c3nc4cc(C)c([C@H](OC(C)(C)C)C(=O)O)c(-c5ccc(Cl)cc5)c4s3)c2)cn1] | D | 574.1 | 574.2 | $^1$H NMR (400 MHz, CD$_3$OD): δ 0.89 (s, 2H), 8.29 (s, 1H), 8.02 (d, J = 3.8 Hz, 1H), 7.85 (s, 1H), 7.78 (d, J = 4 Hz, 1H), 7.68 (d, J = 4.2 Hz, 1H), 7.63-7.58 (m, 4H), 5.26 (s, 1H), 4.06 (s, 3H), 2.61 (s, 3H), 0.97 (s, 9H). |
| 144 | 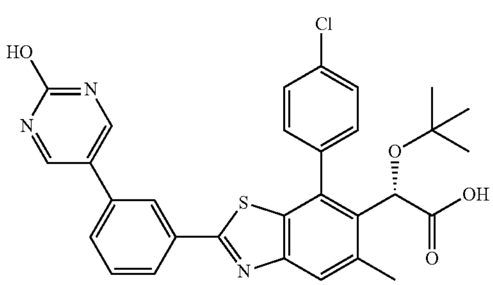 [SMILES: Cc1cc2nc(-c3cccc(-c4cnc(O)nc4)c3)sc2c(-c2ccc(Cl)cc2)c1[C@H](OC(C)(C)C)C(=O)O] | D | 560.07 | 560.2 | $^1$H NMR (400 MHz, CD$_3$OD): δ 8.65 (s, 2H), 8.14 (s, 1H), 7.91 (d, J = 4 Hz, 1H), 7.74 (s, 1H), 7.65-7.46 (m, 6H), 5.26 (s, 1H), 2.51 (s, 3H), 0.87 (s, 9H). |

| Compound Number | Structure | Method | Parent MW | LCMS-ESI+ | 1H NMR |
|---|---|---|---|---|---|
| 145 | 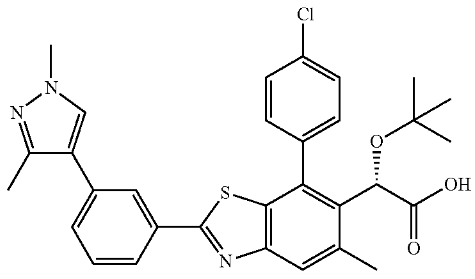 [SMILES: Cc1cc2nc(-c3cccc(-c4cn(C)nc4C)c3)sc2c(-c2ccc(Cl)cc2)c1[C@H](OC(C)(C)C)C(=O)O] | B | 560.12 | 560.2 | ¹H NMR (400 MHz, CD₃OD): δ 7.98 (s, 1H), 7.79-7.73 (m, 3H), 7.60-7.587 (m, 3H), 7.50-7.48 (m, 4H), 7.43-7.39 (m, 1H), 5.16 (s, 1H), 3.78 (s, 3H), 2.52 (s, 3H), 2.31 (s, 3H), 0.88 (s, 9H). |
| 146 | 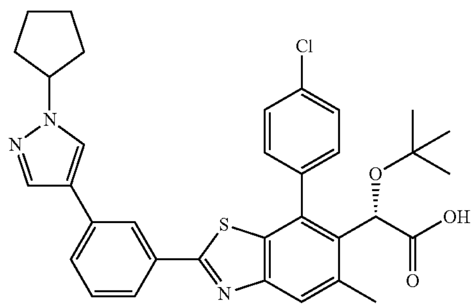 [SMILES: Cc1cc2nc(-c3cccc(-c4cnn(C5CCCC5)c4)c3)sc2c(-c2ccc(Cl)cc2)c1[C@H](OC(C)(C)C)C(=O)O] | B | 600.18 | 600.2 | 1H NMR (400 MHz, CD3OD): δ 8.22 (s, 1H), 8.15 (s, 1H), 7.92 (s, 1H), 7.85-7.82 (m, 2H), 7.73-7.67 (m, 2H), 7.60-7.58 (m, 3H), 7.50-7.46 (m, 1H), 5.26 (s, 1H), 4.76-4.72 (m, 1H), 2.62 (s, 3H), 2.22-2.19 (m, 2H), 2.07-2.03 (m, 2H), 1.93-1.91 (m, 2H), 1.78-1.73 (m, 2H), 0.97 (s, 9H). |
| 147 | 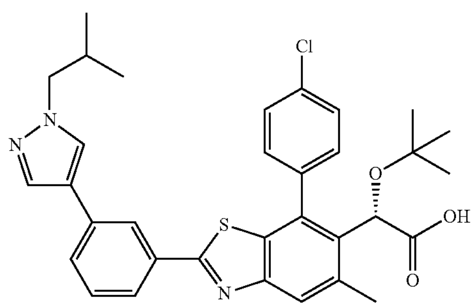 [SMILES: Cc1cc2nc(-c3cccc(-c4cnn(CC(C)C)c4)c3)sc2c(-c2ccc(Cl)cc2)c1[C@H](OC(C)(C)C)C(=O)O] | B | 588.17 | 588.2 | ¹H NMR (400 MHz, CD₃OD): δ 8.21 (s, 1H), 8.09 (s, 1H), 7.92 (s, 1H), 7.83-7.81 (m, 2H), 7.72-7.67 (m, 2H), 7.59-7.58 (m, 3H), 7.49-7.45 (m, 1H), 5.25 (s, 1H), 5.25 (s, 1H), 3.98 (d, J = 3.6 Hz, 2H), 2.61 (s, 3H), 2.24-2.20 (m, 1H), 0.97 (s, 9H), 0.94 (d, J = 3.4 Hz, 6H). |
| 148 | 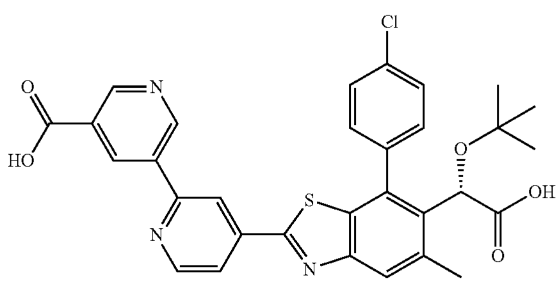 [SMILES: Cc1cc2nc(-c3ccnc(-c4cncc(C(=O)O)c4)c3)sc2c(-c2ccc(Cl)cc2)c1[C@H](OC(C)(C)C)C(=O)O] | C | 588.08 | 588.1 | ¹H NMR (400 MHz, CD₃OD) δ 9.49 (s, 1H), 9.22 (s, 1H), 9.14-9.10 (m, 1H), 8.86 (d, J = 5.1 Hz, 1H), 8.62 (s, 1H), 8.02 (dd, J = 5.1, 1.3 Hz, 1H), 7.97 (s, 1H), 7.73-7.68 (m, 1H), 7.64-7.59 (m, 3H), 5.28 (s, 1H), 2.64 (s, 1H), 2.64 (s, 3H), 0.98 (s, 9H). |
| 149 | 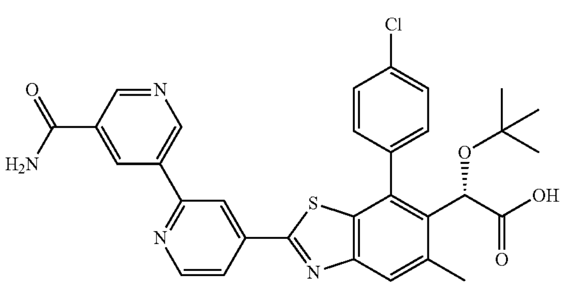 [SMILES: Cc1cc2nc(-c3ccnc(-c4cncc(C(N)=O)c4)c3)sc2c(-c2ccc(Cl)cc2)c1[C@H](OC(C)(C)C)C(=O)O] | C | 587.1 | 587.2 | ¹H NMR (400 MHz, CD₃OD) δ 9.49 (s, 1H), 9.14 (s, 1H), 9.10 (s, 1H), 8.86 (d, J = 5.1 Hz, 1H), 8.63 (s, 1H), 8.04 (d, J = 5.2 Hz, 1H), 7.95 (s, 1H), 7.73-7.67 (m, 1H), 7.63-7.58 (m, 3H), 5.28 (s, 1H), 2.64 (s, 3H), 0.99 (s, 9H). |

-continued

| Compound Number | Structure | Method | Parent MW | LCMS-ESI+ | 1H NMR |
|---|---|---|---|---|---|
| 150 | 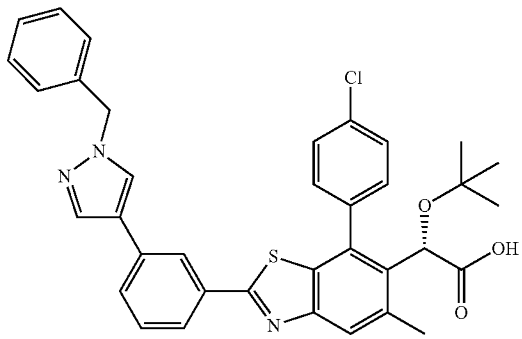 [SMILES: Cc1cc2nc(-c3cccc(-c4cnn(Cc5ccccc5)c4)c3)sc2c(-c2ccc(Cl)cc2)c1[C@H](OC(C)(C)C)C(=O)O] | B | 622.19 | 622.2 | ¹H NMR (400 MHz, CD₃OD): δ 8.21 (s, 1H), 8.17 (s, 1H), 7.96 (s, 1H), 7.83-7.28 (m, 13H), 5.38 (s, 2H), 5.25 (s, 1H), 2.61 (s, 3H), 0.97 (s, 9H). |
| 151 | 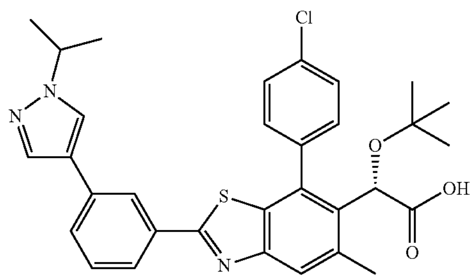 [SMILES: Cc1cc2nc(-c3cccc(-c4cnn(C(C)C)c4)c3)sc2c(-c2ccc(Cl)cc2)c1[C@H](OC(C)(C)C)C(=O)O] | B | 574.14 | 574.2 | 1H NMR (400 MHz, CD3OD): δ 8.22 (s, 1H), 8.16 (s, 1H), 7.92 (s, 1H), 7.84-7.82 (m, 2H), 7.73-7.59 (m, 5H), 7.50-7.46 (m, 1H), 5.26 (s, 1H), 4.59-4.55 (m, 1H), 2.61 (s, 3H), 1.54 (d, J = 3.2 Hz, 6H), 0.97 (s, 9H). |
| 152 | 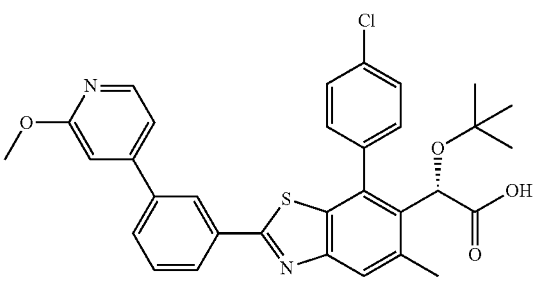 [SMILES: COc1cc(-c2cccc(-c3nc4cc(C)c([C@H](OC(C)(C)C)C(=O)O)c(-c5ccc(Cl)cc5)c4s3)c2)ccn1] | B | 573.11 | 573.2 | ¹H NMR (400 MHz, CD₃OD): δ 8.38 (s, 1H), 8.22 (d, J = 2.8 Hz, 1H), 8.08-8.06 (m, 1H), 7.89-7.87 (m, 2H), 7.70-7.58 (m, 5H), 7.35-7.34 (m, 1H), 7.18 (s, 1H), 5.26 (s, 1H), 3.99 (s, 3H), 2.62 (s, 3H), 0.97 (s, 9H). |
| 153 | 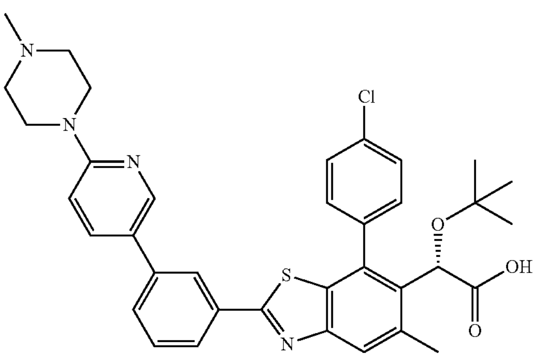 [SMILES: Cc1cc2nc(-c3cccc(-c4ccc(N5CCN(C)CC5)nc4)c3)sc2c(-c2ccc(Cl)cc2)c1[C@H](OC(C)(C)C)C(=O)O] | B | 641.23 | 641.2 | ¹H NMR (400 MHz, CD₃OD): δ 8.54 (d, J = 1 Hz, 1H), 8.27 (s, 1H), 8.02-7.94 (m, 2H), 7.87 (s, 1H), 7.77-7.68 (m, 2H), 7.60-7.58 (m, 4H), 7.07 (d, J = 4.4 Hz), 5.26 (s, 1H), 4.0-4.50 (m, 2H), 3.65-3.55 (m, 2H), 3.3-3.15 (m, 4H), 2.98 (s, 3H), 2.62 (s, 3H), 0.97 (s, 9H). |
| 154 | 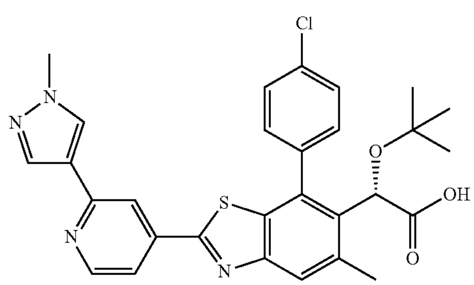 [SMILES: Cc1cc2nc(-c3ccnc(-c4cnn(C)c4)c3)sc2c(-c2ccc(Cl)cc2)c1[C@H](OC(C)(C)C)C(=O)O] | C | 547.08 | 547.2 | ¹H NMR (400 MHz, CD₃OD) δ 8.64 (d, J = 5.7 Hz, 1H), 8.41 (s, 1H), 8.40 (s, 1H), 8.18 (s, 1H), 8.02 (d, J = 5.5 Hz, 1H), 7.98 (s, 1H), 7.70 (d, J = 7.8 Hz, 1H), 7.65-7.58 (m, 3H), 5.28 (s, 1H), 3.99 (s, 3H), 2.64 (s, 3H), 0.98 (s, 9H). |

-continued

| Compound Number | Structure | Method | Parent MW | LCMS-ESI+ | 1H NMR |
|---|---|---|---|---|---|
| 155 | 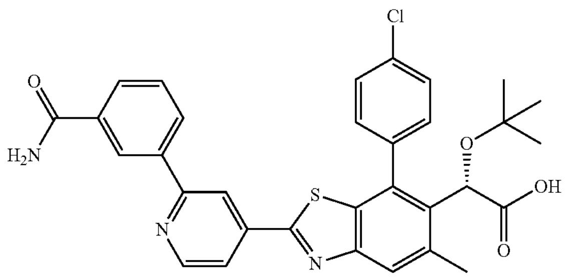 [SMILES: Cc1cc2nc(-c3ccnc(-c4cccc(C(N)=O)c4)c3)sc2c(-c2ccc(Cl)cc2)c1[C@H](OC(C)(C)C)C(=O)O] | C | 586.11 | 586.1 | ¹H NMR (400 MHz, CD₃OD) δ 8.79 (d, J = 5.3 Hz, 1H), 8.57 (s, 1H), 8.53 (s, 1H), 8.26 (d, J = 7.7 Hz, 1H), 8.04-7.99 (m, 2H), 7.94 (s, 1H), 7.72-7.68 (m, 1H), 7.67-7.58 (m, 4H), 5.28 (s, 1H), 2.63 (s, 3H), 0.98 (s, 9H). |
| 156 | 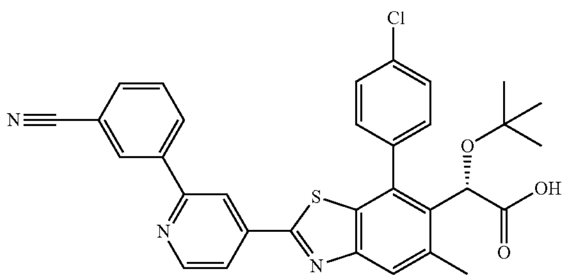 [SMILES: Cc1cc2nc(-c3ccnc(-c4cccc(C#N)c4)c3)sc2c(-c2ccc(Cl)cc2)c1[C@H](OC(C)(C)C)C(=O)O] | C | 568.1 | 568.1 | ¹H NMR (400 MHz, CD₃OD) δ 8.77 (d, J = 5.2 Hz, 1H), 8.47 (s, 1H), 8.45 (s, 1H), 8.36 (d, J = 7.9 Hz, 1H), 7.95-7.88 (m, 2H), 7.82 (d, J = 7.6 Hz, 1H), 7.73-7.65 (m, 2H), 7.62-7.57 (m, 3H), 5.28 (s, 1H), 2.63 (s, 3H), 0.98 (s, 9H). |
| 157 | 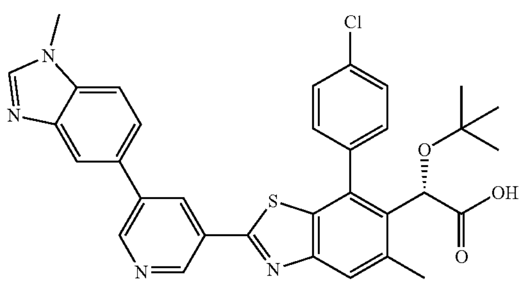 [SMILES: Cc1cc2nc(-c3cncc(-c4ccc5c(c4)ncn5C)c3)sc2c(-c2ccc(Cl)cc2)c1[C@H](OC(C)(C)C)C(=O)O] | | 597.14 | 597.2, 599.2 | ¹H NMR (400 MHz, CD₃OD) δ 9.48 (s, 1H), 9.26 (s, 1H), 9.07 (s, 1H), 8.82 (s, 1H), 8.24 (s, 1H), 8.10 (s, 2H), 7.93 (s, 1H), 7.69 (d, J = 8.9 Hz, 1H), 7.60 (d, J = 6.0 Hz, 3H), 5.27 (s, 1H), 4.21 (s, 3H), 2.63 (s, 3H), 0.98 (s, 9H). |
| 158 | 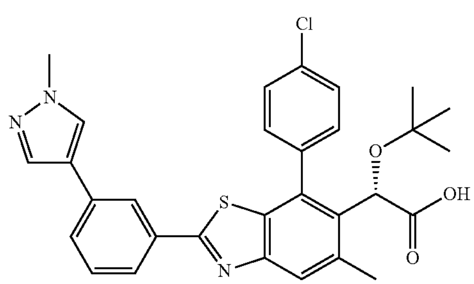 [SMILES: Cc1cc2nc(-c3cccc(-c4cnn(C)c4)c3)sc2c(-c2ccc(Cl)cc2)c1[C@H](OC(C)(C)C)C(=O)O] | B | 546.09 | 546.1 | ¹H NMR (400 MHz, CD₃OD): δ 8.20 (s, 1H), 8.06 (s, 1H), 7.90 (s, 1H), 7.84-7.82 (m, 2H), 7.71-7.59 (m, 5H), 7.50-7.48 (s, 1H), .5.26 (s, 1H), 3.94 (s, 3H), 2.61 (s, 3H), 0.97 (s, 9H). |
| 159 | 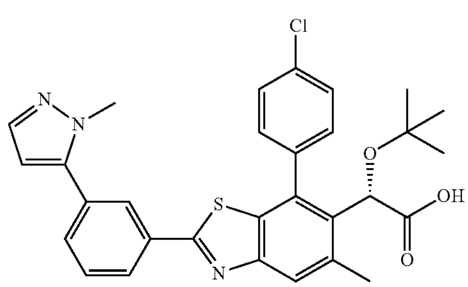 [SMILES: Cc1cc2nc(-c3cccc(-c4ccnn4C)c3)sc2c(-c2ccc(Cl)cc2)c1[C@H](OC(C)(C)C)C(=O)O] | B | 546.09 | 546.2 | ¹H NMR (400 MHz, CD₃OD): δ 8.16 (s, 1H), 8.07 (d, J = 3.6 Hz, 1H), 7.86 (s, 1H), 7.69-7.854 (m, 7H), 6.47 (d, J = 0.8 Hz, 1H), 5.25 (s, 1H), 3.92 (s, 3H), 2.61 (s, 3H), 0.97 (s, 9H). |

| Compound Number | Structure | Method | Parent MW | LCMS-ESI+ | 1H NMR |
|---|---|---|---|---|---|
| 160 | 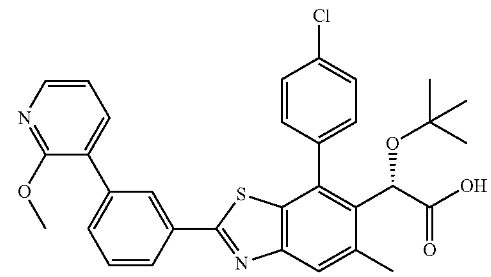 [SMILES: COc1ncccc1-c1cccc(-c2nc3cc(C)c([C@H](OC(C)(C)C)C(=O)O)c(-c4ccc(Cl)cc4)c3s2)c1] | B | 573.11 | 573.1 | ¹H NMR (400 MHz, CD₃OD): δ 8.21-8.16 (m, 3H), 7.99-7.85 (m, 2H), 7.79-7.67 (m, 3H), 7.59-7.53 (m, 4H), 7.10-7.07 (m, 1H), 5.25 (s, 1H), 3.96 (s, 3H), 2.61 (s, 3H), 0.97 (s, 9H). |
| 161 | 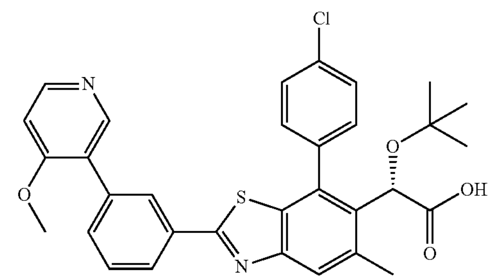 [SMILES: COc1ccncc1-c1cccc(-c2nc3cc(C)c([C@H](OC(C)(C)C)C(=O)O)c(-c4ccc(Cl)cc4)c3s2)c1] | B | 573.11 | 573.2 | ¹H NMR (400 MHz, CD₃OD): δ 8.63-8.60 (m, 2H), 8.16 (s, 1H), 8.03 (d, J = 4 Hz, 1H), 7.77 (s, 1H), 7.66-7.49 (m, 7H), 5.16 (s, 1H), 4.07 (s, 3H), 2.52 (s, 3H), 0.88 (s, 9H). |
| 162 | 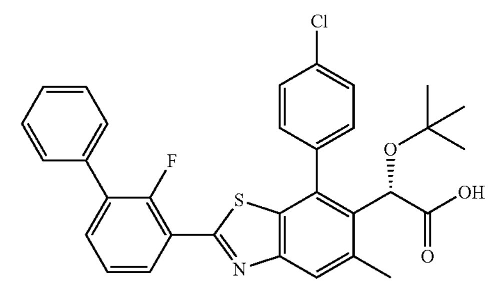 [SMILES: Cc1cc2nc(-c3cccc(-c4ccccc4)c3F)sc2c(-c2ccc(Cl)cc2)c1[C@H](OC(C)(C)C)C(=O)O] | G | 560.09 | 560.2 | ¹H NMR (400 MHz, CD₃OD): δ 8.22 (t, J = 7.2 Hz, 1H), 7.82 (s, 1H), 7.60-7.48 (m, 7H), 7.40-7.311 (m, 4H), 5.17 (s, 1H), 2.35 (s, 3H), 0.87 (s, 9H). |
| 163 | 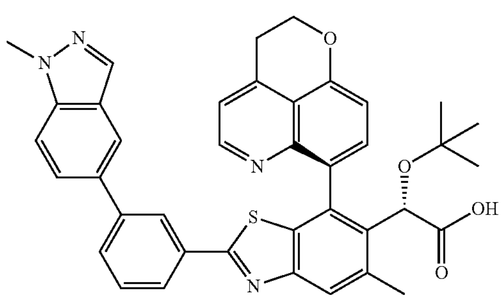 | G | 654.79 | 655.1 | ¹H NMR (400 MHz, CD₃OD): δ 8.77 (d, J = 2.8 Hz, 1H), 8.27-8.26 (m, 1H), 8.09 (s, 1H), 8.05 (d, J = 0.4 Hz, 1H), 8.03-8.02 (m, 1H), 7.94-7.90 (m, 2H), 7.84-7.82 (m, 1H), 7.78-7.73 (m, 2H), 7.65-7.63 (m, 1H), 7.58-7.54 (m, 1H), 7.41 (d, J = 4.2 Hz, 1H), 5.26 (s, 1H), 4.71-4.70 (m, 2H), 4.09 (s, 3H), 3.63 (t, J = 5.8 Hz, 2H), 2.79 (s, 3H), 0.93 (s, 9H). |
| 164 | 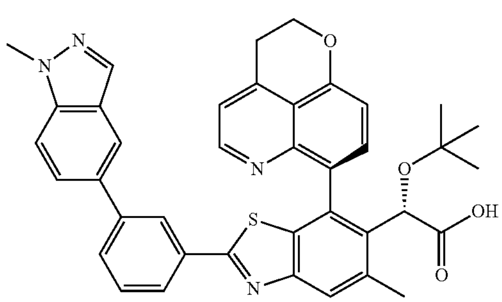 | G | 654.79 | 655.1 | ¹H NMR (400 MHz, CD₃OD): δ 8.64 (d, J = 2.6 Hz, 1H), 8.24-8.18 (m, 2H), 8.05-8.04 (m, 2H), 8.013-8.01 (m, 2H), 7.90-7.88 (m, 1H), 7.82-7.80 (m, 1H), 7.75-7.72 (m, 1H), 7.64-7.62 (m, 2H), 7.57-7.53 (m, 1H), 7.40 (d, J = 4.2 Hz, 1H), 5.31 (s, 1H), 4.67-4.66 (m, 2H), 4.09 (s, 3H), 3.57-3.56 (m, 2H), 2.74 (s, 3H), 0.91 (s, 9H). |

| Compound Number | Structure | Method | Parent MW | LCMS-ESI+ | 1H NMR |
|---|---|---|---|---|---|
| 165 | 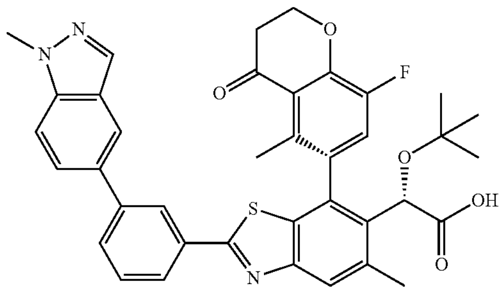 | G | 663.77 | 664.2 | ¹H NMR (400 MHz, CD₃OD): δ 8.32 (s, 1H), 8.08 (s, 2H), 7.97-7.7.79 (m, 4H), 7.65-7.53 (m, 3H), 5.20 (s, 1H), 4.71 (t, J = 6.4 Hz, 2H), 4.11 (s, 3H), 2.94 (t, J = 6.4 Hz, 2H), 2.67 (s, 3H), 2.30 (s, 3H), 1.06 (s, 9H). |
| 166 | 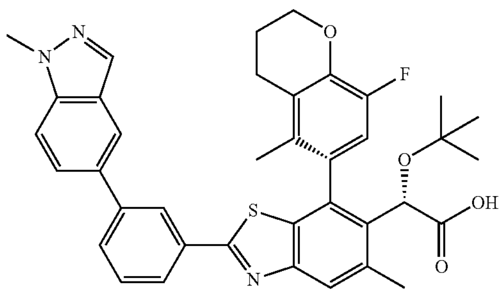 | G | 649.78 | 650.2 | ¹H NMR (400 MHz, CD₃OD): δ 8.32 (s, 1H), 8.09 (s, 2H), 7.97 (d, J = 4 Hz, 1H), 7.85-7.79 (m, 3H), 7.68-7.57 (m, 2H), 7.17 (d, J = 5.8 Hz, 1H), 5.27 (s, 1H), 4.30-4.25 (m, 2H), 4.11 (s, 3H), 2.78-2.69 (s, 2H), 2.63 (s, 3H), 2.16-2.13 (m, 2H), 1.92 (s, 3H), 1.02 (s, 9H). |
| 167 | 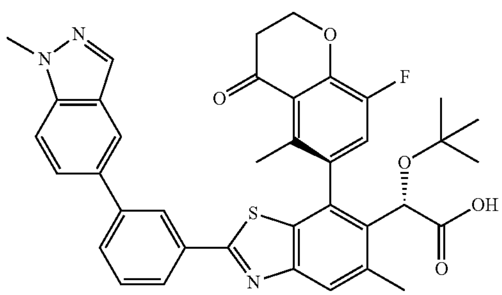 | G | 663.77 | 664.2 | ¹H NMR (400 MHz, CD₃OD): δ 8.21 (s, 1H), 7.98-7.97 (m, 2H), 7.85 (d, J = 3.8 Hz, 1H), 7.80 (s, 1H), 7.75-7.68 (m, 2H), 7.57-7.50 (m, 2H), 7.10 (d, J = 5.4 Hz, 1H), 5.11 (s, 1H), 4.60 (t, J = 6.6 Hz, 2H), 4.01 (s, 3H), 2.85 (t, J = 6.4 Hz, 2H), 2.63 (s, 3H), 2.24 (s, 3H), 1.04 (s, 9H). |
| 168 | 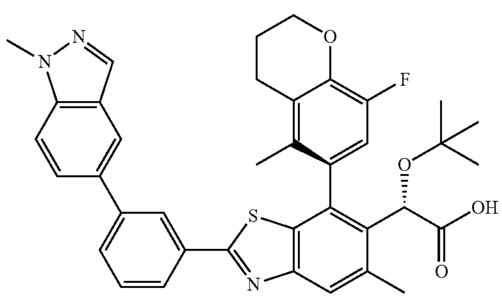 | G | 649.78 | 650.2 | ¹H NMR (400 MHz, CD₃OD): δ 8.31 (s, 1H), 8.08-8.07 (m, 2H), 7.95 (d, J = 4 Hz), 7.85-7.78 (m, 3H), 7.67-7.58 (m, 2H), 6.81 (d, J = 5.6 Hz, 1H), 5.19 (s, 1H), 4.27 (t, J = 2.6 Hz, 2H), 4.10 (s, 3H), 2.77-2.75 (m, 2H), 2.69 (s, 3H), 2.15-2.14 (m, 2H), 1.91 (s, 3H), 1.14 (s, 9H). |
| 169 | 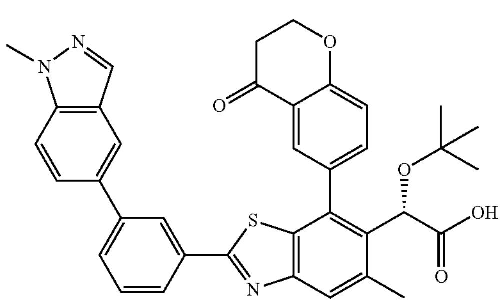 [SMILES: Cc1cc2nc(-c3cccc(-c4ccc5c(cnn5C)c4)c3)sc2c(-c2ccc3c(c2)C(=O)CCO3)c1[C@H](OC(C)(C)C)C(=O)O] | G | 631.75 | 632.2 | ¹H NMR (300 MHz, CD₃OD): δ 8.30 (s, 1H), 8.19-7.94 (m, 3H), 7.85-7.7.57 (m, 6H), 7.22-7.19 (m, 1H), 5.28 (s, 0.5H), 5.24 (s, 0.5H), 4.66-4.64 (m, 2H), 4.01 (s, 3H), 2.90-2.88 (m, 2H), 2.63 (s, 3H), 0.99 (s, 9H). |

| Compound Number | Structure | Method | Parent MW | LCMS-ESI+ | 1H NMR |
|---|---|---|---|---|---|
| 170 | 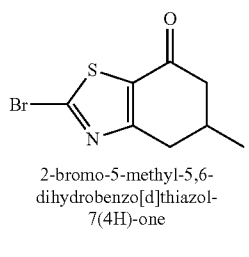 | G | 617.77 | 618.2 | ¹H NMR (300 MHz, CD$_3$OD): δ 8.23 (s, 1H), 7.98 (s, 2H), 7.81-7.70 (m, 3H), 7.57-7.48 (m, 2H), 7.28-7.16 (m, 2H), 6.82 (s, 1H), 5.30 (s, 1H), 4.17-1.15 (m, 2H), 4.01 (s, 3H), 2.78-2.74 (m, 2H), 2.50 (s, 3H), 1.97 (M, 2H), 0.88 (s, 9H). |

Example 40

Preparation of (S)-ethyl 2-tert-butoxy-2-(7-(4-chlorophenyl)-2-(2-chloropyridin-4-yl)-5-methylbenzo[d]thiazol-6-yl)acetate (171)

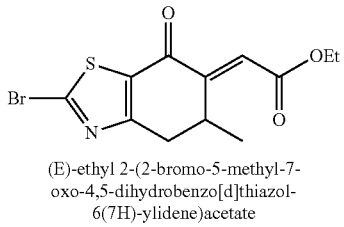

2-bromo-5-methyl-5,6-dihydrobenzo[d]thiazol-7(4H)-one

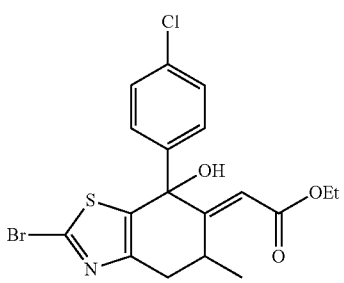

(E)-ethyl 2-(2-bromo-5-methyl-7-oxo-4,5-dihydrobenzo[d]thiazol-6(7H)-ylidene)acetate

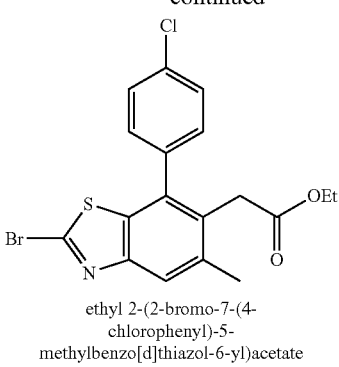

ethyl 2-(2-bromo-7-(4-chlorophenyl)-5-methylbenzo[d]thiazol-6-yl)acetate

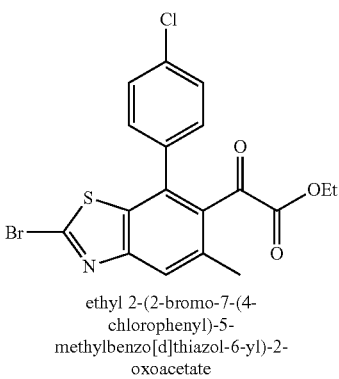

ethyl 2-(2-bromo-7-(4-chlorophenyl)-5-methylbenzo[d]thiazol-6-yl)-2-oxoacetate

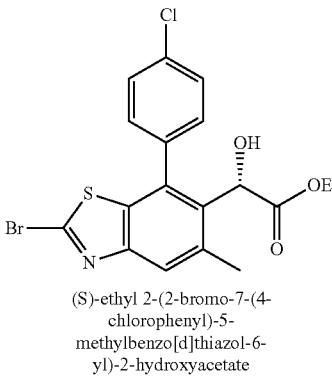

(S)-ethyl 2-(2-bromo-7-(4-chlorophenyl)-5-methylbenzo[d]thiazol-6-yl)-2-hydroxyacetate (E)-ethyl 2-(2-bromo-7-(4-chlorophenyl)-7-hydroxy-5-methyl-4,5-dihydrobenzo[d]thiazol-6(7H)-ylidene)acetate

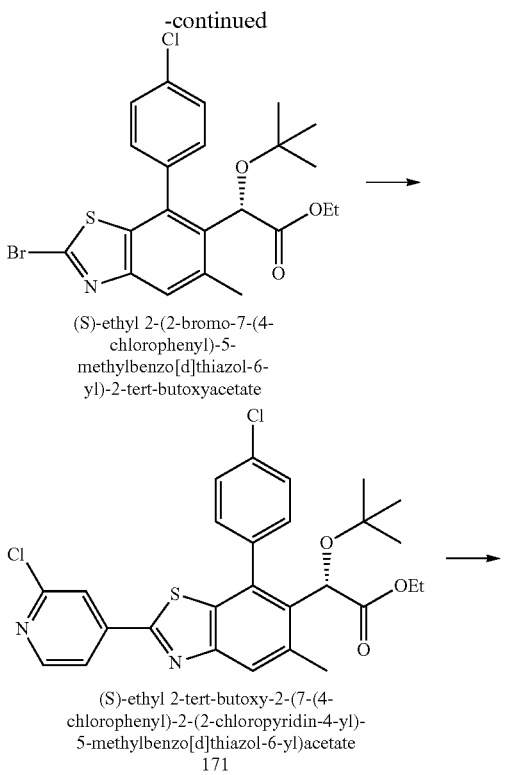

(S)-ethyl 2-(2-bromo-7-(4-chlorophenyl)-5-methylbenzo[d]thiazol-6-yl)-2-tert-butoxyacetate (S)-ethyl 2-tert-butoxy-2-(7-(4-chlorophenyl)-2-(2-chloropyridin-4-yl)-5-methylbenzo[d]thiazol-6-yl)acetate

171

Preparation of (E)-ethyl 2-(2-bromo-5-methyl-7-oxo-4,5-dihydrobenzo[d]thiazol-6(7H)-ylidene)acetate: A 3.0 L round-bottom flask was charged with 2-bromo-5-methyl-5,6-dihydrobenzo[d]thiazol-7(4H)-one (75.0 g, 305 mmol, 1.00 equiv), anhydrous THF (750 mL), and a 50% w/v solution of ethylglyoxylate in toluene (211 mL, 1.07 mol, 3.50 equiv). The resulting solution was placed in a water bath. Solid lithium tert-butoxide (48.9 g, 610 mmol, 2.0 equiv) was steadily added over a 1 min period. The reaction was capped and stirred for 4.5 h. TLC (20% EtOAc/80% hexane indicated full consumption of 2-bromo-5-methyl-5,6-dihydrobenzo[d]thiazol-7(4H)-one). Saturated aqueous NH$_4$Cl (750 mL) was added quickly. The reaction was stirred for 15 min. H$_2$O (250 mL) was added. Most of the solids dissolved. 1.0 M aqueous HCl (180 mL) was added over a 5 min period. After a short time the pH of the aqueous layer was ~3.5. The organic phase was collected, and the aqueous layer was extracted with EtOAc (2×375 mL). Combined organic layers were washed with brine (500 mL), dried (MgSO$_4$), filtered, and concentrated to a minimum volume with a bath temperature of 50-60° C. and 10 mmHg vacuum. DCM (40 mL) was added. The resulting solution was transferred to a Combiflash XL solid loading cartridge by gravity loading. The solid cartridge was assembled in line with a 1.5 kg Combiflash XL silica gel column equilibrated with hexane. The following gradient elution sequence was used: [100% Hexane (5 column volumes, isocratic)→10% EtOAc/90% Hexane (10 column volumes, linear gradient)→10% EtOAc/90% Hexane (7 column volumes, isocratic))→100% EtOAc (8 column volumes, isocratic)]. Fractions containing product were combined, concentrated, and dried under high vacuum to give desired product. LCMS-ESI$^+$ calc'd for C$_{12}$H$_{12}$BrNO$_3$S: 330.0 and 332.0 (M+H$^+$); found: 330.0 and 332.0 (M+H$^+$). $^1$H NMR (400 MHz, CDCl$_3$): δ 6.77 (s, 1H), 4.60-4.53 (m, 1H), 4.30-4.21 (m, 2H), 3.23 (dd, J=17.6, 5.8 Hz, 1H), 3.07 (d, J=5.8 Hz, 1H), 1.33 (t, J=7.2 Hz, 3H), 1.23 (d, J=7.0 Hz, 3H).

Preparation of (E)-ethyl 2-(2-bromo-7-(4-chlorophenyl)-7-hydroxy-5-methyl-4,5-dihydrobenzo[d]thiazol-6(7H)-ylidene)acetate: A 3-liter flask equipped with a mechanical stirrer, addition funnel, and nitrogen inlet was charged with (E)-ethyl 2-(2-bromo-5-methyl-7-oxo-4,5-dihydrobenzo[d]thiazol-6(7H)-ylidene)acetate (24.1 g, 73 mmol, 1.0 equiv) and then diluted with THF (800 mL). To the resulting solution was added 0.6M LaCl$_3$.2LiCl (243 mL, 146 mmol, 2.0 equiv) and then the reaction mixture was cooled to −65° C. by the aid of a dry-ice acetone bath. The addition funnel was then charged with 1.0M 4-chlorophenylmagnesium bromide (146 mL, 146 mmol, 2.0 equiv) and then slowly added to the reaction mixture over a 25 minute period. Upon completion of the addition, TLC analysis showed full consumption of the starting material (TLC of the starting material in 20% EtOAc/Hex has Rf=0.50; TLC of the product in 20% EtOAc/Hex has Rf=0.38), and the reaction was quenched with saturated NH$_4$Cl (100 mL) and then diluted with EtOAc (1 L) and H$_2$O (1.5 L). The cooling bath was removed and the mixture was allowed to warm to room temperature with stirring. The layers were separated and the aqueous extract was washed with EtOAc (1 L). The combined organics were dried over Na$_2$SO$_4$, filtered through a small plug of silica gel eluting with EtOAc, and then concentrated in vacuo. The resulting crude residue was chromatographed using a 330 g RediSep normal phase silica gel cartridge (EtOAc/Hex, 5%→15%) on a CombiFlash system to afford desired product. TLC (20% EtOAc/Hex) Rf=0.38; $^1$H NMR (400 MHz, CDCl$_3$) δ 7.31 (d, J=8.6 Hz, 2H), 7.26 (d, J=8.6 Hz, 2H), 5.62 (s, 1H), 4.57-4.40 (m, 1H), 4.22-4.04 (m, 2H), 3.03 (qd, J=16.6, 3.8 Hz, 2H), 2.61 (br s, 1H), 1.38 (d, J=7.2 Hz, 3H), 1.25 (t, J=7.1 Hz, 3H).

Preparation of ethyl 2-(2-bromo-7-(4-chlorophenyl)-5-methylbenzo[d]thiazol-6-yl)acetate: Polyphosphoric acid (PPA) (140 g) and THF (210 mL) were heated to 75° C. in a 1 L recovery flask. (E)-ethyl 2-(2-bromo-7-(4-chlorophenyl)-7-hydroxy-5-methyl-4,5-dihydrobenzo[d]thiazol-6(7H)-ylidene)acetate (31.0 g, 70.0 mmol) was added via addition funnel in THF (70 mL) over 2 min. The funnel was rinsed with THF (20 mL). The reaction mixture was heated at 80° C. for 2.5 h. After cooling to rt, the mixture was poured onto a 1 M K$_2$HPO$_4$ (1.5 L) solution followed by EtOAc (700 mL). The layers were separated, and the organic layer was washed with brine (500 mL). The organic layer was dried, filtered, and concentrated in vacuo to give desired product that was used without further purification. $^1$H NMR (400 MHz, CDCl$_3$): δ 7.81 (s, 1H), 7.45 (d, 2H, J=8 Hz), 7.29 (d, 2H, J=8 Hz), 4.13 (q, 2H, J=7 Hz), 3.57 (s, 2H), 2.45 (s, 3H), 1.23 (t, 3H, J=7 Hz).

Preparation of ethyl 2-(2-bromo-7-(4-chlorophenyl)-5-methylbenzo[d]thiazol-6-yl)-2-oxoacetate: To a solution of the ethyl 2-(2-bromo-7-(4-chlorophenyl)-5-methylbenzo[d]thiazol-6-yl)acetate (15.4 g, 36.4 mmol) in THF (146 mL) at −78° C. was added a solution of KHMDS (1 M in THF, 43.6 mmol, 43.6 mL) over 5 min. After 30 min, a solution of 3-phenyl-2-(phenylsulfonyl)-1,2-oxaziridine (11.4 g, 43.6 mmol) in THF (29 mL) was added. After 1 h, a saturated solution of NH$_4$Cl was added (200 mL). The reaction mixture was warmed to rt. The layers were separated, and the aqueous layer was extracted with EtOAc. The combined organic layers were dried, filtered, and concentrated in vacuo and were used without further purification.

To the above residue was added CH$_2$Cl$_2$ (240 mL) followed by Dess-Martin periodinane (16.9 g, 40.0 mmol). After 2 h, a saturated solution of Na$_2$S$_2$O$_3$ (150 mL) and a saturated solution of NaHCO$_3$ (150 mL) and water (100 mL) were added. The mixture was stirred at room temperature for 2 h. The layers were separated, and the aqueous layer was extracted with CH$_2$Cl$_2$. The combined organic layers were dried, filtered, and concentrated in vacuo. A mixture of hexanes/EtOAc (9:1) was added. The mixture was filtered, the solids were washed with additional hex/EtOAc (9:1), and the filtrate was concentrated. The crude oil was purified by column chromatography (5%-10% EtOAc/hex) to give desired product. $^1$H NMR (400 MHz, CDCl$_3$): δ 7.88 (s, 1H), 7.45 (d, 2H, J=8 Hz), 7.28 (d, 2H, J=8 Hz), 3.91 (q, 2H, J=7 Hz), 2.52 (s, 3H), 1.08 (t, 3H, J=7 Hz).

Preparation of (S)-ethyl 2-(2-bromo-7-(4-chlorophenyl)-5-methylbenzo[d]thiazol-6-yl)-2-hydroxyacetate:

Catalyst Preparation: A 25 mL flask was charged with dichloro(pentamethylcyclopentadienyl)rhodium(III) dimer (94 mg, 0.15 mmol, 1.0 equiv) and the ligand N-((1S,2S)-2-amino-1,2-diphenylethyl)-4-nitrobenzenesulfonamide (153 mg, 0.39 mmol, 2.6 equiv) and sealed with a rubber septum. The flask was purged with argon and then ACN (1.5 mL) and NEt$_3$ (0.15 mL) were added to the flask and an additional septum was fitted. The resulting red solution was stirred at room temperature under argon for a minimum of 45 minutes, but not more than 6 hours, which resulted in a heterogeneous orange suspension.

A 100 mL flask was charged with ethyl 2-(2-bromo-7-(4-chlorophenyl)-5-methylbenzo[d]thiazol-6-yl)-2-oxoacetate (2.4 g, 5.5 mmol, 1.0 equiv) and sealed with a rubber septum. The flask was purged with argon and to this was charged ACN (11 mL) and NEt$_3$ (1.9 mL, 13.6 mmol, 2.5 equiv) and stirring was initiated. The solution was cooled to 0° C. and then HCO$_2$H (0.63 mL, 16.7 mmol, 3.0 equiv) was added to the solution at a rate to maintain an internal temperature not more than 20° C. Upon completion of the addition, the solution was allowed to cool back to 0° C. Argon was then bubbled through the solution using a porous gas dispersion unit. To the stirring solution at 0° C. was charged the prepared catalyst solution (0.5 mL, 0.05 equiv) from the catalyst preparation above. The solution was stirred at 0° C. with the bubbling of argon through the solution until TLC indicated complete consumption of starting material (10-18 h). The reaction was quenched with H$_2$O then diluted with EtOAc and allowed to warm to room temperature. The layers were separated and the organic extract was washed once more with H$_2$O. The organic extract was then dried over Na$_2$SO$_4$, filtered through a small pad of silica gel eluting with EtOAc, and concentrated in vacuo. The resulting crude residue was chromatographed using a 80 g RediSep normal phase silica gel cartridge (EtOAc/Hex, 5%→20%) on a CombiFlash system to give the desired product. TLC (20% EtOAc/Hex) Rf=0.27; $^1$H NMR (400 MHz, CDCl$_3$) δ 7.79 (s, 1H), 7.53-7.43 (m, 2H), 7.37 (m, 2H), 5.23 (d, J=2.2 Hz, 1H), 4.19 (m, 2H), 3.29 (d, J=2.2 Hz, 1H), 2.48 (d, J=0.5 Hz, 3H), 1.21 (t, J=7.1 Hz, 3H).

Alternative preparation of (S)-ethyl 2-(2-bromo-7-(4-chlorophenyl)-5-methylbenzo[d]thiazol-6-yl)-2-hydroxyacetate: A solution of ethyl 2-(2-bromo-7-(4-chlorophenyl)-5-methylbenzo[d]thiazol-6-yl)-2-oxoacetate (10.60 g, 25.0 mmol) in PhMe (100 mL) was cooled to −30° C. (R)-Me-CBS catalyst (1.39 g, 5.00 mmol) was added, followed immediately by distilled catecholborane (4.00 mL, 37.5 mmol). At 1.2 h, additional (R)-Me-CBS catalyst (1.39 g, 5.00 mmol) was added. After another 1 h had passed, additional (R)-Me-CBS catalyst (700 mg, 2.50 mmol) was added. After 30 min, the reaction was quenched with EtOAc (30 mL). Saturated aqueous NaHCO$_3$ (50 mL) was added, and the reaction was warmed to 23° C. and stirred for an additional 30 min. The organic phase was collected, washed with saturated aqueous NaHCO$_3$ (1×), dried (MgSO$_4$), filtered, and concentrated. Benzene was added and the resulting solution was purified by silica gel column, eluting by 0-100% EtOAc in hexanes to give the product. LCMS-ESI$^+$: calc'd for C$_{18}$H$_{15}$BrClNO$_3$S: 440.0, 442.0, 440.0 (M+H$^+$); Found: 440.2, 442.1, 444.1 (M+H$^+$). $^1$H NMR (400 MHz, CDCl$_3$) δ: 7.80 (s, 1H), 7.54-7.43 (m, 2H), 7.42-7.32 (m, 2H), 5.23 (s, 1H), 4.31-4.12 (m, 2H), 2.47 (s, 3H), 1.23 (t, J=7.1 Hz, 3H).

Preparation of (S)-ethyl 2-(2-bromo-7-(4-chlorophenyl)-5-methylbenzo[d]thiazol-6-yl)-2-tert-butoxyacetate: A suspension of (S)-ethyl 2-(2-bromo-7-(4-chlorophenyl)-5-methylbenzo[d]thiazol-6-yl)-2-hydroxyacetate (7.20 g, 16.9 mmol) in neat t-BuOAc (100 mL) was cooled to 0° C. in an ice bath. 70% w/v aqueous HClO$_4$ (293 μL, 3.4 mmol) was added dropwise over 5 min. The reaction was warmed to 23° C., then stirred for 2.3 h. At this point the reaction was transferred to an addition funnel. The reaction was added to a 23° C. solution of sat aqueous NaHCO$_3$ (400 mL) over 30 min. Once addition was complete, the reaction was stirred for another 15 min. The resulting system was extracted with EtOAc (2×150 mL). Combined organic layers were dried (Na$_2$SO$_4$), filtered, and concentrated in vacuo. Some residual t-BuOAc remained. Hexane (200 mL) was added and the slurry was concentrated once more. The resulting residue (reasonably free of t-BuOAc) was treated with Benzene and loaded onto a 330 g "gold" ISCO silica gel column. The following gradient elution sequence was used: [100% Hexane (5 column volumes, isocratic)→10% EtOAc/90% Hexane (5 column volumes, linear gradient→10% EtOAc/90% Hexane (5 column volumes, isocratic ((S)-ethyl 2-(2-bromo-7-(4-chlorophenyl)-5-methylbenzo[d]thiazol-6-yl)-2-tert-butoxyacetate elutes))→100% EtOAc (10 column volumes, isocratic, (unreacted (S)-ethyl 2-(2-bromo-7-(4-chlorophenyl)-5-methylbenzo[d]thiazol-6-yl)-2-hydroxyacetate elutes))]. Product-containing fractions were pooled, concentrated, co-evarporated with Et$_2$O (100 mL) to give desired product. LCMS-ESI+ calc'd for C$_{22}$H$_{23}$BrClNO$_3$S: 496.0, 498.0 and 500.0 (M+H$^+$); found: 496.2, 498.2, and 500.1 (M+H+). $^1$H NMR (400 MHz, CDCl$_3$): δ 7.77 (s, 1H), 7.48 (m, 3H), 7.37 (m, 1H), 5.12 (s, 1H), 4.20 (m, 2H), 2.57 (s, 3H), 1.24 (t, 3H, J=7 Hz), 0.96 (s, 9H).

Preparation of (S)-ethyl 2-tert-butoxy-2-(7-(4-chlorophenyl)-2-(2-chloropyridin-4-yl)-5-methylbenzo[d]thiazol-6-yl)acetate: To a solution of (S)-ethyl 2-(2-bromo-7-(4-chlorophenyl)-5-methylbenzo[d]thiazol-6-yl)-2-tert-butoxyacetate (858 mg, 1.733 mmol) and 2-chloropyridine-4-boronic acid (327 mg, 2.080 mmol) in dioxane (14.6 mL) was added Pd(PPh$_3$)$_4$ (160 mg, 0.139 mmol) and 2N K$_2$CO$_3$ (3.6 mL, 7.280 mmol). The reaction was degassed for 5 minutes with N$_2$ and then heated at 90° C. for 6 h. After cooling, the reaction mixture was diluted with EtOAc, extracted with H$_2$O, brine, dried over Na$_2$SO$_4$, filtered and concentrated and purified by flash column chromatography (silica gel, 0 to 100% ethyl acetate/hexanes) to give the desired product. LCMS-ESI+ (m/z): [M+H]+ calcd for C$_{27}$H$_{27}$Cl$_2$N$_2$O$_3$S: 529.1; found: 529.2.

Example 41

Preparation of (S)-ethyl 2-tert-butoxy-2-(2-chloro-5-methyl-7-(trifluoromethylsulfonyloxy)benzo[d]thiazol-6-yl)acetate (172)

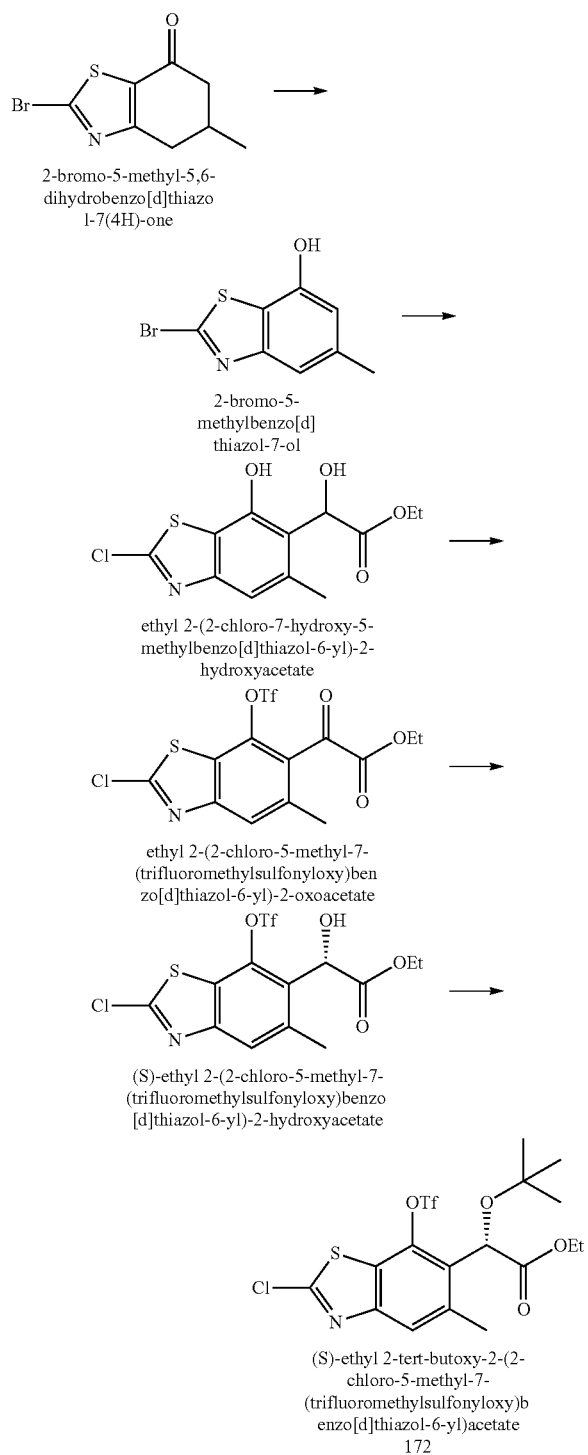

Preparation of 2-bromo-5-methylbenzo[d]thiazol-7-ol: To a solution of 2-bromo-5-methyl-5,6-dihydrobenzo[d]thiazol-7(4H)-one (17.5 g, 71.24 mmol) in acetic acid (142 mL) at 80° C. was added dropwise bromine (3.30 mL, 64.12 mmol) over 30 minutes. Reaction mixture was stirred for 1 h at 80° C., cooled to room temperature and resulting solid collected by filtration. The filter cake was partitioned between dichloromethane/saturated sodium bicarbonate solution. The organic layer was washed with saturated sodium bicarbonate solution, brine, dried (MgSO$_4$), filtered and concentrated. The residue was dissolved in dichloromethane (250 mL) and added dropwise over 2.5 h to a solution of 1,8-Diazabicyclo[5.4.0]undec-7-ene (19.5 mL, 130 mmol) in dichloromethane (1.5 L) at 0° C. Reaction mixture was stirred for 30 minutes, quenched with 1N HCl and stirred for 5 minutes. The organic layer was washed with brine, dried (MgSO$_4$), filtered and concentrated. Purification by CombiFlash (220 g, 5 to 40% EtOAc/Hex) gave impure product. Recystallization from hot EtOAc/Hex gave pure product. NMR (400 MHz, CDCl$_3$): δ 7.42 (s, 1H), 6.65 (s, 1H), 2.44 (s, 3H).

Preparation of ethyl 2-(2-chloro-7-hydroxy-5-methylbenzo[d]thiazol-6-yl)-2-hydroxyacetate: To a mixture of 2-bromo-5-methylbenzo[d]thiazol-7-ol (2.48 g, 10.16 mmol) in dichloromethane (100 mL) at 0° C. was added triethylamine (1.42 mL, 10.16 mmol) to give a clear solution. Titaniuim(IV) chloride (1.0M in CH$_2$Cl$_2$, 10.67 mL, 10.67 mmol) was added slowly to give an orange reaction mixture that was stirred for 30 minutes. A solution of cracked ethyl glyoxalate (1.04 g, 10.16 mmol) in CH$_2$Cl$_2$ (1 mL) was added over 2 minutes and reaction mixture was stirred at room temperature for 2.5 h. Reaction mixture was quenched with Rochelle's salt and stirred at room temperature for 2 h, diluted with CH$_2$Cl$_2$, and aqueous layer extracted with CH$_2$Cl$_2$ (2×). The combined organic layer was dried (MgSO$_4$), filtered and concentrated. Purification by CombiFlash (40 g, 0 to 30% EtOAc/Hex) gave product contaminated with ethyl 2-(2-bromo-7-hydroxy-5-methylbenzo[d]thiazol-6-yl)-2-hydroxyacetate. LCMS-ESI$^+$: calc'd for C$_{12}$H$_{13}$ClNO$_3$S: 302.8 (M+H$^+$); Found: 302.1 (M+H$^+$).

Preparation of ethyl 2-(2-chloro-5-methyl-7-(trifluoromethylsulfonyloxy)benzo[d]thiazol-6-yl)-2-oxoacetate: To a solution of ethyl 2-(2-chloro-7-hydroxy-5-methylbenzo[d]thiazol-6-yl)-2-hydroxyacetate (1.006 g, 3.33 mmol) in CH$_2$Cl$_2$ (33 mL) at −78° C. was added 2,6-lutidine (0.846 mL, 7.33 mmol). Reaction mixture was stirred for 1 h, then trifluoromethanesulfonyl anhydride (0.616 mL, 3.66 mmol) was added over 15 minutes. Reaction was stirred for 1 h, then more trifluoromethanesulfonyl anhydride was added (0.062 mL, 3.66 mmol) and reaction continued for 30 minutes. Reaction mixture was quenched with brine, stirred for 5 minutes, diluted with CH$_2$Cl$_2$, washed with 1N HCl/brine. Organic layer was dried (MgSO$_4$), filtered, concentrated and used in next step without further purification.

The above residue was dissolved in CH$_2$Cl$_2$ (33 mL), cooled to 0° C. and Dess-Martin periodinane (2.54 g, 5.99 mmol) was added portion-wise. After stirring for 2 h, more Dess-Martin periodinane (0.25 g, 5.99 mmol) was added. After 1 h, reaction was quenched with Na$_2$S$_2$O$_3$ solution and stirred for 30 minutes. The mixture was diluted with CH$_2$Cl$_2$, washed with water, saturated sodium bicarbonate solution, brine and dried (MgSO$_4$), filtered, concentrated and purified by CombiFlash (0 to 20% EtOAc/Hex) to give product contaminated with ethyl 2-(2-bromo-5-methyl-7-(trifluoromethylsulfonyloxy)benzo[d]thiazol-6-yl)-2-oxoacetate $^1$H NMR (400 MHz, CDCl$_3$): δ 7.88 (s, 1H), 4.42 (q, J=7.2 Hz, 2H), 2.49 (s, 3H), 1.40 (t, J=7.2 Hz, 3H).

Preparation of (S)-ethyl 2-(2-chloro-5-methyl-7-(trifluoromethylsulfonyloxy)benzo[d]thiazol-6-yl)-2-hydroxyacetate: To a solution of ethyl 2-(2-chloro-5-methyl-7-(trifluoromethylsulfonyloxy)benzo[d]thiazol-6-yl)-2-oxoacetate (0.6621 g, 1.53 mmol), and (R)-2-methyl-CBS-oxazaborolidine (0.098 g, 0.35 mmol) in toluene (6 mL) was added a solution of distilled catecholborane (0.254 g, 2.39 mmol) in toluene (1 mL) over 15 minutes, then stirred for another 45 minutes. The reaction was quenched with saturated sodium carbonate solution and stirred at room temperature for 15 minutes. Product extracted with EtOAc and organic layer washed with saturated sodium carbonate (3×), brine, dried (MgSO$_4$), filtered, concentrated and purified by CombiFlash (0 to 25% EtOAc/Hex) to give product contaminated with (S)-ethyl 2-(2-bromo-5-methyl-7-(trifluoromethylsulfonyloxy)benzo[d]thiazol-6-yl)-2-hydroxyacetate. LCMS-ESI$^+$: calc'd for C$_{13}$H$_{12}$ClF$_3$NO$_6$S$_2$: 434.0 (M+H$^+$); Found: 433.9 (M+H$^+$).

Preparation of (S)-ethyl 2-tert-butoxy-2-(2-chloro-5-methyl-7-(trifluoromethylsulfonyloxy)benzo[d]thiazol-6-yl)acetate: To a solution of (S)-ethyl 2-(2-chloro-5-methyl-7-(trifluoromethylsulfonyloxy)benzo[d]thiazol-6-yl)-2-hydroxyacetate (0.5691 g, 1.31 mmol) in tert-butyl acetate (65 mL) was added 70% perchloric acid (65 µL, 1.57 mmol).

Reaction mixture was stirred for 1.5 h and quenched with solid sodium bicarbonate. Saturated sodium bicarbonate solution was carefully added until basic and mixture was extracted with ethyl acetate. The organic layer was washed with saturated sodium bicarbonate solution, brine, dried (MgSO$_4$), filtered, concentrated and purified by CombiFlash (0 to 15% EtOAc/Hex) to give product contaminated with (S)-ethyl 2-tert-butoxy-2-(2-bromo-5-methyl-7-(trifluoromethylsulfonyloxy)benzo[d]thiazol-6-yl)acetate. $^1$H NMR (400 MHz, CDCl$_3$): δ 7.78 (s, 1H), 5.59 (s, 1H), 4.4-4.1 (m, 2H), 2.55 (s, 3H), 1.20 (s, 9H), 1.16 (t, J=7.2 Hz, 3H).

Example 42

(Method K): Preparation of (S)-2-tert-butoxy-2-(7-(4-chlorophenyl)-2-(2-(2-ethyl-2H-indazol-5-yl)pyridin-4-yl)-5-methylbenzo[d]thiazol-6-yl)acetic acid (173) and (S)-2-tert-butoxy-2-(7-(4-chlorophenyl)-2-(2-(1-ethyl-1H-indazol-5-yl)pyridin-4-yl)-5-methylbenzo[d]thiazol-6-yl)acetic acid (174)

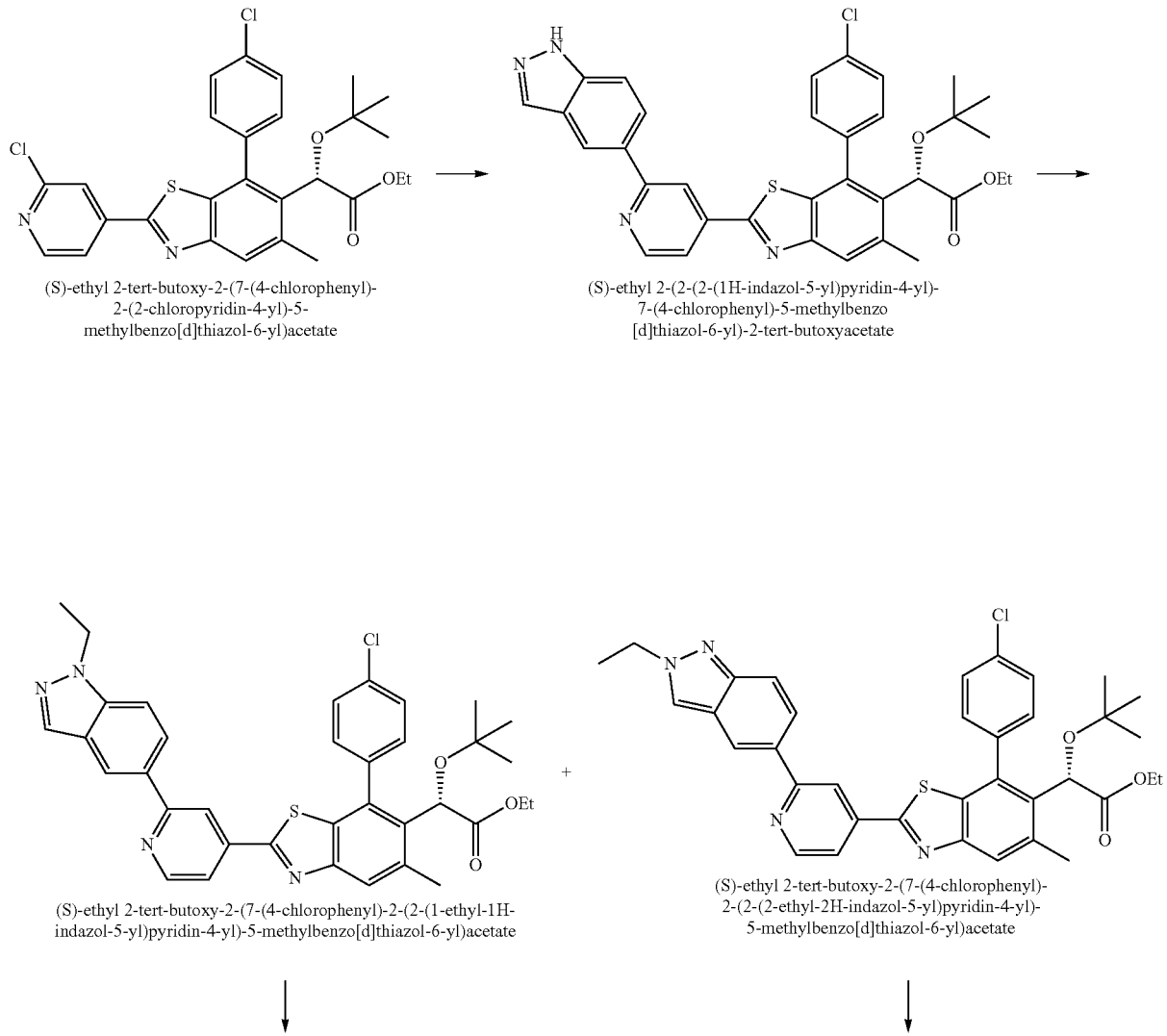

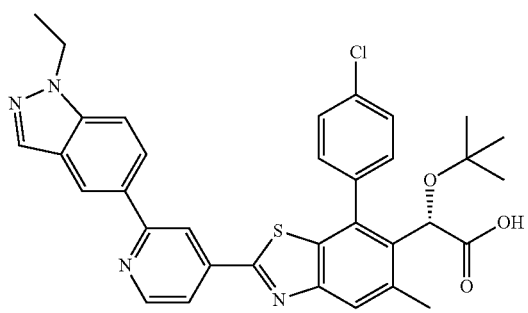

(S)-2-tert-butoxy-2-(7-(4-chlorophenyl)-
2-(2-(1-ethyl-1H-indazol-5-yl)pyridin-4-yl)-5-
methylbenzo[d]thiazol-6-yl)acetic acid
174

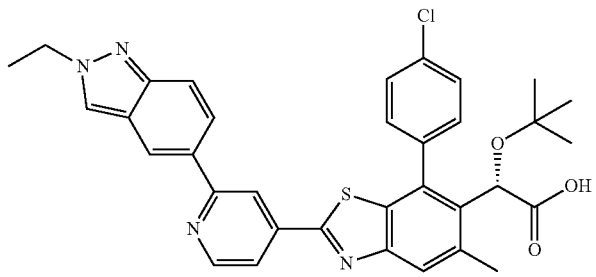

(S)-2-tert-butoxy-2-(7-(4-chlorophenyl)-2-
(2-(2-ethyl-2H-indazol-5-yl)pyridin-4-yl)-
5-methylbenzo[d]thiazol-6-yl)acetic acid
173

Preparation of (S)-ethyl 2-(2-(2-(1H-indazol-5-yl)pyridin-4-yl)-7-(4-chlorophenyl)-5-methylbenzo[d]thiazol-6-yl)-2-tert-butoxyacetate: (S)-ethyl 2-(2-(2-(1H-indazol-5-yl)pyridin-4-yl)-7-(4-chlorophenyl)-5-methylbenzo[d]thiazol-6-yl)-2-tert-butoxyacetate was made by the similar method to make (S)-2-tert-butoxy-2-(7-(4-chlorophenyl)-2-(5′-methoxy-2,3′-bipyridin-4-yl)-5-methylbenzo[d]thiazol-6-yl) ethyl pivalate in method C. LCMS-ESI$^+$: calc'd for $C_{34}H_{31}ClN_4O_3S$: 611.2 (M+H$^+$); found: 611.2.

Preparation of (S)-ethyl 2-tert-butoxy-2-(7-(4-chlorophenyl)-2-(2-(1-ethyl-1H-indazol-5-yl)pyridin-4-yl)-5-methylbenzo[d]thiazol-6-yl)acetate and (S)-ethyl 2-tert-butoxy-2-(7-(4-chlorophenyl)-2-(2-(2-ethyl-2H-indazol-5-yl)pyridin-4-yl)-5-methylbenzo[d]thiazol-6-yl)acetate: To a solution of (S)-ethyl 2-(2-(2-(1H-indazol-5-yl)pyridin-4-yl)-7-(4-chlorophenyl)-5-methylbenzo[d]thiazol-6-yl)-2-tert-butoxyacetate (32 mg, 0.052 mmol) in DMF (1 mL), was added $Cs_2CO_3$ (34 mg, 0.104 mmol), iodoethane (5 μL, 0.062 mmol). The reaction was reacted at room temperature. After the reaction finished, the reaction mixture was washed by water, extracted by EtOAc, the organic phase was dried over $MgSO_4$, filtered, concentrated down, purified by silica gel column, eluting by 0-100% EtOAc in hexanes to give (S)-ethyl 2-tert-butoxy-2-(7-(4-chlorophenyl)-2-(2-(1-ethyl-1H-indazol-5-yl)pyridin-4-yl)-5-methylbenzo[d]thiazol-6-yl)acetate. LCMS-ESI$^+$: calc'd for $C_{36}H_{35}ClN_4O_3S$: 639.2 (M+H$^+$). found: 639.4;

(S)-ethyl 2-tert-butoxy-2-(7-(4-chlorophenyl)-2-(2-(2-ethyl-2H-indazol-5-yl)pyridin-4-yl)-5-methylbenzo[d]thiazol-6-yl)acetate was also isolated. LCMS-ESI$^+$: calc'd for $C_{36}H_{35}ClN_4O_3S$: 639.2 (M+H$^+$); found: 639.3.

Preparation of (S)-2-tert-butoxy-2-(7-(4-chlorophenyl)-2-(2-(1-ethyl-1H-indazol-5-yl)pyridin-4-yl)-5-methylbenzo[d]thiazol-6-yl)acetic acid: (S)-2-tert-butoxy-2-(7-(4-chlorophenyl)-2-(2-(1-ethyl-1H-indazol-5-yl)pyridin-4-yl)-5-methylbenzo[d]thiazol-6-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI$^+$: calc'd for $C_{34}H_{31}ClN_4O_3S$: 611.2 (M+H$^+$); found: 611.2.

$^1$H NMR (400 MHz, CD$_3$OD) δ: 8.74 (s, 2.6 Hz, 1H), 8.56 (s, 1H), 8.45 (s, 1H), 8.17 (s, 1H), 8.09-8.03 (M, 2H), 7.94 (s, 1H), 7.76-7.69 (m, 2H), 7.61-7.59 (m, 3H), 5.28 (s, 1H), 4.53-4.48 (m, 2H), 2.63 (s, 3H), 1.50 (t, J=7.2 Hz, 3H), 0.98 (s, 9H).

Preparation of (S)-2-tert-butoxy-2-(7-(4-chlorophenyl)-2-(2-(2-ethyl-2H-indazol-5-yl)pyridin-4-yl)-5-methylbenzo[d]thiazol-6-yl)acetic acid: (S)-2-tert-butoxy-2-(7-(4-chlorophenyl)-2-(2-(2-ethyl-2H-indazol-5-yl)pyridin-4-yl)-5-methylbenzo[d]thiazol-6-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI$^+$: calc'd for $C_{34}H_{31}ClN_4O_3S$: 611.2 (M+H$^+$); found: 611.2.

$^1$H NMR (400 MHz, CD$_3$OD) δ: 8.70 (d, J=2.8 Hz, 1H), 8.50 (d, 1H), 8.41-8.40 (m, 2H), 7.99-7.91 (m, 2H), 7.76-7.68 (m, 2H), 7.60-7.58 (m, 3H), 5.27 (s, 1H), 4.53-4.50 (m, 2H), 2.62 (s, 3H), 1.62 (t, J=6.8 Hz, 3H), 0.97 (s, 9H).

Example 43

Method L: Preparation of (S)-2-tert-butoxy-2-(7-(4-chlorophenyl)-2-(2-(1-cyclopropyl-1H-indazol-5-yl)pyridin-4-yl)-5-methylbenzo[d]thiazol-6-yl)acetic acid (175)

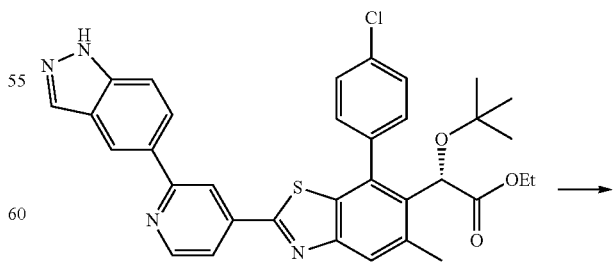

(S)-ethyl 2-(2-(2-(1H-indazol-5-yl)pyridin-4-yl)-
7-(4-chlorophenyl)-5-methylbenzo
[d]thiazol-6-yl)-2-tert-butoxyacetate

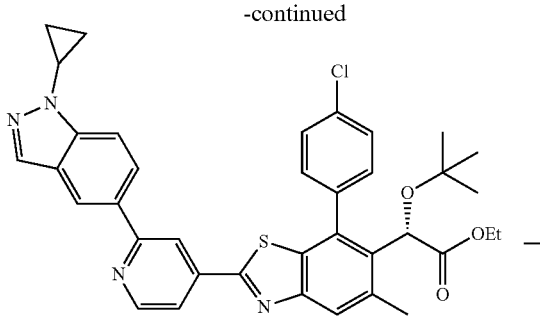

(S)-ethyl 2-tert-butoxy-2-(7-(4-chlorophenyl)-
2-(2-(1-cyclopropyl-1H-indazol-5-yl)pyridin-4-yl)-5-
methylbenzo[d]thiazol-6-yl)acetate

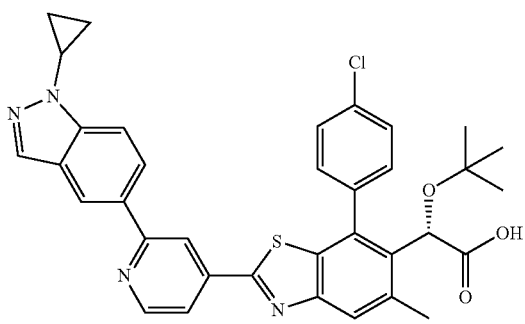

(S)-2-tert-butoxy-2-(7-(4-chlorophenyl)-2-
(2-(1-cyclopropyl-1H-indazol-5-yl)pyridin-4-yl)-
5-methylbenzo[d]thiazol-6-yl)acetic acid
175

Preparation of (S)-ethyl 2-tert-butoxy-2-(7-(4-chlorophenyl)-2-(2-(1-cyclopropyl-1H-indazol-5-yl)pyridin-4-yl)-5-methylbenzo[d]thiazol-6-yl)acetate: To a solution of (S)-ethyl 2-(2-(2-(1H-indazol-5-yl)pyridin-4-yl)-7-(4-chlorophenyl)-5-methylbenzo[d]thiazol-6-yl)-2-tert-butoxyacetate (30 mg, 0.049 mmol) in dichloroethane (1 mL) was added Cu(OAc)$_2$ (9 mg, 0.049 mmol), 2-2'-dipyridyl (7.7 mg, 0.049 mmol), cyclopropylboronic acid (8.4 mg, 0.1 mmol), Na$_2$CO$_3$ (10.4 mg, 0.1 mmol). The reaction mixture was heated at 70° C. for 3 hours under air. The reaction mixture was washed by water, extracted by EtOAc, the organic phase was dried over MgSO$_4$, filtered, concentrated down, purified by silica gel column, eluting by 0-100% EtOAc in hexanes to give the product. LCMS-ESI$^+$: calc'd for C$_{37}$H$_{35}$ClN$_4$O$_3$S: 651.2 (M+H$^+$). found: 651.3.

Preparation of (S)-2-tert-butoxy-2-(7-(4-chlorophenyl)-2-(2-(1-cyclopropyl-1H-indazol-5-yl)pyridin-4-yl)-5-methylbenzo[d]thiazol-6-yl)acetic acid: (S)-2-tert-butoxy-2-(7-(4-chlorophenyl)-2-(2-(1-cyclopropyl-1H-indazol-5-yl)pyridin-4-yl)-5-methylbenzo[d]thiazol-6-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI$^+$: calc'd for C$_{34}$H$_{31}$ClN$_4$O$_3$S: 623.2 (M+H$^+$); found: 623.2. $^1$H NMR (400 MHz, CD$_3$OD) δ: 8.73 (d, J=2.6 Hz, 1H), 8.49 (s, 1H), 8.43 (s, 1H), 8.15-8.10 (m, 2H), 7.93-7.92 (m, 2H), 7.82 (d, J=4.6 Hz, 1H), 7.69 (d, J=4.0 Hz, 1H), 7.61-7.60 (m, 3H), 5.28 (s, 1H), 3.67-3.72 (m, 1H), 2.63 (s, 3H), 1.23-1.20 (m, 4H), 0.98 (s, 9H).

Example 44

Method M: Preparation of (S)-2-tert-butoxy-2-(7-(4-chlorophenyl)-2-(2-(2-(difluoromethyl)-2H-indazol-5-yl)pyridin-4-yl)-5-methylbenzo[d]thiazol-6-yl) acetic acid (176) and (S)-2-tert-butoxy-2-(7-(4-chlorophenyl)-2-(2-(1-(difluoromethyl)-1H-indazol-5-yl)pyridin-4-yl)-5-methylbenzo[d]thiazol-6-yl) acetic acid (177)

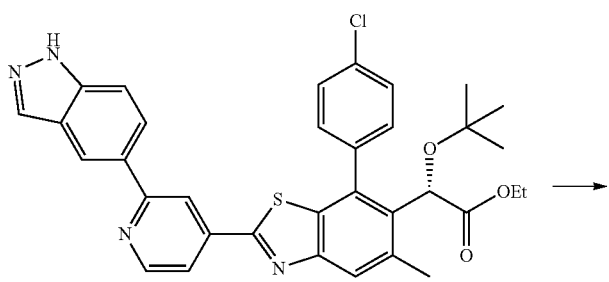

(S)-ethyl 2-(2-(2-(1H-indazol-5-yl)pyridin-4-yl)-
7-(4-chlorophenyl)-5-methylbenzo
[d]thiazol-6-yl)-2-tert-butoxyacetate

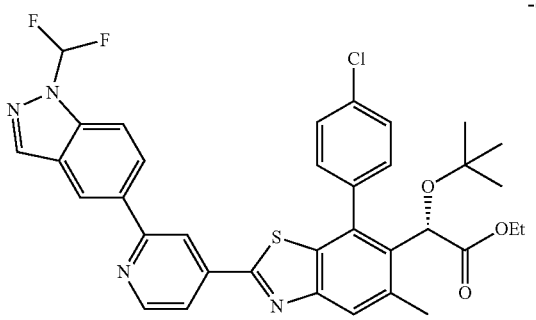

(S)-ethyl 2-tert-butoxy-2-(7-(4-chlorophenyl)-2-(2-(1-(difluoromethyl)-1H-indazol-5-yl)pyridin-4-yl)-5-methylbenzo[d]thiazol-6-yl)acetate

+

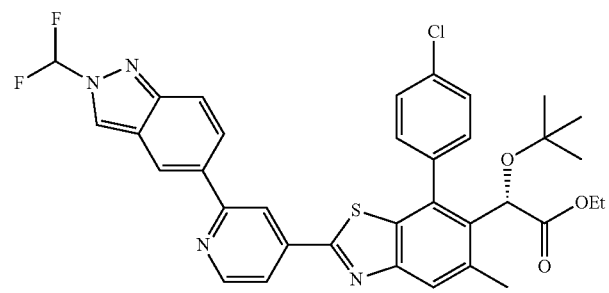

(S)-ethyl 2-tert-butoxy-2-(7-(4-chlorophenyl)-2-(2-(2-(difluoromethyl)-2H-indazol-5-yl)pyridin-4-yl)-5-methylbenzo[d]thiazol-6-yl)acetate

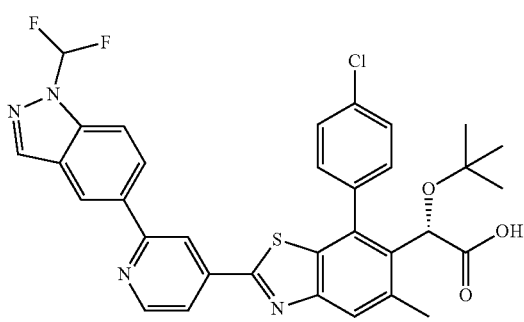

(S)-2-tert-butoxy-2-(7-(4-chlorophenyl)-2-(2-(1-(difluoromethyl)-1H-indazol-5-yl)pyridin-4-yl)-5-methylbenzo[d]thiazol-6-yl)acetic acid
177

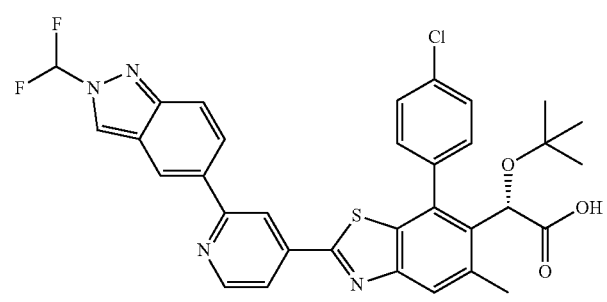

(S)-2-tert-butoxy-2-(7-(4-chlorophenyl)-2-(2-(2-(difluoromethyl)-2H-indazol-5-yl)pyridin-4-yl)-5-methylbenzo[d]thiazol-6-yl)acetic acid
176

Preparation of (S)-ethyl 2-tert-butoxy-2-(7-(4-chlorophenyl)-2-(2-(1-(difluoromethyl)-1H-indazol-5-yl)pyridin-4-yl)-5-methylbenzo[d]thiazol-6-yl)acetate: To a solution of (S)-ethyl 2-(2-(2-(1H-indazol-5-yl)pyridin-4-yl)-7-(4-chlorophenyl)-5-methylbenzo[d]thiazol-6-yl)-2-tert-butoxyacetate (20 mg, 0.0327 mmol) in DMF (1 mL) was added $Cs_2CO_3$ (53 mg, 0.163 mmol), methyl 2-chloro-2,2-difluoroacetate (4 μL, 0.039 mmol). The reaction mixture was heated at 60° C. overnight. Then more methyl 2-chloro-2,2-difluoroacetate (6 μL, 0.058 mmol) was added and heated at 60° C. for 1 day. The reaction mixture was washed by water, extracted by EtOAc, the organic phase was dried over $MgSO_4$, filtered, concentrated down, purified by silica gel column, eluting by 0-50% EtOAc in hexanes to give (S)-ethyl 2-tert-butoxy-2-(7-(4-chlorophenyl)-2-(2-(1-(difluoromethyl)-1H-indazol-5-yl)pyridin-4-yl)-5-methylbenzo[d]thiazol-6-yl)acetate LCMS-ESI⁺: calc'd for $C_{35}H_{31}ClF_2N_4O_3S$: 661.2 (M+H⁺); found: 661.2; and (S)-ethyl 2-tert-butoxy-2-(7-(4-chlorophenyl)-2-(2-(2-(difluoromethyl)-2H-indazol-5-yl)pyridin-4-yl)-5-methylbenzo[d]thiazol-6-yl)acetate. LCMS-ESI⁺: calc'd for $C_{35}H_{31}ClF_2N_4O_3S$: 661.2 (M+H⁺); found: 661.3.

Preparation of (S)-2-tert-butoxy-2-(7-(4-chlorophenyl)-2-(2-(1-(difluoromethyl)-1H-indazol-5-yl)pyridin-4-yl)-5-methylbenzo[d]thiazol-6-yl)acetic acid: (S)-2-tert-butoxy-2-(7-(4-chlorophenyl)-2-(2-(1-(difluoromethyl)-1H-indazol-5-yl)pyridin-4-yl)-5-methylbenzo[d]thiazol-6-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI⁺: calc'd for $C_{33}H_{27}ClF_2N_4O_3S$: 633.2 (M+H⁺); found: 633.2. ¹H NMR (400 MHz, $CD_3OD$) δ: 8.77 (d, J=2.8 Hz, 1H), 8.56 (s, 1H), 8.52 (s, 1H), 8.34 (s, 1H), 8.28 (d, J=4.4 Hz, 1H), 7.96-7.60 (m, 8H), 5.28 (s, 1H), 2.64 (s, 3H), 0.98 (s, 9H). ¹⁹F NMR (400 MHz, $CD_3OD$) δ: −97.70 (dm J=27.8 Hz, 2F).

Preparation of (S)-2-tert-butoxy-2-(7-(4-chlorophenyl)-2-(2-(2-(difluoromethyl)-2H-indazol-5-yl)pyridin-4-yl)-5-methylbenzo[d]thiazol-6-yl)acetic acid: (S)-2-tert-butoxy-2-(7-(4-chlorophenyl)-2-(2-(2-(difluoromethyl)-2H-indazol-5-yl)pyridin-4-yl)-5-methylbenzo[d]thiazol-6-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI⁺: calc'd for $C_{33}H_{27}ClF_2N_4O_3S$: 633.2 (M+H⁺); found: 633.2. ¹H NMR (400 MHz, $CD_3OD$) δ: 8.83 (s. 1H), 8.76 (d, J=2.6 Hz, 1H), 8.54 (d, J=0.4 Hz, 1H), 8.49 (s, 1H), 8.08-7.84 (m, 5H), 7.71-7.60 (m, 4H), 5.28 (s, 1H), 2.63 (s, 3H), 0.98 (s, 9H). ¹⁹F NMR (400 MHz, $CD_3OD$) δ: −97.17 (d, J=31.6 Hz, 2F).

Example 45

Method N: Preparation of (S)-2-tert-butoxy-2-(7-(4-chlorophenyl)-5-methyl-2-(2-(1-(trifluoromethyl)-1H-indazol-5-yl)pyridin-4-yl)benzo[d]thiazol-6-yl)acetic acid (178)

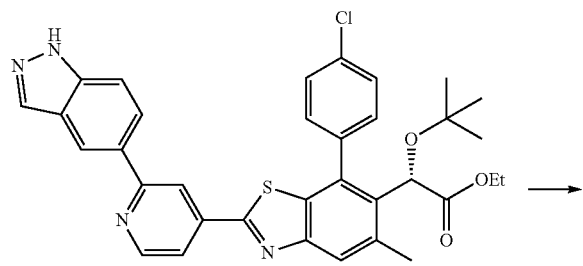

(S)-ethyl 2-(2-(2-(1H-indazol-5-yl)pyridin-4-yl)-7-(4-chlorophenyl)-5-methylbenzo[d]thiazol-6-yl)-2-tert-butoxyacetate

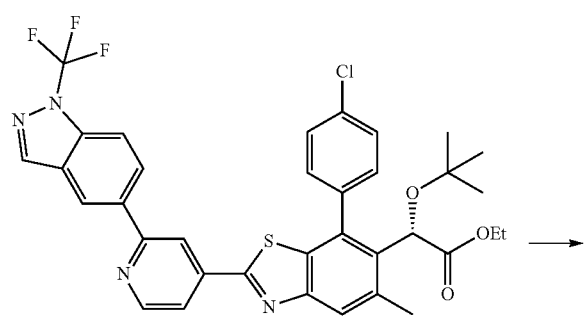

(S)-ethyl 2-tert-butoxy-2-(7-(4-chlorophenyl)-5-methyl-2-(2-(1-(trifluoromethyl)-1H-indazol-5-yl)pyridin-4-yl)benzo[d]thiazol-6-yl)acetate

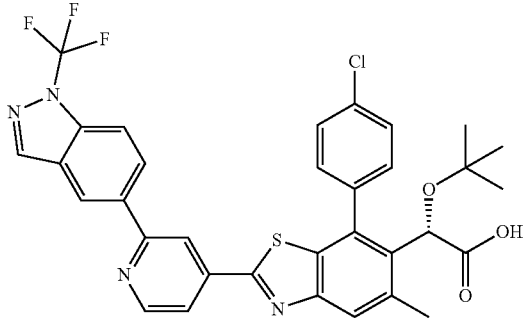

(S)-2-tert-butoxy-2-(7-(4-chlorophenyl)-5-methyl-2-(2-(1-(trifluoromethyl)-1H-indazol-5-yl)pyridin-4-yl)benzo[d]thiazol-6-yl)acetic acid
178

Preparation of (S)-ethyl 2-tert-butoxy-2-(7-(4-chlorophenyl)-5-methyl-2-(2-(1-(trifluoromethyl)-1H-indazol-5-yl)pyridin-4-yl)benzo[d]thiazol-6-yl)acetate: To a solution of (S)-ethyl 2-(2-(2-(1H-indazol-5-yl)pyridin-4-yl)-7-(4-chlorophenyl)-5-methylbenzo[d]thiazol-6-yl)-2-tert-butoxyacetate (40 mg, 0.065 mmol) in $CS_2$ (1.5 mL), was added 1-Trifluoromethyl-3,3-dimethyl-1,2-benziodoxole (64 mg, 0.195 mmol), bis(trifluoromethane)sulfonimide (27 mg, 0.0975 mmol). The reaction mixture was heated at 60° C. in sealed microwave vial for 1d. The reaction mixture was washed by saturated $NaHCO_3$, extracted by EtOAc, the organic phase was dried over $MgSO_4$, filtered, concentrated down, purified by silica gel column, eluting by 0-50% EtOAc in hexanes to give the product. LCMS-ESI$^+$: calc'd for $C_{35}H_{30}ClF_3N_4O_3S$: 679.2 (M+H$^+$); found: 679.2.

Preparation of (S)-2-tert-butoxy-2-(7-(4-chlorophenyl)-5-methyl-2-(2-(1-(trifluoromethyl)-1H-indazol-5-yl)pyridin-4-yl)benzo[d]thiazol-6-yl)acetic acid: (S)-2-tert-butoxy-2-(7-(4-chlorophenyl)-5-methyl-2-(2-(1-(trifluoromethyl)-1H-indazol-5-yl)pyridin-4-yl)benzo[d]thiazol-6-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI$^+$: calc'd for $C_{33}H_{26}ClF_2N_4O_3S$: 651.1 (M+H$^+$); found: 651.2. $^1$H NMR (400 MHz, $CD_3OD$) δ: 8.96 (s, 1H), 8.77 (d, J=2.6 Hz, 1H), 8.50 (s, 2H), 8.20-8.17 (m, 1H), 7.93-7.92 (m, 2H), 7.85-7.65 (m, 2H), 7.61 (s, 3H), 5.28 (s, 1H), 2.63 (s, 3H), 0.98 (s, 9H). $^{19}$F NMR (400 MHz, $CD_3OD$) δ: −62.05 (s, 3F).

Example 46

Method O: Preparation of (S)-2-(2-(2-(1-(azetidin-3-yl)-1H-indazol-5-yl)pyridin-4-yl)-7-(4-chlorophenyl)-5-methylbenzo[d]thiazol-6-yl)-2-tert-butoxyacetic acid (179)

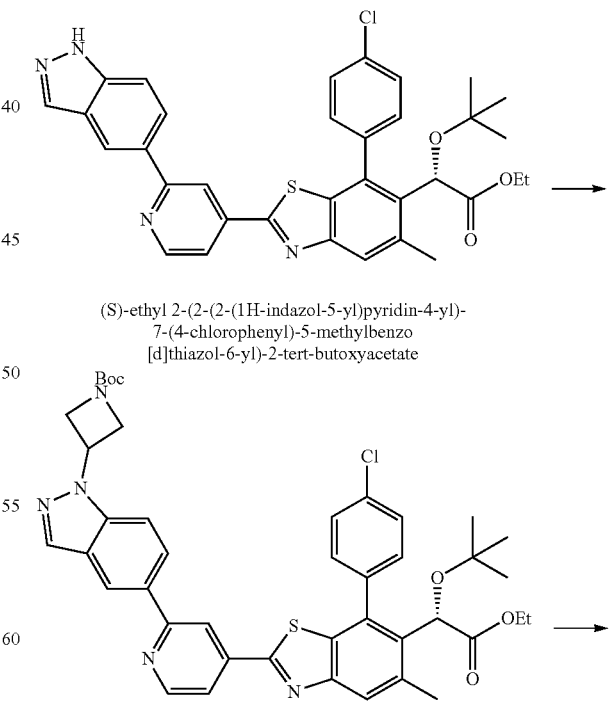

(S)-ethyl 2-(2-(2-(1H-indazol-5-yl)pyridin-4-yl)-7-(4-chlorophenyl)-5-methylbenzo[d]thiazol-6-yl)-2-tert-butoxyacetate (S)-tert-butyl 3-(5-(4-(6-(1-tert-butoxy-2-ethoxy-2-oxoethyl)-7-(4-chlorophenyl)-5-methylbenzo[d]thiazol-2-yl)pyridin-2-yl)-1H-indazol-1-yl)azetidine-1-carboxylate -continued

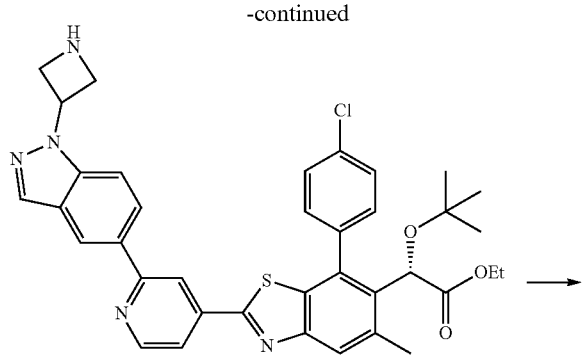

(S)-ethyl 2-(2-(2-(1-(azetidin-3-yl)1H-indazol-5-yl)
pyridin-4-yl)-7-(4-chlorophenyl)-5-methylbenzo
[d]thiazol-6-yl)-2-tert-butoxyacetate

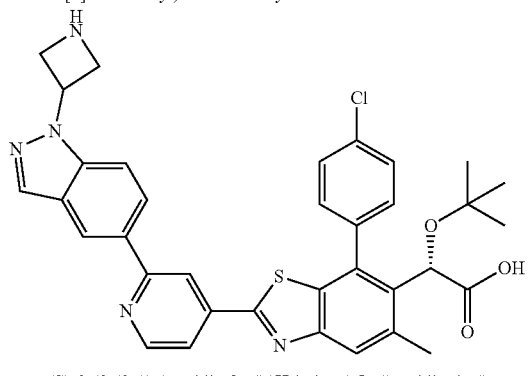

(S)-2-(2-(2-(1-(azetidin-3-yl)1H-indazol-5-yl)pyridin-4-yl)
-7-(4-chlorophenyl)-5-methylbenzo[d]
thiazol-6-yl)-2-tert-butoxyacetic acid
179

Preparation of (S)-tert-butyl 3-(5-(4-(6-(1-tert-butoxy-2-ethoxy-2-oxoethyl)-7-(4-chlorophenyl)-5-methylbenzo[d]thiazol-2-yl)pyridin-2-yl)-1H-indazol-1-yl)azetidine-1-carboxylate: To a solution of (S)-ethyl 2-(2-(2-(1H-indazol-5-yl)pyridin-4-yl)-7-(4-chlorophenyl)-5-methylbenzo[d]thiazol-6-yl)-2-tert-butoxyacetate (110 mg, 0.18 mmol) in DMF (3 mL) was added $Cs_2CO_3$ (117 mg, 0.36 mmol) and 1-Boc-3-iodoazetidine (76 mg, 0.27 mmol). The reaction mixture was heated at 60° C. overnight. The reaction mixture was washed by saturated $NaHCO_3$, extracted by EtOAc, the organic phase was dried over $MgSO_4$, filtered, concentrated down, purified by silica gel column, eluting by 0-60% EtOAc in hexanes to give the product. LCMS-ESI$^+$: calc'd for $C_{42}H_{44}ClN_5O_5S$: 766.3 (M+H$^+$); found: 766.3.

Preparation of (S)-ethyl 2-(2-(2-(1-(azetidin-3-yl)-1H-indazol-5-yl)pyridin-4-yl)-7-(4-chlorophenyl)-5-methylbenzo[d]thiazol-6-yl)-2-tert-butoxyacetate: To a solution of (S)-tert-butyl 3-(5-(4-(6-(1-tert-butoxy-2-ethoxy-2-oxoethyl)-7-(4-chlorophenyl)-5-methylbenzo[d]thiazol-2-yl)pyridin-2-yl)-1H-indazol-1-yl)azetidine-1-carboxylate (54 mg, 0.070 mmol) in isopropanol (3 mL) was added HCl in Dioxane (3 mL, 4 N in dioxane). The reaction mixture was stirred at room temperature. After the reaction finished, the reaction mixture was diluted by EtOAc, washed by saturated $NaHCO_3$, back-extracted by EtOAc, the organic phase was dried over $MgSO_4$, filtered, concentrated down, purified by silica gel column, eluting by 0-100% EtOAc in hexanes to give the product. LCMS-ESI$^+$: calc'd for $C_{37}H_{36}ClN_5O_3S$: 666.2 (M+H$^+$); found: 666.3.

Preparation of (S)-2-(2-(2-(1-(azetidin-3-yl)-1H-indazol-5-yl)pyridin-4-yl)-7-(4-chlorophenyl)-5-methylbenzo[d]thiazol-6-yl)-2-tert-butoxyacetic acid: (S)-2-(2-(2-(1-(azetidin-3-yl)-1H-indazol-5-yl)pyridin-4-yl)-7-(4-chlorophenyl)-5-methylbenzo[d]thiazol-6-yl)-2-tert-butoxyacetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI$^+$: calc'd for $C_{35}H_{32}ClN_5O_3S$: 638.2 (M+H$^+$); found: 638.2. NMR (400 MHz, CD$_3$OD) δ: 8.75 (d, J=2.6 Hz), 8.50 (s, 2H), 8.37 (s, 1H), 8.20-8.18 (m, 1H), 7.94-7.90 (m, 2H), 7.74-7.69 (m, 2H), 7.61 (m, 3H), 5.92-5.88 (m, 1H), 5.28 (s, 1H), 4.67 (d, J=3.8 Hz, 4H), 2.63 (s, 3H), 0.98 (s, 9H).

Example 47

Method P: Preparation of (S)-2-tert-butoxy-2-(7-(4-chlorophenyl)-5-methyl-2-(2-(1-methyl-1H-pyrazolo[4,3-b]pyridin-5-yl)pyridin-4-yl)benzo[d]thiazol-6-yl)acetic acid (180)

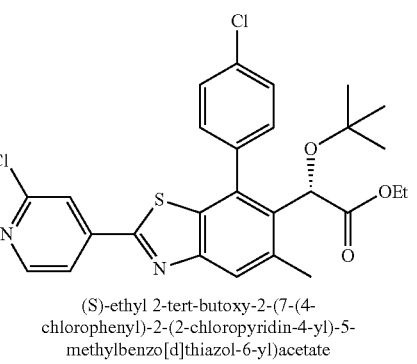

(S)-ethyl 2-tert-butoxy-2-(7-(4-chlorophenyl)-2-(2-chloropyridin-4-yl)-5-methylbenzo[d]thiazol-6-yl)acetate

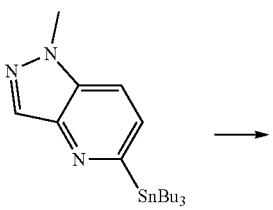

1-methyl-5-
(tributylstannyl)-
1-H-pyrazolo
[4, 3-b]pyridine

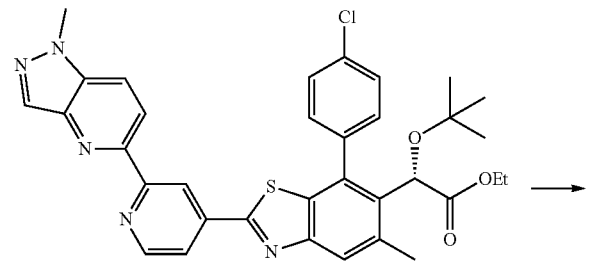

(S)-ethyl 2-tert-butoxy-2-(7-(4-chlorophenyl)
-5-methyl-2-(2-(1-methyl)-1H-pyrazolo
[4, 3-b]pyridin-5-yl)pyridin-4-yl)benzo[d]thiazol-6-
-yl)acetate

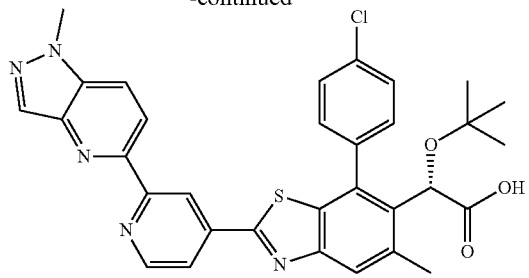

(S)-2-tert-butoxy-2-(7-(4-chlorophenyl)-5-methyl-2-(2-(1-methyl-1H-pyrazolo[4,3-b]pyridin-5-yl)pyridin-4-yl)benzo[d]thiazol-6-yl)acetic acid
180

Preparation of (S)-ethyl 2-tert-butoxy-2-(7-(4-chlorophenyl)-5-methyl-2-(2-(1-methyl-1H-pyrazolo[4,3-b]pyridin-5-yl)pyridin-4-yl)benzo[d]thiazol-6-yl)acetate: To a solution of (S)-ethyl 2-tert-butoxy-2-(7-(4-chlorophenyl)-2-(2-chloropyridin-4-yl)-5-methylbenzo[d]thiazol-6-yl)acetate (48 mg, 0.091 mmol) in microwave vial, was added 1-methyl-5-(tributylstannyl)-1H-pyrazolo[4,3-b]pyridine (47 mg, 0.111 mmol), copper(I) iodide (9 mg, 0.045 mmol), lithium chloride (11 mg, 0.27 mmol), Pd(PPh$_3$)$_4$ (10 mg, 0.009 mmol). The reaction mixture was heated at 120° C. for 4 hours. Then the mixture was washed by saturated NaHCO$_3$, extracted by EtOAc, the organic phase was dried over MgSO$_4$, filtered, concentrated down, purified by silica gel column, eluting by 0-60% EtOAc in hexanes to give the product. LCMS-ESI$^+$: calc'd for C$_{34}$H$_{32}$ClN$_5$O$_3$S: 626.2 (M+H$^+$); found: 626.3.

Preparation of (S)-2-tert-butoxy-2-(7-(4-chlorophenyl)-5-methyl-2-(2-(1-methyl-1H-pyrazolo[4,3-b]pyridin-5-yl)pyridin-4-yl)benzo[d]thiazol-6-yl)acetic acid: (S)-2-tert-butoxy-2-(7-(4-chlorophenyl)-5-methyl-2-(2-(1-methyl-1H-pyrazolo[4,3-b]pyridin-5-yl)pyridin-4-yl)benzo[d]thiazol-6-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI$^+$: calc'd for C$_{32}$H$_{28}$ClN$_5$O$_3$S: 598.2 (M+H$^+$); found: 598.2. $^1$H NMR (400 MHz, CD$_3$OD) S: 8.77 (s, 1H), 8.60 (d, J=2.6 Hz, 1H), 8.32 (d, J=4.6 Hz, 1H), 8.15 (s, 1H), 7.99 (d, J=4.2 Hz, 1H), 7.84 (d, J=2.4 Hz, 1H), 7.76 (s, 1H), 7.61 (d, J=4.4 Hz, 1H), 7.52-7.19 (m, 3H), 5.19 (s, 1H), 3.98 (s, 3H), 2.52 (s, 3H), 0.89 (s, 9H).

Example 48

Method Q: Preparation of (S)-2-tert-butoxy-2-(4-(4-chlorophenyl)-1,6-dimethyl-3-(1-methylpiperidin-4-yl)-2-oxo-2,3-dihydro-1H-benzo[d]imidazol-5-yl)acetic acid (181)

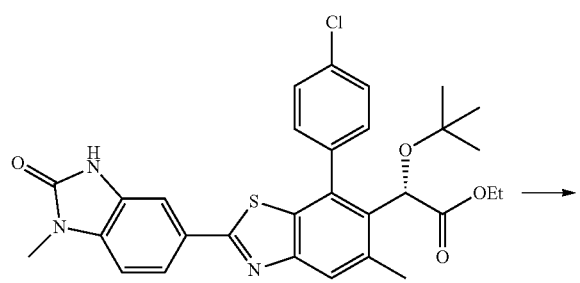

(S)-ethyl 2-tert-butoxy-2-(7-(4-chlorophenyl)-5-methyl-2-(1-methyl-2-oxo-2, 3-dihydro-1H-benzo[d]imidazol-5-yl)benzo[d]thiazol-6-yl)acetate

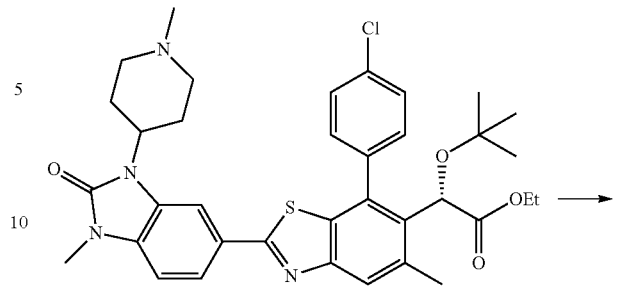

(S)-ethyl 2-tert-butoxy-2-(7-(4-chlorophenyl)-5-methyl-2-(1-methyl-3-(1-methylpiperidin-4-yl)-2-oxo-2, 3-dihydro-1H-benzo[d]imidazol-5-yl)benzo[d]thiazol-6-yl)acetate

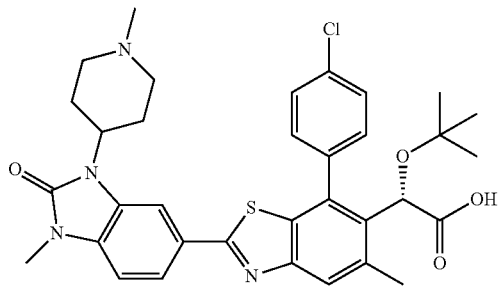

(S)-2-tert-butoxy-2-(7-(4-chlorophenyl)-5-methyl-2-(1-methyl-3-(1-methylpiperidin-4-yl)-2-oxo-2, 3-dihydro-1H-benzo[d]imidazol-5-yl)benzo[d]thiazol-6-yl)acetic acid
181

Preparation of (S)-ethyl 2-tert-butoxy-2-(7-(4-chlorophenyl)-5-methyl-2-(1-methyl-3-(1-methylpiperidin-4-yl)-2-oxo-2,3-dihydro-1H-benzo[d]imidazol-5-yl)benzo[d]thiazol-6-yl)acetate: To a solution of (S)-ethyl 2-tert-butoxy-2-(7-(4-chlorophenyl)-5-methyl-2-(1-methyl-2-oxo-2,3-dihydro-1H-benzo[d]imidazol-5-yl)benzo[d]thiazol-6-yl)acetate (47 mg, 0.083 mmol) in DMF (1 mL), pyridine (0.5 mL), was added N-methyl-4-bromopiperidine (26 mg, 0.146 mmol). The reaction was stirred at 85° C. overnight. Then Cs$_2$CO$_3$ (54 mg) was added, raised temp to 100° C. and stirred overnight. More N-methyl-4-bromopiperidine (50 mg 0.28 mmol), the mixture was heated at 100° C. for 2 days. The reaction was quenched by adding water, extracted by EtOAc, dried by MgSO$_4$, filtered, concentrated down and purified by silica gel column, first 0-100% EtOAc in hexanes to elute (S)-ethyl 2-tert-butoxy-2-(7-(4-chlorophenyl)-5-methyl-2-(1-methyl-2-oxo-2,3-dihydro-1H-benzo[d]imidazol-5-yl)benzo[d]thiazol-6-yl)acetate, then switched to 0-20% MeOH in DCM to elute the product. LCMS-ESI$^+$: calc'd for C$_{36}$H$_{41}$ClN$_4$O$_4$S: 661.2 (M+H$^+$); found: 661.3.

Preparation of (S)-2-tert-butoxy-2-(4-(4-chlorophenyl)-1, 6-dimethyl-3-(1-methylpiperidin-4-yl)-2-oxo-2,3-dihydro-1H-benzo[d]imidazol-5-yl)acetic acid: (S)-2-tert-butoxy-2-(4-(4-chlorophenyl)-1,6-dimethyl-3-(1-methylpiperidin-4-yl)-2-oxo-2,3-dihydro-1H-benzo[d]imidazol-5-yl)acetic acid was made by the similar method to make (S)-2-tert-butoxy-2-(7-(4-chlorophenyl)-5-methyl-2-(3-(pyrimidin-5-yl)phenyl)benzo[d]thiazol-6-yl)acetic acid in method D. LCMS-ESI$^+$: calc'd for C$_{34}$H$_{37}$ClN$_4$O$_4$S: 633.2 (M+H$^+$); found: 633.2. $^1$H NMR (400 MHz, CD$_3$OD) δ: 7.84 (s, 1H), 7.5-7.70 (m, 2H), 7.60-7.57 (m, 1H), 7.51-7.49 (m, 3H), 7.17 (d, J=4.2 Hz), 5.15 (s, 1H), 4.56-4.53 (m, 1H), 3.61-3.57 (m, 2H), 3.34 (s, 3H), 3.19-3.15 (m, 2H), 2.86 (s, 3H), 2.75-2.72 (m, 2H), 2.51 (s, 3H), 2.05-2.02 (m, 2H), 0.88 (s, 9H).

Example 49

Method U: Preparation of (S)-2-tert-butoxy-2-(7-(4-chlorophenyl)-5-methyl-2-(1-(1-methyl-1H-indazol-5-yl)-2-oxo-1,2-dihydropyridin-3-yl)benzo[d]thiazol-6-yl)acetic acid (182)

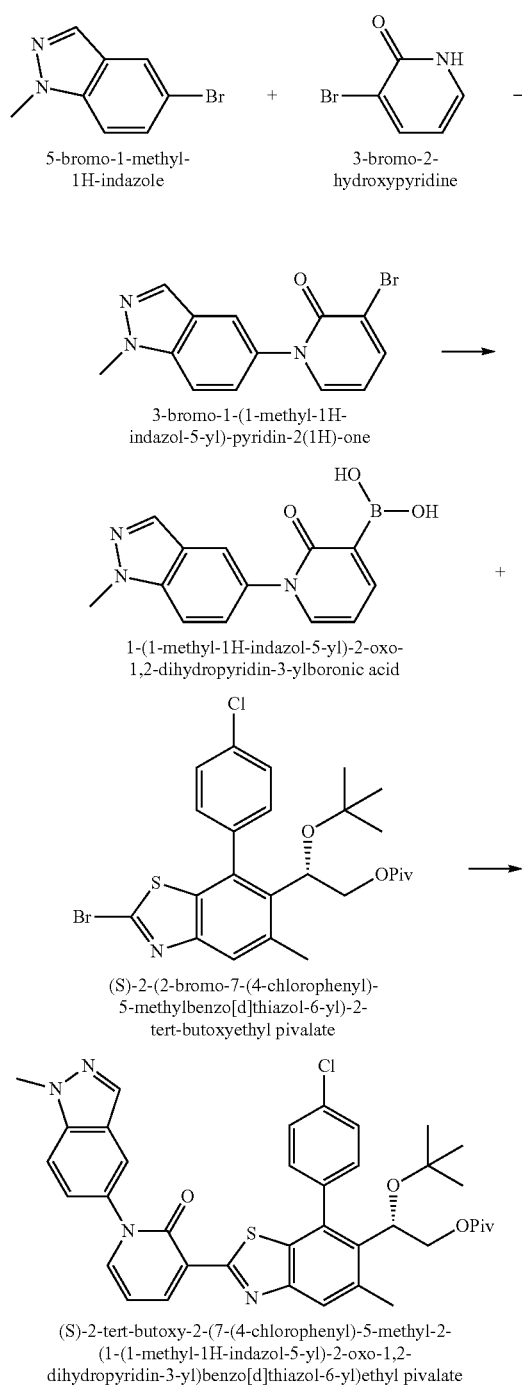
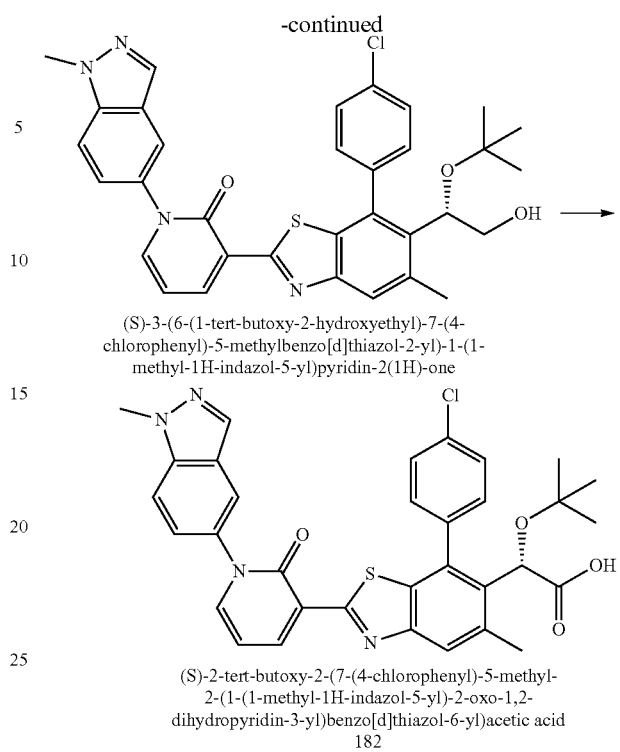

Preparation of 3-bromo-1-(1-methyl-1H-indazol-5-yl)pyridin-2(1H)-one: To a solution of 3-bromo-2-hydroxypyridine (600 mg, 3.448 mmol) in anhydrous DMF (4.0 mL) was added 5-bromo-1-methyl-1H-indazole (1455 mg, 6.896 mmol), CuI (394 mg, 2.069 mmol), trans-$N_1,N_2$-dimethylcyclohexane-1,2-diamine (1.09 mL, 6.896 mmol) and $K_2CO_3$ (1191 mg, 8.621 mmol). The reaction mixture was heated to 110° C. for 15 min. The reaction mixture was purified by reverse phase HPLC, eluting by 0-100% acetonitrile in $H_2O$ with 0.1% TFA to give the TFA salt of the desired product (135 mg, 16%). Then the product was diluted with EtOAc, extracted with saturated $NaHCO_3$, brine, dried over $Na_2SO_4$, filtered and concentrated to give the free base of the desired product. LCMS-ESI+ (m/z): [M+H]+ calcd for $C_{13}H_{11}BrN_3O$: 304.0; found: 304.2.

Preparation of 1-(1-methyl-1H-indazol-5-yl)-2-oxo-1,2-dihydropyridin-3-ylboronic acid: To a stirred and cooled (−78° C.) solution of 3-bromo-1-(1-methyl-1H-indazol-5-yl)pyridin-2(1H)-one (87 mg, 0.287 mmol) and trimethylborate (137 μL, 1.234 mmol) in anhydrous THF (5.0 mL) was added n-BuLi (2.5 M in hexane, 0.71 mL) for 10 min. Quenched the reaction by water and then purified by reverse phase HPLC, eluting by 0-100% acetonitrile in $H_2O$ with 0.1% TFA to give the desired product. LCMS-ESI+ (m/z): [M+H]+ calcd for $C_{13}H_{13}BN_3O_3$: 270.1; found: 270.2.

Preparation of (S)-2-tert-butoxy-2-(7-(4-chlorophenyl)-5-methyl-2-(1-(1-methyl-1H-indazol-5-yl)-2-oxo-1,2-dihydropyridin-3-yl)benzo[d]thiazol-6-3H)ethyl pivalate: To a solution of (S)-2-(2-bromo-7-(4-chlorophenyl)-5-methylbenzo[d]thiazol-6-yl)-2-tert-butoxyethyl pivalate (20.8 mg, 0.039 mmol) and 1-(1-methyl-1H-indazol-5-yl)-2-oxo-1,2-dihydropyridin-3-ylboronic acid (22.2 mg, 0.082 mmol) in DME (0.6 mL) and EtOH (0.6 mL) was added Pd(PPh$_3$)$_4$ (2.0 mg, 0.002 mmol) and 2N $K_2CO_3$ (58 μL, 0.116 mmol). The reaction was degassed for 5 minutes with $N_2$ and then microwaved to 100° C. for 1 h. After cooling, the reaction mixture was diluted with EtOAc, extracted with saturated $NaHCO_3$, brine, dried over Na₂SO₄, filtered and concentrated and purified by flash column chromatography (silica gel, 0 to 100% ethyl acetate/hexanes) to give the desired product. LCMS-ESI+ (m/z): [M+H]+ calcd for C₃₈H₄₀ClN₄O₄S: 683.3; found: 683.4.

Preparation of (S)-3-(6-(1-tert-butoxy-2-hydroxyethyl)-7-(4-chlorophenyl)-5-methylbenzo[d]thiazol-2-yl)-1-(1-methyl-1H-indazol-5-yl)pyridin-2(1H)-one: To a stirred solution of (S)-2-tert-butoxy-2-(7-(4-chlorophenyl)-5-methyl-2-(1-(1-methyl-1H-indazol-5-yl)-2-oxo-1,2-dihydropyridin-3-yl)benzo[d]thiazol-6-yl)ethyl pivalate (15.0 mg, 0.022 mmol) in THF (1.0 mL) and methanol (0.6 mL) was added 1N NaOH solution (0.4 mL, excess). The reaction mixture was stirred at 50° C. for 4 h. The reaction mixture was diluted with EtOAc, extracted with H₂O, brine, dried over Na₂SO₄, filtered and concentrated and purified by flash column chromatography (silica gel, 0 to 100% ethyl acetate/hexanes) to give the desired product. LCMS-ESI+ (m/z): [M+H]+ calcd for C₃₃H₃₂ClN₄O₃S: 599.2; found: 599.3.

Preparation of (S)-2-tert-butoxy-2-(7-(4-chlorophenyl)-5-methyl-2-(1-(1-methyl-1H-indazol-5-yl)-2-oxo-1,2-dihydropyridin-3-yl)benzo[d]thiazol-6-yl)acetic acid: To the solution of (S)-3-(6-(1-tert-butoxy-2-hydroxyethyl)-7-(4-chlorophenyl)-5-methylbenzo[d]thiazol-2-yl)-1-(1-methyl-1H-indazol-5-yl)pyridin-2(1H)-one (7.0 mg, 0.012 mmol) in wet acetonitrile (0.75 w % H₂O, 0.8 mL), was added stock solution of H₅IO₆/CrO₃ (0.439 M in wet acetonitrile, 0.6 mL) at 0° C. for 40 min. The reaction mixture was filtered and purified by reverse phase HPLC, eluting by 0-100% acetonitrile in H₂O with 0.1% TFA to give the desired product. LCMS-ESI+ (m/z): [M+H]+ calcd for C₃₃H₃₀ClN₄O₄S: 613.2; found: 613.2. 1H NMR (400 MHz, CD₃OD) δ 8.84 (dd, J=7.2, 2.0 Hz, 1H), 8.09 (s, 1H), 7.89 (dd, J=6.8, 2.0 Hz, 1H), 7.84 (s, 1H), 7.82 (d, J=1.6 Hz, 1H), 7.69-7.63 (m, 2H), 7.54-7.43 (m, 4H), 6.68 (t, J=6.8 Hz, 1H), 5.26 (s, 1H), 4.12 (s, 3H), 2.62 (s, 3H), 0.95 (s, 9H).

Example 50

Method V: Preparation of (S)-2-tert-butoxy-2-(7-(4-chlorophenyl)-2-(2-(1,3-dimethyl-2-oxo-2,3-dihydro-1H-benzo[d]imidazol-5-yl)pyridin-4-yl)-5-methylbenzo[d]thiazol-6-yl)acetic acid (183)

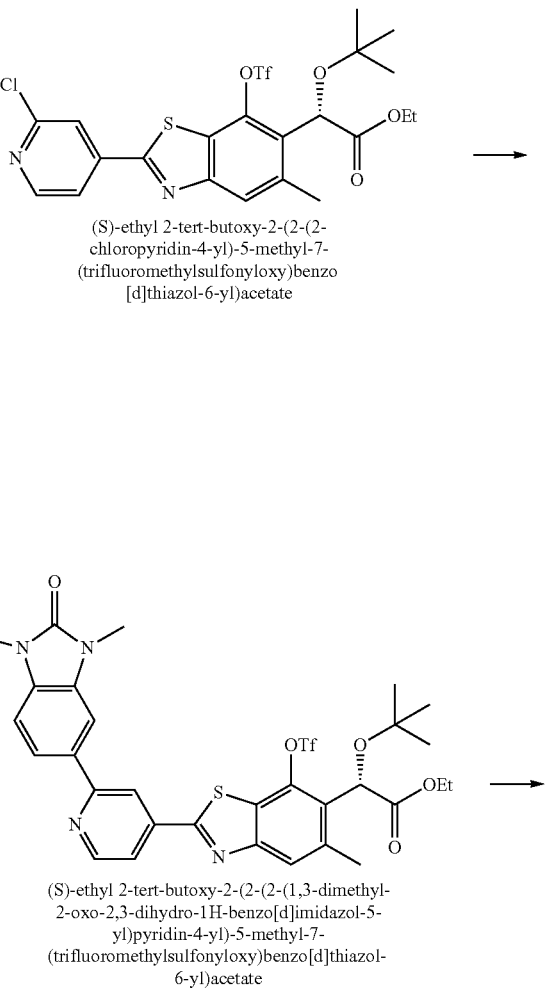

(S)-ethyl 2-tert-butoxy-2-(2-(2-chloropyridin-4-yl)-5-methyl-7-(trifluoromethylsulfonyloxy)benzo[d]thiazol-6-yl)acetate

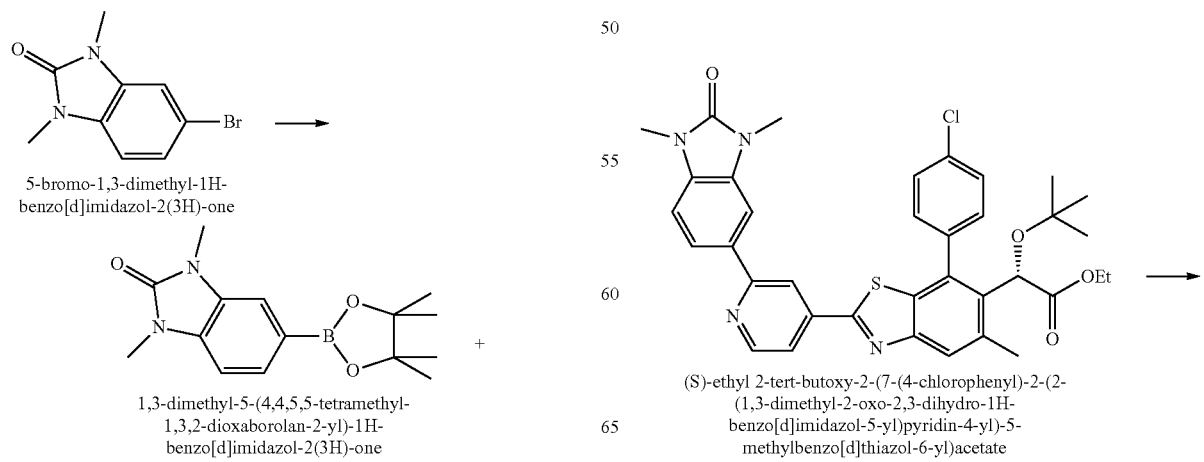

5-bromo-1,3-dimethyl-1H-benzo[d]imidazol-2(3H)-one 1,3-dimethyl-5-(4,4,5,5-tetramethyl-1,3,2-dioxaborolan-2-yl)-1H-benzo[d]imidazol-2(3H)-one (S)-ethyl 2-tert-butoxy-2-(2-(2-(1,3-dimethyl-2-oxo-2,3-dihydro-1H-benzo[d]imidazol-5-yl)pyridin-4-yl)-5-methyl-7-(trifluoromethylsulfonyloxy)benzo[d]thiazol-6-yl)acetate

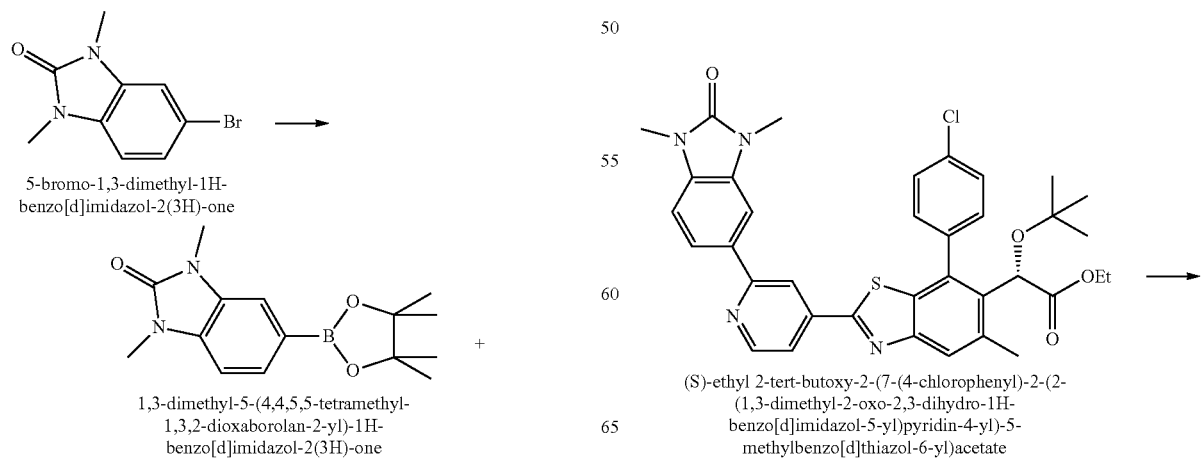

(S)-ethyl 2-tert-butoxy-2-(7-(4-chlorophenyl)-2-(2-(1,3-dimethyl-2-oxo-2,3-dihydro-1H-benzo[d]imidazol-5-yl)pyridin-4-yl)-5-methylbenzo[d]thiazol-6-yl)acetate

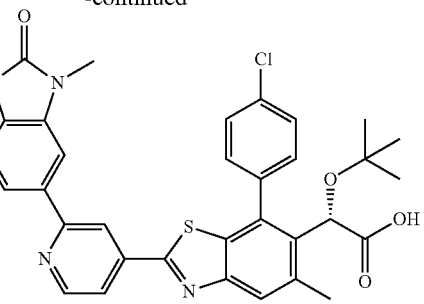

(S)-2-tert-butoxy-2-(7-(4-chlorophenyl)-2-(2-
(1,3-dimethyl-2-oxo-2,3-dihydro-1H-
benzo[d]imidazol-5-yl)pyridin-4-yl)-5-
methylbenzo[d]thiazol-6-yl)acetic acid
183

Preparation of 1,3-dimethyl-5-(4,4,5,5-tetramethyl-1,3,2-dioxaborolan-2-yl)-1H-benzo[d]imidazol-2(3H)-one: A solution of 5-bromo-1,3-dimethyl-1H-benzo[d]imidazol-2(3H)-one (200 mg, 0.830 mmol), bis(pinacolato)diboron (253 mg, 0.996 mmol) and potassium acetate (244 mg, 2.490 mmol) in dioxane (8.2 mL) was degassed for 5 min with $N_2$, then treated with Pd(dppf)Cl$_2$.DCM (34 mg, 0.041 mmol). The resulting mixture was heated at 90° C. overnight. After cooling, the reaction mixture was diluted with EtOAc, extracted with $H_2O$, brine, dried over $Na_2SO_4$, filtered, concentrated and purified by flash column chromatography (silica gel, 0 to 100% ethyl acetate/hexanes) to give the desired product. LCMS-ESI+ (m/z): [M+H]+ calcd for $C_{15}H_{22}BN_2O_3$: 289.2; found: 289.3.

Preparation of (S)-ethyl 2-tert-butoxy-2-(2-(2-(1,3-dimethyl-2-oxo-2,3-dihydro-1H-benzo[d]imidazol-5-yl)pyridin-4-yl)-5-methyl-7-(trifluoromethylsulfonyloxy)benzo[d]thiazol-6-yl)acetate: A solution of (S)-ethyl 2-tert-butoxy-2-(2-(2-chloropyridin-4-yl)-5-methyl-7-(trifluoromethylsulfonyloxy)benzo[d]thiazol-6-yl)acetate (26.0 mg, 0.046 mmol), 1,3-dimethyl-5-(4,4,5,5-tetramethyl-1,3,2-dioxaborolan-2-yl)-1H-benzo[d]imidazol-2(3H)-one (20.0 mg, 0.069 mmol) and $K_3PO_4$ (29.2 mg, 0.138 mmol) in dioxane (1.0 mL) and $H_2O$ (0.1 mL) was degassed for 5 min, treated with PdCl$_2$(dppf) (5.0 mg, 0.007 mmol). The resulting mixture was heated at 100° C. for 8 min. The reaction mixture was diluted with EtOAc, extracted with $H_2O$, brine, dried over $Na_2SO_4$, filtered and concentrated and purified by flash column chromatography (silica gel, 0 to 100% ethyl acetate/hexanes) to give the desired product. LCMS-ESI+ (m/z): [M+H]+ calcd for $C_{31}H_{32}F_3N_4O_7S_2$: 693.2; found: 693.1.

Preparation of (S)-ethyl 2-tert-butoxy-2-(7-(4-chlorophenyl)-2-(2-(1,3-dimethyl-2-oxo-2,3-dihydro-1H-benzo[d]imidazol-5-yl)pyridin-4-yl)-5-methylbenzo[d]thiazol-6-yl)acetate: To a solution of (S)-ethyl 2-tert-butoxy-2-(2-(2-(1,3-dimethyl-2-oxo-2,3-dihydro-1H-benzo[d]imidazol-5-yl)pyridin-4-yl)-5-methyl-7-(trifluoromethylsulfonyloxy)benzo[d]thiazol-6-yl)acetate (15.3 mg, 0.022 mmol), 4-chlorophenylboronic acid (4.0 mg, 0.026 mmol) and $K_2CO_3$ (9.0 mg, 0.066 mmol) in DME (0.5 mL) was added Pd(PPh$_3$)$_4$ (2.0 mg, 1.73×10$^{-3}$ mmol). The reaction was degassed for 5 minutes with $N_2$ and then heated at 120° C. for 6 h. After cooling, the reaction mixture was diluted with EtOAc, extracted with $H_2O$, brine, dried over $Na_2SO_4$, filtered and concentrated and purified by flash column chromatography (silica gel, 0 to 100% ethyl acetate/hexanes) to give the desired product. LCMS-ESI+ (m/z): [M+H]+ calcd for $C_{36}H_{36}ClN_4O_4S$: 655.2; found: 655.3.

Preparation of (S)-2-tert-butoxy-2-(7-(4-chlorophenyl)-2-(2-(1,3-dimethyl-2-oxo-2,3-dihydro-1H-benzo[d]imidazol-5-yl)pyridin-4-yl)-5-methylbenzo[d]thiazol-6-yl)acetic acid: To a stirred solution of (S)-ethyl 2-tert-butoxy-2-(7-(4-chlorophenyl)-2-(2-(1,3-dimethyl-2-oxo-2,3-dihydro-1H-benzo[d]imidazol-5-yl)pyridin-4-yl)-5-methylbenzo[d]thiazol-6-yl)acetate (7.0 mg, 0.011 mmol) in THF (0.5 mL) and methanol (0.5 mL) was added 1N NaOH solution (0.5 mL, excess). The reaction mixture was stirred at 50° C. for 2 h and then purified by reverse phase HPLC, eluting by 0-100% acetonitrile in $H_2O$ with 0.1% TFA to give the desired product. LCMS-ESI+ (m/z): [M+H]+ calcd for $C_{34}H_{32}ClN_4O_4S$: 627.2; found: 627.3. $^1$H NMR (400 MHz, CD$_3$OD) δ 8.68 (d, J=6.0 Hz, 1H), 8.47 (s, 1H), 7.98 (dd, J=5.6, 1.6 Hz, 1H), 7.93 (s, 1H), 7.80 (d, J=1.6 Hz, 1H), 7.78 (s, 1H), 7.71-7.68 (m, 1H), 7.62-7.58 (m, 3H), 7.24 (d, J=8.4 Hz, 1H), 5.28 (s, 1H), 3.47 (s, 3H), 3.42 (s, 3H), 2.63 (s, 3H), 0.98 (s, 9H).

Example 51

Method W: Preparation of (S)-2-tert-butoxy-2-(7-(4-chlorophenyl)-5-methyl-2-(2-(3-oxo-3,4-dihydro-2H-pyrido[3,2-b][1,4]oxazin-7-yl)pyridin-4-yl)benzo[d]thiazol-6-yl)acetic acid (184)

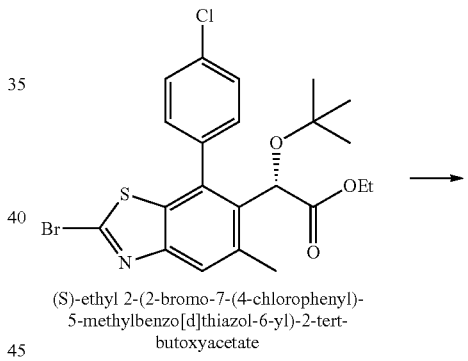

(S)-ethyl 2-(2-bromo-7-(4-chlorophenyl)-
5-methylbenzo[d]thiazol-6-yl)-2-tert-
butoxyacetate

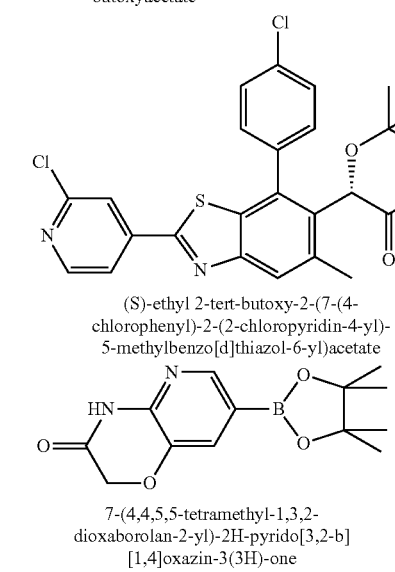

(S)-ethyl 2-tert-butoxy-2-(7-(4-
chlorophenyl)-2-(2-chloropyridin-4-yl)-
5-methylbenzo[d]thiazol-6-yl)acetate 7-(4,4,5,5-tetramethyl-1,3,2-
dioxaborolan-2-yl)-2H-pyrido[3,2-b]
[1,4]oxazin-3(3H)-one -continued

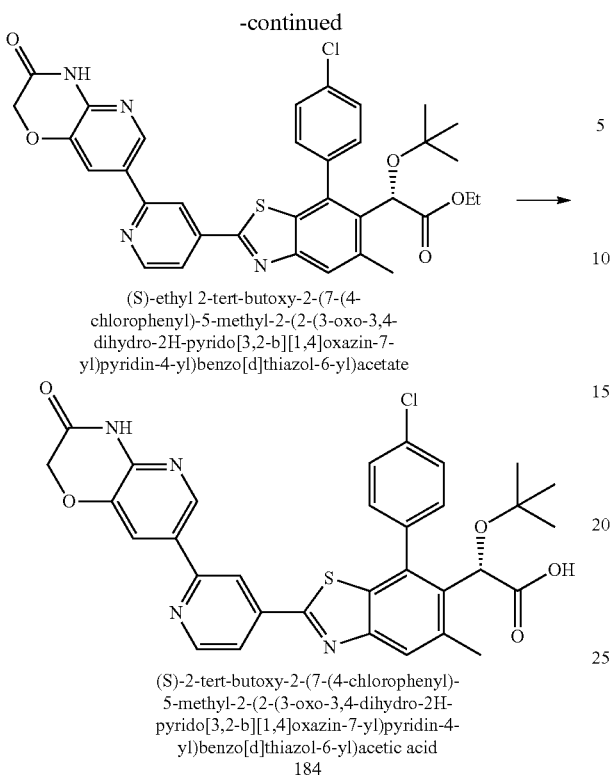

(S)-ethyl 2-tert-butoxy-2-(7-(4-chlorophenyl)-5-methyl-2-(2-(3-oxo-3,4-dihydro-2H-pyrido[3,2-b][1,4]oxazin-7-yl)pyridin-4-yl)benzo[d]thiazol-6-yl)acetate (S)-2-tert-butoxy-2-(7-(4-chlorophenyl)-5-methyl-2-(2-(3-oxo-3,4-dihydro-2H-pyrido[3,2-b][1,4]oxazin-7-yl)pyridin-4-yl)benzo[d]thiazol-6-yl)acetic acid
184

Preparation of (S)-ethyl 2-tert-butoxy-2-(7-(4-chlorophenyl)-2-(2-chloropyridin-4-yl)-5-methylbenzo[d]thiazol-6-yl)acetate: To a solution of (S)-ethyl 2-(2-bromo-7-(4-chlorophenyl)-5-methylbenzo[d]thiazol-6-yl)-2-tert-butoxyacetate (858 mg, 1.73 mmol) and 2-chloropyridine-4-boronic acid (327 mg, 2.08 mmol) in dioxane (14.6 mL) was added Pd(PPh$_3$)$_4$ (160 mg, 0.139 mmol) and 2N K$_2$CO$_3$ (3.6 mL, 7.28 mmol). The reaction was degassed for 5 minutes with N$_2$ and then heated at 90° C. for 6 h. After cooling, the reaction mixture was diluted with EtOAc, extracted with H$_2$O, brine, dried over Na$_2$SO$_4$, filtered, concentrated and purified by flash column chromatography (silica gel, 0 to 100% ethyl acetate/hexanes) to give the desired product. LCMS-ESI+ (m/z): [M+H]+ calcd for C$_{27}$H$_{27}$Cl$_2$N$_2$O$_3$S: 529.1; found: 529.2.

Preparation of (S)-ethyl 2-tert-butoxy-2-(7-(4-chlorophenyl)-5-methyl-2-(2-(3-oxo-3,4-dihydro-2H-pyrido[3,2-b][1,4]oxazin-7-yl)pyridin-4-yl)benzo[d]thiazol-6-yl)acetate: To a solution of (S)-ethyl 2-tert-butoxy-2-(7-(4-chlorophenyl)-2-(2-chloropyridin-4-yl)-5-methylbenzo[d]thiazol-6-yl)acetate (32.0 mg, 0.061 mmol) and 7-(4,4,5,5-tetramethyl-1,3,2-dioxaborolan-2-yl)-2H-pyrido[3,2-b][1,4]oxazin-3(4H)-one (20.0 mg, 0.073 mmol) in dioxane (0.5 mL) was added Pd(PPh$_3$)$_4$ (3.5 mg, 0.003 mmol) and 2N K$_2$CO$_3$ (127 μL, 0.255 mmol). The reaction was degassed for 5 minutes with N$_2$ and then heated at 100° C. for 10 h. After cooling, the reaction mixture was diluted with EtOAc, extracted with H$_2$O, brine, dried over Na$_2$SO$_4$, filtered and concentrated and purified by flash column chromatography (silica gel, 0 to 100% ethyl acetate/hexanes) to give the desired product. LCMS-ESI+ (m/z): [M+H]+ calcd for C$_{34}$H$_{32}$ClN$_4$O$_5$S: 643.2; found: 643.3.

Preparation of (S)-2-tert-butoxy-2-(7-(4-chlorophenyl)-5-methyl-2-(2-(3-oxo-3,4-dihydro-2H-pyrido[3,2-b][1,4]oxazin-7-yl)pyridin-4-yl)benzo[d]thiazol-6-yl)acetic acid: To a stirred solution of (S)-ethyl 2-tert-butoxy-2-(7-(4-chlorophenyl)-5-methyl-2-(2-(3-oxo-3,4-dihydro-2H-pyrido[3,2-b][1,4]oxazin-7-yl)pyridin-4-yl)benzo[d]thiazol-6-yl)acetate (17.1 mg, 0.027 mmol) in THF (1.1 mL) and methanol (1.1 mL) was added 1N NaOH solution (0.8 mL, excess). The reaction mixture was stirred at 50° C. for 2 h and then purified by reverse phase HPLC, eluting by 0-100% acetonitrile in H$_2$O with 0.1% TFA to give (S)-2-tert-butoxy-2-(7-(4-chlorophenyl)-5-methyl-2-(2-(3-oxo-3,4-dihydro-2H-pyrido[3,2-b][1,4]oxazin-7-yl)pyridin-4-yl)benzo[d]thiazol-6-yl)acetic acid. LCMS-ESI+ (m/z): [M+H]+ calcd for C$_{32}$H$_{28}$ClN$_4$O$_5$S: 615.2; found: 615.2. $^1$H NMR (400 MHz, CD$_3$OD) δ 8.74 (d, J=4.8 Hz, 1H), 8.61 (d, J=2.0 Hz, 1H), 8.43 (s, 1H), 7.99 (d, J=2.0 Hz, 1H), 7.94 (s, 1H), 7.91 (dd, J=5.2, 1.6 Hz, 1H), 7.71-7.68 (m, 1H), 7.62-7.59 (m, 3H), 5.28 (s, 1H), 4.72 (s, 2H), 2.63 (s, 3H), 0.97 (s, 9H).

Example 52

Method Y: Preparation of (S)-2-tert-butoxy-2-(7-(4-chlorophenyl)-5-methyl-2-(2-(1-oxo-2,6-naphthyridin-2(1H)-yl)pyridin-4-yl)benzo[d]thiazol-6-yl)acetic acid (186)

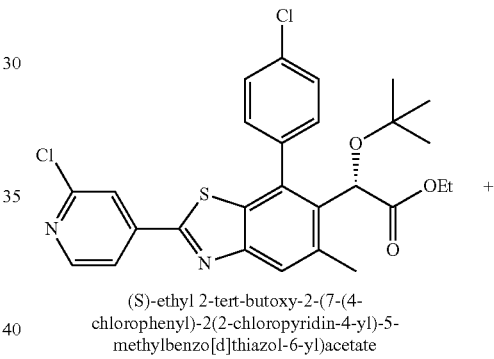

(S)-ethyl 2-tert-butoxy-2-(7-(4-chlorophenyl)-2-(2-chloropyridin-4-yl)-5-methylbenzo[d]thiazol-6-yl)acetate

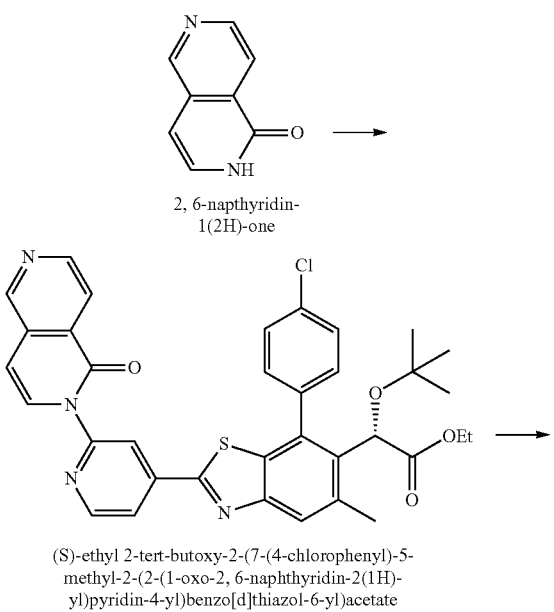

2,6-napthyridin-1(2H)-one (S)-ethyl 2-tert-butoxy-2-(7-(4-chlorophenyl)-5-methyl-2-(2-(1-oxo-2,6-naphthyridin-2(1H)-yl)pyridin-4-yl)benzo[d]thiazol-6-yl)acetate

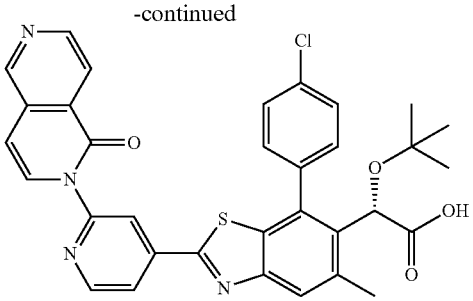

(S)-2-tert-butoxy-2-(7-(4-chlorophenyl)-5-methyl-2-(2-18-oxo-2, 6-naphthyridin-2(1H)-yl)pyridin-4-yl)benzo[d]thiazol-6-yl)acetic acid
186

Preparation of (S)-ethyl 2-tert-butoxy-2-(7-(4-chlorophenyl)-5-methyl-2-(2-(1-oxo-2,6-naphthyridin-2(1H)-yl)pyridin-4-yl)benzo[d]thiazol-6-yl)acetate: To a solution of (S)-ethyl 2-tert-butoxy-2-(7-(4-chlorophenyl)-2-(2-chloropyridin-4-yl)-5-methylbenzo[d]thiazol-6-yl)acetate (26.0 mg, 0.049 mmol) in anhydrous THF (0.6 mL) was added 2,6-naphthyridin-1(2H)-one (11.0 mg, 0.074 mmol), Xantphos (4.0 mg, 0.006 mmol), $Cs_2CO_3$ (27.0 mg, 0.084 mmol) and $Pd_2(dba)_3$ (2.0 mg, 0.002 mmol). The reaction was degassed for 5 minutes with $N_2$ and then heated at 100° C. overnight. After cooling, the reaction mixture was diluted with EtOAc, extracted with $H_2O$, brine, dried over $Na_2SO_4$, filtered, concentrated and purified by flash column chromatography (silica gel, 0 to 90% ethyl acetate/hexanes) to give the desired product. LCMS-ESI+ (m/z): [M+H]+ calcd for $C_{35}H_{32}ClN_4O_4S$: 639.2; found: 639.3.

Preparation of (S)-2-tert-butoxy-2-(7-(4-chlorophenyl)-5-methyl-2-(2-(1-oxo-2,6-naphthyridin-2(1H)-yl)pyridin-4-yl)benzo[d]thiazol-6-yl)acetic acid: To a solution of (S)-ethyl 2-tert-butoxy-2-(7-(4-chlorophenyl)-5-methyl-2-(2-(1-oxo-2,6-naphthyridin-2(1H)-yl)pyridin-4-yl)benzo[d]thiazol-6-yl)acetate (15.5 mg, 0.024 mmol) in pyridine (0.8 mL) was added LiI (100 mg, excess). The reaction mixture was heating in a microwave at 170° C. for 90 min. The mixture was concentrated in vacuo and then purified by reverse phase HPLC, eluting by 0-100% acetonitrile in $H_2O$ with 0.1% TFA to give the desired product. LCMS-ESI+ (m/z): [M+H]+ calcd for $C_{33}H_{28}ClN_4O_4S$: 611.2; found: 611.2. $^1H$ NMR (400 MHz, $CDCl_3$) δ 9.32 (s, 1H), 8.81 (d, J=6.0 Hz, 1H), 8.75-8.71 (m, 2H), 8.60 (s, 1H), 8.27 (d, J=7.6 Hz, 1H), 7.99 (d, J=3.6 Hz, 1H), 7.94 (s, 1H), 7.70 (d, J=8.0 Hz, 1H), 7.53-7.48 (m, 3H), 6.94 (d, J=8.0 Hz, 1H), 5.32 (s, 1H), 2.59 (s, 3H), 1.00 (s, 9H).

Example 53

Method Z: Preparation of (S)-2-tert-butoxy-2-(7-(4-chlorophenyl)-5-methyl-2-(2-(8-oxo-1,7-naphthyridin-7(8H)-yl)pyridin-4-yl)benzo[d]thiazol-6-yl)acetic acid (187)

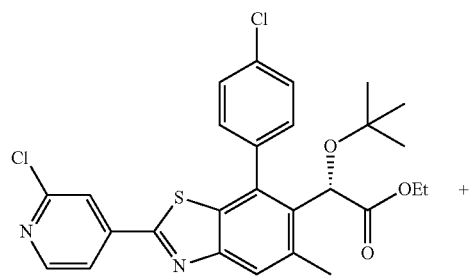

(S)-ethyl 2-tert-butoxy-2-(7-(4-chlorophenyl)-2-(2-chloropyridin-4-yl)-5-methylbenzo[d]thiazol-6-yl)acetate

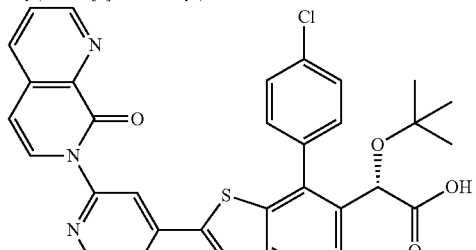

1, 7-napthyridin-8(7H)-one

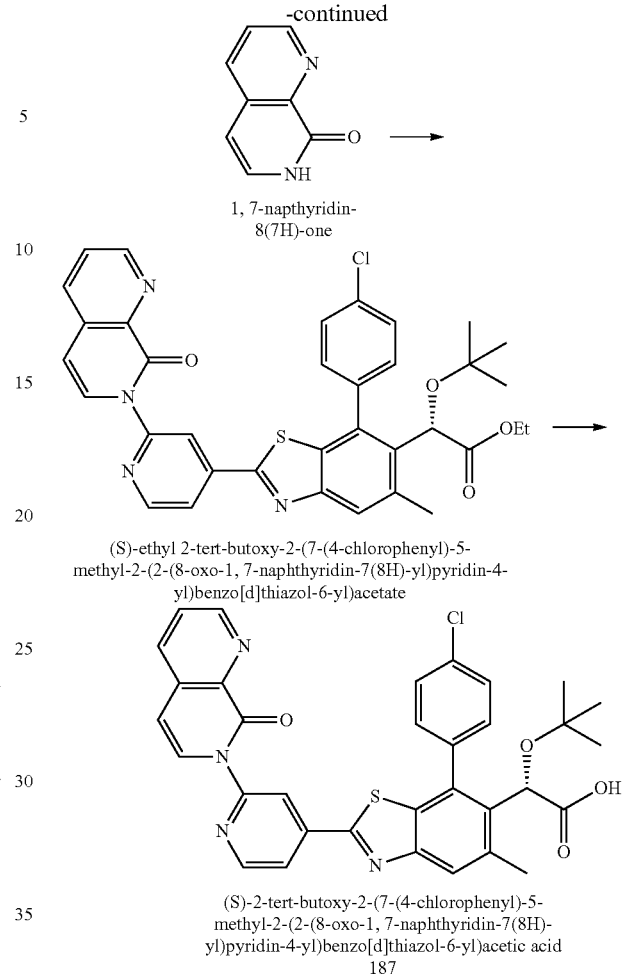

(S)-ethyl 2-tert-butoxy-2-(7-(4-chlorophenyl)-5-methyl-2-(2-(8-oxo-1, 7-naphthyridin-7(8H)-yl)pyridin-4-yl)benzo[d]thiazol-6-yl)acetate (S)-2-tert-butoxy-2-(7-(4-chlorophenyl)-5-methyl-2-(2-(8-oxo-1, 7-naphthyridin-7(8H)-yl)pyridin-4-yl)benzo[d]thiazol-6-yl)acetic acid
187

Preparation of (S)-ethyl 2-tert-butoxy-2-(7-(4-chlorophenyl)-5-methyl-2-(2-(8-oxo-1,7-naphthyridin-7(8H)-yl)pyridin-4-yl)benzo[d]thiazol-6-yl)acetate: A suspension of (S)-ethyl 2-tert-butoxy-2-(7-(4-chlorophenyl)-2-(2-chloropyridin-4-yl)-5-methylbenzo[d]thiazol-6-yl)acetate (27.0 mg, 0.051 mmol), 1,7-naphthyridin-8(7H)-one (22.4 mg, 0.153 mmol) and $Cs_2CO_3$ (66.5 mg, 0.204 mmol) in anhydrous DMF (1.0 mL) was heated in a microwave at 150° C. for 50 min. After cooling, the reaction mixture was diluted with EtOAc, extracted with $H_2O$, brine, dried over $Na_2SO_4$, filtered and concentrated and purified by flash column chromatography (silica gel, 0 to 90% ethyl acetate/hexanes) to give the desired product. LCMS-ESI+ (m/z): [M+H]+ calcd for $C_{35}H_{32}ClN_4O_4S$: 639.2; found: 639.3.

Preparation of (S)-2-tert-butoxy-2-(7-(4-chlorophenyl)-5-methyl-2-(2-(8-oxo-1,7-naphthyridin-7(8H)-yl)pyridin-4-yl)benzo[d]thiazol-6-yl)acetic acid: To a solution of (S)-ethyl 2-tert-butoxy-2-(7-(4-chlorophenyl)-5-methyl-2-(2-(8-oxo-1,7-naphthyridin-7(8H)-yl)pyridin-4-yl)benzo[d]thiazol-6-yl)acetate (7.9 mg, 0.012 mmol) in pyridine (0.6 mL) was added LiI (75 mg, excess). The reaction mixture was heating in a microwave at 170° C. for 90 min. The mixture was concentrated in vacuo and then purified by reverse phase HPLC, eluting by 0-100% acetonitrile in $H_2O$ with 0.1% TFA to give the desired product. LCMS-ESI+ (m/z): [M+H]+ calcd for $C_{33}H_{28}ClN_4O_4S$: 611.2; found: 611.2. $^1H$ NMR (400 MHz, $CDCl_3$) δ 9.06 (d, J=2.8 Hz, 1H), 8.68 (d, J=5.2 Hz, 1H), 8.62 (s, 1H), 8.08 (d, J=8.0 Hz, 1H), 7.99-7.92 (m, 3H), 7.76-7.69 (m, 2H), 7.55-7.49 (m, 3H), 6.66 (d, J=7.6 Hz, 1H), 5.34 (s, 1H), 2.58 (s, 3H), 1.01 (s, 9H).

Example 54

Method AA: Preparation of (S)-2-tert-butoxy-2-(7-(4-chlorophenyl)-2-(2-(1,2-dimethyl-3-oxo-2,3-dihydro-1H-indazol-6-yl)pyridin-4-yl)-5-methylbenzo[d]thiazol-6-yl)acetic acid (188)

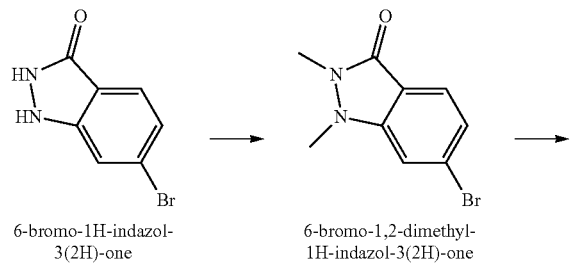

6-bromo-1H-indazol-3(2H)-one 6-bromo-1,2-dimethyl-1H-indazol-3(2H)-one

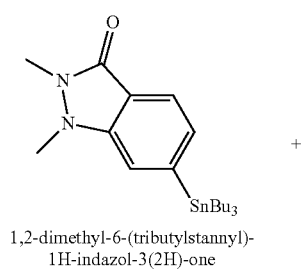

1,2-dimethyl-6-(tributylstannyl)-1H-indazol-3(2H)-one

+

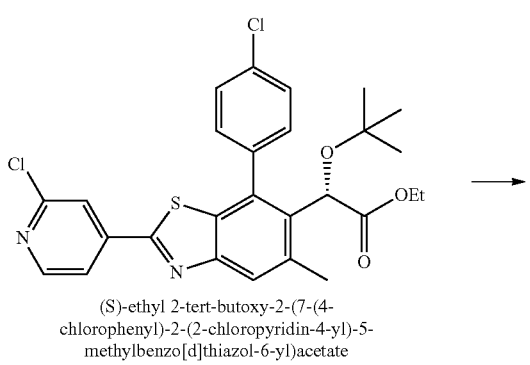

(S)-ethyl 2-tert-butoxy-2-(7-(4-chlorophenyl)-2-(2-chloropyridin-4-yl)-5-methylbenzo[d]thiazol-6-yl)acetate

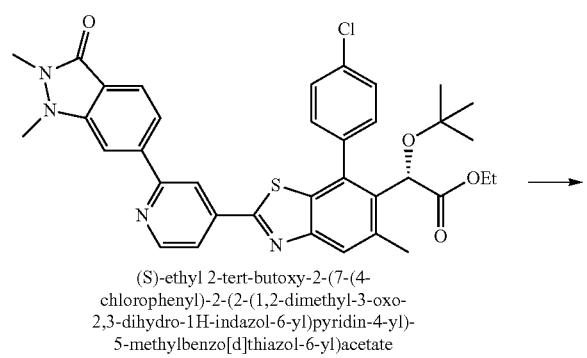

(S)-ethyl 2-tert-butoxy-2-(7-(4-chlorophenyl)-2-(2-(1,2-dimethyl-3-oxo-2,3-dihydro-1H-indazol-6-yl)pyridin-4-yl)-5-methylbenzo[d]thiazol-6-yl)acetate

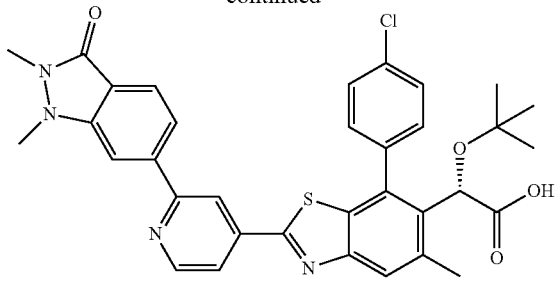

(S)-2-tert-butoxy-2-(7-(4-chlorophenyl)-2-(2-(1,2-dimethyl-3-oxo-2,3-dihydro-1H-indazol-6-yl)pyridin-4-yl)-5-methylbenzo[d]thiazol-6-yl)acetic acid
188

Preparation of 6-bromo-1,2-dimethyl-1H-indazol-3(2H)-one: To a solution of 6-bromo-1H-indazol-3(2H)-one (300 mg, 1.41 mmol) in 1N NaOH (4.2 mL) was added dimethyl sulfate (0.4 mL, 4.22 mmol). The reaction mixture was stirred at room temperature for 6 h and then purified by reverse phase HPLC, eluting by 0-100% acetonitrile in $H_2O$ with 0.1% TFA to give the desired product. LCMS-ESI+ (m/z): [M+H]+ calcd for $C_9H_{10}BrN_2O$: 241.0; found: 241.2.

Preparation of 1,2-dimethyl-6-(tributylstannyl)-1H-indazol-3(2H)-one: To a solution of 6-bromo-1,2-dimethyl-1H-indazol-3(2H)-one (51.0 mg, 0.212 mmol) and bis(tributyltin) (0.12 mL, 0.319 mmol) in toluene (2.0 mL) was added $Pd(PPh_3)_4$ (17.0 mg, 0.015 mmol). The reaction was degassed for 5 minutes with $N_2$ and then heated at 100° C. overnight. After cooling, the reaction mixture was diluted with EtOAc, treated with KF solution and stirred at room temperature for 1 h. The organic layer was washed with $H_2O$, brine, dried over $Na_2SO_4$, filtered and concentrated and purified by flash column chromatography (silica gel, 0 to 100% ethyl acetate/hexanes) to give the desired product. LCMS-ESI+ (m/z): [M+H]+ calcd for $C_{21}H_{37}N_2OSn$: 453.2; found: 453.3

Preparation of (S)-ethyl 2-tert-butoxy-2-(7-(4-chlorophenyl)-2-(2-(1,2-dimethyl-3-oxo-2,3-dihydro-1H-indazol-6-yl)pyridin-4-yl)-5-methylbenzo[d]thiazol-6-yl)acetate: To a solution of (S)-ethyl 2-tert-butoxy-2-(7-(4-chlorophenyl)-2-(2-chloropyridin-4-yl)-5-methylbenzo[d]thiazol-6-yl)acetate (32.0 mg, 0.061 mmol) and 1,2-dimethyl-6-(tributylstannyl)-1H-indazol-3(2H)-one (33.0 mg, 0.073 mmol) in dioxane (0.8 mL) was added $Pd(PPh_3)_4$ (4.0 mg, 0.003 mmol) and CuI (4.0 mg, 0.018 mmol). The reaction was degassed for 5 minutes with $N_2$ and then heated at 100° C. for 2 days. Concentrated in vacuo and then purified by flash column chromatography (silica gel, 0 to 100% ethyl acetate/hexanes) to give the desired product. LCMS-ESI+ (m/z): [M+H]+ calcd for $C_{36}H_{36}ClN_4O_4S$: 655.2; found: 655.3.

Preparation of (S)-2-tert-butoxy-2-(7-(4-chlorophenyl)-2-(2-(1,2-dimethyl-3-oxo-2,3-dihydro-1H-indazol-6-yl)pyridin-4-yl)-5-methylbenzo[d]thiazol-6-yl)acetic acid: To a stirred solution of (S)-ethyl 2-tert-butoxy-2-(7-(4-chlorophenyl)-2-(2-(1,2-dimethyl-3-oxo-2,3-dihydro-1H-indazol-6-yl)pyridin-4-yl)-5-methylbenzo[d]thiazol-6-yl)acetate (9.4 mg, 0.014 mmol) in THF (0.5 mL) and methanol (0.5 mL) was added 1N NaOH solution (0.5 mL, excess). The reaction mixture was stirred at 50° C. for 2 h and then purified by reverse phase HPLC, eluting by 0-100% acetonitrile in $H_2O$ with 0.1% TFA to give the desired product. LCMS-ESI+ (m/z): [M+H]+ calcd for $C_{34}H_{32}ClN_4O_4S$: 627.2; found: 627.2. $^1$H NMR (400 MHz, $CD_3OD$) δ 8.75 (d, J=5.2 Hz, 1H), 8.49 (s, 1H), 8.06 (s, 1H), 7.96 (dd, J=5.2, 1.2 Hz, 1H), 7.90

(s, 1H), 7.85 (q, J=8.4 Hz, 2H), 7.70-7.67 (m, 1H), 7.61-7.56 (m, 3H), 5.27 (s, 1H), 3.51 (s, 3H), 3.47 (s, 3H), 2.62 (s, 3H), 0.98 (s, 9H).

Example 55

Method AE: Preparation of (S)-2-(2-(2-(1H-indazol-1-yl)pyridin-4-yl)-7-(4-chlorophenyl)-5-methyl-benzo[d]thiazol-6-yl)-2-tert-butoxy acetic acid (189)

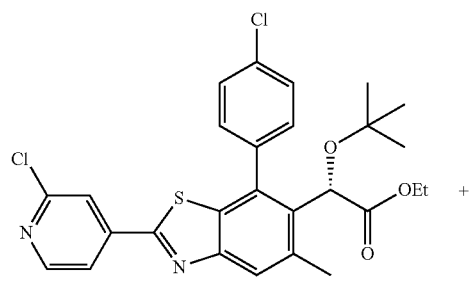

(S)-ethyl 2-tert-butoxy-2-(7-(4-chlorophenyl)-2(2-chloropyridin-4-yl)-5-methylbenzo[d]thiazol-6-yl)acetate

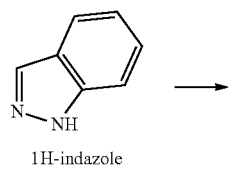

1H-indazole

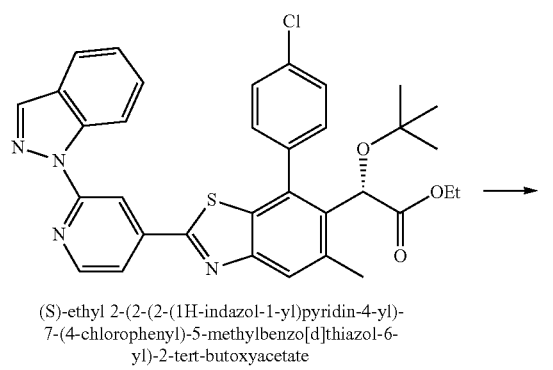

(S)-ethyl 2-(2-(2-(1H-indazol-1-yl)pyridin-4-yl)-7-(4-chlorophenyl)-5-methylbenzo[d]thiazol-6-yl)-2-tert-butoxyacetate

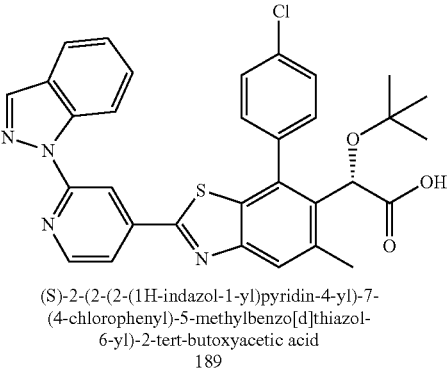

(S)-2-(2-(2-(1H-indazol-1-yl)pyridin-4-yl)-7-(4-chlorophenyl)-5-methylbenzo[d]thiazol-6-yl)-2-tert-butoxyacetic acid
189

Preparation of (S)-ethyl 2-(2-(2-(1H-indazol-1-yl)pyridin-4-yl)-7-(4-chlorophenyl)-5-methylbenzo[d]thiazol-6-yl)-2-tert-butoxyacetate: To a solution of (S)-ethyl 2-tert-butoxy-2-(7-(4-chlorophenyl)-2-(2-chloropyridin-4-yl)-5-methylbenzo[d]thiazol-6-yl)acetate (30 mg, 0.057 mmol) and 1H-indazole (6.0 mg, 0.052 mmol) in DMF (0.5 mL) was added K$_2$CO$_3$ (16.0 mg, 0.117 mmol) and 18-crown-6 (0.1 mg, 5.1×10$^{-4}$ mmol). The reaction mixture was heated in a microwave at 160° C. for 1 h. After cooling, the reaction mixture was diluted with EtOAc, extracted with H$_2$O, brine, dried over Na$_2$SO$_4$, filtered and concentrated and purified by flash column chromatography (silica gel, 0 to 60% ethyl acetate/hexanes) and then purified by reverse phase HPLC, eluting by 0-100% acetonitrile in H$_2$O with 0.1% TFA to give the desired product. LCMS-ESI+ (m/z): [M+H]+ calcd for C$_{34}$H$_{32}$ClN$_4$O$_3$S: 611.2; found: 611.3.

Preparation of (S)-2-(2-(2-(1H-indazol-1-yl)pyridin-4-yl)-7-(4-chlorophenyl)-5-methylbenzo[d]thiazol-6-yl)-2-tert-butoxyacetic acid: To a stirred solution of (S)-ethyl 2-(2-(2-(1H-indazol-1-yl)pyridin-4-yl)-7-(4-chlorophenyl)-5-methylbenzo[d]thiazol-6-yl)-2-tert-butoxyacetate (6.8 mg, 0.011 mmol) in THF (0.4 mL) and methanol (0.4 mL) was added 1N NaOH solution (0.4 mL, excess). The reaction mixture was stirred at 50° C. for 2 h and then purified by reverse phase HPLC, eluting by 0-100% acetonitrile in H$_2$O with 0.1% TFA to give the desired product. LCMS-ESI+ (m/z): [M+H]+ calcd for C$_{32}$H$_{28}$ClN$_4$O$_3$S: 583.2; found: 583.3. $^1$H NMR (400 MHz, CDCl$_3$) δ 8.86 (d, J=8.8 Hz, 1H), 8.63 (d, J=4.8 Hz, 1H), 8.57 (s, 1H), 8.23 (s, 1H), 7.97 (s, 1H), 7.81-7.77 (m, 2H), 7.73 (d, J=7.6 Hz, 1H), 7.58-7.50 (m, 4H), 7.30 (t, J=7.2 Hz, 1H), 5.35 (s, 1H), 2.61 (s, 3H), 1.02 (s, 9H).

Example 56

Method AF: Preparation of (S)-2-tert-butoxy-2-(7-(4-chlorophenyl)-5-methyl-2-(2-(1-methyl-1H-indazol-3-yl)pyridin-4-yl)benzo[d]thiazol-6-yl)acetic acid (190)

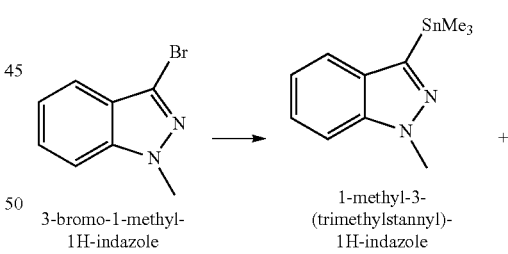

3-bromo-1-methyl-1H-indazole     1-methyl-3-(trimethylstannyl)-1H-indazole

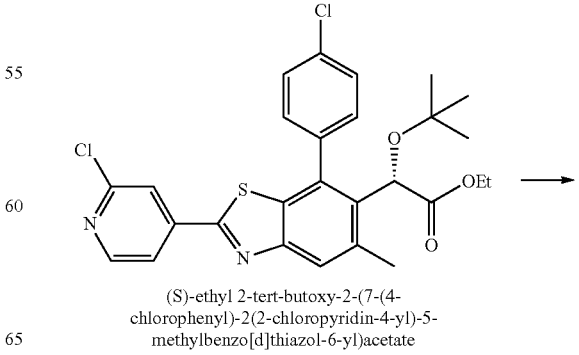

(S)-ethyl 2-tert-butoxy-2-(7-(4-chlorophenyl)-2(2-chloropyridin-4-yl)-5-methylbenzo[d]thiazol-6-yl)acetate

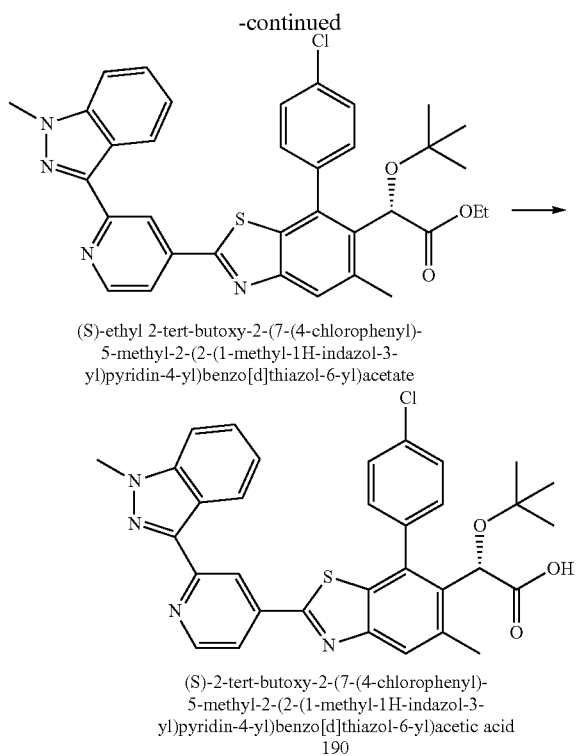

(S)-ethyl 2-tert-butoxy-2-(7-(4-chlorophenyl)-
5-methyl-2-(2-(1-methyl-1H-indazol-3-
yl)pyridin-4-yl)benzo[d]thiazol-6-yl)acetate (S)-2-tert-butoxy-2-(7-(4-chlorophenyl)-
5-methyl-2-(2-(1-methyl-1H-indazol-3-
yl)pyridin-4-yl)benzo[d]thiazol-6-yl)acetic acid
190

Preparation of 1-methyl-3-(trimethylstannyl)-1H-indazole: To a solution of 3-bromo-1-methyl-1H-indazole (100 mg, 0.476 mmol) and hexamethylditin (203 mg, 0.619 mmol) in toluene (3.5 mL) was added Pd(PPh$_3$)$_4$ (198 mg, 0.171 mmol). The reaction was heated at 110° C. for 1 h. After cooling, the reaction mixture was diluted with EtOAc, treated with KF solution and stirred at room temperature for 1 h. The organic layer was washed with H$_2$O, brine, dried over Na$_2$SO$_4$, filtered and concentrated and purified by flash column chromatography (silica gel, 0 to 60% ethyl acetate/hexanes) to give the desired product. LCMS-ESI+ (m/z): [M+H]+ calcd for C$_{11}$H$_{17}$N$_2$Sn: 297.0; found: 297.0.

Preparation of (S)-ethyl 2-tert-butoxy-2-(7-(4-chlorophenyl)-5-methyl-2-(2-(1-methyl-1H-indazol-3-yl)pyridin-4-yl)benzo[d]thiazol-6-yl)acetate: To a solution of (S)-ethyl 2-tert-butoxy-2-(7-(4-chlorophenyl)-2-(2-chloropyridin-4-yl)-5-methylbenzo[d]thiazol-6-yl)acetate (35.0 mg, 0.066 mmol) and 1-methyl-3-(trimethylstannyl)-1H-indazole (24.0 mg, 0.079 mmol) in dioxane (0.9 mL) was added Pd(PPh$_3$)$_4$ (4.0 mg, 3.03×10$^{-3}$ mmol) and CuI (4.0 mg, 0.018 mmol). The reaction was degassed for 5 minutes with N$_2$ and then heated at 100° C. overnight. After cooling, the reaction mixture was diluted with EtOAc, extracted with H$_2$O, brine, dried over Na$_2$SO$_4$, filtered and concentrated and purified by flash column chromatography (silica gel, 0 to 70% ethyl acetate/hexanes) to give the desired product. LCMS-ESI+ (m/z): [M+H]+ calcd for C$_{35}$H$_{34}$ClN$_4$O$_3$S: 625.2; found: 625.3.

Preparation of (S)-2-tert-butoxy-2-(7-(4-chlorophenyl)-5-methyl-2-(2-(1-methyl-1H-indazol-3-yl)pyridin-4-yl)benzo[d]thiazol-6-yl)acetic acid: To a stirred solution of (S)-ethyl 2-tert-butoxy-2-(7-(4-chlorophenyl)-5-methyl-2-(2-(1-methyl-1H-indazol-3-yl)pyridin-4-yl)benzo[d]thiazol-6-yl)acetate (13.5 mg, 0.022 mmol) in THF (0.5 mL) and methanol (0.5 mL) was added 1N NaOH solution (0.5 mL, excess). The reaction mixture was stirred at 50° C. for 2 h and then purified by reverse phase HPLC, eluting by 0-100% acetonitrile in H$_2$O with 0.1% TFA to give the desired product. LCMS-ESI+ (m/z): [M+H]+ calcd for C$_{33}$H$_{30}$ClN$_4$O$_3$S: 597.2; found: 597.2. $^1$H NMR (400 MHz, CDCl$_3$) δ 9.21 (d, J=5.6 Hz, 1H), 8.93 (s, 1H), 8.59 (d, J=7.6 Hz, 1H), 8.22 (d, J=5.2 Hz, 1H), 8.07 (s, 1H), 7.75 (d, J=6.8 Hz, 1H), 7.60-7.46 (m, 6H), 5.36 (s, 1H), 4.29 (s, 3H), 2.65 (s, 3H), 1.02 (s, 9H).

Example 57

Method AG: Preparation of (S)-2-tert-butoxy-2-(7-(4-chlorophenyl)-5-methyl-2-(2-(1-methyl-2-oxo-1,2-dihydroquinolin-6-yl)pyridin-4-yl)benzo[d]thiazol-6-yl)acetic acid (191)

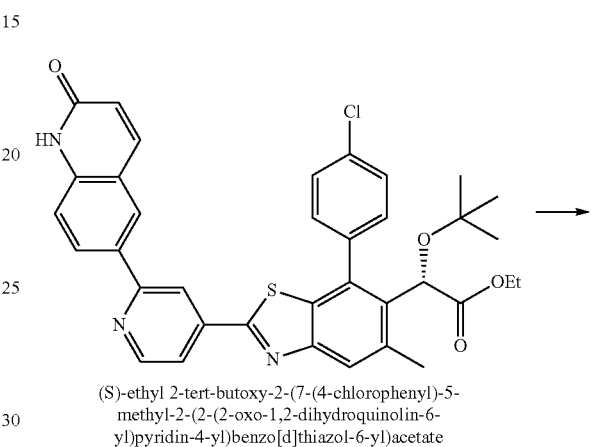

(S)-ethyl 2-tert-butoxy-2-(7-(4-chlorophenyl)-5-methyl-2-(2-(2-oxo-1,2-dihydroquinolin-6-yl)pyridin-4-yl)benzo[d]thiazol-6-yl)acetate

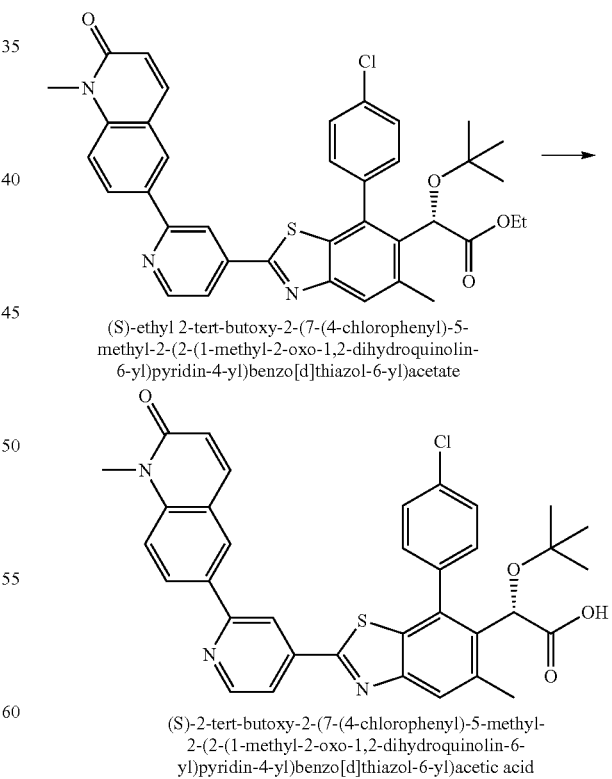

(S)-ethyl 2-tert-butoxy-2-(7-(4-chlorophenyl)-5-methyl-2-(2-(1-methyl-2-oxo-1,2-dihydroquinolin-6-yl)pyridin-4-yl)benzo[d]thiazol-6-yl)acetate (S)-2-tert-butoxy-2-(7-(4-chlorophenyl)-5-methyl-2-(2-(1-methyl-2-oxo-1,2-dihydroquinolin-6-yl)pyridin-4-yl)benzo[d]thiazol-6-yl)acetic acid
191

Preparation of (S)-ethyl 2-tert-butoxy-2-(7-(4-chlorophenyl)-5-methyl-2-(2-(1-methyl-2-oxo-1,2-dihydroquinolin-6- yl)pyridin-4-yl)benzo[d]thiazol-6-yl)acetate: To a solution of (S)-ethyl 2-tert-butoxy-2-(7-(4-chlorophenyl)-5-methyl-2-(2-(2-oxo-1,2-dihydroquinolin-6-yl)pyridin-4-yl)benzo[d]thiazol-6-yl)acetate (13.0 mg, 0.020 mmol) in DMF (0.8 mL) was added $Cs_2CO_3$ (13.0 mg, 0.041 mmol) and methyl iodide (3.0 µL, 0.050 mmol). The reaction mixture was heated at 80° C. for 3 h. After cooling, the reaction mixture was diluted with EtOAc, extracted with $H_2O$, brine, dried over $Na_2SO_4$, filtered and concentrated and purified by flash column chromatography (silica gel, 0 to 100% ethyl acetate/hexanes) to give the desired product. LCMS-ESI+ (m/z): [M+H]+ calcd for $C_{37}H_{35}ClN_3O_4S$: 652.2; found: 652.3.

Preparation of (S)-2-tert-butoxy-2-(7-(4-chlorophenyl)-5-methyl-2-(2-(1-methyl-2-oxo-1,2-dihydroquinolin-6-yl)pyridin-4-yl)benzo[d]thiazol-6-yl)acetic acid: To a stirred solution of (S)-ethyl 2-tert-butoxy-2-(7-(4-chlorophenyl)-5-methyl-2-(2-(1-methyl-2-oxo-1,2-dihydroquinolin-6-yl) pyridin-4-yl)benzo[d]thiazol-6-yl)acetate (5.2 mg, 0.008 mmol) in THF (0.4 mL) and methanol (0.4 mL) was added 1N NaOH solution (0.4 mL, excess). The reaction mixture was stirred at 50° C. for 2 h and then purified by reverse phase HPLC, eluting by 0-100% acetonitrile in $H_2O$ with 0.1% TFA to give the desired product. LCMS-ESI+ (m/z): [M+H]+ calcd for $C_{35}H_{31}ClN_3O_4S$: 624.2; found: 624.2. $^1$H NMR (400 MHz, $CDCl_3$) δ 8.88 (d, J=5.2 Hz, 1H), 8.49 (s, 1H), 8.41 (s, 1H), 8.36 (d, J=7.6 Hz, 1H), 8.00 (s, 1H), 7.94 (s, 1H), 7.85 (d, J=9.6 Hz, 1H), 7.74 (d, J=6.8 Hz, 1H), 7.58-7.47 (m, 4H), 6.81 (d, J=9.6 Hz, 1H), 5.35 (s, 1H), 3.79 (s, 3H), 2.63 (s, 3H), 1.03 (s, 9H).

Example 58

Method AH: Preparation of (S)-2-tert-butoxy-2-(7-(4-chlorophenyl)-5-methyl-2-(2-(2-(methylamino)quinolin-6-yl)pyridin-4-yl)benzo[d]thiazol-6-yl)acetic acid (192)

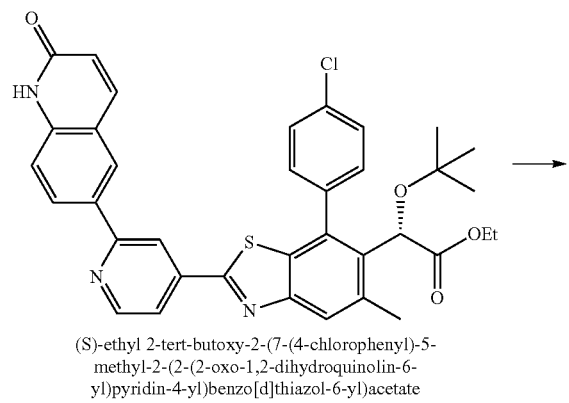

(S)-ethyl 2-tert-butoxy-2-(7-(4-chlorophenyl)-5-methyl-2-(2-(2-oxo-1,2-dihydroquinolin-6-yl)pyridin-4-yl)benzo[d]thiazol-6-yl)acetate

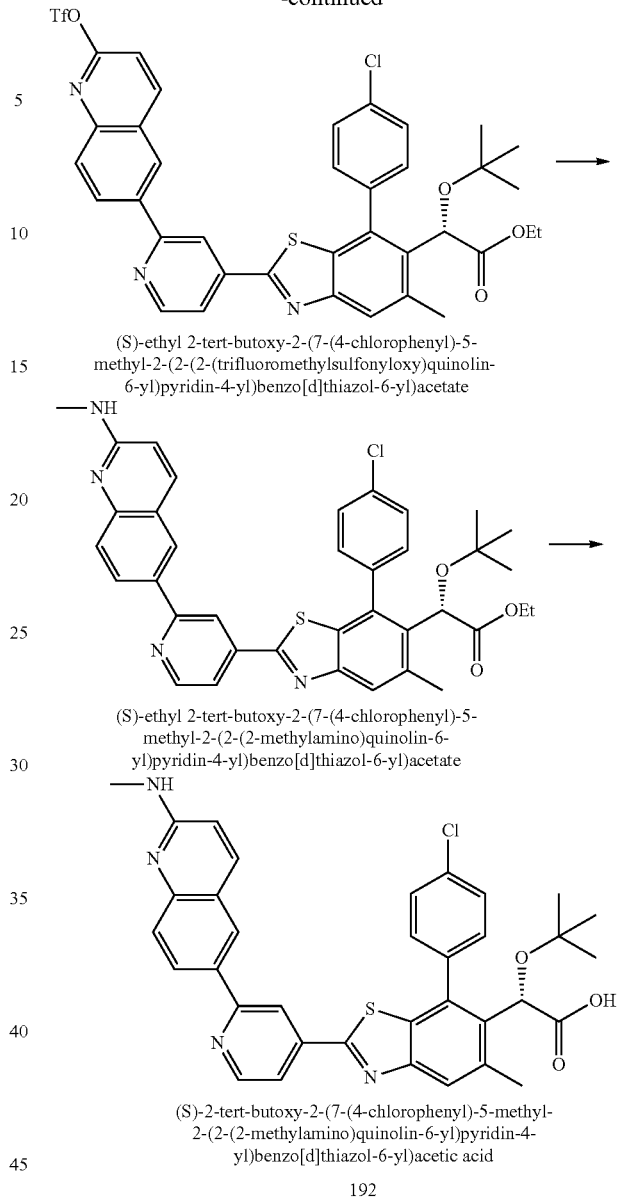

(S)-ethyl 2-tert-butoxy-2-(7-(4-chlorophenyl)-5-methyl-2-(2-(2-(trifluoromethylsulfonyloxy)quinolin-6-yl)pyridin-4-yl)benzo[d]thiazol-6-yl)acetate (S)-ethyl 2-tert-butoxy-2-(7-(4-chlorophenyl)-5-methyl-2-(2-(2-methylamino)quinolin-6-yl)pyridin-4-yl)benzo[d]thiazol-6-yl)acetate (S)-2-tert-butoxy-2-(7-(4-chlorophenyl)-5-methyl-2-(2-(2-methylamino)quinolin-6-yl)pyridin-4-yl)benzo[d]thiazol-6-yl)acetic acid

192

Preparation of (S)-ethyl 2-tert-butoxy-2-(7-(4-chlorophenyl)-5-methyl-2-(2-(2-(trifluoromethylsulfonyloxy)quinolin-6-yl)pyridin-4-yl)benzo[d]thiazol-6-yl)acetate: To a stirred and cooled (−78° C.) solution (S)-ethyl 2-tert-butoxy-2-(7-(4-chlorophenyl)-5-methyl-2-(2-(2-oxo-1,2-dihydroquinolin-6-yl)pyridin-4-yl)benzo[d]thiazol-6-yl)acetate (110 mg, 0.172 mmol) in $CH_2Cl_2$ (2.0 mL) was added pyridine (70 µL, 0.863 mmol), followed by trifluoromethanesulfonic anhydride (116 µL, 0.691 mmol). The solution was warmed to 0° C. over period of 2 h. Quenched the reaction by water and diluted with EtOAc, extracted with saturated $NaHCO_3$, brine, dried over $Na_2SO_4$, filtered and concentrated to give the desired product. LCMS-ESI+ (m/z): [M+H]+ calcd for $C_{37}H_{32}ClF_3N_3O_6S_2$: 770.1; found: 770.1.

Preparation of (S)-ethyl 2-tert-butoxy-2-(7-(4-chlorophenyl)-5-methyl-2-(2-(2-(methylamino)quinolin-6-yl)pyridin-4-yl)benzo[d]thiazol-6-yl)acetate: (S)-ethyl 2-tert-butoxy-2-(7-(4-chlorophenyl)-5-methyl-2-(2-(2-(trifluoromethylsulfonyloxy)quinolin-6-yl)pyridin-4-yl)

benzo[d]thiazol-6-yl)acetate (28.0 mg, 0.036 mmol) and 1.0 mL of methylamine at 2M in THF were heating at 80° C. for 3 days. Concentrated in vacuo and then purified by flash column chromatography (silica gel, 0 to 100% ethyl acetate/hexanes) to give the desired product. LCMS-ESI+ (m/z): [M+H]+ calcd for $C_{37}H_{36}ClN_4O_3S$: 651.2; found: 651.3.

Preparation of (S)-2-tert-butoxy-2-(7-(4-chlorophenyl)-5-methyl-2-(2-(2-(methylamino)quinolin-6-yl)pyridin-4-yl)benzo[d]thiazol-6-yl)acetic acid: To a stirred solution of (S)-ethyl 2-tert-butoxy-2-(7-(4-chlorophenyl)-5-methyl-2-(2-(2-(methylamino)quinolin-6-yl)pyridin-4-yl)benzo[d]thiazol-6-yl)acetate (4.1 mg, 0.006 mmol)) in pyridine (0.4 mL) was added LiI (50 mg, excess). The reaction mixture was heating in a microwave at 170° C. for 90 min. The mixture was concentrated in vacuo and then purified by reverse phase HPLC, eluting by 0-100% acetonitrile in $H_2O$ with 0.1% TFA to give the desired product. LCMS-ESI+ (m/z): [M+H]+ calcd for $C_{35}H_{32}ClN_4O_3S$: 623.2; found: 623.2. $^1$H NMR (400 MHz, $CD_3OD$) δ 8.82 (d, J=5.2 Hz, 1H), 8.60 (s, 1H), 8.57 (s, 1H), 8.53 (d, J=8.8 Hz, 1H), 8.34 (d, J=9.6 Hz, 1H), 8.22-7.20 (m, 3H), 7.70 (d, J=9.2 Hz, 1H), 7.61 (s, 3H), 7.07 (d, J=8.4 Hz, 1H), 5.28 (s, 1H), 3.24 (s, 3H), 2.64 (s, 3H), 0.98 (s, 9H).

Example 59

Method AI: Preparation of (S)-2-(2-(2-(2-aminoquinolin-6-yl)pyridin-4-yl)-7-(4-chlorophenyl)-5-methylbenzo[d]thiazol-6-yl)-2-tert-butoxyacetic acid (193)

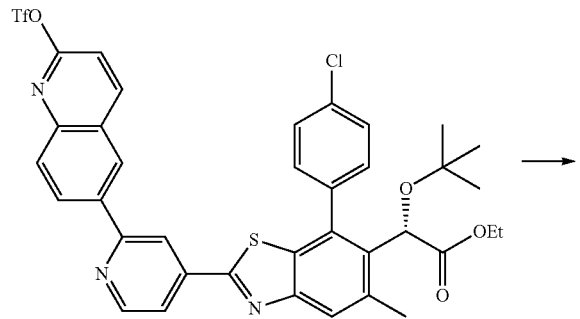

(S)-ethyl 2-tert-butoxy-2-(7-(4-chlorophenyl)-5-methyl-2-(2-(2-(trifluoromethylsulfonyloxy)quinolin-6-yl)pyridin-4-yl)benzo[d]thiazol-6-yl)acetate

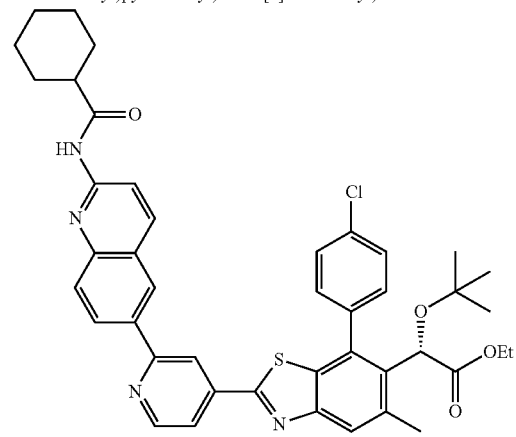

(S)-ethyl 2-tert-butoxy-2-(7-(4-chlorophenyl)-2-(2-(2-(cyclohexanecarboxamido)quinolin-6-yl)pyridin-4-yl)-5-methylbenzo[d]thiazol-6-yl)acetate

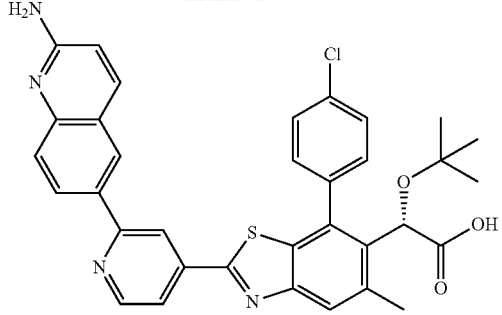

(S)-2-(2-(2-(2-aminoquinolin-6-yl)pyridin-4-yl)-7-(4-chlorophenyl)-5-methylbenzo[d]thiazol-6-yl)-2-tert-butoxyacetic acid

193

Preparation of (S)-ethyl 2-tert-butoxy-2-(7-(4-chlorophenyl)-2-(2-(2-(cyclohexanecarboxamido)quinolin-6-yl)pyridin-4-yl)-5-methylbenzo[d]thiazol-6-yl)acetate: To a solution of (S)-ethyl 2-tert-butoxy-2-(7-(4-chlorophenyl)-5-methyl-2-(2-(2-(trifluoromethylsulfonyloxy)quinolin-6-yl)pyridin-4-yl)benzo[d]thiazol-6-yl)acetate (28.4 mg, 0.037 mmol) in anhydrous dioxane (0.6 mL) was added cyclohexanecarboxamide (7.0 mg, 0.055 mmol), Xantphos (2.0 mg, 0.004 mmol), $Cs_2CO_3$ (36.0 mg, 0.111 mmol) and $Pd_2(dba)_3$ (2.0 mg, 0.002 mmol). The reaction was degassed for 5 minutes with $N_2$ and then heated at 100° C. for 2 h. After cooling, the reaction mixture was diluted with EtOAc, extracted with $H_2O$, brine, dried over $Na_2SO_4$, filtered and concentrated and purified by flash column chromatography (silica gel, 0 to 100% ethyl acetate/hexanes) to give the desired product. LCMS-ESI+ (m/z): [M+H]+ calcd for $C_{43}H_{44}ClN_4O_4S$: 747.3; found: 747.2.

Preparation of (S)-2-(2-(2-(2-aminoquinolin-6-yl)pyridin-4-yl)-7-(4-chlorophenyl)-5-methylbenzo[d]thiazol-6-yl)-2-tert-butoxyacetic acid: To a stirred solution of (S)-ethyl 2-tert-butoxy-2-(7-(4-chlorophenyl)-2-(2-(2-(cyclohexanecarboxamido)quinolin-6-yl)pyridin-4-yl)-5-methylbenzo[d]thiazol-6-yl)acetate (12.0 mg, 0.016 mmol) in THF (0.4 mL) and methanol (0.4 mL) was added 1N NaOH solution (0.4 mL, excess). The reaction mixture was stirred at 50° C. for 2 h and then purified by reverse phase HPLC, eluting by 0-100% acetonitrile in $H_2O$ with 0.1% TFA to give the desired product. LCMS-ESI+ (m/z): [M+H]+ calcd for $C_{34}H_{30}ClN_4O_3S$: 609.2; found: 609.2. $^1$H NMR (400 MHz, $CDCl_3$) δ 8.90 (d, J=5.6 Hz, 1H), 8.51 (s, 1H), 8.45 (s, 1H), 8.29 (d, J=8.4 Hz, 1H), 8.16 (d, J=9.2 Hz, 1H), 8.06 (d, J=0.8 Hz, 1H), 8.00 (s, 1H), 7.90 (d, J=8.8 Hz, 1H), 7.73 (d, J=8.0 Hz, 1H), 7.59-7.45 (m, 3H), 6.94 (d, J=8.8 Hz, 1H), 5.36 (s, 1H), 2.62 (s, 3H), 1.03 (s, 9H).

Example 60

Method AJ: Preparation of (S)-2-tert-butoxy-2-(7-(4-chlorophenyl)-5-methyl-2-(2-(1-methyl-1H-indazol-3-yl)pyridin-4-yl)benzo[d]thiazol-6-yl)acetic acid (194)

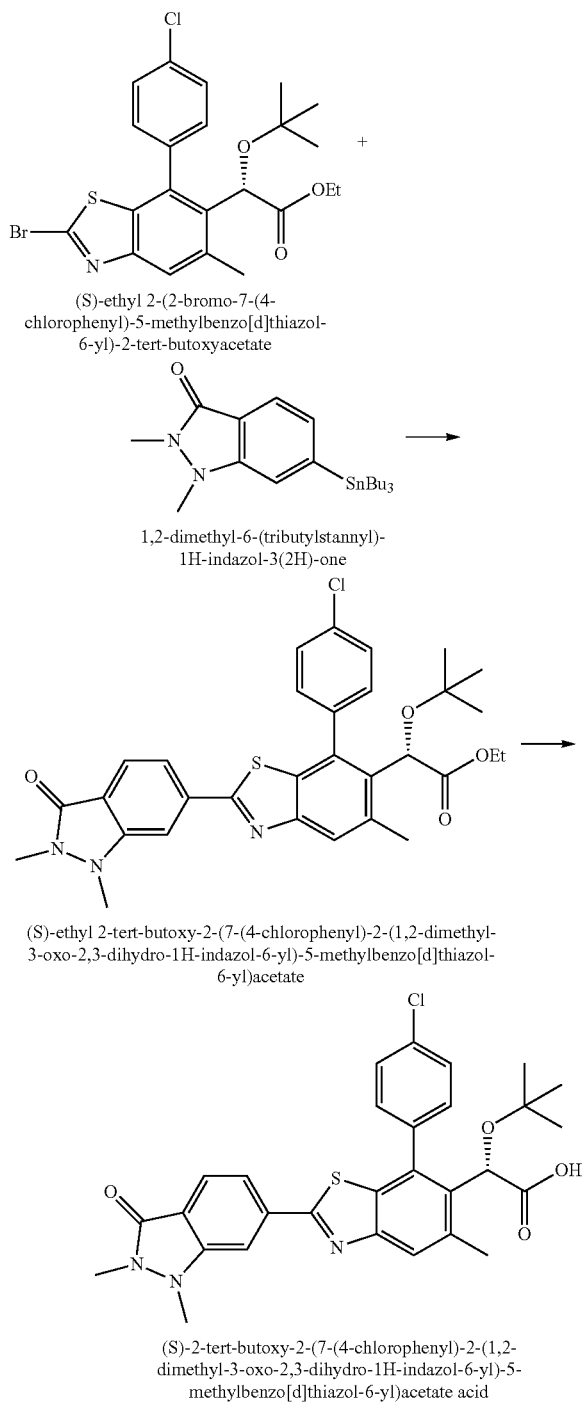

(S)-ethyl 2-(2-bromo-7-(4-chlorophenyl)-5-methylbenzo[d]thiazol-6-yl)-2-tert-butoxyacetate 1,2-dimethyl-6-(tributylstannyl)-1H-indazol-3(2H)-one (S)-ethyl 2-tert-butoxy-2-(7-(4-chlorophenyl)-2-(1,2-dimethyl-3-oxo-2,3-dihydro-1H-indazol-6-yl)-5-methylbenzo[d]thiazol-6-yl)acetate (S)-2-tert-butoxy-2-(7-(4-chlorophenyl)-2-(1,2-dimethyl-3-oxo-2,3-dihydro-1H-indazol-6-yl)-5-methylbenzo[d]thiazol-6-yl)acetate acid

194

Preparation of (S)-ethyl 2-tert-butoxy-2-(7-(4-chlorophenyl)-2-(1,2-dimethyl-3-oxo-2,3-dihydro-1H-indazol-6-yl)-5-methylbenzo[d]thiazol-6-yl)acetate: To a solution of (S)-ethyl 2-(2-bromo-7-(4-chlorophenyl)-5-methylbenzo[d]thiazol-6-yl)-2-tert-butoxyacetate (30.0 mg, 0.060 mmol) and 1,2-dimethyl-6-(tributylstannyl)-1H-indazol-3(2H)-one (32.5 mg, 0.072 mmol) in dioxane (0.7 mL) was added Pd(PPh$_3$)$_4$ (7.0 mg, 0.006 mmol), CuI (4.0 mg, 0.018 mmol) and LiCl (8.0 mg, 0.182 mmol). The reaction was degassed for 5 minutes with N$_2$ and then heated at 100° C. for 7 h. After cooling, the reaction mixture was diluted with EtOAc, extracted with H$_2$O, brine, dried over Na$_2$SO$_4$, filtered and concentrated and purified by flash column chromatography (silica gel, 0 to 100% ethyl acetate/hexanes) to give the desired product. LCMS-ESI+ (m/z): [M+H]+ calcd for C$_{31}$H$_{33}$ClN$_3$O$_4$S: 578.2; found: 578.3.

Preparation of (S)-2-tert-butoxy-2-(7-(4-chlorophenyl)-2-(1,2-dimethyl-3-oxo-2,3-dihydro-1H-indazol-6-yl)-5-methylbenzo[d]thiazol-6-yl)acetic acid: To a stirred solution of (S)-ethyl 2-tert-butoxy-2-(7-(4-chlorophenyl)-2-(1,2-dimethyl-3-oxo-2,3-dihydro-1H-indazol-6-yl)-5-methylbenzo[d]thiazol-6-yl)acetate (27.2 mg, 0.047 mmol) in THF (1.0 mL) and methanol (1.0 mL) was added 1N NaOH solution (0.5 mL, excess). The reaction mixture was stirred at 50° C. for 2 h and then purified by reverse phase HPLC, eluting by 0-100% acetonitrile in H$_2$O with 0.1% TFA to give the desired product. LCMS-ESI+ (m/z): [M+H]+ calcd for C$_{29}$H$_{29}$ClN$_3$O$_4$S: 550.2; found: 550.2. $^1$H NMR (400 MHz, CDCl$_3$) δ 8.07 (s, 1H), 7.96 (s, 1H), 7.93 (d, J=8.0 Hz, 1H), 7.93 (dd, J=8.0, 0.8 Hz, 2H), 7.55-7.49 (m, 3H), 5.33 (s, 1H), 3.50 (s, 3H), 3.39 (s, 3H), 2.60 (s, 3H), 1.01 (s, 9H).

Example 61

Method AK: Preparation of (S)-2-tert-butoxy-2-(7-(4-chlorophenyl)-5-methyl-2-(1-oxo-2,7-naphthyridin-2(1H)-yl)benzo[d]thiazol-6-yl)acetic acid (195)

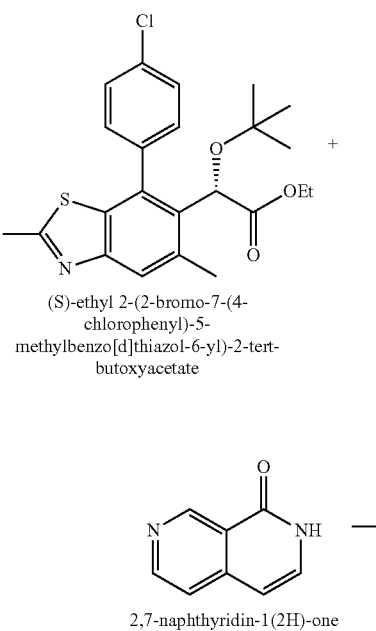

(S)-ethyl 2-(2-bromo-7-(4-chlorophenyl)-5-methylbenzo[d]thiazol-6-yl)-2-tert-butoxyacetate 2,7-naphthyridin-1(2H)-one

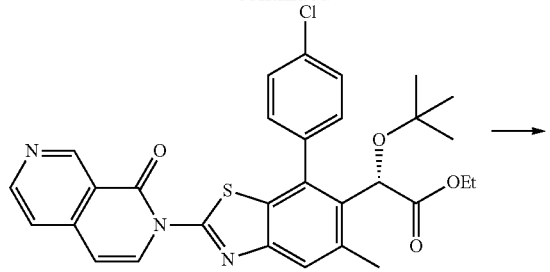

(S)-ethyl 2-tert-butoxy-2-(7-(4-chlorophenyl)-5-methyl-2-(1-oxo-2,7-naphthyridin-2(1H)-yl)benzo[d]thiazol-6-yl)acetate

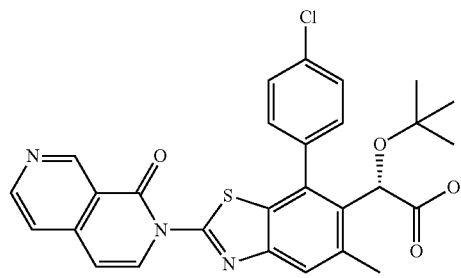

(S)-2-tert-butoxy-2-(7-(4-chlorophenyl)-5-methyl-2-(1-oxo-2,7-naphthyridin-2(1H)-yl)benzo[d]thiazol-6-yl)acetic acid
195

Preparation of (S)-ethyl 2-tert-butoxy-2-(7-(4-chlorophenyl)-5-methyl-2-(1-oxo-2,7-naphthyridin-2(1H)-yl)benzo[d]thiazol-6-yl)acetate: To a solution of (S)-ethyl 2-(2-bromo-7-(4-chlorophenyl)-5-methylbenzo[d]thiazol-6-yl)-2-tert-butoxyacetate (36.7 mg, 0.076 mmol) and 2,7-naphthyridin-1(2H)-one (14.0 mg, 0.092 mmol) in DMF (0.9 mL) was added CuI (9.0 mg, 0.046 mmol) and trans-$N_1,N_2$-dimethylcyclohexane-1,2-diamine (15 µL, 0.092 mmol) and $K_2CO_3$ (21.0 mg, 0.152 mmol). The reaction was heated at 110° C. for 2 h. After cooling, the reaction mixture was diluted with EtOAc, extracted with $H_2O$, brine, dried over $Na_2SO_4$, filtered and concentrated and purified by flash column chromatography (silica gel, 0 to 100% ethyl acetate/hexanes) to give the desired product. LCMS-ESI+ (m/z): [M+H]+ calcd for $C_{30}H_{29}ClN_3O_4S$: 562.2; found: 562.3.

Preparation of (S)-2-tert-butoxy-2-(7-(4-chlorophenyl)-5-methyl-2-(1-oxo-2,7-naphthyridin-2(1H)-yl)benzo[d]thiazol-6-yl)acetic acid: To a stirred solution of (S)-ethyl 2-tert-butoxy-2-(7-(4-chlorophenyl)-5-methyl-2-(1-oxo-2,7-naphthyridin-2(1H)-yl)benzo[d]thiazol-6-yl)acetate (18.8 mg, 0.034 mmol)) in pyridine (0.8 mL) was added LiI (100 mg, excess). The reaction mixture was heating in a microwave at 170° C. for 90 min. The mixture was concentrated in vacuo and then purified by reverse phase HPLC, eluting by 0-100% acetonitrile in $H_2O$ with 0.1% TFA to give the desired product. LCMS-ESI+ (m/z): [M+H]+ calcd for $C_{28}H_{25}ClN_3O_4S$: 534.1; found: 534.2. $^1$H NMR (400 MHz, $CDCl_3$) δ 9.69 (s, 1H), 9.27 (d, J=7.6 Hz, 1H), 8.93 (s, 1H), 7.89 (s, 1H), 7.79 (s, 1H), 7.70 (d, J=8.0 Hz, 1H), 7.58-7.50 (m, 3H), 6.93 (d, J=7.6 Hz, 1H), 5.36 (s, 1H), 2.59 (s, 3H), 1.01 (s, 9H).

Example 62

Method AL: Preparation of (S)-2-tert-butoxy-2-(7-(4-chlorophenyl)-2-(2-(1,2-dimethyl-1H-pyrrolo[2,3-b]pyridin-5-yl)pyridine-4-yl)-5-methylbenzo[d]thiazol-6-yl)acetic acid (196)

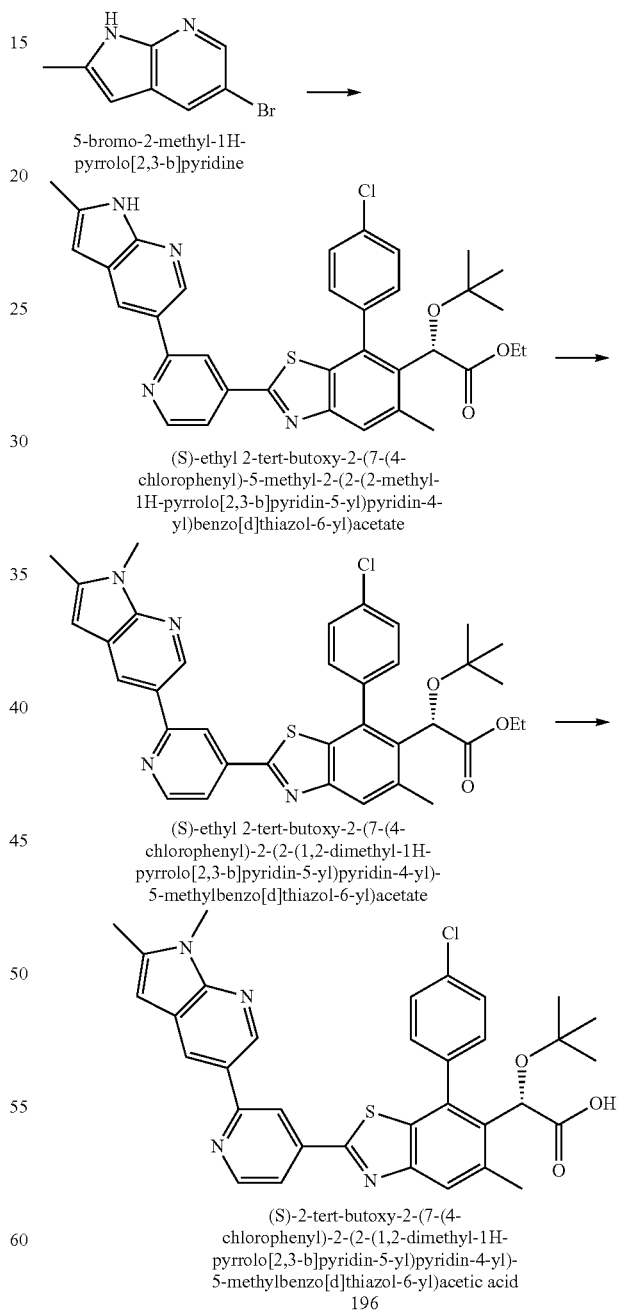

Preparation of (S)-ethyl 2-tert-butoxy-2-(7-(4-chlorophenyl)-5-methyl-2-(2-(2-methyl-1H-pyrrolo[2,3-b]pyridin-5-yl)pyridine-4-yl)benzo[d]thiazol-6-yl)acetate: To a solution of 5-bromo-2-methyl-1H-pyrrolo[2,3-b]pyridine (60 mg, 0.284 mmol) in dioxane (3 mL) was added bis(pinacolato)diboron (87 mg, 0.341 mmol), [1,1'-Bis(diphenylphosphino)ferrocene]dichloropalladium(II) complex with dichloromethane (23 mg, 0.028 mmol), potassium acetate (84 mg, 0.852 mmol). The mixture was degassed and heated at 100° C. for 2 h. The mixture was cooled, and then added (S)-ethyl 2-tert-butoxy-2-(7-(4-chlorophenyl)-2-(2-chloropyridin-4-yl)-5-methylbenzo[d]thiazol-6-yl)acetate (100 mg, 0.189 mmol), tetrakis(triphenylphosphine)palladium(0) (22 mg, 0.019 mmol), $K_2CO_3$ (131 mg, 0.948 mmol) and water (1 mL, degassed). The reaction mixture was heated at 110° C. for 1 h, cooled and partitioned between ethyl acetate and brine. The organic layer was separated, dried over $Na_2SO_4$ and concentrated to give crude which was purified by chromatographic column to afford the desired product. LCMS-ESI$^+$: calc'd for $C_{35}H_{33}ClN_4O_3S$: 625.2 (M+H$^+$); Found: 625.3 (M+H$^+$).

Preparation of (S)-ethyl 2-tert-butoxy-2-(7-(4-chlorophenyl)-2-(2-(1,2-dimethyl-1H-pyrrolo[2,3-b]pyridin-5-yl)pyridine-4-yl)-5-methylbenzo[d]thiazol-6-yl)acetate: To a solution of (S)-ethyl 2-tert-butoxy-2-(7-(4-chlorophenyl)-5-methyl-2-(2-(2-methyl-1H-pyrrolo[2,3-b]pyridin-5-yl)pyridine-4-yl)benzo[d]thiazol-6-yl)acetate (100 mg, 0.16 mmol) in DMF (5 mL) was added cesium carbonate (68 mg, 0.208 mmol). The reaction solution was stirred at room temperature for 5 minutes, iodomethane (30 mg, 0.208 mmol) was added. The reaction solution was stirred for 30 minutes and quenched with water. The mixture was concentrated in vacuo and the residue partitioned between ethyl acetate and water. The organic phase was washed with brine, dried (MgSO$_4$) and concentrated to give crude which was purified by chromatographic column to afford the desired product. LCMS-ESI$^+$: calc'd for $C_{36}H_{35}ClN_4O_3S$: 639.2 (M+H$^+$); Found: 639.3 (M+H$^+$).

Preparation of (S)-2-tert-butoxy-2-(7-(4-chlorophenyl)-2-(2-(1,2-dimethyl-1H-pyrrolo[2,3-b]pyridin-5-yl)pyridine-4-yl)-5-methylbenzo[d]thiazol-6-yl)acetic acid: To a solution of (S)-ethyl 2-tert-butoxy-2-(7-(4-chlorophenyl)-2-(2-(1,2-dimethyl-1H-pyrrolo[2,3-b]pyridin-5-yl)pyridine-4-yl)-5-methylbenzo[d]thiazol-6-yl)acetate (70 mg, 0.110 mmol) in THF/CH$_3$OH (1.0 mL/1.0 mL) was added 2N NaOH (0.55 mL, 1.1 mmol). The reaction mixture was heated at 50° C. for 2 h and the crude was purified by reverse phase HPLC, eluting by 0-100% acetonitrile in H$_2$O with 0.1% TFA to give the product. LCMS-ESI$^+$: calc'd for $C_{34}H_{31}ClN_4O_3S$: 611.2 (M+H$^+$); Found: 612.2 (M+H$^+$), $^1$H NMR (400 MHz, CD$_3$OD) δ 8.91 (s, 1H), 8.83 (d, J=5.2 Hz, 1H), 8.65 (s, 1H), 8.60 (s, 1H), 8.08 (d, J=5.6 Hz, 1H), 8.04 (s, 1H), 7.80 (d, J=8.8 Hz, 1H), 7.71 (s, 2H), 5.59 (s, 1H), 5.38 (s, 1H), 3.91 (s, 3H), 2.73 (s, 3H), 2.60 (s, 3H), 1.08 (s, 9H).

Example 63

Method AM: Preparation of (S)-2-tert-butoxy-2-(7-(4-chlorophenyl)-2-(1,2-dimethyl-1H-pyrrolo[2,3-b]pyridin-5-yl)-5-methylbenzo[d]thiazol-6-yl)acetic acid (197)

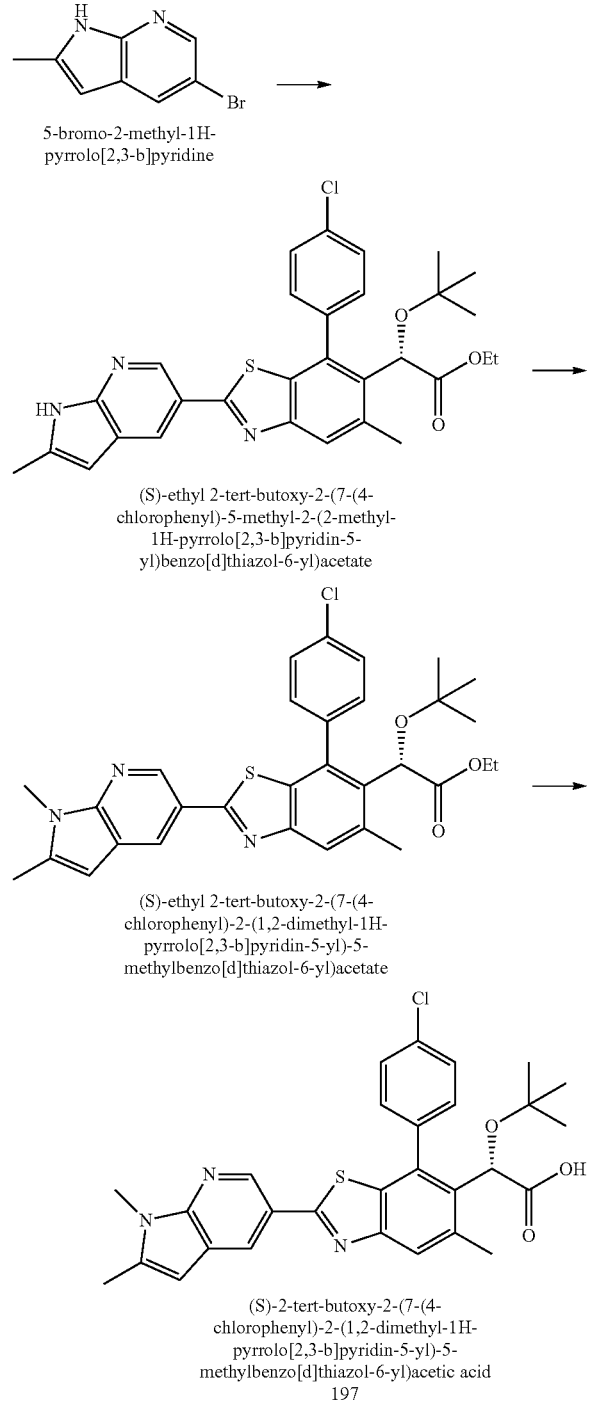

5-bromo-2-methyl-1H-pyrrolo[2,3-b]pyridine (S)-ethyl 2-tert-butoxy-2-(7-(4-chlorophenyl)-5-methyl-2-(2-methyl-1H-pyrrolo[2,3-b]pyridin-5-yl)benzo[d]thiazol-6-yl)acetate (S)-ethyl 2-tert-butoxy-2-(7-(4-chlorophenyl)-2-(1,2-dimethyl-1H-pyrrolo[2,3-b]pyridin-5-yl)-5-methylbenzo[d]thiazol-6-yl)acetate (S)-2-tert-butoxy-2-(7-(4-chlorophenyl)-2-(1,2-dimethyl-1H-pyrrolo[2,3-b]pyridin-5-yl)-5-methylbenzo[d]thiazol-6-yl)acetic acid
197

Preparation of (S)-ethyl 2-tert-butoxy-2-(7-(4-chlorophenyl)-5-methyl-2-(2-methyl-1H-pyrrolo[2,3-b]pyridin-5-yl)

benzo[d]thiazol-6-yl)acetate: To a solution of 5-bromo-2-methyl-1H-pyrrolo[2,3-b]pyridine (85 mg, 0.403 mmol) in dioxane (4 mL) was added bis(pinacolato)diboron (123 mg, 0.483 mmol), [1,1'-bis(diphenylphosphino)ferrocene]dichloropalladium(II) complex with dichloromethane (33 mg, 0.040 mmol), potassium acetate (120 mg, 1.21 mmol). The mixture was degassed and heated at 100° C. for 2 h. The mixture was cooled, and then added (S)-ethyl 2-(2-bromo-7-(4-chlorophenyl)-5-methylbenzo[d]thiazol-6-yl)-2-tert-butoxyacetate (100 mg, 0.201 mmol), tetrakis(triphenylphosphine)palladium(0) (24 mg, 0.02 mmol), $K_2CO_3$ (139 mg, 1.00 mmol) and water (1.3 mL, degassed). The reaction mixture was heated at 100° C. for 1 h, cooled and partitioned between ethyl acetate and brine. The organic layer was separated, dried over $Na_2SO_4$ and concentrated to give crude which was purified by chromatographic column to afford the desired product. LCMS-ESI$^+$: calc'd for $C_{30}H_{30}ClN_3O_3S$: 548.3 (M+H$^+$); Found: 548.3 (M+H$^+$).

Preparation of (S)-ethyl 2-tert-butoxy-2-(7-(4-chlorophenyl)-2-(1,2-dimethyl-1H-pyrrolo[2,3-b]pyridin-5-yl)-5-methylbenzo[d]thiazol-6-yl)acetate: To a solution of (S)-ethyl 2-tert-butoxy-2-(7-(4-chlorophenyl)-5-methyl-2-(2-methyl-1H-pyrrolo[2,3-b]pyridin-5-yl)benzo[d]thiazol-6-yl)acetate (70 mg, 0.128 mmol) in DMF (5 mL) was added cesium carbonate (54 mg, 0.166 mmol). The reaction solution was stirred at room temperature for 5 minutes, then iodomethane (24 mg, 0.166 mmol) was added. The reaction solution was stirred for 30 minutes and quenched with water. Volatiles were removed and the residue partitioned between ethyl acetate and water. The organic phase was washed with brine, dried (MgSO$_4$) and concentrated to give crude which was purified by chromatographic column to afford the desired product. LCMS-ESI$^+$: calc'd for $C_{31}H_{32}ClN_3O_3S$: 562.3 (M+H$^+$); Found: 562.3 (M+H$^+$).

Preparation of (S)-2-tert-butoxy-2-(7-(4-chlorophenyl)-2-(1,2-dimethyl-1H-pyrrolo[2,3-b]pyridin-5-yl)-5-methylbenzo[d]thiazol-6-yl)acetic acid: To a solution of (S)-ethyl 2-tert-butoxy-2-(7-(4-chlorophenyl)-2-(1,2-dimethyl-1H-pyrrolo[2,3-b]pyridin-5-yl)-5-methylbenzo[d]thiazol-6-yl)acetate: (49 mg, 0.09 mmol) in THF/CH$_3$OH (1.0 mL/1.0 mL) was added 2N NaOH (0.44 mL, 0.9 mmol). The reaction mixture was heated at 50° C. for 2 h and the crude was purified by reverse phase HPLC, eluting by 0-100% acetonitrile in H$_2$O with 0.1% TFA to give the product. LCMS-ESI$^+$: calc'd for $C_{29}H_{28}ClN_3O_3S$: 534.2 (M+H$^+$); Found: 534.2 (M+H$^+$); $^1$H NMR (400 MHz, CD$_3$OD) δ 8.82 (d, J=1.6 Hz, 1H), 8.41 (d, J=2 Hz, 1H), 7.82 (s, 1H), 7.70-7.58 (m, 5H), 5.25 (s, 1H), 3.80 (s, 3H), 2.61 (s, 3H), 2.49 (s, 3H), 0.97 (s, 9H).

Example 64

Method AN: Preparation of (S)-2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetic acid (198)

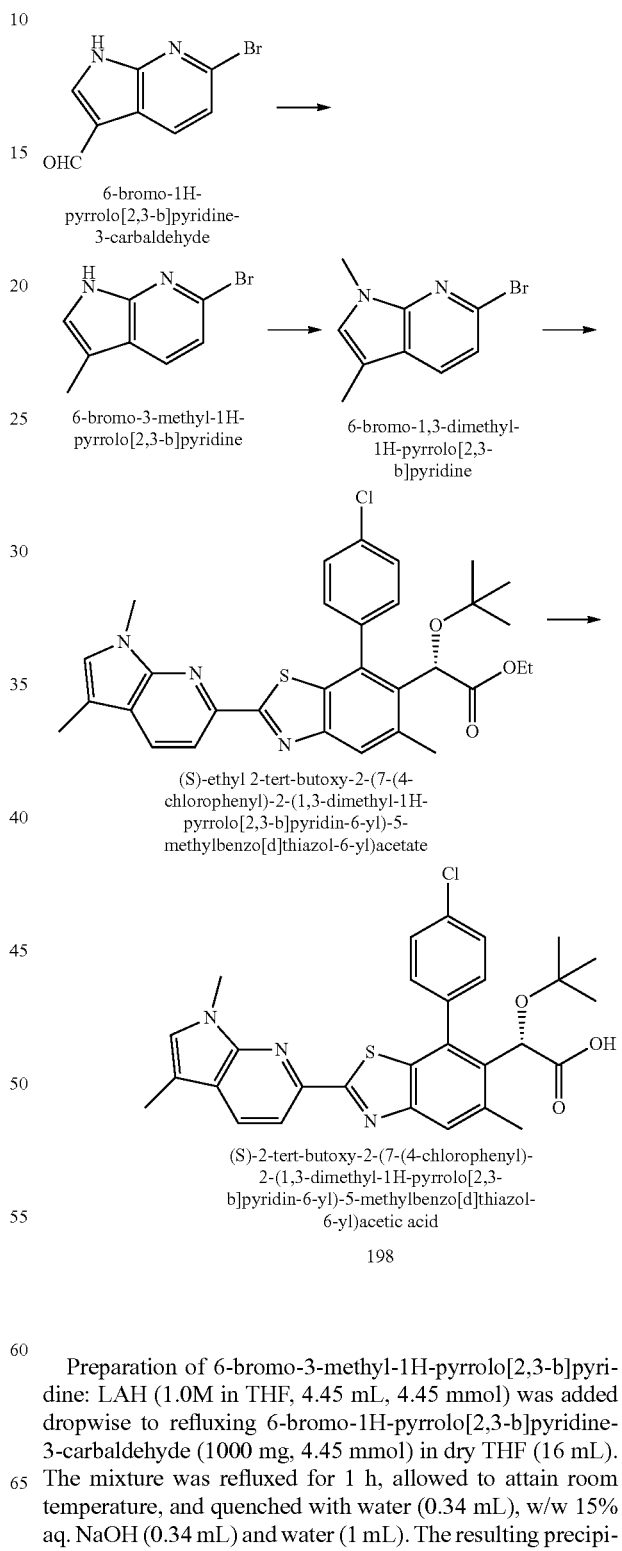

6-bromo-1H-pyrrolo[2,3-b]pyridine-3-carbaldehyde 6-bromo-3-methyl-1H-pyrrolo[2,3-b]pyridine 6-bromo-1,3-dimethyl-1H-pyrrolo[2,3-b]pyridine (S)-ethyl 2-tert-butoxy-2-(7-(4-chlorophenyl)-2-(1,3-dimethyl-1H-pyrrolo[2,3-b]pyridin-6-yl)-5-methylbenzo[d]thiazol-6-yl)acetate (S)-2-tert-butoxy-2-(7-(4-chlorophenyl)-2-(1,3-dimethyl-1H-pyrrolo[2,3-b]pyridin-6-yl)-5-methylbenzo[d]thiazol-6-yl)acetic acid

198

Preparation of 6-bromo-3-methyl-1H-pyrrolo[2,3-b]pyridine: LAH (1.0M in THF, 4.45 mL, 4.45 mmol) was added dropwise to refluxing 6-bromo-1H-pyrrolo[2,3-b]pyridine-3-carbaldehyde (1000 mg, 4.45 mmol) in dry THF (16 mL). The mixture was refluxed for 1 h, allowed to attain room temperature, and quenched with water (0.34 mL), w/w 15% aq. NaOH (0.34 mL) and water (1 mL). The resulting precipitation was filtered off, the filtrate concentrated and the residue was partitioned between aqueous NaOH and DCM. The organic layers were combined, dried and concentrated to give title compound. LCMS-ESI+: calc'd for C8H7BrN2: 211.2 (M+H+); Found: 211.2 (M+H+).

Preparation of 6-bromo-1,3-dimethyl-1H-pyrrolo[2,3-b]pyridine: To a solution of 6-bromo-3-methyl-1H-pyrrolo[2,3-b]pyridine (250 mg, 1.18 mmol) in DMF (6 mL) was added cesium carbonate (502 mg, 1.54 mmol). The reaction solution was stirred at room temperature for 5 minutes, then iodomethane (219 mg, 1.54 mmol) was added. The reaction solution was stirred for 30 minutes and quenched with water. The mixture was concentrated in vacuo and the residue partitioned between ethyl acetate and water. The organic phase was washed with brine, dried (MgSO4) and concentrated to give crude which was purified by chromatographic column to afford the desired product. LCMS-ESI+: calc'd for C9H9BrN2 225.2 (M+H+); Found: 225.2 (M+H+).

Preparation of (S)-ethyl 2-tert-butoxy-2-(7-(4-chlorophenyl)-2-(1,3-dimethyl-1H-pyrrolo[2,3-b]pyridin-6-yl)-5-methylbenzo[d]thiazol-6-yl)acetate: To a solution of 6-bromo-1,3-dimethyl-1H-pyrrolo[2,3-b]pyridine (30 mg, 0.133 mmol) in dioxane (1.4 mL) was added bis(pinacolato)diboron (41 mg, 0.16 mmol), [1,1'-Bis(diphenylphosphino)ferrocene]dichloropalladium(II) complex with dichloromethane (11 mg, 0.013 mmol), potassium acetate (39 mg, 0.4 mmol). The mixture was degassed and heated at 100° C. for 2 h. The mixture was cooled, and then added (S)-ethyl 2-(2-bromo-7-(4-chlorophenyl)-5-methylbenzo[d]thiazol-6-yl)-2-tert-butoxyacetate (33 mg, 0.07 mmol), tetrakis(triphenylphosphine)palladium(0) (8 mg, 0.007 mmol), K2CO3 (48 mg, 0.35 mmol) and water (0.5 mL, degassed). The reaction mixture was heated at 100° C. for 1 h, cooled and partitioned between ethyl acetate and brine. The organic layer was separated, dried over Na2SO4 and concentrated to give crude which was purified by chromatographic column to afford the desired product. LCMS-ESI+: calc'd for C31H32ClN3O3S: 562.3 (M+H+); Found: 562.3 (M+H+).

Preparation of (S)-2-tert-butoxy-2-(7-(4-chlorophenyl)-2-(1,3-dimethyl-1H-pyrrolo[2,3-b]pyridin-5-yl)-5-methylbenzo[d]thiazol-6-yl)acetic acid: To a solution of (S)-ethyl 2-tert-butoxy-2-(7-(4-chlorophenyl)-2-(1,3-dimethyl-1H-pyrrolo[2,3-b]pyridin-6-yl)-5-methylbenzo[d]thiazol-6-yl)acetate: (37 mg, 0.066 mmol) in THF/CH3OH (1.0 mL/1.0 mL) was added 2N NaOH (0.33 mL, 0.66 mmol). The reaction mixture was heated at 50° C. for 2 h and the crude was purified by reverse phase HPLC, eluting by 0-100% acetonitrile in H2O with 0.1% TFA to give the product. LCMS-ESI+: calc'd for C29H28ClN3O3S: 534.2 (M+H+); Found: 534.2 (M+H+); 1H NMR (400 MHz, CD3OD) δ 8.06-8.00 (m, 2H), 7.82 (s, 1H), 7.70-7.60 (m, 4H), 7.24 (s, 1H), 5.26 (s, 1H), 3.81 (s, 3H), 2.61 (s, 3H), 2.32 (s, 3H), 0.87 (s, 9H).

Example 65

Method AO: Preparation of (S)-2-tert-butoxy-2-(7-(4-chlorophenyl)-2-(2-(1,3-dimethyl-1H-pyrrolo[2,3-b]pyridin-5-yl)pyridine-4-yl)-5-methylbenzo[d]thiazol-6-yl)acetic acid (199)

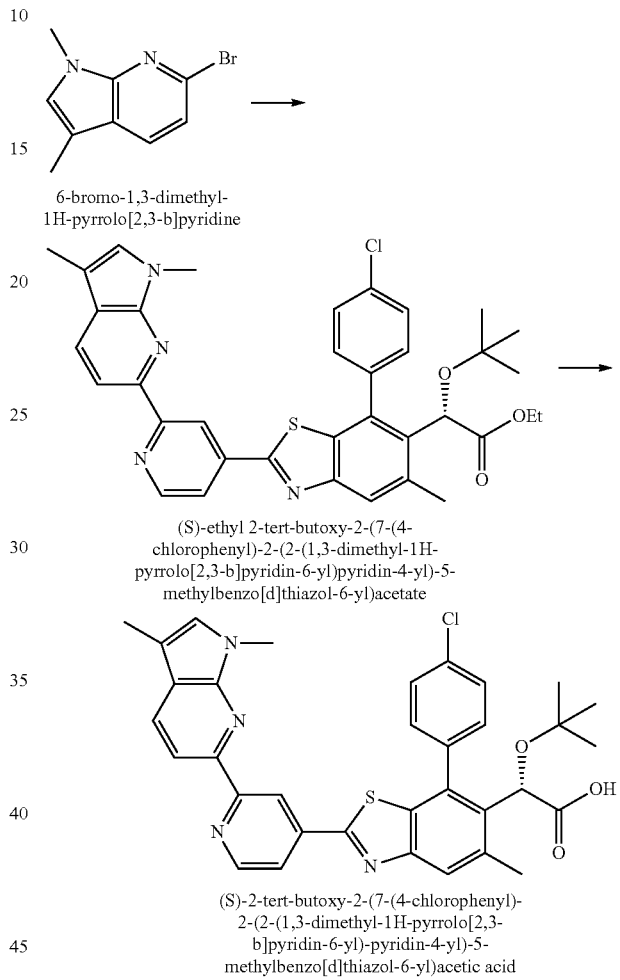

Preparation of (S)-ethyl 2-tert-butoxy-2-(7-(4-chlorophenyl)-2-(2-(1,3-dimethyl-1H-pyrrolo[2,3-b]pyridin-5-yl)pyridine-4-yl)-5-methylbenzo[d]thiazol-6-yl)acetate: To a solution of 6-bromo-1,3-dimethyl-1H-pyrrolo[2,3-b]pyridine (15 mg, 0.067 mmol) in dioxane (1 mL) was added bis(pinacolato)diboron (20 mg, 0.080 mmol), [1,1'-Bis(diphenylphosphino)ferrocene]dichloropalladium(II) complex with dichloromethane (5.5 mg, 0.0067 mmol), potassium acetate (20 mg, 0.201 mmol). The mixture was degassed and heated at 100° C. for 2 h. The mixture was cooled, and then added (R)-ethyl 2-tert-butoxy-2-(7-(4-chlorophenyl)-2-(2-chloropyridin-4-yl)-5-methylbenzo[d]thiazol-6-yl)acetate (24 mg, 0.045 mmol), tetrakis(triphenylphosphine)palladium(0) (5 mg, 0.0045 mmol), K2CO3 (31 mg, 0.227 mmol) and water (0.3 mL, degassed). The reaction mixture was heated at 110° C. for 1 h, cooled and partitioned between ethyl acetate and brine. The organic layer was separated, dried over Na₂SO₄ and concentrated to give crude which was purified by chromatographic column to afford the desired product. LCMS-ESI⁺: calc'd for $C_{36}H_{35}ClN_4O_3S$: 639.3 (M+H⁺); Found: 639.3 (M+H⁺).

Preparation of (S)-2-tert-butoxy-2-(7-(4-chlorophenyl)-2-(2-(1,3-dimethyl-1H-pyrrolo[2,3-b]pyridin-5-yl)pyridine-4-yl)-5-methylbenzo[d]thiazol-6-yl)acetic acid: To a solution of (S)-ethyl 2-tert-butoxy-2-(7-(4-chlorophenyl)-2-(2-(1,3-dimethyl-1H-pyrrolo[2,3-b]pyridin-5-yl)pyridine-4-yl)-5-methylbenzo[d]thiazol-6-yl)acetate: (28 mg, 0.044 mmol) in THF/CH₃OH (1.0 mL/1.0 mL) was added 2N NaOH (0.22 mL, 0.44 mmol). The reaction mixture was heated at 50° C. for 2 h and the crude was purified by reverse phase HPLC, eluting by 0-100% acetonitrile in H₂O with 0.1% TFA to give the product. LCMS-ESI⁺: calc'd for $C_{34}H_{31}ClN_4O_3S$: 611.2 (M+H⁺); Found: 611.2 (M+H⁺); ¹H NMR (400 MHz, CD₃OD) δ 9.11 (s, 1H), 8.79 (d, J=5.6 Hz, 1H), 8.18-7.64 (m, 8H), 7.32 (s, 1H), 5.29 (s, 1H), 3.96 (s, 3H), 2.66 (s, 3H), 2.34 (s, 3H), 0.99 (s, 9H).

Example 66

Method AP: Preparation of (S)-2-tert-butoxy-2-(7-(4-chlorophenyl)-5-methyl-2-(2-methyl-1-((S)-1-methylpyrrolidin-3-yl)-1H-benzo[d]imidazol-6-yl)benzo[d]thiazol-6-yl)acetic acid (200)

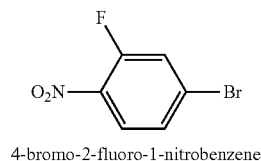

4-bromo-2-fluoro-1-nitrobenzene

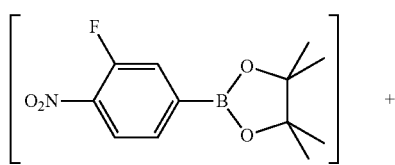

2-(3-fluoro-4-nitrophenyl)-4,4,5,5-tetramethyl-1,3,2-dioxaborolane

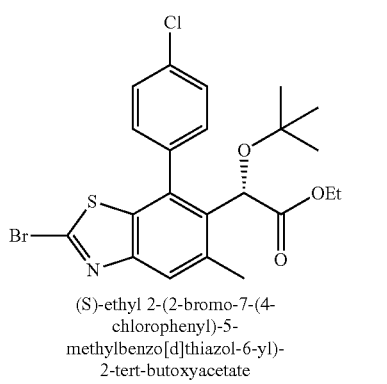

(S)-ethyl 2-(2-bromo-7-(4-chlorophenyl)-5-methylbenzo[d]thiazol-6-yl)-2-tert-butoxyacetate

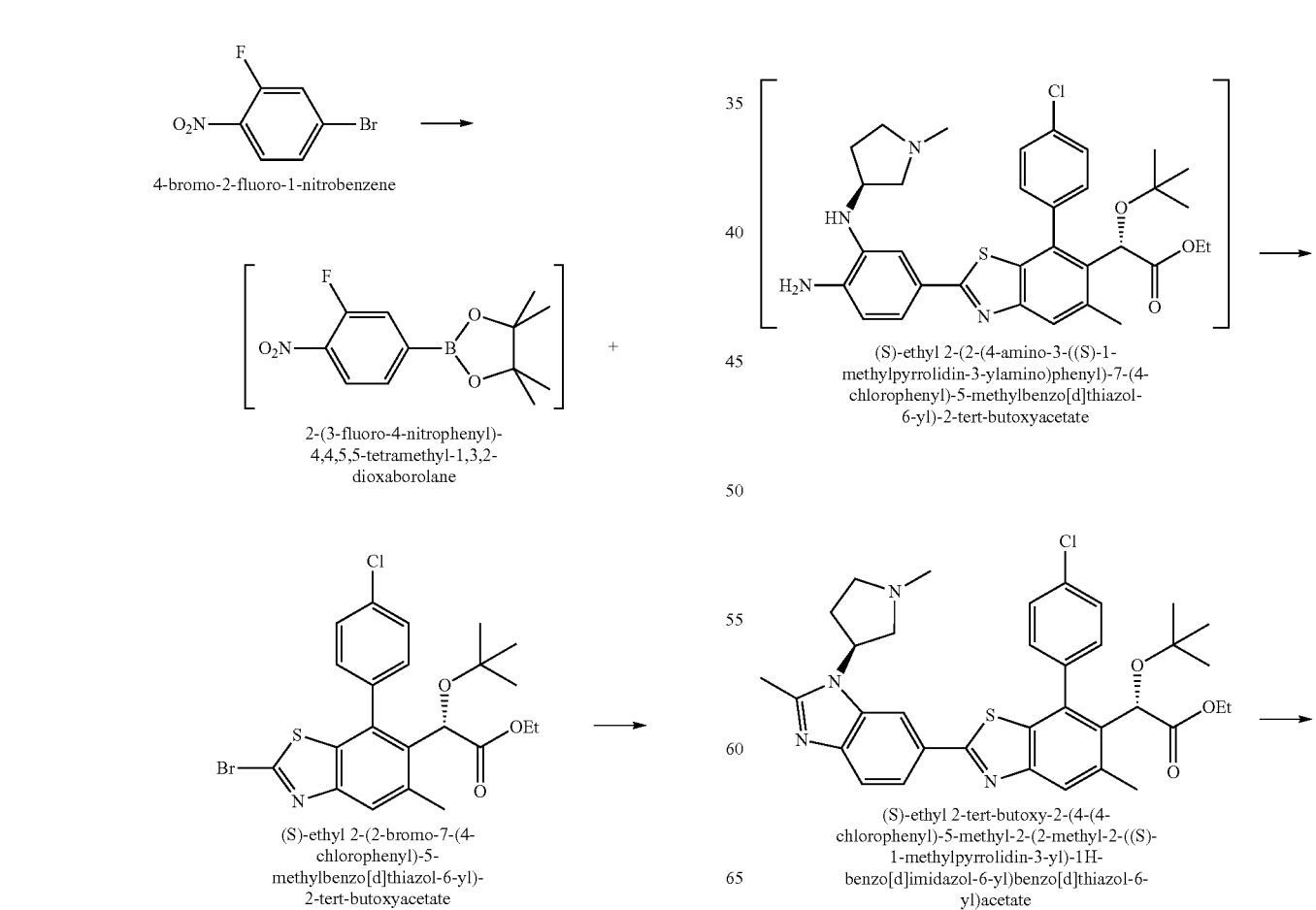

(S)-ethyl 2-tert-butoxy-2-(7-(4-chlorophenyl)-2-(3-fluoro-4-nitrophenyl)-5-methylbenzo[d]thiazol-6-yl)acetate (S)-ethyl 2-tert-butoxy-2-(7-(4-chlorophenyl)-5-methyl-2-(3-((S)-1-1 methylpyrrolidin-3-ylamino)-4-nitrophenyl)benzo[d]thiazol-6-yl)acetate (S)-ethyl 2-(2-(4-amino-3-((S)-1-methylpyrrolidin-3-ylamino)phenyl)-7-(4-chlorophenyl)-5-methylbenzo[d]thiazol-6-yl)-2-tert-butoxyacetate (S)-ethyl 2-tert-butoxy-2-(4-(4-chlorophenyl)-5-methyl-2-(2-methyl-2-((S)-1-methylpyrrolidin-3-yl)-1H-benzo[d]imidazol-6-yl)benzo[d]thiazol-6-yl)acetate -continued

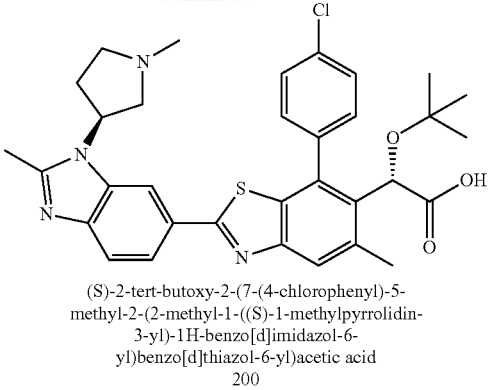

(S)-2-tert-butoxy-2-(7-(4-chlorophenyl)-5-
methyl-2-(2-methyl-1-((S)-1-methylpyrrolidin-
3-yl)-1H-benzo[d]imidazol-6-
yl)benzo[d]thiazol-6-yl)acetic acid
200

Preparation of (S)-ethyl 2-tert-butoxy-2-(7-(4-chlorophenyl)-2-(3-fluoro-4-nitrophenyl)-5-methylbenzo[d]thiazol-6-yl)acetate: A microwave vial was charged with 4-bromo-2-fluoro-1-nitrobenzene (690 mg, 3.14 mmol), bis(pinacolato)diboron (946 mg, 3.73 mmol), PdCl$_2$(dppf).CH$_2$Cl$_2$ (242 mg, 0.30 mmol), then KOAc (926 mg, 9.44 mmol). The vial was flushed with argon, diluted with dioxane (11 mL), sealed, then heated to 100° C. for 1 hour. The reaction mixture was allowed to cool to room temperature and then a portion of this cooled solution (6.1 mL, 1.74 mmol) was added to a vial that was charged with (S)-ethyl 2-(2-bromo-7-(4-chlorophenyl)-5-methylbenzo[d]thiazol-6-yl)-2-tert-butoxyacetate (437 mg, 0.88 mmol) and Pd(PPh$_3$)$_4$ (102 mg, 0.09 mmol). The mixture was diluted with dioxane (2 mL) and to this was added 2M aqueous K$_2$CO$_3$ (1.50 mL, 3.00 mmol). The vial was sealed, heated to 100° C. for 1 hour, and then allowed to cool to room temperature. The mixture was diluted with EtOAc, dried over Na$_2$SO$_4$, filtered, and concentrated in vacuo. The crude residue was purified by silica gel column chromatography (5-30% EtOAc/Hex gradient) to afford the desired product. LCMS-ESI$^+$: calc'd C$_{28}$H$_{27}$ClFN$_2$O$_5$S: 557.1 (M+H$^+$); Found: 557.1 (M+H$^+$).

Preparation of (S)-ethyl 2-tert-butoxy-2-(7-(4-chlorophenyl)-5-methyl-2-(2-methyl-1-((S)-1-methylpyrrolidin-3-yl)-1H-benzo[d]imidazol-6-yl)benzo[d]thiazol-6-yl)acetate: A flask containing (S)-ethyl 2-tert-butoxy-2-(7-(4-chlorophenyl)-2-(3-fluoro-4-nitrophenyl)-5-methylbenzo[d]thiazol-6-yl)acetate (83 mg, 0.15 mmol) was charged with Cs$_2$CO$_3$ (267 mg, 0.82 mmol) and then diluted with DMF (2 mL). The reaction mixture was then treated with (3S)-1-methylpyrrolidin-3-amine (52 mg, 0.52 mmol) at room temperature and allowed to stir for 30 minutes. The mixture was diluted with EtOAc and H$_2$O, the layers were separated, and the aqueous layer was extracted with EtOAc. The combined organic extracts were dried over Na$_2$SO$_4$, filtered, and concentrated in vacuo to afford a crude residue. The flask containing the crude residue was charged with 5 wt % Pt/C (23 mg) and then diluted with 2:1 EtOH/EtOAc (3 mL). The flask was evacuated then backfilled with H$_2$ (3 cycles) and stirred under a hydrogen atmosphere for 20 minutes, at which time, the flask was purged with N$_2$, filtered through a pad of Celite, and concentrated in vacuo to provide a crude residue. The crude residue was taken up in AcOH (3 mL) and MeC(OEt)$_3$ (0.3 mL) was added at room temperature and stirred for 15 minutes. The solution was concentrated in vacuo and the crude residue was purified by reverse phase column chromatography (5-100% ACN/H$_2$O/0.1% TFA gradient) to provide the TFA salt of the product. LCMS-ESI$^+$: calc'd C$_{35}$H$_{40}$ClN$_4$O$_3$S: 631.3 (M+H$^+$); Found: 631.2 (M+H$^+$).

Preparation of (S)-2-tert-butoxy-2-(7-(4-chlorophenyl)-5-methyl-2-(2-methyl-1-((S)-1-methylpyrrolidin-3-yl)-1H-benzo[d]imidazol-6-yl)benzo[d]thiazol-6-yl)acetic acid: To a solution of (S)-ethyl 2-(tert-butoxy)-2-(7-(4-chlorophenyl)-5-methyl-2-(1-(1-methylpiperidin-4-yl)-1H-benzo[d]imidazol-5-yl)benzo[d]thiazol-6-yl)acetate (4 mg, 0.006 mmol) in 2:1 MeOH/THF (1.2 mL) was added 2M aqueous NaOH (0.3 mL, 0.6 mmol) and stirred at 50° C. overnight. The reaction mixture was cooled to room temperature, neutralized with AcOH, filtered, and then purified by reverse phase column chromatography (5-100% ACN/H$_2$O/0.1% TFA gradient). Fractions containing the product were pooled and lyophilized to provide the TFA salt of the product. $^1$H NMR (400 MHz, CD$_3$OD) δ 8.48 (s, 1H), 8.09 (dd, J=8.6, 1.4 Hz, 1H), 7.90 (s, 1H), 7.85 (d, J=8.6 Hz, 1H), 7.75-7.67 (m, 1H), 7.67-7.53 (m, 3H), 5.85-5.61 (br m, 1H), 5.27 (s, 1H), 4.35-3.98 (br m, 2H), 3.99-3.81 (br m, 1H), 3.65 (br s, 1H), 3.19 (s, 3H), 3.04-2.74 (br m, 2H), 2.88 (s, 3H), 2.65 (s, 3H), 0.99 (s, 9H). LCMS-ESI$^+$: calc'd C$_{33}$H$_{36}$ClN$_4$O$_3$S: 603.2 (M+H$^+$); Found: 603.3 (M+H$^+$).

Example 67

Method AR: Preparation of (S)-2-tert-butoxy-2-(7-(4-chlorophenyl)-5-methyl-2-(6-(1-methyl-1H-indazol-5-yl)pyridazin-4-yl)benzo[d]thiazol-6-yl)acetic acid (201)

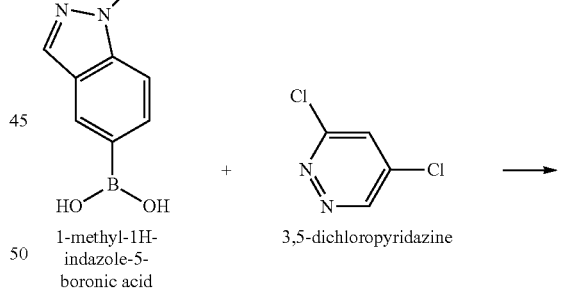

1-methyl-1H-indazole-5-boronic acid 3,5-dichloropyridazine

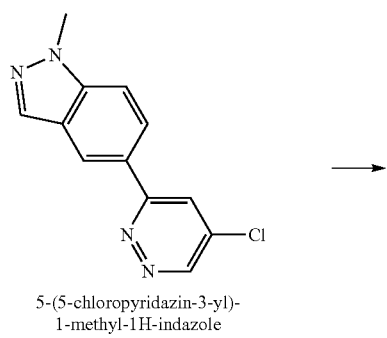

5-(5-chloropyridazin-3-yl)-1-methyl-1H-indazole

-continued

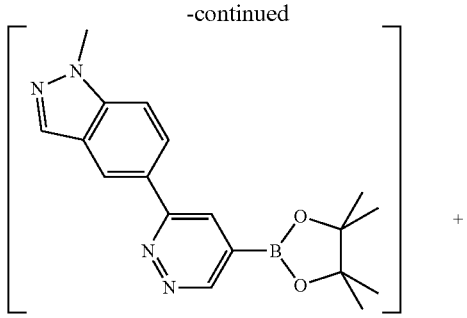

1-methyl-5-(5-(4,4,5,5-
tetramethyl-1,3,2-
dioxaborolan-2-yl)pyridazin-
3-yl)-1H-indazole

+

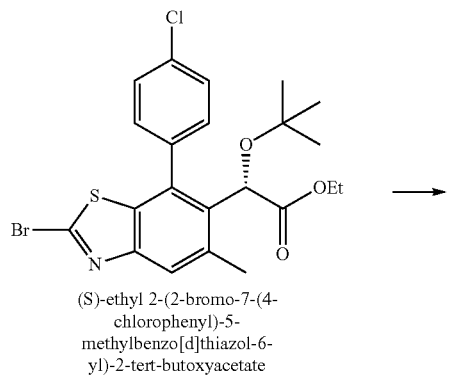

(S)-ethyl 2-(2-bromo-7-(4-
chlorophenyl)-5-
methylbenzo[d]thiazol-6-
yl)-2-tert-butoxyacetate

→

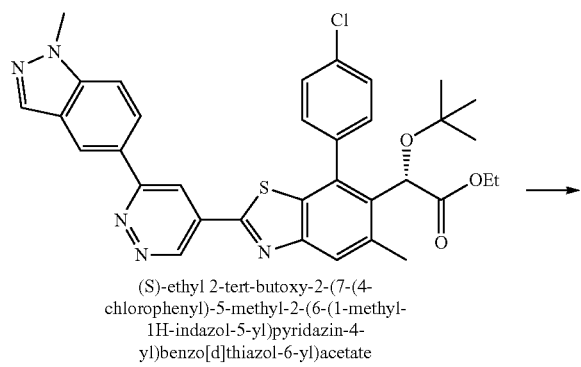

(S)-ethyl 2-tert-butoxy-2-(7-(4-
chlorophenyl)-5-methyl-2-(6-(1-methyl-
1H-indazol-5-yl)pyridazin-4-
yl)benzo[d]thiazol-6-yl)acetate

→

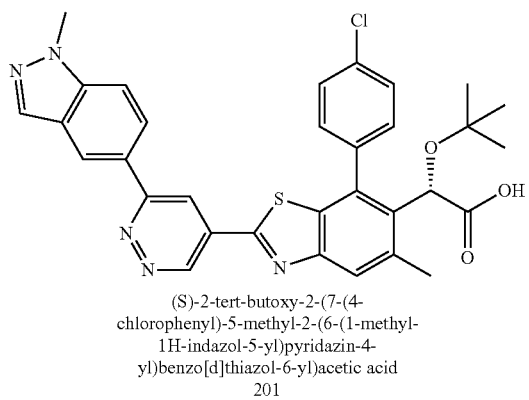

(S)-2-tert-butoxy-2-(7-(4-
chlorophenyl)-5-methyl-2-(6-(1-methyl-
1H-indazol-5-yl)pyridazin-4-
yl)benzo[d]thiazol-6-yl)acetic acid
201

Preparation of 5-(5-chloropyridazin-3-yl)-1-methyl-1H-indazole: 3,5-dichloropyridazine (200 mg, 1.34 mmol), 1-methyl-1H-indazole-5-boronic acid (260 mg, 1.48 mmol), $K_2CO_3$ (556.6 mg, 4.03 mmol), and tetrakis(triphenylphosphine)palladium(0) (233, 0.20 mmol) were taken in a microwave vial, and the vial was vacuum pumped and flushed with argon three times. To this mixture was added degassed 1,4-dioxane (10 mL) and degassed water (2.5 mL). The reaction mixture was heated at 95° C. for 2 h then cooled to room temperature. The reaction mixture was filtered through Celite (ethyl acetate eluent) and concentrated. Purification by flash column chromatography on silica gel (hexanes/ethyl acetate eluent) provided the product. LCMS-ESI$^+$: calc'd for $C_{14}H_{10}ClN_4$: 245.1 (M+H$^+$); Found: 245.2 (M+H$^+$). $^1$H NMR (400 MHz, Chloroform-d) δ 9.15 (d, J=2.2 Hz, 1H), 8.44 (s, 1H), 8.21 (dd, J=8.8, 1.5 Hz, 1H), 8.11 (s, 1H), 7.97 (s, 1H), 7.56 (d, J=8.8 Hz, 1H), 4.14 (s, 3H).

Preparation of (S)-ethyl 2-tert-butoxy-2-(7-(4-chlorophenyl)-5-methyl-2-(6-(1-methyl-1H-indazol-5-yl)pyridazin-4-yl)benzo[d]thiazol-6-yl)acetate: 5-(5-chloropyridazin-3-yl)-1-methyl-1H-indazole (75.0 mg, 0.307 mmol), bis(pinacolato)diboron (101.2 mg, 0.398 mmol), [1,1'Bis(diphenylphosphino)ferrocene]dichloropalladium(II) complex with dichloromethane (37.5 mg, 0.046 mmol), and potassium acetate (90.2 mg, 0.920 mmol) were taken in a microwave vial, and the vial was vacuum pumped and flushed with argon three times. To this mixture was added degassed DMF (3 mL). The reaction mixture was heated at 110° C. for 2 h then cooled. To the cooled reaction mixture was added (S)-ethyl 2-(2-bromo-7-(4-chlorophenyl)-5-methylbenzo[d]thiazol-6-yl)-2-tert-butoxyacetate (180.0 mg, 0.368 mmol), tetrakis(triphenylphosphine)palladium(0) (53.1 mg, 0.046 mmol), $K_2CO_3$ (127.1 mg, 0.920 mmol) and degassed water (0.5 mL). The reaction mixture was heated to 110° C. for 2 h, cooled, filtered through Celite (ethyl acetate eluent), and concentrated. Purification by flash column chromatography on silica gel (hexanes/ethyl acetate eluent) provided the product. LCMS-ESI$^+$ calc'd for $C_{34}H_{33}ClN_5O_3S$ (M+H$^+$): 626.2; Found: 625.5 (M+H$^+$).

Preparation of (S)-2-tert-butoxy-2-(7-(4-chlorophenyl)-5-methyl-2-(6-(1-methyl-1H-indazol-5-yl)pyridazin-4-yl)benzo[d]thiazol-6-yl)acetic acid: To (S)-ethyl 2-tert-butoxy-2-(7-(4-chlorophenyl)-5-methyl-2-(6-(1-methyl-1H-indazol-5-yl)pyridazin-4-yl)benzo[d]thiazol-6-yl)acetate (92.2 mg, 0.147 mmol) in THF (1.2 mL) and methanol (1.2 mL) was added NaOH (1.2 mL of a 2N solution). The reaction mixture was heated at 45° C. for 5 h, filtered, and purified by reverse phase HPLC, eluting with 5-100% acetonitrile in water with 0.1% TFA. Fractions containing the product were pooled and lyophilized to provide the TFA salt of the product. The product was taken in THF (0.5 mL) and methanol (0.5 mL), then made basic by addition of NaOH (0.5 mL of a 2N solution). The mixture was purified by reverse phase HPLC, eluting with 5-100% acetonitrile in water. Fractions containing the product were pooled and lyophilized to provide the sodium salt of the product. LCMS-ESI$^+$: calc'd for $C_{32}H_{29}ClN_5O_3S$ (M+H$^+$): 598.2; Found: 598.1 (M+H$^+$). $^1$H NMR (400 MHz, CD$_3$OD) δ 9.72 (d, J=1.8 Hz, 1H), 8.66 (s, 1H), 8.62 (s, 1H), 8.34-8.27 (m, 1H), 8.18 (s, 1H), 8.01-7.94 (m, 2H), 7.76 (d, J=7.6 Hz, 1H), 7.68-7.62 (m, 1H), 7.62-7.54 (m, 2H), 5.17 (s, 1H), 4.14 (s, 3H), 2.70 (s, 3H), 0.95 (s, 9H).

Example 68

Method AS: Preparation of (S)-2-tert-butoxy-2-(7-(4-chlorophenyl)-2-(2-(4-isopropylpiperazin-1-yl)pyrimidin-4-yl)-5-methylbenzo[d]thiazol-6-yl)acetic acid (202)

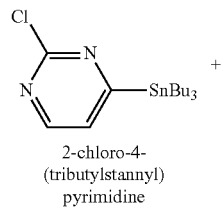

2-chloro-4-(tributylstannyl)pyrimidine

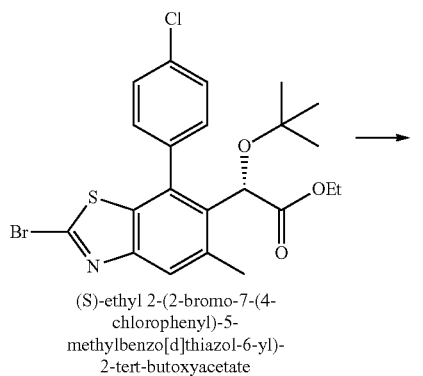

(S)-ethyl 2-(2-bromo-7-(4-chlorophenyl)-5-methylbenzo[d]thiazol-6-yl)-2-tert-butoxyacetate

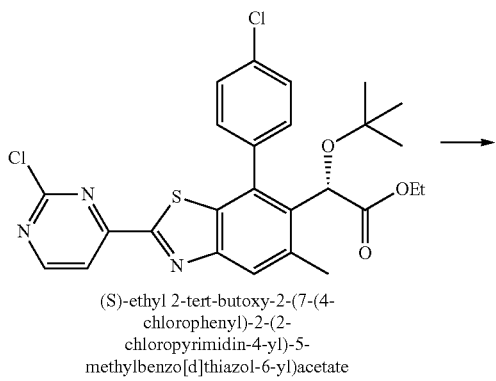

(S)-ethyl 2-tert-butoxy-2-(7-(4-chlorophenyl)-2-(2-chloropyrimidin-4-yl)-5-methylbenzo[d]thiazol-6-yl)acetate

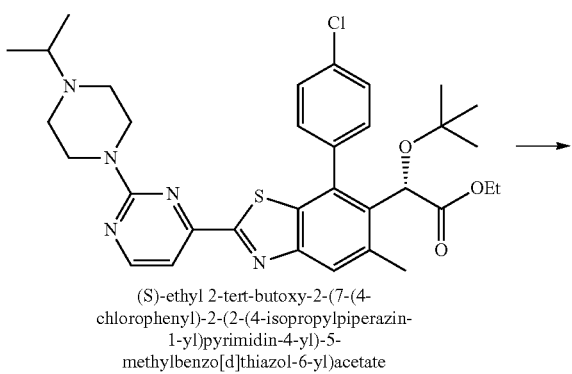

(S)-ethyl 2-tert-butoxy-2-(7-(4-chlorophenyl)-2-(2-(4-isopropylpiperazin-1-yl)pyrimidin-4-yl)-5-methylbenzo[d]thiazol-6-yl)acetate

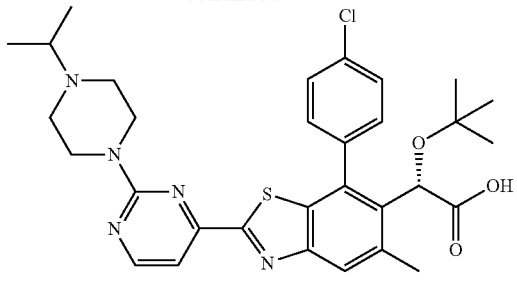

(S)-2-tert-butoxy-2-(7-(4-chlorophenyl)-2-(2-(4-isopropylpiperazin-1-yl)pyrimidin-4-yl)-5-methylbenzo[d]thiazol-6-yl)acetic acid

202

Preparation of (S)-ethyl 2-tert-butoxy-2-(7-(4-chlorophenyl)-2-(2-chloropyrimidin-4-yl)-5-methylbenzo[d]thiazol-6-yl)acetate: (S)-ethyl 2-(2-bromo-7-(4-chlorophenyl)-5-methylbenzo[d]thiazol-6-yl)-2-tert-butoxyacetate (500 mg, 1.01 mmol), tetrakis(triphenylphosphine)palladium(0) (174 mg, 0.15 mmol), lithium chloride (128 mg, 3.02 mmol), and copper(I) iodide (57.5 mg, 0.3 mmol) were taken in a microwave vial, and the vial was vacuum pumped and flushed with argon three times. To this mixture was added 2-chloro-4-(tributyl)stannyl pyrimidine (447 mg, 1.11 mmol) in 1,4-dioxane (10 mL). The reaction mixture was heated at 90° C. overnight, then cooled, filtered through Celite (ethyl acetate eluent), and concentrated. Purification by flash column chromatography on silica gel (hexanes/ethyl acetate eluent) provided the product. LCMS-ESI$^+$ calc'd for $C_{26}H_{26}Cl_2N_3O_3S$ (M+H$^+$): 530.1; Found: 529.5 (M+H$^+$).

Preparation of (S)-ethyl 2-tert-butoxy-2-(7-(4-chlorophenyl)-2-(2-(4-isopropylpiperazin-1-yl)pyrimidin-4-yl)-5-methylbenzo[d]thiazol-6-yl)acetate: To (S)-ethyl 2-tert-butoxy-2-(7-(4-chlorophenyl)-2-(2-chloropyrimidin-4-yl)-5-methylbenzo[d]thiazol-6-yl)acetate (250 mg, 0.471 mmol) in 1,4-dioxane (5 mL) was added 1-isopropylpiperazine (302 mg, 2.36 mmol). The reaction mixture was stirred at room temperature for 2.5 h and concentrated to give the product which was used without further purification. LCMS-ESI$^+$ calc'd for $C_{33}H_{41}ClN_5O_3S$ (M+H$^+$): 622.3; Found: 622.2 (M+H$^+$).

Preparation of (S)-2-tert-butoxy-2-(7-(4-chlorophenyl)-2-(2-(4-isopropylpiperazin-1-yl)pyrimidin-4-yl)-5-methylbenzo[d]thiazol-6-yl)acetic acid: To crude (S)-ethyl 2-tert-butoxy-2-(7-(4-chlorophenyl)-2-(2-(4-isopropylpiperazin-1-yl)pyrimidin-4-yl)-5-methylbenzo[d]thiazol-6-yl)acetate in THF (2.5 mL) and methanol (2.5 mL) was added NaOH (2.63 mL of a 2N solution). The reaction mixture was heated at 45° C. for 1.5 h then 50° C. for 1.5 h, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{31}H_{37}ClN_5O_3S$ (M+H$^+$): 594.2; Found: 593.9 (M+H$^+$). $^1$H NMR (400 MHz, CD$_3$OD) δ 8.62 (d, J=5.0 Hz, 1H), 7.92 (s, 1H), 7.69-7.64 (m, 1H), 7.64-7.47 (m, 4H), 5.25 (s, 1H), 5.02 (br d, J=13.7 Hz, 2H), 3.66-3.51 (m, 3H), 3.29-3.14 (m, 4H), 2.63 (s, 3H), 1.40 (d, J=6.7 Hz, 6H), 0.98 (s, 9H).

Example 69

Method AT: Preparation of (S)-2-tert-butoxy-2-(7-(4-chlorophenyl)-2-(2-(3,4-dimethoxyphenyl)pyrimidin-4-yl)-5-methylbenzo[d]thiazol-6-yl)acetic acid (203)

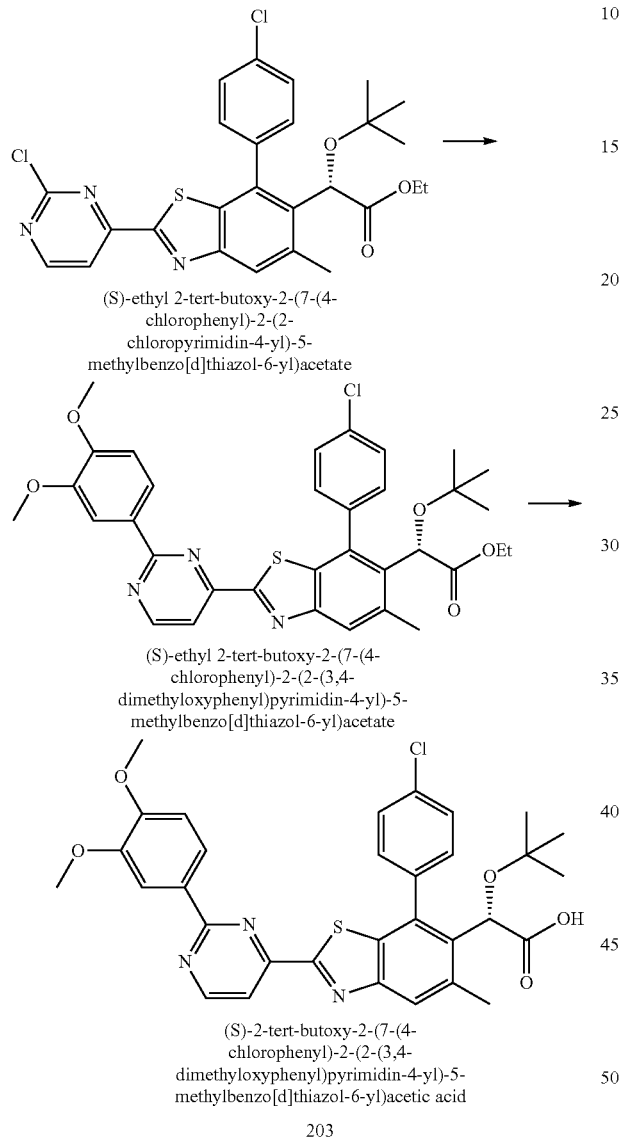

Preparation of (S)-ethyl 2-tert-butoxy-247-(4-chlorophenyl)-2-(2-(3,4-dimethoxyphenyl)pyrimidin-4-yl)-5-methylbenzo[d]thiazol-6-yl)acetate: (S)-ethyl 2-tert-butoxy-2-(7-(4-chlorophenyl)-2-(2-chloropyrimidin-4-yl)-5-methylbenzo[d]thiazol-6-yl)acetate (50.0 mg, 0.094 mmol), 3,4-dimethoxyphenylboronic acid (20.6 mg, 0.113 mmol), tetrakis(triphenylphosphine)palladium(0) (16.4 mg, 0.014 mmol), and $K_2CO_3$ (39.2 mg, 0.283 mmol) were taken in a microwave vial, and the vial was vacuum pumped and flushed with argon three times. To this mixture was added degassed 1,4-dioxane (1 mL) and degassed water (0.25 mL). The reaction mixture was stirred at 110° C. for 1.5 h, filtered through Celite (ethyl acetate eluent), and concentrated. Purification by flash column chromatography on silica gel (hexanes/ethyl acetate eluent) provided the product. LCMS-ESI+ calc'd for $C_{34}H_{35}ClN_3O_5S$ (M+H+): 632.2; Found: 632.2 (M+H+).

Preparation of (S)-2-tert-butoxy-2-(7-(4-chlorophenyl)-2-(2-(3,4-dimethoxyphenyl)pyrimidin-4-yl)-5-methylbenzo[d]thiazol-6-yl)acetic acid: To (S)-ethyl 2-tert-butoxy-2-(7-(4-chlorophenyl)-2-(2-(3,4-dimethoxyphenyl)pyrimidin-4-yl)-5-methylbenzo[d]thiazol-6-yl)acetate (51.2 mg, 0.081 mmol) in THF (0.85 mL) and methanol (0.85 mL) was added NaOH (0.85 mL of a 2N solution). The reaction mixture was heated at 30° C. overnight, cooled, filtered, and purified by reverse phase HPLC, eluting with 5-100% acetonitrile in water with 0.1% TFA. Fractions containing the product were pooled and lyophilized to provide the TFA salt of the product. LCMS-ESI+: calc'd for $C_{32}H_{31}ClN_3O_5S$ (M+H+): 604.2; Found: 604.1 (M+H+). $^1$H NMR (400 MHz, CD$_3$OD) δ 8.96 (d, J=5.1 Hz, 1H), 8.12 (dd, J=8.5, 2.0 Hz, 1H), 8.08 (d, J=5.1 Hz, 1H), 8.06 (d, J=2.0 Hz, 1H), 7.95 (s, 1H), 7.75-7.68 (m, 1H), 7.67-7.61 (m, 3H), 7.09 (d, J=8.6 Hz, 1H), 5.29 (s, 1H), 3.92 (s, 3H), 3.91 (s, 3H), 2.65 (s, 3H), 0.98 (s, 9H).

Example 70

Method AU: Preparation of (S)-2-tert-butoxy-2-(7-(4-chlorophenyl)-2-(4-(1,5-dimethyl-1H-pyrazol-4-yl)phenyl)-5-methylbenzo[d]thiazol-6-yl)acetic acid (204)

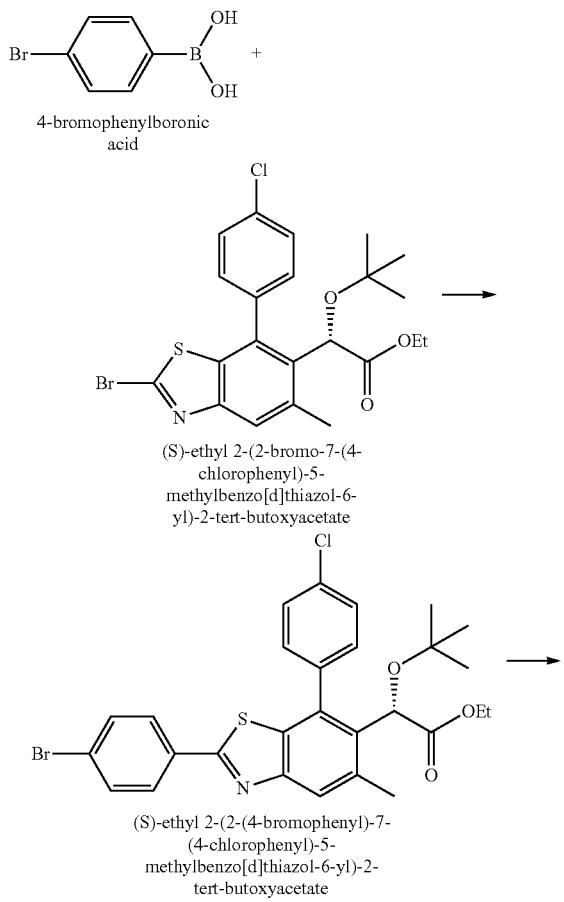

-continued

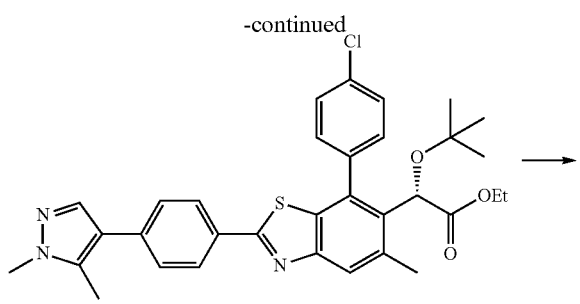

(S)-ethyl 2-tert-butoxy-2-(7-(4-chlorophenyl)-2-(4-(1,5-dimethyl-1H-pyrazol-4-yl)phenyl)-5-methylbenzo[d]thiazol-6-yl)acetate

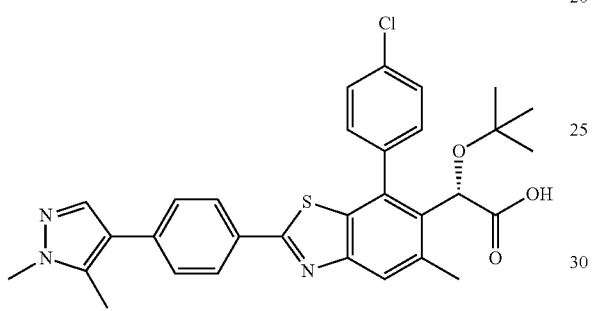

(S)-2-tert-butoxy-2-(7-(4-chlorophenyl)-2-(4-(1,5-dimethyl-1H-pyrazol-4-yl)phenyl)-5-methylbenzo[d]thiazol-6-yl)acetic acid

204

Preparation of (S)-ethyl 2-(2-(4-bromophenyl)-7-(4-chlorophenyl)-5-methylbenzo[d]thiazol-6-yl)-2-tert-butoxyacetate: (S)-ethyl 2-(2-bromo-7-(4-chlorophenyl)-5-methylbenzo[d]thiazol-6-yl)-2-tert-butoxyacetate (200 mg, 0.403 mmol), 4-bromophenylboronic acid (113 mg, 0.564 mmol), tetrakis(triphenylphosphine)palladium(0) (69.8 mg, 0.060 mmol), and $K_2CO_3$ (167 mg, 1.208 mmol) were taken in a microwave vial, and the vial was vacuum pumped and flushed with argon three times. To this mixture was added degassed 1,4-dioxane (4 mL) and degassed water (1 mL). The reaction mixture was stirred at 75° C. for 5 h, filtered through Celite (ethyl acetate eluent), and concentrated. Purification by flash column chromatography on silica gel (hexanes/ethyl acetate eluent) provided the product. LCMS-ESI$^+$ calc'd for $C_{28}H_{28}BrClNO_3S$ (M+H$^+$): 572.1 and 573.9; Found: 574.2 (M+H$^+$).

Preparation of (S)-ethyl 2-tert-butoxy-2-(7-(4-chlorophenyl)-2-(4-(1,5-dimethyl-1H-pyrazol-4-yl)phenyl)-5-methylbenzo[d]thiazol-6-yl)acetate: (S)-ethyl 2-(2-(4-bromophenyl)-7-(4-chlorophenyl)-5-methylbenzo[d]thiazol-6-yl)-2-tert-butoxyacetate (50.0 mg, 0.087 mmol), 1,5-Dimethyl-1H-pyrazole-4-boronic acid, pinacol ester (24.7 mg, 0.105 mmol), tetrakis(triphenylphosphine)palladium(0) (15.1 mg, 0.013 mmol), and $K_2CO_3$ (36.2 mg, 0.262 mmol) were taken in a microwave vial, and the vial was vacuum pumped and flushed with argon three times. To this mixture was added degassed 1,4-dioxane (0.8 mL) and degassed water (0.2 mL). The reaction mixture was stirred at 100° C. for 2.5 h, filtered through Celite (ethyl acetate eluent), and concentrated. Purification by flash column chromatography on silica gel (hexanes/ethyl acetate eluent) provided the product. LCMS-ESI$^+$ calc'd for $C_{33}H_{35}ClN_3O_3S$ (M+H$^+$): 588.2; Found: 588.3 (M+H$^+$).

Preparation of (S)-2-tert-butoxy-2-(7-(4-chlorophenyl)-2-(4-(1,5-dimethyl-1H-pyrazol-4-yl)phenyl)-5-methylbenzo[d]thiazol-6-yl)acetic acid: To (S)-ethyl 2-tert-butoxy-2-(7-(4-chlorophenyl)-2-(4-(1,5-dimethyl-1H-pyrazol-4-yl)phenyl)-5-methylbenzo[d]thiazol-6-yl)acetate in THF (0.5 mL) and water (0.5 mL) was added NaOH (0.5 mL of a 2N solution). The reaction mixture was heated at 30° C. overnight, cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{31}H_{31}ClN_3O_3S$ (M+H$^+$): 560.2; Found: 560.1 (M+H$^+$). $^1$H NMR (400 MHz, CD$_3$OD) δ 8.08-8.03 (m, 2H), 7.83 (s, 1H), 7.71-7.67 (m, 2H), 7.64-7.51 (m, 5H), 5.26 (s, 1H), 3.86 (s, 3H), 2.61 (s, 3H), 2.46 (s, 3H), 0.98 (s, 9H).

Example 71

Method AV: Preparation of (S)-2-tert-butoxy-2-(7-(4-chlorophenyl)-5-methyl-2-(2-(1-methylpiperidin-4-yl)pyrimidin-4-yl)benzo[d]thiazol-6-yl)acetic acid (205)

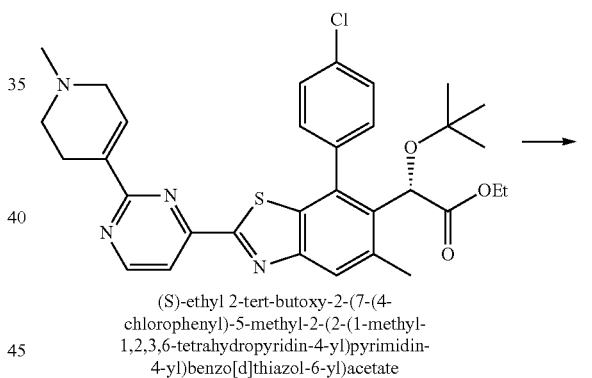

(S)-ethyl 2-tert-butoxy-2-(7-(4-chlorophenyl)-5-methyl-2-(2-(1-methyl-1,2,3,6-tetrahydropyridin-4-yl)pyrimidin-4-yl)benzo[d]thiazol-6-yl)acetate

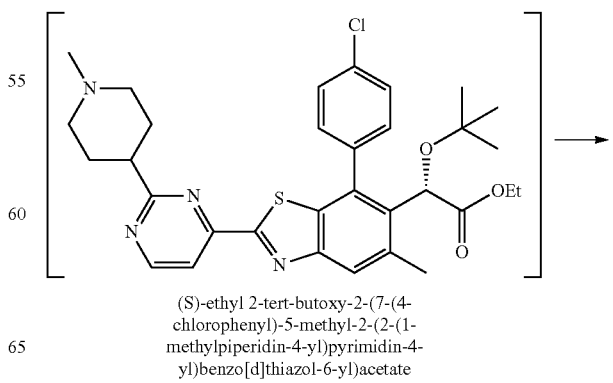

(S)-ethyl 2-tert-butoxy-2-(7-(4-chlorophenyl)-5-methyl-2-(2-(1-methylpiperidin-4-yl)pyrimidin-4-yl)benzo[d]thiazol-6-yl)acetate

371
-continued

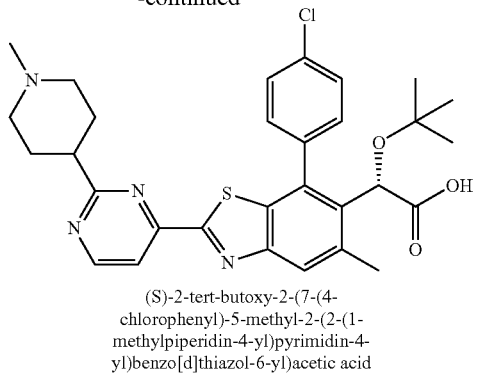

(S)-2-tert-butoxy-2-(7-(4-chlorophenyl)-5-methyl-2-(2-(1-methylpiperidin-4-yl)pyrimidin-4-yl)benzo[d]thiazol-6-yl)acetic acid
205

Preparation of (S)-2-tert-butoxy-2-(7-(4-chlorophenyl)-5-methyl-2-(2-(1-methylpiperidin-4-yl)pyrimidin-4-yl)benzo[d]thiazol-6-yl)acetic acid: To (S)-ethyl 2-tert-butoxy-2-(7-(4-chlorophenyl)-5-methyl-2-(2-(1-methyl-1,2,3,6-tetrahydropyridin-4-yl)pyrimidin-4-yl)benzo[d]thiazol-6-yl)acetate (14.4 mg, 0.024 mmol) in ethanol (0.5 mL) was added rhodium on alumina (2.5 mg, 5 wt. % loading material). The reaction flask was evacuated and flushed with hydrogen three times, then left under a balloon of hydrogen. After 4 h, additional rhodium on alumina (5.0 mg) was added, and the reaction flask evacuated and flushed with hydrogen three additional times. After another 3 h, additional rhodium on alumina (5.0 mg) was added, and the reaction flask evacuated and flushed with hydrogen three additional times. The reaction mixture was stirred under a balloon of hydrogen for 2 days. Upon completion of the reduction, as indicated by LC/MS, the hydrogen balloon was removed. To the crude reaction mixture was added THF (0.5 mL) and NaOH (0.5 mL of a 2N solution). The reaction mixture was heated at 30° C. overnight, cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{30}H_{34}ClN_4O_3S$ (M+H$^+$): 565.2; Found: 565.1 (M+H$^+$). $^1$H NMR (400 MHz, CD$_3$OD) δ 8.94 (d, J=5.3 Hz, 1H), 8.18 (d, J=5.2 Hz, 1H), 7.95 (s, 1H), 7.72-7.65 (m, 1H), 7.65-7.51 (m, 3H), 5.27 (s, 1H), 3.63 (br d, J=12.2 Hz, 2H), 3.25-3.14 (m, 3H), 2.91 (s, 3H), 2.64 (s, 3H), 2.38 (br d, J=16.0 Hz, 2H), 2.12 (br d, J=12.3 Hz, 2H), 0.98 (s, 9H).

Example 72

Method AW: Preparation of (S)-2-tert-butoxy-2-(7-(4-chlorophenyl)-2-(3-(dimethylamino)-1-methyl-1H-indazol-6-yl)-5-methylbenzo[d]thiazol-6-yl)acetic acid (206)

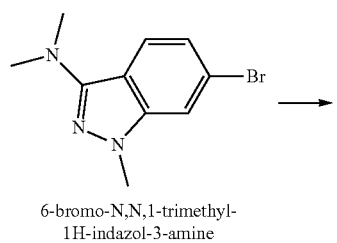

6-bromo-N,N,1-trimethyl-1H-indazol-3-amine

372
-continued

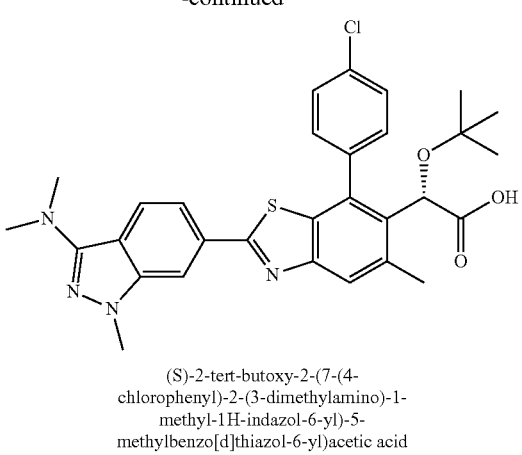

(S)-2-tert-butoxy-2-(7-(4-chlorophenyl)-2-(3-dimethylamino)-1-methyl-1H-indazol-6-yl)-5-methylbenzo[d]thiazol-6-yl)acetic acid
206

Preparation of (S)-2-tert-butoxy-2-(7-(4-chlorophenyl)-2-(3-(dimethylamino)-1-methyl-1H-indazol-6-yl)-5-methyl-benzo[d]thiazol-6-yl)acetic acid: A vial was charged with 6-bromo-N,N,1-trimethyl-1H-indazol-3-amine (102 mg, 0.402 mmol), bis-pinacolatodiboron (112 mg, 0.442 mmol), PdCl$_2$(dppf).DCM (33 mg, 40 μmol), glacial AcOH (25 μL, 0.44 mmol), KOAc (130 mg, 1.33 mmol), and dioxane (2.0 mL). The reaction was heated to 100° C. for 30 min. To this reaction was added (S)-ethyl 2-(2-bromo-7-(4-chlorophenyl)-5-methylbenzo[d]thiazol-6-yl)-2-tert-butoxyacetate (150 mg, 0.302 mmol), 2 M aq K$_2$CO$_3$ (884 μL), and Pd(PPh$_3$)$_4$ (46 mg, 40 mop). The reaction was heated for another 1 h at 100° C. Finally, EtOH (absolute, 1.7 mL) and 2 M aqueous NaOH (884 μL) were added. The reaction was heated to 100° C. for another 1 h. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for $C_{30}H_{31}ClN_4O_3S$: 563.2, 565.2 (M+H$^+$); Found: 563.2, 565.2 (M+H$^+$). $^1$H NMR (400 MHz, CD$_3$OD): δ 8.01 (s, 1H), 7.93 (d, J=8.6 Hz, 1H), 7.84 (s, 1H), 7.69 (dd, J=6.3, 3.2 Hz, 1H), 7.65 (dd, J=8.6, 1.2 Hz, 1H), 7.62-7.56 (m, 3H), 5.26 (s, 1H), 3.90 (s, 3H), 3.12 (s, 6H), 2.61 (d, J=4.8 Hz, 3H), 0.98 (d, J=4.1 Hz, 9H).

Example 73

Method AX: Preparation of (S)-2-tert-butoxy-2-(7-(4-chlorophenyl)-2-(7,8-dihydro-1,6-naphthyridin-6(5H)-yl)-5-methylbenzo[d]thiazol-6-yl)acetic acid (207)

5,6,7,8-tetrahydro-1,6-naphthyridine, dihydrochloride, hydrate

373
-continued

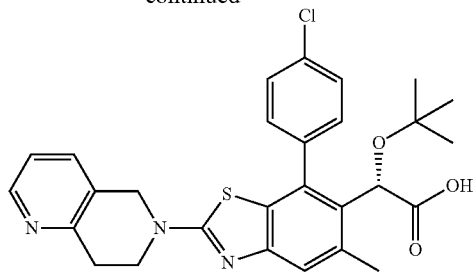

(S)-2-tert-butoxy-2-(7-(4-chlorophenyl)-2-(7,8-dihydro-
1,6-naphthyridin-6(5H)-yl)-5-methylbenzo[d]thiazol-6-
yl)acetic acid

207

Preparation of (S)-2-tert-butoxy-2-(7-(4-chlorophenyl)-2-(7,8-dihydro-1,6-naphthyridin-6(5H)-yl)-5-methylbenzo[d]thiazol-6-yl)acetic acid: A vial was charged with 5,6,7,8-tetrahydro-1,6-naphthyridine, dihydrochloride, hydrate (125 mg), DCM (1.5 mL), and 50% w/v aq KOH (200 µL). The vial was shaken. Then H$_2$O (1.3 mL) was added. The organic phase was collected, dried with a small amount of Na$_2$SO$_4$, decanted, and concentrated to give the free base. N,N-dimethylacetamide (500 µL), and (S)-ethyl 2-(2-bromo-7-(4-chlorophenyl)-5-methylbenzo[d]thiazol-6-yl)-2-tert-butoxyacetate (25 mg, 50 µmol) were added. The vessel was sealed and heated to 100° C. for 30 min. Then THF (1 mL), EtOH (absolute, 500 µL), and 5 M aq NaOH (500 µL) were added. The reaction was heated to 100° C. for 30 min. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for C$_{28}$H$_{28}$ClN$_3$O$_3$S: 522.2, 524.2 (M+H$^+$); Found: 522.3, 524.2 (M+H$^+$). NMR (400 MHz, CD$_3$OD): δ 8.62 (d, J=5.6 Hz, 1H), 8.29 (d, J=8.1 Hz, 1H), 7.78 (dd, J=7.9, 5.6 Hz, 1H), 7.63 (dd, J=8.5, 1.9 Hz, 1H), 7.58-7.52 (m, 2H), 7.52-7.44 (m, 1H), 7.38 (app. s, 1H), 5.15 (s, 1H), 4.96 (s, broad, 2H), 4.03 (t, J=5.9 Hz, 2H), 3.31-3.23 (m, 2H), 2.51 (s, 3H), 0.95 (s, 9H).

Example 74

Method AY: Preparation of (S)-2-tert-butoxy-2-(7-(4-chlorophenyl)-2-(3,4-dihydroisoquinolin-2(1H)-yl)-5-methylbenzo[d]thiazol-6-yl)acetic acid (208)

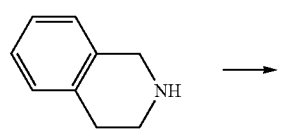

1,2,3,4-tetrahydroisoquinoline

374
-continued

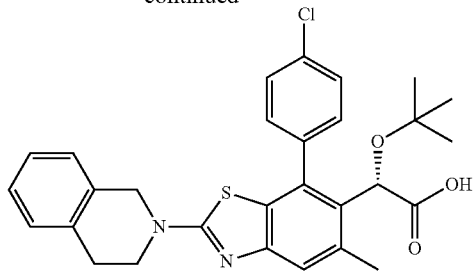

(S)-2-tert-butoxy-2-(7-(4-chlorophenyl)-2-(3,4-
dihydroisoquinolin-2(1H)-yl)-5-methylbenzo[d]thiazol-6-
yl)acetic acid

208

Preparation of (S)-2-tert-butoxy-2-(7-(4-chlorophenyl)-2-(3,4-dihydroisoquinolin-2(1H)-yl)-5-methylbenzo[d]thiazol-6-yl)acetic acid: A vial was charged with (S)-ethyl 2-(2-bromo-7-(4-chlorophenyl)-5-methylbenzo[d]thiazol-6-yl)-2-tert-butoxyacetate (25 mg, 50 µmol), N,N-dimethylacetamide and 1,2,3,4-tetrahydroisoquinoline (50 µL). The reaction was heated to 100° C. for 30 min. Then THF (1 mL), EtOH (absolute, 500 µL), and 5 M aq NaOH (500 µL) were introduced. The reaction was heated for another 30 min at 100° C. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for C$_{29}$H$_{29}$ClN$_2$O$_3$S: 521.2, 523.2 (M+H$^+$); Found: 521.2, 523.2 (M+H$^+$). $^1$H NMR (400 MHz, CD$_3$OD): δ 7.71-7.47 (m, 4H), 7.38 (s, 1H), 7.30-7.22 (m, 4H), 5.17 (s, 1H), 4.79 (s, 2H), 3.84 (t, J=6.0 Hz, 2H), 3.09 (t, J=6.0 Hz, 2H), 2.54 (s, 3H), 0.96 (s, 9H).

Example 75

Method AZ: Preparation of (S)-2-tert-butoxy-2-(7-(4-chlorophenyl)-2-(1,3-dimethyl-1H-indazol-6-yl)-5-methylbenzo[d]thiazol-6-yl)acetic acid (209)

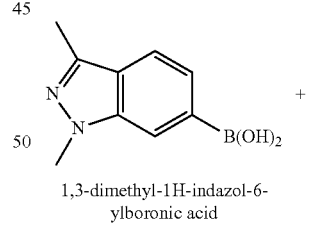

1,3-dimethyl-1H-indazol-6-
ylboronic acid

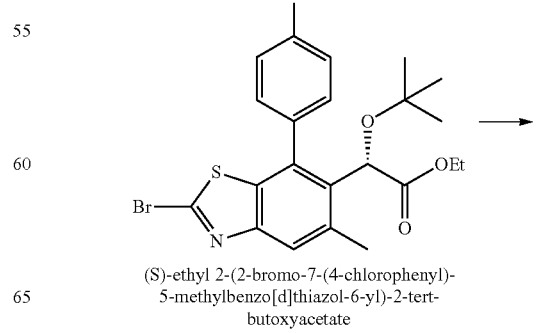

(S)-ethyl 2-(2-bromo-7-(4-chlorophenyl)-
5-methylbenzo[d]thiazol-6-yl)-2-tert-
butoxyacetate (q, J=8.7 Hz, 3H), 7.57 (d, J=6.1 Hz, 3H), 5.25 (s, 1H), 3.98 (s, 3H), 2.59 (s, 3H), 2.51 (s, 3H), 0.97 (s, 9H).

Example 76

Method BA: Preparation of (S)-2-tert-butoxy-2-(7-(4-chlorophenyl)-5-methyl-2-(1-methyl-1H-benzo[d][1,2,3]triazol-5-yl)benzo[d]thiazol-6-yl)acetic acid (210)

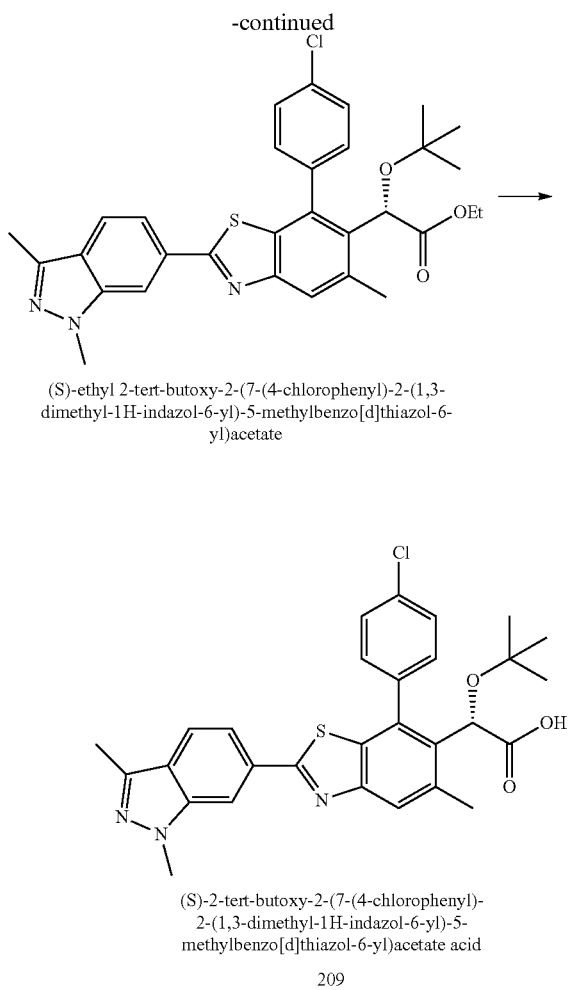

(S)-ethyl 2-tert-butoxy-2-(7-(4-chlorophenyl)-2-(1,3-dimethyl-1H-indazol-6-yl)-5-methylbenzo[d]thiazol-6-yl)acetate (S)-2-tert-butoxy-2-(7-(4-chlorophenyl)-2-(1,3-dimethyl-1H-indazol-6-yl)-5-methylbenzo[d]thiazol-6-yl)acetate acid

209

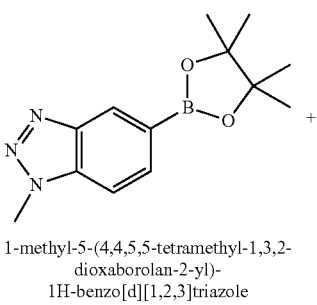

1-methyl-5-(4,4,5,5-tetramethyl-1,3,2-dioxaborolan-2-yl)-1H-benzo[d][1,2,3]triazole

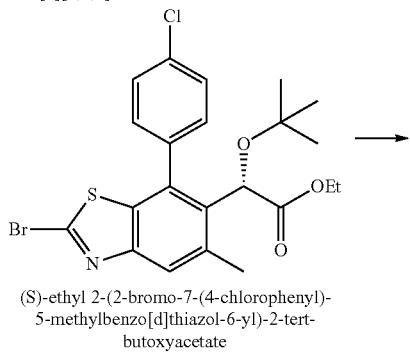

(S)-ethyl 2-(2-bromo-7-(4-chlorophenyl)-5-methylbenzo[d]thiazol-6-yl)-2-tert-butoxyacetate

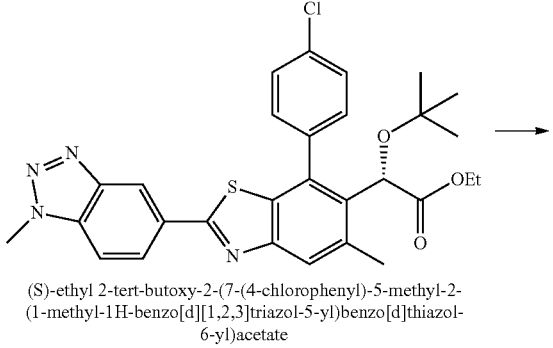

(S)-ethyl 2-tert-butoxy-2-(7-(4-chlorophenyl)-5-methyl-2-(1-methyl-1H-benzo[d][1,2,3]triazol-5-yl)benzo[d]thiazol-6-yl)acetate

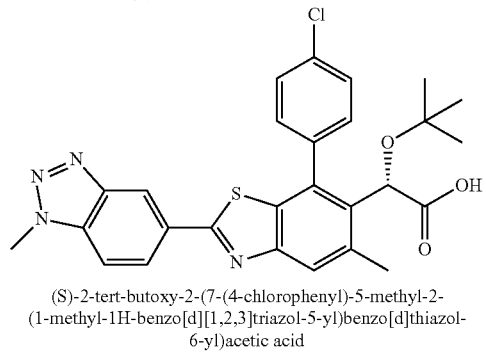

(S)-2-tert-butoxy-2-(7-(4-chlorophenyl)-5-methyl-2-(1-methyl-1H-benzo[d][1,2,3]triazol-5-yl)benzo[d]thiazol-6-yl)acetic acid

210

Preparation of (S)-ethyl 2-tert-butoxy-2-(7-(4-chlorophenyl)-2-(1,3-dimethyl-1H-indazol-6-yl)-5-methylbenzo[d]thiazol-6-yl)acetate: To a vial flushed with argon was added (S)-ethyl 2-(2-bromo-7-(4-chlorophenyl)-5-methylbenzo[d]thiazol-6-yl)-2-tert-butoxyacetate (100 mg, 0.202 mmol), 1,3-dimethyl-1H-indazol-6-ylboronic acid (76 mg, 0.4 mmol), Pd(PPh$_3$)$_4$ (23 mg, 20 μmol), and K$_2$CO$_3$ (83 mg, 0.6 mmol). De-gassed dioxane (1.6 mL) and water (0.4 mL) were then added, and the reaction was heated to 100° C. for 1 h. After cooling to 23° C., the reaction was filtered over a plug of Celite, concentrated, and purified by column chromatography (gradient 0 to 30% EtOAc in hexanes) to give the product. LCMS-ESI$^+$: calc'd for C$_{31}$H$_{33}$ClN$_3$O$_3$S: 562.2 (M+H$^+$); Found: 562.3 (M+H$^+$).

Preparation of (S)-2-tert-butoxy-2-(7-(4-chlorophenyl)-2-(1,3-dimethyl-1H-indazol-6-yl)-5-methylbenzo[d]thiazol-6-yl)acetic acid: To a vial was dissolved (S)-ethyl 2-tert-butoxy-2-(7-(4-chlorophenyl)-2-(1,3-dimethyl-1H-indazol-6-yl)-5-methylbenzo[d]thiazol-6-yl)acetate (100 mg, 0.178 mmol) in THF (4 mL) and EtOH (2 mL). 1M NaOH (2 mL) was added, and the mixture was heated to 50° C. overnight. The reaction was cooled to 23° C., and filtered (0.45 micron teflon syringe filter). The filtrate was purified by reverse phase HPLC, eluting with 5-100% acetonitrile in H$_2$O with 0.1% TFA to give the desired product. LCMS-ESI$^+$: calc'd for C$_{29}$H$_{29}$ClN$_3$O$_3$S: 534.1 (M+H$^+$); Found: 534.2 (M+H$^+$). $^1$H NMR (400 MHz, CD$_3$OD): δ 8.04 (s, 1H), 7.77 (s, 1H), 7.70

Preparation of (S)-ethyl 2-tert-butoxy-2-(7-(4-chlorophenyl)-5-methyl-2-(1-methyl-1H-benzo[d][1,2,3]triazol-5-yl)

benzo[d]thiazol-6-yl)acetate: To a vial flushed with argon was added (S)-ethyl 2-(2-bromo-7-(4-chlorophenyl)-5-methylbenzo[d]thiazol-6-yl)-2-tert-butoxyacetate (100 mg, 0.202 mmol), 1-methyl-5-(4,4,5,5-tetramethyl-1,3,2-dioxaborolan-2-yl)-1H-benzo[d][1,2,3]triazole (62 mg, 0.24 mmol), Pd(PPh$_3$)$_4$ (23 mg, 20 µmol), and K$_2$CO$_3$ (83 mg, 0.6 mmol). De-gassed dioxane (2 mL) and water (0.5 mL) were then added, and the reaction was heated to 100° C. for 1 h. After cooling to 23° C., the reaction was filtered over a plug of Celite, concentrated, and purified by column chromatography (gradient 0 to 35% EtOAc in hexanes) to give the product. $^1$H NMR (400 MHz, CDCl$_3$) δ 8.62 (s, 1H), 8.31 (dd, J=8.7, 1.4 Hz, 1H), 7.90 (s, 1H), 7.66-7.44 (m, 5H), 5.17 (s, 1H), 4.33 (s, 3H), 4.26-4.16 (m, 2H), 2.61 (s, 3H), 1.30-1.22 (m, 3H), 0.98 (s, 9H).

Preparation of (S)-2-tert-butoxy-2-(7-(4-chlorophenyl)-5-methyl-2-(1-methyl-1H-benzo[d][1,2,3]triazol-5-yl)benzo[d]thiazol-6-yl)acetic acid: To a vial was dissolved (S)-ethyl 2-tert-butoxy-2-(7-(4-chlorophenyl)-5-methyl-2-(1-methyl-1H-benzo[d][1,2,3]triazol-5-yl)benzo[d]thiazol-6-yl)acetate (100 mg, 0.182 mmol) in THF (3 mL) and EtOH (1.5 mL). 1M NaOH (1.5 mL) was added, and the mixture was heated to 50° C. overnight. The reaction was cooled to 23° C., and filtered (0.45 micron teflon syringe filter). The filtrate was purified by reverse phase HPLC, eluting with 5-100% acetonitrile in H$_2$O with 0.1% TFA to give the desired product. LCMS-ESI$^+$: calc'd for C$_{27}$H$_{26}$ClN$_4$O$_3$S: 521.0 (M+H$^+$); Found: 521.2 (M+H$^+$). $^1$H NMR (400 MHz, CD$_3$OD) δ 8.60 (s, 1H), 8.26 (dd, J=8.8, 1.5 Hz, 1H), 7.87 (d, J=9.0 Hz, 2H), 7.70 (dd, J=7.4, 2.4 Hz, 1H), 7.65-7.56 (m, 3H), 5.26 (s, 1H), 4.35 (s, 3H), 2.62 (s, 3H), 0.98 (s, 9H).

Example 78

Method BC: Preparation of (S)-2-tert-butoxy-2-(7-(4-chlorophenyl)-5-methyl-2-(1-methyl-3-(pyridin-3-yl)-1H-indazol-5-yl)benzo[d]thiazol-6-yl)acetic acid (212)

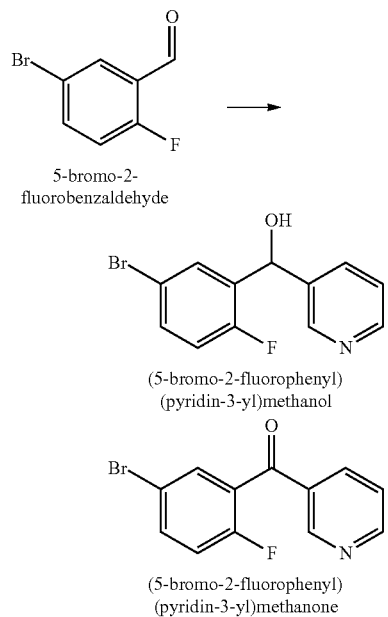

5-bromo-2-fluorobenzaldehyde (5-bromo-2-fluorophenyl)(pyridin-3-yl)methanol (5-bromo-2-fluorophenyl)(pyridin-3-yl)methanone

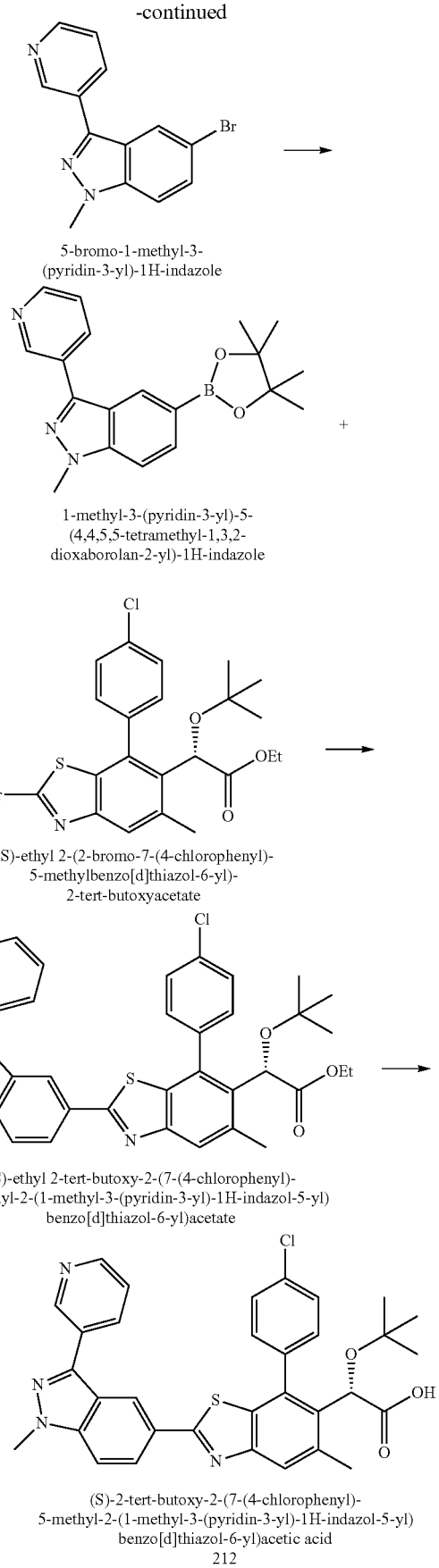

5-bromo-1-methyl-3-(pyridin-3-yl)-1H-indazole 1-methyl-3-(pyridin-3-yl)-5-(4,4,5,5-tetramethyl-1,3,2-dioxaborolan-2-yl)-1H-indazole (S)-ethyl 2-(2-bromo-7-(4-chlorophenyl)-5-methylbenzo[d]thiazol-6-yl)-2-tert-butoxyacetate (S)-ethyl 2-tert-butoxy-2-(7-(4-chlorophenyl)-5-methyl-2-(1-methyl-3-(pyridin-3-yl)-1H-indazol-5-yl)benzo[d]thiazol-6-yl)acetate (S)-2-tert-butoxy-2-(7-(4-chlorophenyl)-5-methyl-2-(1-methyl-3-(pyridin-3-yl)-1H-indazol-5-yl)benzo[d]thiazol-6-yl)acetic acid
212

Preparation of (5-bromo-2-fluorophenyl)(pyridin-3-yl)methanol: To an oven-dried flask was added anhydrous THF (20 mL) and 3-bromopyridine (2 mL, 20 mmol). Isopropylmagnesium chloride in THF (11 mL, 2.0 M solution) was then added dropwise over several minutes. The mixture was stirred at room temperature for 1 hour, and then 5-bromo-2-fluorobenzaldehyde (2.4 mL, 20 mmol) was added. After stirring for 1 further hour at room temperature, the reaction was quenched with saturated aqueous $NH_4Cl$. The aqueous layer was extracted with EtOAc, dried over $MgSO_4$, and purified by column chromatography (gradient 0 to 50% EtOAc in hexanes) to afford the product. $^1H$ NMR (400 MHz, $CDCl_3$) δ 8.51 (d, J=1.9 Hz, 1H), 8.41 (dd, J=4.8, 1.5 Hz, 1H), 7.78-7.68 (m, 2H), 7.38 (ddd, J=8.7, 4.6, 2.6 Hz, 1H), 7.27 (dd, J=8.6, 4.2 Hz, 1H), 6.95-6.85 (m, 1H), 6.10 (s, 1H), 4.22 (br s, 1H).

Preparation of (5-bromo-2-fluorophenyl)(pyridin-3-yl)methanone: To a stirring solution of (5-bromo-2-fluorophenyl)(pyridin-3-yl)methanol (3.75 g, 13.3 mmol) in DCM (50 mL) was added Dess-Martin periodinane (6.21 g, 14.6 mmol) portion-wise over several minutes. The reaction was then quenched with saturated 1:1 $Na_2S_2O_3/NaHCO_3$ solution (140 mL) and stirred until gas evolution ceased. The aqueous layer was extracted with DCM, dried over $MgSO_4$, and purified by column chromatography (gradient 0 to 30% EtOAc in hexanes) to give the product. $^1H$ NMR (400 MHz, $CDCl_3$) δ 8.98 (s, 1H), 8.83 (dd, J=4.9, 1.7 Hz, 1H), 8.14 (dd, J=7.9, 0.6 Hz, 1H), 7.73 (dd, J=6.0, 2.5 Hz, 1H), 7.68 (ddd, J=8.7, 4.5, 2.6 Hz, 1H), 7.47 (dd, J=8.0, 4.9 Hz, 1H), 7.09 (t, J=9.0 Hz, 1H).

Preparation of 5-bromo-1-methyl-3-(pyridin-3-yl)-1H-indazole: A heavy wall pressure flask was charged with (5-bromo-2-fluorophenyl)(pyridin-3-yl)methanone (3.417 g, 12.2 mmol) and dioxane (30 mL). Methylhydrazine (1.4 mL, 26.6 mmol) was then added, and the mixture was heated to 100° C. for 16 hours. The crude mixture was concentrated, and purified by column chromatography (gradient 0 to 55% EtOAc in hexanes) to give the product. $^1H$ NMR (400 MHz, $CDCl_3$) δ 9.19 (d, J=2.1 Hz, 1H), 8.65 (dd, J=4.9, 1.5 Hz, 1H), 8.28 (d, J=8.0 Hz, 1H), 8.13 (d, J=1.6 Hz, 1H), 7.54 (dd, J=8.9, 1.7 Hz, 1H), 7.49 (dd, J=8.0, 4.9 Hz, 1H), 7.35 (d, J=8.9 Hz, 1H), 4.15 (s, 3H).

Preparation of 1-methyl-3-(pyridin-3-yl)-5-(4,4,5,5-tetramethyl-1,3,2-dioxaborolan-2-yl)-1H-indazole: To a vial flushed with argon was added 5-bromo-1-methyl-3-(pyridin-3-yl)-1H-indazole (432 mg, 1.5 mmol), $PdCl_2$(dppf).DCM (123 mg, 0.15 mmol), bis(pinacolato)diboron (419 mg, 1.65 mmol), and KOAc (442 mg, 4.5 mmol). Anhydrous dioxane (8 mL) was added, and the mixture was heated to 90° C. for 3 hours. After cooling to room temperature, the crude reaction was filtered over a plug of Celite, concentrated, and purified by column chromatography (gradient 0 to 60% EtOAc in hexanes) to give the product. $^1H$ NMR (400 MHz, $CDCl_3$) δ 9.28 (d, J=1.6 Hz, 1H), 8.64 (dd, J=4.8, 1.4 Hz, 1H), 8.50 (s, 1H), 8.30 (dt, J=7.8, 1.8 Hz, 1H), 7.86 (d, J=8.5 Hz, 1H), 7.49-7.39 (m, 2H), 4.14 (s, 3H), 1.38 (s, 12H).

Preparation of (S)-ethyl 2-tert-butoxy-2-(7-(4-chlorophenyl)-5-methyl-2-(1-methyl-3-(pyridin-3-yl)-1H-indazol-5-yl)benzo[d]thiazol-6-yl)acetate: To a vial flushed with argon was added (S)-ethyl 2-(2-bromo-7-(4-chlorophenyl)-5-methylbenzo[d]thiazol-6-yl)-2-tert-butoxyacetate (75 mg, 0.15 mmol), 1-methyl-3-(pyridin-3-yl)-5-(4,4,5,5-tetramethyl-1,3,2-dioxaborolan-2-yl)-1H-indazole (60.4 mg, 0.18 mmol), $Pd(PPh_3)_4$ (17.4 mg, 15 μmol), and $K_2CO_3$ (62.2 mg, 0.45 mmol). De-gassed dioxane (1.6 mL) and water (0.4 mL) were then added, and the reaction was heated to 100° C. for 1 h. After cooling to 23° C., the reaction was filtered over a plug of Celite, concentrated, and purified by column chromatography (gradient 0 to 70% EtOAc in hexanes) to give the product. $^1H$ NMR (400 MHz, $CDCl_3$) δ 9.26 (s, 1H), 8.67 (d, J=3.6 Hz, 1H), 8.58 (s, 1H), 8.33 (d, J=7.7 Hz, 1H), 8.19 (dd, J=8.8, 1.0 Hz, 1H), 7.87 (s, 1H), 7.60-7.45 (m, 6H), 5.17 (s, 1H), 4.34-4.08 (m, 5H), 2.61 (s, 3H), 1.25 (t, J=7.1 Hz, 3H), 0.99 (s, 9H).

Preparation of (S)-2-tert-butoxy-2-(7-(4-chlorophenyl)-5-methyl-2-(1-methyl-3-(pyridin-3-yl)-1H-indazol-5-yl)benzo[d]thiazol-6-yl)acetic acid: To a vial was dissolved (S)-ethyl 2-tert-butoxy-2-(7-(4-chlorophenyl)-5-methyl-2-(1-methyl-3-(pyridin-3-yl)-1H-indazol-5-yl)benzo[d]thiazol-6-yl)acetate (69 mg, 0.11 mmol) in THF (2 mL) and EtOH (1 mL). 1M NaOH (1 mL) was added, and the mixture was heated to 50° C. for 15 hours. The reaction was cooled to 23° C., and filtered (0.45 micron teflon syringe filter). The filtrate was purified by reverse phase HPLC, eluting with 5-100% acetonitrile in $H_2O$ with 0.1% TFA to give the desired product as a light yellow powder. LCMS-ESI$^+$: calc'd for $C_{33}H_{30}ClN_4O_3S$: 597.1 (M+H$^+$); Found: 597.2 (M+H$^+$). $^1H$ NMR (400 MHz, $CD_3OD$) δ 9.32 (s, 1H), 8.89 (d, J=8.1 Hz, 1H), 8.72 (d, J=4.5 Hz, 1H), 8.66 (s, 1H), 8.09 (dd, J=8.9, 1.4 Hz, 1H), 7.95 (dd, J=7.9, 5.5 Hz, 1H), 7.79 (s, 1H), 7.76-7.67 (m, 2H), 7.63-7.52 (m, 3H), 5.26 (s, 1H), 4.17 (s, 3H), 2.61 (s, 3H), 0.98 (s, 9H).

Example 79

Method BD: Preparation of (S)-2-tert-butoxy-2-(7-(4-chlorophenyl)-5-methyl-2-(1-methyl-3-(pyridin-4-yl)-1H-indazol-5-yl)benzo[d]thiazol-6-yl)acetic acid (213)

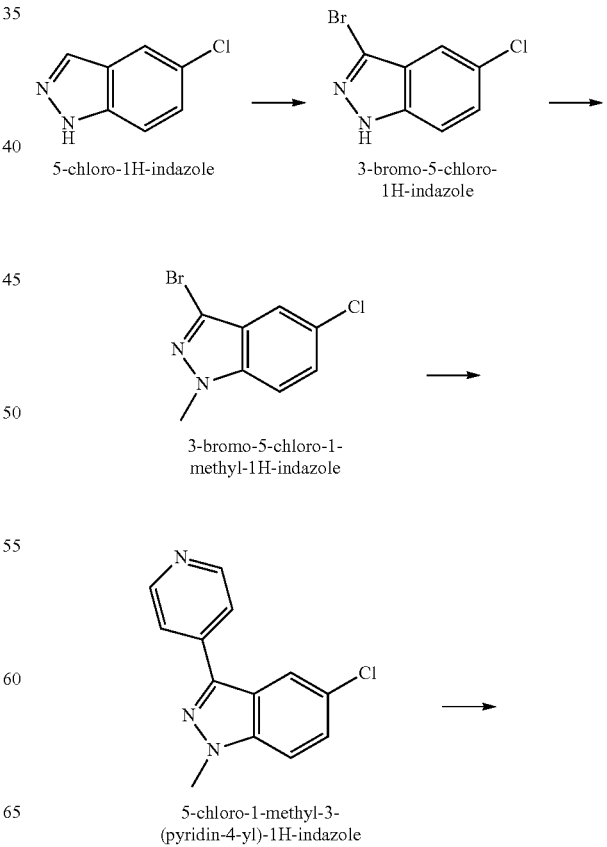

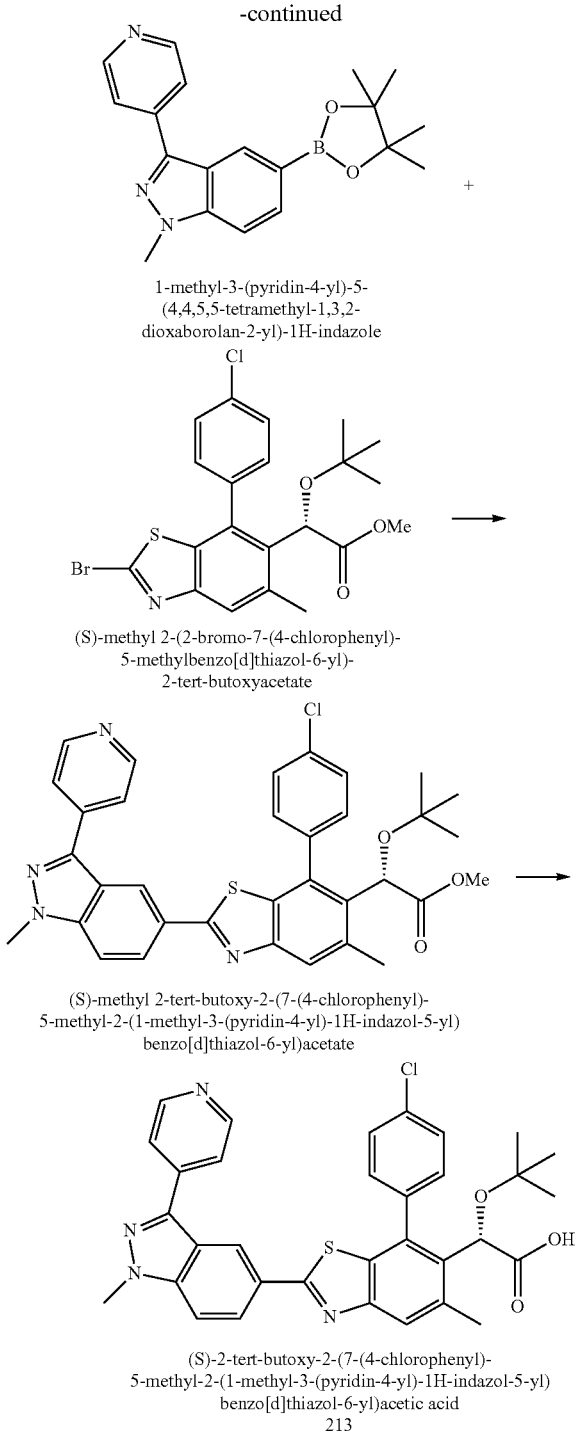

1-methyl-3-(pyridin-4-yl)-5-(4,4,5,5-tetramethyl-1,3,2-dioxaborolan-2-yl)-1H-indazole (S)-methyl 2-(2-bromo-7-(4-chlorophenyl)-5-methylbenzo[d]thiazol-6-yl)-2-tert-butoxyacetate (S)-methyl 2-tert-butoxy-2-(7-(4-chlorophenyl)-5-methyl-2-(1-methyl-3-(pyridin-4-yl)-1H-indazol-5-yl)benzo[d]thiazol-6-yl)acetate (S)-2-tert-butoxy-2-(7-(4-chlorophenyl)-5-methyl-2-(1-methyl-3-(pyridin-4-yl)-1H-indazol-5-yl)benzo[d]thiazol-6-yl)acetic acid
213

Preparation of 3-bromo-5-chloro-1H-indazole: A flask was charged with 5-chloro-1H-indazole (4.9 g, 32.11 mmol) and DMF (30 mL). It was then cooled to 0° C., and a solution of bromine (2.4 mL, 46.86 mmol) in DMF (30 mL) was added over several minutes. After addition was complete, the flask was warmed to rt and stirred for 4 hours. Additional bromine (0.89 mL, 16 mmol) was added, and the reaction stirred at room temperature for 20 minutes. The reaction was poured into 600 mL of ice-cold 1% (w/v) $Na_2S_2O_3$ solution, and the precipitated product was filtered off. The product was redissolved in EtOAc (500 mL), washed with saturated aqueous NaHCO$_3$ then brine, dried over $Na_2SO_4$, and concentrated to afford the product. $^1$H NMR (400 MHz, DMSO-d$_6$) δ 13.60 (br s, 1H), 7.68-7.54 (m, 2H), 7.44 (dd, J=9.0, 1.8 Hz, 1H).

Preparation of 3-bromo-5-chloro-1-methyl-1H-indazole: 3-bromo-5-chloro-1H-indazole (7.5 g, 32.4 mmol) was dissolved in anhydrous DMF (60 mL) then cooled to 0° C. With vigorous stirring, cesium carbonate (13.36 g, 41 mmol) was added in one portion followed by dropwise addition of iodomethane (2.55 mL, 41 mmol). The reaction was then stirred at 0° C. for 1 hour. The reaction was diluted with distilled water (80 mL), and extracted with EtOAc (3×60 mL). The organic extracts were washed with brine (2×), dried over $Na_2SO_4$, and purified by column chromatography (gradient 0 to 15% EtOAc/hexanes) to afford the product. $^1$H NMR (400 MHz, CDCl$_3$) δ 7.58 (d, J=1.8 Hz, 1H), 7.38 (dd, J=8.9, 1.9 Hz, 1H), 7.30 (d, J=8.9 Hz, 1H), 4.04 (s, 3H).

Preparation of 5-chloro-1-methyl-3-(pyridin-4-yl)-1H-indazole: To a pressure flask was added 3-bromo-5-chloro-1-methyl-1H-indazole (0.737 g, 3 mmol), pyridine-4-boronic acid (0.996 g, 8.1 mmol), PdCl$_2$(dppf).DCM (0.490 g, 0.6 mmol), and K$_3$PO$_4$ (3.184 g, 15 mmol). The flask was flushed with argon for 5 minutes, then dry DME (15 mL) was added and the flask sealed under argon. The reaction was then heated to 90° C. for 4 hours. Additional PdCl$_2$(dppf).DCM (0.245 g, 0.3 mmol) and pyridine-4-boronic acid (0.370 g, 3 mmol) were added, and heating was continued for another 14 h at 90° C. After cooling to room temperature, the crude reaction was filtered over a plug of Celite, concentrated, dissolved in DCM, and purified by column chromatography (gradient 0 to 75% EtOAc/hexanes) to afford the product. $^1$H NMR (400 MHz, CDCl$_3$) δ 8.73 (d, J=6.0 Hz, 2H), 8.02 (d, J=0.6 Hz, 1H), 7.87 (d, J=6.1 Hz, 2H), 7.53-7.32 (m, 2H), 4.15 (s, 3H).

Preparation of 1-methyl-3-(pyridin-4-yl)-5-(4,4,5,5-tetramethyl-1,3,2-dioxaborolan-2-yl)-1H-indazole: To a microwave tube was added 5-chloro-1-methyl-3-(pyridin-4-yl)-1H-indazole (171 mg, 0.7 mmol), bis(pinacolato)diboron (533 mg, 2.1 mmol), Pd(OAc)$_2$ (3.1 mg, 0.014 mmol), X-Phos (13 mg, 0.028 mmol), and KOAc (206 mg, 2.1 mmol). The tube was flushed with argon for 5 minutes, anhydrous dioxane (5 mL) was then added, and the reaction heated to 110° C. for 1 hour. After cooling to room temperature, the crude reaction was filtered over a plug of Celite, concentrated, and purified by column chromatography (gradient 0 to 70% EtOAc/hexanes) to afford the product. $^1$H NMR (400 MHz, CDCl$_3$) δ 8.73 (d, J=6.2 Hz, 2H), 8.53 (s, 1H), 8.05 (d, J=5.3 Hz, 2H), 7.89 (d, J=8.4 Hz, 1H), 7.53-7.39 (m, 1H), 4.14 (s, 3H), 1.39 (s, 12H).

Preparation of (S)-methyl 2-tert-butoxy-2-(7-(4-chlorophenyl)-5-methyl-2-(1-methyl-3-(pyridin-4-yl)-1H-indazol-5-yl)benzo[d]thiazol-6-yl)acetate: To a vial flushed with argon was added (S)-methyl 2-(2-bromo-7-(4-chlorophenyl)-5-methylbenzo[d]thiazol-6-yl)-2-tert-butoxyacetate (100 mg, 0.207 mmol), 1-methyl-3-(pyridin-4-yl)-5-(4,4,5,5-tetramethyl-1,3,2-dioxaborolan-2-yl)-1H-indazole (53 mg, 0.16 mmol), Pd(PPh$_3$)$_4$ (18 mg, 16 μmol), and K$_2$CO$_3$ (66 mg, 0.47 mmol). De-gassed dioxane (2 mL) and water (0.5 mL) were then added, and the reaction was heated to 100° C. for 1 h. After cooling to 23° C., the reaction was filtered over a plug of Celite, concentrated, and purified by column chromatography (gradient 0 to 75% EtOAc in hexanes) to give the product. $^1$H NMR (400 MHz, CDCl$_3$) δ 8.77 (d, J=5.9 Hz, 2H), 8.64 (s, 1H), 8.17 (d, J=8.8 Hz, 1H), 7.94 (d, J=5.9 Hz, 2H), 7.89 (s, 1H), 7.61-7.39 (m, 5H), 5.21 (s, 1H), 4.18 (s, 3H), 3.75 (s, 3H), 2.60 (s, 3H), 0.99 (s, 9H).

Preparation of (S)-2-tert-butoxy-2-(7-(4-chlorophenyl)-5-methyl-2-(1-methyl-3-(pyridin-4-yl)-1H-indazol-5-yl)benzo[d]thiazol-6-yl)acetic acid: In a vial was dissolved (S)- methyl 2-tert-butoxy-2-(7-(4-chlorophenyl)-5-methyl-2-(1-methyl-3-(2-methylpyridin-3-yl)-1H-indazol-5-yl)benzo[d]thiazol-6-yl)acetate (100 mg, 0.16 mmol) in THF (3 mL) and EtOH (1.5 mL). 1M NaOH (1.5 mL) was added, and the mixture was heated to 50° C. overnight. The reaction was cooled to 23° C., and filtered (0.45 micron teflon syringe filter). The filtrate was purified by reverse phase HPLC, eluting with 5-100% acetonitrile in H$_2$O with 0.1% TFA to give the desired product. LCMS-ESI+: calc'd for C$_{33}$H$_{30}$ClN$_4$O$_3$S: 597.2 (M+H$^+$); Found: 597.2 (M+H$^+$). $^1$H NMR (400 MHz, CD$_3$OD) δ 8.77 (d, J=6.1 Hz, 2H), 8.73 (s, 1H), 8.47 (d, J=6.3 Hz, 2H), 8.06 (d, J=8.9 Hz, 1H), 7.78-7.70 (m, 3H), 7.60 (dt, J=11.1, 7.5 Hz, 3H), 5.26 (s, 1H), 4.18 (s, 3H), 2.61 (s, 3H), 0.98 (s, 9H).

Example 80

Method BE: Preparation of (S)-2-tert-butoxy-2-(7-(4-chlorophenyl)-5-methyl-2-(1-methyl-3-(pyridin-2-yl)-1H-indazol-5-yl)benzo[d]thiazol-6-yl)acetic acid (2H)

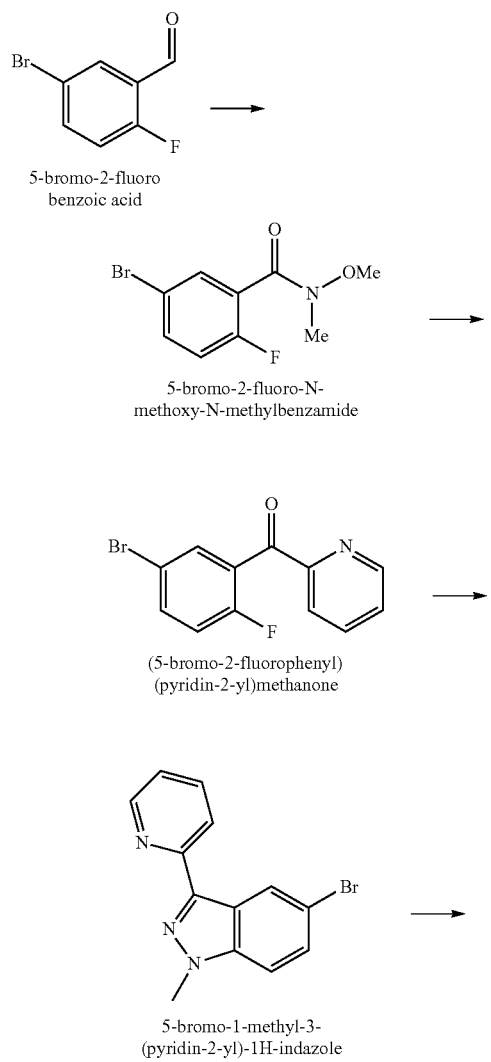

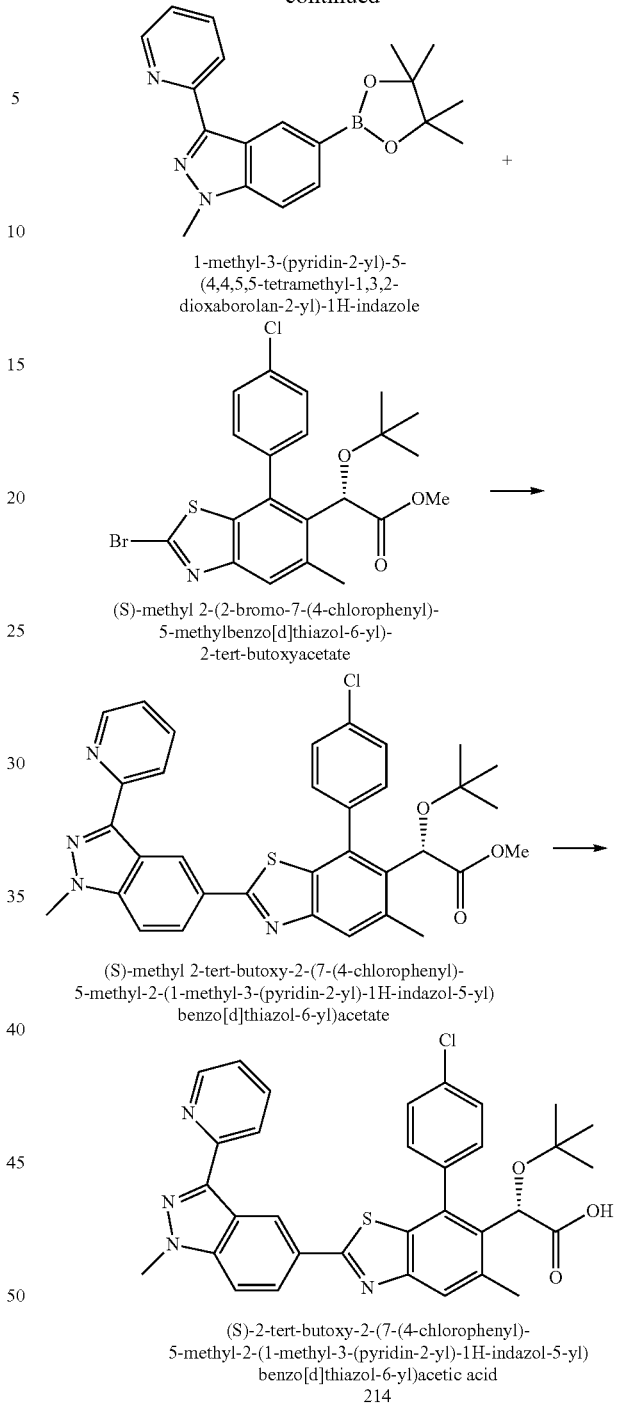

Preparation of 5-bromo-2-fluoro-N-methoxy-N-methylbenzamide: To a suspension of 5-bromo-2-fluorobenzoic acid (29 g, 132 mmol) in anhydrous DCM (500 mL) was added oxalyl chloride (16.8 mL, 199 mmol) and 5 drops of DMF. The suspension was stirred at room temperature for 2 hours. The solvent and excess oxalyl chloride were removed by rotary evaporation, and the residue was dissolved in anhydrous DCM (500 mL). With vigorous stirring, N,O-dimethylhydroxylamine hydrochloride (16.8 g, 172.3 mmol) was added in one portion, followed by triethylamine (80 mL, 574 mmol). The thick suspension was stirred for 1 hour at room temperature and then filtered. The organic layer was washed sequentially with 1M HCl, 1M NaOH, and water, dried over Na$_2$SO$_4$, and concentrated to afford the product. $^1$H NMR (400 MHz, CDCl$_3$) δ 7.55 (dd, J=5.7, 2.5 Hz, 1H), 7.50 (ddd, J=8.7, 4.6, 2.5 Hz, 1H), 7.00 (t, J=8.8 Hz, 1H), 3.56 (s, 3H), 3.34 (s, 3H).

Preparation of (5-bromo-2-fluorophenyl)(pyridin-2-yl)methanone: An oven-dried flask was cooled under argon, then charged with anhydrous THF (40 mL) and 2-bromopyridine (1.76 mL, 18 mmol). Isopropylmagnesium chloride in tetrahydrofuran (2.0 M in THF, 11 mL) was then added dropwise at room temperature. The mixture was then stirred at room temperature for 2 hours, then cooled to 0° C., whereupon a THF solution (5 mL) of 5-bromo-2-fluoro-N-methoxy-N-methylbenzamide (3.93 g, 15 mmol) was added. The mixture was then allowed to warm to room temperature and stirred for 2 hours. The reaction was quenched with saturated NH$_4$Cl, extracted with EtOAc, washed with 10% HCl, dried over Na$_2$SO$_4$, and purified by column chromatography (gradient 0 to 10% EtOAc/hexanes) to afford the product. $^1$H NMR (400 MHz, CDCl$_3$) δ 8.69 (d, J=4.6 Hz, 1H), 8.09 (d, J=7.8 Hz, 1H), 7.92 (t, J=7.7 Hz, 1H), 7.79 (dd, J=5.8, 1.4 Hz, 1H), 7.67-7.59 (m, 1H), 7.52 (dd, J=7.4, 4.9 Hz, 1H), 7.04 (t, J=9.0 Hz, 1H).

Preparation of 5-bromo-1-methyl-3-(pyridin-2-yl)-1H-indazole: A heavy wall pressure flask was charged with (5-bromo-2-fluorophenyl)(pyridin-2-yl)methanone (0.98 g, 3.5 mmol) and dioxane (10 mL). Methylhydrazine (0.4 mL, 7.7 mmol) was then added, and the mixture was heated to 100° C. for 15 hours. The crude mixture was concentrated, and purified by column chromatography (gradient 0 to 20% EtOAc in hexanes) to give the product. NMR (400 MHz, CDCl$_3$) δ 8.84 (s, 1H), 8.73 (d, J=4.8 Hz, 1H), 8.11 (d, J=8.0 Hz, 1H), 7.76 (t, J=7.7 Hz, 1H), 7.50 (d, J=8.8 Hz, 1H), 7.28 (d, J=8.8 Hz, 1H), 7.24 (d, J=7.3 Hz, 1H), 4.12 (s, 3H).

Preparation of 1-methyl-3-(pyridin-2-yl)-5-(4,4,5,5-tetramethyl-1,3,2-dioxaborolan-2-yl)-1H-indazole: To a vial flushed with argon was added 5-bromo-1-methyl-3-(pyridin-2-yl)-1H-indazole (576 mg, 2 mmol), PdCl$_2$(dppf).DCM (163 mg, 0.2 mmol), bis(pinacolato)diboron (559 mg, 2.2 mmol), and KOAc (589 mg, 6 mmol). Anhydrous dioxane (10 mL) was added, and the mixture was heated to 90° C. for 3 hours. After cooling to room temperature, the crude reaction was filtered over a plug of Celite, concentrated, and purified by column chromatography (gradient 0 to 25% EtOAc in hexanes) to give the product. $^1$H NMR (400 MHz, CDCl$_3$) δ 9.01 (s, 1H), 8.79 (d, J=4.8 Hz, 1H), 8.12 (d, J=8.0 Hz, 1H), 7.85 (dd, J=8.5, 0.6 Hz, 1H), 7.77 (td, J=7.7, 1.8 Hz, 1H), 7.40 (d, J=8.5 Hz, 1H), 7.25-7.22 (m, 1H), 4.15 (s, 3H), 1.38 (s, 12H).

Preparation of (S)-methyl 2-tert-butoxy-2-(7-(4-chlorophenyl)-5-methyl-2-(1-methyl-3-(pyridin-2-yl)-1H-indazol-5-yl)benzo[d]thiazol-6-yl)acetate: To a vial flushed with argon was added (S)-methyl 2-(2-bromo-7-(4-chlorophenyl)-5-methylbenzo[d]thiazol-6-yl)-2-tert-butoxyacetate (100 mg, 0.207 mmol), 1-methyl-3-(pyridin-2-yl)-5-(4,4,5,5-tetramethyl-1,3,2-dioxaborolan-2-yl)-1H-indazole (83.3 mg, 0.25 mmol), Pd(PPh$_3$)$_4$ (24 mg, 21 mmol), and K$_2$CO$_3$ (86 mg, 0.62 mmol). De-gassed dioxane (2 mL) and water (0.5 mL) were then added, and the reaction was heated to 100° C. for 1 h. After cooling to rt, the reaction was filtered over a plug of Celite, concentrated, and purified by column chromatography (gradient 0 to 40% EtOAc in hexanes) to give the product. $^1$H NMR (400 MHz, CDCl$_3$) δ 9.21-9.15 (m, 1H), 8.84-8.77 (m, 1H), 8.25 (dd, J=8.8, 1.7 Hz, 1H), 8.14 (d, J=8.0 Hz, 1H), 7.88 (d, J=8.1 Hz, 1H), 7.78 (td, J=7.7, 1.7 Hz, 1H), 7.59-7.49 (m, 4H), 7.47 (d, J=8.9 Hz, 1H), 7.29-7.24 (m, 1H), 5.21 (s, 1H), 4.17 (s, 3H), 3.75 (s, 3H), 2.59 (s, 3H), 0.98 (s, 9H).

Preparation of (S)-2-tert-butoxy-2-(7-(4-chlorophenyl)-5-methyl-2-(1-methyl-3-(pyridin-2-yl)-1H-indazol-5-yl)benzo[d]thiazol-6-yl)acetic acid: To a vial was dissolved (S)-methyl 2-tert-butoxy-2-(7-(4-chlorophenyl)-5-methyl-2-(1-methyl-3-(pyridin-2-yl)-1H-indazol-5-yl)benzo[d]thiazol-6-yl)acetate (122 mg, 0.2 mmol) in THF (3 mL) and EtOH (1.5 mL). 1M NaOH (1.5 mL) was added, and the mixture was heated to 50° C. overnight. The reaction was cooled to rt, and filtered (0.45 micron teflon syringe filter). The filtrate was purified by reverse phase HPLC, eluting with 5-100% acetonitrile in H$_2$O with 0.1% TFA to give the desired product as a bright yellow powder. LCMS-ESI$^+$: calc'd for C$_{33}$H$_{30}$ClN$_4$O$_3$S: 597.1 (M+H$^+$); Found: 597.2 (M+H$^+$). $^1$H NMR (400 MHz, CD$_3$OD) δ 8.79 (s, 1H), 8.66 (d, J=4.7 Hz, 1H), 8.33 (d, J=8.1 Hz, 1H), 8.23 (dd, J=11.1, 4.5 Hz, 1H), 8.02 (dd, J=8.9, 1.3 Hz, 1H), 7.76 (s, 1H), 7.75-7.68 (m, 1H), 7.65-7.53 (m, 5H), 5.26 (s, 1H), 4.14 (s, 3H), 2.61 (s, 3H), 0.98 (s, 9H).

Example 81

Method BF: Preparation of (S)-2-tert-butoxy-2-(7-(4-chlorophenyl)-2-(2-(1,7-dimethyl-1H-indazol-5-yl)pyridin-4-yl)-5-methylbenzo[d]thiazol-6-yl)acetic acid (215) and (S)-2-tert-butoxy-2-(7-(4-chlorophenyl)-2-(2-(2,7-dimethyl-2H-indazol-5-yl)pyridin-4-yl)-5-methylbenzo[d]thiazol-6-yl)acetic acid (216)

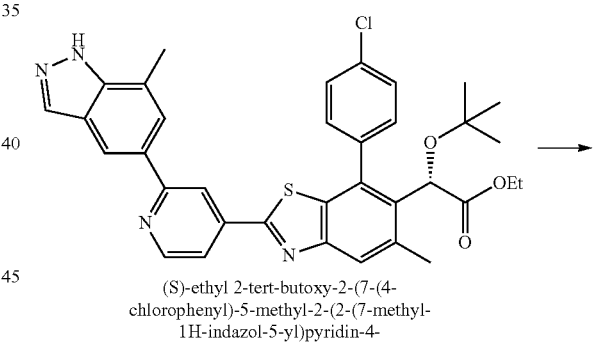

(S)-ethyl 2-tert-butoxy-2-(7-(4-chlorophenyl)-5-methyl-2-(2-(7-methyl-1H-indazol-5-yl)pyridin-4-yl)benzo[d]thiazol-6-yl)acetate

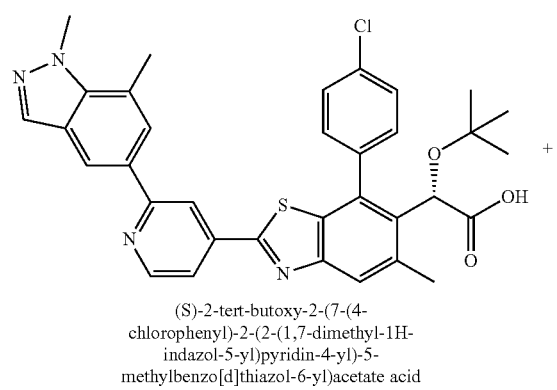

(S)-2-tert-butoxy-2-(7-(4-chlorophenyl)-2-(1,7-dimethyl-1H-indazol-5-yl)pyridin-4-yl)-5-methylbenzo[d]thiazol-6-yl)acetate acid

215

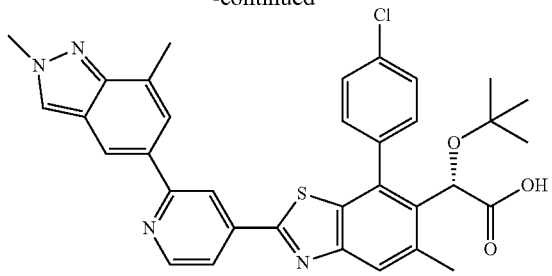

(S)-2-tert-butoxy-2-(7-(4-chlorophenyl)-2-(2-(2,7-dimethyl-2H-indazol-5-yl)pyridin-4-yl)-5-methylbenzo[d]thiazol-6-yl)acetate acid

216

Preparation of (S)-2-tert-butoxy-2-(7-(4-chlorophenyl)-2-(2-(1,7-dimethyl-1H-indazol-5-yl)pyridin-4-yl)-5-methylbenzo[d]thiazol-6-yl)acetic acid and (S)-2-tert-butoxy-2-(7-(4-chlorophenyl)-2-(2-(2,7-dimethyl-2H-indazol-5-yl)pyridin-4-yl)-5-methylbenzo[d]thiazol-6-yl)acetic acid: To a solution of (S)-ethyl 2-tert-butoxy-2-(7-(4-chlorophenyl)-5-methyl-2-(2-(7-methyl-1H-indazol-5-yl)pyridin-4-yl)benzo[d]thiazol-6-yl)acetate, prepared according to Method F (100 mg, 0.16 mmol) in DMF (2 mL) was added sodium hydride (60%, 7.7 mg, 0.19 mmol). After 30 min, iodomethane (~100 µL) was added. After 2 h, a saturated solution of NH$_4$Cl was added and EtOAc. The layers were separated, and the organic layer was washed with brine. The organic layer was dried, filtered, and concentrated in vacuo. MeOH (2 mL) and THF (2 mL) were added followed by sodium hydroxide solution (2 M aqueous, 500 µL). The reaction mixture was stirred at 50° C. for 4 h. The mixture was purified using reverse phase HPLC, eluting by 5-100% acetonitrile in H$_2$O with 0.1% TFA to give the products.

(S)-2-tert-butoxy-2-(7-(4-chlorophenyl)-2-(2-(1,7-dimethyl-1H-indazol-5-yl)pyridin-4-yl)-5-methylbenzo[d]thiazol-6-yl)acetic acid LCMS-ESI$^+$: calc'd for C$_{34}$H$_{32}$ClN$_4$O$_3$S: 611.2 (M+H$^+$); Found: 611.2 (M+H$^+$); $^1$H NMR (400 MHz, CD$_3$OD): δ 8.63 (d, J=6.0 Hz, 1H), 8.48 (s, 1H), 8.15 (s, 1H), 8.01 (m, 2H), 7.87 (s, 1H), 7.67 (s, 1H), 7.61 (m, 1H), 7.52 (m, 3H), 5.20 (s, 1H), 4.23 (s, 3H), 2.77 (s, 3H), 2.55 (s, 3H), 0.89 (s, 9H).

(S)-2-tert-butoxy-2-(7-(4-chlorophenyl)-2-(2-(2,7-dimethyl-2H-indazol-5-yl)pyridin-4-yl)-5-methylbenzo[d]thiazol-6-yl)acetic acid: LCMS-ESI$^+$: calc'd for C$_{34}$H$_{32}$ClN$_4$O$_3$S: 611.2 (M+H$^+$); Found: 611.2 (M+H$^+$); $^1$H NMR (400 MHz, CD$_3$OD): δ 8.64 (d, J=5.6 Hz, 1H), 8.56 (s, 1H), 8.31 (s, 1H), 8.18 (s, 1H), 8.12 (dd, J=5.6, 1.6 Hz, 1H), 7.90 (s, 1H), 7.61 (m, 1H), 7.53 (m, 4H), 5.20 (s, 1H), 4.17 (s, 3H), 2.57 (s, 3H), 2.56 (s, 3H), 0.89 (s, 9H).

Example 82

Method BG: Preparation of (S)-2-tert-butoxy-2-(7-(4-chlorophenyl)-2-(1,2-dimethyl-1H-benzo[d]imidazol-5-yl)-5-methylbenzo[d]thiazol-6-yl)acetic acid (217)

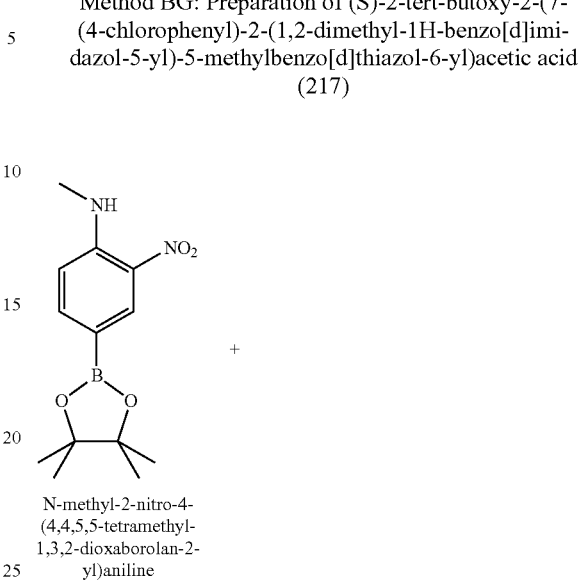

N-methyl-2-nitro-4-(4,4,5,5-tetramethyl-1,3,2-dioxaborolan-2-yl)aniline

+

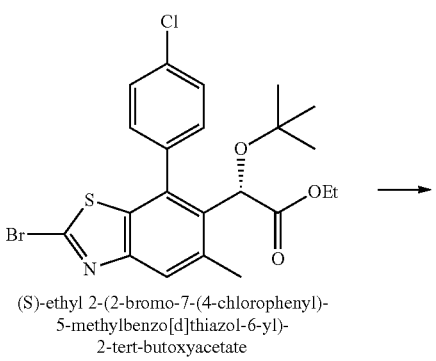

(S)-ethyl 2-(2-bromo-7-(4-chlorophenyl)-5-methylbenzo[d]thiazol-6-yl)-2-tert-butoxyacetate

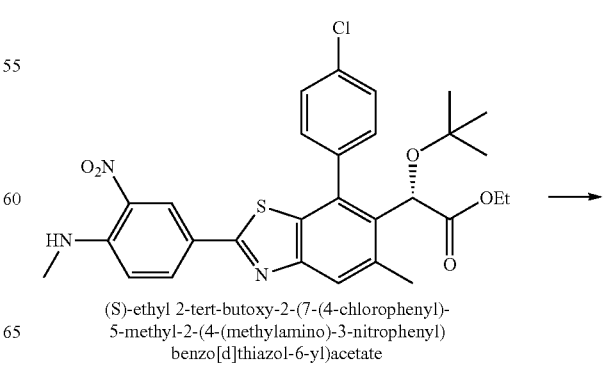

(S)-ethyl 2-tert-butoxy-2-(7-(4-chlorophenyl)-5-methyl-2-(4-(methylamino)-3-nitrophenyl)benzo[d]thiazol-6-yl)acetate

→

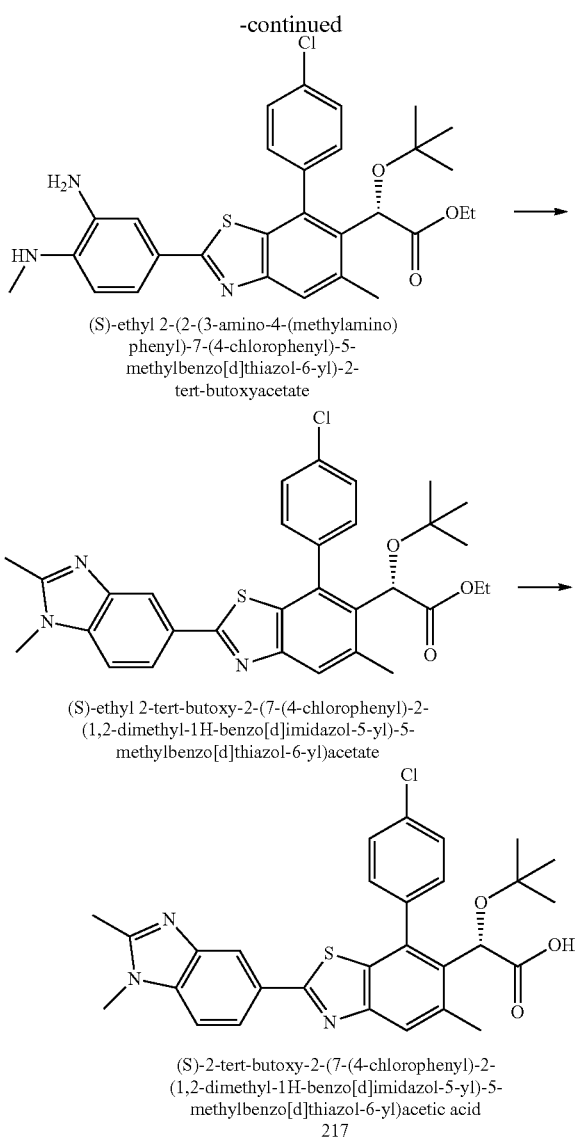

(S)-ethyl 2-(2-(3-amino-4-(methylamino)
phenyl)-7-(4-chlorophenyl)-5-
methylbenzo[d]thiazol-6-yl)-2-
tert-butoxyacetate (S)-ethyl 2-tert-butoxy-2-(7-(4-chlorophenyl)-2-
(1,2-dimethyl-1H-benzo[d]imidazol-5-yl)-5-
methylbenzo[d]thiazol-6-yl)acetate (S)-2-tert-butoxy-2-(7-(4-chlorophenyl)-2-
(1,2-dimethyl-1H-benzo[d]imidazol-5-yl)-5-
methylbenzo[d]thiazol-6-yl)acetic acid
217

Preparation of (S)-ethyl 2-tert-butoxy-2-(7-(4-chlorophenyl)-5-methyl-2-(4-(methylamino)-3-nitrophenyl)benzo[d]thiazol-6-yl)acetate: To a solution of (S)-ethyl 2-(2-bromo-7-(4-chlorophenyl)-5-methylbenzo[d]thiazol-6-yl)-2-tert-butoxyacetate (497 mg, 1.00 mmol) in 1,4-dioxane (6 mL) was added N-methyl-2-nitro-4-(4,4,5,5-tetramethyl-1,3,2-dioxaborolan-2-yl)aniline (417 mg, 1.50 mmol), Pd(PPh$_3$)$_4$ (58 mg, 0.05 mmol) and potassium carbonate solution (2 M aqueous, 1.5 mL, 3.0 mmol). The reaction mixture was stirred at 105° C. for 3 h and was then cooled to rt. EtOAc and H$_2$O were added. The layers were separated, and the organic layer was dried, filtered, and concentrated in vacuo. The crude mixture was purified by CombiFlash (EtOAc/Hex) to give (S)-ethyl 2-tert-butoxy-2-(7-(4-chlorophenyl)-5-methyl-2-(4-(methylamino)-3-nitrophenyl)benzo[d]thiazol-6-yl)acetate. $^1$H NMR (400 MHz, CD$_3$OD): δ 8.71 (s, 1H), 8.40 (m, 1H), 8.05 (dd, J=8.8, 2.4 Hz, 1H), 7.73 (s, 1H), 7.51-7.58 (m, 4H), 7.06 (d, J=8.8 Hz, 1H), 5.22 (s, 1H), 4.22 (m, 2H), 3.05 (d, J=4.8 Hz, 3H), 2.55 (s, 3H), 1.22 (t, J=7 Hz, 3H), 0.97 (s, 9H).

Preparation of (S)-ethyl 2-(2-(3-amino-4-(methylamino)phenyl)-7-(4-chlorophenyl)-5-methylbenzo[d]thiazol-6-yl)-2-tert-butoxyacetate: To a solution of (S)-ethyl 2-tert-butoxy-2-(7-(4-chlorophenyl)-5-methyl-2-(4-(methylamino)-3-nitrophenyl)benzo[d]thiazol-6-yl)acetate (510 mg) in EtOH (4 mL) and EtOAc (2 mL) was added 5% Pt/C (150 mg). The reaction mixture was flushed with hydrogen gas and stirred under hydrogen atmosphere (using a balloon) for 1.5 h. The mixture was filtered through celite and concentrated in vacuo and (S)-ethyl 2-(2-(3-amino-4-(methylamino)phenyl)-7-(4-chlorophenyl)-5-methylbenzo[d]thiazol-6-yl)-2-tert-butoxyacetate was used without further purification. LCMS-ESI$^+$: calc'd for C$_{29}$H$_{33}$ClN$_3$O$_3$S: 538.2 (M+H$^+$); Found: 538.2 (M+H$^+$).

Preparation of (S)-ethyl 2-tert-butoxy-2-(7-(4-chlorophenyl)-2-(1,2-dimethyl-1H-benzo[d]imidazol-5-yl)-5-methylbenzo[d]thiazol-6-yl)acetate: To a solution of (S)-ethyl 2-(2-(3-amino-4-(methylamino)phenyl)-7-(4-chlorophenyl)-5-methylbenzo[d]thiazol-6-yl)-2-tert-butoxyacetate (40 mg, 0.07 mmol) in acetic acid (2 mL) was added triethyl orthoacetate (~200 μL). After 30 min, MeOH (20 mL) was added and the mixture was concentrated in vacuo and (S)-ethyl 2-tert-butoxy-2-(7-(4-chlorophenyl)-2-(1,2-dimethyl-1H-benzo[d]imidazol-5-yl)-5-methylbenzo[d]thiazol-6-yl)acetate was used without further purification. LCMS-ESI$^+$: calc'd for C$_{31}$H$_{33}$ClN$_3$O$_3$S: 562.2 (M+H$^+$); Found: 562.2 (M+H$^+$).

Preparation of (S)-2-tert-butoxy-2-(7-(4-chlorophenyl)-2-(1,2-dimethyl-1H-benzo[d]imidazol-5-yl)-5-methylbenzo[d]thiazol-6-yl)acetic acid: To a solution of (S)-ethyl 2-tert-butoxy-2-(7-(4-chlorophenyl)-2-(1,2-dimethyl-1H-benzo[d]imidazol-5-yl)-5-methylbenzo[d]thiazol-6-yl)acetate in MeOH (2 mL) and THF (2 mL) was added a sodium hydroxide solution (2 M aqueous, 500 μL). The reaction mixture was stirred at 50° C. for 4 h. The mixture was purified using reverse phase HPLC, eluting by 5-100% acetonitrile in H$_2$O with 0.1% TFA to give the product. LCMS-ESI$^+$: calc'd for C$_{29}$H$_{29}$ClN$_3$O$_3$S: 534.2 (M+H$^+$); Found: 534.2 (M+H$^+$); $^1$H NMR (400 MHz, CD$_3$OD): δ 8.38 (s, 1H), 8.23 (d, J=8.8 Hz, 1H), 7.93 (d, J=8.8 Hz, 1H), 7.87 (s, 1H), 7.69 (m, 1H), 7.60 (m, 3H), 5.26 (s, 1H), 4.00 (s, 3H), 2.87 (s, 3H), 2.62 (s, 3H), 0.97 (s, 9H).

Example 83

Preparation of (S)-2-tert-butoxy-2-(7-(4-chlorophenyl)-5-methyl-2-(2-morpholinopyridin-4-yl)benzo[d]thiazol-6-yl)acetic acid (218)

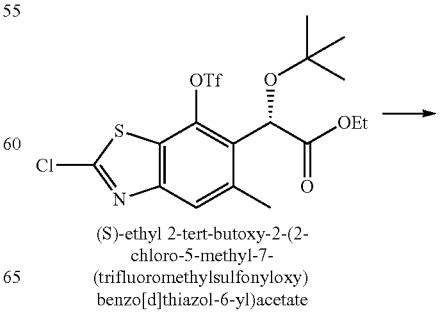

(S)-ethyl 2-tert-butoxy-2-(2-
chloro-5-methyl-7-
(trifluoromethylsulfonyloxy)
benzo[d]thiazol-6-yl)acetate

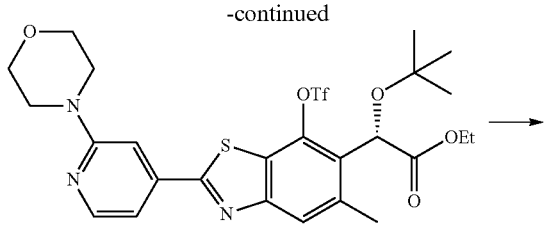

(S)-ethyl 2-tert-butoxy-2-(5-methyl-2-(2-morpholinopyridin-4-yl)-7-(trifluoromethylsulfonyloxy)benzo[d]thiazol-6-yl)acetate

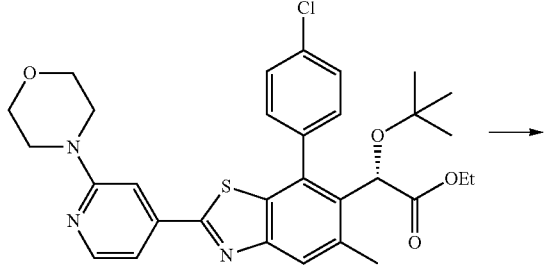

(S)-ethyl 2-tert-butoxy-2-(7-(4-chlorophenyl)-5-methyl-2-(2-morpholinopyridin-4-yl)benzo[d]thiazol-6-yl)acetate

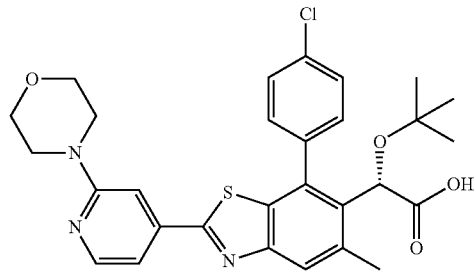

(S)-2-tert-butoxy-2-(7-(4-chlorophenyl)-5-methyl-2-(2-morpholinopyridin-4-yl)benzo[d]thiazol-6-yl)acetate acid

218

Preparation of (S)-ethyl 2-tert-butoxy-2-(5-methyl-2-(2-(4-methylpiperazin-1-yl)pyridin-4-yl)-7-(trifluoromethylsulfonyloxy)benzo[d]thiazol-6-yl)acetate: A mixture of (S)-ethyl 2-tert-butoxy-2-(2-chloro-5-methyl-7-(trifluoromethylsulfonyloxy)benzo[d]thiazol-6-yl)acetate (16 mg, 0.0327 mmol), 2-morpholinopyridine-4-boronic acid (10 mg, 0.049 mmol), $PdCl_2(dppf)$ (2.7 mg, 0.00327 mmol) and powdered potassium carbonate (18 mg, 0.131 mmol) in anhydrous dimethoxyethane (0.5 mL) was sparged with nitrogen for 10 minutes, then heated overnight at 80° C. Reaction mixture was diluted with ethyl acetate, washed with brine, dried ($MgSO_4$), filtered, concentrated and purified by CombiFlash (0 to 60% EtOAc/Hex) to give product. LCMS-ESI$^+$: calc'd for $C_{26}H_{31}F_3N_3O_7S_2$: 618.2 (M+H$^+$); Found: 618.1 (M+H$^+$).

Preparation of (S)-ethyl 2-tert-butoxy-2-(7-(4-chlorophenyl)-5-methyl-2-(2-morpholinopyridin-4-yl)benzo[d]thiazol-6-yl)acetate: A mixture of (S)-ethyl 2-tert-butoxy-2-(5-methyl-2-(2-(4-methylpiperazin-1-yl)pyridin-4-yl)-7-(trifluoromethylsulfonyloxy)benzo[d]thiazol-6-yl)acetate (20 mg, 0.0324 mmol), 4-chlorophenyboronic acid (10 mg, 0.063 mmol), SPhos precatalyst (3.3 mg, 0.0049 mmol) and powdered potassium carbonate (18 mg, 0.129 mmol) in anhydrous dimethoxyethane (0.75 mL) was sparged with nitrogen for 5 minutes, then heated in microwave at 120° C. for 1.5 h. Added more 4-chlorophenyboronic acid and SPhos precatalyst (3.3 mg, 0.0049 mmol) and continued reaction. Reaction mixture was diluted with ethyl acetate, washed with brine, dried ($MgSO_4$), filtered, concentrated and purified by CombiFlash (0 to 40% EtOAc/Hex) to give product. LCMS-ESI$^+$: calc'd for $C_{31}H_{35}ClN_3O_4S$: 580.2 (M+H$^+$); Found: 580.3 (M+H$^+$).

Preparation of (S)-2-tert-butoxy-2-(7-(4-chlorophenyl)-5-methyl-2-(2-morpholinopyridin-4-yl)benzo[d]thiazol-6-yl)acetic acid: A solution of (S)-ethyl 2-tert-butoxy-2-(7-(4-chlorophenyl)-5-methyl-2-(2-morpholinopyridin-4-yl)benzo[d]thiazol-6-yl)acetate (4.2 mg, 0.00724 mmol) 5M NaOH (29 µL) in methanol (0.2 mL) and THF (1.0 mL) was stirred at 40° C. overnight. Acetic acid (1 drop) and DMF (0.3 mL) were added and mixture concentrated to ~0.5 mL, diluted with DMF/$H_2O$, filtered and purified by Gilson HPLC (Gemini, 5 to 100% ACN/$H_2O$+0.1% TFA) to give product after lyophilization. LCMS-ESI$^+$: calc'd for $C_{29}H_{31}ClN_3O_4S$: 552.2 (M+H$^+$); Found: 552.3 (M+H$^+$); $^1$H NMR (400 MHz, $CD_3OD$) δ 8.12 (d, J=6.2 Hz, 1H), 7.94 (s, 1H), 7.69 (s, 1H), 7.67 (d, J=2.1 Hz, 1H), 7.61 (d, J=2.1 Hz, 1H), 7.59 (dd, J=4.2, 2.1 Hz, 2H), 7.47 (dd, J=6.2, 1.5 Hz, 1H), 5.26 (s, 1H), 3.91-3.79 (m, 4H), 3.74-3.62 (m, 4H), 2.63 (s, 3H), 0.97 (s, 9H).

Example 84

Preparation of (S)-2-tert-butoxy-2-(7-(4-chlorophenyl)-5-methyl-2-(2-(4-methylpiperazin-1-yl)pyridin-4-yl)benzo[d]thiazol-6-yl)acetic acid Preparation of (S)-2-tert-butoxy-2-(7-(4-chlorophenyl)-5-methyl-2-(2-(4-methylpiperazin-1-yl)pyridin-4-yl)benzo[d]thiazol-6-yl)acetic acid (219)

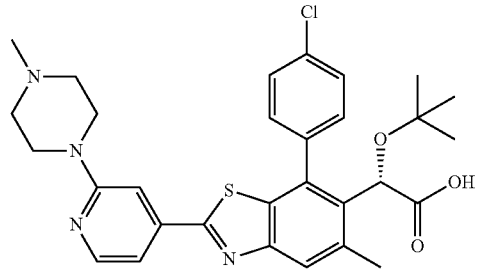

219

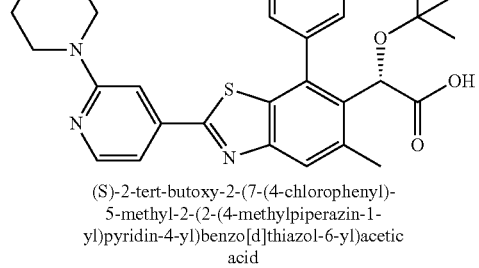

(S)-2-tert-butoxy-2-(7-(4-chlorophenyl)-5-methyl-2-(2-(4-methylpiperazin-1-yl)pyridin-4-yl)benzo[d]thiazol-6-yl)acetic acid Preparation of (S)-2-tert-butoxy-2-(7-(4-chlorophenyl)-5-methyl-2-(2-(4-methylpiperazin-1-yl)pyridin-4-yl)benzo[d]thiazol-6-yl)acetic acid: Prepared in a manner similar to (S)-2-tert-butoxy-2-(7-(4-chlorophenyl)-5-methyl-2-(2-morpholinopyridin-4-yl)benzo[d]thiazol-6-yl)acetic acid except 2-(4-methylpiperazino)pyridine-4-pyridine boronic acid using instead of 2-morpholinopyridine-4-boronic acid. LCMS-ESI$^+$: calc'd for $C_{30}H_{34}ClN_3O_3S$: 565.2 (M+H$^+$); Found: 565.3 (M+H$^+$); $^1$H NMR (400 MHz, $CD_3OD$) δ 8.30 (d, J=4.8 Hz, 1H), 7.89 (s, 1H), 7.68 (d, J=8.9 Hz, 1H), 7.64-7.47 (m, 4H), 7.34 (d, J=5.1 Hz, 1H), 5.26 (s, 1H), 4.77-4.38 (m, 2H), 3.78-3.04 (m, 2H), 2.97 (s, 3H), 2.62 (s, 3H), 0.97 (s, 9H).

Example 85

Preparation of (S)-2-tert-butoxy-2-(7-(4-chlorophenyl)-2-(2-(4-ethylpiperazin-1-yl)pyridin-4-yl)-5-methylbenzo[d]thiazol-6-yl)acetic acid (220) and (S)-2-tert-butoxy-2-(7-(4-chlorophenyl)-2-(2-(4-isopropylpiperazin-1-yl)pyridin-4-yl)-5-methylbenzo[d]thiazol-6-yl)acetic acid (221)

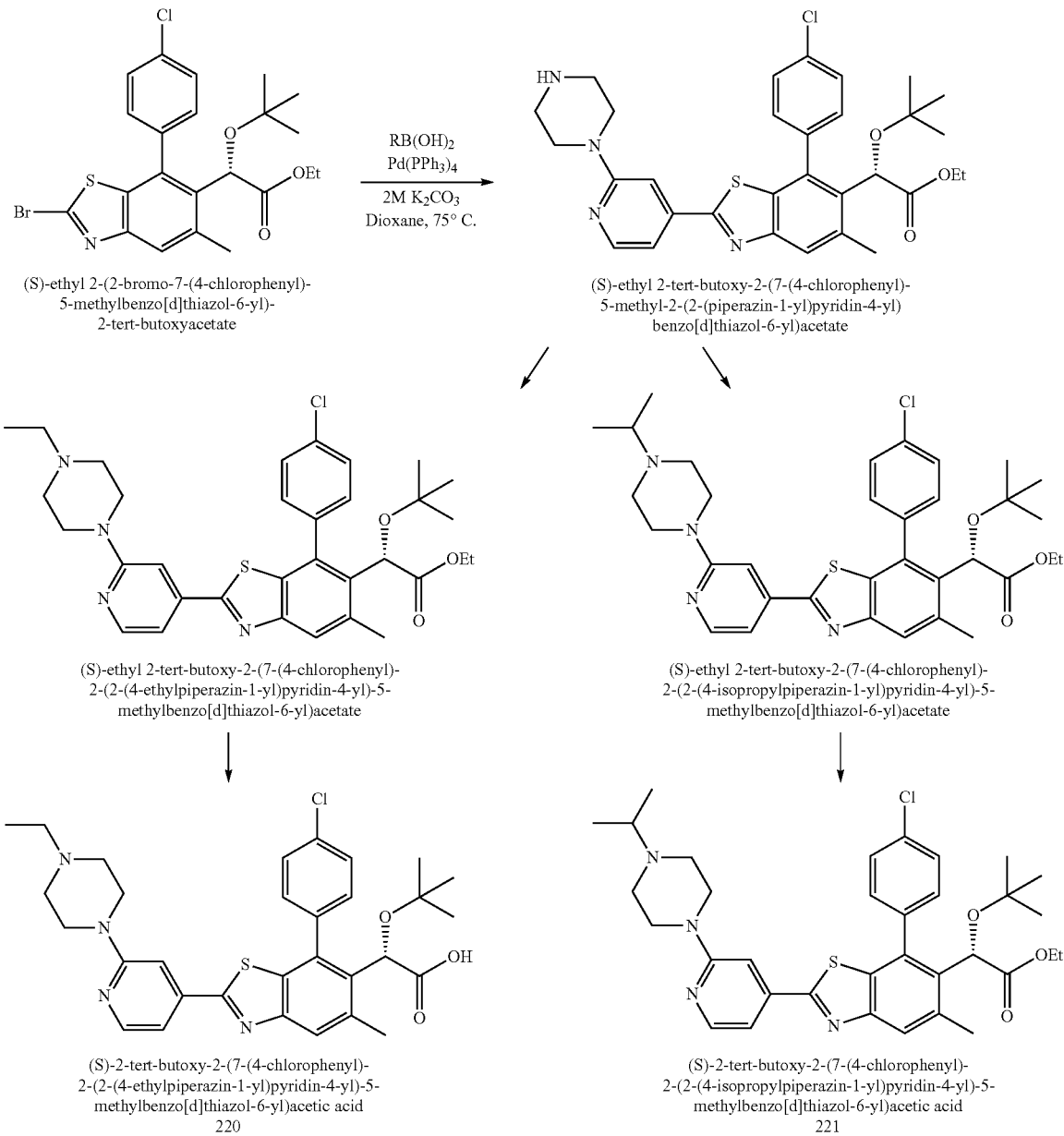

Preparation of (S)-ethyl 2-tert-butoxy-2-(7-(4-chlorophenyl)-5-methyl-2-(2-(piperazin-1-yl)pyridin-4-yl)benzo[d]thiazol-6-yl)acetate: A mixture of (S)-ethyl 2-(2-bromo-7-(4-chlorophenyl)-5-methylbenzo[d]thiazol-6-yl)-2-tert-butoxyacetate (106.5 mg, 0.214 mmol), 2-(1-piperazinyl)-pyridine-4-boronic acid, pinacol ester (93 mg, 0.322 mmol), Pd(PPh$_3$)$_4$ (25 mg, 0.02147 mmol) and 2M potassium carbonate (0.321 mL, 0.642 mmol) in anhydrous dioxane (1.0 mL) was sparged with nitrogen for 5 minutes, then heated in microwave for 1 h at 100° C. Reaction mixture was diluted with ethyl acetate, washed with brine, dried (MgSO$_4$), filtered, concentrated and used in next step without further purification. LCMS-ESI$^+$: calc'd for $C_{36}H_{36}ClN_4O_3S$: 579.2 (M+H$^+$); Found: 579.1 (M+H$^+$).

Preparation of (S)-ethyl 2-tert-butoxy-2-(7-(4-chlorophenyl)-2-(2-(4-ethylpiperazin-1-yl)pyridin-4-yl)-5-methylbenzo[d]thiazol-6-yl)acetate: To a solution of crude (S)-ethyl 2-tert-butoxy-2-(7-(4-chlorophenyl)-5-methyl-2-(2-(piperazin-1-yl)pyridin-4-yl)benzo[d]thiazol-6-yl)acetate (~0.144 mmol) in DMF (1.5 mL) was added cesium carbonate (0.094 g, 0.288 mmol), followed by iodoethane (12.6 µL, 0.158 mmol). Reaction mixture was stirred for 1 h, then more iodoethane (5 µL) was added and reaction mixture stirred for 2 h. LC/MS showed incomplete reaction, so more iodoethane (5 µL) was added and reaction mixture stirred overnight. Reaction mixture was diluted with ethyl acetate, washed with 5% lithium chloride solution (2×), brine, dried (MgSO₄), filtered, concentrated and purified by CombiFlash (0 to 10% MeOH/CH₂Cl₂) to give product. LCMS-ESI⁺: calc'd for C₃₃H₄₀ClN₄O₃S: 607.2 (M+H⁺); Found: 607.3 (M+H⁺).

Preparation of (S)-2-tert-butoxy-2-(7-(4-chlorophenyl)-2-(2-(4-ethylpiperazin-1-yl)pyridin-4-yl)-5-methylbenzo[d]thiazol-6-yl)acetic acid: A solution of (S)-ethyl 2-tert-butoxy-2-(7-(4-chlorophenyl)-2-(2-(4-ethylpiperazin-1-yl)pyridin-4-yl)-5-methylbenzo[d]thiazol-6-yl)acetate (26.7 mg, 0.044 mmol), 5M NaOH (176 µL, 0.879 mmol)) in methanol (0.2 mL) and THF (1.0 mL) was stirred at 45° C. for 2 h, then stirred overnight at rt. Acetic acid (1 drop) and DMF (0.3 mL) were added and mixture concentrated to ~0.3 mL, diluted with methanol, filtered and purified by Gilson HPLC (Gemini, 5 to 100% ACN/H₂O+0.1% TFA) to give product after lyophilization. LCMS-ESI⁺: calc'd for C₃₁H₃₆ClN₄O₃S: 579.2 (M+H⁺); Found: 579.3 (M+H⁺); ¹H NMR (400 MHz, CD₃OD) δ 8.27 (d, J=5.4 Hz, 1H), 7.84 (s, 1H), 7.66 (dd, J=8.5, 1.7 Hz, 1H), 7.63-7.52 (m, 3H), 7.50 (s, 1H), 7.32 (dd, J=5.4, 1.3 Hz, 1H), 5.25 (s, 1H), 4.81-4.18 (m, 2H), 4.81-4.18 (m, 2H), 3.7-2.99 (m, 4H), 3.27 (dd, J=14.8, 7.5 Hz, 3H), 2.59 (s, 3H), 1.39 (t, J=7.3 Hz, 3H), 0.96 (s, 9H).

Preparation of (S)-ethyl 2-tert-butoxy-2-(7-(4-chlorophenyl)-2-(2-(4-isopropylpiperazin-1-yl)pyridin-4-yl)-5-methylbenzo[d]thiazol-6-yl)acetate: To a solution of crude (S)-ethyl 2-tert-butoxy-2-(7-(4-chlorophenyl)-5-methyl-2-(2-(piperazin-1-yl)pyridin-4-yl)benzo[d]thiazol-6-yl)acetate (0.144 mmol) in ethanol (2.0 mL) was added acetone (0.21 mL) and acetic acid (12 µL, 0.21 mmol) at 0° C. Reaction mixture was stirred for 15 minutes, then sodium cyanoborohydride (10 mg, 0.158 mmol) was added and reaction mixture was warmed to room temperature over 2 h. Reaction mixture was diluted with ethyl acetate, washed with saturated sodium bicarbonate/brine, dried (MgSO₄), filtered, concentrated and purified by CombiFlash (0 to 10% MeOH/CH₂Cl₂) to give product. LCMS-ESI⁺: calc'd for C₃₄H₄₂ClN₄O₃S: 622.2 (M+H⁺); Found: 621.3 (M+H⁺).

Preparation of (S)-2-tert-butoxy-2-(7-(4-chlorophenyl)-2-(2-(4-isopropylpiperazin-1-yl)pyridin-4-yl)-5-methylbenzo[d]thiazol-6-yl)acetic acid: A solution of (S)-ethyl 2-tert-butoxy-2-(7-(4-chlorophenyl)-2-(2-(4-isopropylpiperazin-1-yl)pyridin-4-yl)-5-methylbenzo[d]thiazol-6-yl)acetate (36.7 mg, 0.059 mmol), 5M NaOH (236 µL, 1.18 mmol)) in methanol (0.2 mL) and THF (1.0 mL) was stirred at 45° C. for 2 h, then stirred overnight at rt. Acetic acid (1 drop) and DMF (0.3 mL) were added and mixture concentrated to ~0.3 mL, diluted with DMF/methanol, filtered and purified by Gilson HPLC (Gemini, 5 to 100% ACN/H₂O+0.1% TFA) to give product after lyophilization. LCMS-ESI⁺: calc'd for C₃₂H₃₈ClN₄O₃S: 593.2 (M+H⁺); Found: 593.3 (M+H⁺); ¹H NMR (400 MHz, CD₃OD) δ 8.26 (d, J=5.5 Hz, 1H), 7.84 (s, 1H), 7.66 (dd, J=8.5, 1.8 Hz, 1H), 7.61-7.48 (m, 4H), 7.33 (dd, J=5.4, 1.3 Hz, 1H), 5.24 (s, 1H), 4.77-4.40 (m, J=33.2 Hz, 2H), 3.58 (td, J=13.2, 6.6 Hz, 1H), 3.50-3.14 (m, 4H), 2.58 (s, 3H), 1.41 (d, J=6.7 Hz, 6H), 0.95 (s, 9H).

Example 86

Preparation of (S)-2-tert-butoxy-2-(7-(4-chlorophenyl)-5-methyl-2-(2-(3-(trifluoromethyl)-5,6-dihydro-[1,2,4]triazolo[4,3-a]pyrazin-7(8H)-yl)pyridin-4-yl)benzo[d]thiazol-6-yl)acetic acid (222)

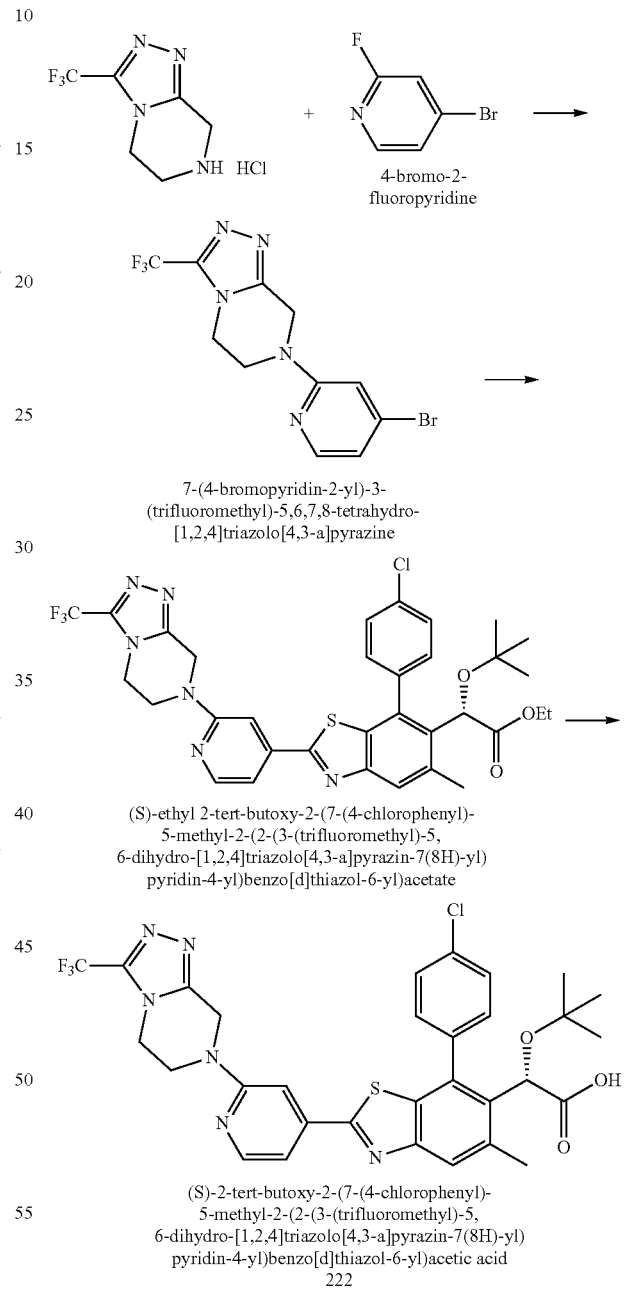

Preparation of 7-(4-bromopyridin-2-yl)-3-(trifluoromethyl)-5,6,7,8-tetrahydro-[1,2,4]triazolo[4,3-a]pyrazine: A mixture of 4-bromo-2-fluoropyridine (0.216 mL, 2.1 mmol), 3-(trifluoromethyl)-5,6,7,8-tetrahydro-[1,2,4]triazolo[4,3-a]pyrazine hydrochloride (0.399 g, 1.75 mmol) and potassium carbonate (0.482 g, 3.49 mmol) in anhydrous DMF (7.0 mL)

was heated at 100° C. for 16 h. Reaction mixture was cooled, diluted with ethyl acetate, washed with 5% lithium chloride solution (2×), brine, dried (MgSO$_4$), filtered, concentrated and purified by CombiFlash (0 to 50% EtOAc/Hex) to give product. LCMS-ESI$^+$: calc'd for C$_{11}$H$_{10}$BrF$_3$N$_5$: 348.0. (M+H$^+$); Found: 348.2 (M+H$^+$).

Preparation of (S)-ethyl 2-tert-butoxy-2-(7-(4-chlorophenyl)-5-methyl-2-(2-(3-(trifluoromethyl)-5,6-dihydro-[1,2,4]triazolo[4,3-a]pyrazin-7(8H)-yl)pyridin-4-yl)benzo[d]thiazol-6-yl)acetate: A mixture of 7-(4-bromopyridin-2-yl)-3-(trifluoromethyl)-5,6,7,8-tetrahydro-[1,2,4]triazolo[4,3-a]pyrazine (22.7 mg, 0.065 mmol), bis(pinacolato)diboron (33 mg, 0.13 mmol), potassium acetate (32 mg, 0.325 mmol) and PdCl$_2$(dppf) (4.8 mg, 0.0065 mmol) in anhydrous dioxane (1.0 mL) was heated at 120° C. for 30 minutes. Cooled to room temperature and used directly in the next step.

To the above reaction mixture were added (S)-ethyl 2-tert-butoxy-2-(7-(4-chlorophenyl)-2-(2-chloropyridin-4-yl)-5-methylbenzo[d]thiazol-6-yl)acetate (38.8 mg, 0.078 mmol), 2M potassium carbonate solution (0.13 mL, 0.26 mmol), and Pd(PPh$_3$)$_4$ (7.5 mg, 0.0065 mmol). Reaction mixture was heated at 95° C. overnight, diluted with ethyl acetate, and washed with brine. Aqueous layer was back-extracted with ethyl acetate and combined organic layer was dried (MgSO$_4$), filtered, concentrated and purified by CombiFlash (0 to 40% EtOAc/Hex) to give product. LCMS-ESI$^+$: calc'd for C$_{33}$H$_{33}$ClF$_3$N$_6$O$_3$S: 685.2. (M+H$^+$); Found: 685.3 (M+H$^+$).

Preparation of (S)-2-tert-butoxy-2-(7-(4-chlorophenyl)-5-methyl-2-(2-(3-(trifluoromethyl)-5,6-dihydro-[1,2,4]triazolo[4,3-a]pyrazin-7(8H)-yl)pyridin-4-yl)benzo[d]thiazol-6-yl)acetic acid: A solution of (S)-ethyl 2-tert-butoxy-2-(7-(4-chlorophenyl)-5-methyl-2-(2-(3-(trifluoromethyl)-5,6-dihydro-[1,2,4]triazolo[4,3-a]pyrazin-7(8H)-yl)pyridin-4-yl)benzo[d]thiazol-6-yl)acetate (35 mg, 0.052 mmol) and 5M sodium hydroxide (0.21 mL, 1.04 mmol) in methanol (0.3 mL) and THF (1.0 mL) was heated 45° C. for 2 h. Acetic acid (1 drop) and DMF (0.3 mL) were added and mixture concentrated to ~0.3 mL, diluted with methanol, filtered and purified by Gilson HPLC (Gemini, 5 to 100% ACN/H$_2$O+0.1% TFA) to give product after lyophilization. LCMS-ESI$^+$: calc'd for C$_{31}$H$_{29}$ClF$_3$N$_6$O$_3$S: 657.2 (M+H$^+$); Found: 657.3 (M+H$^1$); NMR (400 MHz, CD$_3$OD) δ 8.22 (d, J=5.5 Hz, 1H), 7.81 (s, 1H), 7.66 (dd, J=8.7, 1.8 Hz, 1H), 7.62-7.49 (m, J=10.0, 7.3 Hz, 4H), 7.32 (dd, J=5.5, 1.3 Hz, 1H), 5.24 (s, 1H), 5.07 (s, 2H), 4.36 (t, J=5.2 Hz, 2H), 4.20 (t, J=5.3 Hz, 2H), 2.57 (s, 3H), 0.95 (s, 9H).

Example 87

Preparation of (S)-2-tert-butoxy-2-(7-(4-chlorophenyl)-2-(2-(5,6-dihydro-[1,2,4]triazolo[4,3-a]pyrazin-7(8H)-yl)pyridin-4-yl)-5-methylbenzo[d]thiazol-6-yl)acetic acid (223)

Preparation of (S)-2-tert-butoxy-2-(7-(4-chlorophenyl)-2-(2-(5,6-dihydro-[1,2,4]triazolo[4,3-a]pyrazin-7(8H)-yl)pyridin-4-yl)-5-methylbenzo[d]thiazol-6-yl)acetic acid: (S)-2-tert-butoxy-2-(7-(4-chlorophenyl)-2-(2-(5,6-dihydro-[1,2,4]triazolo[4,3-a]pyrazin-7(8H)-yl)pyridin-4-yl)-5-methylbenzo[d]thiazol-6-yl)acetic acid was prepared in a similar manner as (S)-2-tert-butoxy-2-(7-(4-chlorophenyl)-5-methyl-2-(2-(3-(trifluoromethyl)-5,6-dihydro-[1,2,4]triazolo[4,3-a]pyrazin-7(8H)-yl)pyridin-4-yl)benzo[d]thiazol-6-yl)acetic acid except starting with 5,6,7,8-tetrahydro-[1,2,4]triazolo[4,3-a]pyrazine hydrochloride instead of 3-(trifluoromethyl)-5,6,7,8-tetrahydro-[1,2,4]triazolo[4,3-a]pyrazine hydrochloride. LCMS-ESI$^+$: calc'd for C$_{30}$H$_{30}$ClN$_6$O$_3$S: 589.2 (M+H$^+$); Found: 589.3 (M+H$^+$); $^1$H NMR (400 MHz, CD$_3$OD) δ 9.11 (s, 1H), 8.28 (d, J=5.4 Hz, 1H), 7.85 (s, 1H), 7.67 (dd, J=8.5, 1.7 Hz, 1H), 7.63-7.51 (m, 4H), 7.34 (d, J=5.3 Hz, 1H), 5.25 (s, 1H), 5.15 (s, 2H), 4.40 (t, J=5.3 Hz, 2H), 4.22 (t, J=5.4 Hz, 2H), 2.60 (s, 3H), 0.96 (s, 9H).

Example 88

Preparation of (S)-2-tert-butoxy-2-(7-(4-chlorophenyl)-2-(2-(1,3-dimethyl-6,7-dihydro-1H-pyrazolo[4,3-c]pyridin-5(4H)-yl)pyridin-4-yl)-5-methylbenzo[d]thiazol-6-yl)acetic acid (224)

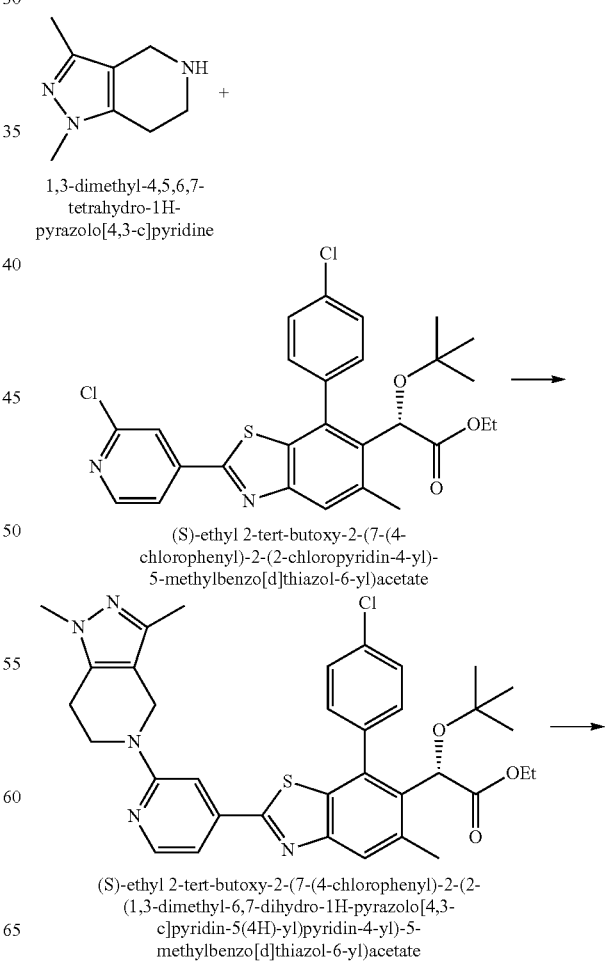

1,3-dimethyl-4,5,6,7-tetrahydro-1H-pyrazolo[4,3-c]pyridine (S)-ethyl 2-tert-butoxy-2-(7-(4-chlorophenyl)-2-(2-chloropyridin-4-yl)-5-methylbenzo[d]thiazol-6-yl)acetate (S)-ethyl 2-tert-butoxy-2-(7-(4-chlorophenyl)-2-(2-(1,3-dimethyl-6,7-dihydro-1H-pyrazolo[4,3-c]pyridin-5(4H)-yl)pyridin-4-yl)-5-methylbenzo[d]thiazol-6-yl)acetate

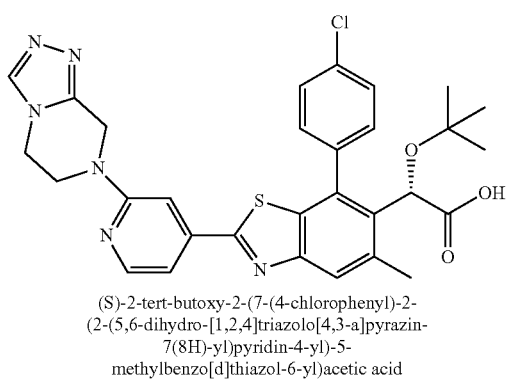

(S)-2-tert-butoxy-2-(7-(4-chlorophenyl)-2-(2-(5,6-dihydro-[1,2,4]triazolo[4,3-a]pyrazin-7(8H)-yl)pyridin-4-yl)-5-methylbenzo[d]thiazol-6-yl)acetic acid

399

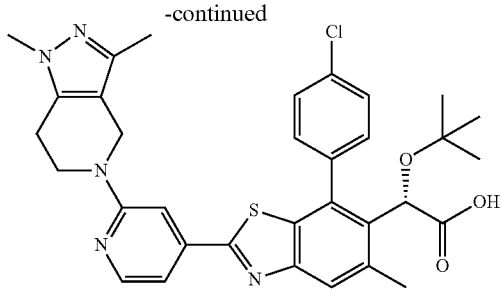

(S)-2-tert-butoxy-2-(7-(4-chlorophenyl)-2-(2-(1,3-dimethyl-6,7-dihydro-1H-pyrazolo[4,3-c]pyridin-5(4H)-yl)pyridin-4-yl)-5-methylbenzo[d]thiazol-6-yl)acetic acid

224

Preparation of (S)-ethyl 2-tert-butoxy-2-(7-(4-chlorophenyl)-2-(2-(1,3-dimethyl-6,7-dihydro-1H-pyrazolo[4,3-c]pyridin-5(4H)-yl)pyridin-4-yl)-5-methylbenzo[d]thiazol-6-yl)acetate: A mixture of 1,3-dimethyl-4,5,6,7-tetrahydro-1H-pyrazolo[4,3-c]pyridine (47.6 mg, 0.315 mmol), (S)-ethyl 2-tert-butoxy-2-(7-(4-chlorophenyl)-2-(2-chloropyridin-4-yl)-5-methylbenzo[d]thiazol-6-yl)acetate (32 mg, 0.060 mmol) in anhydrous NMP (1.0 mL) was heated at 90-110° C. for 40 h. Reaction mixture was cooled to room temperature, filtered through a syringe filter and purified by Gilson HPLC (Gemini, 5 to 100% ACN/H$_2$O+0.1% TFA). Product-containing fractions were diluted with ethyl acetate, washed with saturated sodium bicarbonate solution. Aqueous layer was back-extracted with ethyl acetate and the combined organic layer was washed with brine, dried (MgSO$_4$), filtered, and concentrated to give product. LCMS-ESI$^+$: calc'd for C$_{35}$H$_{39}$ClN$_5$O$_3$S: 644.2 (M+H$^+$); Found: 644.3 (M+H$^+$).

Preparation of (S)-2-tert-butoxy-2-(7-(4-chlorophenyl)-2-(2-(1,3-dimethyl-6,7-dihydro-1H-pyrazolo[4,3-c]pyridin-5(4H)-yl)pyridin-4-yl)-5-methylbenzo[d]thiazol-6-yl)acetic acid: A solution of (S)-ethyl 2-tert-butoxy-2-(7-(4-chlorophenyl)-2-(2-(1,3-dimethyl-6,7-dihydro-1H-pyrazolo[4,3-c]pyridin-5(4H)-yl)pyridin-4-yl)-5-methylbenzo[d]thiazol-6-yl)acetate: A mixture of 1,3-dimethyl-4,5,6,7-tetrahydro-1H-pyrazolo[4,3-c]pyridine (7.7 mg, 0.012 mmol) and 5M sodium hydroxide (47 µL, 0.24 mmol) in methanol (0.1 mL) and THF (0.5 mL) was heated 45° C. for 2 h. Acetic acid (1 drop) and DMF (0.3 mL) were added and mixture concentrated to ~0.3 mL, diluted with methanol, filtered and purified by Gilson HPLC (Gemini, 5 to 100% ACN/H$_2$O+0.1% TFA) to give product after lyophilization. LCMS-ESI$^+$: calc'd for C$_{32}$H$_{34}$ClN$_5$O$_3$S: 616.2 (M+H$^+$); Found: 616.3 (M+H$^+$); $^1$H NMR (400 MHz, CD$_3$OD) δ 8.11 (d, J=6.3 Hz, 1H), 7.96 (s, 1H), 7.83 (s, 1H), 7.68 (dd, J=8.5, 1.7 Hz, 1H), 7.67-7.54 (m, 3H), 7.47 (dd, J=6.3, 1.3 Hz, 1H), 5.27 (s, 1H), 4.63 (s, 2H), 4.07 (t, J=5.7 Hz, 2H), 3.72 (s, 3H), 2.93 (t, J=5.5 Hz, 2H), 2.64 (s, 3H), 2.24 (s, 3H), 0.97 (s, 9H).

400

Example 89

Preparation of (S)-2-tert-butoxy-2-(7-(4-chlorophenyl)-2-(2-(3-fluoro-1-methyl-1H-indazol-6-yl)pyridin-4-yl)-5-methylbenzo[d]thiazol-6-yl)acetic acid (225)

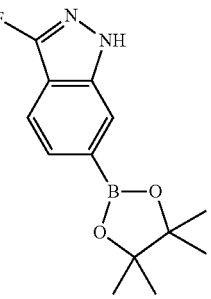

3-fluoro-6-(4,4,5,5-tetramethyl-1,3,2-dioxaborolan-2-yl)-1H-indazole

+

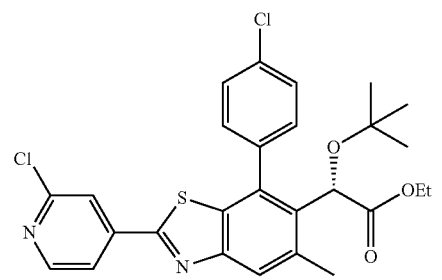

(S)-ethyl 2-tert-butoxy-2-(7-(4-chlorophenyl)-2-(2-chloropyridin-4-yl)-5-methylbenzo[d]thiazol-6-yl)acetate

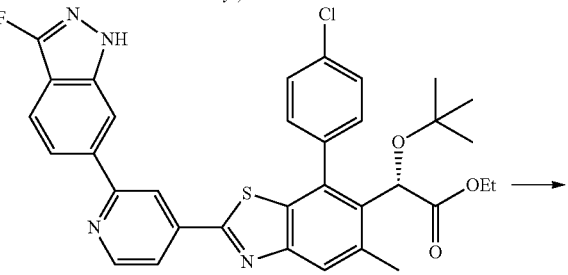

(S)-ethyl 2-tert-butoxy-2-(7-(4-chlorophenyl)-2-(2-(3-fluoro-1H-indazol-6-yl)pyridin-4-yl)-5-methylbenzo[d]thiazol-6-yl)acetate

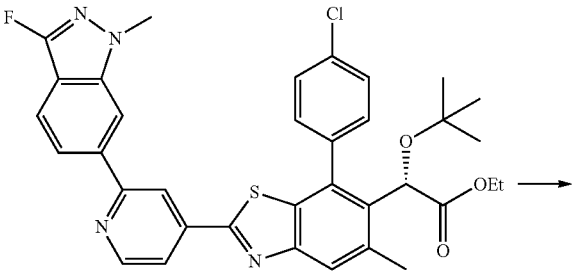

(S)-ethyl 2-tert-butoxy-2-(7-(4-chlorophenyl)-2-(2-(3-fluoro-1-methyl-1H-indazol-6-yl)pyridin-4-yl)-5-methylbenzo[d]thiazol-6-yl)acetate

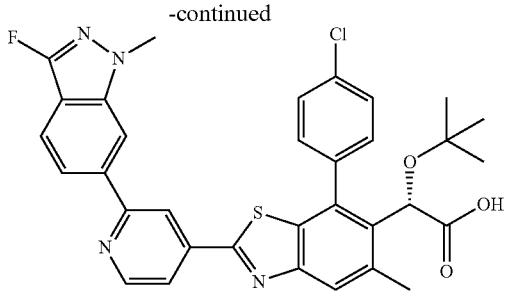

(S)-2-tert-butoxy-2-(7-(4-chlorophenyl)-
2-(2-(3-fluoro-1-methyl-1H-indazol-6-yl)
pyridin-4-yl)-5-methylbenzo[d]
thiazol-6-yl)acetic acid
225

Preparation of (S)-ethyl 2-tert-butoxy-2-(7-(4-chlorophenyl)-2-(2-(3-fluoro-1H-indazol-6-yl)pyridin-4-yl)-5-methylbenzo[d]thiazol-6-yl)acetate: A mixture of 3-fluoro-6-(4,4,5,5-tetramethyl-1,3,2-dioxaborolan-2-yl)-1H-indazole (prepared according to WO201059658, 48 mg, 0.184 mmol), (S)-ethyl 2-tert-butoxy-2-(7-(4-chlorophenyl)-2-(2-chloro-pyridin-4-yl)-5-methylbenzo[d]thiazol-6-yl)acetate (75 mg, 0.142 mmol) and 2M potassium carbonate solution (0.28 mL, 0.568 mmol) in dioxane (1.0 mL) was sparged with nitrogen for 10 minutes, Pd(PPh$_3$)$_4$ (16 mg, 0.014 mmol) was added and reaction mixture was heated in microwave at 100° C. for 1 h. Reaction mixture was diluted with ethyl acetate, washed with brine. The aqueous layer was back extracted with ethyl acetate and the combined organic layer was dried (MgSO$_4$), filtered, concentrated and purified by CombiFlash (0 to 40% EtOAc/Hex) to give product. LCMS-ESI$^+$: calc'd for C$_{34}$H$_{31}$ClFN$_4$O$_3$S: 629.2 (M+H$^+$); Found: 629.3 (M+H$^+$).

Preparation of (S)-ethyl 2-tert-butoxy-2-(7-(4-chlorophenyl)-2-(2-(3-fluoro-1-methyl-1H-indazol-6-yl)pyridin-4-yl)-5-methylbenzo[d]thiazol-6-yl)acetate: To a mixture of (S)-ethyl 2-tert-butoxy-2-(7-(4-chlorophenyl)-2-(2-(3-fluoro-1H-indazol-6-yl)pyridin-4-yl)-5-methylbenzo[d]thiazol-6-yl)acetate (39.7 mg, 0.0631 mmol) and cesium carbonate (62 mg, 0.189 mmol) in anhydrous DMF (1.0 mL) at 0° C. was added iodomethane (5.9 μL, 0.0947 mmol) and reaction stirred for 1 h. More iodomethane (3.0 μL) was added and reaction was stirred for 30 minutes, and stored in freezer overnight. Reaction mixture was diluted with ethyl acetate, washed with 5% lithium chloride solution (3×), brine, dried (MgSO$_4$), filtered, concentrated and purified by CombiFlash (0 to 40% EtOAc/Hex) to give product. LCMS-ESI$^+$: calc'd for C$_{35}$H$_{33}$ClFN$_4$O$_3$S: 643.2 (M+H$^+$); Found: 643.2 (M+H$^+$).

Preparation of (S)-2-tert-butoxy-2-(7-(4-chlorophenyl)-2-(2-(3-fluoro-1-methyl-1H-indazol-6-yl)pyridin-4-yl)-5-methylbenzo[d]thiazol-6-yl)acetic acid: A solution of (S)-ethyl 2-tert-butoxy-2-(7-(4-chlorophenyl)-2-(2-(3-fluoro-1-methyl-1H-indazol-6-yl)pyridin-4-yl)-5-methylbenzo[d]thiazol-6-yl)acetate (37 mg, 0.058 mmol) and 5M NaOH (0.23 mL, 1.15 mmol) in MeOH (0.5 mL) and THF (2 mL) was stirred at 45° C. for 2 hours. DMF (0.3 mL) and acetic acid (73 μL) were added and reaction mixture was concentrated to ~0.3 mL, filtered using a syringe filter, diluted with methanol. Purified using Gilson HPLC (Gemini, 5 to 100% ACN/H$_2$O+ 0.1% TFA) and lyophilized to give product. LCMS-ESI$^+$: calc'd for C$_{33}$H$_{29}$ClFN$_4$O$_3$S: 615.2 (M+H$^+$); Found: 615.2 (M+H$^+$). $^1$H NMR (400 MHz, CD$_3$OD) δ 8.80 (d, J=5.4 Hz, 1H), 8.58 (s, 1H), 8.20 (s, 1H), 8.02 (dd, J=5.3, 1.6 Hz, 1H), 7.95 (s, 1H), 7.83 (dd, J=28.4, 8.6 Hz, 2H), 7.76-7.67 (m, 1H), 7.60 (br s, 3H), 5.28 (s, 1H), 4.01 (s, 3H), 2.64 (s, 3H), 0.98 (s, 9H).

Example 90

Preparation of (S)-2-tert-butoxy-2-(7-(4-chlorophenyl)-2-(2-(3-ethylpyrazolo[1,5-a]pyrimidin-6-yl)pyridin-4-yl)-5-methylbenzo[d]thiazol-6-yl)acetic acid (226) and (S)-2-tert-butoxy-2-(7-(4-chlorophenyl)-2-(3-ethylpyrazolo[1,5-a]pyrimidin-6-yl)-5-methylbenzo[d]thiazol-6-yl)acetic acid (227)

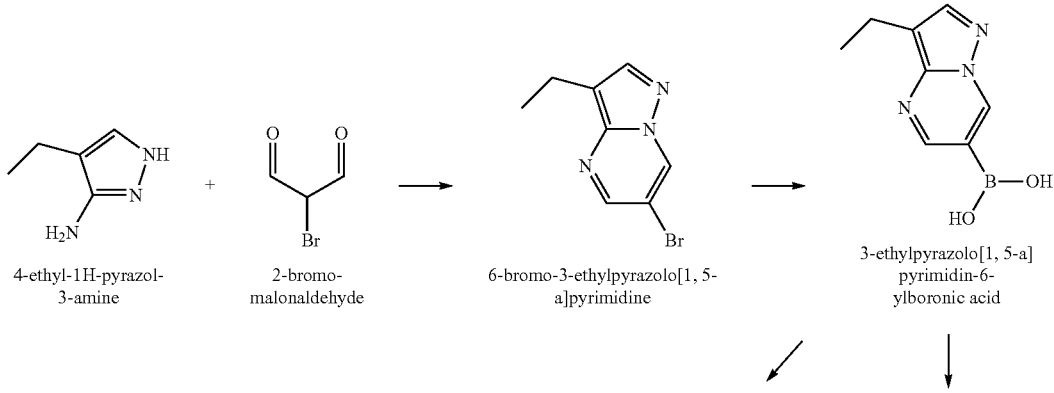

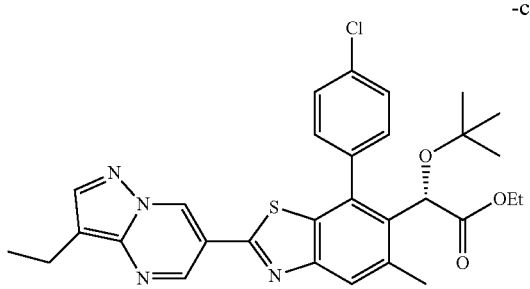

(S)-ethyl 2-tert-butoxy-2-(7-(4-chlorophenyl)-2-(3-ethylpyrazolo[1,5-a]pyrimidin-6-yl)-5-methylbenzo[d]thiazol-6-yl)acetate

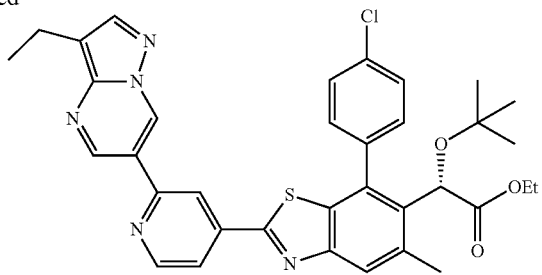

(S)-ethyl 2-tert-butoxy-2-(7-(4-chlorophenyl)-2-(2-(3-ethylpyrazolo[1,5-a]pyrimidin-6-yl)-pyridin-4-yl)-5-methylbenzo[d]thiazol-6-yl)acetate

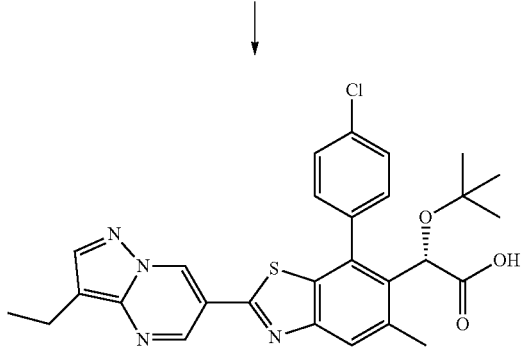

(S)-2-tert-butoxy-2-(7-(4-chlorophenyl)-2-(3-ethylpyrazolo[1,5-a]pyrimidin-6-yl)-5-methylbenzo[d]thiazol-6-yl)acetic acid
226

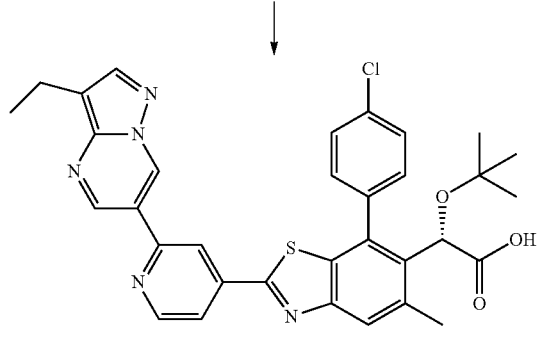

(S)-2-tert-butoxy-2-(7-(4-chlorophenyl)-2-(2-(3-ethylpyrazolo[1,5-a]pyrimidin-6-yl)-pyridin-4-yl)-5-methylbenzo[d]thiazol-6-yl)acetic acid
227

Preparation of 6-bromo-3-ethylpyrazolo[1,5-a]pyrimidine: To a solution of 4-ethyl-1H-pyrazol-3-amine (0.50 g, 4.50 mmol) and 2-bromo-malonaldehyde (1.47 g, 9.72 mmol) in ethanol (8.0 mL) was added acetic acid (1.21 mL, 21.2 mmol). The reaction mixture was refluxed for 4 h, then stored in a freezer overnight. The mixture was warmed to rt, the resulting precipitate was removed by filtration and the filtrate concentrated. The resulting residue was portioned between ethyl acetate and 1M sodium hydroxide and the organic layer was washed with brine, dried (MgSO$_4$), filtered, concentrated and purified by CombiFlash (0 to 50% EtOAc/Hex) to give product. LCMS-ESI$^+$: calc'd for $C_8H_9BrN_3$: 226.0 (M+H$^+$); Found: 226.1 (M+H$^+$).

Preparation of (S)-ethyl 2-tert-butoxy-2-(7-(4-chlorophenyl)-2-(2-(3-ethylpyrazolo[1,5-a]pyrimidin-6-yl)pyridin-4-yl)-5-methylbenzo[d]thiazol-6-yl)acetate: A mixture of 6-bromo-3-ethylpyrazolo[1,5-a]pyrimidine (415 mg, 1.84 mmol), bis(pinacolato)diboron (932 mg, 3.67 mmol), potassium acetate (902 mg, 9.2 mmol) and PdCl$_2$(dppf).CH$_2$Cl$_2$ (150 mg, 0.184 mmol) in anhydrous dioxane (10.0 mL) was sparged with nitrogen for 10 minutes, then heated in a microwave at 100° C. for 1 h. LC/MS showed clean conversion to 3-ethylpyrazolo[1,5-a]pyrimidin-6-ylboronic acid that was used crude.

To a mixture of the above crude 3-ethylpyrazolo[1,5-a]pyrimidin-6-ylboronic acid in dioxane (~0.18M, 0.68 mL, 0.123 mmol) was added (S)-ethyl 2-tert-butoxy-2-(7-(4-chlorophenyl)-2-(2-chloropyridin-4-yl)-5-methylbenzo[d]thiazol-6-yl)acetate (50 mg, 0.0944 mmol), Pd(PPh$_3$)$_4$ (11 mg, 0.0094 mmol) and 2M potassium carbonate (0.19 mL, 0.378 mmol) was heated in a microwave at 110° C. for 1 h. Reaction mixture was stored overnight at rt, diluted with ethyl acetate and washed with brine, dried (MgSO$_4$), filtered, concentrated and purified by CombiFlash (0 to 40% EtOAc/Hex) to give product. LCMS-ESI$^+$: calc'd for $C_{35}H_{35}ClN_5O_3S$: 640.2 (M+H$^+$); Found: 640.3 (M+H$^+$).

Preparation of (S)-2-tert-butoxy-2-(7-(4-chlorophenyl)-2-(2-(3-ethylpyrazolo[1,5-a]pyrimidin-6-yl)pyridin-4-yl)-5-methylbenzo[d]thiazol-6-yl)acetic acid: A mixture of (S)-ethyl 2-tert-butoxy-2-(7-(4-chlorophenyl)-2-(2-(3-ethylpyrazolo[1,5-a]pyrimidin-6-yl)pyridin-4-yl)-5-methylbenzo[d]thiazol-6-yl)acetate (31 mg, 0.048 mmol) and lithium iodide (200 mg) in pyridine (0.5 mL) was heated in microwave at 170° C. for 1 h. Reaction mixture was diluted with ethyl acetate, washed with 5% acetic acid solution, brine, dried (MgSO$_4$), filtered, concentrated and purified by CombiFlash (0 to 10% MeOH/CH$_2$Cl$_2$). Lyophilization gave desired product. LCMS-ESI$^+$: calc'd for $C_{33}H_{31}ClN_5O_3S$: 612.2 (M+H$^+$); Found: 612.2 (M+H$^+$). $^1$H NMR (400 MHz, CD$_3$OD) δ 9.33 (d, J=2.1 Hz, 1H), 9.02 (d, J=2.1 Hz, 1H), 8.60 (d, J=5.1 Hz, 1H), 8.56-8.49 (m, 2H), 8.29 (s, 1H), 8.02 (s, 1H), 7.85 (tt, J=7.7, 1.8 Hz, 1H), 7.77-7.61 (m, 4H), 7.61-7.49 (m, 3H), 7.43 (ddd, J=7.7, 4.4, 1.5 Hz, 2H), 5.24 (s, 1H), 2.78 (q, J=7.6 Hz, 2H), 2.56 (s, 3H), 1.30 (t, J=7.6 Hz, 3H), 0.96 (d, J=6.8 Hz, 9H).

Preparation of (S)-ethyl 2-tert-butoxy-2-(7-(4-chlorophenyl)-2-(3-ethylpyrazolo[1,5-a]pyrimidin-6-yl)-5-methylbenzo[d]thiazol-6-yl)acetate: To a mixture of the crude 3-ethylpyrazolo[1,5-a]pyrimidin-6-ylboronic acid in dioxane (~0.18M, 0.68 mL, 0.123 mmol) was added (S)-ethyl 2-(2-bromo-7-(4-chlorophenyl)-5-methylbenzo[d]thiazol-6-yl)-2-tert-butoxyacetate (50 mg, 0.101 mmol), Pd(PPh$_3$)$_4$ (12 mg, 0.010 mmol) and 2M potassium carbonate (0.20 mL, 0.404 mmol) was heated in a microwave at 110° C. for 1 h. Reaction mixture was stored overnight at rt, diluted with ethyl acetate and washed with brine, dried (MgSO$_4$), filtered, concentrated and purified by CombiFlash (0 to 30% EtOAc/Hex) to give product. LCMS-ESI$^+$: calc'd for $C_{30}H_{32}ClN_4O_3S$: 563.2 (M+H$^+$); Found: 563.3 (M+H$^+$).

Preparation of (S)-2-tert-butoxy-2-(7-(4-chlorophenyl)-2-(3-ethylpyrazolo[1,5-a]pyrimidin-6-yl)-5-methylbenzo[d]thiazol-6-yl)acetic acid: A mixture of (S)-ethyl 2-tert-butoxy-2-(7-(4-chlorophenyl)-2-(3-ethylpyrazolo[1,5-a]pyrimidin-6-yl)-5-methylbenzo[d]thiazol-6-yl)acetate (24.9 mg, 0.044 mmol) and lithium iodide (200 mg) in pyridine (0.5 mL) was heated in microwave at 170° C. for 1 h. Reaction mixture was diluted with ethyl acetate, washed with 5% acetic acid solution, brine, dried (MgSO$_4$), filtered, concentrated and purified by CombiFlash (0 to 30% MeOH/CH$_2$Cl$_2$). Lyophilization gave desired product. LCMS-ESI$^+$: calc'd for $C_{28}H_{28}ClN_4O_3S$: 535.2. (M+H$^+$); Found: 535.2 (M+H$^+$). $^1$H NMR (400 MHz, CDCl$_3$) δ 9.22 (dd, J=2.8, 1.6 Hz, 1H), 8.95 (dd, J=2.8, 1.6 Hz, 1H), 8.07 (s, 1H), 7.89 (s, 1H), 7.70 (d, J=7.8 Hz, 1H), 7.58-7.37 (m, 3H), 5.31 (s, 1H), 2.86 (q, J=7.6 Hz, 2H), 2.58 (s, 3H), 1.34 (dd, J=7.8, 7.3 Hz, 3H), 0.99 (s, 9H).

Example 91

Preparation of (S)-2-tert-butoxy-2-(7-(4-chlorophenyl)-5-methyl-2-(3-(5-methyl-2,4-dioxo-3,4-dihydropyrimidin-1(2H)-yl)phenyl)benzo[d]thiazol-6-yl)acetic acid (228)

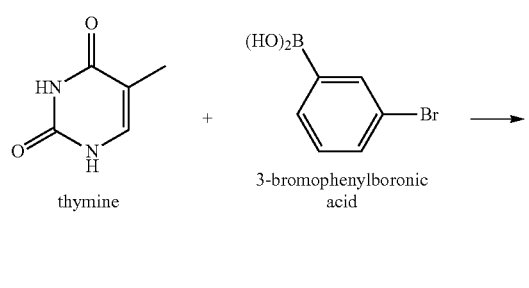

thymine + 3-bromophenylboronic acid

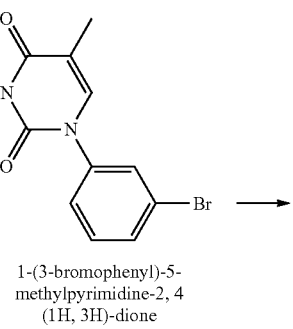

1-(3-bromophenyl)-5-methylpyrimidine-2,4(1H,3H)-dione

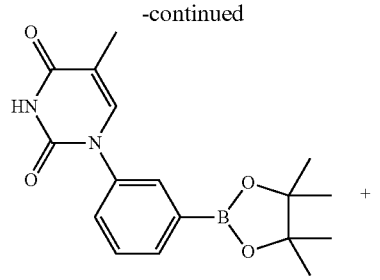

5-methyl-1-(3-(4, 4, 5, 5-tetramethyl-1, 3, 2-dioxaborolan-2-yl)phenyl)pyrimidine-2, 4(1H, 3H)-dione

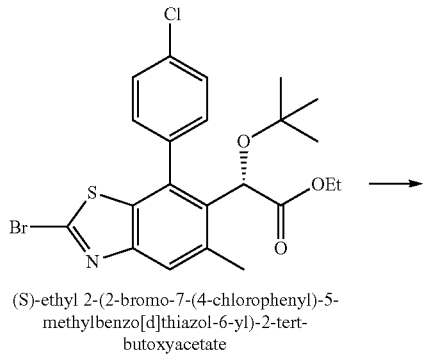

(S)-ethyl 2-(2-bromo-7-(4-chlorophenyl)-5-methylbenzo[d]thiazol-6-yl)-2-tert-butoxyacetate

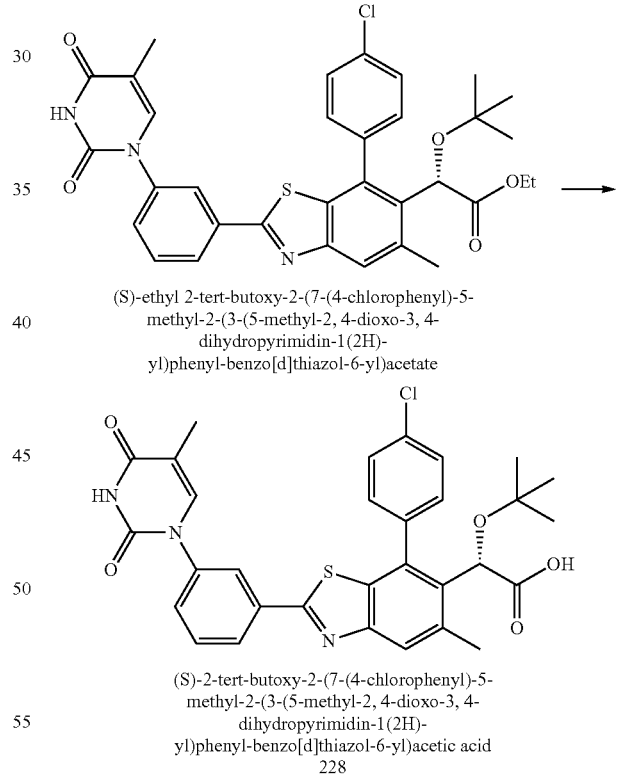

(S)-ethyl 2-tert-butoxy-2-(7-(4-chlorophenyl)-5-methyl-2-(3-(5-methyl-2, 4-dioxo-3, 4-dihydropyrimidin-1(2H)-yl)phenyl-benzo[d]thiazol-6-yl)acetate (S)-2-tert-butoxy-2-(7-(4-chlorophenyl)-5-methyl-2-(3-(5-methyl-2, 4-dioxo-3, 4-dihydropyrimidin-1(2H)-yl)phenyl-benzo[d]thiazol-6-yl)acetic acid 228

Preparation of 1-(3-bromophenyl)-5-methylpyrimidine-2,4(1H,3H)-dione: A 500 mL round bottom flask was charged with thymine (0.314 g, 2.49 mmol), 3-bromophenylboronic acid (1.00 g, 4.98 mmol), tetramethylethyldiamine (0.75 mL, 4.98 mmol), copper(II) acetate monohydrate (0.497 g, 2.49 mmol), methanol (200 mL), and H$_2$O (50 mL). The blue reaction mixture was stirred for 48 h, concentrated and purified by CombiFlash (0 to 8% MeOH/CH$_2$Cl$_2$) to give desired product. LCMS-ESI⁺: calc'd for $C_{11}H_9BrN_2O_2$: 281.0 (M+H⁺); Found: 281.1 (M+H⁺).

Preparation of 5-methyl-1-(3-(4,4,5,5-tetramethyl-1,3,2-dioxaborolan-2-yl)phenyl)pyrimidine-2,4(1H,3H)-dione: A mixture of 1-(3-bromophenyl)-5-methylpyrimidine-2,4(1H,3H)-dione (163 mg, 0.58 mmol), bis(pinacolato)diboron (294 mg, 1.16 mmol), potassium acetate (284 mg, 2.90 mmol) and PdCl$_2$(dppf).CH$_2$Cl$_2$ (47 mg, 0.058 mmol) in anhydrous dioxane (6.0 mL) was sparged with nitrogen for 20 minutes, then heated at 100° C. for 0.5 h. Reaction mixture was concentrated, dissolved in dichloromethane, adsorbed onto silica gel and purified by CombiFlash (0 to 8% MeOH/CH$_2$Cl$_2$) to give desired product. LCMS-ESI⁺: calc'd for $C_{17}H_{22}BN_2O_4$: 329.2 (M+H⁺); Found: 329.1 (M+H⁺).

Preparation of (S)-ethyl 2-tert-butoxy-2-(7-(4-chlorophenyl)-5-methyl-2-(3-(5-methyl-2,4-dioxo-3,4-dihydropyrimidin-1(2H)-yl)phenyl)benzo[d]thiazol-6-yl)acetate: A mixture 5-methyl-1-(3-(4,4,5,5-tetramethyl-1,3,2-dioxaborolan-2-yl)phenyl)pyrimidine-2,4(1H,3H)-dione (50 mg, 0.154 mmol), (S)-ethyl 2-(2-bromo-7-(4-chlorophenyl)-5-methylbenzo[d]thiazol-6-yl)-2-tert-butoxyacetate (51 mg, 0.103 mmol), Pd(PPh$_3$)$_4$ (12 mg, 0.01034 mmol) and 2M potassium carbonate (0.15 mL, 0.309 mmol) was heated at 105-120° C. for 5 h. Reaction mixture was stirred over the weekend at rt, diluted with ethyl acetate and washed with brine, dried (MgSO$_4$), filtered, concentrated and purified by Gilson HPLC (Gemini, 5 to 100% ACN/H$_2$O+0.1% TFA). Product-containing fractions were diluted with ethyl acetate, washed with saturated sodium bicarbonate solution/brine. Organic layer was dried (MgSO$_4$), filtered, and concentrated to give desired product. LCMS-ESI⁺: calc'd for $C_{33}H_{33}ClN_3O_5S$: 618.2 (M+H⁺); Found: 618.2 (M+H⁺).

Preparation of (S)-2-tert-butoxy-2-(7-(4-chlorophenyl)-5-methyl-2-(3-(5-methyl-2,4-dioxo-3,4-dihydropyrimidin-1(2H)-yl)phenyl)benzo[d]thiazol-6-yl)acetic acid: A solution of (S)-ethyl 2-tert-butoxy-2-(7-(4-chlorophenyl)-5-methyl-2-(3-(5-methyl-2,4-dioxo-3,4-dihydropyrimidin-1(2H)-yl)phenyl)benzo[d]thiazol-6-yl)acetate (12.9 mg, 0.0212 mmol) and 5M NaOH (85 μL, 0.424 mmol) in MeOH (0.1 mL) and THF (1.2 mL) was stirred at 50° C. for 1.5 hours. DMF (0.3 mL) and acetic acid (75 μL) were added and reaction mixture was concentrated to ~0.3 mL, filtered using a syringe filter, diluted with methanol. Purified using Gilson HPLC (Gemini, 5 to 100% ACN/H$_2$O+0.1% TFA) and lyophilized to give product. LCMS-ESI⁺: calc'd for $C_{31}H_{29}ClN_3O_5S$: 590.1 (M+H⁺); Found: 590.2 (M+H⁺). ¹H NMR (400 MHz, CD$_3$OD) δ 8.07 (d, J=8.5 Hz, 1H), 7.94 (dd, J=1.8 Hz, 1H), 7.84 (s, 1H), 7.71-7.47 (m, 5H), 7.43-7.22 (m, 2H), 5.25 (s, 1H), 2.60 (s, 3H), 1.92 (d, J=5.2 Hz, 3H), 1.34 (s, 3H), 0.96 (s, 9H).

Example 92

Preparation of (S)-2-tert-butoxy-2-(7-(4-chlorophenyl)-2-(3-(2,4-dioxo-3,4-dihydropyrimidin-1(2H)-yl)phenyl)-5-methylbenzo[d]thiazol-6-yl)acetic acid (229)

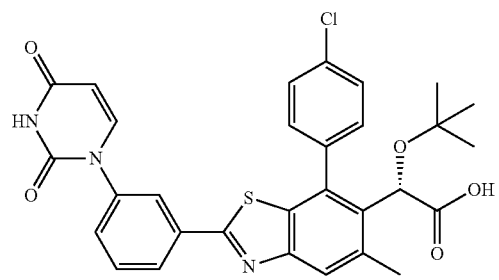

(S)-2-tert-butoxy-2-(7-(4-chlorophenyl)-2-(3-(2,4-dioxo-3,4-dihydropyrimidin-1(2H)-yl)phenyl)-5-methylbenzo[d]thiazol-6-yl)acetic acid Preparation of (S)-2-tert-butoxy-2-(7-(4-chlorophenyl)-2-(3-(2,4-dioxo-3,4-dihydropyrimidin-1(2H)-yl)phenyl)-5-methylbenzo[d]thiazol-6-yl)acetic acid: Prepared in a similar manner as (S)-2-tert-butoxy-2-(7-(4-chlorophenyl)-5-methyl-2-(3-(5-methyl-2,4-dioxo-3,4-dihydropyrimidin-1(2H)-yl)phenyl)benzo[d]thiazol-6-yl)acetic acid, except starting with uracil instead of thymine. LCMS-ESI⁺: calc'd for $C_{30}H_{279}ClN_3O_5S$: 576.1 (M+H⁺); Found: 576.2 (M+H⁺). ¹H NMR (400 MHz, CD$_3$OD) δ 8.10-8.02 (m, 1H), 7.95 (t, J=1.8 Hz, 1H), 7.83 (s, 1H), 7.72-7.54 (m, 6H), 7.50 (d, J=7.7 Hz, 1H), 7.44-7.37 (m, 1H), 5.81 (d, J=7.7 Hz, 1H), 5.25 (s, 1H), 2.60 (s, 3H), 0.96 (s, 9H).

Example 93

Preparation of (S)-2-tert-butoxy-2-(7-(4-chlorophenyl)-5-methyl-2-(2-(6-oxo-1,6-dihydropyridin-3-yl)pyridin-4-yl)benzo[d]thiazol-6-yl)acetic acid (230)

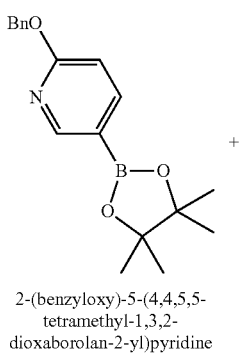

2-(benzyloxy)-5-(4,4,5,5-tetramethyl-1,3,2-dioxaborolan-2-yl)pyridine

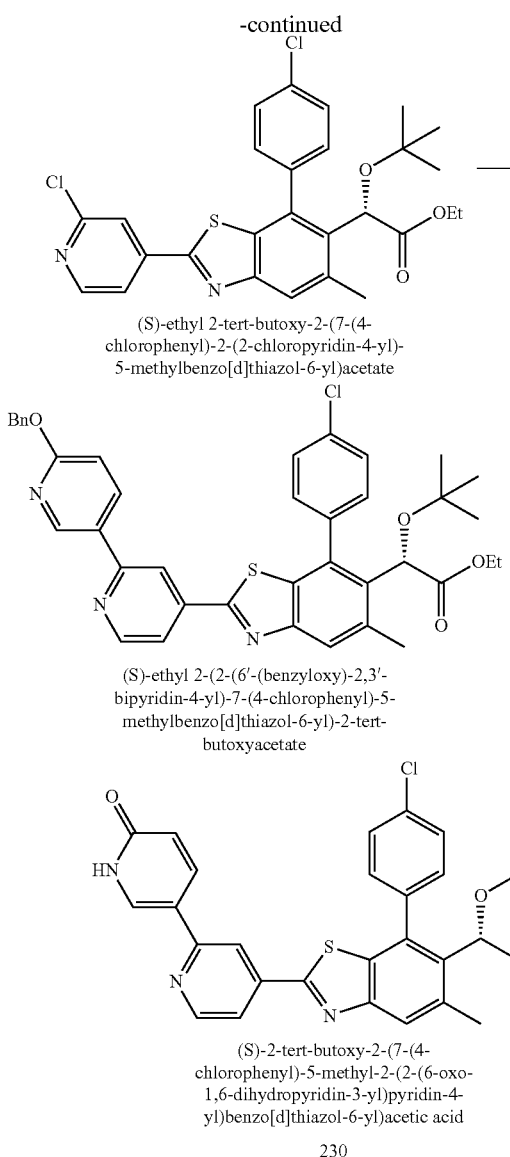

(S)-ethyl 2-tert-butoxy-2-(7-(4-chlorophenyl)-2-(2-chloropyridin-4-yl)-5-methylbenzo[d]thiazol-6-yl)acetate (S)-ethyl 2-(2-(6'-(benzyloxy)-2,3'-bipyridin-4-yl)-7-(4-chlorophenyl)-5-methylbenzo[d]thiazol-6-yl)-2-tert-butoxyacetate (S)-2-tert-butoxy-2-(7-(4-chlorophenyl)-5-methyl-2-(2-(6-oxo-1,6-dihydropyridin-3-yl)pyridin-4-yl)benzo[d]thiazol-6-yl)acetic acid

230

Preparation of (S)-ethyl 2-(2-(6'-(benzyloxy)-2,3'-bipyridin-4-yl)-7-(4-chlorophenyl)-5-methylbenzo[d]thiazol-6-yl)-2-tert-butoxyacetate: A mixture of 2-(benzyloxy)-5-(4,4,5,5-tetramethyl-1,3,2-dioxaborolan-2-yl)pyridine (15 mg, 0.048 mmol), (S)-ethyl 2-tert-butoxy-2-(7-(4-chlorophenyl)-2-(2-chloropyridin-4-yl)-5-methylbenzo[d]thiazol-6-yl)acetate (17 mg, 032 mmol) and 2M potassium carbonate solution (48 µL, 0.096 mmol) in dioxane (0.5 mL) was sparged with nitrogen for 10 minutes, Pd(PPh₃)₄ (3.7 mg, 0.0032 mmol) was added and reaction mixture was heated at 100° C. for 4 h. Reaction mixture was diluted with ethyl acetate, washed with brine. The aqueous layer was back extracted with ethyl acetate and the combined organic layer was dried (MgSO₄), filtered, concentrated and purified by CombiFlash (0 to 20% EtOAc/Hex) to give product. LCMS-ESI⁺: calc'd for $C_{39}H_{37}ClN_3O_4S$: 678.2 (M+H⁺); Found: 678.3 (M+H⁺).

Preparation of (S)-2-tert-butoxy-2-(7-(4-chlorophenyl)-5-methyl-2-(2-(6-oxo-1,6-dihydropyridin-3-yl)pyridin-4-yl)benzo[d]thiazol-6-yl)acetic acid: A mixture of (S)-ethyl 2-(2-(6'-(benzyloxy)-2,3'-bipyridin-4-yl)-7-(4-chlorophenyl)-5-methylbenzo[d]thiazol-6-yl)-2-tert-butoxyacetate (21.2 mg, 0.031 mmol) and 5% rhodium on alumina (61 mg) in absolute ethanol (5.0 mL) was placed under vacuum for 5 minutes, back-filled with hydrogen and stirred under hydrogen balloon for 3 h to give ~70% conversion based on LC/MS. Reaction mixture was filtered through a pad of Celite, concentrated and used in next step without further purification.

A solution of above residue and 5M NaOH (0.12 mL, 0.62 mmol) in methanol (0.2 mL) and THF (1.5 mL) was stirred at 50° C. for 2 h. Acetic acid (21 equivalents) and DMF (0.3 mL) were added and reaction mixture was concentrated to ~0.3 mL, filtered using a syringe filter, diluted with methanol and purified using Gilson HPLC (Gemini, 5 to 100% ACN/H₂O+ 0.1% TFA). Product containing fractions were pooled, diluted with ethyl acetate and washed with saturated sodium bicarbonate solution/brine. Aqueous layer was back-extracted with ethyl acetate (3×) and combined organic layer was dried (MgSO₄), filtered and concentrated. Product suspended in acetonitrile/H₂O, acidified with TFA and lyophilized to give desired product. LCMS-ESI⁺: calc'd for $C_{30}H_{27}ClN_3O_4S$: 560.1 (M+H⁺); Found: 560.2 (M+H⁺). NMR of Na salt (400 MHz, CD₃OD) δ 8.64 (d, J=5.2 Hz, 1H), 8.30 (dd, J=9.6, 2.6 Hz, 1H), 8.24-8.16 (m, 2H), 7.87-7.74 (m, 3H), 7.57 (s, 2H), 7.56 (d, J=9.9 Hz, 1H), 6.64 (d, J=9.6 Hz, 1H), 5.20 (s, 1H), 2.63 (s, 3H), 0.95 (s, 9H).

Example 94

Preparation of (S)-2-tert-butoxy-2-(7-(4-chlorophenyl)-5-methyl-2-(2-(2-oxo-1,2-dihydropyridin-3-yl)pyridin-4-yl)benzo[d]thiazol-6-yl)acetic acid (232) and (S)-2-tert-butoxy-2-(7-(4-chlorophenyl)-2-(2'-methoxy-2,3'-bipyridin-4-yl)-5-methylbenzo[d]thiazol-6-yl)acetic acid (233) was also isolated

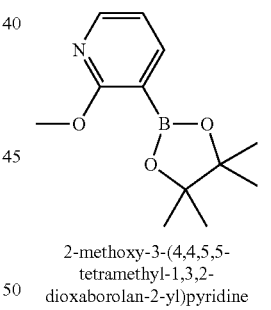

2-methoxy-3-(4,4,5,5-tetramethyl-1,3,2-dioxaborolan-2-yl)pyridine

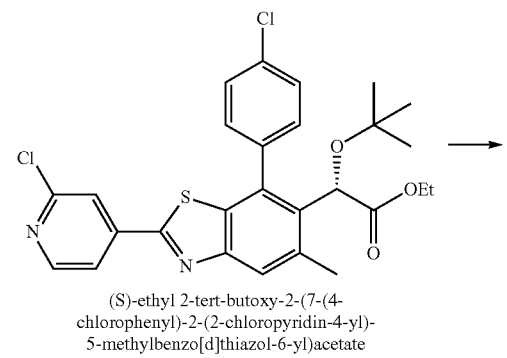

(S)-ethyl 2-tert-butoxy-2-(7-(4-chlorophenyl)-2-(2-chloropyridin-4-yl)-5-methylbenzo[d]thiazol-6-yl)acetate

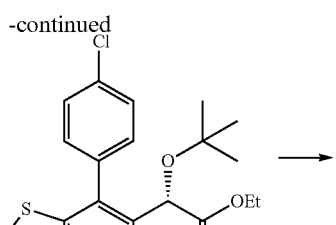

(S)-ethyl 2-tert-butoxy-2-(7-(4-chlorophenyl)-2-(2'-methoxy-2,3'-bipyridin-4-yl)-5-methylbenzo[d]thiazol-6-yl)acetate

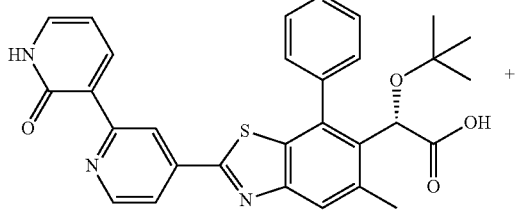

(S)-2-tert-butoxy-2-(7-(4-chlorophenyl)-5-methyl-2-(2-(2-oxo-1,2-dihydropyridin-3-yl)pyridin-4-yl)benzo[d]thiazol-6-yl)acetic acid

232

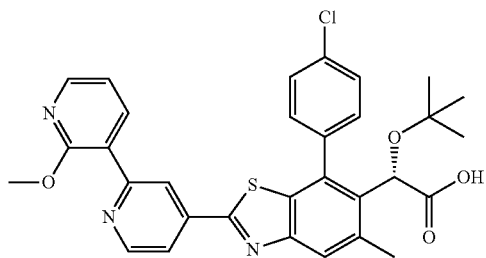

(S)-2-tert-butoxy-2-(7-(4-chlorophenyl)-2-(2'-methoxy-2,3'-bipyridin-4-yl)-5-methylbenzo[d]thiazol-6-yl)acetic acid

233

Preparation of (S)-ethyl 2-tert-butoxy-2-(7-(4-chlorophenyl)-2-(2'-methoxy-2,3'-bipyridin-4-yl)-5-methylbenzo[d]thiazol-6-yl)acetate: A mixture of 2-methoxy-3-(4,4,5,5-tetramethyl-1,3,2-dioxaborolan-2-yl)pyridine (13 mg, 0.0878 mmol), (S)-ethyl 2-tert-butoxy-2-(7-(4-chlorophenyl)-2-(2-chloropyridin-4-yl)-5-methylbenzo[d]thiazol-6-yl)acetate (31 mg, 0585 mmol) and 2M potassium carbonate solution (88 µL, 0.178 mmol) in dioxane (0.5 mL) was sparged with nitrogen for 10 minutes. Pd(PPh$_3$)$_4$ (6.9 mg, 0.0059 mmol) was added and reaction mixture was heated in microwave at 100° C. for 1 h . Reaction mixture was diluted with ethyl acetate, washed with brine. The aqueous layer was back extracted with ethyl acetate and the combined organic layer was dried (MgSO$_4$), filtered, concentrated and purified by CombiFlash (0 to 40% EtOAc/Hex) to give product. LCMS-ESI$^+$: calc'd for C$_{33}$H$_{33}$ClN$_3$O$_4$S: 602.1 (M+H$^+$); Found: 602.3 (M+H$^+$).

Preparation of (S)-2-tert-butoxy-2-(7-(4-chlorophenyl)-5-methyl-2-(2-(2-oxo-1,2-dihydropyridin-3-yl)pyridin-4-yl)benzo[d]thiazol-6-yl)acetic acid: A mixture of (S)-ethyl 2-tert-butoxy-2-(7-(4-chlorophenyl)-2-(2'-methoxy-2,3'-bipyridin-4-yl)-5-methylbenzo[d]thiazol-6-yl)acetate (24.2 mg, 0.040 mmol) and lithium iodide (150 mg) in pyridine (2.0 mL) was heated in microwave at 170° C. for 3.5 hours. Reaction mixture was cooled to room temperature and allowed to stand for 14 days, diluted with ethyl acetate. Organic layer was washed with 5% AcOH solution (3×), brine, dried (MgSO$_4$), filtered, concentrated, and purified using Gilson HPLC (Gemini, 5 to 100% ACN/H$_2$O+0.1% TFA) to give desired product. LCMS-ESI$^+$: calc'd for C$_{30}$H$_{27}$ClN$_3$O$_4$S: 560.1 (M+H$^+$); Found: 560.2 (M+H$^+$). $^1$H NMR (400 MHz, CD$_3$OD) δ 8.99 (s, 1H), 8.78 (dd, J=11.1, 6.9 Hz, 2H), 8.28 (d, J=6.0 Hz, 1H), 7.94 (s, 1H), 7.85 (d, J=6.1 Hz, 1H), 7.69 (d, J=8.6 Hz, 1H), 7.64-7.53 (m, 3H), 6.73 (dd, J=6.8 Hz, 1H), 5.28 (s, 1H), 2.62 (s, 3H), 0.97 (s, 9H).

(S)-2-tert-butoxy-2-(7-(4-chlorophenyl)-2-(2'-methoxy-2,3'-bipyridin-4-yl)-5-methylbenzo[d]thiazol-6-yl)acetic acid was also isolated: LCMS-ESI$^+$: calc'd for C$_{31}$H$_{29}$ClN$_3$O$_4$S: 574.2 (M+H$^+$); Found: 574.2 (M+H$^+$). $^1$H NMR (400 MHz, CD$_3$OD) δ 9.05 (s, 1H), 8.81 (d, J=6.2 Hz, 1H), 8.72 (d, J=7.9 Hz, 1H), 8.32 (d, J=6.2 Hz, 1H), 8.08 (d, J=6.4 Hz, 1H), 8.00 (s, 1H), 7.70 (d, J=8.4 Hz, 1H), 7.62 (d, J=7.6 Hz, 3H), 6.71 (dd, J=6.5, 6.5 Hz, 1H), 5.28 (s, 1H), 3.75 (s, 3H), 2.65 (s, 3H), 0.98 (s, 9H).

Example 95

Preparation of (S)-2-tert-butoxy-2-(7-(4-chlorophenyl)-2-(2-(1,3-dimethyl-1H-pyrazolo[3,4-c]pyridin-5-yl)pyridin-4-yl)-5-methylbenzo[d]thiazol-6-yl)acetic acid (234) and (S)-2-tert-butoxy-2-(7-(4-chlorophenyl)-2-(1,3-dimethyl-1H-pyrazolo[3,4-c]pyridin-5-yl)-5-methylbenzo[d]thiazol-6-yl)acetic acid (235)

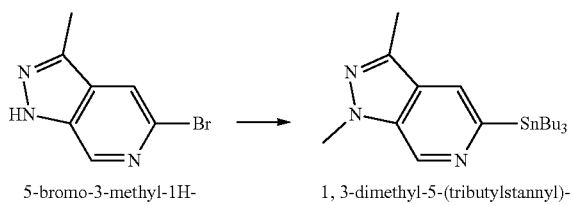

5-bromo-3-methyl-1H-pyrazolo[3,4-c]pyridine → 1,3-dimethyl-5-(tributylstannyl)-1H-pyrazolo[3,4-c]pyridine

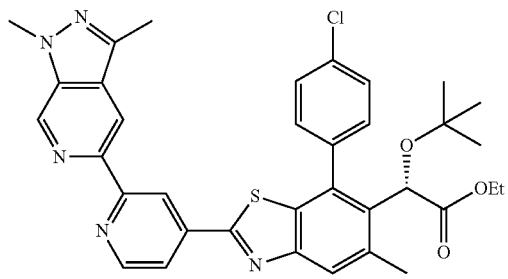

(S)-ethyl 2-tert-butoxy-2-(7-(4-chlorophenyl)-2-(2-(1, 3-dimethyl-1H-pyrazolo[3, 4-c]pyridin-5-yl)pyridine-4-yl)-5-methylbenzo[d]thiazol-6-yl)acetate

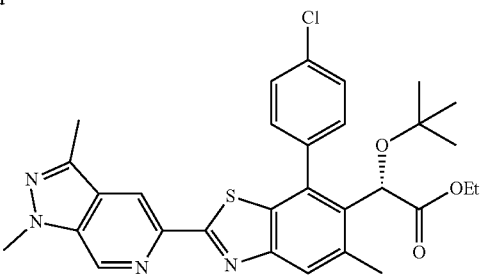

(S)-ethyl 2-tert-butoxy-2-(7-(4-chlorophenyl)-2-(1, 3-dimethyl-1H-pyrazolo[3, 4-c]pyridin-5-yl)-5-methylbenzo[d]thiazol-6-yl)acetate

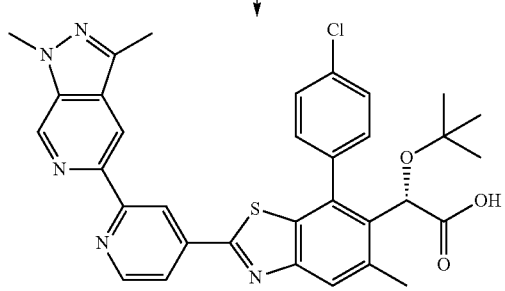

(S)-2-tert-butoxy-2-(7-(4-chlorophenyl)-2-(2-(1, 3-dimethyl-1H-pyrazolo[3, 4-c]pyridin-5-yl)pyridin-4-yl)-5-methylbenzo[d]thiazol-6-yl)acetic acid
234

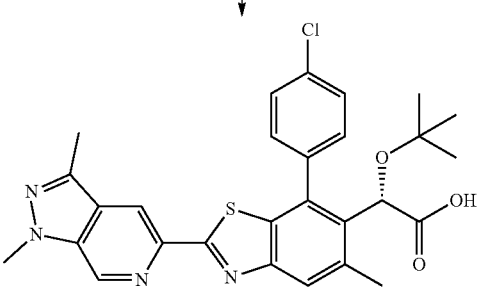

(S)-2-tert-butoxy-2-(7-(4-chlorophenyl)-2-(1, 3-dimethyl-1H-pyrazolo[3, 4-c]pyridin-5-yl)-5-methylbenzo[d]thiazol-6-yl)acetic acid
235

Preparation of 1,3-dimethyl-5-(tributylstannyl)-1H-pyrazolo[3,4-c]pyridine: To a solution of 5-bromo-3-methyl-1H-pyrazolo[3,4-c]pyridine (0.5 g, 2.36 mmol) in DMF (12 mL) at 0° C. was added cesium carbonate (2.305 g, 7.074 mmol), followed by iodomethane (0.22 mL, 3.537 mmol). After stirring for 1 h, LC/MS showed reaction was complete. Reaction mixture was diluted with ethyl acetate, washed with 5% lithium chloride solution (3×), brine and dried (MgSO4). Filtration and concentration gave product that was used in the next step without further purification.

The above residue was dissolved in toluene (10 mL) and hexabutylditin (1.239 mL, 2.473 mmol) was added, followed by tetrakis(triphenylphosphine)palladium(0) (0.22 g, 0.19 mmol). The yellow reaction mixture was stirred at 140° C. in a sealed reaction vessel for 2 hours. Temperature was increased to 170° C. and stirred for 45 min to give a black mixture. Reaction mixture was cooled to rt, diluted with diethyl ether and added aqueous KF solution and stirred vigorously for 1 hr. The biphasic mixture was filtered through a pad of Celite, diluted with ethyl acetate and washed with aqueous KF solution, brine, dried (MgSO$_4$), filtered and concentrated to give a yellow solid. Dissolved solid in DCM, adsorbed onto silica gel and purified by CombiFlash (0 to 50% EtOAc/Hex) to give desired product. LCMS-ESI$^+$: calc'd for $C_{20}H_{36}N_3Sn$: 438.2 (M+H$^+$); Found: 438.2 (M+H$^+$).

Preparation of (S)-ethyl 2-tert-butoxy-2-(7-(4-chlorophenyl)-2-(2-(1,3-dimethyl-1H-pyrazolo[3,4-c]pyridin-5-yl)pyridin-4-yl)-5-methylbenzo[d]thiazol-6-yl)acetate: A mixture of 1,3-dimethyl-5-(tributylstannyl)-1H-pyrazolo[3,4-c]pyridine (31 mg, 0.071 mmol), (S)-ethyl 2-tert-butoxy-2-(7-(4-chlorophenyl)-2-(2-chloropyridin-4-yl)-5-methylbenzo[d]thiazol-6-yl)acetate (30.1 mg, 0.057 mmol), copper(I) iodide (13.5 mg, 0.071 mmol) and lithium chloride (15.1 mg, 0.355 mmol) in dioxane (0.5 mL) was sparged with nitrogen for 10 minutes. Tetrakis(triphenylphosphine)palladium(0) (8.9 mg, 0.0008 mmol) and trans-dichlorobis(triphenylphosphine) palladium (II) (5.2 mg, 0.007 mmol) were added and reaction mixture was heated at 120° C. for 5 hours. Reaction mixture was cooled to rt, diluted with dichloromethane, adsorbed onto silica gel and purified by CombiFlash (0 to 70% EtOAc/Hex) to give product contaminated with tributylstannane impurity. LCMS-ESI$^+$: calc'd for $C_{35}H_{35}ClN_5O_3S$: 640.2 (M+H$^+$); Found: 640.4 (M+H$^+$).

Preparation of (S)-2-tert-butoxy-2-(7-(4-chlorophenyl)-2-(2-(1,3-dimethyl-1H-pyrazolo[3,4-c]pyridin-5-yl)pyridin-4-yl)-5-methylbenzo[d]thiazol-6-yl)acetic acid: A solution of (S)-ethyl 2-tert-butoxy-2-(7-(4-chlorophenyl)-2-(2-(1,3-dimethyl-1H-pyrazolo[3,4-c]pyridin-5-yl)pyridin-4-yl)-5-methylbenzo[d]thiazol-6-yl)acetate (5.6 mg, 0.009 mmol) and 5M NaOH (0.035 mL, 0.175 mmol) in MeOH (0.1 mL) and THF (0.5 mL) was stirred at 50° C. for 3 hours, then stored in freezer overnight. DMF (0.3 mL) and acetic acid (0.011 mL) were added and reaction mixture was concentrated to ~0.3 mL, filtered using a syringe filter, diluted with methanol. Purified using Gilson HPLC (Gemini, 5 to 100% ACN/H$_2$O+0.1% TFA) and lyophilized to give desired product. LCMS-ESI$^+$: calc'd for $C_{33}H_{31}ClN_5O_3S$: 612.2 (M+H$^+$); Found: 612.3 (M+H$^+$); $^1$H NMR (400 MHz, CD$_3$OD) δ 7.95 (s, 2H), 7.8-7.6 (m, 8H), 5.26 (s, 1H), 4.13 (s, 3H), 2.69 (s, 3H), 2.64 (s, 3H), 0.97 (s, 9H).

Preparation of (S)-ethyl 2-tert-butoxy-2-(7-(4-chlorophenyl)-2-(1,3-dimethyl-1H-pyrazolo[3,4-c]pyridin-5-yl)-5-methylbenzo[d]thiazol-6-yl)acetate: A mixture of 1,3-dimethyl-5-(tributylstannyl)-1H-pyrazolo[3,4-c]pyridine (31 mg, 0.071 mmol), (S)-ethyl 2-(2-bromo-7-(4-chlorophenyl)-5-methylbenzo[d]thiazol-6-yl)-2-tert-butoxyacetate (42 mg, 0.085 mmol), copper(I) iodide (14 mg, 0.071 mmol) and lithium chloride (15 mg, 0.355 mmol) in dioxane (0.5 mL) was sparged with nitrogen for 10 minutes. Tetrakis(triphenylphosphine)palladium(0) (9 mg, 0.0008 mmol) and trans-dichlorobis(triphenylphosphine)palladium (II) (5 mg, 0.007 mmol) were added and reaction mixture was heated at 120° C. for 5 hours. Reaction mixture was cooled to rt, diluted with dichloromethane, adsorbed onto silica gel and purified by CombiFlash (0 to 70% EtOAc/Hex) to give product contaminated with tributylstannane impurity. LCMS-ESI⁺: calc'd for $C_{35}H_{35}ClN_5O_3S$: 640.2 (M+H⁺); Found: 640.4 (M+H⁺).

Preparation of (S)-2-tert-butoxy-2-(7-(4-chlorophenyl)-2-(1,3-dimethyl-1H-pyrazolo[3,4-c]pyridin-5-yl)-5-methylbenzo[d]thiazol-6-yl)acetic acid: A solution of (S)-ethyl 2-tert-butoxy-2-(7-(4-chlorophenyl)-2-(1,3-dimethyl-1H-pyrazolo[3,4-c]pyridin-5-yl)-5-methylbenzo[d]thiazol-6-yl)acetate (17.9 mg, 0.032 mmol) and 5M NaOH (0.127 mL, 0.636 mmol) in MeOH (0.2 mL) and THF (1.2 mL) was stirred at 50° C. for 3 hours, then stored in freezer overnight. DMF (0.3 mL) and acetic acid (0.011 mL) were added and reaction mixture was concentrated to ~0.3 mL, filtered using a syringe filter, diluted with methanol. Purified using Gilson HPLC (Gemini, 5 to 100% ACN/H₂O+0.1% TFA) and lyophilized to give desired product. LCMS-ESI⁺: calc'd for $C_{28}H_{28}ClN_4O_3S$: 535.2 (M+H⁺); Found: 535.3 (M+H⁺); ¹H NMR (400 MHz, CD₃OD) δ 8.83 (s, 1H), 8.45 (s, 1H), 7.73 (s, 1H), 7.70 (d, J=8.4 Hz, 1H), 7.58 (d, J=8.4 Hz, 1H), 7.57 (s, 1H), 5.26 (s, 1H), 4.02 (s, 3H), 2.59 (s, 3H), 2.53 (s, 3H), 0.97 (s, 9H).

Example 96

Preparation of (S)-2-tert-butoxy-2-(7-(4-chlorophenyl)-5-methyl-2-(2-(1-methyl-2-oxoindolin-4-yl)pyridin-4-yl)benzo[d]thiazol-6-yl)acetic acid (236)

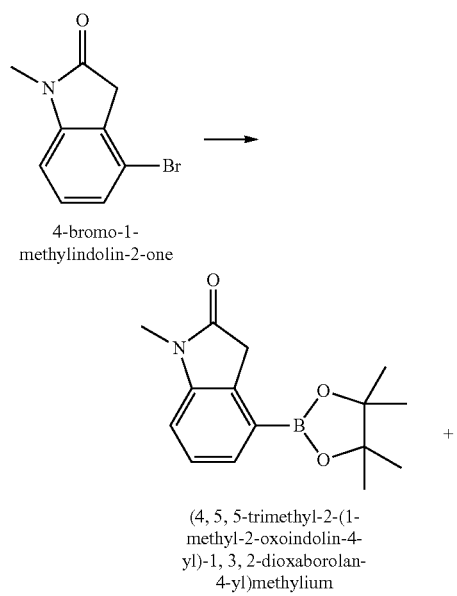

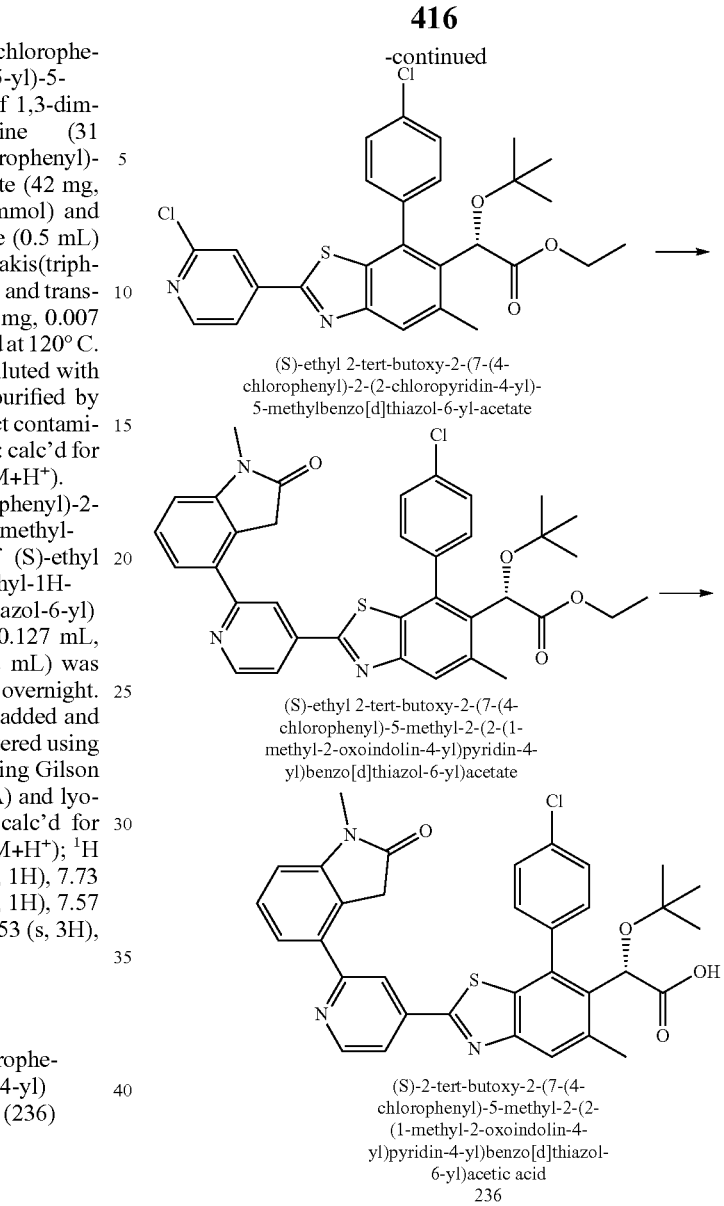

Preparation of (4,5,5-trimethyl-2-(1-methyl-2-oxoindolin-4-yl)-1,3,2-dioxaborolan-4-yl)methylium: To a solution of 4-bromo-1-methylindolin-2-one (154 mg, 0.68 mmol) in anhydrous dioxane (4 mL, degassed) was added Pd(dppf)Cl₂ (74 mg, 0.15 eq.), bis(pinacolato)diboron (173 mg, 1 eq.) and KOAc (200 mg, 3 eq.). The reaction mixture was heated at 110° C. for 40 minutes, cooled and partitioned between ethyl acetate and brine. The organic layer was separated, dried over Na₂SO₄, filtered and concentrated to give crude product which was purified by chromatographic column to afford the desired product. LCMS-ESI⁺: calc'd for $C_{15}H_{20}BNO_3$: 274.2 (M+H⁺); Found: 274.2 (M+H⁺).

Preparation of Preparation of (S)-ethyl 2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetate: To a solution of (S)-ethyl 2-tert-butoxy-2-(7-(4-chlorophenyl)-2-(2-chloropyridin-4-yl)-5-methylbenzo[d]thiazol-6-yl)acetate (20 mg, 0.038 mmol) in dioxane (1.2 mL, degassed) was added (4,5,5-trimethyl-2-(1-methyl-2-oxoindolin-4-yl)-1,3,2-dioxaborolan-4-yl)methylium (16 mg, 1.5 eq.), Pd(PPh₃)₄ (6 mg, 0.05 eq.), K₂CO₃ (16 mg, 2 eq.) and water (0.1 mL). The reaction mixture was heated at 110° C. for 2 h, cooled and partitioned between ethyl acetate and brine. The organic layer was separated, dried over Na$_2$SO$_4$, filtered and concentrated to give crude which was purified by chromatographic column to afford the desired product. LCMS-ESI$^+$: calc'd for C$_{36}$H$_{35}$ClN$_3$O$_4$S: 640.2 (M+H$^+$); Found: 640.3 (M+H$^+$).

Preparation of (S)-2-tert-butoxy-2-(7-(4-chlorophenyl)-5-methyl-2-(2-(1-methyl-2-oxoindolin-4-yl)pyridin-4-yl)benzo[d]thiazol-6-yl)acetic acid: To a solution of (S)-ethyl 2-tert-butoxy-2-(7-(4-chlorophenyl)-5-methyl-2-(2-(1-methyl-2-oxoindolin-4-yl)pyridin-4-yl)benzo[d]thiazol-6-yl)acetate (11 mg, 0.017 mmol) in pyridine (2 mL) was added ethyl iodide (100 mg, excess). The reaction mixture was heated at 170° C. in microwave reactor for 90 minutes and the crude was concentrated and purified by reverse phase HPLC, eluting by 0-100% acetonitrile in H$_2$O with 0.1% TFA to give the product as TFA salt. LCMS-ESI$^+$: calc'd for C$_{34}$H$_{31}$ClN$_3$O$_4$S: 612.1 (M+H$^+$); Found: 612.2 (M+H$^+$); $^1$H NMR (400 MHz, CD$_3$OD): δ 8.77 (d, 1H), 8.35 (s, 1H), 7.93-7.92 (m, 2H), 7.70-7.68 (m, 1H), 7.61-7.59 (m, 3H), 7.55-7.53 (m, 1H), 7.50-7.46 (m, 1H), 7.08 (d, 1H), 5.27 (s, 1H), 3.89 (s, 2H), 3.25 (s, 3H), 2.63 (s, 3H), 0.97 (s, 9H).

Example 97

Preparation of (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid (237)

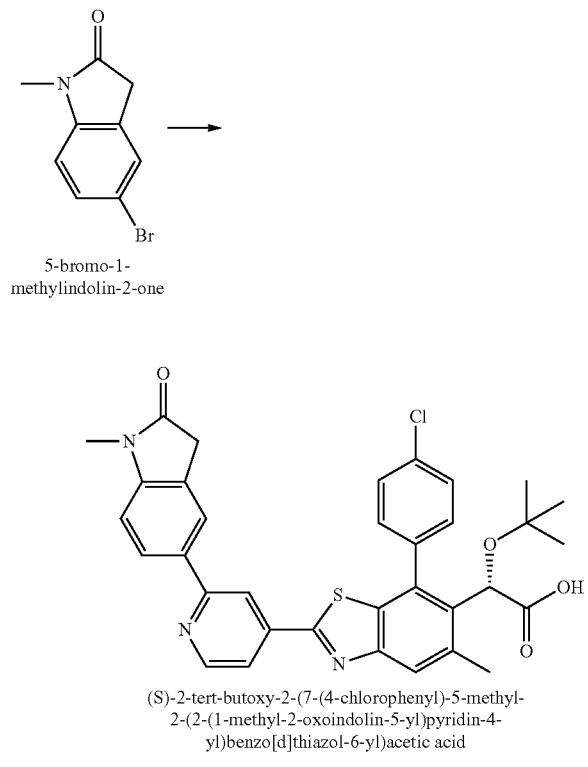

5-bromo-1-methylindolin-2-one (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid

237

Preparation of (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid: (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid was prepared using in a similar manner as (S)-2-tert-butoxy-2-(7-(4-chlorophenyl)-5-methyl-2-(2-(1-methyl-2-oxoindolin-4-yl)pyridin-4-yl)benzo[d]thiazol-6-yl)acetic acid, except 5-bromo-1-methylindolin-2-one was used instead of 4-bromo-1-methylindolin-2-one. LCMS-ESI$^+$: calc'd for C$_{34}$H$_{31}$ClN$_3$O$_4$S: 612.1 (M+H$^+$); Found: 612.2 (M+H$^+$). $^1$H NMR (400 MHz, CD$_3$OD) δ: 8.61 (d, 1H), 8.36 (s, 1H), 7.94 (d, 1H), 7.89 (m, 1H), 7.84 (m, 2H), 7.61-7.59 (m, 1H), 7.54-7.50 (m, 3H), 7.03 (d, 1H), 5.18 (s, 1H), 3.55 (s, 2H), 3.14 (s, 3H), 2.53 (s, 3H), 0.89 (s, 9H).

Example 98

Preparation of (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid (238)

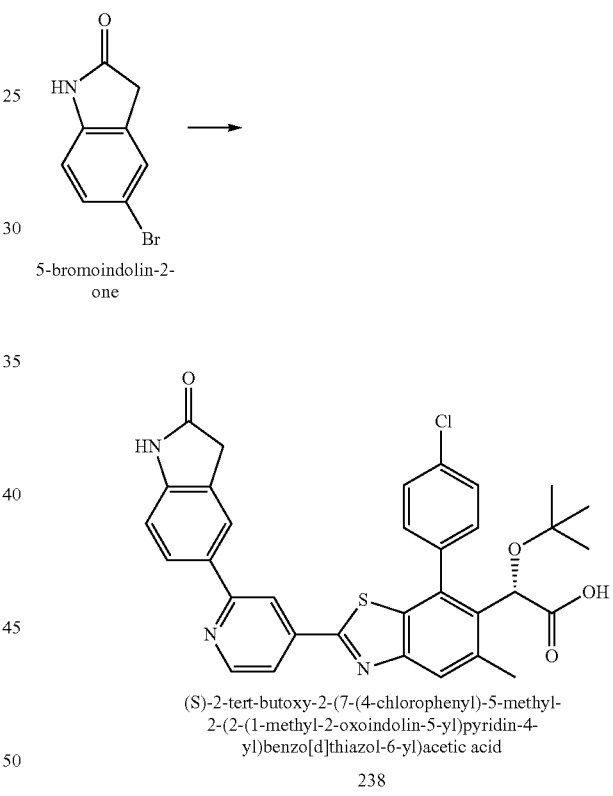

5-bromoindolin-2-one (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid

238

Preparation of (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid: (S)-2-tert-butoxy-2-(7-(4-chlorophenyl)-5-methyl-2-(2-(1-methyl-2-oxoindolin-5-yl)pyridin-4-yl)benzo[d]thiazol-6-yl)acetic acid was prepared in a similar manner as (S)-2-tert-butoxy-2-(7-(4-chlorophenyl)-5-methyl-2-(2-(1-methyl-2-oxoindolin-4-yl)pyridin-4-yl)benzo[d]thiazol-6-yl)acetic acid except 5-bromoindolin-2-one was used instead of 4-bromo-1-methylindolin-2-one. LCMS-ESI$^+$: calc'd for C$_{33}$H$_{29}$ClN$_3$O$_4$S: 598.2 (M+H$^+$); Found: 598.3 (M+H$^+$); $^1$H NMR (400 MHz, CD$_3$OD) δ: 8.71 (d, 1H), 8.45 (s, 1H), 8.01 (d, 1H), 8.00-7.91 (m, 3H), 7.68 (m, 1H), 7.60 (m, 3H), 7.06 (d, 1H), 5.27 (s, 1H), 3.63 (s, 2H), 2.63 (s, 3H), 2.35 (s, 3H), 0.98 (s, 9H).

Example 99

Preparation of (S)-2-tert-butoxy-2-(7-(4-chlorophenyl)-5-methyl-2-(1-methyl-2-oxoindolin-5-yl)benzo[d]thiazol-6-yl)acetic acid (239)

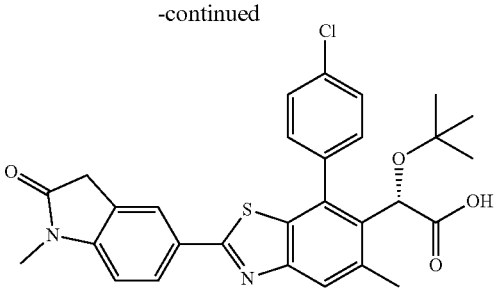

(S)-2-tert-butoxy-2-(7-(4-chlorophenyl)-5-methyl-2-(1-methyl-2-oxoindolin-5-yl)benzo[d]thiazol-6-yl)acetic acid
239

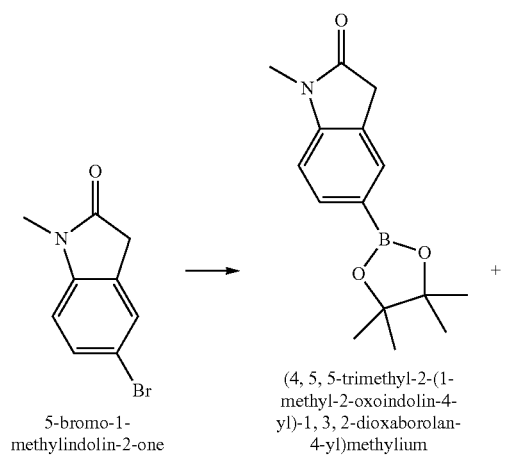

5-bromo-1-methylindolin-2-one (4, 5, 5-trimethyl-2-(1-methyl-2-oxoindolin-4-yl)-1, 3, 2-dioxaborolan-4-yl)methylium Preparation of 1-methyl-5-(4,4,5,5-tetramethyl-1,3,2-dioxaborolan-2-yl)indolin-2-one: To a solution of 5-bromo-1-methylindolin-2-one (79 mg, 0.35 mmol) in anhydrous dioxane (4 mL, degassed) was added Pd(dppf)Cl$_2$ (38 mg, 0.15 eq.), bis(pinacolato)diboron (89 mg, 1 eq.) and KOAc (69 mg, 3 eq.). The reaction mixture was heated at 110° C. for 40 minutes, cooled and partitioned between ethyl acetate and brine. The organic layer was separated, dried over Na$_2$SO$_4$, filtered and concentrated to give crude which was purified by chromatographic column to afford the desired product. LCMS-ESI$^+$: calc'd for C$_{15}$H$_{21}$BNO$_3$: 274.2 (M+H$^+$); Found: 274.2 (M+H$^+$).

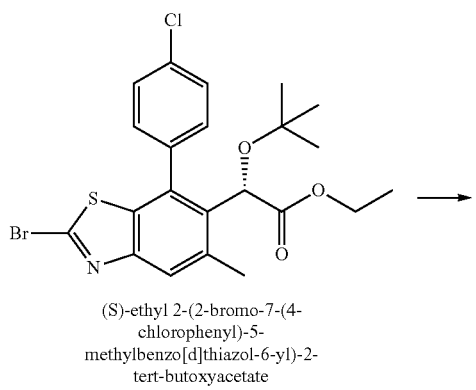

(S)-ethyl 2-(2-bromo-7-(4-chlorophenyl)-5-methylbenzo[d]thiazol-6-yl)-2-tert-butoxyacetate Preparation of (S)-ethyl 2-tert-butoxy-2-(7-(4-chlorophenyl)-5-methyl-2-(2-(1-methyl-2-oxoindolin-4-yl)pyridin-4-yl)benzo[d]thiazol-6-yl)acetate: To a solution of (S)-ethyl 2-(2-bromo-7-(4-chlorophenyl)-5-methylbenzo[d]thiazol-6-yl)-2-tert-butoxyacetate (50 mg, 0.1 mmol) in dioxane (1.2 mL, degassed) was added 1-methyl-5-(4,4,5,5-tetramethyl-1,3,2-dioxaborolan-2-yl)indolin-2-one (30 mg, 1.1 eq.), Pd(PPh$_3$)$_4$ (17 mg, 0.05 eq.), K$_2$CO$_3$ (42 mg, 2 eq.) and water (0.1 mL). The reaction mixture was heated at 110° C. for 2 h, cooled and partitioned between ethyl acetate and brine. The organic layer was separated, dried over Na$_2$SO$_4$, filtered and concentrated to give crude which was purified by chromatographic column to afford the desired product. LCMS-ESI$^+$: calc'd for C$_{31}$H$_{32}$ClN$_2$O$_4$S: 563.2 (M+H$^+$); Found: 563.3 (M+H$^+$).

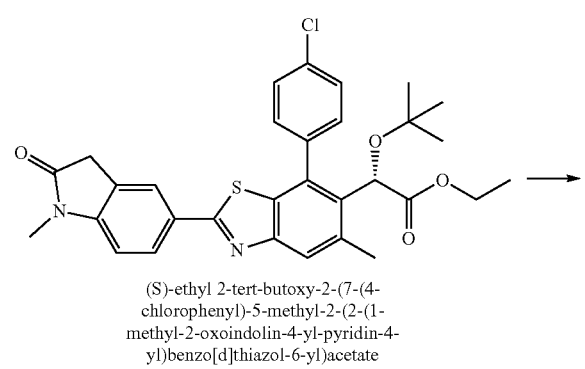

(S)-ethyl 2-tert-butoxy-2-(7-(4-chlorophenyl)-5-methyl-2-(2-(1-methyl-2-oxoindolin-4-yl-pyridin-4-yl)benzo[d]thiazol-6-yl)acetate Preparation (S)-2-tert-butoxy-2-(7-(4-chlorophenyl)-5-methyl-2-(1-methyl-2-oxoindolin-5-yl)benzo[d]thiazol-6-yl)acetic acid: To a solution of (S)-ethyl 2-tert-butoxy-2-(7-(4-chlorophenyl)-5-methyl-2-(2-(1-methyl-2-oxoindolin-4-yl)pyridin-4-yl)benzo[d]thiazol-6-yl)acetate (11 mg, 0.017 mmol) in pyridine (2 mL) was added ethyl iodide (100 mg, excess). The reaction mixture was heated at 170° C. in microwave reactor for 90 minutes and the crude was concentrated and purified by reverse phase HPLC, eluting by 0-100% acetonitrile in H$_2$O with 0.1% TFA to give the product as TFA salt. LCMS-ESI$^+$: calc'd for C$_{29}$H$_{28}$ClN$_2$O$_4$S: 535.1 (M+H$^+$); Found: 535.2 (M+H$^+$). $^1$H NMR (400 MHz, CD$_3$OD) δ: 7.96-7.84 (m, 2H), 7.67 (s, 1H), 7.59-7.56 (m, 2H), 7.49-7.47 (m, 2H), 6.95 (d, 1H), 5.14 (s, 1H), 3.52 (s, 2H), 3.13 (s, 3H), 2.50 (s, 3H), 0.87 (s, 9H).

Example 100

Preparation of (S)-2-tert-butoxy-2-(7-(4-chlorophenyl)-5-methyl-2-(2-oxoindolin-5-yl)benzo[d]thiazol-6-yl)acetic acid (240)

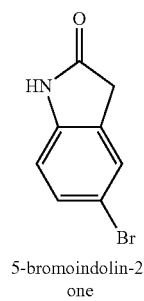

5-bromoindolin-2-one

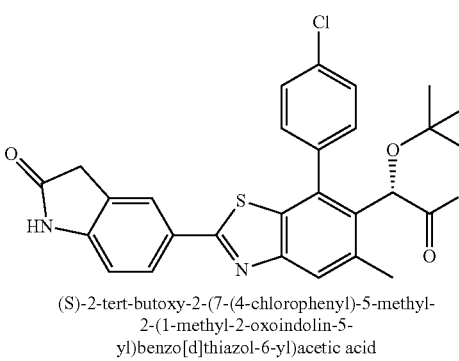

(S)-2-tert-butoxy-2-(7-(4-chlorophenyl)-5-methyl-2-(1-methyl-2-oxoindolin-5-yl)benzo[d]thiazol-6-yl)acetic acid
240

Preparation of (S)-2-tert-butoxy-2-(7-(4-chlorophenyl)-5-methyl-2-(2-oxoindolin-5-yl)benzo[d]thiazol-6-yl)acetic acid: (S)-2-tert-butoxy-2-(7-(4-chlorophenyl)-5-methyl-2-(2-oxoindolin-5-yl)benzo[d]thiazol-6-yl)acetic acid was prepared in a similar manner as (S)-2-tert-butoxy-2-(7-(4-chlorophenyl)-5-methyl-2-(1-methyl-2-oxoindolin-5-yl)benzo[d]thiazol-6-yl)acetic acid except 5-bromoindolin-2-one was used instead of 5-bromo-1-methylindolin-2-one. LCMS-ESI⁺: calc'd $C_{28}H_{26}ClN_2O_4S$: 521.1 (M+H⁺); Found: 521.2 (M+H⁺). ¹H NMR (400 MHz, CD₃OD) δ: 7.91-7.88 (m, 2H), 7.77 (s, 1H), 7.66 (m, 1H), 7.59-7.56 (m, 2H), 6.99 (d, 1H), 5.23 (s, 1H), 3.61 (s, 2H), 2.63 (s, 3H), 2.59 (s, 3H), 0.96 (s, 9H).

Example 101

Preparation of (S)-2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetic acid (241)

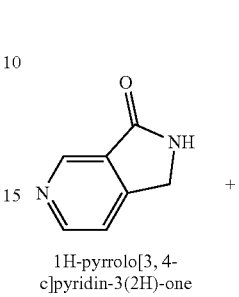

1H-pyrrolo[3,4-c]pyridin-3(2H)-one
+

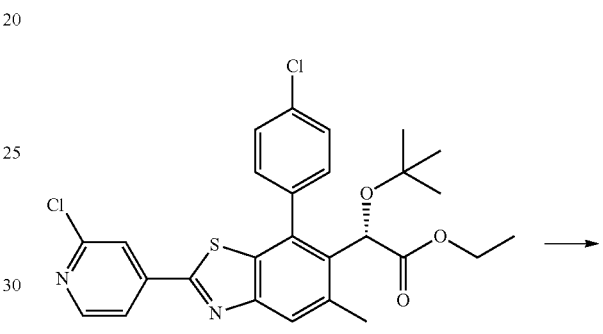

(S)-ethyl 2-tert-butoxy-2-(7-(4-chlorophenyl)-2-(2-chloropyridin-4-yl)-5-methylbenzo[d]thiazol-6-yl)acetate

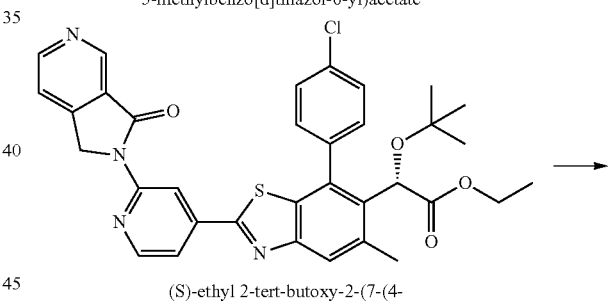

(S)-ethyl 2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetate

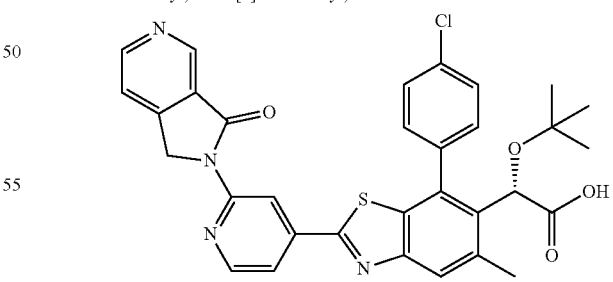

(S)-2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetic acid
241

Preparation of (S)-ethyl 2-tert-butoxy-2-(7-(4-chlorophenyl)-5-methyl-2-(2-(3-oxo-1H-pyrrolo[3,4-c]pyridin-2(3H)- yl)pyridin-4-yl)benzo[d]thiazol-6-yl)acetate: To a solution of (S)-ethyl 2-tert-butoxy-2-(7-(4-chlorophenyl)-2-(2-chloropyridin-4-yl)-5-methylbenzo[d]thiazol-6-yl)acetate (28 mg, 0.053 mmol) in anhydrous THF (1.2 mL, degassed) was added $Pd_2(dba)_3$ (3 mg, 0.05 eq.), XantPhos (5 mg, 0.15 eq.), 1H-pyrrolo[3,4-c]pyridin-3(2H)-one (14 mg, 2 eq.) and $Cs_2CO_3$ (35 mg, 2 eq.). The reaction mixture was heated at 100° C. for 2 h, cooled and partitioned between ethyl acetate and brine. The organic layer was separated, dried over $Na_2SO_4$, filtered and concentrated to give crude which was purified by chromatographic column to afford the desired product. LCMS-ESI$^+$: calc'd for $C_{34}H_{32}ClN_4O_4S$: 627.2 (M+H$^+$); Found: 627.3 (M+H$^+$).

Preparation of (S)-2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetic acid: To a solution of (S)-ethyl 2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetate (28 mg, 0.044 mmol) in pyridine (2 mL) was added ethyl iodide (200 mg, excess). The reaction mixture was heated at 170° C. in microwave reactor for 90 minutes and the crude was concentrated and purified by reverse phase HPLC, eluting by 0-100% acetonitrile in $H_2O$ with 0.1% TFA to give the product. LCMS-ESI$^+$: calc'd for $C_{32}H_{28}ClN_4O_4S$: 599.1 (M+H$^+$); Found: 599.2 (M+H$^+$). $^1$H NMR (400 MHz, CD$_3$OD) δ: 8.80 (s, 1H), 8.58 (s, 2H), 8.18 (d, 1H), 7.57 (m, 2H), 7.50-7.43 (m, 4H), 7.33 (s, 1H), 5.14 (s, 1H), 4.68 (d, 2H), 2.33 (s, 3H), 0.90 (s, 9H).

Example 102

Preparation of (S)-2-tert-butoxy-2-(7-(4-chlorophenyl)-5-methyl-2-(1-methyl-2-oxoindolin-5-yl)benzo[d]thiazol-6-yl)acetic acid (242)

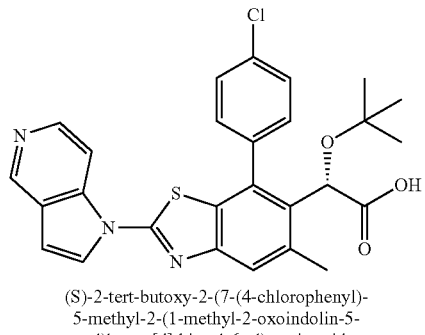

(S)-2-tert-butoxy-2-(7-(4-chlorophenyl)-5-methyl-2-(1-methyl-2-oxoindolin-5-yl)benzo[d]thiazol-6-yl)acetic acid Preparation of (S)-2-tert-butoxy-2-(7-(4-chlorophenyl)-5-methyl-2-(1-methyl-2-oxoindolin-5-yl)benzo[d]thiazol-6-yl)acetic acid: (S)-2-tert-butoxy-2-(7-(4-chlorophenyl)-5-methyl-2-(1-methyl-2-oxoindolin-5-yl)benzo[d]thiazol-6-yl)acetic acid was prepared in a similar manner as (S)-2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetic acid except (S)-ethyl 2-(2-bromo-7-(4-chlorophenyl)-5-methylbenzo[d]thiazol-6-yl)-2-tert-butoxyacetate was used instead of (S)-ethyl 2-tert-butoxy-2-(7-(4-chlorophenyl)-2-(2-chloropyridin-4-yl)-5-methylbenzo[d]thiazol-6-yl)acetate, 1H-pyrrolo[3,2-c]pyridine was used instead 1H-pyrrolo[3,4-c]pyridin-3(2H)-one and Pd(P-tBu$_3$)$_2$ was used instead of Pd$_2$(dba)$_3$ LCMS-ESI$^+$: calc'd $C_{27}H_{25}ClN_3O_3S$: 506.0 (M+H$^+$); Found: 506.2 (M+H$^+$). $^1$H NMR (400 MHz, CD$_3$OD) δ: 9.31 (s, 1H), 9.18 (d, 1H), 8.66 (d, 1H), 8.31 (d, 1H), 7.90 (s, 1H), 7.72-7.70 (m, 1H), 7.63-7.61 (m, 3H), 7.32 (d, 1H), 5.26 (s, 1H), 2.63 (s, 3H), 0.98 (s, 9H).

Example 103

Preparation of (S)-2-tert-butoxy-2-(7-(4-chlorophenyl)-5-methyl-2-(5-methylindolin-1-yl)benzo[d]thiazol-6-yl)acetic acid (243)

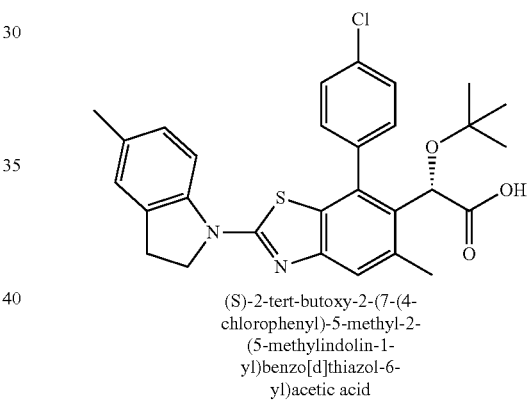

(S)-2-tert-butoxy-2-(7-(4-chlorophenyl)-5-methyl-2-(5-methylindolin-1-yl)benzo[d]thiazol-6-yl)acetic acid Preparation of (S)-2-tert-butoxy-2-(7-(4-chlorophenyl)-5-methyl-2-(5-methylindolin-1-yl)benzo[d]thiazol-6-yl)acetic acid: (S)-2-tert-butoxy-2-(7-(4-chlorophenyl)-5-methyl-2-(5-methylindolin-1-yl)benzo[d]thiazol-6-yl)acetic acid was prepared in similar manner as (S)-2-tert-butoxy-2-(7-(4-chlorophenyl)-5-methyl-2-(2-(3-oxo-1H-pyrrolo[3,4-c]pyridin-2(3H)-yl)pyridin-4-yl)benzo[d]thiazol-6-yl)acetic acid except (S)-ethyl 2-(2-bromo-7-(4-chlorophenyl)-5-methylbenzo[d]thiazol-6-yl)-2-tert-butoxyacetate was used instead of (S)-ethyl 2-tert-butoxy-2-(7-(4-chlorophenyl)-2-(2-chloropyridin-4-yl)-5-methylbenzo[d]thiazol-6-yl)acetate, 5-Methylindoline was used instead 1H-pyrrolo[3,4-c]pyridin-3(2H)-one and Pd(P-tBu$_3$)$_2$ was used instead of Pd$_2$(dba)$_3$. LCMS-ESI$^+$: $C_{29}H_{30}ClN_2O_3S$: 521.2 (M+H$^+$); Found: 521.2 (M+H$^+$); $^1$H NMR (400 MHz, CD$_3$OD) δ: 7.75 (s, 1H), 7.67-7.64 (m, 1H), 7.57-7.50 (m, 3H), 7.44 (s, 1H), 7.12 (d, 1H), 6.84 (d, 1H), 5.17 (s, 1H), 4.07 (dd, 2H), 3.19 (dd, 2H), 2.53 (s, 3H), 2.35 (s, 3H), 0.95 (s, 9H).

Example 105

Preparation of (S)-2-tert-butoxy-2-(7-(4-chlorophenyl)-2-(2-(2,3-dihydro-1H-pyrrolo[3,2-c]pyridin-1-yl)pyridin-4-yl)-5-methylbenzo[d]thiazol-6-yl)acetic acid (245)

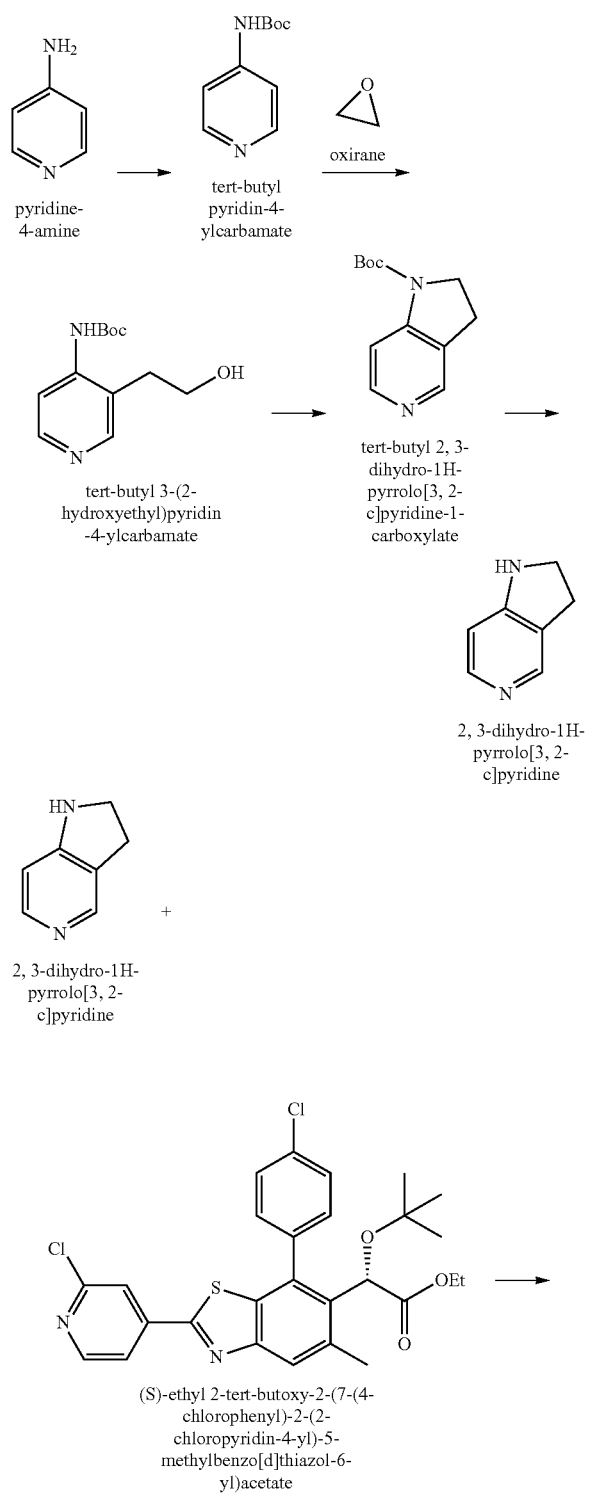

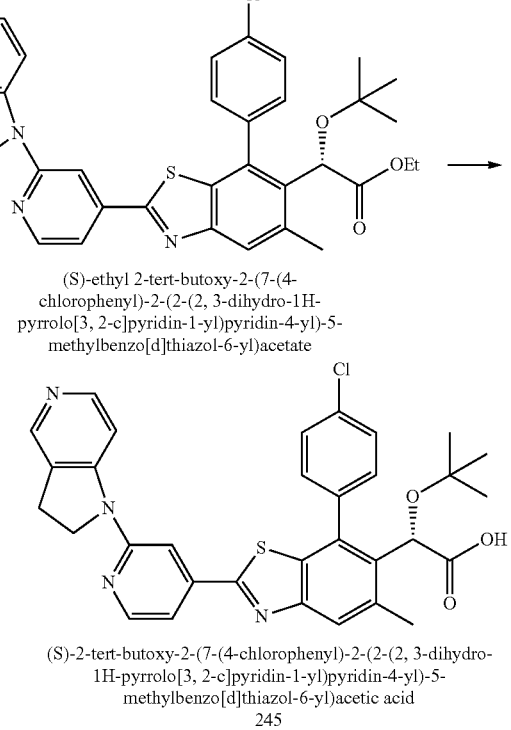

Preparation of tert-butyl 2,3-dihydro-1H-pyrrolo[3,2-c]pyridine-1-carboxylate: Followed reference procedure (Spivey, Alan C. et al. *J. Org. Chem.* 1999, 64(26), 9430-9443) using pyridin-4-amine. LCMS-ESI+: calc'd for $C_{12}H_{17}N_2O_2$: 221.1 (M+H+); Found: 221.0 (M+H+).

Preparation 2,3-dihydro-1H-pyrrolo[3,2-c]pyridine: tent-Butyl 2,3-dihydro-1H-pyrrolo[3,2-c]pyridine-1-carboxylate (280 mg) was dissolved in 5 mL DCM. TFA (1 mL) was added room temperature. The reaction was stirred at room temperature for 1 hour. Concentrated down the reaction mixture and the crude material was used in next step without purification. Crude $^1$H NMR (400 MHz, CD$_3$OD): δ 8.43 (d, 1H), 8.37 (s, 1 H), 8.07 (d, 1H), 4.22 (dd, 2 H), 3.36 (m, 2H).

Preparation of (S)-ethyl 2-tert-butoxy-2-(7-(4-chlorophenyl)-2-(2-(2,3-dihydro-1H-pyrrolo[3,2-c]pyridin-1-yl)pyridin-4-yl)-5-methylbenzo[d]thiazol-6-yl)acetate: In a 5 mL microwave reaction tube, 2,3-dihydro-1H-pyrrolo[3,2-c]pyridine TFA salt (excess), (S)-ethyl 2-tert-butoxy-2-(7-(4-chlorophenyl)-2-(2-chloropyridin-4-yl)-5-methylbenzo[d]thiazol-6-yl)acetate (26 mg, 0.05 mmol), bis(tri-tert-butylphosphine)palladium(0) (4 mg, 15%), cetyltrimethylammonium bromide (3 mg) were charged with 1 mL toluene, then 1 drop of 50% KOH aqueous solution was added. The reaction was heated to 105° C. for 1 hour. LC-MS of the reaction crude show desired product. The reaction crude was extracted using ethyl acetate form brine. The organic layer was separated, dried over Na$_2$SO$_4$, filtered and concentrated to give crude which was purified by chromatographic column to afford the desired product. LCMS-ESI+: calc'd for $C_{34}H_{34}ClN_4O_3S$: 613.1 (M+H+); Found: 613.3 (M+H+).

Preparation of (S)-2-tert-butoxy-2-(7-(4-chlorophenyl)-2-(2-(2,3-dihydro-1H-pyrrolo[3,2-c]pyridin-1-yl)pyridin-4-yl)-5-methylbenzo[d]thiazol-6-yl)acetic acid: To a solution of (S)-ethyl 2-tert-butoxy-2-(7-(4-chlorophenyl)-2-(2-(2,3-dihydro-1H-pyrrolo[3,2-c]pyridin-1-yl)pyridin-4-yl)-5-methylbenzo[d]thiazol-6-yl)acetate (18 mg, 0.017 mmol) in THF (0.3 mL) and methanol (0.3 mL) was added NaOH (0.1 mL of 2N solution). The reaction mixture was heated at 45° C. for 2 h, cooled, filtered, and purified by reverse phase HPLC. Fractions containing the product were pooled and lyophilized to provide the TFA salt of the product. LCMS-ESI⁺: calc'd for $C_{32}H_{30}ClN_4O_3S$: 585.1 (M+H⁺); Found: 585.2 (M+H⁺); ¹H NMR (400 MHz, CD₃OD) δ 8.62(d, 1H), 8.58 (d, 1H), 8.33 (d, 1H), 8.23 (s, 1H), 7.87 (s, 1H), 7.66-7.61 (m, 3), 7.59-7.49 (m, 3H), 5.24 (s, 1H), 4.43 (m, 2H), 3,42(m, 2H), 2.61 (s, 3H), 0.98 (s, 9H).

Example 106

Preparation of (S)-2-tert-butoxy-2-(7-(4-chlorophenyl)-2-(4-(4-isopropylpiperazin-yl)thiazol-2-yl)-5-methylbenzo[d]thiazol-6-yl)acetic acid (246)

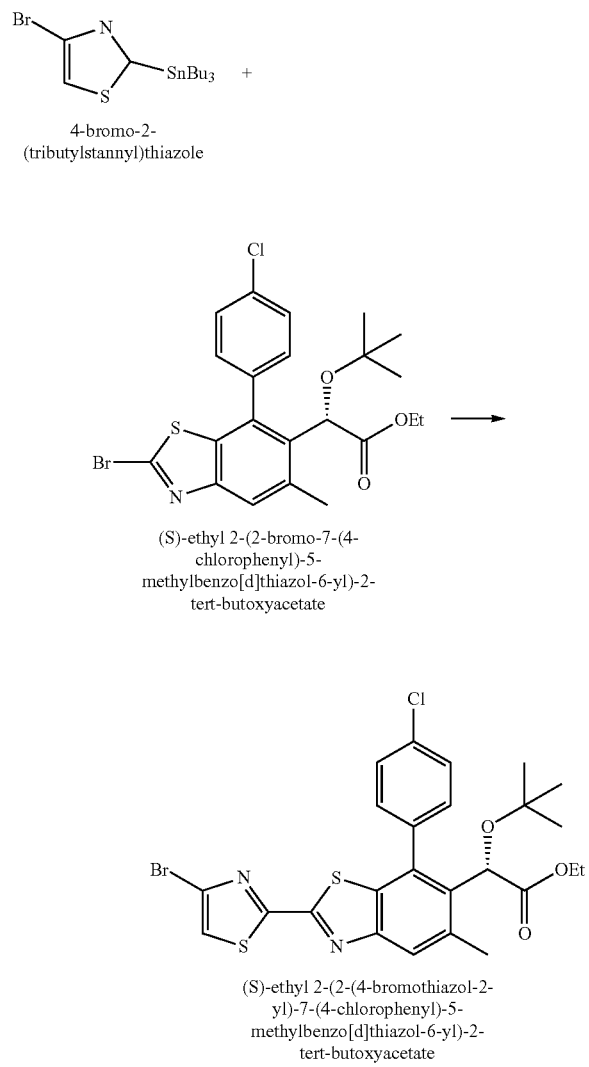

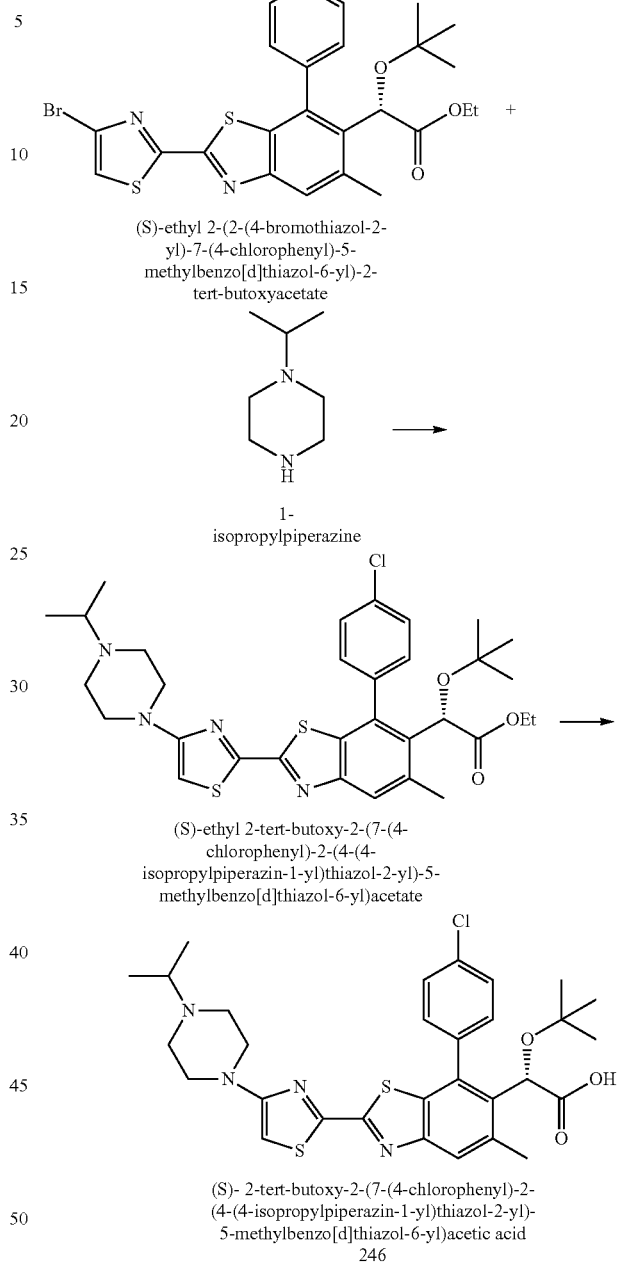

Preparation of (S)-ethyl 2-(2-(4-bromothiazol-2-yl)-7-(4-chlorophenyl)-5-methylbenzo[d]thiazol-6-yl)-2-tert-butoxyacetate: In a 5 mL microwave reaction tube, (S)-ethyl 2-(2-bromo-7-(4-chlorophenyl)-5-methylbenzo[d]thiazol-6-yl)-2-tert-butoxyacetate (240 mg, 0.5 mmol), 4-bromo-2-(tributylstannyl)thiazole (0.25 mL, 1.5 eq.), Pd(PPh₃)₄ (84 mg, 15%) and CuI (14 mg, 15%) were charged, then 4 mL dioxane was added. The reaction mixture was purged N₂, then heated to 100° C. for 3 hour. LC-MS of reaction crude showed desired product mass. The reaction crude was partitioned using ethyl acetate and brine. The organic layer was concentrated and purified via CombiFlash column (0-50% ethyl acetate/hexane) to give desired product. LCMS-ESI⁺: calc'd for $C_{25}H_{25}BrClN_2O_3S_2$: 565.9, found. 567.0 (M+H⁺).

Preparation of (S)-methyl 2-tert-butoxy-2-(7-(4-chlorophenyl)-2-(4-(4-isopropylpiperazin-1-yl)thiazol-2-yl)-5-methylbenzo[d]thiazol-6-yl)acetate: In a 5 mL microwave reaction tube, (S)-methyl 2-(2-(4-bromothiazol-2-yl)-7-(4-chlorophenyl)-5-methylbenzo[d]thiazol-6-yl)-2-tert-butoxyacetate (50 mg, 0.08 mmol), isopropylpiperazine (34 mg, 3 eq.), Bis(tri-t-butylphosphine)palladium(0) (3 mg, 15%), cetyltrimethylammonium bromide (4 mg, 0.5 eq.) were charged with 1 mL toluene, then 1 drop of 50% KOH aqueous solution (excess) was added. The reaction was heated to 105° C. for 1 hour. Reaction mixture was purified by HPLC (0.1% TFA in ACN and water) to give desired product. LCMS-ESI$^+$: calc'd for $C_{31}H_{38}ClN_4O_3S_2$: 613.2 (M+H$^+$); Found: 613.4 (M+H$^+$).

Preparation of (S)-2-tert-butoxy-2-(7-(4-chlorophenyl)-2-(4-(4-isopropylpiperazin-1-yl)thiazol-2-yl)-5-methylbenzo[d]thiazol-6-yl)acetic acid: To a solution of (4 mg) in THF (0.3 mL) and methanol (0.3 mL) was added NaOH (0.1 mL of a 2N solution). The reaction mixture was heated at 50° C. for 2 h, cooled, filtered, and purified by reverse phase HPLC. Fractions containing the product were pooled and lyophilized to provide the TFA salt of the product. LCMS-ESI$^+$: calc'd for $C_{30}H_{36}ClN_4O_3S_2$: 599.2 (M+H$^+$); Found: 599.1. (M+H$^+$). $^1$H NMR (400 MHz, CD$_3$OD) δ 7.84 (s, 1H), 8.68-7.66 (m, 1H), 7.60-7.56 (m, 3H), 6.65 (s, 1H), 5.25 (s, 1H), 3.60-3.56 (m, 4H), 3.30-3.10 (m, 5H), 2.63 (s, 3H), 1.41 (d, 6H), 0.99 (s, 9H).

Example 107

Preparation of (S)-2-tert-butoxy-2-(7-(4-chlorophenyl)-2-(4-(4-isopropylpiperazin-1-yl)thiazol-2-yl)-5-methylbenzo[d]thiazol-6-yl)acetic acid (247)

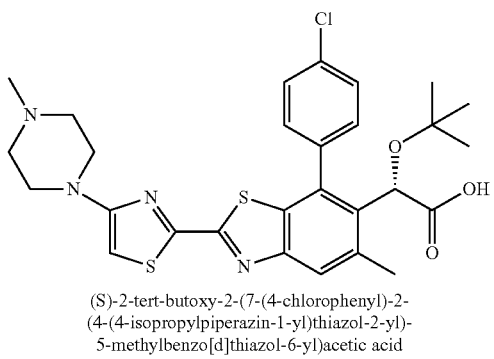

(S)-2-tert-butoxy-2-(7-(4-chlorophenyl)-2-(4-(4-isopropylpiperazin-1-yl)thiazol-2-yl)-5-methylbenzo[d]thiazol-6-yl)acetic acid Preparation of (S)-2-tert-butoxy-2-(7-(4-chlorophenyl)-2-(4-(4-isopropylpiperazin-1-yl)thiazol-2-yl)-5-methylbenzo[d]thiazol-6-yl)acetic acid: (S)-2-tert-butoxy-2-(7-(4-chlorophenyl)-2-(4-(4-isopropylpiperazin-1-yl)thiazol-2-yl)-5-methylbenzo[d]thiazol-6-yl)acetic acid was prepared in a similar manner as (S)-2-tert-butoxy-2-(7-(4-chlorophenyl)-2-(4-(4-isopropylpiperazin-1-yl)thiazol-2-yl)-5-methylbenzo[d]thiazol-6-yl)acetic acid except using 1-methylpiperazine instead of 1-isopropylpiperazine. LCMS-ESI$^+$: calc'd for $C_{28}H_{32}ClN_4O_3S_2$: 571.2 (M+H$^+$); Found: 570.9. (M+H$^+$). $^1$H NMR (400 MHz, CD$_3$OD) δ 7.84 (s, 1H), 8.68-7.66 (m, 1H), 7.60-7.56 (m, 3H), 6.65 (s, 1H), 5.25 (s, 1H), 3.56-3.30 (m, 8H), 2.96 (s, 3H), 2.61 (s, 3H), 0.96 (s, 9H).

Example 108

Preparation of (S)-2-tert-butoxy-2-(7-(4-chlorophenyl)-5-methyl-2-(2-methyl-1-oxoisoindolin-5-yl)benzo[d]thiazol-6-yl)acetic acid (248)

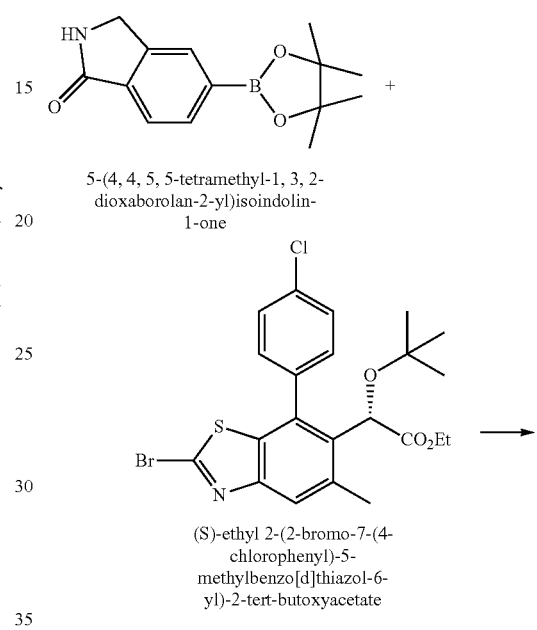

5-(4, 4, 5, 5-tetramethyl-1, 3, 2-dioxaborolan-2-yl)isoindolin-1-one (S)-ethyl 2-(2-bromo-7-(4-chlorophenyl)-5-methylbenzo[d]thiazol-6-yl)-2-tert-butoxyacetate

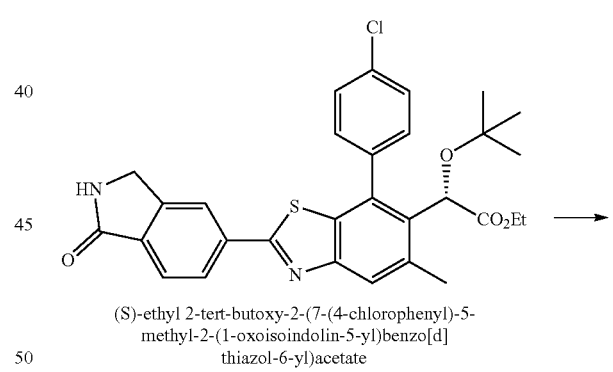

(S)-ethyl 2-tert-butoxy-2-(7-(4-chlorophenyl)-5-methyl-2-(1-oxoisoindolin-5-yl)benzo[d]thiazol-6-yl)acetate

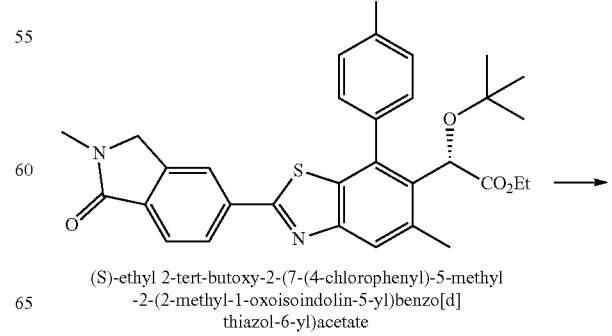

(S)-ethyl 2-tert-butoxy-2-(7-(4-chlorophenyl)-5-methyl-2-(2-methyl-1-oxoisoindolin-5-yl)benzo[d]thiazol-6-yl)acetate

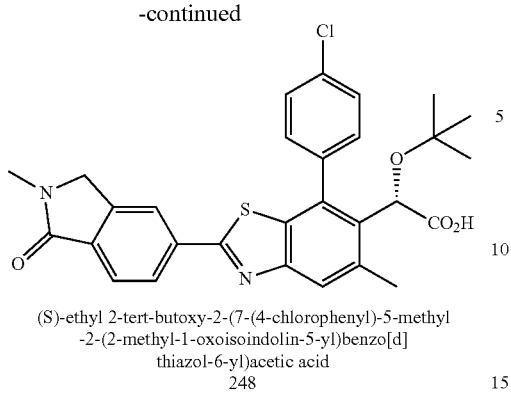

(S)-ethyl 2-tert-butoxy-2-(7-(4-chlorophenyl)-5-methyl-2-(2-methyl-1-oxoisoindolin-5-yl)benzo[d]thiazol-6-yl)acetic acid
248

Preparation of (S)-ethyl 2-tert-butoxy-2-(7-(4-chlorophenyl)-5-methyl-2-(1-oxoisoindolin-5-yl)benzo[d]thiazol-6-yl)acetate: (S)-ethyl 2-tert-butoxy-2-(7-(4-chlorophenyl)-5-methyl-2-(1-oxoisoindolin-5-yl)benzo[d]thiazol-6-yl)acetate was prepared in a similar manner as (S)-methyl 2-tert-butoxy-2-(7-(4-chlorophenyl)-5-methyl-2-(3-methyl-1H-pyrrolo[2,3-b]pyridin-5-yl)benzo[d]thiazol-6-yl)acetate in Method J, except using 5-(4,4,5,5-tetramethyl-1,3,2-dioxaborolan-2-yl)isoindolin-1-one. LCMS-ESI$^+$: calc'd for $C_{30}H_{29}ClN_2O_4S$: 549.2 (M+H$^+$); found: 549.2 (M+H$^+$).

Preparation of (S)-ethyl 2-tert-butoxy-2-(7-(4-chlorophenyl)-5-methyl-2-(2-methyl-1-oxoisoindolin-5-yl)benzo[d]thiazol-6-yl)acetate: To a solution of (S)-ethyl 2-tert-butoxy-2-(7-(4-chlorophenyl)-5-methyl-2-(1-oxoisoindolin-5-yl)benzo[d]thiazol-6-yl)acetate (94 mg, 0.171 mmol) in DMF (2.0 mL) was added NaH (~10 mg, 60% oil dispersion) at 0° C. After 15 min, iodomethane (0.016 mL, 0.256 mmol) was added and after 30 min the reaction was allowed to warm to room temperature. Satd. aqueous NH$_4$Cl was added and the reaction was diluted with EtOAc, washed sequentially with 5% aqueous LiCl and brine. The organic layer was dried over Na$_2$SO$_4$, concentrated and purified by flash column chromatography on silica gel using EtOAc to provide the title compound. LCMS-ESI$^+$: calc'd for $C_{31}H_{31}ClN_2O_4S$: 563.2 (M+H$^+$); found: 563.2 (M+H$^+$).

Preparation of (S)-2-tert-butoxy-2-(7-(4-chlorophenyl)-5-methyl-2-(2-methyl-1-oxoisoindolin-5-yl)benzo[d]thiazol-6-yl)acetic acid: (S)-ethyl 2-tert-butoxy-2-(7-(4-chlorophenyl)-5-methyl-2-(2-methyl-1-oxoisoindolin-5-yl)benzo[d]thiazol-6-yl)acetate (36 mg, 0.064 mmol) dissolved in THF/MeOH (1.25 mL/1.25 mL) and 2N NaOH (0.160 mL) was heated at 50° C. for 2 h and the crude was purified by reverse phase HPLC, eluting by 0-100% acetonitrile in H$_2$O with 0.1% TFA to give the title compound. LCMS-ESI$^+$: calc'd for $C_{29}H_{27}ClN_2O_4S$: 535.1 (M+H$^+$); found: 535.2 (M+H$^+$). $^1$H NMR (400 MHz, DMSO-d$_6$): δ 8.22 (s, 1H), 8.08 (d, J=8.0 Hz, 1H), 7.87 (s, 1H), 7.70 (d, J=8.0 Hz, 1H), 7.65-7.51 (m, 4H), 5.03 (s, 1H), 4.46 (s, 2H), 3.03 (s, 3H), 2.48 (s, 3H), 0.83 (s, 9H).

Example 109

Preparation of (S)-2-tert-butoxy-2-(7-(4-chlorophenyl)-5-methyl-2-(1-methyl-3-(pyridin-3-yl)-1H-pyrrolo[2,3-b]pyridin-5-yl)benzo[d]thiazol-6-yl)acetic acid (249)

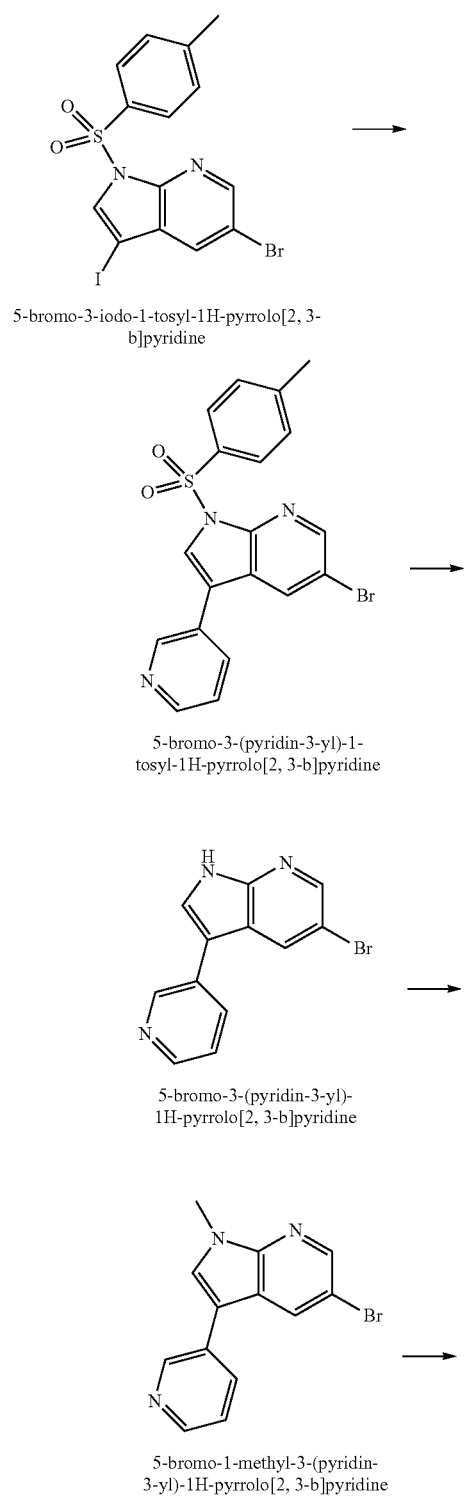

5-bromo-3-iodo-1-tosyl-1H-pyrrolo[2,3-b]pyridine 5-bromo-3-(pyridin-3-yl)-1-tosyl-1H-pyrrolo[2,3-b]pyridine 5-bromo-3-(pyridin-3-yl)-1H-pyrrolo[2,3-b]pyridine 5-bromo-1-methyl-3-(pyridin-3-yl)-1H-pyrrolo[2,3-b]pyridine

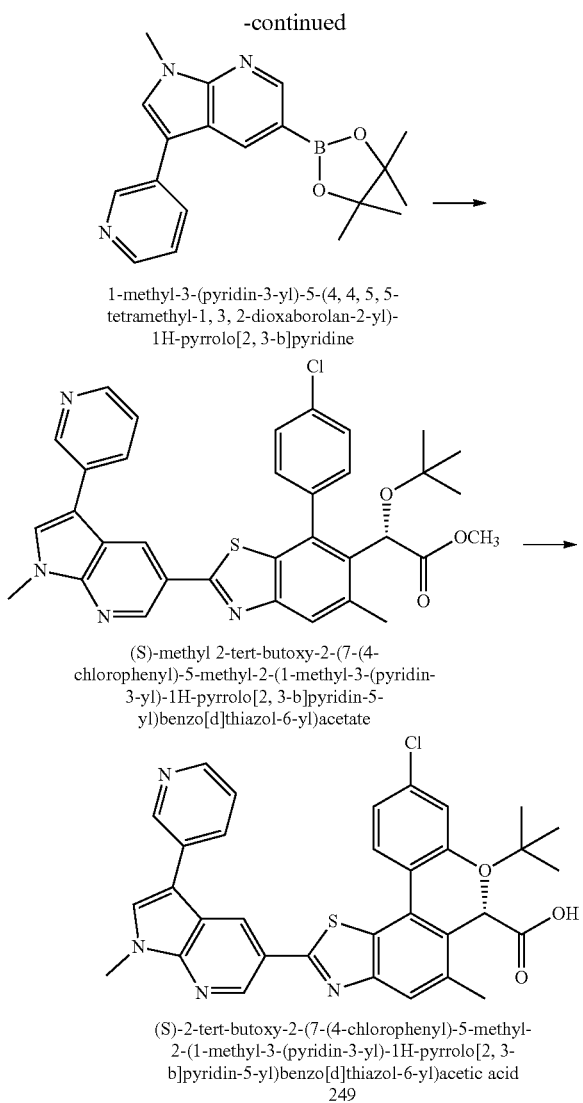

1-methyl-3-(pyridin-3-yl)-5-(4, 4, 5, 5-tetramethyl-1, 3, 2-dioxaborolan-2-yl)-1H-pyrrolo[2, 3-b]pyridine (S)-methyl 2-tert-butoxy-2-(7-(4-chlorophenyl)-5-methyl-2-(1-methyl-3-(pyridin-3-yl)-1H-pyrrolo[2, 3-b]pyridin-5-yl)benzo[d]thiazol-6-yl)acetate (S)-2-tert-butoxy-2-(7-(4-chlorophenyl)-5-methyl-2-(1-methyl-3-(pyridin-3-yl)-1H-pyrrolo[2, 3-b]pyridin-5-yl)benzo[d]thiazol-6-yl)acetic acid
249

Preparation of 5-bromo-3-(pyridin-3-yl)-1-tosyl-1H-pyrrolo[2,3-b]pyridine: To a screw top reaction tube was placed 5-bromo-3-iodo-1-tosyl-1H-pyrrolo[2,3-b]pyridine (1.2 g, 2.52 mmol, prepared according to WO2011/149950), pyridin-3-ylboronic acid (371 mg, 3.02 mmol) and trans-dichlorobis(triphenylphosphine)palladium (II) (177 mg, 0.25 mmol). Degassed acetonitrile (16 mL) and 1 N $Na_2CO_3$ (16 mL) was added and the reaction tube was purged with argon, sealed and heated at 60° C. for 2 h. The reaction was cooled, filtered through a Celite pad and concentrated under reduced pressure. The residue was partitioned between EtOAc/water and extracted. The organic layer was washed with brine, dried over $Na_2SO_4$ and concentrated to give a solid. Trituration of the solid with hexanes and dichloromethane gave the desired compound. LCMS-ESI$^+$: calc'd for $C_{19}H_{14}BrN_3O_2S$: 428.0 (M+H$^+$); found: 428.2 (M+H$^+$).

Preparation of 5-bromo-3-(pyridin-3-yl)-1H-pyrrolo[2,3-b]pyridine: To a solution of 5-bromo-3-(pyridin-3-yl)-1-tosyl-1H-pyrrolo[2,3-b]pyridine (662 mg, 1.55 mmol) in acetone (30 mL) and methanol (20 mL) was added 2N NaOH (1.8 mL). The reaction was heated in a 65° C. oil bath for 1 h and then evaporated to near dryness. The crude reaction product was partitioned between EtOAc and 1N NaOH and extracted. The organic layer was washed with brine, dried over $Na_2SO_4$ and concentrated to give product that was used for the next step without any further purification. LCMS-ESI$^+$: calc'd for $C_{12}H_8BrN_3$: 274.0 (M+H$^+$); found: 274.1 (M+H$^+$).

Preparation of 5-bromo-1-methyl-3-(pyridin-3-yl)-1H-pyrrolo[2,3-b]pyridine: To a solution of the crude material (assume 0.43 mmol) from the previous reaction in DMF (15 mL) was added NaH (93 mg of a 60% oil dispersion, 2.32 mmol) in several portions at 0° C. After 15 min, iodomethane (0.145 mL, 0.33 mmol) was added and the reaction allowed to slowly warm to room temperature and stirred for 2 h. The bulk of the DMF was removed under reduced pressure and the residue partitioned between EtOAc/water. The organic layer was separated and washed with 5% LiCl, brine, dried over $Na_2SO_4$ and concentrated to give a dark orange residue. The crude material was passed through a short column of silica gel eluting with 100% EtOAc to provide the desired product. LCMS-ESI$^+$: calc'd for $C_{13}H_{10}BrN_3$: 288.0 (M+H$^+$); found: 288.1 (M+H$^+$).

Preparation of 1-methyl-3-(pyridin-3-yl)-5-(4,4,5,5-tetramethyl-1,3,2-dioxaborolan-2-yl)-1H-pyrrolo[2,3-b]pyridine: To a large microwave vial was placed -bromo-1-methyl-3-(pyridin-3-yl)-1H-pyrrolo[2,3-b]pyridine (90 mg, 0.31 mmol), bis(pinacolato)diboron (87 mg, 0.34 mmol), dichloro 1,1-bis(diphenylphosphino)ferrocene palladium(II) dichloromethane (26 mg, 0.031 mmol) and potassium acetate (92 mg, 0.94 mmol). Degassed 1,4-dioxane (3.0 mL) was added and the vial was sealed after purging with argon and heated in a 90° C. oil bath for 2.5 h. The reaction was cooled, filtered through a short plug of silica gel on Celite using EtOAc and concentrated to give product that was used in the next step without any further purification. LCMS-ESI$^+$: calc'd for $C_{19}H_{22}BN_3O_2$: 336.2 (M+H$^+$); found: 336.2 (M+H$^+$).

Preparation of (S)-methyl 2-tert-butoxy-2-(7-(4-chlorophenyl)-5-methyl-2-(1-methyl-3-(pyridin-3-yl)-1H-pyrrolo[2,3-b]pyridin-5-yl)benzo[d]thiazol-6-yl)acetate: To a microwave vial containing the crude material from the previous reaction (assume 0.31 mmol) was added (S)-methyl 2-(2-bromo-7-(4-chlorophenyl)-5-methylbenzo[d]thiazol-6-yl)-2-tert-butoxyacetate (136 mg, 0.28 mmol) and tetrakis(triphenylphosphine)palladium 936 mg, 0.03 mmol). Degassed 1,4-dioxane (3.0 mL) and 2N $K_2CO_3$ (0.47 mL) was added and the vial was sealed after purging with argon and heated in a 100° C. oil bath for 2.5 h. The reaction was cooled, partitioned between EtOAc/water and extracted. The organic layer was washed with brine, dried over $Na_2SO_4$ and concentrated to give the crude material. Purification of the residue by flash column chromatography on silica gel using a gradient of EtOAc to 30% MeOH in EtOAc provided the desired compound. LCMS-ESI$^+$: calc'd for $C_{34}H_{31}ClN_4O_3S$: 611.2 (M+H$^+$); found: 611.2 (M+H$^+$).

Preparation of (S)-2-tert-butoxy-2-(7-(4-chlorophenyl)-5-methyl-2-(1-methyl-3-(pyridin-3-yl)-1H-pyrrolo[2,3-b]pyridin-5-yl)benzo[d]thiazol-6-yl)acetic acid: A solution of the material from the previous reaction was dissolved in THF/MeOH (4.0 mL/4.0 mL) and 2N NaOH (0.70 mL). The reaction was heated at 45° C. overnight and then evaporated to dryness. Water (~0.50 mL) was added followed by HOAc (~10 drops). Acetonitrile was added dropwise to produce a tan precipitate that was collected by filtration. The collected solid was washed with water/acetonitrile and dried under vacuum to give the desire product. LCMS-ESI$^+$: calc'd for $C_{33}H_{29}ClN_4O_3S$: 597.2 (M+H$^+$); found: 597.3 (M+H$^+$). $^1$H NMR (400 MHz, CD$_3$OD): δ 8.86 (bs, 2H), 8.71 (s, 1H), 8.44 (d, J=4.7 Hz, 1H), 8.13 (d, J=7.4 Hz, 1H), 7.84 (s, 1H), 7.77

(s, 1H), 7.71 (d, J=8.6 Hz, 1H), 7.60 (s, 3H), 7.52-7.47 (m, 1H), 5.26 (s, 1H), 3.90 (s, 3H), 2.60 (s, 3H), 0.97 (s, 9H).

Example 110

(S)-2-tert-butoxy-2-(7-(4-chlorophenyl)-5-methyl-2-(3-(trifluoromethyl)-5,6-dihydro-[1,2,4]triazolo[4,3-a]pyrazin-7(8H)-yl)benzo[d]thiazol-6-yl)acetic acid (250)

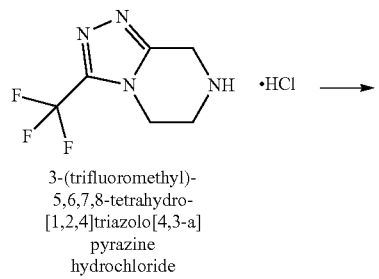

3-(trifluoromethyl)-5,6,7,8-tetrahydro-[1,2,4]triazolo[4,3-a]pyrazine hydrochloride

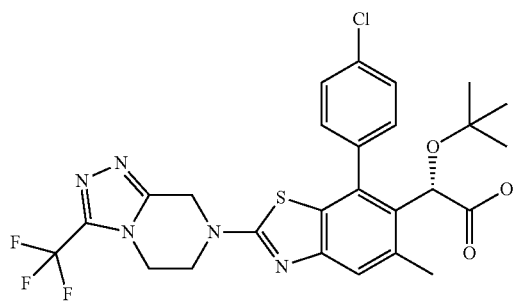

(S)-2-tert-butoxy-2-(7-(4-chlorohenyl)-5-methyl-2-(3-(trifluoromethyl)-5,6-dihydro-[1,2,4]triazolo[4,3-a]pyrazin-7(8H)-yl)benzo[d]thiazol-6-yl)acetic acid
250

Prepared in a similar manner as (S)-2-tert-butoxy-2-(7-(4-chlorophenyl)-2-(7,8-dihydro-1,6-naphthyridin-6(5H)-yl)-5-methylbenzo[d]thiazol-6-yl)acetic acid except using 3-(trifluoromethyl)-5,6,7,8-tetrahydro-[1,2,4]triazolo[4,3-a]pyrazine hydrochloride instead of 5,6,7,8-tetrahydro-1,6-naphthyridine, dihydrochloride, hydrate. LCMS-ESI⁺: calc'd for $C_{26}H_{25}ClF_3N_5O_3S$: 580.1, 582.1 (M+H⁺); Found: 580.2, 582.2 (M+H⁺). ¹H NMR (400 MHz, CD₃OD): δ 7.72-7.45 (m, 4H), 7.41 (s, 1H), 5.16 (s, 1H), 5.09 (s, 2H), 4.38 (t, J=5.4 Hz, 2H), 4.11 (t, J=5.5 Hz, 2H), 2.51 (s, 3H), 0.95 (s, 2H).

Example 111

Preparation of 1,3-dimethyl-4,5,6,7-tetrahydro-1H-pyrazolo[4,3-c]pyridine trifluoroacetic acid salt (252) and 2,3-dimethyl-4,5,6,7-tetrahydro-2H-pyrazolo[4,3-c]pyridine trifluoroacetic acid salt (253)

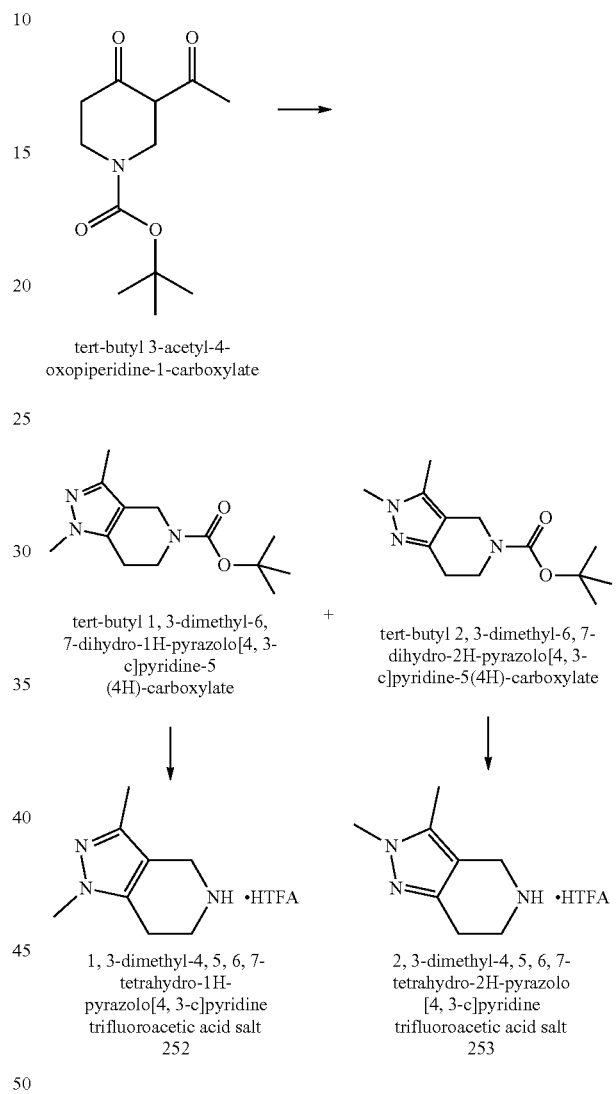

Preparation of tert-butyl 1,3-dimethyl-6,7-dihydro-1H-pyrazolo[4,3-c]pyridine-5(4H)-carboxylate and tert-butyl 2,3-dimethyl-6,7-dihydro-2H-pyrazolo[4,3-c]pyridine-5(4H)-carboxylate: A vial was charged with glacial AcOH (2.0 mL). N-Methylhydrazine (500 μL) was added dropwise over 3 min at an initial temperature of 23° C. The reaction became warm. Once the reaction had cooled back to 23° C., a solution of tert-butyl 3-acetyl-4-oxopiperidine-1-carboxylate (500 mg, 2.07 mmol) in glacial AcOH (500 μL) was added. The reaction was heated to 80° C. for 1 h. The reaction was carefully added to saturated aq NaHCO₃ (100 mL)(bubbling). The system was extracted with EtOAc (1×). The extract was dried over Na₂SO₄, filtered, and concentrated. The residue was treated with DCM and purification by flash column chromatography on silica gel (DCM to DCM/MeOH 4:1, detection at 210 nM) provided the two title compounds.

tert-butyl 1,3-dimethyl-6,7-dihydro-1H-pyrazolo[4,3-c]pyridine-5(4H)-carboxylate: LCMS-ESI+: calc'd for $C_{13}H_{21}N_3O_2$: 252.2 (M+H+); Found: 252.0 (M+H+). $^1$H NMR (400 MHz, CDCl$_3$): δ 4.38-4.22 (m, broad, 2H), 3.68 (s, 3H), 3.68 (s, broad, 2H) 2.63 (dd, broad, J=13.1, 7.6 Hz, 2H), 2.17 (s, 3H), 1.49 (s, 9H).

tert-butyl 2,3-dimethyl-6,7-dihydro-2H-pyrazolo[4,3-c]pyridine-5(4H)-carboxylate: LCMS-ESI+: calc'd for $C_{13}H_{21}N_3O_2$: 252.2 (M+H+); Found: 252.0 (M+H+). $^1$H NMR (400 MHz, CDCl$_3$): δ 4.42-4.25 (m, 2H), 3.72 (s, 3H), 3.67 (s, broad, 2H), 2.68 (dd, broad, J=18.1, 12.6 Hz, 2H), 2.16 (s, 3H), 1.47 (s, 9H).

Preparation of 1,3-dimethyl-4,5,6,7-tetrahydro-1H-pyrazolo[4,3-c]pyridine trifluoroacetic acid salt: A solution of tert-butyl 1,3-dimethyl-6,7-dihydro-1H-pyrazolo[4,3-c]pyridine-5(4H)-carboxylate (all of the product from the previous reaction above) in DCM (2.0 mL) was treated with TFA (500 μL), then stirred for 3 h at 23° C. The reaction was then concentrated, giving the desired product in crude form. The material was immediately used in the next reaction. LCMS-ESI+: calc'd for $C_8H_{13}N_3$: 152.1 (M+H+); Found: 152.0 (M+H+).

Preparation of 2,3-dimethyl-4,5,6,7-tetrahydro-2H-pyrazolo[4,3-c]pyridine trifluoroacetic acid salt: Prepared in a manner similar to 1,3-dimethyl-4,5,6,7-tetrahydro-1H-pyrazolo[4,3-c]pyridine trifluoroacetic acid salt, except using tert-butyl 2,3-dimethyl-6,7-dihydro-2H-pyrazolo[4,3-c]pyridine-5(4H)-carboxylate instead of tert-butyl 1,3-dimethyl-6,7-dihydro-1H-pyrazolo[4,3-c]pyridine-5(4H)-carboxylate. LCMS-ESI+: calc'd for $C_8H_{13}N_3$: 152.1 (M+H+); Found: 152.0 (M+H+).

Example 112

Preparation of (S)-2-tert-butoxy-2-(7-(4-chlorophenyl)-2-(1,3-dimethyl-1H-indazol-5-yl)-5-methylbenzo[d]thiazol-6-yl)acetic acid (254)

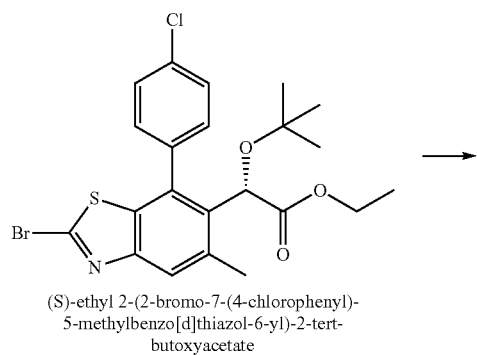

(S)-ethyl 2-(2-bromo-7-(4-chlorophenyl)-5-methylbenzo[d]thiazol-6-yl)-2-tert-butoxyacetate

→

-continued

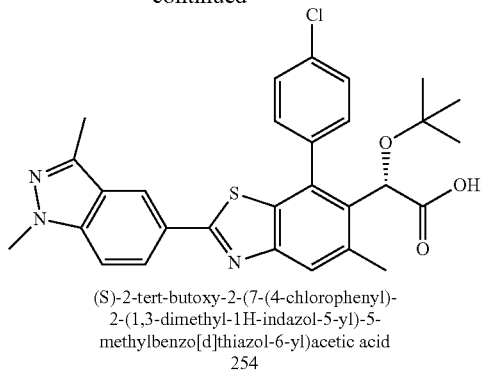

(S)-2-tert-butoxy-2-(7-(4-chlorophenyl)-2-(1,3-dimethyl-1H-indazol-5-yl)-5-methylbenzo[d]thiazol-6-yl)acetic acid
254

Preparation of (S)-2-tert-butoxy-2-(7-(4-chlorophenyl)-2-(1,3-dimethyl-1H-indazol-5-yl)-5-methylbenzo[d]thiazol-6-yl)acetic acid: A vial was charged with (S)-ethyl 2-(2-bromo-7-(4-chlorophenyl)-5-methylbenzo[d]thiazol-6-yl)-2-tert-butoxyacetate (100 mg, 0.202 mmol), 1,3-dimethylindazole-5-boronic acid (42 mg, 0.22 mmol), Pd(PPh$_3$)$_4$ (23 mg, 20 μmol), 2 M aq K$_2$CO$_3$ (800 μL), and dioxane (3.2 mL). The reaction was heated to 100° C. for 2 h. The reaction was treated with absolute EtOH (1.6 mL) and 10 M aq NaOH (800 μL). After heating to 100° C. for 2 h, the reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI+: calc'd for $C_{29}H_{28}ClN_3O_3S$: 534.2, 536.2 (M+H+). Found: 534.3, 536.3 (M+H+). $^1$H NMR (400 MHz, CD$_3$OD): δ 8.35 (s, 1H), 8.08 (dd, J=8.9, 1.6 Hz, 1H), 7.81 (s, 1H), 7.75-7.64 (m, 1H), 7.62-7.52 (m, 4H), 5.26 (s, 1H), 4.01 (s, 3H), 2.61 (s, 3H), 2.57 (s, 3H), 0.98 (s, 9H).

Example 113

Preparation of (S)-2-tert-butoxy-2-(7-(4-chlorophenyl)-2-(2-(1,3-dimethyl-1H-indazol-5-yl)-6-(4-methylpiperazin-1-yl)pyridin-4-yl)-5-methylbenzo[d]thiazol-6-yl)acetic acid (255)

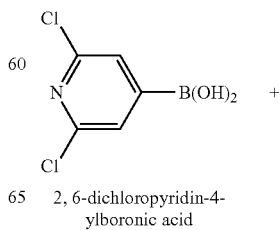 +

2,6-dichloropyridin-4-ylboronic acid

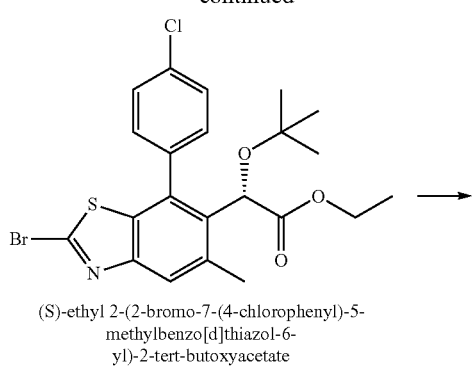

(S)-ethyl 2-(2-bromo-7-(4-chlorophenyl)-5-methylbenzo[d]thiazol-6-yl)-2-tert-butoxyacetate

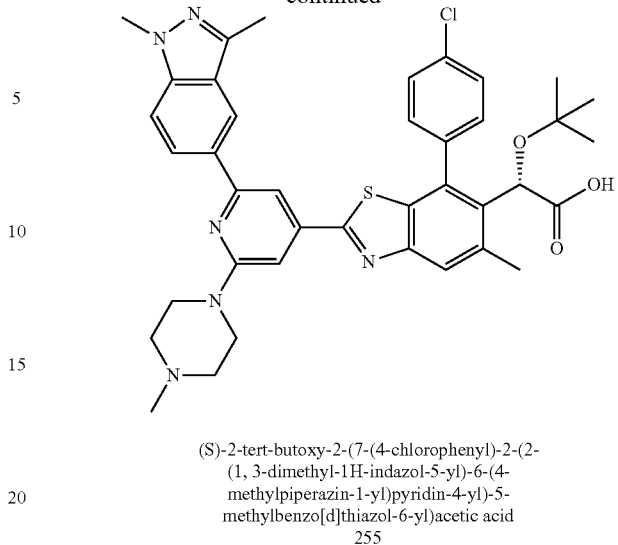

(S)-2-tert-butoxy-2-(7-(4-chlorophenyl)-2-(2-(1,3-dimethyl-1H-indazol-5-yl)-6-(4-methylpiperazin-1-yl)pyridin-4-yl)-5-methylbenzo[d]thiazol-6-yl)acetic acid
255

Preparation of (S)-ethyl 2-tert-butoxy-2-(7-(4-chlorophenyl)-2-(2,6-dichloropyridin-4-yl)-5-methylbenzo[d]thiazol-6-yl)acetate: A microwave tube was charged with Pd(PPh$_3$)$_4$ (4 mg), (S)-ethyl 2-(2-bromo-7-(4-chlorophenyl)-5-methylbenzo[d]thiazol-6-yl)-2-tert-butoxyacetate (25 mg), the 2,6-dichloropyridin-4-ylboronic acid (10 mg), dioxane (250 µL) and 2M aq K$_2$CO$_3$ (100 µL). The vessel was sealed and heated to 100° C. overnight. At 16 h, the reaction had only reached ~60% conversion. The reaction was cooled to 23° C., diluted with absolute EtOH (1.5 mL) and H$_2$O (500 µL), and was purified by reverse phase HPLC, eluting by 5-100% acetonitrile in H$_2$O with 0.1% TFA to give the desired product. LCMS-ESI$^+$: calc'd for C$_{27}$H$_{25}$Cl$_3$N$_2$O$_3$S: 563.1, 565.1, 567.1 (M+H$^+$); Found: 563.1, 565.0, 567.1 (M+H$^+$).

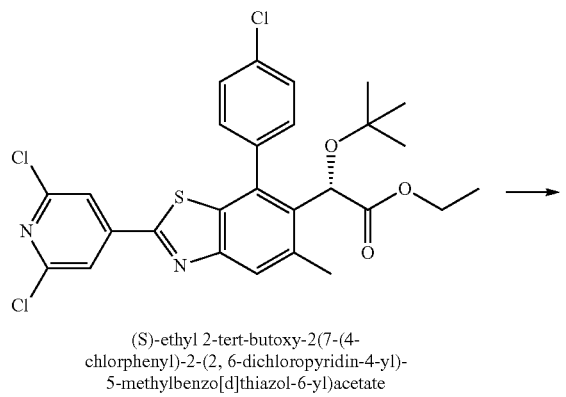

(S)-ethyl 2-tert-butoxy-2(7-(4-chlorphenyl)-2-(2,6-dichloropyridin-4-yl)-5-methylbenzo[d]thiazol-6-yl)acetate Preparation of (S)-ethyl 2-tert-butoxy-2-(2-(2-chloro-6-(4-methylpiperazin-1-yl)pyridin-4-yl)-7-(4-chlorophenyl)-5-methylbenzo[d]thiazol-6-yl)acetate: A solution of (S)-ethyl 2-tert-butoxy-2-(7-(4-chlorophenyl)-2-(2,6-dichloropyridin-4-yl)-5-methylbenzo[d]thiazol-6-yl)acetate (10 mg), N-methylpiperazine (10 mg), and DMA (250 µL) were combined in a microwave tube and heated to 100° C. for 30 min. Reaction was cooled to 23° C. and diluted with absolute ethanol and was purified by reverse phase HPLC, eluting by 5-100% acetonitrile in H$_2$O with 0.1% TFA to give the title compound. LCMS-ESI$^+$: calc'd for C$_{32}$H$_{36}$Cl$_2$N$_4$O$_3$S: 627.2, 629.2 (M+H$^+$); Found: 627.2, 629.2 (M+H$^+$).

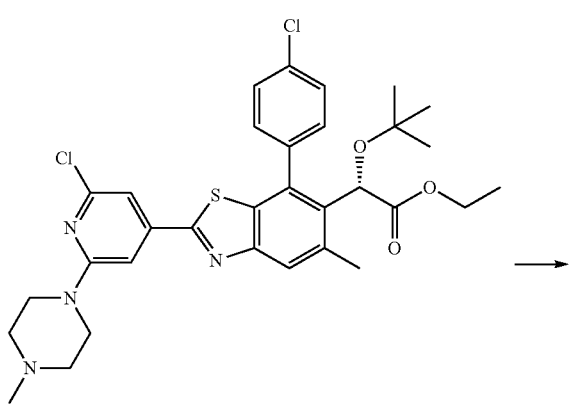

(S)-ethyl 2-tert-butoxy-2(2-(2-chloro-6-(4-methylpiperazin-1-yl)pyridin-4-yl)-7-(4-chlorophenyl)-5-methylbenzo[d]thiazol-6-yl)acetate Preparation of (S)-2-tert-butoxy-2-(7-(4-chlorophenyl)-2-(2-(1,3-dimethyl-1H-indazol-5-yl)-6-(4-methylpiperazin-1-yl)pyridin-4-yl)-5-methylbenzo[d]thiazol-6-yl)acetic acid: Prepared in a similar manner as (S)-2-tert-butoxy-2-(7-(4-chlorophenyl)-2-(1,3-dimethyl-1H-indazol-5-yl)-5-methylbenzo[d]thiazol-6-yl)acetic acid. LCMS-ESI$^+$: calc'd for C$_{39}$H$_{42}$ClN$_6$O$_3$S: 709.3, 711.3 (M+H$^+$); Found: 709.4, 711.2. (M+H$^+$). $^1$H NMR (400 MHz, CD$_3$OD): δ 8.44 (s, 1H), 8.23 (d, J=9.1 Hz, 1H), 7.93 (app. s, 2H), 7.74-7.47 (m, 5H), 7.41

(s, 1H), 5.28 (s, 1H), 4.86-4.68 (m, 2H), 3.99 (s, 3H), 3.80-3.52 (m, 2H), 3.39-3.12 (m, 4H), 2.99 (s, 3H), 2.64 (s, 3H), 2.61 (s, 3H), 0.98 (s, 9H).

Example 114

Preparation of (S)-2-tert-butoxy-2-(7-(4-chlorophenyl)-5-methyl-2-(1,3,3-trimethyl-2-oxoindolin-5-yl)benzo[d]thiazol-6-yl)acetic acid (256)

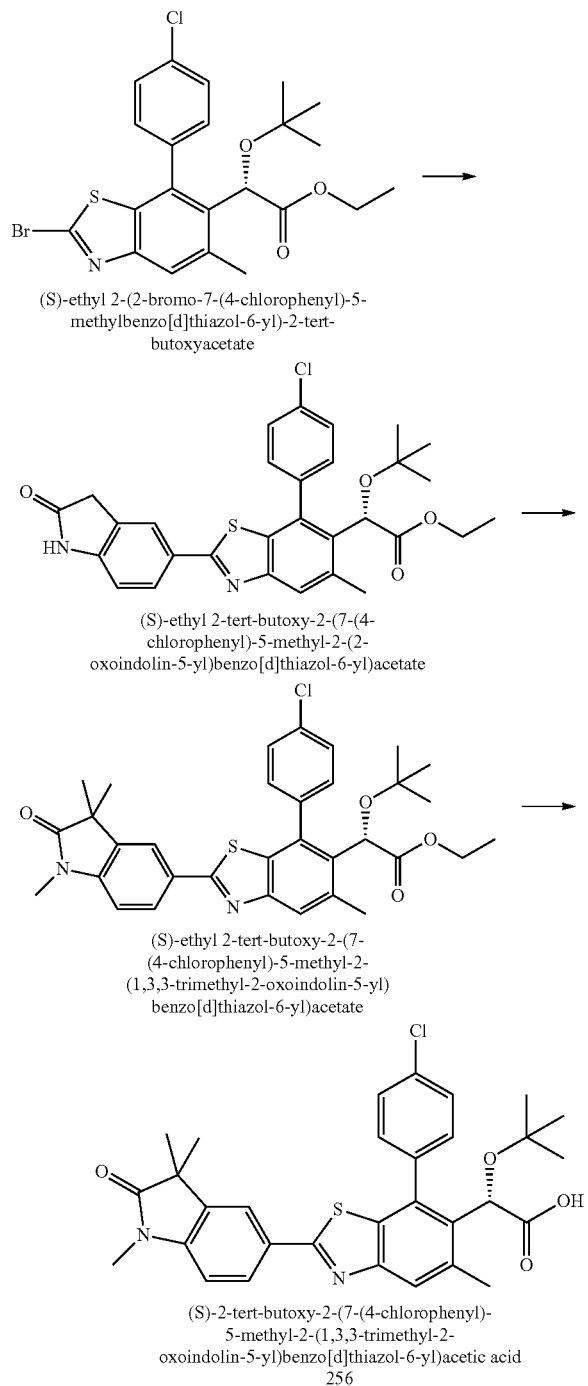

acetate: A vial was charged with (S)-ethyl 2-(2-bromo-7-(4-chlorophenyl)-5-methylbenzo[d]thiazol-6-yl)-2-tert-butoxyacetate (100 mg, 0.202 mmol), 2-(oxindole-5′-yl)-4,4,5,5-tetramethyl-1,3,2-dioxaborolane (58 mg, 0.221 mmol), Pd(PPh$_3$)$_4$ (23 mg, 20 µmol), solid K$_2$CO$_3$ (92 mg, 0.66 mmol), dioxane (1.6 mL), and H$_2$O (400 µL). The vessel was sealed and heated to 100° C. for 1.5 h. The reaction was diluted with water and extracted with EtOAc (2×). Combined organic layers were dried (Na$_2$SO$_4$), filtered, and concentrated. The residue was treated with benzene and purification by flash column chromatography on silica gel (hexanes/ethyl acetate eluent) provided the product. LCMS-ESI$^+$: calc'd for C$_{30}$H$_{29}$ClN$_2$O$_4$S: 549.2, 551.2 (M+H$^+$); Found: 549.3, 551.2 (M+H$^+$). $^1$H NMR (400 MHz, CD$_3$CN): δ 8.60 (s, broad, 1H), 7.92-7.77 (m, 2H), 7.76 (s, 1H), 7.62-7.42 (m, 4H), 6.91 (d, J=8.1 Hz, 1H), 5.17 (s, 1H), 4.29-3.93 (m, 2H), 3.48 (s, 2H), 2.53 (s, 3H), 1.28-1.11 (m, 3H), 0.93 (s, 9H).

Preparation of (S)-ethyl 2-tert-butoxy-2-(7-(4-chlorophenyl)-5-methyl-2-(1,3,3-trimethyl-2-oxoindolin-5-yl)benzo[d]thiazol-6-yl)acetate: A vial was charged with (S)-ethyl 2-tert-butoxy-2-(7-(4-chlorophenyl)-5-methyl-2-(2-oxoindolin-5-yl)benzo[d]thiazol-6-yl)acetate (45 mg, 82 µmol), Cs$_2$CO$_3$ (134 mg, 0.410 mmol), iodomethane (51 µL, 0.82 mmol), and DMF (500 µL). The reaction was warmed to 50° C. for 2 h. The reaction was diluted with EtOAc and washed with 5% w/v aq LiCl (3×). The organic phase was dried (Na$_2$SO$_4$), filtered, and concentrated, giving the product, which was immediately used in the next step. LCMS-ESI$^+$: calc'd for C$_{30}$H$_{29}$ClN$_2$O$_4$S: 591.2, 593.2 (M+H$^+$); Found: 591.3, 593.3 (M+H$^+$). $^1$H NMR (400 MHz, CD$_3$CN): δ 8.04-7.88 (m, 2H), 7.81 (s, 1H), 7.63-7.48 (m, 4H), 7.02 (d, J=8.1 Hz, 1H), 5.18 (s, 1H), 4.32-4.06 (m, 2H), 3.15 (s, 3H), 2.51 (s, 3H), 1.41 (s, 6H), 1.27-1.12 (m, 3H), 0.94 (s, 9H).

Preparation of (S)-2-tert-butoxy-2-(7-(4-chlorophenyl)-5-methyl-2-(1,3,3-trimethyl-2-oxoindolin-5-yl)benzo[d]thiazol-6-yl)acetic acid: The crude (S)-ethyl 2-tert-butoxy-2-(7-(4-chlorophenyl)-5-methyl-2-(1,3,3-trimethyl-2-oxoindolin-5-yl)benzo[d]thiazol-6-yl)acetate from the reaction above was treated with 1.0 M aq NaOH (2 mL), THF (4 mL), and absolute EtOH (2 mL). The reaction was heated to 50° C. for 19 h. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for C$_{31}$H$_{31}$ClN$_2$O$_4$S: 563.2, 565.2 (M+H$^+$); Found: 563.3, 565.3 (M+H$^+$). $^+$). $^1$H NMR (400 MHz, CD$_3$OD): δ 8.05-7.94 (m, 2H), 7.81 (s, 1H), 7.73-7.64 (m, 1H), 7.64-7.54 (m, 3H), 7.14 (d, J=8.2 Hz, 1H), 5.26 (s, 1H), 3.27 (s, 3H), 2.61 (s, 3H), 1.41 (s, 6H), 0.98 (s, 9H).

Example 115

(S)-2-tert-butoxy-2-(7-(4-chlorophenyl)-5-methyl-2-(1-methyl-3-(4-methylpiperazin-1-yl)-1H-indazol-5-yl)benzo[d]thiazol-6-yl)acetic acid (257)

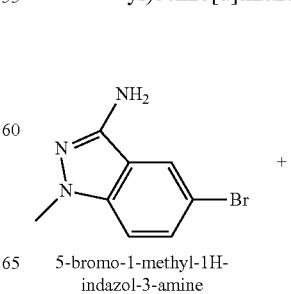

5-bromo-1-methyl-1H-indazol-3-amine

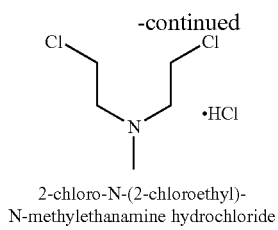

2-chloro-N-(2-chloroethyl)-
N-methylethanamine hydrochloride

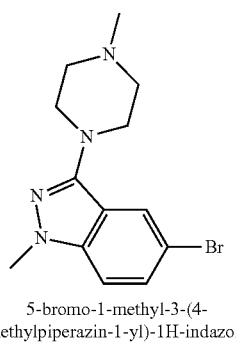

5-bromo-1-methyl-3-(4-
methylpiperazin-1-yl)-1H-indazole

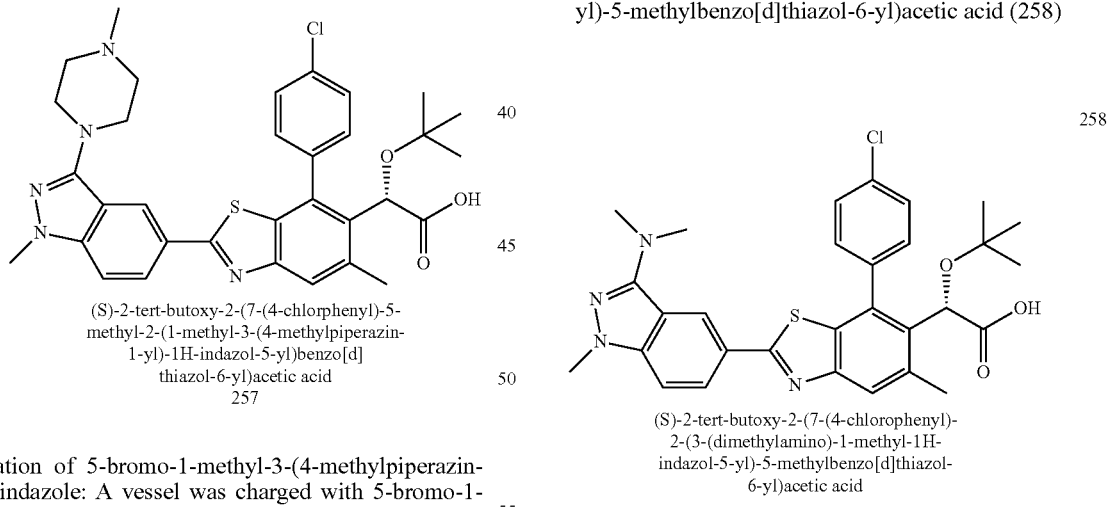

(S)-2-tert-butoxy-2-(7-(4-chlorphenyl)-5-
methyl-2-(1-methyl-3-(4-methylpiperazin-
1-yl)-1H-indazol-5-yl)benzo[d]
thiazol-6-yl)acetic acid
257

Preparation of 5-bromo-1-methyl-3-(4-methylpiperazin-1-yl)-1H-indazole: A vessel was charged with 5-bromo-1-methyl-1H-indazol-3-amine (250 mg, 1.10 mmol), 2-chloro-N-(2-chloroethyl)-N-methylethanamine hydrochloride (230 mg, 1.21 mmol), H$_2$O (250 µL), K$_2$CO$_3$ (500 mg, 3.63 mmol), and DMF (2.5 mL). The vessel was sealed and heated to 100° C. for 18 h. The reaction was poured into EtOAc and washed with 5% w/v aq LiCl (3×), dried (Na$_2$SO$_4$), filtered, and concentrated. The residue was treated with DCM and purification by flash column chromatography on silica gel (hexanes/ethyl acetate to remove side products; then DCM/MeOH eluent to elute product) provided 5-bromo-1-methyl-3-(4-methylpiperazin-1-yl)-1H-indazole. LCMS-ESI$^+$: calc'd for C$_{13}$H$_{17}$BrN$_4$: 309.1, 311.1 (M+H$^+$); Found: 309.2, 311.2 (M+H$^+$).

Preparation of (S)-2-tert-butoxy-2-(7-(4-chlorophenyl)-5-methyl-2-(1-methyl-3-(4-methylpiperazin-1-yl)-1H-indazol-5-yl)benzo[d]thiazol-6-yl)acetic acid: A vial was charged with 5-bromo-1-methyl-3-(4-methylpiperazin-1-yl)-1H-indazole (64.0 mg, 0.208 mmol), bis-pinacolatodiboron (58 mg, 0.23 mmol), PdCl$_2$(dppf).DCM (17 mg, 21 µmol), glacial AcOH (13 µL, 0.23 mmol), KOAc (67 mg, 0.69 mmol), and dioxane (1.6 mL). The reaction was heated to 100° C. for 2 h. To this reaction was added (S)-ethyl 2-(2-bromo-7-(4-chlorophenyl)-5-methylbenzo[d]thiazol-6-yl)-2-tert-butoxyacetate (103 mg, 0.208 mmol), KHCO$_3$ (23 mg, 0.23 mmol), 2 M aq K$_2$CO$_3$ (400 µL), and Pd(PPh$_3$)$_4$ (24 mg, 21 µmol). The reaction was heated for another 1 h at 100° C. Finally, EtOH (absolute, 800 µL) and 10 M aq NaOH (500 µL) were added. The reaction was heated to 100° C. for another 1 h. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for C$_{33}$H$_{36}$ClN$_5$O$_3$S: 618.2, 620.2 (M+H$^+$); Found: 618.4, 620.2 (M+H$^+$). $^1$H NMR (400 MHz, CD$_3$OD): δ 8.43 (s, 1H), 8.05 (d, J=8.9 Hz, 1H), 7.80 (s, 1H), 7.68 (d, J=9.1 Hz, 1H), 7.62-7.47 (m, 4H), 5.24 (s, 1H), 4.31-4.01 (m, 2H), 3.94 (s, 3H), 3.74-3.54 (m, 2H), 3.54-3.35 (m, 2H), 3.32-3.16 (m, 2H), 3.00 (s, 3H), 2.61 (s, 3H), 0.97 (s, 9H).

Example 116

Preparation of (S)-2-tert-butoxy-2-(7-(4-chlorophenyl)-2-(3-(dimethylamino)-1-methyl-1H-indazol-5-yl)-5-methylbenzo[d]thiazol-6-yl)acetic acid (258)

(S)-2-tert-butoxy-2-(7-(4-chlorophenyl)-
2-(3-(dimethylamino)-1-methyl-1H-
indazol-5-yl)-5-methylbenzo[d]thiazol-
6-yl)acetic acid Preparation of (S)-2-tert-butoxy-2-(7-(4-chlorophenyl)-2-(3-(dimethylamino)-1-methyl-1H-indazol-5-yl)-5-methyl-benzo[d]thiazol-6-yl)acetic acid: Prepared in a similar manner as (S)-2-tert-butoxy-2-(7-(4-chlorophenyl)-5-methyl-2-(1-methyl-3-(4-methylpiperazin-1-yl)-1H-indazol-5-yl)benzo[d]thiazol-6-yl)acetic acid, except using 5-bromo-N,N,1-trimethyl-1H-indazol-3-amine instead of 5-bromo-1-methyl-3-(4-methylpiperazin-1-yl)-1H-indazole. LCMS-ESI$^+$: calc'd for C$_{30}$H$_{31}$ClN$_4$O$_3$S: 563.2, 565.2 (M+H$^+$); Found: 563.2, 565.2 (M+H$^+$). $^1$H NMR (400 MHz, CD$_3$OD): δ 8.49 (s, 1H), 7.96 (dd, J=8.9, 1.5 Hz, 1H), 7.78 (s, 1H), 7.74-7.64 (m, 1H), 7.62-7.52 (m, 3H), 7.41 (d, J=8.9 Hz, 1H), 5.25 (s, 1H), 3.86 (s, 3H), 3.16 (s, 6H), 2.60 (s, 3H), 0.97 (s, 9H).

Example 117

(S)-2-tert-butoxy-2-(7-(4-chlorophenyl)-5-methyl-2-(1-methyl-3-(4-methylpiperazin-1-yl)-1H-indazol-6-yl)benzo[d]thiazol-6-yl)acetic acid (259)

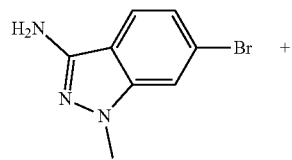

6-bromo-1-methyl-1H-indazol-3-amine

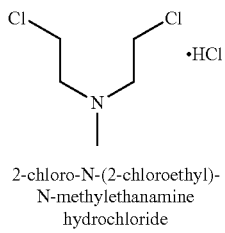

2-chloro-N-(2-chloroethyl)-N-methylethanamine hydrochloride

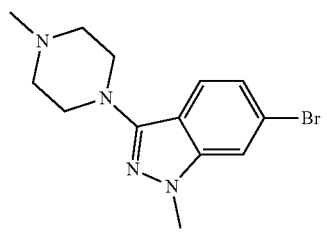

6-bromo-1-methyl-3-(4-methyl piperazin-1-yl)-1H-indazol

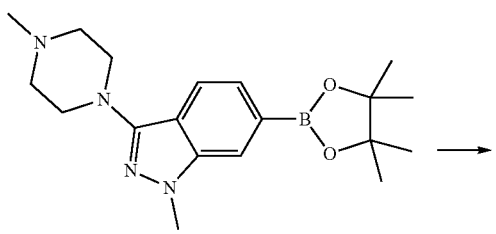

1-methyl-3-(4-methylpiperazin-1-yl)-6-(4, 4, 5, 5-tetramethyl-1, 3, 2-dioxaborolan-2-yl)-1H-indazol

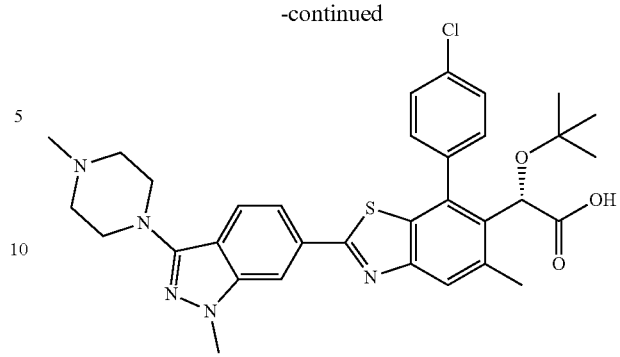

(S)-2-tert-butoxy-2-(7-(4-chlorophenyl)-5-methyl-2-(1-methyl-3-(1-methylpiperidin-1-yl)-1H-indazol-6-yl)benzo[d]thiazol-6-yl)acetic acid
259

Preparation of 6-bromo-1-methyl-3-(4-methylpiperazin-1-yl)-1H-indazole: Prepared in a manner similar to 5-bromo-1-methyl-3-(4-methylpiperazin-1-yl)-1H-indazole but using 6-bromo-1-methyl-1H-indazol-3-amine instead of 5-bromo-1-methyl-1H-indazol-3-amine. LCMS-ESI$^+$: calc'd for $C_{13}H_{17}BrN_4$: 309.1, 311.1 (M+H$^+$); Found: 309.2, 311.2 (M+H$^+$).

Preparation of 1-methyl-3-(4-methylpiperazin-1-yl)-6-(4,4,5,5-tetramethyl-1,3,2-dioxaborolan-2-yl)-1H-indazole: A vial was charged with 6-bromo-1-methyl-3-(4-methylpiperazin-1-yl)-1H-indazole (200 mg, 0.649 mmol), glacial AcOH (41 µL, 0714 mmol), KOAc (210 mg, 2.14 mmol), PdCl$_2$(dppf).DCM (53 mg, 65 µmol), bis-pinacolatodiboron (181 mg, 0.714 mmol), and dioxane (2.0 mL). The reaction was sealed and heated to 100° C. for 1 h. The reaction was cooled to 23° C. and diluted with water. The system was treated with EtOAc and filtered through Celite. The filtrate was extracted with EtOAc (2×). Combined organic extracts were dried (Na$_2$SO$_4$), filtered, and concentrated. The residue was treated with benzene and purification by flash column chromatography on silica gel (hexanes/ethyl acetate (side products elute) then DCM/MeOH eluent to isolate product) provided 1-methyl-3-(4-methylpiperazin-1-yl)-6-(4,4,5,5-tetramethyl-1,3,2-dioxaborolan-2-yl)-1H-indazole. LCMS-ESI$^+$: calc'd for $C_{19}H_{29}BN_4O_2$: 357.2 (M+H$^+$); Found: 357.3 (M+H$^+$).

Preparation of (S)-2-tert-butoxy-2-(7-(4-chlorophenyl)-5-methyl-2-(1-methyl-3-(4-methylpiperazin-1-yl)-1H-indazol-6-yl)benzo[d]thiazol-6-yl)acetic acid: A vial was charged with (S)-ethyl 2-(2-bromo-7-(4-chlorophenyl)-5-methylbenzo[d]thiazol-6-yl)-2-tert-butoxyacetate (75 mg, 0.151 mmol), KHCO$_3$ (15.2 mg, 0.151 mmol), K$_2$CO$_3$ (41.7 mg, 0.302 mmol), 1-methyl-3-(4-methylpiperazin-1-yl)-6-(4,4,5,5-tetramethyl-1,3,2-dioxaborolan-2-yl)-1H-indazole (55 mg, 0.154 mmol), Pd(PPh$_3$)$_4$ (17 mg, 15 µmol), H$_2$O (400 µL), and dioxane (1.6 mL). The vessel was sealed and heated to 100° C. for 2 h. Then EtOH (absolute, 800 µL) and 2 M aq NaOH (400 µL) were added. Heating was continued at 100° C. for 3 h. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for $C_{33}H_{36}ClN_5O_3S$: 618.2, 620.2 (M+H$^+$); Found: 618.3, 620.2 (M+H$^+$). $^1$H NMR (400 MHz, CD$_3$OD): δ 8.10 (s, 1H), 7.93-7.83 (m, 2H), 7.79-7.65 (m, 2H), 7.64-7.55 (m, 3H), 5.16 (s, 2H), 4.09 (d, J=12.9 Hz, 1H), 3.97 (s, 3H), 3.63

(d, J=8.7 Hz, 2H), 3.39 (d, J=11.5 Hz, 2H), 3.36-3.22 (m, 2H), 3.00 (s, 3H), 2.62 (s, 3H), 0.98 (s, 9H).

Example 118

Preparation of 6-bromo-N,1-dimethyl-1H-indazol-3-amine (260) and 6-bromo-N,N,1-trimethyl-1H-indazol-3-amine (261)

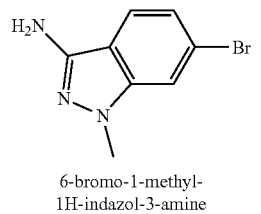

6-bromo-1-methyl-1H-indazol-3-amine

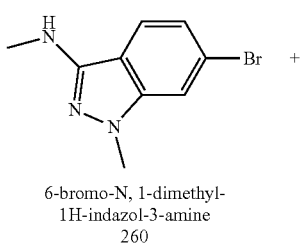

6-bromo-N, 1-dimethyl-1H-indazol-3-amine
260

+

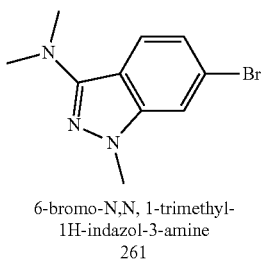

6-bromo-N,N, 1-trimethyl-1H-indazol-3-amine
261

Preparation of 6-bromo-N,1-dimethyl-1H-indazol-3-amine and 6-bromo-N,N,1-trimethyl-1H-indazol-3-amine: A vial was charged with 6-bromo-1-methyl-1H-indazol-3-amine (500 mg, 2.21 mmol), NaBH(OAc)$_3$ (2.33 g, 11.0 mmol), DMF (5.0 mL), and glacial AcOH (630 µL, 11.0 mmol). The reaction was heated to 60° C. and sealed. Then 37% w/w aq formaldehyde (765 µL, 11.0 mmol formaldehyde) was added dropwise over 5 min. Pressure increased during the addition. At 5 h, the reaction was cooled to 23° C. and shaken with 1.0 M aq NaOH (50 mL). EtOAc (100 mL) was added. The organic phase was collected. It was washed with 5% aq LiCl (2×50 mL), dried (Na$_2$SO$_4$), filtered, and concentrated. The residue was treated with DCM/Benzene and purification by flash column chromatography on silica gel (hexanes/ethyl acetate eluent) provided the two title products:

6-bromo-N,1-dimethyl-1H-indazol-3-amine. LCMS-ESI$^+$: calc'd for C$_9$H$_{10}$BrN$_3$: 240.0, 242.0 (M+H$^+$); Found: 240.1, 242.1 (M+H$^+$).

6-bromo-N,N,1-trimethyl-1H-indazol-3-amine. LCMS-ESI$^+$: calc'd for C$_{10}$H$_{12}$BrN$_3$: 254.0, 256.0 (M+H$^+$); Found: 254.2, 256.1 (M+H$^+$).

Example 119

5-bromo-N,1-dimethyl-1H-indazol-3-amine (262) and 5-bromo-N,N,1-trimethyl-1H-indazol-3-amine (263)

5-bromo-1-methyl-1H-indazol-3-amine 5-bromo-N, 1-dimethyl-1H-indazol-3-amine
262

+

5-bromo-N,N, 1-trimethyl-1H-indazol-3-amine
263

Preparation of 5-bromo-N,1-dimethyl-1H-indazol-3-amine and 5-bromo-N,N,1-trimethyl-1H-indazol-3-amine: Each was prepared in a manner similar to 6-bromo-N,1-dimethyl-1H-indazol-3-amine and 6-bromo-N,N,1-trimethyl-1H-indazol-3-amine, respectively except using 5-bromo-1-methyl-1H-indazol-3-amine instead of 6-bromo-1-methyl-1H-indazol-3-amine.

5-bromo-N,1-dimethyl-1H-indazol-3-amine. LCMS-ESI$^+$: calc'd for C$_9$H$_{10}$BrN$_3$: 240.0, 242.0 (M+H$^+$); Found: 240.1, 242.1 (M+H$^+$).

5-bromo-N,N,1-trimethyl-1H-indazol-3-amine. LCMS-ESI$^+$: calc'd for C$_{10}$H$_{12}$BrN$_3$: 254.0, 256.0 (M+H$^+$); Found: 254.1, 256.1 (M+H$^+$).

Example 120

Preparation of (S)-2-tert-butoxy-2-(7-(4-chlorophenyl)-2-(3-cyclopropyl-1-methyl-1H-indazol-5-yl)-5-methylbenzo[d]thiazol-6-yl)acetic acid (264)

5-bromo-3-cyclopropyl-1-methyl-1H-indazole

-continued

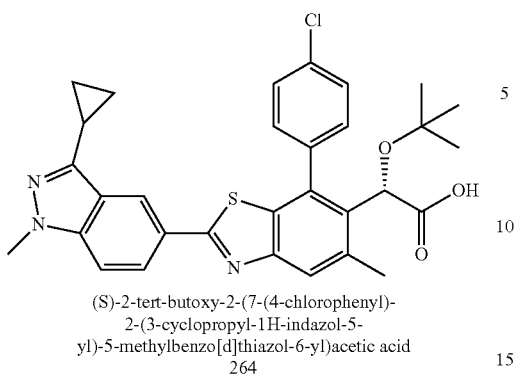

(S)-2-tert-butoxy-2-(7-(4-chlorophenyl)-
2-(3-cyclopropyl-1H-indazol-5-
yl)-5-methylbenzo[d]thiazol-6-yl)acetic acid
264

Preparation of (S)-2-tert-butoxy-2-(7-(4-chlorophenyl)-2-(3-cyclopropyl-1-methyl-1H-indazol-5-yl)-5-methylbenzo[d]thiazol-6-yl)acetic acid: A vial was charged with 5-bromo-3-cyclopropyl-1-methyl-1H-indazole (49 mg, 0.19 mmol), bis-pinacolatodiboron (53 mg, 0.21 mmol), PdCl$_2$(dppf).DCM (15 mg, 19 μmol), KOAc (62 mg, 0.62 mmol), and dioxane (1.6 mL). The reaction was sealed and heated to 100° C. for 2 h. (S)-ethyl 2-(2-bromo-7-(4-chlorophenyl)-5-methylbenzo[d]thiazol-6-yl)-2-tert-butoxyacetate (94 mg, 0.190 mmol), Pd(PPh$_3$)$_4$ (22 mg, 19 μmol), and 2 M aq K$_2$CO$_3$ (400 μL) were added; the reaction was heated at 100° C. for 1.5 h. The reaction was treated with absolute EtOH (2 mL) and 10 M aq NaOH (2 mL). After heating to 100° C. for 1 h, the reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for C$_{31}$H$_{30}$ClN$_3$O$_3$S: 560.2, 562.2 (M+H$^+$); Found: 560.2, 562.2 (M+H$^+$). $^1$H NMR (400 MHz, CD$_3$OD): δ 8.37 (s, 1H), 7.99 (dd, J=8.8, 1.3 Hz, 1H), 7.77 (s, 1H), 7.72-7.66 (m, 1H), 7.58 (d, J=3.2 Hz, 3H), 7.49 (d, J=8.9 Hz, 1H), 5.25 (s, 1H), 3.93 (s, 3H), 2.59 (s, 3H), 2.26 (ddd, J=13.1, 8.3, 5.2 Hz, 1H), 1.16-0.98 (m, 4H), 0.97 (s, 9H).

Example 121

Preparation of (S)-2-tert-butoxy-2-(7-(4-chlorophenyl)-2-(2,3-dimethyl-2H-indazol-5-yl)-5-methylbenzo[d]thiazol-6-yl)acetic acid (265)

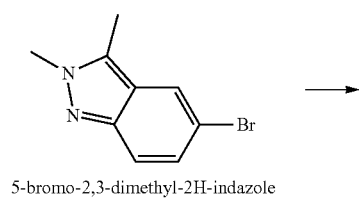

5-bromo-2,3-dimethyl-2H-indazole

-continued

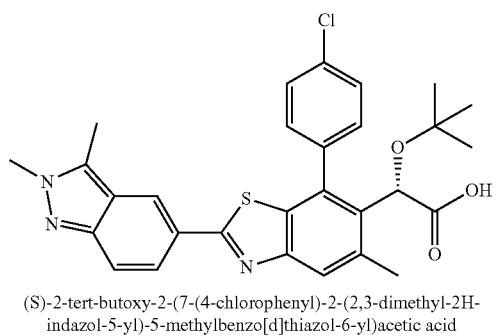

(S)-2-tert-butoxy-2-(7-(4-chlorophenyl)-2-(2,3-dimethyl-2H-indazol-5-yl)-5-methylbenzo[d]thiazol-6-yl)acetic acid
265

Preparation of (S)-2-tert-butoxy-2-(7-(4-chlorophenyl)-2-(2,3-dimethyl-2H-indazol-5-yl)-5-methylbenzo[d]thiazol-6-yl)acetic acid: prepared in a similar manner as the preparation of (S)-2-tert-butoxy-2-(7-(4-chlorophenyl)-2-(3-cyclopropyl-1-methyl-1H-indazol-5-yl)-5-methylbenzo[d]thiazol-6-yl)acetic acid except using 5-bromo-2,3-dimethyl-2H-indazole instead of 5-bromo-3-cyclopropyl-1-methyl-1H-indazole. LCMS-ESI$^+$: calc'd for C$_{29}$H$_{28}$ClN$_3$O$_3$S: 534.2, 536.2 (M+H$^+$); Found: 534.2, 536.2 (M+H$^+$). $^1$H NMR (400 MHz, CD$_3$OD): δ 8.37 (s, 1H), 7.99 (dd, J=9.1, 1.7 Hz, 1H), 7.82 (s, 1H), 7.76-7.66 (m, 1H), 7.66-7.50 (m, J=9.1, 4.8 Hz, 4H), 5.26 (s, 1H), 4.12 (s, 3H), 2.71 (s, 3H), 2.62 (s, 3H), 0.99 (s, 9H).

Example 122

Preparation of (S)-2-(2-(3-amino-1-methyl-1H-indazol-6-yl)-7-(4-chlorophenyl)-5-methylbenzo[d]thiazol-6-yl)-2-tert-butoxyacetic acid (266)

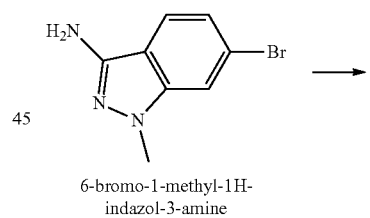

6-bromo-1-methyl-1H-indazol-3-amine

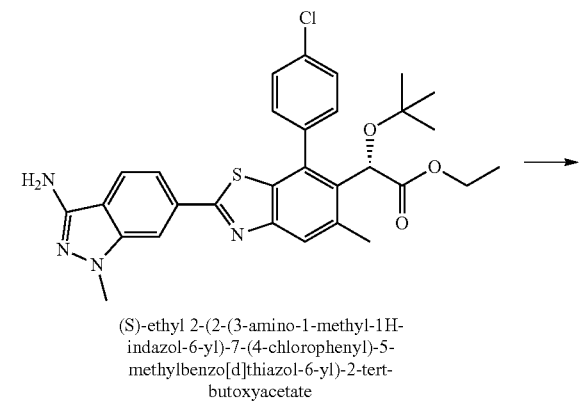

(S)-ethyl 2-(2-(3-amino-1-methyl-1H-indazol-6-yl)-7-(4-chlorophenyl)-5-methylbenzo[d]thiazol-6-yl)-2-tert-butoxyacetate

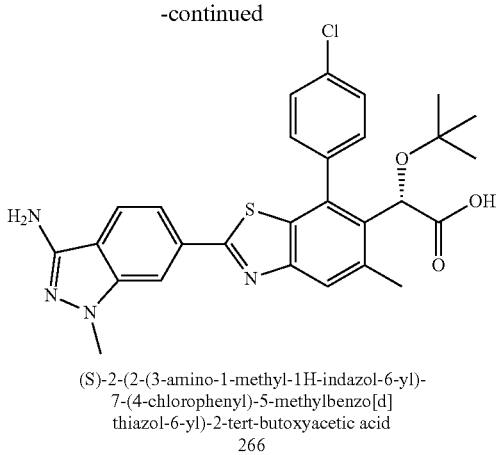

(S)-2-(2-(3-amino-1-methyl-1H-indazol-6-yl)-
7-(4-chlorophenyl)-5-methylbenzo[d]
thiazol-6-yl)-2-tert-butoxyacetic acid
266

Preparation of (S)-ethyl 2-(2-(3-amino-1-methyl-1H-indazol-6-yl)-7-(4-chlorophenyl)-5-methylbenzo[d]thiazol-6-yl)-2-tert-butoxyacetate: A vessel was charged with 6-bromo-1-methyl-1H-indazol-3-amine (191 mg, 0.846 mmol), bis-pinacolatodiboron (236 mg, 0.930 mmol), PdCl$_2$(dppf).DCM (69 mg, 85 μmol), glacial KOAc (273 mg, 2.79 mmol), and dioxane (3.2 mL). The reaction was heated to 100° C. for 1 h. To this reaction was added (S)-ethyl 2-(2-bromo-7-(4-chlorophenyl)-5-methylbenzo[d]thiazol-6-yl)-2-tert-butoxyacetate (420 mg, 0.846 mmol), 2 M aq K$_2$CO$_3$ (800 μL), and Pd(PPh$_3$)$_4$ (98 mg, 85 mmol). The reaction was heated for another 1 h at 100° C. The reaction was diluted with water and extracted with EtOAc (3×). Combined organic layers were dried (Na$_2$SO$_4$), filtered, and concentrated. The residue was treated with benzene and purification by flash column chromatography on silica gel (hexanes/ethyl acetate eluent) gave the title compound in semi-pure form. The mixture was treated with DCM and purification by flash column chromatography on silica gel (DCM/MeOH eluent) giving the title compound. LCMS-ESI$^+$: calc'd for C$_{30}$H$_{31}$ClN$_4$O$_3$S: 563.2, 565.2 (M+H$^+$); Found: 563.3, 565.3 (M+H$^+$).

Preparation of (S)-2-(2-(3-amino-1-methyl-1H-indazol-6-yl)-7-(4-chlorophenyl)-5-methylbenzo[d]thiazol-6-yl)-2-tert-butoxyacetic acid: A vial was charged with (S)-ethyl 2-(2-(3-amino-1-methyl-1H-indazol-6-yl)-7-(4-chlorophenyl)-5-methylbenzo[d]thiazol-6-yl)-2-tert-butoxyacetate (60 mg), THF (1.5 mL), EtOH (absolute, 1 mL), and 2M aq NaOH (1 mL). The vessel was sealed and heated to 100° C. for 2 h. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for C$_{28}$H$_{27}$ClN$_4$O$_3$S: 535.2, 537.2 (M+H$^+$); Found: 535.2, 537.2 (M+H$^+$). $^1$H NMR (400 MHz, CD$_3$OD): δ 8.06 (s, 1H), 7.87 (s, 1H), 7.82 (d, J=8.5 Hz, 1H), 7.78-7.65 (m, 2H), 7.64-7.54 (m, 3H), 5.27 (s, 1H), 3.90 (s, 3H), 2.63 (s, 3H), 0.98 (s, 9H).

Example 123

Preparation of (S)-2-tert-butoxy-2-(7-(4-chlorophenyl)-5-methyl-2-(1-methyl-3-(1-methylpiperidin-4-yl)-1H-indazol-6-yl)benzo[d]thiazol-6-yl)acetic acid
(267)

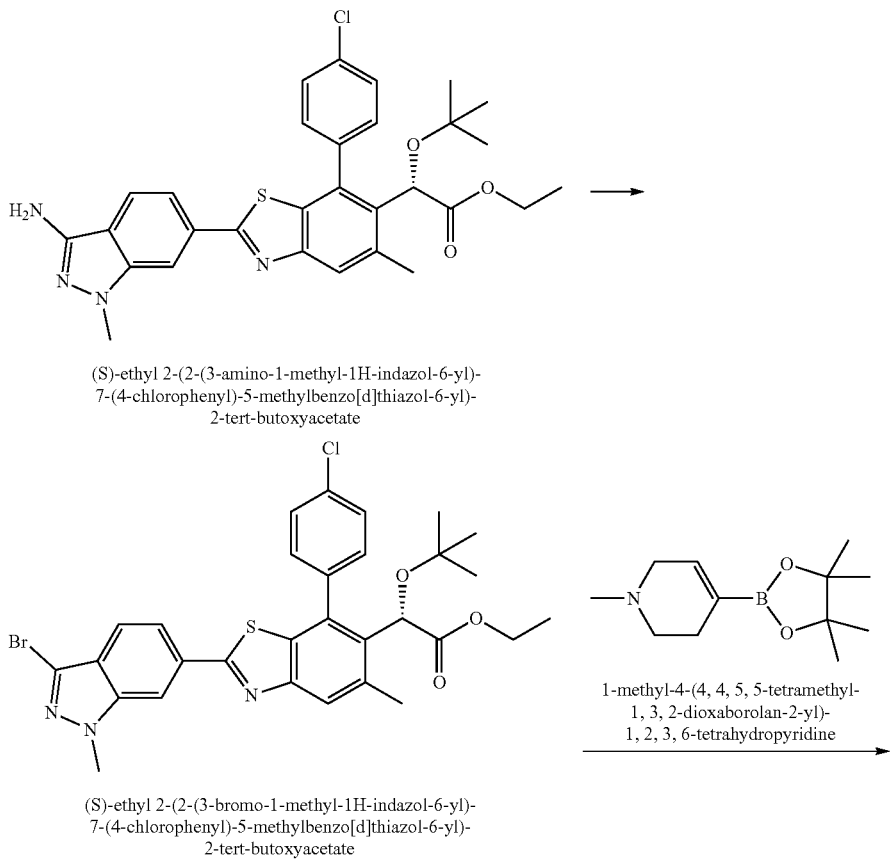

(S)-ethyl 2-(2-(3-amino-1-methyl-1H-indazol-6-yl)-
7-(4-chlorophenyl)-5-methylbenzo[d]thiazol-6-yl)-
2-tert-butoxyacetate (S)-ethyl 2-(2-(3-bromo-1-methyl-1H-indazol-6-yl)-
7-(4-chlorophenyl)-5-methylbenzo[d]thiazol-6-yl)-
2-tert-butoxyacetate 1-methyl-4-(4, 4, 5, 5-tetramethyl-
1, 3, 2-dioxaborolan-2-yl)-
1, 2, 3, 6-tetrahydropyridine -continued

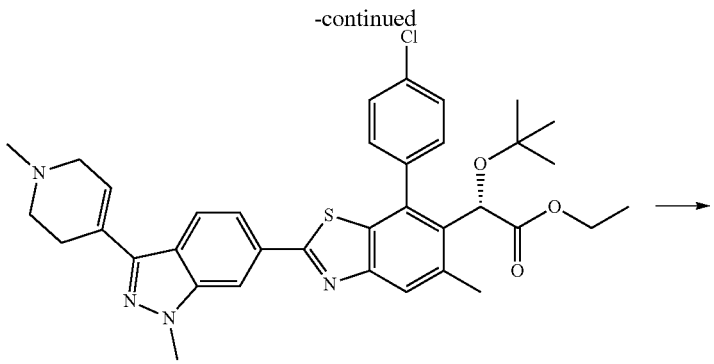

(S)-ethyl 2-tert-butoxy-2(7-(4-chlorophenyl)-
5-methyl-2-(1-methyl-3-(1-methyl-1,2,3,6-
tetrahydropyridin-4-yl)-1H-indazol-
6-yl)benzo[d]thiazol-6-yl)acetate

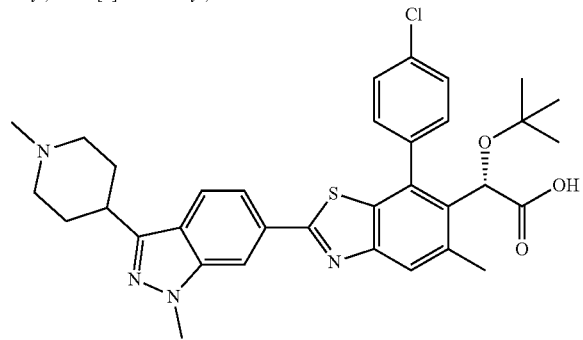

(S)-2-tert-butoxy-2-(7-(4-chlorophenyl)-
5-methyl-2-(1-methyl-3-(1-
methylpiperidin-4-yl)-1H-indazol-6-yl)benzo[d]thiazol-6-yl)acetic acid
267

Preparation of (S)-ethyl 2-(2-(3-bromo-1-methyl-1H-indazol-6-yl)-7-(4-chlorophenyl)-5-methylbenzo[d]thiazol-6-yl)-2-tert-butoxyacetate: A flask was charged with (S)-ethyl 2-(2-(3-amino-1-methyl-1H-indazol-6-yl)-7-(4-chlorophenyl)-5-methylbenzo[d]thiazol-6-yl)-2-tert-butoxyacetate (227 mg, 0.403 mmol) and $CH_3CN$ (4.0 mL). A solution of t-butyl nitrite (46 mg, 0.443 mmol) in $CH_3CN$ (400 µL) was added, followed by $CuBr_2$ (anhydrous, 108 mg, 0.484 mmol). The reaction was fitted with a bubbler and stirred for 30 min at 23° C. The reaction was diluted with water and EtOAc, then filtered through celite. The filtrate was extracted with EtOAc (2×). Combined organic layers were dried ($Na_2SO_4$), filtered, and concentrated. The residue was treated with benzene and purification by flash column chromatography on silica gel (hexanes/ethyl acetate eluent) gave the title compound. LCMS-ESI$^+$: calc'd for $C_{30}H_{29}BrClN_3O_3S$: 626.1, 628.1, 630.1 (M+H$^+$); Found: 626.1, 628.1, 630.2 (M+H$^+$).

Preparation of (S)-ethyl 2-tert-butoxy-2-(7-(4-chlorophenyl)-5-methyl-2-(1-methyl-3-(1-methyl-1,2,3,6-tetrahydropyridin-4-yl)-1H-indazol-6-yl)benzo[d]thiazol-6-yl)acetate: A vial was charged with (S)-ethyl 2-(2-(3-bromo-1-methyl-1H-indazol-6-yl)-7-(4-chlorophenyl)-5-methylbenzo[d]thiazol-6-yl)-2-tert-butoxyacetate (36 mg, 57 mmol), 1-methyl-4-(4,4,5,5-tetramethyl-1,3,2-dioxaborolan-2-yl)-1,2,3,6-tetrahydropyridine (13 mg, 57 mmol), $KHCO_3$ (6.3 mg, 63 µmol), Pd(PPh$_3$)$_4$ (6.7 mg, 5.7 mmol), 2 M aq $K_2CO_3$ (250 mL), and dioxane (1 mL). The vessel was sealed and heated to 100° C. for 1 h. The reaction was cooled to 23° C., and filtered (0.45 micron teflon syringe filter). The filtrate was purified by reverse phase HPLC, eluting by 5-100% acetonitrile in $H_2O$ with 0.1% TFA to give the desired product. LCMS-ESI$^+$: calc'd for $C_{36}H_{39}ClN_4O_3S$: 643.2, 645.2 (M+H$^+$); Found: 643.0, 645.0 (M+H$^+$). $^1$H NMR (400 MHz, CD$_3$OD): δ 8.27 (s, 1H), 8.10 (d, J=8.7 Hz, 1H), 7.97-7.82 (m, 2H), 7.72-7.48 (m, 4H), 6.61 (s, 1H), 5.27 (s, 1H), 4.38-4.18 (m, 2H), 4.14 (s, 3H), 4.06-3.93 (m, 2H), 3.65-3.46 (m, 1H), 3.21-3.07 (m, 3H), 3.03 (s, 3H), 2.61 (s, 3H), 1.26 (t, J=7.1 Hz, 3H), 1.00 (s, 9H).

Preparation of (S)-2-tert-butoxy-2-(7-(4-chlorophenyl)-5-methyl-2-(1-methyl-3-(1-methylpiperidin-4-yl)-1H-indazol-6-yl)benzo[d]thiazol-6-yl)acetic acid: A flask was charged with 5% w/w Rh/Al$_2$O$_3$ (20 mg, 9.6 µmol), (S)-ethyl 2-tert-butoxy-2-(7-(4-chlorophenyl)-5-methyl-2-(1-methyl-3-(1-methyl-1,2,3,6-tetrahydropyridin-4-yl)-1H-indazol-6-yl)benzo[d]thiazol-6-yl)acetate (22.3 mg), and EtOH (absolute, 2 mL). The reaction was evacuated (vacuum) and backfilled from a balloon of H$_2$, then stirred vigorously at 23° C. for 2.5 h. At this point, the reaction was treated with THF (1 mL), and 5 M aq NaOH (1 mL), then heated to 100° C. for 30 min. The reaction was cooled to 23° C., and filtered (0.45 micron teflon syringe filter). The filtrate was purified by reverse phase HPLC, eluting by 5-100% acetonitrile in H$_2$O with 0.1% TFA to give the desired product. LCMS-ESI$^+$: calc'd for $C_{34}H_{37}ClN_4O_3S$: 617.2, 619.2 (M+H$^+$); Found: 617.4, 619.2 (M+H$^+$). $^1$H NMR (400 MHz, CD$_3$OD): δ 8.22 (s, 1H), 7.98-7.78 (m, 3H), 7.71 (d, J=8.4 Hz, 1H), 7.65-7.57 (m, 3H), 5.28 (s, 1H), 4.13 (s, 0.5 H, minor diastereomer), 4.09 (s, 2.5 H, major diastereomer), 3.73-3.60 (m, 2H), 3.54-3.37 (m, 2H), 3.29-3.18 (m, 2H), 2.97 (s, 2.5H, major diastereomer), 2.94 (s, 0.5H, minor diastereomer), 2.64 (s, 3H), 2.45-2.31 (m, 2H), 2.28-2.06 (m 1H), 0.99 (s, 9H).

Example 124

(S)-2-tert-butoxy-2-(7-(4-chlorophenyl)-5-methyl-2-(1-methyl-3-(1-methylpiperidin-4-yl)-1H-indazol-5-yl)benzo[d]thiazol-6-yl)acetic acid (268)

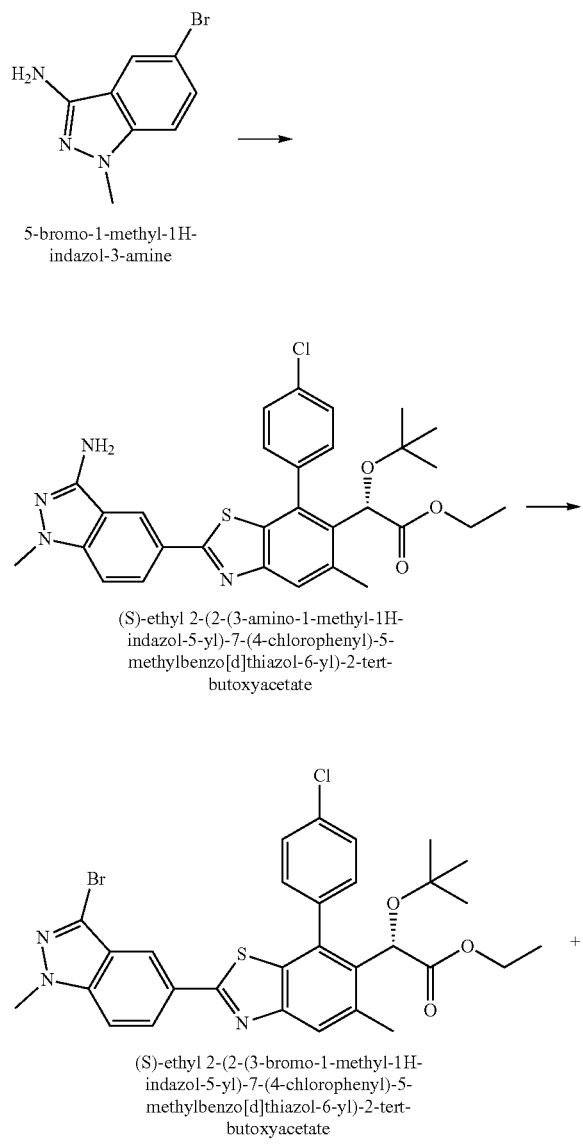

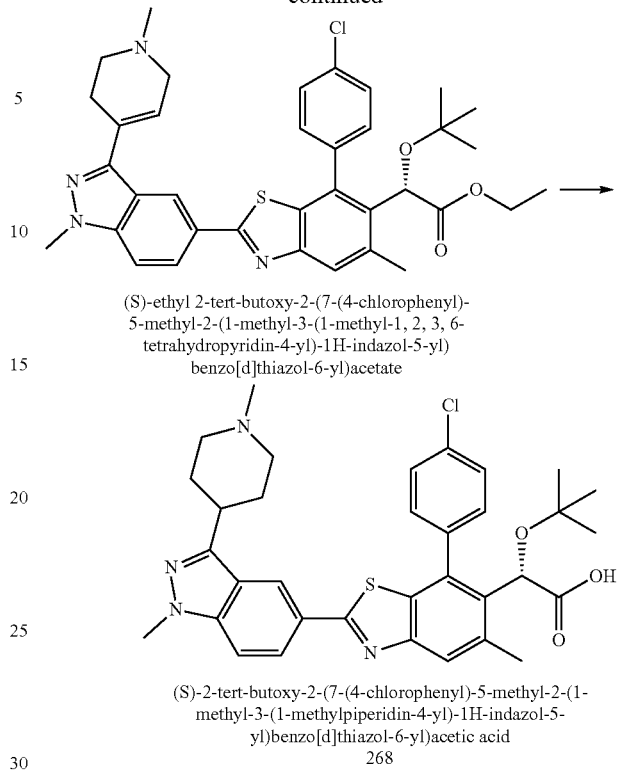

Preparation of (S)-ethyl 2-(2-(3-amino-1-methyl-1H-indazol-5-yl)-7-(4-chlorophenyl)-5-methylbenzo[d]thiazol-6-yl)-2-tert-butoxyacetate: Prepared in a manner similar to (S)-ethyl 2-(2-(3-amino-1-methyl-1H-indazol-6-yl)-7-(4-chlorophenyl)-5-methylbenzo[d]thiazol-6-yl)-2-tert-butoxyacetate except using 5-bromo-1-methyl-1H-indazol-3-amine instead of 6-bromo-1-methyl-1H-indazol-3-amine. LCMS-ESI$^+$: calc'd for $C_{30}H_{31}ClN_4O_3S$: 563.2, 565.2 (M+H$^+$); Found: 563.3, 565.2 (M+H$^+$).

Preparation of (S)-ethyl 2-(2-(3-bromo-1-methyl-1H-indazol-5-yl)-7-(4-chlorophenyl)-5-methylbenzo[d]thiazol-6-yl)-2-tert-butoxyacetate: prepared in a manner similar to (S)-ethyl 2-(2-(3-bromo-1-methyl-1H-indazol-6-yl)-7-(4-chlorophenyl)-5-methylbenzo[d]thiazol-6-yl)-2-tert-butoxyacetate except using (S)-ethyl 2-(2-(3-amino-1-methyl-1H-indazol-5-yl)-7-(4-chlorophenyl)-5-methylbenzo[d]thiazol-6-yl)-2-tert-butoxyacetate instead of (S)-ethyl 2-(2-(3-amino-1-methyl-1H-indazol-6-yl)-7-(4-chlorophenyl)-5-methylbenzo[d]thiazol-6-yl)-2-tert-butoxyacetate. LCMS-ESI$^+$: calc'd for $C_{30}H_{29}BrClN_3O_3S$: 626.1, 628.1, 630.1 (M+H$^+$); Found: 626.1, 628.1, 630.1 (M+H$^+$).

Preparation of (S)-ethyl 2-tert-butoxy-2-(7-(4-chlorophenyl)-5-methyl-2-(1-methyl-3-(1-methyl-1,2,3,6-tetrahydropyridin-4-yl)-1H-indazol-5-yl)benzo[d]thiazol-6-yl)acetate: Prepared in a manner similar to (S)-ethyl 2-tert-butoxy-2-(7-(4-chlorophenyl)-5-methyl-2-(1-methyl-3-(1-methyl-1,2,3,6-tetrahydropyridin-4-yl)-1H-indazol-6-yl)benzo[d]thiazol-6-yl)acetate except using (S)-ethyl 2-(2-(3-bromo-1-methyl-1H-indazol-5-yl)-7-(4-chlorophenyl)-5-methylbenzo[d]thiazol-6-yl)-2-tert-butoxyacetate instead of (S)-ethyl 2-(2-(3-bromo-1-methyl-1H-indazol-6-yl)-7-(4-chlorophenyl)-5-methylbenzo[d]thiazol-6-yl)-2-tert-butoxyacetate. LCMS-ESI$^+$: calc'd for $C_{36}H_{39}ClN_4O_3S$: 643.2, 645.2 (M+H$^+$); Found: 643.1, 645.0 (M+H$^+$). $^1$H NMR (400 MHz, CD$_3$OD):

δ 8.65 (s, 1H), 8.13 (dd, J=8.9, 1.5 Hz, 1H), 7.84 (s, 1H), 7.71 (d, J=8.9 Hz, 1H), 7.65-7.47 (m, 4H), 6.66 (s, 1H), 5.25 (s, 1H), 4.37-4.15 (m, 2H), 4.11 (s, 3H), 4.03-3.87 (m, 2H), 3.87-3.63 (m, 2H), 3.57-3.37 (m, 2H), 3.07 (s, 3H), 2.60 (s, 3H), 1.26 (t, J=7.1 Hz, 3H), 1.00 (s, 9H).

Preparation of (S)-2-tert-butoxy-2-(7-(4-chlorophenyl)-5-methyl-2-(1-methyl-3-(1-methylpiperidin-4-yl)-1H-indazol-5-yl)benzo[d]thiazol-6-yl)acetic acid: Prepared in a similar manner as (S)-2-tert-butoxy-2-(7-(4-chlorophenyl)-5-methyl-2-(1-methyl-3-(1-methylpiperidin-4-yl)-1H-indazol-6-yl)benzo[d]thiazol-6-yl)acetic acid except using (S)-ethyl 2-tert-butoxy-2-(7-(4-chlorophenyl)-5-methyl-2-(1-methyl-3-(1-methyl-1,2,3,6-tetrahydropyridin-4-yl)-1H-indazol-5-yl)benzo[d]thiazol-6-yl)acetate instead of (S)-ethyl 2-tert-butoxy-2-(7-(4-chlorophenyl)-5-methyl-2-(1-methyl-3-(1-methyl-1,2,3,6-tetrahydropyridin-4-yl)-1H-indazol-6-yl)benzo[d]thiazol-6-yl)acetate. LCMS-ESI$^+$: calc'd for $C_{34}H_{37}ClN_4O_3S$: 617.2, 619.2 (M+H$^+$); Found: 617.3, 619.2 (M+H$^+$). $^1$H NMR (400 MHz, CD$_3$OD): δ 8.47 (s, 1H), 8.13 (dd, J=8.9, 1.5 Hz, 1H), 7.83 (s, 1H), 7.74-7.54 (m, 5H), 5.26 (s, 1H), 4.10 (s, 0.3H, minor diastereomer), 4.06 (s, 2.7H, major diastereomer), 3.76-3.60 (m, 2H), 3.58-3.39 (m, 2H), 3.30-3.19 (m, 2H), 2.97 (s, 2.7H, major diastereomer), 2.94 (s, 0.3H, minor diastereomer), 2.63 (s, 3H), 2.49-2.29 (m, 2H), 2.29-2.09 (m, 1H), 0.99 (s, 9H).

Example 125

Preparation of (S)-2-tert-butoxy-2-(7-(4-chlorophenyl)-2-(3-(4-isopropylpiperazin-1-yl)-1-methyl-1H-indazol-5-yl)-5-methylbenzo[d]thiazol-6-yl)acetic acid (269)

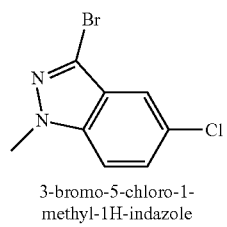

3-bromo-5-chloro-1-methyl-1H-indazole

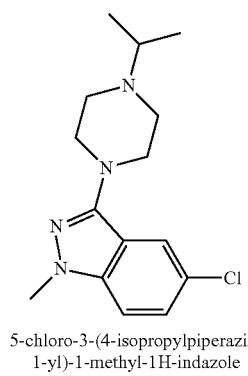

5-chloro-3-(4-isopropylpiperazin-1-yl)-1-methyl-1H-indazole

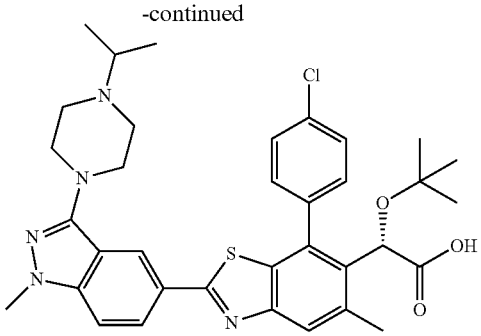

(S)-2-tert-butoxy-2-(7-(4-chlorophenyl)-2-(3-(4-isopropylpiperazin-1-yl)-1-methyl-1H-indazol-5-yl)-5-methylbenzo[d]thiazol-6-yl)acetic acid
269

Preparation of 5-chloro-3-(4-isopropylpiperazin-1-yl)-1-methyl-1H-indazole: A solution of 3-bromo-5-chloro-1-methyl-1H-indazole (500 mg), N-isopropylpiperazine (287 mg), and Dioxane (5.00 mL) was prepared. NaOtBu (294 mg) and Chloro[2-(dicyclohexylphosphino)-3,6-dimethoxy-2',4',6'-triisopropyl-1,1'-biphenyl)][2-(2-aminoethyl)phenyl]Pd(II) (163 mg) were charged and the vessel was sealed and heated to 100° C. overnight. H$_2$O (3 mL) was added and the reaction was filtered (0.45 micron). The filtrate was directly purified on the Gilson C18 column (5 to 100 ACN/H$_2$O+0.1% TFA) giving the title compound. LCMS-ESI$^+$: calc'd for $C_{15}H_{21}ClN_4$: 293.2, 295.1 (M+H$^+$); Found: 293.3, 295.2 (M+H$^+$).

Preparation of (S)-2-tert-butoxy-2-(7-(4-chlorophenyl)-2-(3-(4-isopropylpiperazin-1-yl)-1-methyl-1H-indazol-5-yl)-5-methylbenzo[d]thiazol-6-yl)acetic acid: A microwave vial was charged with Pd(OAc)$_2$ (1.4 mg, trimeric), X-Phos ligand (5.9 mg), bis-pinacolatodiboron (37 mg), and KOAc (53 mg). The vessel was evacuated under vacuum and backfilled with argon. A solution of 5-chloro-3-(4-isopropylpiperazin-1-yl)-1-methyl-1H-indazole (50 mg) in Dioxane (1 mL) was introduced. The reaction was stirred briefly at 23° C., then heated to 110° C. After 1.5 h, The reaction was cooled to 23° C. and charged with (S)-methyl 2-(2-bromo-7-(4-chlorophenyl)-5-methylbenzo[d]thiazol-6-yl)-2-tert-butoxyacetate (83 mg), KHCO$_3$ (12 mg), Pd(PPh$_3$)$_4$ (14 mg), and 2 M aq K$_2$CO$_3$ (500 µL). The reaction was heated to 100° C. for 1 h. EtOH (absolute, 1 mL) and 5 M aq NaOH (1 mL) were added. The reaction was heated at 100° C. for 30 min. The reaction was cooled to 23° C. and directly purified on the Gilson C18 column [5 to 100 ACN/H$_2$O+0.1% TFA] giving the title compound. LCMS-ESI$^+$: calc'd for $C_{35}H_{40}ClN_5O_3S$: 646.3, 648.3 (M+H$^+$); Found: 646.4, 648.2 (M+H$^+$). $^1$H NMR (400 MHz, CD$_3$OD): δ 8.42 (s, 1H), 8.06 (d, J=8.9 Hz, 1H), 7.80 (s, 1H), 7.68 (d, J=9.0 Hz, 1H), 7.62-7.48 (m, 4H), 5.24 (s, 1H), 4.15 (d, J=14.4 Hz, 2H), 3.94 (s, 3H), 3.70-3.52 (m, 3H), 3.47 (s, 2H), 3.35-3.25 (m, 2H), 2.60 (s, 3H), 1.44 (d, J=6.6 Hz, 6H), 0.97 (s, 9H).

Example 126

Preparation of 5-bromo-1-methyl-3-(4-methylpiperazin-1-yl)-1H-pyrrolo[2,3-b]pyridine (270)

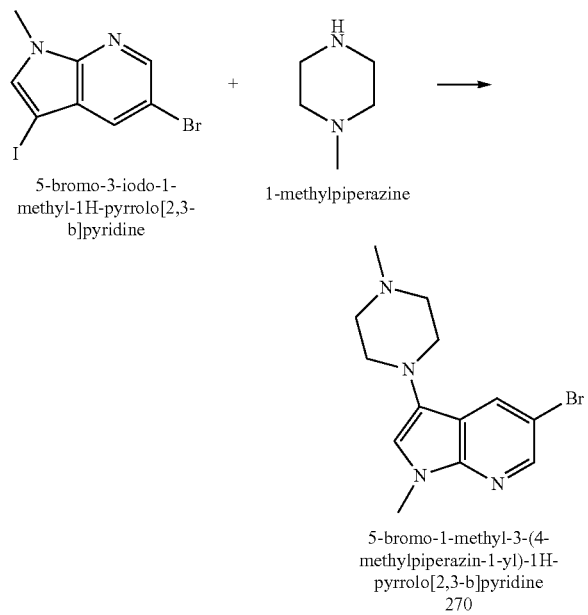

Preparation of 5-bromo-1-methyl-3-(4-methylpiperazin-1-yl)-1H-pyrrolo[2,3-b]pyridine: A solution of 5-bromo-3-iodo-1-methyl-1H-pyrrolo[2,3-b]pyridine (150 mg, 0.445 mmol), 1-methylpiperazine (356.7 mg, 3.56 mmol), copper (I) iodide (84.8 mg, 0.445 mmol), $K_3PO_4$ (378 mg, 1.78 mmol), 1,2-ethanediol (138 mg, 2.225 mmol) in isopropyl alcohol (5 mL) in a sealed tubes was heated at 70° C. for 2 days. After cooling to room temperature, the reaction mixture was filtered through celite. The filtrate was concentrated in vacuo. The residue was taken up in EtOAc and the solution was washed with saturated $NaHCO_3$, dried and concentrated. Purification by flash chromatography afforded the title compound. LCMS-ESI$^+$: calc'd for $C_{13}H_{17}BrN_4$ 309.1 (M+H$^+$); Found: 309.1 (M+H$^+$).

Example 127

Preparation of 5-bromo-1-methyl-3-(1-methyl-1,2,3,6-tetrahydropyridin-4-yl)-1H-pyrrolo-[2,3-b]pyridine (271)

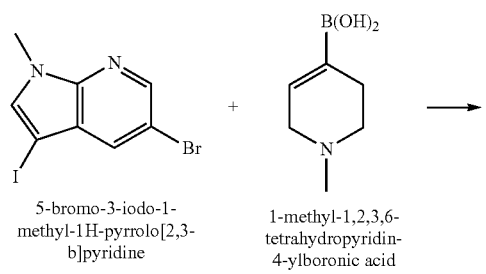

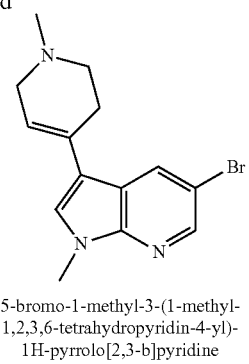

Preparation of 5-bromo-1-methyl-3-(1-methyl-1,2,3,6-tetrahydropyridin-4-yl)-1H-pyrrolo-[2,3-b]pyridine: To a solution of 5-bromo-3-iodo-1-methyl-1H-pyrrolo[2,3-b]pyridine (180 mg, 0.534 mmol) and 1-methyl-1,2,3,6-tetrahydropyridin-4-boronic acid (155 mg, 0.694 mmol) in dioxane (5.4 mL, degassed) was added tetrakis(triphenylphosphine)palladium (0) (75 mg, 0.064 mmol), $K_2CO_3$ (369 mg, 2.67 mmol) and water (1.8 mL, degassed). The reaction mixture was heated at 40° C. for 15 h, cooled and partitioned between ethyl acetate and brine. The organic layer was separated, dried over $Na_2SO_4$, filtered and concentrated to give crude which was purified by chromatographic column to afford the desired product. LCMS-ESI$^+$: calc'd for $C_{14}H_{16}BrN_3$: 306.2 (M+H$^+$); Found: 306.2 (M+H$^+$).

Example 128

Preparation of (S)-2-tert-butoxy-2-(7-(4-chlorophenyl)-2-(3-(3,5-dimethyl-1H-pyrazol-1-yl)phenyl)-5-methylbenzo[d]thiazol-6-yl)acetic acid (272)

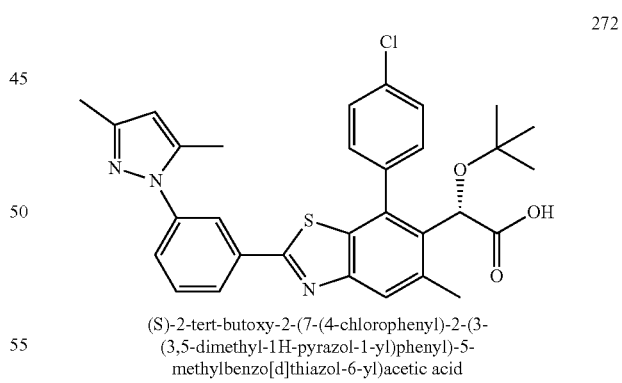

Preparation of (S)-2-tert-butoxy-2-(7-(4-chlorophenyl)-2-(3-(3,5-dimethyl-1H-pyrazol-1-yl)phenyl)-5-methylbenzo[d]thiazol-6-yl)acetic acid: Prepared in a similar manner as (S)-2-tert-butoxy-2-(7-(4-chlorophenyl)-5-methyl-2-(2-morpholinopyridin-4-yl)benzo[d]thiazol-6-yl)acetic acid except 3-(3,5-dimethyl-1H-parazol-1-yl)phenylboronic acid used instead of 2-morpholinopyridine-4-boronic acid. LCMS-ESI$^+$: calc'd for $C_{31}H_{30}ClN_3O_3S$: 560.3 (M+H$^+$); Found: 560.3 (M+H$^+$); $^1$H NMR (400 MHz, CD$_3$OD) δ 8.13

(s, 1H), 8.05 (d, J=7.3, 1H), 7.87 (s, 1H), 7.70-7.59 (m, 6H), 6.12 (s, 1H), 5.26 (s, 1H), 2.61 (s, 3H), 2.35 (s, 3H), 2.27 (s, 3H), 0.97 (s, 9H).

Example 129

Preparation of (S)-2-tert-butoxy-2-(7-(4-chlorophenyl)-5-methyl-2-(3-(1-methyl-1H-indazol-5-yl)-2-oxopyrazin-1(2H)-yl)benzo[d]thiazol-6-yl)acetic acid (273)

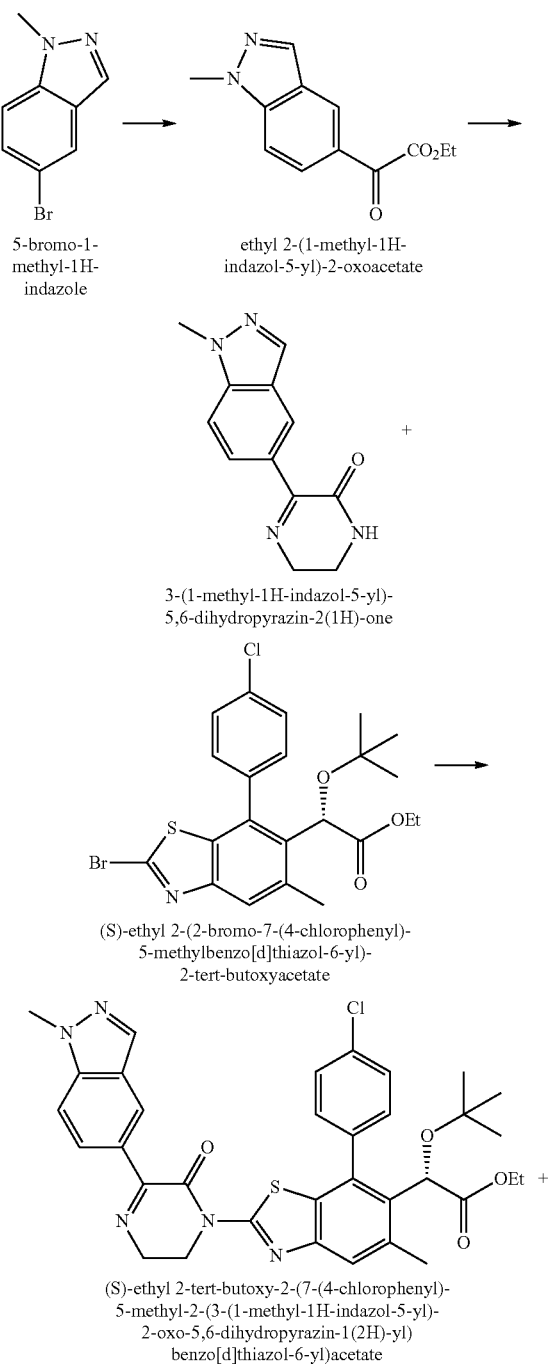

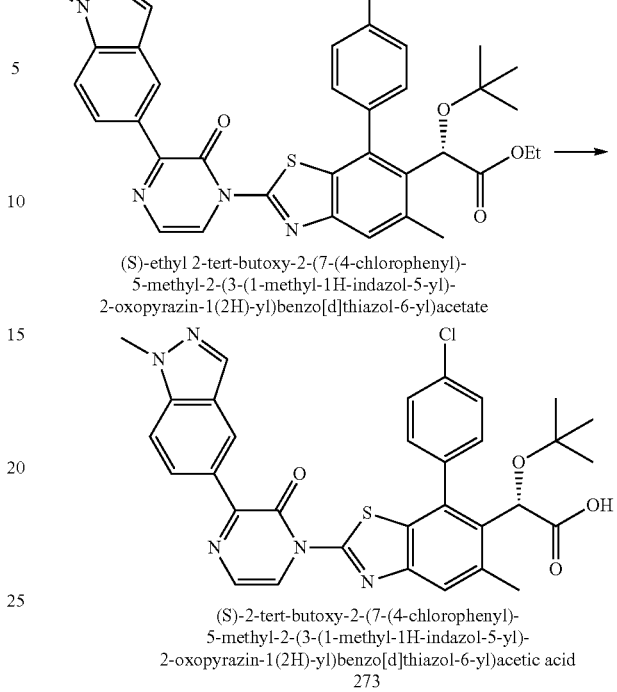

Preparation of ethyl 2-(1-methyl-1H-indazol-5-yl)-2-oxoacetate: To a solution of 5-bromo-1-methyl-1H-indazole (Aldrich, 1.06 g, 5 mmol) in THF (22 mL) at −78° C. was added n-butyllithium (2.2 mL, 2.5 M, 5.5 mmol) slowly. The mixture was stirred for 20 minutes, and the solution of diethyl oxalate (0.68 mL, 5.0 mmol) in THF (5 mL) was added over one minute period. The reaction was kept at −78° C. for 40 minutes, and was quenched with saturated ammonium chloride solution and warmed to 25° C. The mixture was extracted with ethyl acetate, and the organic phase was washed with water, brine, and dried over sodium sulfate. Concentration and purification with flash column chromatography (hexanes/EtOAc) gave ethyl 2-(1-methyl-1H-indazol-5-yl)-2-oxoacetate. LCMS-ESI$^+$: calc'd for $C_{12}H_{13}N_2O_3$: 233.2 (M+H$^+$); Found: 233.0 (M+H$^+$).

Preparation of 3-(1-methyl-1H-indazol-5-yl)-5,6-dihydropyrazin-2(1H)-one: The mixture of 2-(1-methyl-1H-indazol-5-yl)-2-oxoacetate (520 mg, 2.2 mmol), ethylenediamine (0.15 mL, 2.2 mmol), and sodium sulfate in toluene (9 mL) was heated at reflux for 12 hours. The reaction was cooled, and diluted with ethyl acetate. The mixture was filtered through a pad of celite and was washed with ethyl acetate. Concentration and purification with flash column chromatography (EtOAc) gave 3-(1-methyl-1H-indazol-5-yl)-5,6-dihydropyrazin-2(1H)-one. LCMS-ESI$^+$: calc'd for $C_{12}H_{13}N_4O$: 229.3 (M+H$^+$); Found: 229.2 (M+H$^+$).

Preparation of (S)-ethyl 2-tert-butoxy-2-(7-(4-chlorophenyl)-5-methyl-2-(3-(1-methyl-1H-indazol-5-yl)-2-oxo-5,6-dihydropyrazin-1(2H)-yl)benzo[d]thiazol-6-yl)acetate and (S)-ethyl 2-tert-butoxy-2-(7-(4-chlorophenyl)-5-methyl-2-(3-(1-methyl-1H-indazol-5-yl)-2-oxopyrazin-1(2H)-yl)benzo[d]thiazol-6-yl)acetate: The mixture of 3-(1-methyl-1H-indazol-5-yl)-5,6-dihydropyrazin-2(1H)-one (160 mg, 0.70 mmol), (S)-ethyl 2-(2-bromo-7-(4-chlorophenyl)-5-methylbenzo[d]thiazol-6-yl)-2-tert-butoxyacetate (500 mg, 1.05 mmol), tris(2-(2-methoxyethoxy)ethyl)amine (60 μL, 0.2 mmol), potassium carbonate (320 mg, 2.3 mmol), and copper(I) chloride (69 mg, 0.70 mmol) in xylene (16 mL) was degassed with nitrogen, and was heated at 140° C. for 16 hours. The reaction mixture was cooled and diluted with ethyl acetate. The mixture was filtered through a pad of celite and washed with ethyl acetate. The organic solution was washed with water and brine, and was dried over sodium sulfate. Concentration and purification with flash column chromatography (hexanes/EtOAc) gave (S)-ethyl 2-tert-butoxy-2-(7-(4-chlorophenyl)-5-methyl-2-(3-(1-methyl-1H-indazol-5-yl)-2-oxo-5,6-dihydropyrazin-1(2H)-yl)benzo[d]thiazol-6-yl)acetate. LCMS-ESI$^+$: calc'd for $C_{34}H_{34}ClN_5O_4S$: 644.2 (M+H$^+$); Found: 644.3 (M+H$^+$); and (S)-ethyl 2-tert-butoxy-2-(7-(4-chlorophenyl)-5-methyl-2-(3-(1-methyl-1H-indazol-5-yl)-2-oxopyrazin-1(2H)-yl)benzo[d]thiazol-6-yl)acetate (40 mg). LCMS-ESI$^+$: calc'd for $C_{34}H_{33}ClN_5O_4S$: 642.2 (M+H$^+$); Found: 642.3 (M+H$^+$).

Preparation of (S)-2-tert-butoxy-2-(7-(4-chlorophenyl)-5-methyl-2-(3-(1-methyl-1H-indazol-5-yl)-2-oxopyrazin-1(2H)-yl)benzo[d]thiazol-6-yl)acetic acid: The mixture of (S)-ethyl 2-tert-butoxy-2-(7-(4-chlorophenyl)-5-methyl-2-(3-(1-methyl-1H-indazol-5-yl)-2-oxopyrazin-1(2H)-yl)benzo[d]thiazol-6-yl)acetate (6.4 mg) and lithium iodide (100 mg) in pyridine (0.8 mL) was heated at 170° C. for 75 minutes. The mixture was cooled and pyridine was removed under reduced pressure. The mixture was co-evaporated with DMF and was purified with reverse phase HPLC to give (S)-2-tert-butoxy-2-(7-(4-chlorophenyl)-5-methyl-2-(3-(1-methyl-11'-indazol-5-yl)-2-oxopyrazin-1(2H)-yl)benzo[d]thiazol-6-yl)acetic acid. LCMS-ESI$^+$: calc'd for $C_{32}H_{29}ClN_5O_4S$: 614.2 (M+H$^+$); Found: 614.2 (M+H$^+$); $^1$H-NMR 400 MHz, (CDCl$_3$) δ 8.98 (s, 1H), 8.72 (d, J=4.7 Hz, 1H), 8.34 (d, J=8.6 Hz, 1H), 8.06 (s, 1H), 7.84 (s, 1H), 7.70 (m, 2H), 7.55-7.40 (m, 4H), 5.36 (s, 1H), 4.10 (s, 3H), 2.60 (s, 3H), 0.98 (s, 9H).

Example 130

Preparation of (2S)-2-tert-butoxy-2-(7-(4-chlorophenyl)-5-methyl-2-(4-methyl-3-(1-methyl-1H-indazol-5-yl)-2-oxopiperazin-1-yl)benzo[d]thiazol-6-yl)acetic acid (274) and (2S)-2-tert-butoxy-2-(7-(4-chlorophenyl)-5-methyl-2-(3-(1-methyl-1H-indazol-5-yl)-2-oxopiperazin-1-yl)benzo[d]thiazol-6-yl) acetic acid (275)

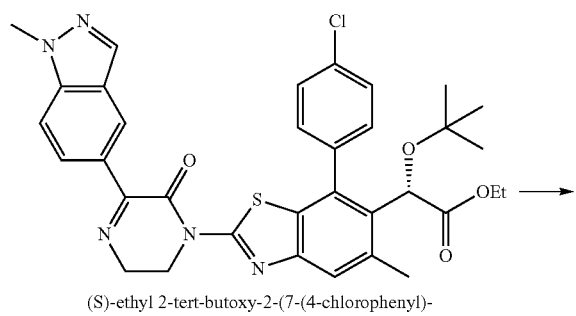

(S)-ethyl 2-tert-butoxy-2-(7-(4-chlorophenyl)-
5-methyl-2-(3-(1-methyl-1H-indazol-5-yl)-
2-oxo-5,6-dihydropyrazin-1(2H)-yl)
benzo[d]thiazol-6-yl)acetate

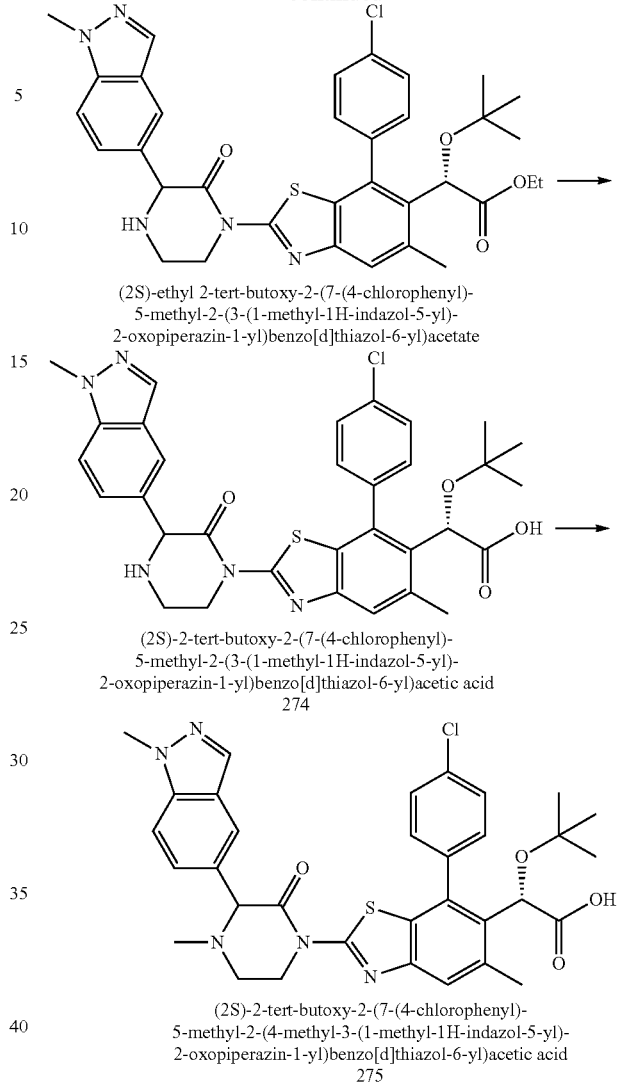

Preparation of (2S)-ethyl 2-tert-butoxy-2-(7-(4-chlorophenyl)-5-methyl-2-(3-(1-methyl-1H-indazol-5-yl)-2-oxopiperazin-1-yl)benzo[d]thiazol-6-yl)acetate: To the solution of (S)-ethyl 2-tert-butoxy-2-(7-(4-chlorophenyl)-5-methyl-2-(3-(1-methyl-1H-indazol-5-yl)-2-oxo-5,6-dihydropyrazin-1(2H)-yl)benzo[d]thiazol-6-yl)acetate (64 mg, 0.1 mmol) in THF (1 mL) was added acetic acid (6 μL, 0.1 mmol), followed by sodium cyanoborohydride (10 mg, 0.2 mmol). The mixture was stirred for 12 hours, and diluted with ethyl acetate. Sodium hydroxide solution (1 N, 5 mL) was added, and the mixture was stirred for 30 minutes. Organic phase was separated, and was washed water and brine, and was dried over sodium sulfate. Concentration and purification with flash column chromatography (hexanes/EtOAc) gave (2S)-ethyl 2-tert-butoxy-2-(7-(4-chlorophenyl)-5-methyl-2-(3-(1-methyl-1H-indazol-5-yl)-2-oxopiperazin-1-yl)benzo[d]thiazol-6-yl)acetate. LCMS-ESI$^+$: calc'd for $C_{34}H_{37}ClN_5O_4S$: 646.2 (M+H$^+$); Found: 646.2 (M+H$^+$).

Preparation of (2S)-2-tert-butoxy-2-(7-(4-chlorophenyl)-5-methyl-2-(3-(1-methyl-1H-indazol-5-yl)-2-oxopiperazin-1-yl)benzo[d]thiazol-6-yl)acetic acid: (2S)-2-tert-butoxy-2-(7-(4-chlorophenyl)-5-methyl-2-(3-(1-methyl-1H-indazol-5-yl)-2-oxopiperazin-1-yl)benzo[d]thiazol-6-yl)acetic acid (5 mg) was prepared in a similar manner as compound (S)-2-tert-butoxy-2-(7-(4-chlorophenyl)-5-methyl-2-(3-(1-methyl-1H-indazol-5-yl)-2-oxopyrazin-1 (2H)-yl)benzo[d]thiazol-6-yl)acetic acid except using (2S)-ethyl 2-tert-butoxy-2-(7-(4-chlorophenyl)-5-methyl-2-(3-(1-methyl-1H-indazol-5-yl)-2-oxopiperazin-1-yl)benzo[d]thiazol-6-yl) acetate instead of (S)-ethyl 2-tert-butoxy-2-(7-(4-chlorophenyl)-5-methyl-2-(3-(1-methyl-1H-indazol-5-yl)-2-oxopyrazin-1(2H)-yl)benzo[d]thiazol-6-yl)acetate. LCMS-ESI$^+$: calc'd for $C_{32}H_{33}ClN_5O_4S$: 618.2 (M+H$^+$); Found: 618.1 (M+H$^+$). $^1$H-NMR 400 MHz, (CDCl$_3$) δ 7.99 (m, 1H), 7.74-7.60 (m, 3H), 7.43-7.35 (m, 4H), 7.3-7.2 (m, 1H), 5.31 (s, 1H), 5.13 (m, 1H), 4.62-4.35 (m, 2H), 4.06 (s, 3H), 3.3 (m, 2H), 2.57 (s, 3H), 0.98 (s, 9H).

Preparation of (2S)-2-tert-butoxy-2-(7-(4-chlorophenyl)-5-methyl-2-(4-methyl-3-(1-methyl-1H-indazol-5-yl)-2-oxopiperazin-1-yl)benzo[d]thiazol-6-yl)acetic acid: To the solution of: (2S)-2-tert-butoxy-2-(7-(4-chlorophenyl)-5-methyl-2-(3-(1-methyl-1H-indazol-5-yl)-2-oxopiperazin-1-yl) benzo[d]thiazol-6-yl)acetic acid (3 mg) in methanol (0.5 mL) was added formaldehyde solution (20 μL, 37%), followed by acetic acid (10 μL) and sodium cyanoborohydride (12 mg). The mixture was stirred for 1 hour, and solvents were removed under reduced pressure. The remaining solid was dissolved with DMF/water (1 mL/0.5 mL), and was purified with reverse phase HPLC to give (2S)-2-tert-butoxy-2-(7-(4-chlorophenyl)-5-methyl-2-(4-methyl-3-(1-methyl-1H-indazol-5-yl)-2-oxopiperazin-1-yl)benzo[d]thiazol-6-yl)acetic acid. LCMS-ESI$^+$: calc'd for $C_{33}H_{35}ClN_5O_4S$: 632.2 (M+H$^+$); Found: 632.2 (M+H$^+$). $^1$H-NMR 400 MHz, (CD$_3$OD) δ 8.0 (m, 1H), 7.82 (m, 1H), 7.68 (s, 1H), 7.62-7.40 (m, 6H), 5.21 (m, 1H), 4.70 (m, 1H), 4.6-4.3 (m, 2H), 4.08/4.05 (s, 3H), 3.5 (m, 2H), 2.57 (s, 3H), 2.40 (m, 3H), 0.93 (s, 9H).

Example 131

Preparation of (2S)-2-tert-butoxy-2-(2-(4-(tert-butoxycarbonyl)-3-(1-methyl-1H-indazol-5-yl)piperazin-1-yl)-7-(4-chlorophenyl)-5-methylbenzo[d]thiazol-6-yl)acetic (276) and (2S)-2-tert-butoxy-2-(7-(4-chlorophenyl)-5-methyl-2-(3-(1-methyl-1H-indazol-5-yl)piperazin-1-yl)benzo[d]thiazol-6-yl) acetic acid (277)

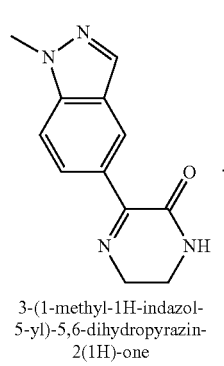

3-(1-methyl-1H-indazol-5-yl)-5,6-dihydropyrazin-2(1H)-one

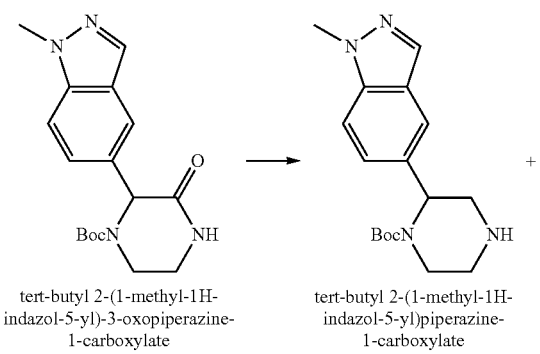

tert-butyl 2-(1-methyl-1H-indazol-5-yl)-3-oxopiperazine-1-carboxylate tert-butyl 2-(1-methyl-1H-indazol-5-yl)piperazine-1-carboxylate

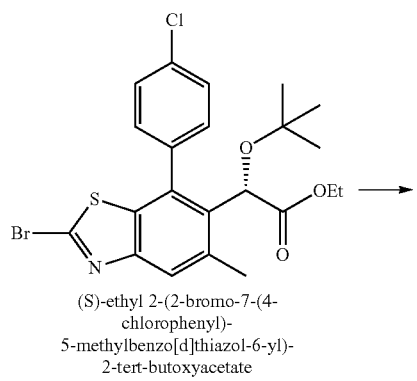

(S)-ethyl 2-(2-bromo-7-(4-chlorophenyl)-5-methylbenzo[d]thiazol-6-yl)-2-tert-butoxyacetate

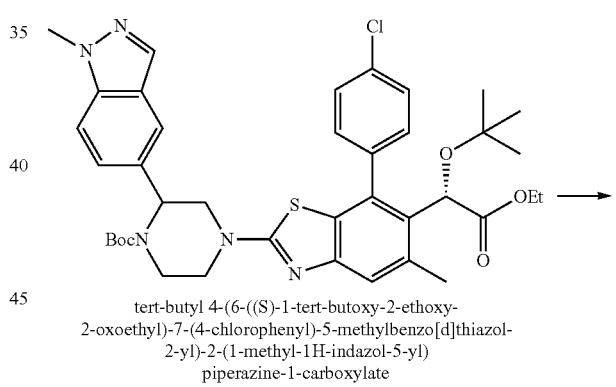

tert-butyl 4-(6-((S)-1-tert-butoxy-2-ethoxy-2-oxoethyl)-7-(4-chlorophenyl)-5-methylbenzo[d]thiazol-2-yl)-2-(1-methyl-1H-indazol-5-yl) piperazine-1-carboxylate

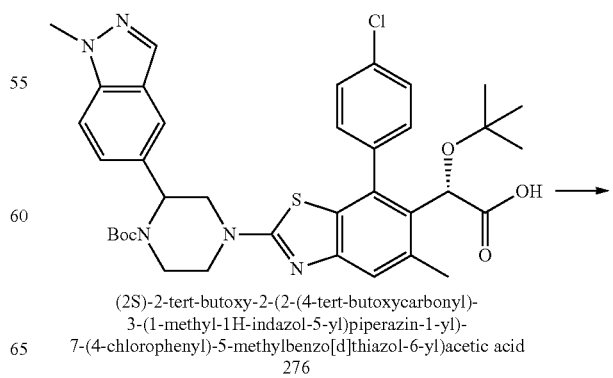

(2S)-2-tert-butoxy-2-(2-(4-tert-butoxycarbonyl)-3-(1-methyl-1H-indazol-5-yl)piperazin-1-yl)-7-(4-chlorophenyl)-5-methylbenzo[d]thiazol-6-yl)acetic acid
276

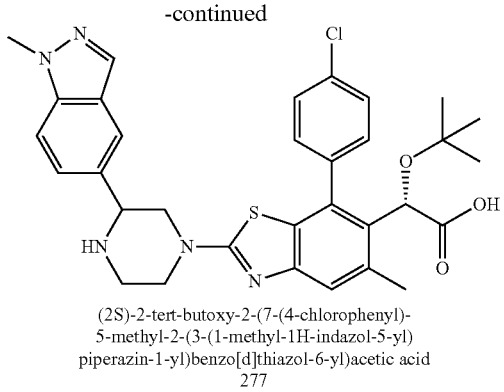

(2S)-2-tert-butoxy-2-(7-(4-chlorophenyl)-
5-methyl-2-(3-(1-methyl-1H-indazol-5-yl)
piperazin-1-yl)benzo[d]thiazol-6-yl)acetic acid
277

Preparation of tert-butyl 2-(1-methyl-1H-indazol-5-yl)-3-oxopiperazine-1-carboxylate: To the solution of 3-(1-methyl-1H-indazol-5-yl)-5,6-dihydropyrazin-2(1H)-one (23 mg, 0.1 mmol) in THF (1 mL) was added acetic acid (6 µL, 0.1 mmol), followed by sodium cyanoborohydride (10 mg, 0.2 mmol). The mixture was stirred for 12 hours, and diisopropylethylamine (35 µL, 0.2 mmol) and di-t-butyl dicarbonate (24 mg, 0.11 mmol) were added. The reaction mixture was stirred for another 16 hours, and was quenched with water. The mixture was diluted with ethyl acetate, and was basified with 1N sodium hydroxide. The organic phase was separated, and was washed with water and brine, and was dried with sodium sulfate. Concentration and purification with flash column chromatography (hexanes/EtOAc) gave tert-butyl 2-(1-methyl-1H-indazol-5-yl)-3-oxopiperazine-1-carboxylate. LCMS-ESI$^+$: calc'd for $C_{17}H_{23}N_4O_3$: 331.2 (M+H$^+$); Found: 330.9 (M+H$^+$).

Preparation of tert-butyl 2-(1-methyl-1H-indazol-5-yl)piperazine-1-carboxylate: To the solution of tert-butyl 2-(1-methyl-1H-indazol-5-yl)-3-oxopiperazine-1-carboxylate (10 mg) in THF (0.5 mL) at 0° C. was added borane in THF (1.0 N, 1 mL) slowly. The mixture was heated at 55° C. for 3 hours, and was cooled. The reaction was quenched with methanol (1 mL), and was stirred for 30 minutes. The mixture was diluted with ethyl acetate, and was made basic with 1 N sodium hydroxide solution. The organic phase was separated, and was washed with water and brine, and was dried with sodium sulfate. Concentration gave tert-butyl 2-(1-methyl-1H-indazol-5-yl)piperazine-1-carboxylate. LCMS-ESI$^+$: calc'd for $C_{17}H_{25}N_4O_2$: 317.2 (M+H$^+$); Found: 317.0 (M+H$^+$).

Preparation of tert-butyl 4-(6-((S)-1-tert-butoxy-2-ethoxy-2-oxoethyl)-7-(4-chlorophenyl)-5-methylbenzo[d]thiazol-2-yl)-2-(1-methyl-1H-indazol-5-yl)piperazine-1-carboxylate: The mixture of tert-butyl 2-(1-methyl-1H-indazol-5-yl)piperazine-1-carboxylate (10 mg, 0.03 mmol), (S)-ethyl 2-(2-bromo-7-(4-chlorophenyl)-5-methylbenzo[d]thiazol-6-yl)-2-tert-butoxyacetate (15 mg, 0.03 mmol), and potassium carbonate (41 mg, 0.3 mmol) in DMF (0.5 mL) was heated at 140° C. for 4 hours. The mixture was cooled, and was quenched with water. The mixture was extracted with ethyl acetate, and the organic phase was washed with water and brine, and was dried with sodium sulfate. Concentration and purification by reverse phase HPLC gave tert-butyl 4-(6-((S)-1-tert-butoxy-2-ethoxy-2-oxoethyl)-7-(4-chlorophenyl)-5-methylbenzo[d]thiazol-2-yl)-2-(1-methyl-1H-indazol-5-yl)piperazine-1-carboxylate. LCMS-ESI$^+$: calc'd for $C_{39}H_{47}ClN_5O_5S_2$: 732.3 (M+H$^+$); Found: 732.2 (M+H$^+$).

Preparation of (2S)-2-tert-butoxy-2-(2-(4-(tert-butoxycarbonyl)-3-(1-methyl-1H-indazol-5-yl)piperazin-1-yl)-7-(4-chlorophenyl)-5-methylbenzo[d]thiazol-6-yl)acetic acid: To the solution of tert-butyl 4-(6-((S)-1-tert-butoxy-2-ethoxy-2-oxoethyl)-7-(4-chlorophenyl)-5-methylbenzo[d]thiazol-2-yl)-2-(1-methyl-1H-indazol-5-yl)piperazine-1-carboxylate (5 mg) in THF/MeOH (0.5 mL/0.5 mL) was added sodium hydroxide solution (0.4 mL, 1.0 N). The mixture was heated at 50° C. for 16 hours. The mixture was cooled, and was acidified with acetic acid (60 µL). Concentration and purification with reverse phase HPLC gave (2S)-2-tert-butoxy-2-(2-(4-(tert-butoxycarbonyl)-3-(1-methyl-1H-indazol-5-yl)piperazin-1-yl)-7-(4-chlorophenyl)-5-methylbenzo[d]thiazol-6-yl)acetic acid. LCMS-ESI$^+$: calc'd for $C_{37}H_{43}ClN_5O_5S$: 704.3 (M+H$^+$); Found: 704.1 (M+H$^+$). $^1$H-NMR 400 MHz, (CD$_3$OD) δ 7.96 (s, 1H), 7.64 (m, 2H), 7.49 (m, 3H), 7.38 (m, 3H), 5.46 (m, 1H), 5.19 (s, 1H), 4.4 (m, 1H), 4.2 (m, 1H), 4.07 (s, 3H), 4.0-3.7 (m, 2H), 3.5 (m, 2H), 2.5 (s, 3H), 1.40 (s, 9H), 0.98 (s, 9H).

Preparation of (2S)-2-tert-butoxy-2-(7-(4-chlorophenyl)-5-methyl-2-(3-(1-methyl-1H-indazol-5-yl)piperazin-1-yl)benzo[d]thiazol-6-yl)acetic acid: To (2S)-2-tert-butoxy-2-(2-(4-(tert-butoxycarbonyl)-3-(1-methyl-1H-indazol-5-yl)piperazin-1-yl)-7-(4-chlorophenyl)-5-methylbenzo[d]thiazol-6-yl)acetic acid (4 mg) was added hydrochloric acid in 2-propanol (3 mL, 0.5 N, 1.5 mmol). The mixture was stirred for 24 hours. Concentration and purification with reverse phase HPLC gave (2S)-2-tert-butoxy-2-(7-(4-chlorophenyl)-5-methyl-2-(3-(1-methyl-1H-indazol-5-yl)piperazin-1-yl)benzo[d]thiazol-6-yl)acetic acid. LCMS-ESI$^+$: calc'd for $C_{32}H_{35}ClN_5O_3S$: 604.2 (M+H$^+$); Found: 604.3 (M+H$^+$). $^1$H-NMR 400 MHz, (CD$_3$OD) δ 8.10 (s, 1H), 7.97 (s, 1H), 7.72 (m, 1H), 7.6-7.4 (m, 5H), 7.38 (s, 1H), 5.15 (s, 1H), 4.7 (m, 1H), 4.45 (m, 1H), 4.26 (m, 1H), 4.11 (s, 3H), 3.8 (m, 1H), 3.65-3.4 (m, 3H), 2.50 (s, 3H), 0.94 (s, 9H);

Example 132

Preparation of (2S)-2-tert-butoxy-2-(7-(4-chlorophenyl)-5-methyl-2-(4-methyl-3-(1-methyl-1H-indazol-5-yl)piperazin-1-yl)benzo[d]thiazol-6-yl)acetic acid (278) and of (2S)-2-tert-butoxy-2-(7-(4-chlorophenyl)-2-(4-isopropyl-3-(1-methyl-1H-indazol-5-yl)piperazin-1-yl)-5-methylbenzo[d]thiazol-6-yl)acetic acid (279)

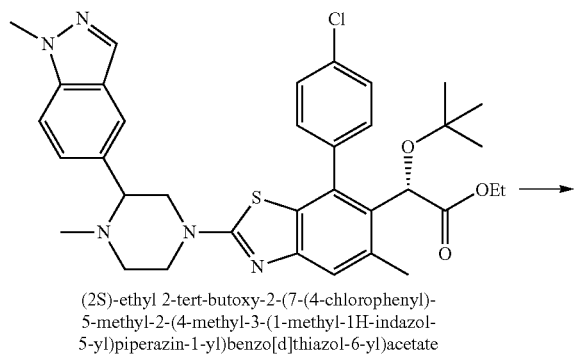

(2S)-ethyl 2-tert-butoxy-2-(7-(4-chlorophenyl)-
5-methyl-2-(4-methyl-3-(1-methyl-1H-indazol-
5-yl)piperazin-1-yl)benzo[d]thiazol-6-yl)acetate

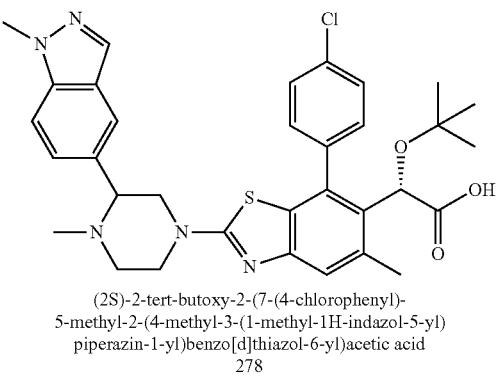 [SMILES: Cc1cc2nc(N3CCNC(c4ccc5c(cnn5C)c4)C3)sc2c(-c2ccc(Cl)cc2)c1[C@H](OC(C)(C)C)C(=O)O]

(2S)-2-tert-butoxy-2-(7-(4-chlorophenyl)-
5-methyl-2-(4-methyl-3-(1-methyl-1H-indazol-5-yl)
piperazin-1-yl)benzo[d]thiazol-6-yl)acetic acid
278

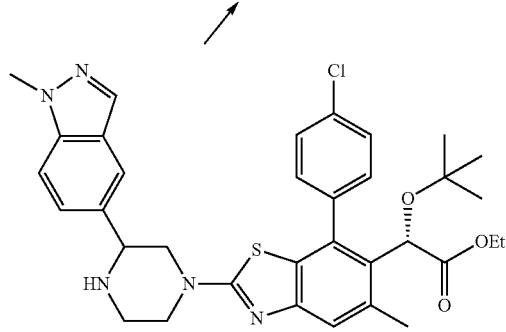

(2S)-ethyl 2-tert-butoxy-2-(7-(4-chlorophenyl)-
5-methyl-2-(3-(1-methyl-1H-indazol-5-yl)
piperazin-1-yl)benzo[d]thiazol-6-yl)acetate

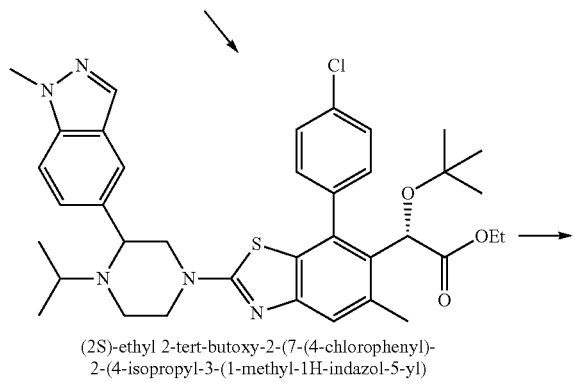

(2S)-ethyl 2-tert-butoxy-2-(7-(4-chlorophenyl)-
2-(4-isopropyl-3-(1-methyl-1H-indazol-5-yl)
piperazin-1-yl)-5-methylbenzo[d]thiazol-6-yl)acetate

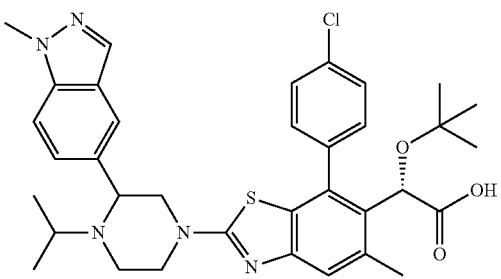

(2S)-2-tert-butoxy-2-(7-(4-chlorophenyl)-
2-(4-isopropyl-3-(1-methyl-1H-indazol-5-yl)
piperazin-1-yl)-5-methylbenzo[d]thiazol-6-yl)acetic acid
279

Preparation of (2S)-ethyl 2-tert-butoxy-2-(7-(4-chlorophenyl)-5-methyl-2-(4-methyl-3-(1-methyl-1H-indazol-5-yl)piperazin-1-yl)benzo[d]thiazol-6-yl)acetate: (2S)-ethyl 2-tert-butoxy-2-(7-(4-chlorophenyl)-5-methyl-2-(4-methyl-3-(1-methyl-1H-indazol-5-yl)piperazin-1-yl)benzo[d]thiazol-6-yl)acetate (16 mg) was prepared in a similar manner as (2S)-2-tert-butoxy-2-(7-(4-chlorophenyl)-5-methyl-2-(4-methyl-3-(1-methyl-1H-indazol-5-yl)-2-oxopiperazin-1-yl)benzo[d]thiazol-6-yl)acetic acid except using (2S)-ethyl 2-tert-butoxy-2-(7-(4-chlorophenyl)-5-methyl-2-(3-(1-methyl-1H-indazol-5-yl)piperazin-1-yl)benzo[d]thiazol-6-yl)acetate instead of (2S)-2-tert-butoxy-2-(7-(4-chlorophenyl)-5-methyl-2-(3-(1-methyl-1H-indazol-5-yl)-2-oxopiperazin-1-yl)benzo[d]thiazol-6-yl)acetic acid. LCMS-ESI$^+$: calc'd for $C_{35}H_{41}ClN_5O_3S$: 646.2 (M+H$^+$); Found: 646.3 (M+H$^+$).

Preparation of (2S)-2-tert-butoxy-2-(7-(4-chlorophenyl)-5-methyl-2-(4-methyl-3-(1-methyl-1H-indazol-5-yl)piperazin-1-yl)benzo[d]thiazol-6-yl)acetic acid: (2S)-2-tert-butoxy-2-(7-(4-chlorophenyl)-5-methyl-2-(4-methyl-3-(1-methyl-1H-indazol-5-yl)piperazin-1-yl)benzo[d]thiazol-6-yl)acetic acid (12 mg) was prepared in a similar manner as compound (2S)-2-tert-butoxy-2-(2-(4-(tert-butoxycarbonyl)-3-(1-methyl-1H-indazol-5-yl)piperazin-1-yl)-7-(4-chlorophenyl)-5-methylbenzo[d]thiazol-6-yl)acetic acid except using (2S)-ethyl 2-tert-butoxy-2-(7-(4-chlorophenyl)-5-methyl-2-(4-methyl-3-(1-methyl-1H-indazol-5-yl)piperazin-1-yl)benzo[d]thiazol-6-yl)acetate instead of tert-butyl 4-(6-((S)-1-tert-butoxy-2-ethoxy-2-oxoethyl)-7-(4-chlorophenyl)-5-methylbenzo[d]thiazol-2-yl)-2-(1-methyl-1H-indazol-5-yl)piperazine-1-carboxylate. LCMS-ESI$^+$: calc'd for $C_{33}H_{37}ClN_5O_3S$: 618.2 (M+H$^+$); Found: 618.4 (M+H$^+$).

$^1$H-NMR 400 MHz, (CD$_3$OD) δ 8.11 (m, 1H), 7.98 (m, 1H), 7.77 (m, 1H), 7.60 (m, 1H), 7.55-7.46 (m, 4H), 7.38 (s, 1H), 5.15 (s, 1H), 4.40 (m, 2H), 4.35 (m, 1H), 4.11 (s, 3H), 3.9-3.7 (m, 3H), 3.45 (m, 1H), 2.68 (s, 3H), 2.50 (s, 3H), 0.94 (s, 9H).

Preparation of (2S)-ethyl 2-tert-butoxy-2-(7-(4-chlorophenyl)-2-(4-isopropyl-3-(1-methyl-1H-indazol-5-yl)piperazin-1-yl)-5-methylbenzo[d]thiazol-6-yl)acetate: (2S)-ethyl 2-tert-butoxy-2-(7-(4-chlorophenyl)-2-(4-isopropyl-3-(1-methyl-1H-indazol-5-yl)piperazin-1-yl)-5-methylbenzo[d]thiazol-6-yl)acetate (16 mg) was prepared in a similar manner as (2S)-2-tert-butoxy-2-(7-(4-chlorophenyl)-5-methyl-2-(4-methyl-3-(1-methyl-1H-indazol-5-yl)-2-oxopiperazin-1-yl)benzo[d]thiazol-6-yl)acetic acid except using (2S)-ethyl 2-tert-butoxy-2-(7-(4-chlorophenyl)-5-methyl-2-(3-(1-methyl-1H-indazol-5-yl)piperazin-1-yl)benzo[d]thiazol-6-yl)acetate, and acetone and 2,2-dimethoxypropane instead of (2S)-2-tert-butoxy-2-(7-(4-chlorophenyl)-5-methyl-2-(3-(1-methyl-1H-indazol-5-yl)-2-oxopiperazin-1-yl)benzo[d]thiazol-6-yl)acetic acid and formaldehyde. LCMS-ESI$^+$: calc'd for $C_{37}H_{45}ClN_5O_3S$: 674.3 (M+H$^+$); Found: 674.3 (M+H$^+$).

Preparation of (2S)-2-tert-butoxy-2-(7-(4-chlorophenyl)-2-(4-isopropyl-3-(1-methyl-1H-indazol-5-yl)piperazin-1-yl)-5-methylbenzo[d]thiazol-6-yl)acetic acid: (2S)-2-tert-butoxy-2-(7-(4-chlorophenyl)-2-(4-isopropyl-3-(1-methyl-1H-indazol-5-yl)piperazin-1-yl)-5-methylbenzo[d]thiazol-6-yl)acetic acid (3.7 mg) was prepared in a similar manner as compound (2S)-2-tert-butoxy-2-(2-(4-(tert-butoxycarbonyl)-3-(1-methyl-1H-indazol-5-yl)piperazin-1-yl)-7-(4-chlorophenyl)-5-methylbenzo[d]thiazol-6-yl)acetic acid except using (2S)-ethyl 2-tert-butoxy-2-(7-(4-chlorophenyl)-2-(4-isopropyl-3-(1-methyl-1H-indazol-5-yl)piperazin-1- yl)-5-methylbenzo[d]thiazol-6-yl)acetate instead of tert-butyl 4-(6-((S)-1-tert-butoxy-2-ethoxy-2-oxoethyl)-7-(4-chlorophenyl)-5-methylbenzo[d]thiazol-2-yl)-2-(1-methyl-1H-indazol-5-yl)piperazine-1-carboxylate. LCMS-ESI⁺: calc'd for $C_{35}H_{41}ClN_5O_3S$: 646.3 (M+H⁺); Found: 646.3 (M+H⁺). ¹H-NMR 400 MHz, (CD₃OD) δ 8.11 (m, 1H), 8.04 (m, 1H), 7.76 (m, 1H), 7.60 (m, 2H), 7.50 (m, 3H), 7.36 (s, 1H), 5.15 (s, 1H), 4.37 (m, 2H), 4.11 (s, 3H), 4.1-3.7 (m, 3H), 3.4 (m, 3H), 2.49 (s, 3H), 1.32 (d, J=6.2 Hz, 3H), 1.24 (d, J=6.7 Hz, 3H), 0.94 (s, 9H).

Example 133

Preparation of (S)-2-tert-butoxy-2-(7-(4-chlorophenyl)-5-methyl-2-(3-(1-methyl-2-oxo-1,2-dihydropyrimidin-5-yl)phenyl)benzo[d]thiazol-6-yl)acetic acid (280)

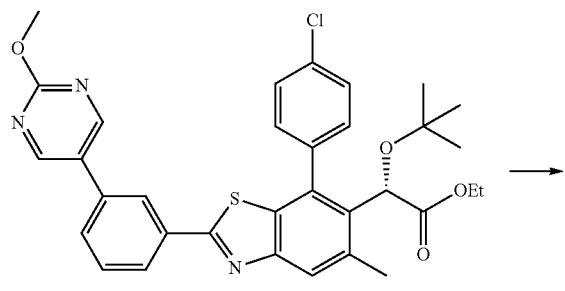

(S)-ethyl 2-tert-butoxy-2-(7-(4-chlorophenyl)-2-(3-(2-methoxypyrimidin-5-yl)phenyl)-5-methylbenzo[d]thiazol-6-yl)acetate

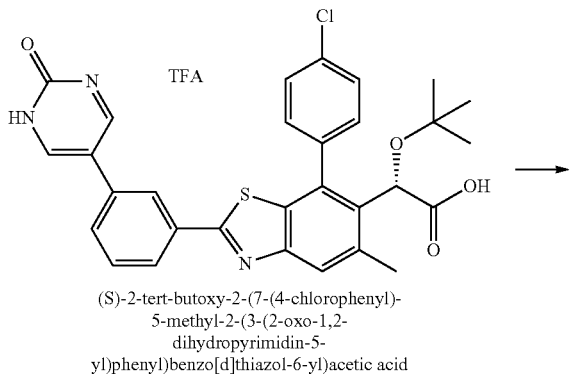

(S)-2-tert-butoxy-2-(7-(4-chlorophenyl)-5-methyl-2-(3-(2-oxo-1,2-dihydropyrimidin-5-yl)phenyl)benzo[d]thiazol-6-yl)acetic acid

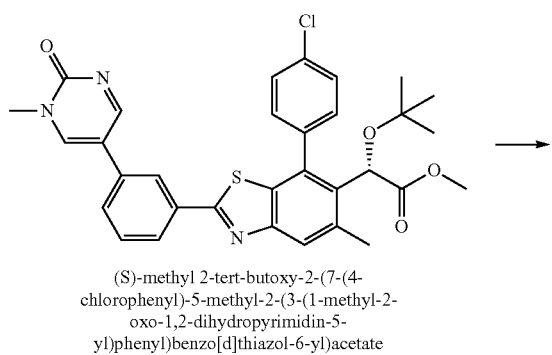

(S)-methyl 2-tert-butoxy-2-(7-(4-chlorophenyl)-5-methyl-2-(3-(1-methyl-2-oxo-1,2-dihydropyrimidin-5-yl)phenyl)benzo[d]thiazol-6-yl)acetate

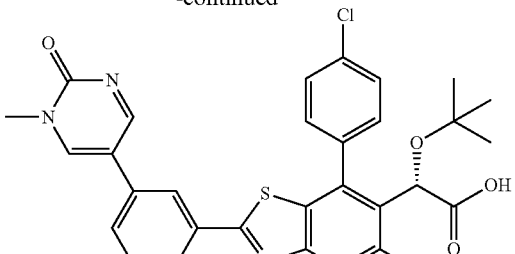

(S)-2-tert-butoxy-2-(7-(4-chlorophenyl)-5-methyl-2-(3-(1-methyl-2-oxo-1,2-dihydropyrimidin-5-yl)phenyl)benzo[d]thiazol-6-yl)acetic acid 280

Preparation of (S)-2-tert-butoxy-2-(7-(4-chlorophenyl)-5-methyl-2-(3-(2-oxo-1,2-dihydropyrimidin-5-yl)phenyl)benzo[d]thiazol-6-yl)acetic acid: To (S)-ethyl 2-tert-butoxy-2-(7-(4-chlorophenyl)-2-(3-(2-methoxypyrimidin-5-yl)phenyl)-5-methylbenzo[d]thiazol-6-yl)acetate (168.5 mg, 0.280 mmol) in THF (2 mL) and water (2 mL) was added NaOH (1.4 mL of a 2N solution). The reaction mixture was heated at 40° C. overnight, cooled, filtered, and purified by reverse phase HPLC, eluting with 5-100% acetonitrile in water with 0.1% TFA. Fractions containing the product were pooled and lyophilized to provide the TFA salt of the product. LCMS-ESI⁺: calc'd for $C_{30}H_{27}ClN_3O_4S$ (M+H⁺): 560.1; Found: 559.7 (M+H⁺).

Preparation of (S)-methyl 2-tert-butoxy-2-(7-(4-chlorophenyl)-5-methyl-2-(3-(1-methyl-2-oxo-1,2-dihydropyrimidin-5-yl)phenyl)benzo[d]thiazol-6-yl)acetate: To the TFA salt of (S)-2-tert-butoxy-2-(7-(4-chlorophenyl)-5-methyl-2-(3-(2-oxo-1,2-dihydropyrimidin-5-yl)phenyl)benzo[d]thiazol-6-yl)acetic acid (94.8 mg, 0.141 mmol) in DMA (3.0 mL) was added K₂CO₃ (194.4 mg, 1.406 mmol) and methyl iodide (199.6 mg, 0.088 mL, 1.406 mmol). The reaction was stirred at room temperature for 45 minutes, filtered through Celite (ethyl acetate eluent), concentrated, and used without further purification. LCMS-ESI⁺: calc'd for $C_{32}H_{31}ClN_3O_4S$ (M+H¹): 588.2; Found: 588.2 (M+H⁺).

Preparation of (S)-2-tert-butoxy-2-(7-(4-chlorophenyl)-5-methyl-2-(3-(1-methyl-2-oxo-1,2-dihydropyrimidin-5-yl)phenyl)benzo[d]thiazol-6-yl)acetic acid: To crude (S)-methyl 2-tert-butoxy-2-(7-(4-chlorophenyl)-5-methyl-2-(3-(1-methyl-2-oxo-1,2-dihydropyrimidin-5-yl)phenyl)benzo[d]thiazol-6-yl)acetate in THF (2.0 mL) and methanol (2.0 mL) was added NaOH (1 mL of a 2N solution). The reaction mixture was heated at 40° C. for 2 h, cooled, filtered, and purified by reverse phase HPLC, eluting with 5-100% acetonitrile in water with 0.1% TFA. Fractions containing the product were pooled and lyophilized to provide the TFA salt of the product. LCMS-ESI⁺: calc'd for $C_{31}H_{29}ClN_3O_4S$ (M+H⁺): 574.1; Found: 574.2 (M+H⁺). ¹H NMR (400 MHz, CD₃OD) δ 9.02 (d, J=3.2 Hz, 1H), 8.71 (d, J=3.2 Hz, 1H), 8.27 (s, 1H), 8.05 (d, J=8.0 Hz, 1H), 7.87 (s, 1H), 7.77 (d, J=7.8 Hz, 1H), 7.72-7.67 (m, 1H), 7.65-7.57 (m, 4H), 5.26 (s, 1H), 3.71 (s, 3H), 2.62 (s, 3H), 0.98 (s, 9H).

Example 134

Preparation of (S)-2-tert-butoxy-2-(7-(4-chlorophenyl)-5-methyl-2-(4-(4-methylpiperazin-1-yl)pyrimidin-2-yl)benzo[d]thiazol-6-yl)acetic acid (281)

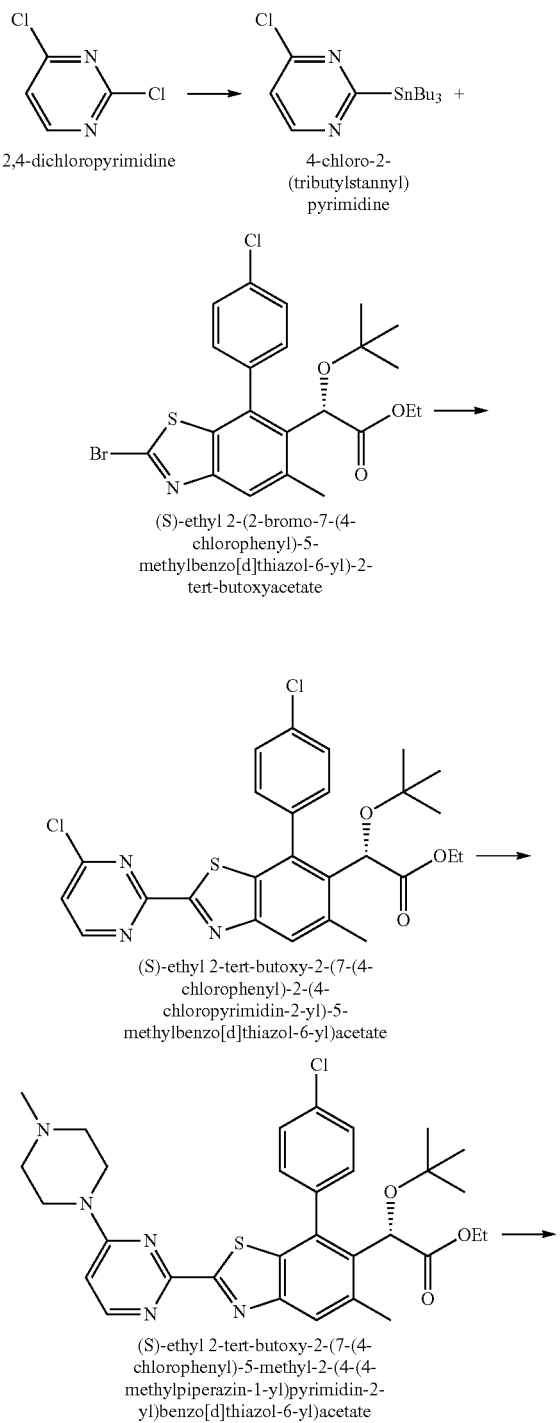

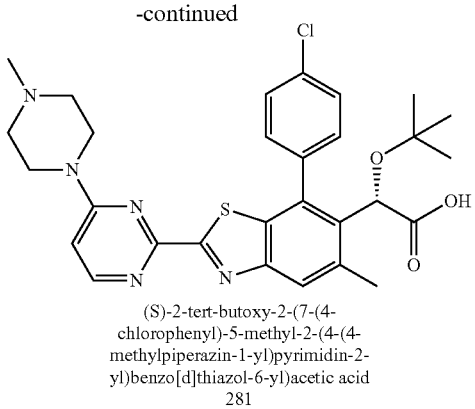

(S)-2-tert-butoxy-2-(7-(4-chlorophenyl)-5-methyl-2-(4-(4-methylpiperazin-1-yl)pyrimidin-2-yl)benzo[d]thiazol-6-yl)acetic acid
281

Preparation of 4-chloro-2-(tributylstannyl)pyrimidine: To a solution of 1.5M (in cyclohexane) lithium diisopropylamide (mono THF) (9.06 mmol, 6.04 mL) in THF (15 mL) at 0° C. was added tri-n-butyltin hydride (2.34 g, 8.05 mmol) in THF (2 mL) dropwise. The reaction mixture was stirred at 0° C. for 15 minutes, then cooled to −78° C. To this solution was added 2,4-dichloropyrimidine (1 g, 6.71 mmol) in THF (7 mL) dropwise. The reaction mixture was stirred at −78° C. for 3 h, then warmed to 0° C. over 30 min. The reaction was quenched with saturated aqueous ammonium chloride (12 mL) at 0° C., then warmed to room temperature and extracted three times with ethyl acetate. The combined organic layers were dried over $Na_2SO_4$, filtered, and concentrated. Purification by flash column chromatography on silica gel (hexanes/DCM eluent) provided the product. LCMS-ESI$^+$ calc'd for $C_{16}H_{30}ClN_2Sn$ (M+H$^+$): 405.1; Found: 405.1 (M+H$^+$). $^1$H NMR (400 MHz, CDCl$_3$) δ 8.53 (dd, J=5.4, 1.3 Hz, 1H), 7.16 (dd, J=5.4, 1.2 Hz, 1H), 1.67-1.49 (m, 6H), 1.38-1.27 (m, 6H), 1.26-1.10 (m, 6H), 0.88 (td, J=7.5, 1.3 Hz, 9H).

Preparation of (S)-ethyl 2-tert-butoxy-2-(7-(4-chlorophenyl)-2-(4-chloropyrimidin-2-yl)-5-methylbenzo[d]thiazol-6-yl)acetate: (S)-ethyl 2-(2-bromo-7-(4-chlorophenyl)-5-methylbenzo[d]thiazol-6-yl)-2-tert-butoxyacetate (500 mg, 1.01 mmol), tetrakis(triphenylphosphine)palladium(0) (174 mg, 0.15 mmol), lithium chloride (128 mg, 3.02 mmol), and copper(I) iodide (58 mg, 0.3 mmol) were taken in a microwave vial, and the vial was vacuum pumped and flushed with argon three times. To this mixture was added 2-(tributylstannyl)-4-chloropyrimidine (447 mg, 1.11 mmol) in dioxane (12 mL) and the resulting mixture was stirred at 90° C. for 18 h. The reaction mixture was then cooled, filtered through Celite (ethyl acetate eluent), and concentrated. Purification by flash column chromatography on silica gel (hexanes/ethyl acetate eluent) provided the product. LCMS-ESI$^+$ calc'd for $C_{26}H_{26}Cl_2N_3O_3S$ (M+H$^+$): 530.1; Found: 530.0 (M+H$^+$).

Preparation of (S)-ethyl 2-tert-butoxy-2-(7-(4-chlorophenyl)-5-methyl-2-(4-(4-methylpiperazin-1-yl)pyrimidin-2-yl)benzo[d]thiazol-6-yl)acetate: To (S)-ethyl 2-tert-butoxy-2-(7-(4-chlorophenyl)-2-(4-chloropyrimidin-2-yl)-5-methylbenzo[d]thiazol-6-yl)acetate (30 mg, 0.06 mmol) in dioxane (1 mL) was added 1-methylpiperazine (56.7 mg, 0.063 mL, 0.566 mmol). The RM was stirred at room temperature for 20 minutes, concentrated, and used without further purification. LCMS-ESI$^+$ calc'd for $C_{31}H_{37}ClN_5O_3S$ (M+H$^+$): 594.2; Found: 593.7 (M+H$^+$).

Preparation of (S)-2-tert-butoxy-2-(7-(4-chlorophenyl)-5-methyl-2-(4-(4-methylpiperazin-1-yl)pyrimidin-2-yl)benzo[d]thiazol-6-yl)acetic acid: To crude (S)-ethyl 2-tert-butoxy-2-(7-(4-chlorophenyl)-5-methyl-2-(4-(4-methylpiperazin-1- yl)pyrimidin-2-yl)benzo[d]thiazol-6-yl)acetate in THF (0.5 mL) and methanol (0.5 mL) was added NaOH (0.5 mL of a 2N solution). The reaction mixture was heated at 30° C. overnight, cooled, filtered, and purified by reverse phase HPLC, eluting with 5-100% acetonitrile in water with 0.1% TFA. Fractions containing the product were pooled and lyophilized to provide the TFA salt of the product. LCMS-ESI+: calc'd for $C_{29}H_{33}ClN_5O_3S$ (M+H+): 566.2; Found: 566.1 (M+H+). 1H NMR (400 MHz, $CD_3OD$) δ 8.43 (d, J=6.1 Hz, 1H), 7.96 (s, 1H), 7.72-7.65 (m, 1H), 7.60 (m, 3H), 7.00 (d, J=5.7 Hz, 1H), 5.26 (s, 1H), 3.37 (br s, 8H), 2.97 (s, 3H), 2.63 (s, 3H), 0.98 (s, 9H).

Example 135

Preparation of (S)-2-tert-butoxy-2-(7-(4-chlorophenyl)-5-methyl-2-(6-(4-methylpiperazin-1-yl)pyrazin-2-yl)benzo[d]thiazol-6-yl)acetic acid (282)

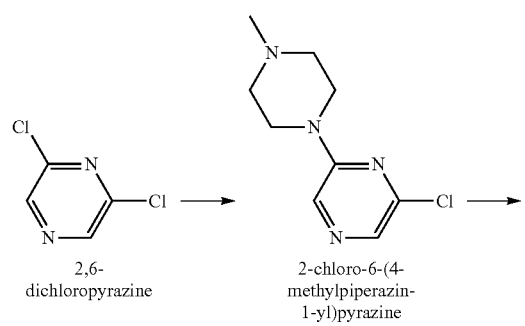

2,6-dichloropyrazine 2-chloro-6-(4-methylpiperazin-1-yl)pyrazine

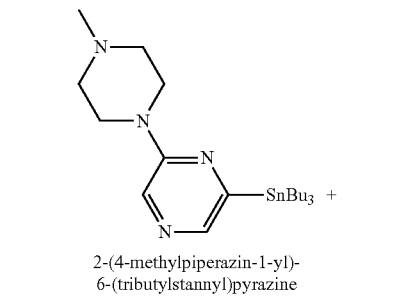

2-(4-methylpiperazin-1-yl)-6-(tributylstannyl)pyrazine

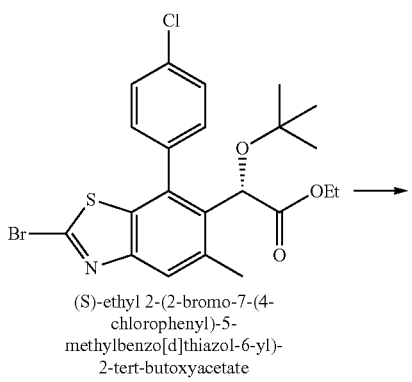

(S)-ethyl 2-(2-bromo-7-(4-chlorophenyl)-5-methylbenzo[d]thiazol-6-yl)-2-tert-butoxyacetate

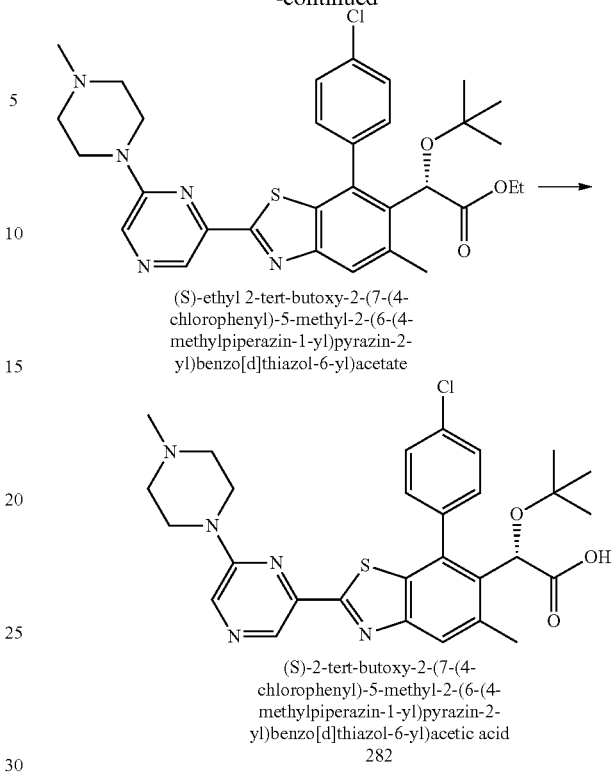

(S)-ethyl 2-tert-butoxy-2-(7-(4-chlorophenyl)-5-methyl-2-(6-(4-methylpiperazin-1-yl)pyrazin-2-yl)benzo[d]thiazol-6-yl)acetate (S)-2-tert-butoxy-2-(7-(4-chlorophenyl)-5-methyl-2-(6-(4-methylpiperazin-1-yl)pyrazin-2-yl)benzo[d]thiazol-6-yl)acetic acid 282

Preparation of 2-chloro-6-(4-methylpiperazin-1-yl)pyrazine: To 2,6-dichloropyrazine (150 mg, 1.007 mmol) in 1,4-dioxane (1.0 mL) was added 1-methylpiperazine (121.0 mg, 0.13 mL, 1.208 mmol) followed by triethylamine (203.8 mg, 0.281 mL, 2.014 mmol). The reaction mixture was stirred at room temperature for 24 h then concentrated. Purification by flash column chromatography on silica gel using 100:5:1 EtOAc/MeOH/NH4OH (0 to 100%) in EtOAc provided the product. LCMS-ESI+ calc'd for $C_9H_{14}ClN_4$ (M+H+): 213.1; Found: 213.2 (M+H+).

Preparation of 2-(4-methylpiperazin-1-yl)-6-(tributylstannyl)pyrazine: tetrakis(triphenylphosphine)palladium(0) (108 mg, 0.093 mmol) and LiCl (39.6 mg, 2.80 mmol) were taken in a microwave vial and the vial vacuum pumped and flushed with argon three times. To this mixture was added 2-chloro-6-(4-methylpiperazin-1-yl)pyrazine (199 mg, 0.933 mmol) and hexabutylditin (541 mg, 0.47 mL, 0.93 mmol) in toluene (10 mL). The reaction mixture was heated to 170° C. for 1.5 h, filtered through Celite, and concentrated. Purification by flash column chromatography on silica gel using 79:20:1 DCM/MeOH/NH3 (0 to 100%) in DCM provided the product. LCMS-ESI+ calc'd for $C_{21}H_{41}N_4Sn$ (M+H+): 469.2; Found: 467.2 (M+H+).

Preparation of (S)-ethyl 2-tert-butoxy-2-(7-(4-chlorophenyl)-5-methyl-2-(6-(4-methylpiperazin-1-yl)pyrazin-2-yl)benzo[d]thiazol-6-yl)acetate: (S)-ethyl 2-(2-bromo-7-(4-chlorophenyl)-5-methylbenzo[d]thiazol-6-yl)-2-tert-butoxyacetate (50.0 mg, 0.101 mmol), tetrakis(triphenylphosphine)palladium(0) (17.4 mg, 0.015 mmol), lithium chloride (12.8 mg, 0.302 mmol), and copper(I) iodide (5.8 mg, 0.030 mmol) were taken in a microwave vial and the vial vacuum pumped and flushed with argon three times. To this mixture was added 2-(4-methylpiperazin-1-yl)-6-(tributylstannyl)pyrazine (56.4 mg, 0.121 mmol) in dioxane (1.0 mL), and the resulting mixture was stirred at 90° C. for 22 h.

Purification by flash column chromatography on silica gel using 79:20:1 DCM/MeOH/NH$_3$ (0 to 100%) in DCM provided the product. LCMS-ESI$^+$ calc'd for C$_{31}$H$_{37}$ClN$_5$O$_3$S (M+H$^+$):594.2; Found: 593.6 (M+H$^+$).

Preparation of (S)-2-tert-butoxy-2-(7-(4-chlorophenyl)-5-methyl-2-(6-(4-methylpiperazin-1-yl)pyrazin-2-yl)benzo[d]thiazol-6-yl)acetic acid: To (S)-ethyl 2-tert-butoxy-2-(7-(4-chlorophenyl)-5-methyl-2-(6-(4-methylpiperazin-1-yl)pyrazin-2-yl)benzo[d]thiazol-6-yl)acetate in THF (0.5 mL) and methanol (0.5 mL) was added NaOH (0.45 mL of a 2N solution). The reaction mixture was heated at 50° C. for 3 h, cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for C$_{29}$H$_{33}$ClN$_5$O$_3$S (M+H$^+$): 566.2; Found: 566.1 (M+H$^+$). $^1$H NMR (400 MHz, CD$_3$OD) δ 8.85 (s, 1H), 8.46 (s, 1H), 7.91 (s, 1H), 7.72-7.64 (m, 1H), 7.64-7.50 (m, 3H), 5.24 (s, 1H), 4.62 (br s, 1H), 3.37 (br s, 7H), 2.97 (s, 3H), 2.63 (s, 3H), 0.98 (s, 9H).

Example 136

Preparation of (S)-2-tert-butoxy-2-(7-(4-chlorophenyl)-5-methyl-2-(1-methyl-1H-benzo[d]imidazol-6-yl)benzo[d]thiazol-6-yl)acetic acid (283)

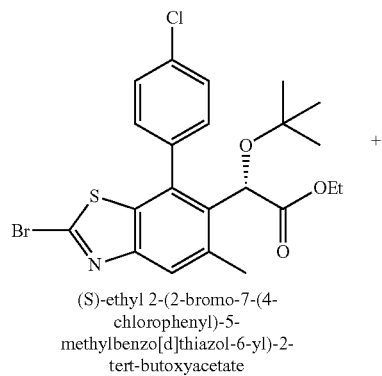

(S)-ethyl 2-(2-bromo-7-(4-chlorophenyl)-5-methylbenzo[d]thiazol-6-yl)-2-tert-butoxyacetate

+

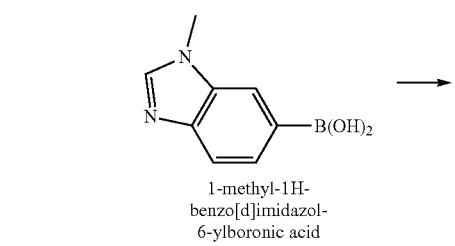

1-methyl-1H-benzo[d]imidazol-6-ylboronic acid

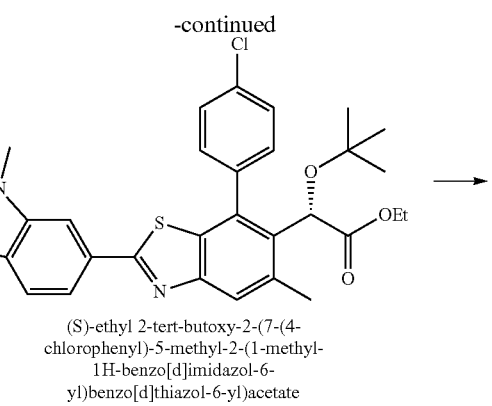

(S)-ethyl 2-tert-butoxy-2-(7-(4-chlorophenyl)-5-methyl-2-(1-methyl-1H-benzo[d]imidazol-6-yl)benzo[d]thiazol-6-yl)acetate

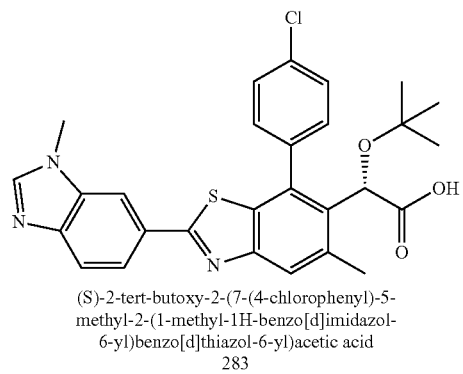

(S)-2-tert-butoxy-2-(7-(4-chlorophenyl)-5-methyl-2-(1-methyl-1H-benzo[d]imidazol-6-yl)benzo[d]thiazol-6-yl)acetic acid
283

Preparation of (S)-ethyl 2-tert-butoxy-2-(7-(4-chlorophenyl)-5-methyl-2-(1-methyl-1H-benzo[d]imidazol-6-yl)benzo[d]thiazol-6-yl)acetate: A microwave vial was charged with (S)-ethyl 2-(2-bromo-7-(4-chlorophenyl)-5-methylbenzo[d]thiazol-6-yl)-2-tert-butoxyacetate (75 mg, 0.15 mmol), 1-methyl-1H-benzo[d]imidazol-6-ylboronic acid (34 mg, 0.19 mmol), then Pd(PPh$_3$)$_4$ (34 mg, 0.03 mmol). The vial was flushed with argon, diluted with dioxane (1.5 mL) and to this was added 2M aqueous K$_2$CO$_3$ (0.25 mL, 0.50 mmol). The vial was sealed, heated to 100° C. for 2 hours, and then allowed to cool to room temperature. The mixture was diluted with EtOAc, dried over Na$_2$SO$_4$, filtered, and concentrated in vacuo. The crude residue was purified by silica gel column chromatography (0-10% MeOH/CH$_2$Cl$_2$ gradient) to afford the desired product. LCMS-ESI$^+$: calc'd for C$_{30}$H$_{31}$ClN$_3$O$_3$S: 548.2 (M+H$^+$); Found: 548.3 (M+H$^+$).

Preparation of (S)-2-tert-butoxy-2-(7-(4-chlorophenyl)-5-methyl-2-(1-methyl-1H-benzo[d]imidazol-6-yl)benzo[d]thiazol-6-yl)acetic acid: To a solution of (S)-ethyl 2-tert-butoxy-2-(7-(4-chlorophenyl)-5-methyl-2-(1-methyl-1H-benzo[d]imidazol-6-yl)benzo[d]thiazol-6-yl)acetate (71 mg, 0.13 mmol) in 1:1 THF/MeOH (1.5 mL) was added 2M aqueous NaOH (0.35 mL, 0.7 mmol) and stirred at 50° C. overnight. The reaction mixture was cooled to room temperature, neutralized with AcOH, filtered, and then purified by reverse phase column chromatography (5-100% ACN/H$_2$O/ 0.1% TFA gradient). Fractions containing the product were pooled and lyophilized to provide the TFA salt of the product. $^1$H NMR (400 MHz, CD$_3$OD) δ 9.34 (s, 1H), 8.55 (d, J=1.0 Hz, 1H), 8.29 (dd, J=8.7, 1.5 Hz, 1H), 7.93 (d, J=8.7 Hz, 1H), 7.87 (s, 1H), 7.72-7.67 (m, 1H), 7.65-7.55 (m, 3H), 5.27 (s, 1H), 4.17 (s, 3H), 2.62 (s, 3H), 0.98 (s, 9H); LCMS-ESI+: calc'd for $C_{28}H_{27}ClN_3O_3S$: 520.2 (M+H+); Found: 520.2 (M+H+).

Example 137

Preparation of (S)-2-(2-(1-benzyl-1H-benzo[d]imidazol-6-yl)-7-(4-chlorophenyl)-5-methylbenzo[d]thiazol-6-yl)-2-tert-butoxyacetic acid (284) and (S)-2-(2-(1-benzyl-1H-benzo[d]imidazol-5-yl)-7-(4-chlorophenyl)-5-methylbenzo[d]thiazol-6-yl)-2-tert-butoxyacetic acid (285)

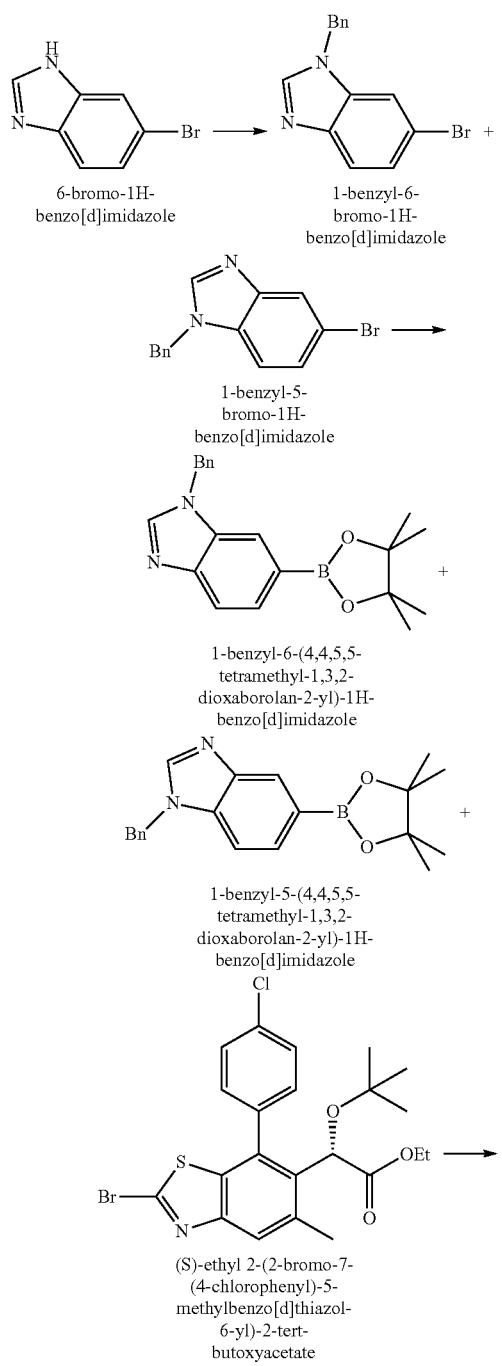

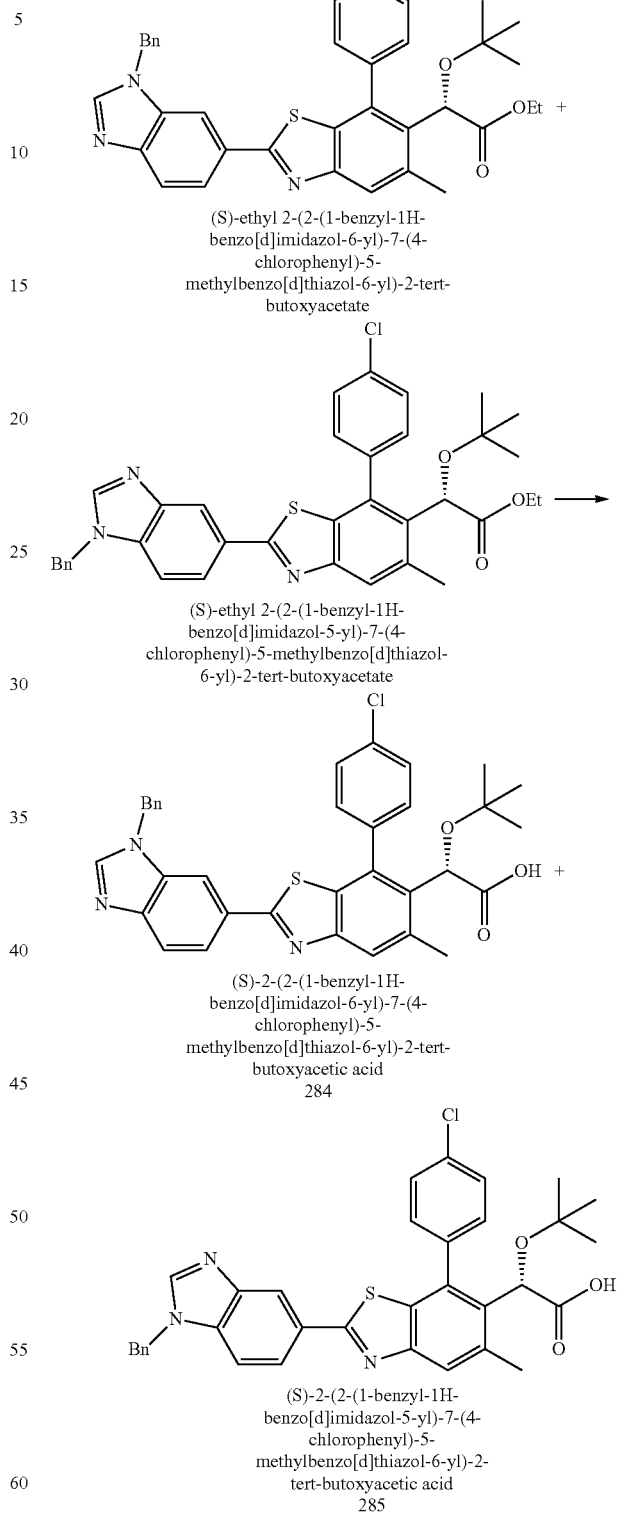

Preparation of 1-benzyl-6-bromo-1H-benzo[d]imidazole and 1-benzyl-5-bromo-1H-benzo[d]imidazole: A flask was charged with 6-bromo-1H-benzo[d]imidazole (595 mg, 3.0 mmol) and $K_2CO_3$ (1.3 g, 3.4 mmol) and then diluted with acetone (15 mL). To this was then added benzyl bromide (0.4 mL, 3.4 mmol) at room temperature and the resulting mixture was allowed to stir overnight. The reaction mixture was diluted with $CH_2Cl_2$ and $H_2O$ and the layers were separated. The aqueous layer was extracted with EtOAc and the combined organic extracts were dried over $Na_2SO_4$, filtered, and concentrated in vacuo. The crude residue was purified by silica gel column chromatography (20-60% EtOAc/Hex gradient) to afford the desired product as a 1:1 isomeric mixture. calc'd for $C_{14}H_{12}BrN_2$: 287.0 (M+H$^+$); Found: 582.3 (M+H$^+$).

Preparation of 1-benzyl-6-(4,4,5,5-tetramethyl-1,3,2-dioxaborolan-2-yl)-1H-benzo[d]imidazole and 1-benzyl-5-(4,4,5,5-tetramethyl-1,3,2-dioxaborolan-2-yl)-1H-benzo[d]imidazole: A microwave vial was charged with a 1:1 isomeric mixture of 1-benzyl-6-bromo-1H-benzo[d]imidazole and 1-benzyl-5-bromo-1H-benzo[d]imidazole (630 mg, 2.19 mmol), bis(pinacolato)diboron (835 mg, 3.29 mmol), $PdCl_2$(dppf).$CH_2Cl_2$ (171 mg, 0.21 mmol), then KOAc (646 mg, 6.58 mmol). The vial was flushed with argon, diluted with dioxane (11 mL), sealed, and then heated to 100° C. for 90 minutes. The reaction mixture was allowed to cool to room temperature, diluted with EtOAc, filtered through a pad of Celite, and concentrated in vacuo. The crude residue was purified by silica gel column chromatography (40-100% EtOAc/Hex gradient) to afford the desired product. LCMS-ESI$^+$: calc'd $C_{20}H_{24}BN_2O_2$: 335.2 (M+H$^+$); Found: 335.3 (M+H$^+$).

Preparation of (S)-ethyl 2-(2-(1-benzyl-1H-benzo[d]imidazol-6-yl)-7-(4-chlorophenyl)-5-methylbenzo[d]thiazol-6-yl)-2-(tert-butoxy)acetate and (S)-ethyl 2-(2-(1-benzyl-1H-benzo[d]imidazol-5-yl)-7-(4-chlorophenyl)-5-methylbenzo[d]thiazol-6-yl)-2-(tert-butoxy)acetate: A microwave vial was charged with (S)-ethyl 2-(2-bromo-7-(4-chlorophenyl)-5-methylbenzo[d]thiazol-6-yl)-2-tert-butoxyacetate (150 mg, 0.30 mmol), a 1:1 mixture of 1-benzyl-6-(4,4,5,5-tetramethyl-1,3,2-dioxaborolan-2-yl)-1H-benzo[d]imidazole and 1-benzyl-5-(4,4,5,5-tetramethyl-1,3,2-dioxaborolan-2-yl)-1H-benzo[d]imidazole (154 mg, 0.46 mmol), then Pd(PPh$_3$)$_4$ (37 mg, 0.03 mmol). The vial was flushed with argon, diluted with dioxane (3 mL) and to this was added 2M aqueous $K_2CO_3$ (0.5 mL, 0.10 mmol). The vial was sealed, heated to 100° C. for 2 hours, and then allowed to cool to room temperature. The mixture was diluted with EtOAc, dried over $Na_2SO_4$, filtered, and concentrated in vacuo. The crude residue was purified by silica gel column chromatography (0-10% MeOH/$CH_2Cl_2$ gradient) to afford the desired product. LCMS-ESI$^+$: calc'd for $C_{36}H_{35}ClN_3O_3S$: 624.2 (M+H$^+$); Found: 624.3 (M+H$^+$).

Preparation of (S)-2-(2-(1-benzyl-1H-benzo[d]imidazol-6-yl)-7-(4-chlorophenyl)-5-methylbenzo[d]thiazol-6-yl)-2-tert-butoxyacetic acid and (S)-2-(2-(1-benzyl-1H-benzo[d]imidazol-5-yl)-7-(4-chlorophenyl)-5-methylbenzo[d]thiazol-6-yl)-2-tert-butoxyacetic acid: To a solution of a 1:1 mixture of (S)-ethyl 2-(2-(1-benzyl-1H-benzo[d]imidazol-6-yl)-7-(4-chlorophenyl)-5-methylbenzo[d]thiazol-6-yl)-2-(tert-butoxy)acetate and (S)-ethyl 2-(2-(1-benzyl-1H-benzo[d]imidazol-5-yl)-7-(4-chlorophenyl)-5-methylbenzo[d]thiazol-6-yl)-2-(tert-butoxy)acetate (187 mg, 0.30 mmol) in 1:1 THF/MeOH (1.5 mL) was added 2M aqueous NaOH (0.35 mL, 0.7 mmol) and stirred at 50° C. overnight. The reaction mixture was cooled to room temperature, neutralized with AcOH, filtered, and then purified by reverse phase column chromatography (5-100% ACN/$H_2O$+0.1% TFA). Fractions containing the product were pooled and lyophilized to provide the TFA salt of the isomeric mixture of products. *1:1 mixture of benzyl-isomers $^1$H NMR (400 MHz, CD$_3$OD) δ 9.39 (s, 1H), 9.37 (s, 1H), 8.47 (s, 1H), 8.43 (s, 1H), 8.22 (dd, J=8.7, 1.5 Hz, 1H), 8.17 (dd, J=8.8, 1.5 Hz, 1H), 7.92 (d, J=8.7 Hz, 1H), 7.87-7.80 (m, 3H), 7.72-7.65 (m, 2H), 7.63-7.53 (m, 6H), 7.51-7.35 (m, 9H), 5.76 (s, 2H), 5.72 (s, 2H), 5.25 (s, 2H), 2.60 (s, 6H), 0.97 (s, 18H). LCMS-ESI$^+$: calc'd for $C_{34}H_{31}ClN_3O_3S$: 596.2 (M+H$^+$); Found: 596.2 (M+H$^+$).

Example 138

Preparation of (S)-2-(tert-butoxy)-2-(7-(4-chlorophenyl)-2-(1,3-dimethyl-2-oxo-2,3-dihydro-1H-benzo[d]imidazol-5-yl)-5-methylbenzo[d]thiazol-6-yl)acetic acid (286)

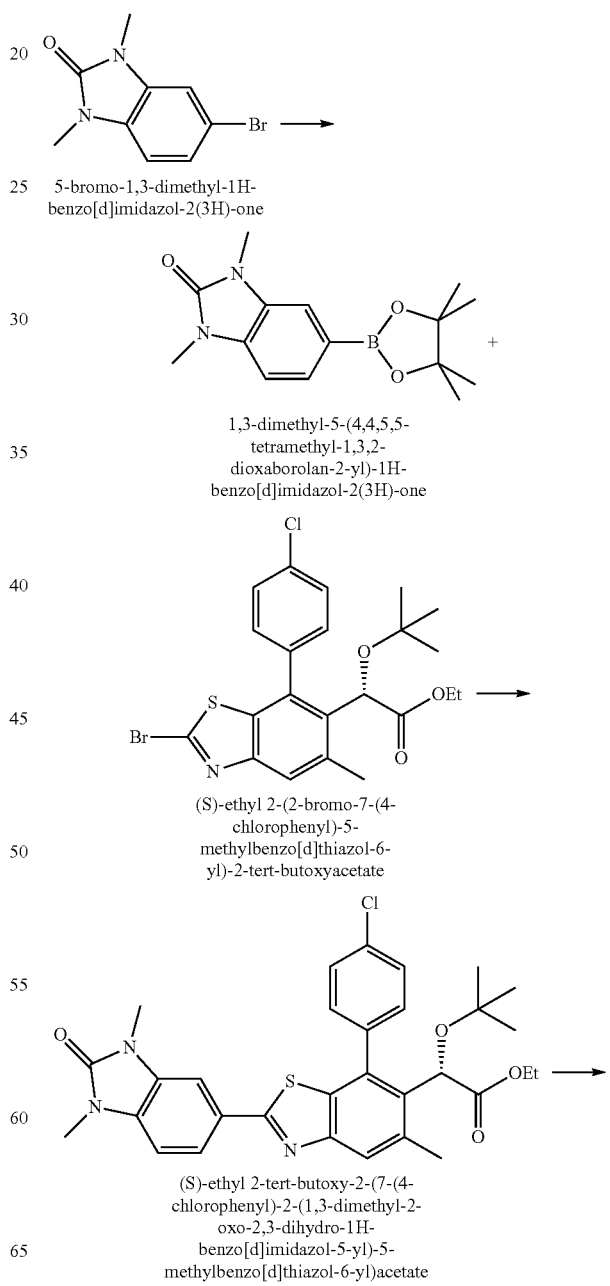

5-bromo-1,3-dimethyl-1H-benzo[d]imidazol-2(3H)-one 1,3-dimethyl-5-(4,4,5,5-tetramethyl-1,3,2-dioxaborolan-2-yl)-1H-benzo[d]imidazol-2(3H)-one (S)-ethyl 2-(2-bromo-7-(4-chlorophenyl)-5-methylbenzo[d]thiazol-6-yl)-2-tert-butoxyacetate (S)-ethyl 2-tert-butoxy-2-(7-(4-chlorophenyl)-2-(1,3-dimethyl-2-oxo-2,3-dihydro-1H-benzo[d]imidazol-5-yl)-5-methylbenzo[d]thiazol-6-yl)acetate

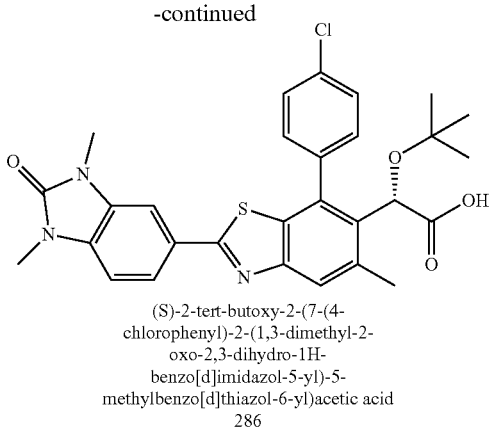

(S)-2-tert-butoxy-2-(7-(4-chlorophenyl)-2-(1,3-dimethyl-2-oxo-2,3-dihydro-1H-benzo[d]imidazol-5-yl)-5-methylbenzo[d]thiazol-6-yl)acetic acid
286

Preparation of 1,3-dimethyl-5-(4,4,5,5-tetramethyl-1,3,2-dioxaborolan-2-yl)-1H-benzo[d]imidazol-2(3H)-one: A microwave vial was charged with 5-bromo-1,3-dimethyl-1H-benzo[d]imidazol-2(3H)-one (250 mg, 1.04 mmol), bis(pinacolato)diboron (395 mg, 1.56 mmol), $PdCl_2(dppf) \cdot CH_2Cl_2$ (84 mg, 0.10 mmol), then KOAc (316 mg, 3.22 mmol). The vial was flushed with argon, diluted with dioxane (5 mL), sealed, then heated to 100° C. for 90 minutes. The reaction mixture was allowed to cool to room temperature, diluted with EtOAc, filtered through a pad of Celite, and concentrated in vacuo. The crude residue was purified by silica gel column chromatography (40-90% EtOAc/Hex gradient) to afford the desired product. LCMS-ESI$^+$: calc'd $C_{15}H_{22}BN_2O_3$: 289.2 (M+H$^+$); Found: 289.3 (M+H$^+$).

Preparation of (S)-ethyl 2-(tert-butoxy)-2-(7-(4-chlorophenyl)-2-(1,3-dimethyl-2-oxo-2,3-dihydro-1H-benzo[d]imidazol-5-yl)-5-methylbenzo[d]thiazol-6-yl)acetate: A microwave vial was charged with (S)-ethyl 2-(2-bromo-7-(4-chlorophenyl)-5-methylbenzo[d]thiazol-6-yl)-2-tert-butoxyacetate (75 mg, 0.15 mmol), 1,3-dimethyl-5-(4,4,5,5-tetramethyl-1,3,2-dioxaborolan-2-yl)-1H-benzo[d]imidazol-2(3H)one (182 mg, 0.63 mmol), then Pd(PPh$_3$)$_4$ (22 mg, 0.02 mmol). The vial was flushed with argon, diluted with dioxane (1.5 mL) and to this was added 2M aqueous K$_2$CO$_3$ (0.25 mL, 0.5 mmol). The vial was sealed, heated to 100° C. for 2 hours, and then allowed to cool to room temperature. The mixture was diluted with EtOAc, dried over Na$_2$SO$_4$, filtered, and concentrated in vacuo. The crude residue was purified by silica gel column chromatography (40-100% EtOAc/Hex gradient) to afford the desired product. LCMS-ESI$^+$: calc'd for $C_{31}H_{33}ClN_3O_4S$: 578.2 (M+H$^+$); Found: 578.3 (M+H$^+$).

Preparation of (S)-2-(tert-butoxy)-2-(7-(4-chlorophenyl)-2-(1,3-dimethyl-2-oxo-2,3-dihydro-1H-benzo[d]imidazol-5-yl)-5-methylbenzo[d]thiazol-6-yl)acetic acid: To a solution of (S)-ethyl 2-(tert-butoxy)-2-(7-(4-chlorophenyl)-2-(1,3-dimethyl-2-oxo-2,3-dihydro-1H-benzo[d]imidazol-5-yl)-5-methylbenzo[d]thiazol-6-yl)acetate (82 mg, 0.14 mmol) in 1:1 THF/MeOH (1.5 mL) was added 2M aqueous NaOH (0.4 mL, 0.8 mmol) and stirred at 50° C. overnight. The reaction mixture was cooled to room temperature, neutralized with AcOH, filtered, and then purified by reverse phase column (5-100% ACN/H$_2$O+0.1% TFA). Fractions containing the product were pooled and lyophilized to provide the TFA salt of the product. $^1$H NMR (400 MHz, CD$_3$OD) δ 7.81 (d, J=7.2 Hz, 3H), 7.68 (s, 1H), 7.59 (s, 3H), 7.25 (s, 1H), 5.25 (s, 1H), 3.48 (s, 3H), 3.45 (s, 3H), 2.61 (s, 3H), 0.98 (s, 9H). LCMS-ESI$^+$: calc'd for $C_{29}H_{29}ClN_3O_4S$: 550.2 (M+H$^+$); Found: 550.2 (M+H$^+$).

Example 139

Preparation of (S)-2-(2-(1H-benzo[d]imidazol-6-yl)-7-(4-chlorophenyl)-5-methylbenzo[d]thiazol-6-yl)-2-(tert-butoxy)acetic acid (287)

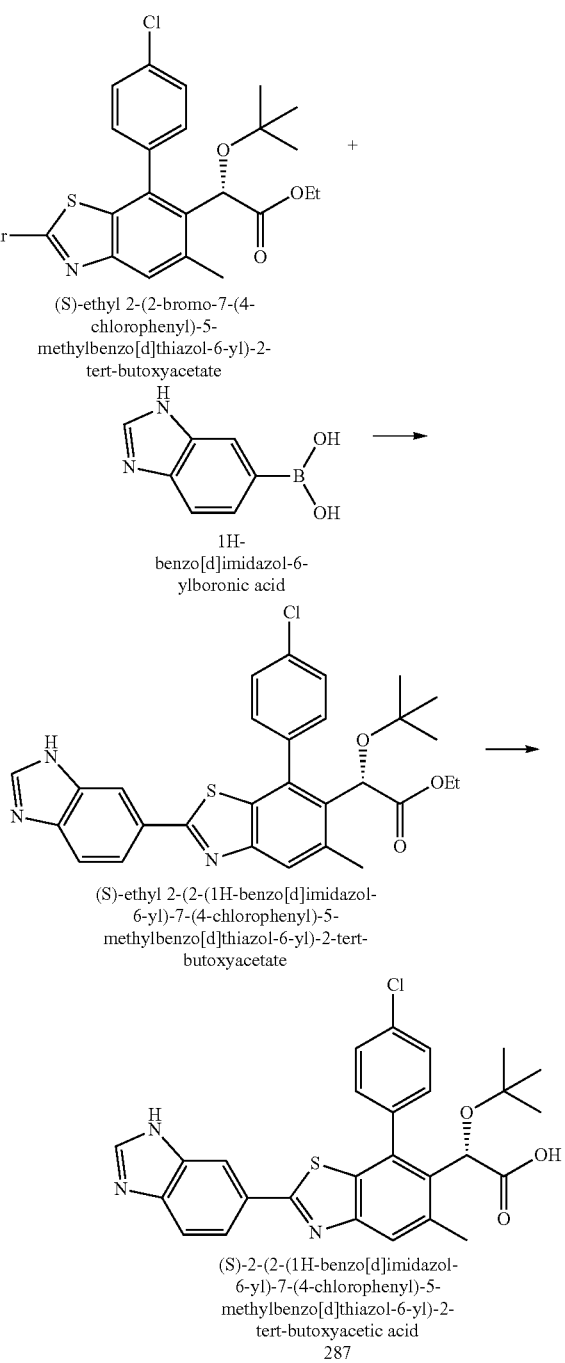

Preparation of (S)-ethyl 2-(2-(1H-benzo[d]imidazol-6-yl)-7-(4-chlorophenyl)-5-methylbenzo[d]thiazol-6-yl)-2-(tert-butoxy)acetate: A microwave vial was charged with (S)-ethyl 2-(2-bromo-7-(4-chlorophenyl)-5-methylbenzo[d]thiazol-6-yl)-2-tert-butoxyacetate (78 mg, 0.16 mmol), (1H-benzo[d]imidazol-6-yl)boronic acid (44 mg, 0.27 mmol), then Pd(PPh$_3$)$_4$ (22 mg, 0.02 mmol). The vial was flushed with argon, diluted with dioxane (1.5 mL) and to this was added 2M aqueous K$_2$CO$_3$ (0.25 mL, 0.5 mmol). The vial was sealed, heated to 100° C. for 2 hours, and then allowed to cool to room temperature. The mixture was diluted with EtOAc, dried over Na$_2$SO$_4$, filtered, and concentrated in vacuo. The crude residue was purified by silica gel column chromatography (0-20% MeOH/CH$_2$Cl$_2$ gradient) to afford the desired product. LCMS-ESI$^+$: calc'd for C$_{29}$H$_{29}$ClN$_3$O$_3$S: 534.2 (M+H$^+$); Found: 534.3 (M+H$^+$).

Preparation of (S)-2-(2-(1H-benzo[d]imidazol-6-yl)-7-(4-chlorophenyl)-5-methylbenzo[d]thiazol-6-yl)-2-(tert-butoxy)acetic acid: To a solution of (S)-ethyl 2-(2-(1H-benzo[d]imidazol-6-yl)-7-(4-chlorophenyl)-5-methylbenzo[d]thiazol-6-yl)-2-(tert-butoxy)acetate (8 mg, 0.015 mmol) in 1:1 THF/MeOH (0.75 mL) was added 2M aqueous NaOH (0.2 mL, 0.4 mmol) and stirred at 50° C. overnight. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 9.37 (s, 1H), 8.51 (s, 1H), 8.28 (d, J=8.8 Hz, 1H), 7.95 (d, J=8.7 Hz, 1H), 7.90 (s, 1H), 7.70 (d, J=8.9 Hz, 1H), 7.66-7.57 (m, 3H), 5.27 (s, 1H), 2.63 (s, 3H), 0.98 (s, 9H). LCMS-ESI$^+$: calc'd for C$_{27}$H$_{25}$ClN$_3$O$_3$S: 506.1 (M+H$^+$); Found: 506.2 (M+H$^+$).

Example 140

Preparation of (S)-2-(tert-butoxy)-2-(7-(4-chlorophenyl)-2-(5-methoxy-2-(1-methyl-1H-indazol-5-yl)pyridin-4-yl)-5-methylbenzo[d]thiazol-6-yl)acetic acid (288)

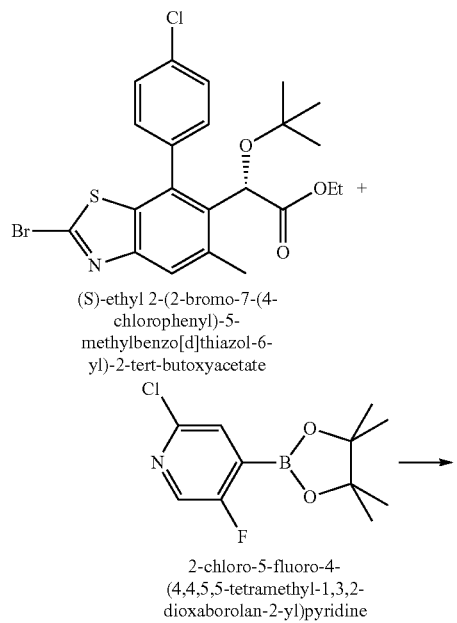

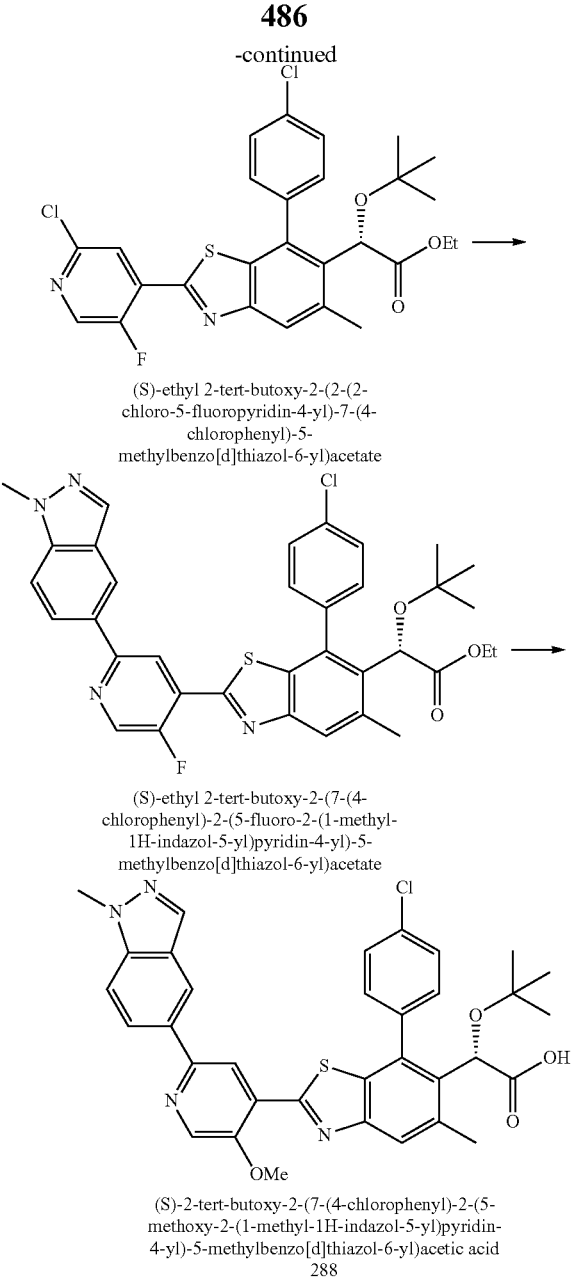

Preparation of (S)-ethyl 2-(tert-butoxy)-2-(2-(2-chloro-5-fluoropyridin-4-yl)-7-(4-chlorophenyl)-5-methylbenzo[d]thiazol-6-yl)acetate: A microwave vial was charged with (S)-ethyl 2-(2-bromo-7-(4-chlorophenyl)-5-methylbenzo[d]thiazol-6-yl)-2-tert-butoxyacetate (104 mg, 0.21 mmol), 2-Chloro-5-fluoropyridine-4-boronic acid pinacol ester (80 mg, 0.31 mmol), then Pd(PPh$_3$)$_4$ (23 mg, 0.02 mmol). The vial was flushed with argon, diluted with dioxane (2.0 mL) and to this was added 2M aqueous K$_2$CO$_3$ (0.30 mL, 0.60 mmol). The vial was sealed, heated to 100° C. for 2 hours, and then allowed to cool to room temperature. The mixture was diluted with EtOAc, dried over Na$_2$SO$_4$, filtered, and concentrated in vacuo. The crude residue was purified by silica gel column chromatography (0-20% EtOAc/Hex gradient) to afford the desired product. LCMS-ESI$^+$: calc'd for C$_{27}$H$_{26}$Cl$_2$FN$_2$O$_3$S: 547.1 (M+H$^+$); Found: 547.2 (M+H$^+$).

Preparation of (S)-ethyl 2-(tert-butoxy)-2-(7-(4-chlorophenyl)-2-(5-fluoro-2-(1-methyl-1H-indazol-5-yl)pyridin-4-yl)-5-methylbenzo[d]thiazol-6-yl)acetate: A microwave vial containing (S)-ethyl 2-(tert-butoxy)-2-(2-(2-chloro-5-fluoropyridin-4-yl)-7-(4-chlorophenyl)-5-methylbenzo[d]thiazol-6-yl)acetate (22 mg, 0.04 mmol) was charged with (1-methyl-1H-indazol-5-yl)boronic acid (19 mg, 0.11 mmol), then Pd(PPh$_3$)$_4$ (9 mg, 0.008 mmol). The vial was flushed with argon, diluted with dioxane (2.0 mL) and to this was added 2M aqueous K$_2$CO$_3$ (0.10 mL, 0.20 mmol). The vial was sealed, heated to 120° C. for 3 hours, and then allowed to cool to room temperature. The mixture was diluted with EtOAc, dried over Na$_2$SO$_4$, filtered, and concentrated in vacuo. The crude residue was purified by silica gel column chromatography (10-40% EtOAc/Hex gradient) to afford the desired product. LCMS-ESI$^+$: calc'd for C$_{35}$H$_{33}$ClFN$_4$O$_3$S: 643.2 (M+H$^+$); Found: 643.2 (M+H$^+$).

Preparation of (S)-2-(tert-butoxy)-2-(7-(4-chlorophenyl)-2-(5-methoxy-2-(1-methyl-1H-indazol-5-yl)pyridin-4-yl)-5-methylbenzo[d]thiazol-6-yl)acetic acid: To a solution of (S)-ethyl 2-(tert-butoxy)-2-(7-(4-chlorophenyl)-2-(5-fluoro-2-(1-methyl-1H-indazol-5-yl)pyridin-4-yl)-5-methylbenzo[d]thiazol-6-yl)acetate (15 mg, 0.023 mmol) in 1:1 THF/MeOH (1.50 mL) was added 2M aqueous NaOH (0.25 mL, 0.5 mmol) and stirred at 50° C. overnight. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 8.95 (s, 1H), 8.60 (s, 1H), 8.39 (s, 1H), 8.16 (s, 1H), 8.06 (dd, J=8.9, 1.6 Hz, 1H), 7.97 (s, 1H), 7.77-7.67 (m, 2H), 7.66-7.56 (m, 3H), 5.29 (s, 1H), 4.16 (s, 3H), 4.13 (s, 3H), 2.65 (s, 3H), 0.98 (s, 9H). LCMS-ESI$^+$: calc'd for C$_{34}$H$_{32}$ClN$_4$O$_4$S: 627.2 (M+H$^+$); Found: 627.2 (M+H$^+$).

Example 141

Preparation of (S)-2-(tert-butoxy)-2-(7-(4-chlorophenyl)-5-methyl-2-(5-methyl-2-(1-methyl-1H-indazol-5-yl)pyridin-4-yl)benzo[d]thiazol-6-yl)acetic acid (289)

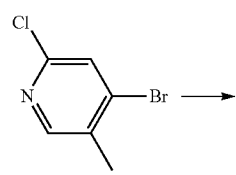

4-bromo-2-chloro-5-methylpyridine

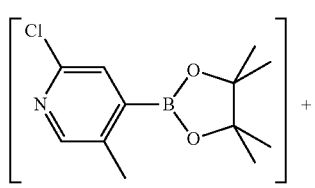

2-chloro-5-methyl-4-(4,4,5,5-tetramethyl-1,3,2-dioxaborolan-2-yl)pyridine

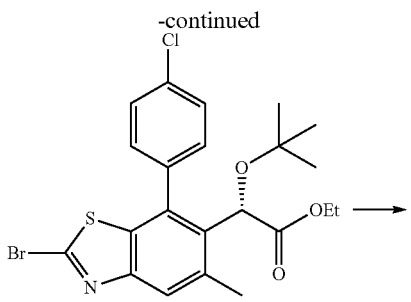

(S)-ethyl 2-(2-bromo-7-(4-chlorophenyl)-5-methylbenzo[d]thiazol-6-yl)-2-tert-butoxyacetate

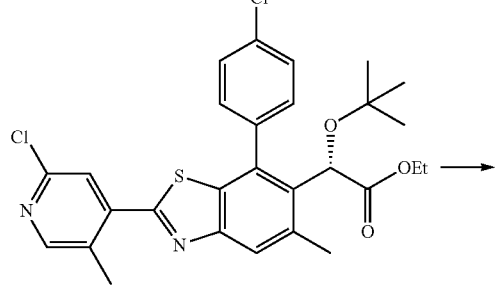

(S)-ethyl 2-tert-butoxy-2-(2-(2-chloro-5-methylpyridin-4-yl)-7-(4-chlorophenyl)-5-methylbenzo[d]thiazol-6-yl)acetate

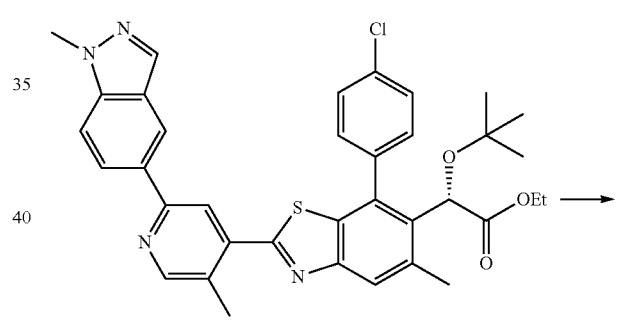

(S)-ethyl 2-tert-butoxy-2-(7-(4-chlorophenyl)-5-methyl-2-(5-methyl-2-(1-methyl-1H-indazol-5-yl)pyridin-4-yl)benzo[d]thiazol-6-yl)acetate

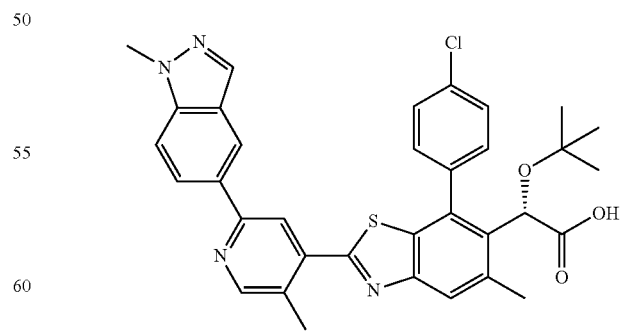

(S)-2-tert-butoxy-2-(7-(4-chlorophenyl)-5-methyl-2-(5-methyl-2-(1-methyl-1H-indazol-5-yl)pyridin-4-yl)benzo[d]thiazol-6-yl)acetic acid
289

Preparation of (S)-ethyl 2-(tert-butoxy)-2-(2-(2-chloro-5-methylpyridin-4-yl)-7-(4-chlorophenyl)-5-methylbenzo[d]thiazol-6-yl)acetate: A microwave vial was charged with 4-bromo-2-chloro-5-methylpyridine (199 mg, 0.96 mmol), Bis(pinacolato)diboron (252 mg, 0.99 mmol), PdCl$_2$(dppf).CH$_2$Cl$_2$ (44 mg, 0.05 mmol), then KOAc (293 mg, 2.98 mmol). The vial was flushed with argon, diluted with dioxane (4 mL), sealed, then heated to 100° C. for 1 hour. The reaction mixture was allowed to cool to room temperature and then a portion of this cooled solution (0.7 mL, 0.17 mmol) was added to a vial that was charged with (S)-ethyl 2-(2-bromo-7-(4-chlorophenyl)-5-methylbenzo[d]thiazol-6-yl)-2-tert-butoxyacetate (80 mg, 0.16 mmol) and Pd(PPh$_3$)$_4$ (9 mg, 0.01 mmol). The mixture was diluted with dioxane (2.0 mL) and to this was added 2M aqueous K$_2$CO$_3$ (0.30 mL, 0.60 mmol). The vial was sealed, heated to 100° C. for 1 hour, and then allowed to cool to room temperature. The mixture was diluted with EtOAc, dried over Na$_2$SO$_4$, filtered, and concentrated in vacuo. The crude residue was purified by silica gel column chromatography (0-20% EtOAc/Hex gradient) to afford the desired product. LCMS-ESI$^+$: calc'd C$_{28}$H$_{29}$Cl$_2$N$_2$O$_3$S: 543.1 (M+H$^+$); Found: 543.2 (M+H$^+$).

Preparation of (S)-ethyl 2-(tert-butoxy)-2-(7-(4-chlorophenyl)-5-methyl-2-(5-methyl-2-(1-methyl-1H-indazol-5-yl)pyridin-4-yl)benzo[d]thiazol-6-yl)acetate: A microwave vial containing (S)-ethyl 2-(tert-butoxy)-2-(2-(2-chloro-5-methylpyridin-4-yl)-7-(4-chlorophenyl)-5-methylbenzo[d]thiazol-6-yl)acetate (68 mg, 0.13 mmol) was charged with (1-methyl-1H-indazol-5-yl)boronic acid (44 mg, 0.25 mmol), then Pd(PPh$_3$)$_4$ (24 mg, 0.02 mmol). The vial was flushed with argon, diluted with dioxane (2.0 mL) and to this was added 2M aqueous K$_2$CO$_3$ (0.20 mL, 0.40 mmol). The vial was sealed, heated to 120° C. for 3 hours, and then allowed to cool to room temperature. The mixture was diluted with EtOAc, dried over Na$_2$SO$_4$, filtered, and concentrated in vacuo. The crude residue was purified by silica gel column chromatography (10-45% EtOAc/Hex gradient) to afford the desired product. LCMS-ESI$^+$: calc'd for C$_{36}$H$_{36}$ClN$_4$O$_3$S: 639.2 (M+H$^+$); Found: 639.2 (M+H$^+$).

Preparation of (S)-2-(tert-butoxy)-2-(7-(4-chlorophenyl)-5-methyl-2-(5-methyl-2-(1-methyl-1H-indazol-5-yl)pyridin-4-yl)benzo[d]thiazol-6-yl)acetic acid: To a solution of (S)-ethyl 2-(tert-butoxy)-2-(7-(4-chlorophenyl)-5-methyl-2-(5-methyl-2-(1-methyl-1H-indazol-5-yl)pyridin-4-yl)benzo[d]thiazol-6-yl)acetate (63 mg, 0.023 mmol) in 1:1 THF/MeOH (1.50 mL) was added 2M aqueous NaOH (0.30 mL, 0.60 mmol) and stirred at 40° C. overnight. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 8.70 (s, 1H), 8.47 (s, 1H), 8.39 (s, 1H), 8.15 (s, 1H), 8.04-7.96 (m, 2H), 7.77-7.67 (m, 2H), 7.64-7.56 (m, 3H), 5.30 (s, 1H), 4.12 (s, 3H), 2.77 (s, 3H), 2.66 (s, 3H), 0.99 (s, 9H); LCMS-ESI$^+$: calc'd for C$_{34}$H$_{32}$ClN$_4$O$_3$S: 611.2 (M+H$^+$); Found: 611.2 (M+H$^+$).

Example 142

Preparation of (S)-2-(tert-butoxy)-2-(7-(4-chlorophenyl)-2-(5-(difluoromethyl)-2-(1-methyl-1H-indazol-5-yl)pyridin-4-yl)-5-methylbenzo[d]thiazol-6-yl) acetic acid (290)

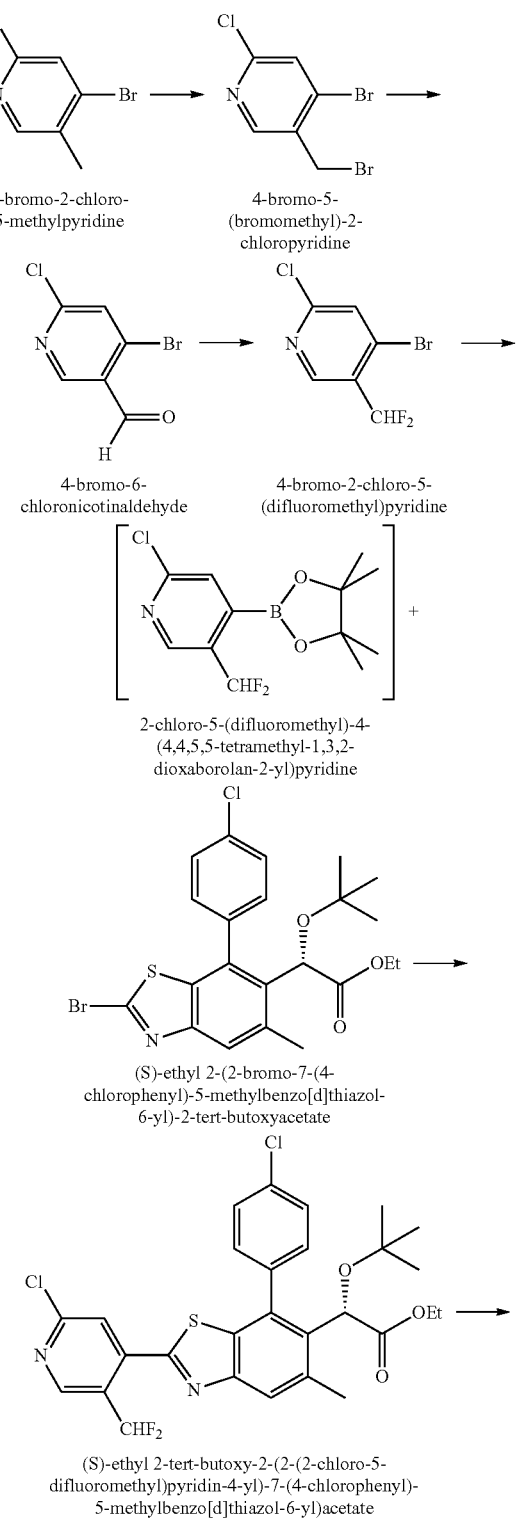

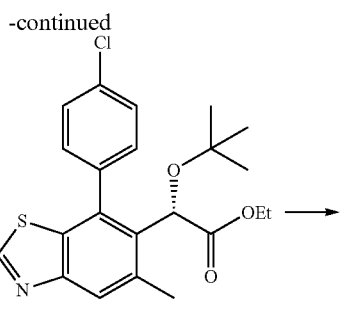

(S)-ethyl 2-tert-butoxy-2-(7-(4-chlorophenyl)-2-(5-(difluoromethyl)-2-(1-methyl-1H-indazol-5-yl)pyridin-4-yl)-5-methylbenzo[d]thiazol-6-yl)acetate

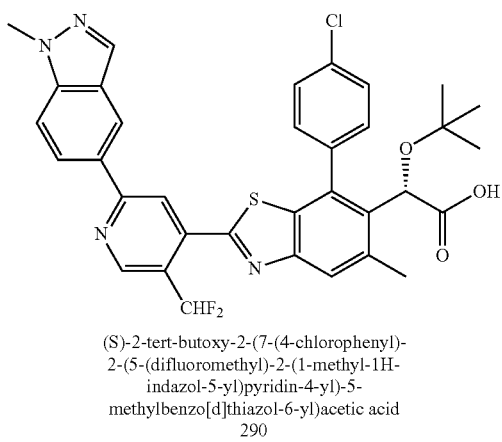

(S)-2-tert-butoxy-2-(7-(4-chlorophenyl)-2-(5-(difluoromethyl)-2-(1-methyl-1H-indazol-5-yl)pyridin-4-yl)-5-methylbenzo[d]thiazol-6-yl)acetic acid
290

Preparation of 4-bromo-5-(bromomethyl)-2-chloropyridine: A flask was charged with 4-bromo-2-chloro-5-methylpyridine (513 mg, 2.48 mmol), (PhCO$_2$)$_2$ (32 mg, 0.13 mmol), and NBS (452 mg, 2.54 mmol) then diluted with CCl$_4$ (9 mL). The reaction mixture was heated to reflux for 2 hours and then allowed to cool to room temperature and diluted with CH$_2$Cl$_2$ and H$_2$O. The layers were separated and the aqueous layer was extracted with CH$_2$Cl$_2$. The combined organic extracts were dried over Na$_2$SO$_4$, filtered, and concentrated in vacuo. The crude residue was purified by silica gel column chromatography (0-20% EtOAc/Hex gradient) to afford the desired product. LCMS-ESI$^+$: calc'd for C$_6$H$_5$Br$_2$ClN 283.9 (M+H$^+$); Found: 283.9 (M+H$^+$).

Preparation of 4-bromo-6-chloronicotinaldehyde: A flask was charged with 4-bromo-5-(bromomethyl)-2-chloropyridine (490 mg, 1.72 mmol), powdered 4 Å molecular sieves, and NMO (2.19 g, 18.74 mmol) then diluted with ACN (17 mL) and stirred at room temperature for 1 h. The reaction mixture was diluted with EtOAc, filtered, and concentrated in vacuo. The crude residue was purified by silica gel column chromatography (0-20% EtOAc/Hex gradient) to afford the desired product. LCMS-ESI$^+$: calc'd for C$_6$H$_4$BrClNO 219.9 (M+H$^+$); Found: 220.0 (M+H$^+$).

Preparation of 4-bromo-2-chloro-5-(difluoromethyl)pyridine: To a solution of 4-bromo-6-chloronicotinaldehyde (165 mg, 0.75 mmol) in CH$_2$Cl$_2$ at 0° C. was slowly added Deoxofluor (0.42 mL, 2.28 mmol) and stirred for 1 hour and then warmed to room temperature and stirred for 1 hour. The reaction mixture was then slowly diluted with saturated aqueous NaHCO$_3$ and then the layers were separated and the aqueous layer was extracted with CH$_2$Cl$_2$. The combined organic extracts were dried over Na$_2$SO$_4$, filtered through a small pad of silica gel, and concentrated in vacuo. The crude residue was purified by silica gel column chromatography (0-10% EtOAc/Hex gradient) to afford the desired product. $^1$H NMR (400 MHz, CDCl$_3$) δ 8.59 (s, 1H), 7.65 (d, J=0.3 Hz, 1H), 6.88 (t, J=54.0 Hz, 1H).

Preparation of (S)-ethyl 2-(tert-butoxy)-2-(2-(2-chloro-5-(difluoromethyl)pyridin-4-yl)-7-(4-chlorophenyl)-5-methylbenzo[d]thiazol-6-yl)acetate: A microwave vial was charged with 4-bromo-2-chloro-5-(difluoromethyl)pyridine (155 mg, 0.64 mmol), Bis(pinacolato)diboron (179 mg, 0.70 mmol), PdCl$_2$(dppf).CH$_2$Cl$_2$ (55 mg, 0.07 mmol), then KOAc (198 mg, 2.00 mmol). The vial was flushed with argon, diluted with dioxane (4 mL), sealed, then heated to 100° C. for 1 hour. The reaction mixture was allowed to cool to room temperature and then a portion of this cooled solution (1.2 mL, 0.19 mmol) was added to a vial that was charged with (S)-ethyl 2-(2-bromo-7-(4-chlorophenyl)-5-methylbenzo[d]thiazol-6-yl)-2-tert-butoxyacetate (58 mg, 0.12 mmol) and PdCl$_2$(dppf).CH$_2$Cl$_2$ (19 mg, 0.02 mmol). The mixture was diluted with dioxane (0.8 mL) and to this was added 2M aqueous K$_2$CO$_3$ (0.20 mL, 0.40 mmol). The vial was sealed, heated to 100° C. for 1 hour, and then allowed to cool to room temperature. The mixture was diluted with EtOAc, dried over Na$_2$SO$_4$, filtered, and concentrated in vacuo. The crude residue was purified by silica gel column chromatography (0-15% EtOAc/Hex gradient) to afford the desired product. LCMS-ESI$^+$: calc'd C$_{28}$H$_{27}$Cl$_2$F$_2$N$_2$O$_3$S: 579.1 (M+H$^+$); Found: 579.1 (M+H$^+$).

Preparation of (S)-ethyl 2-(tert-butoxy)-2-(7-(4-chlorophenyl)-2-(5-(difluoromethyl)-2-(1-methyl-1H-indazol-5-yl)pyridin-4-yl)-5-methylbenzo[d]thiazol-6-yl)acetate: A microwave vial containing (S)-ethyl 2-(tert-butoxy)-2-(2-(2-chloro-5-(difluoromethyl)pyridin-4-yl)-7-(4-chlorophenyl)-5-methylbenzo[d]thiazol-6-yl)acetate (44 mg, 0.076 mmol) was charged with (1-methyl-1H-indazol-5-yl)boronic acid (26 mg, 0.15 mmol), then Pd(PPh$_3$)$_4$ (18 mg, 0.02 mmol). The vial was flushed with argon, diluted with dioxane (1.0 mL) and to this was added 2M aqueous K$_2$CO$_3$ (0.15 mL, 0.30 mmol). The vial was sealed, heated to 120° C. for 3 hours, and then allowed to cool to room temperature. The mixture was diluted with EtOAc, dried over Na$_2$SO$_4$, filtered, and concentrated in vacuo. The crude residue was purified by silica gel column chromatography (10-40% EtOAc/Hex gradient) to afford the desired product. LCMS-ESI$^+$: calc'd for C$_{36}$H$_{34}$ClF$_2$N$_4$O$_3$S: 675.2 (M+H$^+$); Found: 675.2 (M+H$^+$).

Preparation of (S)-2-(tert-butoxy)-2-(7-(4-chlorophenyl)-2-(5-(difluoromethyl)-2-(1-methyl-1H-indazol-5-yl)pyridin-4-yl)-5-methylbenzo[d]thiazol-6-yl)acetic acid: To a solution of (S)-ethyl 2-(tert-butoxy)-2-(7-(4-chlorophenyl)-2-(5-(difluoromethyl)-2-(1-methyl-1H-indazol-5-yl)pyridin-4-yl)-5-methylbenzo[d]thiazol-6-yl)acetate (21 mg, 0.03 mmol) in 1:1 THF/MeOH (1.50 mL) was added 2M aqueous NaOH (0.20 mL, 0.40 mmol) and stirred at 50° C. overnight. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 9.05 (s, 1H), 8.51 (s, 1H), 8.26 (s, 1H), 8.17 (dd, J=8.9, 1.6 Hz, 1H), 8.13 (s, 1H), 7.99 (s, 1H), 7.93 (t, J=54.6 Hz, 1H), 7.75-7.56 (m, 5H), 5.29 (s, 1H), 4.10 (s, 3H), 2.65 (s, 3H), 0.99 (s, 9H). LCMS-ESI+: calc'd for $C_{34}H_{30}ClF_2N_4O_3S$: 647.2 (M+H+). Found: 647.2 (M+H+).

Example 143

Preparation of (S)-2-(tert-butoxy)-2-(7-(4-chlorophenyl)-2-(5-fluoro-2-(1-methyl-1H-indazol-5-yl)pyridin-4-yl)-5-methylbenzo[d]thiazol-6-yl)acetic acid (291)

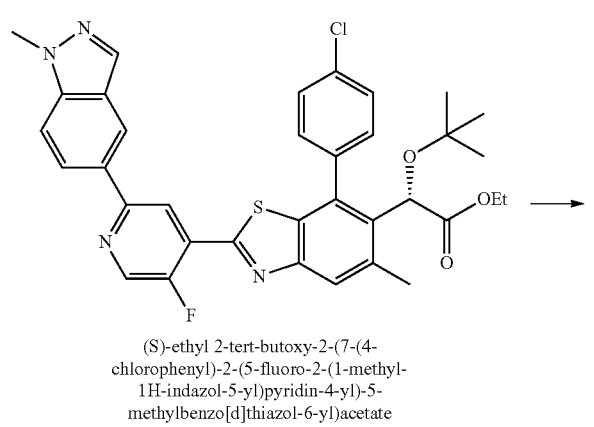

(S)-ethyl 2-tert-butoxy-2-(7-(4-chlorophenyl)-2-(5-fluoro-2-(1-methyl-1H-indazol-5-yl)pyridin-4-yl)-5-methylbenzo[d]thiazol-6-yl)acetate

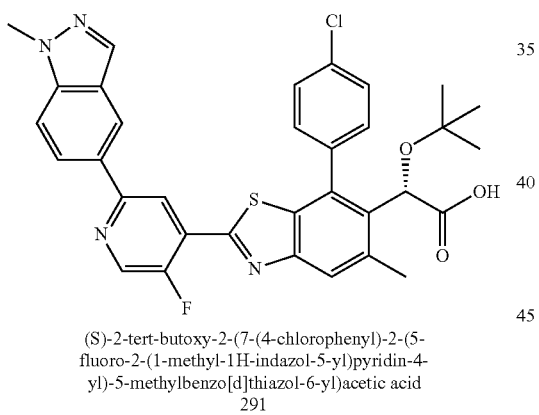

(S)-2-tert-butoxy-2-(7-(4-chlorophenyl)-2-(5-fluoro-2-(1-methyl-1H-indazol-5-yl)pyridin-4-yl)-5-methylbenzo[d]thiazol-6-yl)acetic acid 291

Preparation of (S)-2-(tert-butoxy)-2-(7-(4-chlorophenyl)-2-(5-fluoro-2-(1-methyl-1H-indazol-5-yl)pyridin-4-yl)-5-methylbenzo[d]thiazol-6-yl)acetic acid: To a solution of (S)-ethyl 2-(tert-butoxy)-2-(7-(4-chlorophenyl)-2-(5-fluoro-2-(1-methyl-1H-indazol-5-yl)pyridin-4-yl)-5-methylbenzo[d]thiazol-6-yl)acetate (27 mg, 0.04 mmol) in THF (1.50 mL) was added 2M aqueous NaOH (0.40 mL, 0.80 mmol) and stirred at 90° C. for 2 days. The reaction mixture was cooled to room temperature, neutralized with AcOH, filtered, and then purified by reverse phase column chromatography (5-100% ACN/H2O+0.1% TFA). Fractions containing the product were pooled and lyophilized to provide the TFA salt of the product. $^1$H NMR (400 MHz, CD3OD) δ 8.73 (d, J=5.7 Hz, 1H), 8.66 (d, J=2.3 Hz, 1H), 8.44 (d, J=0.8 Hz, 1H), 8.14 (dd, J=8.9, 1.7 Hz, 1H), 8.12 (d, J=0.8 Hz, 1H), 7.95 (s, 1H), 7.78-7.50 (m, 5H), 5.29 (s, 1H), 4.10 (s, 3H), 2.64 (s, 3H), 0.99 (s, 9H). LCMS-ESI+: calc'd for $C_{33}H_{29}ClFN_4O_3S$: 615.2 (M+H+); Found: 615.2 (M+H+).

Example 144

Preparation of (S)-2-(tert-butoxy)-2-(7-(4-chlorophenyl)-2-(1,2-dimethyl-1H-benzo[d]imidazol-6-yl)-5-methylbenzo[d]thiazol-6-yl)acetic acid (292)

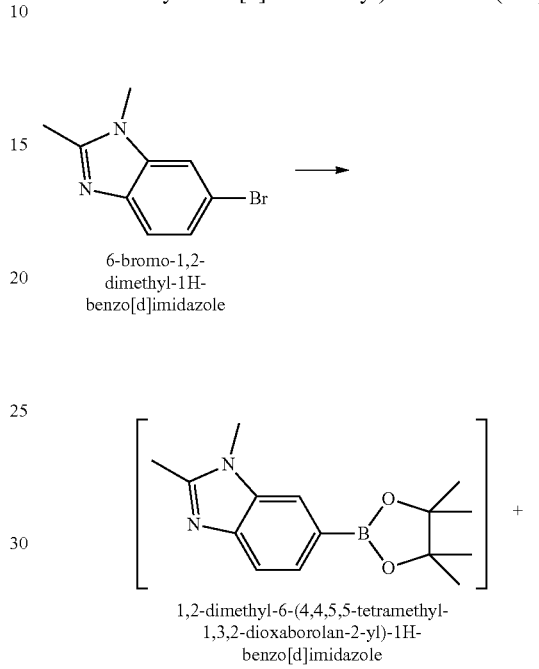

6-bromo-1,2-dimethyl-1H-benzo[d]imidazole 1,2-dimethyl-6-(4,4,5,5-tetramethyl-1,3,2-dioxaborolan-2-yl)-1H-benzo[d]imidazole

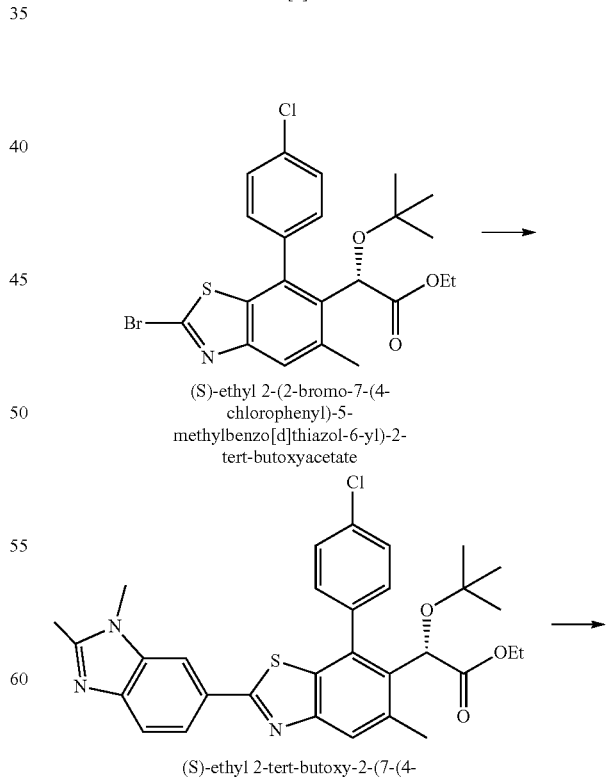

(S)-ethyl 2-(2-bromo-7-(4-chlorophenyl)-5-methylbenzo[d]thiazol-6-yl)-2-tert-butoxyacetate (S)-ethyl 2-tert-butoxy-2-(7-(4-chlorophenyl)-2-(1,2-dimethyl-1H-benzo[d]imidazol-6-yl)-5-methylbenzo[d]thiazol-6-yl)acetate

495

-continued

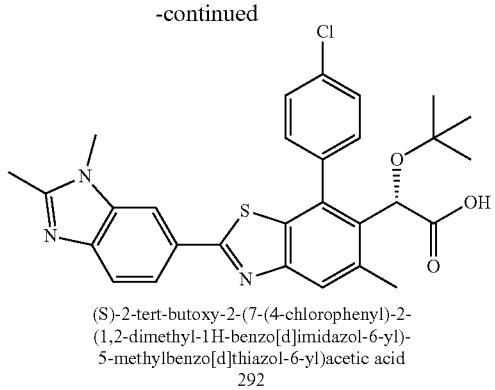

(S)-2-tert-butoxy-2-(7-(4-chlorophenyl)-2-
(1,2-dimethyl-1H-benzo[d]imidazol-6-yl)-
5-methylbenzo[d]thiazol-6-yl)acetic acid
292

Preparation of (S)-ethyl 2-(tert-butoxy)-2-(7-(4-chlorophenyl)-2-(1,2-dimethyl-1H-benzo[d]imidazol-6-yl)-5-methylbenzo[d]thiazol-6-yl)acetate: A microwave vial was charged with 6-bromo-1,2-dimethyl-1H-benzo[d]imidazole (150 mg, 0.67 mmol), Bis(pinacolato)diboron (189 mg, 0.74 mmol), $PdCl_2(dppf) \cdot CH_2Cl_2$ (55 mg, 0.07 mmol), then KOAc (221 mg, 2.25 mmol). The vial was flushed with argon, diluted with dioxane (3 mL), sealed, then heated to 100° C. for 45 minutes. The reaction mixture was allowed to cool to room temperature and then a portion of this cooled solution (1.0 mL, 0.22 mmol) was added to a vial that was charged with (S)-ethyl 2-(2-bromo-7-(4-chlorophenyl)-5-methyl-benzo[d]thiazol-6-yl)-2-tert-butoxyacetate (55 mg, 0.10 mmol) and $Pd(PPh_3)_4$ (12 mg, 0.01 mmol). The mixture was diluted with dioxane (1.5 mL) and to this was added 2M aqueous $K_2CO_3$ (0.21 mL, 0.42 mmol). The vial was sealed, heated to 100° C. for 1 hour, and then allowed to cool to room temperature. The mixture was diluted with EtOAc, dried over $Na_2SO_4$, filtered through a small pad of silica gel, and concentrated in vacuo to afford the desired product. LCMS-ESI$^+$: calc'd $C_{31}H_{33}ClN_3O_3S$: 562.2 (M+H$^+$); Found: 562.3 (M+H$^+$).

Preparation of (S)-2-(tert-butoxy)-2-(7-(4-chlorophenyl)-2-(1,2-dimethyl-1H-benzo[d]imidazol-6-yl)-5-methylbenzo[d]thiazol-6-yl)acetic acid: To a solution of (S)-ethyl 2-(tert-butoxy)-2-(7-(4-chlorophenyl)-2-(1,2-dimethyl-1H-benzo[d]imidazol-6-yl)-5-methylbenzo[d]thiazol-6-yl)acetate (27 mg, 0.05 mmol) in 1:1 THF/MeOH (1.50 mL) was added 2M aqueous NaOH (0.15 mL, 0.30 mmol) and stirred at 50° C. overnight. The reaction mixture was cooled to room temperature, neutralized with AcOH, filtered, and then purified by reverse phase column chromatography (5-100% ACN/H$_2$O+ 0.1% TFA). Fractions containing the product were pooled and lyophilized to provide the TFA salt of the product. $^1$H NMR (400 MHz, CD$_3$OD). δ 8.52 (s, 1H), 8.26 (dd, J=8.6, 1.5 Hz, 1H), 7.90 (s, 1H), 7.85 (d, J=8.6 Hz, 1H), 7.70 (d, J=8.3 Hz, 1H), 7.67-7.57 (m, 3H), 5.27 (s, 1H), 4.05 (s, 3H), 2.88 (s, 3H), 2.63 (s, 3H), 0.98 (s, 9H). LCMS-ESI$^+$: calc'd for $C_{29}H_{29}ClN_3O_3S$: 534.2 (M+H$^+$); Found: 534.2 (M+H$^+$).

496

Example 145

Preparation of (S)-2-tert-butoxy-2-(7-(4-chlorophenyl)-5-methyl-2-(2-methyl-6,7-dihydro-1H-imidazo[4,5-c]pyridin-5(4H)-yl)benzo[d]thiazol-6-yl)acetic acid (293)

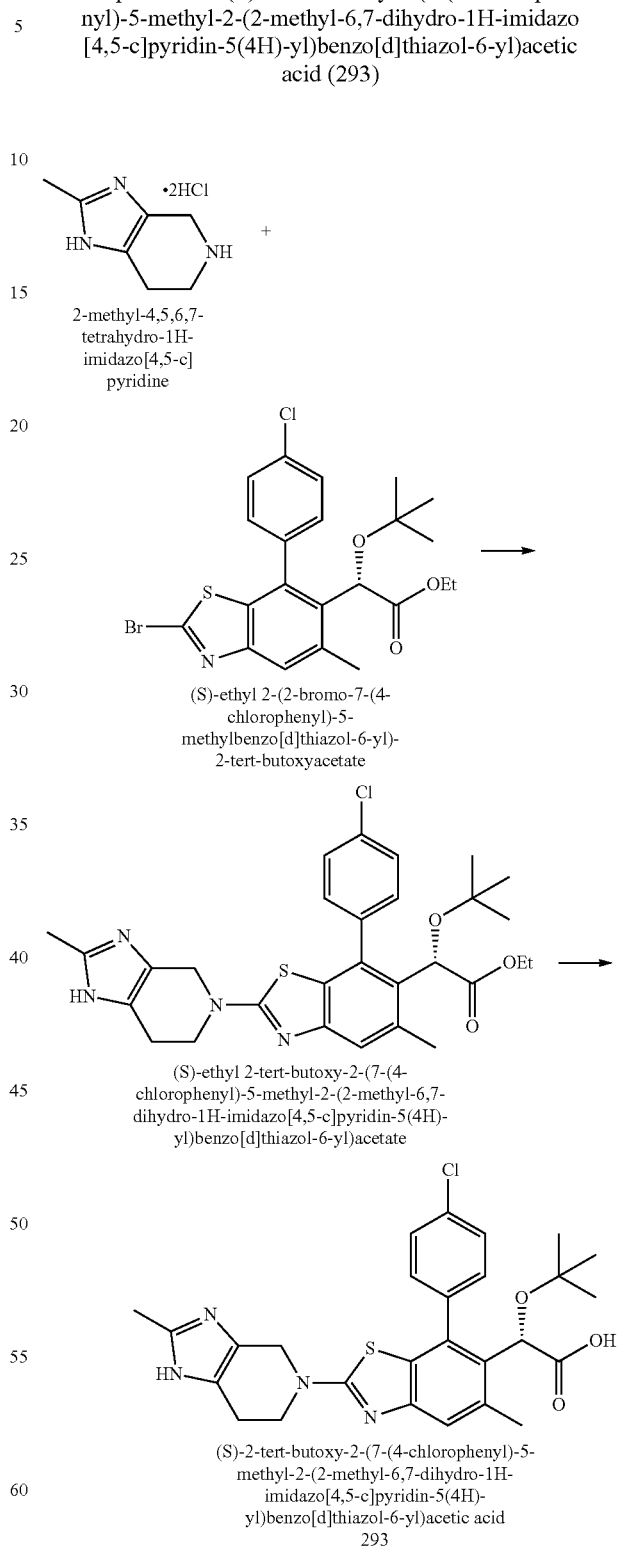

2-methyl-4,5,6,7-
tetrahydro-1H-
imidazo[4,5-c]
pyridine (S)-ethyl 2-(2-bromo-7-(4-
chlorophenyl)-5-
methylbenzo[d]thiazol-6-yl)-
2-tert-butoxyacetate (S)-ethyl 2-tert-butoxy-2-(7-(4-
chlorophenyl)-5-methyl-2-(2-methyl-6,7-
dihydro-1H-imidazo[4,5-c]pyridin-5(4H)-
yl)benzo[d]thiazol-6-yl)acetate (S)-2-tert-butoxy-2-(7-(4-chlorophenyl)-5-
methyl-2-(2-methyl-6,7-dihydro-1H-
imidazo[4,5-c]pyridin-5(4H)-
yl)benzo[d]thiazol-6-yl)acetic acid
293

Preparation of (S)-ethyl 2-tert-butoxy-2-(7-(4-chlorophenyl)-5-methyl-2-(2-methyl-6,7-dihydro-1H-imidazo[4,5-c]pyridin-5(4H)-yl)benzo[d]thiazol-6-yl)acetate: A flask was charged with (S)-ethyl 2-(2-bromo-7-(4-chlorophenyl)-5-methylbenzo[d]thiazol-6-yl)-2-tert-butoxyacetate (100 mg, 0.20 mmol), 2-methyl-4,5,6,7-tetrahydro-1H-imidazo[4,5-c]pyridine (85 mg, 0.40 mmol), Cs$_2$CO$_3$ (325 mg, 1.0 mmol), and then diluted with ACN (4 mL). The suspension was heated to 80° C. for 24 hours and then allowed to cool to room temperature. The resulting mixture was filtered and concentrated in vacuo. The crude residue was purified by reverse phase column chromatography (5-100% ACN/H$_2$O+0.1% TFA)to afford the desired product. LCMS-ESI$^+$: calc'd for C$_{29}$H$_{34}$ClN$_4$O$_3$S: 553.2 (M+H$^+$); Found: 553.2 (M+H$^+$).

Preparation of (S)-2-tert-butoxy-2-(7-(4-chlorophenyl)-5-methyl-2-(2-methyl-6,7-dihydro-1H-imidazo[4,5-c]pyridin-5(4H)-yl)benzo[d]thiazol-6-yl)acetic acid: To a solution of (S)-ethyl 2-tert-butoxy-2-(7-(4-chlorophenyl)-5-methyl-2-(2-methyl-6,7-dihydro-1H-imidazo[4,5-c]pyridin-5(4H)-yl)benzo[d]thiazol-6-yl)acetate (21 mg, 0.04 mmol) in 1:1 THF/MeOH (1.5 mL) was added 2M aqueous NaOH (0.2 mL, 0.4 mmol) and stirred at 50° C. overnight. The reaction mixture was cooled to room temperature, neutralized with AcOH, filtered, and then purified by reverse phase column (5-100% ACN/H$_2$O+0.1% TFA). Fractions containing the product were pooled and lyophilized to provide the TFA salt of the product. $^1$H NMR (400 MHz, CD$_3$OD) δ 7.66-7.43 (m, 4H), 7.36 (s, 1H), 5.14 (s, 1H), 4.76 (br s, 2H), 3.94 (br t, J=5.7 Hz, 2H), 2.87 (br t, J=5.5 Hz, 2H), 2.61 (s, 3H), 2.50 (s, 3H), 0.94 (s, 9H); LCMS-ESI$^+$: calc'd for C$_{27}$H$_{30}$ClN$_4$O$_3$S: 525.2 (M+H$^+$); Found: 525.1 (M+H$^+$).

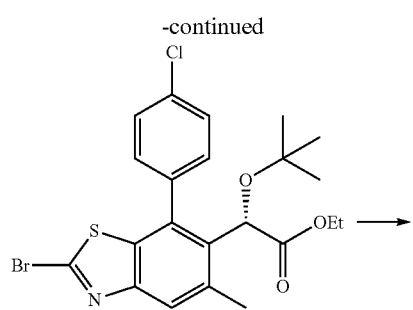

(S)-ethyl 2-(2-bromo-7-(4-chlorophenyl)-5-methylbenzo[d]thiazol-6-yl)-2-tert-butoxyacetate

Example 146

Preparation of (S)-2-(tert-butoxy)-2-(7-(4-chlorophenyl)-5-methyl-2-(2-methyl-1-(1-methylpiperidin-4-yl)-1H-benzo[d]imidazol-5-yl)benzo[d]thiazol-6-yl) acetic acid (294)

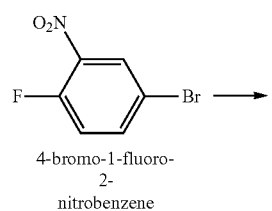

4-bromo-1-fluoro-2-nitrobenzene

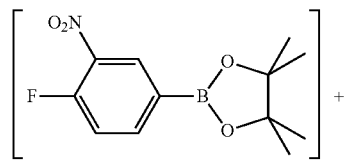

2-(4-fluoro-3-nitrophenyl)-4,4,5,5-tetramethyl-1,3,2-dioxaborolane

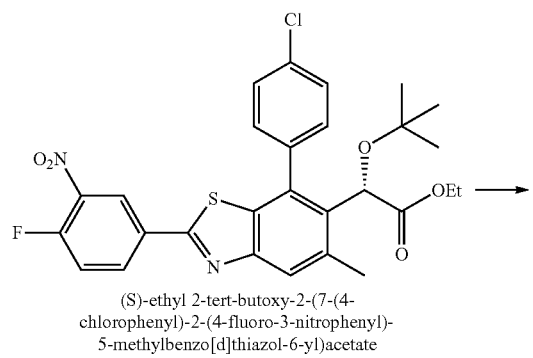

(S)-ethyl 2-tert-butoxy-2-(7-(4-chlorophenyl)-2-(4-fluoro-3-nitrophenyl)-5-methylbenzo[d]thiazol-6-yl)acetate

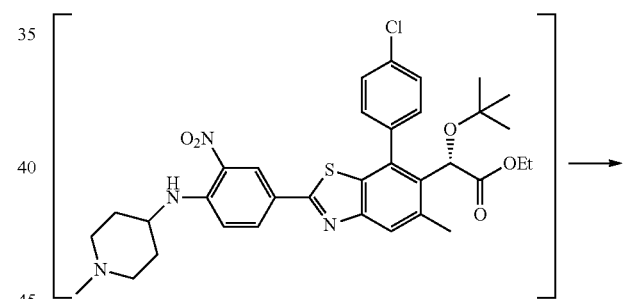

(S)-ethyl 2-tert-butoxy-2-(7-(4-chlorophenyl)-5-methyl-2-(4-(1-methylpiperidin-4-ylamino)-3-nitrophenyl)benzo[d]thiazol-6-yl)acetate

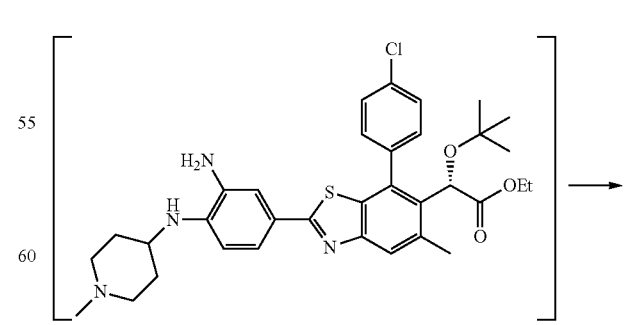

(S)-ethyl 2-(2-(3-amino-4-(1-methylpiperidin-4-ylamino)phenyl)-7-(4-chlorophenyl)-5-methylbenzo[d]thiazol-6-yl)-2-tert-butoxyacetate

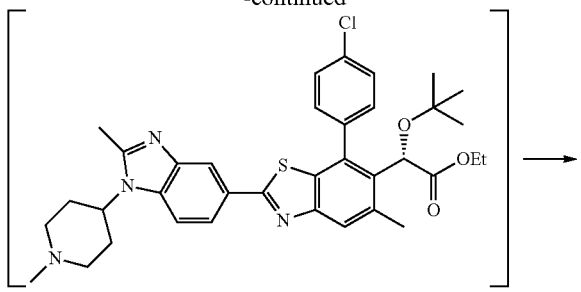

[(S)-ethyl 2-tert-butoxy-2-(7-(4-chlorophenyl)-5-methyl-2-(2-methyl-1-(1-methylpiperidin-4-yl)-1H-benzo[d]imidazol-5-yl)benzo[d]thiazol-6-yl)acetate]

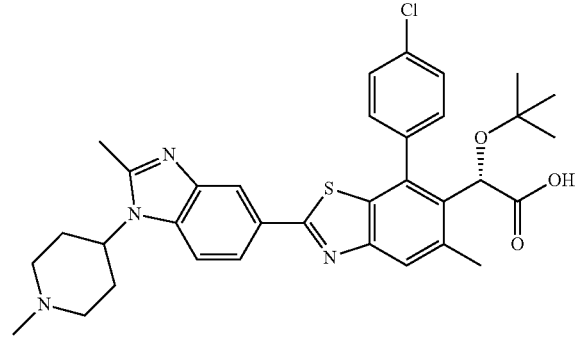

(S)-2-tert-butoxy-2-(7-(4-chlorophenyl)-5-methyl-2-(2-methyl-1-(1-methylpiperidin-4-yl)-1H-benzo[d]imidazol-5-yl)benzo[d]thiazol-6-yl)acetic acid
294

Preparation of (S)-ethyl 2-tert-butoxy-2-(7-(4-chlorophenyl)-2-(4-fluoro-3-nitrophenyl)-5-methylbenzo[d]thiazol-6-yl)acetate: A microwave vial was charged with 4-bromo-1-fluoro-2-nitrobenzene (0.3 mL, 2.41 mmol), Bis(pinacolato)diboron (677 mg, 2.67 mmol), PdCl$_2$(dppf).CH$_2$Cl$_2$ (203 mg, 0.25 mmol), then KOAc (864 mg, 8.80 mmol). The vial was flushed with argon, diluted with dioxane (6 mL), sealed, then heated to 100° C. for 1 hour. The reaction mixture was allowed to cool to room temperature and then a portion of this cooled solution (1.3 mL, 0.52 mmol) was added to a vial that was charged with (S)-ethyl 2-(2-bromo-7-(4-chlorophenyl)-5-methylbenzo[d]thiazol-6-yl)-2-tert-butoxyacetate (130 mg, 0.26 mmol) and Pd(PPh$_3$)$_4$ (44 mg, 0.04 mmol). The mixture was diluted with dioxane (5.0 mL) and to this was added 2M aqueous K$_2$CO$_3$ (0.50 mL, 1.00 mmol). The vial was sealed, heated to 100° C. for 1 hour, and then allowed to cool to room temperature. The mixture was diluted with EtOAc, dried over Na$_2$SO$_4$, filtered, and concentrated in vacuo. The crude residue was purified by silica gel column chromatography (0-25% EtOAc/Hex gradient) to afford the desired product. LCMS-ESI$^+$: calc'd C$_{28}$H$_{27}$ClFN$_2$O$_5$S: 557.1 (M+H$^+$); Found: 557.1 (M+H$^+$).

Preparation of (S)-2-(tert-butoxy)-2-(7-(4-chlorophenyl)-5-methyl-2-(2-methyl-1-(1-methylpiperidin-4-yl)-1H-benzo[d]imidazol-5-yl)benzo[d]thiazol-6-yl)acetic acid: A flask containing (S)-ethyl 2-tert-butoxy-2-(7-(4-chlorophenyl)-2-(4-fluoro-3-nitrophenyl)-5-methylbenzo[d]thiazol-6-yl)acetate (98 mg, 0.18 mmol) was charged with Cs$_2$CO$_3$ (124 mg, 0.38 mmol) and then diluted with DMF (4 mL). The reaction mixture was then treated with 4-amino-1-methylpiperidine (1.0 mL, 0.91 mmol) at room temperature and allowed to stir for 1 hour. The mixture was diluted with EtOAc and H$_2$O, the layers were separated, and the aqueous layer was extracted with EtOAc. The combined organic extracts were dried over Na$_2$SO$_4$, filtered, and concentrated in vacuo to afford a crude residue. The flask containing the crude residue was then charged with 5 wt % Pt/C (33 mg) and diluted with 2:1 EtOH/EtOAc (5 mL). The flask was evacuated then backfilled with H$_2$ (3 cycles) and stirred under a hydrogen atmosphere for 45 minutes, at which time, the flask was purged with N$_2$, filtered through a pad of Celite, and concentrated in vacuo to provide a crude residue that was taken up in AcOH (5 mL). To this was added MeC(OEt)$_3$ (0.3 mL) at room temperature and allowed to stir for 15 minutes. The solution was concentrated in vacuo to provide a crude residue. The crude residue was taken up 1:1 THF/MeOH (1.5 mL) and to this was added 2M aqueous NaOH (0.2 mL, 0.4 mmol) and stirred at 50° C. overnight. The reaction mixture was cooled to room temperature, neutralized with AcOH, filtered, and then purified by reverse phase column chromatography (5-100% ACN/H$_2$O+ 0.1% TFA). Fractions containing the product were pooled and lyophilized to provide the TFA salt of the product. LCMS-ESI$^+$: calc'd C$_{34}$H$_{38}$ClN$_4$O$_3$S: 617.2 (M+H$^+$); Found: 617.3 (M+H$^+$).

Example 147

Preparation of (S)-2-(tert-butoxy)-2-(7-(4-chlorophenyl)-5-methyl-2-(1-(1-methylpiperidin-4-yl)-1H-benzo[d]imidazol-5-yl)benzo[d]thiazol-6-yl)acetic acid (295)

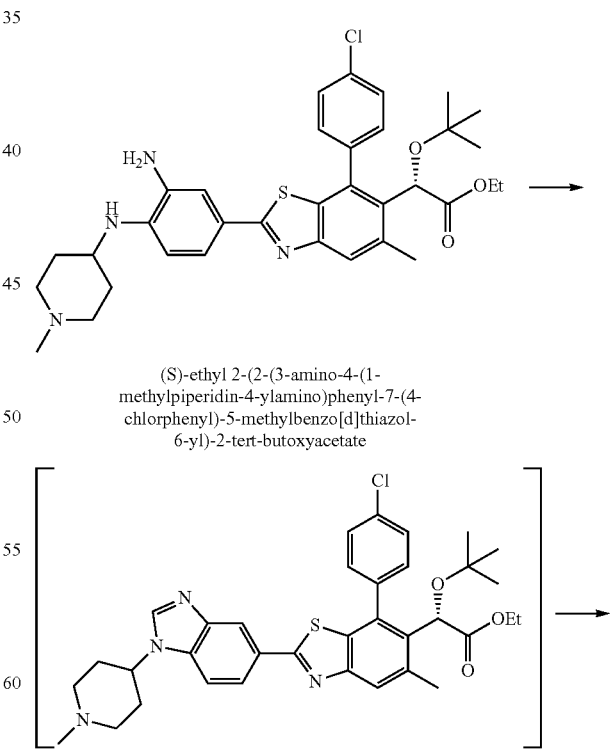

(S)-ethyl 2-(2-(3-amino-4-(1-methylpiperidin-4-ylamino)phenyl-7-(4-chlorphenyl)-5-methylbenzo[d]thiazol-6-yl)-2-tert-butoxyacetate

[(S)-ethyl 2-tert-butoxy-2-(7-(4-chlorophenyl)-5-methyl-2-(1-(1-methylpiperidin-4-yl)-1H-benzo[d]imidazol-5-yl)benzo[d]thiazol-6-yl)acetate]

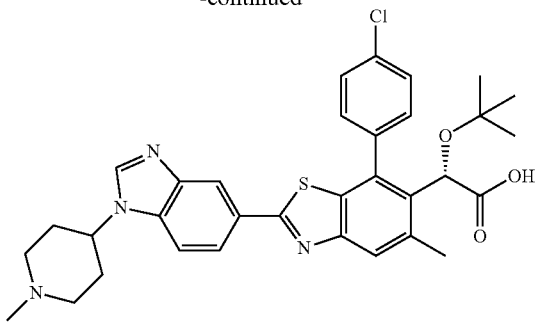

(S)-2-tert-butoxy-2-(7-(4-chlorophenyl)-5-
methyl-2-(1-(1-methylpiperidin-4-yl)-1H-
benzo[d]imidazol-5-yl)benzo[d]thiazol-6-
yl)acetic acid
295

Preparation of (S)-2-(tert-butoxy)-2-(7-(4-chlorophenyl)-5-methyl-2-(1-(1-methylpiperidin-4-yl)-1H-benzo[d]imidazol-5-yl)benzo[d]thiazol-6-yl)acetic acid: To a solution of (S)-ethyl 2-(2-(3-amino-4-((1-methylpiperidin-4-yl)amino)phenyl)-7-(4-chlorophenyl)-5-methylbenzo[d]thiazol-6-yl)-2-(tert-butoxy)acetate (26 mg, 0.04 mmol) in AcOH (3 mL) was added CH(OEt)$_3$ (0.3 mL) at room temperature and stirred for 15 minutes. The solution was concentrated in vacuo to provide a crude residue that was taken up in 1:1 THF/MeOH (1.5 mL) was added 2M aqueous NaOH (0.2 mL, 0.4 mmol) and stirred at 50° C. overnight. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 8.79 (s, 1H), 8.42 (s, 1H), 8.18 (d, J=8.7 Hz, 1H), 7.91 (d, J=8.6 Hz, 1H), 7.87 (s, 1H), 7.70 (d, J=9.5 Hz, 1H), 7.60 (br s, 3H), 5.26 (s, 1H), 5.01-4.89 (m, 1H), 3.90-3.70 (m, 2H), 3.43-3.32 (m, 2H), 3.01 (s, 3H), 2.62 (s, 3H), 2.60-2.34 (m, 4H), 0.98 (s, 9H); LCMS-ESI$^+$: calc'd C$_{33}$H$_{36}$ClN$_4$O$_3$S: 603.2 (M+H$^+$); Found: 603.3 (M+H$^+$).

Example 148

Preparation of (S)-2-tert-butoxy-2-(7-(4-chlorophenyl)-5-methyl-2-(2-methyl-1-((R)-1-methylpyrrolidin-3-yl)-1H-benzo[d]imidazol-6-yl)benzo[d]thiazol-6-yl)acetic acid (296)

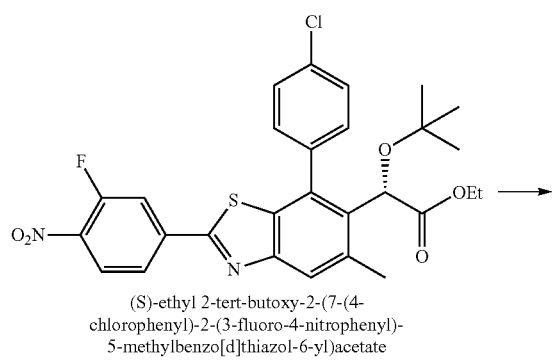

(S)-ethyl 2-tert-butoxy-2-(7-(4-chlorophenyl)-2-(3-fluoro-4-nitrophenyl)-5-methylbenzo[d]thiazol-6-yl)acetate

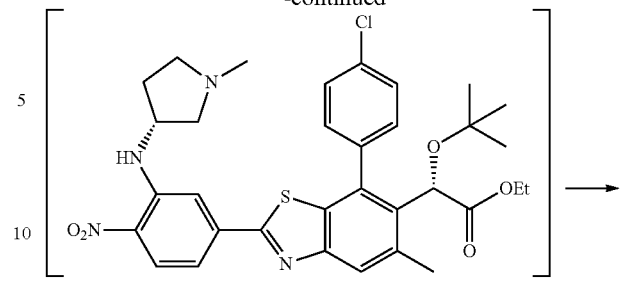

(S)-ethyl 2-tert-butoxy-2-(7-(4-chlorophenyl)-5-methyl-2-(3-((R)-1-methylpyrrolidin-3-ylamino)-4-nitrophenyl)benzo[d]thiazol-6-yl)acetate

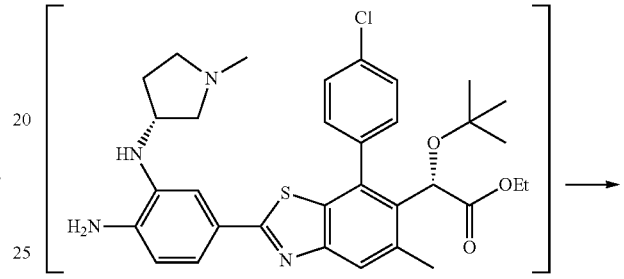

(S)-ethyl 2-(2-(4-amino-3-((R)-1-methylpyrrolidin-3-ylamino)phenyl)-7-(4-chlorophenyl)-5-methylbenzo[d]thiazol-6-yl)-2-tert-butoxyacetate

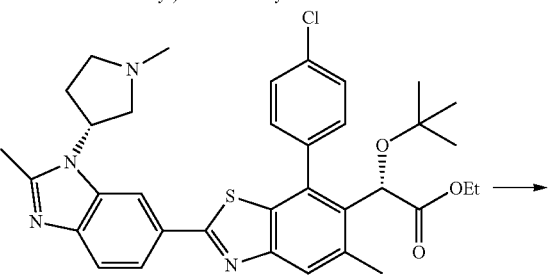

(S)-ethyl 2-tert-butoxy-2-(7-(4-chlorophenyl)-5-methyl-2-(2-methyl-1-((R)-1-methylpyrrolidin-3-yl)-1H-benzo[d]imidazol-6-yl)benzo[d]thiazol-6-yl)acetate

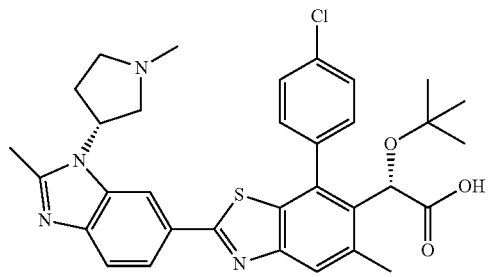

(S)-2-tert-butoxy-2-(7-(4-chlorophenyl)-5-methyl-2-(2-methyl-1-((R)-1-methylpyrrolidin-3-yl)-1H-benzo[d]imidazol-6-yl)benzo[d]thiazol-6-yl)acetic acid
296

Preparation of (S)-ethyl 2-tert-butoxy-2-(7-(4-chlorophenyl)-5-methyl-2-(2-methyl-1-((R)-1-methylpyrrolidin-3-yl)-1H-benzo[d]imidazol-6-yl)benzo[d]thiazol-6-yl)acetate: A flask containing (S)-ethyl 2-tert-butoxy-2-(7-(4-chlorophenyl)-2-(3-fluoro-4-nitrophenyl)-5-methylbenzo[d]thiazol-6-yl)acetate (86 mg, 0.15 mmol) was charged with Cs₂CO₃ (252 mg, 0.77 mmol) and diluted with DMF (3 mL). The reaction mixture was treated with (3R)-1-methylpyrrolidin-3-amine (45 mg, 0.45 mmol) at room temperature and allowed to stir for 30 minutes. The mixture was diluted with EtOAc and H₂O, the layers were separated, and the aqueous layer was extracted with EtOAc. The combined organic extracts were dried over Na₂SO₄, filtered, and concentrated in vacuo to afford a crude residue. The flask containing the crude residue was then charged with 5 wt % Pt/C (23 mg) and then diluted with 2:1 EtOH/EtOAc (3 mL). The flask was evacuated then backfilled with H₂ (3 cycles) and stirred under a hydrogen atmosphere for 20 minutes, at which time, the flask was purged with N₂, filtered through a pad of Celite, and concentrated in vacuo to provide a crude residue. The crude residue was then taken up in AcOH (2 mL) and MeC(OEt)₃ (0.2 mL) was added at room temperature and stirred for 15 minutes. The solution was concentrated in vacuo and the crude residue was purified by reverse phase column chromatography (5-100% ACN/H₂O+0.1% TFA) to provide the TFA salt of the product. LCMS-ESI⁺: calc'd $C_{35}H_{40}ClN_4O_3S$: 631.3 (M+H⁺); Found: 631.2 (M+H⁺).

Preparation of (S)-2-tert-butoxy-2-(7-(4-chlorophenyl)-5-methyl-2-(2-methyl-1-((R)-1-methylpyrrolidin-3-yl)-1H-benzo[d]imidazol-6-yl)benzo[d]thiazol-6-yl)acetic acid: To a solution of (S)-ethyl 2-tert-butoxy-2-(7-(4-chlorophenyl)-5-methyl-2-(2-methyl-1-((R)-1-methylpyrrolidin-3-yl)-1H-benzo[d]imidazol-6-yl)benzo[d]thiazol-6-yl)acetate (8 mg, 0.01 mmol) in 2:1 MeOH/THF (1.2 mL) was added 2M aqueous NaOH (0.3 mL, 0.6 mmol) and stirred at 50° C. overnight. The reaction mixture was cooled to room temperature, neutralized with AcOH, filtered, and then purified by reverse phase column chromatography (5-100% ACN/H₂O+0.1% TFA). Fractions containing the product were pooled and lyophilized to provide the TFA salt of the product. ¹H NMR (400 MHz, CD₃OD) δ 8.44 (s, 1H), 8.04 (dd, J=8.5, 1.4 Hz, 1H), 7.89 (s, 1H), 7.81 (d, J=8.6 Hz, 1H), 7.74-7.66 (m, 1H), 7.66-7.54 (m, 3H), 5.81-5.60 (br m, 1H), 5.27 (s, 1H), 4.29-3.99 (br m, 2H), 3.99-3.84 (m, 1H), 3.60 (br s, 1H), 3.18 (s, 3H), 2.98-2.71 (m, 2H), 2.84 (s, 3H), 2.64 (s, 3H), 0.98 (s, 9H). LCMS-ESI⁺: calc'd $C_{33}H_{36}ClN_4O_3S$: 603.2 (M+H⁺); Found: 603.3 (M+H⁺).

Example 149

Preparation of (S)-2-tert-butoxy-2-(7-(4-chlorophenyl)-5-methyl-2-(2-methyl-1-(1-methylazetidin-3-yl)-1H-benzo[d]imidazol-6-yl)benzo[d]thiazol-6-yl)acetic acid (297)

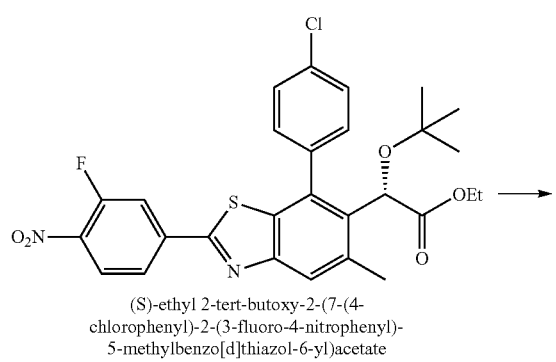

(S)-ethyl 2-tert-butoxy-2-(7-(4-chlorophenyl)-2-(3-fluoro-4-nitrophenyl)-5-methylbenzo[d]thiazol-6-yl)acetate

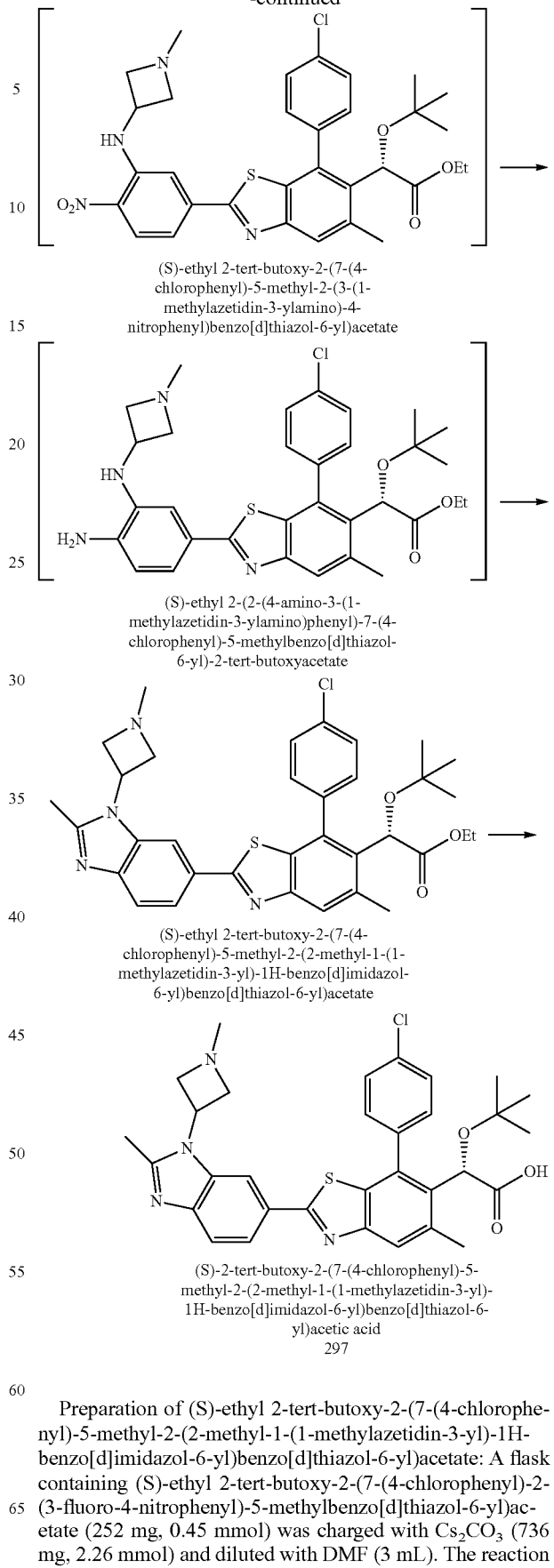

(S)-ethyl 2-tert-butoxy-2-(7-(4-chlorophenyl)-5-methyl-2-(3-(1-methylazetidin-3-ylamino)-4-nitrophenyl)benzo[d]thiazol-6-yl)acetate (S)-ethyl 2-(2-(4-amino-3-(1-methylazetidin-3-ylamino)phenyl)-7-(4-chlorophenyl)-5-methylbenzo[d]thiazol-6-yl)-2-tert-butoxyacetate (S)-ethyl 2-tert-butoxy-2-(7-(4-chlorophenyl)-5-methyl-2-(2-methyl-1-(1-methylazetidin-3-yl)-1H-benzo[d]imidazol-6-yl)benzo[d]thiazol-6-yl)acetate (S)-2-tert-butoxy-2-(7-(4-chlorophenyl)-5-methyl-2-(2-methyl-1-(1-methylazetidin-3-yl)-1H-benzo[d]imidazol-6-yl)benzo[d]thiazol-6-yl)acetic acid
297

Preparation of (S)-ethyl 2-tert-butoxy-2-(7-(4-chlorophenyl)-5-methyl-2-(2-methyl-1-(1-methylazetidin-3-yl)-1H-benzo[d]imidazol-6-yl)benzo[d]thiazol-6-yl)acetate: A flask containing (S)-ethyl 2-tert-butoxy-2-(7-(4-chlorophenyl)-2-(3-fluoro-4-nitrophenyl)-5-methylbenzo[d]thiazol-6-yl)acetate (252 mg, 0.45 mmol) was charged with Cs₂CO₃ (736 mg, 2.26 mmol) and diluted with DMF (3 mL). The reaction mixture was then treated with 1-methylazetidin-3-amine (127 mg, 1.47 mmol) at room temperature and allowed to stir for 30 minutes. The mixture was diluted with EtOAc and H₂O, the layers were separated, and the aqueous layer was extracted with EtOAc. The combined organic extracts were dried over Na₂SO₄, filtered, and concentrated in vacuo to afford a crude residue. The flask containing the crude residue was charged with 5 wt % Pt/C (46 mg) and diluted with 2:1 EtOH/EtOAc (4 mL). The flask was evacuated then backfilled with H₂ (3 cycles) and stirred under a hydrogen atmosphere for 20 minutes, at which time, the flask was purged with N₂, filtered through a pad of Celite, and concentrated in vacuo to provide a crude residue. The crude residue was taken up in AcOH (3 mL) and MeC(OEt)₃ (0.3 mL) was added at room temperature and stirred for 15 minutes. The solution was concentrated in vacuo and the crude residue was purified by reverse phase column chromatography (5-100% ACN/H₂O+ 0.1% TFA)to provide the TFA salt of the product. LCMS-ESI⁺: calc'd $C_{34}H_{38}ClN_4O_3S$: 617.2 (M+H⁺); Found: 617.3 (M+H⁺).

Preparation of (S)-2-tert-butoxy-2-(7-(4-chlorophenyl)-5-methyl-2-(2-methyl-1-(1-methylazetidin-3-yl)-1H-benzo[d]imidazol-6-yl)benzo[d]thiazol-6-yl)acetic acid: To a solution of (S)-ethyl 2-tert-butoxy-2-(7-(4-chlorophenyl)-5-methyl-2-(2-methyl-1-(1-methylazetidin-3-yl)-1H-benzo[d]imidazol-6-yl)benzo[d]thiazol-6-yl)acetate (18 mg, 0.03 mmol) in 4:1 MeOH/THF (1.0 mL) was added 2M aqueous NaOH (0.3 mL, 0.6 mmol) and stirred at 50° C. overnight. The reaction mixture was cooled to room temperature, neutralized with AcOH, filtered, and then purified by reverse phase column chromatography (5-100% ACN/H₂O+0.1% TFA). Fractions containing the product were pooled and lyophilized to provide the TFA salt of the product. ¹H NMR (400 MHz, CD₃OD) δ 8.55 (s, 1H), 8.13 (dd, J=8.6, 1.4 Hz, 1H), 7.96-7.81 (m, 2H), 7.74-7.65 (m, 1H), 7.65-7.53 (m, 3H), 6.00 (br s, 1H), 5.27 (s, 1H), 5.22 (br s, 2H), 4.75 (br s, 2H), 3.25 (s, 3H), 2.84 (s, 3H), 2.64 (s, 3H), 0.99 (s, 9H); LCMS-ESI⁺: calc'd $C_{32}H_{34}ClN_4O_3S$: 589.2 (M+H⁺); Found: 589.2 (M+H⁺).

Example 150

Preparation of (S)-2-(2-(1-(azetidin-3-yl)-2-methyl-1H-benzo[d]imidazol-6-yl)-7-(4-chlorophenyl)-5-methylbenzo[d]thiazol-6-yl)-2-tert-butoxyacetic acid (298)

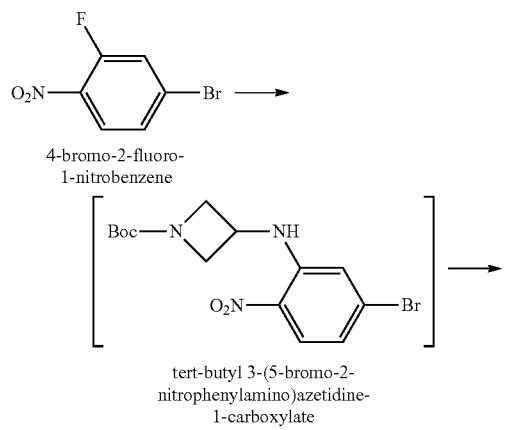

4-bromo-2-fluoro-1-nitrobenzene tert-butyl 3-(5-bromo-2-nitrophenylamino)azetidine-1-carboxylate

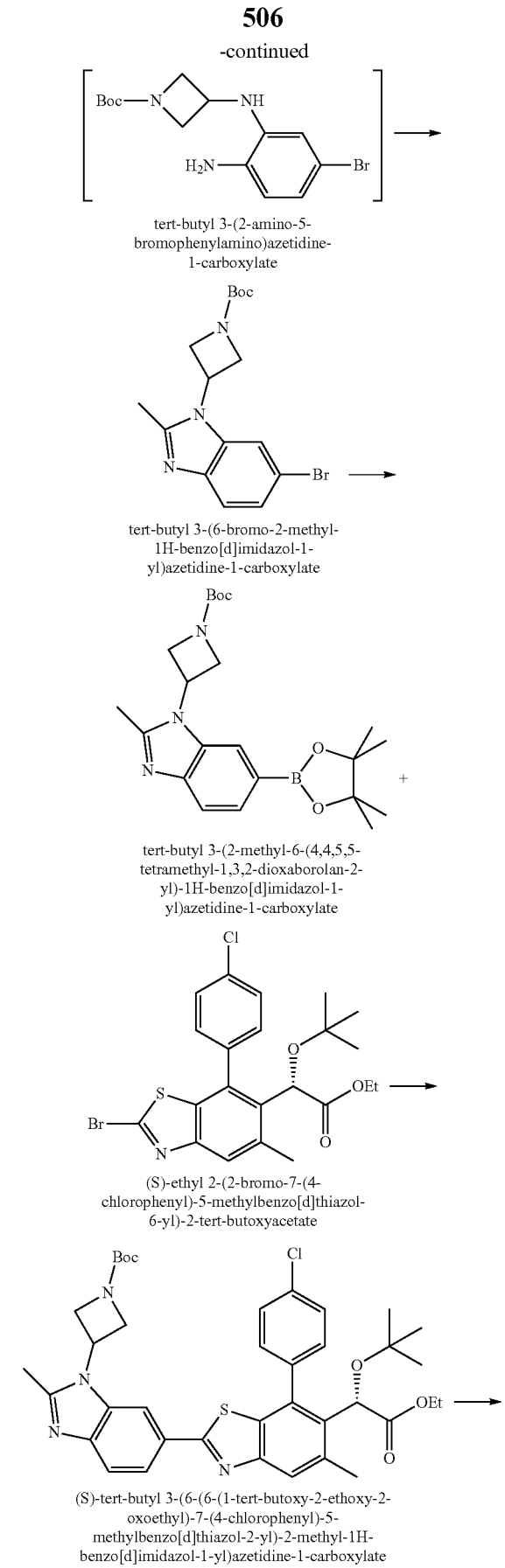

tert-butyl 3-(2-amino-5-bromophenylamino)azetidine-1-carboxylate tert-butyl 3-(6-bromo-2-methyl-1H-benzo[d]imidazol-1-yl)azetidine-1-carboxylate tert-butyl 3-(2-methyl-6-(4,4,5,5-tetramethyl-1,3,2-dioxaborolan-2-yl)-1H-benzo[d]imidazol-1-yl)azetidine-1-carboxylate (S)-ethyl 2-(2-bromo-7-(4-chlorophenyl)-5-methylbenzo[d]thiazol-6-yl)-2-tert-butoxyacetate (S)-tert-butyl 3-(6-(6-(1-tert-butoxy-2-ethoxy-2-oxoethyl)-7-(4-chlorophenyl)-5-methylbenzo[d]thiazol-2-yl)-2-methyl-1H-benzo[d]imidazol-1-yl)azetidine-1-carboxylate

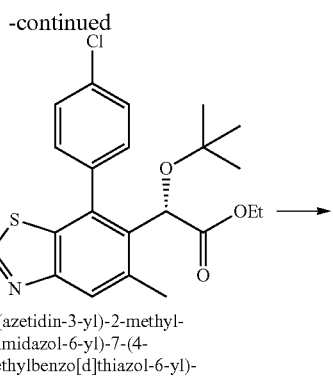

(S)-ethyl 2-(2-(1-(azetidin-3-yl)-2-methyl-
1H-benzo[d]imidazol-6-yl)-7-(4-
chlorophenyl)-5-methylbenzo[d]thiazol-6-yl)-
2-tert-butoxyacetate

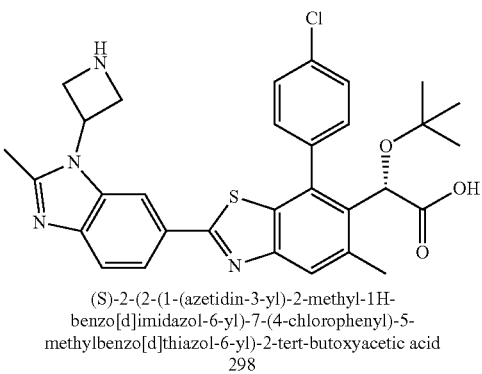

(S)-2-(2-(1-(azetidin-3-yl)-2-methyl-1H-
benzo[d]imidazol-6-yl)-7-(4-chlorophenyl)-5-
methylbenzo[d]thiazol-6-yl)-2-tert-butoxyacetic acid
298

Preparation of tert-butyl 3-(6-bromo-2-methyl-1H-benzo[d]imidazol-1-yl)azetidine-1-carboxylate: A flask was charged with 4-bromo-2-fluoro-1-nitrobenzene (529 mg, 2.41 mmol), Cs$_2$CO$_3$ (2.45 g, 7.52 mmol), and diluted with DMF (6 mL). To this was added tert-butyl 3-aminoazetidine-1-carboxylate (0.75 mL, 4.78 mmol) at room temperature and the reaction mixture was allowed to stir for 16 hours. The mixture was diluted with EtOAc and H$_2$O and the layers were separated. The aqueous layer was extracted with EtOAc and the combined organic extracts were dried over Na$_2$SO$_4$, filtered through a small pad of silica gel eluting with 30% EtOAc/Hex, and concentrated in vacuo to afford a crude residue. The flask containing the crude residue was charged 5 wt % Pt/C (140 mg) and then diluted with 2:1 EtOH/EtOAc (30 mL). The flask was evacuated then backfilled with H$_2$ (3 cycles) and stirred under a hydrogen atmosphere for 20 minutes, at which time, the flask was purged with N$_2$, filtered through a pad of Celite, and concentrated in vacuo to provide a crude residue. The crude residue was taken up in AcOH (10 mL) and MeC(OEt)$_3$ (1 mL) was added at room temperature, stirred for 15 minutes, and then the solution was concentrated in vacuo. The crude residue was purified by silica gel column chromatography (30-70% EtOAc/Hex gradient) to afford the desired product. LCMS-ESI$^+$: calc'd C$_{16}$H$_{21}$BrN$_3$O$_2$: 366.1 (M+H$^+$); Found: 366.1 (M+H$^+$).

Preparation of tert-butyl 3-(2-methyl-6-(4,4,5,5-tetramethyl-1,3,2-dioxaborolan-2-yl)-1H-benzo[d]imidazol-1-yl)azetidine-1-carboxylate: A microwave vial was charged with tert-butyl 3-(6-bromo-2-methyl-1H-benzo[d]imidazol-1-yl)azetidine-1-carboxylate (330 mg, 0.90 mmol), Bis(pinacolato)diboron (275 mg, 1.1 mmol), PdCl$_2$(dppf).CH$_2$Cl$_2$ (74 mg, 0.10 mmol), then KOAc (265 mg, 2.70 mmol). The vial was flushed with argon, diluted with dioxane (9 mL), sealed, and then heated to 100° C. for 90 minutes. The reaction mixture was allowed to cool to room temperature, diluted with EtOAc, filtered through a pad of Celite, and concentrated in vacuo. The crude residue was purified by silica gel column chromatography (50-100% EtOAc/Hex gradient) to afford the desired product. LCMS-ESI$^+$: calc'd C$_{22}$H$_{33}$BN$_3$O$_4$: 414.3 (M+H$^+$); Found: 414.2 (M+H$^+$).

Preparation of (S)-tert-butyl 3-(6-(6-(1-tert-butoxy-2-ethoxy-2-oxoethyl)-7-(4-chlorophenyl)-5-methylbenzo[d]thiazol-2-yl)-2-methyl-1H-benzo[d]imidazol-1-yl)azetidine-1-carboxylate: A microwave vial was charged with (S)-ethyl 2-(2-bromo-7-(4-chlorophenyl)-5-methylbenzo[d]thiazol-6-yl)-2-tert-butoxyacetate (54 mg, 0.11 mmol), tert-butyl 3-(2-methyl-6-(4,4,5,5-tetramethyl-1,3,2-dioxaborolan-2-yl)-1H-benzo[d]imidazol-1-yl)azetidine-1-carboxylate (181 mg, 0.44 mmol), then Pd(PPh$_3$)$_4$ (23 mg, 0.02 mmol). The vial was flushed with argon, diluted with dioxane (2 mL) and to this was added 2M aqueous K$_2$CO$_3$ (0.2 mL, 0.4 mmol). The vial was sealed, heated to 100° C. for 16 hours, and then allowed to cool to room temperature. The mixture was diluted with EtOAc, dried over Na$_2$SO$_4$, filtered, and concentrated in vacuo. The crude residue was purified by silica gel column chromatography (0-10% MeOH/CH$_2$Cl$_2$ gradient) to afford the desired product. LCMS-ESI$^+$: calc'd for C$_{38}$H$_{44}$ClN$_4$O$_5$S C$_{31}$H$_{33}$ClN$_3$O$_4$S: 703.3 (M+H$^+$); Found: 703.5 (M+H$^+$).

Preparation of (S)-ethyl 2-(2-(1-(azetidin-3-yl)-2-methyl-1H-benzo[d]imidazol-6-yl)-7-(4-chlorophenyl)-5-methylbenzo[d]thiazol-6-yl)-2-tert-butoxyacetate: A solution of (S)-tert-butyl 3-(6-(6-(1-tert-butoxy-2-ethoxy-2-oxoethyl)-7-(4-chlorophenyl)-5-methylbenzo[d]thiazol-2-yl)-2-methyl-1H-benzo[d]imidazol-1-yl)azetidine-1-carboxylate (76 mg, 0.11 mmol) in 1.25 M HCl in i-PrOH (20 mL) was stirred at room temperature for 16 hours then at 45° C. for 3 hours. The solution was cooled to room temperature and concentrated in vacuo to provide the desired product. LCMS-ESI$^+$: calc'd for C$_{33}$H$_{36}$ClN$_4$O$_3$S: 603.2 (M+H$^+$); Found: 603.4 (M+H$^+$).

Preparation of (S)-2-(2-(1-(azetidin-3-yl)-2-methyl-1H-benzo[d]imidazol-6-yl)-7-(4-chlorophenyl)-5-methylbenzo[d]thiazol-6-yl)-2-tert-butoxyacetic acid: To a solution of (S)-ethyl 2-(2-(1-(azetidin-3-yl)-2-methyl-1H-benzo[d]imidazol-6-yl)-7-(4-chlorophenyl)-5-methylbenzo[d]thiazol-6-yl)-2-tert-butoxyacetate (69 mg, 0.11 mmol) in 3:1 MeOH/THF (1.3 mL) was added 2M aqueous NaOH (0.3 mL, 0.6 mmol) and stirred at 90° C. for 3 hours. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 8.72 (s, 1H), 8.15 (d, J=8.6 Hz, 1H), 7.94-7.82 (m, 2H), 7.76-7.66 (m, 1H), 7.65-7.52 (m, 3H), 5.97 (p, J=8.7 Hz, 1H), 5.27 (s, 1H), 5.14-5.01 (m, 2H), 4.74-4.62 (m, 2H), 2.87

(s, 3H), 2.64 (s, 3H), 0.98 (s, 9H); LCMS-ESI+: calc'd C$_{31}$H$_{32}$ClN$_4$O$_3$S: 575.2 (M+1-0); Found: 575.3 (M+H+).

Example 151

Preparation of (S)-2-tert-butoxy-2-(7-(4-chlorophenyl)-5-methyl-2-(2-methyl-1-((R)-pyrrolidin-3-yl)-1H-benzo[d]imidazol-6-yl)benzo[d]thiazol-6-yl)acetic acid (299)

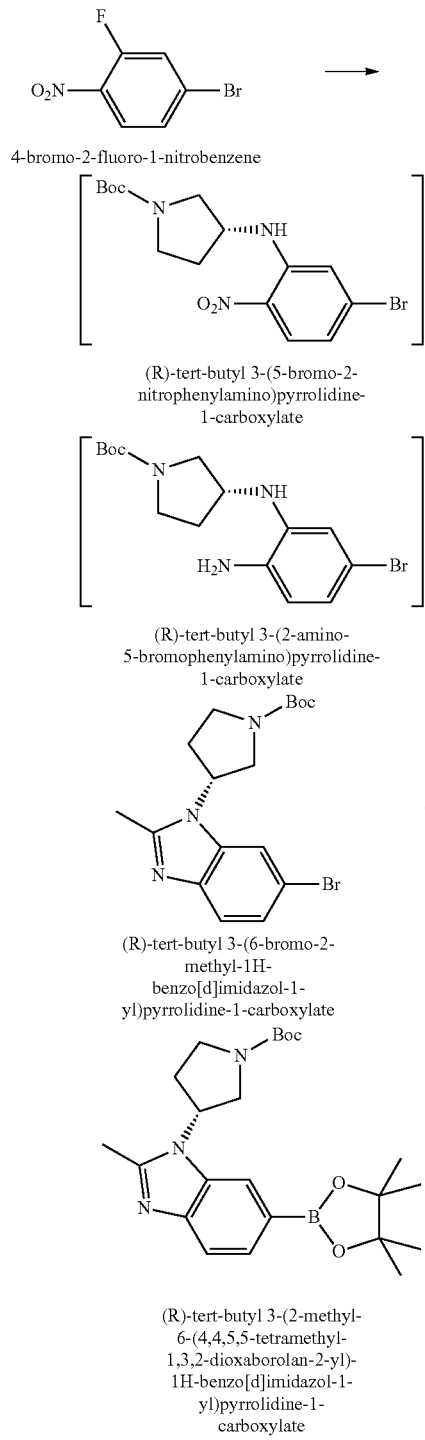

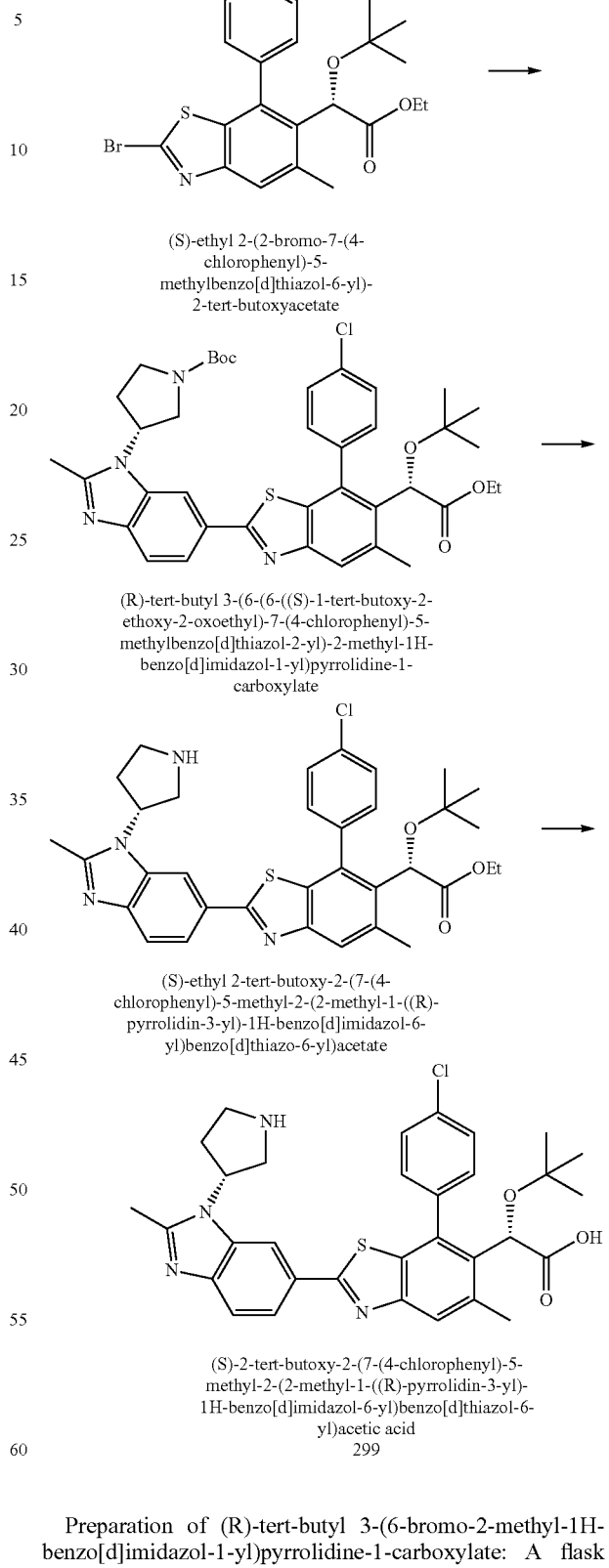

Preparation of (R)-tert-butyl 3-(6-bromo-2-methyl-1H-benzo[d]imidazol-1-yl)pyrrolidine-1-carboxylate: A flask was charged with 4-bromo-2-fluoro-1-nitrobenzene (531 mg, 2.41 mmol) and Cs$_2$CO$_3$ (2.37 g, 7.27 mmol) and diluted with DMF (6 mL). To this was added (R)-tert-butyl 3-aminopyrrolidine-1-carboxylate (0.85 mL, 5.01 mmol) at room temperature and the reaction mixture was allowed to stir for 16 hours. The mixture was diluted with EtOAc and H₂O and the layers were separated. The aqueous layer was extracted with EtOAc and the combined organic extracts were dried over Na₂SO₄, filtered through a small pad of silica gel eluting with 30% EtOAc/Hex, and concentrated in vacuo to afford a crude residue. The flask containing the crude residue was charged with 5 wt % Pt/C (200 mg) and then diluted with 2:1 EtOH/EtOAc (30 mL). The flask was evacuated then backfilled with H₂ (3 cycles) and stirred under a hydrogen atmosphere for 20 minutes, at which time, the flask was purged with N₂, filtered through a pad of Celite, and concentrated in vacuo to provide a crude residue. The crude residue was taken up in AcOH (10 mL) and MeC(OEt)₃ (1 mL) was added at room temperature, stirred for 15 minutes, and concentrated in vacuo. The crude residue was purified by silica gel column chromatography (30-70% EtOAc/Hex gradient) to afford the desired product. LCMS-ESI⁺: calc'd C₁₇H₂₃BrN₃O₂: 380.1 (M+H⁺); Found: 380.1 (M+H⁺).

Preparation of (R)-tert-butyl 3-(2-methyl-6-(4,4,5,5-tetramethyl-1,3,2-dioxaborolan-2-yl)-1H-benzo[d]imidazol-1-yl)pyrrolidine-1-carboxylate: A microwave vial was charged with (R)-tert-butyl 3-(6-bromo-2-methyl-1H-benzo[d]imidazol-1-yl)pyrrolidine-1-carboxylate (337 mg, 0.89 mmol), Bis(pinacolato)diboron (274 mg, 1.1 mmol), PdCl₂(dppf).CH₂Cl₂ (75 mg, 0.10 mmol), then KOAc (271 mg, 2.76 mmol). The vial was flushed with argon, diluted with dioxane (9 mL), sealed, and then heated to 100° C. for 90 minutes. The reaction mixture was allowed to cool to room temperature, diluted with EtOAc, filtered through a pad of Celite, and concentrated in vacuo. The crude residue was purified by silica gel column chromatography (50-100% EtOAc/Hex gradient) to afford the desired product. LCMS-ESI⁺: calc'd C₂₃H₃₅BN₃O₄: 428.3 (M+H⁺); Found: 428.2 (M+H⁺).

Preparation of (R)-tert-butyl 3-(6-(6-((S)-1-tert-butoxy-2-ethoxy-2-oxoethyl)-7-(4-chlorophenyl)-5-methylbenzo[d]thiazol-2-yl)-2-methyl-1H-benzo[d]imidazol-1-yl)pyrrolidine-1-carboxylate: A microwave vial was charged with (S)-ethyl 2-(2-bromo-7-(4-chlorophenyl)-5-methylbenzo[d]thiazol-6-yl)-2-tert-butoxyacetate (53 mg, 0.11 mmol), (R)-tert-butyl 3-(2-methyl-6-(4,4,5,5-tetramethyl-1,3,2-dioxaborolan-2-yl)-1H-benzo[d]imidazol-1-yl)pyrrolidine-1-carboxylate (92 mg, 0.21 mmol), then Pd(PPh₃)₄ (23 mg, 0.02 mmol). The vial was flushed with argon, diluted with dioxane (2 mL) and to this was added 2M aqueous K₂CO₃ (0.2 mL, 0.4 mmol). The vial was sealed then heated to 100° C. for 16 hours and then allowed to cool to room temperature. The mixture was diluted with EtOAc, dried over Na₂SO₄, filtered, and concentrated. The crude residue was purified by silica gel column chromatography (0-10% MeOH/CH₂Cl₂ gradient) to afford the desired product. LCMS-ESI⁺: calc'd for C₃₉H₄₆ClN₄O₅S: 717.3 (M+H⁺); Found: 717.1 (M+H⁺).

Preparation of (S)-ethyl 2-tert-butoxy-2-(7-(4-chlorophenyl)-5-methyl-2-(2-methyl-1-((R)-pyrrolidin-3-yl)-1H-benzo[d]imidazol-6-yl)benzo[d]thiazol-6-yl)acetate: A solution of (R)-tert-butyl 3-(6-(6-((S)-1-tert-butoxy-2-ethoxy-2-oxoethyl)-7-(4-chlorophenyl)-5-methylbenzo[d]thiazol-2-yl)-2-methyl-1H-benzo[d]imidazol-1-yl)pyrrolidine-1-carboxylate (77 mg, 0.11 mmol) in 1.25 M HCl in i-PrOH (12 mL) was stirred at room temperature for 16 hours. The solution was then concentrated in vacuo to provide the desired product. LCMS-ESI⁺: calc'd for C₃₄H₃₈ClN₄O₃S: 617.2 (M+H⁺); Found: 617.2 (M+H⁺).

Preparation of (S)-2-tert-butoxy-2-(7-(4-chlorophenyl)-5-methyl-2-(2-methyl-1-((R)-pyrrolidin-3-yl)-1H-benzo[d]imidazol-6-yl)benzo[d]thiazol-6-yl)acetic acid: To a solution of (S)-ethyl 2-(2-(1-(azetidin-3-yl)-2-methyl-1H-benzo[d]imidazol-6-yl)-7-(4-chlorophenyl)-5-methylbenzo[d]thiazol-6-yl)-2-tert-butoxyacetate (70 mg, 0.11 mmol) in 3:1 MeOH/THF (1.3 mL) was added 2M aqueous NaOH (0.6 mL, 1.2 mmol) and stirred at 90° C. for 3 hours. The reaction mixture was cooled to room temperature, neutralized with AcOH, filtered, and then purified by reverse phase column chromatography (5-100% ACN/H₂O+0.1% TFA). Fractions containing the product were pooled and lyophilized to provide the TFA salt of the product. ¹H NMR (400 MHz, CD₃OD) δ 8.52 (s, 1H), 8.19 (dd, J=8.6, 1.3 Hz, 1H), 7.98-7.79 (br m, 2H), 7.75-7.65 (br m, 1H), 7.65-7.52 (m, 3H), 5.69 (p, J=9.4 Hz, 1H), 5.26 (s, 1H), 4.07-3.83 (m, 3H), 3.58 (td, J=11.4, 7.0 Hz, 1H), 2.96 (s, 3H), 2.95-2.68 (m, 2H), 2.63 (s, 3H), 0.97 (s, 9H); LCMS-ESI⁺: calc'd C₃₂H₃₄ClN₄O₃S: 589.2 (M+H⁺); Found: 589.4 (M+H⁺).

Example 152

Preparation of (S)-2-tert-butoxy-2-(7-(4-chlorophenyl)-2-(1-((R)-1-isopropylpyrrolidin-3-yl)-2-methyl-1H-benzo[d]imidazol-6-yl)-5-methylbenzo[d]thiazol-6-yl)acetic acid (300)

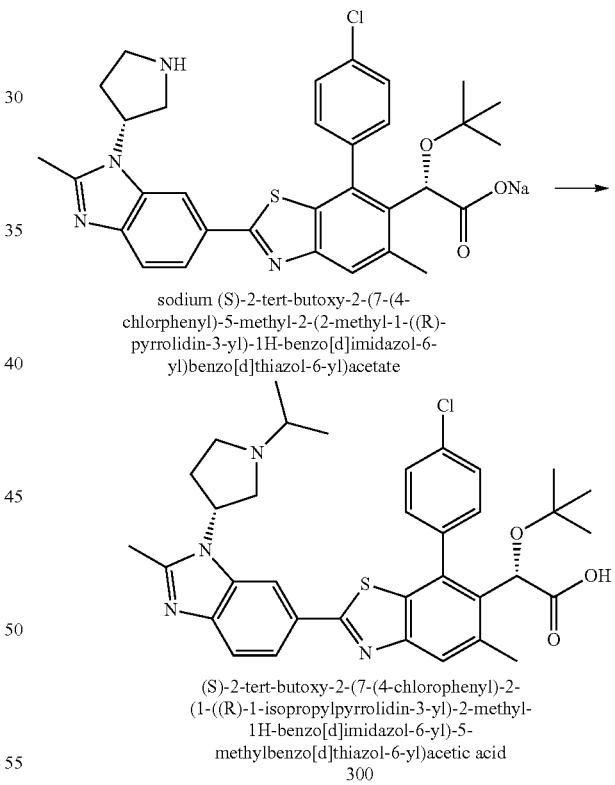

sodium (S)-2-tert-butoxy-2-(7-(4-chlorphenyl)-5-methyl-2-(2-methyl-1-((R)-pyrrolidin-3-yl)-1H-benzo[d]imidazol-6-yl)benzo[d]thiazol-6-yl)acetate (S)-2-tert-butoxy-2-(7-(4-chlorophenyl)-2-(1-((R)-1-isopropylpyrrolidin-3-yl)-2-methyl-1H-benzo[d]imidazol-6-yl)-5-methylbenzo[d]thiazol-6-yl)acetic acid 300

Preparation of (S)-2-tert-butoxy-2-(7-(4-chlorophenyl)-2-(1-((R)-1-isopropylpyrrolidin-3-yl)-2-methyl-1H-benzo[d]imidazol-6-yl)-5-methylbenzo[d]thiazol-6-yl)acetic acid: The sodium salt of (S)-2-tert-butoxy-2-(7-(4-chlorophenyl)-5-methyl-2-(2-methyl-1-((R)-pyrrolidin-3-yl)-1H-benzo[d]imidazol-6-yl)benzo[d]thiazol-6-yl)acetic acid was prepared by dissolving the TFA salt in 1M aqueous NaOH and then filtering the solution through a small plug of reverse phase silica gel initially eluting with H₂O, then eluting with MeOH to obtain the desired sodium salt. A flask was then charged with sodium (S)-2-tert-butoxy-2-(7-(4-chlorophenyl)-5-methyl-2-(2-methyl-1-((R)-pyrrolidin-3-yl)-1H-benzo[d]imidazol-6-yl)benzo[d]thiazol-6-yl)acetate (13 mg, 0.02 mmol) and then diluted with DMF (1 mL). Sodium triacetoxyborohydride (32 mg, 0.15 mmol) and AcOH (20 μL, 0.27 mmol) were added sequentially and the reaction mixture was warmed to 60° C., at which time acetone (20 μL, 0.35 mmol) was added and the resulting mixture was stirred for an additional 30 minutes at that temperature. The mixture was then cooled to room temperature, filtered, and then purified by reverse phase column chromatography (5-100% ACN/H₂O+ 0.1% TFA). Fractions containing the product were pooled and lyophilized to provide the TFA salt of the product. $^1$H NMR (400 MHz, CD$_3$OD) δ 8.51 (s, 1H), 8.10 (dd, J=8.6, 1.3 Hz, 1H), 7.90 (s, 1H), 7.85 (d, J=8.6 Hz, 1H), 7.76-7.67 (m, 1H), 7.67-7.56 (m, 3H), 5.66 (br s, 1H), 5.27 (s, 1H), 4.02 (br s, 3H), 3.70 (br s, 1H), 3.02-2.85 (m, 1H), 2.89 (s, 3H), 2.79 (br s, 1H), 2.64 (s, 3H), 1.50 (d, J=6.4 Hz, 6H), 0.98 (s, 9H); LCMS-ESI$^+$: calc'd C$_{35}$H$_{40}$ClN$_4$O$_3$S: 631.3 (M+H$^+$); Found: 631.3 (M+H$^+$).

Example 153

Preparation of (S)-2-tert-butoxy-2-(7-(4-chlorophenyl)-5-methyl-2-(2-methyl-1-((S)-pyrrolidin-3-yl)-1H-benzo[d]imidazol-6-yl)benzo[d]thiazol-6-yl)acetic acid (301)

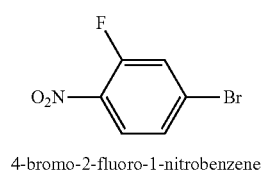

4-bromo-2-fluoro-1-nitrobenzene

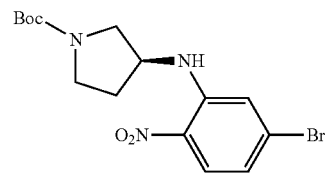

(S)-tert-butyl 3-(5-bromo-2-nitrophenylamino)pyrrolidine-1-carboxylate

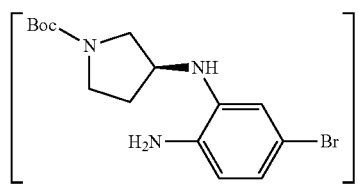

(S)-tert-butyl 3-(2-amino-5-bromophenylamino)pyrrolidine-1-carboxylate

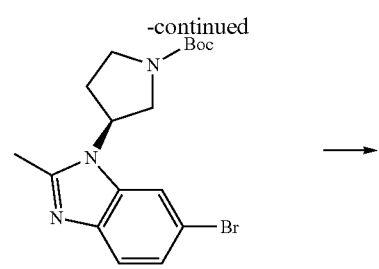

(S)-tert-butyl 3-(6-bromo-2-methyl-1H-benzo[d]imidazol-1-yl)pyrrolidine-1-carboxylate

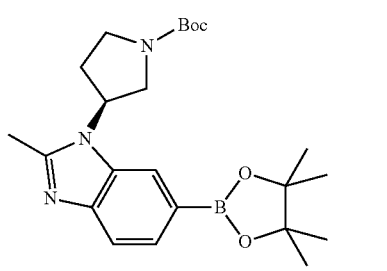

(S)-tert-butyl 3-(2-methyl-6-(4,4,5,5-tetramethyl-1,3,2-dioxaborolan-2-yl)-1H-benzo[d]imidazol-1-yl)pyrrolidine-1-carboxylate

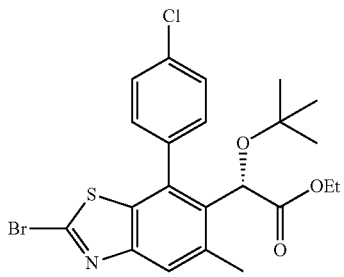

(S)-ethyl 2-(2-bromo-7-(4-chlorophenyl)-5-methylbenzo[d]thiazol-6-yl)-2-tert-butoxyacetate

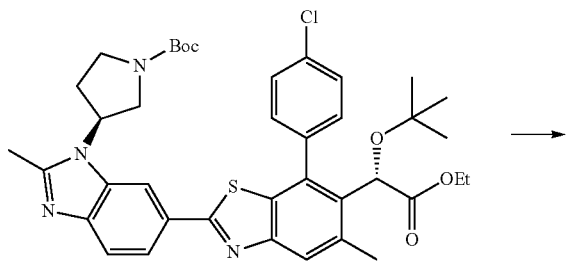

(S)-tert-butyl 3-(6-(6-((S)-1-tert-butoxy-2-ethoxy-2-oxoethyl)-7-(4-chlorophenyl)-5-methylbenzo[d]thiazol-2-yl)-2-methyl-1H-benzo[d]imidazol-1-yl)pyrrolidine-1-carboxylate -continued

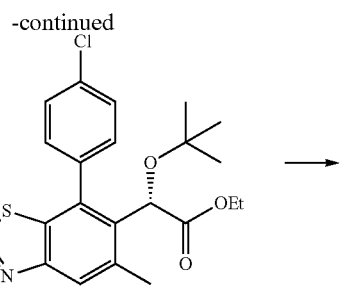

(S)-ethyl 2-tert-butoxy-2-(7-(4-
chlorophenyl)-5-methyl-2-(2-methyl-1-((S)-
pyrrolidin-3-yl)-1H-benzo[d]imidazol-6-
yl)benzo[d]thiazo-6-yl)acetate

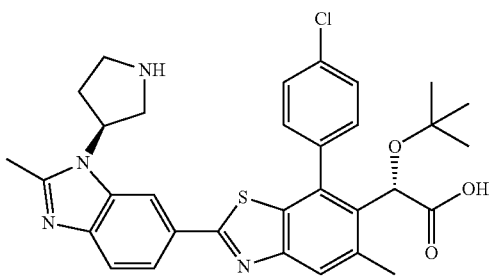

(S)-2-tert-butoxy-2-(7-(4-chlorophenyl)-5-
methyl-2-(2-methyl-1-((S)-pyrrolidin-3-yl)-
1H-benzo[d]imidazol-6-yl)benzo[d]thiazo-6-
yl)acetic acid
301

Preparation of (S)-tert-butyl 3-(6-bromo-2-methyl-1H-benzo[d]imidazol-1-yl)pyrrolidine-1-carboxylate: A flask was charged with 4-bromo-2-fluoro-1-nitrobenzene (531 mg, 2.41 mmol), $Cs_2CO_3$ (2.43 g, 7.46 mmol) and diluted with DMF (6 mL). The reaction mixture was then treated with (S)-tert-butyl 3-aminopyrrolidine-1-carboxylate (0.9 mL, 5.16 mmol) at room temperature and allowed to stir for 16 hours. The mixture was diluted with EtOAc and $H_2O$ and the layers were separated. The aqueous layer was extracted with EtOAc and the combined organic extracts were dried over $Na_2SO_4$, filtered through a small pad of silica gel eluting with 30% EtOAc/Hex, and concentrated in vacuo to afford a crude residue. The flask containing the crude residue was charged with 5 wt % Pt/C (211 mg) and then diluted with 2:1 EtOH/EtOAc (16 mL). The flask was evacuated then backfilled with $H_2$ (3 cycles) and stirred under a hydrogen atmosphere for 20 minutes, at which time, the flask was purged with $N_2$, filtered through a pad of Celite, and concentrated in vacuo to provide a crude residue that was then taken up in AcOH (5 mL). To this was added $MeC(OEt)_3$ (0.5 mL) at room temperature and stirred for 15 minutes, at which time, the solution was concentrated in vacuo. The crude residue was purified by silica gel column chromatography (0-50% $THF/CH_2Cl_2$ gradient) to afford the desired product. LCMS-ESI$^+$: calc'd $C_{17}H_{23}BrN_3O_2$: 380.1 (M+H$^1$); Found: 380.1 (M+H$^+$).

Preparation of (S)-tert-butyl 3-(2-methyl-6-(4,4,5,5-tetramethyl-1,3,2-dioxaborolan-2-yl)-1H-benzo[d]imidazol-1-yl)pyrrolidine-1-carboxylate: A microwave vial was charged with (S)-tert-butyl 3-(6-bromo-2-methyl-1H-benzo[d]imidazol-1-yl)pyrrolidine-1-carboxylate (624 mg, 1.64 mmol), Bis(pinacolato)diboron (500 mg, 2.00 mmol), $PdCl_2$(dppf).$CH_2Cl_2$ (134 mg, 0.16 mmol), then KOAc (483 mg, 4.92 mmol). The vial was flushed with argon, diluted with dioxane (9 mL), sealed, and then heated to 100° C. for 90 minutes. The reaction mixture was allowed to cool to room temperature, diluted with EtOAc, filtered through a pad of Celite, and concentrated in vacuo. The crude residue was purified by silica gel column chromatography (0-50% $THF/CH_2Cl_2$ gradient) to afford the desired product. LCMS-ESI$^+$: calc'd $C_{23}H_{35}BN_3O_4$: 428.3 (M+H$^+$); Found: 428.2 (M+H$^+$).

Preparation of (S)-tert-butyl 3-(6-(6-((S)-1-tert-butoxy-2-ethoxy-2-oxoethyl)-7-(4-chlorophenyl)-5-methylbenzo[d]thiazol-2-yl)-2-methyl-1H-benzo[d]imidazol-1-yl)pyrrolidine-1-carboxylate: A microwave vial was charged with (S)-ethyl 2-(2-bromo-7-(4-chlorophenyl)-5-methylbenzo[d]thiazol-6-yl)-2-tert-butoxyacetate (50 mg, 0.10 mmol), (S)-tert-butyl 3-(2-methyl-6-(4,4,5,5-tetramethyl-1,3,2-dioxaborolan-2-yl)-1H-benzo[d]imidazol-1-yl)pyrrolidine-1-carboxylate (181 mg, 0.42 mmol), then $Pd(PPh_3)_4$ (23 mg, 0.02 mmol). The vial was flushed with argon, diluted with dioxane (2 mL) and to this was added 2M aqueous $K_2CO_3$ (0.2 mL, 0.4 mmol). The vial was sealed then heated to 100° C. for 16 hours and then allowed to cool to room temperature. The mixture was diluted with EtOAc, dried over $Na_2SO_4$, filtered, and concentrated. The crude residue was purified by silica gel column chromatography (0-100% $THF/CH_2Cl_2$ gradient) to afford the desired product. LCMS-ESI$^+$: calc'd for $C_{39}H_{46}ClN_4O_5S$: 717.3 (M+H$^+$); Found: 717.1 (M+H$^+$).

Preparation of (S)-ethyl 2-tert-butoxy-2-(7-(4-chlorophenyl)-5-methyl-2-(2-methyl-1-((S)-pyrrolidin-3-yl)-1H-benzo[d]imidazol-6-yl)benzo[d]thiazol-6-yl)acetate: A solution of (S)-tert-butyl 3-(6-(6-((S)-1-tert-butoxy-2-ethoxy-2-oxoethyl)-7-(4-chlorophenyl)-5-methylbenzo[d]thiazol-2-yl)-2-methyl-1H-benzo[d]imidazol-1-yl)pyrrolidine-1-carboxylate (70 mg, 0.10 mmol) in 1.25 M HCl in i-PrOH (20 mL) was stirred at 35° C. for 4 hours. The solution was then concentrated in vacuo to provide the desired product. LCMS-ESI$^+$: calc'd for $C_{34}H_{38}ClN_4O_3S$: 617.2 (M+H$^+$); Found: 617.2 (M+H$^+$).

Preparation of (S)-2-tert-butoxy-2-(7-(4-chlorophenyl)-5-methyl-2-(2-methyl-1-((S)-pyrrolidin-3-yl)-1H-benzo[d]imidazol-6-yl)benzo[d]thiazol-6-yl)acetic acid: To a solution of (S)-ethyl 2-tert-butoxy-2-(7-(4-chlorophenyl)-5-methyl-2-(2-methyl-1-((S)-pyrrolidin-3-yl)-1H-benzo[d]imidazol-6-yl)benzo[d]thiazol-6-yl)acetate (66 mg, 0.10 mmol) in 10:1 MeOH/THF (2.2 mL) was added 2M aqueous NaOH (0.9 mL, 1.8 mmol) and stirred at 100° C. for 5 hours. The reaction mixture was cooled to room temperature, neutralized with AcOH, filtered, and then purified by reverse phase column chromatography (5-100% ACN/$H_2O$+0.1% TFA). Fractions containing the product were pooled and lyophilized to provide the TFA salt of the product. $^1$H NMR (400 MHz, CD$_3$OD) δ 8.49 (s, 1H), 8.15 (dd, J=8.6, 1.3 Hz, 1H), 7.90 (s, 1H), 7.88 (d, J=8.6 Hz, 1H), 7.75-7.67 (m, 1H), 7.67-7.55 (m, 3H), 5.74-5.57 (m, 1H), 5.27 (s, 1H), 4.05-3.82 (m, 3H), 3.58 (td, J=11.4, 6.9 Hz, 1H), 2.93 (s, 3H), 2.90-2.79 (m, 1H), 2.79-2.68 (m, 1H), 2.64 (s, 3H), 0.99 (s, 9H). LCMS-ESI$^+$: calc'd $C_{32}H_{34}ClN_4O_3S$: 589.2 (M+H$^+$); Found: 589.4 (M+H$^+$).

Example 154

Preparation of (S)-2-tert-butoxy-2-(7-(4-chlorophenyl)-2-(2,3-dimethyl-3H-imidazo[4,5-b]pyridin-6-yl)-5-methylbenzo[d]thiazol-6-yl)acetic acid (302)

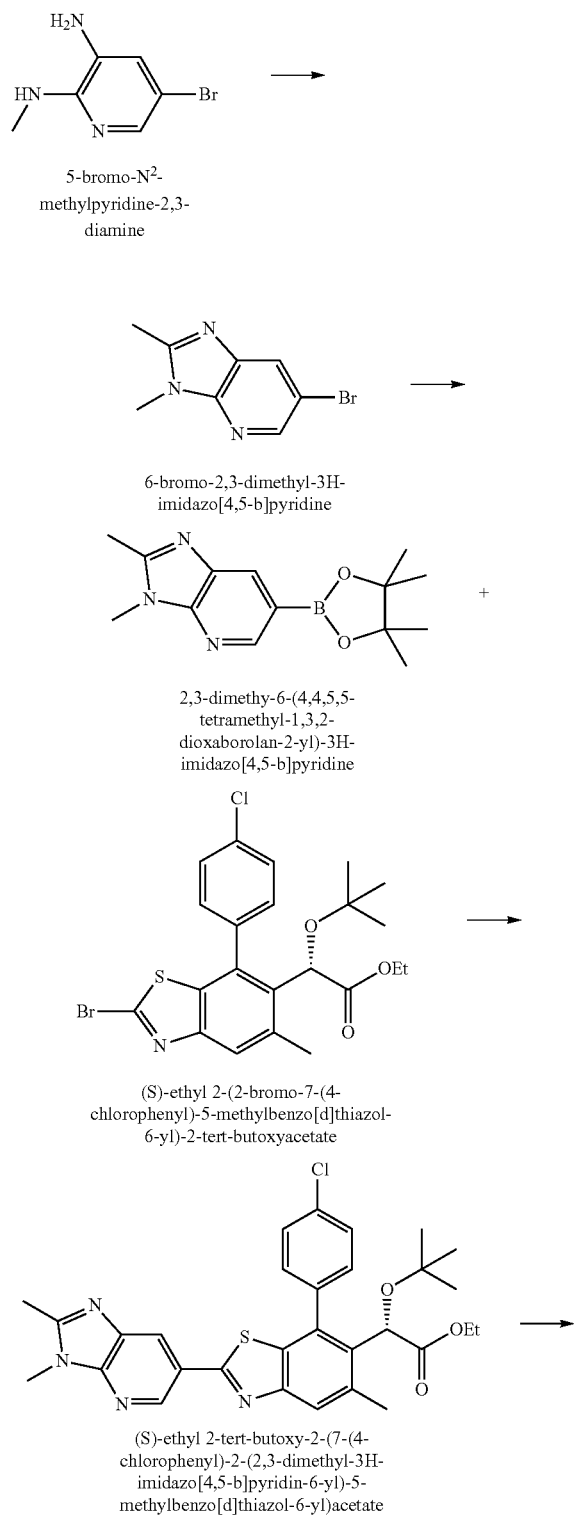

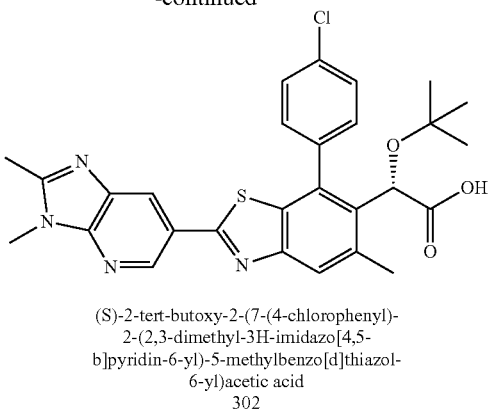

(S)-2-tert-butoxy-2-(7-(4-chlorophenyl)-2-(2,3-dimethyl-3H-imidazo[4,5-b]pyridin-6-yl)-5-methylbenzo[d]thiazol-6-yl)acetic acid
302

Preparation of 6-bromo-2,3-dimethyl-3H-imidazo[4,5-b]pyridine: To a suspension of 5-bromo-$N^2$-methylpyridine-2,3-diamine (510 mg, 2.51 mmol) in AcOH (20 mL) was added MeC(OEt)$_3$ (1 mL) and the solution was warmed to 80° C. for 2 hours. The reaction mixture was allowed to cool to room temperature and was concentrated in vacuo. The crude residue was purified by silica gel column chromatography (0-25% THF/CH$_2$Cl$_2$ gradient) to afford the desired product. $^1$H NMR (400 MHz, CDCl$_3$) δ 8.36 (d, J=1.8 Hz, 1H), 8.06 (d, J=1.9 Hz, 1H), 3.80 (s, 3H), 2.65 (s, 3H).

Preparation of 2,3-dimethyl-6-(4,4,5,5-tetramethyl-1,3,2-dioxaborolan-2-yl)-3H-imidazo[4,5-b]pyridine: A microwave vial was charged with 6-bromo-2,3-dimethyl-3H-imidazo[4,5-b]pyridine (300 mg, 1.32 mmol), Bis(pinacolato)diboron (387 mg, 1.52 mmol), PdCl$_2$(dppf).CH$_2$Cl$_2$ (117 mg, 0.14 mmol), then KOAc (408 mg, 4.16 mmol). The vial was flushed with argon, diluted with dioxane (6 mL), sealed, and then heated to 100° C. for 90 minutes. The reaction mixture was allowed to cool to room temperature, diluted with EtOAc, filtered through a pad of Celite, and concentrated in vacuo. The crude residue was purified by silica gel column chromatography (0-50% THF/CH$_2$Cl$_2$ gradient) to afford the desired product. LCMS-ESI$^+$: calc'd C$_{14}$H$_{21}$BN$_3$O$_2$ 274.2 (M+H$^+$); Found: 274.2 (M+H$^+$).

Preparation of (S)-ethyl 2-tert-butoxy-2-(7-(4-chlorophenyl)-2-(2,3-dimethyl-3H-imidazo[4,5-b]pyridin-6-yl)-5-methylbenzo[d]thiazol-6-yl)acetate: A microwave vial was charged with (S)-ethyl 2-(2-bromo-7-(4-chlorophenyl)-5-methylbenzo[d]thiazol-6-yl)-2-tert-butoxyacetate (50 mg, 0.10 mmol), 2,3-dimethyl-6-(4,4,5,5-tetramethyl-1,3,2-dioxaborolan-2-yl)-3H-imidazo[4,5-b]pyridine (102 mg, 0.37 mmol), then Pd(PPh$_3$)$_4$ (23 mg, 0.02 mmol). The vial was flushed with argon, diluted with dioxane (2 mL) and to this was added 2M aqueous K$_2$CO$_3$ (0.2 mL, 0.4 mmol). The vial was sealed then heated to 100° C. for 16 hours and then allowed to cool to room temperature. The mixture was diluted with EtOAc, dried over Na$_2$SO$_4$, filtered, and concentrated. The crude residue was purified by silica gel column chromatography (0-100% THF/CH$_2$Cl$_2$ gradient) to afford the desired product. LCMS-ESI$^+$: calc'd for C$_{30}$H$_{32}$ClN$_4$O$_3$S: 563.2 (M+H$^+$); Found: 563.2 (M+H$^+$).

Preparation of (S)-2-tert-butoxy-2-(7-(4-chlorophenyl)-2-(2,3-dimethyl-3H-imidazo[4,5-b]pyridin-6-yl)-5-methylbenzo[d]thiazol-6-yl)acetic acid: To a solution of (S)-ethyl 2-tert-butoxy-2-(7-(4-chlorophenyl)-2-(2,3-dimethyl-3H-imidazo[4,5-b]pyridin-6-yl)-5-methylbenzo[d]thiazol-6-yl) acetate (57 mg, 0.10 mmol) in 5:1 MeOH/THF (1.2 mL) was added 2M aqueous NaOH (0.3 mL, 0.6 mmol) and stirred at 50° C. for 16 hours. The reaction mixture was cooled to room

Example 155

Preparation of (S)-2-tert-butoxy-2-(7-(4-chlorophenyl)-5-methyl-2-(1-methyl-2-oxo-2,3-dihydro-1H-benzo[d]imidazol-5-yl)benzo[d]thiazol-6-yl)acetic acid (303)

temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 9.18 (s, 1H), 8.67 (s, 1H), 7.88 (s, 1H), 7.70 (d, J=8.1 Hz, 1H), 7.60 (br s, 3H), 5.27 (s, 1H), 3.99 (s, 3H), 2.86 (s, 3H), 2.62 (s, 3H), 0.98 (s, 9H). LCMS-ESI$^+$: calc'd C$_{28}$H$_{28}$ClN$_4$O$_3$S: 535.2 (M+H$^+$); Found: 535.2 (M+

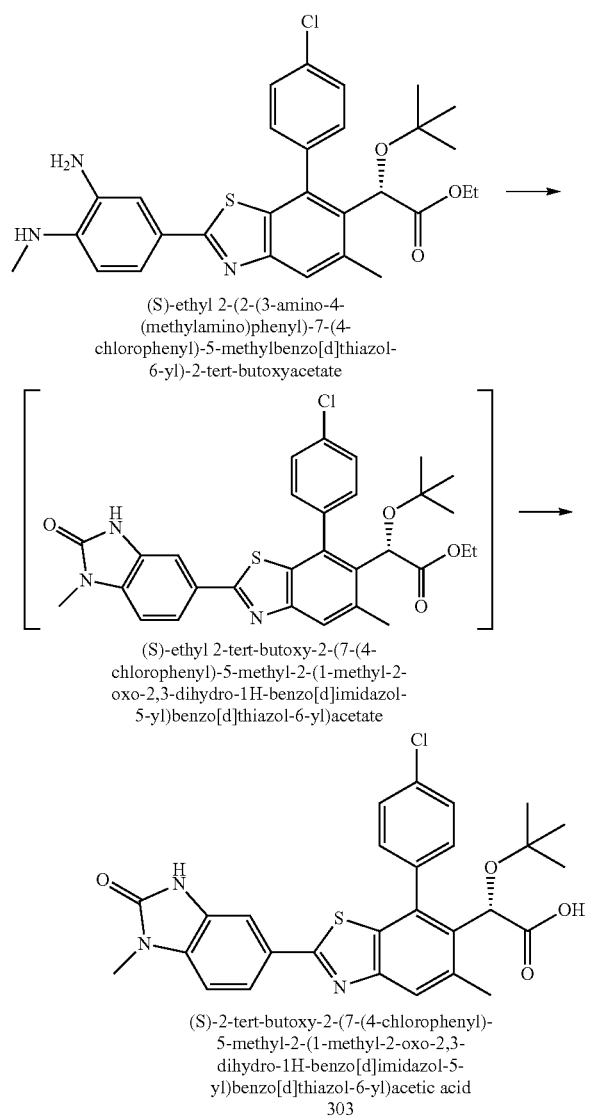

Preparation of (S)-2-tert-butoxy-2-(7-(4-chlorophenyl)-5-methyl-2-(1-methyl-2-oxo-2,3-dihydro-1H-benzo[d]imidazol-5-yl)benzo[d]thiazol-6-yl)acetic acid: To a solution of (S)-ethyl 2-(2-(3-amino-4-(methylamino)phenyl)-7-(4-chlorophenyl)-5-methylbenzo[d]thiazol-6-yl)-2-tert-butoxyacetate (40 mg, 0.07 mmol) in THF (2 mL) was added carbonyldiimidazole (45 mg, 0.28 mmol). After 3 h, LCMS showed complete conversion to (S)-ethyl 2-tert-butoxy-2-(7-(4-chlorophenyl)-5-methyl-2-(1-methyl-2-oxo-2,3-dihydro-1H-benzo[d]imidazol-5-yl)benzo[d]thiazol-6-yl)acetate. LCMS-ESI$^+$: calc'd for C$_{30}$H$_{31}$ClN$_3$O$_4$S: 564.2 (M+H$^+$); Found: 564.2 (M+H$^+$).

MeOH (2 mL) was added to the mixture followed by a sodium hydroxide solution (2 M aqueous, 500 µL). The reaction mixture was stirred at 50° C. for 4 h. The mixture was purified using reverse phase HPLC, eluting by 5-100% acetonitrile in H$_2$O with 0.1% TFA to give the product. LCMS-ESI$^+$: calc'd for C$_{28}$H$_{27}$ClN$_3$O$_4$S: 536.1 (M+H$^+$); Found: 536.2 (M+H$^+$). $^1$H NMR (400 MHz, CD$_3$OD): δ 7.74-7.79 (m, 3H), 7.67 (m, 1H), 7.58 (m, 3H), 7.18 (d, J=8.0 Hz, 1H), 5.24 (s, 1H), 3.41 (s, 3H), 2.60 (s, 3H), 0.97 (s, 9H).

Example 157

Preparation of (S)-2-tert-butoxy-2-(7-(4-chlorophenyl)-5-methyl-2-(6-methyl-5-(1-methyl-1H-indazol-5-yl)pyridin-3-yl)benzo[d]thiazol-6-yl)acetic acid (305)

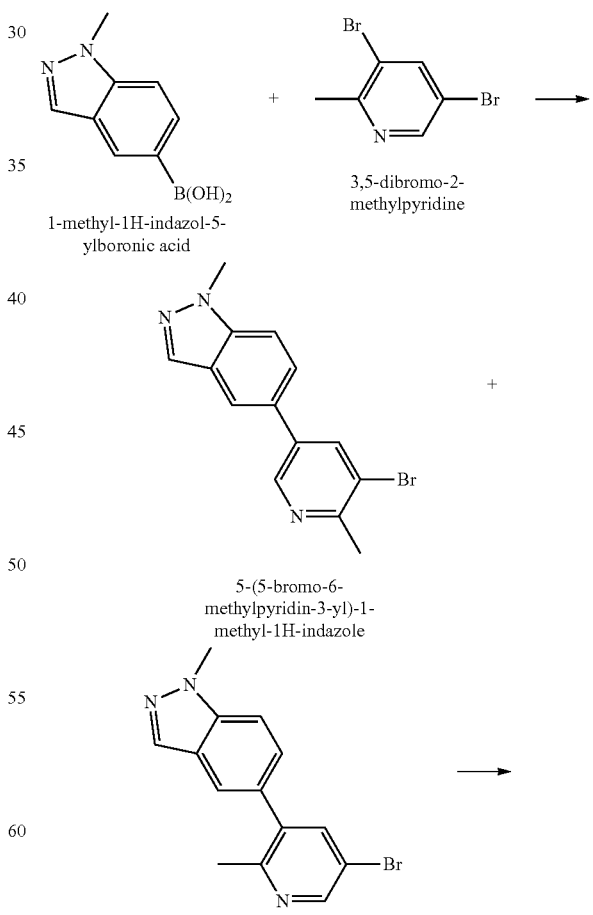

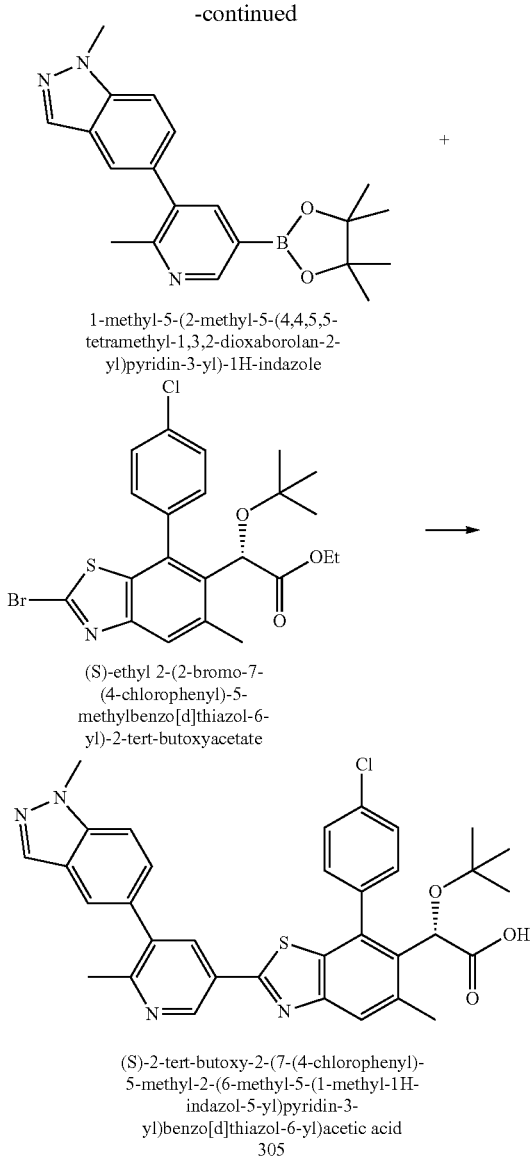

1-methyl-5-(2-methyl-5-(4,4,5,5-tetramethyl-1,3,2-dioxaborolan-2-yl)pyridin-3-yl)-1H-indazole (S)-ethyl 2-(2-bromo-7-(4-chlorophenyl)-5-methylbenzo[d]thiazol-6-yl)-2-tert-butoxyacetate (S)-2-tert-butoxy-2-(7-(4-chlorophenyl)-5-methyl-2-(6-methyl-5-(1-methyl-1H-indazol-5-yl)pyridin-3-yl)benzo[d]thiazol-6-yl)acetic acid
305

Preparation of 5-(5-bromo-2-methylpyridin-3-yl)-1-methyl-1H-indazole and 5-(5-bromo-6-methylpyridin-3-yl)-1-methyl-1H-indazole: To a solution of 3,5-dibromo-2-methylpyridine (1.0 g, 3.99 mmol) and 5-(bromomethyl)-1-methyl-1H-indazole (772 mg, 4.38 mmol) in 1,4-dioxane (12 mL) was added Pd(PPh$_3$)$_4$ (231 mg, 0.20 mmol) and potassium carbonate solution (2 M aqueous, 6 mL, 12 mmol). The reaction mixture was stirred at 105° C. in a sealed tube for 1.5 h. The mixture was diluted with water (15 mL) and EtOAc (20 mL). The layers were separated, and the organic layer was dried, filtered, and concentrated in vacuo. The crude material was purified by CombiFlash (EtOAc w/5% MeOH and Hexanes) to give 5-(5-bromo-2-methylpyridin-3-yl)-1-methyl-1H-indazole and 5-(5-bromo-6-methylpyridin-3-yl)-1-methyl-1H-indazole.

5-(5-bromo-2-methylpyridin-3-yl)-1-methyl-1H-indazole:

$^1$H NMR (400 MHz, CD$_3$OD): δ 8.54 (s, 1H), 8.00 (s, 1H), 7.69 (s, 1H), 7.62 (s, 1H), 7.44 (d, J=8.8 Hz, 1H), 7.29 (d, J=8.8 Hz, 1H), 4.10 (s, 3H), 2.43 (s, 3H).

5-(5-bromo-6-methylpyridin-3-yl)-1-methyl-1H-indazole:

$^1$H NMR (400 MHz, CDCl$_3$): δ 8.68 (d, J=2 Hz, 1H), 8.06 (s, 1H), 8.04 (s, 1H), 7.88 (s, 1H), 7.56 (dd, J=8.8 Hz, 1H), 7.48 (d, J=8.8 Hz, 1H), 4.10 (s, 3H), 2.71 (s, 3H).

Preparation of (S)-2-tert-butoxy-2-(7-(4-chlorophenyl)-5-methyl-2-(6-methyl-5-(1-methyl-1H-indazol-5-yl)pyridin-3-yl)benzo[d]thiazol-6-yl)acetic acid: To a solution of 5-(5-bromo-2-methylpyridin-3-yl)-1-methyl-1H-indazole (80 mg, 0.27 mmol) in DMF (3 mL) was added potassium acetate (78 mg, 0.80 mmol), bis(pinacolato)diboron (99 mg, 0.40 mmol), and PdCl$_2$dppf (9 mg, 0.013 mmol). The reaction mixture was stirred at 110° C. for 45 min. Brine (5 mL) was added and EtOAc (10 mL). The layers were separated, and the organic layer was dried, filtered, and concentrated in vacuo. The crude product was used without purification.

Dioxane (4 mL) was added followed by (S)-ethyl 2-(2-bromo-7-(4-chlorophenyl)-5-methylbenzo[d]thiazol-6-yl)-2-tert-butoxyacetate (45 mg, 0.091 mmol), Pd(PPh$_3$)$_4$ (5 mg, 0.005 mmol) and potassium carbonate solution (2 M aqueous, 200 µL, 0.40 mmol). The reaction mixture was stirred at 105° C. in a sealed tube for 2.5 h. The mixture was diluted with water (5 mL) and EtOAc (5 mL). The layers were separated, and the organic layer was dried, filtered, and concentrated in vacuo.

MeOH (2 mL) and THF (2 mL) were added to the crude material followed by a sodium hydroxide solution (2 M aqueous, 500 µL). The reaction mixture was stirred at 50° C. for 4 h. The mixture was purified using reverse phase HPLC, eluting by 5-100% acetonitrile in H$_2$O with 0.1% TFA to give the product. LCMS-ESI$^+$: calc'd for C$_{34}$H$_{32}$ClN$_4$O$_3$S: 611.2 (M+H$^+$); Found: 611.2 (M+H$^+$). $^1$H NMR (400 MHz, CD$_3$OD): δ 9.17 (s, 1H), 8.59 (s, 1H), 8.11 (s, 1H), 7.91 (s, 1H), 7.89 (s, 1H), 7.69-7.74 (m, 2H), 7.58 (m, 3H), 7.53 (d, J=9.6 Hz, 1H), 5.26 (s, 1H), 4.14 (s, 3H), 2.66 (s, 3H), 2.62 (s, 3H), 0.96 (s, 9H).

Example 158

Preparation of (S)-2-tert-butoxy-2-(7-(4-chlorophenyl)-5-methyl-2-(2-methyl-5-(1-methyl-1H-indazol-5-yl)pyridin-3-yl)benzo[d]thiazol-6-yl)acetic acid (306)

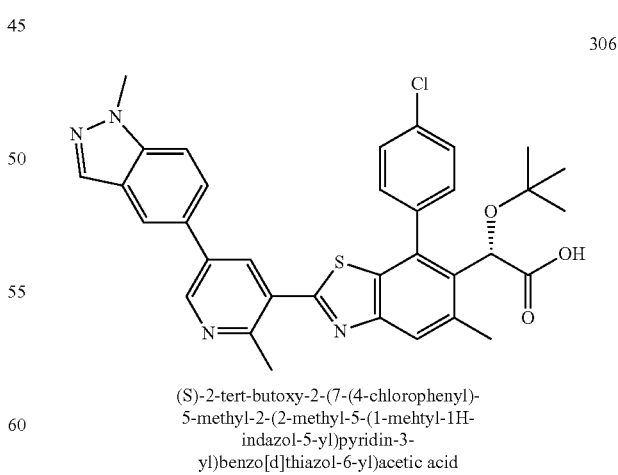

(S)-2-tert-butoxy-2-(7-(4-chlorophenyl)-5-methyl-2-(2-methyl-5-(1-mehtyl-1H-indazol-5-yl)pyridin-3-yl)benzo[d]thiazol-6-yl)acetic acid Preparation of (S)-2-tert-butoxy-2-(7-(4-chlorophenyl)-5-methyl-2-(2-methyl-5-(1-methyl-1H-indazol-5-yl)pyridin-3-yl)benzo[d]thiazol-6-yl)acetic acid: (S)-2-tert-butoxy-2-(7-(4-chlorophenyl)-5-methyl-2-(2-methyl-5-(1-methyl-1H- indazol-5-yl)pyridin-3-yl)benzo[d]thiazol-6-yl)acetic acid was prepared in a similar manner as (S)-2-tert-butoxy-2-(7-(4-chlorophenyl)-5-methyl-2-(6-methyl-5-(1-methyl-1H-indazol-5-yl)pyridin-3-yl)benzo[d]thiazol-6-yl)acetic acid except using 5-(5-bromo-6-methylpyridin-3-yl)-1-methyl-1H-indazole instead of 5-(5-bromo-2-methylpyridin-3-yl)-1-methyl-1H-indazole. LCMS-ESI+: calc'd for $C_{34}H_{32}ClN_4O_3S$: 611.2 (M+H+); Found: 611.2 (M+H+). $^1$H NMR (400 MHz, CD$_3$OD): δ 9.00 (s, 1H), 8.77 (s, 1H), 8.20 (s, 1H), 8.12 (s, 1H), 7.98 (s, 1H), 7.84 (m, 1H), 7.72 (m, 2H), 7.60 (m, 3H), 5.28 (s, 1H), 4.11 (s, 3H), 3.00 (s, 3H), 2.64 (s, 3H), 0.98 (s, 9H).

Example 159

Preparation of (S)-2-tert-butoxy-2-(7-(4-chlorophenyl)-2-(6-(4-isopropylpiperazin-1-yl)pyridin-2-yl)-5-methylbenzo[d]thiazol-6-yl)acetic acid (307)

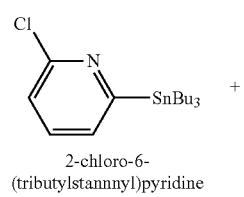

2-chloro-6-(tributylstannnyl)pyridine

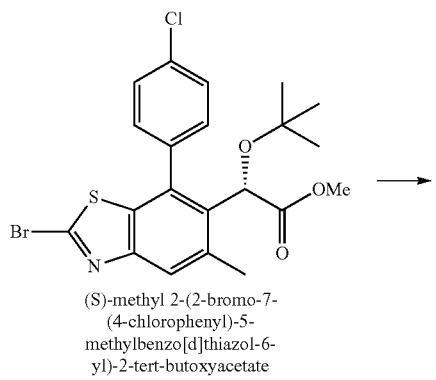

(S)-methyl 2-(2-bromo-7-(4-chlorophenyl)-5-methylbenzo[d]thiazol-6-yl)-2-tert-butoxyacetate

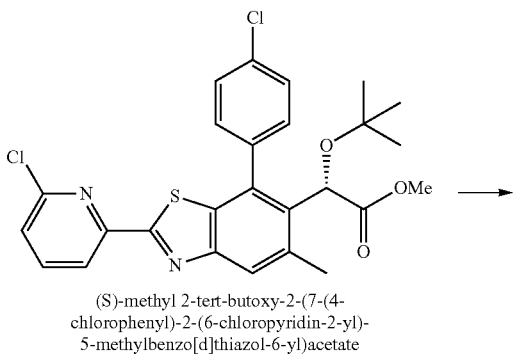

(S)-methyl 2-tert-butoxy-2-(7-(4-chlorophenyl)-2-(6-chloropyridin-2-yl)-5-methylbenzo[d]thiazol-6-yl)acetate

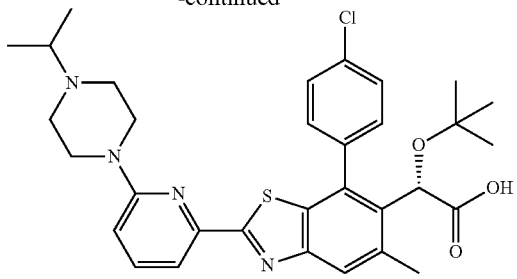

(S)-2-tert-butoxy-2-(7-(4-chlorophenyl)-2-(6-(4-isopropylpiperazin-1-yl)pyridin-2-yl)-5-methylbenzo[d]thiazol-6-yl)acetic acid
307

Preparation of (S)-methyl 2-tert-butoxy-2-(7-(4-chlorophenyl)-2-(6-chloropyridin-2-yl)-5-methylbenzo[d]thiazol-6-yl)acetate: To a solution of (S)-methyl 2-(2-bromo-7-(4-chlorophenyl)-5-methylbenzo[d]thiazol-6-yl)-2-tert-butoxyacetate (241.41 mg, 0.5 mmol) in DMF (2 mL) was added 2-chloro-6-(tributylstannyl)pyridine (241.55 mg, 0.6 mmol), tetrakis(triphenylphosphine)palladium (28.89 mg, 0.03 mmol), copper (I) iodide (9.52 mg, 0.05 mmol), and lithium chloride (21.2 mg, 0.5 mmol). The reaction mixture was stirred at 95° C. for 4 h. Brine was added (5 mL) and EtOAc (10 mL). The layers were separated, and the organic layer was dried, filtered, and concentrated in vacuo. The crude material was purified by CombiFlash (EtOAc/Hexanes) to give (S)-methyl 2-tert-butoxy-2-(7-(4-chlorophenyl)-2-(6-chloropyridin-2-yl)-5-methylbenzo[d]thiazol-6-yl)acetate. LCMS-ESI+: calc'd for $C_{26}H_{25}Cl_2N_2O_3S$: 515.1 (M+H+); Found: 515.1 (M+H+).

Preparation of (S)-2-tert-butoxy-2-(7-(4-chlorophenyl)-2-(6-(4-isopropylpiperazin-1-yl)pyridin-2-yl)-5-methylbenzo[d]thiazol-6-yl)acetic acid: To a solution of (S)-methyl 2-tert-butoxy-2-(7-(4-chlorophenyl)-2-(6-chloropyridin-2-yl)-5-methylbenzo[d]thiazol-6-yl)acetate (75 mg, 0.14 mmol) in 1,4-dioxane (2 mL) and EtOH (2 mL) was added triethylamine (200 μL) and 1-isopropylpiperazine (93 mg, 0.73 mmol). The mixture was heated in the microwave at 160° C. for 5 h (the starting material is not all consumed). A saturated solution of NH$_4$Cl (4 mL) was added and EtOAc (5 mL). The layers were separated, and the organic layer was dried, filtered, concentrated in vacuo and used without further purification. LCMS-ESI+: calc'd for $C_{33}H_{40}ClN_4O_3S$: 607.2 (M+H+); Found: 607.3 (M+H+).

MeOH (2 mL) and THF (2 mL) were added to the crude material followed by a sodium hydroxide solution (2 M aqueous, 500 μL). The reaction mixture was stirred at 50° C. for 4 h. The mixture was purified using reverse phase HPLC, eluting by 5-100% acetonitrile in H$_2$O with 0.1% TFA to give the product. LCMS-ESI+: calc'd for $C_{32}H_{38}ClN_4O_3S$: 593.2 (M+H+); Found: 593.3 (M+H+). $^1$H NMR (400 MHz, CD$_3$OD): δ 7.73-7.82 (m, 3H), 7.69 (m, 1H), 7.53-7.60 (m, 3H), 7.05 (d, J=8 Hz, 1H), 5.23 (s, 1H), 4.59 (br m, 2H), 3.58 (br m, 3H), 3.20 (br m, 4H), 2.61 (s, 3H), 1.39 (d, J=7 Hz, 6H), 0.97 (s, 9H).

Example 160

Preparation of (S)-2-tert-butoxy-2-(7-(4-chlorophenyl)-5-methyl-2-(6-(4-(oxetan-3-yl)piperazin-1-yl)pyridin-2-yl)benzo[d]thiazol-6-yl)acetic acid (308)

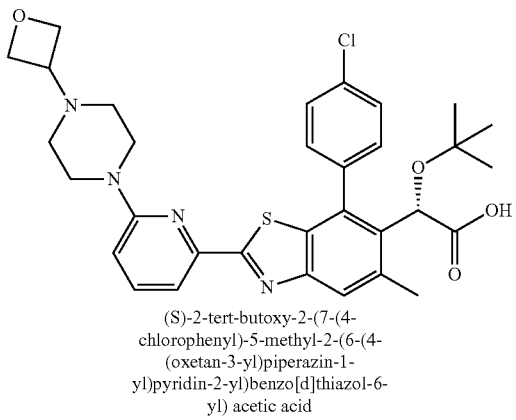

(S)-2-tert-butoxy-2-(7-(4-chlorophenyl)-5-methyl-2-(6-(4-(oxetan-3-yl)piperazin-1-yl)pyridin-2-yl)benzo[d]thiazol-6-yl) acetic acid Preparation of (S)-2-tert-butoxy-2-(7-(4-chlorophenyl)-5-methyl-2-(6-(4-(oxetan-3-yl)piperazin-1-yl)pyridin-2-yl)benzo[d]thiazol-6-yl)acetic acid: (S)-2-tert-butoxy-2-(7-(4-chlorophenyl)-5-methyl-2-(6-(4-(oxetan-3-yl)piperazin-1-yl)pyridin-2-yl)benzo[d]thiazol-6-yl)acetic acid was prepared in a similar manner as (S)-2-tert-butoxy-2-(7-(4-chlorophenyl)-2-(6-(4-isopropylpiperazin-1-yl)pyridin-2-yl)-5-methylbenzo[d]thiazol-6-yl)acetic acid, except using 1-(oxetan-3-yl)piperazine instead of 1-isopropylpiperazine. LCMS-ESI+: calc'd for $C_{32}H_{36}ClN_4O_4S$: 607.2 (M+H+); Found: 607.2 (M+H+); 1H NMR (400 MHz, CD3OD): δ 7.70-7.81 (m, 3H), 7.64 (m, 1H), 7.49-7.56 (m, 3H), 7.04 (d, J=8 Hz, 1H), 5.19 (s, 1H), 4.88 (br m, 2H), 4.77 (br m [under solvent], 4H), 4.35 (m, 1H), 3.80 (br m, 2H), 3.24 (m, [under solvent] 4H), 0.93 (s, 9H).

Example 161

Preparation of (S)-2-tert-butoxy-2-(7-(4-chlorophenyl)-5-methyl-2-(6-(1-methyl-1H-indazol-5-yl)pyridin-2-yl)benzo[d]thiazol-6-yl)acetic acid (309)

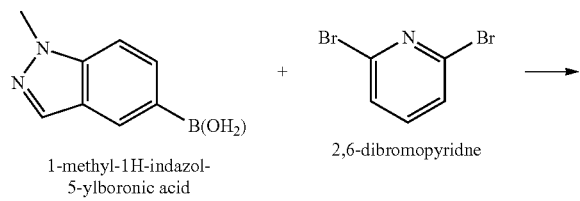

1-methyl-1H-indazol-5-ylboronic acid + 2,6-dibromopyridne

-continued

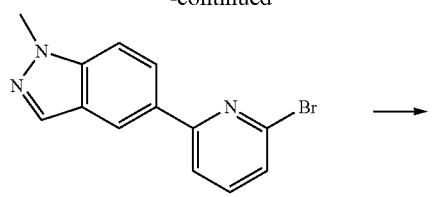

5-(6-bromopyridin-2-yl)-1-methyl-1H-indazole

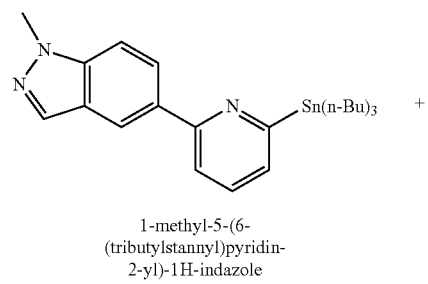

1-methyl-5-(6-(tributylstannyl)pyridin-2-yl)-1H-indazole +

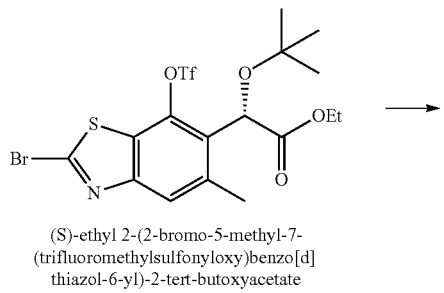

(S)-ethyl 2-(2-bromo-5-methyl-7-(trifluoromethylsulfonyloxy)benzo[d]thiazol-6-yl)-2-tert-butoxyacetate

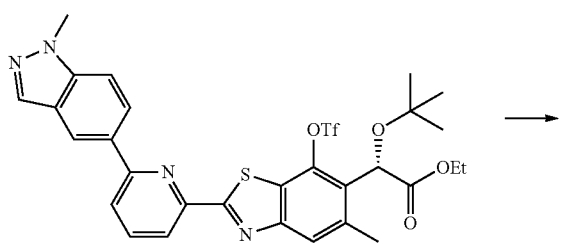

(S)-ethyl 2-tert-butoxy-2-(5-methyl-2-(6-(1-methyl-1H-indazol-5-yl)pyridin-2-yl)-7-(trifluoromethylsulfonyloxy)benzo[d]thiazol-6-yl)acetate

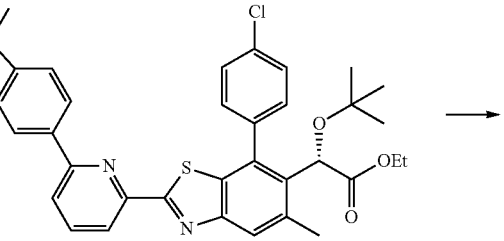

(S)-ethyl 2-tert-butoxy-2-(7-(4-chlorophenyl)-5-methyl-2-(6-(1-methyl-1H-indazol-5-yl)pyridin-2-yl)benzo[d]thiazol-6-yl)acetate

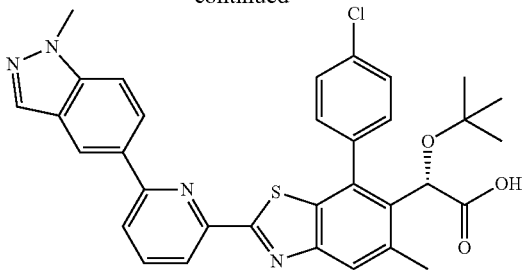

(S)-2-tert-butoxy-2-(7-(4-chlorophenyl)-5-methyl-2-(6-(1-methyl-1H-indazol-5-yl)pyridin-2-yl)benzol[d]thiazol-6-yl)acetic acid
309

Preparation of 5-(6-bromopyridin-2-yl)-1-methyl-1H-indazole: In a 10-20 mL reaction vial, the 1-methyl-1H-indazol-5-ylboronic acid (500 mg, 2.73 mmol) and the 2,6-dibromopyridine (776 mg, 3.27 mmol) were dissolved in dioxane (7 mL) under argon atmosphere. The mixture was bubbled with argon for 5 min and then potassium carbonate (754 mg, 5.46 mmol) and PdCl$_2$(dppf) catalyst were added sequentially. The resulting reaction mixture was then sealed and heated in oil bath at 110° C. for 3 h. Reaction was then diluted with EtOAc (10 mL), filtered and the filtrate was collected and concentrated. Residue was purified on silica gel column with 0-25% EtOAc/Hex to afford the title product. LCMS-ESI$^+$: calc'd for: $C_{13}H_{10}BrN_3$: 288.0, 290.0 (M+H$^+$); Found: 288.2, 290.3 (M+H$^+$).

Preparation of 1-methyl-5-(6-(tributylstannyl)pyridin-2-yl)-1H-indazole: In a 10 mL reaction vial, 5-(6-bromopyridin-2-yl)-1-methyl-1H-indazole (130 mg, 0.453 mmol) was dissolved in dry toluene (5 mL) under argon atmosphere. The solution was bubbled with argon for 5 min. Then Sn$_2$(n-Bu)$_6$ (415 mg, 0.358 mL, 0.68 mmol) and Pd(PPh$_3$)$_4$ (16 mg, 0.014 mmol) were added sequentially. The resulting reaction mixture was sealed and heated in oil bath at 85° C. for 17 h. Reaction mixture was then concentrated and purified on silica gel column with 0-20% EtOAc/Hex to afford a the title product. LCMS-ESI$^+$: calc'd for: $C_{25}H_{37}N_3Sn$: 500.2, 498.2, 499.2, 496.2, 497.2 (M+H$^+$); Found: 500.1, 498.3, 499.5, 496.0, 497.0 (M+H$^+$)

Preparation of (S)-ethyl 2-tert-butoxy-2-(5-methyl-2-(6-(1-methyl-1H-indazol-5-yl)pyridin-2-yl)-7-(trifluoromethylsulfonyloxy)benzo[d]thiazol-6-yl)acetate: In a 10 mL reaction vial, (S)-ethyl 2-(2-bromo-5-methyl-7-(trifluoromethylsulfonyloxy)benzo[d]thiazol-6-yl)-2-tert-butoxyacetate (50 mg, 0.0938 mmol) was dissolved in dry dioxane (1.5 mL) under argon atmosphere. The solution was bubbled with argon for 5 min. Then LiCl (11 mg, 0.256 mmol), CuI (5 mg, 0.026 mmol) and Pd(PPh$_3$)$_4$ (10 mg, 0.0085 mmol) were added sequentially. A solution of 1-methyl-5-(6-(tributylstannyl)pyridin-2-yl)-1H-indazole (43 mg, 0.0853 mmol) in 1.4-dioxane (1.5 mL) was then added dropwise. The resulting reaction mixture was then sealed and heated in oil bath at 100° C. for 3 h. The resulting reaction mixture was diluted with EtOAc (5 mL), filtered and the filtrate was concentrated and purified on silica gel column with 0-40% EtOAc/Hex to afford the title product. LCMS-ESI$^+$: calc'd for: $C_{30}H_{29}F_3N_4O_6S_2$: 663.2, 664.2 (M+H$^+$); Found: 663.1, 664.3 (M+H$^+$).

Preparation of (S)-ethyl 2-tert-butoxy-2-(7-(4-chlorophenyl)-5-methyl-2-(6-(1-methyl-1H-indazol-5-yl)pyridin-2-yl)benzo[d]thiazol-6-yl)acetate: In a 10 mL reaction vial, (S)-ethyl 2-tert-butoxy-2-(5-methyl-2-(6-(1-methyl-1H-indazol-5-yl)pyridin-2-yl)-7-(trifluoromethylsulfonyloxy)benzo[d]thiazol-6-yl)acetate (33 mg, 0.050 mmol) and p-chlorophenyl boronic acid (48 mg, 0.20 mmol) were dissolved in dioxane (2.5 mL) under argon atmosphere. The solution was bubbled with argon for 5 min. Then potassium carbonate (45 mg, 0.32 mmol) and Pd(PPh$_3$)$_4$ (10 mg, 0.0075 mmol) were added sequentially. The reaction mixture was sealed and heated in oil bath at 120° C. for 4.5 h. Reaction was then diluted with EtOAc (10 mL) and filtered to remove solid. The filtrate was concentrated and purified on silica gel column with 0-40% EtOAc/Hex to afford product. LCMS-ESI$^+$: calc'd for: $C_{35}H_{33}ClN_4O_3S$: 625.2, 626.2, 627.2 (M+H$^+$); found: 625.1, 626.2, 627.1 (M+H$^+$).

Preparation of (S)-2-tert-butoxy-2-(7-(4-chlorophenyl)-5-methyl-2-(6-(1-methyl-1H-indazol-5-yl)pyridin-2-yl)benzo[d]thiazol-6-yl)acetic acid: In a 25 mL round bottom flask, (S)-ethyl 2-tert-butoxy-2-(7-(4-chlorophenyl)-5-methyl-2-(6-(1-methyl-1H-indazol-5-yl)pyridin-2-yl)benzo[d]thiazol-6-yl)acetate (5 mg, 0.008 mmol) was dissolved in THF (0.4 mL) EtOH (0.2 mL) and water (0.1 mL). Then aqueous NaOH (2N) (0.1 mL) was added. The reaction mixture was stirred at 40° C. in oil bath for 17 h. The resulting reaction mixture was concentrated and purified on Gilson reverse phase preparative HPLC with 0-95% CH$_3$CN (with 0.1% TFA) in water (with 0.1% TFA) to afford the product as TFA salt. LCMS-ESI$^+$: calc'd for: $C_{33}H_{29}ClN_4O_3S$: 597.2, 599.2, 598.2 (M+H$^+$); found: 597.3, 599.3, 598.2 (M+H$^+$). $^1$H NMR (400 MHz, CD$_3$OD) δ 8.50 (d, J=1.6 Hz, 1H), 8.30-8.18 (m, 2H), 8.12 (s, 1H), 8.08-7.97 (m, 2H), 7.88 (s, 1H), 7.75-7.58 (m, 5H), 5.27 (s, 1H), 4.09 (s, 3H), 2.63 (s, 3H), 0.98 (s, 9H).

Example 162

Preparation of (S)-2-tert-butoxy-2-(7-(4-chlorophenyl)-5-methyl-2-(4-(1-methyl-1H-indazol-5-yl)thiazol-2-yl)benzo[d]thiazol-6-yl)acetic acid (310).

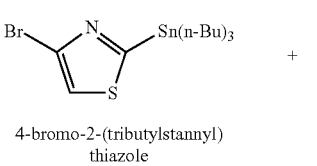

4-bromo-2-(tributylstannyl)thiazole

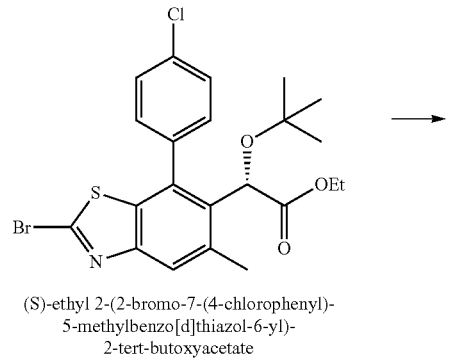

(S)-ethyl 2-(2-bromo-7-(4-chlorophenyl)-5-methylbenzo[d]thiazol-6-yl)-2-tert-butoxyacetate

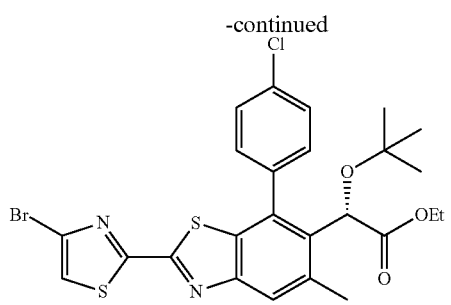

(S)-ethyl 2-(2-(4-bromothiazol-2-yl)-
7-(4-chlorophenyl)-5-methylbenzo
[d]thiazol-6-yl)-2-tert-butoxyacetate

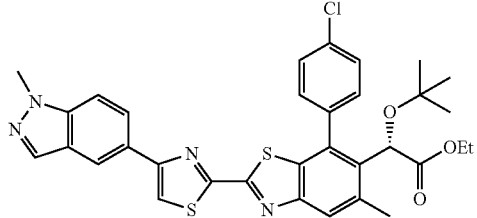

(S)-ethyl 2-tert-butoxy-2-(7-(4-chlorophenyl)-
5-methyl-2-(4-(1-methyl-1H-indazol-5-yl)
thiazol-2-yl)benzo[d]thiazol-6-yl)acetate

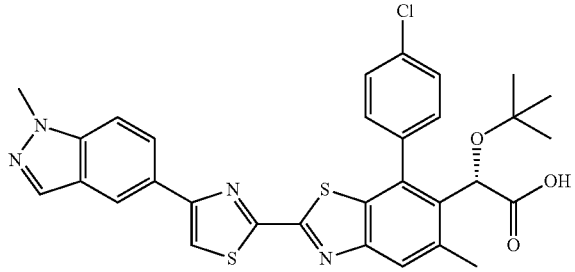

(S)-2-tert-butoxy-2-(7-(4-chlorophenyl)-5-
methyl-2-(4-(1-methyl-1H-indazol-5-yl)
thiazol-2-yl)benzo[d]thiazol-6-yl)acetic acid
310

Preparation of (S)-ethyl 2-(2-(4-bromothiazol-2-yl)-7-(4-chlorophenyl)-5-methylbenzo[d]thiazol-6-yl)-2-tert-butoxyacetate: In a 10 mL reaction vial, 4-bromo-2-(tributylstannyl)thiazole (125 mg, 0.251 mmol) and (S)-ethyl 2-(2-bromo-7-(4-chlorophenyl)-5-methylbenzo[d]thiazol-6-yl)-2-tert-butoxyacetate (114 mg, 0.251 mmol) were dissolved in dioxane (3 mL) at room temperature under argon atmosphere. The solution was bubbled with argon for 5 min. Then CuI (10.6 mg, 0.055 mmol), LiCl (31.7 mg, 0.753 mmol) and Pd(PPh$_3$)$_4$ (52.3 mg, 0.0417 mmol) were added sequentially. The reaction mixture was then sealed and heated in oil bath at 100° C. for 3.5 h. The reaction mixture was then diluted with EtOAc (10 mL), filtered and the filtrate was concentrated and purified on silica gel column with 0-10% EtOAc/Hex to afford title compound. LCMS-ESI$^+$: calc'd for: C$_{25}$H$_{24}$BrClN$_2$O$_3$S$_2$: 581.0, 579.0, 582.0, 583.0, 580.0 (M+H$^+$); found: 581.1, 579.0, 582.2, 583.1, 580.3 (M+H$^+$).

Preparation of (S)-ethyl 2-tert-butoxy-2-(7-(4-chlorophenyl)-5-methyl-2-(4-(1-methyl-1H-indazol-5-yl)thiazol-2-yl)benzo[d]thiazol-6-yl)acetate: In a 10 mL reaction vial, 1-methyl-1H-indazol-5-ylboronic acid (31 mg, 0.173 mmol) and (S)-ethyl 2-(2-(4-bromothiazol-2-yl)-7-(4chlorophenyl)-5methylbenzo[d]thiazol-6-yl)-2-tert-butoxyacetate (100 mg, 0.173 mmol) were mixed with dioxane (5 mL) and water (1 mL). The resulting reaction mixture was bubbled with argon for 5 min. Then potassium carbonate (60 mg, 0.432 mmol) and Pd(PPh$_3$)$_4$ were added sequentially. The reaction mixture was sealed and heated in oil bath at 95° C. for 2 h. The brown mixture was then diluted with EtOAc (20 mL), filtered and the filtrate was concentrated and purified on silica gel column with 0-30% EtOAc/Hex to afford the title compound. LCMS-ESI$^+$: calc'd for: C$_{33}$H$_{31}$ClN$_4$O$_3$S$_2$: 631.2, 633.2, 632.2 (M+H$^+$); found: 631.0, 633.1, 632.1 (M+H$^+$).

Preparation of (S)-2-tert-butoxy-2-(7-(4-chlorophenyl)-5-methyl-2-(4-(1-methyl-1H-indazol-5-yl)thiazol-2-yl)benzo[d]thiazol-6-yl)acetic acid: In a 25 mL round bottom flask, (S)-ethyl 2-tert-butoxy-2-(7-(4-chlorophenyl)-5-methyl-2-(4-(1-methyl-1H-indazol-5-yl)thiazol-2-yl)benzo[d]thiazol-6-yl)acetate (74 mg, 0.117 mmol) was dissolved in THF (3 mL) EtOH (2 mL) and water (1 mL). Then aqueous NaOH (2N) (1.17 mL) was added. The reaction mixture was stirred at 40° C. in oil bath for 17 h. The resulting reaction mixture was concentrated and purified on Gilson reverse phase preparative HPLC with 0-95% acetonitrile (with 0.1% TFA) in water (with 0.1% TFA) to afford product as a TFA salt. LCMS-ESI$^+$: calc'd for: C$_{31}$H$_{27}$ClN$_4$O$_3$S$_2$: 603.1, 605.1, 604.1 (M+H$^+$); found: 603.2, 605.2, 604.0 (M+H$^+$). $^1$H NMR (400 MHz, CD$_3$OD) δ 8.36 (d, J=1.2 Hz, 1H), 8.06-7.98 (m, 3H), 7.82 (s, 1H), 7.70 (dd, J=7.9, 2.4 Hz, 1H), 7.66-7.52 (m, 4H), 5.28 (s, 1H), 4.05 (s, 3H), 2.61 (s, 3H), 0.98 (s, 9H).

Example 163

Preparation of (S)-2-(2-(3-amino-6-(1-methyl-1H-indazol-5-yl)pyridin-2-yl)-7-(4-chlorophenyl)-5-methylbenzo[d]thiazol-6-yl)-2-tert-butoxyacetic acid
(311)

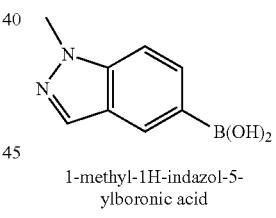

1-methyl-1H-indazol-5-
ylboronic acid

6-bromopyridin-3-amine

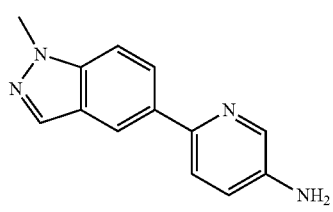

6-(1-methyl-1H-indazol-
5-yl)pyridin-3-amine

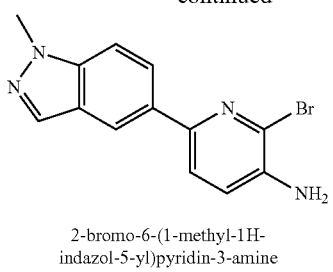

2-bromo-6-(1-methyl-1H-indazol-5-yl)pyridin-3-amine

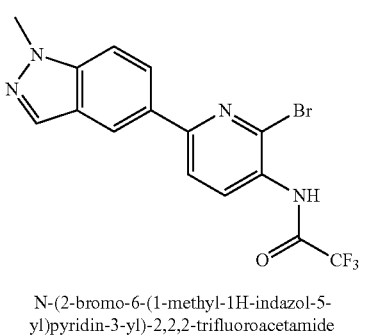

N-(2-bromo-6-(1-methyl-1H-indazol-5-yl)pyridin-3-yl)-2,2,2-trifluoroacetamide

+

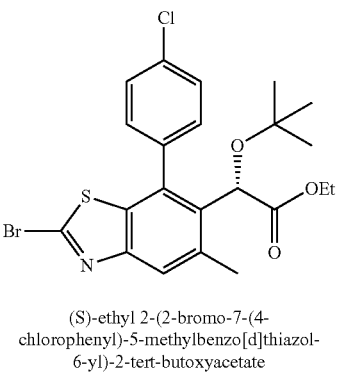

(S)-ethyl 2-(2-bromo-7-(4-chlorophenyl)-5-methylbenzo[d]thiazol-6-yl)-2-tert-butoxyacetate

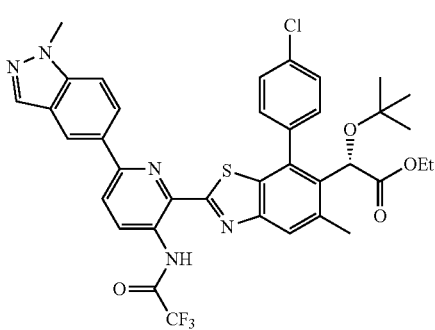

(S)-ethyl 2-tert-butoxy-2-(7-(4-chlorophenyl)-5-methyl-2-(6-(1-methyl-1H-indazol-5-yl)-3-(2,2,2-trifluoroacetamido)pyridin-2-yl)benzo[d]thiazol-6-yl)acetate

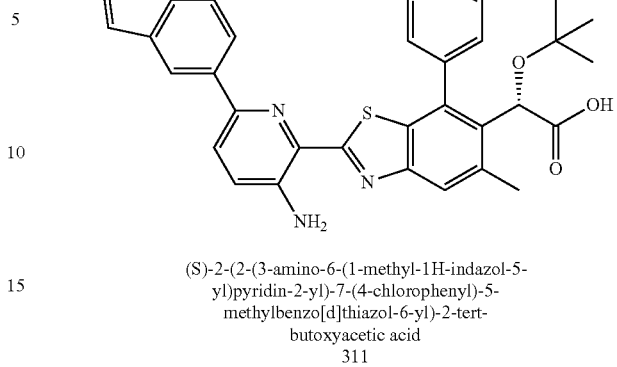

(S)-2-(2-(3-amino-6-(1-methyl-1H-indazol-5-yl)pyridin-2-yl)-7-(4-chlorophenyl)-5-methylbenzo[d]thiazol-6-yl)-2-tert-butoxyacetic acid
311

Preparation of 6-(1-methyl-1H-indazol-5-yl)pyridin-3-amine: In a 10-20 mL reaction vial, the 1-methyl-1H-indazol-5-ylboronic acid (250 mg, 1.34 mmol) and the 6-bromopyridin-3-amine (250 mg, 1.34 mmol) were dissolved in dioxane (7 mL) and water (1.5 mL) under argon atmosphere. The mixture was bubbled with argon for 5 min and then potassium carbonate (368 mg, 2.67 mmol) and Pd(PPh$_3$)$_4$ (231 mg, 0.2 mmol) were added sequentially. The resulting reaction mixture was then sealed and heated in oil bath at 110° C. for 3 h. Reaction was then partitioned between EtOAc (30 mL) and water (30 mL). The organic phase was washed with water (3×20 mL) and was concentrated. Residue was purified on silica gel column with 0-75% EtOAc/Hex to afford the title compound. LCMS-ESI$^+$: calc'd for: C$_{13}$H$_{12}$N$_4$: 225.1 (M+H$^+$); found: 225.2 (M+H$^+$).

Preparation of 2-bromo-6-(1-methyl-1H-indazol-5-yl)pyridin-3-amine: In a 50 mL round bottom flask, 6-(1-methyl-1H-indazol-5-yl)pyridin-3-amine (225 mg, 1.00 mmol) was dissolved in DMF (8 mL) at room temperature and the solution was cooled down to 0° C. for 5 min under argon atmosphere. A solution of NBS (179 mg, 1.00 mmol) in DMF (6 mL) was added dropwise. The resulting reaction mixture was stirred at 0° C. for 30 min and then was poured onto saturated aq NaHCO$_3$ solution (30 mL). EtOAc (3×30 mL) was used for extraction. Organic phase was then washed with water (2×20 mL) and concentrated. Residue was purified on silica gel column with 0-30% to afford product. LCMS-ESI$^+$: calc'd for: C$_{13}$H$_{11}$BrN$_4$: 303.0, 305.0 (M+H$^+$); found: 303.1, 305.1 (M+H$^+$)

Preparation of N-(2-bromo-6-(1-methyl-1H-indazol-5-yl)pyridin-3-yl)-2,2,2-trifluoroacetamide: In a 50m round bottom flask, 2-bromo-6-(1-methyl-1H-indazol-5-yl)pyridin-3-amine (34 mg, 0.112 mmol) was dissolved in DCM (5 mL) at room temperature under a argon atmosphere. Then a solution of trifluoroacetic anhydride (38.5 mg, 0.183 mmol) in DCM (1 mL) was added drop-wise. A few crystals of DMAP (catalytic amount) were added. The resulting reaction mixture was stirred under argon atmosphere for 17 h. The reaction mixture was concentrated and purified on silica gel column with 0-30% EtOAc/Hex to afford product. LCMS-ESI$^+$: calc'd for: C$_{15}$H$_{10}$BrF$_3$N$_4$O: 399.0, 401.0 (M+H$^+$); found: 399.0, 401.0 (M+H$^+$).

Preparation of (S)-ethyl 2-tert-butoxy-2-(7-(4-chlorophenyl)-5-methyl-2-(6-(1-methyl-1H-indazol-5-yl)-3-(2,2,2-trifluoroacetamido)pyridin-2-yl)benzo[d]thiazol-6-yl)acetate: In a 10 mL reaction vial, N-(2-bromo-6-(1-methyl-1H-indazol-5-yl)pyridin-3-yl)-2,2,2-trifluoroacetamide (24 mg, 0.06 mmol) was dissolved in dioxane (3 mL) at room temperature. The solution was bubbled with argon for 5 min. Then Sn$_2$(n-Bu)$_6$ (0.057 mL, 0.108 mmol), LiCl (30 mg, 0.7 mmol), Pd(PPh$_3$)$_2$Cl$_2$ (6.3 mg, 0.009 mmol) and Pd(PPh$_3$)$_4$ (10 mg, 0.009 mmol) were added sequentially. The resulting reaction mixture was sealed and heated to 90° C. in oil bath. To this mixture, a solution of (S)-ethyl 2-(2-bromo-7-(4-chlorophenyl)-5-methylbenzo[d]thiazol-6-yl)-2-tert-butoxyacetate (44 mg, 0.09 mmol) in dioxane (1.5 mmol) was added slowly through syringe pump over 1.5 h. The resulting reaction mixture was stirred at 100° C. in oil bath for 16 h. The reaction was then diluted with EtOAc (20 mL) and filtered to remove solid. The filtrate was concentrated and purified on silica gel column with 0-20% EtOAc/Hex to afford product. LCMS-ESI$^+$: calc'd for: C$_{37}$H$_{33}$ClF$_3$N$_5$O$_4$S: 736.2, 737.2, 738.2 (M+H$^+$); found: 736.1, 737.1, 738.1 (M+H$^+$).

Preparation of (S)-2-(2-(3-amino-6-(1-methyl-1H-indazol-5-yl)pyridin-2-yl)-7-(4-chlorophenyl)-5-methylbenzo[d]thiazol-6-yl)-2-tert-butoxyacetic acid: In a 25 mL round bottom flask, (S)-ethyl 2-tert-butoxy-2-(7-(4-chlorophenyl)-5-methyl-2-(6-(1-methyl-1H-indazol-5-yl)-3-(2,2,2-trifluoroacetamido)pyridin-2-yl)benzo[d]thiazol-6-yl)acetate (9 mg, 0.0122 mmol) was dissolved in THF (1.5 mL) EtOH (0.5 mL) and water (0.5 mL). Then aqueous NaOH (2N) (0.2 mL) was added. The reaction mixture was stirred at 40° C. in oil bath for 17 h. The resulting reaction mixture was concentrated and purified on Gilson reverse phase preparative HPLC with 0-95% acetonitrile (with 0.1% TFA) in water (with 0.1% TFA) to afford product as TFA salt. LCMS-ESI$^+$: calc'd for: C$_{33}$H$_{30}$ClN$_5$O$_3$S: 612.2, 613.2, 614.2 (M+H$^+$); found: 612.2, 613.2, 614.2 (M+H$^+$); $^1$H NMR (400 MHz, CD$_3$OD) δ 8.28 (d, J=1.5 Hz, 1H), 8.21-8.16 (m, 1H), 8.05 (s, 1H), 7.85-7.77 (m, 2H), 7.71 (d, J=8.4 Hz, 1H), 7.65-7.56 (m, 4H), 7.34 (d, J=8.7 Hz, 1H), 5.25 (s, 1H), 4.07 (s, 3H), 2.61 (s, 3H), 0.97 (s, 9H).

Example 164

Preparation of (S)-2-tert-butoxy-2-(7-(4-chlorophenyl)-5-methyl-2-(1-methyl-2-(1-methyl-1H-indazol-5-yl)-1H-imidazol-4-yl)benzo[d]thiazol-6-yl)acetic acid (312)

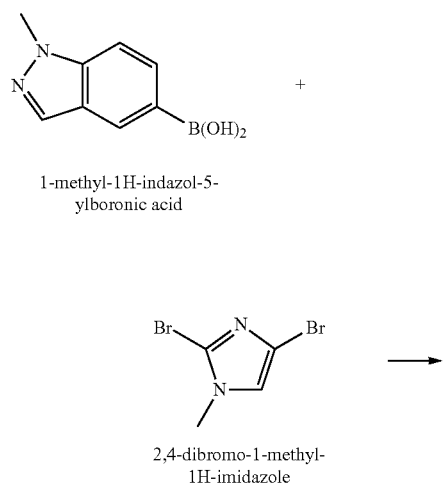

1-methyl-1H-indazol-5-ylboronic acid

+

2,4-dibromo-1-methyl-1H-imidazole

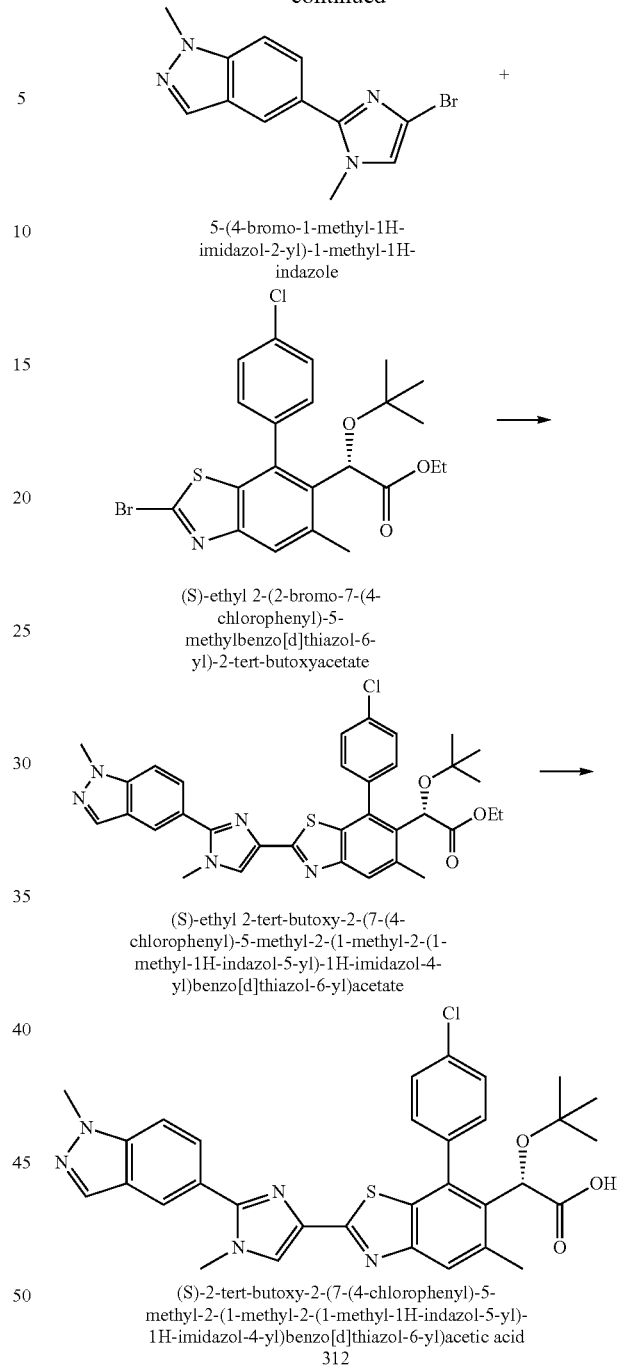

5-(4-bromo-1-methyl-1H-imidazol-2-yl)-1-methyl-1H-indazole (S)-ethyl 2-(2-bromo-7-(4-chlorophenyl)-5-methylbenzo[d]thiazol-6-yl)-2-tert-butoxyacetate (S)-ethyl 2-tert-butoxy-2-(7-(4-chlorophenyl)-5-methyl-2-(1-methyl-2-(1-methyl-1H-indazol-5-yl)-1H-imidazol-4-yl)benzo[d]thiazol-6-yl)acetate (S)-2-tert-butoxy-2-(7-(4-chlorophenyl)-5-methyl-2-(1-methyl-2-(1-methyl-1H-indazol-5-yl)-1H-imidazol-4-yl)benzo[d]thiazol-6-yl)acetic acid 312

Preparation of 5-(4-bromo-1-methyl-1H-imidazol-2-yl)-1-methyl-1H-indazole: In a 10-20 mL reaction vial, the 1-methyl-1H-indazol-5-ylboronic acid (169 mg, 0.966 mmol) and the 2,4-dibromo-1-methyl-1H-imidazole (300 mg, 1.25 mmol) were dissolved in dioxane (4 mL) and water (1 mL) under argon atmosphere. The mixture was bubbled with argon for 5 min and then potassium carbonate (400 mg, 2.895 mmol) and Pd(PPh$_3$)$_4$ (167 mg, 0.145 mmol) were added sequentially. The resulting reaction mixture was then sealed and heated in oil bath at 110° C. for 1.5 h. Reaction was then partitioned between EtOAc (30 mL) and water (30 mL). The organic phase was washed with water (3×20 mL) and was concentrated. Residue was purified on silica gel column with 0-50% EtOAc/Hex to afford the desired product. LCMS-ESI⁺: calc'd for: $C_{12}H_{11}BrN_4$: 291.0, 293.0 (M+H⁺); found: 291.0, 293.0 (M+H⁺)

Preparation of (S)-ethyl 2-tert-butoxy-2-(7-(4-chlorophenyl)-5-methyl-2-(1-methyl-2-(1-methyl-1H-indazol-5-yl)-1H-imidazol-4-yl)benzo[d]thiazol-6-yl)acetate: In a 10 mL reaction vial, 5-(4-bromo-1-methyl-1H-imidazol-2-yl)-1-methyl-1H-indazole (50 mg, 0.172 mmol) was dissolved in dioxane (3 mL) at rt. The solution was bubbled with argon for 5 min. Then $Sn_2(n-Bu)_6$ (0.136 mL, 0.259 mmol), LiCl (60 mg, 1.4 mmol), $Pd(PPh_3)_2Cl_2$ (24 mg, 0.034 mmol) and $Pd(PPh_3)_4$ (40 mg, 0.0344 mmol) were added sequentially. The resulting reaction mixture was sealed and heated to 90° C. in oil bath. To this mixture, a solution of (S)-ethyl 2-(2-bromo-7-(4-chlorophenyl)-5-methylbenzo[d]thiazol-6-yl)-2-tert-butoxyacetate (128 mg, 0.259 mmol) in dioxane (1.5 mmol) was added slowly through syringe pump over 1.5 h. The resulting reaction mixture was stirred at 100° C. in oil bath for 16 h. The reaction was then diluted with EtOAc (20 mL) and filtered to remove solid. The filtrate was concentrated and purified on silica gel column with 0-20% EtOAc/Hex to afford product. LCMS-ESI⁺: calc'd for: $C_{34}H_{34}ClN_5O_3S$: 628.2, 629.2, 630.2 (M+H⁺); found: 628.1, 629.1, 630.1 (M+H⁺)

Preparation of (S)-2-tert-butoxy-2-(7-(4-chlorophenyl)-5-methyl-2-(1-methyl-2-(1-methyl-1H-indazol-5-yl)-1H-imidazol-4-yl)benzo[d]thiazol-6-yl)acetic acid: In a 25 mL round bottom flask, (S)-ethyl 2-tert-butoxy-2-(7-(4-chlorophenyl)-5-methyl-2-(1-methyl-2-(1-methyl-1H-indazol-5-yl)-1H-imidazol-4-yl)benzo[d]thiazol-6-yl)acetate 15 mg, 0.024 mmol) was dissolved in THF (1.5 mL) EtOH (0.7 mL) and water (0.5 mL). Then aqueous NaOH (2 N) (0.4 mL) was added. The reaction mixture was stirred at 30° C. in oil bath for 17 h. The resulting reaction mixture was concentrated. The residue was purified on Gilson reverse phase HPLC with $CH_3CN$ and water (10 mL) to afford the product. LCMS-ESI⁺: calc'd for: $C_{32}H_{30}ClN_5O_3S$: 600.2, 602.2, 601.2 (M+H⁺); Found: 600.3, 602.3, 601.3 (M+H⁺). ¹H NMR (400 MHz, $CD_3OD$) δ 8.03 (d, J=0.8 Hz, 1H), 7.99 (dd, J=1.6, 0.8 Hz, 1H), 7.93-7.88 (m, 1H), 7.83 (s, 1H), 7.67-7.58 (m, 3H), 7.50 (dd, J=8.6, 2.3 Hz, 1H), 7.42 (ddd, J=8.3, 5.5, 2.2 Hz, 2H), 5.01 (s, 1H), 4.03 (d, J=0.7 Hz, 3H), 3.75 (s, 3H), 2.55 (s, 3H), 0.82 (s, 9H).

Example 165

Preparation of (S)-2-tert-butoxy-2-(7-(4-chlorophenyl)-5-methyl-2-(5-methyl-6-(1-methyl-1H-indazol-5-yl)pyridin-2-yl)benzo[d]thiazol-6-yl)acetic acid (313)

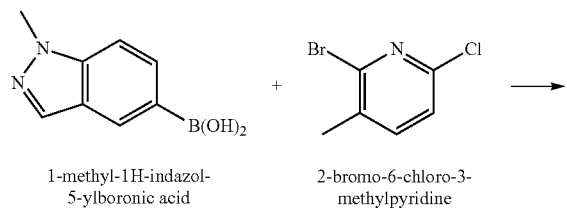

1-methyl-1H-indazol-5-ylboronic acid 2-bromo-6-chloro-3-methylpyridine

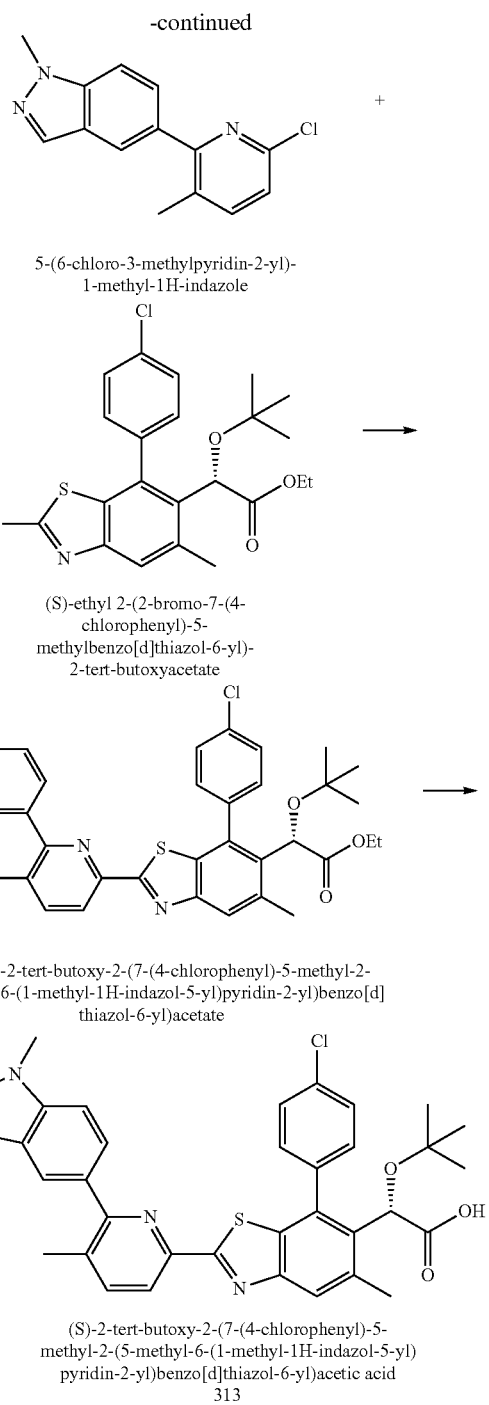

5-(6-chloro-3-methylpyridin-2-yl)-1-methyl-1H-indazole (S)-ethyl 2-(2-bromo-7-(4-chlorophenyl)-5-methylbenzo[d]thiazol-6-yl)-2-tert-butoxyacetate (S)-ethyl-2-tert-butoxy-2-(7-(4-chlorophenyl)-5-methyl-2-(5-methyl-6-(1-methyl-1H-indazol-5-yl)pyridin-2-yl)benzo[d]thiazol-6-yl)acetate (S)-2-tert-butoxy-2-(7-(4-chlorophenyl)-5-methyl-2-(5-methyl-6-(1-methyl-1H-indazol-5-yl)pyridin-2-yl)benzo[d]thiazol-6-yl)acetic acid
313

Preparation of 5-(6-chloro-3-methylpyridin-2-yl)-1-methyl-1H-indazole: In a 10 mL reaction vial, the 1-methyl-1H-indazol-5-ylboronic acid (500 mg, 2.84 mmol) and the 2-bromo-6-chloro-3-methylpyridine (585 mg, 2.84 mmol) were dissolved in dioxane (7 mL) and water (1.7 mL) under argon atmosphere. The mixture was bubbled with argon for 5 min. Then potassium carbonate (979 mg, 7.1 mmol) and $Pd(PPh_3)_4$ (49 3 mg, 0.428 mmol) were added sequentially. The resulting reaction mixture was then sealed and heated in oil bath at 110° C. for 2.5 h. Reaction was then partitioned between EtOAc (30 mL) and water (30 mL).The organic phase was washed with water (3×20 mL) and was concentrated. Residue was purified on silica gel column with 0-50% EtOAc/Hex to afford the title compound. LCMS-ESI+: calc'd for: $C_{14}H_{12}ClN_3$: 258.1 and 260.1 (M+H+); found: 258.0 and 260.0 (M+H+).

Preparation of (S)-ethyl 2-tert-butoxy-2-(7-(4-chlorophenyl)-5-methyl-2-(5-methyl-6-(1-methyl-1H-indazol-5-yl)pyridin-2-yl)benzo[d]thiazol-6-yl)acetate: In a 10 mL reaction vial, 5-(6-chloro-3-methylpyridin-2-yl)-1-methyl-1H-indazole (100 mg, 0.389 mmol) was dissolved in dioxane (5 mL) at rt. The solution was bubbled with argon for 5 min. Then $Sn_2(n-Bu)_6$ (0.253 mL, 0.508 mmol), LiCl (100 mg, 2.38 mmol), $Pd(PPh_3)_2Cl_2$ (27 mg, 0.039 mmol) and $Pd(PPh_3)_4$ (45 mg, 0.039 mmol) were added sequentially. The resulting reaction mixture was sealed and heated to 90° C. in oil bath. To this mixture, a solution of (S)-ethyl 2-(2-bromo-7-(4-chlorophenyl)-5-methylbenzo[d]thiazol-6-yl)-2-tert-butoxyacetate (289 mg, 0.583 mmol) in dioxane (5 mL) was added slowly through syringe pump over 1.5 h. The resulting reaction mixture was stirred at 100° C. in oil bath for 16 h. The reaction was then diluted with EtOAc (20 mL) and filtered to remove solid. The filtrate was concentrated and purified on silica gel column with 0-20% EtOAc/Hex to afford product as. LCMS-ESI+: calc'd for: $C_{36}H_{35}ClN_4O_3S$: 639.2, 640.2, 641.2 (M+H+); found: 639.1, 640.1, 641.1 (M+H+).

Preparation of (S)-2-tert-butoxy-2-(7-(4-chlorophenyl)-5-methyl-2-(5-methyl-6-(1-methyl-1H-indazol-5-yl)pyridin-2-yl)benzo[d]thiazol-6-yl)acetic acid: In a 25 mL round bottom flask, (S)-ethyl 2-tert-butoxy-2-(7-(4-chlorophenyl)-5-methyl-2-(1-methyl-2-(1-methyl-1H-indazol-5-yl)-1H-imidazol-4-yl)benzo[d]thiazol-6-yl)acetate 49 mg, 0.768 mmol) was dissolved in THF (2 mL) EtOH (1 mL) and water (0.5 mL). Then aqueous NaOH (1N) (1 mL) was added. The reaction mixture was stirred at 30° C. in oil bath for 17 h. The resulting reaction mixture was concentrated. The residue was triturated with $CH_3CN$ (10 mL) and water (10 mL) and was filtered. Solid was collected to afford sodium salt of product. LCMS-ESI+: calc'd for: $C_{34}H_{31}ClN_4O_3S$: 611.2, 612.2, 613.2 (M+H+); found: 611.1, 612.1, 613.1 (M+H+). $^1$H NMR (400 MHz, $CD_3OD$) δ 8.16 (d, J=7.9 Hz, 1H), 8.09 (d, J=0.9 Hz, 1H), 8.05-8.01 (m, 1H), 7.98 (dd, J=1.6, 0.9 Hz, 1H), 7.89-7.84 (m, 1H), 7.79 (d, J=0.9 Hz, 1H), 7.71 (dd, J=8.8, 1.5 Hz, 1H), 7.64 (dt, J=8.7, 0.9 Hz, 1H), 7.61-7.55 (m, 1H), 7.52-7.46 (m, 2H), 5.09 (s, 1H), 4.11 (s, 3H), 2.67 (d, J=0.8 Hz, 3H), 2.47 (s, 3H), 0.90 (s, 9H).

Example 166

Preparation of (S)-2-(2-(1-benzyl-3-methyl-1H-indazol-5-yl)-7-(4-chlorophenyl)-5-methylbenzo[d]thiazol-6-yl)-2-tert-butoxyacetic acid (3H) and (S)-2-(2-(2-benzyl-3-methyl-2H-indazol-5-yl)-7-(4-chlorophenyl)-5-methylbenzo[d]thiazol-6-yl)-2-tert-butoxyacetic acid (315)

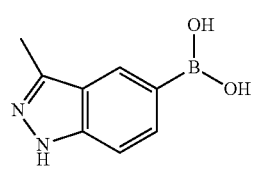

3-methyl-1H-indazol-5-ylboronic acid

-continued

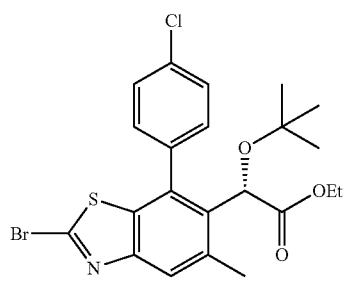

(S)-ethyl 2-(2-bromo-7-(4-chlorophenyl)-5-methylbenzo[d]thiazol-6-yl)-2-tert-butoxyacetate

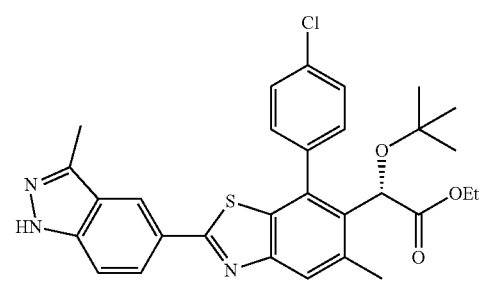

(S)-ethyl 2-tert-butoxy-2-(7-(4-chlorophenyl)-5-methyl-2-(3-methyl-1H-indazol-5-yl)benzo[d]thiazol-6-yl)acetate

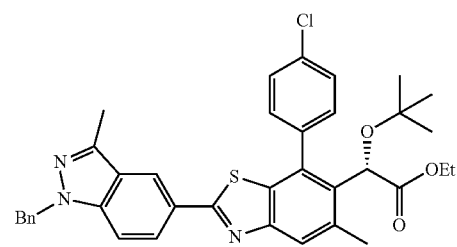

(S)-ethyl 2-(2-(1-benzyl-3-methyl-1H-indazol-5-yl)-7-(4-chlorophenyl)-5-methylbenzo[d]thiazol-6-yl)-2-tert-butoxyacetate

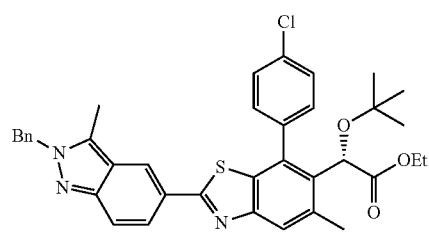

(S)-ethyl 2-(2-(2-benzyl-3-methyl-2H-indazol-5-yl)-7-(4-chlorophenyl)-5-methylbenzo[d]thiazol-6-yl)-2-tert-butoxyacetate

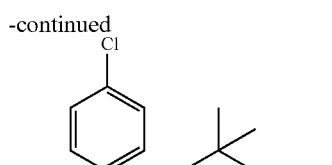

(S)-2-(2-(1-benzyl-3-methyl-1H-indazol-5-yl)-
7-(4-chlorophenyl)-5-methylbenzo[d]thiazol-6-yl)-
2-tert-butoxyacetic acid
314

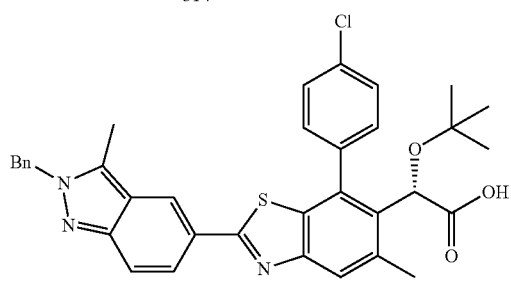

(S)-2-(2-(2-benzyl-3-methyl-2H-indazol-5-yl)-
7-(4-chlorophenyl)-5-methylbenzo[d]thiazol-6-yl)-
2-tert-butoxyacetic acid
315

Preparation of (S)-ethyl 2-tert-butoxy-2-(7-(4-chlorophenyl)-5-methyl-2-(3-methyl-1H-indazol-5-yl)benzo[d]thiazol-6-yl)acetate: Prepared in a manner similar to (S)-ethyl 2-tert-butoxy-2-(7-(4-chlorophenyl)-2-(1,3-dimethyl-1H-indazol-6-yl)-5-methylbenzo[d]thiazol-6-yl)acetate, but using 3-methyl-1H-indazol-5-ylboronic acid instead of 1,3-dimethyl-1H-indazol-6-ylboronic acid. $^1$H NMR (400 MHz, CDCl$_3$) δ 8.35 (s, 1H), 8.07 (dd, J=8.8, 1.4 Hz, 1H), 7.86 (s, 1H), 7.59-7.44 (m, 5H), 5.17 (s, 1H), 4.22 (dtt, J=10.8, 7.4, 3.7 Hz, 2H), 2.64 (s, 3H), 2.60 (s, 3H), 1.26 (t, J=7.1 Hz, 3H), 0.99 (s, 9H).

Preparation of (S)-ethyl 2-(2-(1-benzyl-3-methyl-1H-indazol-5-yl)-7-(4-chlorophenyl)-5-methylbenzo[d]thiazol-6-yl)-2-tert-butoxyacetate and (S)-ethyl 2-(2-(2-benzyl-3-methyl-2H-indazol-5-yl)-7-(4-chlorophenyl)-5-methylbenzo[d]thiazol-6-yl)-2-tert-butoxyacetate: To a stirring solution of (S)-ethyl 2-tert-butoxy-2-(7-(4-chlorophenyl)-5-methyl-2-(3-methyl-1H-indazol-5-yl)benzo[d]thiazol-6-yl)acetate (219 mg, 0.4 mmol) in ACN (5 mL) was added K$_2$CO$_3$ (166 mg, 1.2 mmol) and benzyl bromide (71 μL, 0.6 mmol). The reaction was then heated to 75° C. for 27 hours. After cooling to room temperature, the solids were filtered off, the crude reaction was concentrated and purified by column chromatography (gradient 0 to 20% EtOAc in hexanes) to give (S)-ethyl 2-(2-(1-benzyl-3-methyl-1H-indazol-5-yl)-7-(4-chlorophenyl)-5-methylbenzo[d]thiazol-6-yl)-2-tert-butoxyacetate. $^1$H NMR (400 MHz, CDCl$_3$) δ 8.40 (s, 1H), 8.05 (d, J=8.9 Hz, 1H), 7.92 (s, 1H), 7.60-7.45 (m, 4H), 7.35-7.27 (m, 4H), 7.22-7.18 (m, 2H), 5.54 (s, 2H), 5.16 (s, 1H), 4.21 (dtt, J=10.9, 7.4, 3.7 Hz, 2H), 2.63 (s, 3H), 2.60 (s, 3H), 1.26 (t, J=7.1 Hz, 3H), 0.98 (s, 9H).

(S)-ethyl 2-(2-(2-benzyl-3-methyl-2H-indazol-5-yl)-7-(4-chlorophenyl)-5-methylbenzo[d]thiazol-6-yl)-2-tert-butoxyacetate was also isolated. $^1$H NMR (400 MHz, CDCl$_3$) δ 8.42 (s, 1H), 7.92 (d, J=9.4 Hz, 2H), 7.71 (d, J=9.2 Hz, 1H), 7.62-7.43 (m, 4H), 7.36-7.28 (m, 3H), 7.17 (dd, J=7.5, 1.0 Hz, 2H), 5.61 (s, 2H), 5.16 (s, 1H), 4.21 (ddt, J=10.7, 7.0, 3.6 Hz, 2H), 2.61 (s, 3H), 2.60 (s, 3H), 1.25 (t, J=7.1 Hz, 3H), 0.98 (s, 9H).

Preparation of (S)-2-(2-(1-benzyl-3-methyl-1H-indazol-5-yl)-7-(4-chlorophenyl)-5-methylbenzo[d]thiazol-6-yl)-2-tert-butoxyacetic acid: Prepared in a manner similar to (S)-2-tert-butoxy-2-(7-(4-chlorophenyl)-2-(1,3-dimethyl-1H-indazol-6-yl)-5-methylbenzo[d]thiazol-6-yl)acetic acid, but using (S)-ethyl 2-(2-(1-benzyl-3-methyl-1H-indazol-5-yl)-7-(4-chlorophenyl)-5-methylbenzo[d]thiazol-6-yl)-2-tert-butoxyacetate instead of (S)-ethyl 2-tert-butoxy-2-(7-(4-chlorophenyl)-2-(1,3-dimethyl-1H-indazol-6-yl)-5-methylbenzo[d]thiazol-6-yl)acetate. LCMS-ESI$^+$: calc'd for C$_{35}$H$_{33}$ClN$_3$O$_3$S: 610.2 (M+H$^+$); found: 610.3 (M+H$^+$). $^1$H NMR (400 MHz, CD$_3$OD) δ 8.47 (s, 1H), 8.12 (dd, J=7.6, 1.6 Hz, 1H), 7.89 (s, 1H), 7.78 (d, J=10 Hz, 1H), 7.69-7.62 (m, 4H), 7.40-7.27 (m, 4H), 5.66 (s, 2H), 5.34 (s, 1H), 2.69 (s, 3H), 2.68 (s, 3H), 0.98 (s, 9H).

Preparation of (S)-2-(2-(2-benzyl-3-methyl-2H-indazol-5-yl)-7-(4-chlorophenyl)-5-methylbenzo[d]thiazol-6-yl)-2-tert-butoxyacetic acid: Prepared in a manner similar to (S)-2-tert-butoxy-2-(7-(4-chlorophenyl)-2-(1,3-dimethyl-1H-indazol-6-yl)-5-methylbenzo[d]thiazol-6-yl)acetic acid, but using (S)-ethyl 2-(2-(2-benzyl-3-methyl-2H-indazol-5-yl)-7-(4-chlorophenyl)-5-methylbenzo[d]thiazol-6-yl)-2-tert-butoxyacetate instead of (S)-ethyl 2-tert-butoxy-2-(7-(4-chlorophenyl)-2-(1,3-dimethyl-1H-indazol-6-yl)-5-methylbenzo[d]thiazol-6-yl)acetate. LCMS-ESI$^+$: calc'd for C$_{35}$H$_{33}$ClN$_3$O$_3$S: 610.2 (M+H$^+$); found: 610.3 (M+H$^+$). $^1$H NMR (400 MHz, CD$_3$OD) δ 8.36 (s, 1H), 7.99 (dd, J=9.1, 1.6 Hz, 1H), 7.80 (s, 1H), 7.69 (d, J=8.6 Hz, 1H), 7.65 (d, J=9.1 Hz, 1H), 7.59 (t, J=3.4 Hz, 3H), 7.38-7.26 (m, 3H), 7.17 (d, J=7.0 Hz, 2H), 5.65 (s, 2H), 5.26 (s, 1H), 2.64 (s, 3H), 2.61 (s, 3H), 0.98 (s, 9H).

Example 167

Preparation of (S)-2-tert-butoxy-2-(7-(4-chlorophenyl)-5-methyl-2-(1-methyl-1H-benzo[d][1,2,3]triazol-6-yl)benzo[d]thiazol-6-yl)acetic acid (316)

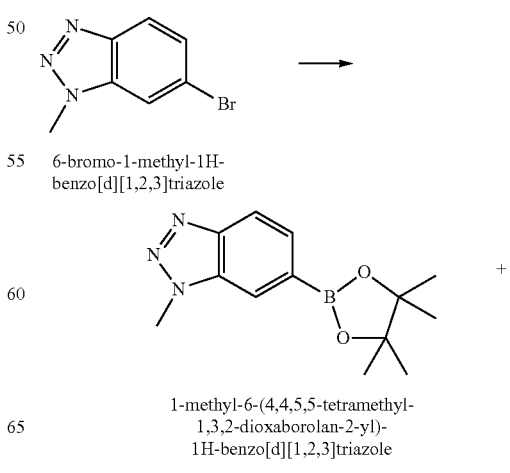

6-bromo-1-methyl-1H-benzo[d][1,2,3]triazole 1-methyl-6-(4,4,5,5-tetramethyl-1,3,2-dioxaborolan-2-yl)-1H-benzo[d][1,2,3]triazole

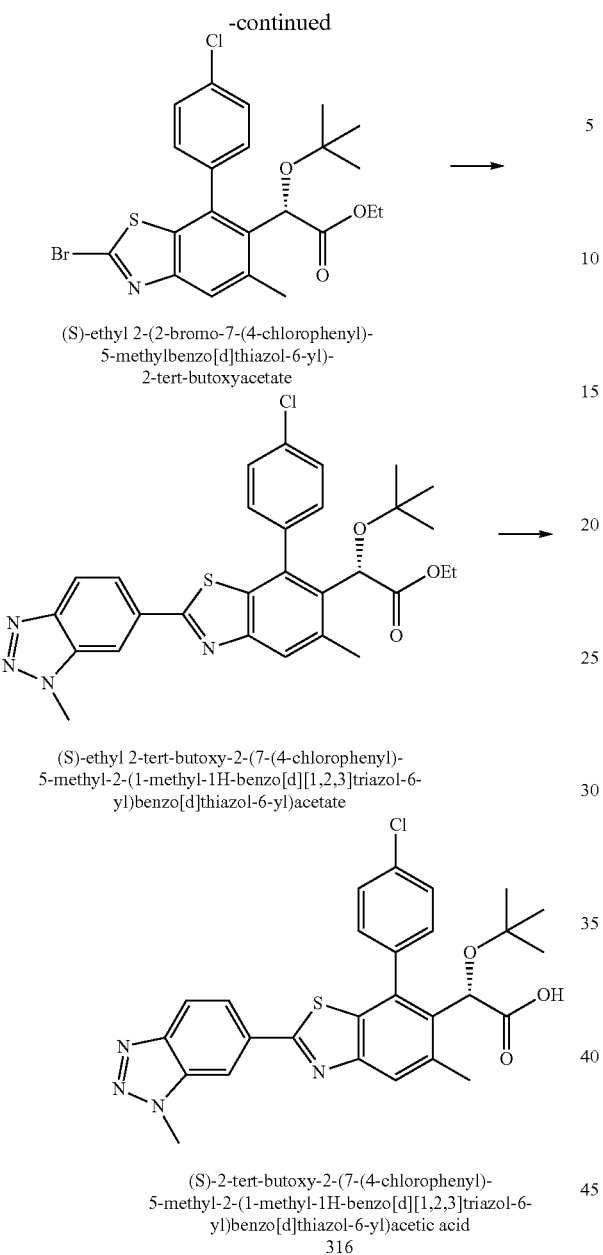

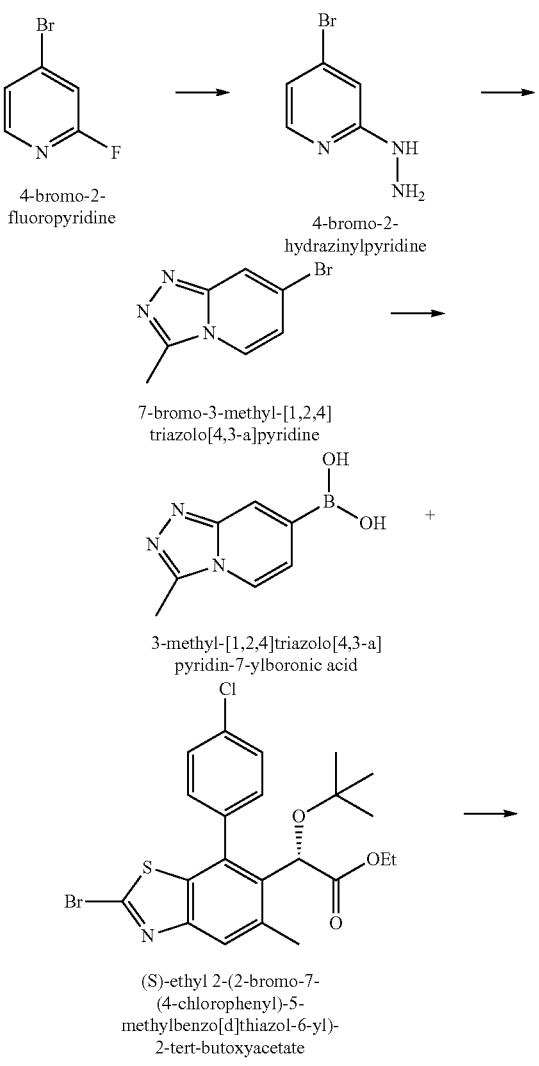

7.60-7.45 (m, 4H), 5.18 (s, 1H), 4.39 (s, 3H), 4.28-4.17 (m, 2H), 2.63 (s, 3H), 1.26 (t, J=8 Hz, 3H), 0.99 (s, 9H).

Preparation of (S)-2-tert-butoxy-2-(7-(4-chlorophenyl)-5-methyl-2-(1-methyl-1H-benzo[d][1,2,3]triazol-6-yl)benzo[d]thiazol-6-yl)acetic acid: Prepared in a manner similar to (S)-2-tert-butoxy-2-(7-(4-chlorophenyl)-5-methyl-2-(1-methyl-1H-benzo[d][1,2,3]triazol-5-yl)benzo[d]thiazol-6-yl) acetic acid, but using (S)-ethyl 2-tert-butoxy-2-(7-(4-chlorophenyl)-5-methyl-2-(1-methyl-1H-benzo[d][1,2,3]triazol-6-yl)benzo[d]thiazol-6-yl)acetate instead of (S)-ethyl 2-tert-butoxy-2-(7-(4-chlorophenyl)-5-methyl-2-(1-methyl-1H-benzo[d][1,2,3]triazol-5-yl)benzo[d]thiazol-6-yl)acetate. LCMS-ESI$^+$: calc'd for $C_{27}H_{26}ClN_4O_3S$: 521.0 (M+H$^+$); Found: 521.2 (M+H$^+$). $^1$H NMR (400 MHz, CD$_3$OD) δ 8.44 (s, 1H), 8.12 (dd, J=8.8, 1.4 Hz, 1H), 8.08 (d, J=8.8 Hz, 1H), 7.87 (s, 1H), 7.70 (d, J=9.5 Hz, 1H), 7.64-7.57 (m, 3H), 5.27 (s, 1H), 4.39 (s, 3H), 2.62 (s, 3H), 0.98 (s, 9H).

Example 168

Preparation of (S)-2-tert-butoxy-2-(7-(4-chlorophenyl)-5-methyl-2-(3-methyl-[1,2,4]triazolo[4,3-a]pyridin-7-yl)benzo[d]thiazol-6-yl)acetic acid (317)

Preparation of 1-methyl-6-(4,4,5,5-tetramethyl-1,3,2-dioxaborolan-2-yl)-1H-benzo[d][1,2,3]triazole: Prepared in a manner similar to 1-methyl-3-phenyl-5-(4,4,5,5-tetramethyl-1,3,2-dioxaborolan-2-yl)-1H-indazole, but using 6-bromo-1-methyl-1H-benzo[d][1,2,3]triazole instead of 5-bromo-1-methyl-3-phenyl-1H-indazole. $^1$H NMR (400 MHz, CDCl$_3$) δ 8.04 (dd, J=6.8, 1.6 Hz, 2H), 7.79 (d, J=8.6 Hz, 1H), 4.33 (s, 3H), 1.39 (s, 12H).

Preparation of (S)-ethyl 2-tert-butoxy-2-(7-(4-chlorophenyl)-5-methyl-2-(1-methyl-1H-benzo[d][1,2,3]triazol-6-yl)benzo[d]thiazol-6-yl)acetate: Prepared in a manner similar to (S)-ethyl 2-tert-butoxy-2-(7-(4-chlorophenyl)-5-methyl-2-(1-methyl-1H-benzo[d][1,2,3]triazol-5-yl)benzo[d]thiazol-6-yl)acetate, but using 1-methyl-6-(4,4,5,5-tetramethyl-1,3,2-dioxaborolan-2-yl)-1H-benzo[d][1,2,3]triazole instead of 1-methyl-5-(4,4,5,5-tetramethyl-1,3,2-dioxaborolan-2-yl)-1H-benzo[d][1,2,3]triazole. $^1$H NMR (400 MHz, CDCl$_3$) δ 8.46 (s, 1H), 8.11 (d, J=8.7 Hz, 1H), 7.96 (d, J=7.6 Hz, 2H),

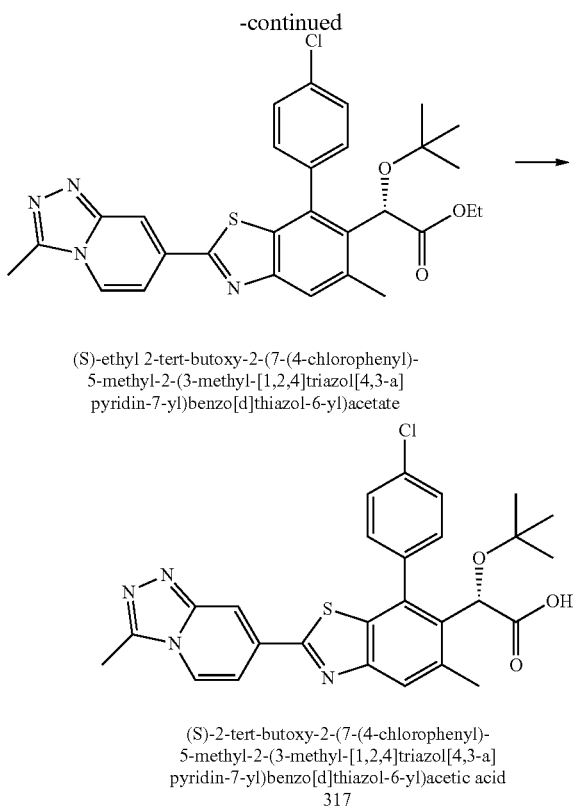

(S)-ethyl 2-tert-butoxy-2-(7-(4-chlorophenyl)-
5-methyl-2-(3-methyl-[1,2,4]triazol[4,3-a]
pyridin-7-yl)benzo[d]thiazol-6-yl)acetate (S)-2-tert-butoxy-2-(7-(4-chlorophenyl)-
5-methyl-2-(3-methyl-[1,2,4]triazol[4,3-a]
pyridin-7-yl)benzo[d]thiazol-6-yl)acetic acid
317

Preparation of 4-bromo-2-hydrazinylpyridine: To a stirring solution of hydrazine monohydrate (16 mL) was added 4-bromo-2-fluoropyridine (3.4 mL, 33.1 mmol). After stirring for 23 hours at room temperature, 4M NaOH (15 mL) and water (30 mL) were added, and the thick suspension was stirred vigorously for 15 minutes. The precipitated solids were filtered off and dried to give the product. $^1$H NMR (400 MHz, CDCl$_3$) δ 7.91 (d, J=5.4 Hz, 1H), 6.97 (d, J=1.3 Hz, 1H), 6.80 (dd, J=5.4, 1.5 Hz, 1H), 6.05 (br s, 1H), 3.65 (br s, 2H).

Preparation of 7-bromo-3-methyl-[1,2,4]triazolo[4,3-a]pyridine: To a vial flushed with argon was added 4-bromo-2-hydrazinylpyridine (1.88 g, 10 mmol) and acetic acid (2.5 mL). The mixture was refluxed at 125° C. under argon for 16 hours. After cooling to room temperature, acetic acid was distilled off, and to the residue was added saturated NaHCO$_3$ (150 mL) and DCM (150 mL). The aqueous layer was extracted with DCM, the organic extracts were combined, dried over MgSO$_4$, and concentrated to give the product. $^1$H NMR (400 MHz, CDCl$_3$) δ 7.95-7.90 (m, 1H), 7.73 (d, J=7.3 Hz, 1H), 6.94 (dd, J=7.3, 1.7 Hz, 1H), 2.74 (s, 3H).

Preparation of 3-methyl-[1,2,4]triazolo[4,3-a]pyridin-7-ylboronic acid: To a vial flushed with argon was added 7-bromo-3-methyl-[1,2,4]triazolo[4,3-a]pyridine (318 mg, 1.5 mmol), PdCl$_2$(dppf).DCM (245 mg, 0.3 mmol), bis(pinacolato)diboron (508 mg, 2 mmol), and KOAc (442 mg, 4.5 mmol). Anhydrous dioxane (8 mL) was added, and the mixture was heated to 100° C. for 3 hours. After cooling to room temperature, the mixture was filtered over a plug of Celite, and concentrated to provide the crude product, which was used directly without further purification. LCMS-ESI$^+$: calc'd for C$_7$H$_9$BN$_3$O$_2$: 178.1 (M+H$^+$); Found: 178.1 (M+H$^+$).

Preparation of (S)-ethyl 2-tert-butoxy-2-(7-(4-chlorophenyl)-5-methyl-2-(3-methyl-[1,2,4]triazolo[4,3-a]pyridin-7-yl)benzo[d]thiazol-6-yl)acetate: Prepared in a manner similar to (S)-ethyl 2-tert-butoxy-2-(7-(4-chlorophenyl)-2-(1,3-dimethyl-1H-indazol-6-yl)-5-methylbenzo[d]thiazol-6-yl)acetate, but using 3-methyl-[1,2,4]triazolo[4,3-a]pyridin-7-ylboronic acid instead of 1,3-dimethyl-1H-indazol-6-ylboronic acid. $^1$H NMR (400 MHz, CDCl$_3$) δ 8.25 (s, 1H), 7.94 (d, J=6.0 Hz, 1H), 7.91 (s, 1H), 7.75 (s, 1H), 7.58-7.49 (m, 3H), 7.49-7.44 (m, 1H), 5.17 (s, 1H), 4.26-4.16 (m, 2H), 2.81 (s, 3H), 2.61 (s, 3H), 1.26 (t, J=7.1 Hz, 3H), 0.98 (s, 9H).

Preparation of (S)-2-tert-butoxy-2-(7-(4-chlorophenyl)-5-methyl-2-(3-methyl-[1,2,4]triazolo[4,3-a]pyridin-7-yl)benzo[d]thiazol-6-yl)acetic acid: Prepared in a manner similar to (S)-2-tert-butoxy-2-(7-(4-chlorophenyl)-2-(1,3-dimethyl-1H-indazol-6-yl)-5-methylbenzo[d]thiazol-6-yl)acetic acid, but using (S)-ethyl 2-tert-butoxy-2-(7-(4-chlorophenyl)-5-methyl-2-(3-methyl-[1,2,4]triazolo[4,3-a]pyridin-7-yl)benzo[d]thiazol-6-yl)acetate instead of (S)-ethyl 2-tert-butoxy-2-(7-(4-chlorophenyl)-2-(1,3-dimethyl-1H-indazol-6-yl)-5-methylbenzo[d]thiazol-6-yl)acetate. LCMS-ESI$^+$: calc'd for C$_{27}$H$_{26}$ClN$_4$O$_3$S: 521.0 (M+H$^+$); Found: 521.2 (M+H$^+$). $^1$H NMR (400 MHz, CD$_3$OD) δ 8.61 (d, J=7.3 Hz, 1H), 8.42 (s, 1H), 7.97 (d, J=7.5 Hz, 2H), 7.74-7.67 (m, 1H), 7.66-7.58 (m, 3H), 5.28 (s, 1H), 2.85 (s, 3H), 2.64 (s, 3H), 0.98 (s, 9H).

Example 169

Preparation of (S)-2-tert-butoxy-2-(7-(4-chlorophenyl)-5-methyl-2-(3-methyl-[1,2,3]triazolo[1,5-a]pyridin-5-yl)benzo[d]thiazol-6-yl)acetic acid (318)

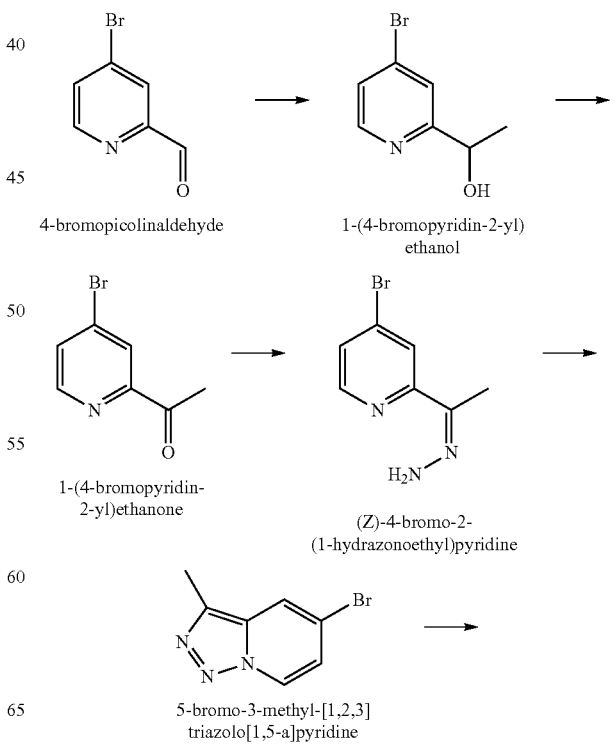

4-bromopicolinaldehyde 1-(4-bromopyridin-2-yl)ethanol 1-(4-bromopyridin-2-yl)ethanone (Z)-4-bromo-2-(1-hydrazonoethyl)pyridine 5-bromo-3-methyl-[1,2,3]triazolo[1,5-a]pyridine

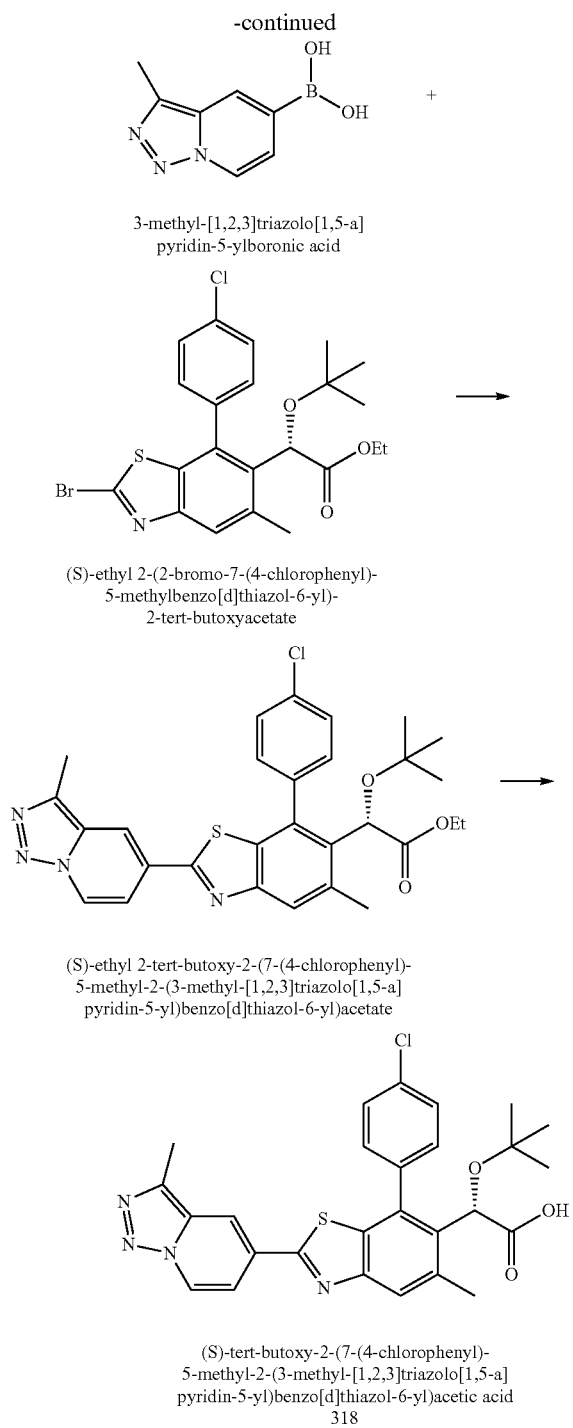

3-methyl-[1,2,3]triazolo[1,5-a]
pyridin-5-ylboronic acid (S)-ethyl 2-(2-bromo-7-(4-chlorophenyl)-
5-methylbenzo[d]thiazol-6-yl)-
2-tert-butoxyacetate (S)-ethyl 2-tert-butoxy-2-(7-(4-chlorophenyl)-
5-methyl-2-(3-methyl-[1,2,3]triazolo[1,5-a]
pyridin-5-yl)benzo[d]thiazol-6-yl)acetate (S)-tert-butoxy-2-(7-(4-chlorophenyl)-
5-methyl-2-(3-methyl-[1,2,3]triazolo[1,5-a]
pyridin-5-yl)benzo[d]thiazol-6-yl)acetic acid
318

Preparation of 1-(4-bromopyridin-2-yl)ethanol: An oven-dried flask was cooled under argon, and to it was added 4-bromopicolinaldehyde (2.98 g, 16 mmol) and anhydrous THF (50 mL). The mixture was cooled to −78° C., and 3M methylmagnesium bromide in Et$_2$O (6.4 mL) was added dropwise. The mixture was then allowed to warm slowly to room temperature, whereupon it was quenched with saturated NH$_4$Cl solution. The aqueous layer was extracted with EtOAc, dried over Na$_2$SO$_4$, concentrated, and purified by column chromatography (gradient 0 to 60% EtOAc in hexanes) to give the product. $^1$H NMR (400 MHz, CDCl$_3$) δ 8.36 (d, J=5.3 Hz, 1H), 7.57-7.48 (m, 1H), 7.38 (dd, J=5.3, 1.4 Hz, 1H), 4.88 (q, J=6.6 Hz, 1H), 3.84 (br s, 1H), 1.51 (d, J=6.6 Hz, 3H).

Preparation of 1-(4-bromopyridin-2-yl)ethanone: To a stirring solution of 1-(4-bromopyridin-2-yl)ethanol (2.93 g, 14.5 mmol) in DCM (50 mL) was added Dess-Martin periodinane (12.93 g, 30.5 mmol) portion-wise over several minutes. The reaction was then quenched with saturated 1:1 Na$_2$S$_2$O$_3$/NaHCO$_3$ solution (200 mL) and stirred until gas evolution ceased. The aqueous layer was extracted with DCM, dried over MgSO$_4$, and purified by column chromatography (gradient 0 to 10% EtOAc in hexanes) to give the product. $^1$H NMR (400 MHz, CDCl$_3$) δ 8.50 (d, J=5.2 Hz, 1H), 8.20 (d, J=1.9 Hz, 1H), 7.64 (dd, J=5.2, 1.9 Hz, 1H), 2.71 (s, 3H).

Preparation of (Z)-4-bromo-2-(1-hydrazonoethyl)pyridine: To a stirring solution of 1-(4-bromopyridin-2-yl)ethanone (2.4 g, 12 mmol) in MeOH (40 mL) was added hydrazine monohydrate (2.9 mL, 60 mmol) in one portion. After stirring at room temperature for 2 hours, the mixture was concentrated to afford the product. $^1$H NMR (400 MHz, CDCl$_3$) δ 8.34 (d, J=5.3 Hz, 1H), 8.14 (d, J=1.8 Hz, 1H), 7.33 (dd, J=5.3, 1.8 Hz, 1H), 5.66 (br s, 2H), 2.23 (s, 3H).

Preparation of 5-bromo-3-methyl-[1,2,3]triazolo[1,5-a]pyridine: To a stirring solution of (Z)-4-bromo-2-(1-hydrazonoethyl)pyridine (2.53 g, 11.8 mmol) in DCM (40 mL) was added (diacetoxyiodo)benzene (3.8 g, 11.8 mmol) in small portions over several minutes and stirred at room temperature for 45 minutes. The reaction was quenched with saturated 1:1 Na$_2$S$_2$O$_3$/NaHCO$_3$ solution (40 mL) and stirred until gas evolution ceased. The aqueous layer was extracted with DCM, dried over MgSO$_4$, and purified by column chromatography (gradient 0 to 45% EtOAc in hexanes) to afford the product. $^1$H NMR (400 MHz, CDCl$_3$) δ 8.50 (d, J=6.9 Hz, 2H), 7.79 (s, 2H), 6.97 (d, J=6.5 Hz, 2H), 2.57 (s, 7H).

Preparation of 3-methyl-[1,2,3]triazolo[1,5-a]pyridin-5-ylboronic acid: To a vial flushed with argon was added 5-bromo-3-methyl-[1,2,3]triazolo[1,5-a]pyridine (424 mg, 2 mmol), PdCl$_2$(dppf)-DCM (327 mg, 0.4 mmol), bis(pinacolato)diboron (660 mg, 2.6 mmol), and KOAc (589 mg, 6 mmol). Anhydrous dioxane (10 mL) was added, and the mixture was heated to 100° C. for 3 hours. After cooling to room temperature, the mixture was filtered over a plug of Celite, and concentrated to provide the crude product, which was used directly without further purification. LCMS-ESI$^+$: calc'd for C$_7$H$_9$BN$_3$O$_2$: 178.1 (M+H$^+$); Found: 178.04 (M+H$^+$).

Preparation of (S)-ethyl 2-tert-butoxy-2-(7-(4-chlorophenyl)-5-methyl-2-(3-methyl-[1,2,3]triazolo[1,5-a]pyridin-5-yl)benzo[d]thiazol-6-yl)acetate: Prepared in a manner similar to (S)-ethyl 2-tert-butoxy-2-(7-(4-chlorophenyl)-2-(1,3-dimethyl-1H-indazol-6-yl)-5-methylbenzo[d]thiazol-6-yl)acetate, but using 3-methyl-[1,2,3]triazolo[1,5-a]pyridin-5-ylboronic acid instead of 1,3-dimethyl-1H-indazol-6-ylboronic acid. $^1$H NMR (400 MHz, CDCl$_3$) δ 8.68 (d, J=7.4 Hz, 1H), 8.21 (s, 1H), 7.91 (s, 1H), 7.66 (dd, J=7.4, 1.6 Hz, 1H), 7.61-7.50 (m, 3H), 7.50-7.43 (m, 1H), 5.17 (s, 1H), 4.27-4.17 (m, 2H), 2.67 (s, 3H), 2.62 (s, 3H), 1.30-1.22 (m, 3H), 0.99 (s, 9H).

Preparation of (S)-2-tert-butoxy-2-(7-(4-chlorophenyl)-5-methyl-2-(3-methyl-[1,2,3]triazolo[1,5-a]pyridin-5-yl)benzo[d]thiazol-6-yl)acetic acid: Prepared in a manner similar to (S)-2-tert-butoxy-2-(7-(4-chlorophenyl)-2-(1,3-dimethyl-1H-indazol-6-yl)-5-methylbenzo[d]thiazol-6-yl)acetic acid, but using (S)-ethyl 2-tert-butoxy-2-(7-(4-chlorophenyl)-5-methyl-2-(3-methyl-[1,2,3]triazolo[1,5-a]pyridin-5-yl)benzo[d]thiazol-6-yl)acetate instead of (S)-ethyl 2-tert-butoxy-2-(7-(4-chlorophenyl)-2-(1,3-dimethyl- 1H-indazol-6-yl)-5-methylbenzo[d]thiazol-6-yl)acetate. LCMS-ESI⁺: calc'd for $C_{27}H_{26}ClN_4O_3S$: 521.0 (M+H⁺); Found: 521.2 (M+H⁺). NMR (400 MHz, CD₃OD) δ 8.87 (d, J=7.4 Hz, 1H), 8.43 (s, 1H), 7.86 (s, 1H), 7.78 (dd, J=7.4, 1.8 Hz, 1H), 7.73-7.67 (m, 1H), 7.65-7.56 (m, 3H), 5.27 (s, 1H), 2.63 (s, 3H), 2.61 (s, 3H), 0.98 (s, 9H).

Example 170

Preparation of (S)-2-tert-butoxy-2-(7-(4-chlorophenyl)-2-(1,3-dimethylimidazo[1,5-a]pyridin-7-yl)-5-methylbenzo[d]thiazol-6-yl)acetic acid (319)

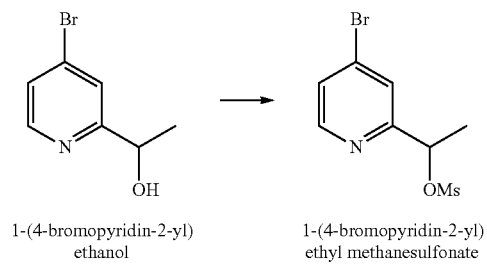

1-(4-bromopyridin-2-yl) ethanol → 1-(4-bromopyridin-2-yl) ethyl methanesulfonate

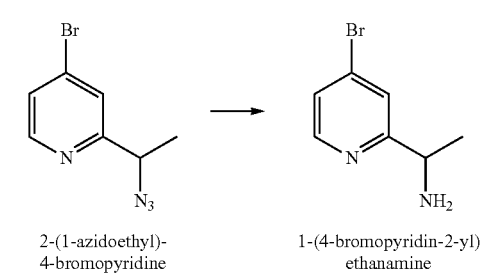

2-(1-azidoethyl)-4-bromopyridine → 1-(4-bromopyridin-2-yl) ethanamine

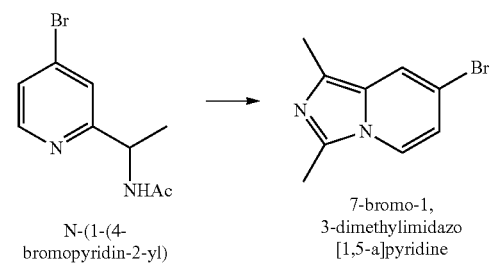

N-(1-(4-bromopyridin-2-yl)ethyl)acetamide → 7-bromo-1,3-dimethylimidazo[1,5-a]pyridine

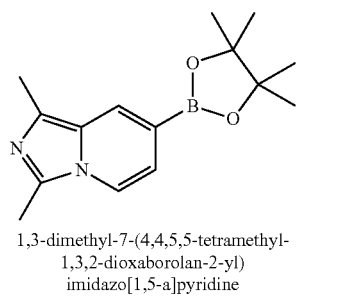

1,3-dimethyl-7-(4,4,5,5-tetramethyl-1,3,2-dioxaborolan-2-yl)imidazo[1,5-a]pyridine

+

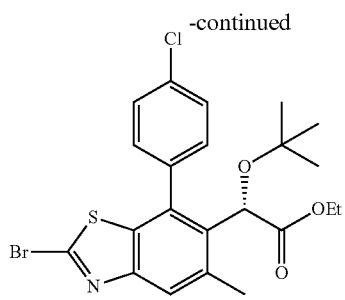

(S)-ethyl 2-(2-bromo-7-(4-chlorophenyl)-5-methylbenzo[d]thiazol-6-yl)-2-tert-butoxyacetate

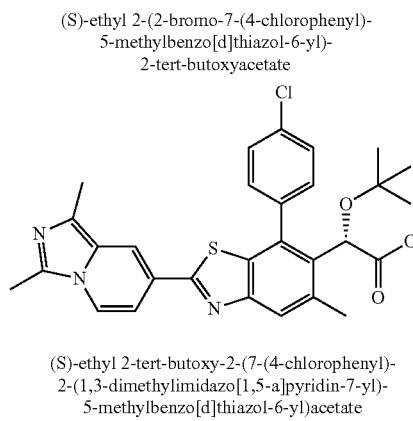

(S)-ethyl 2-tert-butoxy-2-(7-(4-chlorophenyl)-2-(1,3-dimethylimidazo[1,5-a]pyridin-7-yl)-5-methylbenzo[d]thiazol-6-yl)acetate

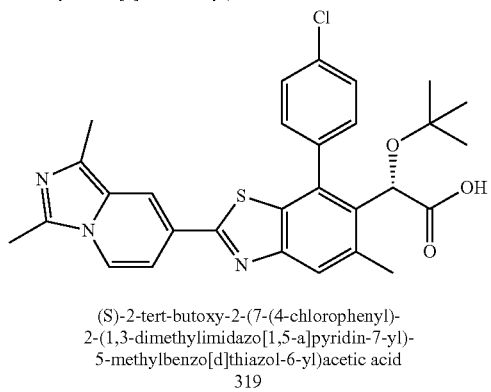

(S)-2-tert-butoxy-2-(7-(4-chlorophenyl)-2-(1,3-dimethylimidazo[1,5-a]pyridin-7-yl)-5-methylbenzo[d]thiazol-6-yl)acetic acid 319

Preparation of 1-(4-bromopyridin-2-yl)ethyl methanesulfonate: A stirring solution of the 1-(4-bromopyridin-2-yl) ethanol (3.72 g, 18.41 mmol and DMAP (4.5 g, 36.82 mmol) in 75 mL of dichloromethane was cooled to 0° C. To it was added mesyl chloride (1.71 mL, 22.09 mmol) dropwise. The mixture was stirred at 0° C. for 10 minutes, then warmed to room temperature and stirred for 15 min. The reaction was quenched with 50 mL ice water, the layers were separated, and the aqueous layer was extracted with dichloromethane (50 mL). The organics were combined, washed with water and brine, dried over Na₂SO₄, and purified by column chromatography (gradient 0 to 45% EtOAc/hexanes) to afford the product. ¹H NMR (400 MHz, CDCl₃) δ 8.40 (d, J=5.3 Hz, 1H), 7.64 (d, J=1.6 Hz, 1H), 7.45 (dd, J=5.3, 1.8 Hz, 1H), 5.75 (q, J=6.6 Hz, 1H), 3.00 (s, 3H), 1.75 (d, J=6.6 Hz, 3H).

Preparation of 2-(1-azidoethyl)-4-bromopyridine: To a stirring solution of 1-(4-bromopyridin-2-yl)ethyl methanesulfonate (4.68 g, 16.71 mmol) in anhydrous DMF (45 mL) DMF was added sodium azide (2.17 g, 33.41 mmol) and stirred at room temperature for 2 hours. The reaction was then diluted with 80 mL of water, then extracted with EtOAc (2×75 mL). The organic extracts were combined, washed with water (50 mL) and brine (50 mL), dried over Na₂SO₄, and concentrated to give the crude product which was used directly without further purification. $^1$H NMR (400 MHz, CDCl$_3$) δ 8.40 (d, J=5.2 Hz, 1H), 7.55 (s, 1H), 7.41 (d, J=5.2 Hz, 1H), 4.65 (q, J=6.8 Hz, 1H), 1.60 (dd, J=6.8, 0.8 Hz, 3H).

Preparation of 1-(4-bromopyridin-2-yl)ethanamine: To a solution of 2-(1-azidoethyl)-4-bromopyridine (4.08 g, 16.54 mmol) in THF (100 mL) and water (10 mL) was added polymer-bound triphenylphosphine (200-400 mesh, ~3 mmol/g loading; 10.97 g, 32.94 mmol). The suspension was then stirred at room temperature for 7 hours. The reaction was filtered over a coarse frit twice, then concentrated to afford the crude product which was used without further purification. $^1$H NMR (400 MHz, CDCl$_3$) δ 8.35 (d, J=5.2 Hz, 1H), 7.52 (s, 1H), 7.32 (dd, J=5.2, 1.6 Hz, 1H), 4.13 (q, J=6.7 Hz, 1H), 1.83 (br s, 2H), 1.41 (d, J=6.7 Hz, 3H).

Preparation of N-(1-(4-bromopyridin-2-yl)ethyl)acetamide: To a solution of 1-(4-bromopyridin-2-yl)ethanamine (2.3 g, 11.44 mmol) in chloroform (30 mL) was added acetic anhydride (2.16 mL, 22.88 mmol) dropwise at 0° C. The reaction was then quenched with ice water (40 mL) and extracted with chloroform (2×50 mL). The organic extracts were combined, then washed with 1M NaOH (50 mL), dried over Na$_2$SO$_4$, concentrated, and purified by column chromatography (gradient 0 to 5% MeOH/DCM) to afford the product. $^1$H NMR (400 MHz, CDCl$_3$) δ 8.35 (d, J=5.3 Hz, 1H), 7.42 (s, 1H), 7.36 (dd, J=5.3, 1.7 Hz, 1H), 6.71 (br s, 1H), 5.10 (p, J=7.0 Hz, 1H), 2.02 (s, 3H), 1.45 (d, J=6.8 Hz, 3H).

Preparation of 7-bromo-1,3-dimethylimidazo[1,5-a]pyridine: N-(1-(4-bromopyridin-2-yl)ethyl)acetamide (2.28 g, 9.38 mmol) was suspended in anhydrous benzene (20 mL), then phosphorus oxychloride (2.2 mL, 23.6 mmol) was added and the reaction heated to reflux for 3 hours. The crude reaction was then added portion-wise to 1M potassium carbonate solution (60 mL) and stirred until gas evolution ceased. The pH was then adjusted to pH 10 with potassium carbonate. The aqueous layer was extracted with DCM (50 mL×2), the organic were combined, dried over Na$_2$SO$_4$, and concentrated to afford the product, which was used without further purification. LCMS-ESI$^+$: calc'd for C$_9$H$_{10}$BrN$_2$: 225.1 (M+H$^+$); Found: 225.05 (M+H$^+$).

Preparation of 1,3-dimethyl-7-(4,4,5,5-tetramethyl-1,3,2-dioxaborolan-2-yl) imidazo[1,5-a]pyridine: To a vial flushed with argon was added 7-bromo-1,3-dimethylimidazo[1,5-a]pyridine (360 mg, 1.6 mmol), PdCl$_2$(dppf).DCM (340 mg, 0.416 mmol), bis(pinacolato)diboron (609 mg, 2.4 mmol), and KOAc (628 mg, 6.4 mmol). Anhydrous dioxane (10 mL) was added, and the mixture was heated to 100° C. for 3 hours. After cooling to room temperature, the mixture was filtered over a plug of Celite, and concentrated to provide the crude product, which was used directly without further purification. LCMS-ESI$^+$: calc'd for C$_{15}$H$_{22}$BN$_2$O$_2$: 273.2 (M+H$^+$); Found: 273.21 (M+H$^+$).

Preparation of (S)-ethyl 2-tert-butoxy-2-(7-(4-chlorophenyl)-2-(1,3-dimethylimidazo[1,5-a]pyridin-7-yl)-5-methylbenzo[d]thiazol-6-yl)acetate: Prepared in manner similar to (S)-ethyl 2-tert-butoxy-2-(7-(4-chlorophenyl)-5-methyl-2-(1-methyl-1H-benzo[d][1,2,3]triazol-5-yl)benzo[d]thiazol-6-yl)acetate, but using 1,3-dimethyl-7-(4,4,5,5-tetramethyl-1,3,2-dioxaborolan-2-yl)imidazo[1,5-a]pyridine instead of 1-methyl-5-(4,4,5,5-tetramethyl-1,3,2-dioxaborolan-2-yl)-1H-benzo[d][1,2,3]triazole. $^1$H NMR (400 MHz, CDCl$_3$) δ 7.94 (s, 1H), 7.82 (s, 1H), 7.61 (d, J=7.6 Hz, 1H), 7.51 (dt, J=14.3, 7.8 Hz, 5H), 5.15 (s, 1H), 4.21 (dd, J=5.9, 3.5 Hz, 2H), 2.67 (s, 3H), 2.59 (s, 3H), 2.54 (s, 3H), 1.25 (t, J=6.0 Hz, 3H), 0.98 (s, 9H).

Preparation of (S)-2-tert-butoxy-2-(7-(4-chlorophenyl)-2-(1,3-dimethylimidazo[1,5-a]pyridin-7-yl)-5-methylbenzo[d]thiazol-6-yl)acetic acid: Prepared in a manner similar to (S)-2-tert-butoxy-2-(7-(4-chlorophenyl)-5-methyl-2-(1-methyl-1H-benzo[d][1,2,3]triazol-5-yl)benzo[d]thiazol-6-yl) acetic acid, but using (S)-ethyl 2-tert-butoxy-2-(7-(4-chlorophenyl)-2-(1,3-dimethylimidazo[1,5-a]pyridin-7-yl)-5-methylbenzo[d]thiazol-6-yl)acetate instead of (S)-ethyl 2-tert-butoxy-2-(7-(4-chlorophenyl)-5-methyl-2-(1-methyl-1H-benzo[d][1,2,3]triazol-5-yl)benzo[d]thiazol-6-yl)acetate. LCMS-ESI$^+$: calc'd for C$_{29}$H$_{29}$ClN$_3$O$_3$S: 534.1 (M+H$^+$); Found: 534.2 (M+H$^+$). $^1$H NMR (400 MHz, CD$_3$OD) δ 8.33 (s, 1H), 8.28 (d, J=7.7 Hz, 1H), 7.87 (s, 1H), 7.76-7.65 (m, 2H), 7.60 (d, J=6.4 Hz, 3H), 5.27 (s, 1H), 2.86 (s, 3H), 2.65 (s, 3H), 2.62 (s, 3H), 0.98 (s, 9H).

Example 171

Preparation of 1-(5-bromo-2-fluorophenyl)-2-methylpropan-1-ol (320)

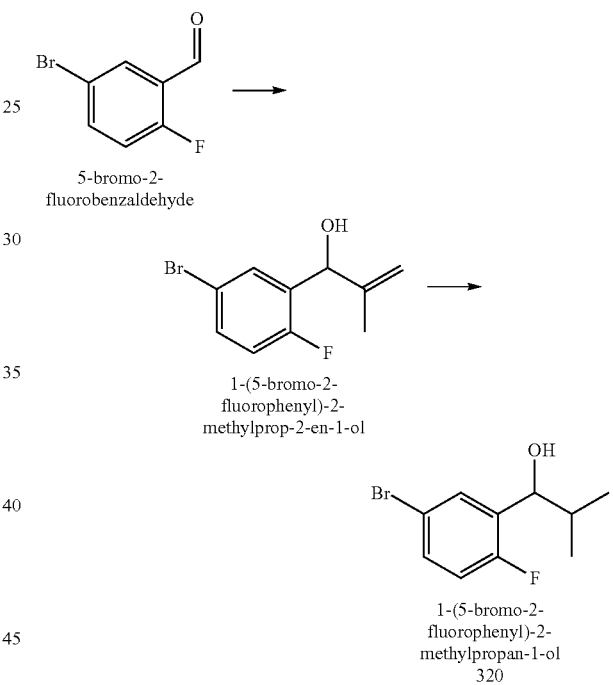

5-bromo-2-fluorobenzaldehyde 1-(5-bromo-2-fluorophenyl)-2-methylprop-2-en-1-ol 1-(5-bromo-2-fluorophenyl)-2-methylpropan-1-ol
320

Preparation of 1-(5-bromo-2-fluorophenyl)-2-methylprop-2-en-1-ol: Prepared in a similar manner to (5-bromo-2-fluorophenyl)(phenyl)methanol, but using 0.5M isopropenylmagnesium bromide in THF instead of 1M phenylmagnesium bromide in THF. $^1$H NMR (400 MHz, CDCl$_3$) δ 7.60 (dd, J=6.4, 2.6 Hz, 1H), 7.36 (ddd, J=8.7, 4.5, 2.6 Hz, 1H), 6.96-6.88 (m, 1H), 5.42 (s, 1H), 5.17 (s, 1H), 4.99 (s, 1H), 2.10 (br s, 1H), 1.66 (s, 3H).

Preparation of 1-(5-bromo-2-fluorophenyl)-2-methylpropan-1-ol: A flask was charged with 1-(5-bromo-2-fluorophenyl)-2-methylprop-2-en-1-ol (5.39 g, 22 mmol), THF (120 mL), and water (120 mL). With vigorous stirring, p-toluenesulfonylhydrazide (20.5 g, 110 mmol) and NaOAc (18.05 g, 220 mmol) were added successively. The mixture was then refluxed at 70° C. for 20 hours. After cooling to room temperature, saturated K$_2$CO$_3$ solution was added, and the mixture stirred for 5 minutes. The aqueous layer was then extracted with Et$_2$O, dried over MgSO$_4$, and purified by column chromatography (gradient 0 to 15% EtOAc in hexanes)

to give the product. $^1$H NMR (400 MHz, CDCl$_3$) δ 7.58 (dd, J=6.3, 2.6 Hz, 1H), 7.34 (ddd, J=8.5, 4.5, 2.6 Hz, 1H), 6.94-6.86 (m, 1H), 4.71 (d, J=6.6 Hz, 1H), 1.97 (dq, J=13.5, 6.7 Hz, 1H), 1.84 (br s, 1H), 0.98 (d, J=6.7 Hz, 3H), 0.88 (d, J=6.8 Hz, 3H).

Example 172

Preparation of (5-bromo-2-fluorophenyl)(pyrazin-2-yl)methanol (321)

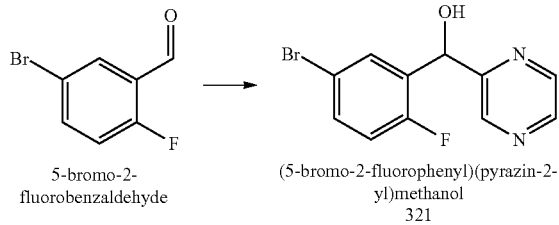 [SMILES: O=Cc1cc(Br)ccc1F ; OC(c1cnccn1)c1cc(Br)ccc1F]

5-bromo-2-fluorobenzaldehyde (5-bromo-2-fluorophenyl)(pyrazin-2-yl)methanol
321

Preparation of (5-bromo-2-fluorophenyl)(pyrazin-2-yl)methanol: To an oven-dried flask was added anhydrous THF (60 mL) and 2-iodopyrazine (3 mL, 20 mmol). The flask was cooled to 0° C., and 2M n-butylmagnesium chloride in THF (11 mL) was then added dropwise over several minutes. The mixture was stirred at 0° C. for 30 minutes, and then 5-bromo-2-fluorobenzaldehyde (2.4 mL, 20 mmol) was added. After stirring for 2 hours at 0° C., the reaction was quenched with saturated aqueous NH$_4$Cl. The aqueous layer was extracted with EtOAc, dried over MgSO$_4$, and purified by column chromatography (gradient 0 to 50% EtOAc in hexanes) to afford the product. $^1$H NMR (400 MHz, CDCl$_3$) δ 8.65 (s, 1H), 8.55 (s, 2H), 7.59 (dd, J=6.4, 2.5 Hz, 1H), 7.46-7.35 (m, 1H), 6.98 (t, J=9.2 Hz, 1H), 6.17 (s, 1H).

Example 173

Preparation of (2S)-2-tert-butoxy-2-(7-(4-chlorophenyl)-2-(2-(4-chlorophenyl)-2-methylmorpholino)-5-methylbenzo[d]thiazol-6-yl)acetic acid (322)

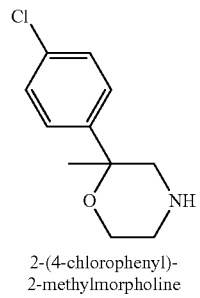

2-(4-chlorophenyl)-2-methylmorpholine

+

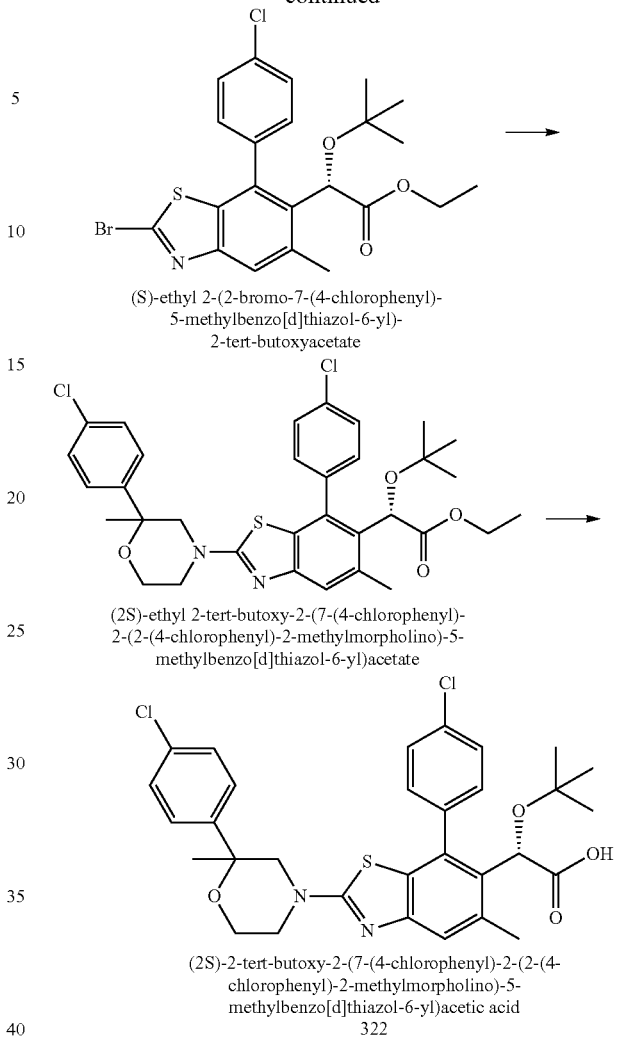

(S)-ethyl 2-(2-bromo-7-(4-chlorophenyl)-5-methylbenzo[d]thiazol-6-yl)-2-tert-butoxyacetate (2S)-ethyl 2-tert-butoxy-2-(7-(4-chlorophenyl)-2-(2-(4-chlorophenyl)-2-methylmorpholino)-5-methylbenzo[d]thiazol-6-yl)acetate (2S)-2-tert-butoxy-2-(7-(4-chlorophenyl)-2-(2-(4-chlorophenyl)-2-methylmorpholino)-5-methylbenzo[d]thiazol-6-yl)acetic acid
322

Preparation of (2S)-ethyl 2-tert-butoxy-2-(7-(4-chlorophenyl)-2-(2-(4-chlorophenyl)-2-methylmorpholino)-5-methylbenzo[d]thiazol-6-yl)acetate: A mixture of (S)-ethyl 2-(2-bromo-7-(4-chlorophenyl)-5-methylbenzo[d]thiazol-6-yl)-2-tert-butoxyacetate, 2-(4-chlorophenyl)-2-methylmorpholine and iPr$_2$NEt (20.1 mg, 0.156 mmol) in DMF was heated at 100° C. for 10 hours. The mixture was evaporated to dryness and separated on CombiFlash, eluting with 0-70% EtOAc/Hex to give title compound. LCMS-ESI$^+$: calc'd for C$_{33}$H$_{36}$Cl$_2$N$_2$O$_4$S: 627.2, 629.2 (M+H$^+$); found: 627.3, 629.3 (M+H$^+$).

Preparation of (2S)-2-tert-butoxy-2-(7-(4-chlorophenyl)-2-(2-(4-chlorophenyl)-2-methylmorpholino)-5-methylbenzo[d]thiazol-6-yl)acetic acid: To a solution of (2S)-ethyl 2-tert-butoxy-2-(7-(4-chlorophenyl)-2-(2-(4-chlorophenyl)-2-methylmorpholino)-5-methylbenzo[d]thiazol-6-yl)acetate (63.7 mg, 0.101 mmol) in CH$_3$OH/THF (1:1, 4 mL) was added NaOH (2N, 1 mL, 2 mmol), the resulting mixture was heated at 50° C. for 14 hr. The mixture was evaporated to a small volume, acidified to pH 3 and taken into partitioned between CH$_2$Cl$_2$ and brine. The organic layer was separated, dried (Na$_2$SO$_4$), filtered and evaporated to dryness. The residue was purified on CombiFlash (50% EtOAc/Hex) to give (2S)-2-tert-butoxy-2-(7-(4-chlorophenyl)-2-(2-(4-chlorophenyl)-2-methylmorpholino)-5-methylbenzo[d]thiazol- 6-yl)acetic acid. LCMS-ESI+: calc'd for $C_{31}H_{32}Cl_2N_2O_4S$: 599.2, 601.2 (M+H+); found: 599.2, 601.2 (M+H+). 1H-NMR: 400 MHz, (CD3OD) δ: 7.62 (m, 1H), 7.44-7.53 (m, 5H), 7.32 (m, 3H), 5.13 (s, 1H), 4.31 (t, J=14.4 Hz, 1H), 3.81 (m, 1H), 3.62 (m, 1H), 3.44-3.53 (m, 3H), 2.50 (s, 3H), 1.46 (s, 3H), 0.95 (s, 9H).

Example 174

Preparation of (2S)-2-tert-butoxy-2-(7-(4-chlorophenyl)-5-methyl-2-(2-methyl-2-p-tolylmorpholino)benzo[d]thiazol-6-yl)acetic acid (323)

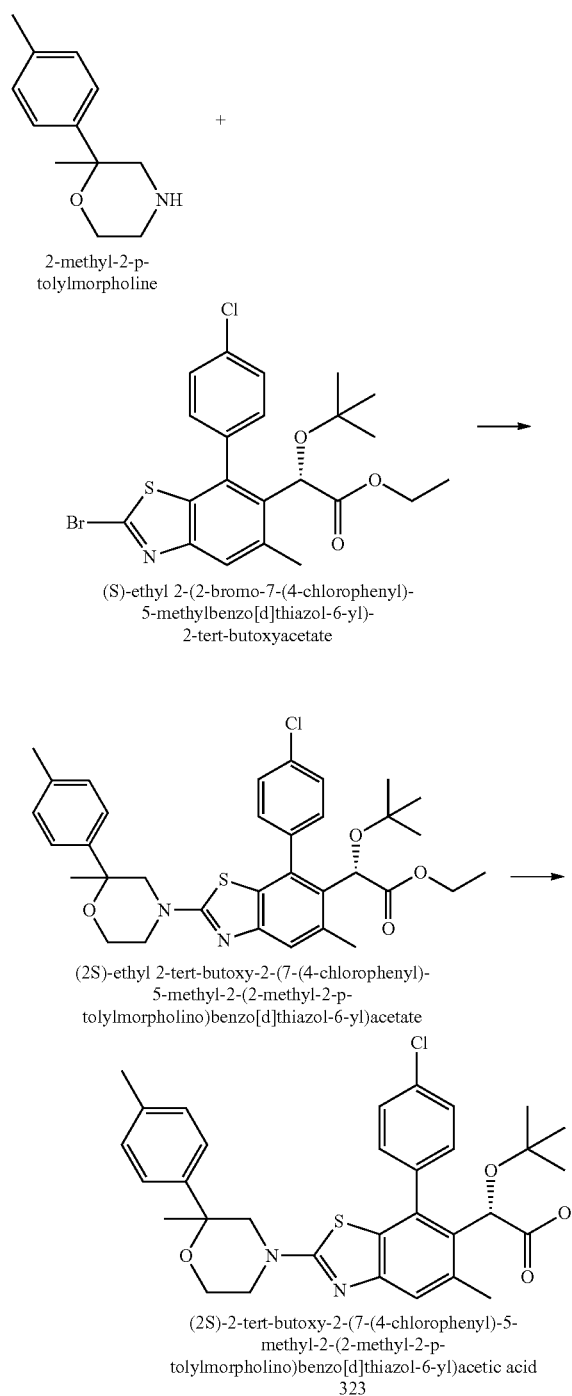

2-methyl-2-p-tolylmorpholine (S)-ethyl 2-(2-bromo-7-(4-chlorophenyl)-5-methylbenzo[d]thiazol-6-yl)-2-tert-butoxyacetate (2S)-ethyl 2-tert-butoxy-2-(7-(4-chlorophenyl)-5-methyl-2-(2-methyl-2-p-tolylmorpholino)benzo[d]thiazol-6-yl)acetate (2S)-2-tert-butoxy-2-(7-(4-chlorophenyl)-5-methyl-2-(2-methyl-2-p-tolylmorpholino)benzo[d]thiazol-6-yl)acetic acid 323

Preparation of (2S)-2-tert-butoxy-2-(7-(4-chlorophenyl)-5-methyl-2-(2-methyl-2-p-tolylmorpholino)benzo[d]thiazol-6-yl)acetic acid: (2S)-2-tert-butoxy-2-(7-(4-chlorophenyl)-5-methyl-2-(2-methyl-2-p-tolylmorpholino)benzo[d]thiazol-6-yl)acetic acid was prepared using the similar procedure as (2S)-2-tert-butoxy-2-(7-(4-chlorophenyl)-2-(2-(4-chlorophenyl)-2-methylmorpholino)-5-methylbenzo[d]thiazol-6-yl)acetic acid except 2-(4-methylphenyl)-2-methylmorpholine was used instead of 2-(4-chlorophenyl)-2-methylmorpholine. LCMS-ESI+: calc'd for $C_{32}H_{35}ClN_2O_4S$: 579.2, 581.2 (M+H+); found: 579.4, 581.3 (M+H+). 1H-NMR: 400 MHz, (CD3OD) δ: 7.62 (m, 1H), 7.47-7.54 (m, 3H), 7.32 (m, 3H), 7.14 (m, 2H), 5.14 (s, 1H), 4.31 (t, J=12.8 Hz, 1H), 3.80 (m, 1H), 3.64 (m, 1H), 3.40-3.51 (m, 3H), 2.50 (s, 3H), 2.28 (s, 3H), 1.44 (s, 3H), 0.95 (s, 9H).

Example 175

Preparation of (2S)-2-tert-butoxy-2-(7-(4-chlorophenyl)-5-methyl-2-(2-(1-methyl-1H-indazol-5-yl)morpholino)benzo[d]thiazol-6-yl)acetic acid (324), (S)-2-tert-butoxy-2-(7-(4-chlorophenyl)-5-methyl-2-((R)-2-(1-methyl-1H-indazol-5-yl)morpholino)benzo[d]thiazol-6-yl)acetic acid (325) and (S)-2-tert-butoxy-2-(7-(4-chlorophenyl)-5-methyl-2-((S)-2-(1-methyl-1H-indazol-5-yl)morpholino)benzo[d]thiazol-6-yl)acetic acid (326)

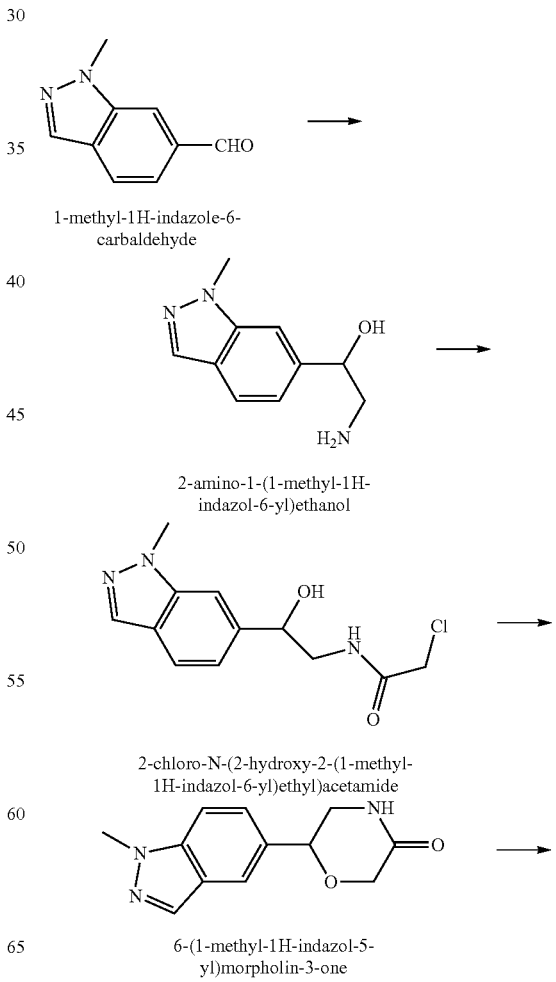

1-methyl-1H-indazole-6-carbaldehyde 2-amino-1-(1-methyl-1H-indazol-6-yl)ethanol 2-chloro-N-(2-hydroxy-2-(1-methyl-1H-indazol-6-yl)ethyl)acetamide 6-(1-methyl-1H-indazol-5-yl)morpholin-3-one -continued

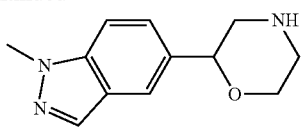

2-(1-methyl-1H-indazol-5-yl)morpholine

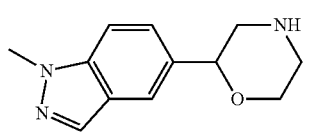

2-(1-methyl-1H-indazol-5-yl)morpholine

+

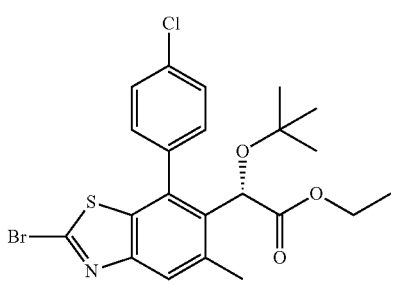

(S)-ethyl 2-(2-bromo-7-(4-chlorophenyl)-5-methylbenzo[d]thiazol-6-yl)-2-tert-butoxyacetate

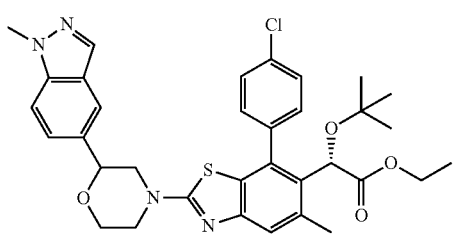

(2S)-ethyl 2-tert-butoxy-2-(7-(4-chlorophenyl)-5-methyl-2-(2-(1-methyl-1H-indazol-5-yl)morpholino)benzo[d]thiazol-6-yl)acetate

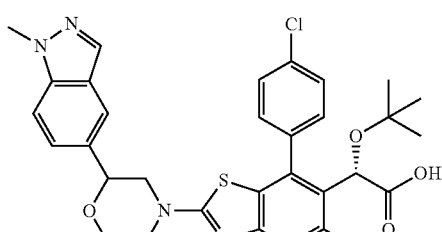

(2S)-2-tert-butoxy-2-(7-(4-chlorophenyl)-5-methyl-2-(2-(1-methyl-1H-indazol-5-yl)morpholino)benzo[d]thiazol-6-yl)acetic acid
324

-continued

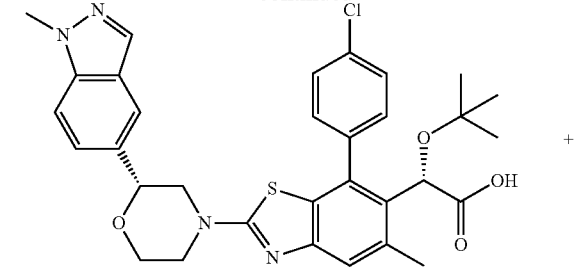

(S)-2-tert-butoxy-2-(7-(4-chlorophenyl)-5-methyl-2-((R)-2-(1-methyl-1H-indazol-5-yl)morpholino)benzo[d]thiazol-6-yl)acetic acid
325

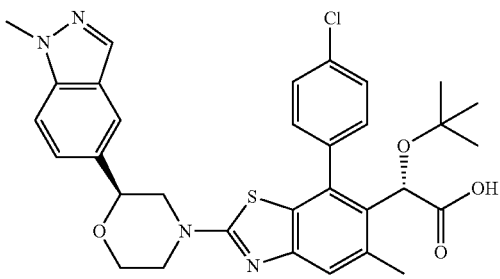

(S)-2-tert-butoxy-2-(7-(4-chlorophenyl)-5-methyl-2-((S)-2-(1-methyl-1H-indazol-5-yl)morpholino)benzo[d]thiazol-6-yl)acetic acid
326

Preparation of 2-chloro-N-(2-hydroxy-2-(1-methyl-1H-indazol-6-yl)ethyl)acetamide: To a solution of 1-methyl-1H-indazole-6-carbaldehyde (532.8 mg, 3.3 mmol) in CH$_2$Cl$_2$ (5 mL) at 0° C. was added ZnI$_2$ (106.1 mg, 0.33 mmol) and cyanotrimethylsilane (0.499 mL, 3.99 mmol), the resulting mixture was stirred at 0° C. for 2 hr, and LC/MS indicated the full formation of TMS-cyanohydrin. Around 3 mL of the above mixture was evaporated to dryness and then re-dissolved in THF, LiAlH$_4$ (2 mL, 1N in THF, 2 mmol) was added, the resulting mixture was stirred at room temperature for 2 hr. The mixture was quenched with EtOAc, added 0.075 mL H$_2$O, 0.075 mL NaOH (15% w/w), then 0.225 mL H$_2$O and then filtered through celite. The filtrate and washings were collected and evaporated to dryness to give crude compound. The crude material, containing around 50% of 2-amino-1-(1-methyl-1H-indazol-6-yl)ethanol, was used for the next step without purified or characterization.

To the crude material 2-amino-1-(1-methyl-1H-indazol-6-yl)ethanol (390.8 mg, ~50%, ~1 mmol) in DMF was then added 2-chloroacetyl chloride (138.7 mg, 1.2 mmol) and iPr$_2$NEt (0.347 mL, 2 mmol). The resulting mixture was stirred at room temperature for 2 hr. The mixture was then taken into partition between EtOAc and brine. The organic layer was separated and the aqueous layer was extracted with EtOAc twice. The combined organic layers were dried dried (Na$_2$SO$_4$), filtered and evaporated to dryness. The residue was purified on CombiFlash (50% EtOAc/Hex) to give 2-chloro-N-(2-hydroxy-2-(1-methyl-1H-indazol-6-yl)ethyl)acetamide. LCMS-ESI$^+$: calc'd for C$_{12}$H$_{14}$ClN$_3$O$_2$: 268.1, 270.1 (M+H$^+$); found: 268.2, 270.2 (M+H$^+$).

Preparation of 6-(1-methyl-1H-indazol-5-yl)morpholin-3-one: To a solution of 2-chloro-N-(2-hydroxy-2-(1-methyl-1H-indazol-6-yl)ethyl)acetamide (70.1 mg, 0.26 mmol) in THF was added tBuOK (38.3 mg, 0.31 mmol). The resulting mixture was stirred at room temperature for 7 hr. The mixture was taken into partition between CH₂Cl₂ and brine. The organic layer was separated, dried (Na₂SO₄), filtered and evaporated to dryness. The residue was purified on Combi-Flash (50% EtOAc/Hex) to give 6-(1-methyl-1H-indazol-5-yl)morpholin-3-one. LCMS-ESI⁺: calc'd for $C_{12}H_{13}N_3O$: 232.1 (M+H⁺); found: 232.1 (M+H⁺).

Preparation of 2-(1-methyl-1H-indazol-5-yl)morpholine: To a solution of 6-(1-methyl-1H-indazol-5-yl)morpholin-3-one (17.8 mg, 0.077 mmol) in THF was added BH₃ in THF (1M, mmol). The resulting mixture was stirred at room temperature for 10 hr. The crude compound was evaporated to dryness and used for the next step without further purification. LCMS-ESI⁺: calc'd for $C_{12}H_{15}N_3O$: 218.1 (M+H⁺); found: 218.2 (M+H⁺).

Preparation of (2S)-2-tert-butoxy-2-(7-(4-chlorophenyl)-5-methyl-2-(2-(1-methyl-1H-indazol-5-yl)morpholino)benzo[d]thiazol-6-yl)acetic acid: (2S)-2-tert-butoxy-2-(7-(4-chlorophenyl)-5-methyl-2-(2-(1-methyl-1H-indazol-5-yl)morpholino)benzo[d]thiazol-6-yl)acetic acid was prepared using the similar procedure as (2S)-2-tert-butoxy-2-(7-(4-chlorophenyl)-2-(2-(4-chlorophenyl)-2-methylmorpholino)-5-methylbenzo[d]thiazol-6-yl)acetic acid except 2-(1-methyl-1H-indazol-5-yl)morpholine was used instead of 2-(4-chlorophenyl)-2-methylmorpholine. LCMS-ESI⁺: calc'd for $C_{32}H_{33}ClN_4O_4S$: 605.2, 607.2 (M+H⁺); found: 605.3, 607.3 (M+H⁺). ¹H-NMR: 400 MHz, (CD₃OD) δ: 7.99 (s, 1H), 7.82 (s, 1H), 7.62 (d, J=7.6 Hz, 1H), 7.49-7.56 (m, 5H), 7.32 (s, 1H), 5.13 (s, 1H), 4.72 (d, J=7.2 Hz, 1H), 4.11 (m, 2H), 4.05 (s, 3H), 3.85 (m, 2H), 3.35 (m, 1H), 3.30 (t, J=12 Hz, 1H), 2.50 (s, 3H), 0.94 (s, 9H).

Preparation of (S)-2-tert-butoxy-2-(7-(4-chlorophenyl)-5-methyl-2-((R)-2-(1-methyl-1H-indazol-5-yl)morpholino)benzo[d]thiazol-6-yl)acetic acid and (S)-2-tert-butoxy-2-(7-(4-chlorophenyl)-5-methyl-2-((S)-2-(1-methyl-1H-indazol-5-yl)morpholino)benzo[d]thiazol-6-yl)acetic acid: The diastereomic mixture of (2S)-2-tert-butoxy-2-(7-(4-chlorophenyl)-5-methyl-2-(2-(1-methyl-1H-indazol-5-yl)morpholino)benzo[d]thiazol-6-yl)acetic acid was separated with 35% CH₃OH/SFC (containing 0.01% TFA) to give enantiomeric pure (S)-2-tert-butoxy-2-(7-(4-chlorophenyl)-5-methyl-2-((R)-2-(1-methyl-1H-indazol-5-yl)morpholino)benzo[d]thiazol-6-yl)acetic acid and (S)-2-tert-butoxy-2-(7-(4-chlorophenyl)-5-methyl-2-((S)-2-(1-methyl-1H-indazol-5-yl)morpholino)benzo[d]thiazol-6-yl)acetic acid respectively. The fast eluting fraction: LCMS-ESI⁺: calc'd for $C_{32}H_{33}ClN_4O_4S$: 605.2, 607.2 (M+H⁺); found: 605.3, 607.3 (M+H⁺). ¹H-NMR: 400 MHz, (CD₃OD) S: 8.00 (s, 1H), 7.83 (s, 1H), 7.62 (d, J=8.0 Hz, 1H), 7.47-7.57 (m, 5H), 7.34 (s, 1H), 5.15 (s, 1H), 4.76 (d, J=10.8 Hz, 1H), 4.14 (m, 2H), 4.06 (s, 3H), 3.89 (m, 2H), 3.47-3.64 (m, 2H), 2.51 (s, 3H), 0.94 (s, 9H).

The slow eluting fraction: LCMS-ESI⁺: calc'd for $C_{32}H_{33}ClN_4O_4S$: 605.2, 607.2 (M+H⁺); Found: 605.3, 607.3 (M+H⁺), ¹H-NMR: 400 MHz, (CD₃OD) δ: 8.00 (s, 1H), 7.84 (s, 1H), 7.62 (d, J=8.8 Hz, 1H), 7.47-7.57 (m, 5H), 7.34 (s, 1H), 5.14 (s, 1H), 4.76 (d, J=10.8 Hz, 1H), 4.15 (t, J=14.4 Hz, 2H), 4.06 (s, 3H), 3.88 (m, 2H), 3.46-3.64 (m, 2H), 2.51 (s, 3H), 0.94 (s, Example 176

Preparation of (2S)-2-tert-butoxy-2-(7-(4-chlorophenyl)-5-methyl-2-(2-phenylmorpholino)benzo[d]thiazol-6-yl)acetic acid (327)

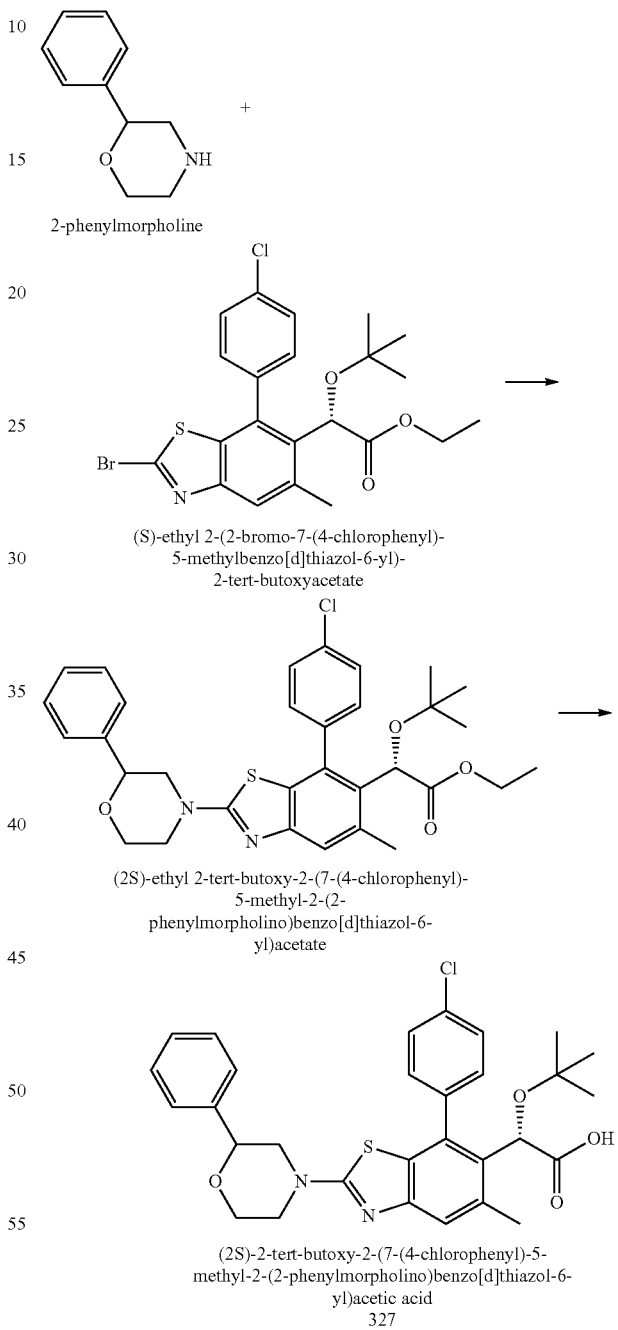

2-phenylmorpholine (S)-ethyl 2-(2-bromo-7-(4-chlorophenyl)-5-methylbenzo[d]thiazol-6-yl)-2-tert-butoxyacetate (2S)-ethyl 2-tert-butoxy-2-(7-(4-chlorophenyl)-5-methyl-2-(2-phenylmorpholino)benzo[d]thiazol-6-yl)acetate (2S)-2-tert-butoxy-2-(7-(4-chlorophenyl)-5-methyl-2-(2-phenylmorpholino)benzo[d]thiazol-6-yl)acetic acid
327

Preparation of (2S)-2-tert-butoxy-2-(7-(4-chlorophenyl)-5-methyl-2-(2-phenylmorpholino)benzo[d]thiazol-6-yl)acetic acid: (2S)-2-tert-butoxy-2-(7-(4-chlorophenyl)-5-methyl-2-(2-phenylmorpholino)benzo[d]thiazol-6-yl)acetic acid was prepared using the similar procedure as (2S)-2-tert-butoxy-2-(7-(4-chlorophenyl)-2-(2-(4-chlorophenyl)-2-methylmorpholino)-5-methylbenzo[d]thiazol-6-yl)acetic acid except 2-(4-methylphenyl)-2-methylmorpholine was used instead of 2-(4-chlorophenyl)-2-methylmorpholine. LCMS-ESI+: calc'd for $C_{30}H_{31}ClN_2O_4S$: 551.2, 553.2 (M+H+); found: 551.3, 553.3 (M+H+). $^1$H-NMR: 400 MHz, (CD$_3$Cl) δ: 7.62 (dd, J1=2.4 Hz, J2=10 Hz, 1H), 7.49 (m, 3H), 7.3-7.4 (m, 6H), 5.13 (s, 1H), 4.58 (d, J=10.8 Hz, 1H), 4.09 (m, 2H), 3.80 (m, 2H), 3.64 (m, 1H), 3.37 (m, 1H), 3.08 (dd, J1=12.8 Hz, J2=10.8 Hz, 1H. 50 (s, 3H), 2.49 (s, 3H), 0.93 (s, 9H).

Example 177

Method AQ: Preparation of (S)-2-tert-butoxy-2-(7-(4-chlorophenyl)-5-methyl-2-(2-(oxetan-3-yl)-2H-indazol-5-yl)benzo[d]thiazol-6-yl)acetic acid (328) and (S)-2-tert-butoxy-2-(7-(4-chlorophenyl)-5-methyl-2-(1-(oxetan-3-yl)-1H-indazol-5-yl)benzo[d]thiazol-6-yl)acetic acid (329)

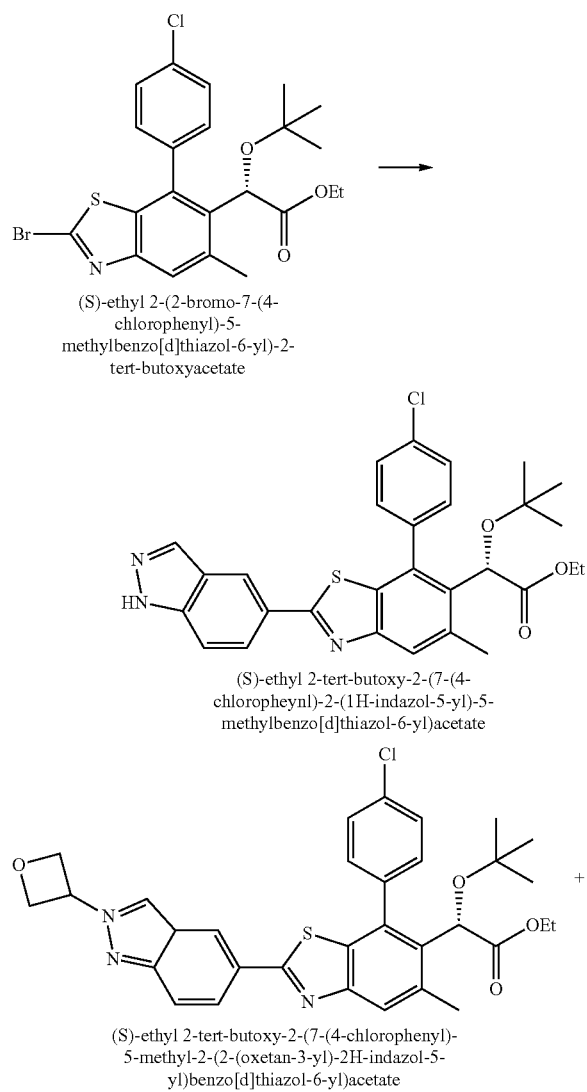

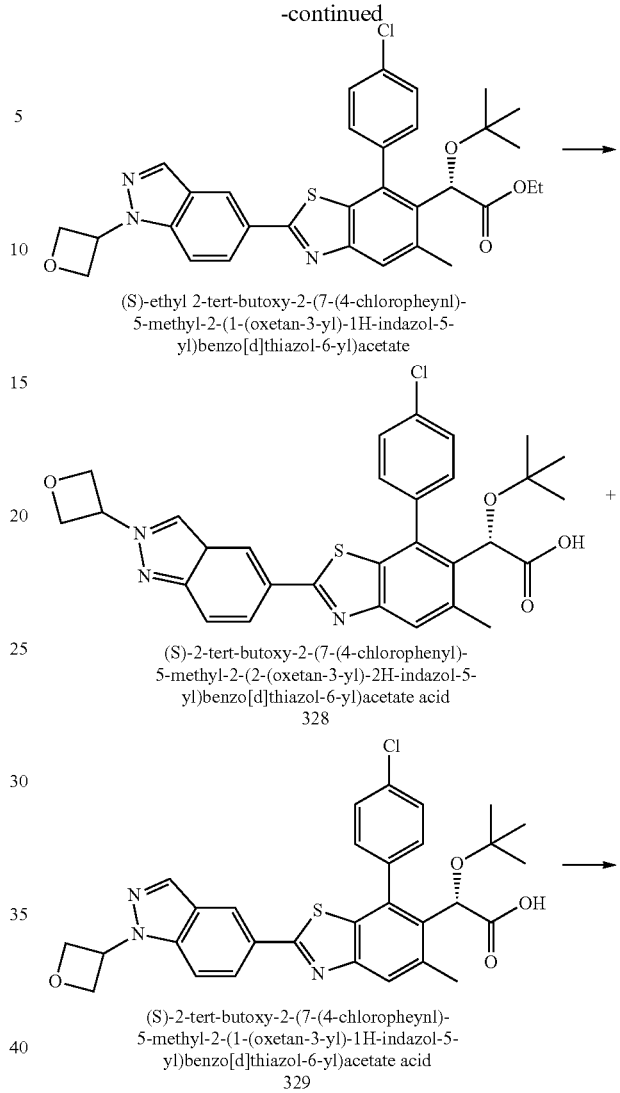

Preparation of (S)-ethyl 2-tert-butoxy-2-(7-(4-chlorophenyl)-2-(1H-indazol-5-yl)-5-methylbenzo[d]thiazol-6-yl)acetate: (S)-ethyl 2-(2-bromo-7-(4-chlorophenyl)-5-methylbenzo[d]thiazol-6-yl)-2-tert-butoxyacetate (300.0 mg, 0.604 mmol), 1H-indazole-5-boronic acid (117.3 mg, 0.725 mmol), potassium carbonate (250.3 mg, 1.811 mmol), and tetrakis(triphenylphosphine)palladium(0) (104.7 mg, 0.091 mmol) were taken in a microwave vial, and the vial was vacuum pumped and flushed with argon three times. To this mixture was added degassed 1,4-dioxane (6 mL) and degassed water (1.5 mL). The reaction mixture was heated at 95° C. for 6.5 h then cooled to room temperature. The reaction mixture was filtered through Celite (ethyl acetate eluent) and concentrated. Purification by flash column chromatography on silica gel (hexanes/ethyl acetate eluent) provided the product. LCMS-ESI+: calc'd for $C_{29}H_{29}ClN_3O_3S$: 534.2 (M+H+); Found: 533.8 (M+H+).

Preparation of (S)-2-tert-butoxy-2-(7-(4-chlorophenyl)-5-methyl-2-(2-(oxetan-3-yl)-2H-indazol-5-yl)benzo[d]thiazol-6-yl)acetic acid and (S)-2-tert-butoxy-2-(7-(4-chlorophenyl)-5-methyl-2-(1-(oxetan-3-yl)-1H-indazol-5-yl) benzo[d]thiazol-6-yl)acetic acid: Prepared in a similar manner as (S)-2-tert-butoxy-2-(7-(4-chlorophenyl)-2-(1,2-dimethyl-1H-pyrrolo[2,3-b]pyridin-5-yl)-5-methylbenzo[d]

thiazol-6-yl)acetic acid except starting from (S)-ethyl 2-tert-butoxy-2-(7-(4-chlorophenyl)-2-(1H-indazol-5-yl)-5-methylbenzo[d]thiazol-6-yl)acetate instead of (S)-ethyl 2-tert-butoxy-2-(7-(4-chlorophenyl)-5-methyl-2-(2-methyl-1H-pyrrolo[2,3-b]pyridin-5-yl)benzo[d]thiazol-6-yl)acetate and 3-bromooxetane instead of iodomethane.

Example 178

Method BB: Preparation of (S)-2-tert-butoxy-2-(7-(4-chlorophenyl)-2-(3-isopropyl-1-methyl-1H-indazol-5-yl)-5-methylbenzo[d]thiazol-6-yl)acetic acid (330)

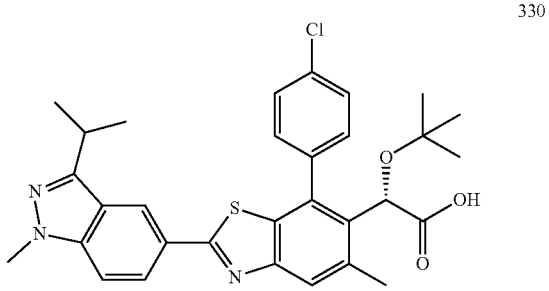 [SMILES: Cc1cc2nc(-c3ccc4c(c3)c(C(C)C)nn4C)sc2c(-c2ccc(Cl)cc2)c1[C@H](OC(C)(C)C)C(=O)O]

Preparation of (S)-2-tert-butoxy-2-(7-(4-chlorophenyl)-2-(3-isopropyl-1-methyl-1H-indazol-5-yl)-5-methylbenzo[d]thiazol-6-yl)acetic acid: (S)-2-tert-butoxy-2-(7-(4-chlorophenyl)-2-(3-isopropyl-1-methyl-1H-indazol-5-yl)-5-methylbenzo[d]thiazol-6-yl)acetic acid was prepared in a similar manner as (S)-2-tert-butoxy-2-(7-(4-chlorophenyl)-5-methyl-2-(1-methyl-3-(pyridin-3-yl)-1H-indazol-5-yl)benzo[d]thiazol-6-yl)acetic acid except 1-(5-bromo-2-fluorophenyl)-2-methylpropan-1-ol was used instead of (5-bromo-2-fluorophenyl)(pyridin-3-yl)methanol. LCMS-ESI$^+$: calc'd for $C_{31}H_{33}ClN_3O_3S$: 562.2 (M+H$^+$); Found 562.3 (M+H$^+$). $^1$H NMR (400 MHz, CD$_3$OD) δ 8.44 (s, 1H), 8.03 (dd, J=8.9, 1.6 Hz, 1H), 7.81 (s, 1H), 7.70 (d, J=8.3 Hz, 1H), 7.58 (dd, J=9.4, 6.9 Hz, 4H), 5.26 (s, 1H), 4.01 (s, 3H), 3.45 (hept, J=7.0 Hz, 1H), 2.61 (s, 3H), 1.46 (d, J=7.0 Hz, 6H), 0.98 (s, 9H).

Example 179

Chemical synthesis and characterization data for compounds 331-463. The compounds were prepared by the general method noted in the table. Based on the general methods described above, the skilled artisan will be able to determine the appropriate reactants that will successfully produce the described compounds.

General Methods (Method C (Example 15), Method F (Example 18), Method H (Example 20), Method J (example 22), Method O (Example 46), Method P (Example 47), Method V (Example 50), Method W (Example 51), Method Y (Example 52), Method AA (Example 54), Method AG (Example 57), Method AJ (Example 60), Method AK (Example 61), Method AL (Example 62), Method AM (Example 63), Method AN (Example 64), Method AO (Example 65), Method AP (Example 66), Method AQ (Example 177), Method AR (Example 67), Method AS (Example 68), Method AT (Example 69), Method AU (Example 70), Method AV (Example 71), Method AW (Example 72), Method AX (Example 73), Method AY (Example 74), Method AZ (Example 75), Method BA (Example 76), Method BC (Example 78), Method BE (Example 80), Method BF (Example 81), Method BG (Example 82).

| Cmpd # | Compound Structure | Method | Parent MW | LCMS-ESI+ | 1H NMR |
|---|---|---|---|---|---|
| 331 | 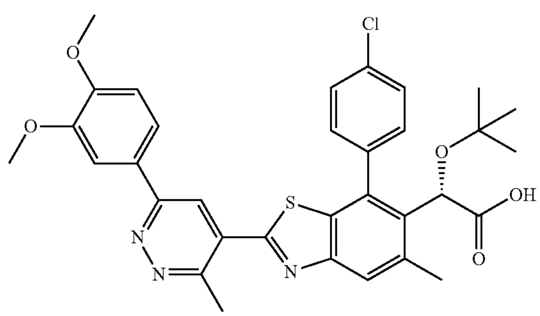 [SMILES: COc1ccc(-c2cc(-c3nc4cc(C)c([C@H](OC(C)(C)C)C(=O)O)c(-c5ccc(Cl)cc5)c4s3)c(C)nn2)cc1OC] | AR | 618.14 | 618.2 | $^1$H NMR (400 MHz, CD$_3$OD) δ 8.36 (s, 1H), 8.03-7.95 (m, 1H), 7.94 (s, 1H), 7.81 (d, J = 2.0 Hz, 1H), 7.68 (dd, J = 8.4, 2.1 Hz, 1H), 7.66-7.60 (m, 1H), 7.60-7.50 (m, 2H), 7.12 (d, J = 8.5 Hz, 1H), 5.15 (s, 1H), 3.95 (s, 3H), 3.91 (s, 3H), 3.04 (s, 3H), 2.69 (s, 3H), 0.94 (s, 9H). |
| 332 | 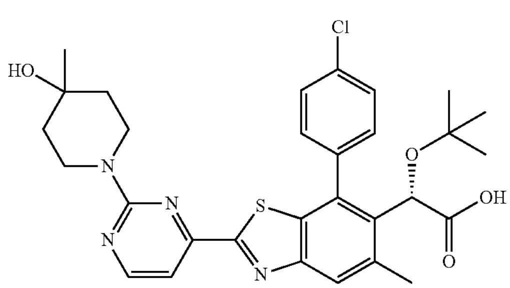 [SMILES: Cc1cc2nc(-c3ccnc(N4CCC(C)(O)CC4)n3)sc2c(-c2ccc(Cl)cc2)c1[C@H](OC(C)(C)C)C(=O)O] | AS | 581.13 | 581.1 | $^1$H NMR (400 MHz, CD$_3$OD) δ 8.47 (d, J = 5.1 Hz, 1H), 7.90 (s, 1H), 7.71-7.64 (m, 1H), 7.64-7.54 (m, 3H), 7.42 (d, J = 5.1 Hz, 1H), 5.26 (s, 1H), 4.32-4.19 (m, 2H), 3.61-3.49 (m, 2H), 2.62 (s, 3H), 1.72-1.52 (m, 4H), 1.25 (s, 3H), 0.97 (s, 9H). |

-continued

| Cmpd # | Compound Structure | Method | Parent MW | LCMS-ESI+ | 1H NMR |
|---|---|---|---|---|---|
| 333 | 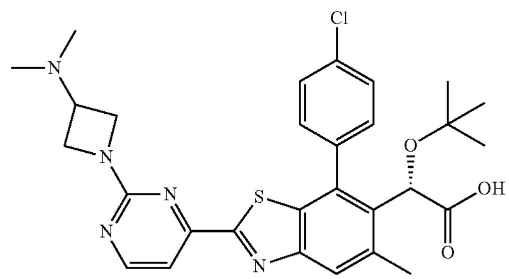 [SMILES: Cc1cc2nc(-c3ccnc(N4CC(N(C)C)C4)n3)sc2c(-c2ccc(Cl)cc2)c1[C@H](OC(C)(C)C)C(=O)O] | AS | 566.11 | 566.1 | ¹H NMR (400 MHz, CD₃OD) δ 8.59 (d, J = 5.1 Hz, 1H), 7.92 (s, 1H), 7.70-7.50 (m, 5H), 5.26 (s, 1H), 4.54-4.44 (m, 2H), 4.34-4.15 (m, 3H), 2.95 (s, 6H), 2.63 (s, 3H), 0.98 (s, 9H). |
| 334 | 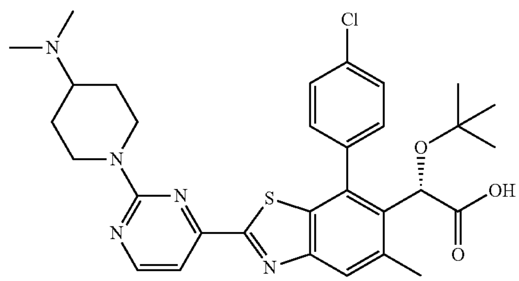 [SMILES: Cc1cc2nc(-c3ccnc(N4CCC(N(C)C)CC4)n3)sc2c(-c2ccc(Cl)cc2)c1[C@H](OC(C)(C)C)C(=O)O] | AS | 594.17 | 593.8 | ¹H NMR (400 MHz, CD₃OD) δ 8.55 (d, J = 5.0 Hz, 1H), 7.91 (s, 1H), 7.71-7.64 (m, 1H), 7.61 (d, J = 8.7 Hz, 2H), 7.58-7.52 (m, 1H), 7.48 (d, J = 5.0 Hz, 1H), 5.25 (s, 1H), 5.02 (br d, J = 13.9 Hz, 2H), 3.56-3.45 (m, 1H), 3.04-2.93 (m, 2H), 2.88 (s, 6H), 2.63 (s, 3H), 2.16 (br d, J = 10.6 Hz, 2H), 1.72-1.55 (m, 2H), 0.98 (s, 9H). |
| 335 | 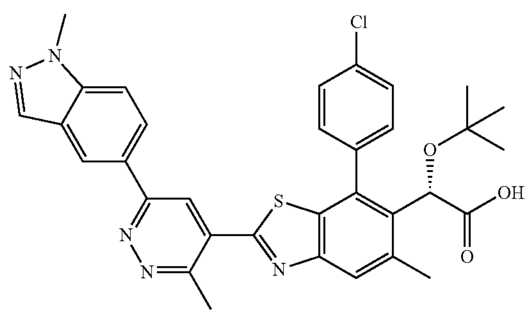 [SMILES: Cc1cc2nc(-c3cc(-c4ccc5c(cnn5C)c4)nnc3C)sc2c(-c2ccc(Cl)cc2)c1[C@H](OC(C)(C)C)C(=O)O] | AR | 612.14 | 611.9 | ¹H NMR (400 MHz, CD₃OD) δ 8.51 (s, 1H), 8.43 (s, 1H), 8.28-8.21 (m, 1H), 8.13 (s, 1H), 7.95 (s, 1H), 7.93-7.86 (m, 1H), 7.70 (d, J = 8.9 Hz, 1H), 7.68-7.60 (m, 1H), 7.60-7.54 (m, 2H), 5.20 (s, 1H), 4.11 (s, 3H), 3.05 (s, 3H), 2.68 (s, 3H), 0.96 (s, 9H). |
| 336 | 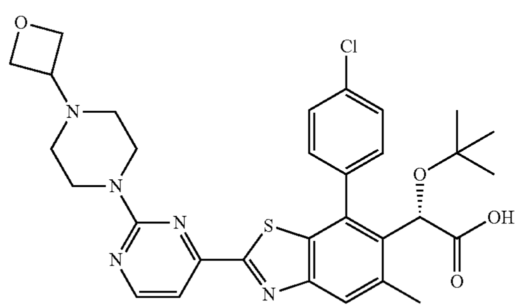 [SMILES: Cc1cc2nc(-c3ccnc(N4CCN(C5COC5)CC4)n3)sc2c(-c2ccc(Cl)cc2)c1[C@H](OC(C)(C)C)C(=O)O] | AS | 608.15 | 608.2 | ¹H NMR (400 MHz, CD₃OD) δ 8.62 (d, J = 5.0 Hz, 1H), 7.92 (s, 1H), 7.70-7.64 (m, 1H), 7.63-7.52 (m, 4H), 5.25 (s, 1H), 4.93-4.88 (m, 2H), 4.83-4.77 (m, 2H), 4.57-3.46 (m, 5H), 3.22 (br s, 4H), 2.63 (s, 3H), 0.98 (s, 9H). |
| 337 | 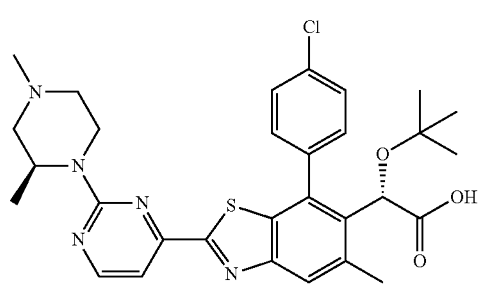 [SMILES: Cc1cc2nc(-c3ccnc(N4CCN(C)C[C@@H]4C)n3)sc2c(-c2ccc(Cl)cc2)c1[C@H](OC(C)(C)C)C(=O)O] | AS | 580.14 | 580.1 | ¹H NMR (400 MHz, CD₃OD) δ 8.63 (d, J = 4.9 Hz, 1H), 7.92 (s, 1H), 7.71-7.63 (m, 1H), 7.63-7.53 (m, 4H), 5.33-5.26 (m, 1H), 5.25 (s, 1H), 4.95-4.89 (m, 1H), 3.65-3.45 (m, 2H), 3.43-3.33 (m, 1H), 3.29-3.23 (m, 1H), 3.17-3.03 (m, 1H), 2.96 (s, 3H), 2.63 (s, 3H), 1.37 (d, J = 7.1 Hz, 3H), 0.98 (s, 9H). |

| Cmpd # | Compound Structure | Method | Parent MW | LCMS-ESI+ | 1H NMR |
|---|---|---|---|---|---|
| 338 | 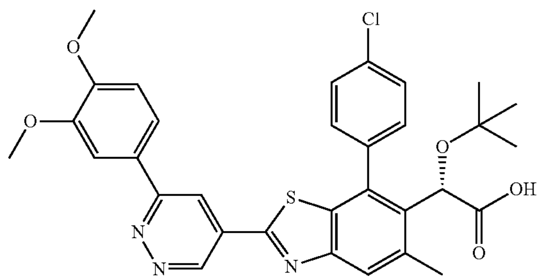 [SMILES: COc1ccc(-c2cc(-c3nc4cc(C)c([C@H](OC(C)(C)C)C(=O)O)c(-c5ccc(Cl)cc5)c4s3)cnn2)cc1OC] | AR | 604.12 | 604.2 | ¹H NMR (400 MHz, CD₃OD) δ 9.67 (d, J = 1.9 Hz, 1H), 8.55 (d, J = 2.0 Hz, 1H), 7.97 (s, 1H), 7.89-7.82 (m, 2H), 7.75 (dd, J = 8.4, 2.0 Hz, 1H), 7.67-7.55 (m, 3H), 7.15 (d, J = 8.5 Hz, 1H), 5.22 (s, 1H), 3.97 (s, 3H), 3.93 (s, 3H), 2.67 (s, 3H), 0.96 (s, 9H). |
| 339 | 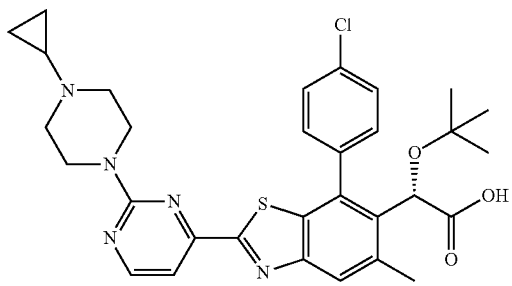 [SMILES: Cc1cc2nc(-c3ccnc(N4CCN(C5CC5)CC4)n3)sc2c(-c2ccc(Cl)cc2)c1[C@H](OC(C)(C)C)C(=O)O] | AS | 592.15 | 592.1 | ¹H NMR (400 MHz, CD₃OD) δ 8.62 (d, J = 5.0 Hz, 1H), 7.92 (s, 1H), 7.72-7.64 (m, 1H), 7.64-7.51 (m, 4H), 5.25 (s, 1H), 4.11 (br s, 3H), 3.46 (m, 5H), 2.77 (br s, 1H), 2.63 (s, 3H), 0.98 (s, 13H). |
| 340 | 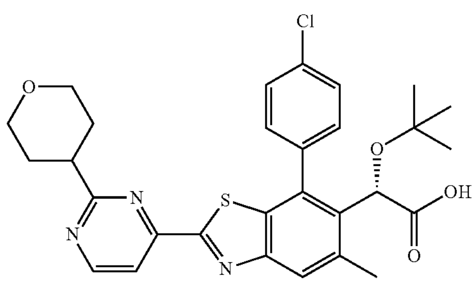 [SMILES: Cc1cc2nc(-c3ccnc(C4CCOCC4)n3)sc2c(-c2ccc(Cl)cc2)c1[C@H](OC(C)(C)C)C(=O)O] | AV | 552.08 | 552.1 | ¹H NMR (400 MHz, CD₃OD) δ 8.90 (d, J = 5.1 Hz, 1H), 8.12 (d, J = 5.2 Hz, 1H), 7.94 (s, 1H), 7.73-7.66 (m, 1H), 7.65-7.55 (m, 3H), 5.28 (s, 1H), 4.05 (dt, J = 11.5, 3.2 Hz, 2H), 3.66-3.53 (m, 2H), 3.24-3.11 (m, 1H), 2.63 (s, 3H), 2.05-1.90 (m, 4H), 0.98 (s, 9H). |
| 341 | 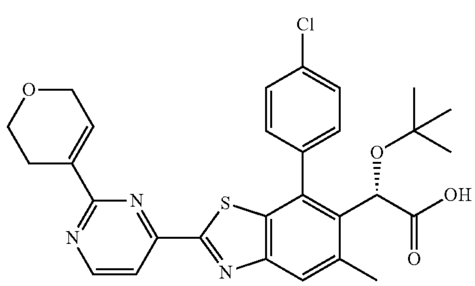 | AT | 550.07 | 550.1 | ¹H NMR (400 MHz, CD₃OD) δ 8.90 (d, J = 5.0 Hz, 1H), 8.08 (d, J = 5.3 Hz, 1H), 7.94 (s, 1H), 7.73-7.65 (m, 1H), 7.65-7.54 (m, 3H), 7.34 (s, 1H), 5.27 (s, 1H), 4.42-4.34 (m, 2H), 3.97-3.87 (m, 2H), 2.75-2.66 (m, 2H), 2.63 (s, 3H), 0.98 (s, 9H). |
| 342 | 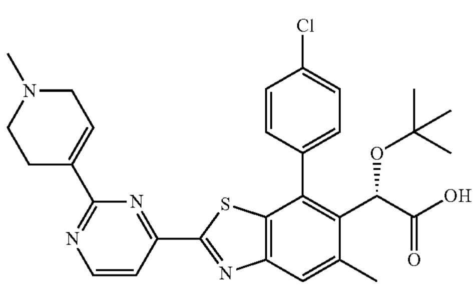 [SMILES: Cc1cc2nc(-c3ccnc(C4=CCN(C)CC4)n3)sc2c(-c2ccc(Cl)cc2)c1[C@H](OC(C)(C)C)C(=O)O] | AT | 563.11 | 563.2 | ¹H NMR (400 MHz, CD₃OD) δ 8.97 (d, J = 5.1 Hz, 1H), 8.18 (d, J = 5.1 Hz, 1H), 7.96 (s, 1H), 7.73-7.65 (m, 1H), 7.65-7.53 (m, 3H), 7.31 (s, 1H), 5.26 (s, 1H), 4.16 (br s, 1H), 3.94 (br s, 1H), 3.75 (br s, 1H), 3.27-2.85 (m, 6H), 2.64 (s, 3H), 0.98 (s, 9H). |

| Cmpd # | Compound Structure | Method | Parent MW | LCMS-ESI+ | 1H NMR |
|---|---|---|---|---|---|
| 343 | 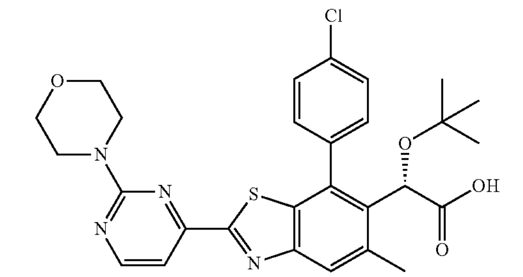 [SMILES: Cc1cc2nc(-c3ccnc(N4CCOCC4)n3)sc2c(-c2ccc(Cl)cc2)c1[C@H](OC(C)(C)C)C(=O)O] | AS | 553.07 | 553.1 | $^1$H NMR (400 MHz, CD$_3$OD) δ 8.52 (d, J = 5.0 Hz, 1H), 7.89 (s, 1H), 7.70-7.64 (m, 1H), 7.63-7.53 (m, 3H), 7.46 (d, J = 5.0 Hz, 1H), 5.25 (s, 1H), 3.84-3.69 (m, 8H), 2.62 (s, 3H), 0.97 (s, 9H). |
| 344 | 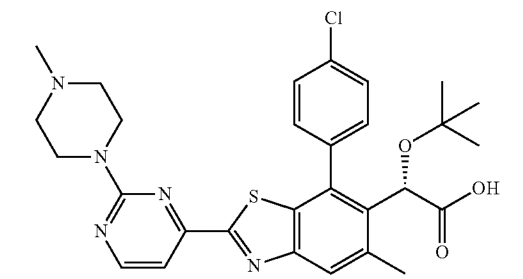 [SMILES: Cc1cc2nc(-c3ccnc(N4CCN(C)CC4)n3)sc2c(-c2ccc(Cl)cc2)c1[C@H](OC(C)(C)C)C(=O)O] | AS | 566.11 | 566.1 | $^1$H NMR (400 MHz, CD$_3$OD) δ 8.62 (d, J = 5.0 Hz, 1H), 7.92 (s, 1H), 7.70-7.65 (m, 1H), 7.64-7.53 (m, 4H), 5.25 (s, 1H), 4.95 (br s, 2H), 3.58 (br s, 2H), 3.15 (br s, 4H), 2.95 (s, 3H), 2.63 (s, 3H), 0.98 (s, 9H). |
| 345 | 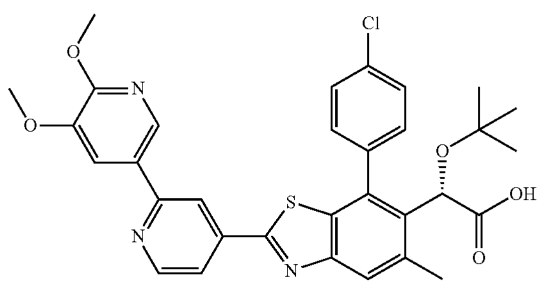 [SMILES: COc1cc(-c2cc(-c3nc4cc(C)c([C@H](OC(C)(C)C)C(=O)O)c(-c5ccc(Cl)cc5)c4s3)ccn2)cnc1OC] | F | 604.12 | 604.1 | $^1$H NMR (400 MHz, CD$_3$OD) δ 8.76 (d, J = 5.3 Hz, 1H), 8.48 (s, 1H), 8.40 (d, J = 2.0 Hz, 1H), 7.97 (s, 1H), 7.95 (dd, J = 5.4, 1.5 Hz, 1H), 7.91 (d, J = 1.9 Hz, 1H), 7.74-7.67 (m, 1H), 7.65-7.56 (m, 3H), 5.28 (s, 1H), 4.03 (s, 3H), 3.97 (s, 3H), 2.65 (s, 3H), 0.98 (s, 9H). |
| 346 | 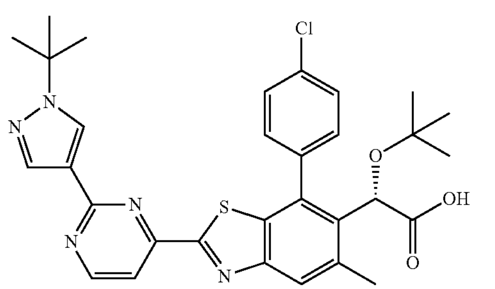 [SMILES: Cc1cc2nc(-c3ccnc(-c4cnn(C(C)(C)C)c4)n3)sc2c(-c2ccc(Cl)cc2)c1[C@H](OC(C)(C)C)C(=O)O] | AT | 590.14 | 590.2 | $^1$H NMR (400 MHz, CD$_3$OD) δ 8.87 (d, J = 5.1 Hz, 1H), 8.42 (s, 1H), 8.18 (s, 1H), 8.04 (d, J = 5.2 Hz, 1H), 7.95 (s, 1H), 7.74-7.68 (m, 1H), 7.68-7.57 (m, 3H), 5.28 (s, 1H), 2.64 (s, 3H), 1.65 (s, 9H), 0.98 (s, 9H). |
| 347 | 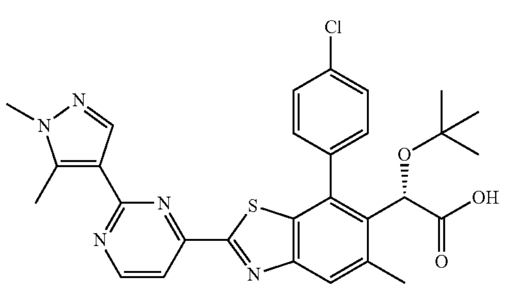 [SMILES: Cc1cc2nc(-c3ccnc(-c4cnn(C)c4C)n3)sc2c(-c2ccc(Cl)cc2)c1[C@H](OC(C)(C)C)C(=O)O] | AT | 562.08 | 561.4 | $^1$H NMR (400 MHz, CD$_3$OD) δ 8.89 (d, J = 5.1 Hz, 1H), 8.11 (s, 1H), 8.00 (d, J = 5.1 Hz, 1H), 7.94 (s, 1H), 7.73-7.68 (m, 1H), 7.65-7.57 (m, 3H), 5.28 (s, 1H), 3.85 (s, 3H), 2.75 (s, 3H), 2.64 (s, 3H), 0.98 (s, 9H). |

-continued

| Cmpd # | Compound Structure | Method | Parent MW | LCMS-ESI+ | 1H NMR |
|---|---|---|---|---|---|
| 348 | 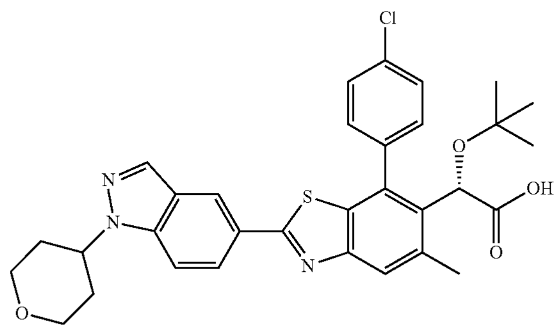 [SMILES: Cc1cc2nc(-c3ccc4c(cnn4C4CCOCC4)c3)sc2c(-c2ccc(Cl)cc2)c1[C@H](OC(C)(C)C)C(=O)O] | AQ | 590.13 | 590.2 | ¹H NMR (400 MHz, CD₃OD) δ 8.45-8.43 (m, 1H), 8.17 (s, 1H), 8.12 (dd, J = 8.9, 1.7 Hz, 1H), 7.83 (s, 1H), 7.79 (d, J = 8.9 Hz, 1H), 7.72-7.66 (m, 1H), 7.64-7.56 (m, 3H), 5.26 (s, 1H), 4.94-4.86 (m, 1H), 4.12 (dd, J = 11.6, 4.5 Hz, 2H), 3.69 (td, J = 12.4, 2.1 Hz, 2H), 2.61 (s, 3H), 2.40-2.25 (m, 2H), 1.98 (dd, J = 12.6, 4.0 Hz, 2H), 0.98 (s, 9H). |
| 349 | 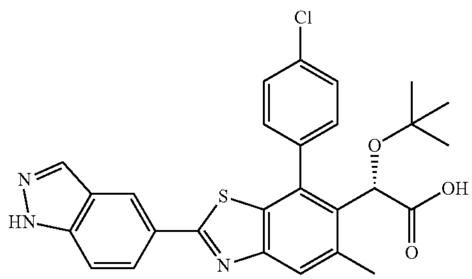 [SMILES: Cc1cc2nc(-c3ccc4[nH]ncc4c3)sc2c(-c2ccc(Cl)cc2)c1[C@H](OC(C)(C)C)C(=O)O] | J | 506.02 | 506.1 | ¹H NMR (400 MHz, CD₃OD) δ 8.47 (s, 1H), 8.18 (s, 1H), 8.14-8.08 (m, 1H), 7.83 (s, 1H), 7.68 (dd, J = 16.2, 8.8 Hz, 2H), 7.63-7.57 (m, 3H), 5.26 (s, 1H), 2.62 (s, 3H), 0.98 (s, 9H). |
| 350 | 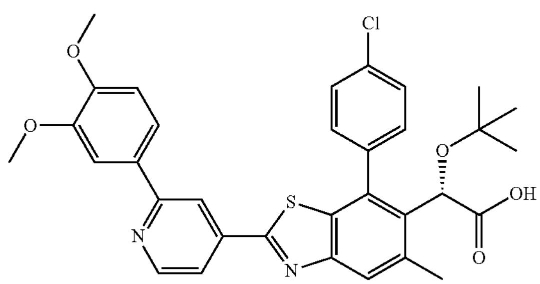 [SMILES: COc1ccc(-c2cc(-c3nc4cc(C)c([C@H](OC(C)(C)C)C(=O)O)c(-c5ccc(Cl)cc5)c4s3)ccn2)cc1OC] | F | 603.13 | 603.1 | ¹H NMR (400 MHz, CD₃OD) δ 8.73 (d, J = 5.6 Hz, 1H), 8.54 (s, 1H), 8.05 (dd, J = 5.4, 1.6 Hz, 1H), 7.99 (s, 1H), 7.73-7.57 (m, 6H), 7.16 (d, J = 8.4 Hz, 1H), 5.29 (s, 1H), 3.97 (s, 3H), 3.93 (s, 3H), 2.65 (s, 3H), 0.99 (s, 9H). |
| 351 | 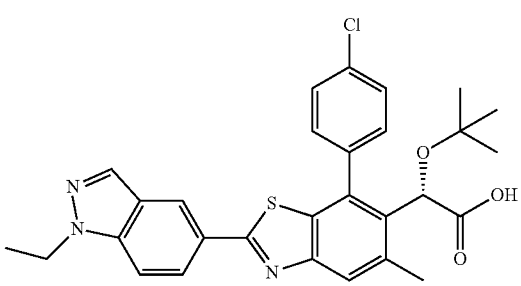 [SMILES: CCn1ncc2cc(-c3nc4cc(C)c([C@H](OC(C)(C)C)C(=O)O)c(-c5ccc(Cl)cc5)c4s3)ccc21] | J | 534.07 | 534 | ¹H NMR (400 MHz, CD₃OD) δ 8.43-8.41 (m, 1H), 8.14 (s, 1H), 8.11 (dd, J = 8.9, 1.7 Hz, 1H), 7.81 (s, 1H), 7.72-7.67 (m, 2H), 7.59 (m, 3H), 5.25 (s, 1H), 4.50 (q, J = 7.2 Hz, 2H), 2.60 (s, 3H), 1.49 (t, J = 7.2 Hz, 3H), 0.98 (s, 9H). |
| 352 | 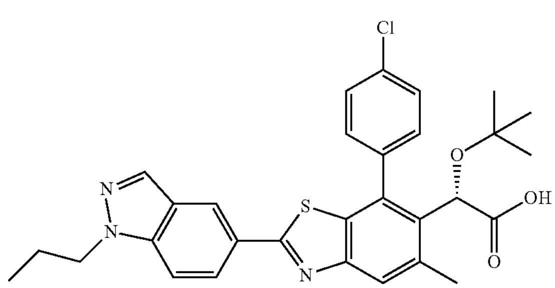 [SMILES: CCCn1ncc2cc(-c3nc4cc(C)c([C@H](OC(C)(C)C)C(=O)O)c(-c5ccc(Cl)cc5)c4s3)ccc21] | J | 548.1 | 548.2 | ¹H NMR (400 MHz, CD₃OD) δ 8.46-8.44 (m, 1H), 8.15 (d, J = 0.9 Hz, 1H), 8.13 (dd, J = 8.9, 1.7 Hz, 1H), 7.83 (s, 1H), 7.75-7.66 (m, 2H), 7.65-7.55 (m, 3H), 5.26 (s, 1H), 4.43 (t, J = 6.9 Hz, 2H), 2.61 (s, 3H), 2.07-1.83 (m, 2H), 0.98 (s, 9H), 0.91 (t, J = 7.4 Hz, 3H). |

| Cmpd # | Compound Structure | Method | Parent MW | LCMS-ESI+ | 1H NMR |
|---|---|---|---|---|---|
| 353 | 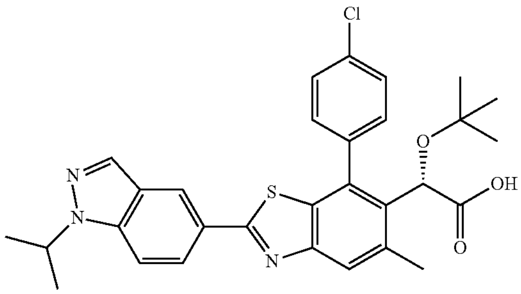 [SMILES: Cc1cc2nc(-c3ccc4c(cnn4C(C)C)c3)sc2c(-c2ccc(Cl)cc2)c1[C@H](OC(C)(C)C)C(=O)O] | J | 548.1 | 548.1 | ¹H NMR (400 MHz, CD₃OD) δ 8.43 (d, J = 1.3 Hz, 1H), 8.15 (s, 1H), 8.11 (dd, J = 8.9, 1.7 Hz, 1H), 7.82 (d, J = 0.9 Hz, 1H), 7.76-7.66 (m, 2H), 7.64-7.56 (m, 3H), 5.26 (s, 1H), 5.01 (hept, J = 6.3 Hz, 1H), 2.61 (s, 3H), 1.58 (d, J = 6.7 Hz, 6H), 0.98 (s, 9H). |
| 354 | 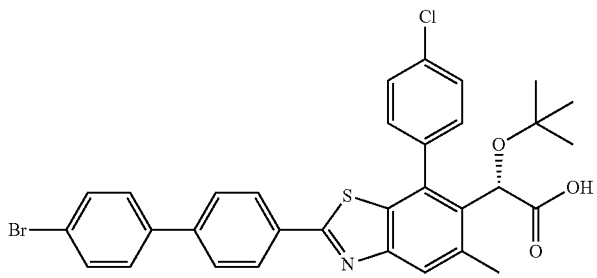 [SMILES: Cc1cc2nc(-c3ccc(-c4ccc(Br)cc4)cc3)sc2c(-c2ccc(Cl)cc2)c1[C@H](OC(C)(C)C)C(=O)O] | AU | 620.98 | 621.5 | ¹H NMR (400 MHz, CD₃OD) δ 8.10-8.05 (m, 2H), 7.83 (s, 1H), 7.79-7.72 (m, 2H), 7.73-7.65 (m, 1H), 7.65-7.54 (m, 7H), 5.26 (s, 1H), 2.61 (s, 3H), 0.97 (s, 9H). |
| 355 | 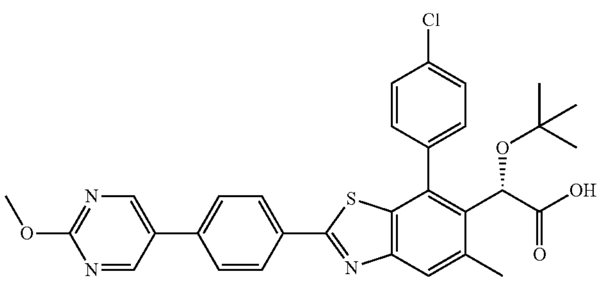 [SMILES: COc1ncc(-c2ccc(-c3nc4cc(C)c([C@H](OC(C)(C)C)C(=O)O)c(-c5ccc(Cl)cc5)c4s3)cc2)cn1] | AU | 574.09 | 574 | ¹H NMR (400 MHz, CD₃OD) δ 8.92 (s, 2H), 8.16 (d, J = 8.6 Hz, 2H), 7.89-7.78 (m, 3H), 7.73-7.66 (m, 1H), 7.63-7.57 (m, 3H), 5.26 (s, 1H), 4.07 (s, 3H), 2.62 (s, 3H), 0.98 (s, 9H). |
| 356 | 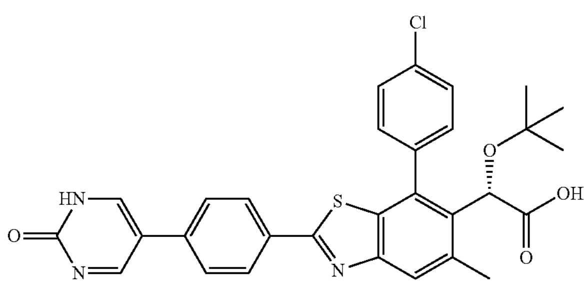 [SMILES: Cc1cc2nc(-c3ccc(-c4cnc(=O)[nH]c4)cc3)sc2c(-c2ccc(Cl)cc2)c1[C@H](OC(C)(C)C)C(=O)O] | AU | 560.06 | 560 | ¹H NMR (400 MHz, CD₃OD) δ 8.74 (s, 2H), 8.14 (d, J = 8.2 Hz, 2H), 7.86 (s, 1H), 7.79-7.66 (m, 3H), 7.64-7.55 (m, 3H), 5.26 (s, 1H), 2.62 (s, 3H), 0.98 (s, 9H). |
| 357 | 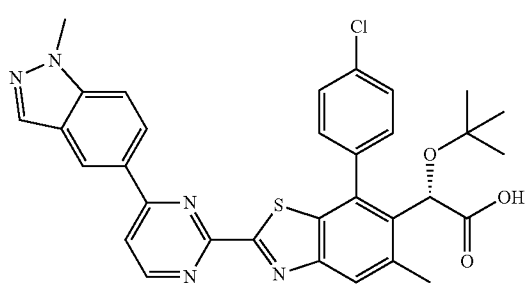 [SMILES: Cc1cc2nc(-c3nccc(-c4ccc5c(cnn5C)c4)n3)sc2c(-c2ccc(Cl)cc2)c1[C@H](OC(C)(C)C)C(=O)O] | H | 598.11 | 598.1 | ¹H NMR (400 MHz, CD₃OD) δ 8.90 (d, J = 5.4 Hz, 1H), 8.79 (s, 1H), 8.41 (dd, J = 9.0, 1.7 Hz, 1H), 8.19 (d, J = 0.9 Hz, 1H), 8.09 (d, J = 5.5 Hz, 1H), 8.00 (s, 1H), 7.75-7.70 (m, 2H), 7.68-7.61 (m, 3H), 5.30 (s, 1H), 4.12 (s, 3H), 2.65 (s, 3H), 0.99 (s, 9H). |

| Cmpd # | Compound Structure | Method | Parent MW | LCMS-ESI+ | 1H NMR |
|---|---|---|---|---|---|
| 358 | 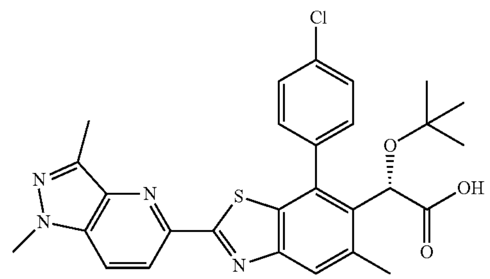 [SMILES: Cc1cc2nc(-c3ccc4c(n3)c(C)nn4C)sc2c(-c2ccc(Cl)cc2)c1[C@H](OC(C)(C)C)C(=O)O] | F | 535.15 | 535.3 | $^1$H NMR (400 MHz, CD$_3$OD) δ: 8.55 (d, J = 2.4 Hz, 1H), 7.99 (s, 1H), 7.72-7.55 (m, 5H), 5.29 (s, 1H), 4.10 (s, 3H), 2.64 (s, 6H), 0.98 (s, 9H). |
| 359 | 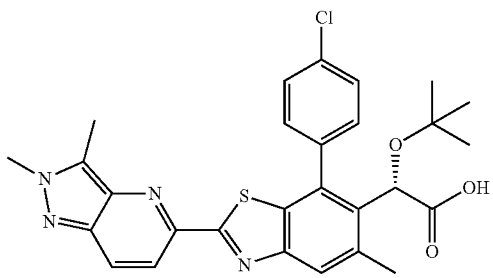 [SMILES: Cc1cc2nc(-c3ccc4nn(C)c(C)c4n3)sc2c(-c2ccc(Cl)cc2)c1[C@H](OC(C)(C)C)C(=O)O] | F | 535.15 | 535.2 | $^1$H NMR (400 MHz, CD$_3$OD) δ: 8.63 (s, J = 2.2 Hz, 1H), 8.25 (d, J = 2.6 Hz, 1H), 7.94 (s, 1H), 7.72-7.61 (m, 4H), 5.27 (s, 1H), 4.18 (s, 3H), 2.72 (s, 3H), 2.64 (s, 3H), 0.98 (s, 9H). |
| 360 | 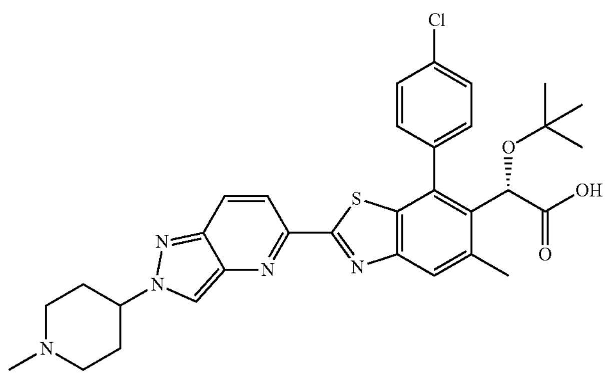 [SMILES: Cc1cc2nc(-c3ccc4nn(C5CCN(C)CC5)cc4n3)sc2c(-c2ccc(Cl)cc2)c1[C@H](OC(C)(C)C)C(=O)O] | F | 604.16 | 604.3 | $^1$H NMR (400 MHz, CD$_3$OD) δ: 8.26-8.24 (m, 1H), 8.14-8.12 (m, 2H), 7.70 (s, 1H), 7.61-7.59 (m, 1H), 7.50-7.47 (m, 3H), 5.17 (s, 1H), 9.63-4.91 (m, 1H), 3.65-3.62 (m, 2H), 3.24-3.22 (m, 2H), 2.89 (s, 3H), 2.50 (s, 3H), 2.47-2.41 (m, 2H), 2.24-2.21 (m, 2H), 0.87 (s, 9H). |
| 361 | 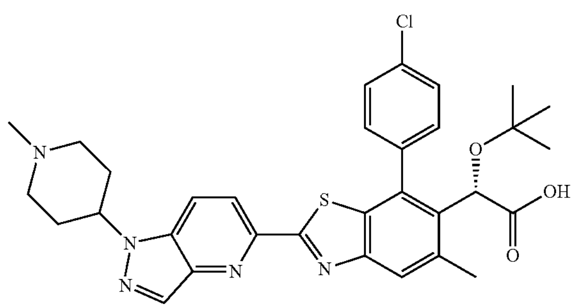 [SMILES: Cc1cc2nc(-c3ccc4c(cnn4C4CCN(C)CC4)n3)sc2c(-c2ccc(Cl)cc2)c1[C@H](OC(C)(C)C)C(=O)O] | F | 604.16 | 604.4 | $^1$H NMR (400 MHz, CD$_3$OD) δ: 8.50 (s, 1H), 8.20-8.08 (s, 2H), 7.74 (s, 1H), 7.60-7.58 (s, 1H), 7.50-7.47 (m, 3H), 5.17 (s, 1H), 4.84-4.83 (m, 1H), 3.63-3.57 (m, 2H), 3.24-3.22 (m, 2H), 2.88 (s, 3H), 2.50 (s, 3H), 2.49-2.41 (m, 4H), 0.87 (s, 9H). |
| 362 | 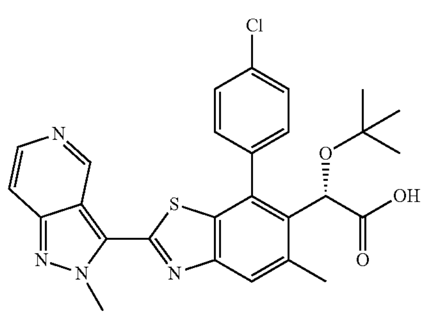 [SMILES: Cc1cc2nc(-c3c4cnccc4nn3C)sc2c(-c2ccc(Cl)cc2)c1[C@H](OC(C)(C)C)C(=O)O] | F | 521.03 | 521.2 | $^1$H NMR (400 MHz, CD$_3$OD) δ: 9.80 (s, 1H), 8.43 (d, J = 3 Hz, 1H), 7.95 (d, J = 3.4 Hz, 1H), 7.82 (s, 1H), 7.64-7.62 (m, 1H), 7.54-7.7.46 (m, 3H), 5.19 (s, 1H), 4.11 (s, 3H), 2.54 (s, 3H), 0.88 (s, 9H). |

-continued

| Cmpd # | Compound Structure | Method | Parent MW | LCMS-ESI+ | 1H NMR |
|---|---|---|---|---|---|
| 363 | 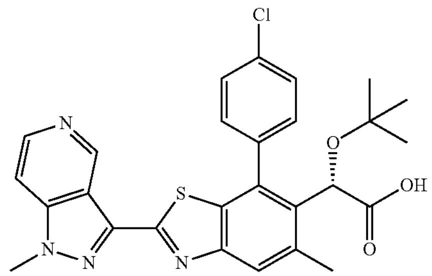 [SMILES: Cc1cc2nc(-c3nn(C)c4ccncc34)sc2c(-c2ccc(Cl)cc2)c1[C@H](OC(C)(C)C)C(=O)O] | F | 521.03 | 521.3 | ¹H NMR (400 MHz, CD₃OD) δ: 9.84 (s, 1H), 8.45 (d, J = 3.2 Hz, 1H), 7.99 (d, J = 3.6 Hz, 1H), 7.83 (s, 1H), 7.75-7.7.53 (m, 4H), 5.28 (s, 1H), 4.15 (s, 3H), 2.63 (s, 3H), 0.96 (s, 9H). |
| 364 | 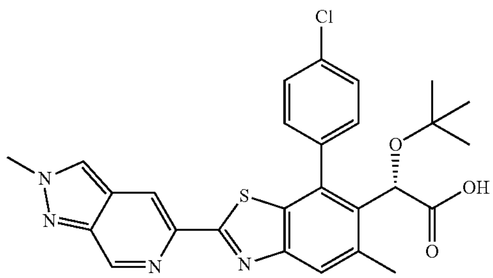 [SMILES: Cc1cc2nc(-c3cc4cn(C)nc4cn3)sc2c(-c2ccc(Cl)cc2)c1[C@H](OC(C)(C)C)C(=O)O] | F | 521.03 | 521.2 | ¹H NMR (400 MHz, CD₃OD) δ: 9.10 (s, 1H), 8.63 (s, 1H), 8.52 (s, 1H), 7.82 (s, 1H), 7.69 (d, J = 4.8 Hz, 1H), 7.60-7.58 (m, 3H), 5.27 (s, 1H), 4.32 (s, 3H), 2.61 (s, 3H), 0.97 (s, 9H). |
| 365 | 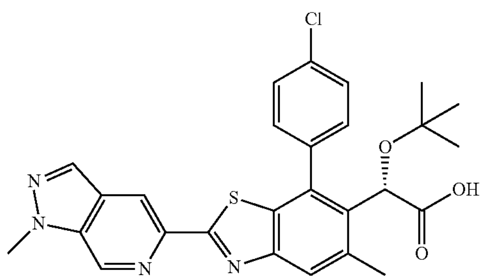 [SMILES: Cc1cc2nc(-c3cc4cnn(C)c4cn3)sc2c(-c2ccc(Cl)cc2)c1[C@H](OC(C)(C)C)C(=O)O] | F | 521.03 | 521.3 | ¹H NMR (400 MHz, CD₃OD) δ: 8.88 (s, 1H), 8.50 (s, 1H), 8.12 (s, 1H), 7.67-7.49 (m, 5H), 5.17 (s, 1H), 4.08 (s, 3H), 2.51 (s, 3H), 0.88 (s, 9H). |
| 366 | 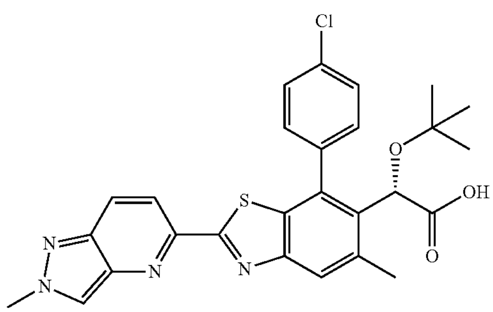 [SMILES: Cc1cc2nc(-c3ccc4nn(C)cc4n3)sc2c(-c2ccc(Cl)cc2)c1[C@H](OC(C)(C)C)C(=O)O] | F | 521.03 | 521.2 | ¹H NMR (400 MHz, CD₃OD) δ: 8.34-8.32 (m, 1H), 8.18-8.10 (m, 2H), 7.81 (s, 1H), 7.70-7.68 (m, 1H), 7.60-7.59 (m, 3H), 5.27 (s, 1H), 4.08 (s, 3H), 2.61 (s, 3H), 0.97 (s, 9H). |
| 367 | 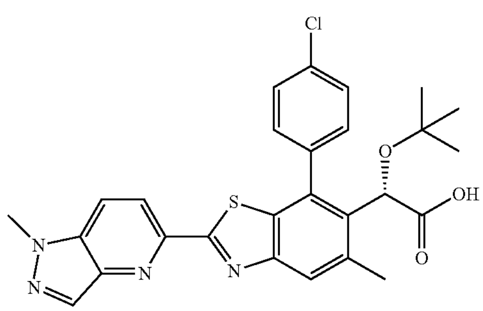 [SMILES: Cc1cc2nc(-c3ccc4c(cnn4C)n3)sc2c(-c2ccc(Cl)cc2)c1[C@H](OC(C)(C)C)C(=O)O] | F | 521.03 | 521.2 | ¹H NMR (400 MHz, CD₃OD) δ: 8.37 (d, J = 4.4 Hz, 1H), 8.21-8.15 (m, 2H), 7.85 (s, 1H), 7.70-7.68 (m, 1H), 7.61-7.59 (m, 3H), 5.27 (s, 1H), 4.12 (s, 3H), 2.61 (s, 3H), 0.97 (s, 9H). |

-continued

| Cmpd # | Compound Structure | Method | Parent MW | LCMS-ESI+ | 1H NMR |
|---|---|---|---|---|---|
| 368 | 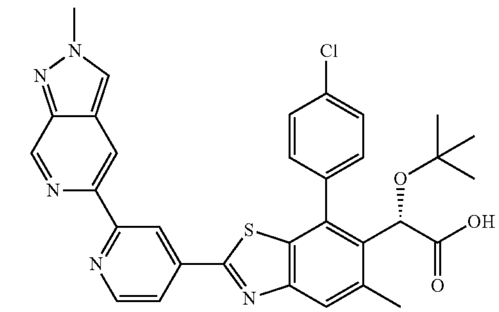 [SMILES: Cc1cc2nc(-c3ccnc(-c4cc5cn(C)nc5cn4)c3)sc2c(-c2ccc(Cl)cc2)c1[C@H](OC(C)(C)C)C(=O)O] | P | 598.11 | 598.2 | ¹H NMR (400 MHz, CD₃OD) δ: 0.923 (S, 1H), 8.71-8.50 (m, 4H), 7./84 (s, 1H), 7.701 (s, 1H), 7.62-7.43 (m, 4J), 5.18 (s, 1H), 4.25 (s, 3H), 2.50 (s, 3H), 0.89 (s, 9H). |
| 369 | 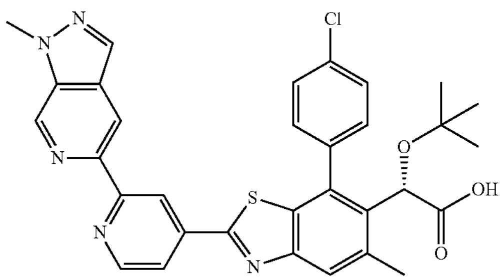 [SMILES: Cc1cc2nc(-c3ccnc(-c4cc5cnn(C)c5cn4)c3)sc2c(-c2ccc(Cl)cc2)c1[C@H](OC(C)(C)C)C(=O)O] | P | 598.11 | 598.2 | ¹H NMR (400 MHz, CD₃OD) δ: 0.916 (s, 1H), 8.72-8.69 (m, 3H), 8.20 (s, 1H), 7.89-7.55 (m, 6H), 5.26 (s, 1H), 4.13 (s, 3H), 2.60 (s, 3H), 0.99 (s, 9H). |
| 370 | 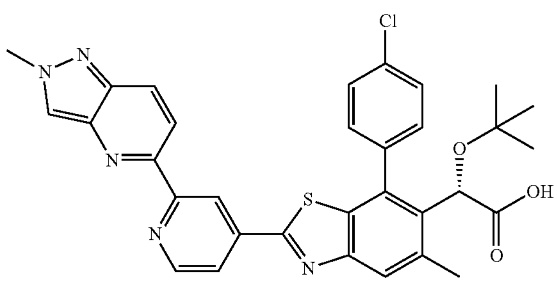 [SMILES: Cc1cc2nc(-c3ccnc(-c4ccc5nn(C)cc5n4)c3)sc2c(-c2ccc(Cl)cc2)c1[C@H](OC(C)(C)C)C(=O)O] | P | 598.11 | 598.3 | ¹H NMR (400 MHz, CD₃OD) δ: 8.45 (s, 1H), 8.41 (d, J = 2.6 Hz, 1H), 8.21 (s, 1H), 8.02 (d, J = 4.4 Hz, 1H), 7.89 (d, J = 4.6 Hz, 1H), 7.63-7.56 (m, 3H), 7.46-7.40 (m, 3H), 5.16 (s, 1H), 4.06 (s, 3H), 2.46 (s, 3H), 0.88 (s, 9H). |
| 371 | 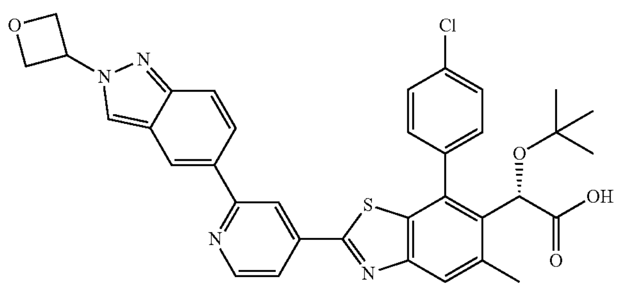 [SMILES: Cc1cc2nc(-c3ccnc(-c4ccc5nn(C6COC6)cc5c4)c3)sc2c(-c2ccc(Cl)cc2)c1[C@H](OC(C)(C)C)C(=O)O] | O | 639.16 | 639.3 | ¹H NMR (400 MHz, CD₃OD) δ: 8.61 (d, J = 2.8 Hz, 1H), 8.42-8.31 (m, 3H), 7.88-7.82 (m, 3H), 7.72 (d, J = 2.8 Hz, 1H), 7.61-7.58 (m, 1H), 7.51-7.48 (m, 3H), 5.80-5.75 (m, 1H), 5.18 (s, 1H), 5.09-5.05 (m, 4H), 2.52 (s, 3H), 0.88 (s, 9H). |
| 372 | 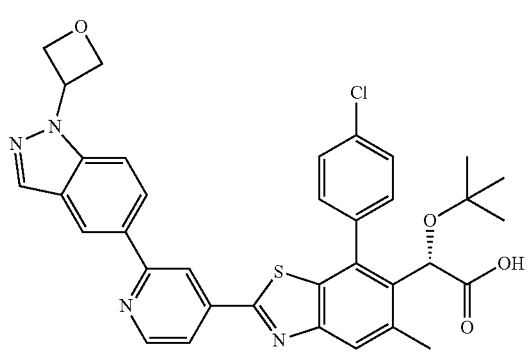 [SMILES: Cc1cc2nc(-c3ccnc(-c4ccc5c(cnn5C5COC5)c4)c3)sc2c(-c2ccc(Cl)cc2)c1[C@H](OC(C)(C)C)C(=O)O] | O | 639.16 | 639.3 | ¹H NMR (400 MHz, CD₃OD) δ: 8.67 (d, J = 2.6 Hz, 1H), 8.49 (s, 1H), 8.39 (s, 1H), 8.21 (s, 1H), 8.01-7.98 (m, 2H), 7.87 (s, 1H), 7.71 (d, J = 4.4 Hz, 1H), 7.62-7.60 (m, 1H), 7.52 (m, 2H), 5.96-5.92 (m, 1H), 5.19 (s, 1H), 5.16-5.06 (m, 4H), 2.55 (s, 3H), 0.89 (s, 9H). |

-continued

| Cmpd # | Compound Structure | Method | Parent MW | LCMS-ESI+ | 1H NMR |
|---|---|---|---|---|---|
| 373 | 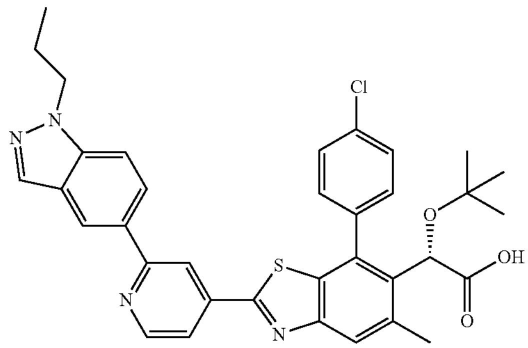 [SMILES: CCCn1ncc2cc(-c3cc(-c4nc5cc(C)c([C@H](OC(C)(C)C)C(=O)O)c(-c6ccc(Cl)cc6)c5s4)ccn3)ccc21] | F | 625.18 | 625.3 | ¹H NMR (400 MHz, CD₃OD) δ: 8.77 (d, J = 2.6 Hz, 1H), 8.59 (s, 1H), 8.49 (s, 1H), 8.19 (s, 1H), 8.14-8.04 (m, 2H), 7.98 (s, 1H), 7.78-7.69 (m, 2H), 7.62-7.61 (m, 3H), 5.28 (s, 1H), 4.45 (t, J = 6.8 Hz, 2H), 2.65 (s, 3H), 1.99-1.64 (m, 2H), 0.98 (s, 9H), 0.925 (t, J = 7.4 Hz, 3H). |
| 374 | 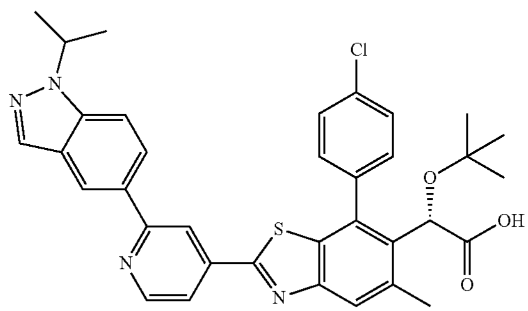 [SMILES: Cc1cc2nc(-c3ccnc(-c4ccc5c(cnn5C(C)C)c4)c3)sc2c(-c2ccc(Cl)cc2)c1[C@H](OC(C)(C)C)C(=O)O] | F | 625.18 | 625.2 | ¹H NMR (400 MHz, CD₃OD) δ: 8.74 (d, J = 2.8 Hz, 1H), 8.52 (s, 1H), 8.46 (s, 1H), 8.17 (s, 1H), 8.11 (d, J = 4.2 Hz, 1H), 7.95-7.94 (m, 2H), 7.76-7.69 (m, 2H), 7.62-7.60 (m, 3H), 5.28 (s, 1H), 5.04-5.00 (m, 1H), 2.64 (s, 3H), 1.60 (s, 3H), 1.58 (s, 3H), 0.98 (s, 9H). |
| 375 | 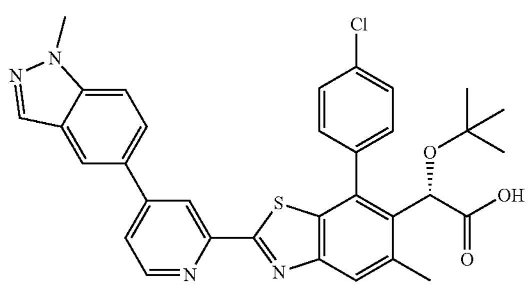 [SMILES: Cc1cc2nc(-c3cc(-c4ccc5c(cnn5C)c4)ccn3)sc2c(-c2ccc(Cl)cc2)c1[C@H](OC(C)(C)C)C(=O)O] | H | 597.13 | 597.1 | ¹H NMR (400 MHz, CD₃OD) δ: 8.59 (s, 1H), 8.53 (d, J = 2.4 Hz, 1H), 8.21 (s, 1H), 8.06 (s, 1H), 7.86-7.75 (m, 3H), 7.67-7.60 (m, 2H), 7.52-7.51 (m, 3H), 5.18 (s, 1H), 4.04 (3H), 2.53 (s, 3H), 0.88 (s, 9H). |
| 376 | 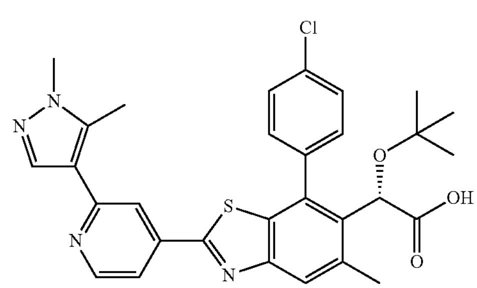 [SMILES: Cc1cc2nc(-c3ccnc(-c4cnn(C)c4C)c3)sc2c(-c2ccc(Cl)cc2)c1[C@H](OC(C)(C)C)C(=O)O] | C | 561.09 | 561.2 | ¹H NMR (400 MHz, CD₃OD) δ: 8.69 (d, J = 2.8 Hz, 1H), 8.28 (s, 1H), 7.99-7.96 (m, 3H), 7.70-7.68 (m, 1H), 7.62-7.60 (m, 3H), 5.27 (s, 1H), 3.89 (s, 3H), 2.64 (s, 3H), 2.62 (s, 3H), 0.97 (s, 9H). |

| Cmpd # | Compound Structure | Method | Parent MW | LCMS-ESI+ | 1H NMR |
|---|---|---|---|---|---|
| 377 | 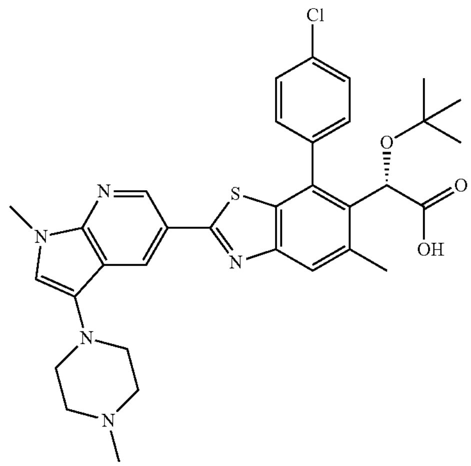 [SMILES: Cc1cc2nc(-c3cnc4c(c3)c(N3CCN(C)CC3)cn4C)sc2c(-c2ccc(Cl)cc2)c1[C@H](OC(C)(C)C)C(=O)O] | AN | 618.23 | 618.39 | ¹H NMR (400 MHz, CD₃OD) δ 8.93 (d, J = 2 Hz, 1H), 8.60 (d, J = 1.6 Hz, 1H), 7.82 (s, 1H), 7.70-7.60 (m, 4H), 7.15 (s, 1H), 5.25 (s, 1H), 3.88 (s, 3H), 3.71- 3.48 (m, 6H), 3.13-3.01 (m, 5H), 2.62 (s, 3H), 0.98 (s, 9H). |
| 378 | 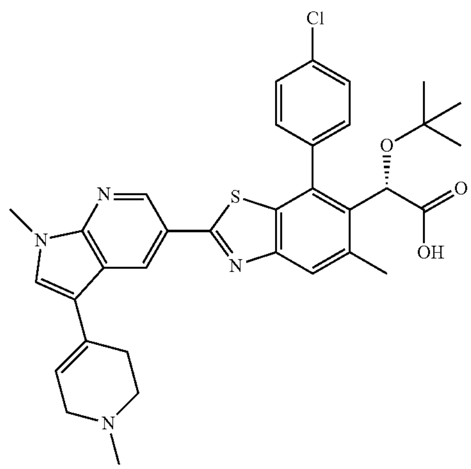 [SMILES: Cc1cc2nc(-c3cnc4c(c3)c(C3=CCN(C)CC3)cn4C)sc2c(-c2ccc(Cl)cc2)c1[C@H](OC(C)(C)C)C(=O)O] | AN | 615.22 | 615.3 | ¹H NMR (400 MHz, CD₃OD) δ 8.96 (d, J = 1.6 Hz, 1H), 8.84 (d, J = 1.6 Hz, 1H), 7.85-7.60 (m, 6H), 6.31 (s, 1H), 5.26 (s, 1H), 4.12-4.00 (m, 1H), 3.91 (s, 3H), 3.74 (s, 1H), 3.48-3.40 (m, 2H), 3.11 (s, 1H), 3.04 (s, 3H), 2.96 (s, 2H), 2.62 (s, 3H), 0.98 (s, 9H). |
| 379 | 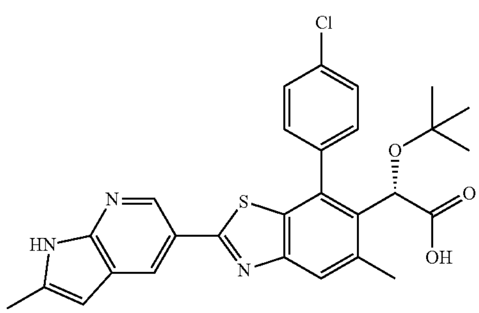 [SMILES: Cc1cc2cc(-c3nc4cc(C)c([C@H](OC(C)(C)C)C(=O)O)c(-c5ccc(Cl)cc5)c4s3)cnc2[nH]1] | AN | 520.04 | 520.2 | ¹H NMR (400 MHz, CD₃OD) δ 8.77 (d, J = 1.6 Hz, 1H), 8.45 (d, J = 1.6 Hz, 1H), 7.83 (s, 1H), 7.70-7.58 (m, 4H), 6.32 (s, 1H), 5.25 (s, 1H), 2.61 (s, 3H), 2.48 (s, 3H), 0.97 (s, 9H). |
| 380 | 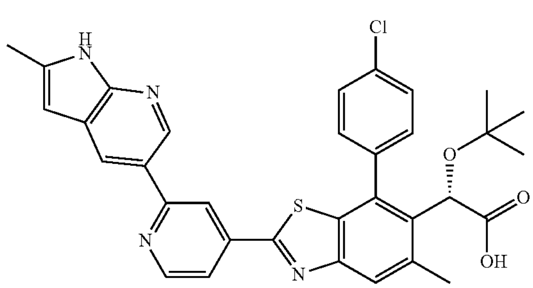 [SMILES: Cc1cc2cc(-c3cc(-c4nc5cc(C)c([C@H](OC(C)(C)C)C(=O)O)c(-c6ccc(Cl)cc6)c5s4)ccn3)cnc2[nH]1] | AO | 597.13 | 597.2 | ¹H NMR (400 MHz, CD₃OD) δ 8.79-8.76 (m, 2H), 8.50-8.48 (m, 2H), 7.97 (s, 1H), 7.91-7.62 (m, 5H), 6.32 (s, 1H), 5.28 (s, 1H), 2.64 (s, 3H), 2.49 (s, 3H), 0.98 (s, 9H). |

-continued

| Cmpd # | Compound Structure | Method | Parent MW | LCMS-ESI+ | 1H NMR |
|---|---|---|---|---|---|
| 381 | 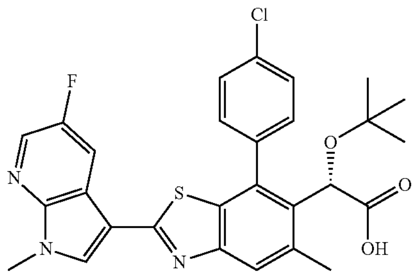 [SMILES: Cc1cc2nc(-c3cn(C)c4ncc(F)cc34)sc2c(-c2ccc(Cl)cc2)c1[C@H](OC(C)(C)C)C(=O)O] | AM | 538.03 | 538.2 | ¹H NMR (400 MHz, CD₃OD) δ 8.44-8.41 (m, 1H), 8.29 (d, J = 2 Hz, 1H), 8.19 (s, 1H), 7.80 (s, 1H), 7.69-7.57 (m, 4H), 5.24 (s, 1H), 3.92 (s, 3H), 2.60 (s, 3H), 0.97 (s, 9H). |
| 382 | 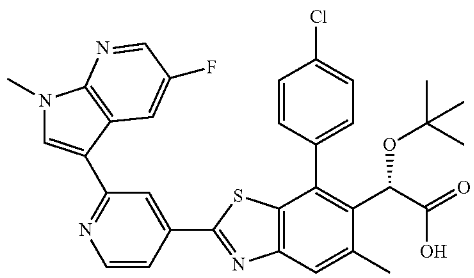 [SMILES: Cc1cc2nc(-c3ccnc(-c4cn(C)c5ncc(F)cc45)c3)sc2c(-c2ccc(Cl)cc2)c1[C@H](OC(C)(C)C)C(=O)O] | AL | 615.12 | 615.2 | ¹H NMR (400 MHz, DMSO) δ 8.75-8.56 (m, 3H), 8.34-8.24 (m, 2H), 7.99 (s, 1H), 7.83-7.58 (m, 5H), 5.09 (s, 1H), 3.89 (s, 3H), 2.56 (s, 3H), 0.89 (s, 9H). |
| 383 | 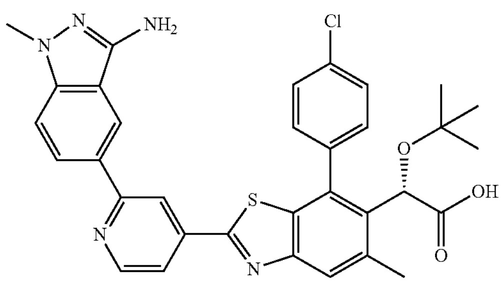 [SMILES: Cc1cc2nc(-c3ccnc(-c4ccc5c(c4)c(N)nn5C)c3)sc2c(-c2ccc(Cl)cc2)c1[C@H](OC(C)(C)C)C(=O)O] | AO | 612.14 | 612.3 | ¹H NMR (400 MHz, CD₃OD) δ 8.74 (d, J = 5.6 Hz, 1H), 8.54 (s, 1H), 8.46 (s, 1H), 8.15-7.62 (m, 7H), 7.51 (d, J = 9.2 Hz, 1H), 5.28 (s, 1H), 3.86 (s, 3H), 2.65 (s, 3H), 0.98 (s, 9H). |
| 384 | 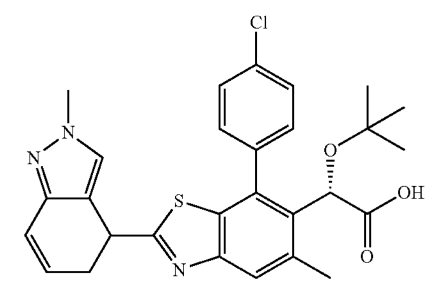 [SMILES: Cc1cc2nc(C3CC=Cc4nn(C)cc43)sc2c(-c2ccc(Cl)cc2)c1[C@H](OC(C)(C)C)C(=O)O] | AM | 520.04 | 520.3 | ¹H NMR (400 MHz, CD₃OD) δ 8.98 (s, 1H), 7.93 (s, 1H), 7.78-7.37 (m, 7H), 5.26 (s, 1H), 4.30 (s, 3H), 2.63 (s, 3H), 0.98 (s, 9H). |
| 385 | 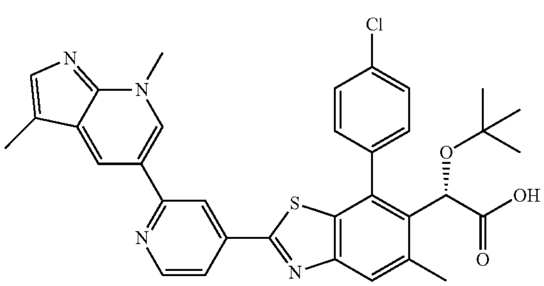 [SMILES: Cc1cnc2n(C)cc(-c3cc(-c4nc5cc(C)c([C@H](OC(C)(C)C)C(=O)O)c(-c6ccc(Cl)cc6)c5s4)ccn3)cc1-2] | AL | 611.15 | 611.2 | ¹H NMR (400 MHz, CD₃OD) δ 8.85 (d, J = 2 Hz, 1H), 8.70-8.68 (m, 1H), 8.59 (d, J = 2.4 Hz, 1H), 8.49 (d, J = 0.8 Hz, 1H), 7.90-7.51 (m, 6H), 7.15 (s, 1H), 5.19 (s, 1H), 3.78 (s, 3H), 2.55 (s, 3H), 2.31 (d, J = 1.2 Hz, 3H), 0.89 (s, 9H). |

-continued

| Cmpd # | Compound Structure | Method | Parent MW | LCMS-ESI+ | 1H NMR |
|---|---|---|---|---|---|
| 386 | 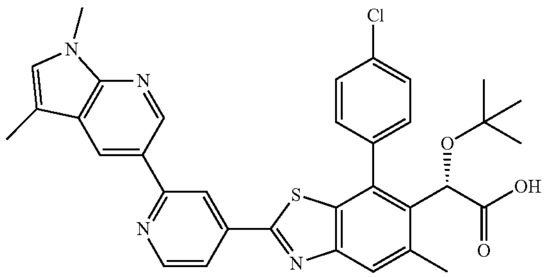 [SMILES: Cc1cc2nc(-c3ccnc(-c4cnc5c(c4)c(C)cn5C)c3)sc2c(-c2ccc(Cl)cc2)c1[C@H](OC(C)(C)C)C(=O)O] | AL | 611.15 | 611.3 | ¹H NMR (400 MHz, CD₃OD) δ 8.92 (d, J = 1.6 Hz, 1H), 8.77-8.70 (m, 2H), 8.58 (d, J = 1.2 Hz, 1H), 8.02-7.61 (m, 6H), 7.24 (d, J = 0.8 Hz, 1H), 5.28 (s, 1H), 3.86 (s, 3H), 2.64 (s, 3H), 2.39 (d, J = 0.8 Hz, 3H), 0.98 (s, 9H). |
| 387 | 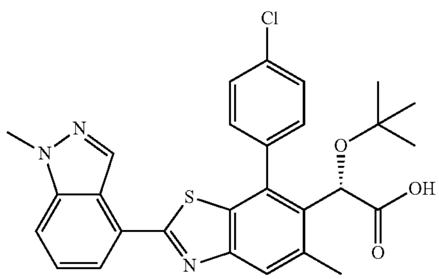 [SMILES: Cc1cc2nc(-c3cccc4c3cnn4C)sc2c(-c2ccc(Cl)cc2)c1[C@H](OC(C)(C)C)C(=O)O] | AM | 520.04 | 520.2 | ¹H NMR (400 MHz, CD₃OD) δ 8.70 (s, 1H), 7.85 (s, 1H), 7.66-7.39 (m, 7H), 5.17 (s, 1H), 4.04 (s, 3H), 2.54 (s, 3H), 0.88 (s, 9H). |
| 388 | 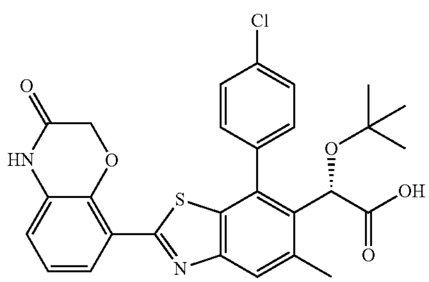 [SMILES: Cc1cc2nc(-c3cccc4c3OCC(=O)N4)sc2c(-c2ccc(Cl)cc2)c1[C@H](OC(C)(C)C)C(=O)O] | J | 537.03 | 537.2 | ¹H NMR (400 MHz, CD₃OD) δ: 7.75 (s, 1H), 7.67-7.65 (m, 1H), 7.57-7.54 (m, 5H), 7.96 (d, 1H), 5.23 (s, 1H), 4.62 (s, 2H), 2.58 (s, 3H), 0.95 (s, 9H). |
| 389 | 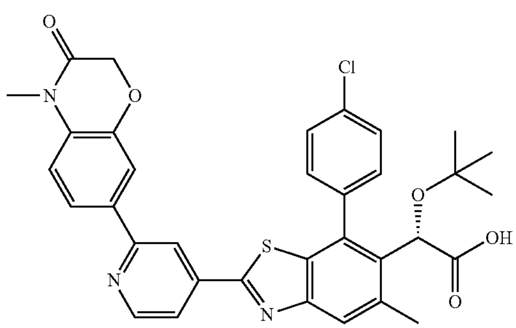 [SMILES: Cc1cc2nc(-c3ccnc(-c4ccc5c(c4)OCC(=O)N5C)c3)sc2c(-c2ccc(Cl)cc2)c1[C@H](OC(C)(C)C)C(=O)O] | F | 628.14 | 628.3 | ¹H NMR (400 MHz, CD₃OD) δ: 8.71 (d, 1H), 8.52 (s, 1H), 8.08 (d, 1H), 7.91 (s, 1H), 7.80 (m, 1H), 7.77-7.68 (m, 2H), 7.64-7.58 (m, 3H), 7.37 (d, 1H), 5.28 (s, 1H), 4.66 (s, 2H), 3.40 (s, 3H), 2.62 (s, 3H), 0.98 (s, 9H). |
| 390 | 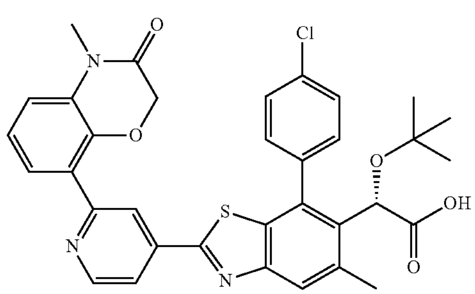 [SMILES: Cc1cc2nc(-c3ccnc(-c4cccc5c4OCC(=O)N5C)c3)sc2c(-c2ccc(Cl)cc2)c1[C@H](OC(C)(C)C)C(=O)O] | F | 628.14 | 628.2 | ¹H NMR (400 MHz, CD₃OD) δ: 8.79 (d, 1H), 8.52 (s, 1H), 8.08 (d, 1H), 7.88 (s, 1H), 7.68 (m, 1H), 7.62-7.58 (m, 3H), 7.54-7.44 (m, 1H), 7.37-7.23 (m, 2H), 5..32 (s, 1H), 4.63 (s, 2H), 3.37 (s, 3H), 2.62 (s, 3H), 1.02 (s, 9H). |

| Cmpd # | Compound Structure | Method | Parent MW | LCMS-ESI+ | 1H NMR |
|---|---|---|---|---|---|
| 391 | 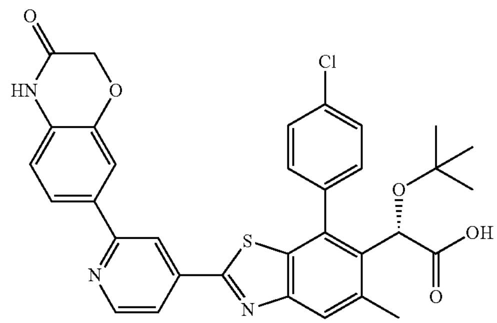 [SMILES: Cc1cc2nc(-c3ccnc(-c4ccc5c(c4)OCC(=O)N5)c3)sc2c(-c2ccc(Cl)cc2)c1[C@H](OC(C)(C)C)C(=O)O] | F | 614.11 | 614.3 | ¹H NMR (400 MHz, CD₃OD) δ: 8.69 (d, 1H), 8.43 (s, 1H), 7.98 (d, 1H), 7.92 (s, 1H), 7.68 (m, 1H), 7.62-7.58 (m, 5H), 7.05 (d, 1H), 5.27 (s, 1H), 4.64 (s, 2H), 2.62 (s, 3H), 0.97 (s, 9H). |
| 392 | 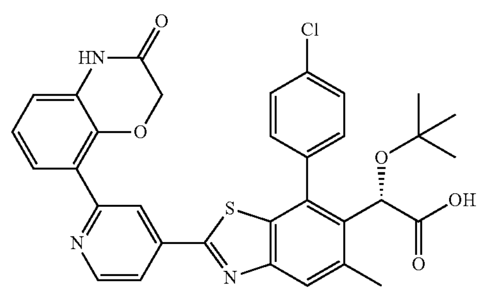 [SMILES: Cc1cc2nc(-c3ccnc(-c4cccc5c4OCC(=O)N5)c3)sc2c(-c2ccc(Cl)cc2)c1[C@H](OC(C)(C)C)C(=O)O] | F | 614.11 | 614.3 | ¹H NMR (400 MHz, CD₃OD) δ: 8.74 (d, 1H), 8.48 (s, 1H), 8.06 (m, 1H), 7.85 (s, 1H), 7.66-7.44 (m, 1H), 7.57-7.51 (m, 3H), 7.38-7.36 (m, 1H), 7.13-7.04 (m, 2H), 5..27 (s, 1H), 4.64 (s, 2H), 2.59 (s, 3H), 0.96 (s, 9H). |
| 393 | 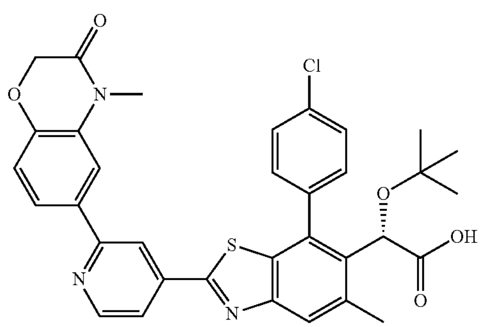 [SMILES: Cc1cc2nc(-c3ccnc(-c4ccc5c(c4)N(C)C(=O)CO5)c3)sc2c(-c2ccc(Cl)cc2)c1[C@H](OC(C)(C)C)C(=O)O] | F | 628.14 | 628.3 | ¹H NMR (400 MHz, CD₃OD) δ: 8.82 (d, 1H), 8.67 (s, 1H), 8.27 (d, 1H), 8.02 (s, 1H), 7.81 (m, 1H), 7.73-7.71 (m, 2H), 7.70-7.62 (m, 3H), 7.23 (m, 1H), 5.30 (s, 1H), 4.75 (s, 2H), 3.49 (s, 3H), 2.67 (s, 3H), 1.008 (s, 9H). |
| 394 | 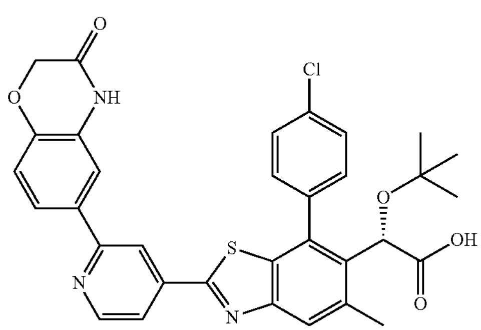 [SMILES: Cc1cc2nc(-c3ccnc(-c4ccc5c(c4)NC(=O)CO5)c3)sc2c(-c2ccc(Cl)cc2)c1[C@H](OC(C)(C)C)C(=O)O] | F | 614.11 | 614.3 | ¹H NMR (400 MHz, CD₃OD) δ: 8.70 (d, 1H), 8.40 (s, 1H), 8.01 (m, 1H), 7.93 (s, 1H), 7.70-7.68 (m, 1H), 7.63-7.59 (m, 4H), 7.54-7.53 (m, 1H), 7.09 (d, 1H), 5.27 (s, 1H), 4.64 (s, 2H), 2.63 (s, 3H), 0.97 (s, 9H). |
| 395 | 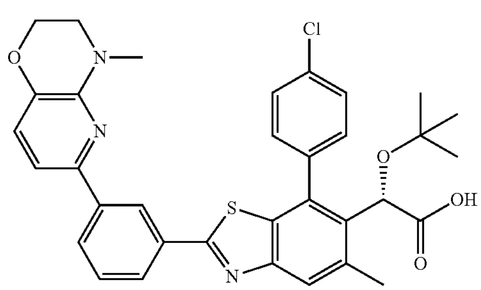 [SMILES: Cc1cc2nc(-c3cccc(-c4ccc5c(n4)N(C)CCO5)c3)sc2c(-c2ccc(Cl)cc2)c1[C@H](OC(C)(C)C)C(=O)O] | H | 614.5 | 614.3 | ¹H NMR (400 MHz, CD₃OD) δ: 8.36 (m, 1H), 8.43 (s, 1H), 7.98 (d, 1H), 7.86 (d, 1H), 7.80 (s, 1H), 7.68-7.65 (m, 1H), 7.56-7.50 (m, 3H), 7.43 (d, 1H), 7.23 (d, 1H), 5..27 (s, 1H), 4.54 (dd, 2H), 3.40 (dd, 2H), 2.97 (s, 3H), 2.60 (s, 3H), 0.97 (s, 9H). |

| Cmpd # | Compound Structure | Method | Parent MW | LCMS-ESI+ | 1H NMR |
|---|---|---|---|---|---|
| 396 | 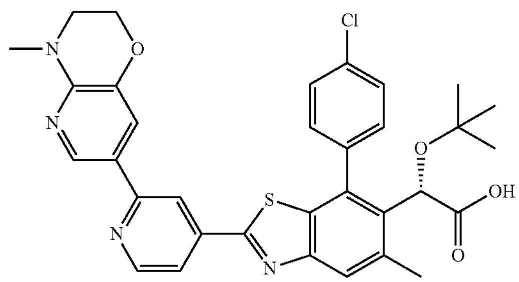 [SMILES: Cc1cc2nc(-c3ccnc(-c4cnc5c(c4)OCCN5C)c3)sc2c(-c2ccc(Cl)cc2)c1[C@H](OC(C)(C)C)C(=O)O] | F | 615.14 | 615.2 | $^1$H NMR (400 MHz, CD$_3$OD) δ: 8.68 (d, 1H), 8.33 (s, 1H), 8.27 (d, 1H), 7.98 (d, 1H), 7.89 (s, 1H), 7.88-7.84 (m, 1H), 7.69-7.67 (m, 1H), 7.61-7.58 (m, 3H), 5..27 (s, 1H), 4.36 (dd, 2H), 3.75 (dd, 2H), 3.30 (s, 3H), 2.62 (s, 3H), 0.97 (s, 9H). |
| 397 | 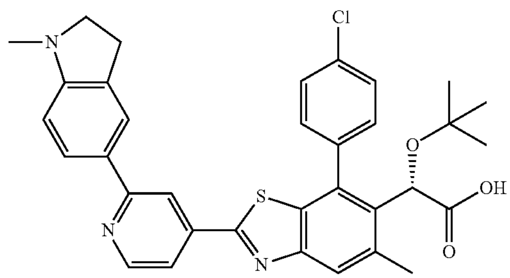 [SMILES: Cc1cc2nc(-c3ccnc(-c4ccc5c(c4)CCN5C)c3)sc2c(-c2ccc(Cl)cc2)c1[C@H](OC(C)(C)C)C(=O)O] | F | 598.15 | 598.3 | $^1$H NMR (400 MHz, CD$_3$OD) δ: 8.57 (d, 1H), 8.51 (s, 1H), 8.05-8.04 (m, 2H), 7.82-7.72 (m, 3H), 7.68-7.66 (m, 3H), 6.64 (d, 1H), 5.35 (s, 1H), 3.61-3.57 (dd, 2H), 3.14-3.10 (dd, 2H), 2.94 (s, 3H), 2.70 (s, 3H), 1.04 (s, 9H). |
| 398 | 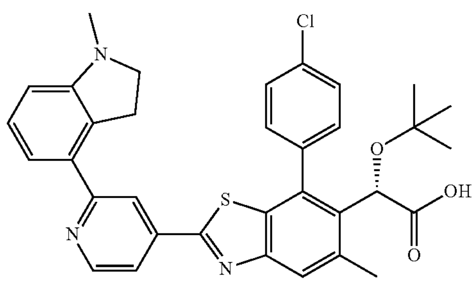 [SMILES: Cc1cc2nc(-c3ccnc(-c4cccc5c4CCN5C)c3)sc2c(-c2ccc(Cl)cc2)c1[C@H](OC(C)(C)C)C(=O)O] | F | 598.15 | 598.3 | $^1$H NMR (400 MHz, CD$_3$OD) δ: 8.77 (d, 1H), 8.35 (s, 1H), 8.10-8.08 (m, 1H), 7.90 (s, 1H), 7.68-7.66 (m, 1H), 7.58-7.56 (m, 3H), 7.40-7.38 (m, 1H), 7.27-7.25 (m, 1H), 7.02 (d, 1H), 5.26 (s, 1H), 3.56-3.53 (dd, 2H), 3.31-3.27 (m, 2H), 2.96 (s, 3H), 2.61 (s, 3H), 0.96 (s, 9H). |
| 399 | 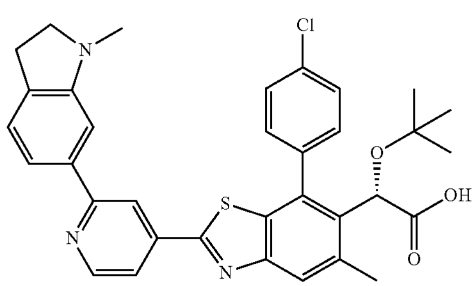 [SMILES: Cc1cc2nc(-c3ccnc(-c4ccc5c(c4)N(C)CC5)c3)sc2c(-c2ccc(Cl)cc2)c1[C@H](OC(C)(C)C)C(=O)O] | F | 598.15 | 598.3 | $^1$H NMR (400 MHz, CD$_3$OD) δ: 8.65 (d, 1H), 8.47 (s, 1H), 8.07-8.06 (m, 1H), 7.88 (s, 1H), 7.68-7.66 (m, 1H), 7.60-7.53 (m, 3H), 7.31-7.29 (m, 1H), 7.24-7.23 (m, 1H), 7.14 (s, 1H), 5.27 (s, 1H), 3.45-3.44 (dd, 2H), 3.04-3.00 (m, 2H), 2.88 (s, 3H), 2.60 (s, 3H), 0.97 (s, 9H). |
| 400 | 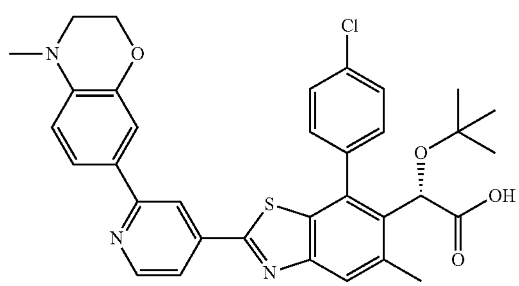 | F | 614.15 | 614.2 | $^1$H NMR (400 MHz, CD$_3$OD) δ: 8.38 (d, 1H), 8.24 (s, 1H), 7.80-7.77 (m, 2H), 7.60-7.58 (m, 1H), 7.51-7.47 (m, 3H), 7.38-7.36 (m, 1H), 7.22-7.21 (m, 1H), 6.66-6.64 (d, 1H), 5.18 (s, 1H), 4.14-4.12 (dd, 2H), 3.28-3.26 (m, 2H), 2.88 (s, 3H), 2.52 (s, 3H), 0.88 (s, 9H). |

| Cmpd # | Compound Structure | Method | Parent MW | LCMS-ESI+ | 1H NMR |
|---|---|---|---|---|---|
| 401 | 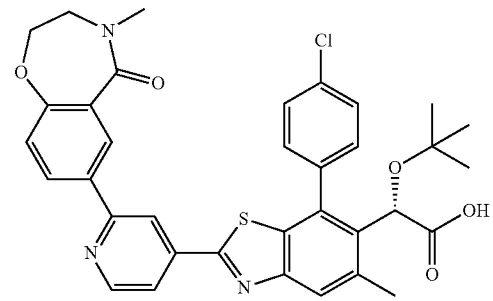 [SMILES: Cc1cc2nc(-c3ccnc(-c4ccc5c(c4)C(=O)N(C)CCO5)c3)sc2c(-c2ccc(Cl)cc2)c1[C@H](OC(C)(C)C)C(=O)O] | F | 642.16 | 642.2 | ¹H NMR (400 MHz, CD₃OD) δ: 8.67 (d, 1H), 8.36 (d, 2H), 8.08-8.06 (m, 1H), 7.96-7.94 (m, 1H), 7.84 (s, 1H), 7.64-7.63 (m, 1H), 7.55-7.53 (m, 3H), 7.12 (d, 1H), 5.25 (s, 1H), 4.49-4.72 (dd, 2H), 3.66-3.63 (dd, 2H), 3.20 (s, 3H), 2.57 (s, 3H), 0.96 (s, 9H). |
| 402 | 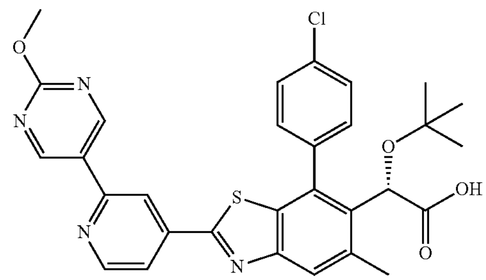 | F | 575.08 | 575.2 | ¹H NMR (400 MHz, CD₃OD) δ: 9.22 (s, 2H), 8.75-8.74 (d, 1H), 8.42 (s, 1H), 7.89 (m, 2H), 7.68-7.67 (m, 1H), 7.60-7.58 (m, 3H), 5.26 (s, 1H), 4.08 (s, 3H), 2.61 (s, 3H), 0.97 (s, 9H). |
| 403 | 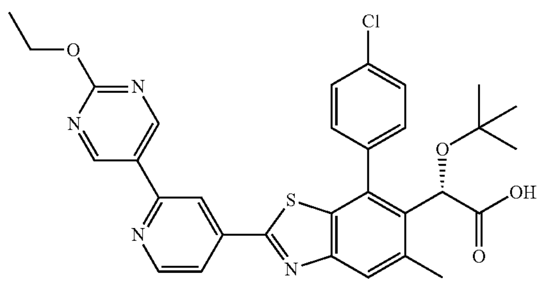 [SMILES: CCOc1ncc(-c2cc(-c3nc4cc(C)c([C@H](OC(C)(C)C)C(=O)O)c(-c5ccc(Cl)cc5)c4s3)ccn2)cn1] | F | 589.1 | 589.2 | ¹H NMR (400 MHz, CD₃OD) δ: 9.22 (s, 2H), 8.77-8.76 (d, 1H), 8.45 (s, 1H), 7.93-7.92 (m, 2H), 7.70-7.68 (m, 1H), 7.60-7.58 (m, 3H), 5.26 (s, 1H), 4.53 (m, 2H), 2.61 (s, 3H), 1.45 (dd, 3H), 0.97 (s, 9H). |
| 404 | 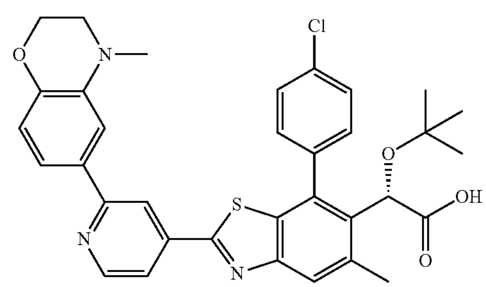 | F | 614.15 | 614.3 | ¹H NMR (400 MHz, CD₃OD) δ: 8.48 (d, 1H), 8.30 (d, 1H), 7.89-7.88 (m, 1H), 7.78 (s, 1H), 7.59-7.57 (m, 1H), 7.50-7.46 (m, 3H), 7.13-7.12 (m, 1H), 7.09-7.06 (m, 1H), 6.71 (d, 1H), 5.18 (s, 1H), 4.21-4.19 (dd, 2H), 3.18-3.16 (m, 2H), 2.86 (s, 3H), 2.52 (s, 3H), 0.88 (s, 9H). |
| 405 | 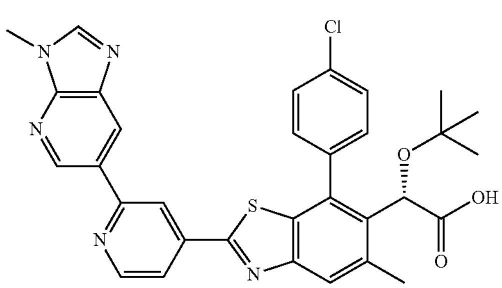 [SMILES: Cc1cc2nc(-c3ccnc(-c4cnc5c(c4)ncn5C)c3)sc2c(-c2ccc(Cl)cc2)c1[C@H](OC(C)(C)C)C(=O)O] | H | 598.11 | 598.2 | ¹H NMR (400 MHz, CD₃OD) δ: 9.00 (d, 1H), 8.63 (d, 1H), 8.57 (s, 1H), 8.32-8.30 (m, 2H), 7.78 (s, 1H), 7.72-7.69 (m, 2H), 7.56-7.54 (m, 3H), 5.24 (s, 1H)), 3.88 (s, 3H), 2.58 (s, 3H), 0.96 (s, 9H). |

| Cmpd # | Compound Structure | Method | Parent MW | LCMS-ESI+ | 1H NMR |
|---|---|---|---|---|---|
| 406 | 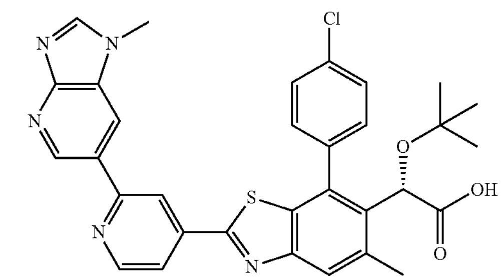 [SMILES: Cc1cc2nc(-c3ccnc(-c4cnc5ncn(C)c5c4)c3)sc2c(-c2ccc(Cl)cc2)c1[C@H](OC(C)(C)C)C(=O)O] | H | 598.11 | 598.2 | ¹H NMR (400 MHz, CD₃OD) δ: 9.34 (s, 1H), 8.99 (d, 1H), 8.82 (m, 2H), 8.59 (s, 1H), 7.98-7.97 (m, 1H), 7.90 (s, 1H), 7.71-7.68 (m, 1H), 7.61-7.59 (m, 3H), 5.27 (s, 1H)), 4.13 (s, 3H), 2.62 (s, 3H), 0.98 (s, 9H). |
| 407 | 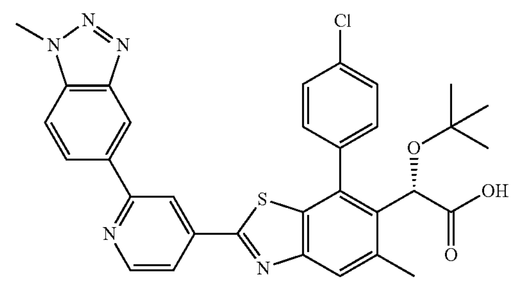 | F | 598.11 | 598.2 | ¹H NMR (400 MHz, CD₃OD) δ: 8.80 (d, 1H), 8.67 (s, 1H), 8.57 (s, 1H), 8.30-8.27 (m, 1H), 7.80-7.99 (m, 1H), 7.95 (s, 1H), 7.91-7.89 (m, 1H), 7.71-7.69 (m, 1H), 7.60-7.58 (m, 3H), 5.27 (s, 1H)), 4.37 (s, 3H), 2.64 (s, 3H), 0.98 (s, 9H). |
| 408 | 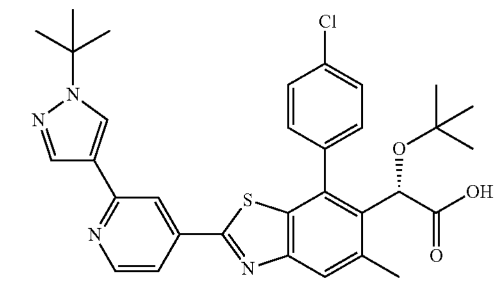 [SMILES: Cc1cc2nc(-c3ccnc(-c4cnn(C(C)(C)C)c4)c3)sc2c(-c2ccc(Cl)cc2)c1[C@H](OC(C)(C)C)C(=O)O] | F | 589.15 | 589.3 | ¹H NMR (400 MHz, CD₃OD) δ: 8.62 (d, 1H), 8.57 (s, 1H), 8.43 (s, 1H), 7.99 (s, 1H), 7.98-7.97 (m, 2H), 7.71-7.68 (m, 1H), 7.62-7.609 (m, 3H), 5.27 (s, 1H)), 2.64 (s, 3H), 1.66 (s, 9H), 0.98 (s, 9H). |
| 409 | 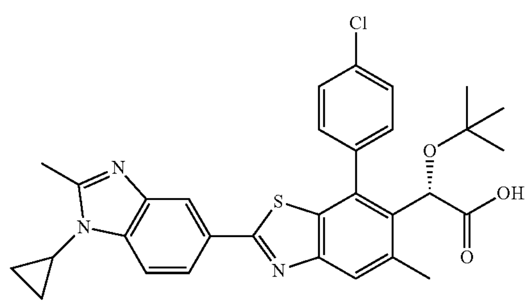 [SMILES: Cc1cc2nc(-c3ccc4c(c3)nc(C)n4C3CC3)sc2c(-c2ccc(Cl)cc2)c1[C@H](OC(C)(C)C)C(=O)O] | BG | 560.17 | 560.2 | ¹H NMR (400 MHz, CD₃OD) δ: 8.39 (s, 1H), 8.22 (d, J = 12 Hz, 1H), 8.02 (d, J = 12 Hz, 1H), 7.87 (s, 1H), 7.68 (m, 1H), 7.60 (m, 3H), 5.26 (s, 1H), 3.58 (m, 1H), 2.93 (s, 3H), 2.62 (s, 3H), 1.43 (m, 2H), 1.27 (m, 2H), 0.97 (s, 9H). |
| 410 | 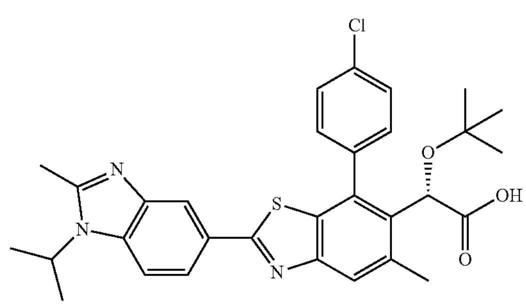 [SMILES: Cc1cc2nc(-c3ccc4c(c3)nc(C)n4C(C)C)sc2c(-c2ccc(Cl)cc2)c1[C@H](OC(C)(C)C)C(=O)O] | BG | 562.19 | 562.2 | ¹H NMR (400 MHz, CD₃OD) δ: 8.41 (s, 1H), 8.14-8.23 (m, 2H), 7.89 (s, 1H), 7.68 (m, 1H), 7.60 (m, 3H), 5.26 (s, 1H), 5.06 (m, 1H), 2.92 (s, 3H), 2.62 (s, 3H), 1.77 (d, J = 8 Hz, 6H), 0.98 (s, 9H). |

-continued

| Cmpd # | Compound Structure | Method | Parent MW | LCMS-ESI+ | 1H NMR |
|---|---|---|---|---|---|
| 411 | 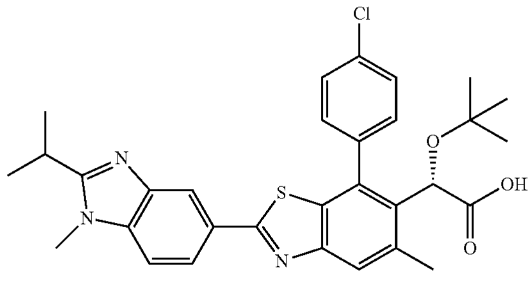 [SMILES: Cc1cc2nc(-c3ccc4c(c3)nc(C(C)C)n4C)sc2c(-c2ccc(Cl)cc2)c1[C@H](OC(C)(C)C)C(=O)O] | BG | 562.19 | 562.2 | ¹H NMR (400 MHz, CD₃OD) δ: 8.41 (s, 1H), 8.26 (d, J = 8.8 Hz, 1H), 7.96 (d, J = 8.8 Hz, 1H), 7.89 (s, 1H), 7.69 (m, 1H), 7.61 (m, 3H), 5.26 (s, 1H), 4.08 (s, 3H), 3.70 (quint, J = 6.8 Hz, 1H), 2.62 (s, 3H), 1.55 (d, J = 6.8 Hz, 6H), 0.97 (s, 9H). |
| 412 | 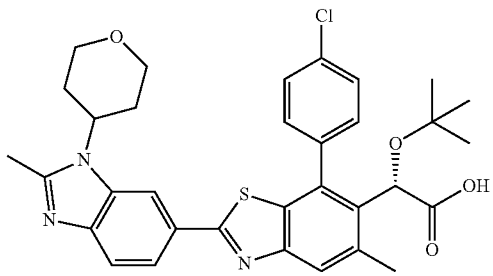 [SMILES: Cc1cc2nc(-c3ccc4nc(C)n(C5CCOCC5)c4c3)sc2c(-c2ccc(Cl)cc2)c1[C@H](OC(C)(C)C)C(=O)O] | AP | 604.16 | 604.2 | ¹H NMR (400 MHz, CD₃OD) δ: 8.64 (s, 1H), 8.15 (dd, J = 8.8, 1.2 Hz, 1H), 7.90 (s, 1H), 7.82 (d, J = 8.8 Hz, 1H), 7.69 (m, 1H), 7.60 (m, 3H), 5.26 (s, 1H), 4.93 (m, 1H), 4.21 (dd, J = 11.2, 4.0 Hz, 2H), 3.71 (t, J = 11.2 Hz, 1H), 2.92 (s, 3H), 2.66 (m, 2H), 2.63 (s, 3H), 2.04 (br d, J = 8.4 Hz, 2H), 0.98 (s, 9H). |
| 413 | 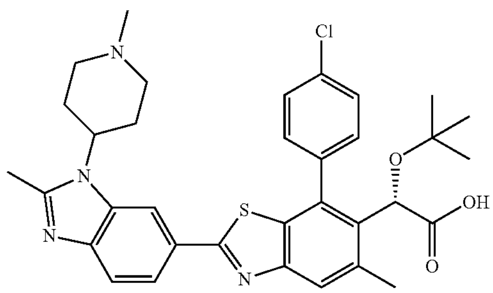 [SMILES: Cc1cc2nc(-c3ccc4nc(C)n(C5CCN(C)CC5)c4c3)sc2c(-c2ccc(Cl)cc2)c1[C@H](OC(C)(C)C)C(=O)O] | AP | 617.2 | 617.2 | ¹H NMR (400 MHz, CD₃OD) δ: 8.84 (s, 1H), 8.14 (d, J = 8.4 Hz, 1H), 7.88 (s, 1H), 7.82 (d, J = 8.4 Hz, 1H), 7.68 (m, 1H), 7.60 (m, 3H), 5.25 (s, 1H), 4.99 (m, 1H), 3.79 (br m, 2H), 3.37 (m, 2H), 3.03 (s, 3H), 2.88 (s, 1H), 2.84 (m, 2H), 2.63 (s, 3H), 2.39 (br m, 2H), 0.98 (s, 9H). |
| 414 | 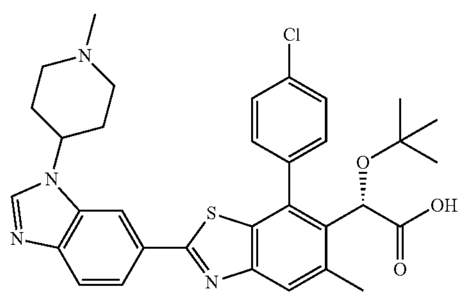 [SMILES: Cc1cc2nc(-c3ccc4ncn(C5CCN(C)CC5)c4c3)sc2c(-c2ccc(Cl)cc2)c1[C@H](OC(C)(C)C)C(=O)O] | AP | 603.17 | 603.3 | ¹H NMR (400 MHz, CD₃OD) δ: 8.55 (s, 1H), 8.42 (s, 1H), 8.06 (d, J = 8.4 Hz, 1H), 7.85 (m, 2H), 7.69 (m, 1H), 7.60 (m, 3H), 5.26 (s, 1H), 4.93 (m, 1H), 3.76 (m, 2H), 3.38 (m, 2H), 3.02 (m, 2H), 3.01 (s, 3H), 2.63 (s, 3H), 2.48 (m, 2H), 0.98 (s, 9H). |
| 415 | 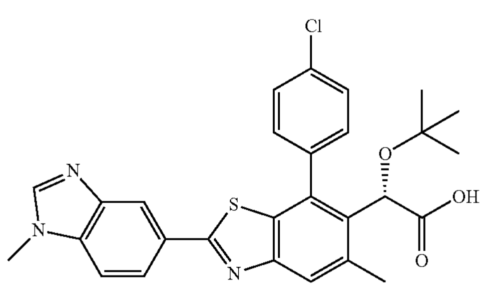 [SMILES: Cc1cc2nc(-c3ccc4c(c3)ncn4C)sc2c(-c2ccc(Cl)cc2)c1[C@H](OC(C)(C)C)C(=O)O] | BG | 520.04 | 520.1 | ¹H NMR (400 MHz, CD₃OD) δ: 9.20 (br s, 1H), 8.43 (s, 1H), 8.24 (d, J = 8.8 Hz, 1H), 7.93 (d, J = 8.8 Hz, 1H), 7.85 (s, 1H), 7.67 (m, 1H), 7.58 (m, 3H), 5.26 (s, 1H), 4.10 (s, 3H), 2.62 (s, 3H), 0.97 (s, 9H). |

| Cmpd # | Compound Structure | Method | Parent MW | LCMS-ESI+ | 1H NMR |
|---|---|---|---|---|---|
| 416 | 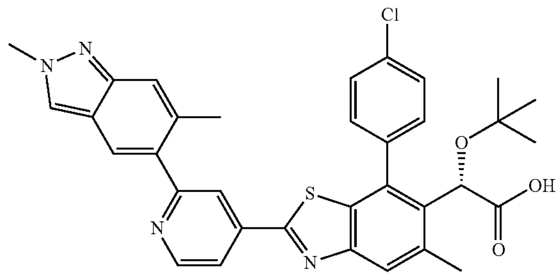 [SMILES: Cc1cc2nn(C)cc2cc1-c1cc(-c2nc3cc(C)c([C@H](OC(C)(C)C)C(=O)O)c(-c4ccc(Cl)cc4)c3s2)ccn1] | BF | 611.15 | 611.1 | ¹H NMR (400 MHz, CD₃OD) δ: 8.83 (d, J = 6.0 Hz, 1H), 8.40 (s, 1H), 8.31 (s, 1H), 8.27 (dd, J = 6.0, 2.0 Hz, 1H), 7.99 (s, 1H), 7.87 (s, 1H), 7.69 (m, 1H), 7.60 (m, 4H), 5.28 (s, 1H), 4.24 (s, 3H), 2.63 (s, 3H), 2.42 (s, 3H), 0.97 (s, 9H). |
| 417 | 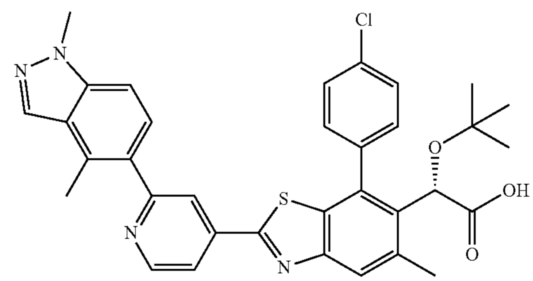 [SMILES: Cc1cc2nc(-c3ccnc(-c4ccc5c(cnn5C)c4C)c3)sc2c(-c2ccc(Cl)cc2)c1[C@H](OC(C)(C)C)C(=O)O] | BF | 611.15 | 611.1 | ¹H NMR (400 MHz, CD₃OD) δ: 8.84 (d, J = 5.6 Hz, 1H), 8.40 (s, 1H), 8.27 (dd, J = 5.6, 1.6 Hz, 1H), 8.23 (s, 1H), 7.99 (s, 1H), 7.69 (m, 1H), 7.55-7.61 (m, 5H), 5.28 (s, 1H), 4.12 (s, 3H), 2.66 (s, 3H), 2.64 (s, 3H), 0.97 (s, 9H). |
| 418 | 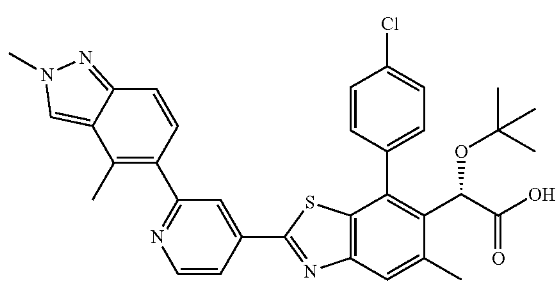 [SMILES: Cc1cc2nc(-c3ccnc(-c4ccc5nn(C)cc5c4C)c3)sc2c(-c2ccc(Cl)cc2)c1[C@H](OC(C)(C)C)C(=O)O] | BF | 611.15 | 611.1 | ¹H NMR (400 MHz, CD₃OD) δ: 8.81 (d, J = 5.6 Hz, 1H), 8.44 (s, 1H), 8.31 (s, 1H), 8.17 (d, J = 5.6 Hz, 1H), 7.98 (s, 1H), 7.69 (m, 1H), 7.60 (m, 4H), 7.43 (d, J = 8.8 Hz, 1H), 5.27 (s, 1H), 4.26 (s, 3H), 2.64 (s, 3H), 2.60 (s, 3H), 0.97 (s, 9H). |
| 419 | 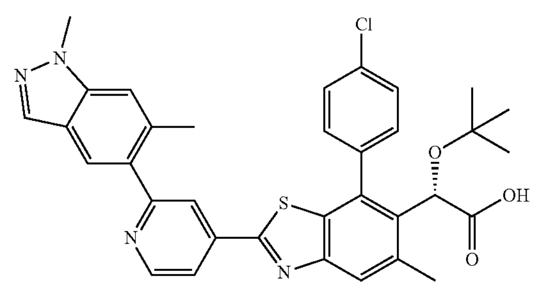 [SMILES: Cc1cc2c(cnn2C)cc1-c1cc(-c2nc3cc(C)c([C@H](OC(C)(C)C)C(=O)O)c(-c4ccc(Cl)cc4)c3s2)ccn1] | BF | 611.15 | 611.1 | ¹H NMR (400 MHz, CD₃OD) δ: 8.84 (d, J = 5.6 Hz, 1H), 8.42 (s, 1H), 8.28 (d, J = 5.6 Hz, 1H), 8.07 (s, 1H), 7.99 (s, 1H), 7.91 (s, 1H), 7.69 (m, 1H), 7.60 (m, 4H), 5.28 (s, 1H), 4.10 (s, 3H), 2.64 (s, 3H), 2.50 (s, 3H), 0.97 (s, 9H). |
| 420 | 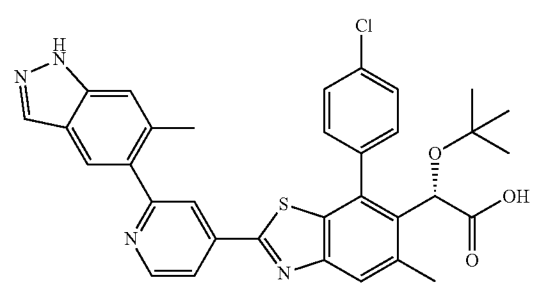 [SMILES: Cc1cc2[nH]ncc2cc1-c1cc(-c2nc3cc(C)c([C@H](OC(C)(C)C)C(=O)O)c(-c4ccc(Cl)cc4)c3s2)ccn1] | F | 597.13 | 597.2 | ¹H NMR (400 MHz, CD₃OD) δ: 8.83 (d, J = 5.6 Hz, 1H), 8.42 (s, 1H), 8.36 (dd, J = 5.6, 2.0 Hz, 1H), 8.12 (s, 1H), 7.99 (s, 1H), 7.93 (s, 1H), 7.69 (m, 1H), 7.56-7.61 (m, 4H), 5.27 (s, 1H), 2.63 (s, 3H), 2.47 (s, 3H), 0.97 (s, 9H). |

| Cmpd # | Compound Structure | Method | Parent MW | LCMS-ESI+ | 1H NMR |
|---|---|---|---|---|---|
| 421 | 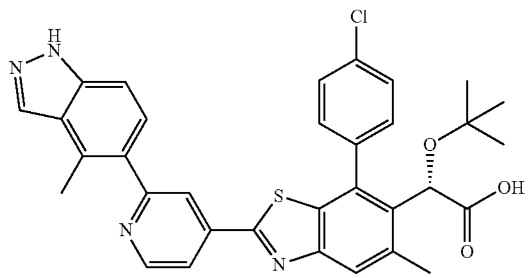 [SMILES: Cc1cc2nc(-c3ccnc(-c4ccc5[nH]ncc5c4C)c3)sc2c(-c2ccc(Cl)cc2)c1[C@H](OC(C)(C)C)C(=O)O] | F | 597.13 | 597.2 | ¹H NMR (400 MHz, CD₃OD) δ: 8.87 (d, J = 6.0 Hz, 1H), 8.49 (s, 1H), 8.36 (dd, J = 6.0, 1.6 Hz, 1H), 8.30 (s, 1H), 8.02 (s, 1H), 7.69 (m, 1H), 7.53-7.61 (m, 5H), 5.28 (s, 1H), 2.69 (s, 3H), 2.64 (s, 3H), 0.97 (s, 9H). |
| 422 | 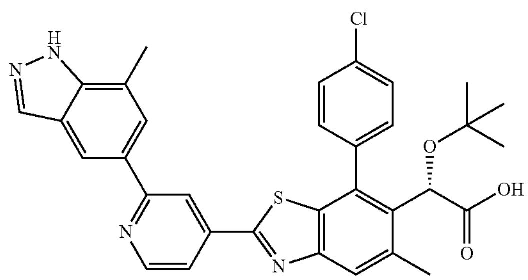 [SMILES: Cc1cc2nc(-c3ccnc(-c4cc(C)c5[nH]ncc5c4)c3)sc2c(-c2ccc(Cl)cc2)c1[C@H](OC(C)(C)C)C(=O)O] | F | 597.13 | 597.2 | ¹H NMR (400 MHz, CD₃OD) δ: 8.76 (d, J = 5.6 Hz, 1H), 8.67 (s, 1H), 8.32 (s, 1H), 8.23 (s, 1H), 8.19 (d, J = 5.6 Hz, 1H), 8.00 (s, 1H), 7.83 (s, 1H), 7.69 (m, 1H), 7.61 (m, 3H), 5.28 (s, 1H), 2.68 (s, 3H), 2.65 (s, 3H), 0.98 (s, 9H). |
| 427 | 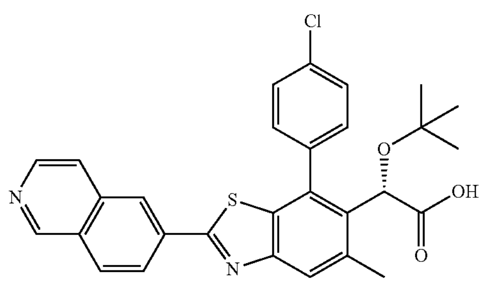 [SMILES: Cc1cc2nc(-c3ccc4cnccc4c3)sc2c(-c2ccc(Cl)cc2)c1[C@H](OC(C)(C)C)C(=O)O] | BA | 517.04 | 517.2 | ¹H NMR (400 MHz, CD₃OD) δ 9.61 (s, 1H), 8.79 (s, 1H), 8.59 (t, J = 7.0 Hz, 2H), 8.47 (d, J = 8.7 Hz, 1H), 8.32 (d, J = 6.3 Hz, 1H), 7.94 (s, 1H), 7.72 (d, J = 8.5 Hz, 1H), 7.62 (s, 3H), 5.28 (s, 1H), 2.64 (s, 3H), 0.99 (s, 9H). |
| 428 | 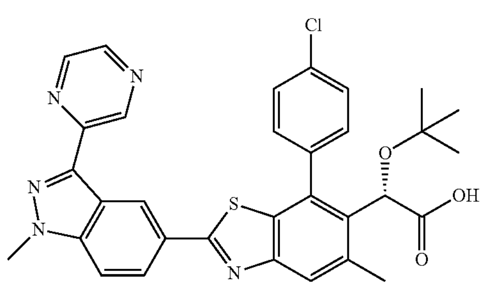 [SMILES: Cc1cc2nc(-c3ccc4c(c3)c(-c3cnccn3)nn4C)sc2c(-c2ccc(Cl)cc2)c1[C@H](OC(C)(C)C)C(=O)O] | BC | 598.11 | 598.2 | ¹H NMR (400 MHz, CD₃OD) δ 9.34 (s, 1H), 9.13 (s, 1H), 8.75 (s, 1H), 8.49 (d, J = 2.6 Hz, 1H), 8.15 (d, J = 9.1 Hz, 1H), 7.83 (s, 1H), 7.70 (t, J = 8.1 Hz, 2H), 7.66-7.57 (m, 3H), 5.26 (s, 1H), 4.18 (s, 3H), 2.62 (s, 3H), 0.98 (s, 9H). |
| 429 | 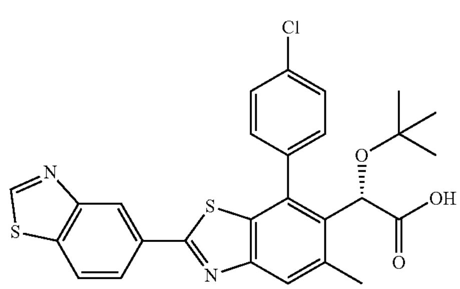 [SMILES: Cc1cc2nc(-c3ccc4scnc4c3)sc2c(-c2ccc(Cl)cc2)c1[C@H](OC(C)(C)C)C(=O)O] | BA | 523.07 | 523.2 | ¹H NMR (400 MHz, CD₃OD) δ 9.34 (s, 1H), 8.68 (d, J = 0.9 Hz, 1H), 8.16 (dt, J = 8.5, 5.0 Hz, 2H), 7.86 (s, 1H), 7.70 (dd, J = 6.2, 3.2 Hz, 1H), 7.60 (d, J = 2.2 Hz, 3H), 5.27 (s, 1H), 2.62 (s, 3H), 0.98 (s, 9H). |

-continued

| Cmpd # | Compound Structure | Method | Parent MW | LCMS-ESI+ | 1H NMR |
|---|---|---|---|---|---|
| 430 | 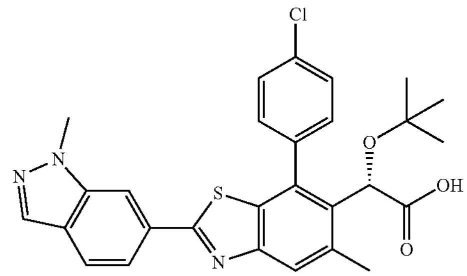 [SMILES: Cc1cc2nc(-c3ccc4cnn(C)c4c3)sc2c(-c2ccc(Cl)cc2)c1[C@H](OC(C)(C)C)C(=O)O] | AZ | 520.04 | 520.2 | $^1$H NMR (400 MHz, CD$_3$OD) δ 8.22 (s, 1H), 8.05 (d, J = 0.8 Hz, 1H), 7.93-7.76 (m, 3H), 7.69 (dd, J = 6.4, 3.1 Hz, 1H), 7.59 (t, J = 3.7 Hz, 3H), 5.27 (s, 1H), 4.12 (s, 3H), 2.61 (s, 3H), 0.98 (s, 9H). |
| 431 | 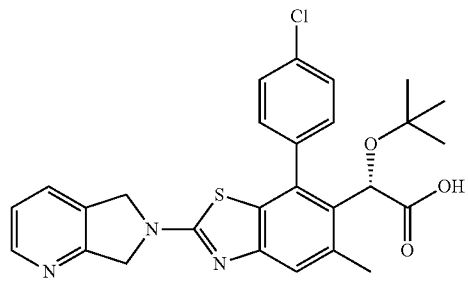 [SMILES: Cc1cc2nc(N3Cc4cccnc4C3)sc2c(-c2ccc(Cl)cc2)c1[C@H](OC(C)(C)C)C(=O)O] | AX | 508.03 | 508.2 | $^1$H NMR (400 MHz, CD$_3$OD) δ 8.50 (d, J = 4.9 Hz, 1H), 7.89 (d, J = 7.8 Hz, 1H), 7.71-7.62 (m, 1H), 7.57 (app. d, J = 8.6 Hz, 2H), 7.55-7.48 (m, 1H), 7.47-7.33 (m, 2H), 5.16 (s, 1H), 4.86 (s, 4H), 2.51 (s, 3H), 0.95 (s, 9H). |
| 432 | 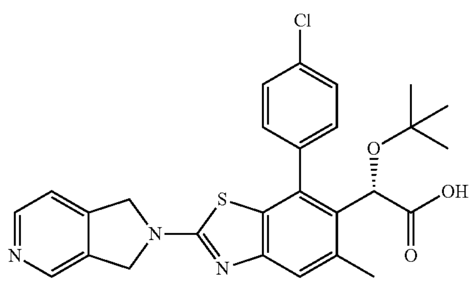 [SMILES: Cc1cc2nc(N3Cc4ccncc4C3)sc2c(-c2ccc(Cl)cc2)c1[C@H](OC(C)(C)C)C(=O)O] | AX | 508.03 | 508.3 | $^1$H NMR (400 MHz, CD$_3$OD) δ 8.85 (s, 1H), 8.74 (d, J = 5.7 Hz, 1H), 7.95 (d, J = 5.7 Hz, 1H), 7.66 (d, J = 7.6 Hz, 1H), 7.62-7.48 (m, 3H), 7.42 (s, 1H), 5.17 (s, 1H), 5.13-4.98 (m, 4H), 2.53 (s, 3H), 0.97 (s, 9H). |
| 433 | 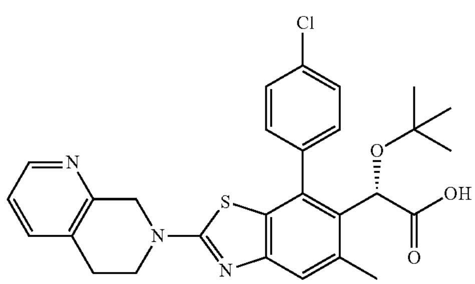 [SMILES: Cc1cc2nc(N3CCc4cccnc4C3)sc2c(-c2ccc(Cl)cc2)c1[C@H](OC(C)(C)C)C(=O)O] | AX | 522.06 | 522.3 | $^1$H NMR (400 MHz, CD$_3$OD) δ 8.52 (d, J = 5.0 Hz, 1H), 7.95 (d, J = 8.0 Hz, 1H), 7.71-7.59 (m, 1H), 7.60-7.43 (m, 4H), 7.38 (s, 1H), 5.16 (s, 1H), 4.93 (s, 2H), 3.91 (t, J = 5.9 Hz, 2H), 3.12 (t, J = 5.7 Hz, 2H), 2.52 (s, 3H), 0.95 (s, 9H). |
| 434 | 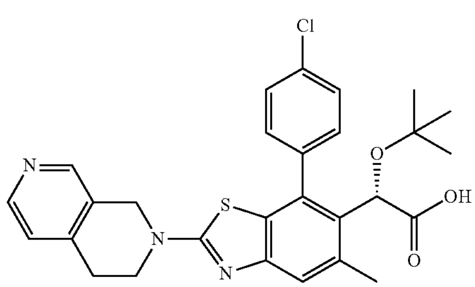 [SMILES: Cc1cc2nc(N3CCc4ccncc4C3)sc2c(-c2ccc(Cl)cc2)c1[C@H](OC(C)(C)C)C(=O)O] | AX | 522.06 | 522.3 | $^1$H NMR (400 MHz, CD$_3$OD) δ 8.70 (s, 1H), 8.55 (d, J = 5.8 Hz, 1H), 7.77 (d, J = 5.8 Hz, 1H), 7.63 (dd, J = 8.4, 1.9 Hz, 1H), 7.59-7.45 (m, 3H), 7.37 (s, 1H), 5.15 (s, 1H), 4.95 (s, 2H), 3.92 (t, J = 5.9 Hz, 2H), 3.25 (t, J = 5.9 Hz, 2H), 2.51 (s, 3H), 0.95 (s, 9H). |

-continued

| Cmpd # | Compound Structure | Method | Parent MW | LCMS-ESI+ | 1H NMR |
|---|---|---|---|---|---|
| 435 | 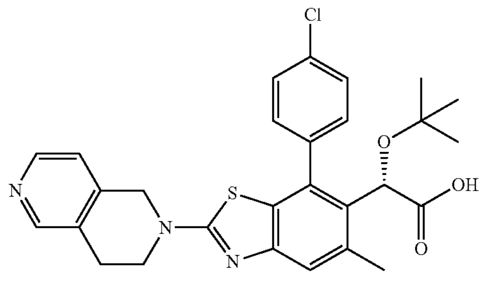 [SMILES: Cc1cc2nc(N3CCc4cnccc4C3)sc2c(-c2ccc(Cl)cc2)c1[C@H](OC(C)(C)C)C(=O)O] | AX | 522.06 | 522.3 | $^1$H NMR (400 MHz, CD$_3$OD) δ 8.69 (s, 1H), 8.60 (d, J = 5.9 Hz, 1H), 7.85 (d, J = 5.9 Hz, 1H), 7.63 (dd, J = 8.2, 2.1 Hz, 1H), 7.59-7.45 (m, 3H), 7.37 (s, 1H), 5.15 (s, 1H), 5.05 (s, 2H), 3.93 (t, J = 5.8 Hz, 2H), 3.17 (dd, J = 14.1, 8.3 Hz, 2H), 2.51 (s, 3H), 0.95 (s, 9H). |
| 436 | 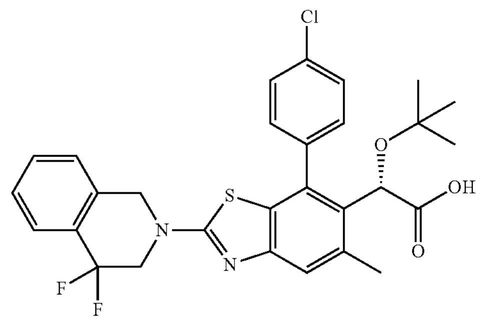 [SMILES: Cc1cc2nc(N3Cc4ccccc4C(F)(F)C3)sc2c(-c2ccc(Cl)cc2)c1[C@H](OC(C)(C)C)C(=O)O] | AX | 557.05 | 557.1 | $^1$H NMR (400 MHz, CD$_3$OD) δ 7.71 (d, J = 7.9 Hz, 1H), 7.63 (dd, J = 8.3, 6.4 Hz, 1H), 7.59-7.32 (m, 7H), 5.16 (s, 1H), 4.89-4.83 (m, 2H), 4.30 (td, J = 11.1, 2.6 Hz, 2H), , 2.52 (s, 3H), 0.95 (s, 9H). |
| 437 | 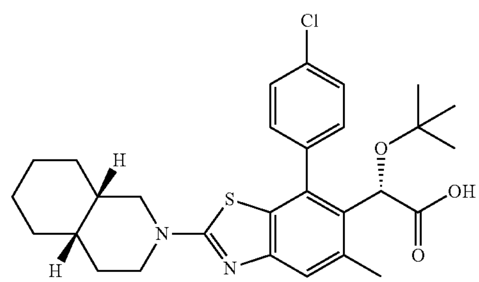 [SMILES: Cc1cc2nc(N3CC[C@@H]4CCCC[C@@H]4C3)sc2c(-c2ccc(Cl)cc2)c1[C@H](OC(C)(C)C)C(=O)O] | AY | 527.12 | 527.3 | $^1$H NMR (400 MHz, CD$_3$OD) δ 7.69-7.52 (m, 3H), 7.48 (dd, J = 8.4, 1.9 Hz, 1H), 7.30 (s, 1H), 5.15 (s, 1H), 4.11-3.94 (m, 1H), 3.94-3.79 (m, 1H), 3.02-2.82 (m, 1H), 2.52 (s, 3H), 1.92-1.53 (m, 5H), 1.53-1.20 (m, 5H), 1.06 (s, 2H), 0.95 (s, 3H). |
| 438 | 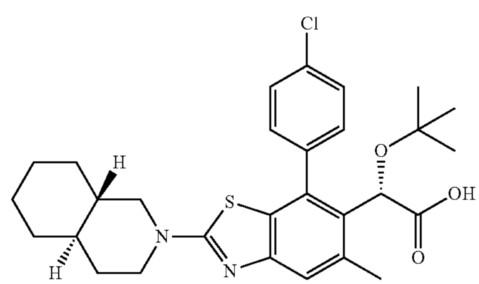 [SMILES: Cc1cc2nc(N3CC[C@H]4CCCC[C@@H]4C3)sc2c(-c2ccc(Cl)cc2)c1[C@H](OC(C)(C)C)C(=O)O] | AY | 527.12 | 527.3 | $^1$H NMR (400 MHz, CD$_3$OD) δ 7.69-7.54 (m, 3H), 7.48 (dd, J = 9.8, 5.1 Hz, 1H), 7.30 (s, 1H), 5.15 (s, 1H), 3.92 (d, J = 14.3 Hz, 1H), 3.75 (d, J = 14.6 Hz, 1H), 3.63-3.36 (m, 2H), 2.53 (s, 3H), 2.11-1.83 (m, 3H), 1.78-1.24 (m, 9H), 0.95 (s, 9H). |
| 439 | 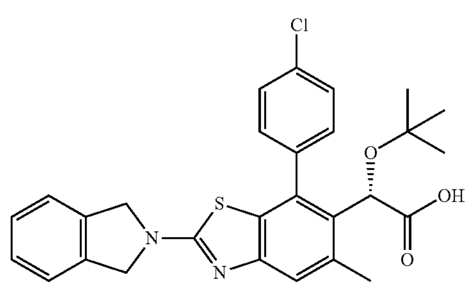 [SMILES: Cc1cc2nc(N3Cc4ccccc4C3)sc2c(-c2ccc(Cl)cc2)c1[C@H](OC(C)(C)C)C(=O)O] | AY | 507.04 | 507.2 | $^1$H NMR (400 MHz, CD$_3$OD) δ 7.71-7.47 (m, 4H), 7.47-7.32 (m, 5H), 5.17 (s, 1H), 5.03-4.87 (m, J = 22.4 Hz, 4H), 2.52 (s, 3H), 0.96 (s, 9H). |

-continued

| Cmpd # | Compound Structure | Method | Parent MW | LCMS-ESI+ | 1H NMR |
|---|---|---|---|---|---|
| 440 | 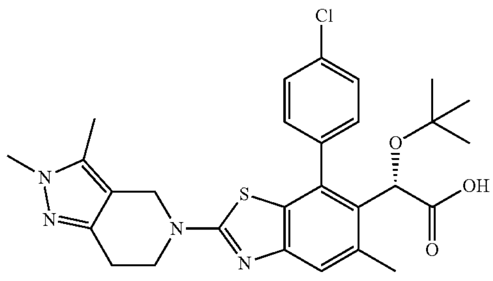 [SMILES: Cc1cc2nc(N3CCc4nn(C)c(C)c4C3)sc2c(-c2ccc(Cl)cc2)c1[C@H](OC(C)(C)C)C(=O)O] | AX | 539.09 | 539.2 | ¹H NMR (400 MHz, CD₃OD) δ 7.69-7.45 (m, 4H), 7.35 (s, 1H), 5.15 (s, 1H), 4.61 (s, 2H), 3.93 (t, J = 5.7 Hz, 2H), 3.74 (s, 1H), 2.86 (t, J = 5.9 Hz, 2H), 2.52 (s, 3H), 2.25 (s, 3H), 0.95 (s, 9H). |
| 441 | 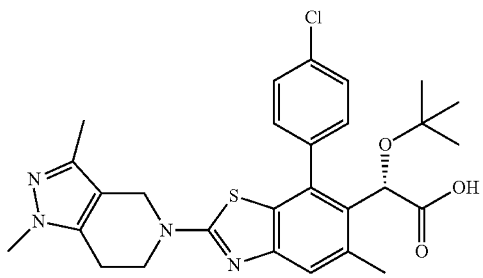 [SMILES: Cc1cc2nc(N3CCc4c(c(C)nn4C)C3)sc2c(-c2ccc(Cl)cc2)c1[C@H](OC(C)(C)C)C(=O)O] | AX | 539.09 | 539.2 | ¹H NMR (400 MHz, CD₃OD) δ 7.71-7.42 (m, 4H), 7.34 (s, 1H), 5.15 (s, 1H), 4.57 (s, 2H), 3.93 (t, J = 5.8 Hz, 2H), 3.69 (s, 3H), 2.87 (t, J = 5.7 Hz, 2H), 2.51 (s, 3H), 2.19 (s, 3H), 0.95 (s, 9H). |
| 442 | 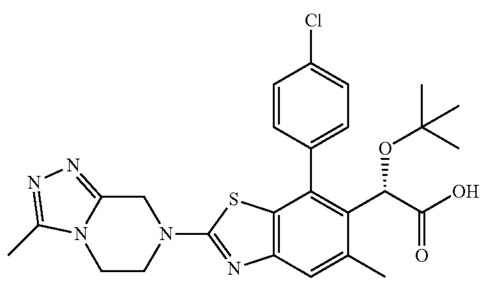 [SMILES: Cc1cc2nc(N3CCn4c(C)nnc4C3)sc2c(-c2ccc(Cl)cc2)c1[C@H](OC(C)(C)C)C(=O)O] | AX | 526.05 | 526.3 | ¹H NMR (400 MHz, CD₃OD) δ 7.68-7.46 (m, J = 9.3, 2.7 Hz, 4H), 7.41 (s, 1H), 5.16 (s, 1H), 5.03 (s, 2H), 4.20 (t, J = 5.4 Hz, 2H), 4.11 (t, J = 5.3 Hz, 2H), 2.51 (s, 3H), 0.95 (s, 9H). |
| 443 | 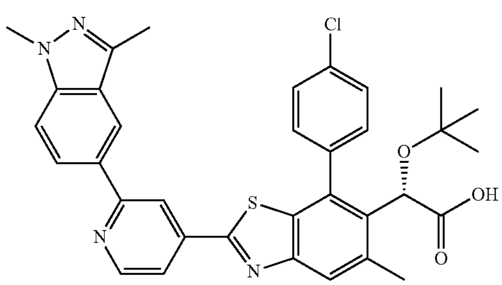 [SMILES: Cc1cc2nc(-c3ccnc(-c4ccc5c(c4)c(C)nn5C)c3)sc2c(-c2ccc(Cl)cc2)c1[C@H](OC(C)(C)C)C(=O)O] | F | 611.15 | 611.2 | ¹H NMR (400 MHz, CD₃OD) δ 8.76 (d, J = 5.6 Hz, 1H), 8.63 (s, 1H), 8.44 (s, 1H), 8.14-8.04 (m, 2H), 7.99 (s, 1H), 7.66 (dt, J = 18.8, 7.8 Hz, 5H), 5.28 (s, 1H), 4.04 (s, 3H), 2.65 (s, 3H), 2.63 (s, 3H), 0.98 (s, 9H). |
| 444 | 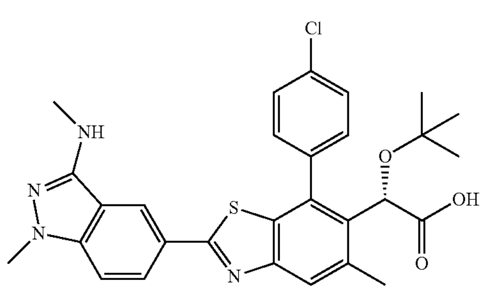 [SMILES: CNc1nn(C)c2ccc(-c3nc4cc(C)c([C@H](OC(C)(C)C)C(=O)O)c(-c5ccc(Cl)cc5)c4s3)cc12] | AW | 549.08 | 549.2 | ¹H NMR (400 MHz, CD₃OD) δ 8.37 (s, 1H), 8.09 (d, J = 10.7 Hz, 1H), 7.79 (s, 1H), 7.70 (d, J = 8.7 Hz, 1H), 7.63-7.57 (m, J = 6.1 Hz, 3H), 7.40 (d, J = 8.8 Hz, 1H), 5.26 (s, 1H), 3.85 (s, 3H), 3.01 (s, 3H), 2.61 (s, 3H), 0.98 (s, 9H). |

| Cmpd # | Compound Structure | Method | Parent MW | LCMS-ESI+ | 1H NMR |
|---|---|---|---|---|---|
| 445 | 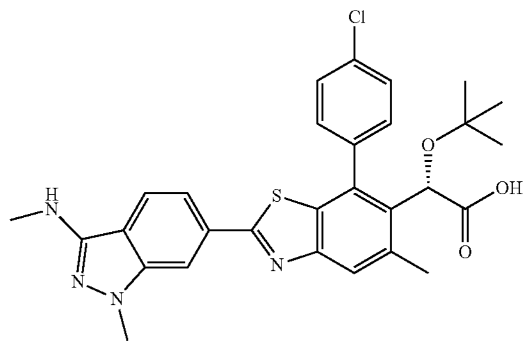 [SMILES: CNc1nn(C)c2cc(-c3nc4cc(C)c([C@H](OC(C)(C)C)C(=O)O)c(-c5ccc(Cl)cc5)c4s3)ccc12] | AW | 549.08 | 549.2 | ¹H NMR (400 MHz, CD₃OD) δ 7.97 (s, 1H), 7.82 (s, 1H), 7.76 (d, J = 8.4 Hz, 1H), 7.71-7.61 (m, 2H), 7.61-7.55 (m, 3H), 5.25 (s, 1H), 3.83 (s, 3H), 3.01 (s, 3H), 2.60 (s, 3H), 0.95 (s, 9H). |
| 446 | 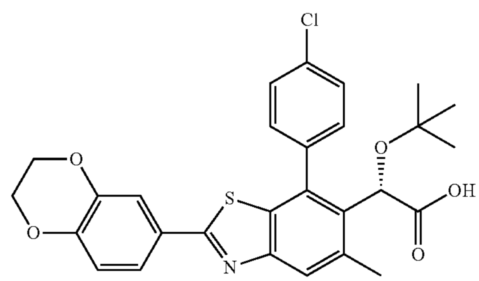 [SMILES: Cc1cc2nc(-c3ccc4c(c3)OCCO4)sc2c(-c2ccc(Cl)cc2)c1[C@H](OC(C)(C)C)C(=O)O] | J | 524.03 | 524.2 | ¹H NMR (400 MHz, CD₃OD) δ 7.77 (s, 1H), 7.70-7.65 (m, 1H), 7.60-7.51 (m, 4H), 7.47 (dd, J = 8.2, 2.2 Hz, 1H), 6.93 (d, J = 8.4, Hz, 1H), 5.23 (s, 1H), 4.35-4.25 (m, 4H), 2.59 (s, 3H), 0.96 (s, 9H). |
| 447 | 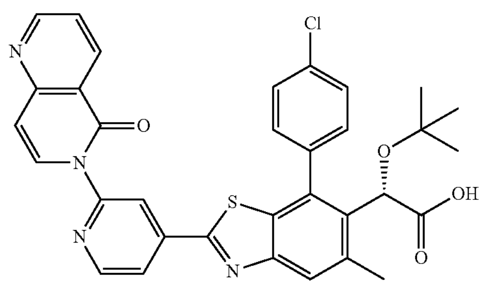 [SMILES: Cc1cc2nc(-c3ccnc(-n4ccc5ncccc5c4=O)c3)sc2c(-c2ccc(Cl)cc2)c1[C@H](OC(C)(C)C)C(=O)O] | Y | 611.11 | 611.2 | ¹H NMR (400 MHz, CDCl₃) δ 9.09 (d, J = 4.4 Hz, 1H), 9.02 (d, J = 8.0 Hz, 1H), 8.70 (d, J = 5.2 Hz, 1H), 8.57 (s, 1H), 8.24 (d, J = 8.0 Hz, 1H), 7.98 (d, J = 5.2 Hz, 1H), 7.94 (s, 1H), 7.72-7.67 (m, 2H), 7.55-7.47 (m, 3H), 6.13 (d, J = 8.4 Hz, 1H), 5.33 (s, 1H), 2.59 (s, 3H), 1.01 (s, 9H). |
| 448 | 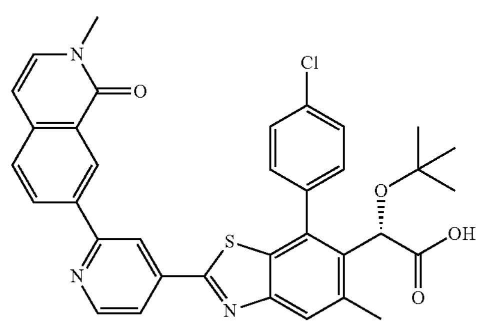 [SMILES: Cc1cc2nc(-c3ccnc(-c4ccc5ccn(C)c(=O)c5c4)c3)sc2c(-c2ccc(Cl)cc2)c1[C@H](OC(C)(C)C)C(=O)O] | AG | 624.15 | 624.4 | ¹H NMR (400 MHz, DMSO-d6) δ 9.00 (s, 1H), 8.85 (d, J = 5.2 Hz, 1H), 8.52-8.50 (m, 2H), 8.05 (s, 1H), 7.98 (d, J = 3.6 Hz, 1H), 7.78 (d, J = 8.4 Hz, 1H), 7.72-7.69 (m, 2H), 7.65-7.59 (m, 2H), 7.54 (d, J = 7.2 Hz, 1H), 6.68 (d, J = 7.2 Hz, 1H), 5.09 (s, 1H), 3.54 (s, 3H), 2.56 (s, 3H), 0.89 (s, 9H). |
| 449 | 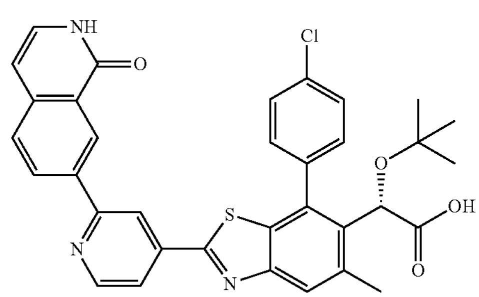 [SMILES: Cc1cc2nc(-c3ccnc(-c4ccc5cc[nH]c(=O)c5c4)c3)sc2c(-c2ccc(Cl)cc2)c1[C@H](OC(C)(C)C)C(=O)O] | W | 610.12 | 610.2 | ¹H NMR (400 MHz, CDCl₃) δ 8.97 (s, 2H), 8.55-8.52 (m, 2H), 8.07 (s, 1H), 7.94 (s, 1H), 7.79 (d, J = 8.8 Hz, 1H), 7.72 (d, J = 7.2 Hz, 1H), 7.57-7.49 (m, 4H), 6.76 (d, J = 6.4 Hz, 1H), 5.34 (s, 1H), 2.60 (s, 3H), 1.01 (s, 9H). |

| Cmpd # | Compound Structure | Method | Parent MW | LCMS-ESI+ | 1H NMR |
|---|---|---|---|---|---|
| 450 | 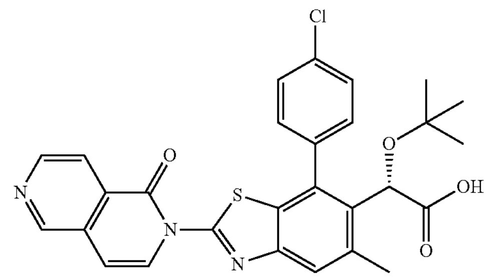 [SMILES: Cc1cc2nc(-n3ccc4cnccc4c3=O)sc2c(-c2ccc(Cl)cc2)c1[C@H](OC(C)(C)C)C(=O)O] | AK | 534.03 | 534.2 | ¹H NMR (400 MHz, CDCl₃) δ 9.69 (s, 1H), 9.27 (d, J = 7.6 Hz, 1H), 8.93 (s, 1H), 7.89 (s, 1H), 7.79 (s, 1H), 7.70 (d, J = 8.0 Hz, 1H), 7.58-7.50 (m, 3H), 6.93 (d, J = 7.6 Hz, 1H), 5.36 (s, 1H), 2.59 (s, 3H), 1.01 (s, 9H). |
| 451 | 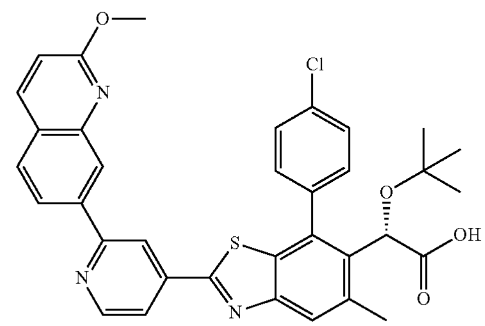 [SMILES: COc1ccc2ccc(-c3cc(-c4nc5cc(C)c([C@H](OC(C)(C)C)C(=O)O)c(-c6ccc(Cl)cc6)c5s4)ccn3)cc2n1] | AG | 624.15 | 624.2 | ¹H NMR (400 MHz, CDCl₃) δ 9.10 (d, J = 6.0 Hz, 1H), 8.72 (s, 1H), 8.52 (s, 1H), 8.24 (d, J = 6.0 Hz, 1H), 8.13-8.09 (m, 2H), 8.04 (s, 1H), 7.98 (d, J = 8.8 Hz, 1H), 7.73 (d, J = 8.4 Hz, 1H), 7.60-7.47 (m, 3H), 7.06 (d, J = 8.8 Hz, 1H), 5.37 (s, 1H), 4.16 (s, 3H), 2.64 (s, 3H), 1.03 (s, 9H). |
| 452 | 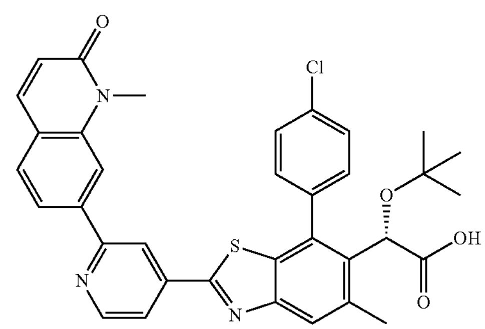 [SMILES: Cc1cc2nc(-c3ccnc(-c4ccc5ccc(=O)n(C)c5c4)c3)sc2c(-c2ccc(Cl)cc2)c1[C@H](OC(C)(C)C)C(=O)O] | AG | 624.15 | 624.2 | ¹H NMR (400 MHz, CDCl₃) δ 9.03 (d, J = 5.6 Hz, 1H), 8.55 (s, 1H), 8.25 (s, 1H), 8.04 (d, J = 5.2 Hz, 1H), 8.01 (s, 1H), 7.86 (d, J = 8.4 Hz, 1H), 7.81-7.73 (m, 3H), 7.58-7.49 (m, 3H), 6.90 (d, J = 9.6 Hz, 1H), 5.35 (s, 1H), 3.91 (s, 3H), 2.63 (s, 3H), 1.03 (s, 9H). |
| 453 | 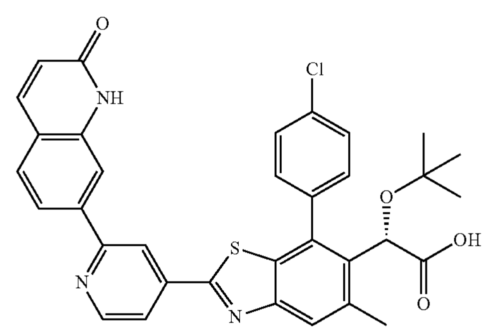 [SMILES: Cc1cc2nc(-c3ccnc(-c4ccc5ccc(=O)[nH]c5c4)c3)sc2c(-c2ccc(Cl)cc2)c1[C@H](OC(C)(C)C)C(=O)O] | W | 610.12 | 610.2 | ¹H NMR (400 MHz, CDCl₃) δ 8.86 (s, 1H), 8.39 (s, 1H), 8.05 (s, 1H), 7.97-7.88 (m, 4H), 7.73-7.64 (m, 2H), 7.48-7.39 (m, 3H), 6.78 (d, J = 8.8 Hz, 1H), 5.27 (s, 1H), 2.54 (s, 3H), 0.94 (s, 9H). |
| 454 | 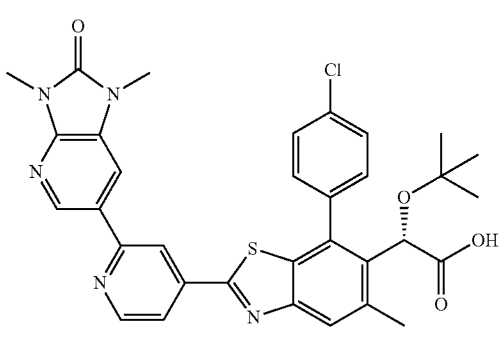 [SMILES: Cc1cc2nc(-c3ccnc(-c4cnc5c(c4)n(C)c(=O)n5C)c3)sc2c(-c2ccc(Cl)cc2)c1[C@H](OC(C)(C)C)C(=O)O] | W | 628.14 | 628.2 | ¹H NMR (400 MHz, CDCl₃) δ 8.96 (d, J = 6.0 Hz, 1H), 8.66 (d, J = 13.6 Hz, 2H), 8.33 (s, 1H), 8.18 (d, J = 4.8 Hz, 1H), 8.03 (s, 1H), 7.71 (d, J = 8.0 Hz, 1H), 7.57-7.47 (m, 3H), 5.35 (s, 1H), 3.58 (s, 3H), 3.56 (s, 3H), 2.62 (s, 3H), 1.01 (s, 9H). |

| Cmpd # | Compound Structure | Method | Parent MW | LCMS-ESI+ | 1H NMR |
|---|---|---|---|---|---|
| 455 | 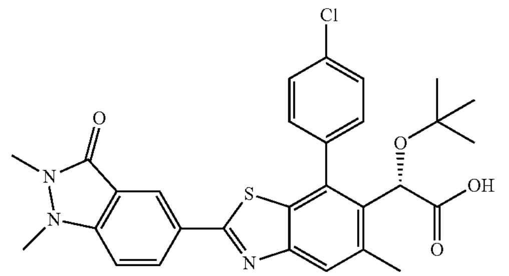 [SMILES: Cc1cc2nc(-c3ccc4c(c3)c(=O)n(C)n4C)sc2c(-c2ccc(Cl)cc2)c1[C@H](OC(C)(C)C)C(=O)O] | AJ | 550.07 | 550.2 | $^1$H NMR (400 MHz, CDCl$_3$) δ 8.48 (d, J = 8.8 Hz, 1H), 8.42 (s, 1H), 7.94 (s, 1H), 7.71 (d, J = 8.4 Hz, 1H), 7.57-7.49 (m, 3H), 7.31 (d, J = 8.4 Hz, 1H), 5.34 (s, 1H), 3.57 (s, 3H), 3.47 (s, 3H), 2.58 (s, 3H), 1.01 (s, 9H). |
| 456 | 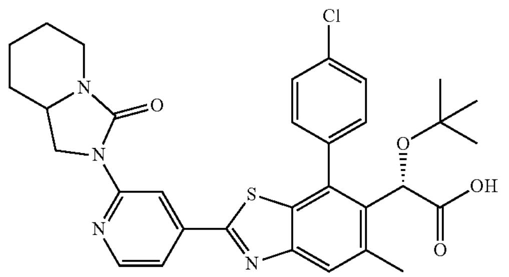 [SMILES: Cc1cc2nc(-c3ccnc(N4CC5CCCCN5C4=O)c3)sc2c(-c2ccc(Cl)cc2)c1[C@H](OC(C)(C)C)C(=O)O] | Y | 605.15 | 605.3 | $^1$H NMR (400 MHz, CDCl$_3$) δ 9.01 (d, J = 4.4 Hz, 1H), 8.44 (d, J = 6.8 Hz, 1H), 7.97 (s, 1H), 7.88 (d, J = 6.4 Hz, 1H), 7.68 (d, J = 7.2 Hz, 1H), 7.56-7.44 (m, 3H), 5.33 (s, 1H), 4.51-4.45 (m, 1H), 4.04 (d, J = 13.2 Hz, 1H), 3.91-3.86 (m, 1H), 3.81-3.76 (m, 1H), 2.93-2.87 (m, 1H), 2.60 (s, 3H), 2.06 (d, J = 12.8 Hz, 1H), 2.01-1.96 (m, 1H), 1.78 (d, J = 9.6 Hz, 1H), 1.55-1.38 (m, 3H), 1.01 (s, 9H). |
| 457 | 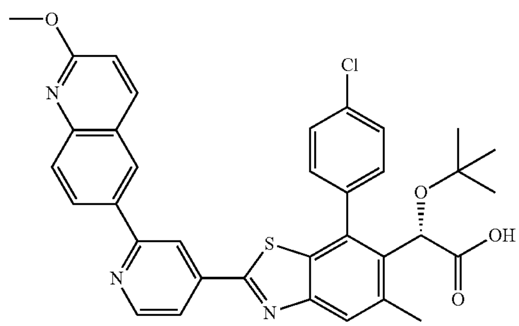 [SMILES: COc1ccc2cc(-c3cc(-c4nc5cc(C)c([C@H](OC(C)(C)C)C(=O)O)c(-c6ccc(Cl)cc6)c5s4)ccn3)ccc2n1] | W | 624.15 | 624.2 | $^1$H NMR (400 MHz, CDCl$_3$) δ 9.05 (d, J = 6.0 Hz, 1H), 8.69 (s, 1H), 8.62 (s, 1H), 8.22-7.20 (m, 3H), 8.09 (d, J = 8.4 Hz, 1H), 8.05 (s, 1H), 7.74 (d, J = 8.4 Hz, 1H), 7.60-7.55 (m, 2H), 7.52-7.49 (m, 1H), 6.05 (d, J = 9.2 Hz, 1H), 5.37 (s, 1H), 4.16 (s, 3H), 2.64 (s, 3H), 1.04 (s, 9H). |
| 458 | 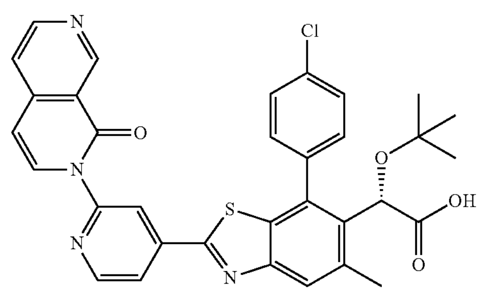 [SMILES: Cc1cc2nc(-c3ccnc(-n4ccc5ccncc5c4=O)c3)sc2c(-c2ccc(Cl)cc2)c1[C@H](OC(C)(C)C)C(=O)O] | Y | 611.1 | 611.2 | $^1$H NMR (400 MHz, CDCl$_3$) δ 10.83 (br. s., 1H), 9.67 (s, 1H), 8.88 (d, J = 6.0 Hz, 1H), 8.69 (d, J = 4.8 Hz, 1H), 8.59 (s, 1H), 8.38 (d, J = 8.0 Hz, 1H), 7.98 (dd, J = 5.2, 1.2 Hz, 1H), 7.93 (s, 1H), 7.81 (d, J = 5.6 Hz, 1H), 7.70 (d, J = 8.4 Hz, 1H), 7.55-7.47 (m, 3H), 6.77 (d, J = 8.0 Hz, 1H), 5.33 (s, 1H), 2.59 (s, 3H), 1.01 (s, 9H). |
| 459 | 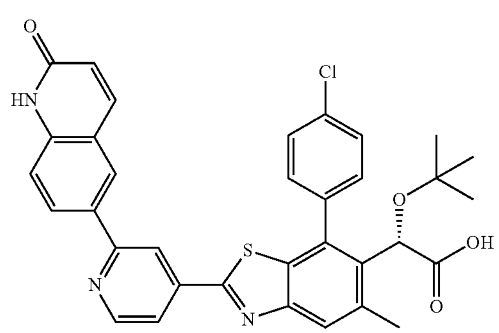 [SMILES: Cc1cc2nc(-c3ccnc(-c4ccc5[nH]c(=O)ccc5c4)c3)sc2c(-c2ccc(Cl)cc2)c1[C@H](OC(C)(C)C)C(=O)O] | W | 610.12 | 610.2 | $^1$H NMR (400 MHz, CDCl$_3$) δ 8.83 (d, J = 5.2 Hz, 1H), 8.37 (d, J = 13.2 Hz, 2H), 8.25 (d, J = 8.4 Hz, 1H), 8.02 (d, J = 7.6 Hz, 1H), 8.00 (s, 1H), 7.81 (d, J = 5.6 Hz, 1H), 7.74 (d, J = 8.0 Hz, 1H), 7.58-7.46 (m, 4H), 6.81 (d, J = 9.2 Hz, 1H), 5.35 (s, 1H), 2.63 (s, 3H), 1.03 (s, 9H). |

| Cmpd # | Compound Structure | Method | Parent MW | LCMS-ESI+ | 1H NMR |
|---|---|---|---|---|---|
| 460 | 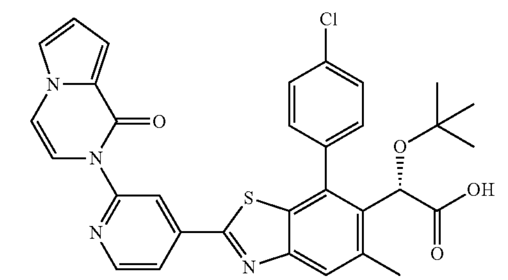 [SMILES: Cc1cc2nc(-c3ccnc(-n4ccn5cccc5c4=O)c3)sc2c(-c2ccc(Cl)cc2)c1[C@H](OC(C)(C)C)C(=O)O] | Y | 599.1 | 599.2 | $^1$H NMR (400 MHz, CD$_3$OD) δ 8.53 (s, 1H), 8.49 (s, 1H), 7.82-7.80 (m, 2H), 7.67-7.65 (m, 1H), 7.55-7.50 (m, 3H), 7.37-7.33 (m, 3H), 7.13 (d, J = 3.2 Hz, 1H), 6.60-6.58 (m, 1H), 5.25 (s, 1H), 2.58 (s, 3H), 0.96 (s, 9H). |
| 461 | 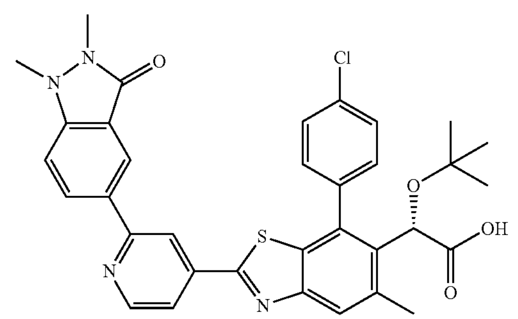 [SMILES: Cc1cc2nc(-c3ccnc(-c4ccc5c(c4)c(=O)n(C)n5C)c3)sc2c(-c2ccc(Cl)cc2)c1[C@H](OC(C)(C)C)C(=O)O] | AA | 627.15 | 627.2 | $^1$H NMR (400 MHz, CD$_3$OD) δ 8.56 (d, J = 5.2 Hz, 1H), 8.25-8.23 (m, 2H), 8.09 (dd, J = 8.4, 1.6 Hz, 1H), 7.82 (dd, J = 5.6, 1.6 Hz, 1H), 7.75 (s, 1H), 7.60-7.58 (m, 1H), 7.51-7.46 (m, 3H), 7.37 (d, J = 9.2 Hz, 1H), 5.18 (s, 1H), 3.39 (s, 3H), 3.36 (s, 3H), 2.50 (s, 3H), 0.88 (s, 9H). |
| 462 | 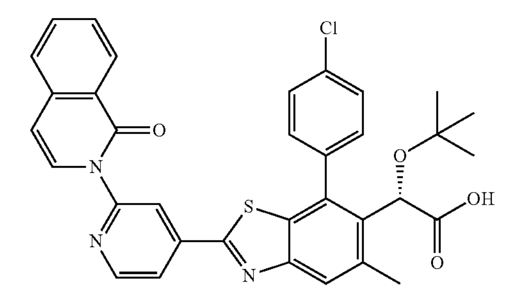 [SMILES: Cc1cc2nc(-c3ccnc(-n4ccc5ccccc5c4=O)c3)sc2c(-c2ccc(Cl)cc2)c1[C@H](OC(C)(C)C)C(=O)O] | Y | 610.12 | 610.2 | $^1$H NMR (400 MHz, CD$_3$OD) δ 8.49 (d, J = 5.6 Hz, 1H), 8.34 (s, 1H), 8.19 (d, J = 8.4 Hz, 1H), 7.77 (d, J = 5.2 Hz, 1H), 7.72 (s, 1H), 7.64-7.56 (m, 3H), 7.51 (d, J = 7.6 Hz, 1H), 7.45-7.39 (m, 4H), 6.61 (d, J = 7.2 Hz, 1H), 5.15 (s, 1H), 2.48 (s, 3H), 0.86 (s, 9H). |
| 463 | 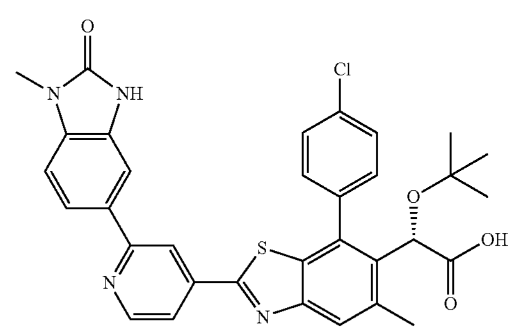 [SMILES: Cc1cc2nc(-c3ccnc(-c4ccc5c(c4)[nH]c(=O)n5C)c3)sc2c(-c2ccc(Cl)cc2)c1[C@H](OC(C)(C)C)C(=O)O] | V | 613.13 | 613.3 | $^1$H NMR (400 MHz, CD$_3$OD) δ 8.71 (d, J = 5.2 Hz, 1H), 8.05 (d, J = 0.8 Hz, 1H), 8.04 (dd, J = 5.6, 1.6 Hz, 1H), 7.96 (s, 1H), 7.78 (dd, J = 8.4, 1.6 Hz, 1H), 7.73-7.68 (m, 2H), 7.65-7.60 (m, 3H), 7.27 (d, J = 8.4 Hz, 1H), 5.28 (s, 1H), 3.43 (s, 3H), 2.64 (s, 3H), 0.98 (s, 9H). |

Example 180

Preparation of (S)-2-tert-butoxy-2-(7-(4-chlorophenyl)-5-methyl-2-(2-(4-(pentan-3-yl)piperazin-1-yl)pyrimidin-4-yl)benzo[d]thiazol-6-yl)acetic acid (464)

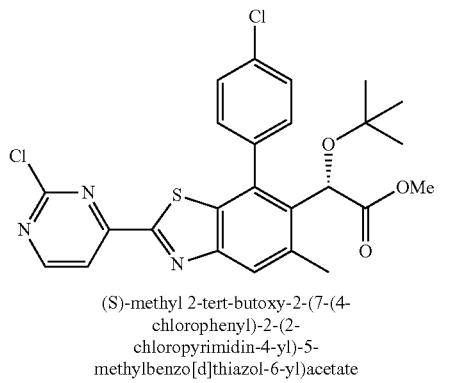

(S)-methyl 2-tert-butoxy-2-(7-(4-chlorophenyl)-2-(2-chloropyrimidin-4-yl)-5-methylbenzo[d]thiazol-6-yl)acetate

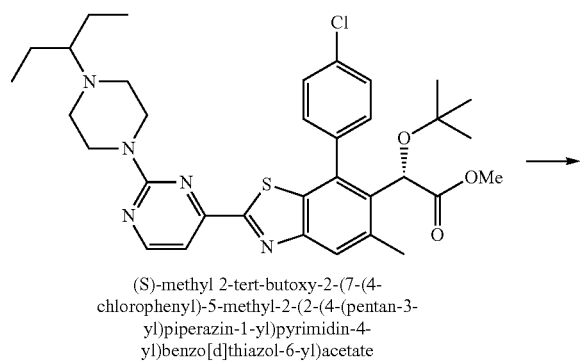

(S)-methyl 2-tert-butoxy-2-(7-(4-chlorophenyl)-5-methyl-2-(2-(4-(pentan-3-yl)piperazin-1-yl)pyrimidin-4-yl)benzo[d]thiazol-6-yl)acetate

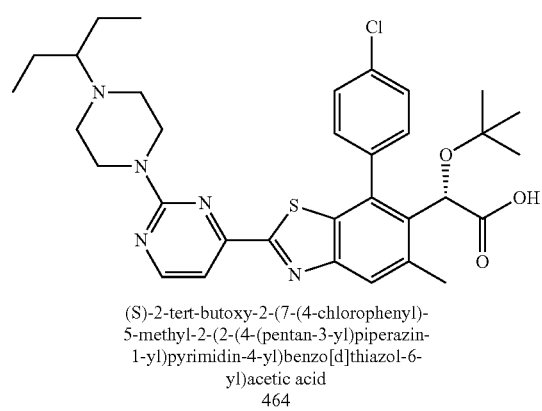

(S)-2-tert-butoxy-2-(7-(4-chlorophenyl)-5-methyl-2-(2-(4-(pentan-3-yl)piperazin-1-yl)pyrimidin-4-yl)benzo[d]thiazol-6-yl)acetic acid
464

Preparation of (S)-methyl 2-tert-butoxy-2-(7-(4-chlorophenyl)-5-methyl-2-(2-(4-(pentan-3-yl)piperazin-1-yl)pyrimidin-4-yl)benzo[d]thiazol-6-yl)acetate: To (S)-methyl 2-tert-butoxy-2-(7-(4-chlorophenyl)-2-(2-chloropyrimidin-4-yl)-5-methylbenzo[d]thiazol-6-yl)acetate (40.0 mg, 0.077 mmol) was added 1-(3-propyl)-piperazine (60.5 mg, 0.387 mmol) in 1,4-dioxane (1 mL). The reaction mixture was stirred at room temperature for 20 min, then 40° C. for 1 h. Upon completion of the reaction, the reaction mixture was filtered through Celite (ethyl acetate eluent), concentrated, and used without further purification. LCMS-ESI$^+$ calc'd for $C_{34}H_{43}ClN_5O_3S$ (M+H$^+$): 636.3; Found: 636.2 (M+H$^+$).

Preparation of (S)-2-tert-butoxy-2-(7-(4-chlorophenyl)-5-methyl-2-(2-(4-(pentan-3-yl)piperazin-1-yl)pyrimidin-4-yl)benzo[d]thiazol-6-yl)acetic acid: To crude (S)-methyl 2-tert-butoxy-2-(7-(4-chlorophenyl)-5-methyl-2-(2-(4-(pentan-3-yl)piperazin-1-yl)pyrimidin-4-yl)benzo[d]thiazol-6-yl)acetate in THF (0.4 mL) and methanol (0.4 mL) was added NaOH (0.39 mL of a 2N solution). The reaction mixture was heated at 30° C. overnight, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{33}H_{41}ClN_5O_3S$ (M+H$^+$): 622.3; Found: 622.3 (M+H$^+$). $^1$H NMR (400 MHz, Methanol-d$_4$) δ 8.62 (d, J=5.0 Hz, 1H), 7.92 (s, 1H), 7.71-7.63 (m, 1H), 7.63-7.52 (m, 4H), 5.25 (s, 1H), 5.08-4.92 (m, 2H), 3.60 (s, 2H), 3.40-3.33 (m, 1H), 3.28-3.08 (m, 4H), 2.63 (s, 3H), 1.97-1.84 (m, 2H), 1.84-1.69 (m, 2H), 1.08 (t, J=7.5 Hz, 6H), 0.98 (s, 9H).

Example 181

Preparation of (S)-2-tert-butoxy-2-(2-(2-(4-tert-butylpiperazin-1-yl)pyrimidin-4-yl)-7-(4-chlorophenyl)-5-methylbenzo[d]thiazol-6-yl)acetic acid (465)

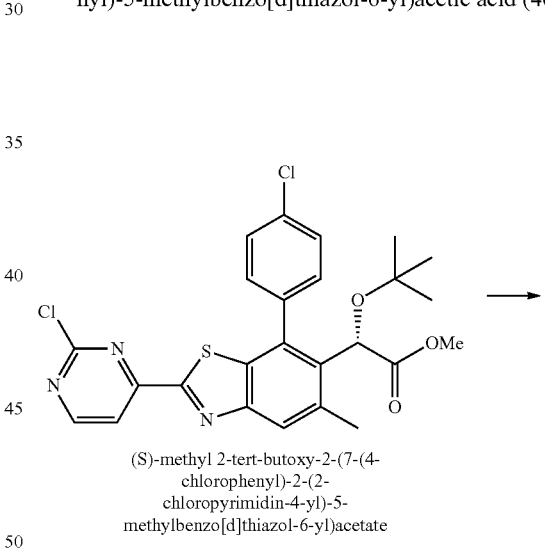

(S)-methyl 2-tert-butoxy-2-(7-(4-chlorophenyl)-2-(2-chloropyrimidin-4-yl)-5-methylbenzo[d]thiazol-6-yl)acetate

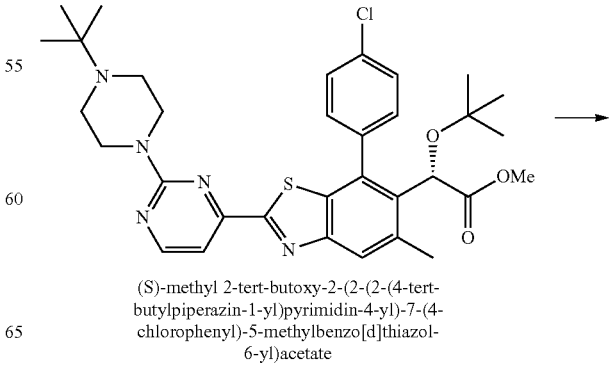

(S)-methyl 2-tert-butoxy-2-(2-(2-(4-tert-butylpiperazin-1-yl)pyrimidin-4-yl)-7-(4-chlorophenyl)-5-methylbenzo[d]thiazol-6-yl)acetate

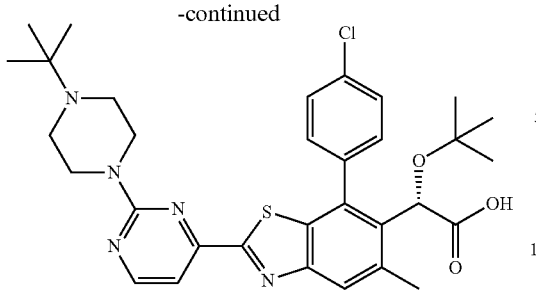

(S)-2-tert-butoxy-2-(2-(2-(4-tert-butylpiperazin-1-yl)pyrimidin-4-yl)-7-(4-chlorophenyl)-5-methylbenzo[d]thiazol-6-yl)acetic acid
465

Preparation of (S)-methyl 2-tert-butoxy-2-(2-(2-(4-tert-butylpiperazin-1-yl)pyrimidin-4-yl)-7-(4-chlorophenyl)-5-methylbenzo[d]thiazol-6-yl)acetate: A flask was charged with (S)-methyl 2-tert-butoxy-2-(7-(4-chlorophenyl)-2-(2-chloropyrimidin-4-yl)-5-methylbenzo[d]thiazol-6-yl)acetate (40.0 mg, 0.077 mmol) and 1-tert-butylpiperazine (33.1 mg, 0.232 mmol). 1,4-Dioxane (1 mL) was added, and the reaction mixture was stirred at room temperature for 3 h. Upon completion of the reaction, the reaction mixture was filtered through Celite (ethyl acetate eluent), concentrated, and used without further purification. LCMS-ESI$^+$ calc'd for $C_{33}H_{41}ClN_5O_3S$ (M+H$^+$): 622.3; Found: 622.2 (M+H$^+$).

Preparation of (S)-2-tert-butoxy-2-(2-(2-(4-tert-butylpiperazin-1-yl)pyrimidin-4-yl)-7-(4-chlorophenyl)-5-methylbenzo[d]thiazol-6-yl)acetic acid:: To crude (S)-methyl 2-tert-butoxy-2-(2-(2-(4-tert-butylpiperazin-1-yl)pyrimidin-4-yl)-7-(4-chlorophenyl)-5-methylbenzo[d]thiazol-6-yl)acetate in THF (0.4 mL) and methanol (0.4 mL) was added NaOH (0.39 mL of a 2N solution). The reaction mixture was heated at 30° C. overnight, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{32}H_{39}ClN_5O_3S$ (M+H$^+$): 608.2; Found: 608.2 (M+H$^+$). $^1$H NMR (400 MHz, Methanol-d$_4$) δ 8.62 (d, J=5.0 Hz, 1H), 7.92 (s, 1H), 7.73-7.49 (m, 5H), 5.25 (s, 1H), 5.04 (d, J=14.0 Hz, 2H), 3.72 (d, J=10.8 Hz, 2H), 3.26 (d, J=13.8 Hz, 2H), 3.21-3.08 (m, 2H), 2.63 (s, 3H), 1.45 (s, 9H), 0.98 (s, 9H).

Example 182

Preparation of (S)-2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetic acid (466).

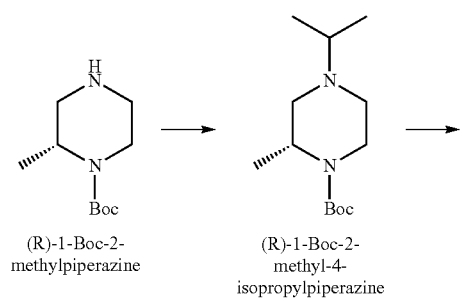

(R)-1-Boc-2-methylpiperazine (R)-1-Boc-2-methyl-4-isopropylpiperazine

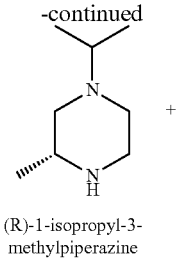

(R)-1-isopropyl-3-methylpiperazine

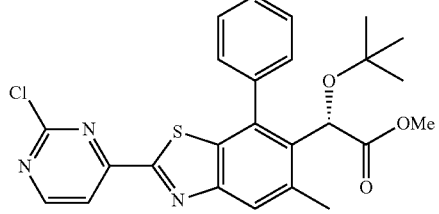

(S)-methyl 2-tert-butoxy-2-(7-(4-chlorophenyl)-2-(2-chloropyrimidin-4-yl)-5-methylbenzo[d]thiazol-6-yl)acetate

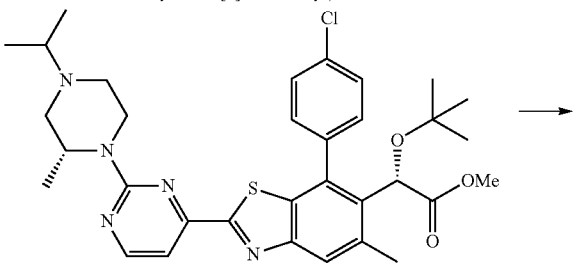

(S)-methyl 2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetate

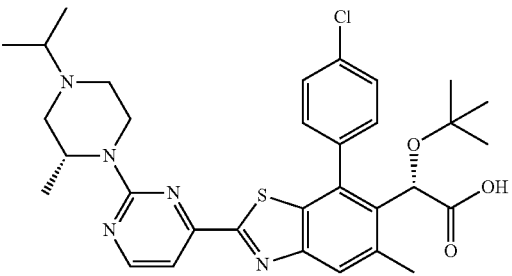

(S)-2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetic acid
466

Preparation of (R)-1-Boc-2-methyl-4-isopropylpiperazine: To (R)-1-Boc-2-methylpiperazine (200.0 mg, 0.999 mmol) and sodium triacetoxyborohydride (444.5 mg, 2.097 mmol) in DMF (5 mL) was added acetone (116 mg, 0.147 mL, 1.997 mmol) and acetic acid (90.0 mg, 86 µL, 1.498 mmol). The reaction mixture was heated at 60° C. for 1 h. The reaction mixture was diluted with water and extracted three times with diethyl ether. The combined organics were dried over sodium sulfate, filtered, concentrated, and used without further purification. LCMS-ESI$^+$: calc'd for $C_{13}H_{27}N_2O_2$ (M+H$^+$): 243.2; Found: 243.1 (M+H$^+$).

Preparation of (R)-1-isopropyl-3-methylpiperazine: To crude (R)-1-Boc-2-methyl-4-isopropylpiperazine in 1,4-dioxane (10 mL) was added HCl (5 mL of a 4M solution in 1,4-dioxane). The reaction mixture was stirred at room temperature for 28 h then concentrated. The resulting solid was suspended in diethyl ether, concentrated and dried on high vacuum for 1 d. The resulting solid was taken up in aq. 2N NaOH and the solution extracted three times with DCM. The combined organic layers were dried over sodium sulfate, filtered, and concentrated to provide the free base of the product which was used without further purification. LCMS-ESI+: calc'd for $C_8H_{18}N_2$ (M+H+): 143.1; Found: 143.7 (M+H+).

Preparation of (S)-methyl 2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetate: To (S)-methyl 2-tert-butoxy-2-(7-(4-chlorophenyl)-2-(2-chloropyrimidin-4-yl)-5-methylbenzo[d]thiazol-6-yl)acetate (40.0 mg, 0.077 mmol) was added (R)-1-isopropyl-3-methylpiperazine (33.1 mg, 0.232 mmol) in 1,4-dioxane (1 mL) and triethylamine (15.7 mg, 22 µL, 0.155 mmol). The reaction mixture was stirred at 60° C. for 4 d, after which the reaction mixture was filtered through Celite (ethyl acetate eluent), concentrated, and used without further purification. LCMS-ESI+ calc'd for $C_{33}H_{41}ClN_5O_3S$ (M+H+): 622.3; Found: 622.2 (M+H+).

Preparation of (S)-2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetic acid: To crude (S)-methyl 2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetate in THF (0.4 mL) and methanol (0.4 mL) was added NaOH (0.39 mL of a 2N solution). The reaction mixture was heated at 30° C. overnight, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI+: calc'd for $C_{32}H_{39}ClN_5O_3S$ (M+H+): 608.2; Found: 608.3 (M+H+). $^1$H NMR (400 MHz, Methanol-$d_4$) δ 8.63 (d, J=4.9 Hz, 1H), 7.92 (s, 1H), 7.71-7.64 (m, 1H), 7.63-7.53 (m, 4H), 5.31 (br s, 1H), 5.25 (s, 1H), 4.95 (d, J=15.0 Hz, 1H), 3.63-3.46 (m, 3H), 3.45-3.34 (m, 1H), 3.28-3.11 (m, 2H), 2.63 (s, 3H), 1.45-1.32 (m, 9H), 0.98 (s, 9H).

Example 183

Preparation of (S)-2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetic acid (467)

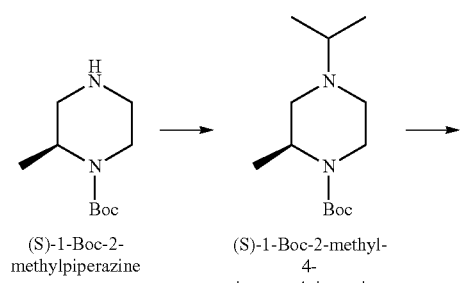

(S)-1-Boc-2-methylpiperazine (S)-1-Boc-2-methyl-4-isopropylpiperazine

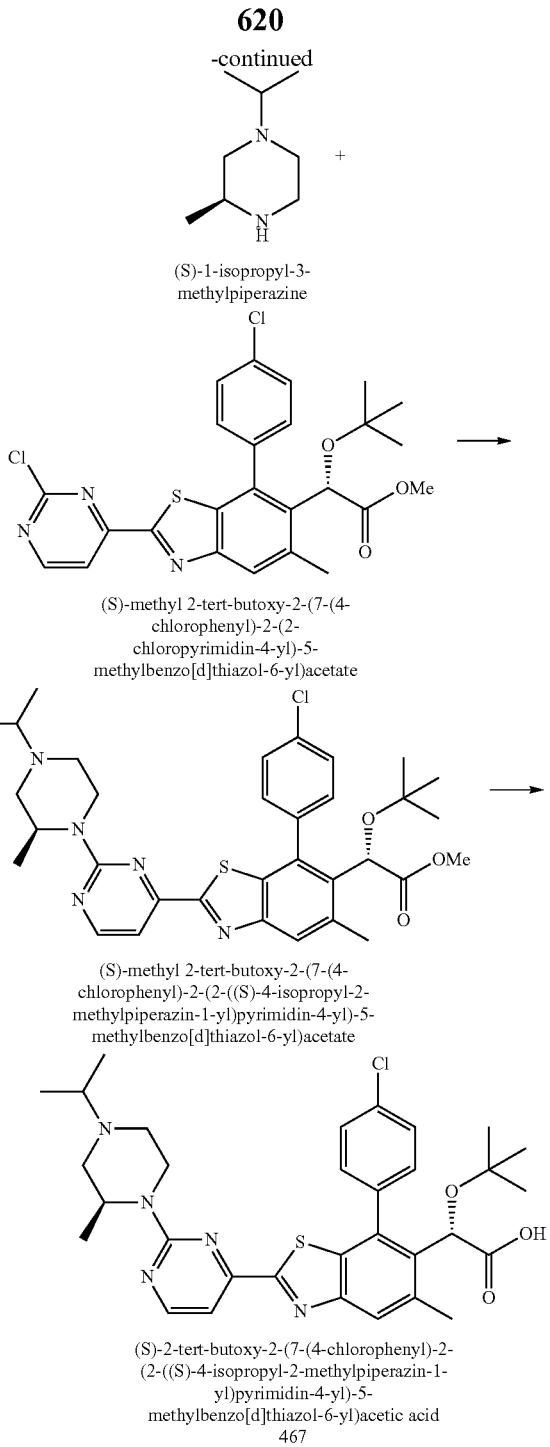

(S)-1-isopropyl-3-methylpiperazine (S)-methyl 2-tert-butoxy-2-(7-(4-chlorophenyl)-2-(2-chloropyrimidin-4-yl)-5-methylbenzo[d]thiazol-6-yl)acetate (S)-methyl 2-tert-butoxy-2-(7-(4-chlorophenyl)-2-(2-((S)-4-isopropyl-2-methylpiperazin-1-yl)pyrimidin-4-yl)-5-methylbenzo[d]thiazol-6-yl)acetate (S)-2-tert-butoxy-2-(7-(4-chlorophenyl)-2-(2-((S)-4-isopropyl-2-methylpiperazin-1-yl)pyrimidin-4-yl)-5-methylbenzo[d]thiazol-6-yl)acetic acid
467

Preparation of (S)-1-Boc-2-methyl-4-isopropylpiperazine: To (R)-1-Boc-2-methylpiperazine (200.0 mg, 0.999 mmol) and sodium triacetoxyborohydride (444.5 mg, 2.097 mmol) in DMF (5 mL) was added acetone (116 mg, 0.147 mL, 1.997 mmol) and acetic acid (90.0 mg, 86 µL, 1.498 mmol). The reaction mixture was heated at 60° C. for 1 h. The reaction mixture was diluted with water and extracted three times with diethyl ether. The combined organics were dried over sodium sulfate, filtered, concentrated, and used without further purification. LCMS-ESI+: calc'd for $C_{13}H_{27}N_2O_2$ (M+H+): 243.2; Found: 243.2 (M+H+).

Preparation of (S)-1-isopropyl-3-methylpiperazine: To crude (S)-1-Boc-2-methyl-4-isopropylpiperazine in 1,4-dioxane (10 mL) was added HCl (5 mL of a 4M solution in 1,4-dioxane). The reaction mixture was stirred at room temperature for 28 h then concentrated. The resulting solid was suspended in diethyl ether, concentrated and dried on high vacuum for 1 d. The resulting solid was taken up in aq. 2N NaOH and the solution extracted three times with DCM. The combined organic layers were dried over sodium sulfate, filtered, and concentrated to provide the free base of the product which was used without further purification. LCMS-ESI⁺: calc'd for $C_8H_{18}N_2$ (M+H⁺): 143.1; Found: 143.7 (M+H⁺).

Preparation of (S)-methyl 2-tert-butoxy-2-(7-(4-chlorophenyl)-2-(2-((S)-4-isopropyl-2-methylpiperazin-1-yl)pyrimidin-4-yl)-5-methylbenzo[d]thiazol-6-yl)acetate: To (S)-methyl 2-tert-butoxy-2-(7-(4-chlorophenyl)-2-(2-chloropyrimidin-4-yl)-5-methylbenzo[d]thiazol-6-yl)acetate (40.0 mg, 0.077 mmol) was added (S)-1-isopropyl-3-methylpiperazine (33.1 mg, 0.232 mmol) in 1,4-dioxane (1 mL) and triethylamine (15.7 mg, 22 µL, 0.155 mmol). The reaction mixture was stirred at 60° C. for 4 d, after which the reaction mixture was filtered through Celite (ethyl acetate eluent), concentrated, and used without further purification. LCMS-ESI⁺ calc'd for $C_{33}H_{41}ClN_5O_3S$ (M+H⁺): 622.3; Found: 622.2 (M+H⁺).

Preparation of (S)-2-tert-butoxy-2-(7-(4-chlorophenyl)-2-(2-((R)-4-isopropyl-2-methylpiperazin-1-yl)pyrimidin-4-yl)-5-methylbenzo[d]thiazol-6-yl)acetic acid: To crude (S)-methyl 2-tert-butoxy-2-(7-(4-chlorophenyl)-2-(2-((S)-4-isopropyl-2-methylpiperazin-1-yl)pyrimidin-4-yl)-5-methylbenzo[d]thiazol-6-yl)acetate in THF (0.4 mL) and methanol (0.4 mL) was added NaOH (0.39 mL of a 2N solution). The reaction mixture was heated at 30° C. overnight, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI⁺: calc'd for $C_{32}H_{39}ClN_5O_3S$ (M+H⁺): 608.2; Found: 608.3 (M+H⁺). ¹H NMR (400 MHz, Methanol-d₄) δ 8.63 (d, J=5.0 Hz, 1H), 7.92 (s, 1H), 7.71-7.63 (m, 1H), 7.63-7.50 (m, 4H), 5.31 (br s, 1H), 5.25 (s, 1H), 4.95 (d, J=14.6 Hz, 1H), 3.63-3.46 (m, 3H), 3.45-3.34 (m, 1H), 3.29-3.11 (m, 2H), 2.63 (s, 3H), 1.46-1.37 (m, 9H), 0.98 (s, 9H).

Example 184

Preparation of (S)-2-tert-butoxy-2-(7-(4-chlorophenyl)-2-(2-((S)-3,4-dimethylpiperazin-1-yl)pyrimidin-4-yl)-5-methylbenzo[d]thiazol-6-yl)acetic acid (468)

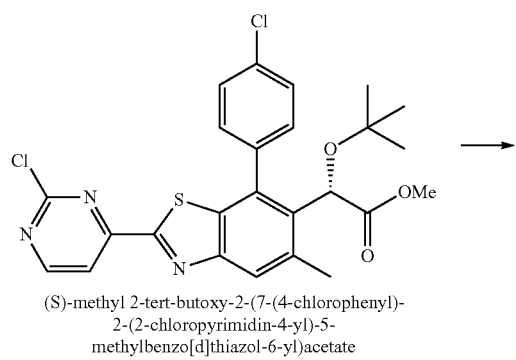

(S)-methyl 2-tert-butoxy-2-(7-(4-chlorophenyl)-2-(2-chloropyrimidin-4-yl)-5-methylbenzo[d]thiazol-6-yl)acetate

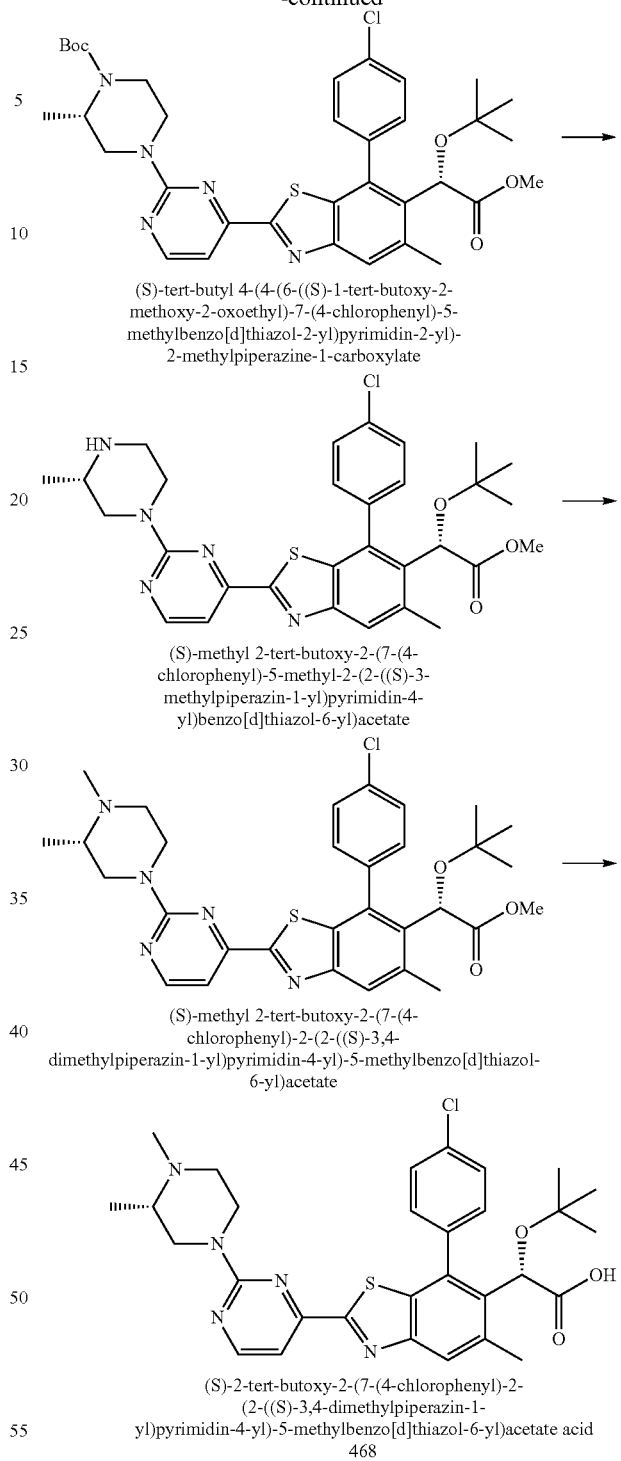

(S)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate (S)-methyl 2-tert-butoxy-2-(7-(4-chlorophenyl)-5-methyl-2-(2-((S)-3-methylpiperazin-1-yl)pyrimidin-4-yl)benzo[d]thiazol-6-yl)acetate (S)-methyl 2-tert-butoxy-2-(7-(4-chlorophenyl)-2-(2-((S)-3,4-dimethylpiperazin-1-yl)pyrimidin-4-yl)-5-methylbenzo[d]thiazol-6-yl)acetate (S)-2-tert-butoxy-2-(7-(4-chlorophenyl)-2-(2-((S)-3,4-dimethylpiperazin-1-yl)pyrimidin-4-yl)-5-methylbenzo[d]thiazol-6-yl)acetate acid 468

Preparation of (S)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate: To (S)-methyl 2-tert-butoxy-2-(7-(4-chlorophenyl)-2-(2-chloropyrimidin-4-yl)-5-methylbenzo[d]thiazol-6-yl)acetate (80.0 mg, 0.155 mmol) and (S)-1-boc-2-methylpiperazine (93.1 mg, 0.465 mmol) in 1,4-dioxane (2 mL) was added triethylamine (156.8 mg, 0.19 mL, 1.549 mmol). The reaction mixture was stirred at 40° C. for 4 h, at room temperature overnight, then at 40° C. for an additional 7 h. The reaction mixture was filtered through Celite (ethyl acetate eluent), concentrated, and used without further purification. LCMS-ESI+ calc'd for $C_{35}H_{43}ClN_5O_5S$ (M+H+): 680.3; Found: 680.0 (M+H+).

Preparation of (S)-methyl 2-tert-butoxy-2-(7-(4-chlorophenyl)-5-methyl-2-(2-((S)-3-methylpiperazin-1-yl)pyrimidin-4-yl)benzo[d]thiazol-6-yl)acetate: To crude (S)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate in 1,4-dioxane (1.25 mL) was added HCl (0.78 mL of a 4M solution in 1,4-dioxane). The reaction mixture was stirred at room temperature for 2.5 h then concentrated. The resulting solid was suspended in diethyl ether, concentrated and dried under high vacuum overnight. The resulting solid was taken up in water, basified with 2N NaOH, and extracted three times with DCM. The combined organic layers were dried over sodium sulfate, filtered, concentrated, and used without further purification. LCMS-ESI+ calc'd for $C_{30}H_{35}ClN_5O_3S$ (M+H+): 580.2; Found: 580.2 (M+H+).

Preparation of (S)-methyl 2-tert-butoxy-2-(7-(4-chlorophenyl)-2-(2-((S)-3,4-dimethylpiperazin-1-yl)pyrimidin-4-yl)-5-methylbenzo[d]thiazol-6-yl)acetate: To crude (S)-methyl 2-tert-butoxy-2-(7-(4-chlorophenyl)-5-methyl-2-(2(S)-3-methylpiperazin-1-yl)pyrimidin-4-yl)benzo[d]thiazol-6-yl)acetate (43.8 mg, 0.075 mmol) and sodium triacetoxyborohydride (80.1 mg, 0.377 mmol) in DMF (1 mL) was added acetic acid (22.7 mg, 21.6 µL, 0.377 mmol). The reaction mixture was heated to 60° C., then 37% w/w aq. formaldehyde (9.1 mg, 21.6 µL, 0.302 mmol) was added dropwise over 1 min. The reaction mixture was heated at 60° C. for 2 h. Upon completion of the reaction, the reaction mixture was filtered through Celite (ethyl acetate eluent) and concentrated. Purification by flash column chromatography on silica gel using 100:5:1 EtOAc/MeOH/NH4OH (0 to 100%) in EtOAc provided the product. LCMS-ESI+ calc'd for $C_{31}H_{37}ClN_5O_3S$ (M+H+): 594.2; Found: 593.6 (M+H+).

Preparation of (S)-2-tert-butoxy-2-(7-(4-chlorophenyl)-2-(2-((S)-3,4-dimethylpiperazin-1-yl)pyrimidin-4-yl)-5-methylbenzo[d]thiazol-6-yl)acetic acid: To (S)-methyl 2-tert-butoxy-2-(7-(4-chlorophenyl)-2-(2-((S)-3,4-dimethylpiperazin-1-yl)pyrimidin-4-yl)-5-methylbenzo[d]thiazol-6-yl)acetate in THF (0.3 mL) and methanol (0.3 mL) was added NaOH (0.30 mL of a 2N solution). The reaction mixture was heated at 30° C. overnight then cooled, filtered, and purified by reverse phase HPLC, eluting with 5-100% acetonitrile in water with 0.1% TFA. Fractions containing the product were pooled and lyophilized to provide the TFA salt of the product. LCMS-ESI+: calc'd for $C_{30}H_{35}ClN_5O_3S$ (M+H+): 580.2; Found: 580.1 (M+H+). 1H NMR (400 MHz, Methanol-d4) δ 8.62 (d, J=4.9 Hz, 1H), 7.92 (s, 1H), 7.72-7.64 (m, 1H), 7.65-7.58 (m, 3H), 7.58-7.53 (m, 1H), 5.25 (s, 1H), 5.01-4.73 (m, 2H), 3.61 (br s, 1H), 3.46-3.02 (m, 4H), 2.96 (s, 3H), 2.63 (s, 3H), 1.44 (br s, 3H), 0.97 (s, 9H).

Example 185

Preparation of (S)-2-tert-butoxy-2-(7-(4-chlorophenyl)-2-(2-((R)-3,4-dimethylpiperazin-1-yl)pyrimidin-4-yl)-5-methylbenzo[d]thiazol-6-yl)acetic acid (469)

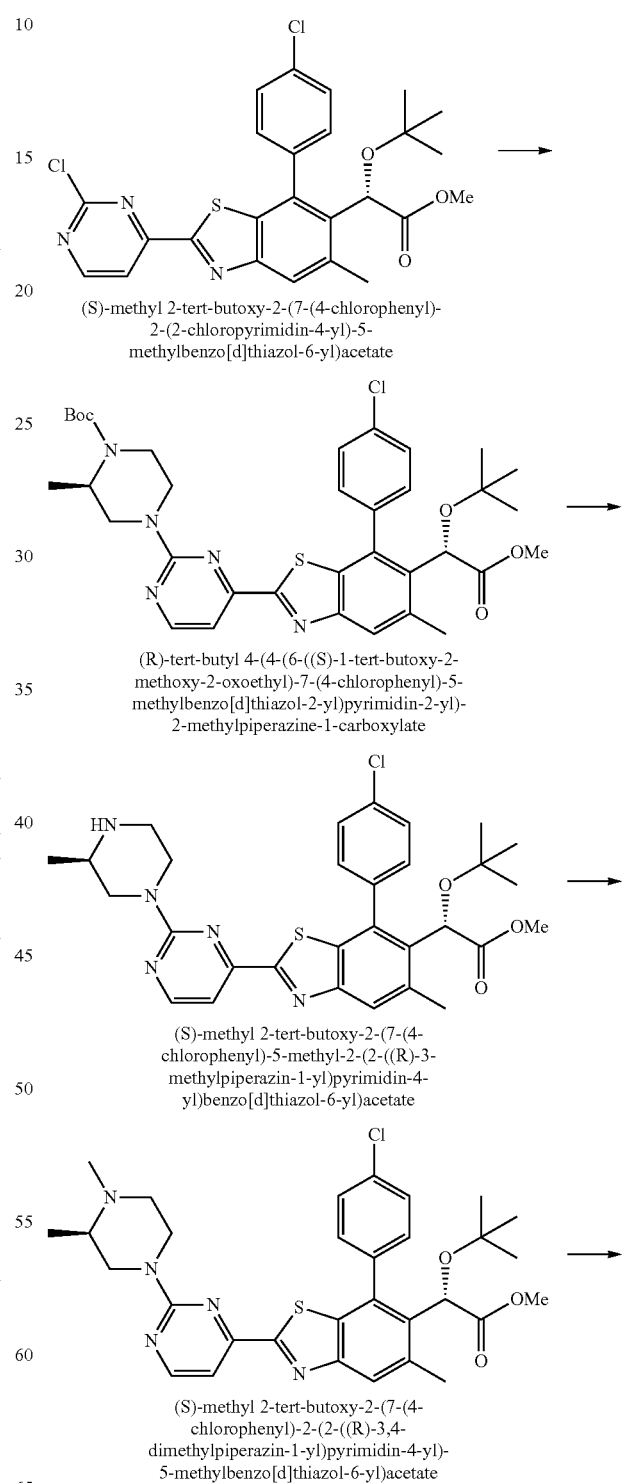

(S)-methyl 2-tert-butoxy-2-(7-(4-chlorophenyl)-2-(2-chloropyrimidin-4-yl)-5-methylbenzo[d]thiazol-6-yl)acetate (R)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate (S)-methyl 2-tert-butoxy-2-(7-(4-chlorophenyl)-5-methyl-2-(2-((R)-3-methylpiperazin-1-yl)pyrimidin-4-yl)benzo[d]thiazol-6-yl)acetate (S)-methyl 2-tert-butoxy-2-(7-(4-chlorophenyl)-2-(2-((R)-3,4-dimethylpiperazin-1-yl)pyrimidin-4-yl)-5-methylbenzo[d]thiazol-6-yl)acetate

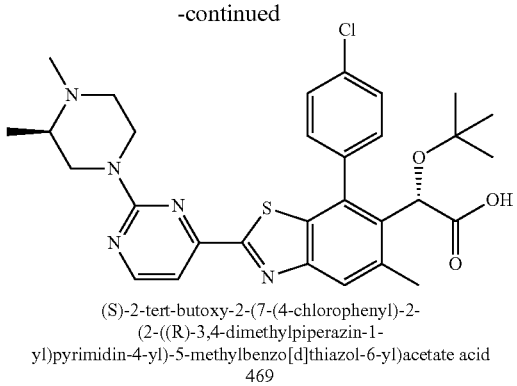

(S)-2-tert-butoxy-2-(7-(4-chlorophenyl)-2-
(2-((R)-3,4-dimethylpiperazin-1-
yl)pyrimidin-4-yl)-5-methylbenzo[d]thiazol-6-yl)acetate acid
469

Preparation of (R)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate: To (S)-methyl 2-tert-butoxy-2-(7-(4-chlorophenyl)-2-(2-chloropyrimidin-4-yl)-5-methylbenzo[d]thiazol-6-yl)acetate (80.0 mg, 0.155 mmol) and (R)-1-boc-2-methylpiperazine (93.1 mg, 0.465 mmol) in 1,4-dioxane (2 mL) was added triethylamine (156.8 mg, 0.19 mL, 1.549 mmol). The reaction mixture was stirred at 40° C. for 4 h, at room temperature overnight, then at 40° C. for an additional 7 h. The reaction mixture was filtered through Celite (ethyl acetate eluent), concentrated, and used without further purification. LCMS-ESI+ calc'd for $C_{35}H_{43}ClN_5O_5S$ (M+H+): 680.3; Found: 680.0 (M+H+).

Preparation of (S)-methyl 2-tert-butoxy-2-(7-(4-chlorophenyl)-5-methyl-2-(2-((R)-3-methylpiperazin-1-yl)pyrimidin-4-yl)benzo[d]thiazol-6-yl)acetate: To crude (R)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate in 1,4-dioxane (1.25 mL) was added HCl (0.78 mL of a 4M solution in 1,4-dioxane). The reaction mixture was stirred at room temperature for 2.5 h then concentrated. The resulting solid was suspended in diethyl ether, concentrated and dried under high vacuum overnight. The resulting solid was taken up in water, basified with 2N NaOH, and extracted three times with DCM. The combined organic layers were dried over sodium sulfate, filtered, concentrated, and used without further purification. LCMS-ESI+ calc'd for $C_{30}H_{35}ClN_5O_3S$ (M+H+): 580.2; Found: 580.2 (M+H+).

Preparation of (S)-methyl 2-tert-butoxy-2-(7-(4-chlorophenyl)-2-(2-((R)-3,4-dimethylpiperazin-1-yl)pyrimidin-4-yl)-5-methylbenzo[d]thiazol-6-yl)acetate: To crude (S)-methyl 2-tert-butoxy-2-(7-(4-chlorophenyl)-5-methyl-2-(2-((R)-3-methylpiperazin-1-yl)pyrimidin-4-yl)benzo[d]thiazol-6-yl)acetate (45.8 mg, 0.079 mmol) and sodium triacetoxyborohydride (83.7 mg, 0.395 mmol) in DMF (1 mL) was added acetic acid (23.7 mg, 22.6 μL, 0.395 mmol). The reaction mixture was heated to 60° C., then 37% w/w aq. formaldehyde (9.48 mg, 23.5 μL, 0.316 mmol) was added dropwise over 1 min. The reaction mixture was heated at 60° C. for 2 h. Upon completion of the reaction, the reaction mixture was filtered through Celite (ethyl acetate eluent) and concentrated. Purification by flash column chromatography on silica gel using 100:5:1 EtOAc/MeOH/NH4OH (0 to 100%) in EtOAc provided the product. LCMS-ESI+ calc'd for $C_{31}H_{37}ClN_5O_3S$ (M+H+): 594.2; Found: 593.7 (M+H+).

Preparation of (S)-2-tert-butoxy-2-(7-(4-chlorophenyl)-2-(2-((R)-3,4-dimethylpiperazin-1-yl)pyrimidin-4-yl)-5-methylbenzo[d]thiazol-6-yl)acetic acid: To (S)-methyl 2-tert-butoxy-2-(7-(4-chlorophenyl)-2-(2-((R)-3,4-dimethylpiperazin-1-yl)pyrimidin-4-yl)-5-methylbenzo[d]thiazol-6-yl)acetate in THF (0.3 mL) and methanol (0.3 mL) was added NaOH (0.30 mL of a 2N solution). The reaction mixture was heated at 30° C. overnight then cooled, filtered, and purified by reverse phase HPLC, eluting with 5-100% acetonitrile in water with 0.1% TFA. Fractions containing the product were pooled and lyophilized to provide the TFA salt of the product. LCMS-ESI+: calc'd for $C_{30}H_{35}ClN_5O_3S$ (M+H+): 580.2; Found: 580.1 (M+H+). 1H NMR (400 MHz, Methanol-d4) δ 8.62 (d, J=4.8 Hz, 1H), 7.92 (s, 1H), 7.71-7.65 (m, 1H), 7.65-7.58 (m, 3H), 7.58-7.53 (m, 1H), 5.25 (s, 1H), 5.07-4.70 (m, 2H), 3.61 (d, J=13.4 Hz, 1H), 3.37-3.03 (m, 4H), 2.96 (s, 3H), 2.63 (s, 3H), 1.53-1.37 (m, 3H), 0.97 (s, 9H).

Example 186

Preparation of (S)-2-tert-butoxy-2-(7-(4-chlorophenyl)-2-(2-((S)-4-isopropyl-3-methylpiperazin-1-yl)pyrimidin-4-yl)-5-methylbenzo[d]thiazol-6-yl)acetic acid (470)

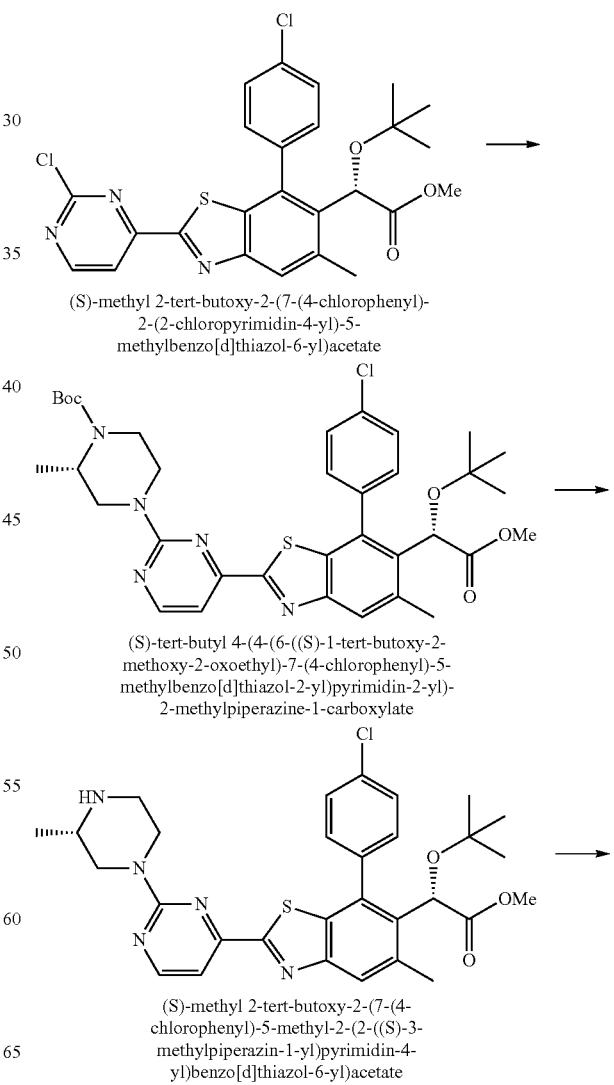

(S)-methyl 2-tert-butoxy-2-(7-(4-chlorophenyl)-2-(2-chloropyrimidin-4-yl)-5-methylbenzo[d]thiazol-6-yl)acetate (S)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate (S)-methyl 2-tert-butoxy-2-(7-(4-chlorophenyl)-5-methyl-2-(2-((S)-3-methylpiperazin-1-yl)pyrimidin-4-yl)benzo[d]thiazol-6-yl)acetate

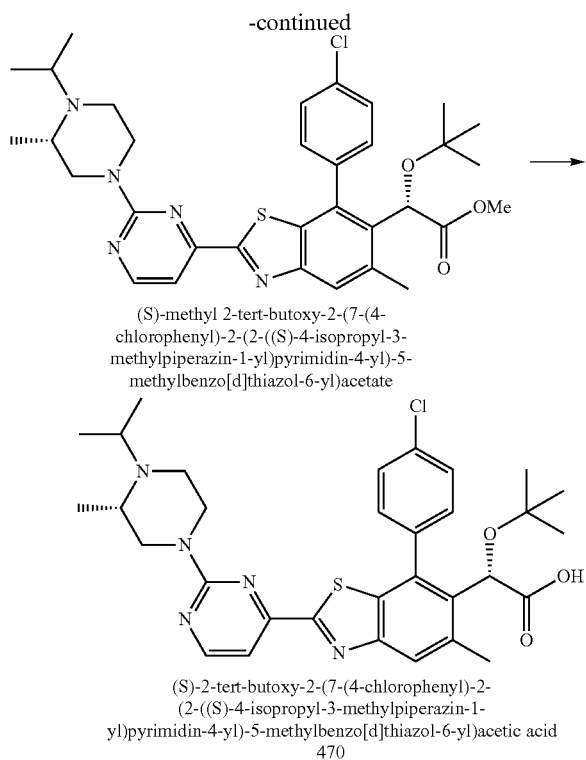

(S)-methyl 2-tert-butoxy-2-(7-(4-chlorophenyl)-2-(2-((S)-4-isopropyl-3-methylpiperazin-1-yl)pyrimidin-4-yl)-5-methylbenzo[d]thiazol-6-yl)acetate (S)-2-tert-butoxy-2-(7-(4-chlorophenyl)-2-(2-((S)-4-isopropyl-3-methylpiperazin-1-yl)pyrimidin-4-yl)-5-methylbenzo[d]thiazol-6-yl)acetic acid 470

Preparation of (S)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate: To (S)-methyl 2-tert-butoxy-2-(7-(4-chlorophenyl)-2-(2-chloropyrimidin-4-yl)-5-methylbenzo[d]thiazol-6-yl)acetate (80.0 mg, 0.155 mmol) and (S)-1-boc-2-methylpiperazine (93.1 mg, 0.465 mmol) in 1,4-dioxane (2 mL) was added triethylamine (156.8 mg, 0.19 mL, 1.549 mmol). The reaction mixture was stirred at 40° C. for 4 h, at room temperature overnight, then at 40° C. for an additional 7 h. The reaction mixture was filtered through Celite (ethyl acetate eluent), concentrated, and used without further purification. LCMS-ESI$^+$ calc'd for $C_{35}H_{43}ClN_5O_5S$ (M+H$^+$): 680.3; Found: 680.0 (M+H$^+$).

Preparation of (S)-methyl 2-tert-butoxy-2-(7-(4-chlorophenyl)-5-methyl-2-(2-((S)-3-methylpiperazin-1-yl)pyrimidin-4-yl)benzo[d]thiazol-6-yl)acetate: To crude (S)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate in 1,4-dioxane (1.25 mL) was added HCl (0.78 mL of a 4M solution in 1,4-dioxane). The reaction mixture was stirred at room temperature for 2.5 h then concentrated. The resulting solid was suspended in diethyl ether, concentrated and dried under high vacuum overnight. The resulting solid was taken up in water, basified with 2N NaOH, and extracted three times with DCM. The combined organic layers were dried over sodium sulfate, filtered, concentrated, and used without further purification. LCMS-ESI$^+$ calc'd for $C_{30}H_{35}ClN_5O_3S$ (M+H$^+$): 580.2; Found: 580.2 (M+H$^+$).

Preparation of (S)-methyl 2-tert-butoxy-2-(7-(4-chlorophenyl)-2-(2-((S)-4-isopropyl-3-methylpiperazin-1-yl)pyrimidin-4-yl)-5-methylbenzo[d]thiazol-6-yl)acetate: To crude (S)-methyl 2-tert-butoxy-2-(7-(4-chlorophenyl)-5-methyl-2-(2-((S)-3-methylpiperazin-1-yl)pyrimidin-4-yl)benzo[d]thiazol-6-yl)acetate (43.8 mg, 0.075 mmol) and sodium triacetoxyborohydride (80.1 mg, 0.377 mmol) in DMF (1 mL) was added acetic acid (22.7 mg, 21.6 µL, 0.377 mmol) and acetone (17.6 mg, 22.2 µL, 0.302 mmol). The reaction mixture was heated at 60° C. for 6.5 h. Upon completion of the reaction, the reaction mixture was filtered through Celite (ethyl acetate eluent) and concentrated. Purification by flash column chromatography on silica gel using 100:5:1 EtOAc/MeOH/NH$_4$OH (0 to 100%) in EtOAc provided the product. LCMS-ESI$^+$ calc'd for $C_{33}H_{41}ClN_5O_3S$ (M+H$^1$): 622.3; Found: 622.2 (M+H$^+$).

Preparation of (S)-2-tert-butoxy-2-(7-(4-chlorophenyl)-2-(2-((S)-4-isopropyl-3-methylpiperazin-1-yl)pyrimidin-4-yl)-5-methylbenzo[d]thiazol-6-yl)acetic acid: To (S)-methyl 2-tert-butoxy-2-(7-(4-chlorophenyl)-2-(2-((S)-4-isopropyl-3-methylpiperazin-1-yl)pyrimidin-4-yl)-5-methylbenzo[d]thiazol-6-yl)acetate in THF (0.3 mL) and methanol (0.3 mL) was added NaOH (0.35 mL of a 2N solution). The reaction mixture was heated at 30° C. overnight then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{32}H_{39}ClN_5O_3S$ (M+H$^+$): 608.2; Found: 608.2 (M+H$^+$). $^1$H NMR (400 MHz, Methanol-d$_4$) δ 8.62 (d, J=5.3 Hz, 1H), 7.92 (s, 1H), 7.70-7.65 (m, 1H), 7.64-7.58 (m, 3H), 7.58-7.53 (m, 1H), 5.25 (s, 1H), 5.03-4.75 (m, 2H), 4.11-3.93 (m, 1H), 3.70-3.05 (m, 5H), 2.63 (s, 3H), 1.48-1.39 (m, 6H), 1.34-1.23 (m, 3H), 0.98 (s, 9H).

Example 187

Preparation of (S)-2-tert-butoxy-2-(7-(4-chlorophenyl)-2-(2-((R)-4-isopropyl-3-methylpiperazin-1-yl)pyrimidin-4-yl)-5-methylbenzo[d]thiazol-6-yl)acetic acid (471)

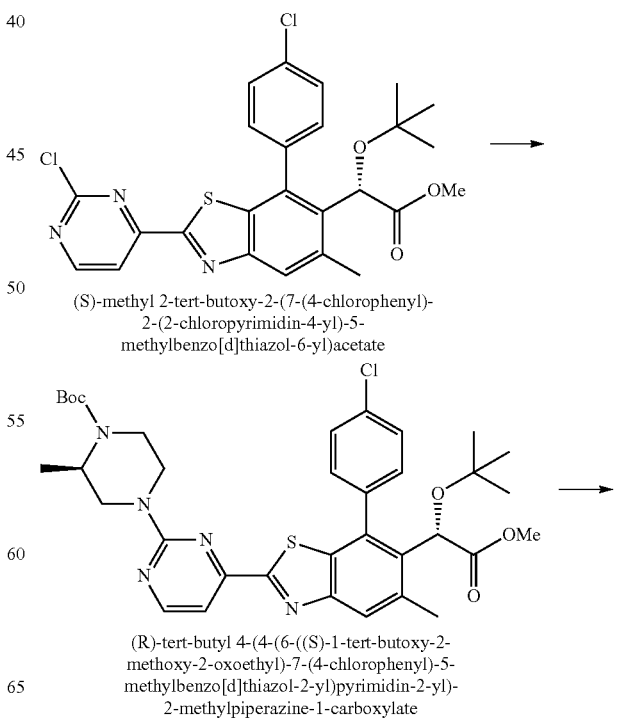

(S)-methyl 2-tert-butoxy-2-(7-(4-chlorophenyl)-2-(2-chloropyrimidin-4-yl)-5-methylbenzo[d]thiazol-6-yl)acetate (R)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate

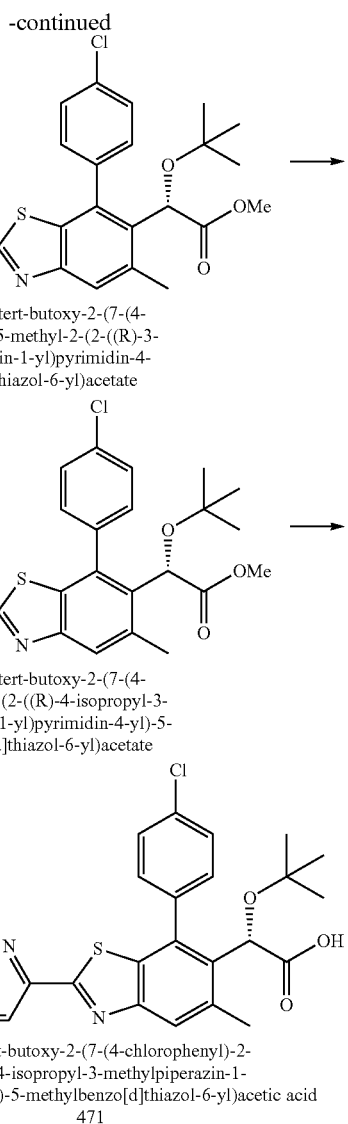

(S)-methyl 2-tert-butoxy-2-(7-(4-chlorophenyl)-5-methyl-2-(2-((R)-3-methylpiperazin-1-yl)pyrimidin-4-yl)benzo[d]thiazol-6-yl)acetate (S)-methyl 2-tert-butoxy-2-(7-(4-chlorophenyl)-2-(2-((R)-4-isopropyl-3-methylpiperazin-1-yl)pyrimidin-4-yl)-5-methylbenzo[d]thiazol-6-yl)acetate (S)-2-tert-butoxy-2-(7-(4-chlorophenyl)-2-(2-((R)-4-isopropyl-3-methylpiperazin-1-yl)pyrimidin-4-yl)-5-methylbenzo[d]thiazol-6-yl)acetic acid
471

Preparation of (R)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate: To (S)-methyl 2-tert-butoxy-2-(7-(4-chlorophenyl)-2-(2-chloropyrimidin-4-yl)-5-methylbenzo[d]thiazol-6-yl)acetate (80.0 mg, 0.155 mmol) and (R)-1-boc-2-methylpiperazine (93.1 mg, 0.465 mmol) in 1,4-dioxane (2 mL) was added triethylamine (156.8 mg, 0.19 mL, 1.549 mmol). The reaction mixture was stirred at 40° C. for 4 h, at room temperature overnight, then at 40° C. for an additional 7 h. The reaction mixture was filtered through Celite (ethyl acetate eluent), concentrated, and used without further purification. LCMS-ESI$^+$ calc'd for $C_{35}H_{43}ClN_5O_5S$ (M+H$^+$): 680.3; Found: 680.0 (M+H$^+$).

Preparation of (S)-methyl 2-tert-butoxy-2-(7-(4-chlorophenyl)-5-methyl-2-(2-((R)-3-methylpiperazin-1-yl)pyrimidin-4-yl)benzo[d]thiazol-6-yl)acetate: To crude (R)-tert-butyl 4-(4-(6-((S)-1-tert-butoxy-2-methoxy-2-oxoethyl)-7-(4-chlorophenyl)-5-methylbenzo[d]thiazol-2-yl)pyrimidin-2-yl)-2-methylpiperazine-1-carboxylate in 1,4-dioxane (1.25 mL) was added HCl (0.78 mL of a 4M solution in 1,4-dioxane). The reaction mixture was stirred at room temperature for 2.5 h then concentrated. The resulting solid was suspended in diethyl ether, concentrated and dried under high vacuum overnight. The resulting solid was taken up in water, basified with 2N NaOH, and extracted three times with DCM. The combined organic layers were dried over sodium sulfate, filtered, concentrated, and used without further purification. LCMS-ESI$^+$ calc'd for $C_{30}H_{35}ClN_5O_3S$ (M+H$^+$): 580.2; Found: 580.2 (M+H$^+$).

Preparation of (S)-methyl 2-tert-butoxy-2-(7-(4-chlorophenyl)-2-(2-((R)-4-isopropyl-3-methylpiperazin-1-yl)pyrimidin-4-yl)-5-methylbenzo[d]thiazol-6-yl)acetate: To crude (S)-methyl 2-tert-butoxy-2-(7-(4-chlorophenyl)-5-methyl-2-(2-((R)-3-methylpiperazin-1-yl)pyrimidin-4-yl)benzo[d]thiazol-6-yl)acetate (45.8 mg, 0.079 mmol) and sodium triacetoxyborohydride (83.7 mg, 0.395 mmol) in DMF (1 mL) was added acetic acid (23.7 mg, 22.6 µL, 0.395 mmol) and acetone (18.3 mg, 23.2 µL, 0.316 mmol). The reaction mixture was heated at 60° C. for 6.5 h. Upon completion of the reaction, the reaction mixture was filtered through Celite (ethyl acetate eluent) and concentrated. Purification by flash column chromatography on silica gel using 100:5:1 EtOAc/MeOH/NH$_4$OH (0 to 100%) in EtOAc provided the product. LCMS-ESI$^+$ calc'd for $C_{33}H_{41}ClN_5O_3S$ (M+H$^+$): 622.3; Found: 622.2 (M+H$^+$).

Preparation of (S)-2-tert-butoxy-2-(7-(4-chlorophenyl)-2-(2-((R)-4-isopropyl-3-methylpiperazin-1-yl)pyrimidin-4-yl)-5-methylbenzo[d]thiazol-6-yl)acetic acid: To (S)-methyl 2-tert-butoxy-2-(7-(4-chlorophenyl)-2-(2-((R)-4-isopropyl-3-methylpiperazin-1-yl)pyrimidin-4-yl)-5-methylbenzo[d]thiazol-6-yl)acetate in THF (0.33 mL) and methanol (0.33 mL) was added NaOH (0.33 mL of a 2N solution). The reaction mixture was heated at 30° C. overnight then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{32}H_{39}ClN_5O_3S$ (M+H$^+$): 608.2; Found: 608.2 (M+H$^+$). $^1$H NMR (400 MHz, Methanol-d$_4$) δ 8.62 (d, J=4.9 Hz, 1H), 7.92 (s, 1H), 7.70-7.65 (m, 1H), 7.64-7.57 (m, 3H), 7.57-7.53 (m, 1H), 5.25 (s, 1H), 5.04-4.76 (m, 2H), 4.09-3.97 (m, 1H), 3.69-3.04 (m, 5H). 2.63 (s, 3H), 1.48-1.39 (m, 6H), 1.34-1.23 (m, 3H), 0.98 (s, 9H Example 188

Preparation of (S)-2-tert-butoxy-2-(7-(4-chlorophenyl)-2-(2-(4-(dimethylcarbamoyl)piperazin-1-yl)pyrimidin-4-yl)-5-methylbenzo[d]thiazol-6-yl)acetic acid (472)

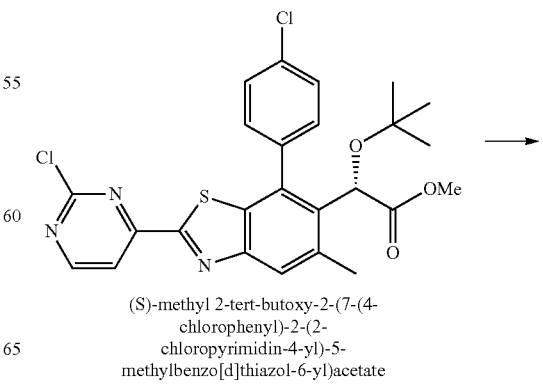

(S)-methyl 2-tert-butoxy-2-(7-(4-chlorophenyl)-2-(2-chloropyrimidin-4-yl)-5-methylbenzo[d]thiazol-6-yl)acetate

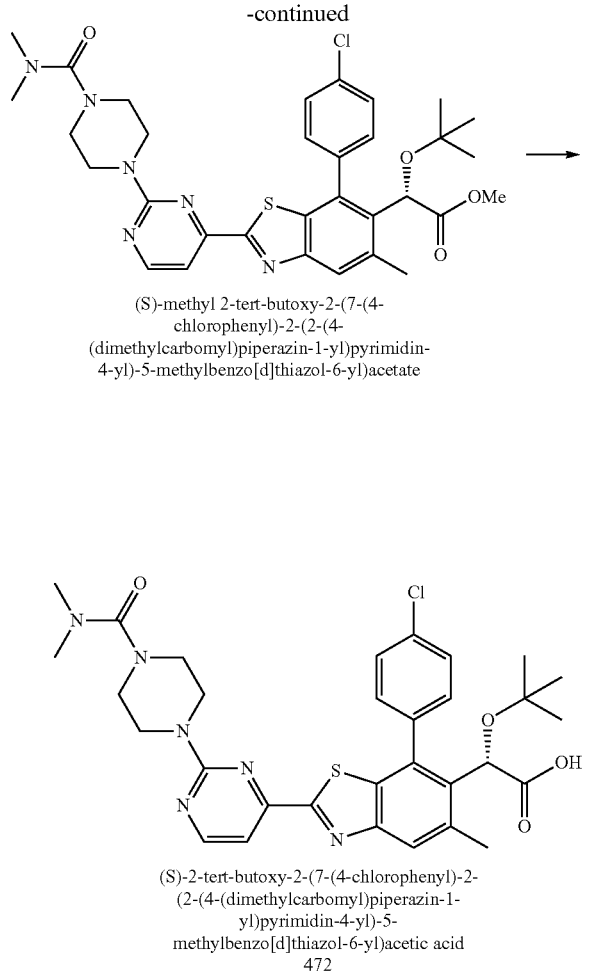

(S)-methyl 2-tert-butoxy-2-(7-(4-chlorophenyl)-2-(2-(4-(dimethylcarbomyl)piperazin-1-yl)pyrimidin-4-yl)-5-methylbenzo[d]thiazol-6-yl)acetate (S)-2-tert-butoxy-2-(7-(4-chlorophenyl)-2-(2-(4-(dimethylcarbomyl)piperazin-1-yl)pyrimidin-4-yl)-5-methylbenzo[d]thiazol-6-yl)acetic acid
472

Preparation of (S)-methyl 2-tert-butoxy-2-(7-(4-chlorophenyl)-2-(2-(4-(dimethylcarbamoyl)piperazin-1-yl)pyrimidin-4-yl)-5-methylbenzo[d]thiazol-6-yl)acetate: To (S)-methyl 2-tert-butoxy-2-(7-(4-chlorophenyl)-2-(2-chloropyrimidin-4-yl)-5-methylbenzo[d]thiazol-6-yl)acetate (30.0 mg, 0.058 mmol) was added piperazine-1-carboxylic acid dimethylamide (36.6 mg, 0.232 mmol) in 1,4-dioxane (1 mL). The reaction mixture was stirred at 40° C. for 4 h, then at room temperature overnight. The reaction mixture was filtered through Celite (ethyl acetate eluent), concentrated, and used without further purification. LCMS-ESI$^+$ calc'd for $C_{32}H_{38}ClN_6O_4S$ (M+H$^+$): 637.2; Found: 637.2 (M+H$^+$).

Preparation of (S)-2-tert-butoxy-2-(7-(4-chlorophenyl)-2-(2-(4-(dimethylcarbamoyl)piperazin-1-yl)pyrimidin-4-yl)-5-methylbenzo[d]thiazol-6-yl)acetic acid: To crude (S)-methyl 2-tert-butoxy-2-(7-(4-chlorophenyl)-2-(2-(4-(dimethylcarbamoyl)piperazin-1-yl)pyrimidin-4-yl)-5-methylbenzo[d]thiazol-6-yl)acetate in THF (0.3 mL) and methanol (0.3 mL) was added NaOH (0.29 mL of a 2N solution). The reaction mixture was heated at 40° C. for 4 h, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{31}H_{36}ClN_6O_4S$ (M+H$^+$): 623.2; Found: 623.2 (M+H$^+$). $^1$H NMR (400 MHz, DMSO-d$_6$) δ 12.95 (br s, 1H), 8.60 (d, J=4.9 Hz, 1H), 7.98 (s, 1H), 7.75-7.65 (m, 2H), 7.65-7.54 (m, 2H), 7.43 (d, J=4.8 Hz, 1H), 5.07 (s, 1H), 3.81-3.69 (m, 4H), 3.22-3.13 (m, 4H), 2.77 (s, 6H), 2.55 (s, 3H), 0.88 (s, 9H).

Example 189

Preparation of (S)-2-tert-butoxy-2-(7-(4-chlorophenyl)-2-(2-(4-ethyl-3-oxopiperazin-1-yl)pyrimidin-4-yl)-5-methylbenzo[d]thiazol-6-yl)acetic acid (473)

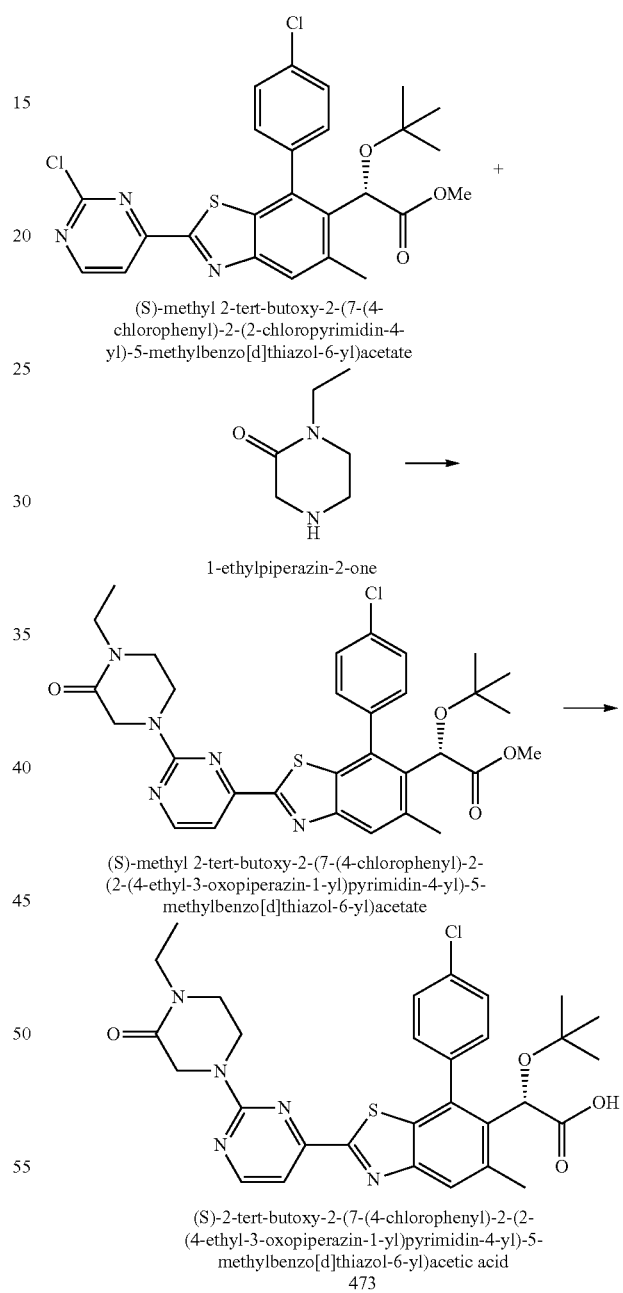

(S)-methyl 2-tert-butoxy-2-(7-(4-chlorophenyl)-2-(2-chloropyrimidin-4-yl)-5-methylbenzo[d]thiazol-6-yl)acetate 1-ethylpiperazin-2-one (S)-methyl 2-tert-butoxy-2-(7-(4-chlorophenyl)-2-(2-(4-ethyl-3-oxopiperazin-1-yl)pyrimidin-4-yl)-5-methylbenzo[d]thiazol-6-yl)acetate (S)-2-tert-butoxy-2-(7-(4-chlorophenyl)-2-(2-(4-ethyl-3-oxopiperazin-1-yl)pyrimidin-4-yl)-5-methylbenzo[d]thiazol-6-yl)acetic acid
473

Preparation of (S)-methyl 2-tert-butoxy-2-(7-(4-chlorophenyl)-2-(2-(4-ethyl-3-oxopiperazin-1-yl)pyrimidin-4-yl)-5-methylbenzo[d]thiazol-6-yl)acetate: To a solution of (S)-methyl 2-tert-butoxy-2-(7-(4-chlorophenyl)-2-(2-chloropyrimidin-4-yl)-5-methylbenzo[d]thiazol-6-yl)acetate (15.0 mg, 0.029 mmol) in DMF (0.4 mL) was added 1-ethylpiperazin-2-one (7.4 mg, 0.058 mmol). The reaction mixture was heated at 100° C. overnight. Reaction mixture was concentrated in vacuo and purified by flash column chromatography (silica gel, 0 to 100% ethyl acetate/hexanes) to give the product. LCMS-ESI⁺: calc'd for $C_{31}H_{35}ClN_5O_4S$: 608.2 (M+H⁺); Found: 608.2 (M+H⁺).

Preparation of (S)-2-tert-butoxy-2-(7-(4-chlorophenyl)-2-(2-(4-ethyl-3-oxopiperazin-1-yl)pyrimidin-4-yl)-5-methylbenzo[d]thiazol-6-yl)acetic acid: To a solution of (9-methyl 2-tert-butoxy-2-(7-(4-chlorophenyl)-2-(2-(4-ethyl-3-oxopiperazin-1-yl)pyrimidin-4-yl)-5-methylbenzo[d]thiazol-6-yl)acetate (4.1 mg, 0.007 mmol) in pyridine (0.4 mL) was added LiI (50 mg, excess). The reaction mixture was heated in a microwave at 170° C. for 90 min. The mixture was concentrated in vacuo and then purified by reverse phase HPLC, eluting by 0-100% acetonitrile in H₂O with 0.1% TFA to give the TFA salt of the product. ¹H NMR (400 MHz, CD₃OD) δ 8.56 (d, J=5.0 Hz, 1H), 7.89 (s, 1H), 7.74-7.48 (m, 5H), 5.25 (s, 1H), 4.35 (s, 2H), 4.07 (t, J=5.4 Hz, 2H), 3.55-3.43 (m, 4H), 2.62 (s, 3H), 1.16 (t, J=7.2 Hz, 3H), 0.97 (s, 9H); LCMS-ESI⁺: calc'd for $C_{30}H_{33}ClN_5O_4S$: 594.2 (M+H⁺); Found: 594.2 (M+H⁺).

A vial was charged with a solution of (S)-methyl 2-tert-butoxy-2-(7-(4-chlorophenyl)-2-(2-chloropyrimidin-4-yl)-5-methylbenzo[d]thiazol-6-yl)acetate (10 mg), dioxane (500 µL), H₂O (200 µL), Et₃N (50 µL), and 1-((2R/2S)-1,1,1-trifluoropropan-2-yl)piperazine (30 mg). The reaction was heated to 60° C. for 1 h. Ethanol (absolute, 500 µL) and 5 M aq NaOH (500 µL) were added and the reaction was heated to 60° C. for 30 min. The reaction was cooled to 23° C. and directly purified by reverse phase HPLC (5-100% ACN/H₂O+0.1% TFA) giving the title compound. ¹H NMR (400 MHz, CD₃OD) δ 8.50 (d, J=5.0 Hz, 1H), 7.89 (s, 1H), 7.70-7.51 (m, 5H), 7.43 (d, J=4.9 Hz, 1H), 5.25 (s, 1H), 3.92-3.71 (m, 4H), 2.94-2.70 (m, 4H), 2.62 (s, 3H), 1.27 (d, J=7.1 Hz, 3H), 0.97 (s, 9H).). LCMS-ESI⁺: calc'd for $C_{31}H_{34}ClF_3N_5O_3S$ [M+H⁺]: 648.2, 650.2; Found: 648.2, 650.2 (M+H⁺).

Example 191

Preparation of (S)-2-tert-butoxy-2-(7-(4-chlorophenyl)-2-(2-(4-ethylpiperazin-1-yl)pyrimidin-4-yl)-5-methylbenzo[d]thiazol-6-yl)acetic acid (475)

Example 190

Preparation of (2S)-2-tert-butoxy-2-(7-(4-chlorophenyl)-5-methyl-2-(2-(4-((2R/2S)-1,1,1-trifluoropropan-2-yl)piperazin-1-yl)pyrimidin-4-yl)benzo[d]thiazol-6-yl)acetic acid (474)

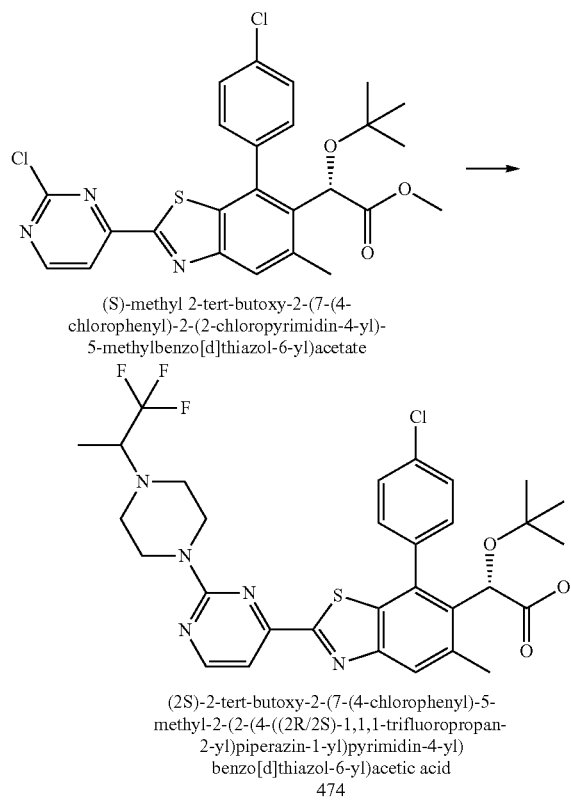

(S)-methyl 2-tert-butoxy-2-(7-(4-chlorophenyl)-2-(2-chloropyrimidin-4-yl)-5-methylbenzo[d]thiazol-6-yl)acetate (2S)-2-tert-butoxy-2-(7-(4-chlorophenyl)-5-methyl-2-(2-(4-((2R/2S)-1,1,1-trifluoropropan-2-yl)piperazin-1-yl)pyrimidin-4-yl)benzo[d]thiazol-6-yl)acetic acid 474

Preparation of (2S)-2-tert-butoxy-2-(7-(4-chlorophenyl)-5-methyl-2-(2-(4-((2R/2S)-1,1,1-trifluoropropan-2-yl)piperazin-1-yl)pyrimidin-4-yl)benzo[d]thiazol-6-yl)acetic acid:

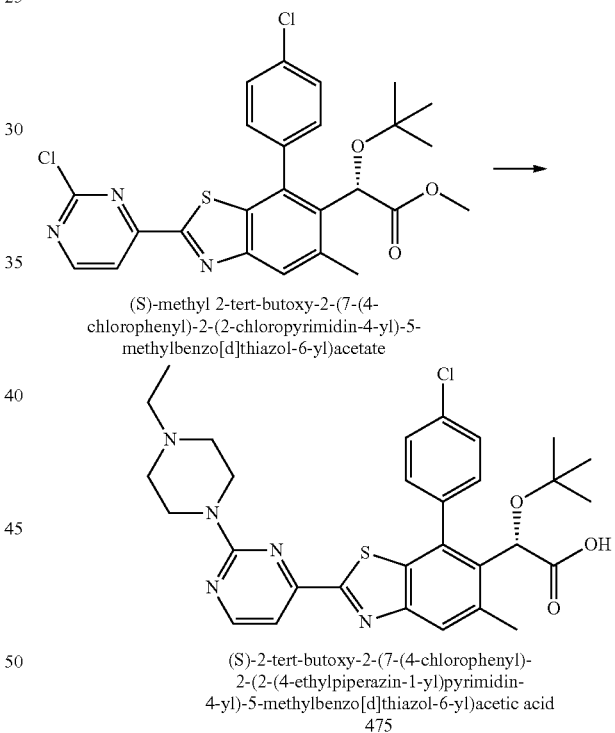

(S)-methyl 2-tert-butoxy-2-(7-(4-chlorophenyl)-2-(2-chloropyrimidin-4-yl)-5-methylbenzo[d]thiazol-6-yl)acetate (S)-2-tert-butoxy-2-(7-(4-chlorophenyl)-2-(2-(4-ethylpiperazin-1-yl)pyrimidin-4-yl)-5-methylbenzo[d]thiazol-6-yl)acetic acid 475

Preparation of (S)-2-tert-butoxy-2-(7-(4-chlorophenyl)-2-(2-(4-ethylpiperazin-1-yl)pyrimidin-4-yl)-5-methylbenzo[d]thiazol-6-yl)acetic acid: A vial was charged with solid LiAlH₄ (100 mg). A solution of N-Acetylpiperazine (120 mg) in anhydrous Et₂O (4.0 mL) was added dropwise over 2 min at 23° C. The vessel was placed under N₂ and stirred for 30 min. Water (100 µL) was added and the mixture was stirred for 3 min. 10 M aq NaOH (50 µL) was added and the mixture was stirred for 5 min. Finally, H₂O (300 µL) was added, the mixture was stirred for 15 min, and filtered. The filtrate was concentrated and vacuum dried (briefly, because product is volatile) giving N-ethylpiperazine, which was immediately used in the next reaction.

(S)-Methyl 2-tert-butoxy-2-(7-(4-chlorophenyl)-2-(2-chloropyrimidin-4-yl)-5-methylbenzo[d]thiazol-6-yl)acetate (10 mg), dioxane (500 µL), and H$_2$O (200 µL) were added. The reaction was heated to 90° C. for 1 h. Ethanol (absolute, 500 µL) and 5 M aq NaOH (500 µL) were added and the reaction was heated to 90° C. for 30 min. The reaction was cooled to 23° C. and directly purified by reverse phase HPLC (5-100% ACN/H$_2$O+0.1% TFA) giving the title compound. $^1$H NMR (400 MHz, CD$_3$OD) δ 8.62 (d, J=5.0 Hz, 1H), 7.91 (s, 1H), 7.74-7.49 (m, 5H), 5.24 (s, 1H), 3.37-3.28 (m, 8H), 3.24 (q, J=7.4 Hz, 2H), 2.62 (s, 3H), 1.38 (t, J=7.3 Hz, 2H), 0.97 (s, 9H). LCMS-ESI$^+$: calc'd for C$_{30}$H$_{35}$ClN$_5$O$_3$S [M+H$^+$]: 580.2, 582.2; Found: 580.4, 582.2 (M+H$^+$).

Example 192

Preparation of (S)-2-tert-butoxy-2-(7-(4-chlorophenyl)-5-methyl-2-(2-(piperazin-1-yl)pyrimidin-4-yl)benzo[d]thiazol-6-yl)acetic acid (476)

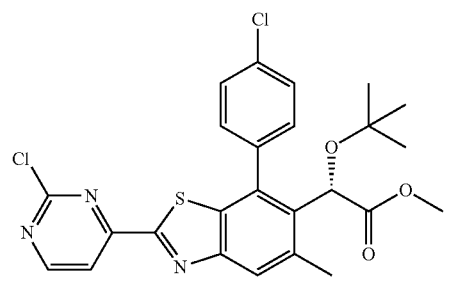

(S)-methyl 2-tert-butoxy-2-(7-(4-chlorophenyl)-2-(2-chloropyrimidin-4-yl)-5-methylbenzo[d]thiazol-6-yl)acetate

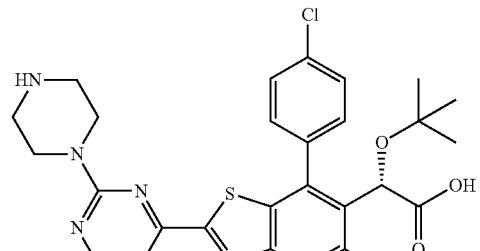

(S)-2-tert-butoxy-2-(7-(4-chlorophenyl)-5-methyl-2-(2-(piperazin-1-yl)pyrimidin-4-yl)benzo[d]thiazol-6-yl)acetic acid 476

Preparation of (S)-2-tert-butoxy-2-(7-(4-chlorophenyl)-5-methyl-2-(2-(piperazin-1-yl)pyrimidin-4-yl)benzo[d]thiazol-6-yl)acetic acid: A vial was charged with a solution of (S)-methyl 2-tert-butoxy-2-(7-(4-chlorophenyl)-2-(2-chloropyrimidin-4-yl)-5-methylbenzo[d]thiazol-6-yl)acetate (10 mg), dioxane (500 µL), H$_2$O (200 µL), Et$_3$N (50 µL), and piperazine (40 mg). The reaction was heated to 60° C. for 1 h. Ethanol (absolute, 500 µL) and 5 M aq NaOH (500 µL) were added. The reaction was heated to 60° C. for 30 min. The reaction was cooled to 23° C. and directly purified by reverse phase HPLC (5-100% ACN/H$_2$O+0.1% TFA) giving the title compound. $^1$H NMR (400 MHz, CD$_3$OD) δ 8.49 (d, J=5.0 Hz, 1H), 8.03 (d, J=8.4 Hz, 1H), 7.81 (s, 1H), 7.68-7.44 (m, 3H), 7.41 (d, J=5.0 Hz, 1H), 5.08 (s, 1H), 3.92-3.69 (m, 4H), 2.85 (dd, J=18.8, 13.9 Hz, 4H), 2.66 (s, 3H), 0.91 (s, 9H). LCMS-ESI$^+$: calc'd for C$_{20}$H$_{31}$ClN$_5$O$_3$S [M+H$^+$]: 552.2, 554.2; Found: 552.4, 552.2 (M+H$^+$).

Example 193

Preparation of (S)-2-tert-butoxy-2-(7-(4-chlorophenyl)-5-methyl-2-(2-(4-methyl-1,4-diazepan-1-yl)pyrimidin-4-yl)benzo[d]thiazol-6-yl)acetic acid (477)

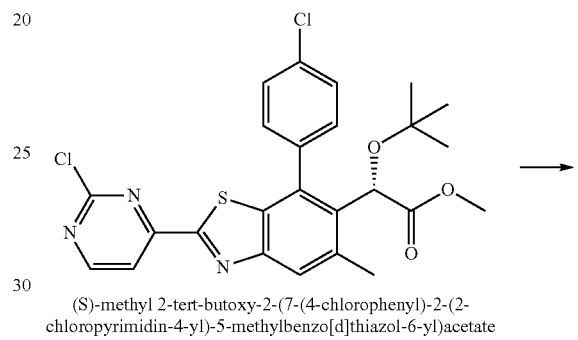

(S)-methyl 2-tert-butoxy-2-(7-(4-chlorophenyl)-2-(2-chloropyrimidin-4-yl)-5-methylbenzo[d]thiazol-6-yl)acetate

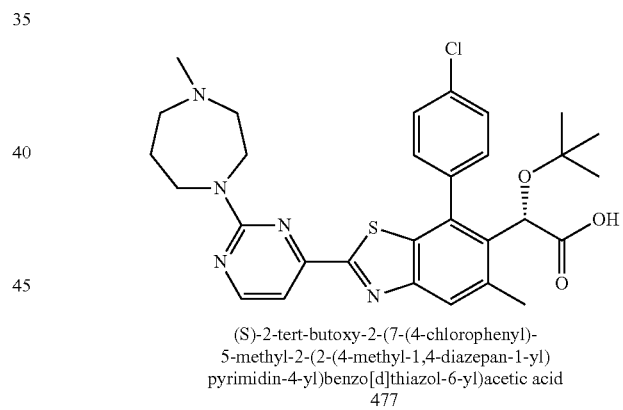

(S)-2-tert-butoxy-2-(7-(4-chlorophenyl)-5-methyl-2-(2-(4-methyl-1,4-diazepan-1-yl)pyrimidin-4-yl)benzo[d]thiazol-6-yl)acetic acid 477

Preparation of (S)-2-tert-butoxy-2-(7-(4-chlorophenyl)-5-methyl-2-(2-(4-methyl-1,4-diazepan-1-yl)pyrimidin-4-yl)benzo[d]thiazol-6-yl)acetic acid: A vial was charged with a solution of (S)-methyl 2-tert-butoxy-2-(7-(4-chlorophenyl)-2-(2-chloropyrimidin-4-yl)-5-methylbenzo[d]thiazol-6-yl)acetate (10 mg), dioxane (500 µL), H$_2$O (200 µL), Et$_3$N (50 µL), and 1-methyl-1,4-diazepane (40 mg). The reaction was heated to 90° C. for 1 h. Ethanol (absolute, 500 µL) and 5 M aq NaOH (500 µL) were added. The reaction was heated to 90° C. for 30 min. The reaction was cooled to 23° C. and directly purified by reverse phase HPLC (5-100% ACN/H$_2$O+0.1% TFA) giving the title compound. $^1$H NMR (400 MHz, CD$_3$OD) δ 8.59 (d, J=5.1 Hz, 1H), 7.92 (s, 1H), 7.74-7.47 (m, 5H), 5.24 (s, 1H), 4.67-3.39 (m, 6H), 3.39-3.20 (m, 2H), 2.92 (s, 3H), 2.63 (s, 3H), 2.29-2.10 (m, 2H), 0.97 (s, 9H). LCMS-ESI$^+$: calc'd for $C_{30}H_{35}ClN_5O_3S$ [M+H±]: 580.2, 582.2; Found: 580.4, 582.2 (M+H$^+$).

Example 194

Preparation of (S)-2-tert-butoxy-2-(7-(4-chlorophenyl)-2-(2-((S)-3-(dimethylamino)pyrrolidin-1-yl)pyrimidin-4-yl)-5-methylbenzo[d]thiazol-6-yl)acetic acid (478)

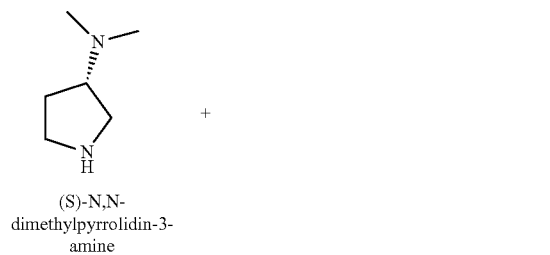

(S)-N,N-dimethylpyrrolidin-3-amine

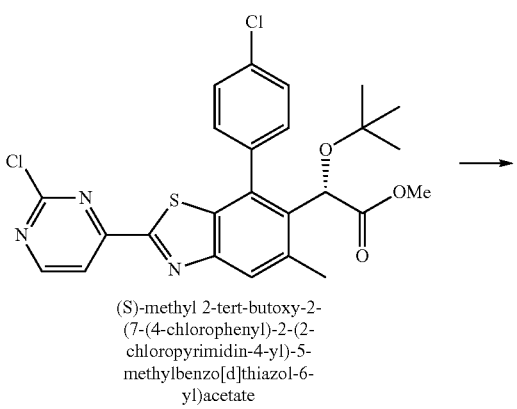

(S)-methyl 2-tert-butoxy-2-(7-(4-chlorophenyl)-2-(2-chloropyrimidin-4-yl)-5-methylbenzo[d]thiazol-6-yl)acetate

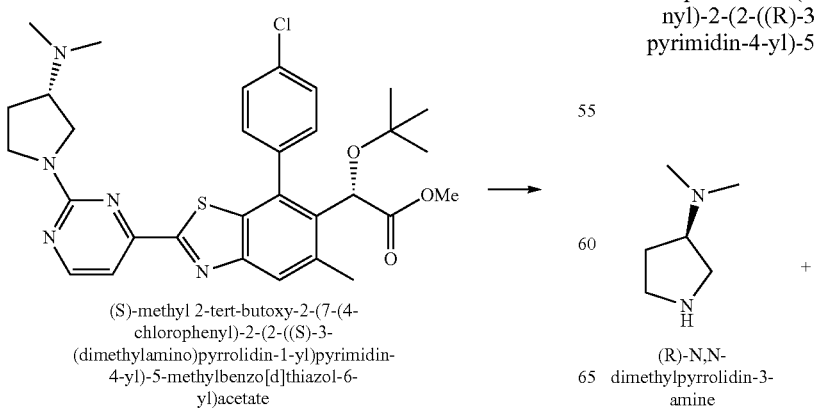

(S)-methyl 2-tert-butoxy-2-(7-(4-chlorophenyl)-2-(2-((S)-3-(dimethylamino)pyrrolidin-1-yl)pyrimidin-4-yl)-5-methylbenzo[d]thiazol-6-yl)acetate

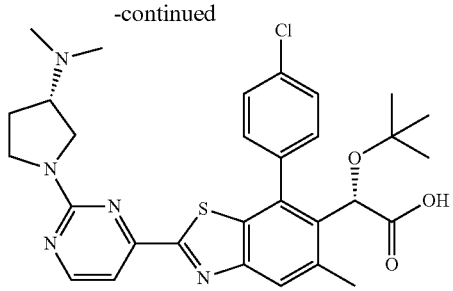

(S)-2-tert-butoxy-2-(7-(4-chlorophenyl)-2-(2-((S)-3-(dimethylamino)pyrrolidin-1-yl)pyrimidin-4-yl)-5-methylbenzo[d]thiazol-6-yl)acetic acid
478

Preparation of (S)-methyl 2-tert-butoxy-2-(7-(4-chlorophenyl)-2-(2-((S)-3-(dimethylamino)pyrrolidin-1-yl)pyrimidin-4-yl)-5-methylbenzo[d]thiazol-6-yl)acetate: To a solution of (S)-methyl 2-tert-butoxy-2-(7-(4-chlorophenyl)-2-(2-chloropyrimidin-4-yl)-5-methylbenzo[d]thiazol-6-yl)acetate (40 mg, 0.08 mmol) in dioxane (1 mL) was added (S)—N,N-dimethylpyrrolidin-3-amine (89 mg, 0.78 mmol) at room temperature. The reaction mixture was allowed to stir for an additional 30 minutes and then concentrated in vacuo to provide the desired product. LCMS-ESI$^+$: calc'd for $C_{31}H_{37}ClN_5O_3S$: 594.2 (M+H$^+$); Found: 594.4 (M+H$^+$).

Preparation of (S)-2-tert-butoxy-2-(7-(4-chlorophenyl)-2-(2-((S)-3-(dimethylamino)pyrrolidin-1-yl)pyrimidin-4-yl)-5-methylbenzo[d]thiazol-6-yl)acetic acid: To a solution of (9-methyl 2-tert-butoxy-2-(7-(4-chlorophenyl)-2-(2-((S)-3-(dimethylamino)pyrrolidin-1-yl)pyrimidin-4-yl)-5-methylbenzo[d]thiazol-6-yl)acetate (46 mg, 0.08 mmol) in 1:5 THF/MeOH (1.2 mL) was added 2M aqueous NaOH (0.2 mL, 0.4 mmol) and stirred at 40° C. overnight. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 8.53 (d, J=5.1 Hz, 1H), 7.90 (s, 1H), 7.67 (dd, J=8.4, 2.0 Hz, 1H), 7.64-7.50 (m, 4H), 5.25 (s, 1H), 4.13-3.95 (m, 2H), 3.95-3.80 (m, 1H), 3.76 (dd, J=11.4, 5.7 Hz, 1H), 3.60 (dt, J=11.4, 7.9 Hz, 1H), 2.97 (s, 6H), 2.62 (s, 3H), 2.60-2.49 (m, 1H), 2.40-2.17 (m, 1H),z 0.97 (s, 9H); LCMS-ESI$^+$: calc'd for $C_{30}H_{35}ClN_5O_3S$: 580.2 (M+H$^+$); Found: 580.3 (M+H$^+$).

Example 195

Preparation of (S)-2-tert-butoxy-2-(7-(4-chlorophenyl)-2-(2-((R)-3-(dimethylamino)pyrrolidin-1-yl)pyrimidin-4-yl)-5-methylbenzo[d]thiazol-6-yl)acetic acid (479)

(R)-N,N-dimethylpyrrolidin-3-amine

-continued

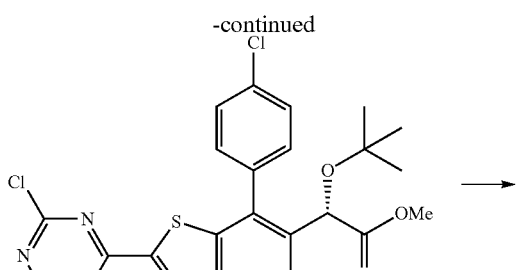

(S)-methyl 2-tert-butoxy-2-
(7-(4-chlorophenyl)-2-(2-
chloropyrimidin-4-yl)-5-
methylbenzo[d]thiazol-6-
yl)acetate

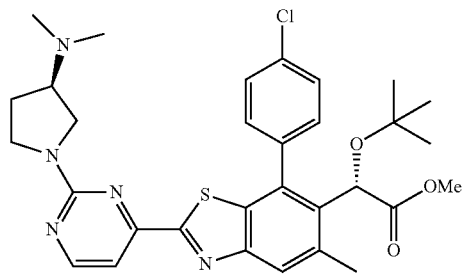

(S)-methyl 2-tert-butoxy-2-(7-(4-chlorophenyl)-2-
(2-((R)-3-(dimethylamino)pyrrolidin-1-
yl)pyrimidin-4-yl)-5-methylbenzo[d]thiazol-6-
yl)acetate

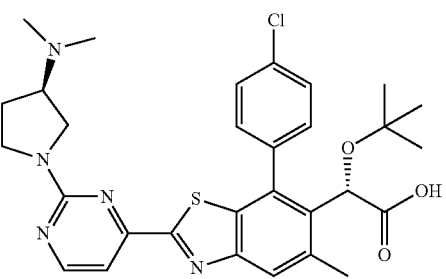

(S)-2-tert-butoxy-2-(7-(4-chlorophenyl)-2-
(2-((R)-3-(dimethylamino)pyrrolidin-1-
yl)pyrimidin-4-yl)-5-methylbenzo[d]thiazol-
6-yl)acetic acid
479

Preparation of (S)-methyl 2-tert-butoxy-2-(7-(4-chlorophenyl)-2-(2-((R)-3-(dimethylamino)pyrrolidin-1-yl)pyrimidin-4-yl)-5-methylbenzo[d]thiazol-6-yl)acetate: To a solution of (9-methyl 2-tert-butoxy-2-(7-(4-chlorophenyl)-2-(2-chloropyrimidin-4-yl)-5-methylbenzo[d]thiazol-6-yl)acetate (37 mg, 0.07 mmol) in dioxane (1 mL) was added (R)—N,N-dimethylpyrrolidin-3-amine (89 mg, 0.78 mmol) at room temperature. The reaction mixture was allowed to stir for an additional 30 minutes and then concentrated in vacuo to provide the desired product. LCMS-ESI$^+$: calc'd for $C_{31}H_{37}ClN_5O_3S$: 594.2 (M+H$^+$); Found: 594.4 (M+H$^+$).

Preparation of (S)-2-tert-butoxy-2-(7-(4-chlorophenyl)-2-(2-((R)-3-(dimethylamino)pyrrolidin-1-yl)pyrimidin-4-yl)-5-methylbenzo[d]thiazol-6-yl)acetic acid: To a solution of (9-methyl 2-tert-butoxy-2-(7-(4-chlorophenyl)-2-(2-((R)-3-(dimethylamino)pyrrolidin-1-yl)pyrimidin-4-yl)-5-methylbenzo[d]thiazol-6-yl)acetate (43 mg, 0.07 mmol) in 1:5 THF/MeOH (1.2 mL) was added 2M aqueous NaOH (0.2 mL, 0.4 mmol) and stirred at 40° C. overnight. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 8.52 (d, J=5.1 Hz, 1H), 7.89 (s, 1H), 7.67 (dd, J=8.5, 1.8 Hz, 1H), 7.64-7.47 (m, 4H), 5.25 (s, 1H), 4.12-3.97 (m, 2H), 3.97-3.80 (m, 1H), 3.75 (dd, J=11.1, 5.5 Hz, 1H), 3.58 (dt, J=11.4, 8.0 Hz, 1H), 2.97 (s, 6H), 2.62 (s, 3H), 2.59-2.46 (m, 1H), 2.36-2.21 (m, 1H), 0.97 (s, 9H).; LCMS-ESI$^+$: calc'd for $C_{30}H_{35}ClN_5O_3S$: 580.2 (M+H$^+$); Found: 580.3 (M+H$^+$).

Example 196

Preparation of (S)-2-tert-butoxy-2-(7-(4-chlorophenyl)-2-(6-(4-isopropylpiperazin-1-yl)pyrazin-2-yl)-5-methylbenzo[d]thiazol-6-yl)acetic acid (480)

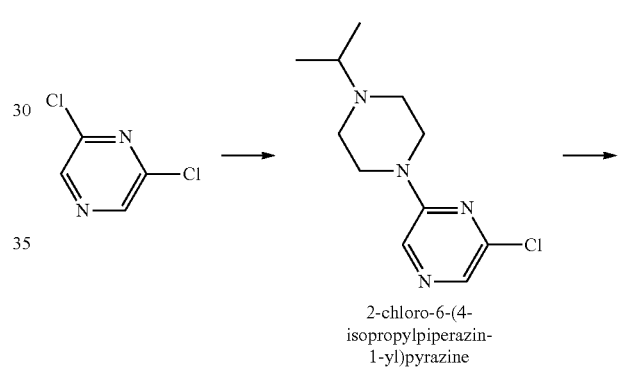

2-chloro-6-(4-
isopropylpiperazin-
1-yl)pyrazine

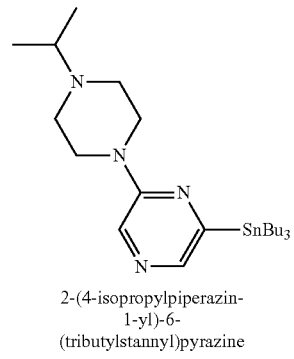

2-(4-isopropylpiperazin-
1-yl)-6-
(tributylstannyl)pyrazine

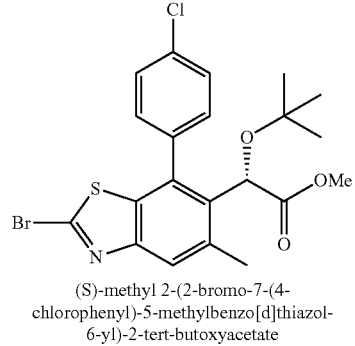

(S)-methyl 2-(2-bromo-7-(4-
chlorophenyl)-5-methylbenzo[d]thiazol-
6-yl)-2-tert-butoxyacetate

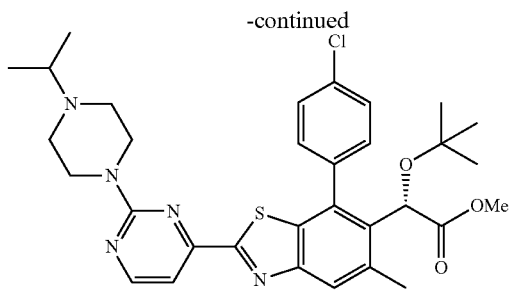

(S)-methyl 2-tert-butoxy-2-(7-(4-chlorophenyl)-2-(6-(4-isopropylpiperazin-1-yl)pyrazin-2-yl)-5-methylbenzo[d]thiazol-6-yl)acetate

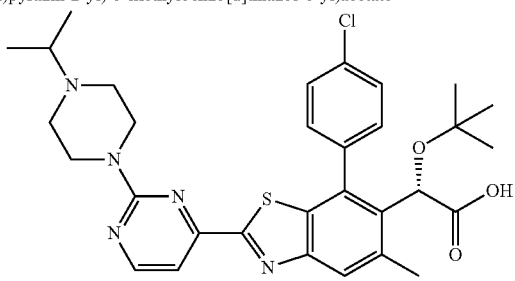

(S)-2-tert-butoxy-2-(7-(4-chlorophenyl)-2-(6-(4-isopropylpiperazin-1-yl)pyrazin-2-yl)-5-methylbenzo[d]thiazol-6-yl)acetic acid
480

Preparation of 2-chloro-6-(4-isopropylpiperazin-1-yl)pyrazine: To 2,6-dichloropyrazine (250.0 mg, 1.678 mmol) in 1,4-dioxane (2 mL) was added 1-isopropylpiperazine (0.29 mL, 2.014 mmol) and triethylamine (0.70 mL, 5.034 mmol). The reaction mixture was stirred at room temperature for 1 day, filtered through Celite (1,4-dioxane eluent) then concentrated. Purification by flash column chromatography on silica gel using 100:5:1 EtOAc/MeOH/NH$_4$OH (0 to 100%) in EtOAc provided the product. LCMS-ESI$^+$ calc'd for C$_{11}$H$_{18}$ClN$_4$ (M+H$^+$): 241.1; Found: 241.2 (M+H$^+$).

Preparation of 2-(4-isopropylpiperazin-1-yl)-6-(tributylstannyl)pyrazine: Tetrakis(triphenylphosphine)palladium(0) (120.0 mg, 0.104 mmol) and LiCl (132.1 mg, 3.115 mmol) were taken in a microwave vial and the vial vacuum pumped and flushed with argon three times. To this mixture was added 2-chloro-6-(4-isopropylpiperazin-1-yl)pyrazine (250.0 mg, 1.038 mmol) and hexabutylditin (903.7 mg, 0.79 mL, 1.558 mmol) in toluene (10 mL). The reaction mixture was heated at 140° C. for 1.5 h, filtered through Celite, and concentrated. Purification by flash column chromatography on silica gel using 79:20:1 DCM/MeOH/NH$_3$ (0 to 100%) in DCM provided the product. LCMS-ESI$^+$ calc'd for C$_{23}$H$_{44}$N$_4$Sn (M+H$^+$): 497.3; Found: 496.6 (M+H$^+$).

Preparation of (S)-methyl 2-tert-butoxy-2-(7-(4-chlorophenyl)-2-(6-(4-isopropylpiperazin-1-yl)pyrazin-2-yl)-5-methylbenzo[d]thiazol-6-yl)acetate: (S)-methyl 2-(2-bromo-7-(4-chlorophenyl)-5-methylbenzo[d]thiazol-6-yl)-2-tert-butoxyacetate (60.0 mg, 0.124 mmol), tetrakis(triphenylphosphine)palladium(0) (21.5 mg, 0.019 mmol), lithium chloride (15.8 mg, 0.373 mmol), and copper(I) iodide (7.1 mg, 0.037 mmol) were taken in a microwave vial and the vial vacuum pumped and flushed with argon three times. To this mixture was added 2-(4-isopropylpiperazin-1-yl)-6-(tributylstannyl)pyrazine (73.9 mg, 0.149 mmol) in dioxane (1.5 mL), and the resulting mixture was stirred at 100° C. for 4.5 h. The reaction mixture was cooled, filtered through Celite (ethyl acetate eluent), and concentrated. Purification by flash column chromatography on silica gel using 79:20:1 DCM/MeOH/NH$_3$ (0 to 100%) in DCM provided the product. LCMS-ESI$^+$ calc'd for C$_{32}$H$_{39}$ClN$_5$O$_3$S (M+H$^+$): 608.2; Found: 608.3 (M+H$^+$).

Preparation of (S)-2-tert-butoxy-2-(7-(4-chlorophenyl)-2-(6-(4-isopropylpiperazin-1-yl)pyrazin-2-yl)-5-methylbenzo[d]thiazol-6-yl)acetic acid: To (S)-methyl 2-tert-butoxy-2-(7-(4-chlorophenyl)-2-(6-(4-isopropylpiperazin-1-yl)pyrazin-2-yl)-5-methylbenzo[d]thiazol-6-yl)acetate (52.9 mg, 0.087 mmol) in THF (0.45 mL) and methanol (0.45 mL) was added NaOH (0.44 mL of a 2N solution). The reaction mixture was heated at 30° C. overnight, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for C$_{31}$H$_{37}$ClN$_5$O$_3$S (M+H$^+$): 594.2; Found: 594.4 (M+H$^+$). $^1$H NMR (400 MHz, Methanol-d$_4$) δ 8.84 (s, 1H), 8.46 (s, 1H), 7.91 (s, 1H), 7.70-7.64 (m, 1H), 7.63-7.48 (m, 3H), 5.24 (s, 1H), 4.68 (br s, 2H), 3.76-3.50 (m, 3H), 3.26 (br s, 4H), 2.63 (s, 3H), 1.41 (d, J=6.6 Hz, 6H), 0.98 (s, 9H).

Example 197

Preparation of (9-2-tert-butoxy-2-(7-(4-chlorophenyl)-2-(5-(4-isopropylpiperazin-1-yl)pyridin-3-yl)-5-methylbenzo[d]thiazol-6-yl)acetic acid (481)

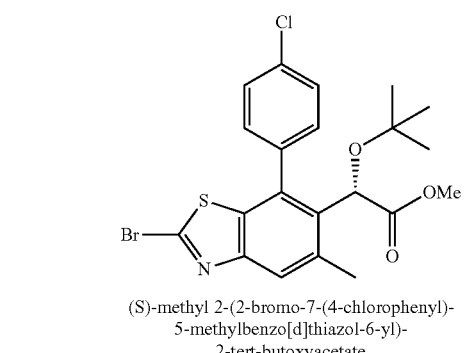

(S)-methyl 2-(2-bromo-7-(4-chlorophenyl)-5-methylbenzo[d]thiazol-6-yl)-2-tert-butoxyacetate

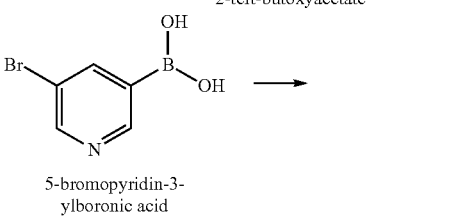

5-bromopyridin-3-ylboronic acid

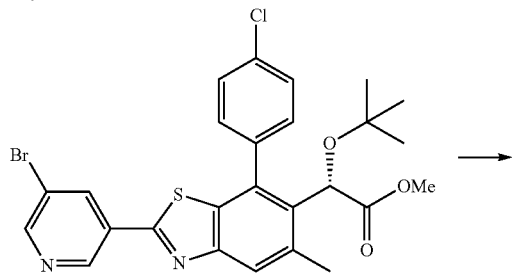

(S)-methyl 2-(2-(6-bromopyridin-2-yl)-7-(4-chlorophenyl)-5-methylbenzo[d]thiazol-6-yl)-2-tert-butoxyacetate

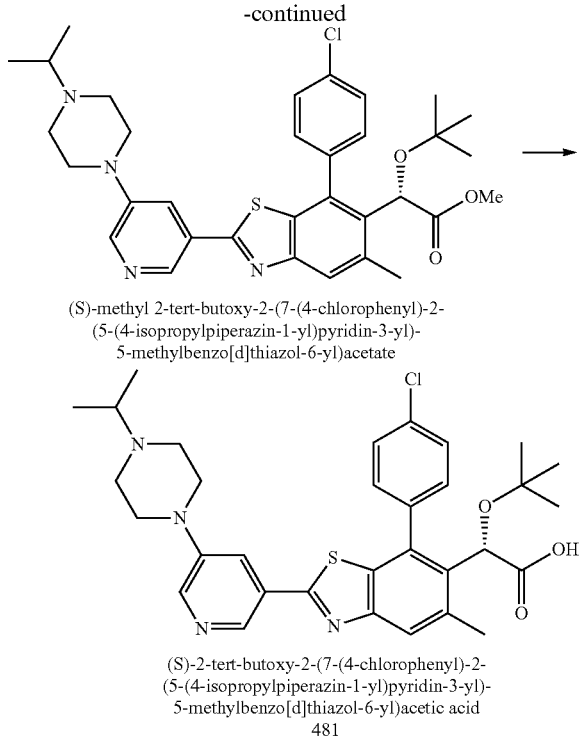

(S)-methyl 2-tert-butoxy-2-(7-(4-chlorophenyl)-2-
(5-(4-isopropylpiperazin-1-yl)pyridin-3-yl)-
5-methylbenzo[d]thiazol-6-yl)acetate (S)-2-tert-butoxy-2-(7-(4-chlorophenyl)-2-
(5-(4-isopropylpiperazin-1-yl)pyridin-3-yl)-
5-methylbenzo[d]thiazol-6-yl)acetic acid
481

Preparation of (9-methyl 2-(2-(6-bromopyridin-2-yl)-7-(4-chlorophenyl)-5-methylbenzo[d]thiazol-6-yl)-2-tert-butoxyacetate: To a solution of (S)-methyl 2-(2-bromo-7-(4-chlorophenyl)-5-methylbenzo[d]thiazol-6-yl)-2-tert-butoxyacetate (121 mg, 0.25 mmol) and 5-bromopyridin-3-ylboronic acid (61 mg, 0.30 mmol) in 1,4-dioxane (3 mL) was added potassium carbonate solution (0.50 mL, 2 M aqueous) and tetrakis(triphenylphosphine)palladium (14 mg, 0.013 mmol). The reaction was stirred at 105° C. for 3 h. Diluted with brine and EtOAc. Layer separated and the organic layer was dried, filtered, concentrated in vacuo and purified by CombiFlash (EtOAc/Hex) to give desired product. LCMS-ESI$^+$: calc'd for $C_{26}H_{25}ClBrN_2O_3S$: 559.0 (M+H$^+$); Found: 559.1 (M+H$^+$).

Preparation of (S)-methyl 2-tert-butoxy-2-(7-(4-chlorophenyl)-2-(5-(4-isopropylpiperazin-1-yl)pyridin-3-yl)-5-methylbenzo[d]thiazol-6-yl)acetate: To a solution of (S)-methyl 2-(2-(6-bromopyridin-2-yl)-7-(4-chlorophenyl)-5-methylbenzo[d]thiazol-6-yl)-2-tert-butoxyacetate (54 mg, 0.096 mmol) in 1,4-dioxane (1 mL) was added isopropylpiperazine (16 mg, 0.13 mmol), cesium carbonate (41 mg, 0.13 mmol), and Pd BrettPhos precatalyst (2 mg, 0.003 mmol). Reaction mixture was stirred at 110° C. in a sealed vial for 20 h and taken on crude. LCMS-ESI$^+$: calc'd for $C_{33}H_{40}ClN_4O_3S$: 607.2 (M+H$^+$); Found: 607.3 (M+H$^+$).

Preparation of (S)-2-tert-butoxy-2-(7-(4-chlorophenyl)-2-(5-(4-isopropylpiperazin-1-yl)pyridin-3-yl)-5-methylbenzo[d]thiazol-6-yl)acetic acid: MeOH (2 mL) was added to the reaction mixture above followed by sodium hydroxide solution (0.20 mL, 2 M aqueous). The mixture was stirred at 60° C. for 4 h and was then filtered and purified using reverse phase HPLC, eluting by 2-100% acetonitrile in H$_2$O with 0.1% TFA to give the product. $^1$H NMR (400 MHz, CD$_3$OD) δ 8.71 (s, 1H), 8.46 (d, J=2.4 Hz, 1H), 8.06 (br s, 1H), 7.89 (s, 1H), 7.67 (m, 1H), 7.59 (m, 3H), 5.26 (s, 1H), 4.11 (m, 2H), 3.62 (m, 4H), 3.20 (m, 3H), 2.62 (s, 3H), 1.43 (d, J=7 Hz, 6H), 0.97 (s, 9H). LCMS-ESI$^+$: calc'd for $C_{32}H_{38}ClN_4O_3S$: 593.2 (M+H$^+$); Found: 593.3 (M+H$^+$).

Example 198

Preparation of (S)-2-tert-butoxy-2-(7-(4-chlorophenyl)-5-methyl-2-(5-(4-(oxetan-3-yl)piperazin-1-yl)pyridin-3-yl)benzo[d]thiazol-6-yl)acetic acid (482)

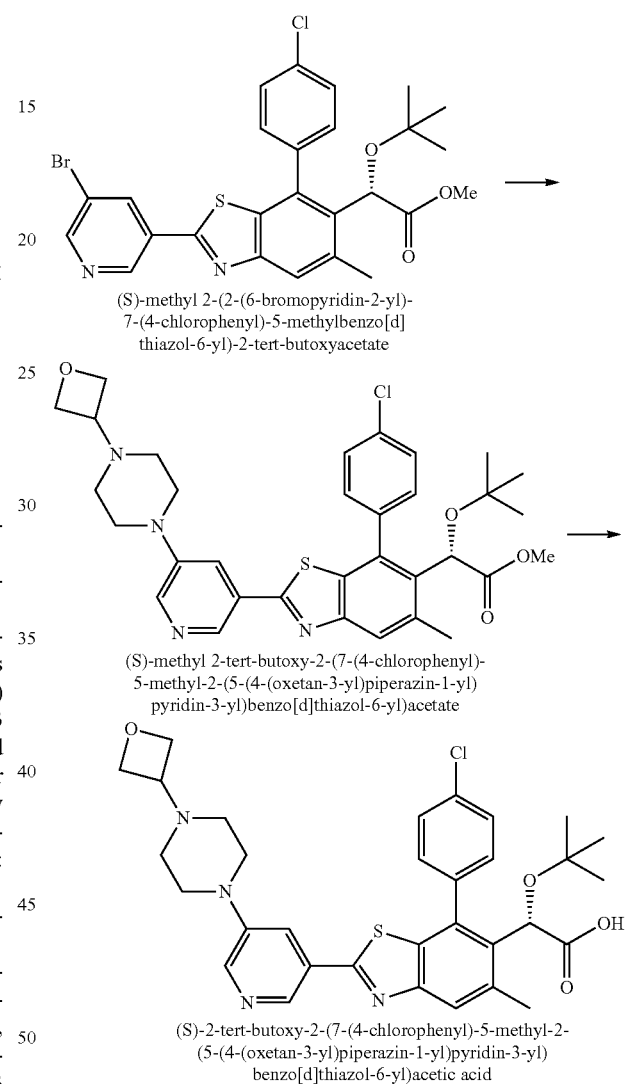

(S)-methyl 2-(2-(6-bromopyridin-2-yl)-
7-(4-chlorophenyl)-5-methylbenzo[d]
thiazol-6-yl)-2-tert-butoxyacetate (S)-methyl 2-tert-butoxy-2-(7-(4-chlorophenyl)-
5-methyl-2-(5-(4-(oxetan-3-yl)piperazin-1-yl)
pyridin-3-yl)benzo[d]thiazol-6-yl)acetate (S)-2-tert-butoxy-2-(7-(4-chlorophenyl)-5-methyl-2-
(5-(4-(oxetan-3-yl)piperazin-1-yl)pyridin-3-yl)
benzo[d]thiazol-6-yl)acetic acid Preparation of (S)-methyl 2-tert-butoxy-2-(7-(4-chlorophenyl)-5-methyl-2-(5-(4-(oxetan-3-yl)piperazin-1-yl)pyridin-3-yl)benzo[d]thiazol-6-yl)acetate: To a solution of (S)-methyl 2-(2-(6-bromopyridin-2-yl)-7-(4-chlorophenyl)-5-methylbenzo[d]thiazol-6-yl)-2-tert-butoxyacetate (54 mg, 0.096 mmol) in 1,4-dioxane (1 mL) was added 1-(oxetan-3-yl)piperazine (18 mg, 0.13 mmol), cesium carbonate (41 mg, 0.13 mmol), and Pd BrettPhos precatalyst (2 mg, 0.003 mmol). Reaction mixture was stirred at 110° C. in a sealed vial for 20 h and taken on crude. LCMS-ESI$^+$: calc'd for $C_{33}H_{38}ClN_4O_4S$: 621.2 (M+H$^+$); Found: 621.2 (M+H$^+$).

Preparation of (S)-2-tert-butoxy-2-(7-(4-chlorophenyl)-5-methyl-2-(5-(4-(oxetan-3-yl)piperazin-1-yl)pyridin-3-yl)benzo[d]thiazol-6-yl)acetic acid: MeOH (2 mL) was added to the reaction mixture above followed by sodium hydroxide solution (0.20 mL, 2 M aqueous). The mixture was stirred at 60° C. for 4 h and was then filtered and purified using reverse phase HPLC, eluting by 2-100% acetonitrile in H₂O with 0.1% TFA to give the product. ¹H NMR (400 MHz, CD₃OD) δ 8.72 (s, 1H), 8.47 (s, 1H), 8.08 (s, 1H), 7.89 (s, 1H), 7.68 (m, 1H), 7.60 (m, 3H), 5.26 (s, 1H), 4.94 (m, 2H), 4.86 (m, 2H), 4.38 (m, 1H), 3.63 (m, 4H), 3.33 (m, 4H), 2.62 (s, 3H), 0.97 (s, 9H). LCMS-ESI⁺: calc'd for $C_{32}H_{36}ClN_4O_4S$: 607.2 (M+H⁺); Found: 607.2 (M+H⁺).

Example 199

Preparation of (S)-2-tert-butoxy-2-(7-(4-chlorophenyl)-2-(3-(4-isopropylpiperazin-1-yl)phenyl)-5-methylbenzo[d]thiazol-6-yl)acetic acid (483)

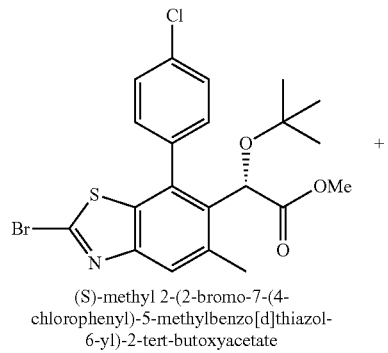

(S)-methyl 2-(2-bromo-7-(4-chlorophenyl)-5-methylbenzo[d]thiazol-6-yl)-2-tert-butoxyacetate

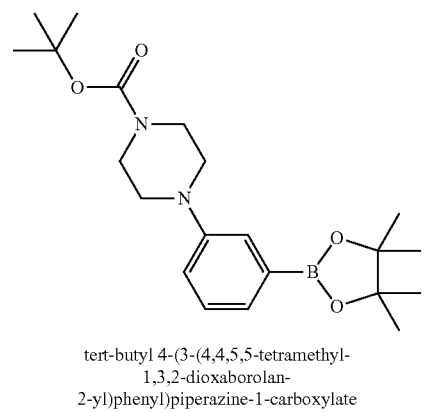

tert-butyl 4-(3-(4,4,5,5-tetramethyl-1,3,2-dioxaborolan-2-yl)phenyl)piperazine-1-carboxylate

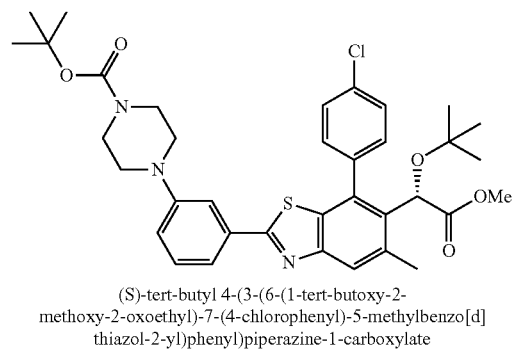

(S)-tert-butyl 4-(3-(6-(1-tert-butoxy-2-methoxy-2-oxoethyl)-7-(4-chlorophenyl)-5-methylbenzo[d]thiazol-2-yl)phenyl)piperazine-1-carboxylate

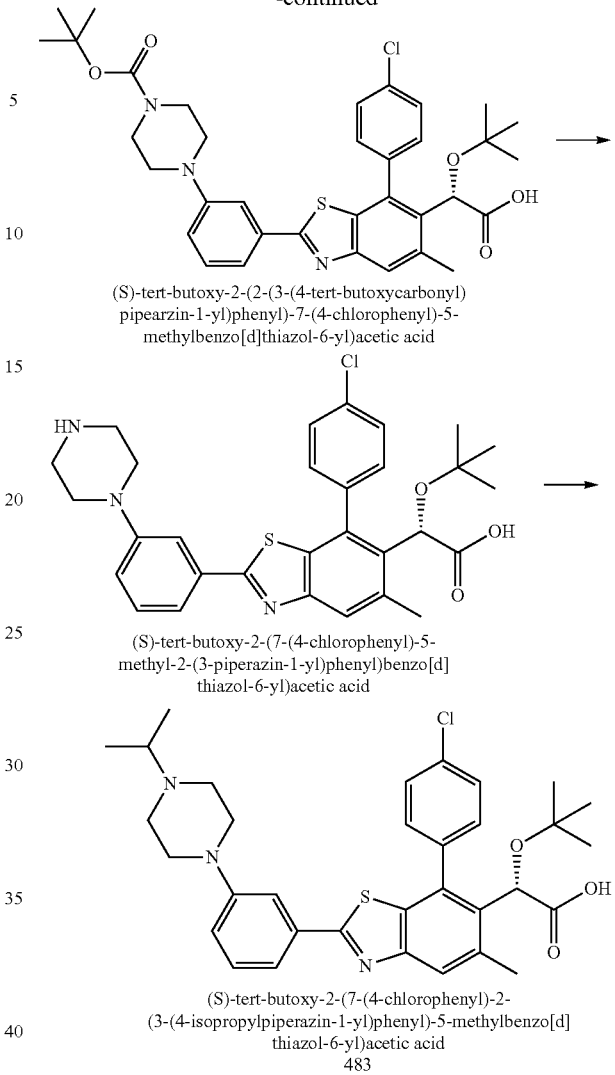

(S)-tert-butoxy-2-(2-(3-(4-tert-butoxycarbonyl)pipearzin-1-yl)phenyl)-7-(4-chlorophenyl)-5-methylbenzo[d]thiazol-6-yl)acetic acid (S)-tert-butoxy-2-(7-(4-chlorophenyl)-5-methyl-2-(3-piperazin-1-yl)phenyl)benzo[d]thiazol-6-yl)acetic acid (S)-tert-butoxy-2-(7-(4-chlorophenyl)-2-(3-(4-isopropylpiperazin-1-yl)phenyl)-5-methylbenzo[d]thiazol-6-yl)acetic acid
483

Preparation of (S)-tert-butyl 4-(3-(6-(1-tert-butoxy-2-methoxy-2-oxoethyl)-7-(4-chlorophenyl)-5-methylbenzo[d]thiazol-2-yl)phenyl)piperazine-1-carboxylate: To a solution of (S)-methyl 2-(2-bromo-7-(4-chlorophenyl)-5-methylbenzo[d]thiazol-6-yl)-2-tert-butoxyacetate (193 mg, 0.40 mmol) and tert-butyl 4-(3-(4,4,5,5-tetramethyl-1,3,2-dioxaborolan-2-yl)phenyl)piperazine-1-carboxylate (217 mg, 0.56 mmol) in 1,4-dioxane (3 mL) was added potassium carbonate solution (0.80 mL, 1.6 mmol, 2 M aqueous solution) and Pd(PPh₃)₄ (23 mg, 0.02 mmol). The reaction mixture was stirred at 105° C. for 3 h. The mixture was diluted with brine (5 mL) and EtOAc (5 mL). The layers were separated, and the organic layer was dried, filtered, and concentrated in vacuo and used without further purification. LCMS-ESI⁺: calc'd for $C_{36}H_{43}ClN_3O_5S$: 664.3 (M+H⁺); Found: 664.3 (M+H⁺).

Preparation of (S)-2-tert-butoxy-2-(2-(3-(4-(tert-butoxycarbonyl)piperazin-1-yl)phenyl)-7-(4-chlorophenyl)-5-methylbenzo[d]thiazol-6-yl)acetic acid: To a solution of (S)-tert-butyl 4-(3-(6-(1-tert-butoxy-2-methoxy-2-oxoethyl)-7-(4-chlorophenyl)-5-methylbenzo[d]thiazol-2-yl)phenyl)piperazine-1-carboxylate (from above) in THF (4 mL) and methanol (4 mL) was added sodium hydroxide solution (1.0 mL, 2 mmol, 2 M aqueous solution). The mixture was stirred at 60° C. for 18 h. A saturated solution of NH₄Cl (20 mL) and EtOAc (15 mL) were added. The layers were separated, and the organic layer was dried, filtered, and concentrated in vacuo and used without further purification. LCMS-ESI⁺: calc'd for $C_{35}H_{41}ClN_3O_5S$: 650.2 (M+H⁺); Found: 650.2 (M+H⁺).

Preparation of (S)-2-tert-butoxy-2-(7-(4-chlorophenyl)-5-methyl-2-(3-(piperazin-1-yl)phenyl)benzo[d]thiazol-6-yl)acetic acid: To a solution of (S)-2-tert-butoxy-2-(2-(3-(4-(tert-butoxycarbonyl)piperazin-1-yl)phenyl)-7-(4-chlorophenyl)-5-methylbenzo[d]thiazol-6-yl)acetic acid (from above) in 1,4-dioxane (5 mL) was added 4M HCl in 1,4-dioxane (1 mL, 4 mmol). The reaction was stirred at rt for 6 h. A saturated solution of NaHCO₃ (10 mL) was added carefully. The layers were separated, and the organic layer was dried, filtered, and concentrated in vacuo and used without further purification. LCMS-ESI⁺: calc'd for $C_{30}H_{33}ClN_3O_3S$: 550.2 (M+H⁺); Found: 550.2 (M+H⁺).

Preparation of (S)-2-tert-butoxy-2-(7-(4-chlorophenyl)-2-(3-(4-isopropylpiperazin-1-yl)phenyl)-5-methylbenzo[d]thiazol-6-yl)acetic acid: To a solution of (S)-2-tert-butoxy-2-(7-(4-chlorophenyl)-5-methyl-2-(3-(piperazin-1-yl)phenyl)benzo[d]thiazol-6-yl)acetic acid (30 mg, 0.055 mmol) in MeOH (1 mL) was added acetone (0.20 mL), acetic acid (0.08 mL), and sodium triacetoxyborohydride (58 mg, 0.27 mmol). Stirred at rt for 18 h then 60° C. for 3 h (reaction not to completion). H₂O added (1 mL) and purified using reverse phase HPLC, eluting by 2-100% acetonitrile in H₂O with 0.1% TFA to give the product. ¹H NMR (400 MHz, CD₃OD) δ 7.83 (s, 1H), 7.68 (m, 2H), 7.58 (m, 3H), 7.43 (t, J=8 Hz, 1H), 7.21 (d, J=8 Hz, 1H), 5.25 (s, 1H), 4.02 (m, 2H), 3.60 (m, 4H), 3.12 (m, 3H), 2.61 (s, 3H), 1.43 (d, J=7 Hz, 6H), 0.97 (s, 9H). LCMS-ESI⁺: calc'd for $C_{33}H_{39}ClN_3O_3S$: 592.2 (M+H⁺); Found: 592.3 (M+H⁺).

Example 200

Preparation of (S)-2-tert-butoxy-2-(7-(4-chlorophenyl)-2-(2-(4-isopropylpiperazin-1-yl)thiazol-4-yl)-5-methylbenzo[d]thiazol-6-yl)acetic acid (484)

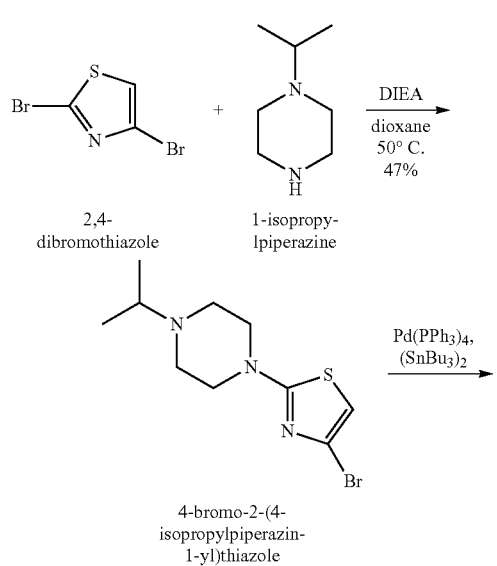

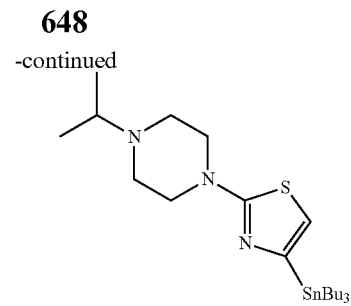

2-(4-isopropylpiperazin-1-yl)-4-(tributylstannyl)thiazole

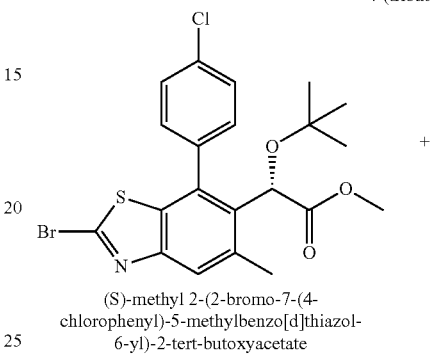

(S)-methyl 2-(2-bromo-7-(4-chlorophenyl)-5-methylbenzo[d]thiazol-6-yl)-2-tert-butoxyacetate

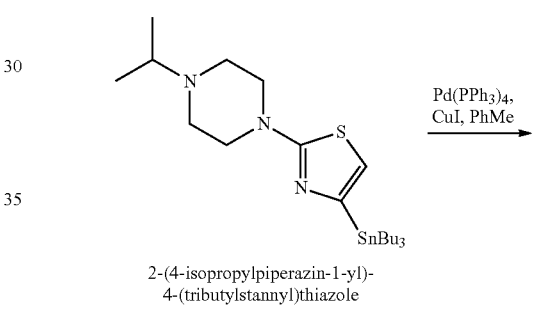

2-(4-isopropylpiperazin-1-yl)-4-(tributylstannyl)thiazole

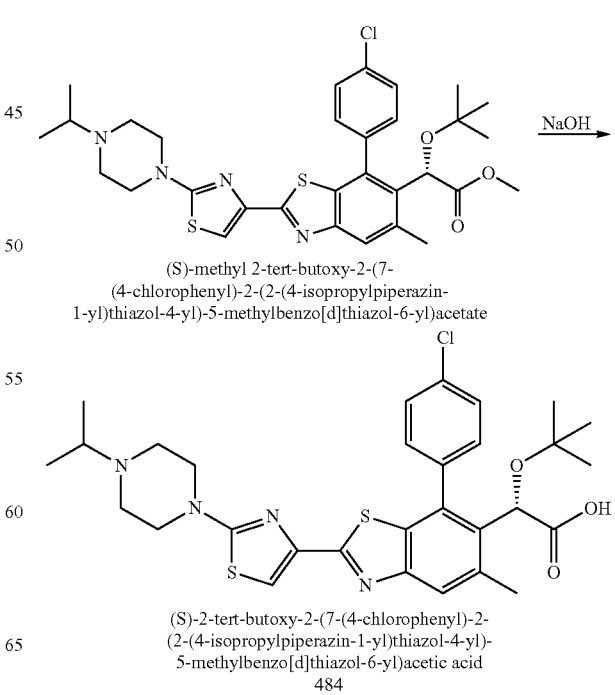

(S)-methyl 2-tert-butoxy-2-(7-(4-chlorophenyl)-2-(2-(4-isopropylpiperazin-1-yl)thiazol-4-yl)-5-methylbenzo[d]thiazol-6-yl)acetate (S)-2-tert-butoxy-2-(7-(4-chlorophenyl)-2-(2-(4-isopropylpiperazin-1-yl)thiazol-4-yl)-5-methylbenzo[d]thiazol-6-yl)acetic acid 484

Preparation of 4-bromo-2-(4-isopropylpiperazin-1-yl)thiazole: In a 50 mL round bottom flask, 1-isopropylpiperazine (306 mg, 2.38 mmol) was dissolved in 4 mL dioxane. 2,4-Dibromothiazole (870 mg, 1.5 eq.) was added and the reaction was stirred at room temperature overnight. TLC and LC-MS showed desired product. DIEA (0.83 mL, 2 eq.) was added. The reaction was stirred at room temperature for 4 hours, then heated to 50° C. for 5 hours. Reaction was cooled and extracted using ethyl acetate/brine. The organic layer was concentrated and purified via combiflash to give desired compound. LCMS-ESI$^+$: calc'd for $C_{10}H_{17}BrN_3S$: 290.0 (M+H$^+$); Found: 290.2 (M+H$^+$).

Preparation of 2-(4-isopropylpiperazin-1-yl)-4-(tributylstannyl)thiazole: A 5 mL microwave reaction tube was charged with 4-bromo-2-(4-isopropylpiperazin-1-yl)thiazole (61 mg, 0.21 mmol), Pd(PPh$_3$)$_4$ (37 mg, 15 mol %), bis(tributyltin) (183 mg, 2 eq.) and toluene (1.5 mL). The reaction was heated to 140° C. in oil bath for 1 hour. LC-MS of the reaction crude show desired product. Reaction mixture was diluted with ethyl acetate and saturated NaF aqueous solution was added and stirred for 30 minutes. Extracted with ethyl acetate and the organic layer was concentrated and purified via Combiflash (0-100% Ethyl acetate in hexane) to desired compound. LCMS-ESI$^+$: calc'd for $C_{22}H_{44}N_4SSn$: 502.2 (M+H$^+$); Found: 502.2 (M+H$^+$).

Preparation of (S)-methyl 2-tert-butoxy-2-(7-(4-chlorophenyl)-2-(2-(4-isopropylpiperazin-1-yl)thiazol-4-yl)-5-methylbenzo[d]thiazol-6-yl)acetate: A 5 mL microwave reaction tube was charged with 2-(4-isopropylpiperazin-1-yl)-4-(tributylstannyl)thiazole (33 mg, 0.066 mmol), (S)-methyl 2-(2-bromo-7-(4-chlorophenyl)-5-methylbenzo[d]thiazol-6-yl)-2-tert-butoxyacetate (40 mg, 1.2 eq.), Pd(PPh$_3$)$_4$ (15 mg, 15 mol %), CuI (5 mg, 30 mol %) and dioxane (1 mL). The reaction was heated to 110° C. in oil bath for 1 hour. Reaction mixture was diluted with ethyl acetate and saturated NaF aqueous solution was added and stirred for 30 minutes. Extracted with ethyl acetate and the organic layer was concentrated and purified via Combiflash (0-100% ethyl acetate in hexane) to give desired compound. LCMS-ESI$^+$: calc'd for $C_{31}H_{38}ClN_4O_3S_2$: 613.2 (M+H$^+$); Found: 613.4 (M+H$^+$).

Preparation of (S)-2-tert-butoxy-2-(7-(4-chlorophenyl)-2-(2-(4-isopropylpiperazin-1-yl)thiazol-4-yl)-5-methylbenzo[d]thiazol-6-yl)acetic acid: To a solution of (S)-methyl 2-tert-butoxy-2-(7-(4-chlorophenyl)-2-(2-(4-isopropylpiperazin-1-yl)thiazol-4-yl)-5-methylbenzo[d]thiazol-6-yl)acetate (30 mg, 0.04 mmol) in 1:1 THF/MeOH (1.5 mL) was added 2M aqueous NaOH (0.2 mL, 0.4 mmol) and stirred at 40° C. overnight. The reaction mixture was cooled to room temperature, neutralized with AcOH, filtered, and then purified by reverse phase column chromatography (5-100% ACN/H$_2$O+ 0.1% TFA). Fractions containing the product were pooled and lyophilized to provide the TFA salt of the product. $^1$H NMR (400 MHz, CD$_3$OD) δ 7.67 (s, 1H), 7.58-7.55 (m, 2H), 7.49-7.41 (m, 3H), 5.14 (s, 1H), 3.74 (m, 4H), 3.51-3.49 (m, 4H), 3.33 (m, 4H), 2.50 (s, 3H), 1.30 (d, J=6.65 Hz, 6H), 0.86 (s, 9H); LCMS-ESI$^+$: calc'd for $C_{30}H_{36}ClN_4O_3S_2$: 599.2 (M+H$^+$); Found: 599.4 (M+H$^+$).

Example 201

Preparation of (S)-2-tert-butoxy-2-(7-(4-chlorophenyl)-2-(2-(4-isopropylpiperazin-1-yl)thiazol-5-yl)-5-methylbenzo[d]thiazol-6-yl)acetic acid (485)

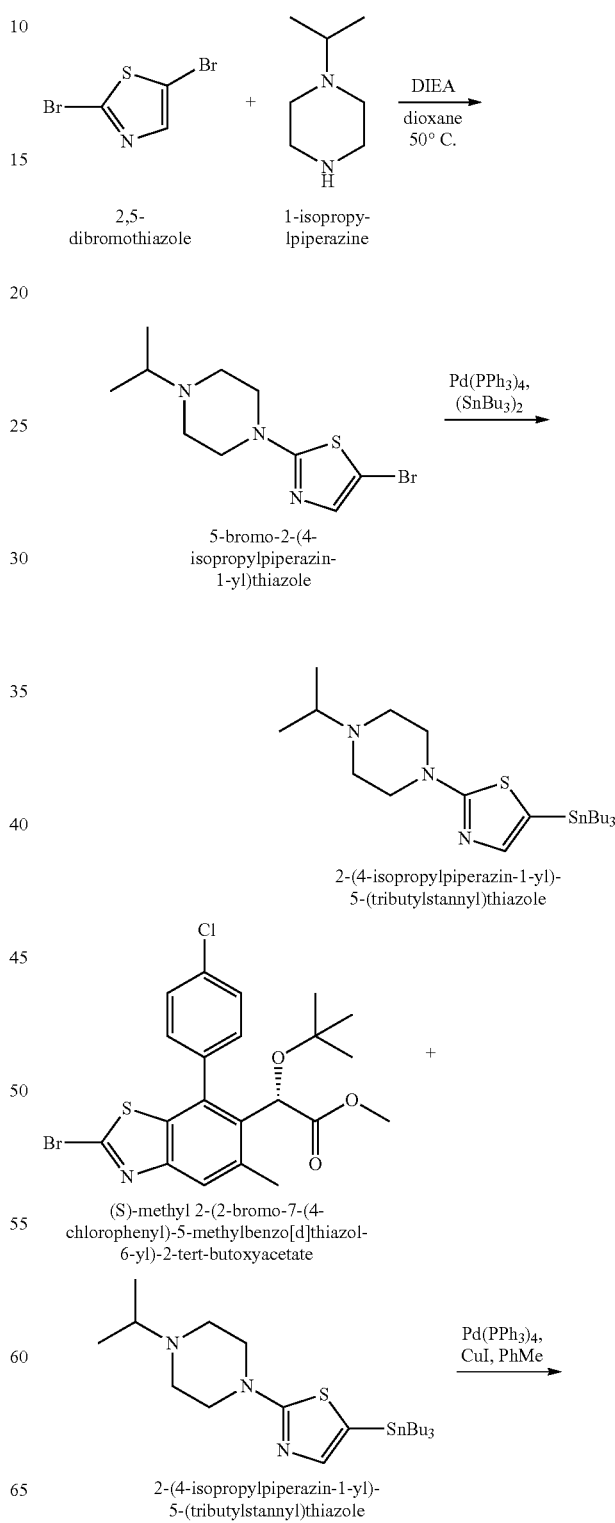

-continued

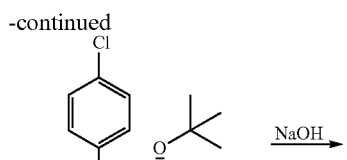

(S)-methyl 2-tert-butoxy-2-(7-
(4-chlorophenyl)-2-(2-(4-isopropylpiperazin-
5-yl)thiazol-4-yl)-5-methylbenzo[d]thiazol-6-yl)acetate

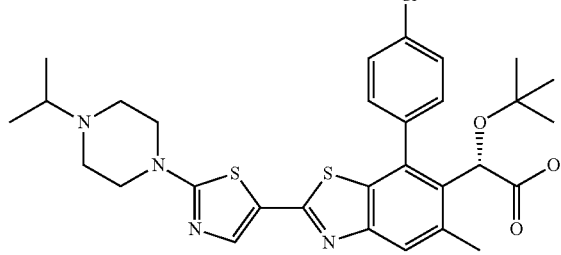

(S)-2-tert-butoxy-2-(7-(4-chlorophenyl)-2-
(2-(4-isopropylpiperazin-1-yl)thiazol-5-yl)-
5-methylbenzo[d]thiazol-6-yl)acetic acid
485

Preparation of 5-bromo-2-(4-isopropylpiperazin-1-yl) thiazole: In a 50 mL round bottom flask, 1-isopropylpiperazine (224 mg, 1.74 mmol) was dissolved in 4 mL dioxane. 2,5-Dibromothiazole (650 mg, 1.5 eq.) and DIEA (670 mg, 3 eq.) were added and the reaction was heated to 50° C. overnight. Reaction mixture was cooled and extracted using ethyl acetate /brine. The organic layer was concentrated and purified via combiflash to give desired compound. LCMS-ESI⁺: calc'd for $C_{10}H_{17}BrN_3S$: 290.0 (M+H⁺); Found: 290.2 (M+H⁺).

Preparation of 2-(4-isopropylpiperazin-1-yl)-5-(tributylstannyl)thiazole: A 5 mL microwave reaction tube was charged with 5-bromo-2-(4-isopropylpiperazin-1-yl)thiazole (100 mg, 0.34 mmol), Pd(PPh₃)₄ (60 mg, 15 mol %), Bis(tributyltin) (300 mg, 2 eq.) and toluene (1.5 mL). The reaction was heated to 140° C. in oil bath for 1 hour. LC-MS of the reaction crude show desired product. Reaction mixture was diluted using ethyl acetate, saturated NaF aqueous solution was added and stirred for 30 minutes. Extracted with ethyl acetate and the organic layer was concentrated and purified via Combiflash (0-100% Ethyl acetate in hexane) to give desired compound. LCMS-ESI⁺: calc'd for $C_{22}H_{44}N_4SSn$: 502.2 (M+H⁺); Found: 502.2 (M+H⁺).

Preparation of (S)-methyl 2-tert-butoxy-2-(7-(4-chlorophenyl)-2-(2-(4-isopropylpiperazin-1-yl)thiazol-5-yl)-5-methylbenzo[d]thiazol-6-yl)acetate: A 5 mL microwave reaction tube was charged with 2-(4-isopropylpiperazin-1-yl)-5-(tributylstannyl)thiazole (39 mg, 0.078 mmol), (S)-methyl 2-(2-bromo-7-(4-chlorophenyl)-5-methylbenzo[d]thiazol-6-yl)-2-tert-butoxyacetate (40 mg, 1.1 eq.), Pd(PPh₃)₄ (15 mg, 15 mol %), CuI (5 mg, 30 mol %) and dioxane (1 mL). The reaction was heated to 110° C. in oil bath for 1 hour. Reaction mixture was diluted with ethyl acetate and saturated NaF aqueous solution was added and stirred for 30 minutes. Extracted with ethyl acetate and the organic layer was concentrated and purified via Combiflash (0-100% Ethyl acetate in hexane) to give desired compound. LCMS-ESI⁺: calc'd for $C_{31}H_{38}ClN_4O_3S_2$: 613.2 (M+H⁺); Found: 613.2 (M+H⁺).

Preparation of (S)-2-tert-butoxy-2-(7-(4-chlorophenyl)-2-(2-(4-isopropylpiperazin-1-yl)thiazol-5-yl)-5-methylbenzo[d]thiazol-6-yl)acetic acid: To a solution of (S)-methyl 2-tert-butoxy-2-(7-(4-chlorophenyl)-2-(2-(4-isopropylpiperazin-1-yl)thiazol-5-yl)-5-methylbenzo[d]thiazol-6-yl)acetate (30 mg, 0.04 mmol) in 1:1 THF/MeOH (1.5 mL) was added 2M aqueous NaOH (0.2 mL, 0.4 mmol) and stirred at 40° C. overnight. The reaction mixture was cooled to room temperature, neutralized with AcOH, filtered, and then purified by reverse phase column chromatography (5-100% ACN/H₂O+ 0.1% TFA). Fractions containing the product were pooled and lyophilized to provide the TFA salt of the product. ¹H NMR (400 MHz, CD₃OD) δ 7.77 (s, 1H), 7.66-7.64 (m, 2H), 7.57-7.50 (m, 3H), 5.21 (s, 1H), 3.65-3.57 (m, 1H), 3.57-3.30 (m, 8H), 2.56 (s, 3H), 1.41 (d, J=6.65 Hz, 6H), 0.95 (s, 9H); LCMS-ESI⁺: calc'd for $C_{30}H_{36}ClN_4O_3S_2$: 599.2 (M+H⁺); Found: 599.4 (M+H⁺).

Example 202

Preparation of (S)-2-tert-butoxy-2-(7-(4-chlorophenyl)-2-(5-(4-isopropylpiperazin-1-yl)thiazol-2-yl)-5-methylbenzo[d]thiazol-6-yl)acetic acid (486)

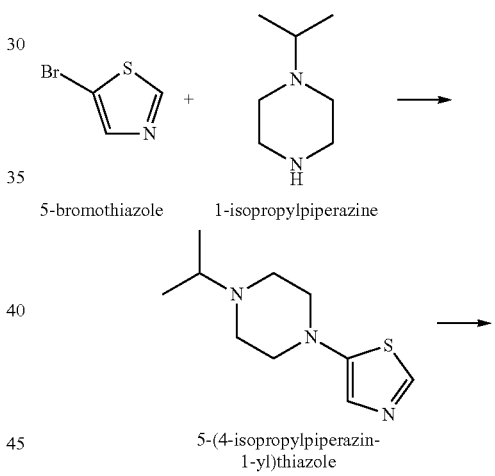

5-bromothiazole    1-isopropylpiperazine 5-(4-isopropylpiperazin-1-yl)thiazole

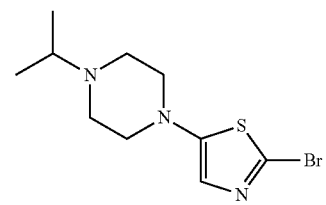

2-bromo-5-(4-isopropylpiperazin-1-yl)thiazole

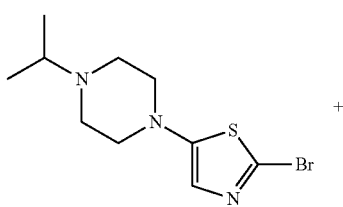

+

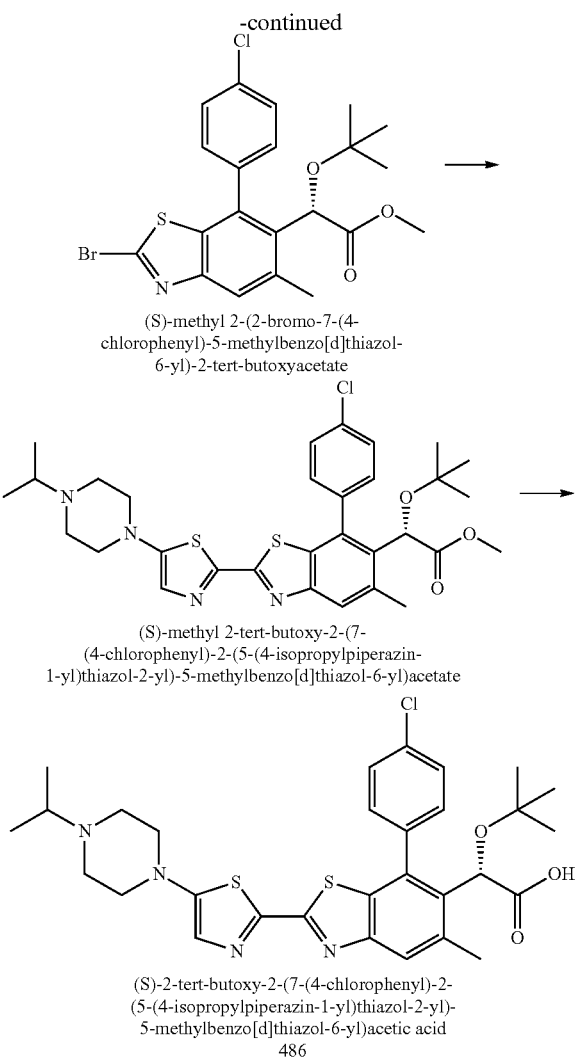

(S)-methyl 2-(2-bromo-7-(4-chlorophenyl)-5-methylbenzo[d]thiazol-6-yl)-2-tert-butoxyacetate (S)-methyl 2-tert-butoxy-2-(7-(4-chlorophenyl)-2-(5-(4-isopropylpiperazin-1-yl)thiazol-2-yl)-5-methylbenzo[d]thiazol-6-yl)acetate (S)-2-tert-butoxy-2-(7-(4-chlorophenyl)-2-(5-(4-isopropylpiperazin-1-yl)thiazol-2-yl)-5-methylbenzo[d]thiazol-6-yl)acetic acid
486

Preparation of 5-(4-isopropylpiperazin-1-yl)thiazole: To a 5 mL microwave reaction tube containing 5-bromothiazole (359 mg, 2.19 mmol), isopropylpiperazine (330 mg, 1.1 eq.), Bis(tri-t-butylphosphine)palladium (0) (22 mg, 15 mol %), cetyltrimethylammonium bromide (15 mg, 30 mol %), toluene (3 mL) was added one drop of 50% KOH aqueous solution. The reaction was heated to 110° C. for 4 hours. The reaction was cooled down and extracted using ethyl acetate/brine. The organic layers were concentrated and purified via Combiflash (0-20% MeOH/Ethyl acetate) to give desired product. LCMS-ESI$^+$: calc'd for $C_{10}H_{18}N_3S$: 212.1 (M+H$^+$); Found: 212.1 (M+H$^+$).

Preparation of 2-bromo-5-(4-isopropylpiperazin-1-yl)thiazole: At −78° C., n-butyl lithium (2.5 N in hexane, 0.27 mL, 2 eq.) was added to 5-(4-isopropylpiperazin-1-yl)thiazole (28 mg, 0.132 mmol) in 1 mL THF. CBr$_4$ (22 mg, 0.5 eq.) was added after 30 minutes. The reaction was stirred at −78° C. for 2 hours. The reaction was quenched by adding water. The reaction crude was extracted using EtOAc. The organic layers were concentrated and purified via Combiflash (0-20% MeOH in EtOAc) to give desired product. LCMS-ESI$^+$: calc'd for $C_{10}H_{17}BrN_3S$: 290.0 (M+H$^+$); Found: 290.1 (M+H$^+$).

Preparation of (S)-methyl 2-tert-butoxy-2-(7-(4-chlorophenyl)-2-(5-(4-isopropylpiperazin-1-yl)thiazol-2-yl)-5-methylbenzo[d]thiazol-6-yl)acetate: A 5 mL microwave reaction tube was charged with 2-bromo-5-(4-isopropylpiperazin-1-yl)thiazole (12 mg, 0.041 mmol), Pd(PPh$_3$)$_4$ (7 mg, 15 mol %), CuI (4 mg, 30 mol %) and (SnBu$_3$)$_2$ (48 mg, 2 eq.) and toluene (0.5 mL). The reaction was heated to 110° C. in oil bath. (S)-methyl 2-(2-bromo-7-(4-chlorophenyl)-5-methylbenzo[d]thiazol-6-yl)-2-tert-butoxyacetate (20 mg, 1.1 eq.) in toluene (4 mL) was added slowly (over 1.5 hours). The reaction was heated at 110° C. in oil bath for 2 hours. The reaction crude was partitioned between ethyl acetate and brine. The organic layer were concentrated and purified by reverse phase column chromatography (5-100% ACN/H$_2$O+0.1% TFA) to give desired product. LCMS-ESI$^+$: calc'd for $C_{31}H_{38}ClN_4O_3S_2$: 613.2 (M+H$^+$); Found: 613.2 (M+H$^+$).

Preparation of (S)-2-tert-butoxy-2-(7-(4-chlorophenyl)-2-(5-(4-isopropylpiperazin-1-yl)thiazol-2-yl)-5-methylbenzo[d]thiazol-6-yl)acetic acid: To a solution of (S)-methyl 2-tert-butoxy-2-(7-(4-chlorophenyl)-2-(5-(4-isopropylpiperazin-1-yl)thiazol-2-yl)-5-methylbenzo[d]thiazol-6-yl)acetate in 1:1 THF/MeOH (1.5 mL) was added 2M aqueous NaOH (0.2 mL, 0.4 mmol) and stirred at 40° C. for 2 days. The reaction mixture was cooled to room temperature, neutralized with AcOH, filtered, and then purified by reverse phase column chromatography (5-100% ACN/H$_2$O+0.1% TFA). Fractions containing the product were pooled and lyophilized to provide the TFA salt of the product. $^1$H NMR (400 MHz, CD$_3$OD) δ 7.77 (s, 1H), 7.67-7.65 (m, 2H), 7.60-7.50 (m, 3H), 5.23 (s, 1H), 3.65-3.60 (m, 1H), 3.60-3.36 (m, 8H), 2.59 (s, 3H), 1.42 (d, J=6.65 Hz, 6H), 0.95 (s, 9H); LCMS-ESI$^+$: calc'd for $C_{30}H_{36}ClN_4O_3S_2$: 599.2 (M+H$^+$); Found: 599.4 (M+H$^+$).

Example 203

Preparation of (S)-2-tert-butoxy-2-(7-(4-chlorophenyl)-2-(1,3-dimethyl-1H-pyrazolo[4,3-d]pyrimidin-5-yl)-5-methylbenzo[d]thiazol-6-yl)acetic acid (487)

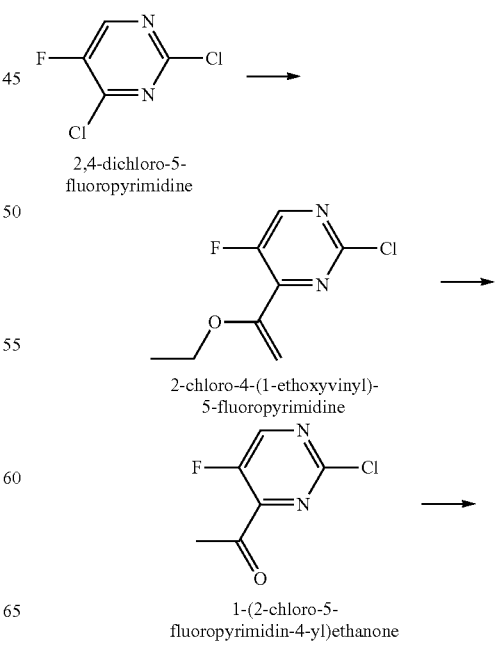

2,4-dichloro-5-fluoropyrimidine 2-chloro-4-(1-ethoxyvinyl)-5-fluoropyrimidine 1-(2-chloro-5-fluoropyrimidin-4-yl)ethanone

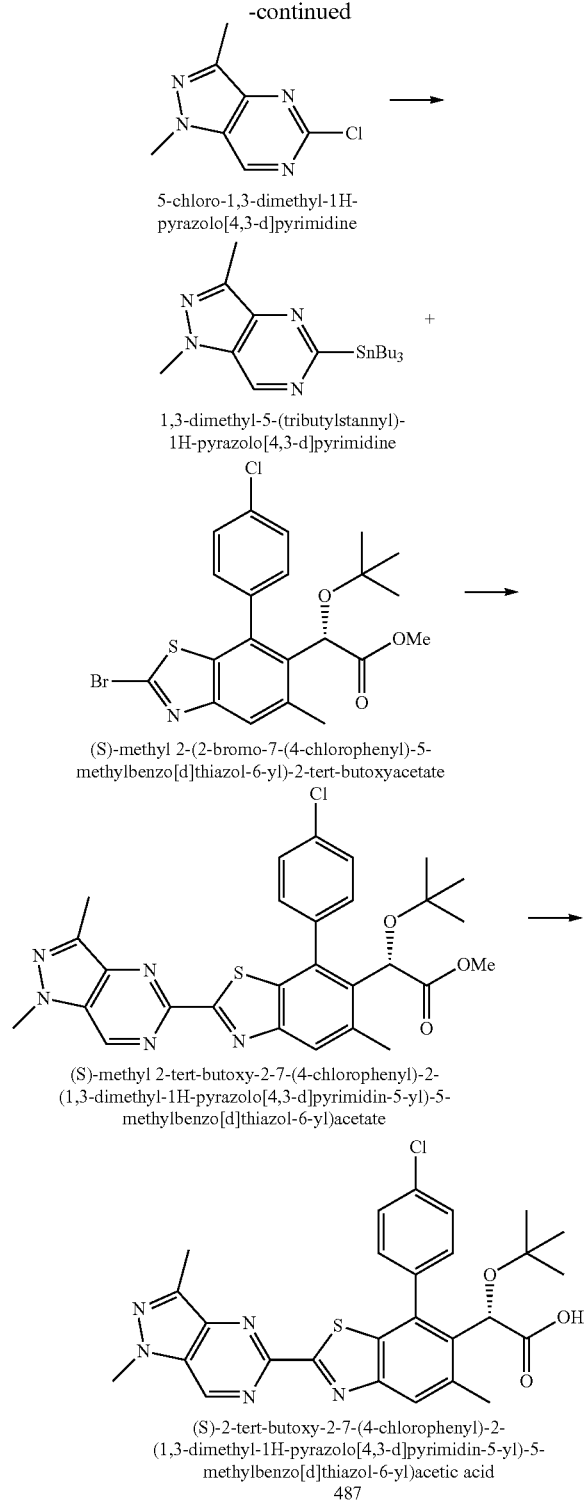

5-chloro-1,3-dimethyl-1H-pyrazolo[4,3-d]pyrimidine 1,3-dimethyl-5-(tributylstannyl)-1H-pyrazolo[4,3-d]pyrimidine (S)-methyl 2-(2-bromo-7-(4-chlorophenyl)-5-methylbenzo[d]thiazol-6-yl)-2-tert-butoxyacetate (S)-methyl 2-tert-butoxy-2-7-(4-chlorophenyl)-2-(1,3-dimethyl-1H-pyrazolo[4,3-d]pyrimidin-5-yl)-5-methylbenzo[d]thiazol-6-yl)acetate (S)-2-tert-butoxy-2-7-(4-chlorophenyl)-2-(1,3-dimethyl-1H-pyrazolo[4,3-d]pyrimidin-5-yl)-5-methylbenzo[d]thiazol-6-yl)acetic acid
487

Preparation of 2-chloro-4-(1-ethoxyvinyl)-5-fluoropyrimidine: To a solution of 2,4-dichloro-5-fluoro-pyrimidine (5.2 g, 31.14 mmol) in DMF (60 mL) was added tributyl-(1-ethoxy-vinyl)-stannane (12.37 g, 361.2 mmol), followed by dichlorobis(triphenylphosphine) palladium(II) (0.438 g, 0.623 mmol). The mixture was heated at 75° C. for 2 hours, cooled to rt and concentrated. The oily residue was dissolved in ethyl ether and a saturated solution of aqueous potassium fluoride was added and the mixture was stirred at room temperature for 18 hours. After dilution with EtOAc and filtration through Celite, the organic phase was washed with water, brine and concentrated. The crude material was purified by CombiFlash (0 to 10% EtOAc/Hex) to give desired product. LCMS-ESI$^+$: calc'd for $C_8H_9ClFN_2O$: 203.0 (M+H$^+$); Found: 203.1 (M+H$^+$); $^1$H NMR (400 MHz, Chloroform-d) δ 8.45 (d, J=2.8 Hz, 1H), 5.30 (d, J=3.1 Hz, 1H), 4.71 (d, J=3.1 Hz, 1H), 3.96 (q, J=7.0 Hz, 2H), 1.42 (t, J=7.0 Hz, 3H).

Preparation of 1-(2-chloro-5-fluoropyrimidin-4-yl)ethanone: A mixture of 2-chloro-4-(1-ethoxyvinyl)-5-fluoropyrimidine (5.23 g, 25.81 mmol) in 3N HCl (100 mL) was stirred at rt for 6 h. Potassium hydroxide (50%) was added to give a cloudy mixture (pH was still less than 1) and extracted cloudy mixture with EtOAc. More potassium hydroxide (50%) was added and extracted with EtOAc. Again, more potassium hydroxide (50%) was added until pH=7 and extracted with EtOAc. The combined organic layer dried (MgSO$_4$), filtered, concentrated and purified by CombiFlash (0 to 25% EtOAc/Hex) to give the desired product. $^1$H NMR (400 MHz, CDCl$_3$) δ 8.69 (d, J=2 Hz, 1H), 2.71 (2, 3H); $^{19}$F (376 MHz, CDCl$_3$) δ −138.26.

Preparation of 5-chloro-1,3-dimethyl-1H-pyrazolo[4,3-d]pyrimidine: A solution of 1-(2-chloro-5-fluoropyrimidin-4-yl)ethanone (4.00 g, 22.91 mmol) and methylhydrazine (0.724 mL, 13.75 mmol) in ethylene glycol was heated at 120° C. for 2 h. Reaction mixture was cooled to rt, diluted with H$_2$O and extracted with ethyl acetate (3×). The combined organic layer was washed with H$_2$O (2×), brine, dried (MgSO$_4$), filtered and concentrated. The residue was purified by CombiFlash (0 to 30% EtOAc/Hex) to give the title compound. LCMS-ESI$^+$: calc'd for $C_7H_8ClN_4$: 183.0 (M+H$^+$); Found: 183.0 (M+H$^+$); $^1$H NMR (400 MHz, CDCl$_3$) δ 8.90 (s, 1H), 4.12 (s, 3H), 2.61 (s, 3H).

Preparation of 1,3-dimethyl-5-(tributylstannyl)-1H-pyrazolo[4,3-d]pyrimidine: 5-chloro-1,3-dimethyl-1H-pyrazolo[4,3-d]pyrimidine (0.193 g, 1.057 mmol) was dissolved in toluene (5 mL) and hexabutylditin (0.688 mL, 1.374 mmol) and tetrakis(triphenylphosphine)palladium(0) (0.122 g, 0.106 mmol) were added. Reaction mixture was stirred at 170° C. for 2 h to give a black mixture, cooled to rt, concentrated to ~2 mL and purified by CombiFlash (0 to 30% EtOAc/Hex) to give title compound. LCMS-ESI$^+$: calc'd for $C_{19}H_{35}N_4Sn$: 439.2 (M+H$^+$). Found: 438.9 (M+H$^+$); $^1$H NMR (400 MHz, Chloroform-d) δ 9.03 (s, 1H), 4.07 (s, 3H), 2.65 (s, 3H), 1.73-1.49 (m, 6H), 1.42-1.09 (m, 12H), 0.89 (q, J=7.9, 7.3 Hz, 9H).

Preparation of (S)-methyl 2-tert-butoxy-2-(7-(4-chlorophenyl)-2-(1,3-dimethyl-1H-pyrazolo[4,3-d]pyrimidin-5-yl)-5-methylbenzo[d]thiazol-6-yl)acetate: A mixture of (S)-methyl 2-(2-bromo-7-(4-chlorophenyl)-5-methylbenzo[d]thiazol-6-yl)-2-tert-butoxyacetate (0.055 g, 0.107 mmol), 1,3-dimethyl-5-(tributylstannyl)-1H-pyrazolo[4,3-d]pyrimidine (0.058 mg, 0.133 mmol), copper(I) iodide (6 mg, 0.032 mmol) and tetrakis(triphenylphosphine)palladium(0) (11 mg, 0.012 mmol) in dioxane (1 mL) was heated at 90° C. for 16 hr. Reaction mixture was cooled to rt, filtered through a syringe filter and purified by CombiFlash (0 to 70% EtOAc/Hex) to give title product. LCMS-ESI$^+$: calc'd for $C_{28}H_{29}ClN_5O_3S$: 550.2 (M+H$^+$); Found: 550.3 (M+H$^+$); $^1$H NMR (400 MHz, Methanol-d$_4$) δ 9.32 (s, 1H), 7.88 (s, 1H), 7.70-7.53 (m, 4H), 5.30 (s, 1H), 4.13 (s, 3H), 3.75 (s, 3H), 2.57 (s, 3H), 2.54 (s, 3H), 0.97 (s, 9H).

Preparation of (S)-2-tert-butoxy-2-(7-(4-chlorophenyl)-2-(1,3-dimethyl-1H-pyrazolo[4,3-d]pyrimidin-5-yl)-5-methylbenzo[d]thiazol-6-yl)acetic acid: A solution of (S)-methyl 2-tert-butoxy-2-(7-(4-chlorophenyl)-2-(1,3-dimethyl-1H-pyrazolo[4,3-d]pyrimidin-5-yl)-5-methylbenzo[d]thiazol-6- yl)acetate (38 mg, 0.07 mmol) and 5M sodium hydroxide (0.28 mL, 1.4 mmol) in THF (2 mL) and MeOH (0.5 mL) was stirred at 50° C. for 2 h. Reaction mixture was cooled to rt, acetic acid (88 µL) and DMF (0.3 mL) were added and reaction mixture was concentrated to ~0.3 mL, filtered, purified by Gilson HPLC (Gemini, 5 to 100% ACN/H₂O+0.1% TFA) and lyophilized to give desired product. LCMS-ESI⁺: calc'd for $C_{27}H_{27}ClN_5O_3S$: 536.1 (M+H⁺); Found: 536.2 (M+H⁺); ¹H NMR (400 MHz, CD₃OD) δ 9.29 (s, 1H), 7.92 (s, 1H), 7.71 (d, J=8.0 Hz, 1H), 7.62 (br s, 3H), 5.28 (s, 1H), 4.13 (s, 3H), 2.63 (s, 6H), 0.98 (s, 9H).

Example 204

Preparation of (S)-2-tert-butoxy-2-(7-(4-chlorophenyl)-2-(2-(1,3-dimethyl-1H-pyrazolo[4,3-d]pyrimidin-5-yl)pyridin-4-yl)-5-methylbenzo[d]thiazol-6-yl) acetic acid (488)

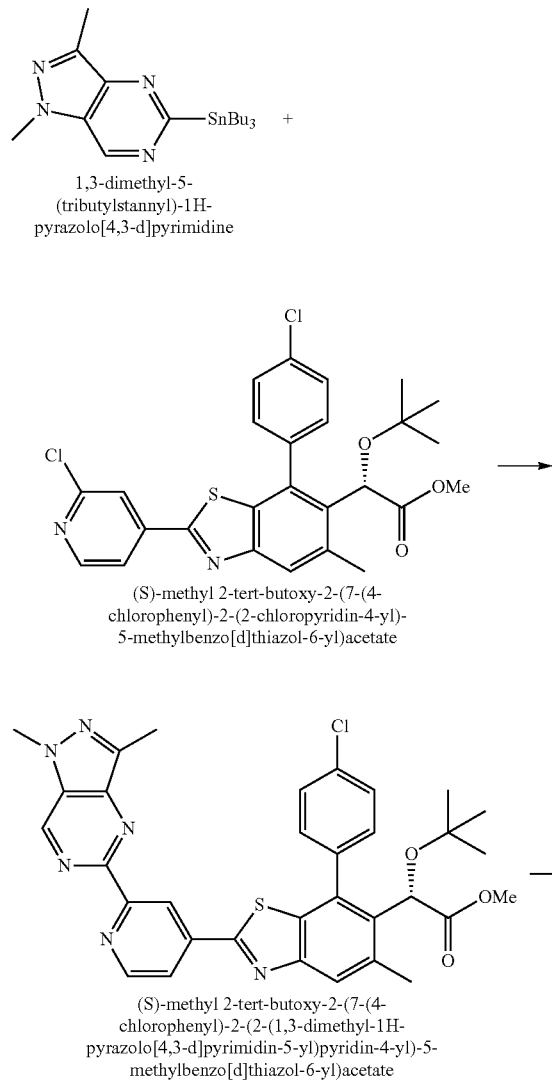

1,3-dimethyl-5-(tributylstannyl)-1H-pyrazolo[4,3-d]pyrimidine (S)-methyl 2-tert-butoxy-2-(7-(4-chlorophenyl)-2-(2-chloropyridin-4-yl)-5-methylbenzo[d]thiazol-6-yl)acetate (S)-methyl 2-tert-butoxy-2-(7-(4-chlorophenyl)-2-(2-(1,3-dimethyl-1H-pyrazolo[4,3-d]pyrimidin-5-yl)pyridin-4-yl)-5-methylbenzo[d]thiazol-6-yl)acetate

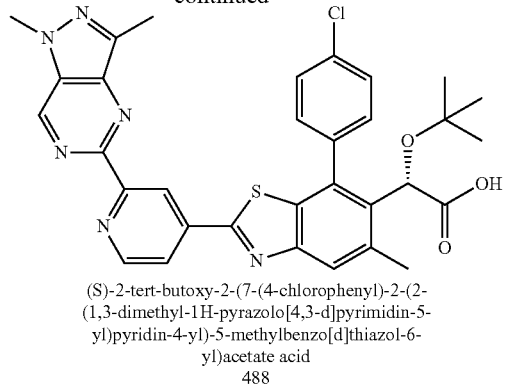

(S)-2-tert-butoxy-2-(7-(4-chlorophenyl)-2-(2-(1,3-dimethyl-1H-pyrazolo[4,3-d]pyrimidin-5-yl)pyridin-4-yl)-5-methylbenzo[d]thiazol-6-yl)acetate acid
488

Preparation of (S)-methyl 2-tert-butoxy-2-(7-(4-chlorophenyl)-2-(2-(1,3-dimethyl-1H-pyrazolo[4,3-d]pyrimidin-5-yl)pyridin-4-yl)-5-methylbenzo[d]thiazol-6-yl)acetate: A mixture of (S)-methyl 2-tert-butoxy-2-(7-(4-chlorophenyl)-2-(2-chloropyridin-4-yl)-5-methylbenzo[d]thiazol-6-yl)acetate (0.055 g, 0.107 mmol), 1,3-dimethyl-5-(tributylstannyl)-1H-pyrazolo[4,3-d]pyrimidine (0.058 mg, 0.133 mmol), copper(I) iodide (6 mg, 0.032 mmol) and tetrakis(triphenylphosphine)palladium(0) (11 mg, 0.012 mmol) in dioxane was heated at 90° C. for 16 hr. Reaction mixture was cooled to rt, filtered through a syringe filter and purified by CombiFlash (12 g, Gold, 10-100% EtOAc/Hex, then 15% MeOH/CH₂Cl₂ to elute product) to give impure product that was used in next step without further purification. LCMS-ESI⁺: calc'd for $C_{33}H_{32}ClN_6O_3S$: 627.2 (M+H⁺); Found: 627.2 (M+H⁺).

Preparation of (S)-2-tert-butoxy-2-(7-(4-chlorophenyl)-2-(2-(1,3-dimethyl-1H-pyrazolo[4,3-d]pyrimidin-5-yl)pyridin-4-yl)-5-methylbenzo[d]thiazol-6-yl)acetic acid: A solution of (S)-methyl 2-tert-butoxy-2-(7-(4-chlorophenyl)-2-(2-(1,3-dimethyl-1H-pyrazolo[4,3-d]pyrimidin-5-yl)pyridin-4-yl)-5-methylbenzo[d]thiazol-6-yl)acetate (7.7 mg, 0.012 mmol) and 5M sodium hydroxide (20 µL, 0.012 mmol) in THF (1 mL) and MeOH (0.2 mL) was stirred at 50° C. for 2 h. Reaction mixture was cooled to rt, acetic acid (15 µL) and DMF (0.3 mL) were added and reaction mixture was concentrated to ~0.3 mL, filtered, purified by Gilson HPLC (Gemini, 5 to 100% ACN/H₂O+0.1% TFA) and lyophilized to give desired product. LCMS-ESI⁺: calc'd for $C_{32}H_{30}ClN_6O_3S$: 613.2 (M+H⁺); Found: 613.2 (M+H⁺); ¹H NMR (400 MHz, CD₃OD) δ 9.41 (s, 1H), 9.28 (s, 1H), 8.85 (s, 1H), 8.25 (s, 1H), 7.99 (s, 1H), 7.76-7.43 (m, 4H), 5.28 (s, 1H), 4.16 (s, 3H), 2.71 (s, 3H), 2.65 (s, 3H), 0.98 (s, 9H).

Example 205

Preparation of (S)-2-(2-(2-(2-aminoquinolin-6-yl)pyrimidin-4-yl)-7-(4-chlorophenyl)-5-methylbenzo[d]thiazol-6-yl)-2-tert-butoxyacetic acid (489)

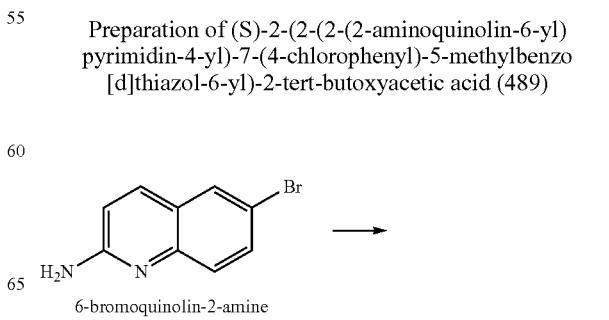

6-bromoquinolin-2-amine

-continued

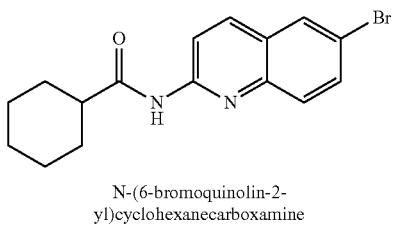

N-(6-bromoquinolin-2-yl)cyclohexanecarboxamine

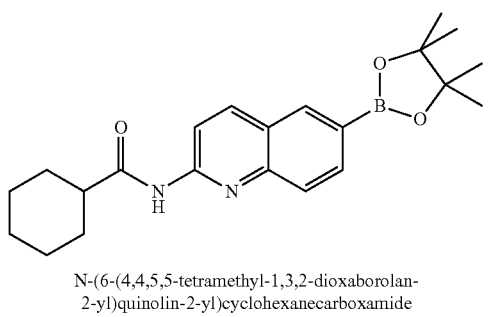

N-(6-(4,4,5,5-tetramethyl-1,3,2-dioxaborolan-2-yl)quinolin-2-yl)cyclohexanecarboxamide

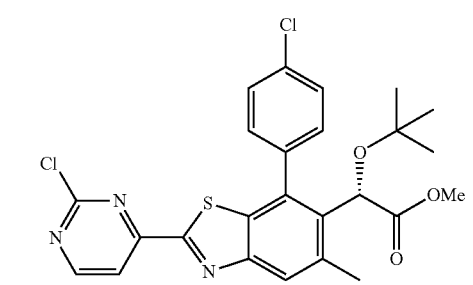

(S)-methyl 2-tert-butoxy-2-(7-(4-chlorophenyl)-2-(2-chloropyrimidin-4-yl)-5-methylbenzo[d]thiazol-6-yl)acetate

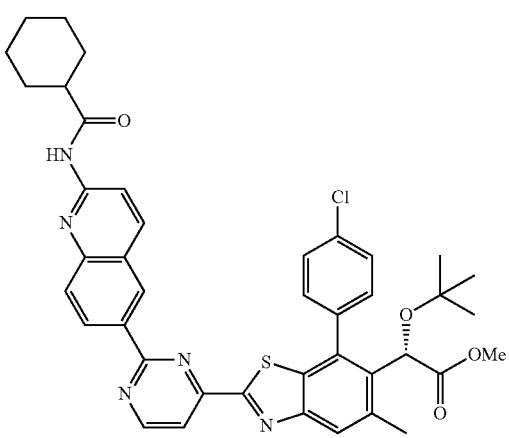

(S)-methyl 2-tert-butoxy-2-(7-(4-chlorophenyl)-2-(2-(2-(cyclohexanecarboxamido)quinolin-6-yl)pyrimidin-4-yl)-5-methylbenzo[d]thiazol-6-yl)acetate -continued

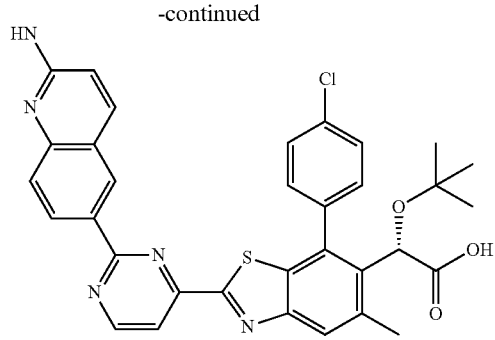

(S)-2-(2-(2-(2-aminoquinolin-6-yl)pyrimidin-4-yl)-7-(4-chlorophenyl)-5-methylbenzo[d]thiazol-6-yl)-2-tert-butoxyacetic acid
489

Preparation of N-(6-bromoquinolin-2-yl)cyclohexanecarboxamide: To a solution of 2-amino-6-bromoquinoline (250 mg, 1.121 mmol) in $CH_2Cl_2$ (7 mL) was added $Et_3N$ (0.94 mL, 6.726 mmol) and DMAP (137 mg, 1.121 mmol) followed by cyclohexanecarbonyl chloride (0.46 mL, 3.362 mmol). The reaction mixture was stirred at rt for 20 min and then diluted with EtOAc, washed with $H_2O$, brine, dried over $Na_2SO_4$, filtered and concentrated and purified by flash column chromatography (silica gel, 0 to 40% ethyl acetate/hexanes) to give the product. LCMS-ESI$^+$: calc'd for $C_{16}H_{18}BrN_2O$: 333.0 (M+H$^+$); found: 333.1 (M+H$^+$).

Preparation of N-(6-(4,4,5,5-tetramethyl-1,3,2-dioxaborolan-2-yl)quinolin-2-yl)cyclohexanecarboxamide: A solution of N-(6-bromoquinolin-2-yl)cyclohexanecarboxamide (100 mg, 0.300 mmol), bis(pinacolato)diboron (91 mg, 0.360 mmol) and potassium acetate (88 mg, 0.900 mmol) in dioxane (2.8 mL) was degassed for 5 min with $N_2$, then treated with Pd(dppf)Cl$_2$.DCM (12 mg, 0.015 mmol). The resulting mixture was heated at 90° C. for 90 min. After cooling, the reaction mixture was diluted with EtOAc, extracted with $H_2O$, brine, dried over $Na_2SO_4$, filtered and concentrated and purified by flash column chromatography (silica gel, 0 to 50% ethyl acetate/hexanes) to give the desired product. LCMS-ESI$^+$: calc'd for $C_{22}H_{30}BN_2O_3$: 381.2 (M+H$^+$); Found: 381.3 (M+H$^+$).

Preparation of (S)-methyl 2-tert-butoxy-2-(7-(4-chlorophenyl)-2-(2-(2-(cyclohexanecarboxamido)quinolin-6-yl)pyrimidin-4-yl)-5-methylbenzo[d]thiazol-6-yl)acetate: To a solution of (S)-methyl 2-tert-butoxy-2-(7-(4-chlorophenyl)-2-(2-chloropyrimidin-4-yl)-5-methylbenzo[d]thiazol-6-yl)acetate (20.0 mg, 0.038 mmol) and N-(6-(4,4,5,5-tetramethyl-1,3,2-dioxaborolan-2-yl)quinolin-2-yl)cyclohexanecarboxamide (17.2 mg, 0.045 mmol) in dioxane (0.4 mL) was added Pd(PPh$_3$)$_4$ (2.2 mg, 0.002 mmol) and 2N $K_2CO_3$ (79 µL, 0.158 mmol). The reaction was degassed for 5 minutes with $N_2$ and then heated at 90° C. for 10 h. After cooling, the reaction mixture was diluted with EtOAc, extracted with $H_2O$, brine, dried over $Na_2SO_4$, filtered and concentrated and purified by flash column chromatography (silica gel, 0 to 50% ethyl acetate/hexanes) to give the product. LCMS-ESI$^+$: calc'd for $C_{41}H_{41}ClN_5O_4S$: 734.3 (M+H$^+$); found: 734.3 (M+H$^+$).

Preparation of (S)-2-(2-(2-(2-aminoquinolin-6-yl)pyrimidin-4-yl)-7-(4-chlorophenyl)-5-methylbenzo[d]thiazol-6-yl)-2-tert-butoxyacetic acid: To a stirred solution of (S)-methyl 2-tert-butoxy-2-(7-(4-chlorophenyl)-2-(2-(2-(cyclohexanecarboxamido)quinolin-6-yl)pyrimidin-4-yl)-5-methylbenzo[d]thiazol-6-yl)acetate (28.0 mg, 0.038 mmol)

in THF (1.0 mL) and methanol (0.6 mL) was added 1N NaOH solution (0.6 mL, excess). The reaction mixture was stirred at 50° C. for 2 h. The mixture was acidified with TFA and concentrated and purified by flash column chromatography (silica gel, 0 to 20% methanol/dichloromethane) to give the TFA salt of the product. $^1$H NMR (400 MHz, DMSO-$d_6$) δ 9.12 (d, J=5.1 Hz, 1H), 8.81 (d, J=2.4 Hz, 1H), 8.64-8.55 (m, 1H), 8.34 (s, 1H), 8.17 (d, J=5.1 Hz, 1H), 8.03 (s, 1H), 7.77-7.64 (m, 4H), 7.61 (dd, J=8.6, 2.1 Hz, 1H), 6.96 (d, J=9.2 Hz, 1H), 5.09 (s, 1H), 2.56 (s, 3H), 0.88 (s, 9H); LCMS-ESI$^+$: calc'd for $C_{33}H_{29}ClN_5O_3S$: 610.2 (M+H$^+$); found: 610.2 (M+H$^+$).

Example 206

Preparation of (S)-2-tert-butoxy-2-(7-(4-chlorophenyl)-5-methyl-2-(6-methyl-5-(1-methyl-1H-pyrazolo[4,3-b]pyridin-5-yl)pyridin-3-yl)benzo[d]thiazol-6-yl)acetic acid (490)

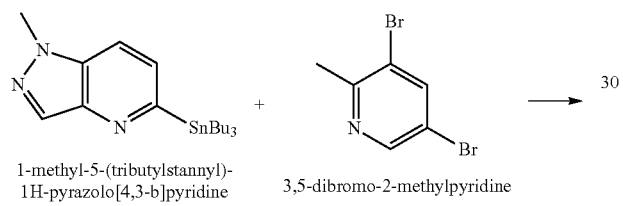

1-methyl-5-(tributylstannyl)-1H-pyrazolo[4,3-b]pyridine 3,5-dibromo-2-methylpyridine

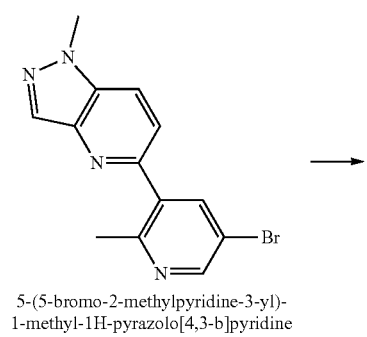

5-(5-bromo-2-methylpyridine-3-yl)-1-methyl-1H-pyrazolo[4,3-b]pyridine

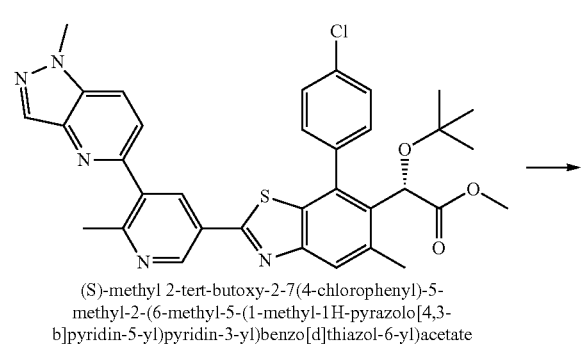

(S)-methyl 2-tert-butoxy-2-7(4-chlorophenyl)-5-methyl-2-(6-methyl-5-(1-methyl-1H-pyrazolo[4,3-b]pyridin-5-yl)pyridin-3-yl)benzo[d]thiazol-6-yl)acetate

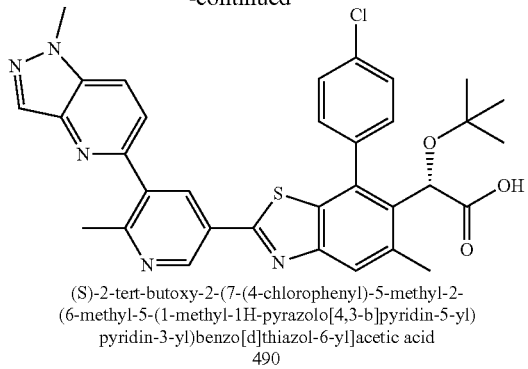

(S)-2-tert-butoxy-2-(7-(4-chlorophenyl)-5-methyl-2-(6-methyl-5-(1-methyl-1H-pyrazolo[4,3-b]pyridin-5-yl)pyridin-3-yl)benzo[d]thiazol-6-yl]acetic acid
490

Preparation of 5-(5-bromo-2-methylpyridin-3-yl)-1-methyl-1H-pyrazolo[4,3-b]pyridine: To a solution of 3,5-dibromo-2-methylpyridine (320 mg, 1.28 mmol) in dioxane (10 mL), was added 1-methyl-5-(tributylstannyl)-1H-pyrazolo[4,3-b]pyridine (540 mg, 1.28 mmol), CuI (73 mg, 0.38 mmol), LiCl (271 mg, 6.4 mmol) and Pd(PPh$_3$)$_4$ (147 mg, 0.12 mmol). The reaction mixture was heated at 100° C. for 2 h. The reaction was cooled down, washed by sat. NaHCO$_3$, extracted by EtOAc, dried over MgSO$_4$, filtered, concentrated down and purified by silica gel column, eluting by 0-100% EtOAc in hexanes give the product. LCMS-ESI$^+$: calc'd for $C_{13}H_{11}BrN_4$: 303.0 (M+H$^+$); Found: 303.2 (M+H$^+$).

Preparation of (S)-methyl 2-tert-butoxy-2-(7-(4-chlorophenyl)-5-methyl-2-(6-methyl-5-(1-methyl-1H-pyrazolo[4,3-b]pyridin-5-yl)pyridin-3-yl)benzo[d]thiazol-6-yl)acetate: To a solution of -(5-bromo-2-methylpyridin-3-yl)-1-methyl-1H-pyrazolo[4,3-b]pyridine (67 mg, 0.221 mmol) in dioxane (2 mL), was added bis(pinacolato)diboron (67 mg, 0.265 mmol), KOAc (86 mg, 0.884 mmol), PdCl$_2$(dppf) (16 mg, 0.022 mmol). The reaction mixture was heated at 100° C. for 3 h. Then the reaction was cooled down and to the mixture was added (S)-methyl 2-(2-bromo-7-(4-chlorophenyl)-5-methylbenzo[d]thiazol-6-yl)-2-tert-butoxyacetate (106 mg, 0.221 mmol), Pd(PPh$_3$)$_4$ (12 mg, 0.011 mmol). The mixture was heated at 90° C. for 3 h. The reaction was cooled down, washed by sat. NaHCO$_3$, extracted by EtOAc, dried over MgSO$_4$, filtered, concentrated down and purified by silica gel column, eluting with 0-70% EtOAc in hexanes to give the product. LCMS-ESI$^+$: calc'd for $C_{34}H_{32}ClN_5O_3S$: 626.2 (M+H$^+$); Found: 626.2 (M+H$^+$).

Preparation of (S)-2-tert-butoxy-2-(7-(4-chlorophenyl)-5-methyl-2-(6-methyl-5-(1-methyl-1H-pyrazolo[4,3-b]pyridin-5-yl)pyridin-3-yl)benzo[d]thiazol-6-yl)acetic acid: To a solution of (S)-methyl 2-tert-butoxy-2-(7-(4-chlorophenyl)-5-methyl-2-(6-methyl-5-(1-methyl-1H-pyrazolo[4,3-b]pyridin-5-yl)pyridin-3-yl)benzo[d]thiazol-6-yl)acetate (26 mg, 0.042 mmol) in THF (0.5 mL) and MeOH (0.5 mL) was added 2N NaOH (410 μL). The reaction mixture was heated at 60° C. for 3 h. The reaction mixture was concentrated down, the residue was dissolved in DMF and MeOH, filtered and purified by reverse phase HPLC, (10-100% ACN/H$_2$O+0.1% TFA) to give the product. $^1$H NMR (400 MHz, CD$_3$OD) δ 9.11 (d, J=0.8 Hz, 1H), 8.59 (d, J=1.0 Hz, 1H), 8.22-8.18 (m, 2H), 7.81 (s, 1H), 7.69-7.62 (m, 2H), 7.53-7.51 (m, 3H), 5.23

(s, 1H), 4.15 (s, 3H), 2.67 (s, 3H), 2.57 (s, 1H), 0.95 (s, 9H). LCMS-ESI$^+$: calc'd for $C_{33}H_{30}ClN_5O_3S$: 612.2 (M+H$^+$); Found: 612.1 (M+H$^+$).

Example 207

Preparation of (S)-2-tert-butoxy-2-(7-(4-chlorophenyl)-5-methyl-2-((S)-4-methyl-3-(1-methyl-1H-indazol-5-yl)piperazin-1-yl)benzo[d]thiazol-6-yl)acetic acid (491) and (S)-2-tert-butoxy-2-(7-(4-chlorophenyl)-5-methyl-2-((R)-4-methyl-3-(1-methyl-1H-indazol-5-yl)piperazin-1-yl)benzo[d]thiazol-6-yl)acetic acid (492)

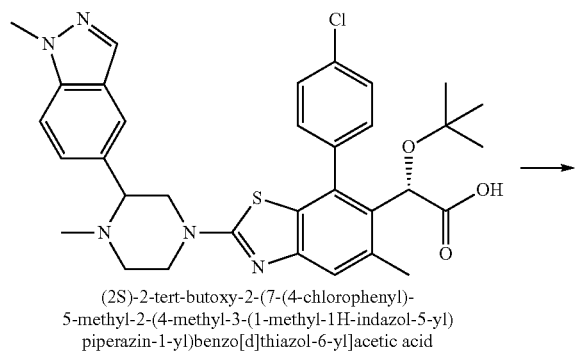

(2S)-2-tert-butoxy-2-(7-(4-chlorophenyl)-5-methyl-2-(4-methyl-3-(1-methyl-1H-indazol-5-yl)piperazin-1-yl)benzo[d]thiazol-6-yl]acetic acid

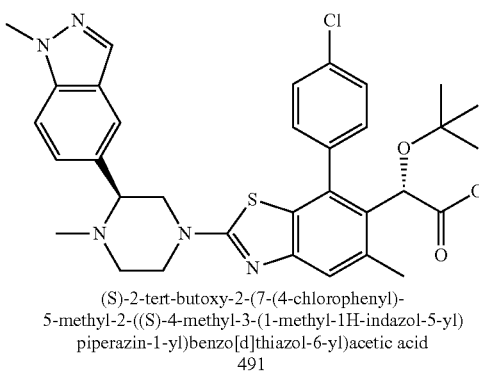

(S)-2-tert-butoxy-2-(7-(4-chlorophenyl)-5-methyl-2-((S)-4-methyl-3-(1-methyl-1H-indazol-5-yl)piperazin-1-yl)benzo[d]thiazol-6-yl)acetic acid
491

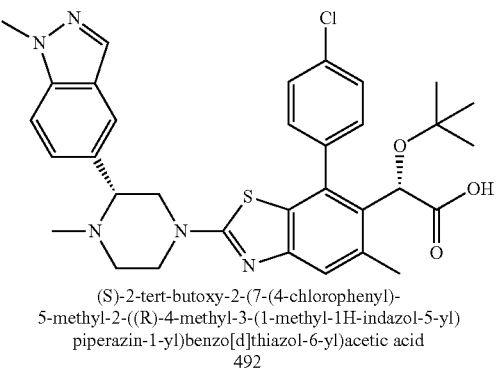

(S)-2-tert-butoxy-2-(7-(4-chlorophenyl)-5-methyl-2-((R)-4-methyl-3-(1-methyl-1H-indazol-5-yl)piperazin-1-yl)benzo[d]thiazol-6-yl)acetic acid
492

Preparation of (S)-2-tert-butoxy-2-(7-(4-chlorophenyl)-5-methyl-2-((S)-4-methyl-3-(1-methyl-1H-indazol-5-yl)piperazin-1-yl)benzo[d]thiazol-6-yl)acetic acid and (S)-2-tert-butoxy-2-(7-(4-chlorophenyl)-5-methyl-2-((R)-4-methyl-3-(1-methyl-1H-indazol-5-yl)piperazin-1-yl)benzo[d]thiazol-6-yl)acetic acid: (2S)-2-tert-butoxy-2-(7-(4-chlorophenyl)-5-methyl-2-(4-methyl-3-(1-methyl-1H-indazol-5-yl)piperazin-1-yl)benzo[d]thiazol-6-yl)acetic acid (8 mg, a mixture of two diastereoisomers) was dissolved in heptane/isopropanol (1 mL, 70/30) and was purified by Chiralpac Chiral Column (AZ-H) with heptane/isopropanol (70/30). Two fractions were collected.

Less polar fraction: $^1$H-NMR 400 MHz, (CD$_3$OD) δ 8.0 (s, 1H), 7.8 (s, 1H), 7.62-7.59 (m, 2H), 7.58-7.46 (m, 4H), 7.29 (s, 1H), 5.12 (s, 1H), 4.07 (s, 3H), 4.0 (m, 2H), 3.52-3.3 (m, 3H), 3.2 (m, 1H), 2.54 (m, 1H), 2.48 (s, 3H), 2.12 (s, 3H), 0.93 (s, 9H); LCMS-ESI$^+$: calc'd for $C_{33}H_{36}ClN_5O_3S$: 618.2 (M+H$^+$); Found: 618.4 (M+H$^+$).

More polar fraction: $^1$H-NMR 400 MHz, (CD$_3$OD) δ 7.99 (s, 1H), 7.79 (s, 1H), 7.64-7.45 (m, 6H), 7.28 (s, 1H), 5.12 (s, 1H), 4.06 (s, 3H), 3.98 (m, 2H), 3.48 (m, 1H), 3.30 (m, 2H), 3.10 (m, 1H), 2.50 (m, 1H), 2.48 (s, 3H), 2.10 (s, 3H), 0.93 (s, 9H); LCMS-ESI$^+$: calc'd for $C_{33}H_{36}ClN_5O_3S$: 618.2 (M+H$^+$); Found: 618.4 (M+H$^+$).

Example 208

Preparation of (2S)-2-tert-butoxy-2-(7-(4-chlorophenyl)-5-methyl-2-(1-methyl-3-(4-((2R/2S)-1,1,1-trifluoropropan-2-yl)piperazin-1-yl)-1H-indazol-5-yl)benzo[d]thiazol-6-yl)acetic acid (493)

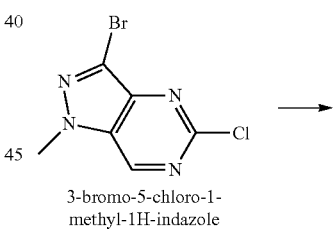

3-bromo-5-chloro-1-methyl-1H-indazole

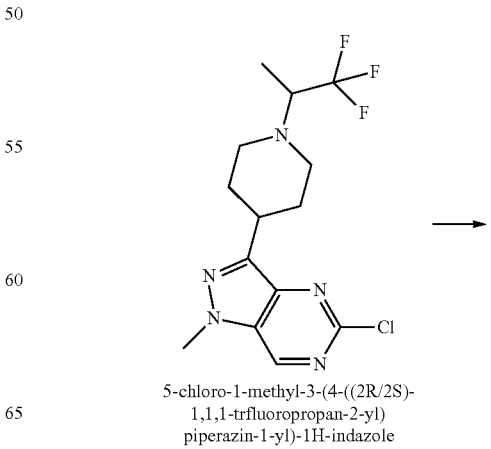

5-chloro-1-methyl-3-(4-((2R/2S)-1,1,1-trfluoropropan-2-yl)piperazin-1-yl)-1H-indazole -continued

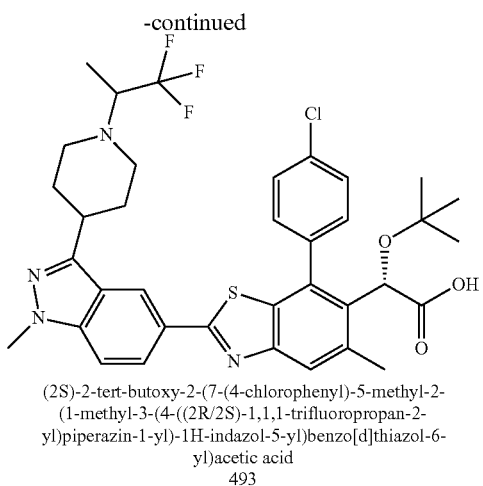

(2S)-2-tert-butoxy-2-(7-(4-chlorophenyl)-5-methyl-2-(1-methyl-3-(4-((2R/2S)-1,1,1-trifluoropropan-2-yl)piperazin-1-yl)-1H-indazol-5-yl)benzo[d]thiazol-6-yl)acetic acid
493

Preparation of 5-chloro-1-methyl-3-(4-((2R/2S)-1,1,1-trifluoropropan-2-yl)piperazin-1-yl)-1H-indazole: A solution of 3-bromo-5-chloro-1-methyl-1H-indazole (160 mg, 0.652 mmol), 1-((2R/2S)-1,1,1-trifluoropropan-2-yl)piperazine (119 mg, 0.652 mmol), and Dioxane (1.00 mL) was prepared. NaOtBu (94 mg, 0.978 mmol) and Chloro[2-(dicyclohexylphosphino)-3,6-dimethoxy-2',4',6'-triisopropyl-1,1'-biphenyl)][2-(2-aminoethyl)phenyl]Pd(II) (52 mg, 65 μmol) were charged and the vessel was sealed and heated to 100° C. overnight. Water (3 mL) was added and the reaction was filtered (0.45 micron). The filtrate was directly purified by reverse phase column chromatography (5-100% ACN/H$_2$O+ 0.1% TFA) giving the title compound. LCMS-ESI$^+$: calc'd for C$_{15}$H$_{19}$ClF$_3$N$_4$: 347.2, 349.2 (M+H$^+$); Found: 347.1, 349.1 (M+H$^+$).

Preparation of (2S)-2-tert-butoxy-2-(7-(4-chlorophenyl)-5-methyl-2-(1-methyl-3-(4-((2R/2S)-1,1,1-trifluoropropan-2-yl)piperazin-1-yl)-1H-indazol-5-yl)benzo[d]thiazol-6-yl)acetic acid: A vial was charged with Pd(OAc)$_2$ (1.1 mg, trimeric), X-Phos ligand (4.5 mg), bis-pinacolatodiboron (29 mg), and KOAc (21 mg). The vessel was evacuated under vacuum and backfilled with argon. A solution of 5-chloro-1-methyl-3-(4-1((2R/2S)-1,1,1-trifluoropropan-2-yl)piperazin-1-yl)-1H-indazole (50 mg) in dioxane (1.5 mL) was introduced. The reaction was stirred briefly at 23° C., then heated to 110° C. After 1.5 h, The reaction was cooled to 23° C. and charged with (S)-methyl 2-(2-bromo-7-(4-chlorophenyl)-5-methylbenzo[d]thiazol-6-yl)-2-tert-butoxyacetate (35 mg), KHCO$_3$ (7 mg), Pd(PPh$_3$)$_4$ (2 mg), and 2 M aq K$_2$CO$_3$ (250 μL). The reaction was heated to 100° C. for 1 h. Ethanol (absolute, 0.5 mL) and 5 M aq NaOH (0.5 mL) were added. The reaction was heated at 100° C. for 30 min. The reaction was cooled to 23° C. and directly purified by reverse phase column chromatography (5-100% ACN/H$_2$O+0.1% TFA) giving the title compound. $^1$H NMR (400 MHz, CD$_3$OD): δ 8.44 (s, 1H), 7.99 (d, J=9.4 Hz, 1H), 7.80 (s, 1H), 7.69 (d, J=7.5 Hz, 2H), 7.65-7.54 (m, 5H), 7.48 (d, J=9.0 Hz, 1H), 5.25 (s, 1H), 3.90 (s, 3H), 3.54-3.40 (m, 4H), 3.13-2.93 (m, 4H), 2.61 (s, 3H), 1.34 (d, J=7.1 Hz, 3H), 0.97 (s, 9H).

LCMS-ESI$^+$: calc'd for C$_{35}$H$_{37}$ClF$_3$N$_5$O$_3$S [M+H±]: 700.2, 702.2; Found: 700.2, 702.2 (M+H$^+$).

Example 209

Preparation of (S)-2-tert-butoxy-2-(7-(4-chlorophenyl)-2-(3-(4,4-dimethylpiperazin-1-ium-1-yl)-1-methyl-1H-indazol-5-yl)-5-methylbenzo[d]thiazol-6-yl)acetate (494)

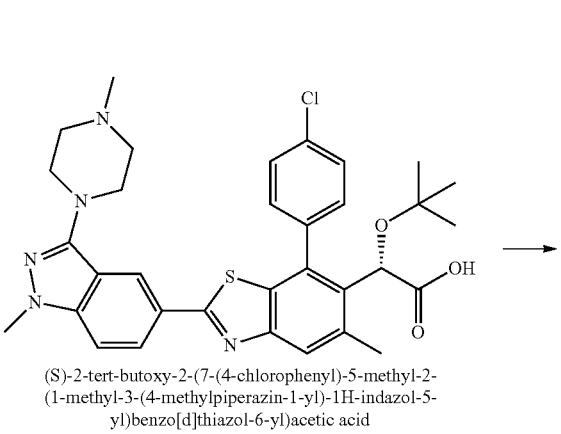

(S)-2-tert-butoxy-2-(7-(4-chlorophenyl)-5-methyl-2-(1-methyl-3-(4-methylpiperazin-1-yl)-1H-indazol-5-yl)benzo[d]thiazol-6-yl)acetic acid

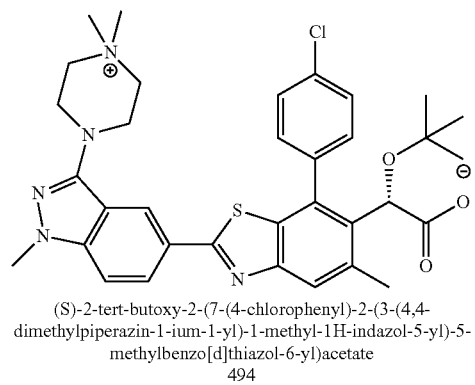

(S)-2-tert-butoxy-2-(7-(4-chlorophenyl)-2-(3-(4,4-dimethylpiperazin-1-ium-1-yl)-1-methyl-1H-indazol-5-yl)-5-methylbenzo[d]thiazol-6-yl)acetate
494

Preparation of (S)-2-tert-butoxy-2-(7-(4-chlorophenyl)-2-(3-(4,4-dimethylpiperazin-1-ium-1-yl)-1-methyl-1H-indazol-5-yl)-5-methylbenzo[d]thiazol-6-yl)acetate: A vessel was charged with (S)-2-tert-butoxy-2-(7-(4-chlorophenyl)-5-methyl-2-(1-methyl-3-(4-methylpiperazin-1-yl)-1H-indazol-5-yl)benzo[d]thiazol-6-yl)acetic acid (15 mg), N,N-dimethylacetamide (500 μL), iodomethane (250 mg), and Cs$_2$CO$_3$ (50 mg). The vessel was sealed and warmed to 60° C. for 15 h. Ethanol (absolute, 0.5 mL) and 5M aq NaOH (0.5 mL) were added. Heating was continued at 60° C. Then after 30 min, dioxane (0.5 mL) was added. Reaction was heated to 90° C. for 1 h. The reaction was cooled to 23° C. and directly purified by reverse phase column chromatography (5-100% ACN/H$_2$O+0.1% TFA) giving the title compound. $^1$H NMR (400 MHz, CD$_3$OD) δ 8.45 (s, 1H), 8.05 (d, J=9.4 Hz, 1H), 7.80 (s, 1H), 7.69 (d, J=9.5 Hz, 1H), 7.64-7.47 (m, 4H), 5.24

(s, 1H), 3.94 (s, 3H), 3.83 (d, J=4.7 Hz, 4H), 3.75-3.67 (m, 4H), 2.69 (s, 6H), 2.61 (s, 3H), 0.96 (s, 9H).

Example 210

Preparation of (S)-2-tert-butoxy-2-(7-(4-chlorophenyl)-5-methyl-2-(1-methyl-3-(4-methylpiperazin-1-yl)-1H-pyrazolo[4,3-b]pyridin-5-yl)benzo[d]thiazol-6-yl)acetic acid (495)

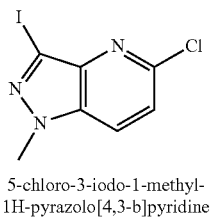

5-chloro-3-iodo-1-methyl-1H-pyrazolo[4,3-b]pyridine

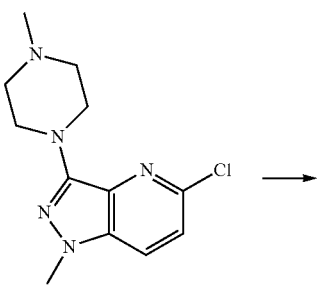

5-chloro-1-methyl-3-(4-methylpiperazin-1-yl)-1H-pyrazolo[4,3-b]pyridine

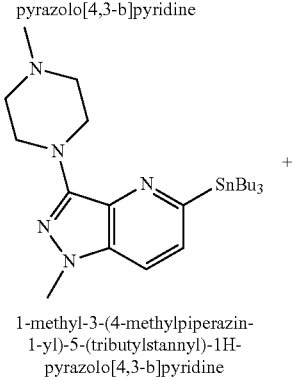

1-methyl-3-(4-methylpiperazin-1-yl)-5-(tributylstannyl)-1H-pyrazolo[4,3-b]pyridine

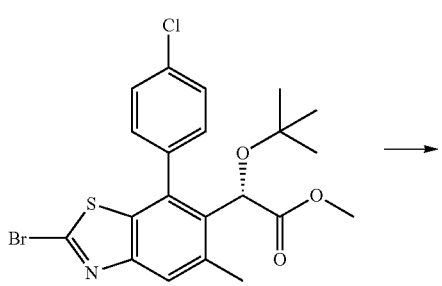

(S)-methyl 2-(2-bromo-7-(4-chlorophenyl)-5-methylbenzo[d]thiazol-6-yl)-2-tert-butoxyacetate

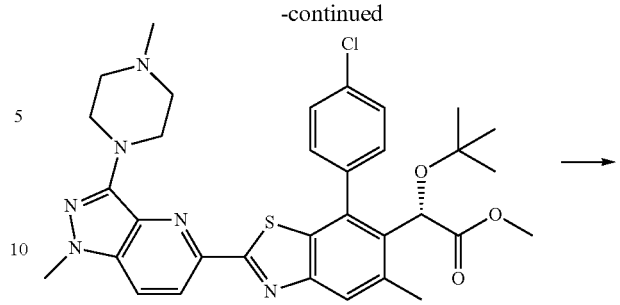

(S)-methyl 2-tert-butoxy-2-7-(4-chlorophenyl)-5-methyl-2-(1-methyl-3-(4-methylpiperazin-1-yl)-1H-pyrazolo[4,3-d]pyrimidin-5-yl)-5-methylbenzo[d]thiazol-6-yl)acetate

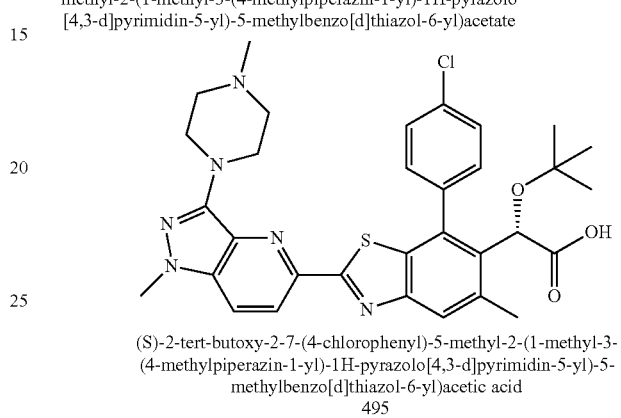

(S)-2-tert-butoxy-2-7-(4-chlorophenyl)-5-methyl-2-(1-methyl-3-(4-methylpiperazin-1-yl)-1H-pyrazolo[4,3-d]pyrimidin-5-yl)-5-methylbenzo[d]thiazol-6-yl)acetic acid
495

Preparation of 5-chloro-1-methyl-3-(4-methylpiperazin-1-yl)-1H-pyrazolo[4,3-b]pyridine: To a solution of 5-chloro-3-iodo-1-methyl-1H-pyrazolo[4,3-b]pyridine (104 mg, 0.354 mmol, containing the isomer 5-chloro-3-iodo-2-methyl-2H-pyrazolo[4,3-b]pyridine (360 mg, 1.22 mmol) was added 1-methylpiperazine (184 mg, 1.84 mmol), CuI (70 mg, 0.368 mmol), L-proline (84 mg, 0.736 mmol). The reaction mixture was heated at 100° C. for 4 h. The reaction was cooled, washed by sat. NaHCO$_3$, extracted with EtOAc, dried over MgSO$_4$, filtered, concentrated and purified by silica gel column, eluting by 0-100% EtOAc in hexanes to give the product. LCMS-ESI$^+$: calc'd for $C_{12}H_{16}ClN_5$: 266.1 (M+H$^+$); Found: 266.2 (M+H$^+$).

Preparation of 1-methyl-3-(4-methylpiperazin-1-yl)-5-(tributylstannyl)-1H-pyrazolo[4,3-b]pyridine: To a solution of 5-chloro-1-methyl-3-(4-methylpiperazin-1-yl)-1H-pyrazolo[4,3-b]pyridine (56 mg, 0.211 mmol) in toluene (12 mL), was added bis(tributyltin) (244 mg, 0.42 mmol) and Pd(PPh$_3$)$_4$ (24 mg, 0.021 mmol). The reaction mixture was heated at 170° C. for 1 hr. The reaction mixture was cooled down, washed with H$_2$O, extracted by EtOAc, the organic phase was dried over MgSO$_4$, filtered, concentrated and purified by silica gel column to give the product. LCMS-ESI$^+$: calc'd for $C_{24}H_{43}N_5Sn$: 522.2 (M+H$^+$); Found: 522.1 (M+H$^+$).

Preparation of (S)-methyl 2-tert-butoxy-2-(7-(4-chlorophenyl)-5-methyl-2-(1-methyl-3-(4-methylpiperazin-1-yl)-1H-pyrazolo[4,3-b]pyridin-5-yl)benzo[d]thiazol-6-yl)acetate: To a solution of (S)-methyl 2-(2-bromo-7-(4-chlorophenyl)-5-methylbenzo[d]thiazol-6-yl)-2-tert-butoxyacetate (22 mg, 0.046 mmol) in dioxane (2 mL), was added 1-methyl-3-(4-methylpiperazin-1-yl)-5-(tributylstannyl)-1H-pyrazolo[4,3-b]pyridine (20 mg, 0.038 mmol), CuI (7 mg, 0.038 mmol), LiCl (8 mg, 0.19 mmol) and Pd(PPh$_3$)$_4$ (4.4 mg, 0.004 mmol). The reaction mixture was heated at 100° C. for 2 h. The reaction was cooled, washed with sat.

NaHCO₃, extracted with EtOAc, dried over MgSO₄, filtered, concentrated down and purified by silica gel column, first eluting by 0-100% EtOAc in hexanes, then eluting by 0-20% MeOH in dichloromethane to give the product. LCMS-ESI⁺: calc'd for $C_{33}H_{37}ClN_6O_3S$: 633.2 (M+H⁺); Found: 633.3 (M+H⁺).

Preparation of (S)-2-tert-butoxy-2-(7-(4-chlorophenyl)-5-methyl-2-(1-methyl-3-(4-methylpiperazin-1-yl)-1H-pyrazolo[4,3-b]pyridin-5-yl)benzo[d]thiazol-6-yl)acetic acid: To a solution of (S)-methyl 2-tert-butoxy-2-(7-(4-chlorophenyl)-5-methyl-2-(1-methyl-3-(4-methylpiperazin-1-yl)-1H-pyrazolo[4,3-b]pyridin-5-yl)benzo[d]thiazol-6-yl)acetate (11 mg, 0.017 mmol) in THF (0.5 mL) and MeOH (0.5 mL) was added 2N NaOH (174 μL). The reaction mixture was heated at 45° C. overnight. The reaction mixture was concentrated, the residue was dissolved in DMF and MeOH, filtered and purified by reverse phase HPLC (10-100% ACN/H₂O+ 0.1% TFA) to give the product. ¹H NMR (400 MHz, CD₃OD) δ 8.33 (d, J=4.4 Hz, 1H), 7.97 (d, J=4.4 Hz, 1H), 7.85 (s, 1H), 7.70-7.57 (m, 4H), 5.22 (s, 1H), 4.75-4.74 (m, 2H), 3.92 (s, 3H), 3.61-3.59 (m, 2H), 3.36-3.34 (m, 4H), 2.94 (s, 3H), 2.61 (s, 3H), 0.96 (s, 9H). LCMS-ESI⁺: calc'd for $C_{32}H_{35}ClN_6O_3S$: 619.2 (M+H⁺); Found: 619.3 (M+H⁺).

Example 211

Preparation of (S)-2-tert-butoxy-2-(7-(4-chlorophenyl)-5-methyl-2-(1-methyl-3-(pyridin-3-yl)-1H-pyrazolo[4,3-b]pyridin-5-yl)benzo[d]thiazol-6-yl)acetic acid (496)

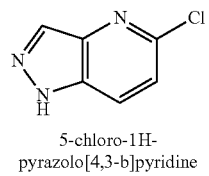

5-chloro-1H-pyrazolo[4,3-b]pyridine

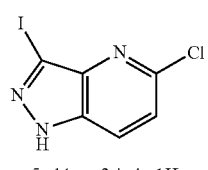

5-chloro-3-iodo-1H-pyrazolo[4,3-b]pyridine

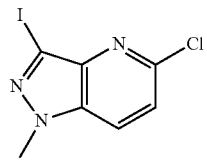

5-chloro-3-iodo-1-methyl-1H-pyrazolo[4,3-b]pyridine

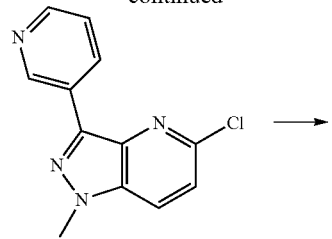

5-chloro-1-methyl-3-(pyridin-3-yl)-1H-pyrazolo[4,3-b]pyridine

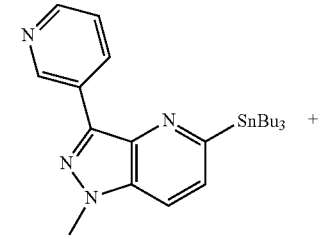

1-methyl-3-(pyridin-3-yl)-5-(tributylstannyl)-1H-pyrazolo[4,3-b]pyridine +

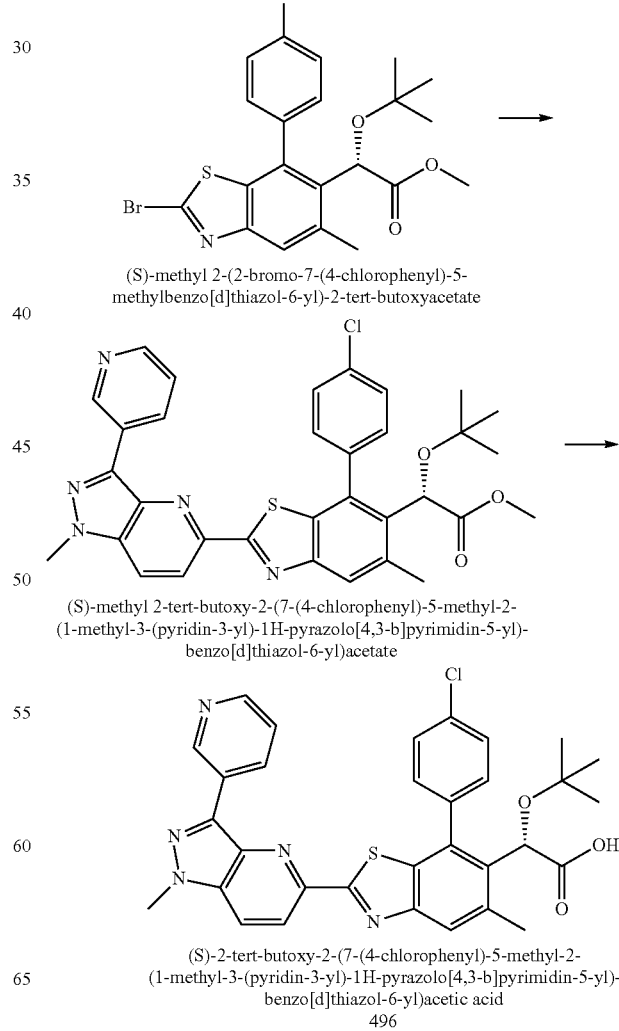

(S)-methyl 2-(2-bromo-7-(4-chlorophenyl)-5-methylbenzo[d]thiazol-6-yl)-2-tert-butoxyacetate (S)-methyl 2-tert-butoxy-2-(7-(4-chlorophenyl)-5-methyl-2-(1-methyl-3-(pyridin-3-yl)-1H-pyrazolo[4,3-b]pyrimidin-5-yl)-benzo[d]thiazol-6-yl)acetate (S)-2-tert-butoxy-2-(7-(4-chlorophenyl)-5-methyl-2-(1-methyl-3-(pyridin-3-yl)-1H-pyrazolo[4,3-b]pyrimidin-5-yl)-benzo[d]thiazol-6-yl)acetic acid
496

Preparation of 5-chloro-3-iodo-1H-pyrazolo[4,3-b]pyridine: To a solution of 5-chloro-1H-pyrazolo[4,3-b]pyridine (100 mg, 0.65 mmol) in DMF (5 mL), was added KOH (91 mg, 1.63 mmol), I$_2$ (247 mg, 0.98 mmol) at 0° C. The reaction mixture was stirred at 0° C. for 5 min and then stirred at room temperature overnight. The reaction mixture was diluted with EtOAc and water. The organic phase was washed by sat. NaHSO$_3$, dried over MgSO$_4$, filtered, concentrated, and purified by silica gel column, eluting by 0-70% EtOAc in hexanes to give the product. LCMS-ESI$^+$: calc'd for C$_6$H$_3$ClIN$_3$: 279.9 (M+H$^+$); Found: 279.3 (M+H$^+$).

Preparation of 5-chloro-3-iodo-1-methyl-1H-pyrazolo[4,3-b]pyridine: To a solution of 5-chloro-3-iodo-1H-pyrazolo[4,3-b]pyridine (102 mg, 0.365 mmol) in DMF (3 mL), was added Cs$_2$CO$_3$ (237 mg, 0.73 mmol), MeI (35 μL, 0.55 mmol). The reaction mixture was stirred at room temperature for 3 hours. The reaction mixture was diluted with EtOAc and water, the organic phase was dried over MgSO$_4$, filtered, concentrated and purified by silica gel column, eluting by 0-50% EtOAc in hexanes to give the product containing the isomer 5-chloro-3-iodo-2-methyl-2H-pyrazolo[4,3-b]pyridine (in about 1.5:1 ratio). LCMS-ESI$^+$: calc'd for C$_7$H$_5$Cl$_1$N$_3$: 293.9 (M+H$^+$); Found: 294.1 (M+H$^+$).

Preparation of 5-chloro-1-methyl-3-(pyridin-3-yl)-1H-pyrazolo[4,3-b]pyridine: To a solution of 5-chloro-3-iodo-1-methyl-1H-pyrazolo[4,3-b]pyridine (104 mg, 0.354 mmol, containing the isomer 5-chloro-3-iodo-2-methyl-21-1-pyrazolo[4,3-b]pyridine) was added pyridin-3-ylboronic acid (52 mg, 0.425 mmol). The reaction mixture was heated at 70° C. for 1 hr. Then the temperature was raised to 90° C. and the reaction was stirred at 90° C. for 2 h. The reaction was cooled down, washed with sat. NaHCO$_3$, extracted with EtOAc, dried over MgSO$_4$, filtered, concentrated down and purified by silica gel column to give the product. LCMS-ESI$^+$: calc'd for C$_{12}$H$_9$ClN$_4$: 245.0 (M+H$^+$); Found: 245.3 (M+H$^+$).

Preparation of 1-methyl-3-(pyridin-3-yl)-5-(tributylstannyl)-1H-pyrazolo[4,3-b]pyridine: To a solution of 5-chloro-1-methyl-3-(pyridin-3-yl)-1H-pyrazolo[4,3-b]pyridine (40 mg, 0.163 mmol) in toluene (5 mL), was added bis(tributyltin) (142 mg, 0.245 mmol) and Pd(PPh$_3$)$_4$ (19 mg, 0.016 mmol). The reaction mixture was heated at 170° C. for 1 hr. The reaction mixture was cooled down, washed with H$_2$O, extracted with EtOAc. The organic phase was dried over MgSO$_4$, filtered, concentrated and purified by silica gel column to give the product. LCMS-ESI$^+$: calc'd for C$_{24}$H$_{36}$N$_4$Sn: 501.2 (M+H$^+$); Found: 501.1 (M+H$^+$).

Preparation of (S)-methyl 2-tert-butoxy-2-(7-(4-chlorophenyl)-5-methyl-2-(1-methyl-3-(pyridin-3-yl)-1H-pyrazolo[4,3-b]pyridin-5-yl)benzo[d]thiazol-6-yl)acetate: To a solution of (S)-methyl 2-(2-bromo-7-(4-chlorophenyl)-5-methylbenzo[d]thiazol-6-yl)-2-tert-butoxyacetate (8 mg, 0.018 mmol) in dioxane (2 mL), was added 1-methyl-3-(pyridin-3-yl)-5-(tributylstannyl)-1H-pyrazolo[4,3-b]pyridine (9 mg, 0.018 mmol), CuI (3.4 mg, 0.018 mmol), LiCl (3.8 mg, 0.09 mmol) and Pd(PPh$_3$)$_4$ (2 mg, 0.002 mmol). The reaction mixture was heated at 100° C. for 2 h. The reaction was cooled, washed with sat. NaHCO$_3$, extracted by EtOAc, dried over MgSO$_4$, filtered, concentrated down and purified by silica gel column, eluting with 0-100% EtOAc in hexanes to give the product. LCMS-ESI$^+$: calc'd for C$_{33}$H$_{30}$ClN$_5$O$_3$S: 612.2 (M+H$^+$); Found: 612.2 (M+H$^+$).

Preparation of (S)-2-tert-butoxy-2-(7-(4-chlorophenyl)-5-methyl-2-(1-methyl-3-(pyridin-3-yl)-1H-pyrazolo[4,3-b]pyridin-5-yl)benzo[d]thiazol-6-yl)acetic acid: To a solution of (S)-methyl 2-tert-butoxy-2-(7-(4-chlorophenyl)-5-methyl-2-(1-methyl-3-(pyridin-3-yl)-1H-pyrazolo[4,3-b]pyridin-5-yl)benzo[d]thiazol-6-yl)acetate (6 mg, 0.01 mmol) in THF (0.5 mL) and MeOH (0.5 mL) was added 2N NaOH (100 μL). The reaction mixture was heated at 45° C. overnight. The reaction mixture was concentrated, the residue was dissolved in DMF and MeOH, filtered and purified by reverse phase HPLC (10-100% ACN/H$_2$O+0.1% TFA) to give the product (3 mg). $^1$H NMR (400 MHz, CD$_3$OD) δ 9.70 (bs, 1H), 8.97 (d, J=3.8 Hz, 1H), 8.60 (bs, 1H), 8.37 (d, J=4.4 Hz, 1H), 8.14 (d, J=4.2 Hz, 1H), 7.84-7.56 (m, 6H), 5.24 (s, 1H), 4.13 (s, 3H), 2.63 (s, 3H), 0.98 (s, 9H). LCMS-ESI$^+$: calc'd for C$_{32}$H$_{28}$ClN$_5$O$_3$S: 598.2 (M+H$^+$); Found: 598.2 (M+H$^+$).

Example 212

Preparation of (S)-2-tert-butoxy-2-(7-(4-chlorophenyl)-5-methyl-2-(1-methyl-3-(pyrimidin-5-yl)-1H-indazol-5-yl)benzo[d]thiazol-6-yl)acetic acid (497)

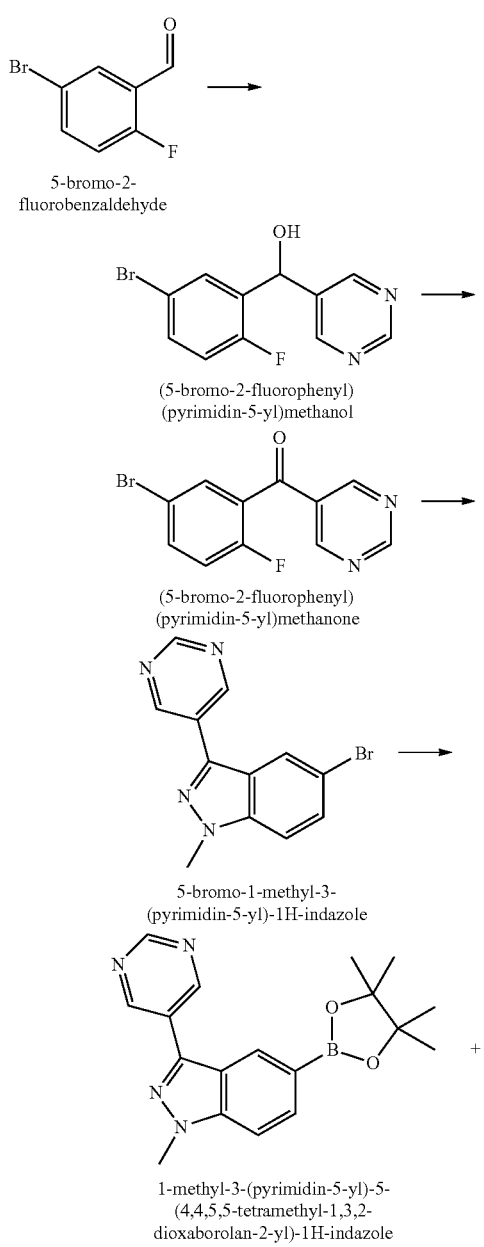

5-bromo-2-fluorobenzaldehyde (5-bromo-2-fluorophenyl)(pyrimidin-5-yl)methanol (5-bromo-2-fluorophenyl)(pyrimidin-5-yl)methanone 5-bromo-1-methyl-3-(pyrimidin-5-yl)-1H-indazole 1-methyl-3-(pyrimidin-5-yl)-5-(4,4,5,5-tetramethyl-1,3,2-dioxaborolan-2-yl)-1H-indazole

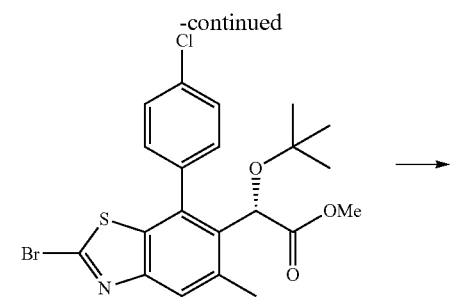

(S)-methyl 2-(2-bromo-7-(4-chlorophenyl)-5-methylbenzo[d]thiazol-6-yl)-2-tert-butoxyacetate

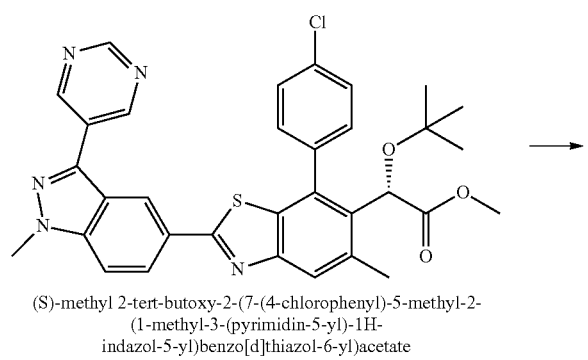

(S)-methyl 2-tert-butoxy-2-(7-(4-chlorophenyl)-5-methyl-2-(1-methyl-3-(pyrimidin-5-yl)-1H-indazol-5-yl)benzo[d]thiazol-6-yl)acetate

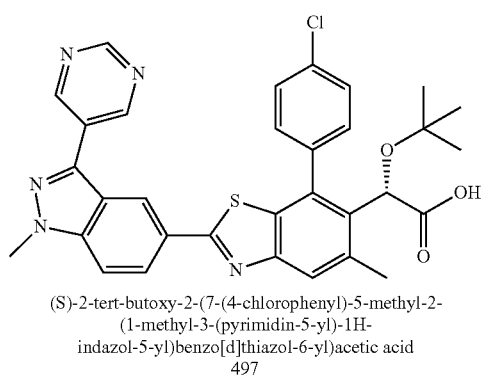

(S)-2-tert-butoxy-2-(7-(4-chlorophenyl)-5-methyl-2-(1-methyl-3-(pyrimidin-5-yl)-1H-indazol-5-yl)benzo[d]thiazol-6-yl)acetic acid
497

Preparation of (5-bromo-2-fluorophenyl)(pyrimidin-5-yl)methanol: To an oven-dried flask was added anhydrous THF (40 mL) and 5-bromopyrimidine (6.36 g, 40 mmol). 2M isopropylmagnesium chloride in THF (22 mL) was then added dropwise over several minutes at 0° C. The mixture was stirred at 0° C. for 30 minutes, and then 5-bromo-2-fluorobenzaldehyde (2.4 mL, 20 mmol) was added. After warming to room temperature, the reaction was quenched with saturated aqueous NH$_4$Cl. The aqueous layer was extracted with EtOAc, dried over MgSO$_4$, and purified by column chromatography (gradient 0 to 60% EtOAc in hexanes) to afford the product. $^1$H NMR (400 MHz, CDCl$_3$) δ 9.10 (s, 1H), 8.74 (s, 2H), 7.71 (dd, J=6.4, 2.5 Hz, 1H), 7.43 (ddd, J=8.7, 4.6, 2.6 Hz, 1H), 6.95 (dd, J=9.5, 8.9 Hz, 1H), 6.15 (s, 1H).

Preparation of (5-bromo-2-fluorophenyl)(pyrimidin-5-yl)methanone: To a stirring solution of (5-bromo-2-fluorophenyl)(pyrimidin-5-yl)methanol (2.42 g, 8.55 mmol) in DCM (40 mL) was added Dess-Martin periodinane (4 g, 9.4 mmol) portion-wise over several minutes. The reaction was then quenched with saturated 1:1 Na$_2$S$_2$O$_3$/NaHCO$_3$ solution (80 mL) and stirred until gas evolution ceased. The aqueous layer was extracted with DCM, dried over MgSO$_4$, and purified by column chromatography (gradient 0 to 30% EtOAc in hexanes) to give the product. $^1$H NMR (400 MHz, CDCl$_3$) δ 9.41 (s, 1H), 9.09 (d, J=1.6 Hz, 2H), 7.81 (dd, J=6.0, 2.6 Hz, 1H), 7.74 (ddd, J=8.8, 4.5, 2.6 Hz, 1H), 7.13 (t, J=9.1 Hz, 1H).

Preparation of 5-bromo-1-methyl-3-(pyrimidin-5-yl)-1H-indazole: A heavy wall pressure flask was charged with (5-bromo-2-fluorophenyl)(pyrimidin-5-yl)methanone (2.08 g, 7.4 mmol) and dioxane (20 mL). Methylhydrazine (0.86 mL, 16.3 mmol) was then added, and the mixture was heated to 100° C. for 16 hours. The crude mixture was concentrated, and the residue suspended in DCM. After storing at −10° C. for 2 hours, the precipitated solids were filtered off to give the product. $^1$H NMR (400 MHz, DMSO-d$_6$) δ 9.35 (s, 2H), 9.22 (s, 1H), 8.39 (d, J=1.1 Hz, 1H), 7.76 (d, J=8.9 Hz, 1H), 7.62 (dd, J=8.9, 1.7 Hz, 1H), 4.15 (s, 3H).

Preparation of 1-methyl-3-(pyrimidin-5-yl)-5-(4,4,5,5-tetramethyl-1,3,2-dioxaborolan-2-yl)-1H-indazole: To a vial flushed with argon was added 5-bromo-1-methyl-3-(pyrimidin-5-yl)-1H-indazole (376 mg, 1.3 mmol), PdCl$_2$(dppf).DCM (107 mg, 0.13 mmol), bis(pinacolato)diboron (363 mg, 1.43 mmol), and KOAc (383 mg, 3.9 mmol). Anhydrous dioxane (7 mL) was added, and the mixture was heated to 90° C. for 3 hours. After cooling to room temperature, the crude reaction was filtered over a plug of Celite, concentrated, and the crude product used directly without further purification. LCMS-ESI$^+$: calc'd for C$_{18}$H$_{22}$BN$_4$O$_2$: 337.2 (M+H$^+$); Found: 337.3 (M+H$^+$).

Preparation of (S)-methyl 2-tert-butoxy-2-(7-(4-chlorophenyl)-5-methyl-2-(1-methyl-3-(pyrimidin-5-yl)-1H-indazol-5-yl)benzo[d]thiazol-6-yl)acetate: To a vial flushed with argon was added (S)-methyl 2-(2-bromo-7-(4-chlorophenyl)-5-methylbenzo[d]thiazol-6-yl)-2-tert-butoxyacetate (110 mg, 0.23 mmol), 1-methyl-3-(pyridin-3-yl)-5-(4,4,5,5-tetramethyl-1,3,2-dioxaborolan-2-yl)-1H-indazole (92 mg, 0.27 mmol), Pd(PPh$_3$)$_4$ (26 mg, 23 µmol), and K$_2$CO$_3$ (95 mg, 0.68 mmol). De-gassed dioxane (2 mL) and water (0.5 mL) were then added, and the reaction was heated to 100° C. for 1 h. After cooling to room temperature, the reaction was filtered over a plug of Celite, concentrated, and purified by column chromatography (gradient 0 to 50% EtOAc in hexanes) to give the product. $^1$H NMR (400 MHz, CDCl$_3$) δ 9.37 (s, 2H), 9.27 (s, 1H), 8.56 (s, 1H), 8.22 (dd, J=8.9, 1.3 Hz, 1H), 7.88 (s, 1H), 7.59-7.45 (m, 5H), 5.22 (s, 1H), 4.19 (s, 3H), 3.75 (s, 3H), 2.60 (s, 3H), 0.99 (s, 9H).

Preparation of (S)-2-tert-butoxy-2-(7-(4-chlorophenyl)-5-methyl-2-(1-methyl-3-(pyrimidin-5-yl)-1H-indazol-5-yl)benzo[d]thiazol-6-yl)acetic acid: To a vial was dissolved (S)-methyl 2-tert-butoxy-2-(7-(4-chlorophenyl)-5-methyl-2-(1-methyl-3-(pyrimidin-5-yl)-1H-indazol-5-yl)benzo[d]thiazol-6-yl)acetate (130 mg, 0.212 mmol) in THF (3 mL) and MeOH (1.5 mL) 1M NaOH (1.5 mL) was added, and the mixture was heated to 50° C. for 3 hours. The reaction was cooled to room temperature, and filtered (0.45 micron teflon syringe filter). The filtrate was purified by reverse phase column chromatography (5-100% ACN/H$_2$O+0.1% TFA). Fractions containing the product were pooled and lyophilized to provide the TFA salt of the product. LCMS-ESI$^+$: calc'd for C$_{32}$H$_{29}$ClN$_5$O$_3$S: 598.1 (M+H$^+$); Found: 598.2 (M+H$^+$). $^1$H NMR (400 MHz, CD$_3$OD) δ 9.34 (s, 2H), 9.14 (s, 1H), 8.57 (s, 1H), 8.01 (d, J=8.9 Hz, 1H), 7.77 (s, 1H), 7.70 (d, J=8.9 Hz, 1H), 7.65 (d, J=8.9 Hz, 1H), 7.58 (d, J=6.0 Hz, 3H), 5.25 (s, 1H), 4.13 (s, 3H), 2.61 (s, 3H), 0.98 (s, 9H).

Example 213

Preparation of (S)-2-tert-butoxy-2-(7-(4-chlorophenyl)-5-methyl-2-(2-(4-(oxetan-3-yl)piperazin-1-yl)pyrimidin-4-yl)benzo[d]thiazol-6-yl)acetic acid (336)

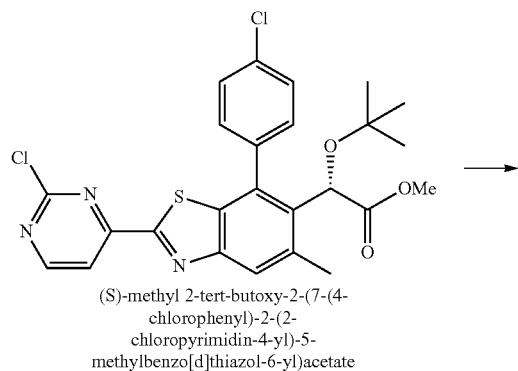

(S)-methyl 2-tert-butoxy-2-(7-(4-chlorophenyl)-2-(2-chloropyrimidin-4-yl)-5-methylbenzo[d]thiazol-6-yl)acetate

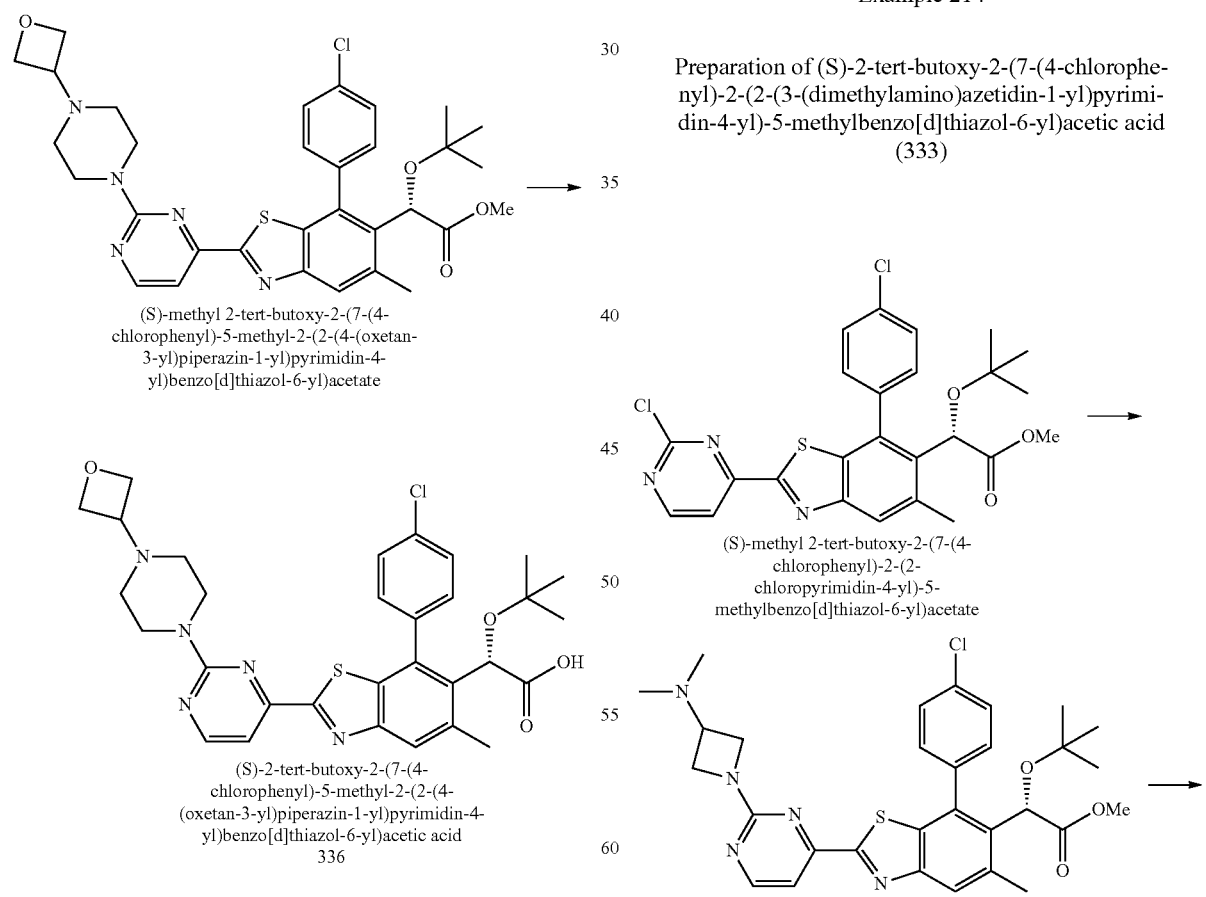

(S)-methyl 2-tert-butoxy-2-(7-(4-chlorophenyl)-5-methyl-2-(2-(4-(oxetan-3-yl)piperazin-1-yl)pyrimidin-4-yl)benzo[d]thiazol-6-yl)acetate (S)-2-tert-butoxy-2-(7-(4-chlorophenyl)-5-methyl-2-(2-(4-(oxetan-3-yl)piperazin-1-yl)pyrimidin-4-yl)benzo[d]thiazol-6-yl)acetic acid 336

Preparation of (S)-methyl 2-tert-butoxy-2-(7-(4-chlorophenyl)-5-methyl-2-(2-(4-(oxetan-3-yl)piperazin-1-yl)pyrimidin-4-yl)benzo[d]thiazol-6-yl)acetate: To (S)-methyl 2-tert-butoxy-2-(7-(4-chlorophenyl)-2-(2-chloropyrimidin-4-yl)-5-methylbenzo[d]thiazol-6-yl)acetate (49.0 mg, 0.095 mmol) was added 1-(oxetan-3-yl)piperazine (27.0 mg, 0.190 mmol) in 1,4-dioxane (1 mL). The reaction mixture was stirred at room temperature for 6 h. Upon completion of the reaction, the reaction mixture was filtered through Celite (ethyl acetate eluent), concentrated, and used without further purification. LCMS-ESI$^+$ calc'd for $C_{32}H_{37}ClN_5O_4S$ (M+H$^+$): 622.2; Found: 622.2 (M+H$^+$).

Preparation of (S)-2-tert-butoxy-2-(7-(4-chlorophenyl)-5-methyl-2-(2-(4-(oxetan-3-yl)piperazin-1-yl)pyrimidin-4-yl)benzo[d]thiazol-6-yl)acetic acid: To crude (S)-methyl 2-tert-butoxy-2-(7-(4-chlorophenyl)-5-methyl-2-(2-(4-(oxetan-3-yl)piperazin-1-yl)pyrimidin-4-yl)benzo[d]thiazol-6-yl)acetate in THF (0.5 mL) and methanol (0.5 mL) was added NaOH (0.47 mL of a 2N solution). The reaction mixture was heated at 30° C. overnight, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{31}H_{35}ClN_5O_4S$ (M+H$^+$): 608.2; Found: 608.2 (M+H$^+$). $^1$H NMR (400 MHz, Methanol-d$_4$) δ 8.62 (d, J=5.0 Hz, 1H), 7.92 (s, 1H), 7.70-7.64 (m, 1H), 7.63-7.52 (m, 4H), 5.25 (s, 1H), 4.93-4.88 (m, 2H), 4.83-4.77 (m, 2H), 4.57-3.46 (m, 5H), 3.22 (br s, 4H), 2.63 (s, 3H), 0.98 (s, 9H).

Example 214

Preparation of (S)-2-tert-butoxy-2-(7-(4-chlorophenyl)-2-(2-(3-(dimethylamino)azetidin-1-yl)pyrimidin-4-yl)-5-methylbenzo[d]thiazol-6-yl)acetic acid (333)

(S)-methyl 2-tert-butoxy-2-(7-(4-chlorophenyl)-2-(2-chloropyrimidin-4-yl)-5-methylbenzo[d]thiazol-6-yl)acetate (S)-methyl 2-tert-butoxy-2-(7-(4-chlorophenyl)-2-(2-)3-(dimethylamino)azetidin-1-yl)pyrimidin-4-yl)-5-methylbenzo[d]thiazol-6-yl)acetate

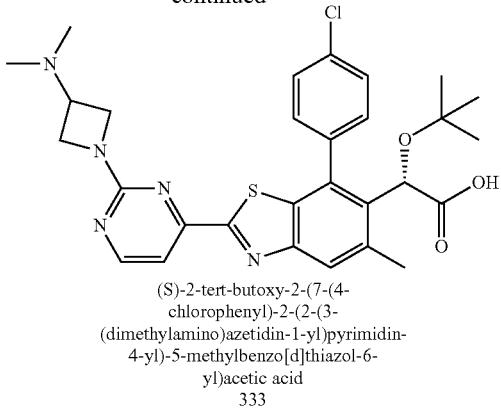

(S)-2-tert-butoxy-2-(7-(4-chlorophenyl)-2-(2-(3-(dimethylamino)azetidin-1-yl)pyrimidin-4-yl)-5-methylbenzo[d]thiazol-6-yl)acetic acid
333

Preparation of (S)-methyl 2-tert-butoxy-2-(7-(4-chlorophenyl)-2-(2-(3-(dimethylamino)azetidin-1-yl)pyrimidin-4-yl)-5-methylbenzo[d]thiazol-6-yl)acetate: To (S)-methyl 2-tert-butoxy-2-(7-(4-chlorophenyl)-2-(2-chloropyrimidin-4-yl)-5-methylbenzo[d]thiazol-6-yl)acetate (30.0 mg, 0.058 mmol) and 3-(dimethylamino)azetidine dihydrochloride (30.2 mg. 0.174 mmol) in 1,4-dioxane (1 mL) was added triethylamine (58.8 mg, 81.0 µL, 0.581 mmol). The reaction mixture was heated at 50° C. for 1 h. Upon completion of the reaction, the reaction mixture was filtered through Celite (ethyl acetate eluent), concentrated, and used without further purification. LCMS-ESI$^+$ calc'd for $C_{30}H_{35}ClN_5O_3S$ (M+H$^+$): 580.2; Found: 580.1 (M+H$^+$).

Preparation of (S)-2-tert-butoxy-2-(7-(4-chlorophenyl)-2-(2-(3-(dimethylamino)azetidin-1-yl)pyrimidin-4-yl)-5-methylbenzo[d]thiazol-6-yl)acetic acid: To crude (S)-methyl 2-tert-butoxy-2-(7-(4-chlorophenyl)-2-(2-(3-(dimethylamino)azetidin-1-yl)pyrimidin-4-yl)-5-methylbenzo[d]thiazol-6-yl)acetate in THF (0.5 mL) and methanol (0.5 mL) was added NaOH (0.29 mL of a 2N solution). The reaction mixture was heated at 30° C. overnight, then cooled, filtered, and purified by reverse phase HPLC, eluting with 5-100% acetonitrile in water with 0.1% TFA. Fractions containing the product were pooled and lyophilized to provide the TFA salt of the product. LCMS-ESI$^+$: calc'd for $C_{29}H_{33}ClN_5O_3S$ (M+H$^+$): 566.2; Found: 566.1 (M+H$^+$). $^1$H NMR (400 MHz, Methanol-d$_4$) δ 8.59 (d, J=5.1 Hz, 1H), 7.92 (s, 1H), 7.70-7.50 (m, 5H), 5.26 (s, 1H), 4.54-4.44 (m, 2H), 4.34-4.15 (m, 3H), 2.95 (s, 6H), 2.63 (s, 3H), 0.98 (s, 9H).

Example 215

Preparation of (S)-2-tert-butoxy-2-(7-(4-chlorophenyl)-5-methyl-2-(2-(3-methyl-1H-pyrrolo[2,3-b]pyridin-5-yl)pyridin-4-yl)benzo[d]thiazol-6-yl)acetic acid (498)

498

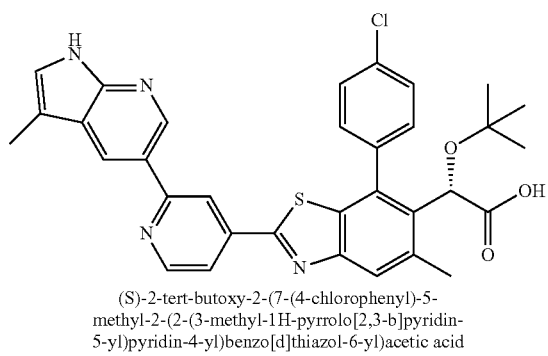

(S)-2-tert-butoxy-2-(7-(4-chlorophenyl)-5-methyl-2-(2-(3-methyl-1H-pyrrolo[2,3-b]pyridin-5-yl)pyridin-4-yl)benzo[d]thiazol-6-yl)acetic acid Preparation of (S)-2-tert-butoxy-2-(7-(4-chlorophenyl)-5-methyl-2-(2-(3-methyl-1H-pyrrolo[2,3-b]pyridin-5-yl)pyridin-4-yl)benzo[d]thiazol-6-yl)acetic acid: (S)-2-tert-Butoxy-2-(7-(4-chlorophenyl)-5-methyl-2-(2-(3-methyl-1H-pyrrolo[2,3-b]pyridin-5-yl)pyridin-4-yl)benzo[d]thiazol-6-yl)acetic acid can be prepared from the ethyl ester ((S)-ethyl 2-(tert-butoxy)-2-(7-(4-chlorophenyl)-5-methyl-2-(2-(3-methyl-1H-pyrrolo[2,3-b]pyridin-5-yl)pyridin-4-yl)benzo[d]thiazol-6-yl)acetate) by the following the hydrolysis step described in method H. LCMS-ESI$^+$: calc'd for $C_{33}H_{29}ClN_4O_3S$: 597.2 (M+H$^+$); found: 597.2 (M+H$^+$). $^1$H NMR (400 MHz, CD$_3$OD): δ 8.99 (s, 1H), 8.96 (s, 1H), 8.82 (d, J=5.6 Hz, 1H), 8.66 (s, 1H), 8.06-8.03 (m, 1H), 7.98 (s, 1H), 7.73-7.65 (m, 1H), 7.65-7.60 (m, 3H), 7.37 (s, 1H), 5.28 (s, 1H), 2.65 (s, 3H), 2.45 (s, 3H), 0.98 (s, 9H).

Example 216

Preparation of (S)-2-(tert-butoxy)-2-(7-(4-chlorophenyl)-5-methyl-2-(2-(4-(N-methylacetamido)phenyl)pyridin-4-yl)benzo[d]thiazol-6-yl)acetic acid (499)

499

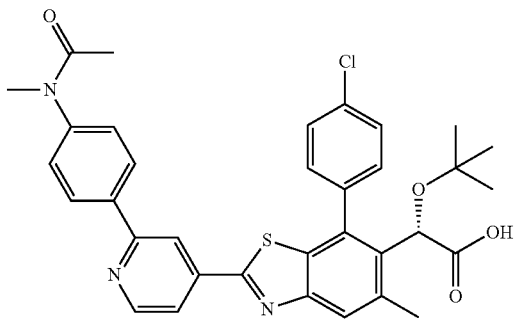

Preparation of (S)-2-(tert-butoxy)-2-(7-(4-chlorophenyl)-5-methyl-2-(2-(4-(N-methylacetamido)phenyl)pyridin-4-yl)benzo[d]thiazol-6-yl)acetic acid: (S)-2-(tert-Butoxy)-2-(7-(4-chlorophenyl)-5-methyl-2-(2-(4-(N-methylacetamido)phenyl)pyridin-4-yl)benzo[d]thiazol-6-yl)acetic acid was prepared following the procedure of method W . LCMS-ESI$^+$: calc'd for $C_{34}H_{32}ClN_3O_4S$: 614.15 (M+H$^+$); found: 614.2 (M+H$^+$). $^1$H NMR (400 MHz, CD$_3$OD) δ 8.66 (d, J=4.8 Hz, 1H), 8.41 (s, 1H), 8.04 (d, J=8.0 Hz, 2H), 7.89 (d, J=5.2 Hz, 1H), 7.81 (s, 1H), 7.60 (d, J=8.4 Hz, 1H), 7.51-7.48 (m, 3H), 7.40 (d, J=8.0 Hz, 2H), 5.18 (s, 1H), 3.21 (s, 3H), 2.52 (s, 3H), 1.87 (s, 3H), 0.88 (s, 9H).

Example 217

Preparation of (S)-methyl 2-tert-butoxy-2-(7-(4-chlorophenyl)-2-(2-chloropyrimidin-4-yl)-5-methylbenzo[d]thiazol-6-yl)acetate

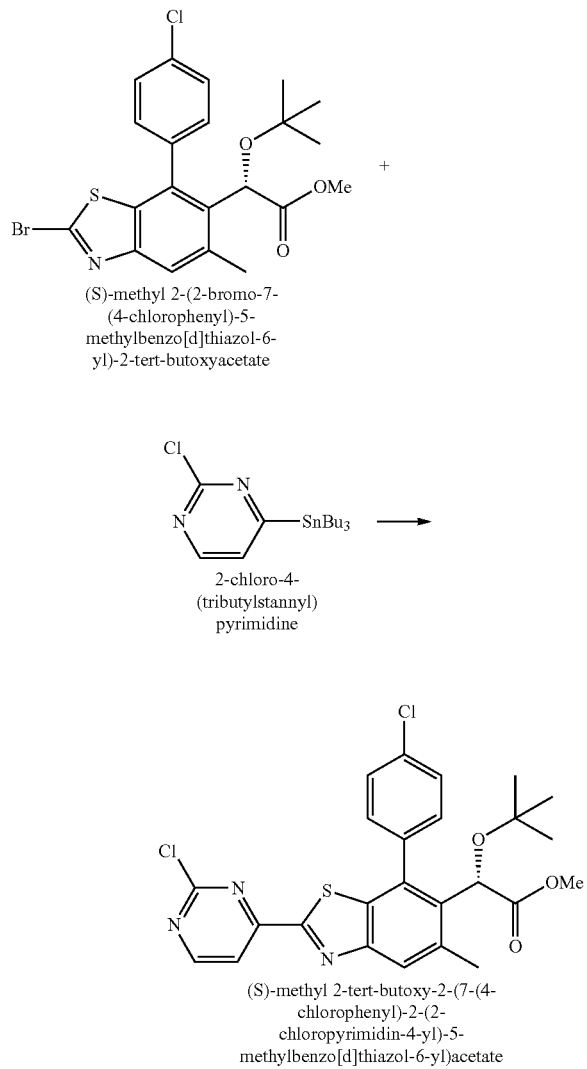

(S)-methyl 2-(2-bromo-7-(4-chlorophenyl)-5-methylbenzo[d]thiazol-6-yl)-2-tert-butoxyacetate 2-chloro-4-(tributylstannyl)pyrimidine (S)-methyl 2-tert-butoxy-2-(7-(4-chlorophenyl)-2-(2-chloropyrimidin-4-yl)-5-methylbenzo[d]thiazol-6-yl)acetate Preparation of (S)-methyl 2-tert-butoxy-2-(7-(4-chlorophenyl)-2-(2-chloropyrimidin-4-yl)-5-methylbenzo[d]thiazol-6-yl)acetate: A microwave vial was charged with (S)-methyl 2-(2-bromo-7-(4-chlorophenyl)-5-methylbenzo[d]thiazol-6-yl)-2-tert-butoxyacetate (496.3 mg, 1.03 mmol), tetrakis(triphenylphosphine)palladium(0) (178.2 mg, 0.15 mmol), lithium chloride (43.6 mg, 1.03 mmol), and copper(I) iodide (58.7 mg, 0.31 mmol) and the vial was evacuated and backfilled with argon (3×). To this mixture was added 2-chloro-4-(tributyl)stannyl pyrimidine (456.3 mg, 1.13 mmol) in 1,4-dioxane (10 mL). The reaction mixture was heated at 90° C. overnight, then cooled, filtered through Celite (ethyl acetate eluent), and concentrated. Purification by flash column chromatography on silica gel (hexanes/ethyl acetate eluent) provided the product. LCMS-ESI+ calc'd for $C_{25}H_{23}Cl_2N_3O_3S$ (M+H+): 516.1; Found: 516.2 (M+H+).

Example 218

The following illustrate representative pharmaceutical dosage forms, containing a compound of formula I or I' ('Compound X'), for therapeutic or prophylactic use in humans.

|  | mg/tablet |
|---|---|
| (i) Tablet 1 |  |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |
| (ii) Tablet 2 |  |
| Compound X = | 20.0 |
| Microcrystalline cellulose | 410.0 |
| Starch | 50.0 |
| Sodium starch glycolate | 15.0 |
| Magnesium stearate | 5.0 |
|  | 500.0 |
| (iii) Capsule | mg/capsule |
| Compound X = | 10.0 |
| Colloidal silicon dioxide | 1.5 |
| Lactose | 465.5 |
| Pregelatinized starch | 120.0 |
| Magnesium stearate | 3.0 |
|  | 600.0 |
|  | mg/ml |
| (iv) Injection 1 (1 mg/ml) |  |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) |  |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |
| (vi) Aerosol | mg/can |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound, or a pharmaceutically acceptable salt thereof, of formula I':

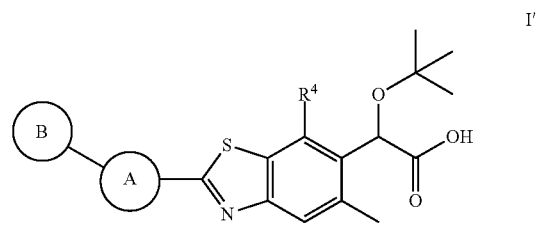

wherein:
R⁴ is:

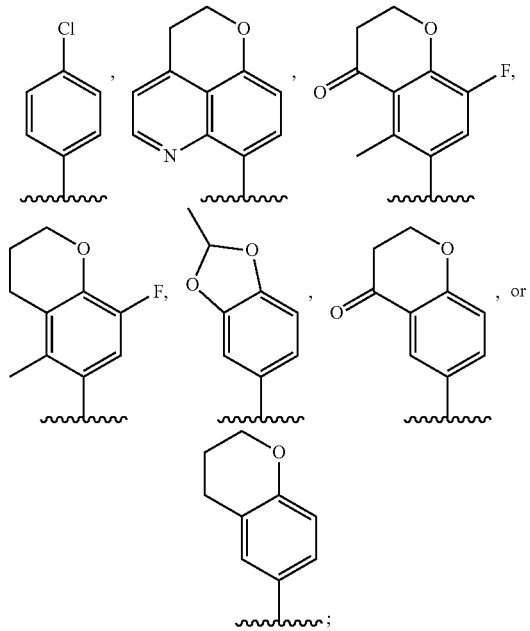

A is phenyl, 6-membered N-heteroaryl, thiazolyl, pyridinyl-2(1H)-one, tetrahydropyrimidin-2(1H)-one, imidazolidinyl-2-one, pyrrolidinyl-2-one, pyrrolidinyl, pyrazin-2(1H)-one, piperazinyl-2-one, piperazinyl, morpholinyl, or piperidinyl, wherein A is optionally substituted with 1 to 5 $Z^{1a}$ groups;

B is $(C_6$-$C_{20})$aryl, heteroaryl or heterocycle, wherein B is optionally substituted with 1 to 5 $Z^{1b}$ groups; or A and B together form a bicyclic $(C_9$-$C_{14})$aryl, bicyclic heteroaryl or bicyclic heterocycle, wherein bicyclic $(C_9$-$C_{14})$aryl, bicyclic heteroaryl or bicyclic heterocycle is optionally substituted with 1 to 5 $Z^{1b}$ groups;

each $Z^{1a}$ is independently halo, $(C_1$-$C_3)$alkyl, $(C_2$-$C_3)$alkenyl, $(C_2$-$C_3)$alkynyl, $(C_1$-$C_3)$haloalkyl, $(C_3$-$C_7)$carbocycle, heterocycle, —O$(C_1$-$C_3)$alkyl, —O$(C_2$-$C_3)$ alkenyl, —O($C_2$-$C_3$)alkynyl, —$NR_cR_d$, —$R_aC(O)R_a$, —C(O)$OR_b$ or —C(O)$NR_cR_d$, wherein any ($C_3$-$C_7$)carbocycle and heterocycle of $Z^{1a}$ is optionally substituted with 1 to 5 halogen or ($C_1$-$C_6$)alkyl;

each $Z^{1b}$ is independently halo, CN, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)carbocycle, heteroaryl, heterocycle, ($C_6$-$C_{20}$)aryl($C_1$-$C_6$)alkyl-, —OH, —O($C_1$-$C_6$)alkyl, —O($C_2$-$C_6$)alkenyl, —O($C_2$-$C_6$)alkynyl, —$NR_cR_d$, —$NR_aC(O)R_a$, —C(O)$OR_b$ or —C(O)$NR_cR_d$, wherein any ($C_3$-$C_7$)carbocycle and heterocycle of $Z^{1b}$ is optionally substituted with 1 to 5 halogen or ($C_1$-$C_6$)alkyl; and $R_a$, $R_b$, $R_c$ and $R_d$ are each independently H or ($C_1$-$C_6$)alkyl;

wherein each heteroaryl, as a monocyclic ring or portion of a 2 to 3 ring system, has 1 to 6 carbon atoms and 1 to 4 heteroatoms selected from the group consisting of oxygen, nitrogen and sulfur, and each heterocycle, as a monocyclic ring or portion of a 2 to 3 ring system, has 1 to 6 carbon atoms and 1 to 3 heteroatoms selected from the group consisting of oxygen, nitrogen and sulfur.

2. The compound of claim 1, or a pharmaceutically acceptable salt thereof, wherein:
A is pyridinyl, pyrimidinyl or pyrazinyl, optionally substituted with 1 to 5 $Z^{1a}$ groups; and
B is ($C_6$-$C_{20}$)aryl, heteroaryl or heterocycle, optionally substituted with 1 to 5 $Z^{1b}$ groups.

3. The compound of claim 1, or a pharmaceutically acceptable salt thereof, wherein:
A is pyridinyl, pyrimidinyl or pyrazinyl; and
B is heteroaryl or heterocycle, optionally substituted with 1 to 5 $Z^{1b}$ groups.

4. The compound of claim 1, or a pharmaceutically acceptable salt thereof, wherein:
A is pyridinyl, pyrimidinyl or pyrazinyl; and
B is a 4-6 membered monocyclic heterocycle optionally substituted with 1 to 5 $Z^{1b}$ groups.

5. The compound of claim 1, or a pharmaceutically acceptable salt thereof, wherein:
A is pyridinyl, pyrimidinyl or pyrazinyl; and
B is phenyl, pyridinyl, indazolyl, pyrazolo[4,3-b]pyridinyl, pyrimidinyl, pyrazolyl, benzo[d]imidazolyl, indazolyl, 1H-benzo[d]imidazolyl-2(3H)-one, 2H-pyrido[3,2-b][1,4]oxazinyl-3(4H)-one, 2,6-naphthyridin-1(2H)-one, 1,7-naphthyridinyl-8(7H)-one, 1H-indazolyl-3(2H)-one, quinolinyl-2(1H)-one, quinolinyl, pyrrolo[2,3-b]pyridinyl, pyrrolidinyl, piperazinyl, phenyl, imidazolyl, piperidinyl, morpholinyl, 5,6,7,8-tetrahydro-[1,2,4]triazolo[4,3-a]pyrazinyl, 4,5,6,7-tetrahydropyrazolo[4,3-c]pyridinyl, pyrazolo[1,5-a]pyrimidinyl, pyrimidinyl-2,4(1H,3H)-dionyl, pyridinyl-2(1H)-one, 1H-pyrazolo[3,4-c]pyridinyl, indolinyl-2-one, 1H-pyrrolo[3,4-c]pyridinyl-3(2H)-one, 2,3-dihydro-1H-pyrrolo[3,2-c]pyridinyl, pyrazolyl, pyrimidinyl-2(1H)-one, azetidinyl, tetrahydro-2H-pyranyl, 3,6-dihydro-2H-pyranyl, 1,2,3,6-tetrahydropyridine, 1H-pyrazolo[3,4-b]pyridinyl, 2H-benzo[b][1,4]oxazinyl-3(4H)-one, 3,4-dihydro-2H-pyrido[3,2-b][1,4]oxazinyl, indolinyl, 3,4-dihydrobenzo[f][1,4]oxazepin-5(2H)-one, 3H-imidazo[4,5-b]pyridinyl or 1H-benzo[d][1,2,3]triazolyl, wherein B is optionally substituted with 1 to 5 $Z^{1b}$ groups.

6. The compound of claim 1, or a pharmaceutically acceptable salt thereof, wherein A is pyridinyl, pyrimidinyl or pyrazinyl, and B is piperazinyl or azetidinyl, optionally substituted with 1 to 5 $Z^{1b}$ groups.

7. The compound of claim 1, or a pharmaceutically acceptable salt thereof, wherein A is not substituted with $Z^{1a}$.

8. The compound of claim 1, or a pharmaceutically acceptable salt thereof, wherein $Z^{1b}$ is ($C_1$-$C_6$)alkyl.

9. The compound of claim 1, or a pharmaceutically acceptable salt thereof, wherein A is not substituted with $Z^{1a}$; and $Z^{1b}$ is ($C_1$-$C_6$)alkyl.

10. The compound of claim 1, or a pharmaceutically acceptable salt thereof, wherein A and B together form a bicyclic ($C_9$-$C_{14}$)aryl, bicyclic heteroaryl or bicyclic heterocycle, wherein bicyclic ($C_9$-$C_{14}$)aryl, bicyclic heteroaryl or bicyclic heterocycle is optionally substituted with 1 to 5 $Z^{1b}$ groups.

11. The compound of claim 1, or a pharmaceutically acceptable salt thereof, wherein each $Z^{1b}$ is independently CN, ($C_2$-$C_6$)alkenyl, ($C_2$-$C_6$)alkynyl, ($C_1$-$C_6$)haloalkyl, ($C_3$-$C_7$)carbcycle, heteroaryl, heterocycle, ($C_6$-$C_{20}$)aryl($C_1$-$C_6$)alkyl-, —OH, —O($C_1$-$C_6$)alkyl, —O($C_2$-$C_6$)alkenyl, —O($C_2$-$C_6$)alkynyl, —$NR_cR_d$, —$NR_aC(O)R_a$, or —C(O)$NR_cR_d$.

12. The compound of claim 1, or a pharmaceutically acceptable salt thereof, selected from the group consisting of:

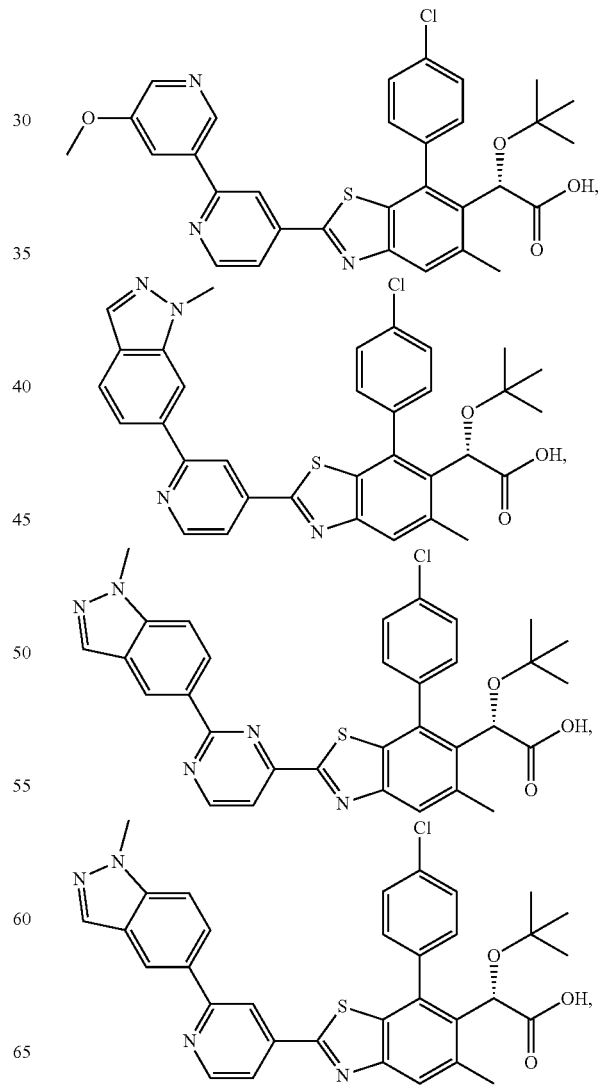

685
-continued
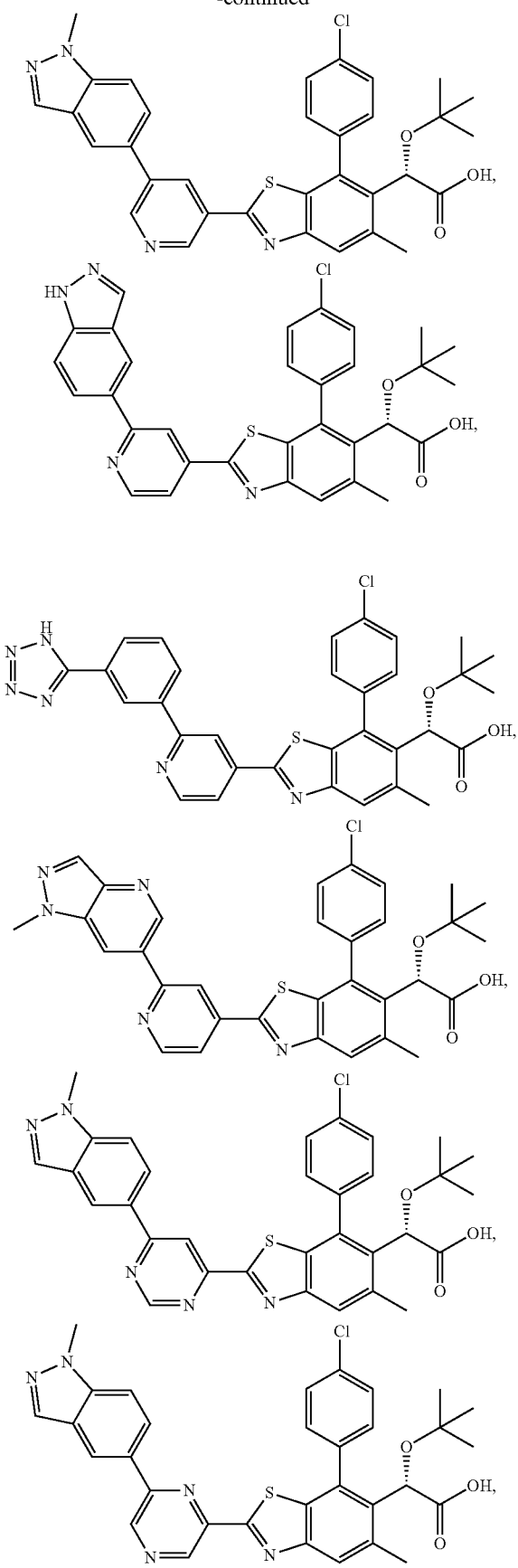
686
-continued
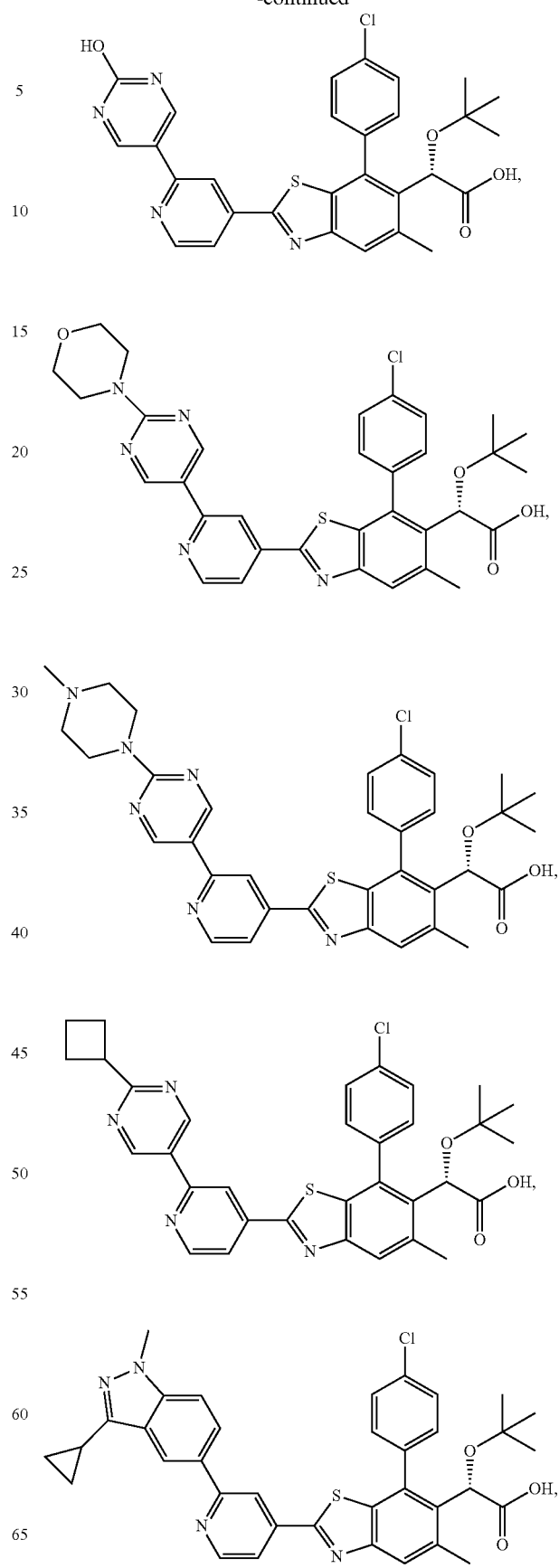

687
-continued
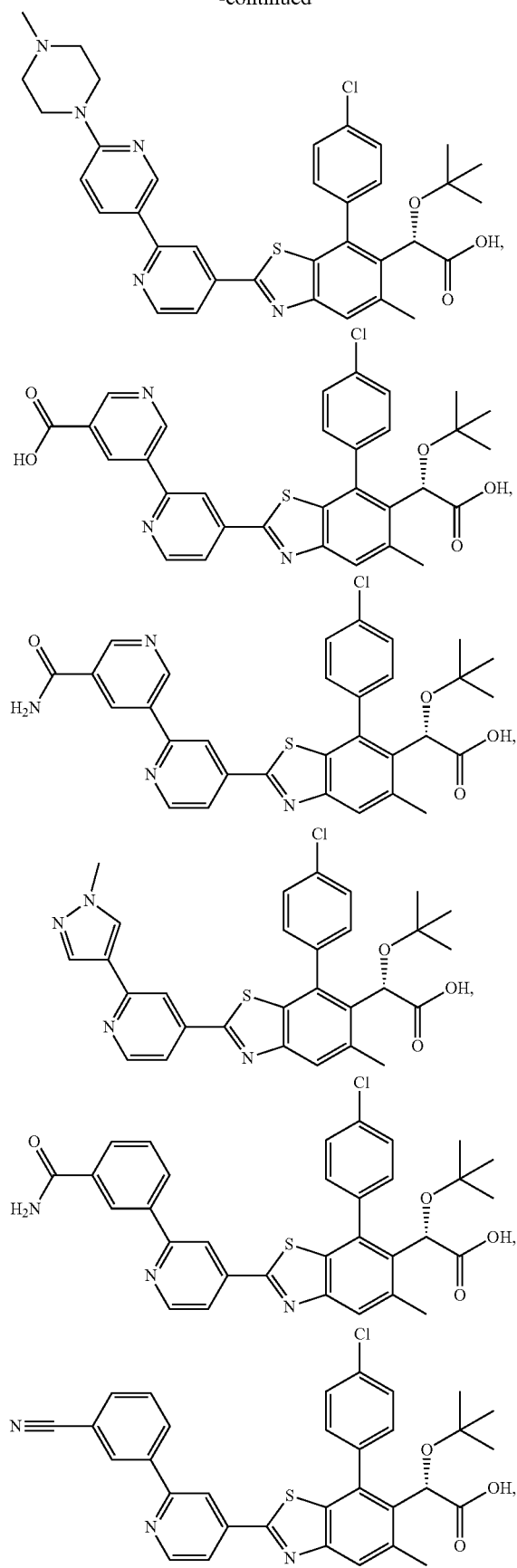
688
-continued
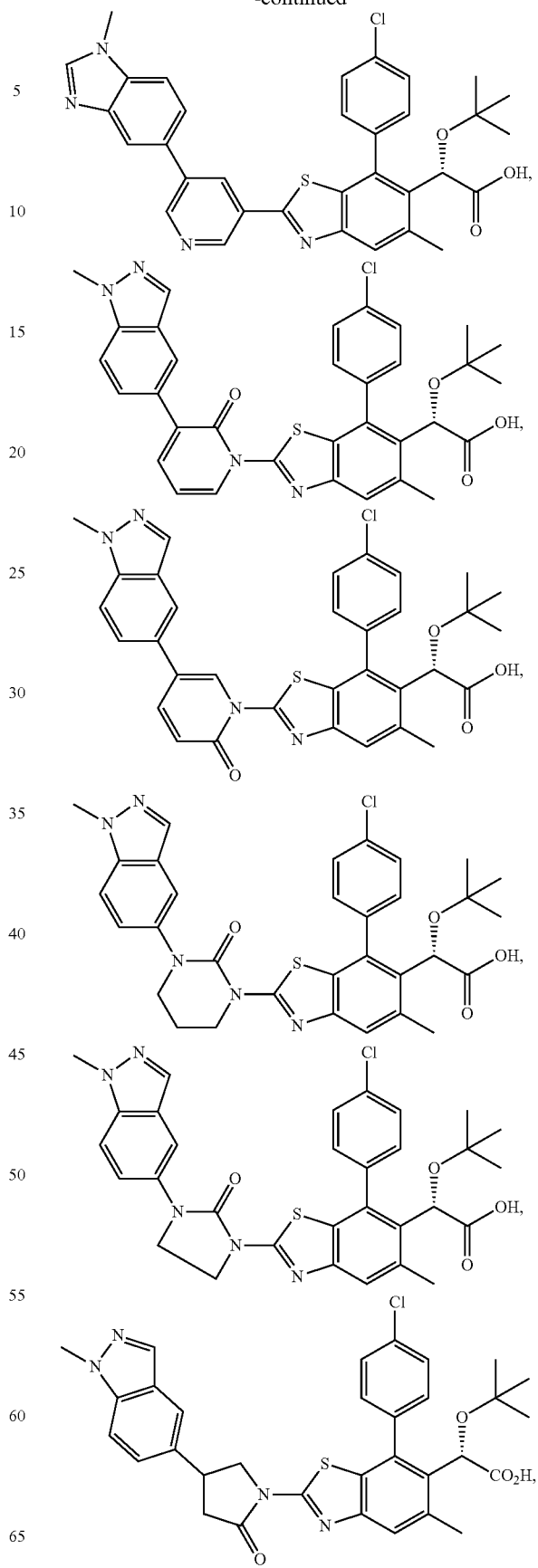

689
-continued
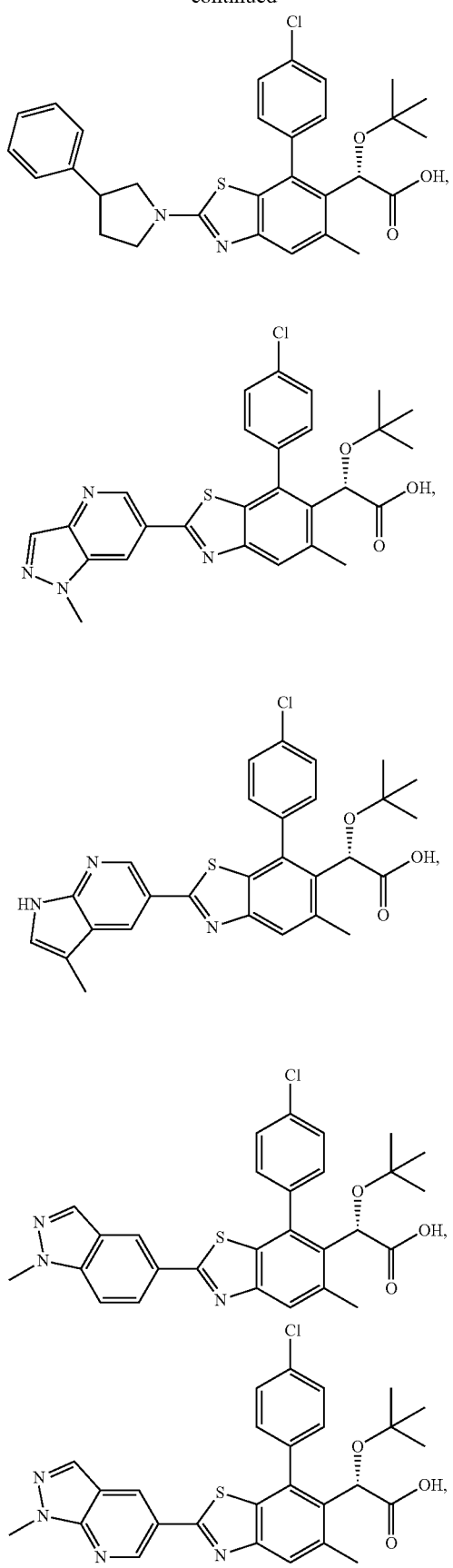
690
-continued
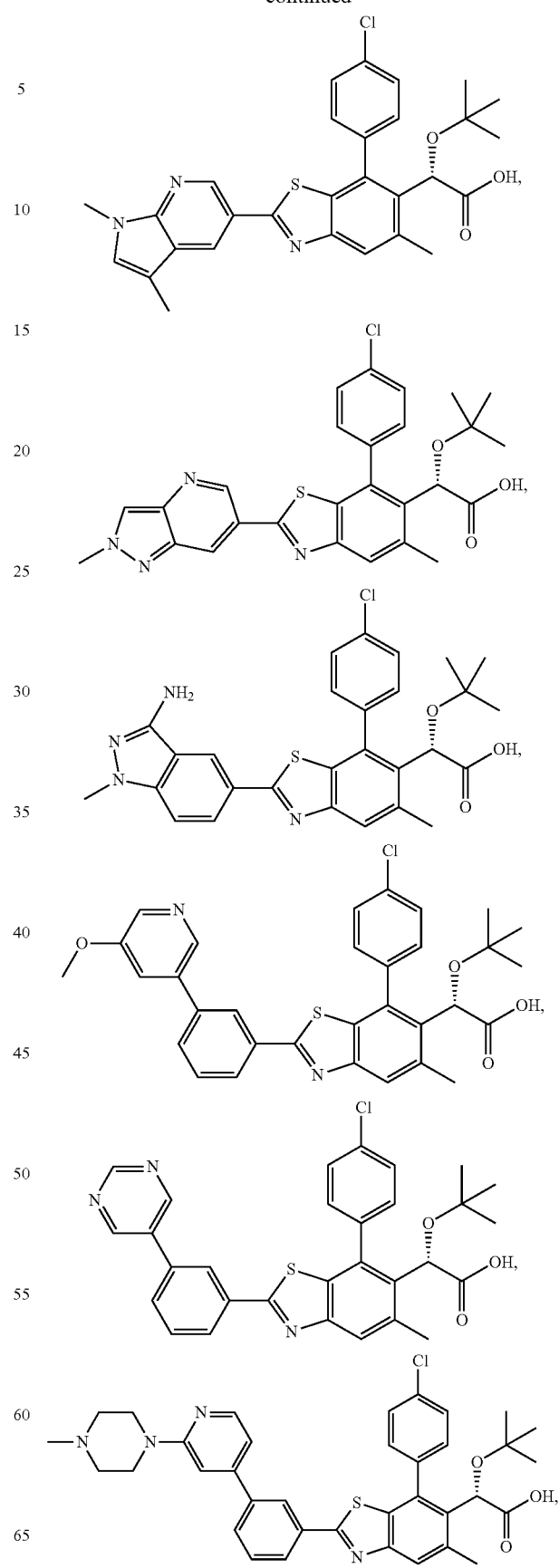

691
-continued
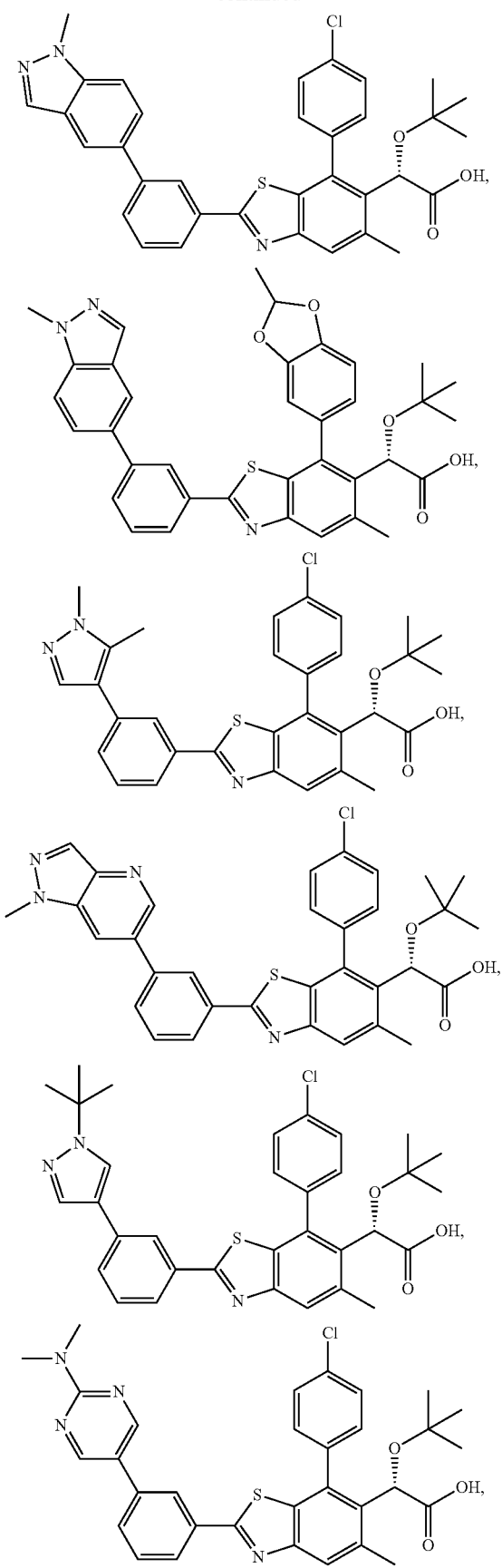
692
-continued
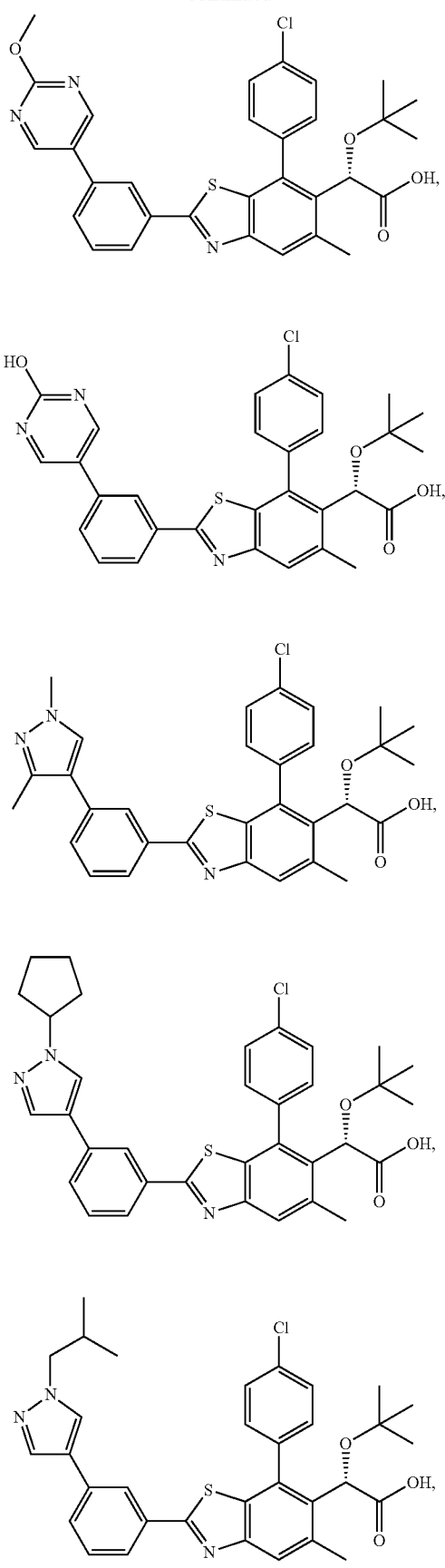

693
-continued
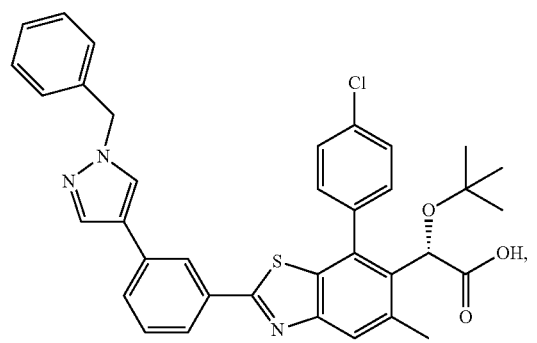
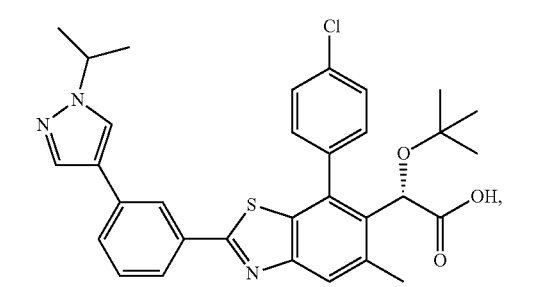
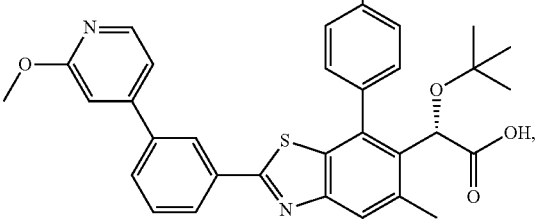
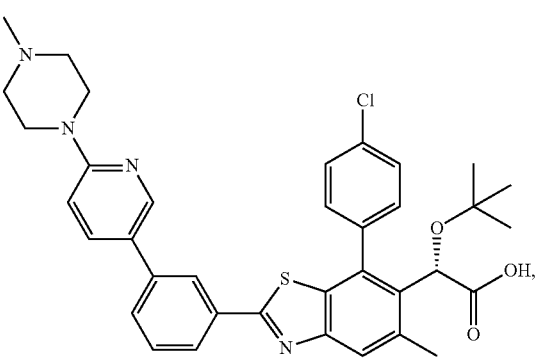
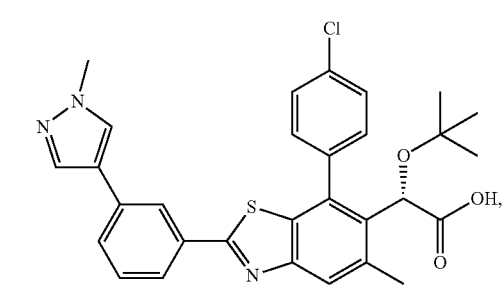
694
-continued
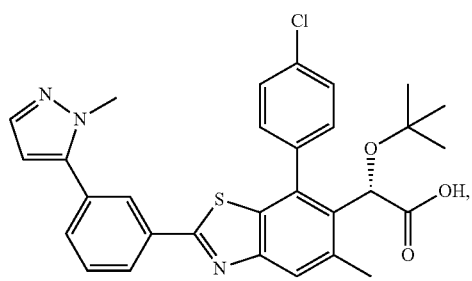
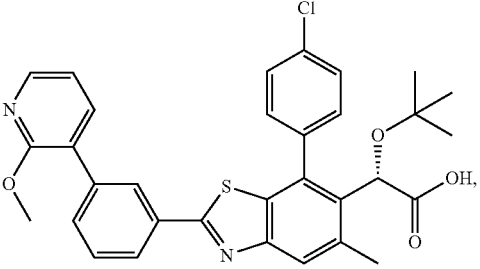
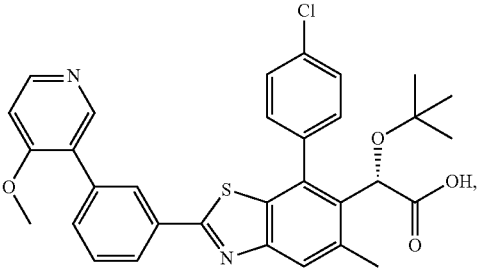
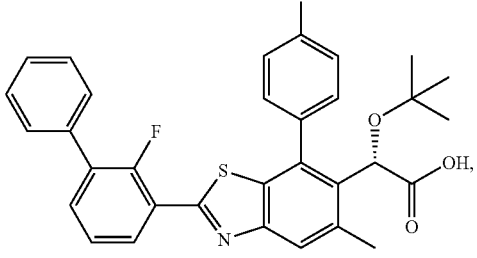
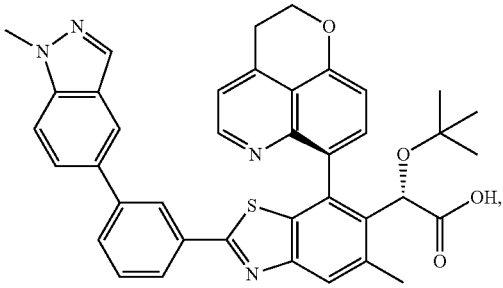
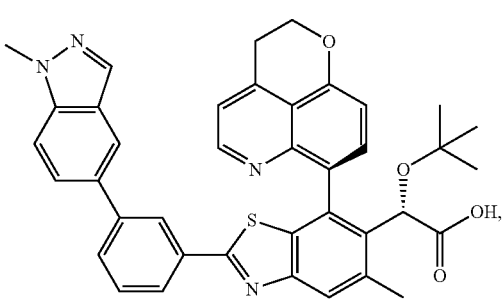

695
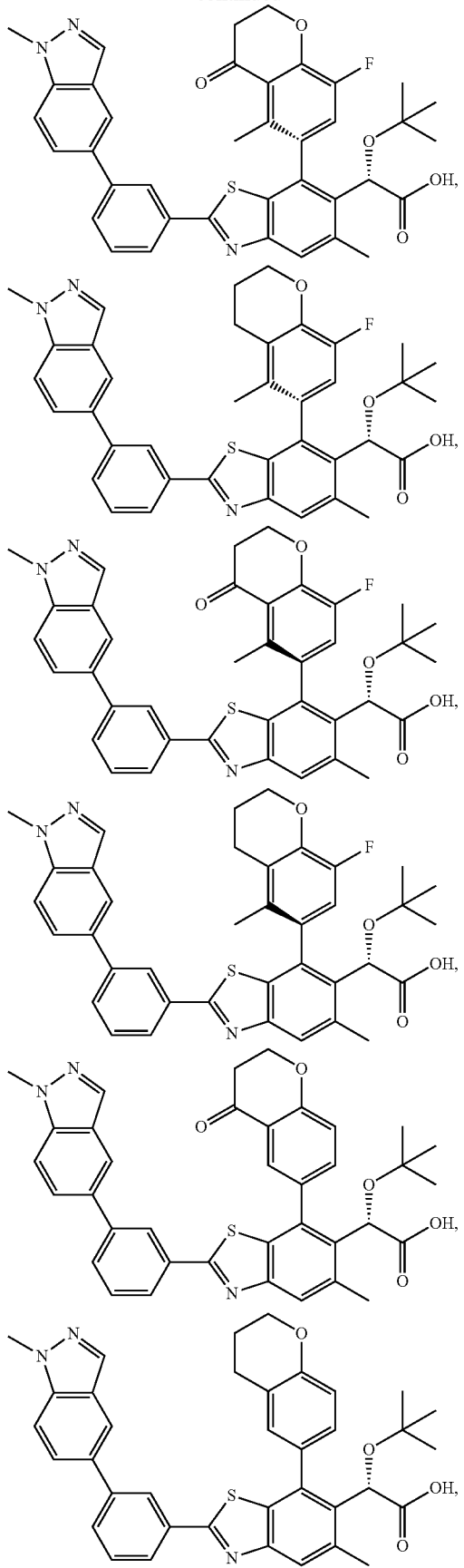
696
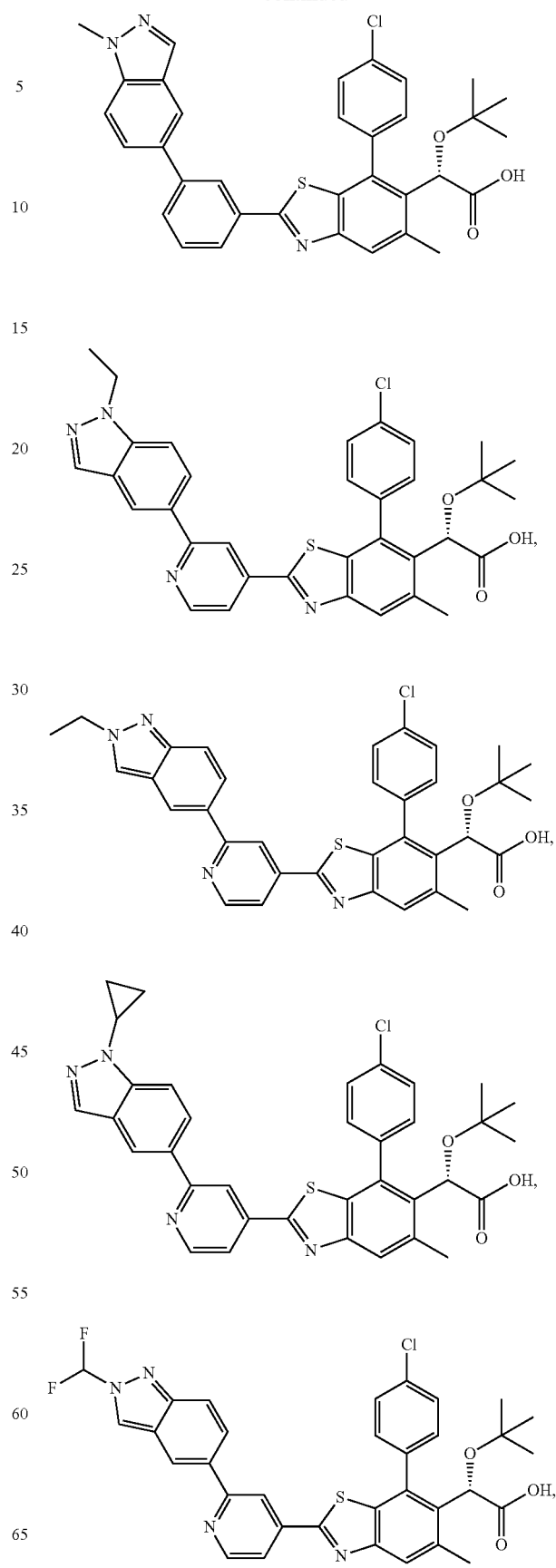

697
-continued
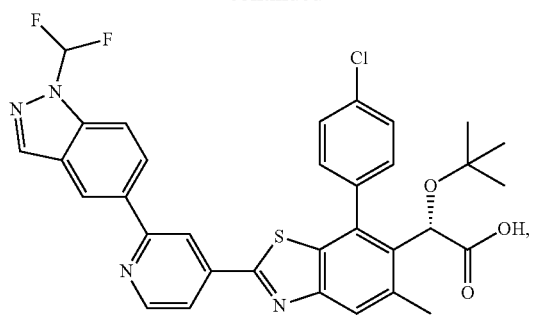
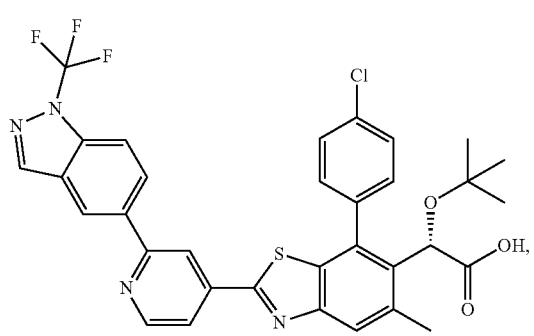
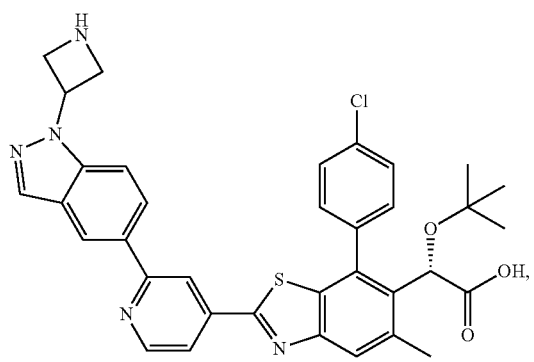
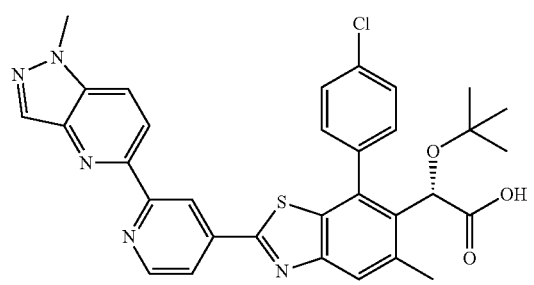
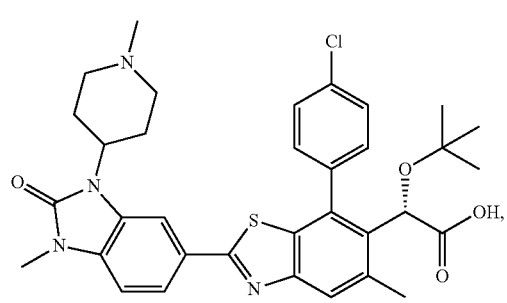
698
-continued
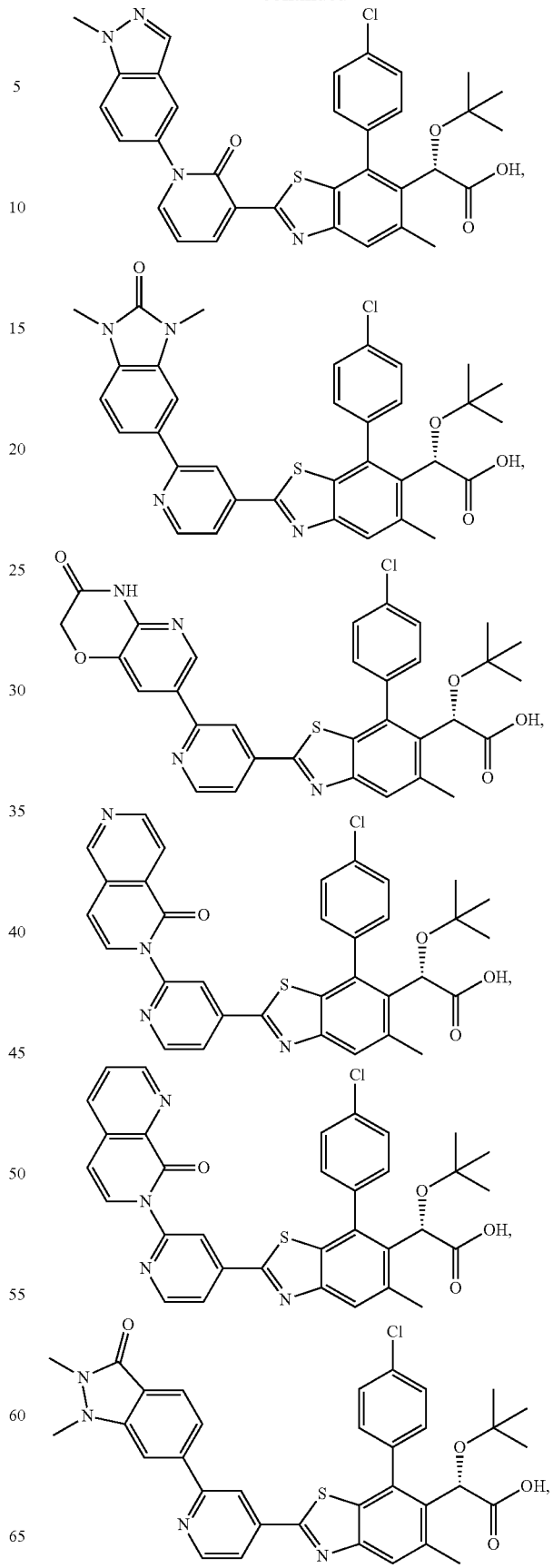

699
-continued
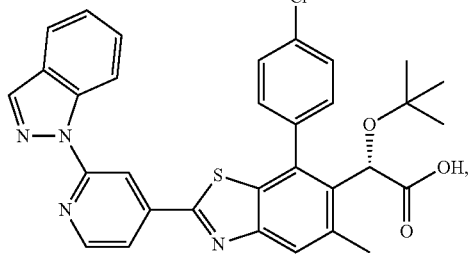
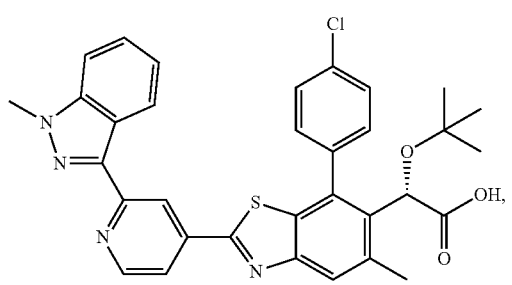
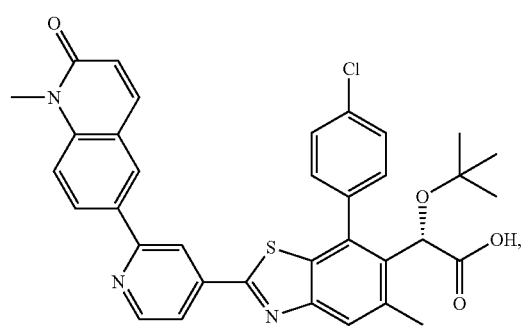
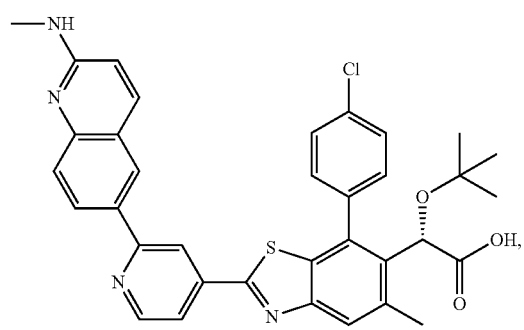
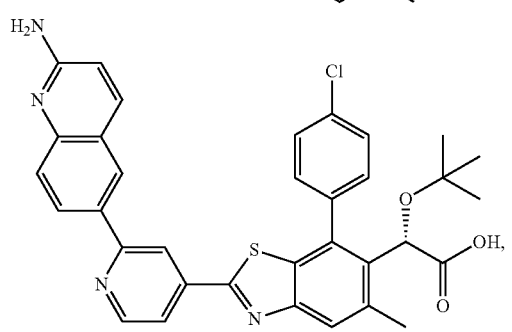
700
-continued
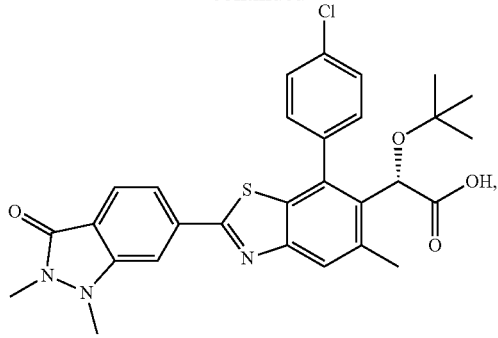
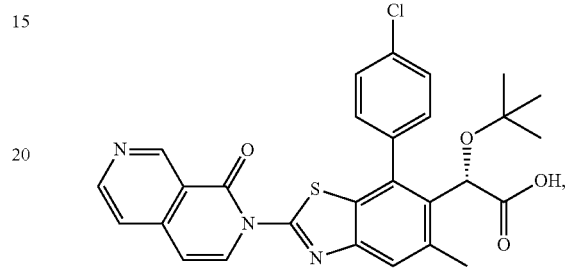
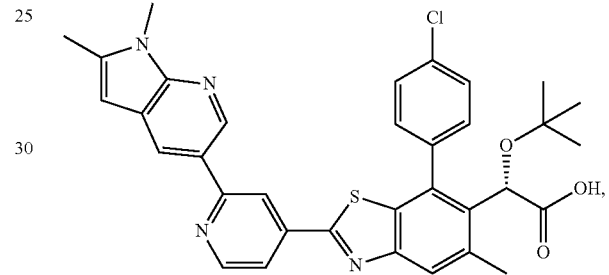
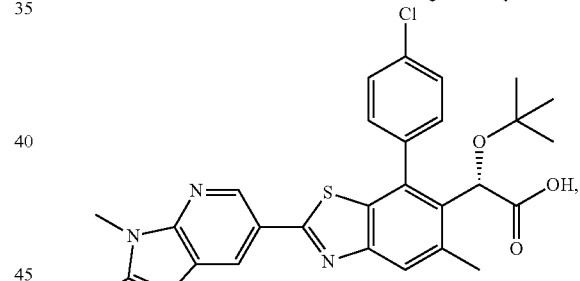
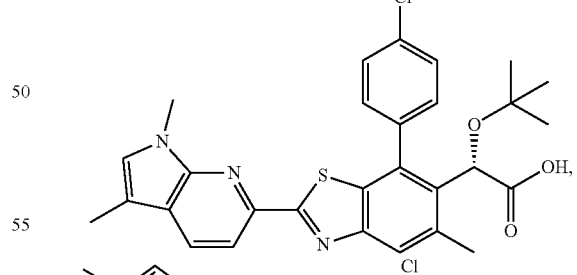
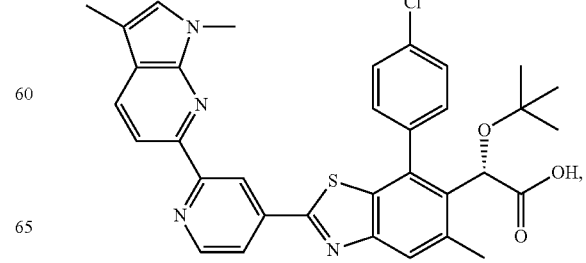

701
-continued
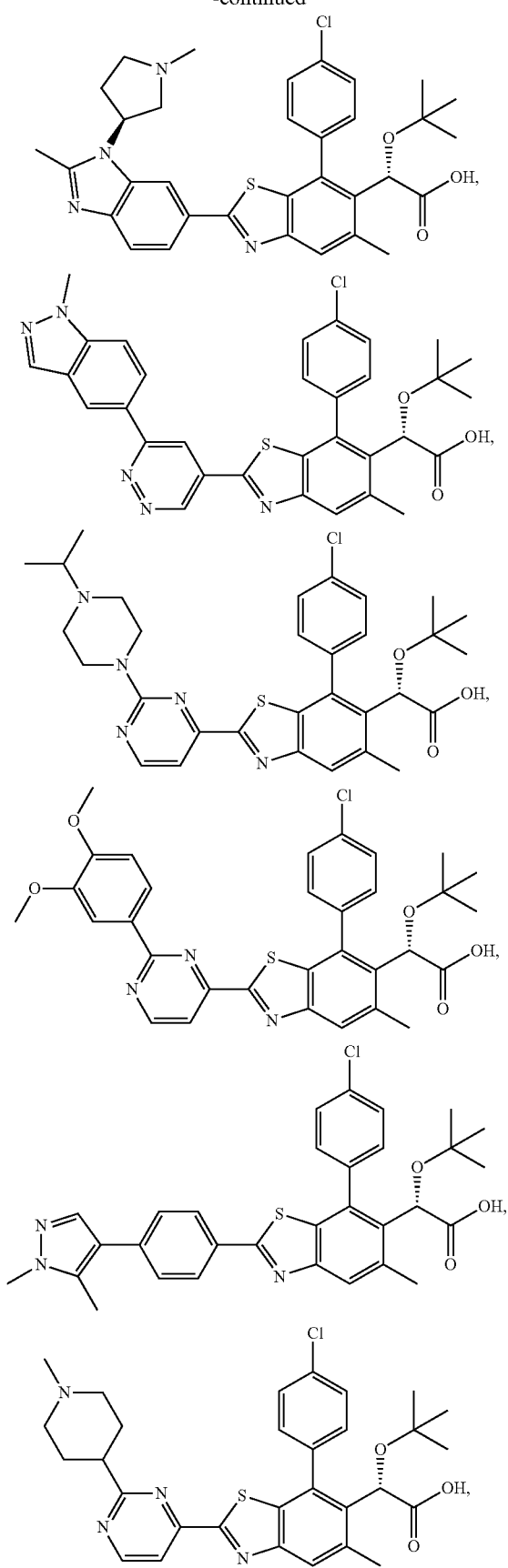
702
-continued
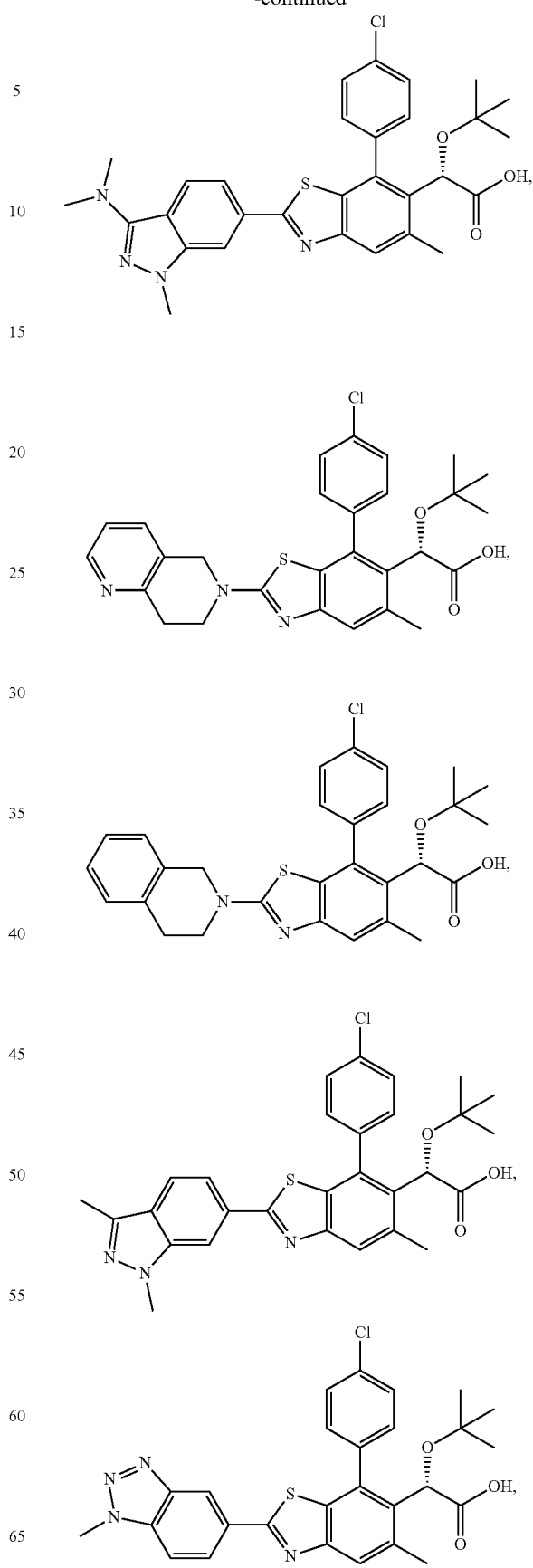

703
-continued
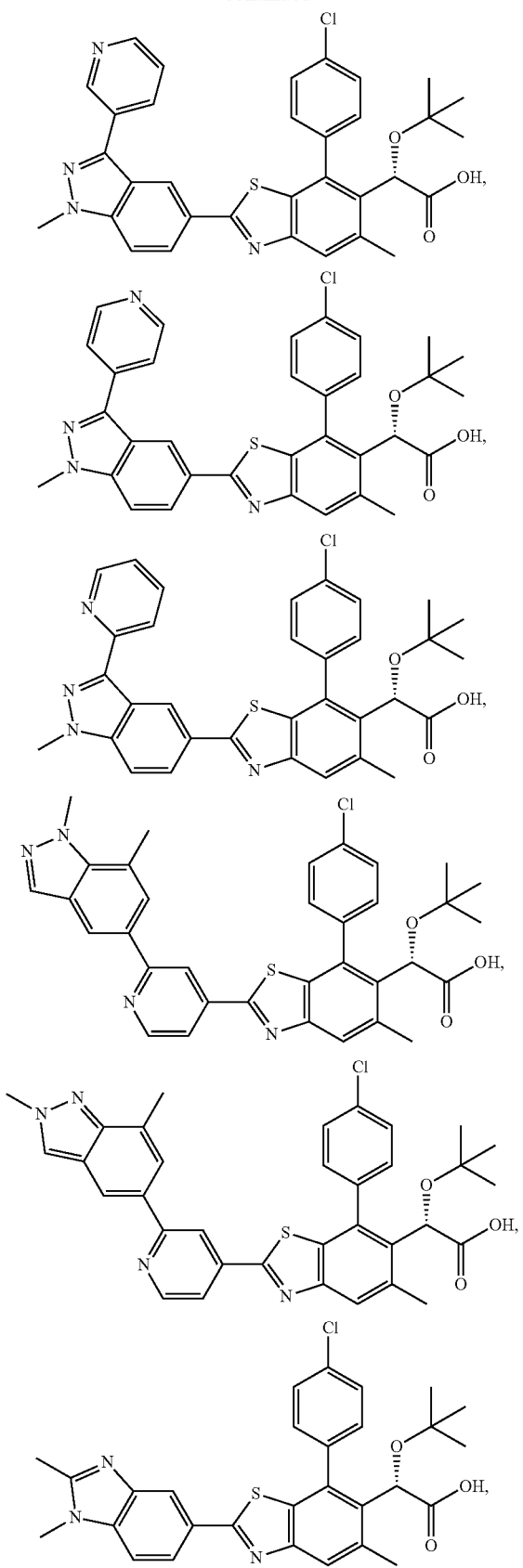
704
-continued
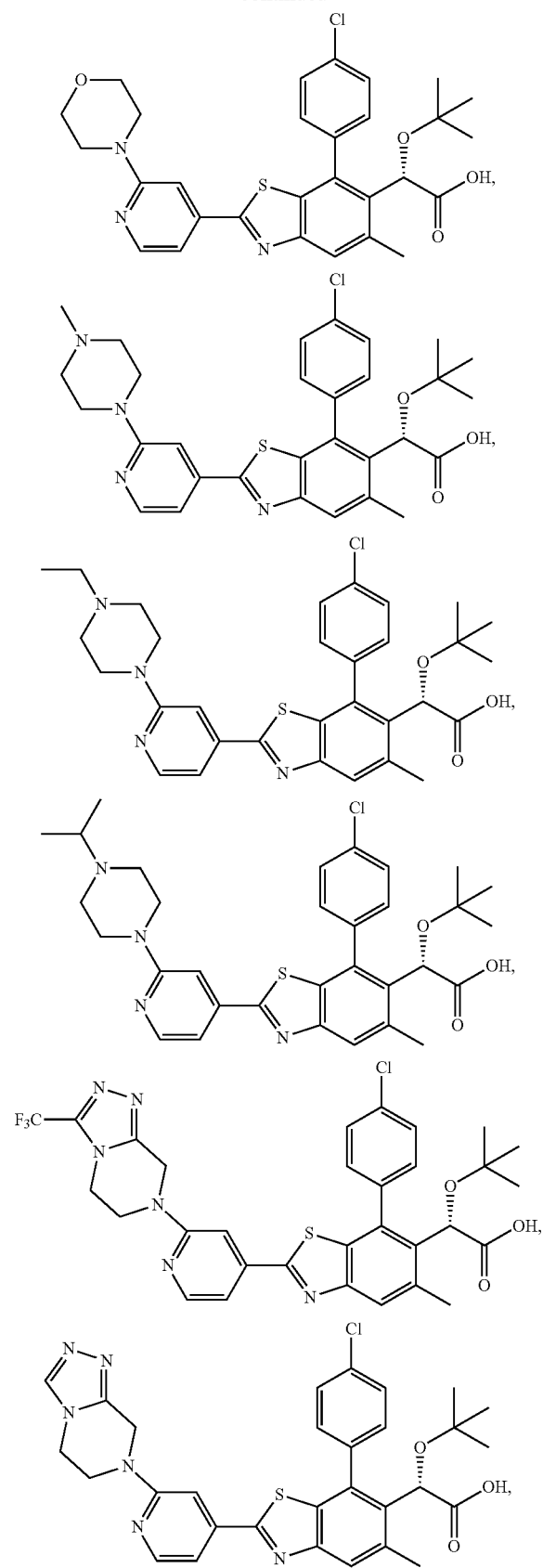

705
-continued
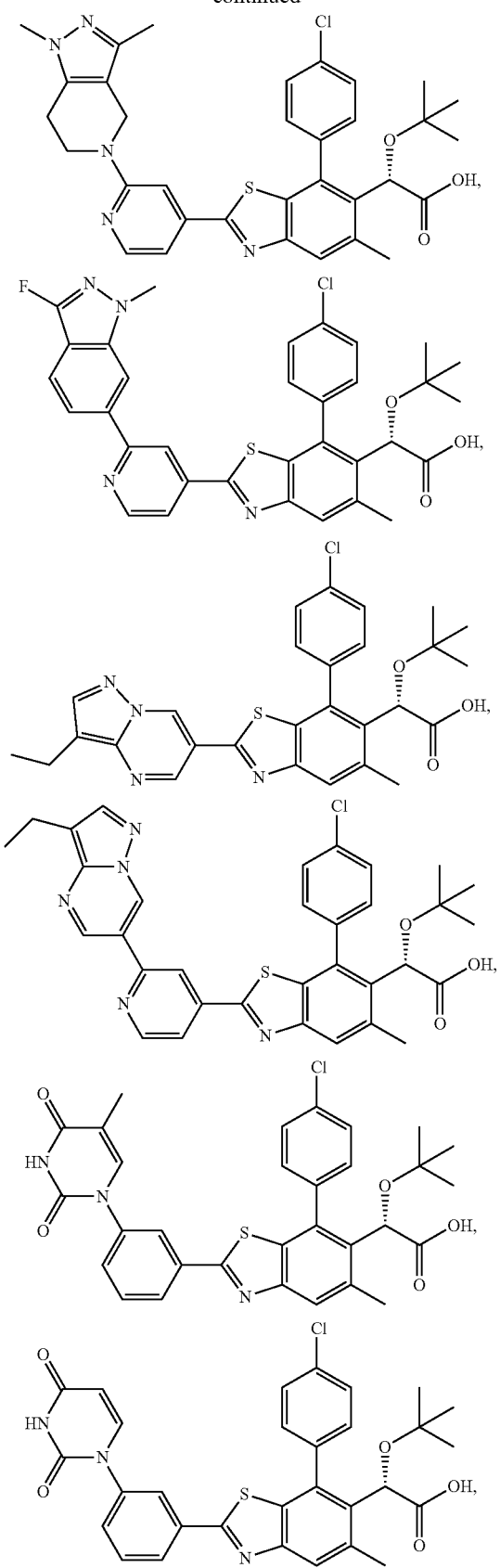
706
-continued
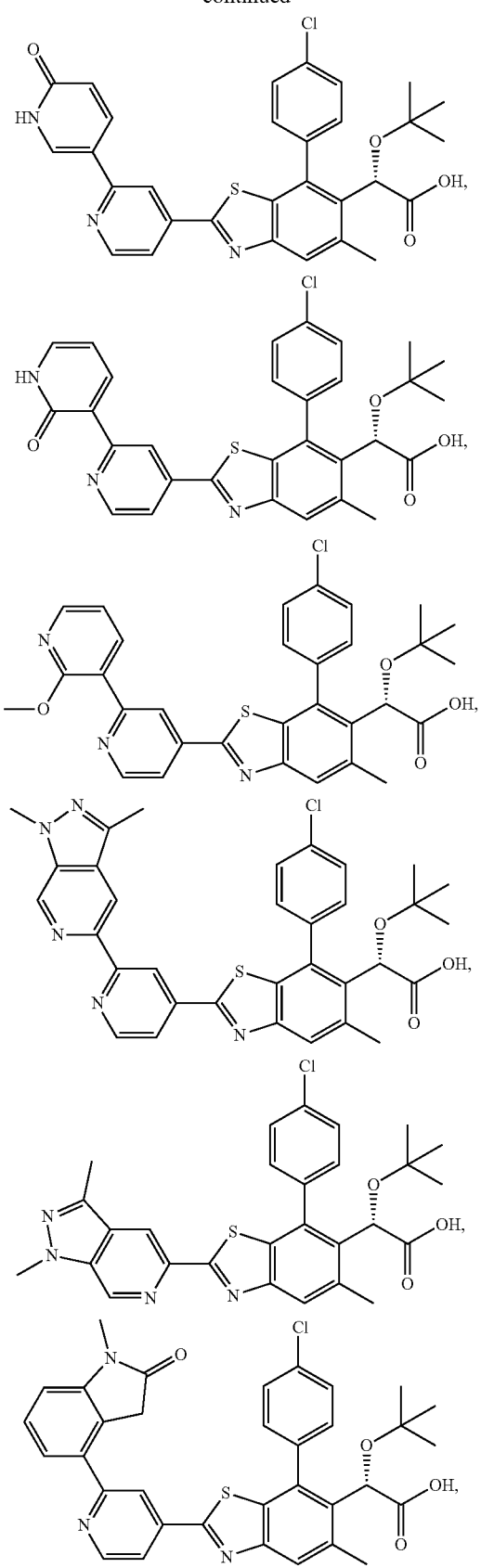

707
-continued
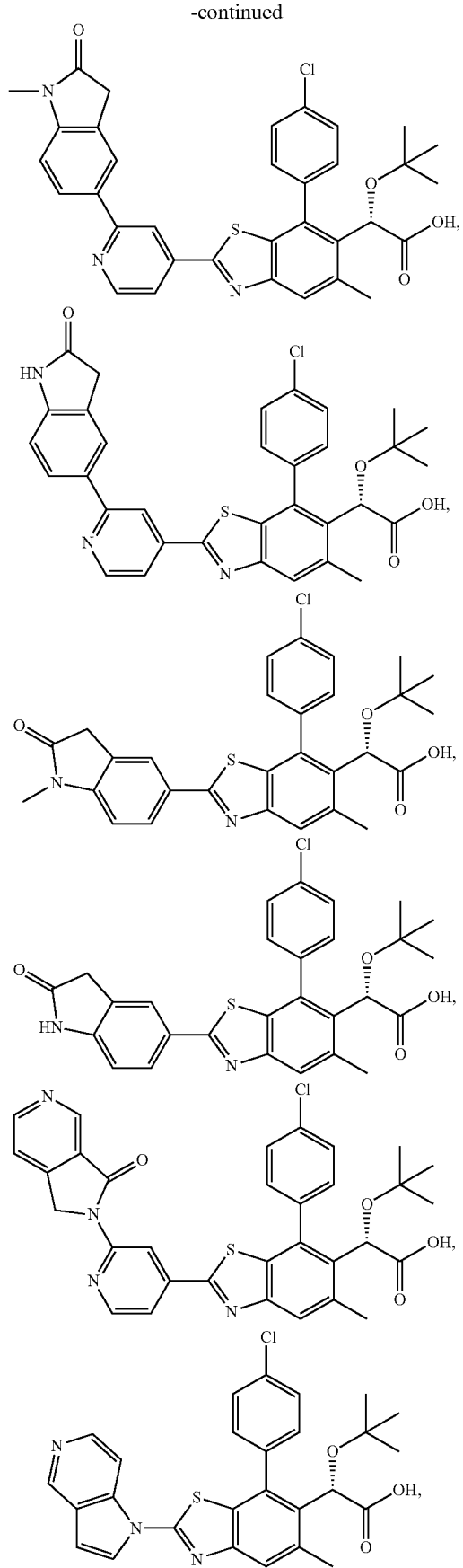
708
-continued
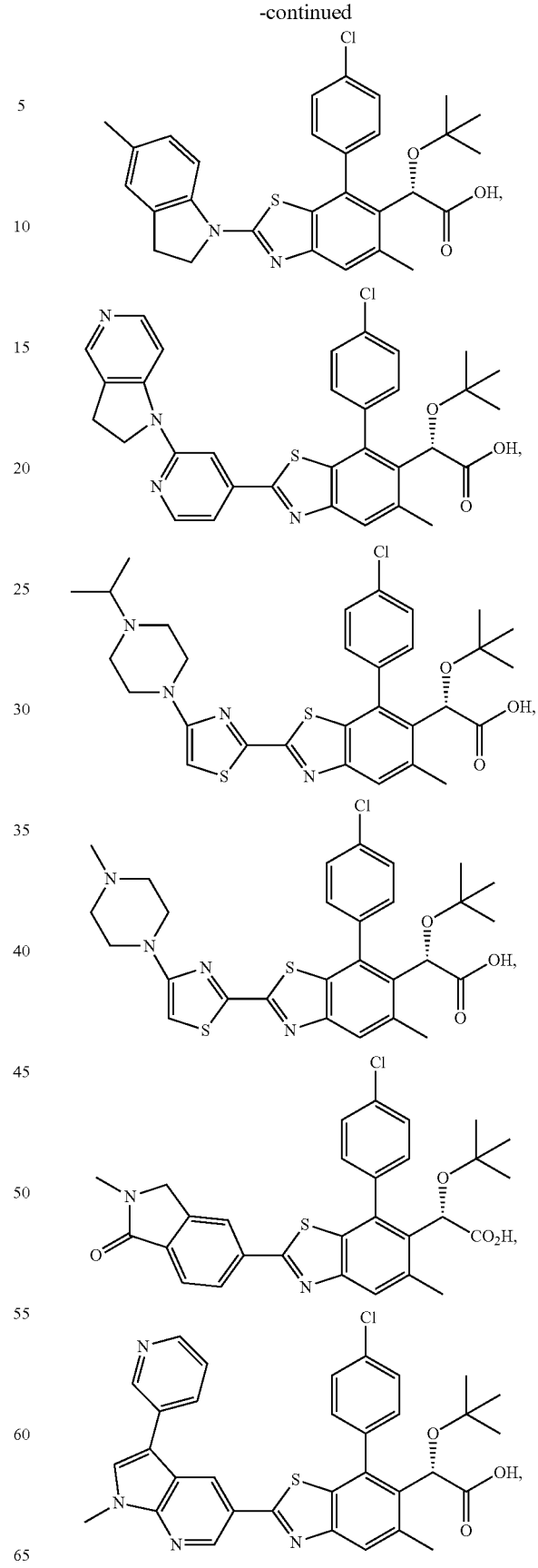

709
-continued
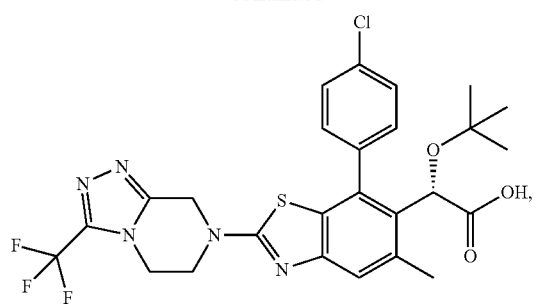
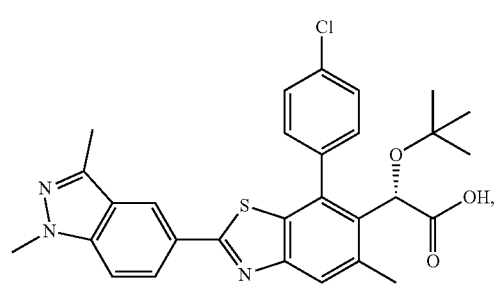
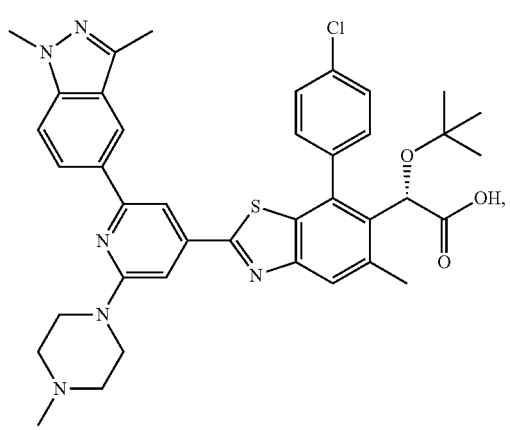
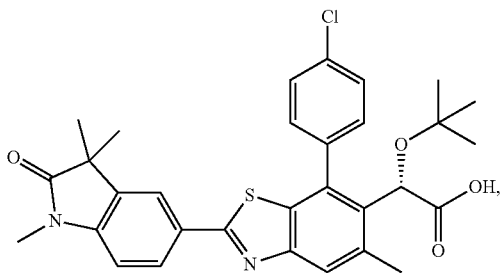
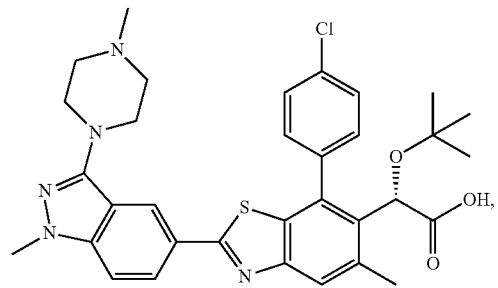
710
-continued
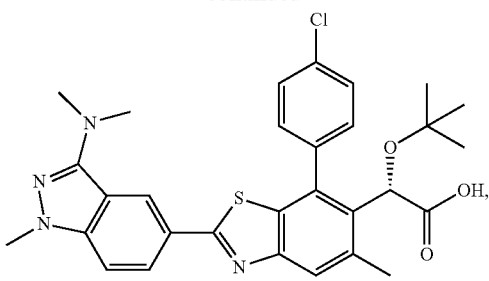
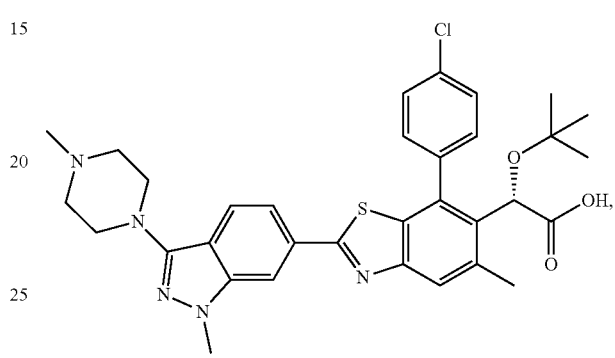
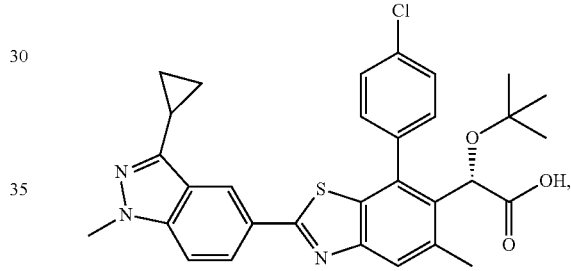
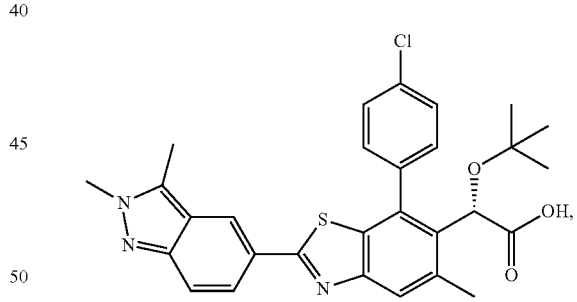
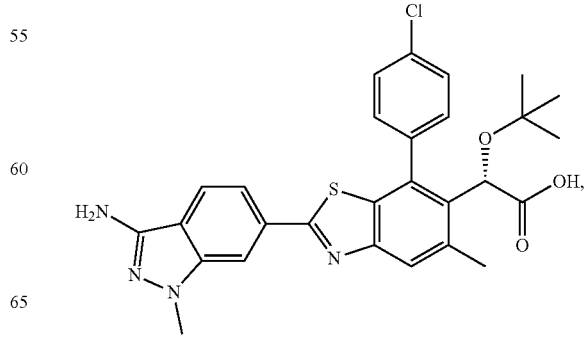

711
-continued
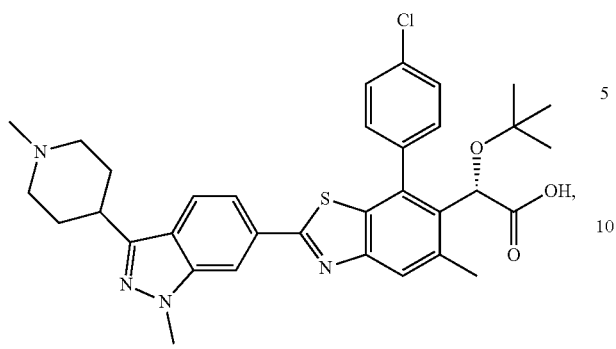
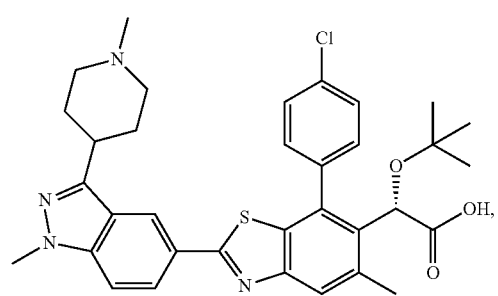
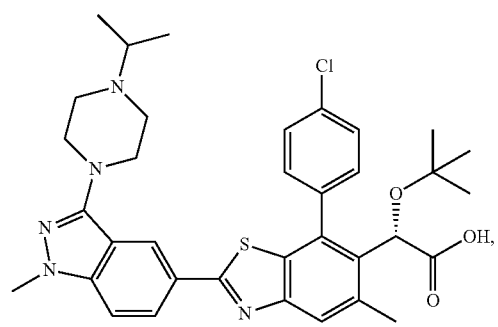
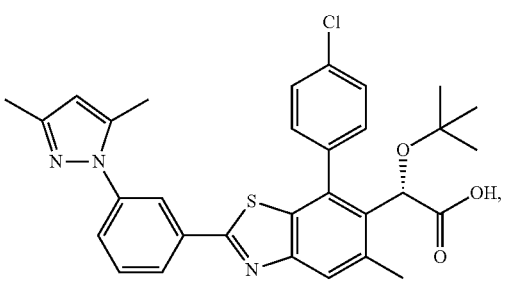
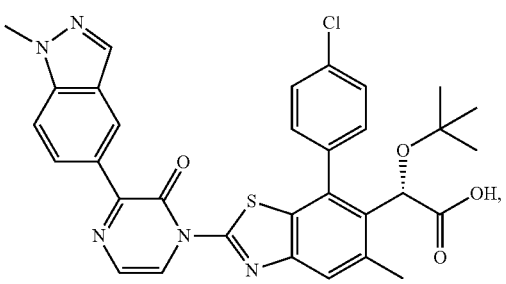
712
-continued
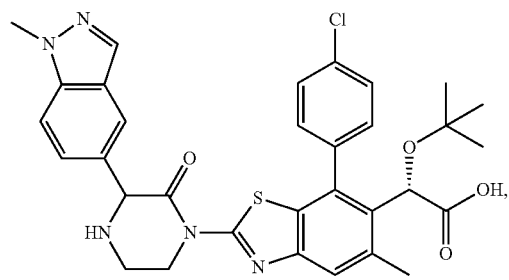
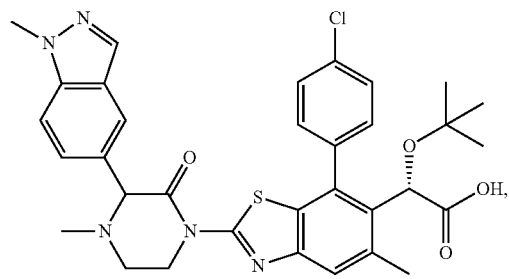
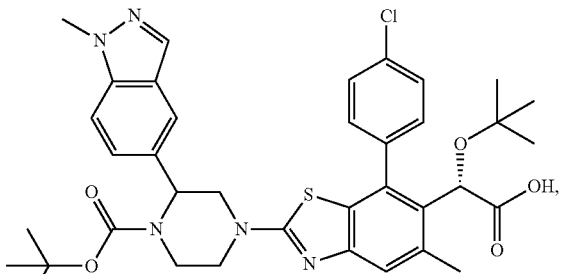
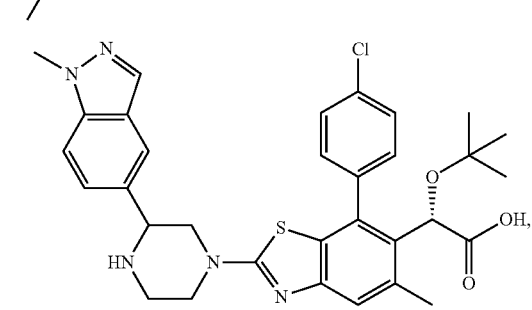
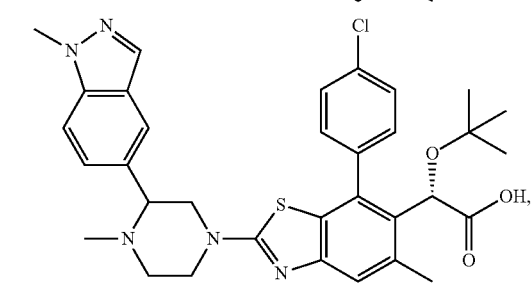
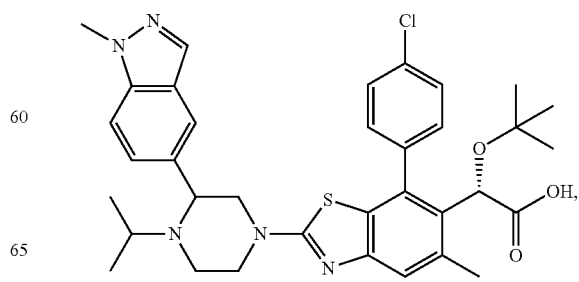

713
-continued
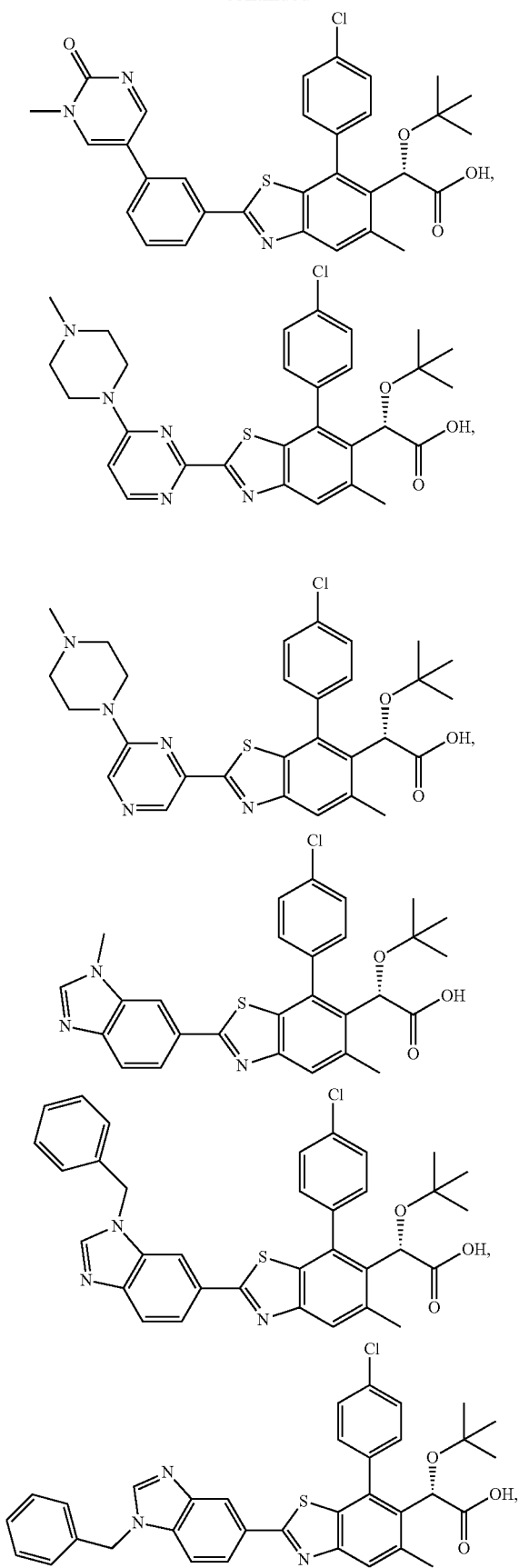
714
-continued
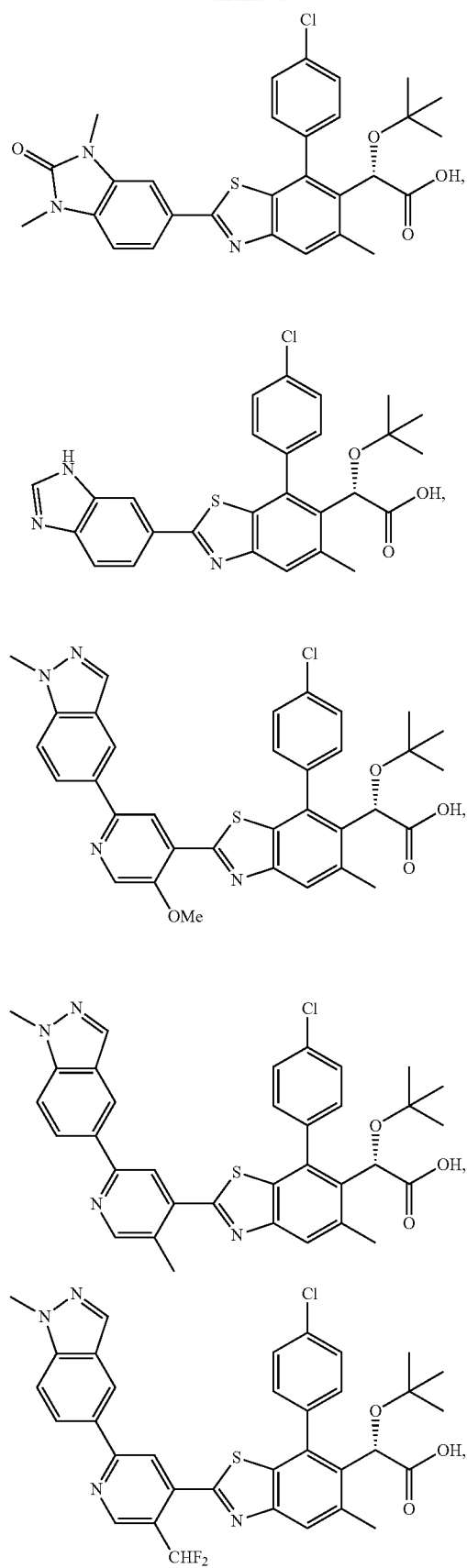

715
-continued
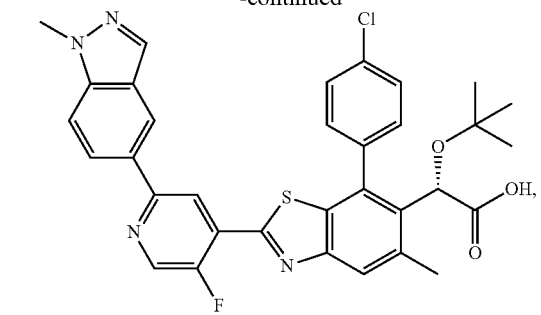
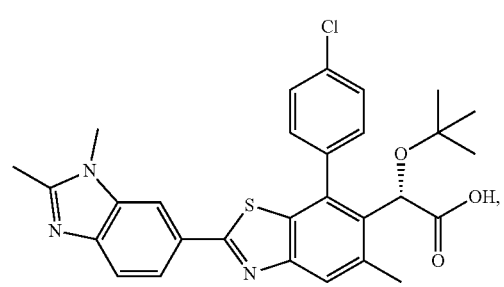
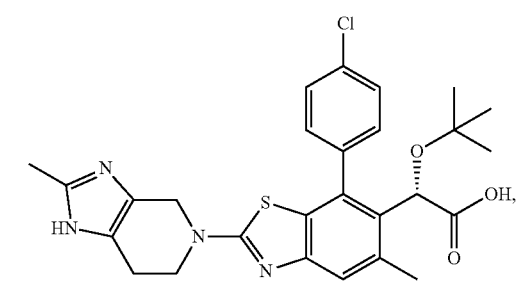
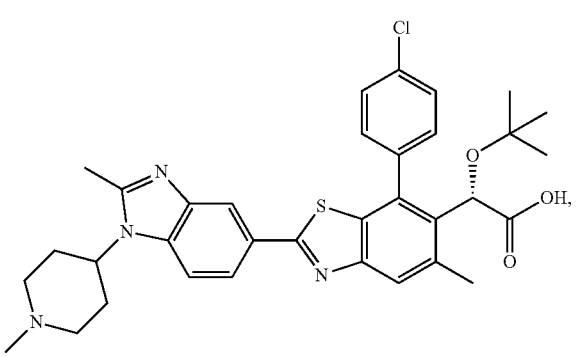
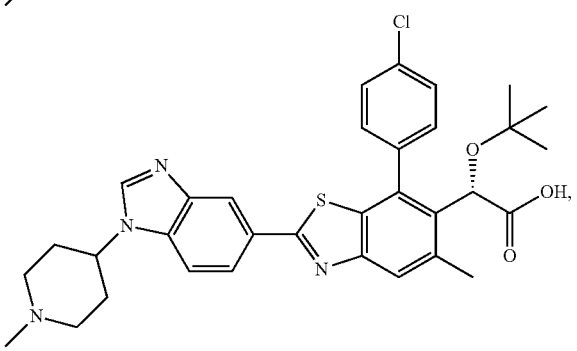
716
-continued
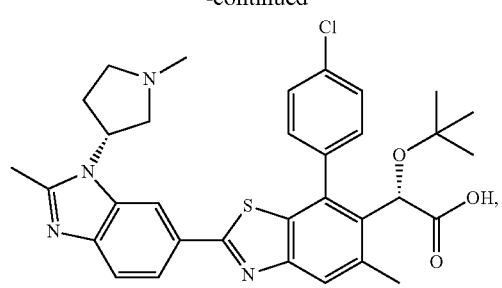
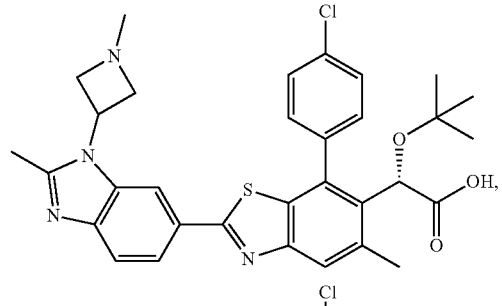
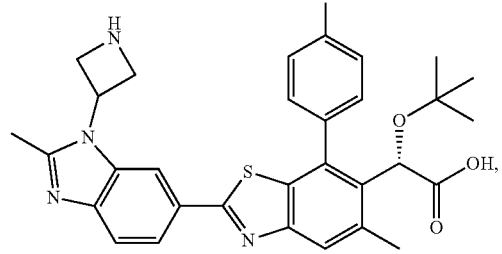
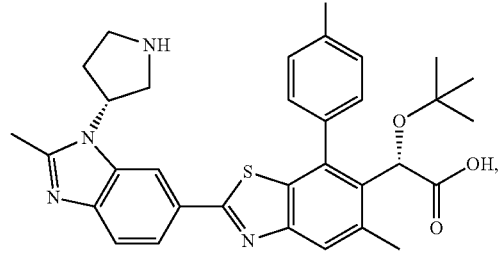
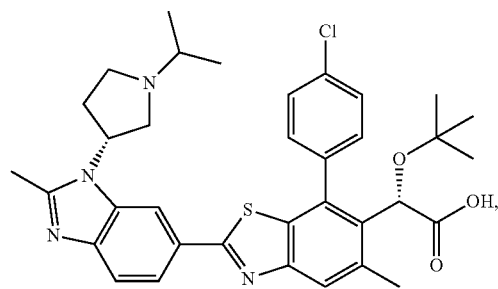
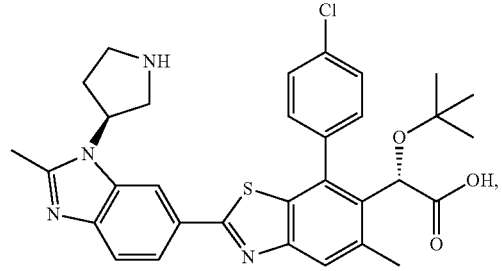

717
-continued
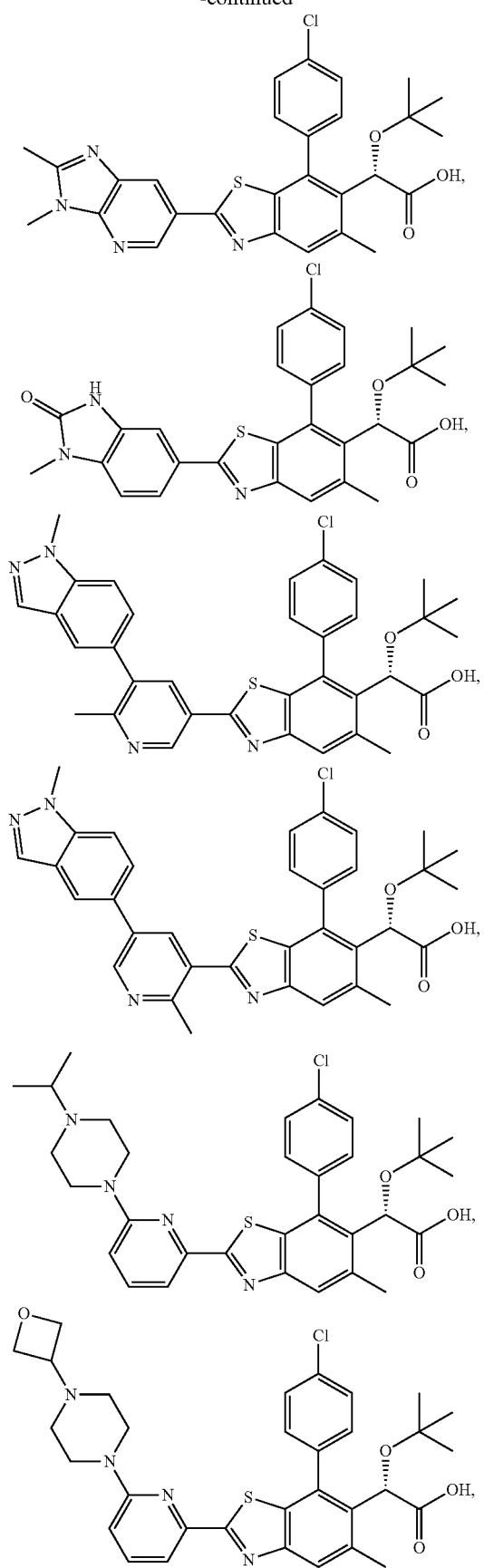
718
-continued
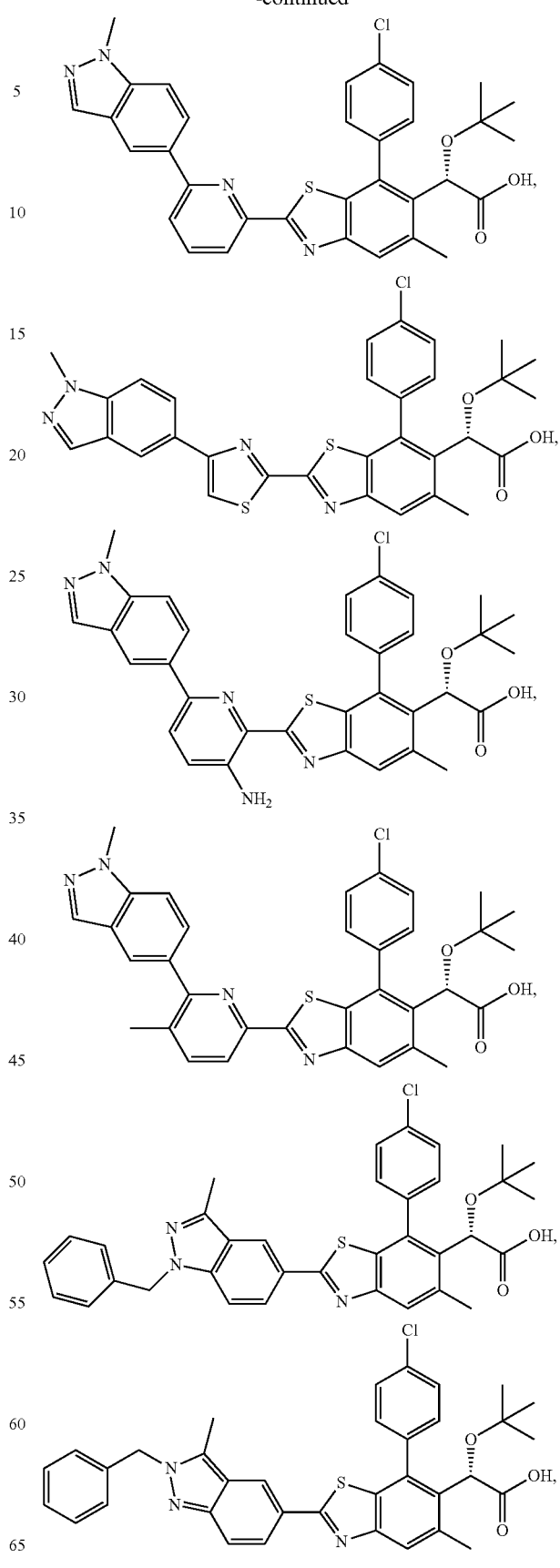

719
-continued
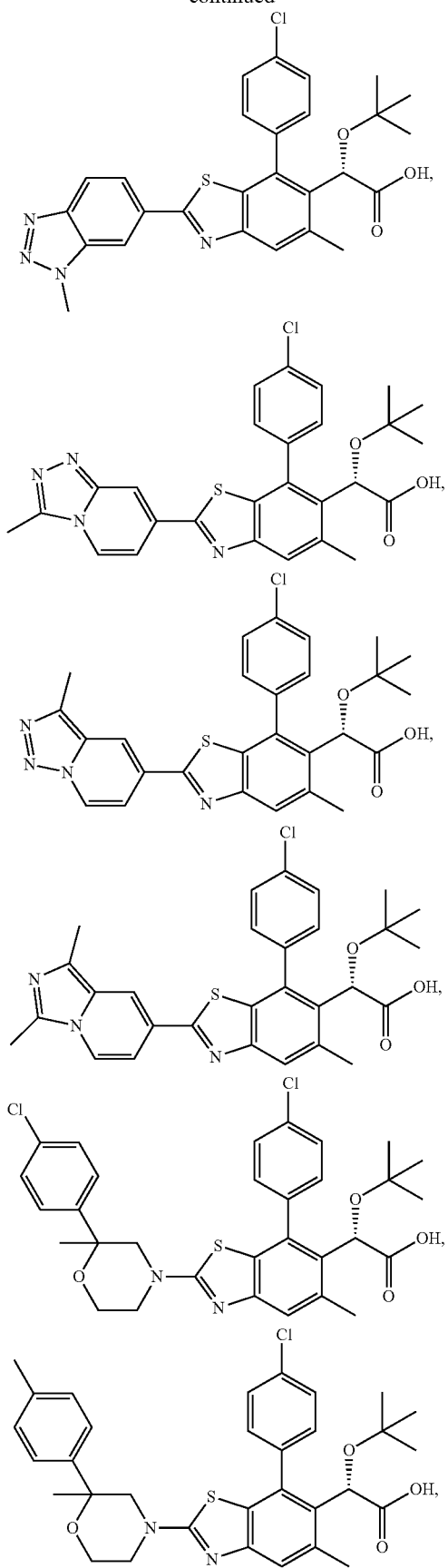
720
-continued
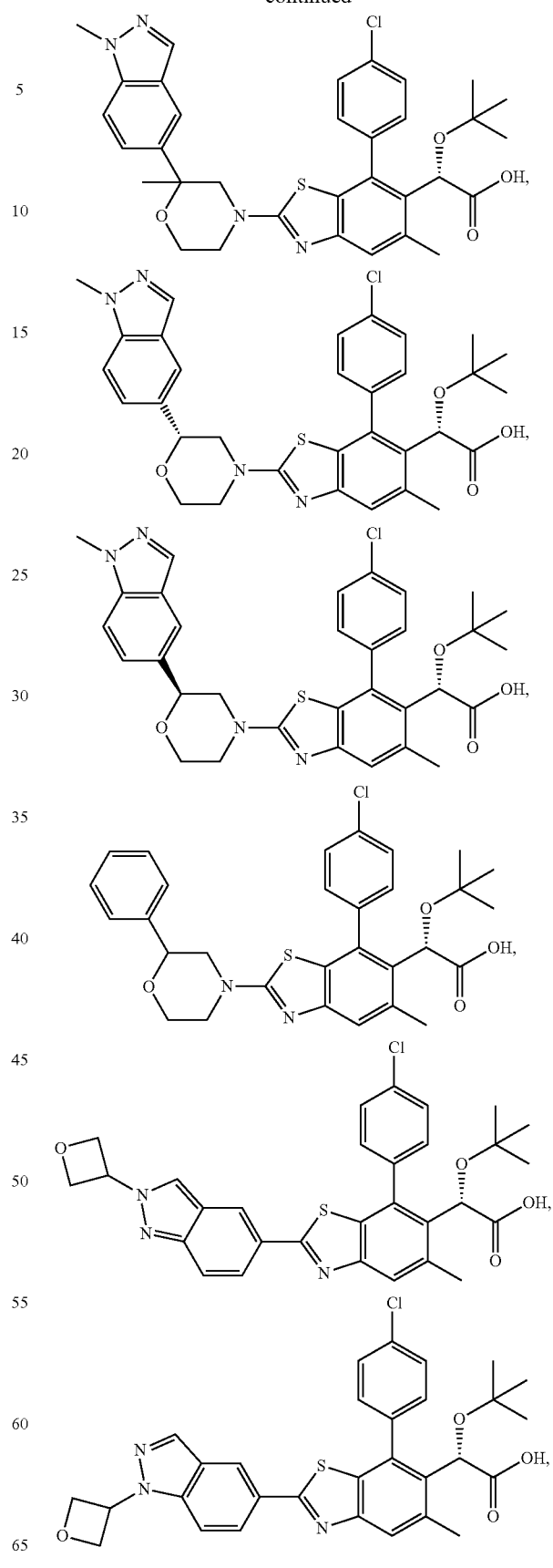

721
-continued
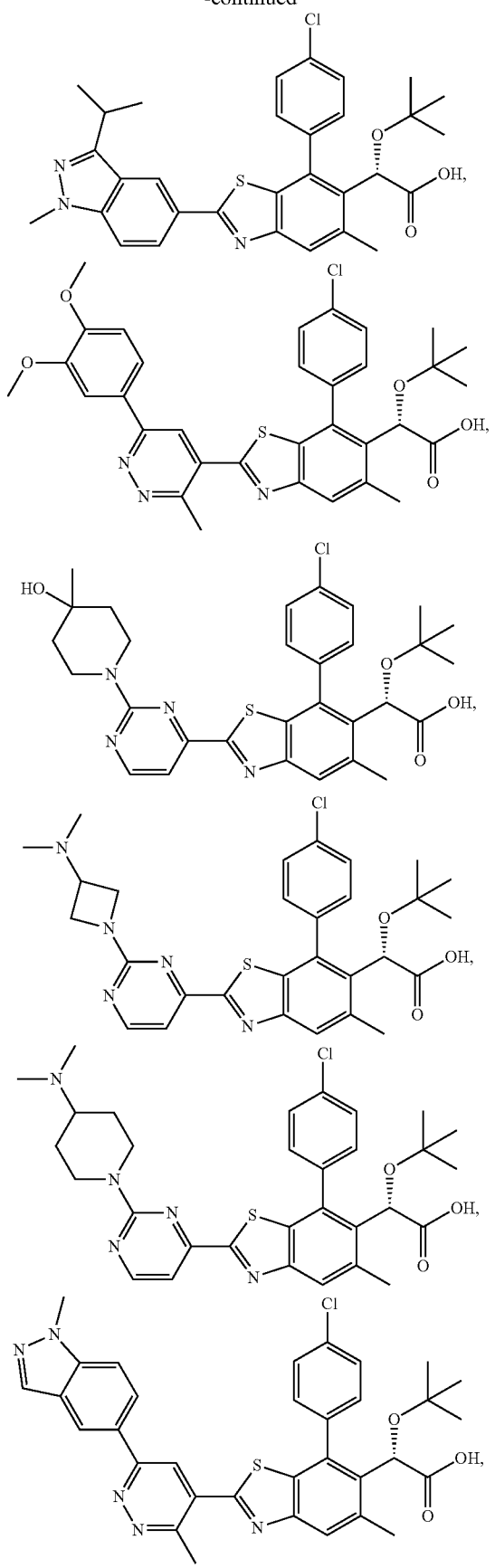
722
-continued
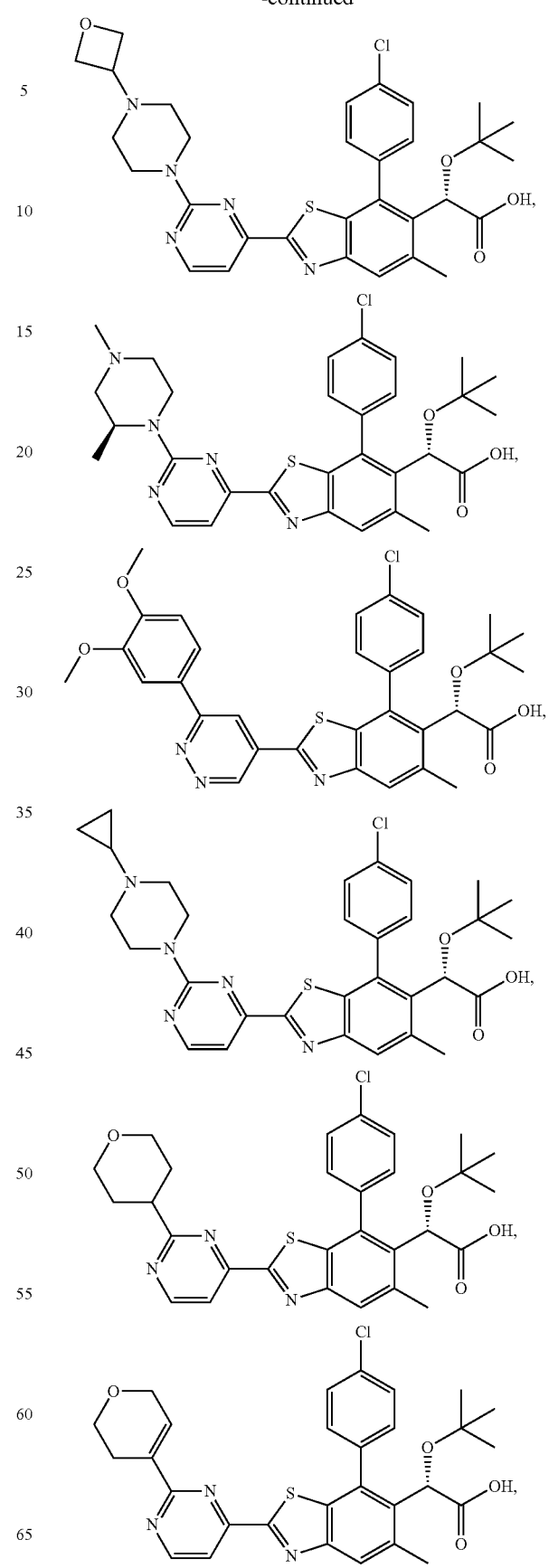

723
-continued
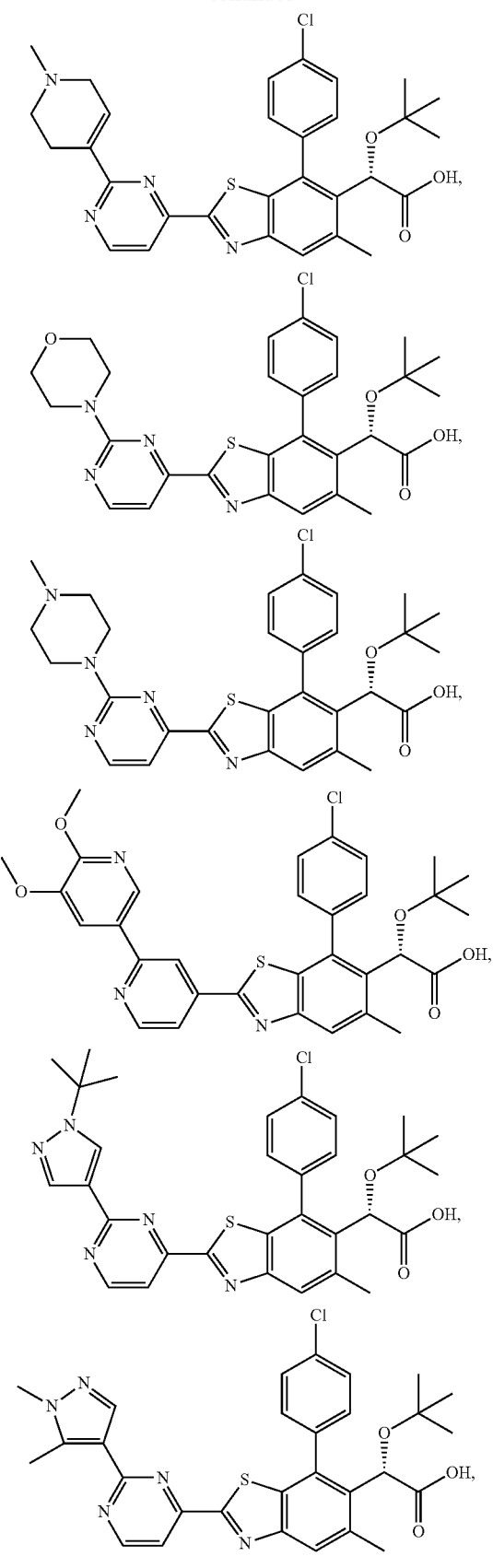
724
-continued
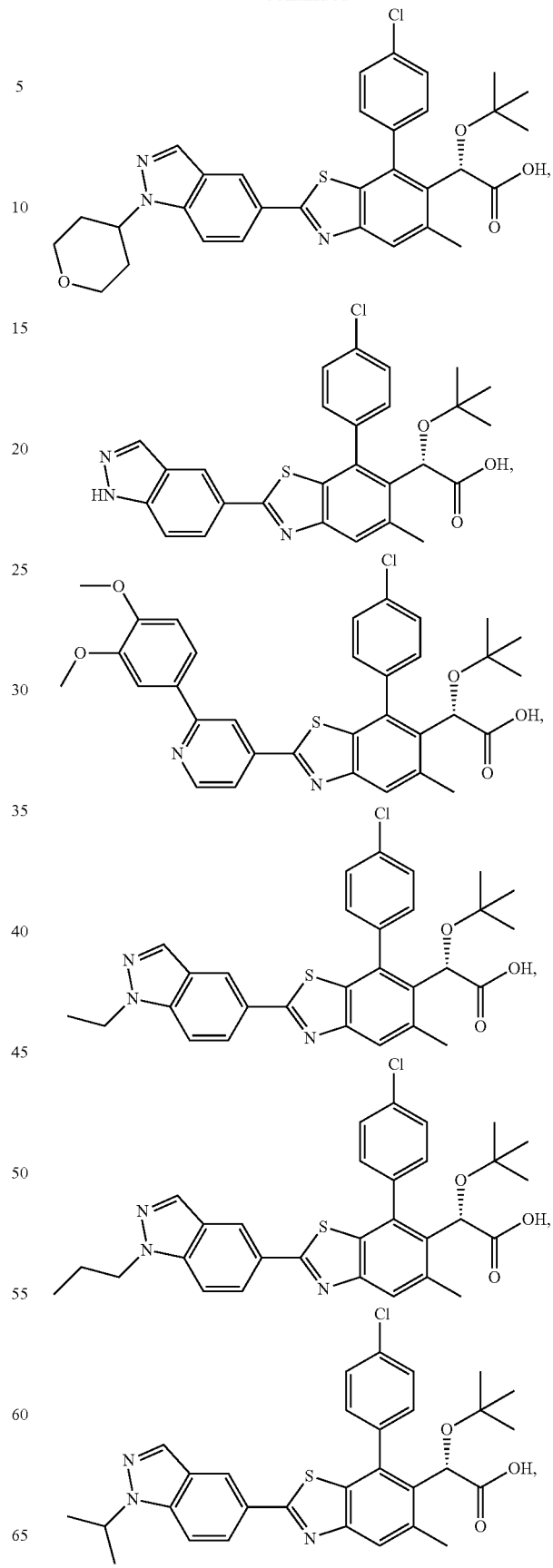

725
-continued
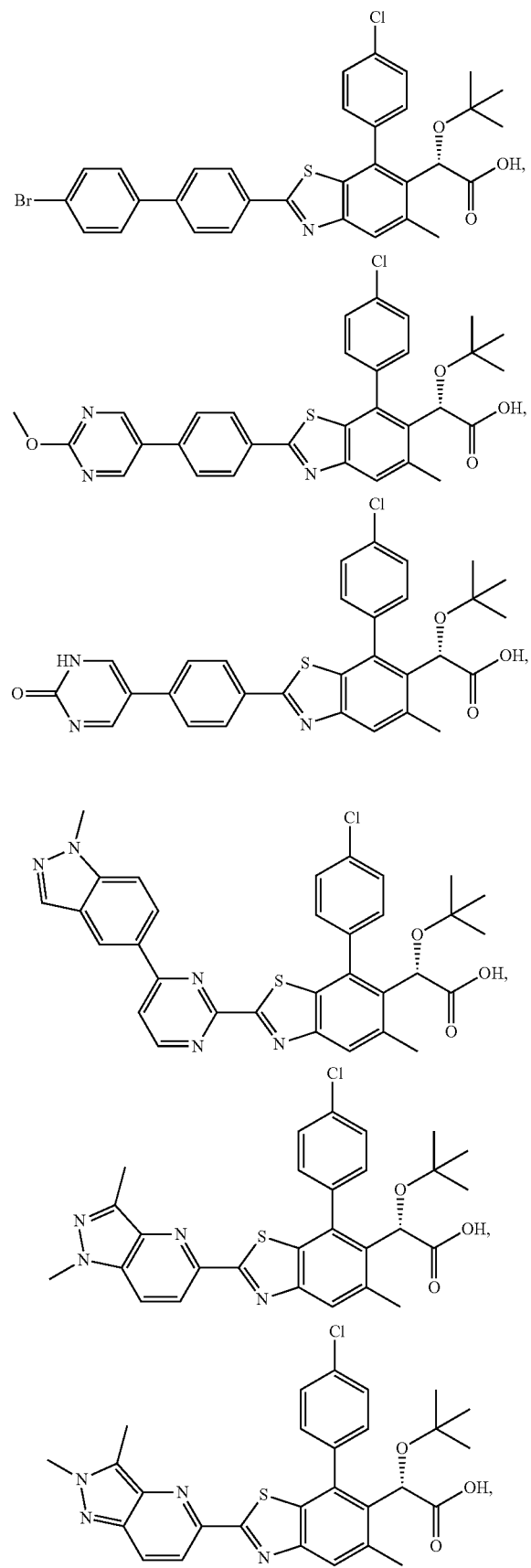
726
-continued
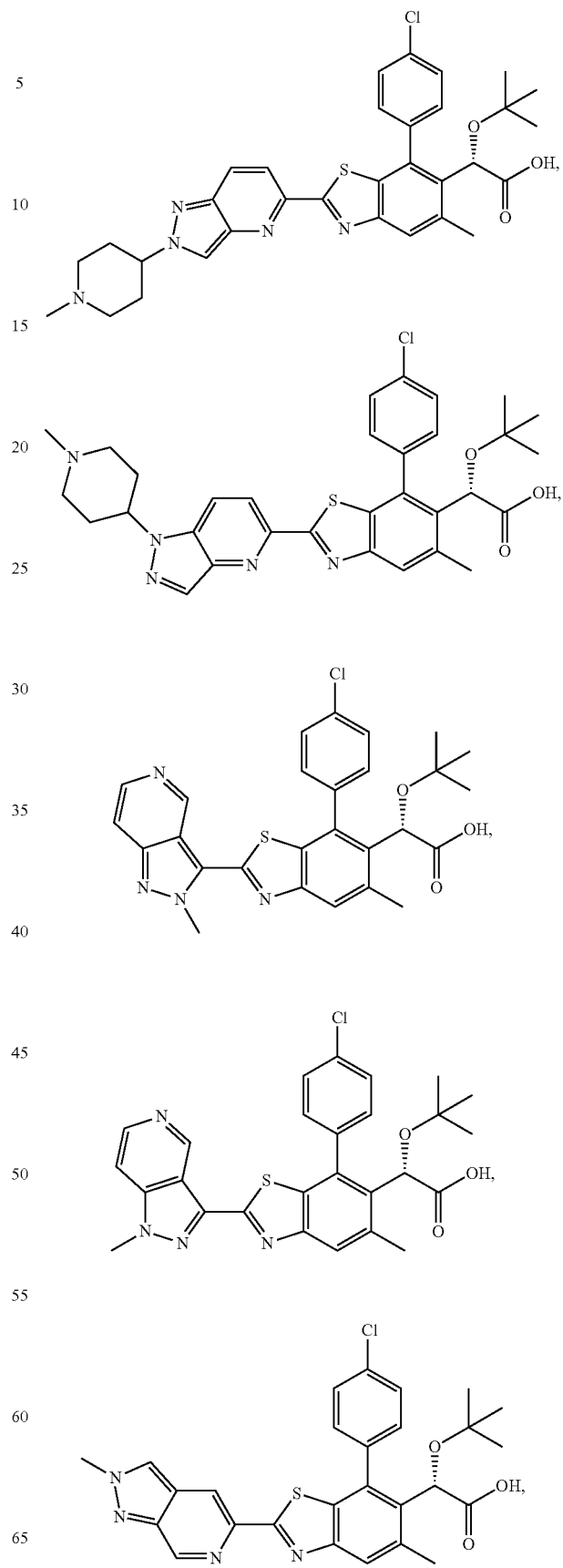

727
-continued
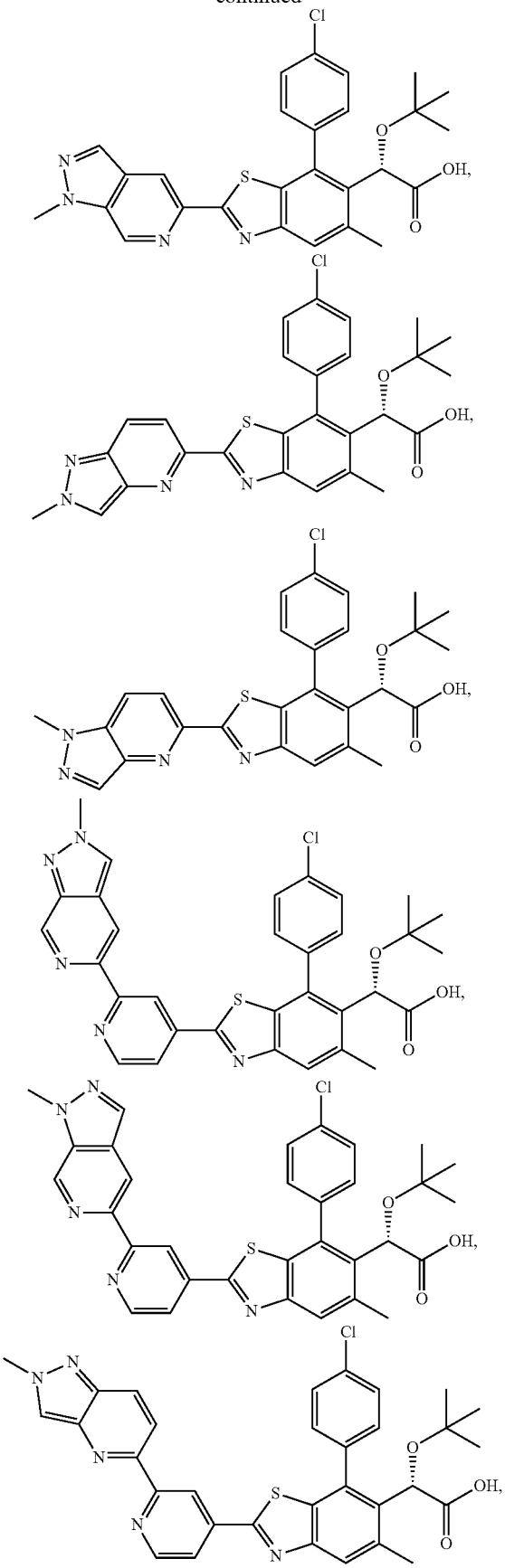
728
-continued
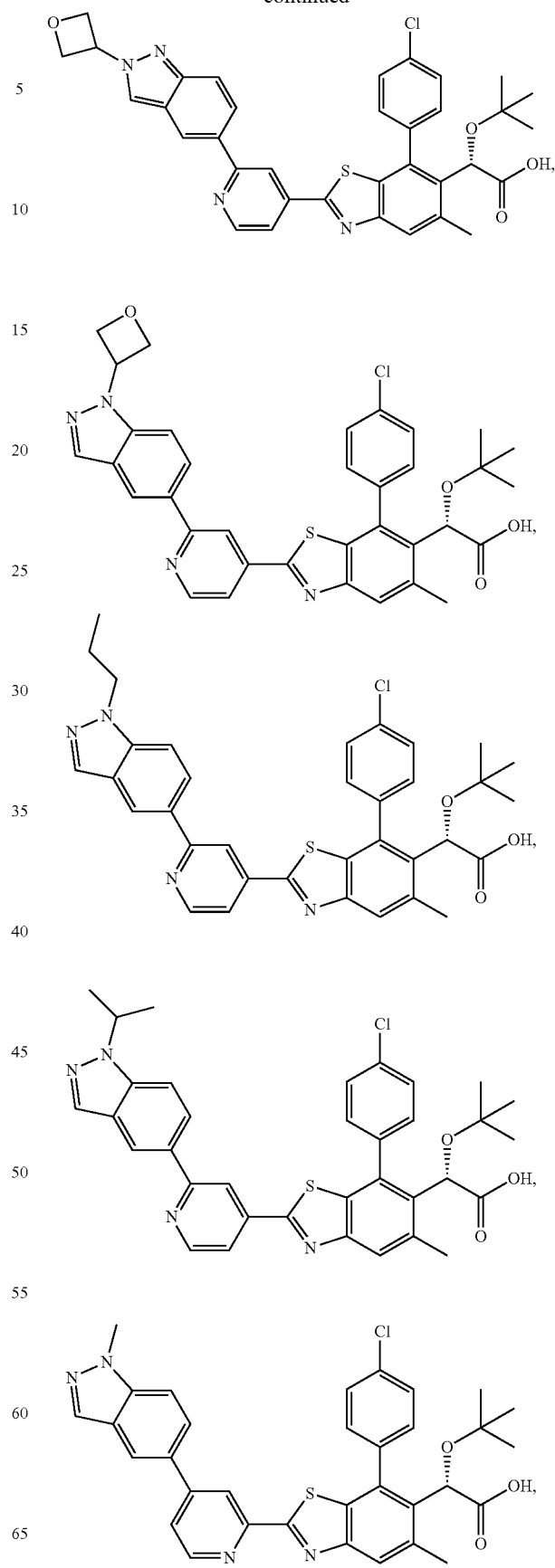

729
-continued
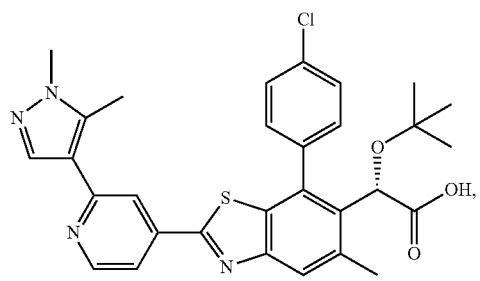
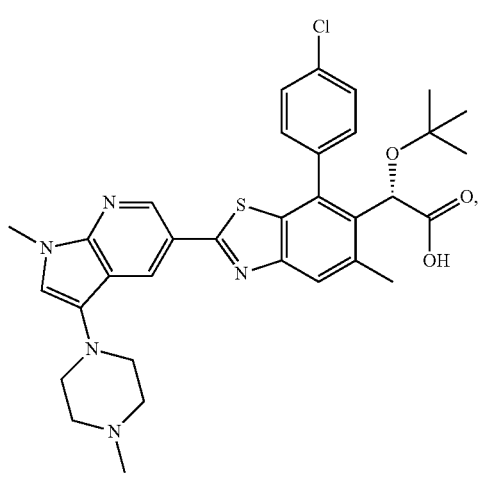
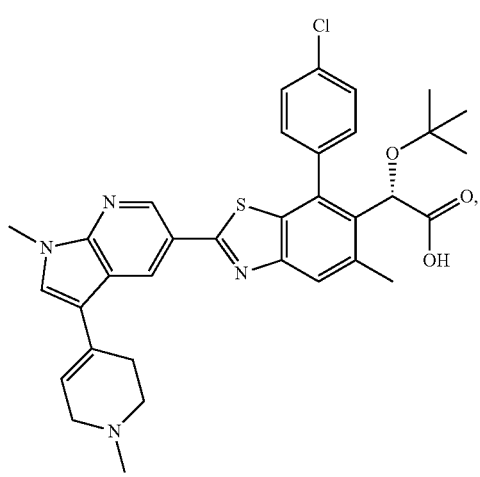
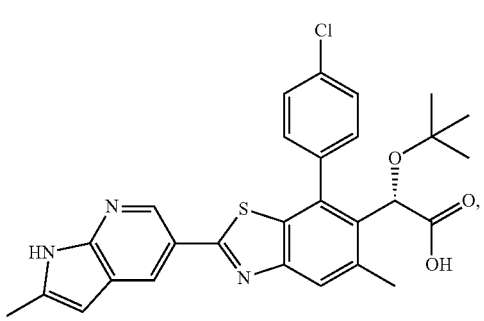
730
-continued
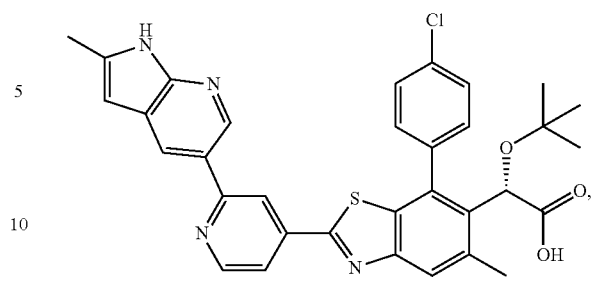
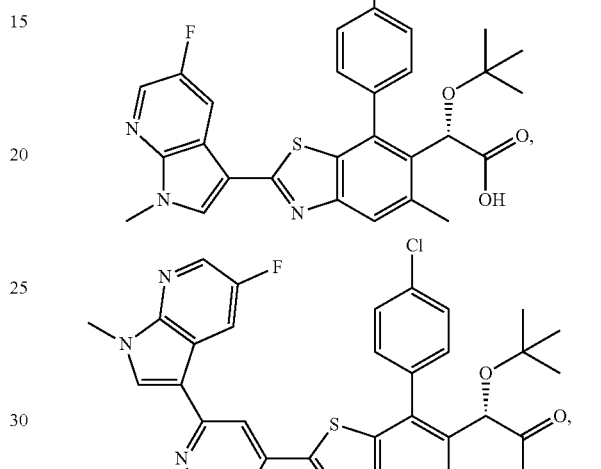
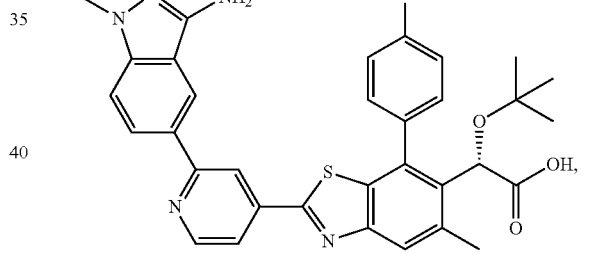
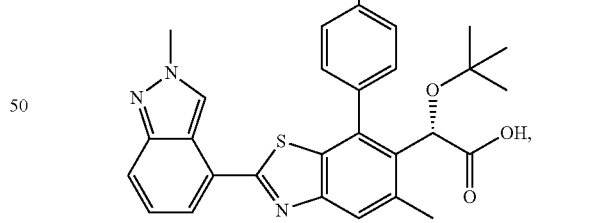
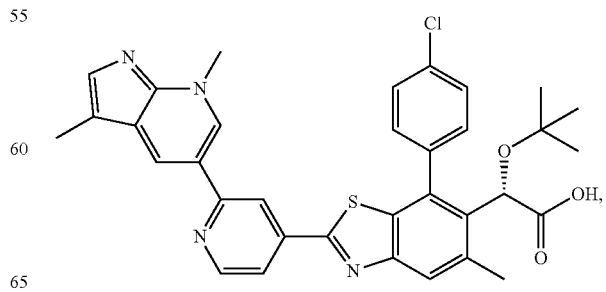

731
-continued
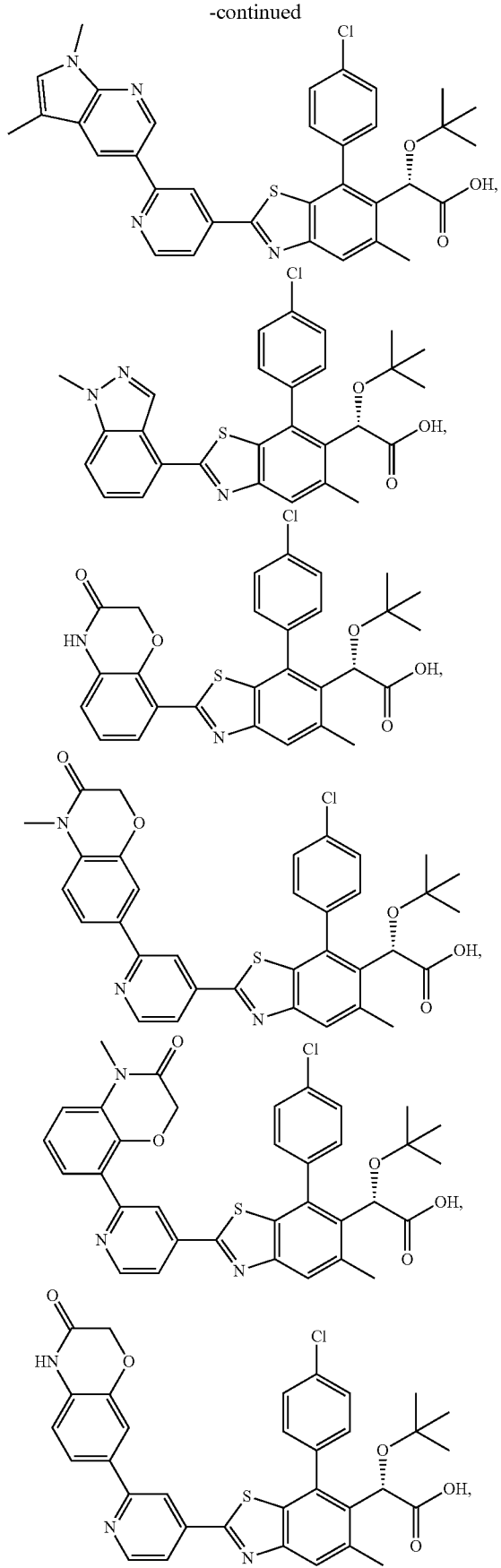
732
-continued
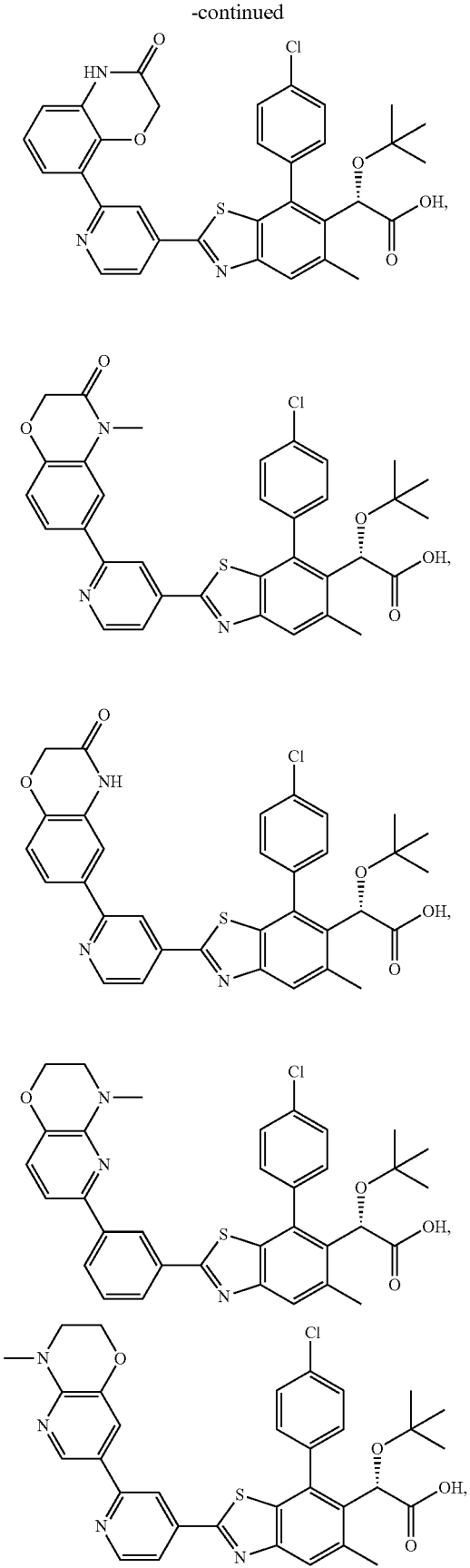

733
-continued
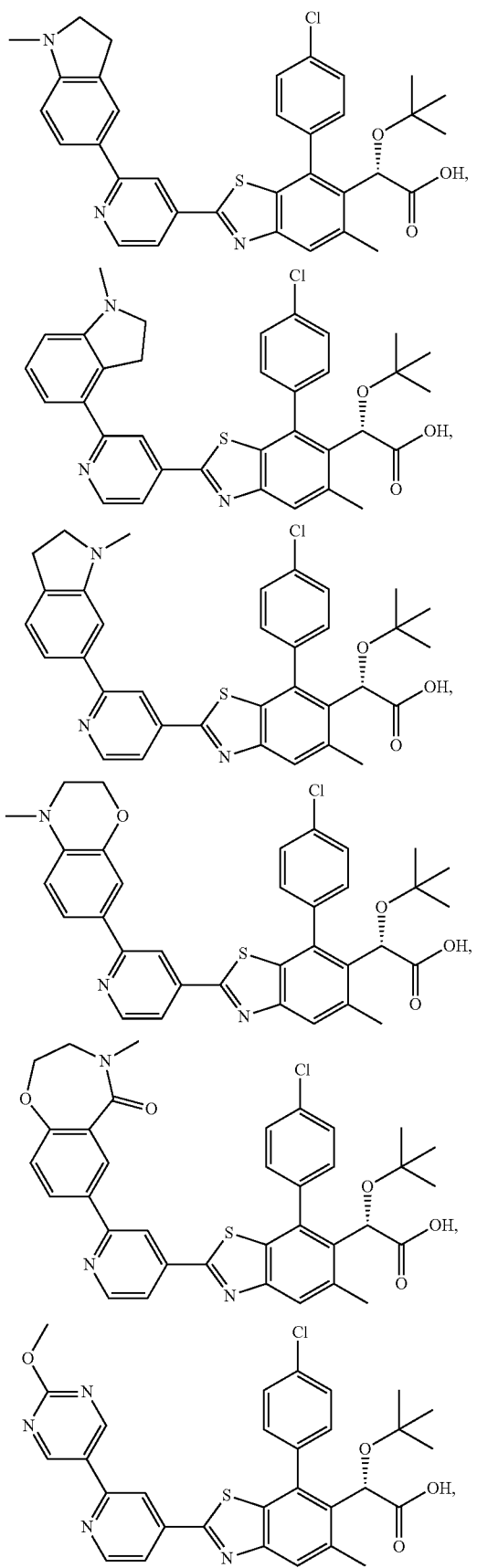
734
-continued
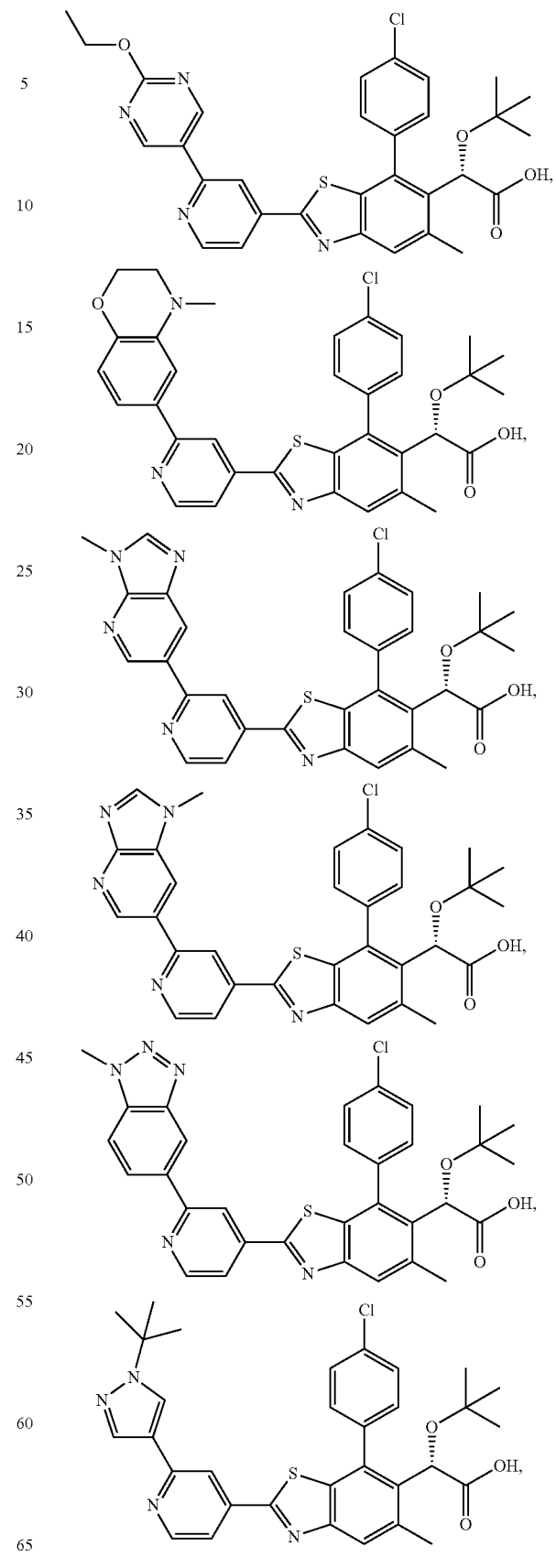

735
-continued
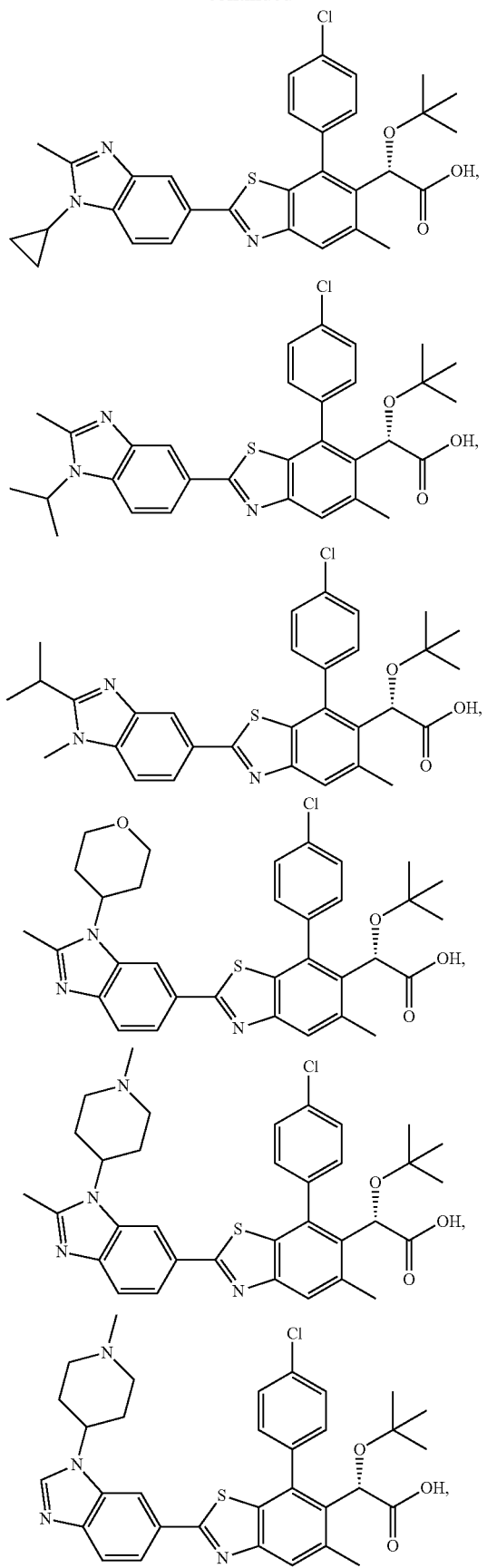
736
-continued
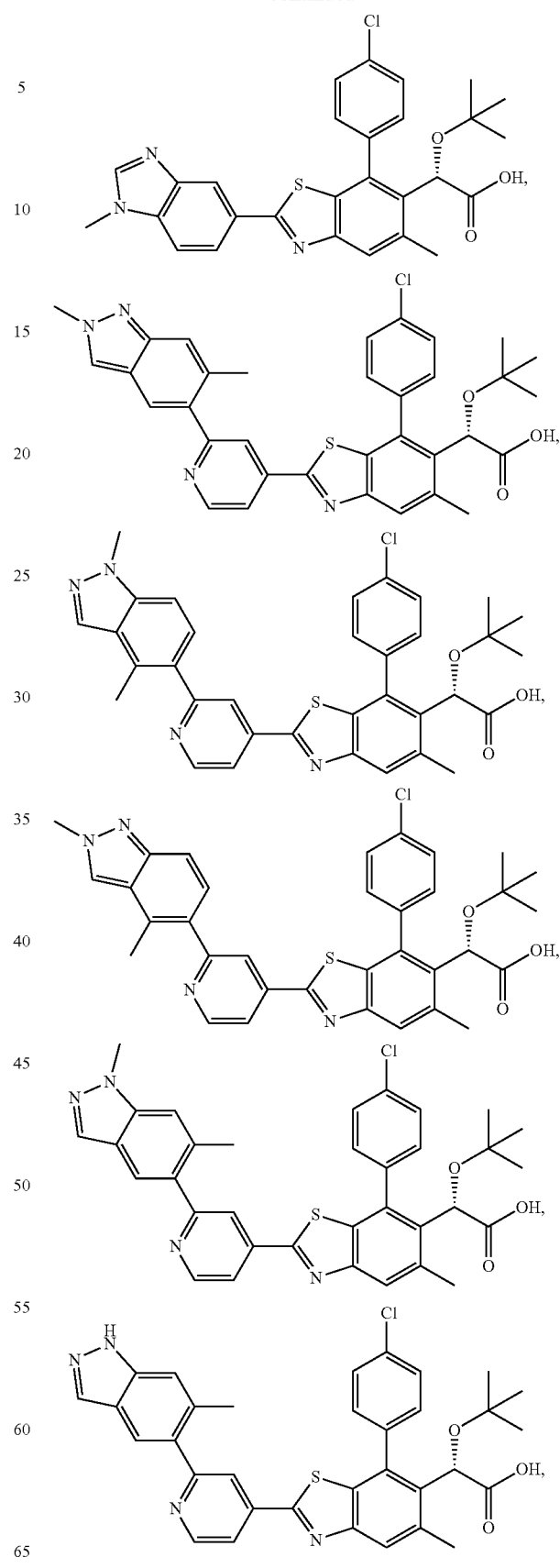

737
-continued
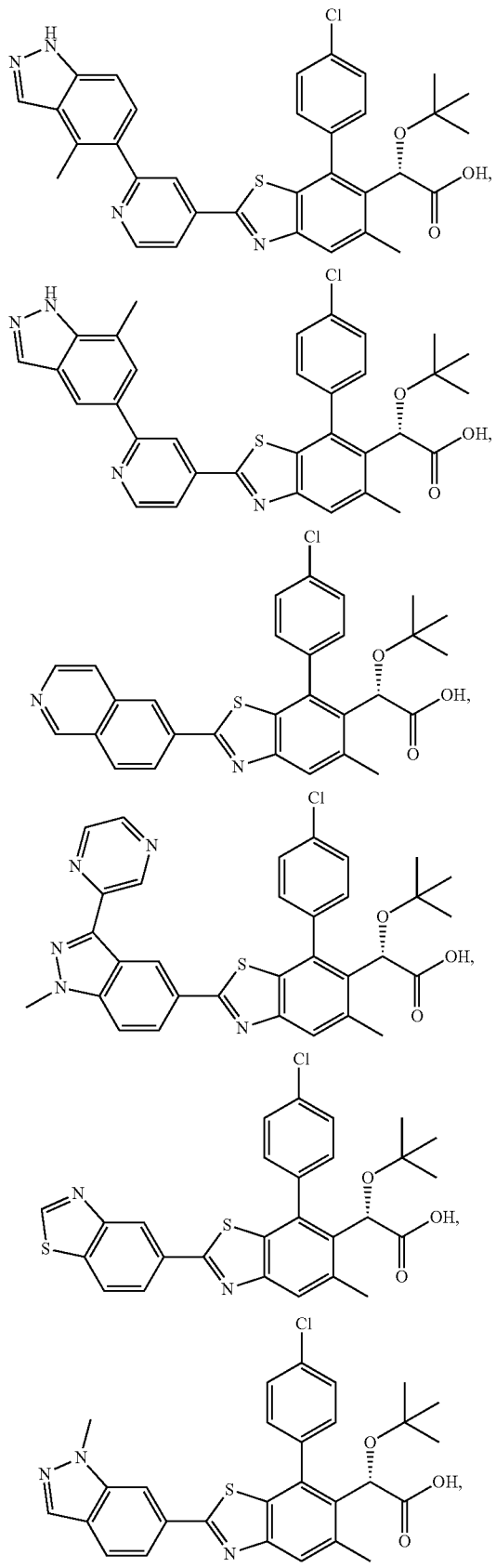
738
-continued
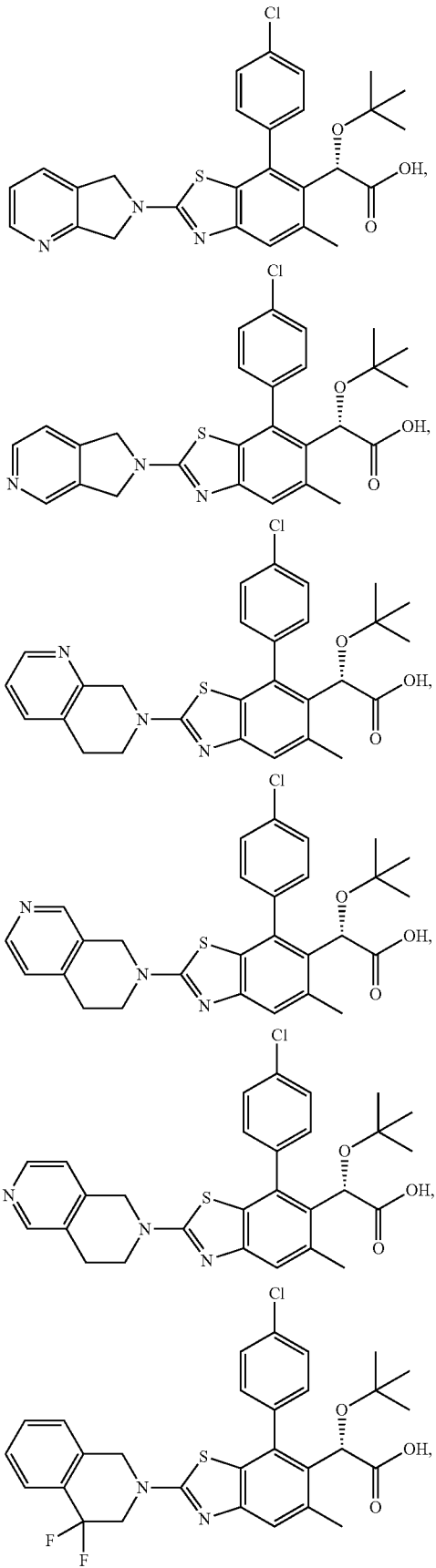

739
-continued
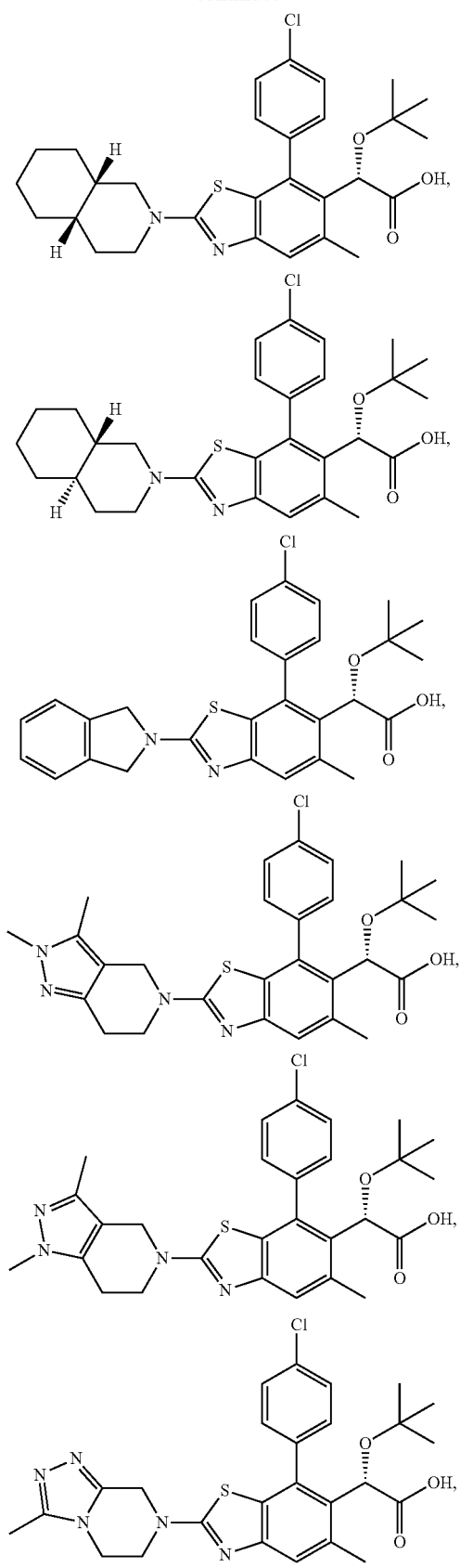
740
-continued
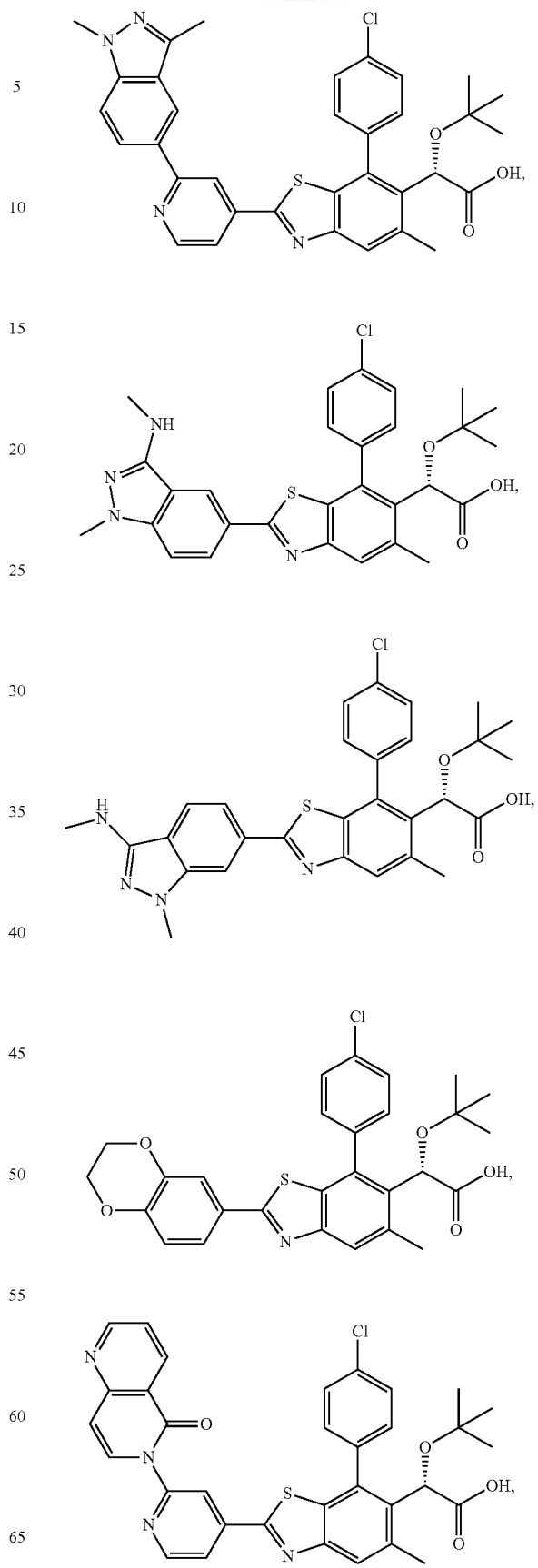

741
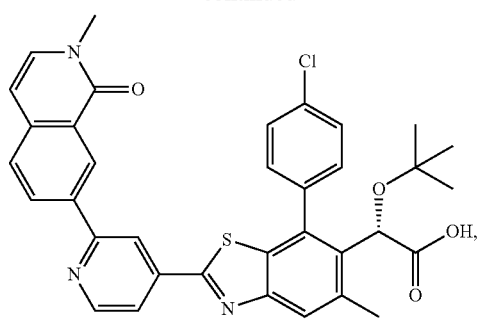
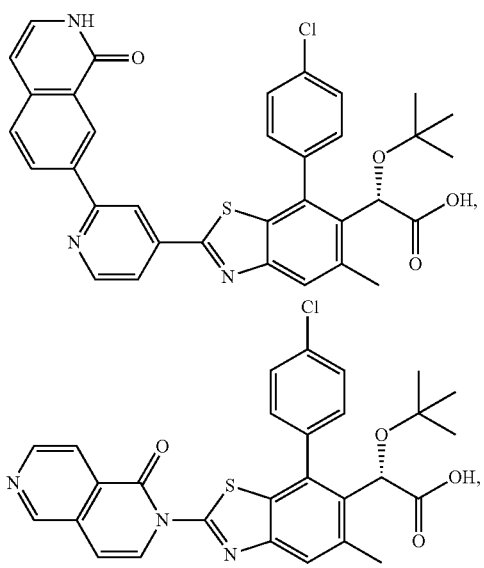
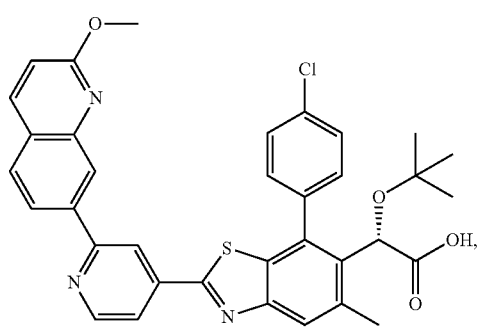
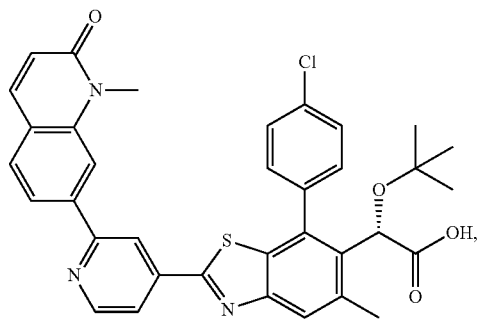
742
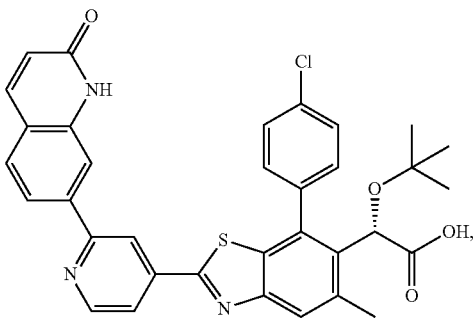
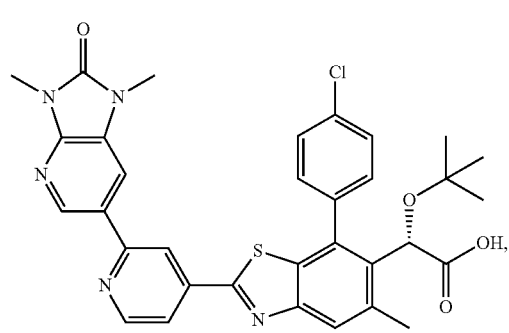
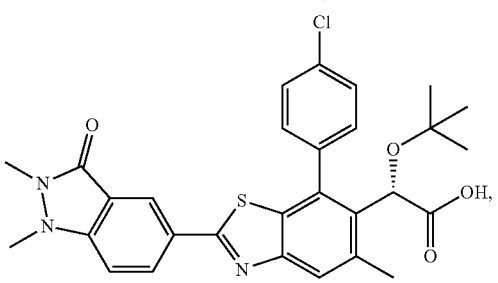
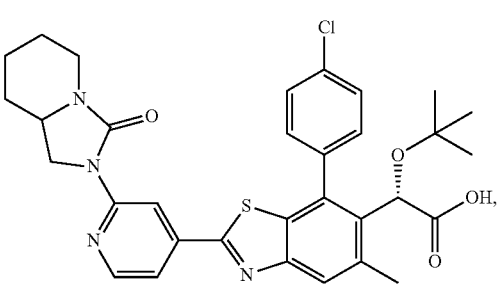

743
-continued
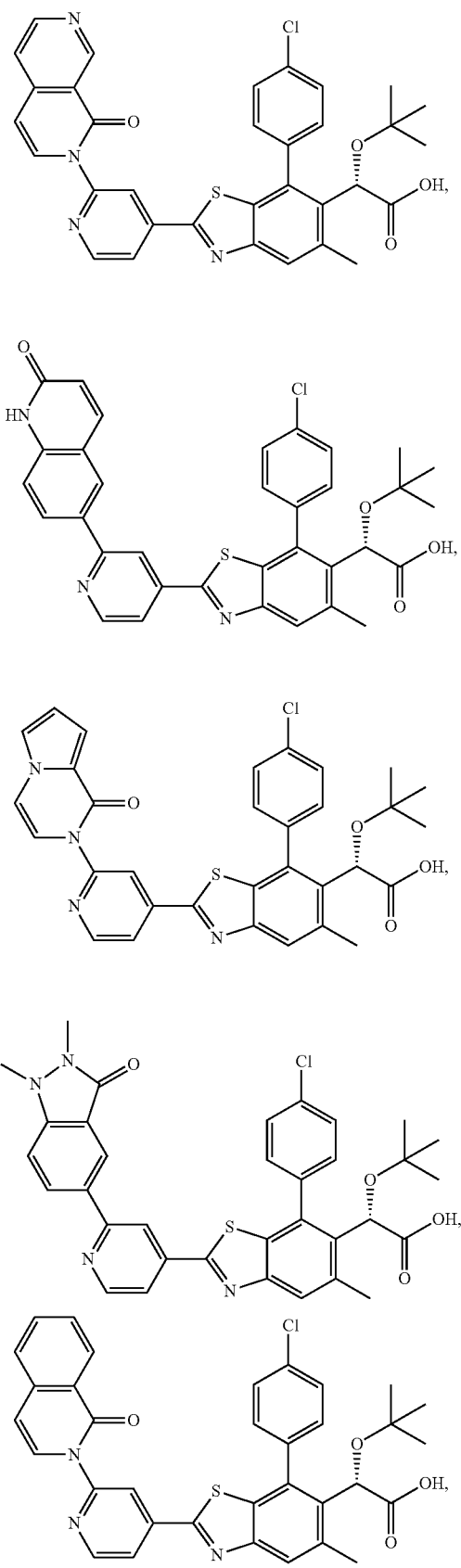
744
-continued
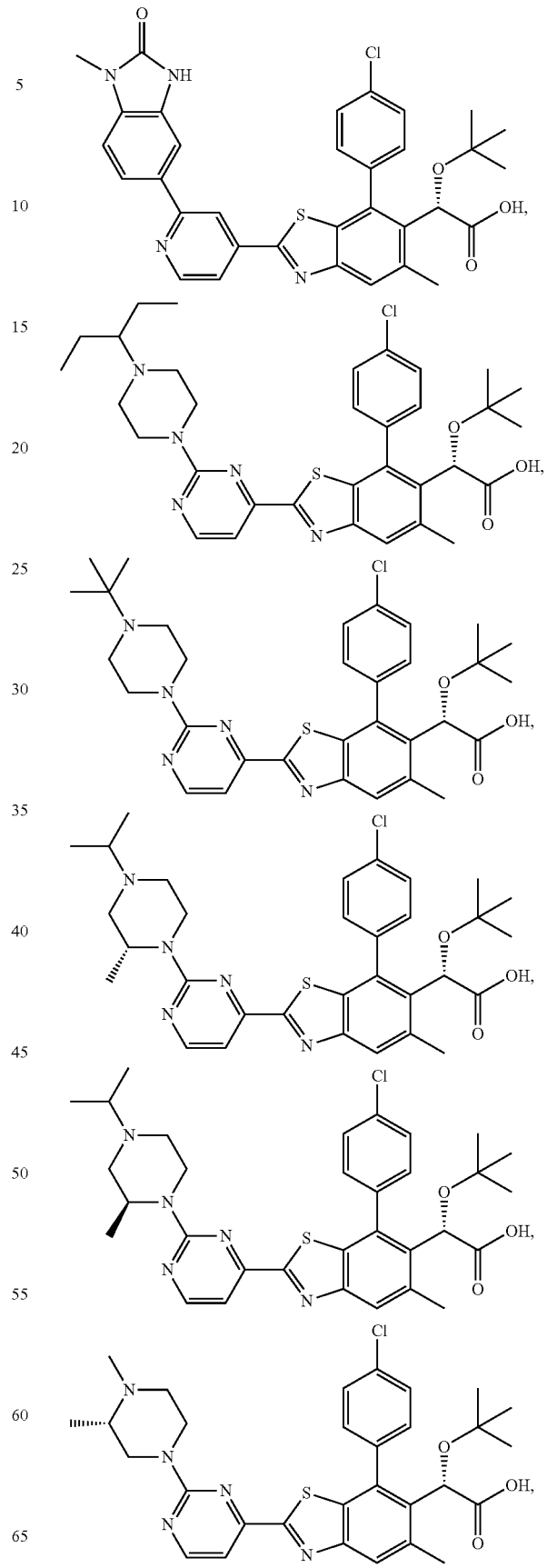

745
-continued
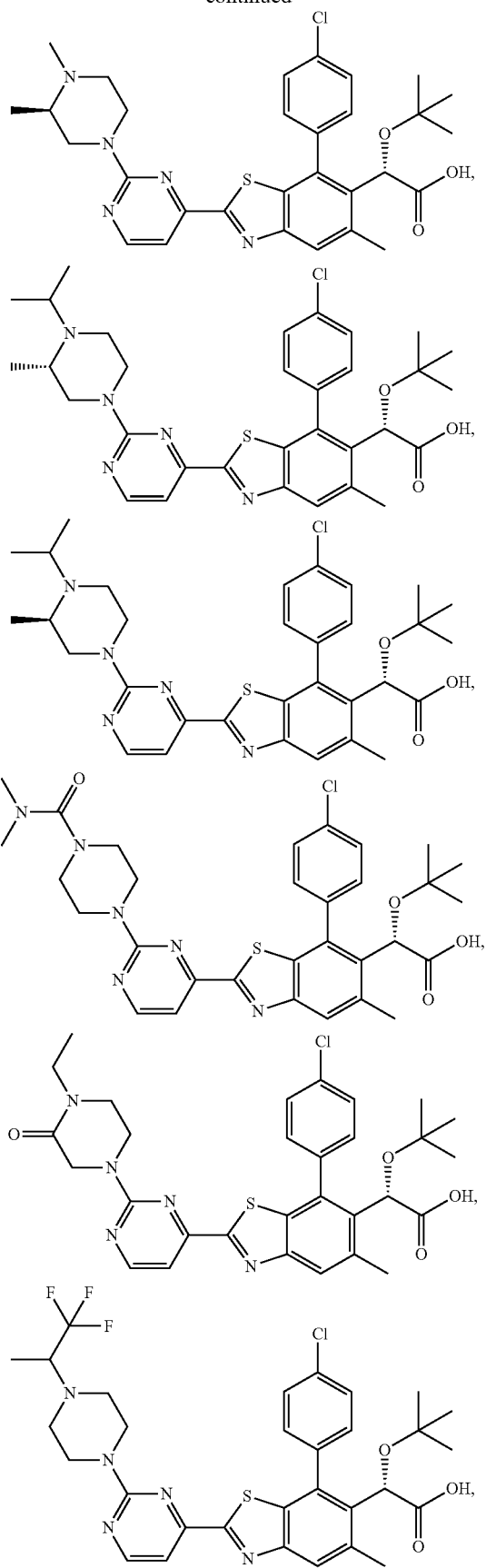
746
-continued
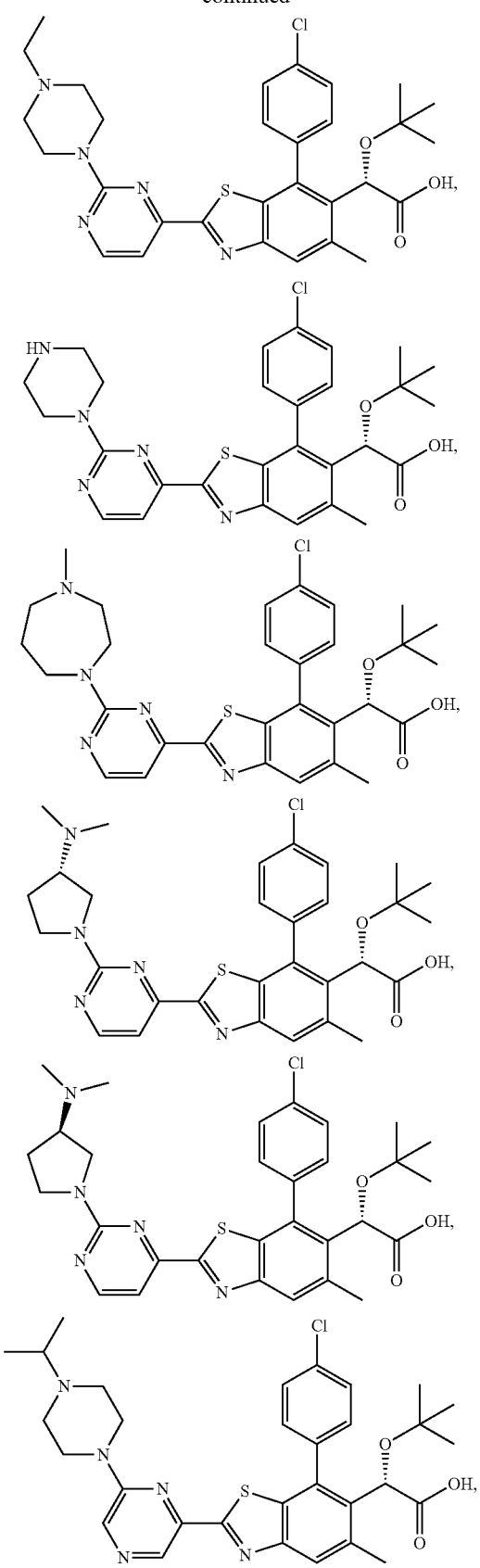

747
-continued
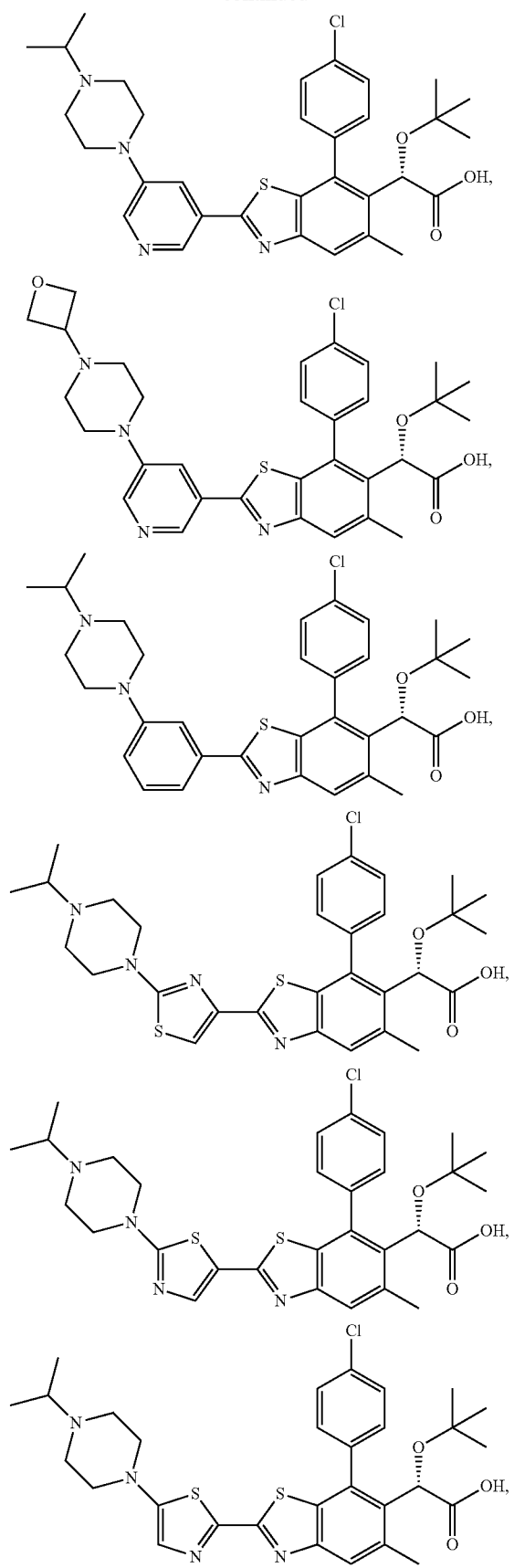
748
-continued
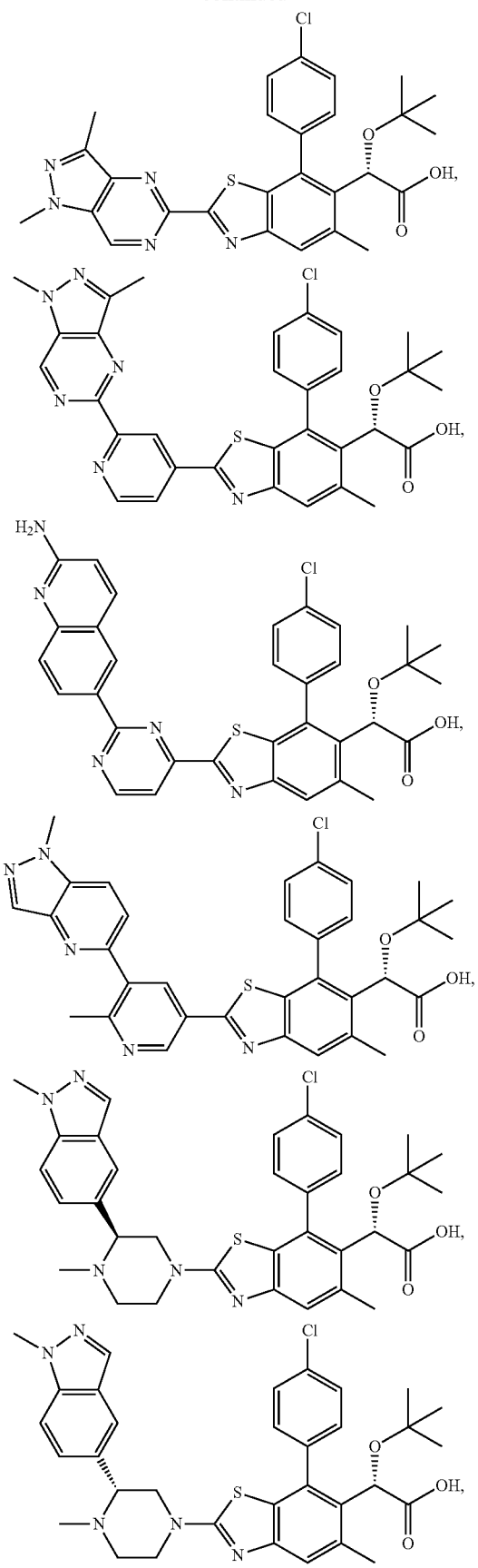

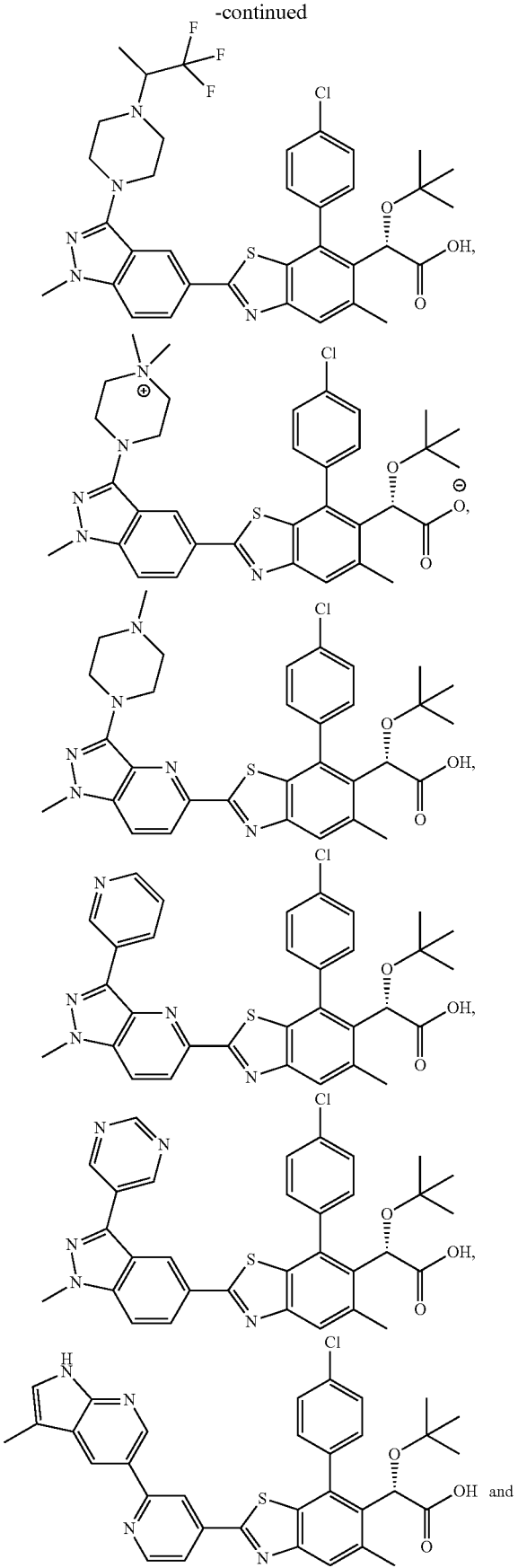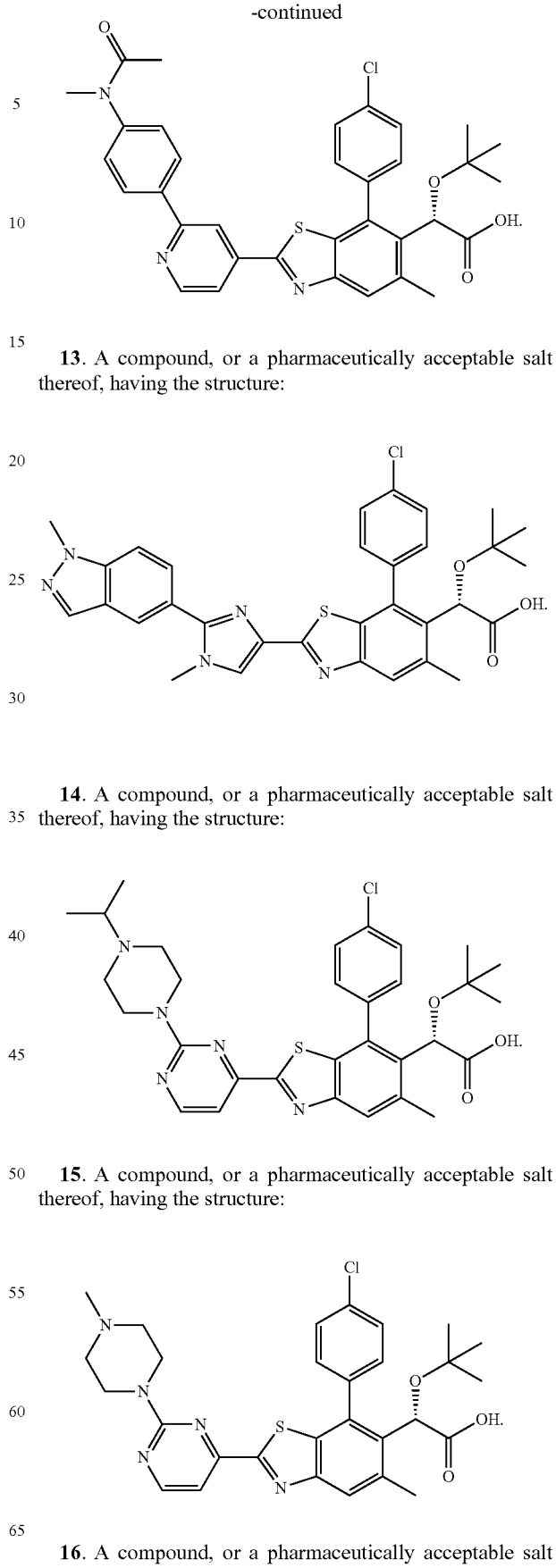
13. A compound, or a pharmaceutically acceptable salt thereof, having the structure:
14. A compound, or a pharmaceutically acceptable salt thereof, having the structure:
15. A compound, or a pharmaceutically acceptable salt thereof, having the structure:
16. A compound, or a pharmaceutically acceptable salt thereof, having the structure:

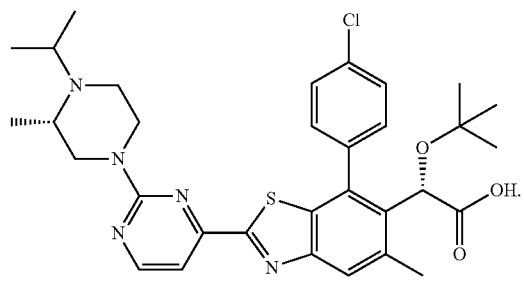 [SMILES: Cc1cc2nc(-c3ccnc(N4CCN(C(C)C)[C@@H](C)C4)n3)sc2c(-c2ccc(Cl)cc2)c1[C@H](OC(C)(C)C)C(=O)O]

17. A compound, or a pharmaceutically acceptable salt thereof, having the structure:

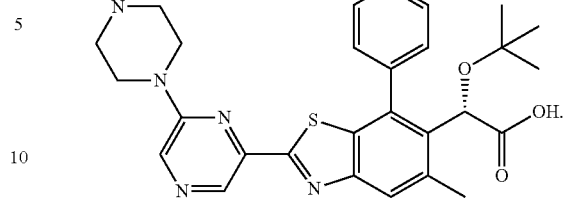

19. A compound, or a pharmaceutically acceptable salt thereof, having the structure:

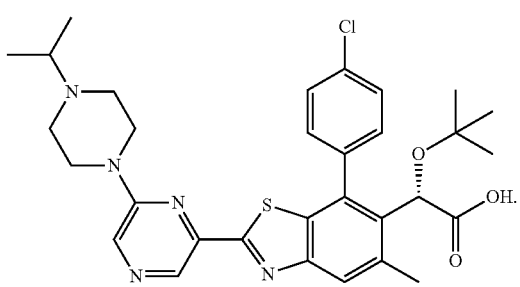 [SMILES: Cc1cc2nc(-c3cncc(N4CCN(C(C)C)CC4)n3)sc2c(-c2ccc(Cl)cc2)c1[C@H](OC(C)(C)C)C(=O)O]

18. A compound, or a pharmaceutically acceptable salt thereof, having the structure:

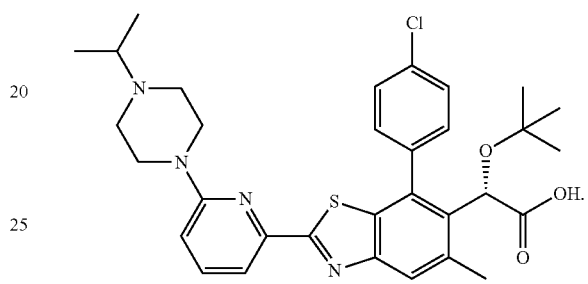

20. A pharmaceutical composition comprising a compound according to claim 1, or a pharmaceutically acceptable salt thereof, and a pharmaceutically acceptable carrier.

* * * * *